US012110499B2

United States Patent
(12) United States Patent
Scharenberg et al.

(10) Patent No.: US 12,110,499 B2
(45) Date of Patent: Oct. 8, 2024

(54) HOMOLOGY DIRECTED REPAIR COMPOSITIONS FOR THE TREATMENT OF HEMOGLOBINOPATHIES

(71) Applicants: Seattle Children's Hospital, Seattle, WA (US); Fred Hutchinson Cancer Center, Seattle, WA (US)

(72) Inventors: Andrew Scharenberg, Seattle, WA (US); Kyle Jacoby, Seattle, WA (US); Hans-Peter Kiem, Seattle, WA (US); David J. Rawlings, Seattle, WA (US); Christopher Lux, Bremerton, WA (US); Sowmya Pattabhi, Bellevue, WA (US); Olivier M. Humbert, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 554 days.

(21) Appl. No.: 16/608,182

(22) PCT Filed: Apr. 24, 2018

(86) PCT No.: PCT/US2018/029235
§ 371 (c)(1),
(2) Date: Oct. 24, 2019

(87) PCT Pub. No.: WO2018/200597
PCT Pub. Date: Nov. 1, 2018

(65) Prior Publication Data

US 2021/0222201 A1 Jul. 22, 2021

Related U.S. Application Data

(60) Provisional application No. 62/488,927, filed on Apr. 24, 2017.

(51) Int. Cl.

| | |
|---|---|
| ***C12N 15/90*** | (2006.01) |
| ***A61K 35/28*** | (2015.01) |
| ***A61P 9/00*** | (2006.01) |
| ***C07K 14/805*** | (2006.01) |
| ***C12N 15/11*** | (2006.01) |
| ***C12N 15/86*** | (2006.01) |

(52) U.S. Cl.
CPC ............ *C12N 15/907* (2013.01); *A61K 35/28* (2013.01); *A61P 9/00* (2018.01); *C07K 14/805* (2013.01); *C12N 15/11* (2013.01); *C12N 15/86* (2013.01); *C12N 2310/20* (2017.05); *C12N 2750/14143* (2013.01); *C12N 2800/80* (2013.01)

(58) Field of Classification Search
CPC ...... C12N 15/907; C12N 15/11; C12N 15/86; C12N 2310/20; C12N 2750/14143; C12N 2800/80; C12N 15/102; C12N 15/10; A61K 35/28; A61K 48/00; A61P 9/00; C07K 14/805
See application file for complete search history.

(56) References Cited

U.S. PATENT DOCUMENTS

| | | | | |
|---|---|---|---|---|
| 6,051,402 | A | 4/2000 | LeBoulch et al. | |
| 7,901,671 | B2 | 3/2011 | Leboulch et al. | |
| 9,017,967 | B2 | 4/2015 | Bonas et al. | |
| 9,068,199 | B2 | 6/2015 | Leboulch et al. | |
| 2014/0080216 | A1 | 3/2014 | Cost et al. | |
| 2015/0133528 | A1 | 5/2015 | Krieg et al. | |
| 2015/0166969 | A1 | 6/2015 | Takeuchi et al. | |
| 2020/0255857 | A1* | 8/2020 | Gori ..................... | C12N 5/0602 |

FOREIGN PATENT DOCUMENTS

| | | | |
|---|---|---|---|
| WO | WO-2014/036219 | A2 | 3/2014 |
| WO | WO-2017/115268 | A1 | 7/2017 |
| WO | WO-2017/218948 | A2 | 12/2017 |
| WO | WO2002088346 | A2 | 11/2022 |

OTHER PUBLICATIONS

Finotti et al. "Recent trends in the gene therapy of β-thalassemia." Journal of blood medicine 6 (2015): 69 (Year: 2015).*
Choi et al. "Optimization of AAV expression cassettes to improve packaging capacity and transgene expression in neurons." Molecular brain 7.1 (2014): 1-10 (Year: 2014).*
Dever, et al., "CRISPR/Cas9 β-Globin Gene Targeting in Human Hematopoietic Stem Cells," *Nature*, 539 (7629):384-389, (Nov. 17, 2016).
Hoban, et al., "Correction of the Sickle Cell Disease Mutation in Human Hematopoietic Stem/Progenitor Cells," *Blood*, 725:2597-2604, (Apr. 23, 2015).
Pattabhi, et al., "In Vivo Outcome of Homology-Directed Repair at the HBB Gene in HSC Using Alternative Donor Template Delivery Methods," *Molecular Therapy Nucleic Acids*, 77:277-288, (Sep. 1, 2019).
Balazs and Godbey, "Liposomes for use in gene delivery," J. Drug Deliv., vol. 2011, No. 326497, 2011, 12 pages.
Cong, et al., "Multiplex genome engineering using CRISPR/Cas systems," Science, vol. 339, No. 6121, 2013, pp. 819-823.
Office Action dated Dec. 20, 2021 for European Application No. 18789938, 5 pages.
Gilman, et al., "Distal CCAAT box deletion in the A gamma globin gene of two black adolescents with elevated fetal A gamma globin," Nucleic Acids Res., vol. 16, No. 22, 1988, pp. 10635-10642.

(Continued)

*Primary Examiner* — Janet L Epps-Smith
*Assistant Examiner* — Alexander W Nicol
(74) *Attorney, Agent, or Firm* — C. Rachal Winger; Lee & Hayes PC

(57) ABSTRACT

The present disclosure provides improved compositions for the homology directed repair of the human globin locus for the prevention, treatment, or amelioration of at least one symptom of a hemoglobinopathy.

18 Claims, 98 Drawing Sheets

Specification includes a Sequence Listing.

(56) References Cited

OTHER PUBLICATIONS

Huang and Yen, “Role of the hepatitis B virus posttranscriptional regulatory element in export of intronless transcripts,” Mol. Cell. Biol., vol. 15, No. 7, 1995, pp. 3864-3869.
Jinek, et al., “A programmable dual-RNA-guided DNA endonuclease in adaptive bacterial immunity,” Science, vol. 337, No. 6096, 2012, pp. 816-821.
Jinek, et al., “RNA-programmed genome editing in human cells,” eLife 2:e00471, 2013, 9 pages.
Liu and Mertz, “HnRNP L binds a cis-acting RNA sequence element that enables intron-dependent gene expression,” Genes Dev., vol. 9, No. 14, 1995, pp. 1766.
Liu, et al., “Poly(cationic lipid)-mediated in vivo gene delivery to mouse liver,” Gene Therapy., vol. 10, No. 2, 2003, pp. 180-187.
Mali, et al., “RNA-guided human genome engineering via Cas9,” Science, vol. 339, No. 6121, 2013, pp. 823-826.
Qi, et al., “Repurposing CRISPR as an RNA-guided platform for sequence-specific control of gene expression,” Cell, vol. 152, No. 5, 2013, pp. 1173-1183.
Ran, et al., “Genome engineering using the CRISPR-Cas9 system,” Nature Protocols, vol. 8, No. 11, 2013, pp. 2281-2308.
Segal, “Bacteria herald a new era of gene editing,” eLife 2:e00563, 2013, 3 pages.
Wall, et al., “The human B-globin gene 3' enhanver contains multiple binding sites for an erythroid-specific protein,” Cen. Dev , vol. 2, 1988, 1089-1100.
Zetsche, et al., “Cpf1 is a single RNA-guided endonuclease of a class 2 CRISPR-Cas system,” Cell, vol. 163, No. 3, 2015, pp. 759-771.
Zufferey, et al., “Woodchuck hepatitis virus posttranscriptional regulatory element enhances expression of transgenes delivered by retroviral vectors,” J. Virol., vol. 73, No. 4, 1999, pp. 2886-2892.
Manca, et al., “Disorders of the Synthesis of Human Fetal Hemoglobin,” *IUBMB Life*, 60(2):94-111, (Feb. 2008).
Kiem, et al., Abstract “Novel Gene Editing Approaches for Hemoglobinopathies,” National Institutes of Health Grant No. HL136135 (Funding Start Date Jan. 17, 2017).
International Search Report from PCT/US2018/029235, dated Oct. 2, 2018.
Office Action dated Feb. 2, 2023, in European Application No. 18789938, 6 pages.

* cited by examiner

Day 0
Thaw hPBSCs
SCGM w/
SCF/Flt3/TPO/IL3
2
TALEN mRNA
Transfection
30°C/37°C
3
37°C
5
Erythroid
Differentiation
IMDM w/ EPO/SCF/IL3
17-20
Erythroid
Analysis
FACS/HPLC Count
CD235a (BV421)
TALEN
Mock
HbF (APC)
TALEN
Mock %HbF (FACS)
TALEN mRNA (μg)
37°C
30°C β-Globin (HPLC)
TALEN mRNA (μg)
37°C
30°C
HBG1
HBG2
HBB 3.5kb, 1.3kb HPFH deletion repair templates

- Generate a large deletion to drive fetal hemoglobin expression

| | | |
|---|---|---|
| d3.5kb | 1240 | pAAV d3.5kb(600) MND>GFP.wPRE-O.BGHpA |
| | 1241 | pAAV d3.5kb(600) HPFH-2.MND>GFP.wPRE-O.BGHpA |
| d1.3kb | 1255 | pAAV HBG1d-1.3kb,-382(600) MND>GFP.wPRE3.SV40USE.pA |
| | 1256 | pAAV HBG1d-1.3kb,-1(600) MND>GFP.wPRE3.SV40USE.pA;HBBp> |

FIG. 9

HBG1 Round 1 Repair Templates

- V1&3 – uses the d13 HBG1 promoter to drive T87Q globin expression
- V4 – uses HBB promoter in the HBG1 locus to drive T87Q globin expression HBG1 Round 2 Repair Templates

- New versions based on data from V1

| | | |
|---|---|---|
| HBG1 Round1 | V1E1 | pAAV HBG1.d-667,-1(600) MND>GFP.wPREO.BGHpA;HBBp> (Upstream) |
| | V1E4 | pAAV HBG1(200-600).d13&dATG,stop>HBB(T87Q).3'enh;MND>GFP *200-600bp HA |
| | V1E5/1303 | pAAV HBG1(400).d13min>HBB(T87Q).3'enh;MND>GFP.SV40pA |
| | V3E5 | pAAV HBG1(200-600).d13>HBB(T87Q).3'enhCore;MND>GFP::T2A::Ex2 *200-600bp HA |
| | V3E6/1260 | V3E5 (400) corrected polyA |
| | V3E7/1292 | pAAV HBG1(600).d13min>HBB(T87Q).3'enhCore;MND>GFP.SV40pA |
| | V4E4 | pAAV HBG1d-247(200-600).HBBp>HBB(T87Q).3'enh;MND>MGMT::T2A::Ex2 *200-600bp HA |
| | V4E5/1304 | pAAV HBG1(400).d-141,-1 HBBp>HBB(T87Q).3'enh;MND>GFP.SV40pA |
| HBG1 Round2 | 1238 | pAAV HBG1(400).d13>HBBopt(T87Q).wPRE-O.BGHpA;MND>GFP::P2A:Ex2 * |
| | 1239 | pAAV HBG1(400).d13>HBBopt(T87Q).wPRE-O.BGHpA;HPFH2.MND>GFP::P2A:Ex2 * |
| | 1291 | HBG1(400).d13min>HBBopt(T87Q).wPRE-O.BGHpA;HPFH2.MND>GFP.SV40pA (like 1238) |

| | | |
|---|---|---|
| 1324 | HBG1(1k,900).d13 [MND>GFP.SV40pA];HPFH2.HS40.HBG1d13p> | Alt-HR Version |
| 1325 | HBG1(1k,900).d13 [MND>GFP.SV40pA];HPFH2.HS40.HBG1d13p> | deletional variant of 1324 |
| 1323 | HBG1d-141,-1(459,600) [MND>GFP.wPRE3.SV40USE.pA];HPFH-2.HS40.HBBp> | like 1293 GFP inverted |

FIG. 10

HBG1 Round 3 Repair Templates

- Improved 3rd generation based on previous HBG1 templates
- Drives T87Q Expression with HBG1 promoter

| | | |
|---|---|---|
| HBG1 Round3 | 1343 | HBG1(650).d0 HBBp>HBB(T87Q).core3'enh;PGK>MGMT(P140K).SV40pA |
| | 1344 | HBG1(500).d0 HBBp>HBB(T87Q).core3'enh;PGK>MGMT(P140K).wPRE3.SV40pA |
| | 1345 | HBG1(650).d0 HBBp>HBB(T87Q).core3'enh;MND>GFP.SV40pA |
| | 1346 | HBG1(650).d0 HBG1d13>HBB(T87Q).core3'enh;PGK>MGMT(P140K).SV40pA |
| | 1333 | HBG1d-141,-1(459,600) MND>MGMT.wPRE3.SV40USE.pA;HPFH-2.HS40.HBBp> |
| | 1334 | HBG1d-141,-1(459,600) hPGK>MGMT.wPRE3.SV40USE.pA;HPFH-2.HS40.HBBp> |
| | 1336 | HBG1(600).d-114,488 HG1d13>HBB(T87Q).core3'enh;PGK>MGMT.T2A.Ex2 |

Simple repair template with 2kb homology arms flanking a 13bp deletion

| | | |
|---|---|---|
| d13 Repair | 1315 | pAAV HBG1(2.2kb)d13 repair only |

FIG. 11

Rhesus Repair Templates

| | | | |
|---|---|---|---|
| Rhesus | 1268 | V3E6(400) in AAV (corrected polyA) | RHESUS V3E6 |
| | 1308 | HBG1d-141,-1(900,1kb)<br>MND>GFP.wPRE3.SV40USE.pA;HBBp> | RHESUS 1295 |
| | 1347 | HBG1(650).d0<br>HBBp>HBB(T87Q).core3'enh;PGK>MGMT(P140K).SV40pA | RHESUS 1343 'ideal' |
| | 1348 | HBG1(650).d0<br>HBBp>HBB(T87Q).core3'enh;MND>GFP.SV40pA | RHESUS 1345 |

FIG. 12 d13 deletion driving HBG1 (Human)

| Gilman HR | |
|---|---|
| AMS#1324 pAAV HBG1(1k,900).d13 [MND>GFP.SV40pA];HPFH2.HS40.HBG1 d13p> | Incidental homology in the template: could be a alternate HR site<br>GFP is upstream in reverse orientation<br>HS40 enhancer<br>Direct repeat of the d13 promoter (at the 5' HR arm and end of HR template)<br>0 bp deletion |

d13 deletion driving HBG1 (Human)

| Gilman HR | |
|---|---|
| AMS#1325 pAAV HBG1(1k,900).d13 [MND>GFP.SV40pA];HPFH2.HS40.HBG1d13 p> | GFP is upstream in reverse orientation<br>d13 promoter in the 5' HR arm is deleted so no direct repeat<br>d13 promoter only at the end of HR template<br>281 bp deletion could lower HR rates |

1345 drives 3.5% HDR on day 13

HbF increases with RNP + HDR template delivery

HBB promoter driving T87Q (Human)

Gilman HR

AMS#1345 pAAV HBG1(650).d0
HBBp>HBB(T87Q).core3'enh;MND>GFP.SV40pA

HBB promoter drives T87Q
GFP
0 bp deletion

HBB promoter driving T87Q (Rhesus)

AMS#1348 Rhesus pAAV HBG1(650).d0
HBBp>HBB(T87Q).core3'enh;MND>GFP.SV40pA

HBB promoter drives T87Q
GFP
0 bp deletion

MGMT Cassettes (Human)

| | |
|---|---|
| AMS#1346 pAAV HBG1(650).d0<br>HBG1d13>HBB(T87Q).core3'enh;PGK>MGMT(P140K).SV40pA | HBG1>T87Q,<br>has direct repeat,<br>MGMT,<br>281 bp deletion |
| AMS#1343 pAAV HBG1(650).d0<br>HBBp>HBB(T87Q).core3'enh;PGK>MGMT(P140K).SV40pA | HBB>T87Q,<br>MGMT<br>0 bp deletion |

FIG. 30

HBB promoter driving T87Q (Rhesus)

| | |
|---|---|
| AMS#1347 Rhesus pAAV HBG1(650).d0 HBBp>HBB(T87Q).core3'enh;PGK>MGMT(P140K).SV40pA | HBB promoter drives T87Q<br>MGMT selection<br>0 bp deletion |

| Animal ID | A17117 | A17114 | A17112 | A17116 | A17115 | A17113 |
|---|---|---|---|---|---|---|
| Target cells | $CD34^+$ | $CD34^+$ | $CD34^+$ | $CD90^+$ | $CD90^+$ | $CD90^+$ |
| Date of infusion | 7/14/17 | 8/4/17 | 2/8/18 | 9/28/17 | 11/17/17 | 3/23/18 |
| Animal Weight [kg] | 5 | 4.9 | 7.3 | 5.25 | 4.5 | 4.55 |
| | | | | | | |
| Cell-sorting parameters: | | | | | | |
| # of cells before sort | 95.2E+06 | 90.0E+06 | 144E+06 | 287E+06 | 290E+06 | 155E+06 |
| # of $CD90^+$ sorted | - | - | - | 10.0E+06 | 11.3E+06 | 14.0E+06 |
| # of $CD90^-$ sorted | - | - | - | 125E+06 | 199E+06 | 103E+06 |
| | | | | | | |
| Infusion product parameters: | | | | | | |
| # in $CD34^+$ fraction | 125E+06 | 83.5E+06 | 204E+06 | - | - | - |
| # in $CD90^+$ fraction | - | - | - | 15.0E+06 | 8.65E+06 | 5.15E+06 |
| # in $CD90^-$ fraction | - | - | - | 266E+06 | 213E+06 | 50.0E+06 |
| Total cells infused | 125E+06 | 83.5E+06 | 204E+06 | 281E+06 | 221E+06 | 55.2E+06 |
| | | | | | | |
| Calculated number of cells infused: | | | | | | |
| # of $CD34^+$ cells | 53.0E+06 | 33.5E+06 | 148E+06 | 64.6E+06 | 77.4E+06 | 15.7E+06 |
| # of $CD90^+$ cells | 3,537,500 | 3,582,150 | 4,998,000 | 5,223,540 | 3,053,730 | 1,639,000 |
| | | | | | | |
| # of $CD34^+$ cells/kg | 10.6E+06 | 6.84E+06 | 20.3E+06 | 12.3E+06 | 17.2E+06 | 3.45E+06 |
| # of $CD90^+$ cells/kg | 707,500 | 731,051 | 684,657 | 994,960 | 678,606 | 360,219 |
| | | | | | | |

FIG. 46

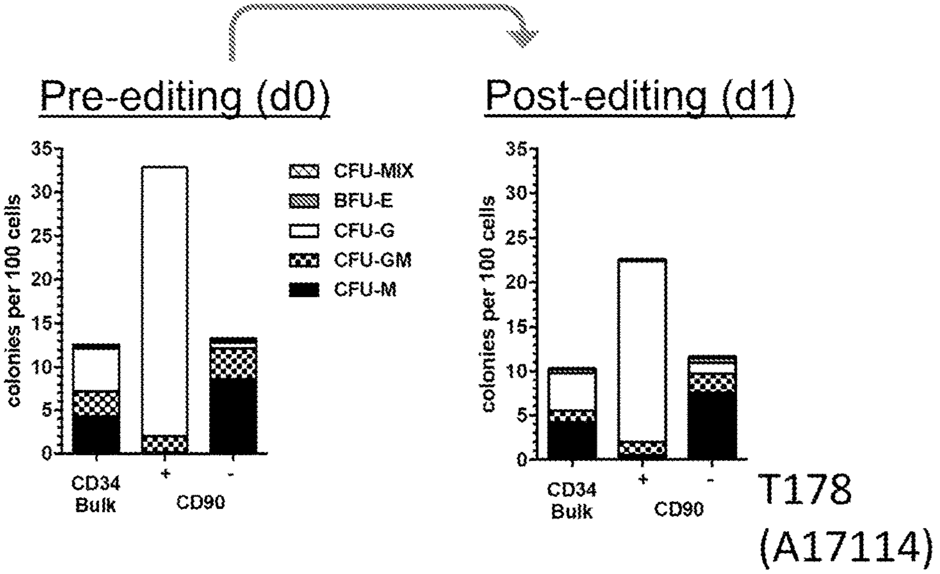
FIG. 54B
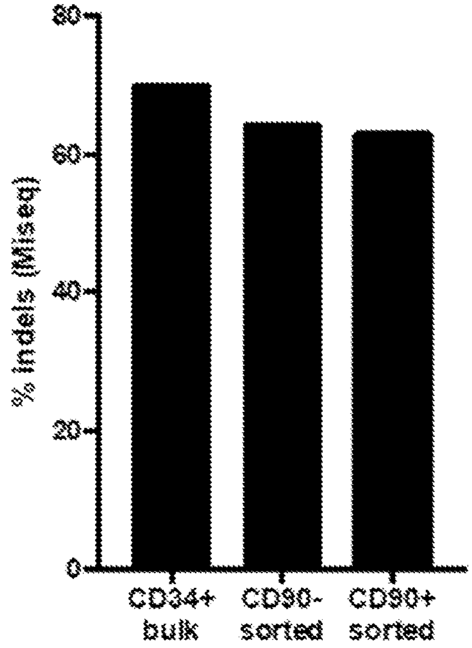
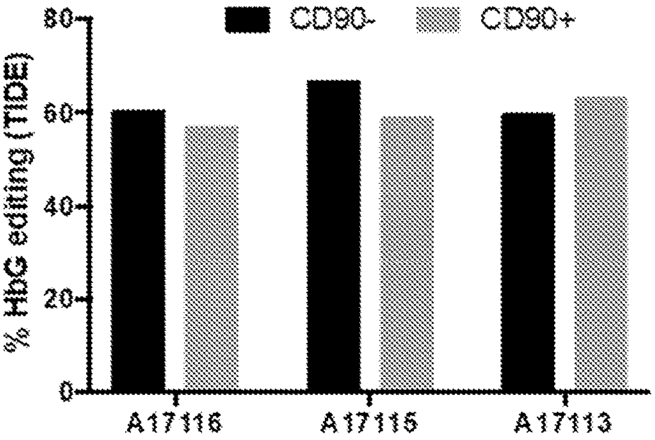
FIG. 54C
FIG. 54D

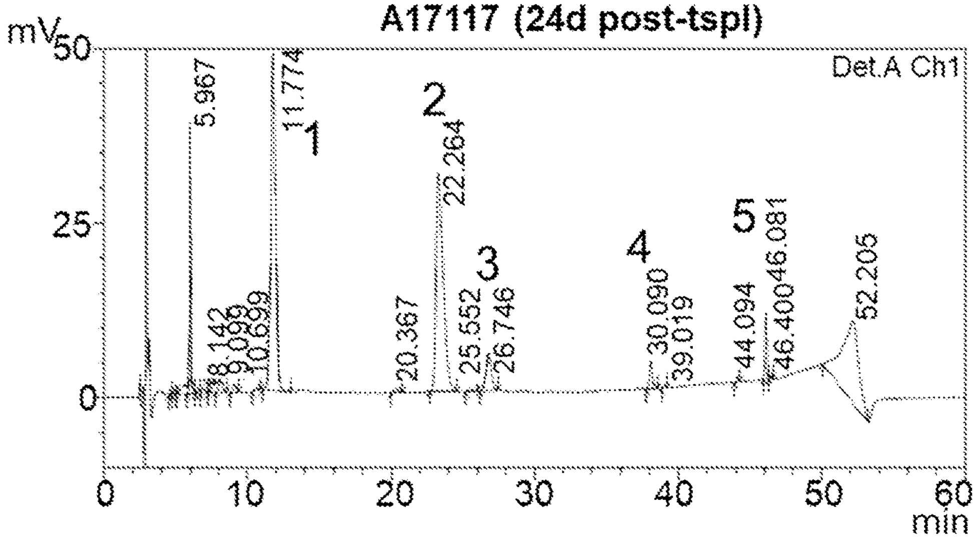

| | Description | # PSMs |
|---|---|---|
| | Globin A1 OS=Macaca mulatta GN=HBB PE=2 SV=1 | 1352 |
| 1 | Hemoglobin subunit beta OS=Macaca mulatta GN=HBB PE=1 SV=1 | 1264 |
| | Uncharacterized protein OS=Macaca mulatta GN=LOC715607 PE=3 SV=2 | 224 |
| | Hemoglobin subunit epsilon OS=Macaca mulatta GN=HBE1 PE=2 SV=3 | 186 |

| | | |
|---|---|---|
| | Hemoglobin alpha chain OS=Macaca mulatta GN=HBA2 PE=2 SV=1 | 768 |
| 2 | Uncharacterized protein OS=Macaca mulatta PE=3 SV=2 | 482 |
| | Hemoglobin subunit beta OS=Macaca mulatta GN=HBB PE=1 SV=1 | 312 |
| | Hemoglobin subunit gamma OS=Macaca mulatta GN=HBG PE=1 SV=2 | 135 |

| | | |
|---|---|---|
| | Hemoglobin alpha chain OS=Macaca mulatta GN=HBA2 PE=2 SV=1 | 371 |
| 3 | Hemoglobin subunit beta OS=Macaca mulatta GN=HBB PE=1 SV=1 | 206 |
| | Hemoglobin subunit gamma OS=Macaca mulatta GN=HBG PE=1 SV=2 | 118 |

| | | |
|---|---|---|
| | Hemoglobin subunit gamma OS=Macaca mulatta GN=HBG PE=1 SV=2 | 155 |
| | Hemoglobin subunit beta OS=Macaca mulatta GN=HBB PE=1 SV=1 | 68 |
| 4 | | |
| | Keratin 5 OS=Macaca mulatta GN=KRT5 PE=3 SV=2 | 87 |
| | Gamma-globin OS=Macaca mulatta GN=LOC715607 PE=3 SV=1 | 86 |

FIG. 58

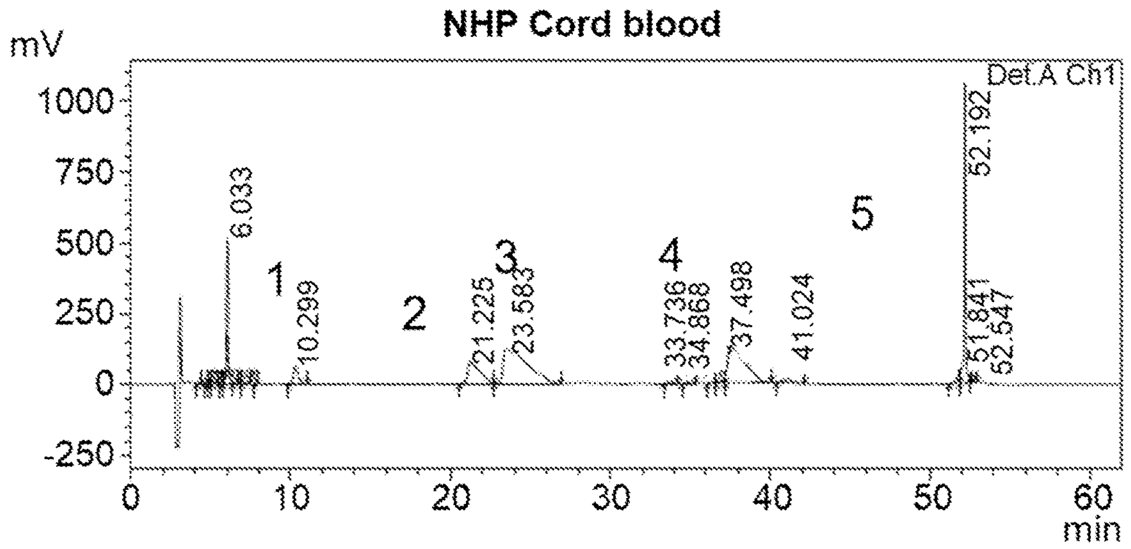

| | Description | # PSMs |
|---|---|---|
| | Globin A1 OS=Macaca mulatta GN=HBB PE=2 SV=1 | 265 |
| 1 | Hemoglobin subunit beta OS=Macaca mulatta GN=HBB PE=1 SV=1 | 248 |
| | Hemoglobin alpha chain OS=Macaca mulatta GN=HBA2 PE=2 SV=1 | 60 |
| | Hemoglobin subunit gamma OS=Macaca mulatta GN=HBG PE=1 SV=2 | 42 |
| | Hemoglobin alpha chain OS=Macaca mulatta GN=HBA2 PE=2 SV=1 | 187 |
| 2 | Hemoglobin subunit alpha OS=Macaca mulatta GN=HBA PE=1 SV=2 | 183 |
| | Uncharacterized protein OS=Macaca mulatta PE=3 SV=2 | 138 |
| 3 | Hemoglobin alpha chain OS=Macaca mulatta GN=HBA2 PE=2 SV=1 | 233 |
| | Uncharacterized protein OS=Macaca mulatta PE=3 SV=2 | 139 |
| | Hemoglobin subunit gamma OS=Macaca mulatta GN=HBG PE=1 SV=2 | 310 |
| 4 | Globin A1 OS=Macaca mulatta GN=HBB PE=2 SV=1 | 31 |
| | Hemoglobin subunit epsilon OS=Macaca mulatta GN=HBE1 PE=2 SV=3 | 28 |
| | Hemoglobin alpha chain OS=Macaca mulatta GN=HBA2 PE=2 SV=1 | 21 |
| | Gamma-globin OS=Macaca mulatta GN=LOC715607 PE=3 SV=1 | 371 |
| 5 | Arachidonate 15-lipoxygenase OS=Macaca mulatta GN=ALOX15 PE=3 SV=1 | 37 |

FIG. 58 (Continued)

AAV5 donor construct 1348:
HBG1(650).d0 HBBp>HBB(T87Q).core3'enh;MND>GFP.SV40pA

HOMOLOGY DIRECTED REPAIR COMPOSITIONS FOR THE TREATMENT OF HEMOGLOBINOPATHIES

RELATED APPLICATIONS

This application is a national stage filing under 35 U.S.C. 371 of International Application No. PCT/US2018/029235, filed Apr. 24, 2018, which claims the benefit of U.S. Provisional Application No. 62/488,927, filed on Apr. 24, 2017. The entire teachings of the above applications are incorporated herein by reference.

GOVERNMENT SUPPORT

This invention was made with government support under HL136135 awarded by the National Institutes of Health. The government has certain rights in the invention.

REFERENCE TO SEQUENCE LISTING

The Sequence Listing associated with this application is provided in text format in lieu of a paper copy and is hereby incorporated by reference into the specification. The name of the text file containing the Sequence Listing is 5281-0038US_ST25.txt. The text file is 544 KB, was created on Oct. 27, 2022, and is being submitted electronically via PatentCenter.

BACKGROUND

Technical Field

The present disclosure relates to improved compositions for use in homology directed repair of the human globin locus. More particularly, the disclosure relates to improved donor repair templates for editing the human globin locus for the prevention, treatment, or amelioration of at least one symptom of a hemoglobinopathy.

Description of the Related Art

Hemoglobinopathies are a diverse group of inherited monogenetic blood disorders that result from variations in the structure and/or synthesis of hemoglobin. The most common hemoglobinopathies are sickle cell disease (SCD), α-thalassemia, and β-thalassemia. Approximately 5% of the world's population carries a globin gene mutation. The World Health Organization estimates that more than 300,000 infants are born each year with major hemoglobin disorders. Hemoglobinopathies manifest highly variable clinical manifestations that range from mild hypochromic anemia to moderate hematological disease to severe, lifelong, transfusion-dependent anemia with multiorgan involvement.

The only potentially curative treatment available for hemoglobinopathies is allogeneic hematopoietic stem cell transplantation. However, it is estimated that HLA-compatible HSC transplants are available to less than 20% of affected individuals and long term toxicities are substantial. In addition, HSC transplants are also associated with significant mortality and morbidity in subjects that have SCD or severe thalassemias. The significant mortality and morbidity is due in part to pre-HSC transplantation transfusion-related iron overload, graft-versus-host disease (GVHD), and high doses of chemotherapy/radiation required for pre-transplant conditioning of the subject, among others.

Supportive treatments for hemoglobinopathies include periodic blood transfusions for life, combined with iron chelation, and in some cases splenectomy. Additional treatments for SCD include analgesics, antibiotics, ACE inhibitors, and hydroxyurea. However, the side effects associated with hydroxyurea treatment include cytopenia, hyperpigmentation, weight gain, opportunistic infections, azoospermia, hypomagnesemia, and cancer.

At best, patients treated with existing methods have a projected lifespan of 50 to 60 years.

BRIEF SUMMARY

The present disclosure generally relates, in part, to improved donor repair templates used for editing a human γ-globin gene.

In particular embodiments, a DNA donor repair template is contemplated comprising: a 5' homology arm and a 3' homology arm, wherein the donor repair template comprises a polynucleotide sequence within at least about 1 kb, at least about 1.5 kb, or at least about 2 kb upstream of the transcription start site of a human gamma globin gene and further comprises a deletion of Chr11: 5249959-5249971.

In particular embodiments, a DNA donor repair template is contemplated comprising: a 5' homology arm; a selection cassette; an erythroid expression control sequence; and a 3' homology arm.

In certain embodiments, the length of the 5' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 5' homology arm comprises a polynucleotide sequence within at least about 1 kb, at least about 1.5 kb, or at least about 2 kb upstream of the transcription start site of a human gamma globin gene.

In some embodiments, the 5' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 5' homology arm comprises a polynucleotide sequence within 1 kb upstream of the transcription start site of a human gamma globin gene and the 5' homology arm comprises a deletion in the region of Chr11: 5249957-5249977.

In certain embodiments, the deletion in the region of Chr11: 5249957-5249977 is a deletion associated with hereditary persistence of fetal hemoglobin.

In some embodiments, the deletion in the region of Chr11: 5249957-5249977 is a deletion associated with derepression of gamma globin expression.

In particular embodiments, the deletion in the region of Chr11: 5249957-5249977, comprises a deletion of the polynucleotide sequence of any one of SEQ ID NOs: 1-6.

In particular embodiments, the deletion in the region of Chr11: 5249957-5249977, comprises a deletion of the polynucleotide sequence of Chr11: 5249959-5249971.

In further embodiments, the selection cassette comprises a ubiquitous promoter, a constitutive promoter, an inducible promoter, or hematopoietic stem cell promoter, operably linked to a polynucleotide sequence encoding a selectable marker, and one or more post-transcription regulatory elements.

In certain embodiments, the promoter is selected from the group consisting of: a cytomegalovirus (CMV) immediate early promoter, a viral simian virus 40 (SV40) promoter, a Moloney murine leukemia virus (MoMLV) LTR promoter, a Rous sarcoma virus (RSV) LTR promoter, a herpes simplex virus (HSV) (thymidine kinase) promoter, a H5, P7.5, or P11 vaccinia virus promoter, a short elongation factor 1-alpha (EF1a-short) promoter, a long elongation factor 1-alpha (EF1a-long) promoter, an early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin (β-KIN) promoter, a human ROSA 26 promoter, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter.

In particular embodiments, the selectable marker is selected from the group consisting of: a hygromycin-B phosphotransferase (HPH) gene, an amino 3'-glycosyl phosphotransferase (NEO) gene, a dihydrofolate reductase (DHFR) gene, an adenosine deaminase (ADA) gene, a multi-drug resistance (MDR) gene, an $O^6$-methylguanine-DNA-methyltransferase (MGMT) gene, a bleomycin (BLE) gene, and a blasticidin-S deaminase (BSR) gene.

In certain embodiments, the one or more post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence.

In some embodiments, the polyadenylation sequence is selected from the group consisting of: an ideal poly(A) sequence, an SV40 poly(A) sequence, a bovine growth hormone (BGH) poly(A) sequence, and a rabbit β-globin poly(A) sequence.

In some embodiments, the erythroid expression control sequence comprises a human β-globin LCR responsive promoter.

In particular embodiments, the erythroid expression control sequence comprises an ankyrin gene promoter, an α-spectrin gene promoter, a β-spectrin gene promoter, or a β-globin gene promoter, optionally in combination with an HPFH-2 enhancer, an HS40 enhancer, or a β-globin gene 3' enhancer.

In further embodiments, the erythroid expression control sequence is positioned to be operably linked to an endogenous gamma globin gene when the DNA donor repair template is integrated into the human genome.

In certain embodiments, the endogenous gamma globin gene is the A-gamma globin gene (HBGA; HBG1).

In further embodiments, the endogenous gamma globin gene is the G-gamma globin gene (HBGG; HBG2).

In additional embodiments, DNA donor repair template is integrated into the human genome at both the HBG1 locus and the HBG2 locus and the erythroid expression control sequence of the DNA donor repair template integrated at the HBG1 locus is positioned to be operably linked to the endogenous HBG1 gene and the erythroid expression control sequence of the DNA donor repair template integrated at the HBG2 locus is positioned to be operably linked to the endogenous HBG2 gene.

In particular embodiments, the length of the 3' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 3' homology arm comprises a polynucleotide sequence downstream of the 5' homology arm and upstream of the start codon of the human gamma globin gene.

In particular embodiments, a DNA donor repair template is contemplated comprising: a 5' homology arm; a polynucleotide encoding a therapeutic globin and one or more post-transcriptional control elements; a selection cassette; and a 3' homology arm.

In particular embodiments, the length of the 5' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 5' homology arm comprises a polynucleotide sequence within 1 kb upstream of the transcription start site of a human gamma globin gene and the 5' homology arm comprises a deletion in the region of Chr11: 5249957-5249977.

In some embodiments, the deletion in the region of Chr11: 5249957-5249977 is a deletion associated with hereditary persistence of fetal hemoglobin.

In certain embodiments, the deletion in the region of Chr11: 5249957-5249977 is a deletion associated with derepression of gamma globin expression.

In some embodiments, the deletion in the region of Chr11: 5249957-5249977, comprises a deletion of the polynucleotide sequence of any one of SEQ ID NOs: 1-6.

In particular embodiments, the deletion in the region of Chr11: 5249957-5249977, comprises a deletion of the polynucleotide sequence of Chr11: 5249959-5249971.

In further embodiments, the endogenous gamma globin promoter is operably linked to the polynucleotide encoding the therapeutic globin.

In particular embodiments, the therapeutic globin is γ-globin, β-globin, δ-globin, or an anti-sickling β-globin.

In certain embodiments, the anti-sickling β-globin is selected from the group consisting of: β-globin$^{A-T87Q}$, β-globin$^{A-T87Q/K120E/K95E}$, and β-globin$^{A-T87Q/G16D/E22A}$.

In additional embodiments, the one or more post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence.

In particular embodiments, the polyadenylation sequence is selected from the group consisting of: an ideal poly(A) sequence, an SV40 poly(A) sequence, a bovine growth hormone (BGH) poly(A) sequence, and a rabbit β-globin poly(A) sequence.

In particular embodiments, the DNA donor repair template further comprises an erythroid enhancer that enhances the expression of the polynucleotide encoding the therapeutic globin.

In certain embodiments, the erythroid enhancer is selected from an HPFH-2 enhancer, an HS40 enhancer, or a β-globin gene 3' enhancer.

In some embodiments, the selection cassette comprises a ubiquitous promoter, a constitutive promoter, an inducible promoter, or hematopoietic stem cell promoter, operably linked to a polynucleotide sequence encoding a selectable marker, and optionally one or more post-transcription regulatory elements.

In some embodiments, the promoter is selected from the group consisting of: a cytomegalovirus (CMV) immediate early promoter, a viral simian virus 40 (SV40) promoter, a Moloney murine leukemia virus (MoMLV) LTR promoter, a Rous sarcoma virus (RSV) LTR promoter, a herpes simplex virus (HSV) (thymidine kinase) promoter, a H5, P7.5, or P11 vaccinia virus promoter, a short elongation factor 1-alpha (EF1a-short) promoter, a long elongation factor 1-alpha (EF1a-long) promoter, an early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin 03-KIN) promoter, a human ROSA 26 promoter, a Ubiquitin C (UBC) promoter, a phosphoglycerate kinase-1 (PGK) promoter, a cytomegalovirus enhancer/chicken (3-actin (CAG) promoter, a β-actin promoter and a myeloproliferative sarcoma virus enhancer, negative control region deleted, d1587rev primer-binding site substituted (MND) promoter.

In particular embodiments, the selectable marker is selected from the group consisting of: a hygromycin-B phosphotransferase (HPH) gene, an amino 3'-glycosyl phosphotransferase (NEO) gene, a dihydrofolate reductase (DHFR) gene, an adenosine deaminase (ADA) gene, a multi-drug resistance (MDR) gene, an $O^6$-methylguanine-DNA-methyltransferase (MGMT) gene, a bleomycin (BLE) gene, and a blasticidin-S deaminase (BSR) gene.

In certain embodiments, the one or more post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence.

In some embodiments, the polyadenylation sequence is selected from the group consisting of: an ideal poly(A) sequence, an SV40 poly(A) sequence, a bovine growth hormone (BGH) poly(A) sequence, and a rabbit β-globin poly(A) sequence.

In particular embodiments, the selection cassette comprises a ubiquitous promoter, a constitutive promoter, an inducible promoter, or hematopoietic stem cell promoter, operably linked to a polynucleotide sequence encoding a selectable marker, and a ribosomal skipping sequence or viral self-cleaving peptide.

In certain embodiments, the length of the 3' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 3' homology arm comprises a polynucleotide sequence downstream of the start codon of the gamma globin gene.

In certain embodiments, the gamma globin gene is the A-gamma globin gene (HBGA; HBG1).

In various embodiments, a viral vector comprises a DNA donor repair template contemplated herein.

In particular embodiments, the viral vector is a recombinant adeno-associated viral vector (rAAV) or a retrovirus.

In some embodiments, the rAAV has one or more ITRs from AAV2.

In further embodiments, the rAAV has a serotype selected from the group consisting of: AAV1, AAV2, AAV3, AAV4, AAV5, AAV6, AAV7, AAV8, AAV9, and AAV10.

In certain embodiments, the rAAV has an AAV6 serotype.

In additional embodiments, the retrovirus is a lentivirus.

In particular embodiments, the lentivirus is an integrase deficient lentivirus.

In some embodiments, a cell comprises a DNA donor repair template or a viral vector contemplated herein.

In some embodiments, the DNA donor repair template has been inserted into a human gamma globin gene target site by homology directed repair.

In further embodiments, the target site is an engineered nuclease target site set forth in SEQ ID NO: 7 or SEQ ID NO: 8.

In particular embodiments, the cell is a hematopoietic cell.

In certain embodiments, the cell is $CD34^+$ cell.

In particular embodiments, the cell is $CD133^+$ cell.

In various embodiments, a method for increasing gamma globin expression in a hematopoietic stem or progenitor cell comprising introducing one or more engineered nucleases that cleave a target site set forth in SEQ ID NO: 9 and a DNA donor repair template contemplated herein into the cell, whereby the DNA donor repair template is inserted into the cell genome by homology directed repair at a double strand break introduced by the one or more engineered nucleases.

In particular embodiments, a method for increasing therapeutic globin expression in a hematopoietic stem or progenitor cell comprises introducing one or more engineered nucleases that cleave a target site set forth in SEQ ID NO: 7 or SEQ ID NO: 8 and a DNA donor repair template contemplated herein into the cell, whereby the DNA donor repair template is inserted into the cell genome by homology directed repair at a double strand break introduced by the one or more engineered nucleases.

In some embodiments, a genome edited cell produced by a HDR with a donor repair template contemplated herein is provided.

In various embodiments, a composition comprises a DNA donor repair template, a viral vector, or a cell contemplated herein.

In various embodiments, a composition comprises a physiologically acceptable excipient and a DNA donor repair template, a viral vector, or a cell contemplated herein.

In further embodiments, a method of treating a hemoglobinopathy in a subject comprises administering the subject a cell or composition contemplated herein.

In various embodiments, a method of ameliorating at least one symptom, of a hemoglobinopathy in a subject comprises administering the subject a cell or composition contemplated herein.

In particular embodiments, the β-globin alleles of the subject are $\beta^E/\beta^0$, $\beta^C/\beta^0$, $\beta^0/\beta^0$, $\beta^E/\beta^E$, $\beta^C/\beta^+$, $\beta^E/\beta^+$, $\beta^E/\beta^+$, $\beta^0/\beta^+$, $\beta^+/\beta^+$, $\beta^E/\beta^S$, $\beta^0/\beta^S$, $\beta^C/\beta^S$, $\beta^+/\beta^S$ or $\beta^S/\beta^S$.

In additional embodiments, a method of treating a thalassemia in a subject comprises administering the subject an effective amount of a cell or composition contemplated herein.

In certain embodiments, the thalassemia is a β-thalassemia.

In particular embodiments, the β-globin alleles of the subject are $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In certain embodiments, a method of treating sickle cell disease in a subject comprises administering the subject an effective amount of a cell or composition contemplated herein.

In particular embodiments, the β-globin alleles of the subject are $\beta^E/\beta^S$, $\beta^0/\beta^S$, $\beta^C/\beta^S$, $\beta^+/\beta^S$ or $\beta^S/\beta^S$.

In some embodiments, a method of treating a β-thalassemia in a subject comprises administering the subject an effective amount of a cell or composition contemplated herein.

In particular embodiments, the β-globin alleles of the subject are $β^E/β^0$, $β^C/β^0$, $β^0/β^0$, $β^C/β^C$, $β^E/β^E$, $β^E/β^+$, $β^C/β^E$, $β^C/β^+$, $β^0/β^+$, or $β^+/β^+$.

BRIEF DESCRIPTION OF SEVERAL VIEWS OF THE DRAWINGS

FIG. 4A shows a diagram of the human β hemoglobin locus on Chromosome 11 highlighting the Aγ(HBG1) promoter structure. FIG. 4B provides a schematic of repressive elements that bind the γ-hemoglobin promoter including the CCAAT Displacement Protein (CDP/CUX1), DRED Complex (in conjunction with COUP-TFII), BCL11a (associated with the NURD complex which also partners with LRF) and the NF-Y binding sites. Negative transcription factors are shown in red. Positive transcriptions factors are shown in green. The putative BCL11a binding sequence (TGACCA) is underlined in red. The distal and proximal CCAAT boxes are underlined in green. Green * indicate the location of published HPFH SNPs. The bracketed green line highlights the 13 bp HPFH deletion as labeled. FIG. 4C shows TALENs selected in silico and tested. Blue boxes represent Repeat Variable Diresidues (RVDs) and their corresponding nucleotide is listed below. Scissors represent FokI endonuclease and the dotted line and indicated bp numbers represent the spacer length between the TALEN pairs.

FIG. 5A provides an experimental timeline for TALEN transfection of hPBSCs. FIG. 5B shows cell viability (right axis) and total cell number (left axis) assessed at two recovery temperatures (37° C. and 30° C.) and over increasing TALEN mRNA doses measured at 24 hours post transfection. (n=6/condition, p-values *<0.05, <0.005, *<0.0005)). TALEN mRNA doses higher than 1 ug had a significant negative impact on transfected cells and the effect was more pronounced with a 30° C. recovery step. FIG. 5C provides schematic of a novel ddPCR fall off assay designed to detect NHEJ events at both the HBG1 and HBG2 promoters. A common set of primers (green) are used to amplify the HBG1 and HGB2 alleles. A common NHEJ ddPCR Probe linked to HEX bind over the TALEN target cut site and is designed to fall off if single base insertion or deletion is present in the binding region. Unique HBG1 and HBG2 Ref ddPCR Probes linked to FAM bind to a region with three unique nucleotides allowing for editing of HBG1 and HBG2 to be assessed independently. FIG. 5D shows ddPCR results for hPBSCs edited with TALEN mRNA at increasing concentrations and two recovery temperatures. All cells transfected with TALEN mRNA result in significant indel generation. 30° C. recovery results in significantly higher rates of NHEJ than 37° C. but decreases with doses of TALEN mRNA over 1 ug. HBG1 NHEJ editing rates detected by this assay are roughly 50% of HBG2 due to the presence of large intergenic deletions. FIG. 5E shows rates of NHEJ following 1 ug mRNA transfection and detected by ddPCR do not vary by donor (n=3 donors). FIG. 5F shows NHEJ assessment by Next Gen Sequencing (Illumina MiSeq) detects editing rates lower than the ddPCR assay but demonstrate a consistent doubling in editing following 30° C. recovery. FIG. 5G shows indel frequency by size (bp) demonstrating higher editing rates following 30° C. recovery (bottom, blue) also result in higher rates of 13 bp deletion as well as an increased frequency of larger (5-8 bp) deletions than 37° C. (above, black) recovery where 1 bp deletions predominate. Solid bars represent HBG1, Outlined bars represent HBG2.

FIG. 6A provides an experimental timeline for erythroid differentiation following transfection. FIG. 6B shows representative flow at 14 days of differentiation comparing the erythroid progeny of mock and TALEN edited hPBSCs. The left panel demonstrates that the overall CD235a+ staining profile is nearly identical between mock (82.5%, blue) and TALEN edited cells (88.5%, orange). Isotype control is shown in brown. The right panel shows HbF expression is significantly higher in TALEN edited cells (61.1%) compared to mock (27.4%). FIG. 6C shows combined analysis of HbF expression at increasing doses of TALEN mRNA and at different recovery temperatures demonstrating a significant increase in HbF expression in all TALEN transfected cells compared to mock (p<0.0005) and a greater increase seen at 30° C. recovery (outlined blue circles) compared to 37° C. (filled black circles). Cells transfected with 1 ug TALEN result in significantly more HbF expression with 37° C. recovery resulting in 44±3% HbF and 30° C. recovery resulting in 57±3% HbF compared to mock HbF expression of 24±2 (30° C.) or 24±5 (37° C.). FIG. 6D shows hemoglobin protein expression detected by HPLC demonstrates a significant increase in overall HbF expression at 1 ug TALEN mRNA. There is a 2.4 fold increase (26±3% total HbF protein) seen with 37° C. culture following 1 ug transfection. 30° C. cold shock treatment resulted in a 4.6 fold increase in HbF protein expression to 41±8% when transfected with 1 ug mRNA (p<0.005).

FIG. 7A provides experimental timeline for editing of hPBSCs followed by both primary and secondary transplants. FIG. 7B shows human engraftment (% hCD45 positive) at sac for both the primary and secondary transplants. Shapes correspond to experimental cohorts. Primary and secondary transplant average engraftment was not significantly different following TALEN editing (Primary mock 67±3% n=4, TALEN 71±8% n=9. Secondary: mock 3.6±1.9% n=2, TALEN 2.8±1.4% n=5). FIG. 7C provides summary of FACS analysis of primary transplants at sac (Transplant 1 at 16 weeks, Transplant 2 at 24 weeks) with multilineage engraftment in mice transfused with either mock or TALEN edited cells. CD19+ engraftment is more robust at 24 weeks with population profiles otherwise similar. FIG. 7D shows NHEJ rates detected by ddPCR at sac for both the primary and secondary transplants. Transplant 1 had a higher input editing rate (HBG1=56%, HBG2=46%) than transplant 2 (HBG1=20%, HBG2=28%). Editing rates drop by approximately 50% post transplant but are maintained following secondary transplant.

FIG. 7E shows indel frequency measured by Next Gen Sequencing demonstrates the edits maintained post transplant tend to be in the 2-7 bp range with a relative decrease in the 13 bp HPFH deletion. FIG. 7F shows comparison of percent modification (deletion) seen at each nucleotide indicates that the majority of deletions occur over the BCL11a binding site (red line) and distal CCAAT box (green line)

with a relative decrease in retained deletions post transplant of the 3' end of the 13 bp HPFH deletion. FIG. 7G shows flow analysis at the time of harvest shows that human HbF is significantly upregulated in mice that receive TALEN edited hPBSCs (Mock=21±1%, TALEN 33±15%). FIG. 7H shows flow analysis following ex vivo liquid differentiation demonstrates significantly higher HbF in animals that received TALEN edited hPBSCs (Mock=59±2%, TALEN=70±6%).

FIG. 9 provides templates that rely on large genomic deletions to induce fetal hemoglobin.

FIG. 10 provides templates designed to express T87Q using the HBG1 promoter or drive the endogenous HBG1 gene using the d13 HPFH promoter or the HBB promoter.

FIG. 11 provides 'Round 3' repair templates designed to express T87Q using the HBG1 promoter or drive the endogenous HBG1 gene using the d13 HPFH promoter or the HBB promoter and some containing an MGMT chemo selection cassette.

FIG. 12 provides a summary of Rhesus related constructs.

FIG. 30 demonstrates Construct 1343 is a rAAV construct that can drive homology-dependent repair into the human HBG1 locus. The donor template introduces a HBB promoter that drives T87Q globin expression and allows for chemo therapeutic selection, as it has a PGK-promoter driving P140K MGMT expression. Construct 1346 is a rAAV construct that can drive homology-dependent repair into the human HBG1 locus. The donor template introduces a HBG1 d13 promoter that drives T87Q globin expression and allows for chemo therapeutic selection, as it has a PGK-promoter driving P140K MGMT expression.

FIG. 46 provides a transplants summary for various animals tested.

FIG. 47A shows recapitulation of 13-nucleotide HPFH deletion by CRISPR/Cas9 gene editing. FIG. 47B shows immunophenotypic separation of HSPC subsets from bone marrow enriched-CD34+ cells (A17117) by surface antibody staining. FIG. 47C shows HbG gene editing efficiency measured at 24 h post CRISPR RNPs electroporation in sorted HSPCs subset. Results are means and standard deviations from 2 donors. FIG. 47D shows proportion of 13-nt HPFH deletion relative to all other deletions in reactions from FIG. 47C. * denotes statistically significant decrease (t-test, $P<0.05$) in 13-nt deletion in CD90+ subset as compared to CD34+ cells. FIG. 47E shows colony-forming cells in CD34+ and HSPC subsets plated on methylcellulose media at 24 h post mock electroporation. FIG. 47F shows colony-forming cells in CD34+ and HSPC subsets plated on methylcellulose media at 24 h post CRISPR/Cas9 RNPs electroporation. Results are from the same donor. FIG. 47G shows deletion profile in CD34+-edited cells (A17117) at 4 days post electroporation. Each color box shows deletion with a frequency higher than 1% and the white portion at the bottom shows combined deletions that contributes less than 1%. FIG. 47H provides sequences of the most common deletions (color-coded) from FIG. 47G. FIG. 47I shows in vitro HbF expression (defined as ratio of HbF/HbA measured by flow cytometry) in differentiated erythroblast as function of HbG editing levels (measured by TIDE). Results are from 4 different donors and HbF/HbA ratio was normalized to mock-treated samples in each donor for comparison.

FIG. 49A shows HbG editing efficiency by Miseq analysis measured over days post transplantation. FIG. 49B shows percent HPFH 13-nt deletion by Miseq analysis measured over days post transplantation. FIGS. 49C-49D show mutant frequency for animals A17114 and A17116.

FIGS. 51A-51B show immunophenotypic separation of HSPC subsets from bone marrow enriched-CD34+ cells by surface antibody staining, as well as showing colony-forming cells in CD34+ and HSPC subsets for animal models A17114 (FIG. 51A) and A17116 (FIG. 51B). FIG. 51C shows HbG editing efficiency (measured by TIDE) for three animal models measuring CD34+ cells, CD45RA+ cells, CD50− cells, and CD90+ cells. FIGS. 51D and 51E provide flow cytometry sorting of HSPCs subsets. FIG. 51F shows HbG editing efficiency (measured by TIDE) for three animal models measuring T cells, B cells, Gran cells, mono cells, 71+ erythroid cells. FIG. 51G shows mutant frequency for animal model A17114 in multiple cell types.

FIG. 53A shows titration of molar ratios of Cas9 protein to gRNA for optimization of HbG editing efficiency (determined by Surveyor assay). Circles show individual data points and bar shows mean. Results are from 3 different NHP donors. FIG. 53B shows size distribution of HbG deletions in edited NHP CD34+ cells 4 days post treatment. Results are from Miseq analysis using 1 donor and deletion frequency was normalized to 100%. FIG. 53C shows flow cytometry sorting of HSPCs subsets from A17114 after CD34+ enrichment. FIG. 53D shows HbG editing efficiency in HSPCs sorted subsets from FIG. 53C determined by Miseq analysis. FIG. 53E shows flow cytometry sorting of HSPCs subsets from A17117 after CD34+ enrichment. FIG. 53F shows HbG editing efficiency in HSPCs sorted subsets from FIG. 53E determined by Miseq analysis.

FIGS. 54A-54D demonstrates validation of CD90+ editing approach. FIGS. 54A-54D show results pre-editing and post-editing, including flow cytometry sorting (FIG. 54A), showing colony forming cells (FIG. 54B), measuring percent indels by Miseq analysis (FIG. 54C), and measuring HbG editing efficiency (measured by TIDE) (FIG. 55D).

FIG. 58 shows validation of RP-HPLC approach for analysis of hemoglobin expression from NHP peripheral blood.

FIG. 61A shows longitudinal analysis of gamma globin (HbG) editing in peripheral blood of transplanted animals as determined by TIDE analysis. FIG. 61B shows frequency of circulating F-cells in transplanted animals as compared to control transplants (grey) and to an untransplanted control (black).

FIG. 62A provides a schematic of targeted integration strategy using combination of CRISPR/Cas9 and AAV donor delivery. FIG. 62B shows HDR time course experiment in rhesus CD34+ cells treated with or without CRISPR/Cas9 RNPs and with 2 different doses of AAV donor. FIG. 62C provides representative flow plots of treated cells (day 7) showing GFP positive cells as surrogate for HDR events.

BRIEF DESCRIPTION OF THE SEQUENCE IDENTIFIERS

Figure 1:
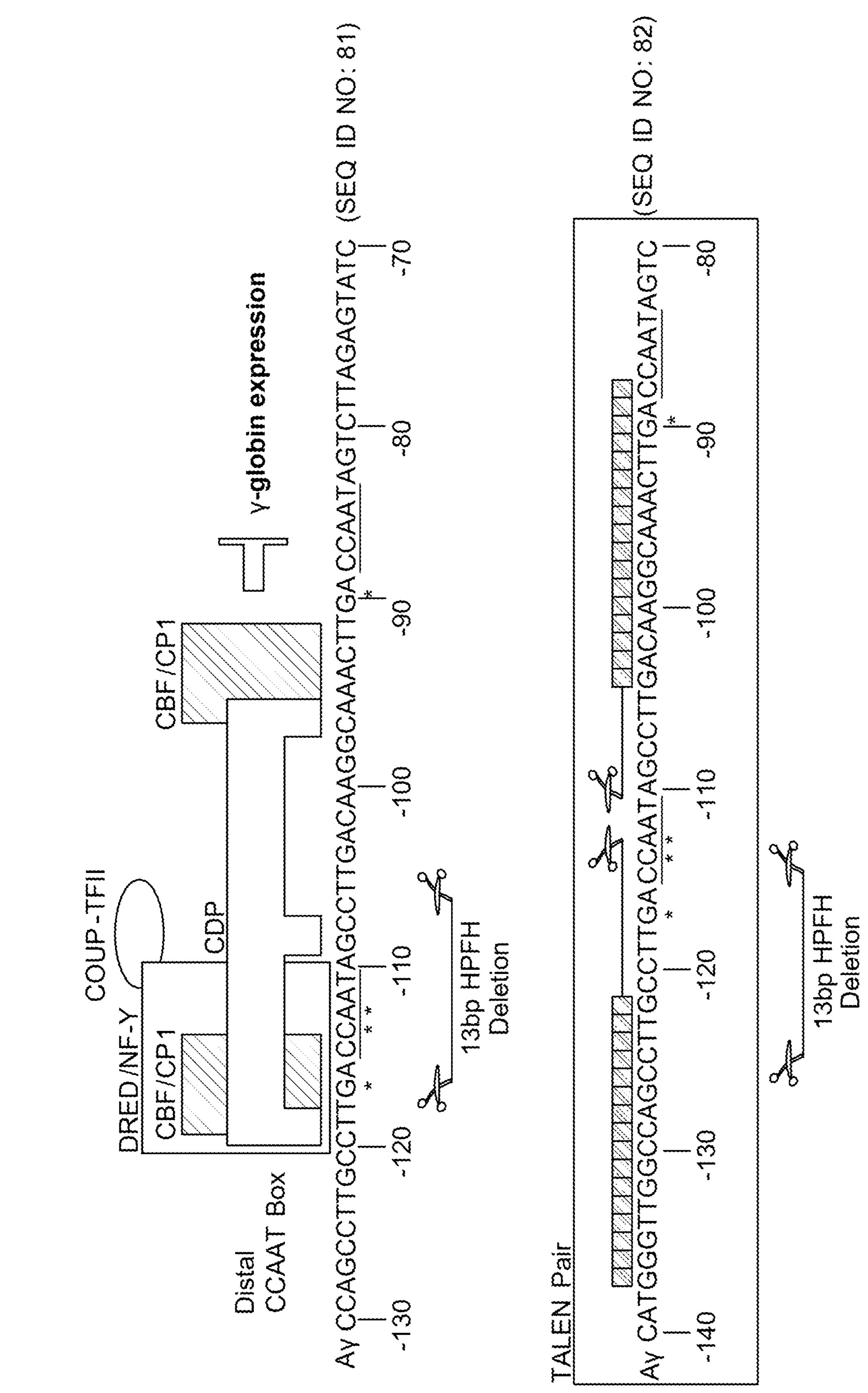
FIG. 1 shows an upstream region of the γ-globin promoter, including the 13 bp sequence responsible for repression of γ-globin gene expression (top panel) and a nuclease target site strategy for disruption of the 13 bp sequence.

SEQ ID NOs: 1-6 set forth polynucleotide sequences in the human γ-globin promoter, that when disrupted, are associated with HPFH.

SEQ ID NOs: 7-8 set forth polynucleotide sequence of the human γ-globin gene and its reverse complement, both of which can be used to target donor repair templates contemplated herein.

SEQ ID NO: 9 sets forth a polynucleotide sequence of 1 kb upstream of the transcriptional start site of the human γ-globin gene.

SEQ ID NOs: 10-57 set forth various AAV donor templates.

SEQ ID NOs: 58-59 set forth TALEN plasmid sequences.

SEQ ID NOs: 60-69 set forth polynucleotide sequences for exemplary 2A sites. SEQ ID NOs: 70-80 set forth linker sequences.

DETAILED DESCRIPTION

A. Overview

The present disclosure generally relates to, in part, improved genome editing compositions for use in homology directed repair (HDR). Without wishing to be bound by any particular theory, the DNA donor repair templates contemplated herein are used to increase the amount of a therapeutic globin in a cell and to select the cells. The therapeutic cells can be used to treat, prevent, or ameliorate at least one symptom associated with a hemoglobinopathy.

Normal adult hemoglobin comprises a tetrameric complex of two alpha-(α) globin proteins and two beta-(β-) globin proteins. In development, the fetus produces fetal hemoglobin (HbF), which comprises two gamma-(γ) globin proteins instead of the two β-globin proteins. At some point during perinatal development, a "globin switch" occurs; erythrocytes down-regulate γ-globin expression and switch to predominantly producing β-globin. This switch results primarily from decreased transcription of the γ-globin genes and increased transcription of β-globin genes.

There is a segment of the human population that has deletions in various regions of the globin locus that lead to a condition known as Hereditary Persistence of Fetal Hemoglobin (HPFH). The deletions associated with HPFH are associated with increases in HbF in adulthood and are referred to herein collectively as HPFH deletions, a number of which are described herein, and others that are known in the art. HPFH is not associated with any significant clinical manifestations, even when 100% of the individual's hemoglobin is HbF. Thus, individuals that have a hemoglobinopathy that also have HPFH, have increased HbF expression, which can lessen the severity of the disease.

In particular preferred embodiments, the genome editing compositions contemplated herein are used to engineer the globin locus to phenocopy a 13 bp deletion in the γ-globin promoter associated with HPFH (Gilman et al. *Nucleic Acids Res.* 1988 Nov. 25; 16(22): 10635-10642). Without wishing to be bound by any particular theory, it is contemplated that the DNA donor repair templates contemplated herein can be used to derepress the γ-globin locus to drive expression of a therapeutic globin gene and to select genome edited cells. The DNA donor repair templates contemplated herein are also advantageous because they can be designed to alter both the A-γ-globin gene and the G-γ-globin gene. A further advantage is that the engineered nuclease(s) used to introduce a DSB into the locus to facilitate HDR in the presence of a DNA donor repair template, can still lead to therapeutic editing in the absence of a DNA donor repair template because cleavage of the 13 bp target sequence will be repaired by NHEJ, thereby producing indels at the target site, disrupting the repressive function of the intact 13 bp sequence, and derepressing γ-globin expression.

In other particular preferred embodiments, the genome edited compositions contemplated herein are used to increase expression of endogenous γ-globin and select for edited cells. Without wishing to be bound by any particular theory, it is contemplated that the DNA donor repair templates contemplated herein can be used for selection and to introduce a β-globin LCR responsive promoter in operable linkage to an endogenous γ-globin gene to drive expression of endogenous γ-globin. The DNA donor repair templates contemplated herein are also advantageous because they can be designed to alter both the A-γ-globin gene and the G-γ-globin gene. A further advantage is that the engineered nuclease(s) used to introduce a DSB into the locus to facilitate HDR in the presence of a DNA donor repair template, can still lead to therapeutic editing in the absence of a DNA donor repair template because cleavage of the 13 bp target sequence will be repaired by NHEJ, thereby producing indels at the target site, disrupting the repressive function of the intact 13 bp sequence, and derepressing γ-globin expression.

The engineered nucleases contemplated herein can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

Genome edited cells engineered by HDR with a DNA donor repair template and one or more engineered nucleases are contemplated in particular embodiments.

Genome edited cells and compositions comprising the same are also contemplated for use in the treatment, prevention, and/or amelioration of at least one symptom of a hemoglobinopathy.

Accordingly, the methods and compositions contemplated herein represent a quantum improvement compared to existing gene editing strategies for the treatment of hemoglobinopathies.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined and in some cases elaborated on below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words “comprise”, “comprises” and “comprising” will be understood to imply the inclusion of a stated step or element or group of steps or elements but not the exclusion of any other step or element or group of steps or elements. By “consisting of” is meant including, and limited to, whatever follows the phrase “consisting of.” Thus, the phrase “consisting of” indicates that the listed elements are required or mandatory, and that no other elements may be present. By “consisting essentially of” is meant including any elements listed after the phrase, and limited to other elements that do not interfere with or contribute to the activity or action specified in the disclosure for the listed elements. Thus, the phrase “consisting essentially of” indicates that the listed elements are required or mandatory, but that no other elements are present that materially affect the activity or action of the listed elements.

Reference throughout this specification to “one embodiment,” “an embodiment,” “a particular embodiment,” “a related embodiment,” “a certain embodiment,” “an additional embodiment,” or “a further embodiment” or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term “ex vivo” refers generally to activities that take place outside an organism, such as experimentation or measurements done in or on living tissue in an artificial environment outside the organism, preferably with minimum alteration of the natural conditions. In particular embodiments, “ex vivo” procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be “in vitro,” though in certain embodiments, this term can be used interchangeably with ex vivo.

The term “in vivo” refers generally to activities that take place inside an organism. In one embodiment, cellular genomes are engineered, edited, or modified in vivo.

By “enhance” or “promote” or “increase” or “expand” or “potentiate” refers generally to the ability of a DNA donor repair template, genome editing composition, or genome edited cell contemplated herein to produce, elicit, or cause a greater response (i.e., physiological response) compared to the response caused by either vehicle or control. A measurable response may include an increase in γ-globin expression, HbF expression, and/or an increase in transfusion independence, among others apparent from the understanding in the art and the description herein. An “increased” or “enhanced” amount is typically a “statistically significant” amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or control.

By “decrease” or “lower” or “lessen” or “reduce” or “abate” or “ablate” or “inhibit” or “dampen” refers generally to the ability of a DNA donor repair template, genome editing composition, or genome edited cell contemplated herein to produce, elicit, or cause a lesser response (i.e., physiological response) compared to the response caused by either vehicle or control. A measurable response may include a decrease in endogenous β-globin, transfusion dependence, RBC sickling, and the like. A “decrease” or “reduced” amount is typically a “statistically significant” amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, or control.

By “maintain,” or “preserve,” or “maintenance,” or “no change,” or “no substantial change,” or “no substantial decrease” refers generally to the ability of a DNA donor repair template, genome editing composition, or genome edited cell contemplated herein to produce, elicit, or cause a substantially similar or comparable physiological response (i.e., downstream effects) in as compared to the response caused by either vehicle or control. A comparable response is one that is not significantly different or measurably different from the reference response.

A “target site” or “target sequence” is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO that references only one strand of a target site or target sequence, it would be understood that the target site or target sequence bound and/or cleaved by a nuclease variant is double-stranded and comprises the reference sequence and its complement. In a preferred embodiment, the target site is a sequence in the human gamma globin gene that when disrupted, is associated with an HPFH phenotype.

“Recombination” refers to a process of exchange of genetic information between two polynucleotides, including but not limited to, donor capture by non-homologous end joining (NHEJ) and homologous recombination. For the purposes of this disclosure, “homologous recombination (HR)” refers to the specialized form of such exchange that takes place, for example, during repair of double-strand breaks in cells via homology-directed repair (HDR) mechanisms. This process requires nucleotide sequence homology, uses a “donor” molecule as a template to repair a “target” molecule (i.e., the one that experienced the double-strand break), and is variously known as “non-crossover gene conversion” or “short tract gene conversion,” because it leads to the transfer of genetic information from the donor to the target. Without wishing to be bound by any particular theory, such transfer can involve mismatch correction of heteroduplex DNA that forms between the broken target and the donor, and/or “synthesis-dependent strand annealing,” in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may bias repair towards an altNHEJ pathway.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins, for example, endogenous globins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extrachromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., SEQ ID NOs: 1-9), typically where the variant maintains at least one biological activity of the reference sequence. In various illustrative embodiments, viral vector and transfer plasmid polynucleotide sequences and compositions comprising the same are contemplated. In particular embodiments, polynucleotides encoding one or more therapeutic polypeptides and/or other genes of interest are contemplated.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

As used herein, the term "isolated" means material, e.g., a polynucleotide, a polypeptide, a cell, that is substantially or essentially free from components that normally accompany it in its native state. In particular embodiments, the term "obtained" or "derived" is used synonymously with isolated. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., Current Protocols in Molecular Biology, John Wiley & Sons Inc., 1994-1998, Chapter 15.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

The terms "complementary" and "complementarity" refer to polynucleotides (i.e., a sequence of nucleotides) related by the base-pairing rules. For example, the complementary strand of the DNA sequence 5' AGTCATG 3' is 3' TCAGTAC 5'. The latter sequence is often written as the reverse complement with the 5' end on the left and the 3' end on the right, 5' CATGACT 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express a polynucleotide. In one embodiment, the nucleic acid cassette contains a polynucleotide(s)-of-interest. In another embodiment, the nucleic acid cassette contains one or more expression control sequences, e.g., a promoter, enhancer, post-transcriptional regulatory element, poly(A) sequence, and a polynucleotide(s)-of-interest. Vectors may comprise one, two, three, four, five or more nucleic acid cassettes. The nucleic acid cassette is positionally and sequentially oriented within the vector such that the nucleic acid in the cassette can be transcribed into RNA. Preferably, the cassette has its 3' and 5' ends adapted for ready insertion into a vector, e.g., it has restriction endonuclease sites at each end. In a preferred embodiment, the nucleic acid cassette one or more expression control sequences operably linked to a polynucleotide encoding a therapeutic RNA, e.g., a shmiR, and/or a polypeptide, that can be used to treat, prevent, or ameliorate a genetic disorder. The cassette can be removed and inserted into a plasmid or viral vector as a single unit.

As used herein, the term "polynucleotide(s)-of-interest" refers to one or more polynucleotides, e.g., a polynucleotide encoding a polypeptide (i.e., a polypeptide-of-interest), inserted into an expression vector that is desired to be expressed. In preferred embodiments, polynucleotides comprise one or more polynucleotides-of-interest that encode one or more therapeutic globins. In particular embodiments, the polynucleotide-of-interest is a transgene that encodes a polypeptide that provides a therapeutic function for the treatment of a hemoglobinopathy, e.g., α-globin, β-globin$^{A\text{-}T87Q}$, anti-sickling globins, γ-globin, and δ globin.

Polynucleotides, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

The term "expression control sequence" refers to a polynucleotide sequence that comprises one or more promoters, enhancers, or other transcriptional control elements or combinations thereof that are capable of directing, increasing, regulating, or controlling the transcription or expression of an operatively linked polynucleotide. In particular embodiments, vectors of the invention comprise one or more expression control sequences that are specific to particular erythroid cells, erythroid cell types, or erythroid cell lineages. In preferred embodiments, vectors comprise one or more expression control sequences specific to erythroid cells, e.g., an erythroid specific expression control sequence.

An "endogenous" expression control sequence is one which is naturally linked to a given gene in the genome. An "exogenous" expression control sequence is one which is placed in juxtaposition to a gene by means of genetic manipulation (i.e., molecular biological techniques) such that transcription of that gene is directed by the linked enhancer/promoter. A "heterologous" expression control sequence is an exogenous sequence that is from a different species than the cell being genetically manipulated. A "synthetic" expression control sequence may comprise elements of one or more endogenous and/or exogenous sequences, and/or sequences determined in vitro or in silico that provide optimal promoter and/or enhancer activity for the particular gene therapy. In particular embodiments, a vector comprises exogenous, endogenous, or heterologous expression control sequences such as promoters and/or enhancers.

The term "promoter" as used herein refers to an expression control sequence that comprises a recognition site of a polynucleotide (DNA or RNA) to which an RNA polymerase binds. The term "enhancer" refers to an expression control sequence that comprises a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer or other expression control sequence) and a second polynucleotide sequence, e.g., a polynucleotide-of-interest, wherein the expression control sequence directs transcription of the nucleic acid corresponding to the second sequence.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Illustrative examples of polypeptides include, but are not limited to globin polypeptides, suitable for use in the compositions and methods of particular embodiments. Also, see, e.g., U.S. Pat. Nos. 6,051,402; 7,901,671; and 9,068,199, the full disclosure and claims of which are specifically incorporated herein by reference in their entireties.

Particular embodiments contemplated herein, also include polypeptide "variants." The recitation polypeptide "variant" refers to polypeptides that are distinguished from a reference polypeptide by the addition, deletion, truncations, modifications, and/or substitution of at least one amino acid residue, and that retain a biological activity. In certain embodiments, a polypeptide variant is distinguished from a reference polypeptide by one or more substitutions, which may be conservative or non-conservative, as known in the art. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, amino acid additions or deletions occur at the C-terminal end and/or the N-terminal end of the reference polypeptide.

Polypeptides contemplated in particular embodiments include fusion polypeptides. "Fusion polypeptides" or "fusion proteins" refer to a polypeptide having at least two, three, four, five, six, seven, eight, nine, or ten polypeptide segments, including, but not limited to one or more linker and/or self-cleaving polypeptides.

A peptide "linker" sequence refers to a polypeptide sequence that may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between. Exemplary linkers include, but are not limited to the following amino acid sequences: glycine polymers (G)n; glycine-serine polymers (G1-5S1-5)n, where n is an integer of at least one, two, three, four, or five; glycine-alanine polymers; alanine-serine polymers; GGG (SEQ ID NO: 70); DGGGS (SEQ ID NO: 71); TGEKP (SEQ ID NO: 72) (see e.g., Liu et al., PNAS 5525-5530

(1997)); GGRR (SEQ ID NO: 73) (Pomerantz et al. 1995, supra); (GGGGS)n wherein n=1, 2, 3, 4 or 5 (SEQ ID NO: 74) (Kim et al., PNAS 93, 1156-1160 (1996.); EGKSSGSGSESKVD (SEQ ID NO: 75) (Chaudhary et al., 1990, Proc. Natl. Acad. Sci. U.S.A. 87:1066-1070); KESGSVSSEQLAQFRSLD (SEQ ID NO: 76) (Bird et al., 1988, Science 242:423-426), GGRRGGGS (SEQ ID NO: 77); LRQRDGERP (SEQ ID NO: 78); LRQKDGGGSERP (SEQ ID NO: 79); LRQKD(GGGS)2ERP (SEQ ID NO: 80). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods.

C. Engineered Nucleases

In particular embodiments, HDR at target sites comprises introducing one or more double strand breaks (DSB) at a target site using one or more engineered nucleases in the presence of a DNA donor repair template contemplated herein. The terms "reprogrammed nuclease," "engineered nuclease," or "nuclease variant" are used interchangeably and refer to a nuclease comprising one or more DNA binding domains and one or more DNA cleavage domains, wherein the nuclease has been designed and/or modified from a parental or naturally occurring nuclease, to bind and cleave a double-stranded DNA target sequence. The nuclease variant may be designed and/or modified from a naturally occurring nuclease or from a previous nuclease variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerase or template-independent DNA polymerase activity.

Illustrative examples of nucleases that may be engineered to bind and cleave a target sequence include, but are not limited to homing endonucleases (meganucleases), megaTALs, transcription activator-like effector nucleases (TALENs), zinc finger nucleases (ZFNs), and clustered regularly-interspaced short palindromic repeats (CRISPR)/Cas nuclease systems.

I. Homing Endonucleases/Meganucleases

In various embodiments, a plurality of homing endonucleases or meganucleases are introduced into a cell and engineered to bind to, and to introduce single-stranded nicks or double-strand breaks (DSBs) at a target site in a human γ-globin gene, e.g., a polynucleotide sequence as set for the in any one of SEQ ID NOs: 1-9. "Homing endonuclease" and "meganuclease" are used interchangeably and refer to naturally-occurring nucleases or engineered meganucleases that recognize 12-45 base-pair cleavage sites and are commonly grouped into five families based on sequence and structure motifs: LAGLIDADG, GIY-YIG, HNH, His-Cys box, and PD-(D/E)XK.

Engineered HEs do not exist in nature and can be obtained by recombinant DNA technology or by random mutagenesis. Engineered HEs may be obtained by making one or more amino acid alterations, e.g., mutating, substituting, adding, or deleting one or more amino acids, in a naturally occurring HE or previously engineered HE. In particular embodiments, an engineered HE comprises one or more amino acid alterations to the DNA recognition interface.

Engineered HEs contemplated in particular embodiments may further comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, engineered HEs are introduced into a hematopoietic cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The HE and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or engineered HE. By way of non-limiting example, an engineered HE contemplated in particular embodiments may be derived by constructing libraries of HE variants in which one or more amino acid residues localized in the DNA recognition interface of the natural HE (or a previously engineered HE) are varied. The libraries may be screened for target cleavage activity against each predicted target site using cleavage assays (see e.g., Jarjour et al., 2009. *Nuc. Acids Res.* 37(20): 6871-6880).

LAGLIDADG homing endonucleases (LHE) are the most well studied family of meganucleases, are primarily encoded in archaea and in organellar DNA in green algae and fungi, and display the highest overall DNA recognition specificity. LHEs comprise one or two LAGLIDADG catalytic motifs per protein chain and function as homodimers or single chain monomers, respectively. Structural studies of LAGLIDADG proteins identified a highly conserved core structure (Stoddard 2005), characterized by an αββαββα fold, with the LAGLIDADG motif belonging to the first helix of this fold. The highly efficient and specific cleavage of LHE's represent a protein scaffold to derive novel, highly specific endonucleases. However, engineering LHEs to bind and cleave a non-natural or non-canonical target site requires selection of the appropriate LHE scaffold, examination of the target locus, selection of putative target sites, and extensive alteration of the LHE to alter its DNA contact points and cleavage specificity, at up to two-thirds of the base-pair positions in a target site.

Illustrative examples of LHEs from which engineered LHEs may be designed include, but are not limited to I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

Other illustrative examples of LHEs from which engineered LHEs may be designed include, but are not limited to I-CreI and I-SceI.

In one embodiment, the engineered LHE is selected from the group consisting of: I-CpaMI, I-HjeMI, I-OnuI, I-PanMI, and SmaMI.

In one embodiment, the engineered LHE is I-OnuI.

In a particular embodiment, the engineered I-OnuI LHE comprises one or more amino acid substitutions in the DNA recognition interface. In particular embodiments, the I-OnuI LHE comprises at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the DNA recognition interface of I-OnuI (Taekuchi et al. 2011. *Proc Natl Acad Sci U.S.A* 2011 Aug. 9; 108(32): 13077-13082) or an engineered variant of I-OnuI.

In one embodiment, the I-OnuI LHE comprises at least 70%, more preferably at least 80%, more preferably at least 85%, more preferably at least 90%, more preferably at least 95%, more preferably at least 97%, more preferably at least 99% sequence identity with the DNA recognition interface of I-OnuI (Taekuchi et al. 2011. *Proc Natl Acad Sci U.S.A* 2011 Aug. 9; 108(32): 13077-13082) or an engineered variant of I-OnuI.

In a particular embodiment, an engineered I-OnuI LHE comprises one or more amino acid substitutions or modifications in the DNA recognition interface, particularly in the subdomains situated from positions 24-50, 68 to 82, 180 to 203 and 223 to 240 of I-OnuI.

In one embodiment, an engineered I-OnuI LHE comprises one or more amino acid substitutions or modifications at additional positions situated anywhere within the entire I-OnuI sequence. The residues which may be substituted and/or modified include but are not limited to amino acids that contact the nucleic acid target or that interact with the nucleic acid backbone or with the nucleotide bases, directly or via a water molecule. In one non-limiting example an engineered I-OnuI LHE contemplated herein comprises one or more substitutions and/or modifications, preferably at least 5, preferably at least 10, preferably at least 15, more preferably at least 20, even more preferably at least 25 in at least one position selected from the position group consisting of positions: 19, 24, 26, 28, 30, 32, 34, 35, 36, 37, 38, 40, 42, 44, 46, 48, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, 240 of 1-OnuI.

2. MegaTALs

In various embodiments, one or more megaTALs are introduced into a hematopoietic cell and engineered to bind and introduce DSBs at a target site in a human γ-globin gene, e.g., a polynucleotide sequence as set for the in any one of SEQ ID NOs: 1-9. A "megaTAL" refers to an engineered nuclease comprising an engineered TALE DNA binding domain and an engineered meganuclease, and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a megaTAL can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. *Science* 318:648-651). TALE DNA binding domains contemplated in particular embodiments are engineered de novo or from naturally occurring TALEs, e.g., AvrBs3 from *Xanthomonas campestris* pv. *vesicatoria, Xanthomonas gardneri, Xanthomonas translucens, Xanthomonas axonopodis, Xanthomonas perforans, Xanthomonas alfalfa, Xanthomonas citri, Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S*for recognition of A or T or G or C, wherein (*) means that the amino acid at position 13 is absent. Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-16 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-13.5 repeat units, more preferably 7.5-12.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises an "N-terminal domain (NTD)" polypeptide, one or more TALE repeat domains/units, a "C-terminal domain (CTD)" polypeptide, and an engineered meganuclease.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids+1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas TALE protein. In one embodiment, a megaTAL contemplated herein comprises an NTD polypeptide of at least amino acids*+1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids −20 to −1 of a *Xanthomonas* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids −20 to −1 of a *Ralstonia* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a meganuclease engineered to bind and cleave a target sequence, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to an engineered meganuclease. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the meganuclease. In this way, the megaTALs contemplated herein, increase the specificity and efficiency of genome editing.

In particular embodiments, a megaTAL contemplated herein, comprises one or more TALE DNA binding repeat units and an engineered LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD, one or more TALE DNA binding repeat units, a CTD, and an engineered LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD, about 9.5 to about 15.5 TALE DNA binding repeat units, and an engineered I-OnuI LHE selected from the group consisting of: I-AabMI, I-AaeMI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an engineered I-OnuI LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

3. Talens

In various embodiments, a plurality of transcription activator-like effector nucleases (TALENs) are introduced into a cell and engineered to bind to, and to introduce single-stranded nicks or double-strand breaks (DSBs) at a target site in a human γ-globin gene, e.g., a polynucleotide sequence as set forth in any one of SEQ ID NOs: 1-9. A "TALEN" refers to an engineered nuclease comprising an engineered TALE DNA binding domain contemplated elsewhere herein and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a TALEN can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The TALEN and 3' processing enzyme may be introduced separately, e.g., in different vectors or separate mRNAs, or together, e.g., as a fusion protein, or in a polycistronic construct separated by a viral self-cleaving peptide or an IRES element.

In one embodiment, targeted double-stranded cleavage is achieved with two TALENs, each comprising an endonuclease half-domain can be used to reconstitute a catalytically active cleavage domain. In another embodiment, targeted double-stranded cleavage is achieved using a single polypeptide comprising a TALE DNA binding domain and two endonuclease half-domains.

TALENs contemplated in particular embodiments comprise an NTD, a TALE DNA binding domain comprising about 3 to 30 repeat units, e.g., about 3, 4, 5, 6, 7, 8, 9, 10, 11, 12, 13, 14, 15, 16, 17, 18, 19, 20, 21, 22, 23, 24, 25, 26, 27, 28, 29, or 30 repeat units, and an endonuclease domain or half-domain.

TALENs contemplated in particular embodiments comprise an NTD, a TALE DNA binding domain comprising about 3.5 to 30.5 repeat units, e.g., about 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 repeat units, a CTD, and an endonuclease domain or half-domain TALENs contemplated in particular embodiments comprise an NTD of about 121 amino acids to about 137 amino acids as disclosed elsewhere herein, a TALE DNA binding domain comprising about 9.5 to about 15.5 repeat units (i.e., about 9.5, about 10.5, about 11.5, about 12.5, about 13.5, about 14.5, or about 15.5 repeat units), a CTD of about 20 amino acids to about 85 amino acids, and an endonuclease domain or half domain In particular embodiments, a TALEN comprises an endonuclease domain of a type restriction endonuclease. Restriction endonucleases (restriction enzymes) are present in many species and are capable of sequence-specific binding to DNA (at a recognition site), and cleaving DNA at or near the site of binding. Certain restriction enzymes (e.g., Type-IIS) cleave DNA at sites removed from the recognition site and have separable binding and endonuclease domains. In one embodiment, TALENs comprise the endonuclease domain (or endonuclease half-domain) from at least one Type-IIS restriction enzyme and one or more TALE DNA-binding domains contemplated elsewhere herein.

Illustrative examples of Type-IIS restriction endonuclease domains suitable for use in TALENs contemplated in particular embodiments include endonuclease domains of the at least 1633 Type-IIS restriction endonucleases disclosed at "rebase.neb.com/cgi-bin/sublist?S."

Additional illustrative examples of Type-IIS restriction endonuclease domains suitable for use in TALENs contemplated in particular embodiments include those of endonucleases selected from the group consisting of: Aar I, Ace III, Aci I, Alo I, Alw26 I, Bae I, Bbr7 I, Bbv I, Bbv II, BbvC I, Bcc I, Bce83 I, BceA I, Bcef I, Bcg I, BciV I, Bfi I, Bin I, Bmg I, Bpu10 I, BsaX I, Bsb I, BscA I, BscG I, BseR I, BseY I, Bsi I, Bsm I, BsmA I, BsmF I, Bsp24 I, BspG I, BspM I, BspNC I, Bsr I, BsrB I, BsrD I, BstF5 I, Btr I, Bts I, Cdi I, CjeP I, Drd II, EarI, Eci I, Eco31 I, Eco57 I, Eco57M I, Esp3 I, Fau I, Fin I, Fok I, Gdi II, Gsu I, Hga I, Hin4 II, Hph I, Ksp632 I, Mbo II, Mly I, Mme I, Mnl I, Pfl1108, I Ple I, Ppi I Psr I, RleA I, Sap I, SfaN I, Sim I, SspD5 I, Sth132 I, Sts I, TspDT I, TspGW I, Tth111 II, UbaP I, Bsa I, and BsmB I.

In one embodiment, a TALEN contemplated herein comprises an endonuclease domain of the Fok I Type-IIS restriction endonuclease.

In one embodiment, a TALEN contemplated herein comprises a TALE DNA binding domain and an endonuclease half-domain from at least one Type-IIS restriction endonuclease to enhance cleavage specificity, optionally wherein the endonuclease half-domain comprises one or more amino acid substitutions or modifications that minimize or prevent homodimerization.

Illustrative examples of cleavage half-domains suitable for use in particular embodiments contemplated in particular embodiments include those disclosed in U.S. Patent Publication Nos. 20050064474; 20060188987, 20080131962, 20090311787; 20090305346; 20110014616, and 20110201055, each of which are incorporated by reference herein in its entirety.

4. Zinc Finger Nucleases

In various embodiments, a plurality of zinc finger nucleases (ZFNs) are introduced into a cell and engineered to bind to, and to introduce single-stranded nicks or double-strand breaks (DSBs) at a target site in a human γ-globin gene, e.g., a polynucleotide sequence as set for the in any one of SEQ ID NOs: 1-9. A "ZFN" refers to an engineered nuclease comprising one or more zinc finger DNA binding domains and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a ZFN can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The ZFN and 3' processing enzyme may be introduced separately, e.g., in different vectors or separate mRNAs, or together, e.g., as a fusion protein, or in a polycistronic construct separated by a viral self-cleaving peptide or an IRES element. In one embodiment, targeted double-stranded cleavage is achieved using two ZFNs, each comprising an endonuclease half-domain can be used to reconstitute a catalytically active cleavage domain. In another embodiment, targeted double-stranded cleavage is achieved with a single polypeptide comprising one or more zinc finger DNA binding domains and two endonuclease half-domains.

In one embodiment, a ZNF comprises a TALE DNA binding domain contemplated elsewhere herein, a zinc finger DNA binding domain, and an endonuclease domain (or endonuclease half-domain) contemplated elsewhere herein.

In one embodiment, a ZNF comprises a zinc finger DNA binding domain, and a meganuclease contemplated elsewhere herein.

In particular embodiments, the ZFN comprises a zinc finger DNA binding domain that has one, two, three, four, five, six, seven, or eight or more zinc finger motifs and an endonuclease domain (or endonuclease half-domain) Typically, a single zinc finger motif is about 30 amino acids in length. Zinc fingers motifs include both canonical $C_2H_2$ zinc fingers, and non-canonical zinc fingers such as, for example, $C_3H$ zinc fingers and $C_4$ zinc fingers.

Zinc finger binding domains can be engineered to bind any DNA sequence. Candidate zinc finger DNA binding domains for a given 3 bp DNA target sequence have been identified and modular assembly strategies have been devised for linking a plurality of the domains into a multi-finger peptide targeted to the corresponding composite DNA target sequence. Other suitable methods known in the art can also be used to design and construct nucleic acids encoding zinc finger DNA binding domains, e.g., phage display, random mutagenesis, combinatorial libraries, computer/rational design, affinity selection, PCR, cloning from cDNA or genomic libraries, synthetic construction and the like. (See, e.g., U.S. Pat. No. 5,786,538; Wu et al., *PNAS* 92:344-348 (1995); Jamieson et al., *Biochemistry* 33:5689-5695 (1994); Rebar & Pabo, *Science* 263:671-673 (1994); Choo & Klug, *PNAS* 91:11163-11167 (1994); Choo & Klug, *PNAS* 91: 11168-11172 (1994); Desjarlais & Berg, *PNAS* 90:2256-2260 (1993); Desjarlais & Berg, *PNAS* 89:7345-7349 (1992); Pomerantz et al., *Science* 267:93-96 (1995); Pomerantz et al., *PNAS* 92:9752-9756 (1995); Liu et al., *PNAS* 94:5525-5530 (1997); Griesman & Pabo, *Science* 275:657-661 (1997); Desjarlais & Berg, *PNAS* 91:11-99-11103 (1994)).

Individual zinc finger motifs bind to a three or four nucleotide sequence. The length of a sequence to which a zinc finger binding domain is engineered to bind (e.g., a target sequence) will determine the number of zinc finger motifs in an engineered zinc finger binding domain. For example, for ZFNs in which the zinc finger motifs do not bind to overlapping subsites, a six-nucleotide target sequence is bound by a two-finger binding domain; a nine-nucleotide target sequence is bound by a three-finger binding domain, etc. In particular embodiments, DNA binding sites for individual zinc fingers motifs in a target site need not be contiguous, but can be separated by one or several nucleotides, depending on the length and nature of the linker sequences between the zinc finger motifs in a multi-finger binding domain.

In particular embodiments, ZNFs contemplated herein comprise, a zinc finger DNA binding domain comprising two, three, four, five, six, seven or eight or more zinc finger motifs, and an endonuclease domain or half-domain from at least one Type-IIS restriction enzyme and one or more TALE DNA-binding domains contemplated elsewhere herein.

In particular embodiments, ZNFs contemplated herein comprise, a zinc finger DNA binding domain comprising three, four, five, six, seven or eight or more zinc finger motifs, and an endonuclease domain or half-domain from at least one Type-IIS restriction enzyme selected from the group consisting of: Aar I, Ace III, Aci I, Alo I, Alw26 I, Bae I, Bbr7 I, Bbv I, Bbv II, BbvC I, Bcc I, Bce83 I, BceA I, Bcef I, Bcg I, BciV I, Bfi I, Bin I, Bmg I, Bpu10 I, BsaX I, Bsb I, BscA I, BscG I, BseR I, BseY I, Bsi I, Bsm I, BsmA I, BsmF I, Bsp24 I, BspG I, BspM I, BspNC I, Bsr I, BsrB I, BsrD I, BstF5 I, Btr I, Bts I, Cdi I, CjeP I, Drd II, Earl, Eci I, Eco31 I, Eco57 I, Eco57M I, Esp3 I, Fau I, Fin I, Fok I, Gdi II, Gsu I, Hga I, Hin4 II, Hph I, Ksp632 I, Mbo II, Mly I, Mme I, Mnl I, Pfl1108, I Ple I, Ppi I Psr I, RleA I, Sap I, SfaN I, Sim I, SspD5 I, Sth132 I, Sts I, TspDT I, TspGW I, Tth111 II, UbaP I, Bsa I, and BsmB I.

In particular embodiments, ZNFs contemplated herein comprise, a zinc finger DNA binding domain comprising three, four, five, six, seven or eight or more zinc finger motifs, and an endonuclease domain or half-domain from the Fok I Type-IIS restriction endonuclease.

In one embodiment, a ZFN contemplated herein comprises a zinc finger DNA binding domain and an endonuclease half-domain from at least one Type-IIS restriction endonuclease to enhance cleavage specificity, optionally wherein the endonuclease half-domain comprises one or more amino acid substitutions or modifications that minimize or prevent homodimerization.

5. CRISPR/Cas Nuclease System

In various embodiments, a CRISPR (Clustered Regularly Interspaced Short Palindromic Repeats)/Cas (CRISPR Associated) nuclease system is introduced into a cell and engineered to bind to, and to introduce single-stranded nicks or double-strand breaks (DSBs) at a target site in a human γ-globin gene, e.g., a polynucleotide sequence as set forth in any one of SEQ ID NOs: 1-9. The CRISPR/Cas nuclease system is an engineered nuclease system based on a bacterial system that can be used for mammalian genome engineering. See, e.g., Jinek et al. (2012) *Science* 337:816-821; Cong et al. (2013) *Science* 339:819-823; Mali et al. (2013) *Science* 339:823-826; Qi et al. (2013) *Cell* 152:1173-1183; Jinek et al. (2013), *eLife* 2:e00471; David Segal (2013) *eLife* 2:e00563; Ran et al. (2013) *Nature Protocols* 8(11):2281-2308; Zetsche et al. (2015) *Cell* 163(3):759-771, each of which is incorporated herein by reference in its entirety.

In one embodiment, the CRISPR/Cas nuclease system comprises Cas nuclease and one or more RNAs that recruit the Cas nuclease to the target site, e.g., a transactivating cRNA (tracrRNA) and a CRISPR RNA (crRNA), or a single guide RNA (sgRNA). crRNA and tracrRNA can engineered into one polynucleotide sequence referred to herein as a "single guide RNA" or "sgRNA."

In one embodiment, the Cas nuclease is engineered as a double-stranded DNA endonuclease or a nickase or catalytically dead Cas, and forms a target complex with a crRNA and a tracrRNA, or sgRNA, for site specific DNA recognition and site-specific cleavage of the protospacer target sequence located within one or more target sites in a human γ-globin gene, e.g., a polynucleotide sequence as set forth in any one of SEQ ID NOs: 1-9. The protospacer motif abuts a short protospacer adjacent motif (PAM), which plays a role in recruiting a Cas/RNA complex. Cas polypeptides recognize PAM motifs specific to the Cas polypeptide. Accordingly, the CRISPR/Cas system can be used to target and cleave either or both strands of a double-stranded polynucleotide sequence flanked by particular 3' PAM sequences specific to a particular Cas polypeptide. PAMs may be identified using bioinformatics or using experimental approaches. Esvelt et al., 2013, *Nature Methods*. 10(11): 1116-1121, which is hereby incorporated by reference in its entirety.

In one embodiment, the Cas nuclease comprises one or more heterologous DNA binding domains, e.g., a TALE DNA binding domain or zinc finger DNA binding domain Fusion of the Cas nuclease to TALE or zinc finger DNA binding domains increases the DNA cleavage efficiency and specificity. In a particular embodiment, a Cas nuclease optionally comprises one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a Cas nuclease can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The Cas nuclease and 3' processing enzyme may be introduced separately, e.g., in different vectors or separate mRNAs, or together, e.g., as a fusion protein, or in a polycistronic construct separated by a viral self-cleaving peptide or an IRES element.

In various embodiments, the Cas nuclease is Cas9 or Cpf1.

Illustrative examples of Cas9 polypeptides suitable for use in particular embodiments contemplated in particular embodiments may be obtained from bacterial species including, but not limited to: *Enterococcus faecium, Enterococcus italicus, Listeria innocua, Listeria monocytogenes, Listeria seeligeri, Listeria ivanovii, Streptococcus agalactiae, Streptococcus anginosus, Streptococcus bovis, Streptococcus dysgalactiae, Streptococcus equinus, Streptococcus gallolyticus, Streptococcus macacae, Streptococcus mutans, Streptococcus pseudoporcinus, Streptococcus pyogenes, Streptococcus thermophilus, Streptococcus gordonii, Streptococcus infantarius, Streptococcus macedonicus, Streptococcus mitis, Streptococcus pasteurianus, Streptococcus suis, Streptococcus vestibularis, Streptococcus sanguinis, Streptococcus downei, Neisseria bacilliformis, Neisseria cinerea, Neisseria flavescens, Neisseria lactamica, Neisseria meningitidis, Neisseria subflava, Lactobacillus brevis, Lactobacillus buchneri, Lactobacillus casei, Lactobacillus paracasei, Lactobacillus fermentum, Lactobacillus gasseri, Lactobacillus jensenii, Lactobacillus johnsonii, Lactobacillus rhamnosus, Lactobacillus ruminis, Lactobacillus salivarius, Lactobacillus sanfranciscensis, Corynebacterium accolens, Corynebacterium diphtheriae, Corynebacterium matruchotii, Campylobacter jejuni, Clostridium perfringens, Treponema vincentii, Treponema phagedenis*, and *Treponema denticola*.

Illustrative examples of Cpf1 polypeptides suitable for use in particular embodiments contemplated in particular embodiments may be obtained from bacterial species including, but not limited to: *Francisella* spp., *Acidaminococcus* spp., *Prevotella* spp., *Lachnospiraceae* spp., among others.

Conserved regions of Cas9 orthologs include a central HNH endonuclease domain and a split RuvC/RNase H domain. Cpf1 orthologs possess a RuvC/RNase H domain but no discernable HNH domain. The HNH and RuvC-like domains are each responsible for cleaving one strand of the double-stranded DNA target sequence. The HNH domain of the Cas9 nuclease polypeptide cleaves the DNA strand complementary to the tracrRNA:crRNA or sgRNA. The RuvC-like domain of the Cas9 nuclease cleaves the DNA strand that is not-complementary to the tracrRNA:crRNA or sgRNA. Cpf1 is predicted to act as a dimer wherein each RuvC-like domain of Cpf1 cleaves either the complementary or non-complementary strand of the target site. In particular embodiments, a Cas9 nuclease variant (e.g., Cas9 nickase) is contemplated comprising one or more amino acids additions, deletions, mutations, or substitutions in the HNH or RuvC-like endonuclease domains that decreases or eliminates the nuclease activity of the variant domain Illustrative examples of Cas9 HNH mutations that decrease or eliminate the nuclease activity in the domain include, but are not limited to: *S. pyogenes* (D10A); *S. thermophilis* (D9A); *T. denticola* (D13A); and *N. meningitidis* (D16A).

Illustrative examples of Cas9 RuvC-like domain mutations that decrease or eliminate the nuclease activity in the domain include, but are not limited to: *S. pyogenes* (D839A, H840A, or N863A); *S. thermophilis* (D598A, H599A, or N622A); *T. denticola* (D878A, H879A, or N902A); and *N. meningitidis* (D587A, H588A, or N611A).

6. End-Processing Enzymes

Genome editing compositions and methods contemplated in particular embodiments comprise editing cellular genomes using a nuclease variant and an end-processing enzyme. In particular embodiments, a single polynucleotide encodes a homing endonuclease variant and an end-processing enzyme, separated by a linker, a self-cleaving peptide sequence, e.g., 2A sequence, or by an IRES sequence. In particular embodiments, genome editing compositions comprise a polynucleotide encoding a nuclease variant and a separate polynucleotide encoding an end-processing enzyme.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using a homing endonuclease variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include, but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, ExoI, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising a homing endonuclease variant or megaTAL and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, *E. coli* ExoI, hTREX2, mouse TREX2, rat TREX2, hTREX1, mouse TREX1, rat TREX1, and Rat TREX1.

In particular embodiments, the DNA end-processing enzyme is a 3' or 5' exonuclease, preferably Trex 1 or Trex2, more preferably Trex2, and even more preferably human or mouse Trex2.

D. Target Sites

The engineered nucleases contemplated herein are designed to bind to any suitable target sequence and can have a novel binding specificity, compared to a naturally-occurring nuclease. In particular embodiments, the target site is a regulatory region of a γ-globin gene including, but not limited to transcription factor binding sites. In particular embodiments, the nuclease target site is in a polynucleotide sequence that when deleted or disrupted is associated with HPFH, e.g., at position −120 to −102 relative to the transcriptional start site of a γ-globin gene; preferably the nuclease target site is at, or disrupts or deletes, a 13 bp polynucleotide sequence in a γ-globin gene associated with HPFH (SEQ ID NO: 3); more preferably the nuclease target site is at, or disrupts or deletes, a CCAAT polynucleotide sequence at position −115 to −111 (relative to the transcriptional start site) of the promoter of the HBG1 gene; and even more preferably the nuclease target site is at, or disrupts or deletes, a CAAT polynucleotide sequence at position −114 to −111 (relative to the transcriptional start site) of the HBG1 gene.

In particular embodiments, the nuclease target site is in, or near, the region of Chr11: 5249957-5249977.

In particular embodiments, the nuclease target site is in, or near, the polynucleotide sequence of any one of SEQ ID NOs: 1-6 in the region of Chr11: 5249957-5249977.

In particular embodiments, the nuclease target site is in, or near, the region of Chr11: 5249959-5249971 (in the HBG1 gene).

In particular embodiments, the engineered nucleases introduce a DSB in, near, or flanking the 5' and/or 3' sequences of a 13 bp polynucleotide sequence in a γ-globin gene associated with HPFH (SEQ ID NO: 3), so that in the event that a DNA donor repair template is not inserted into the target site, the target site will still be disrupted by NHEJ in the absence of a DNA donor repair template, and thus, either HDR or NHEJ events at the target site will lead to derepression of γ-globin gene expression and/or therapeutic globin expression (either endogenous γ-globin expression or heterologous expression of another therapeutic globin, including but not limited to, γ-globin, β-globin, or an anti-sickling form of β-globin.

In a preferred embodiment, an engineered nuclease cleaves double-stranded DNA and introduces a DSB into the polynucleotide sequence set forth in any one of SEQ ID NOs: 1-9, more preferably, in the human HBG1 and/or HBG2 gene.

E. Donor Repair Templates

In preferred embodiments, one or more engineered nucleases are used to introduce a DSB in a target sequence in the presence of a donor repair template. The donor repair template may comprise single-stranded or double-stranded DNA or RNA. In the presence of a donor repair template the DSB may be repaired through homology directed repair (HDR) mechanisms.

In particular embodiments, a donor repair template comprises a pair of homology arms, a selection cassette and an erythroid expression control sequence. In preferred embodiments, the donor repair template is inserted into a γ-globin gene and the erythroid expression control sequence is positioned such that it is operably linked to the endogenous polynucleotide sequence encoding a γ-globin.

In particular embodiments, a donor repair template comprises a pair of homology arms, a polynucleotide encoding a therapeutic globin and one or more post-transcriptional control elements; and a selection cassette. In preferred embodiments, the donor repair template is inserted into a γ-globin gene at a site that derepresses the γ-globin promoter, thereby operably linking a derepressed γ-globin promoter to the polynucleotide encoding a therapeutic globin. In other preferred embodiments, the 5' homology arm encodes a deletion in a site that derepresses the γ-globin promoter thereby operably linking a derepressed γ-globin promoter to the polynucleotide encoding a therapeutic globin.

A "pair of homology arms" refers to a group of two homology arms. In particular embodiments a pair of homology arms comprises a 5' homology arm and a 3' homology arm. A "5' homology arm" refers to a polynucleotide sequence that is identical, or nearly identical, or homologous to a DNA sequence 5' of a target site (e.g., double strand break site). A "3' homology arm" refers to a polynucleotide sequence that is identical, or nearly identical, or homologous to a DNA sequence 3' of the target site. In particular embodiments, a pair of homology arms comprises a homology arm comprising a polynucleotide sequence that includes a target site for a double strand break with a mutation in the target site to minimize recleavage of the target site. In particular preferred embodiments, the 5' homology arm comprises a polynucleotide sequence within 1 kb upstream of a γ-globin transcriptional start site (SEQ ID NO: 9). In more particular preferred embodiments, the 5' homology arm comprises a polynucleotide sequence within 1 kb upstream of a γ-globin transcriptional start site and further comprises a deletion of, or lacks the polynucleotide sequence set forth in any one of SEQ ID NOs: 1-6.

In some embodiments, where the donor repair template is designed to derepress a γ-globin promoter and operably link the derepressed promoter to a polynucleotide encoding a therapeutic globin, the 5' homology arm comprises a polynucleotide sequence within 1 kb upstream of a γ-globin transcriptional start site and further comprises a deletion of, or lacks the polynucleotide sequence set forth in any one of SEQ ID NOs: 1-6 and the 3' homology arm comprises a sequence downstream of the 5' homology arm. In some embodiments, the donor repair template disrupts endogenous γ-globin gene expression, optionally through deletion of genomic sequence encoding γ-globin.

In some embodiments, where the donor repair template is designed to operably link a β-globin LCR responsive expression control sequence to an endogenous genomic sequence encoding a γ-globin, the 5' homology arm comprises a polynucleotide sequence within 1 kb upstream of a γ-globin transcriptional start site and may further comprise a deletion of, or lack the polynucleotide sequence set forth in any one of SEQ ID NOs: 1-6 and the 3' homology arm comprises a sequence downstream of the 5' homology arm, but upstream of a γ-globin gene transcription start site.

In particular embodiments, either one of, or both, homology arms in a pair of homology arms is independently located about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, from the target site, including all intervening distances from the target site.

Illustrative examples of suitable lengths of homology arms contemplated in particular embodiments, may be independently selected, and include but are not limited to: about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 600 bp, about 100 bp to about 500 bp, about 100 bp to about 400 bp, about 100 bp to about 300 bp, about 100 bp to about 200 bp, about 200 bp to about 600 bp, about 200 bp to about 500 bp, about 200 bp to about 400 bp, about 200 bp to about 300 bp, about 300 bp to about 600 bp, about 300 bp to about 500 bp, about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of any 5' and 3' homology arms present in a DNA donor repair template are independently selected from about 100 bp, about 200 bp, about 300 bp, about 400 bp, about 500 bp, or about 600 bp. In one embodiment, a 5'homology arm is about 300 bp and a 3' homology arm is about 300 bp.

Donor repair templates contemplated herein comprise a selection cassette. As used herein, the term "selection cassette" refers to an expression cassette that comprises one or more expression control sequences operably linked to a polynucleotide sequence encoding a selectable marker and one or more post-transcriptional elements or a ribosomal skipping polypeptide.

Illustrative examples of expression control sequences suitable for use in selection cassettes contemplated herein include but are not limited to: a constitutive promoter, a conditional promoter, or hematopoietic stem cell promoter. As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) promoter, a Moloney murine leukemia virus (MoMLV) LTR promoter, a Rous sarcoma virus (RSV) LTR promoter, a herpes simplex virus (HSV) (thymidine kinase) promoter, a H5, P7.5, or P11 vaccinia virus promoter, a short elongation factor 1-alpha (EF1a-short) promoter, a long elongation factor 1-alpha (EF1a-long) promoter, an early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin 03-KIN) promoter, a human ROSA 26 promoter, a Ubiquitin C promoter (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., *J Virol.* 69(2):748-55 (1995)).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

Illustrative examples of tissue specific promoters include, but are not limited to: an B29 promoter (B cell expression), a runt transcription factor (CBFa2) promoter (stem cell specific expression), an CD14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fms-related tyrosine kinase 1 (FLT1) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-β) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), an interferon beta (IFN-β) promoter (hematopoietic cell expression), an α-spectrin promoter (erythroid cell expression), a (3-spectrin promoter (erythroid cell expression), a β-globin LCR (erythroid cell expression), a γ-globin promoter (erythroid cell expression), a β-globin promoter (erythroid cell expression), an α-globin HS40 enhancer (erythroid cell expression), an ankyrin-1 promoter (erythroid cell expression), and a Wiskott-Aldrich syndrome protein (WASP) promoter (hematopoietic cell expression).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc.

In particular embodiments, a selection cassette comprises an EF1α promoter or an MND promoter operably linked to a polynucleotide encoding a selectable marker.

Illustrative examples of selectable markers suitable for use in selection cassettes contemplated herein include, but are not limited to: hygromycin-B phosphotransferase (HPH) which may be positively selected for with hygromycin B; amino 3'-glycosyl phosphotransferase (NEO), which may be positively selected for with G418; dihydrofolate reductase (DHFR), which may be positively selected for with methotrexate; adenosine deaminase (ADA), which may be positively selected for with 2'-deoxycoformycin; multi-drug resistance protein (MDR), which may be positively selected for by anti-cancer drugs including, but not limited to *vinca* alkaloids, taxanes, anthracyclines, epipodophyllotoxins, colchicine, doxorubicin, and actinomycin D; $O^6$-methylguanine-DNA-methyltransferase (MGMT), which may be selected for by $O^6$-benzylguanine/1,3-bis(2-chloroethyl)-1-nitrosourea (BG/BCNU); Sh ble (BLE), which may be positively selected for with bleocin or zeocin; and blasticidin-S deaminase (BSR), which may be positively selected for with blastocidin.

In particular embodiments, a selection cassette comprises a ubiquitous promoter operably linked to a polynucleotide encoding MGMT.

Illustrative examples of post-transcriptional control sequences for use in selection cassettes include, but are not limited to: woodchuck hepatitis virus post-transcriptional response element (WPRE) or variant thereof, a hepatitis B virus post-transcriptional response element (HPRE) or variant thereof, and a polyadenylation sequence.

As used herein, the terms "post-transcriptional control sequences," "posttranscriptional regulatory element" or "PRE" refer to a cis-acting element that regulates expression at the mRNA level by, for example, regulating capping, splicing, poly(A) tail addition, and mRNA stability. Illustrative examples of PTE include, but are not limited to, woodchuck hepatitis virus posttranscriptional regulatory element (WPRE; Zufferey et al., 1999, *J. Virol.,* 73:2886); the posttranscriptional regulatory element present in hepatitis B virus (HPRE) (Huang and Yen, 1995, *Mol. Cell. Biol.,* 5:3864); and the like (Liu et al., 1995, *Genes Dev.,* 9:1766).

The term "poly(A) site" or "poly(A) sequence" as used herein denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is a synthetic poly(A) sequence (e.g., AATAAA, ATTAAA, AGTAAA). Illustrative examples of poly(A) sequences include, but are not limited to an SV40 poly(A) sequence, a bovine growth hormone poly(A) sequence (BGHpA), a rabbit β-globin poly(A) sequence (eβgpA), or another suitable heterologous or endogenous poly(A) sequence known in the art.

In particular embodiments, the polynucleotide encoding the selectable marker is fused to a polynucleotide encoding a viral self-cleaving peptide or ribosomal skipping sequence.

Illustrative examples of ribosomal skipping sequences include, but are not limited to: a 2A or 2A-like site, sequence or domain (Donnelly et al., 2001. *J. Gen. Virol.* 82:1027-

1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 1.

TABLE 1

| Exemplary 2A sites include the following sequences: | |
|---|---|
| SEQ ID NO: 60 | LLNFDLLKLAGDVESNPGP |
| SEQ ID NO: 61 | TLNFDLLKLAGDVESNPGP |
| SEQ ID NO: 62 | LLKLAGDVESNPGP |
| SEQ ID NO: 63 | NFDLLKLAGDVESNPGP |
| SEQ ID NO: 64 | QLLNFDLLKLAGDVESNPGP |
| SEQ ID NO: 65 | APVKQTLNFDLLKLAGDVESNPGP |
| SEQ ID NO: 66 | VTELLYRMKRAETYCPRPLLAIHPTEARHKQKIV APVKQT |
| SEQ ID NO: 67 | LNFDLLKLAGDVESNPGP |
| SEQ ID NO: 68 | LLAIHPTEARHKQKIVAPVKQTLNFDLLKLAGDV ESNPGP |
| SEQ ID NO: 69 | EARHKQKIVAPVKQTLNFDLLKLAGDVESNPGP |

In some embodiments, where the donor repair template is designed to derepress a γ-globin promoter and operably link the derepressed promoter to a polynucleotide encoding a therapeutic globin.

The term "globin" as used herein refers to proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are included by the term globin. The term excludes hemocyanins Examples of globins include α-globin or variant thereof, β-globin or variant thereof, a γ-globin or a variant thereof, and δ-globin or a variant thereof.

In particular embodiments, the therapeutic globin or anti-sickling variant thereof includes, but is not limited to is β-globin, δ-globin, γ-globin, β-globinA-T87Q, β-globinA-T87Q/K120E/K95E, or β-globinA-T87Q/G16D/E22A.

In some embodiments, the expression of the therapeutic globin is enhanced or improved by including one or more post-transcriptional elements and/or erythroid enhancers.

Illustrative examples of post-transcriptional elements and/or erythroid enhancers suitable for use in particular embodiments of donor repair templates contemplated herein include, but are not limited to: post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence and an erythroid enhancer selected from the group consisting of: an HPFH-2 enhancer, an HS40 enhancer, and a β-globin gene 3' enhancer.

In particular embodiments, a donor repair template is designed to operably link an erythroid expression control sequence to an endogenous genomic sequence encoding a γ-globin.

Illustrative examples of erythroid expression control sequences include, but are not limited to: a human β-globin LCR responsive promoter, an ankyrin gene promoter, an α-spectrin gene promoter, a β-spectrin gene promoter, or a β-globin gene promoter, optionally in combination with an HPFH-2 enhancer, an HS40 enhancer, and a β-globin gene 3' enhancer.

In particular embodiments, a donor repair template is inserted into a γ-globin locus to both derepress a γ-globin promoter to enable erythroid expression of a therapeutic globin and to select for genetically modified cells comprising the donor repair template. Derepression of the γ-globin promoter may occur through selection of the nuclease target sites or through engineering a deletion into one of the homology arms of the donor repair template. In particular embodiments, it is advantageous to engineer the nuclease to cleave at a transcription factor binding site associated with repression of a γ-globin gene, that way, derepression can occur by HDR; or in absence of HDR, the repressive site can still be disrupted by NHEJ, which also leads to derepression of the γ-globin gene. In preferred embodiments, the nuclease target site is designed to delete or disrupt a polynucleotide sequence associated with HPFH, e.g., at position −120 to −102 relative to the transcriptional start site of a γ-globin gene (see SEQ ID NOs: 1-6); preferably, a 13 bp polynucleotide sequence in a γ-globin gene associated with HPFH (SEQ ID NO: 3); more preferably a CCAAT polynucleotide sequence at position −115 to −111 (relative to the transcriptional start site of a γ-globin gene); and even more preferably the nuclease target site is at, or disrupts or deletes, a CAAT polynucleotide sequence at position −114 to −111 (relative to the transcriptional start site) of the HBG1 gene. In some embodiments, the donor repair template is also designed to disrupt endogenous γ-globin expression in favor of expressing the therapeutic globin of the donor repair template.

In other particular embodiments, a donor repair template is inserted into a γ-globin locus to derepress a γ-globin promoter, to enable selection of genetically modified cells comprising the template, and to enable erythroid expression of endogenous γ-globin. Derepression of the γ-globin promoter may occur through selection of the nuclease target sites or through engineering a deletion into one of the homology arms of the donor repair template. In particular embodiments, it is advantageous to engineer the nuclease to cleave at a transcription factor binding site associated with repression of a γ-globin gene, that way, γ-globin expression can occur by through HDR; or through NHEJ and derepression of the γ-globin gene. In preferred embodiments, the nuclease target site is designed to delete or disrupt a polynucleotide sequence associated with HPFH, e.g., at position −120 to −102 relative to the transcriptional start site of a γ-globin gene (see SEQ ID NOs: 1-6); preferably, a 13 bp polynucleotide sequence in a γ-globin gene associated with HPFH (SEQ ID NO: 3); more preferably a CCAAT polynucleotide sequence at position −115 to −111 (relative to the transcriptional start site of a γ-globin gene); and even more preferably the nuclease target site is at, or disrupts or deletes, a CAAT polynucleotide sequence at position −114 to −111 (relative to the transcriptional start site) of the HBG1 gene.

In various embodiments, an engineered nuclease is introduced into a hematopoietic cell, e.g., a hematopoietic stem or progenitor cell, or CD34+ cell, using non-viral or viral based methods and a donor repair template is introduced into a hematopoietic cell using viral methods by transducing the cell with an adeno-associated virus (AAV), retrovirus, e.g., lentivirus, IDLY, etc., herpes simplex virus, adenovirus, or vaccinia virus vector comprising the donor repair template.

In particular embodiments, delivery of one or more polynucleotides encoding nucleases and/or donor repair templates may be provided by the same method or by different methods, and/or by the same vector or by different vectors.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) Gene Therapy. 10:180-187; and Balazs et al. (2011) Journal of Drug Delivery. 2011:1-12. Antibody-targeted, bacterially derived, non-living nanocell-based delivery is also contemplated in particular embodiments.

Illustrative examples of viral vector systems suitable for use in particular embodiments contemplated herein include, but are not limited to adeno-associated virus (AAV), retrovirus, herpes simplex virus, adenovirus, and vaccinia virus vectors.

In various embodiments, one or more polynucleotides encoding a nuclease variant and/or donor repair template are introduced into a hematopoietic cell, e.g., a hematopoietic stem or progenitor cell, or CD34+ cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding a nuclease variant and/or donor repair template are introduced into a hematopoietic cell, e.g., a hematopoietic stem or progenitor cell, or CD34+ cell, by transducing the cell with a retrovirus, e.g., lentivirus, comprising the one or more polynucleotides. In one embodiment, a nuclease variant and/or donor repair template are introduced into a hematopoietic cell, e.g., a hematopoietic stem or progenitor cell, or CD34+ cell, by transducing the cell with an integrase deficient lentivirus.

As used herein, the term "integration defective lentivirus" or "IDLY" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In one embodiment, the HIV-1 integrase deficient pol gene comprises a D64V, D116I, D116A, E152G, or E152A mutation; D64V, D116I, and E152G mutations; or D64V, D116A, and E152A mutations.

In one embodiment, the HIV-1 integrase deficient pol gene comprises a D64V mutation.

F. Genome Edited Cells

The genome edited cells manufactured by the methods contemplated in particular embodiments provide improved cell-based therapeutics for the treatment of hemoglobinopathies. Without wishing to be bound to any particular theory, it is believed that the compositions and methods contemplated herein enable therapeutic globin expression and more robust selection of genome edited cells that may be used to treat, and in some embodiments potentially cure, hemoglobinopathies.

Genome edited cells contemplated in particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

Illustrative examples of cell types whose genome can be edited using the compositions and methods contemplated herein include, but are not limited to, cell lines, primary cells, stem cells, progenitor cells, and differentiated cells.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Symmetric cell division produces two identical daughter cells. "Proliferation" or "expansion" of cells refers to symmetrically dividing cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

In particular embodiments, the cell is a primary cell. The term "primary cell" as used herein is known in the art to refer to a cell that has been isolated from a tissue and has been established for growth in vitro or ex vivo. Corresponding cells have undergone very few, if any, population doublings and are therefore more representative of the main functional component of the tissue from which they are derived in comparison to continuous cell lines, thus representing a more representative model to the in vivo state. Methods to obtain samples from various tissues and methods to establish primary cell lines are well-known in the art (see, e.g., Jones and Wise, Methods Mol Biol. 1997). Primary cells for use in the methods contemplated herein are derived from umbilical cord blood, placental blood, mobilized peripheral blood and bone marrow. In one embodiment, the primary cell is a hematopoietic stem or progenitor cell.

In one embodiment, the genome edited cell is an embryonic stem cell.

In one embodiment, the genome edited cell is an adult stem or progenitor cell.

In one embodiment, the genome edited cell is primary cell.

In a preferred embodiment, the genome edited cell is a hematopoietic cell, e.g., hematopoietic stem cell, hematopoietic progenitor cell, an erythroid cell, or cell population comprising hematopoietic cells.

As used herein, the term "population of cells" refers to a plurality of cells that may be made up of any number and/or combination of homogenous or heterogeneous cell types, as described elsewhere herein. For example, for transduction of hematopoietic stem or progenitor cells, a population of cells may be isolated or obtained from umbilical cord blood, placental blood, bone marrow, or mobilized peripheral blood. A population of cells may comprise about 10%, about 20%, about 30%, about 40%, about 50%, about 60%, about 70%, about 80%, about 90%, or about 100% of the target cell type to be edited. In certain embodiments, hematopoietic stem or progenitor cells may be isolated or purified from a population of heterogeneous cells using methods known in the art.

Illustrative sources to obtain hematopoietic cells include, but are not limited to: cord blood, bone marrow or mobilized peripheral blood.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

Additional illustrative examples of hematopoietic stem or progenitor cells suitable for use with the methods and compositions contemplated herein include hematopoietic cells that are $CD34^+CD38^{Lo}CD90^+CD45^{RA-}$, hematopoietic cells that are $CD34^+$, $CD59^+$, $Thy1/CD90^+$, $CD38^{Lo/-}$, C-kit/$CD117^+$, and $Lin^{(-)}$, and hematopoietic cells that are $CD133^+$.

Various methods exist to characterize hematopoietic hierarchy. One method of characterization is the SLAM code. The SLAM (Signaling lymphocyte activation molecule) family is a group of >10 molecules whose genes are located mostly tandemly in a single locus on chromosome 1 (mouse), all belonging to a subset of immunoglobulin gene superfamily, and originally thought to be involved in T-cell stimulation. This family includes CD48, CD150, CD244, etc., CD150 being the founding member, and, thus, also called slamF1, i.e., SLAM family member 1. The signature SLAM code for the hematopoietic hierarchy is hematopoietic stem cells (HSC)—$CD150^+CD48^-CD244^-$; multipotent progenitor cells (MPPs)—$CD150^-CD48^-CD244^{\pm}$; lineage-restricted progenitor cells (LRPs)—$CD150^-CD48^+CD244^{\pm}$; common myeloid progenitor (CMP)—lin-SCA-1-c-$kit^+$ $CD34^+CD16/32^{mid}$; granulocyte-macrophage progenitor (GMP)—$kit^+CD34^+CD16/32^{hi}$; and megakaryocyte-erythroid progenitor (MEP)—$kit^+CD34^-CD16/32^{low}$.

Preferred target cell types edited with the compositions and methods contemplated herein include, hematopoietic cells, preferably human hematopoietic cells, more preferably human hematopoietic stem and progenitor cells, and even more preferably $CD34^+$ human hematopoietic stem cells. The term "CD34+ cell," as used herein refers to a cell expressing the CD34 protein on its cell surface. "CD34," as used herein refers to a cell surface glycoprotein (e.g., sialomucin protein) that often acts as a cell-cell adhesion factor. CD34+ is a cell surface marker of both hematopoietic stem and progenitor cells.

In one embodiment, the genome edited hematopoietic cells are $CD150^+CD48^-CD244^-$ cells.

In one embodiment, the genome edited hematopoietic cells are $CD34^+$CD133+ cells.

In one embodiment, the genome edited hematopoietic cells are $CD133^+$ cells.

In one embodiment, the genome edited hematopoietic cells are $CD34^+$ cells.

In particular embodiments, a population of hematopoietic cells comprising hematopoietic stem and progenitor cells (HSPCs) comprises an edited γ-globin gene, wherein the edit is a DSB preferably repaired by HDR in the presence of a donor repair template that derepresses the γ-globin promoter, and enables therapeutic globin expression and cell selection, but where a DSB repaired by NHEJ may also be advantageous in derepressing the γ-globin promoter in certain embodiments.

In particular embodiments, the genome edited cells comprise erythroid cells.

In particular embodiments, the genome edited cells comprise one or more mutations in a β-globin gene. In one embodiment, the β-globin alleles of the subject are selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$, or $\beta^S/\beta^S$.

In particular embodiments, the genome edited cells comprise one or more one or more mutations in a β-globin gene that result in a thalassemia. In one embodiment, the thalassemia is an α-thalassemia. In one embodiment, the thalassemia is a β-thalassemia. In one embodiment, the β-globin alleles of the subject are selected from the group consisting of: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In particular embodiments, the genome edited cells comprise one or more one or more mutations in a β-globin gene that result in sickle cell disease. In one embodiment, the β-globin alleles of the subject are selected from the group consisting of: $\beta^E/\beta^S$, $\beta^0/\beta^S$, $\beta^C/\beta^S$, $\beta^+/\beta^S$ or $\beta^S/\beta^S$.

G. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing a target site in a human γ-globin gene in a cell or a population of cells. In preferred embodiments, the cell is a hematopoietic cell, e.g., a hematopoietic stem or progenitor cell, or a $CD34^+$ cell.

In particular embodiments, the compositions contemplated herein comprise a population of cells, an engineered nuclease, and a donor repair template. In particular embodiments, the compositions contemplated herein comprise a population of cells, an engineered nuclease, an end-processing enzyme, and a donor repair template.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified hematopoietic stem and/or progenitor cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a nontoxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the genome edited hematopoietic stem and/or progenitor cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of genome edited cells, e.g., hematopoietic stem and progenitor cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions include, but are not limited to QBSF-60 (Quality Biological, Inc.), StemPro-34 (Life Technologies), and X-VIVO 10.

In a preferred embodiment, the compositions comprising genome edited hematopoietic stem and/or progenitor cells are formulated in PlasmaLyte.

In various embodiments, compositions comprising hematopoietic stem and/or progenitor cells are formulated in a cryopreservation medium. For example, cryopreservation media with cryopreservation agents may be used to maintain a high cell viability outcome post-thaw. Illustrative examples of cryopreservation media used in particular compositions include, but are not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of mycoplasma, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contains about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more reprogrammed nucleases, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intraarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. $22^{nd}$ Edition. Edited by Loyd V. Allen Jr. Philadelphia, Pa.: Pharmaceutical Press; 2012, which is incorporated by reference herein, in its entirety.

H. Genome Edited Cell Therapies

The genome edited cells manufactured by the methods contemplated in particular embodiments provide improved drug products for use in the prevention, treatment, and amelioration of a hemoglobinopathy or for preventing, treating, or ameliorating at least one symptom associated with a hemoglobinopathy or a subject having a hemoglobinopathic mutation in a β-globin gene. As used herein, the term "drug product" refers to genetically modified cells produced using the compositions and methods contemplated herein. In particular embodiments, the drug product comprises genetically modified hematopoietic stem or progenitor cells, e.g., $CD34^+$ cells. The genetically modified hematopoietic stem or progenitor cells can be selected through positive selection in vitro, ex vivo or in vivo and give rise to adult erythroid cells with increased γ-globin gene expression and allow treatment of subjects having no or minimal expression of the γ-globin gene in vivo, thereby significantly expanding the opportunity to bring genome edited cell therapies to subjects for which this type of treatment was not previously a viable treatment option.

In particular embodiments, genome edited hematopoietic stem or progenitor cells comprise a selection cassette and a mechanism to express a therapeutic globin through derepression of a γ-globin promoter or through operably linking an erythroid expression control sequence to an endogenous γ-globin coding sequence. The genetically modified cells may be positively selected for a selectable marker in a donor repair template through in vitro or ex vivo culture with the appropriate drug, or though in vivo selection by administration of the drug to a subject that has been administered a population of cells comprising the genetically modified cells that comprise the donor repair template. Drug-based selection, including dose and dosing schedule may be determined using methods known in the art.

In particular embodiments, genome edited hematopoietic stem or progenitor cells provide a curative, preventative, or ameliorative therapy to a subject diagnosed with or that is suspected of having a hemoglobinopathy.

As used herein, "hematopoiesis," refers to the formation and development of blood cells from progenitor cells, as well as formation of progenitor cells from stem cells. Blood cells include but are not limited to erythrocytes or red blood cells (RBCs), reticulocytes, monocytes, neutrophils, megakaryocytes, eosinophils, basophils, B-cells, macrophages, granulocytes, mast cells, thrombocytes, and leukocytes.

As used herein, the term "hemoglobinopathy" or "hemoglobinopathic condition" refers to a diverse group of inherited blood disorders that involve the presence of abnormal hemoglobin molecules resulting from alterations in the structure and/or synthesis of hemoglobin. Normally, hemoglobin consists of four protein subunits: two subunits of β-globin and two subunits of α-globin. Each of these protein subunits is attached (bound) to an iron-containing molecule called heme; each heme contains an iron molecule in its center that can bind to one oxygen molecule. Hemoglobin within red blood cells binds to oxygen molecules in the lungs. These cells then travel through the bloodstream and deliver oxygen to tissues throughout the body.

Hemoglobin A (HbA) is the designation for the normal hemoglobin that exists after birth. Hemoglobin A is a tetramer with two alpha chains and two beta chains ($\alpha_2\beta_2$). Hemoglobin A2 is a minor component of the hemoglobin found in red cells after birth and consists of two alpha chains and two delta chains ($\alpha_2\delta_2$). Hemoglobin A2 generally comprises less than 3% of the total red cell hemoglobin. Hemoglobin F (HbF) is the predominant hemoglobin during fetal development. The molecule is a tetramer of two alpha chains and two gamma chains ($\alpha_2\gamma_2$). In preferred embodiments, subjects are administered genome edited hematopoietic stem or progenitor cells that give rise to erythroid cells that have increased γ-globin gene expression and/or decreased hemoglobinopathic β-globin gene expression, thereby increasing the amount of HbF in the subject.

The most common hemoglobinopathies include sickle cell disease, β-thalassemia, and α-thalassemia.

In particular embodiments, the compositions and methods contemplated herein provide genome edited cell therapies for subjects having a sickle cell disease. The term "sickle cell anemia" or "sickle cell disease" is defined herein to include any symptomatic anemic condition which results from sickling of red blood cells. Sickle cell anemia $\beta^S/\beta^S$, a common form of sickle cell disease (SCD), is caused by Hemoglobin S (HbS). HbS is generated by replacement of glutamic acid (E) with valine (V) at position 6 in β-globin, noted as Glu6Val or E6V. Replacing glutamic acid with valine causes the abnormal HbS subunits to stick together and form long, rigid molecules that bend red blood cells into a sickle (crescent) shape. The sickle-shaped cells die prematurely, which can lead to a shortage of red blood cells (anemia). In addition, the sickle-shaped cells are rigid and can block small blood vessels, causing severe pain and organ damage.

Additional mutations in the β-globin gene can also cause other abnormalities in β-globin, leading to other types of sickle cell disease. These abnormal forms of β-globin are often designated by letters of the alphabet or sometimes by a name. In these other types of sickle cell disease, one β-globin subunit is replaced with HbS and the other β-globin subunit is replaced with a different abnormal variant, such as hemoglobin C (HbC; β-globin allele noted as $\beta^C$) or hemoglobin E (HbE; β-globin allele noted as $\beta^E$).

In hemoglobin SC (HbSC) disease, the β-globin subunits are replaced by HbS and HbC. HbC results from a mutation in the β-globin gene and is the predominant hemoglobin found in people with HbC disease ($\alpha_2\beta^C{}_2$). HbC results when the amino acid lysine replaces the amino acid glutamic acid at position 6 in β-globin, noted as Glu6Lys or E6K. HbC disease is relatively benign, producing a mild hemolytic anemia and splenomegaly. The severity of HbSC disease is variable, but it can be as severe as sickle cell anemia.

HbE is caused when the amino acid glutamic acid is replaced with the amino acid lysine at position 26 in β-globin, noted as Glu26Lys or E26K. People with HbE disease have a mild hemolytic anemia and mild splenomegaly. HbE is extremely common in Southeast Asia and in some areas equals hemoglobin A in frequency. In some cases, the HbE mutation is present with HbS. In these cases, a person may have more severe signs and symptoms associated with sickle cell anemia, such as episodes of pain, anemia, and abnormal spleen function.

Other conditions, known as hemoglobin sickle-β-thalassemias (HbSBetaThal), are caused when mutations that produce hemoglobin S and β-thalassemia occur together. Mutations that combine sickle cell disease with beta-zero ($\beta^0$; gene mutations that prevent β-globin production) thalassemia lead to severe disease, while sickle cell disease combined with beta-plus ($\beta^+$; gene mutations that decrease β-globin production) thalassemia is milder.

As used herein, "thalassemia" refers to a hereditary disorder characterized by defective production of hemoglobin. Examples of thalassemias include α- and β-thalassemia.

In particular embodiments, the compositions and methods contemplated herein provide genome edited cell therapies for subjects having a β-thalassemia. β-thalassemias are caused by a mutation in the β-globin chain, and can occur in a major or minor form. Nearly 400 mutations in the β-globin gene have been found to cause (3-thalassemia. Most of the mutations involve a change in a single DNA building block (nucleotide) within or near the β-globin gene. Other mutations insert or delete a small number of nucleotides in the β-globin gene. As noted above, β-globin gene mutations that decrease β-globin production result in a type of the condition called beta-plus Or) thalassemia. Mutations that prevent cells from producing any beta-globin result in beta-zero ($\beta^0$) thalassemia. In the major form of β-thalassemia, children are normal at birth, but develop anemia during the first year of life. The minor form of β-thalassemia produces small red blood cells. Thalassemia minor occurs if you receive the defective gene from only one parent. Persons with this form of the disorder are carriers of the disease and usually do not have symptoms.

HbE/β-thalassemia results from combination of HbE and β-thalassemia ($\beta^E/\beta^0$, $\beta^E/\beta^+$) and produces a condition more severe than is seen with either HbE trait or β-thalassemia trait. The disorder manifests as a moderately severe thalassemia that falls into the category of thalassemia intermedia. HbE/β-thalassemia is most common in people of Southeast Asian background.

In a preferred embodiment, genome edited cell therapies contemplated herein are used to treat, prevent, or ameliorate a hemoglobinopathy is selected from the group consisting of: hemoglobin C disease, hemoglobin E disease, sickle cell anemia, sickle cell disease (SCD), thalassemia, β-thalassemia, thalassemia major, thalassemia intermedia, hemoglobin Bart syndrome and hemoglobin H disease.

In various embodiments, the genome editing compositions are administered by direct injection to a cell, tissue, or organ of a subject in need of gene therapy, in vivo, e.g., bone marrow. In various other embodiments, cells are edited in vitro or ex vivo, and optionally selected and expanded ex vivo. The genome edited cells are then administered to a subject in need of therapy. In certain embodiments, the cells are edited in vitro or ex vivo and selected in vivo after administration to a subject in need of therapy.

Preferred cells for use in the genome editing methods contemplated herein include autologous/autogeneic ("self") cells, preferably hematopoietic cells, more preferably hematopoietic stem or progenitor cell, and even more preferably CD34+ cells.

As used herein, the terms "individual" and "subject" are often used interchangeably and refer to any animal that exhibits a symptom of a hemoglobinopathy that can be treated with the reprogrammed nucleases, genome editing compositions, gene therapy vectors, genome editing vectors, genome edited cells, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects include human patients that have, have been diagnosed with, or are at risk of having a hemoglobinopathy.

As used herein, the term "patient" refers to a subject that has been diagnosed with hemoglobinopathy that can be treated with the reprogrammed nucleases, genome editing compositions, gene therapy vectors, genome editing vectors, genome edited cells, and methods contemplated elsewhere herein.

As used herein "treatment" or "treating," includes any beneficial or desirable effect on the symptoms or pathology of a hemoglobinopathy or hemoglobinopathic condition, and may include even minimal reductions in one or more measurable markers of the hemoglobinopathy or hemoglobinopathic condition. Treatment can optionally involve delaying of the progression of the hemoglobinopathy or hemoglobinopathic condition. "Treatment" does not necessarily indicate complete eradication or cure of the hemoglobinopathy or hemoglobinopathic condition, or associated symptoms thereof.

As used herein, "prevent," and similar words such as "prevention," "prevented," "preventing" etc., indicate an approach for preventing, inhibiting, or reducing the likelihood of the occurrence or recurrence of, hemoglobinopathy or hemoglobinopathic condition. It also refers to delaying the onset or recurrence of a hemoglobinopathy or hemoglobinopathic condition or delaying the occurrence or recurrence of the symptoms of hemoglobinopathy or hemoglobinopathic condition. As used herein, "prevention" and similar words also includes reducing the intensity, effect, symptoms and/or burden of a hemoglobinopathy or hemoglobinopathic condition prior to its onset or recurrence.

As used herein, the phrase "ameliorating at least one symptom of" refers to decreasing one or more symptoms of the hemoglobinopathy or hemoglobinopathic condition for which the subject is being treated, e.g., thalassemia, sickle cell disease, etc. In particular embodiments, the hemoglobinopathy or hemoglobinopathic condition being treated is β-thalassemia, wherein the one or more symptoms ameliorated include, but are not limited to, weakness, fatigue, pale appearance, jaundice, facial bone deformities, slow growth, abdominal swelling, dark urine, iron deficiency (in the absence of transfusion), requirement for frequent transfusions. In particular embodiments, the hemoglobinopathy or hemoglobinopathic condition being treated is sickle cell disease (SCD) wherein the one or more symptoms ameliorated include, but are not limited to, anemia; unexplained episodes of pain, such as pain in the abdomen, chest, bones or joints; swelling in the hands or feet; abdominal swelling; fever; frequent infections; pale skin or nail beds; jaundice; delayed growth; vision problems; signs or symptoms of stroke; iron deficiency (in the absence of transfusion), requirement for frequent transfusions.

As used herein, the term "amount" refers to "an amount effective" or "an effective amount" of a nuclease variant, genome editing composition, or genome edited cell sufficient to achieve a beneficial or desired prophylactic or therapeutic result, including clinical results.

A "prophylactically effective amount" refers to an amount of a nuclease variant, genome editing composition, or genome edited cell sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a nuclease variant, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

The genome edited cells may be administered as part of a bone marrow or cord blood transplant in an individual that has or has not undergone bone marrow ablative therapy. In one embodiment, genome edited cells contemplated herein are administered in a bone marrow transplant to an individual that has undergone chemoablative or radioablative bone marrow therapy.

In one embodiment, a dose of genome edited cells is delivered to a subject intravenously. In preferred embodiments, genome edited hematopoietic stem cells are intravenously administered to a subject.

In one illustrative embodiment, the effective amount of genome edited cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of genome edited cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of genome edited cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

Some variation in dosage will necessarily occur depending on the condition of the subject being treated. The person responsible for administration will, in any event, determine the appropriate dose for the individual subject.

In particular embodiments, a genome edited cell therapy is used to treat, prevent, or ameliorate a hemoglobinopathy, or condition associated therewith, comprising administering to subject having a β-globin genotype selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$, a therapeutically effective amount of the genome edited cells contemplated herein.

In particular embodiments, genome edited cell therapies contemplated herein are used to treat, prevent, or ameliorate a thalassemia, or condition associated therewith. Thalassemias treatable with the genome edited cell contemplated herein include, but are not limited to α-thalassemias and β-thalassemias. In particular embodiments, a genome edited cell therapy is used to treat, prevent, or ameliorate a β-thalassemia, or condition associated therewith, comprising administering to subject having a β-globin genotype selected from the group consisting of: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$, a therapeutically effective amount of the genome edited cells contemplated herein.

In particular embodiments, genome edited cell therapies contemplated herein are used to treat, prevent, or ameliorate a sickle cell disease or condition associated therewith. In particular embodiments, a genome edited cell therapy is used to treat, prevent, or ameliorate a sickle cell disease or condition associated therewith, comprising administering to subject having a β-globin genotype selected from the group consisting of: $\beta^E/\beta^S$, $\beta^0/\beta^S$, $\beta^C/\beta^S$, $\beta^+/\beta^S$ or $\beta^S/\beta^S$, a therapeutically effective amount of the genome edited cells contemplated herein.

One of ordinary skill in the art would be able to use routine methods in order to determine the appropriate route of administration and the correct dosage of an effective amount of a composition comprising genome edited cells contemplated herein. It would also be known to those having ordinary skill in the art to recognize that in certain therapies, multiple administrations of pharmaceutical compositions contemplated herein may be required to effect therapy.

One of the prime methods used to treat subjects amenable to treatment with genome edited hematopoietic stem and progenitor cell therapies is blood transfusion. Thus, one of the chief goals of the compositions and methods contemplated herein is to reduce the number of, or eliminate the need for, transfusions.

In particular embodiments, the drug product is administered once.

In certain embodiments, the drug product is administered 1, 2, 3, 4, 5, 6, 7, 8, 9, or 10 or more times over a span of 1 year, 2 years, 5, years, 10 years, or more.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Genome Editing Strategies for Treatment of Hemoglobinopathies

Figure 2:
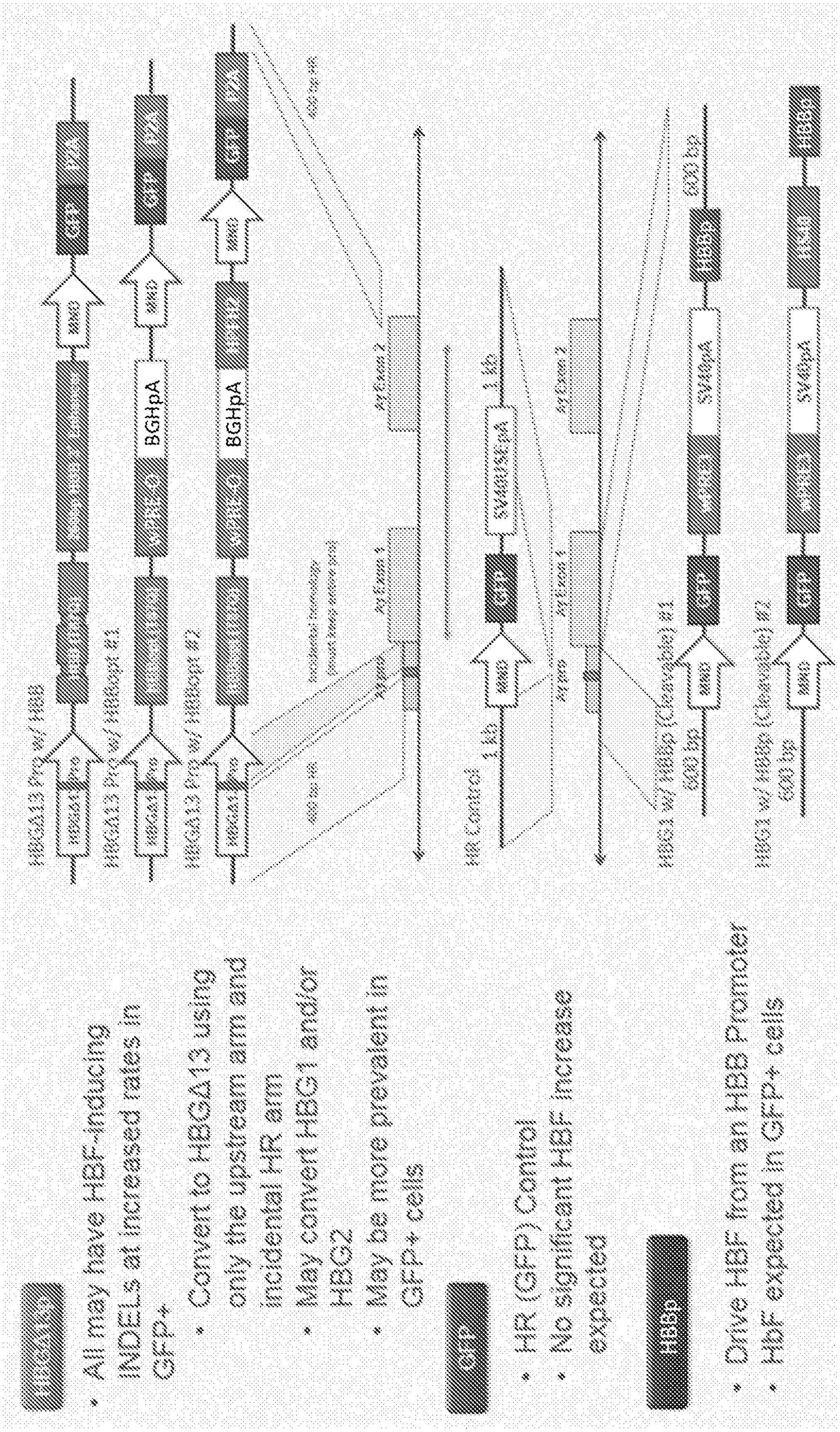
FIG. 2 shows a diagram of the various illustrative donor repair templates that were integrated into the γ-globin locus by homology directed repair.
Figure 3:
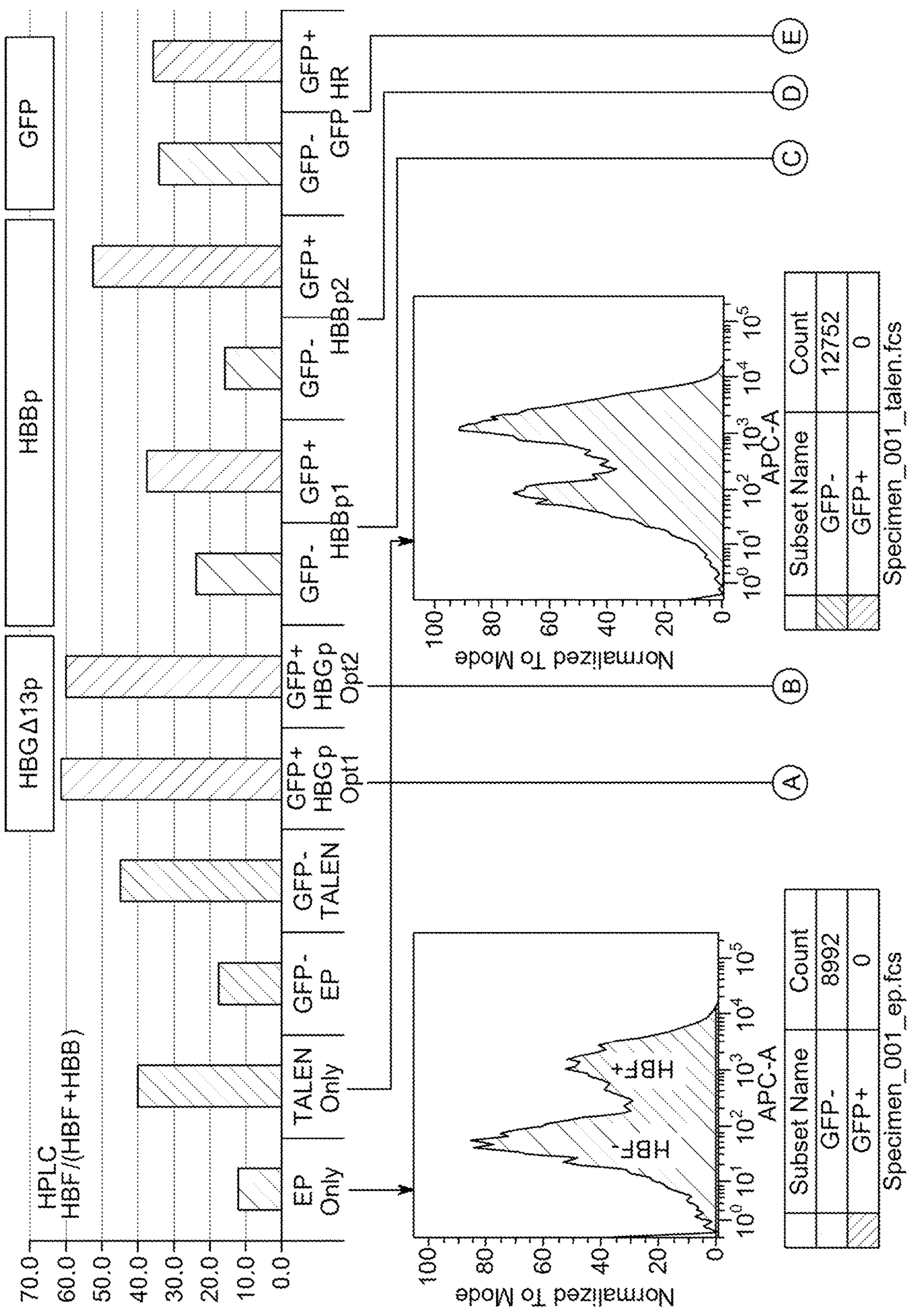
FIG. 3 shows the flow cytometric analysis of HbF expression by HPLC following erythroid differentiation.
Figure 3:
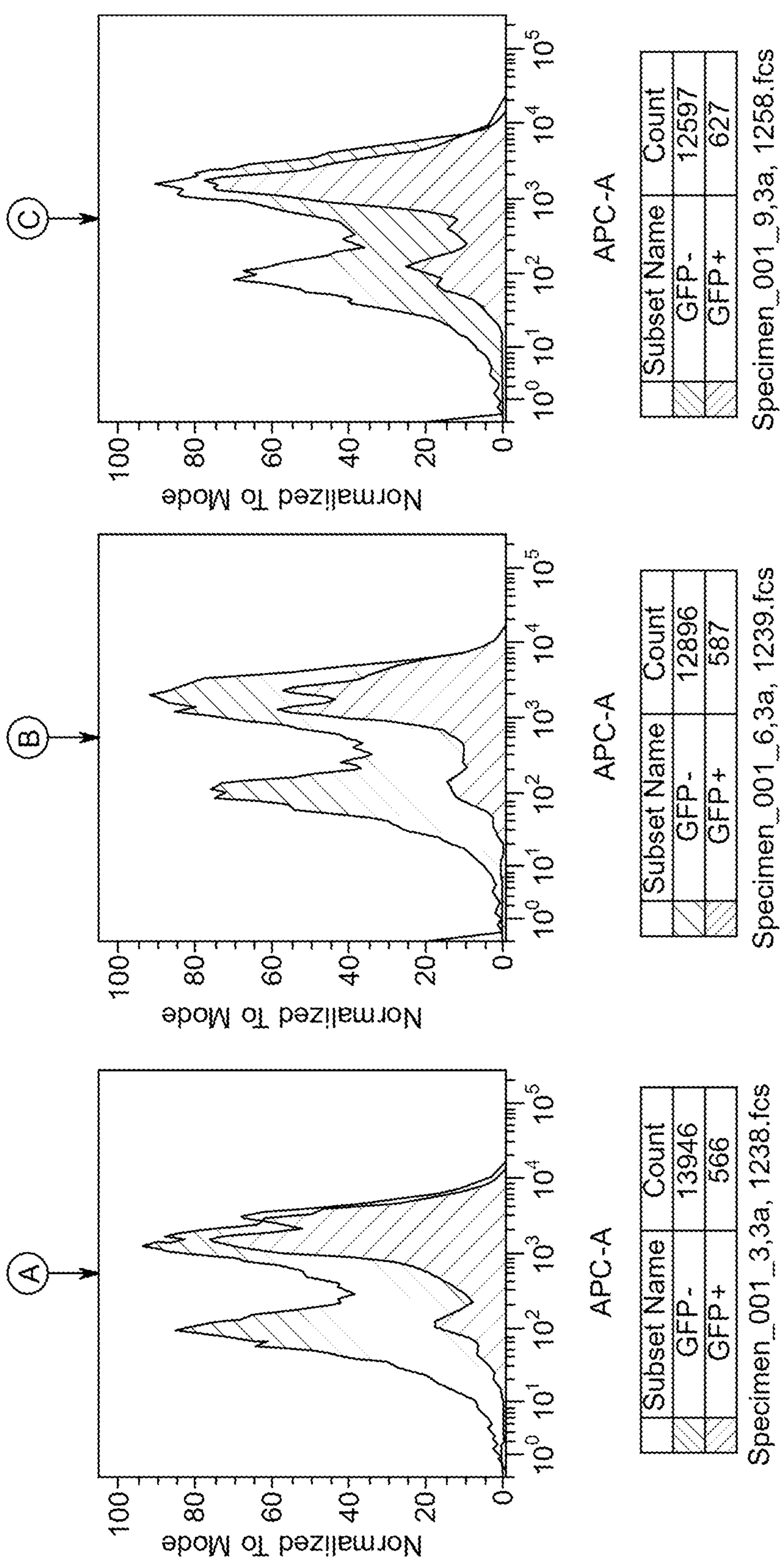
Figure 3:
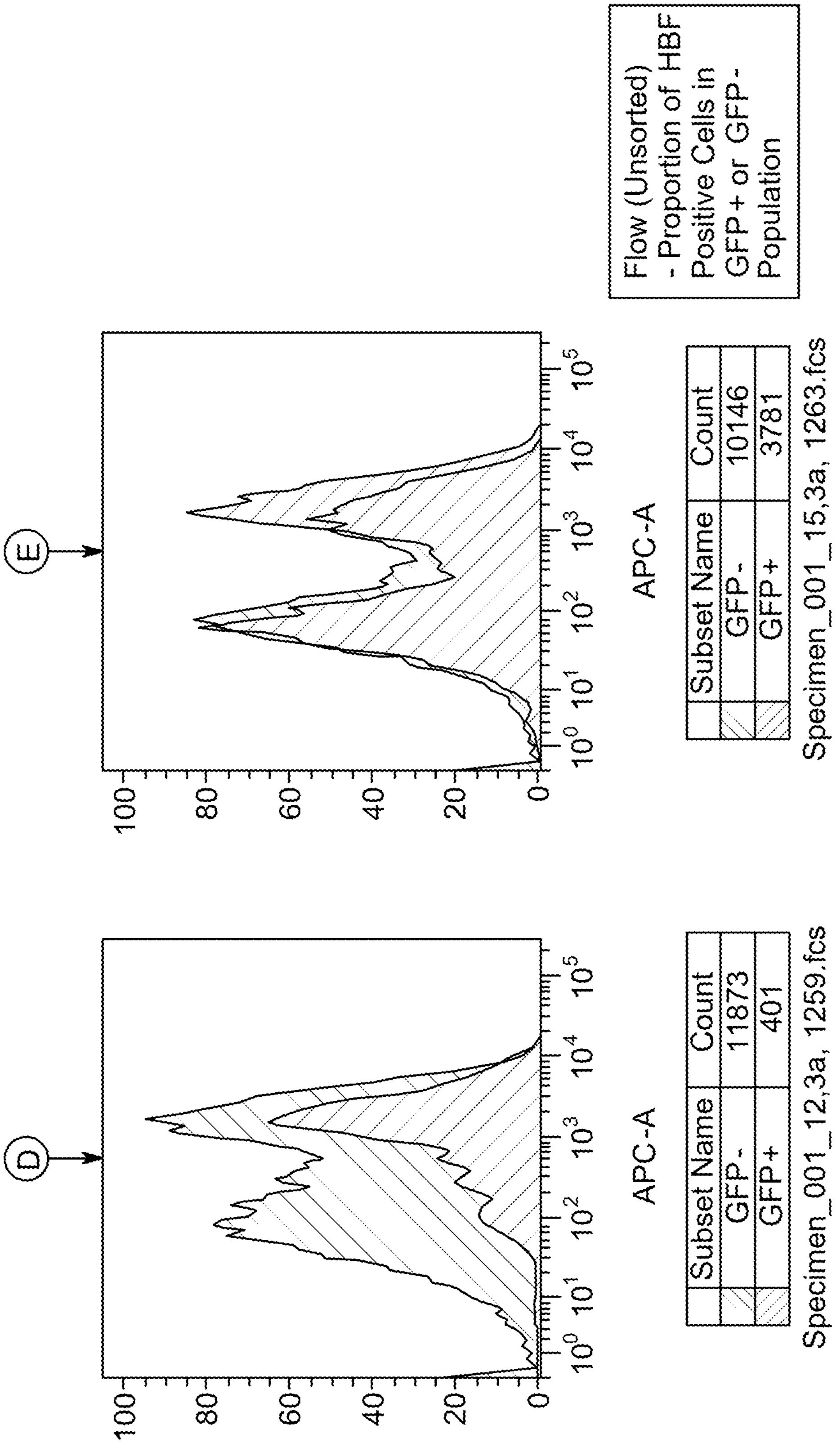

Human $CD34^+$ hematopoietic stem and progenitor cells were selected and cultured for 48-72 hours in growth medium containing SCF, TPO, and FLT3. The $hCD34^+$ cells were then centrifuged, re-suspended in electroporation media, and electroporated with a polynucleotide encoding a nuclease. In this particular example, $hCD34^+$ cells were electroporated with an mRNA encoding TALENs nucleases that target a 13 base pair region (SEQ ID NO: 3) in the γ-globin promoter (e.g., SEQ ID NO: 9), that when deleted, has shown to be associated with HPFH. FIG. 1. The electroporated $hCD34^+$ cells were cultured for 4 hours and were then transduced with AAV vectors (packaged with AAV6 capsid) comprising the cassettes schematized in FIG. 2. The transduced $hCD34^+$ cells were then cultured in methylcellulose to assess CFU potential and flow cytometric analysis of fetal globin expression following erythroid differentiation. FIG. 3.

The γ-globin locus was targeted by HDR using the illustrative donor repair templates and TALENs nucleases and resulted in upregulation of fetal globin (HbF) expression ($2^{nd}$, and $4^{th}$ bars), and was also detectable when a GFP selection cassette was used ($11^{th}$ and $12^{th}$ bars). Analysis of erythroid-differentiated colonies in CFU assays from cells targeted with the GFP-vector showed GFP expression, thereby demonstrating that integration of a donor repair template comprising a selection cassette into this region of the γ-globin gene did not disrupt γ-globin expression or erythroid differentiation. HbF expression was further increased when the nuclease was co-transfected with donor repair templates that comprised a 13 bp deletion in the γ-globin promoter associated with HPFH or the β-globin promoter (see bars 5/6, and 7-10 respectively).

Example 2

Approach

A gene editing strategy was developed with TALEN's or Crispr/Cas9 ribonucleoprotein (RNP) delivery to create clinically useful deletions, including a naturally occurring 13 bp deletion, at the HBG1 and HBG2 promoter region that drives increased fetal hemoglobin expression. The deletions created by these designer nucleases eliminate suppressive elements that function to block fetal globin expression. Upon editing this region at the HBG1 or HBG2 loci, fetal hemoglobin is induced. Re-induction of fetal hemoglobin can be therapeutic in sickle-cell and β-thalassemia patients and potentially curative to alleviate symptoms. In parallel with generation of clinically useful indels/deletions, we have developed AAV gene delivery cassettes that, following introduction by homology-directed-repair (HDR), will mediate expression of functional hemoglobin based upon a series of alternative strategies described below. This overall approach thereby effectively partners: a) deletional events that promote fetal hemoglobin induction with b) additional HDR-mediated gene expression events that drive therapeutic hemoglobin production, that together, synergize to provide increased overall therapeutic benefit.

Strategies

Multiple strategies have been optimized for inducing hemoglobin at the HBG1 and HBG2 loci:

1. Nucleases (TALEN's and Crispr/Cas9) that edit at HBG1 and HBG2 loci and drive indels and re-induce both G1 and G2 globin.
2. Early parental constructs that integrate at the HBG1 locus and test expression of globin.
3. Optimized homology-directed repair templates that integrate at the HBG1 locus and drive: (A) HBG1 expression or (B) $\beta^{T87Q}$ expression in human or non-human primate cells.
4. Optimized homology-directed repair templates that integrate at the HBG1 locus and drive HBG1 expression or $\beta^{T87Q}$ expression and, in parallel, allow for chemo-therapeutic selection of HDR-edited human or non-human primate cells.

Strategy 1: Nucleases (TALEN's and Crispr/Cas9) that Edit at HBG1 and HBG2 Loci in Mobilized Primary Human $CD34^{+}$ HSC Cells Drive Indels and Re-Induce Both G1 and G2 Globin.

Figure 4A:
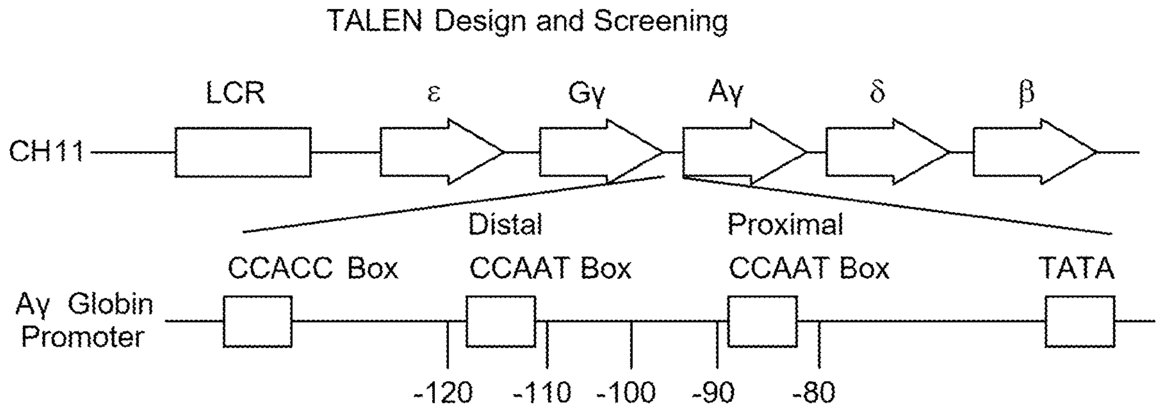
FIGS. 4A-4C show TALEN design and screening.
Figure 4B:
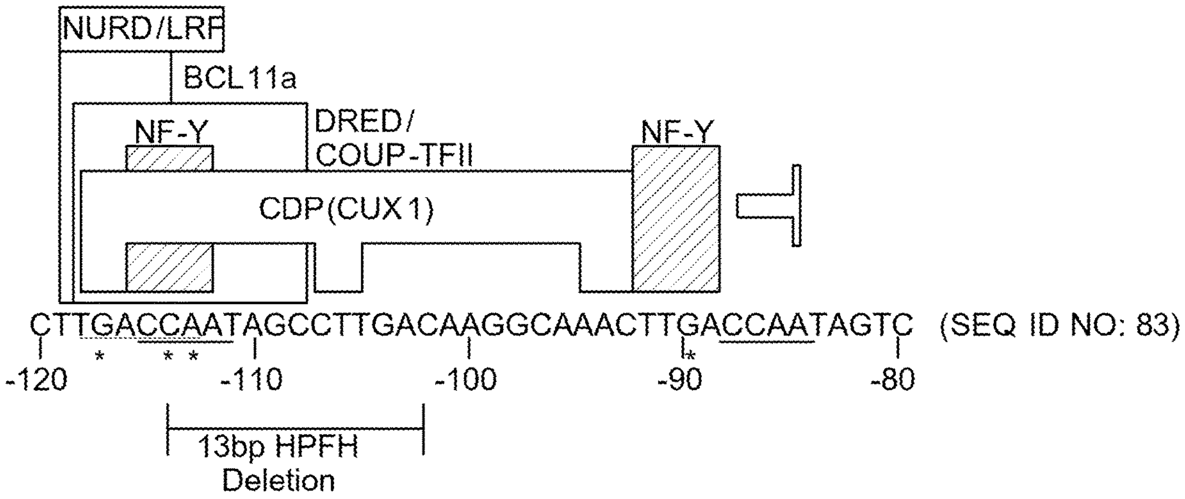
Figure 4C:
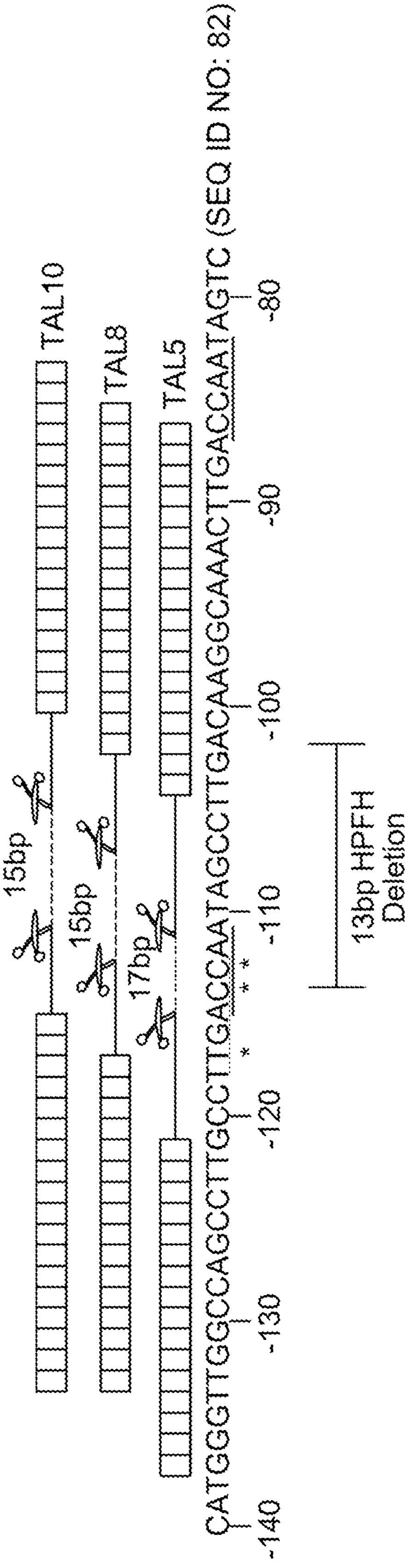
Figure 5A:
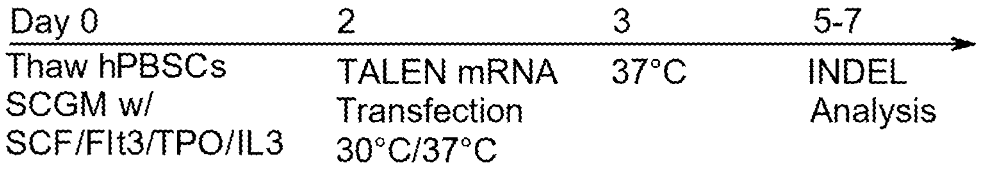
FIGS. 5A-5G demonstrate optimizing TALEN editing conditions to maximize efficiency.
Figure 5B:
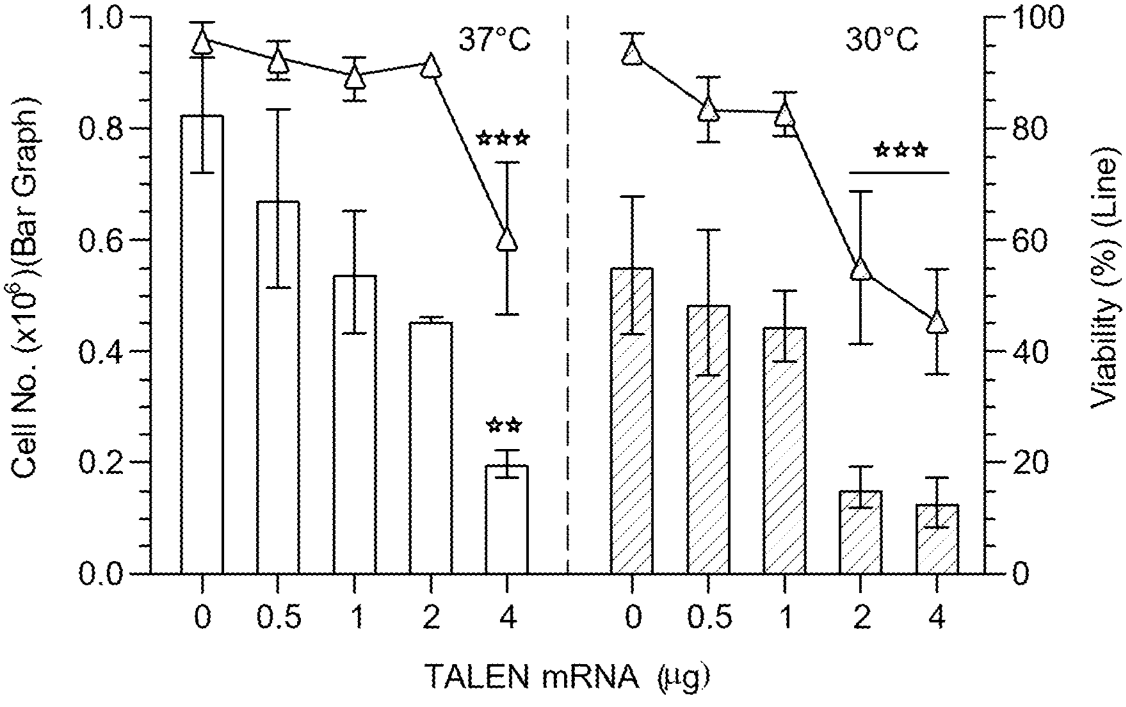
Figure 5C:
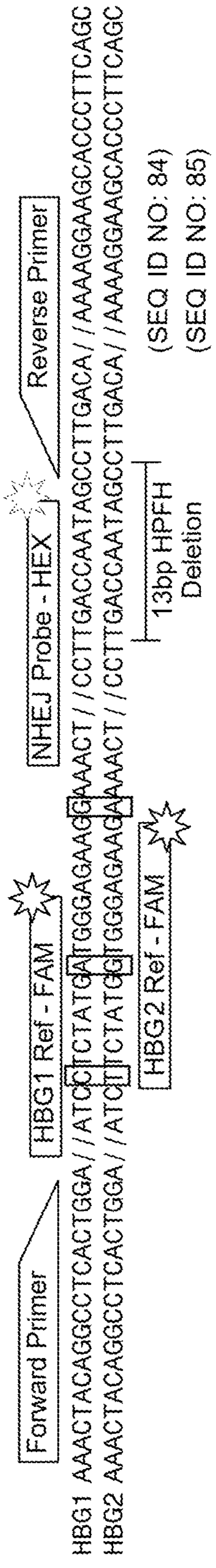
Figure 5D:
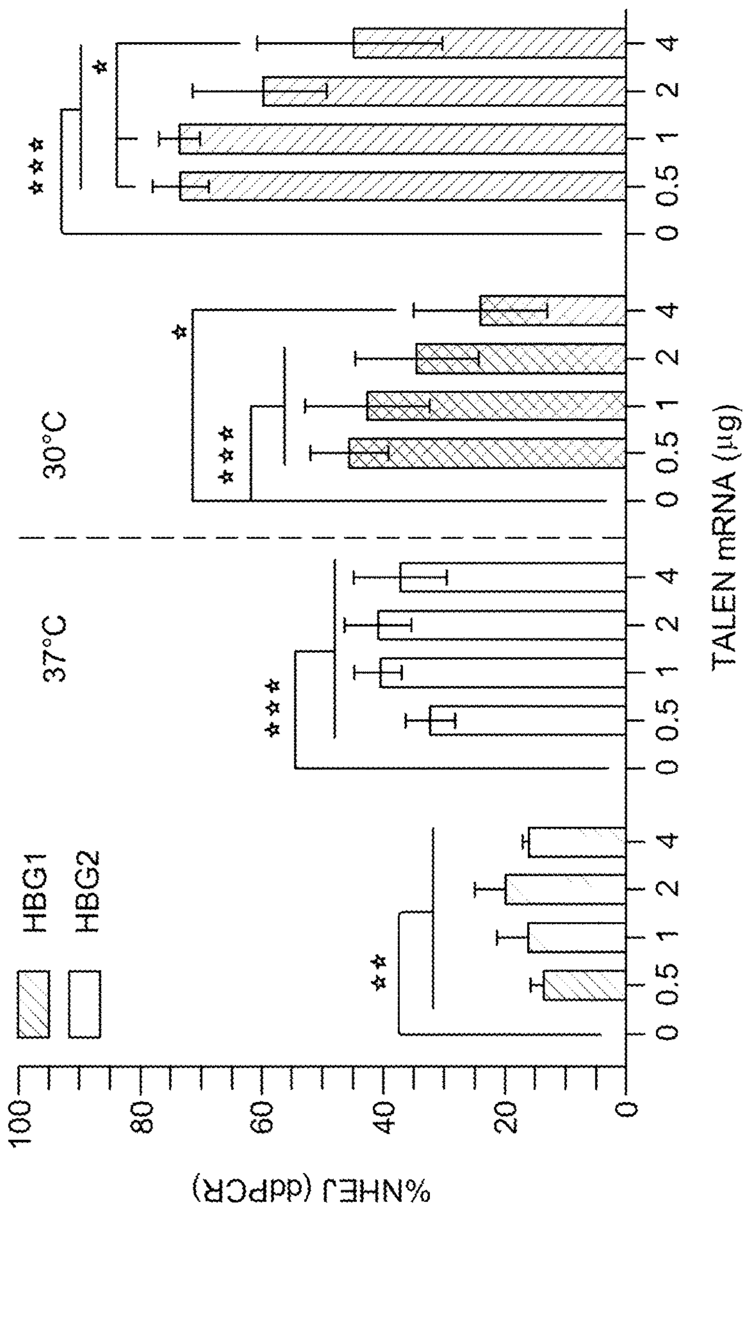
Figure 5E:
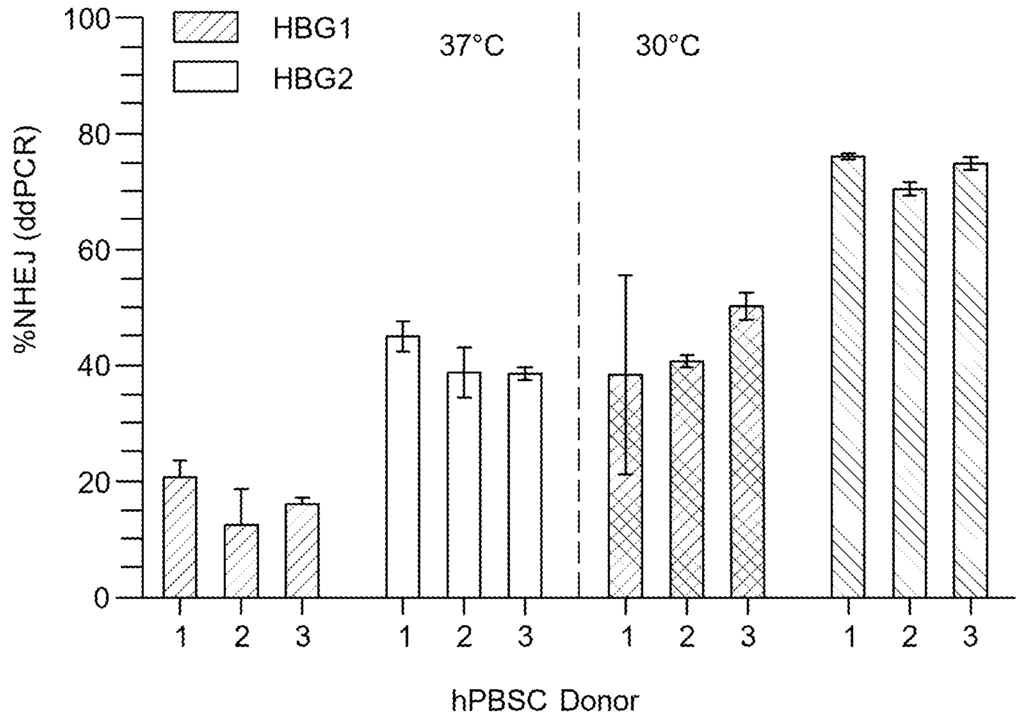
Figure 5F:
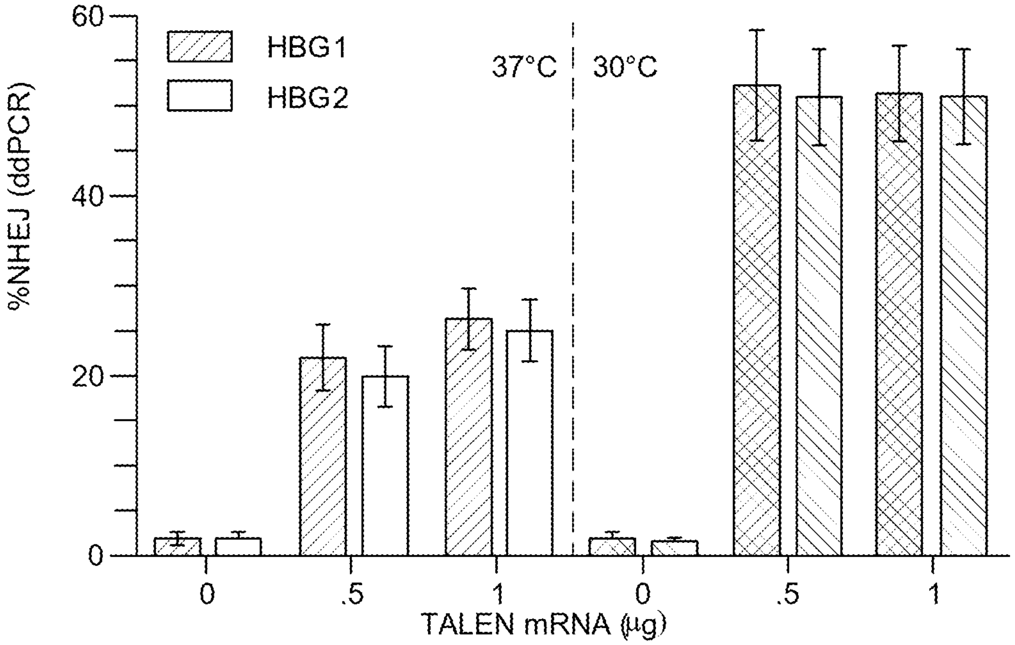
Figure 5G:
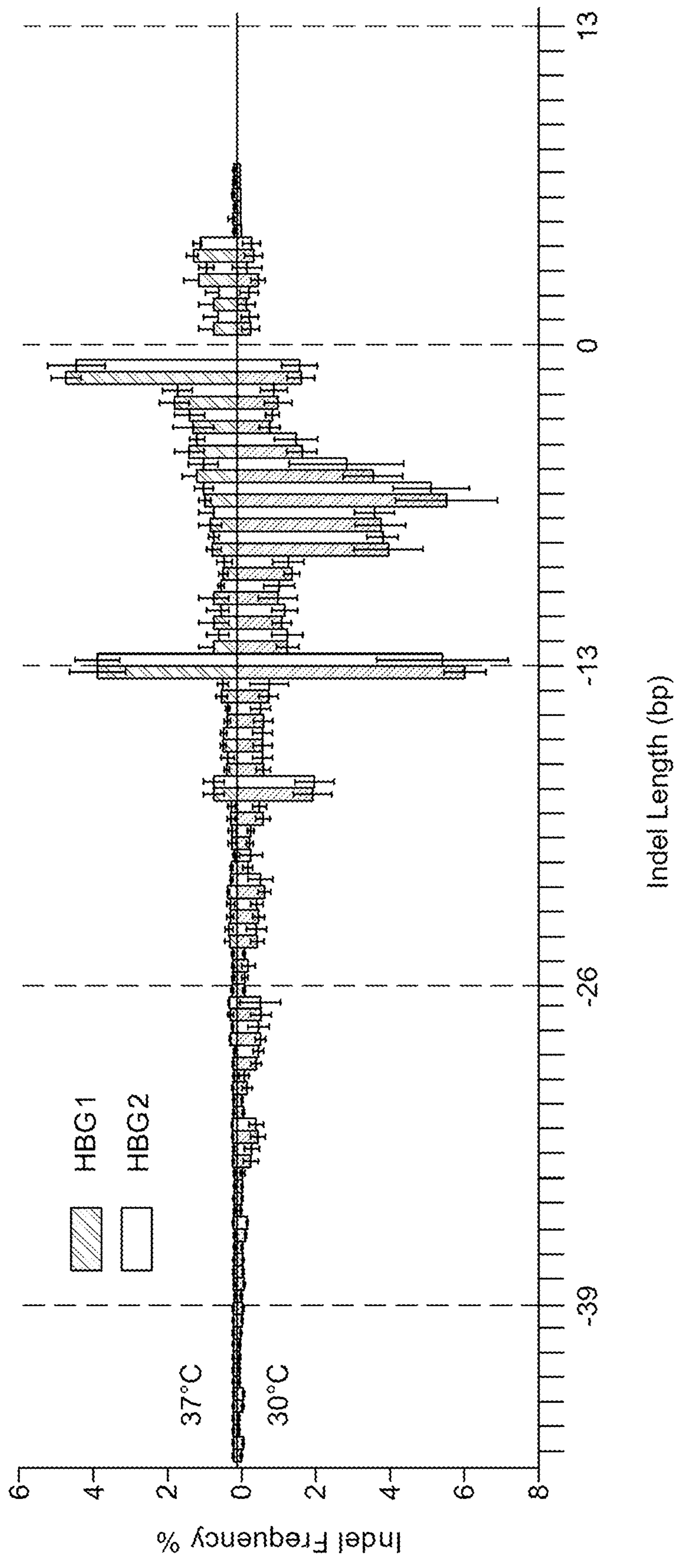
Figures 6A, 6B, 6C, 6D:
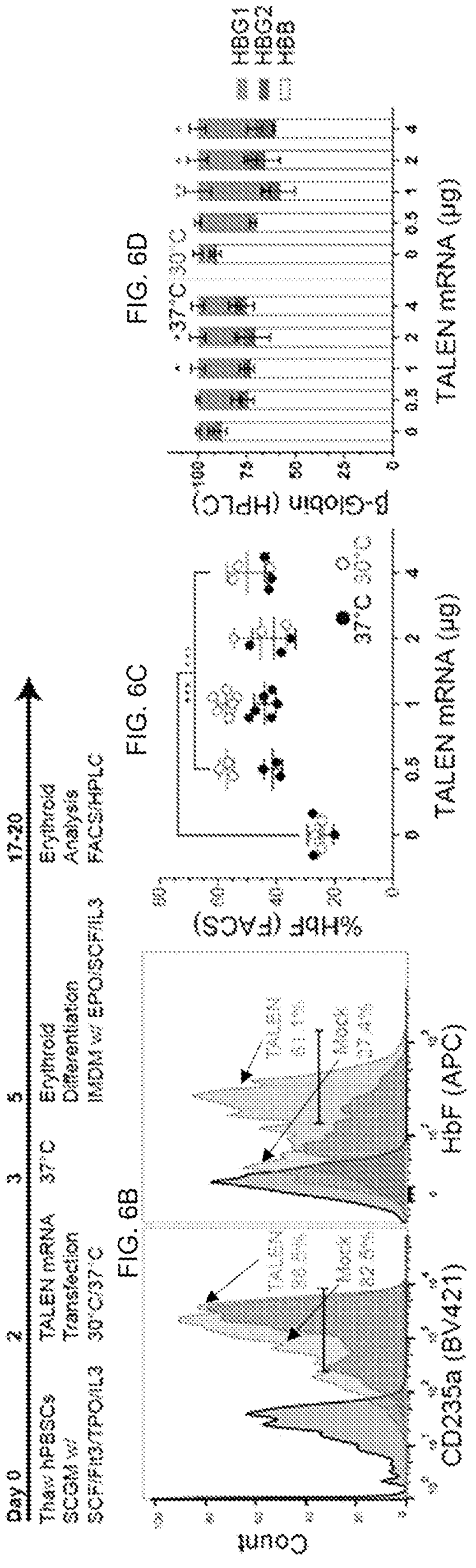
FIGS. 6A-6D demonstrate TALEN-induced ds breaks drive fetal hemoglobin expression in differentiated hPBSCs.
Figure 7A:
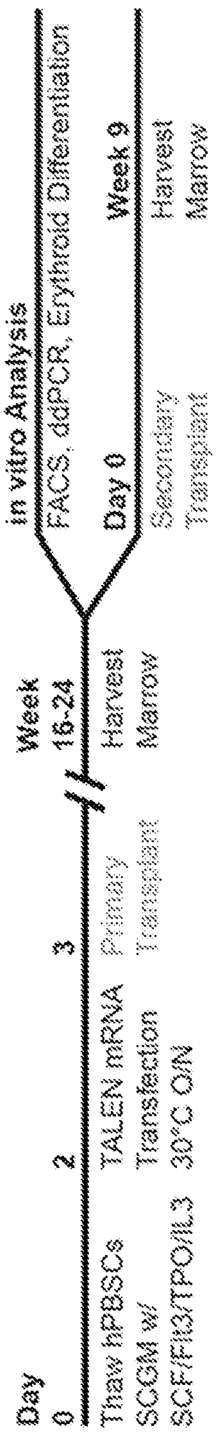
FIGS. 7A-7H demonstrates sustained multi-lineage engraftment of TALEN edited hPBSCs in recipient W41 mice.
Figure 7B:
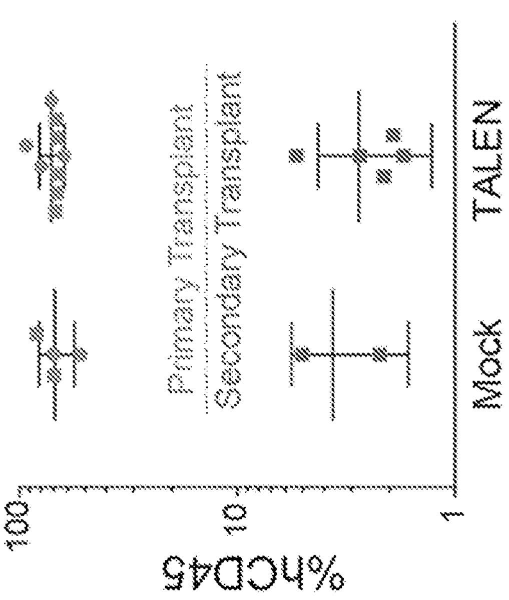
Figure 7C:
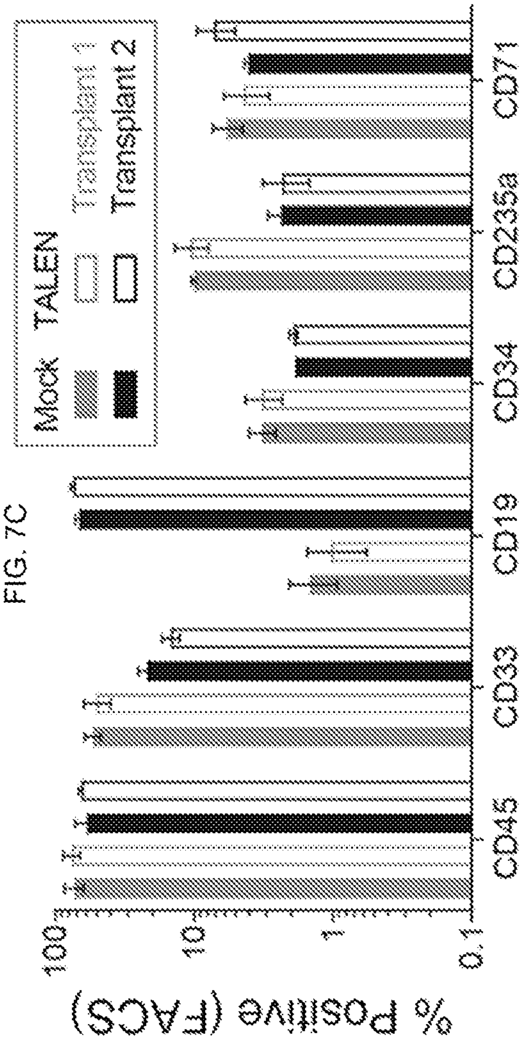
Figure 7D:
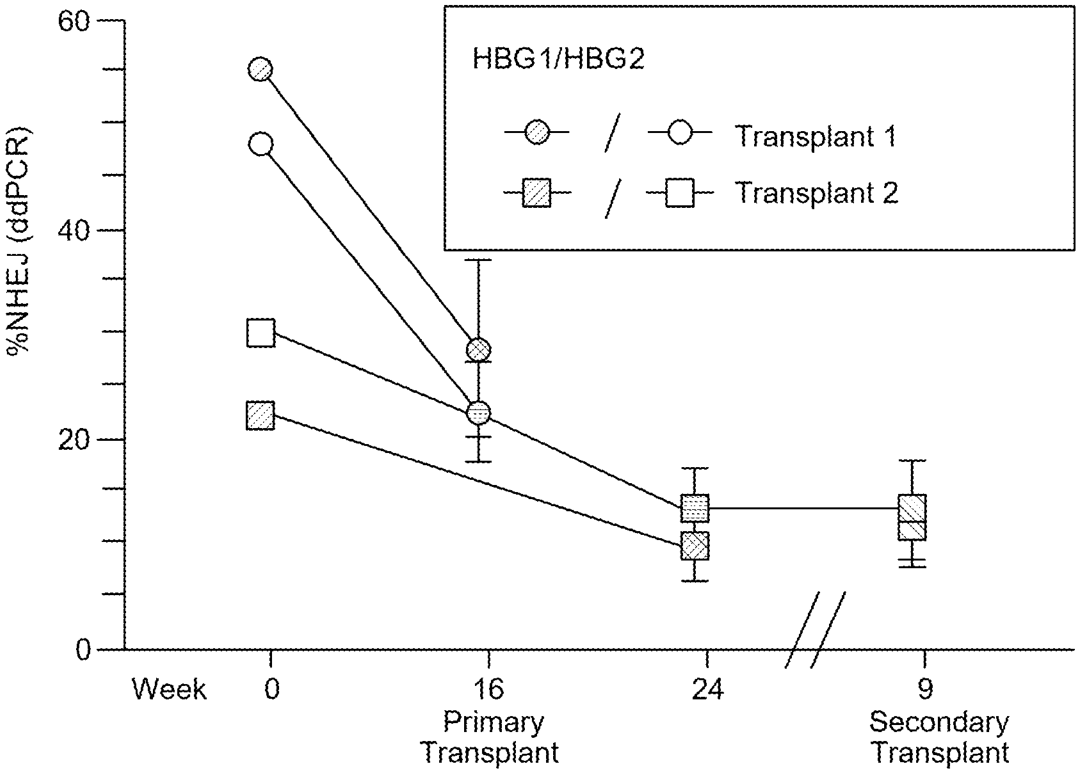
Figure 7E:
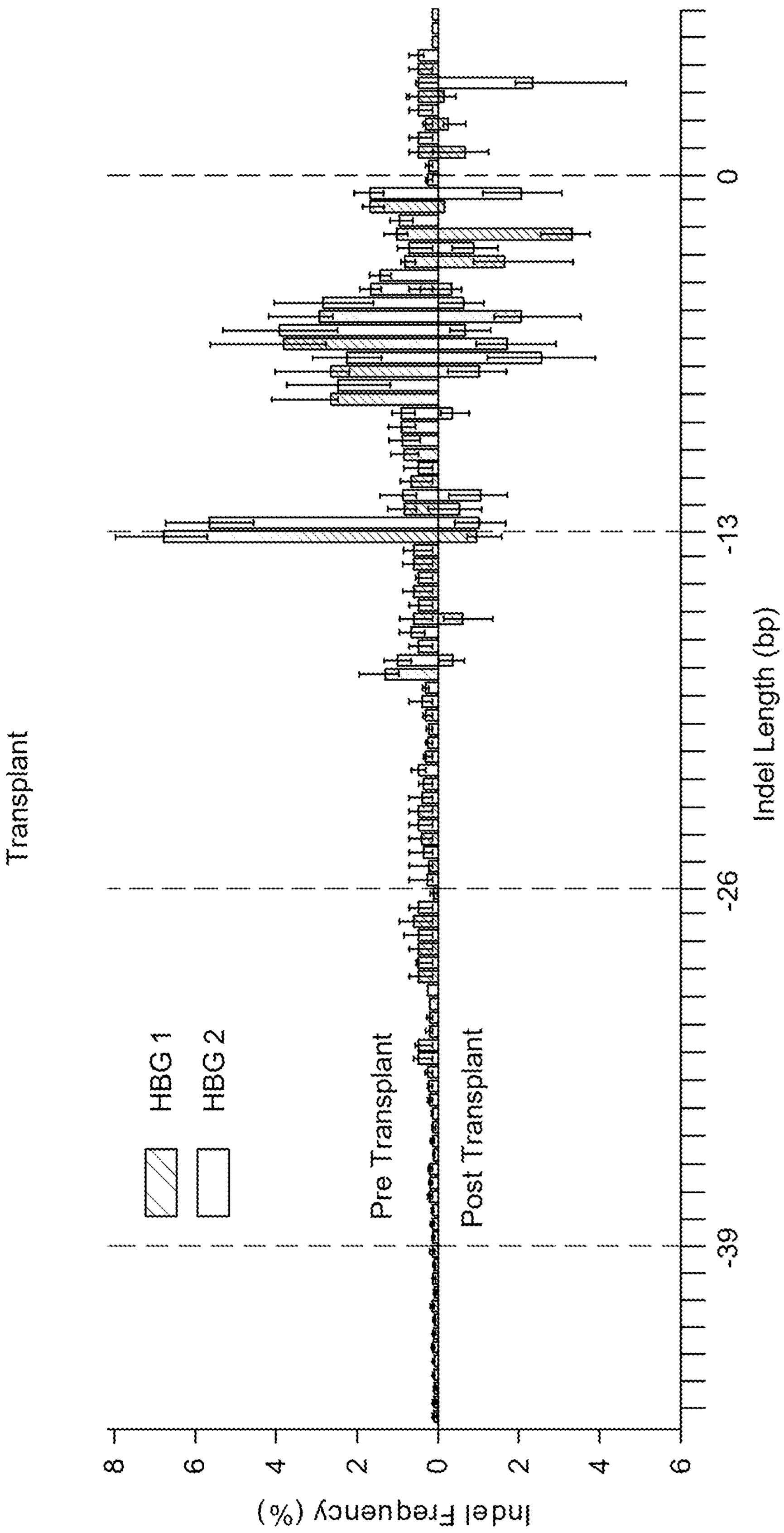
Figure 7F:
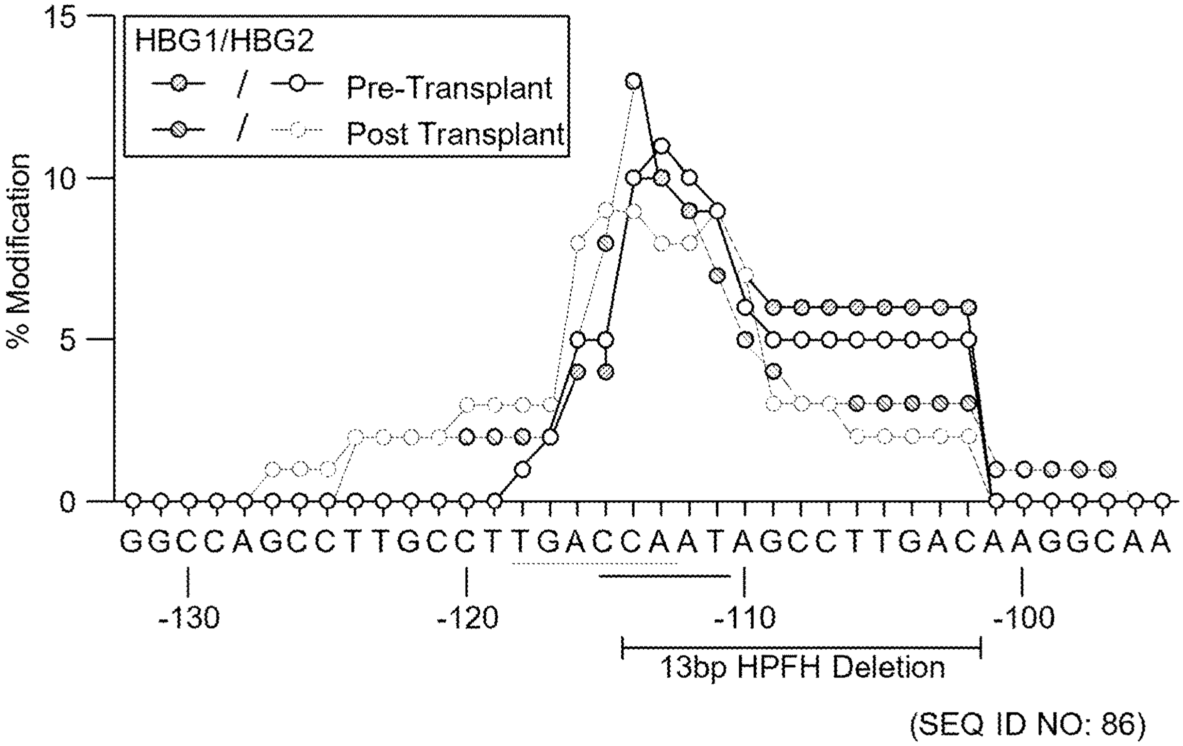
Figure 7G:
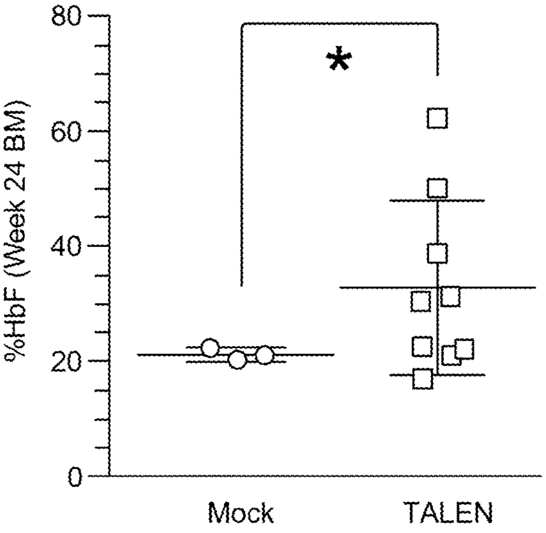
Figure 7H:
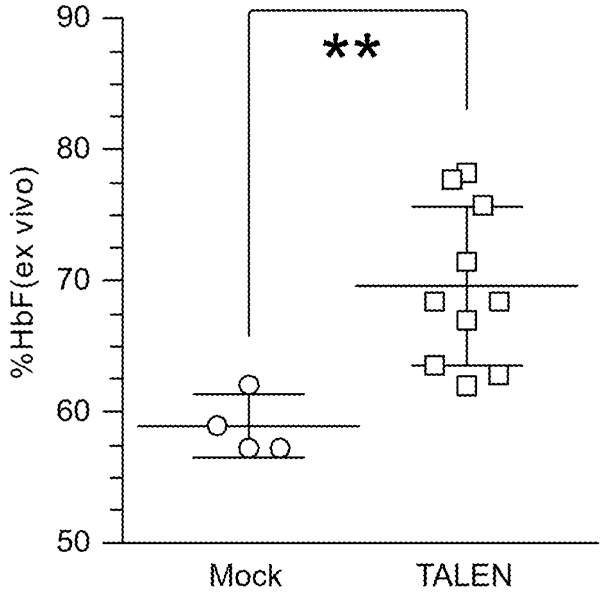

1A. 13 bp deletion drives fetal hemoglobin expression in gene edited mobilized primary human CD34+ HSC cells. (FIGS. 4-6) TALEN and RNP nucleases drive non-homologus end joining (NHEJ) mediated re-creation of 13 bp deletion and other useful deletions at the HBG1 and HBG2 loci. These deletions obliterate the distal CCAAT box along with sites that bind multiple transcription factors including the BCL11A binding site TGACCA and results in the induction of both HBG1 and HBG2 fetal hemoglobin.

Figure 8:
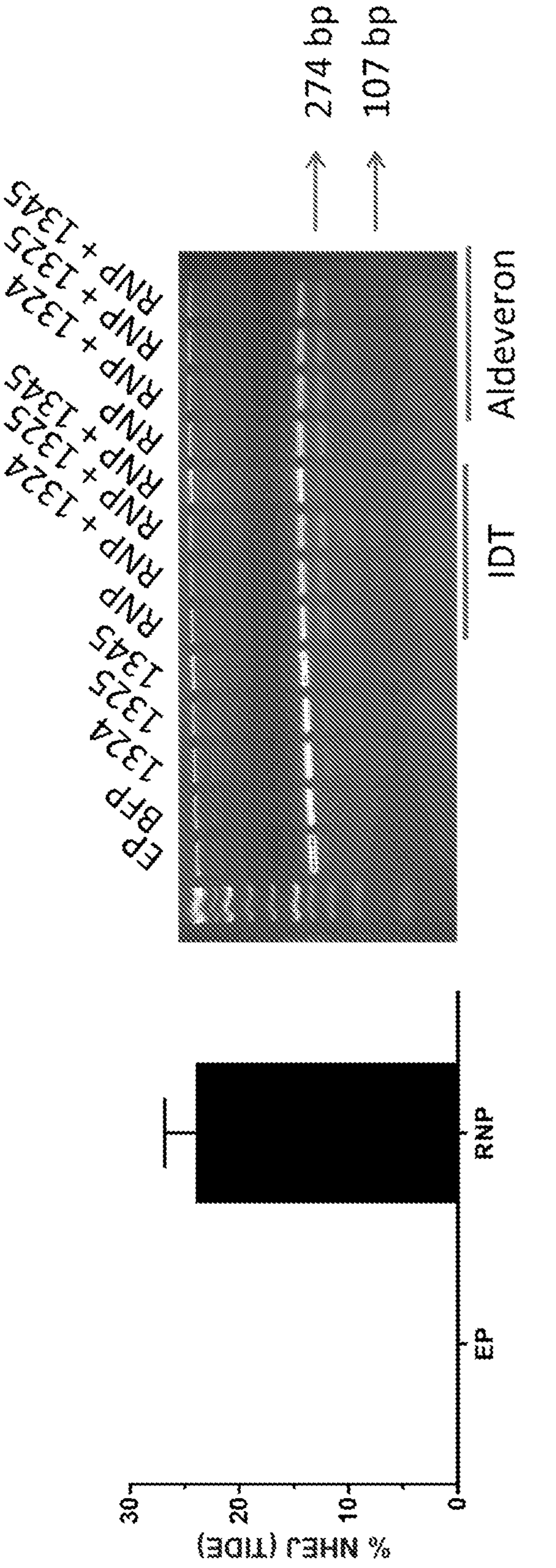
FIG. 8 demonstrates ribonuceloprotein delivery with Cas9 and sgRNA has been optimized for editing at the HBG1 and G2 loci. The panel on the left shows ~26% overall editing at the HbG1 and HbG2 loci by TIDE analysis. The panel on the right shows a T7 endonuclease assay that shows, no Indels in the electroporation only samples and the presence of Indels in the RNP and RNP+AAV samples.
Figure 13:
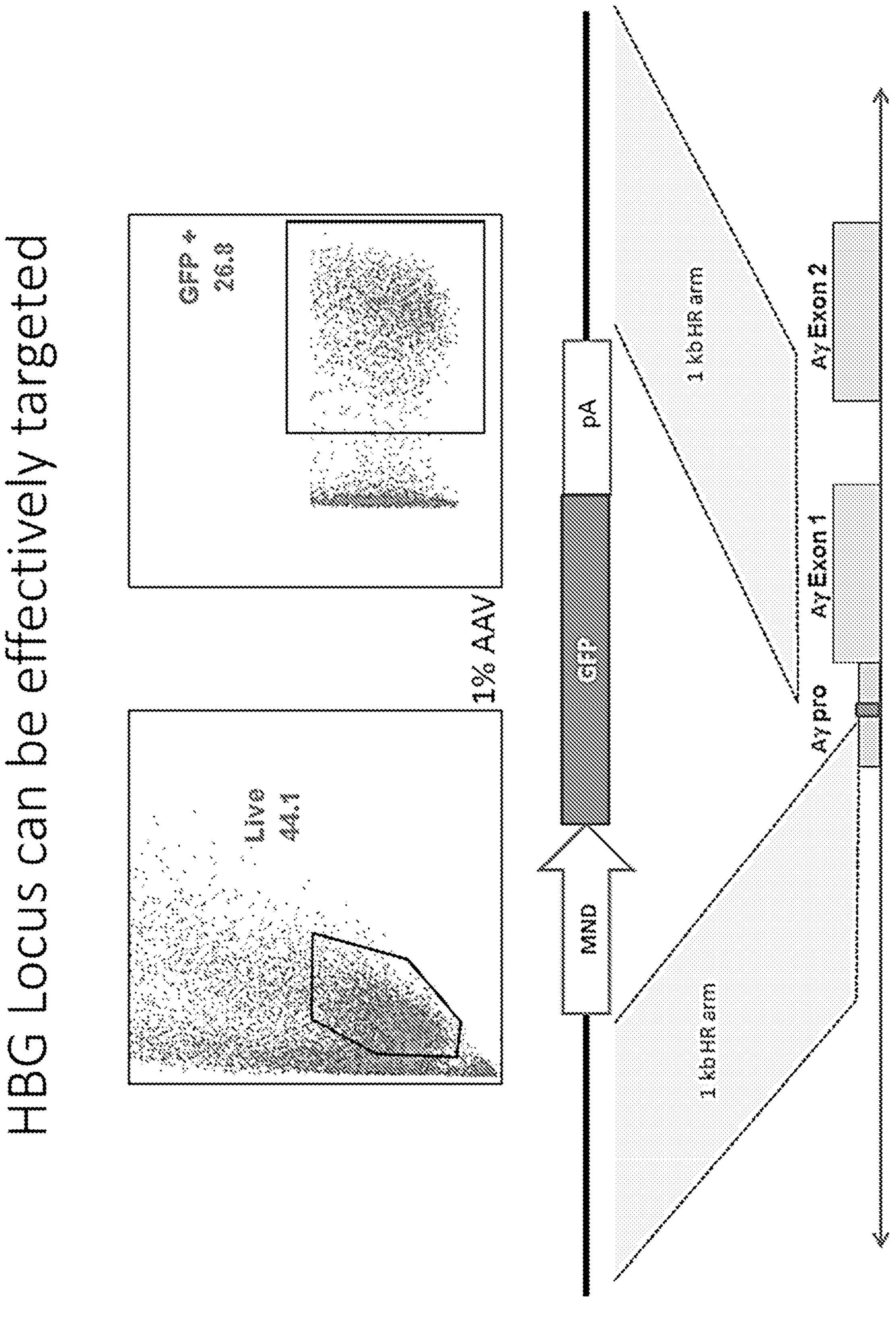
FIG. 13 shows construct 1263-GFP Control repair template. This template is used to assess HDR rates at the HGB1 locus. The data demonstrates efficient HDR within this locus. The HDR rates are comparable to our own and others published results at other genetic loci in human CD34+ HSC. This construct is used to compare to other HDR constructs that create deletions and/or have smaller HR arms, etc, and this acts as a benchmark for editing.
Figure 14:
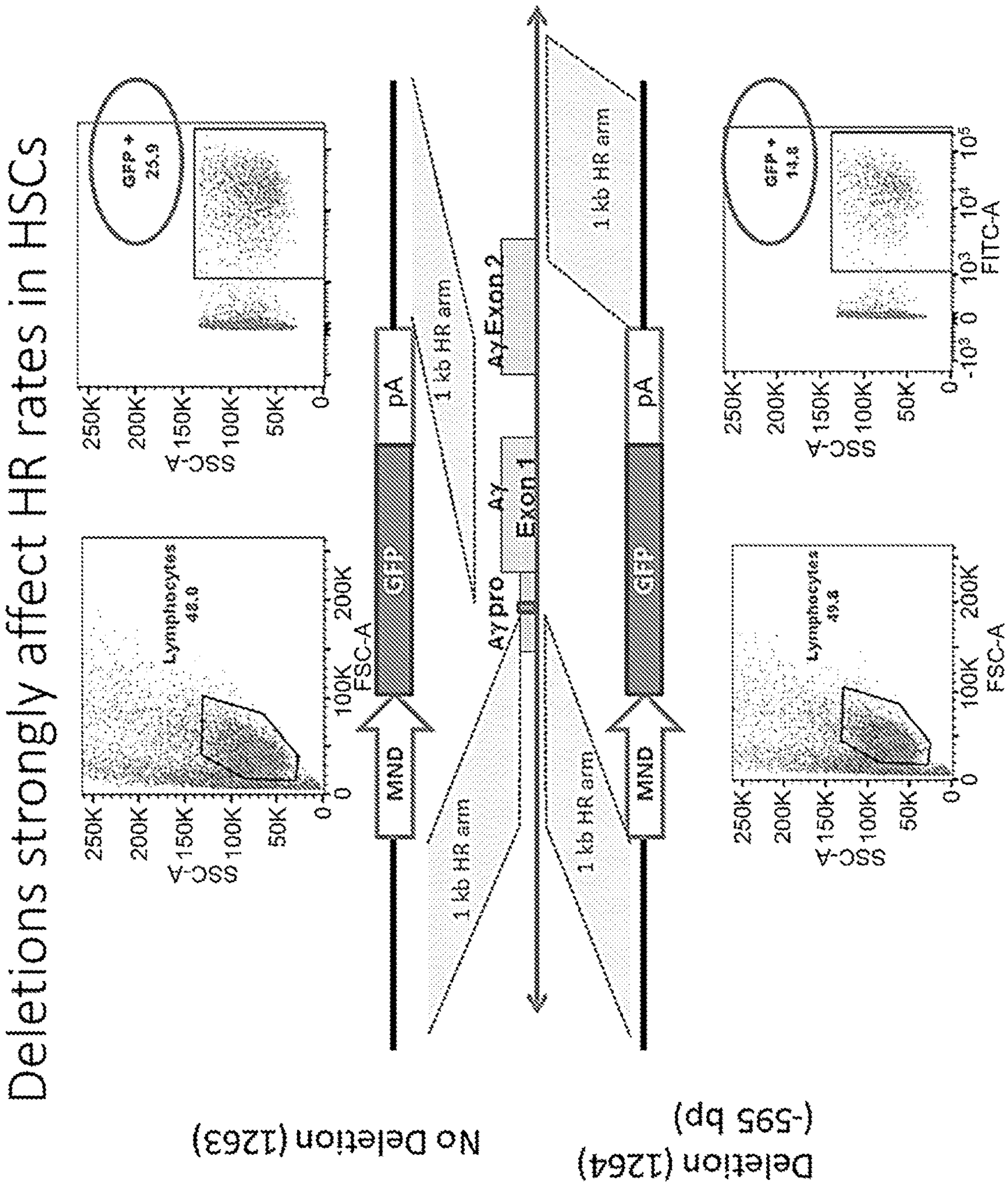
FIG. 14 shows when HR arms bind to sequences distant from each other in the genome, they require a deletion event to occur and decrease HR efficiency.
Figure 15:
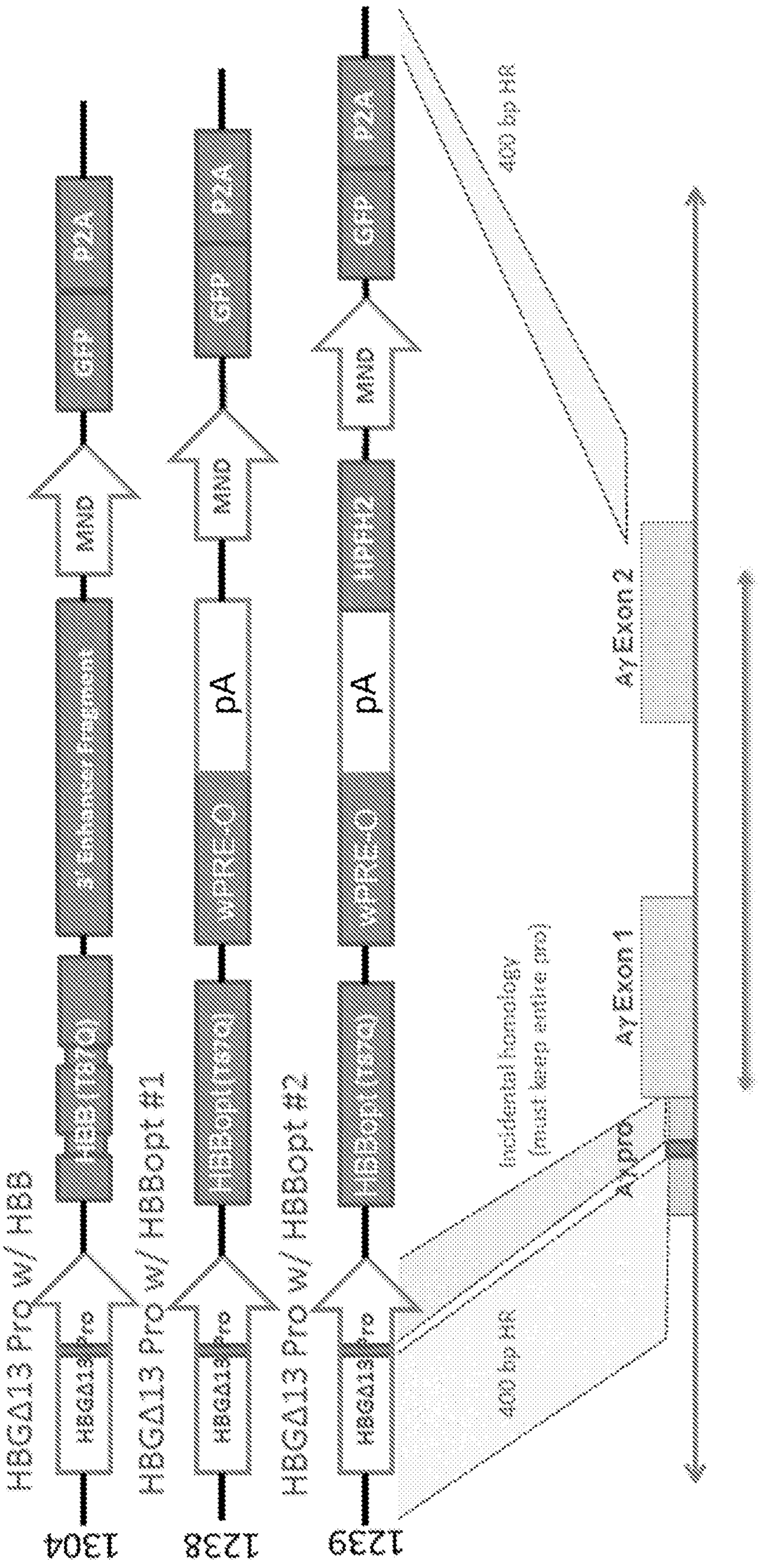
FIG. 15 provides alternative constructs using the HBGd13 Promoter driving HBB T87Q anti-sickling globin.

1B. Edited mobilized primary human CD34+ HSC cells engraft and retain deletions in the gamma hemoglobin promoter (including the 13 bp and other useful deletions) in their LT-HSC population (FIG. 7) which allows for the de-repression of fetal hemoglobin. TALEN-edited cells were engrafted into W41 NSG mice and the data supports that the edited cells robustly drive multi-lineage engraftment. The edits remain in the erythroid population up to 24 weeks and are sustained across multiple animals in three independent transplant experiments. Edits remain detectable in LT-HSC populations that engraft and re-populate the bone marrow in primary and secondary transplant recipients. These data prove that creating deletions in the gamma hemoglobin promoter that drive fetal hemoglobin (including the 13 bp deletion) may be an effective long-term therapeutic approach. FIG. 8 shows use of RNPs to efficiently target the same region in HBG1 and 2 in mobilized primary human CD34+ HSC cells.

Strategy 2: Development and Testing of Initial/Parental Constructs for HDR Based Editing of the HBG1 Locus (FIGS. 9-18).

The initial constructs tested various elements including alternative promoters, enhancers, polyA tails, introns, varying homology arm lengths, deletional versus non-deletional constructs to identify the best design to maximize globin expression. Various constructs were designed and tested to identify the best regulatory regions to promote maximal globin expression. The data supports the following:

- HBB and HBG1-d13 promoters work equally well with respect to globin expression.
- Tissue-specific enhancers like HS-40, HPFH-2 produce the maximum protein expression from the donor templates.
- wPRE-3, wPRE-O elements work well and enhance stability of the mRNA and therefore globin expression.
- Longer HR arms mediated higher rates of HDR using AAV donor templates.
- Deletional templates (e.g. ones that had deletions near the nuclease cleavage site) yielded lower HR rates than non-deletional templates.

The early designs helped identify that HBG1 locus is amenable to HDR and with a positive control AAV delivering GFP, a 30% HR rate was observed at the HBG1 locus.

The basic function of elements described in the naming conventions of the described templates are as follows:

- HPFH2 Enhancer—used in HBG1 cassettes to enhance promoter activity;
- d13HBG1 Promoter—HBG1 promoter with 13 bp HPFH deletion that promotes HBG1 expression;
- HBBpro—utilizes the endogenous HBB promoter to drive HBG1 expression;
- HS40 Enhancer—used in combination with HBBpro and HBG1pro to enhance the promoter activity;
- T2A—used in constructs to use the exons and polyA from the native gene;
- wPRE3.SV40USE.pA—"minimal" wPRE and modified SV40 polyA;
- MND—denotes MND-CMV1 short version promoter;
- T87Q—Anti-sickling hemoglobin gene;
- MGMT—Anti-sickling P140K mutant MGMT for chemoselection; and
- GFP—Green Fluorescent Protein.

Data optimizing HDR templates with GFP include control templates expressing only GFP (Constructs 1263 and 1264);

templates inducing G1 globin (Constructs 1324 and 1325); and templates driving $\beta^{T87Q}$ (Construct 1345).

Strategy 3: Homology-Directed Repair Templates that Integrate at the HBG1 Locus and Drive: (A) HBG1 Expression or (B) $\beta^{T87Q}$ Expression in Mobilized Primary Human CD34+ HSC Cells and Non-Human Primate BM CD34+ Cells (FIGS. 19-27).

rAAV-6 and rAAV-5 delivery of HDR templates have been designed and optimized for delivery of donor templates into human and Rhesus cells, respectively.

3A. Homology-directed repair templates that integrate at the HBG1 locus and drive HBG1 expression. Constructs 1324 and 1325 (FIGS. 19-20) are donor templates with optimized promoters (HBG1, HBB, PGK) and enhancers (HS-40, HPFH2), poly-A tail (SV-40) with varying homology arm lengths (400-1000 bp) and drive insertion at the HBG1 promoter region and recapitulates the 13 bp deletion that drives HBG1 native promoter-mediated induction of Gamma 1 globin. Data shown demonstrates results following co-delivery of these templates with AAV and RNP in mobilized primary human CD34+ HSC cells.

Figure 28:
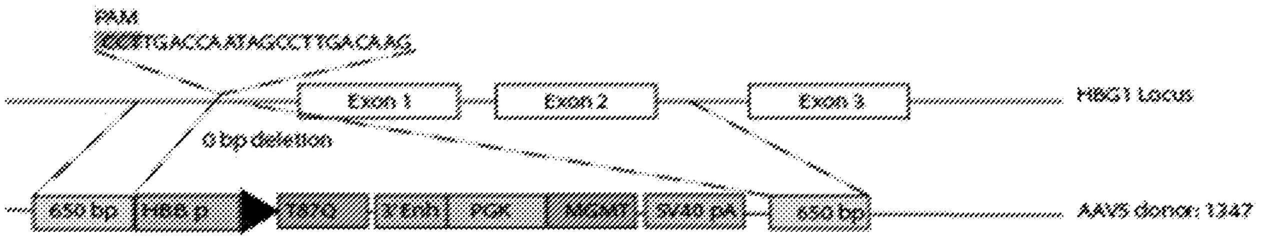
FIG. 28 demonstrates Construct 1347 is a rAAV construct that can drive homology-dependent repair into the Rhesus HBG1 locus. The donor template introduces a HBB promoter that drives T87Q globin.
Figure 29:
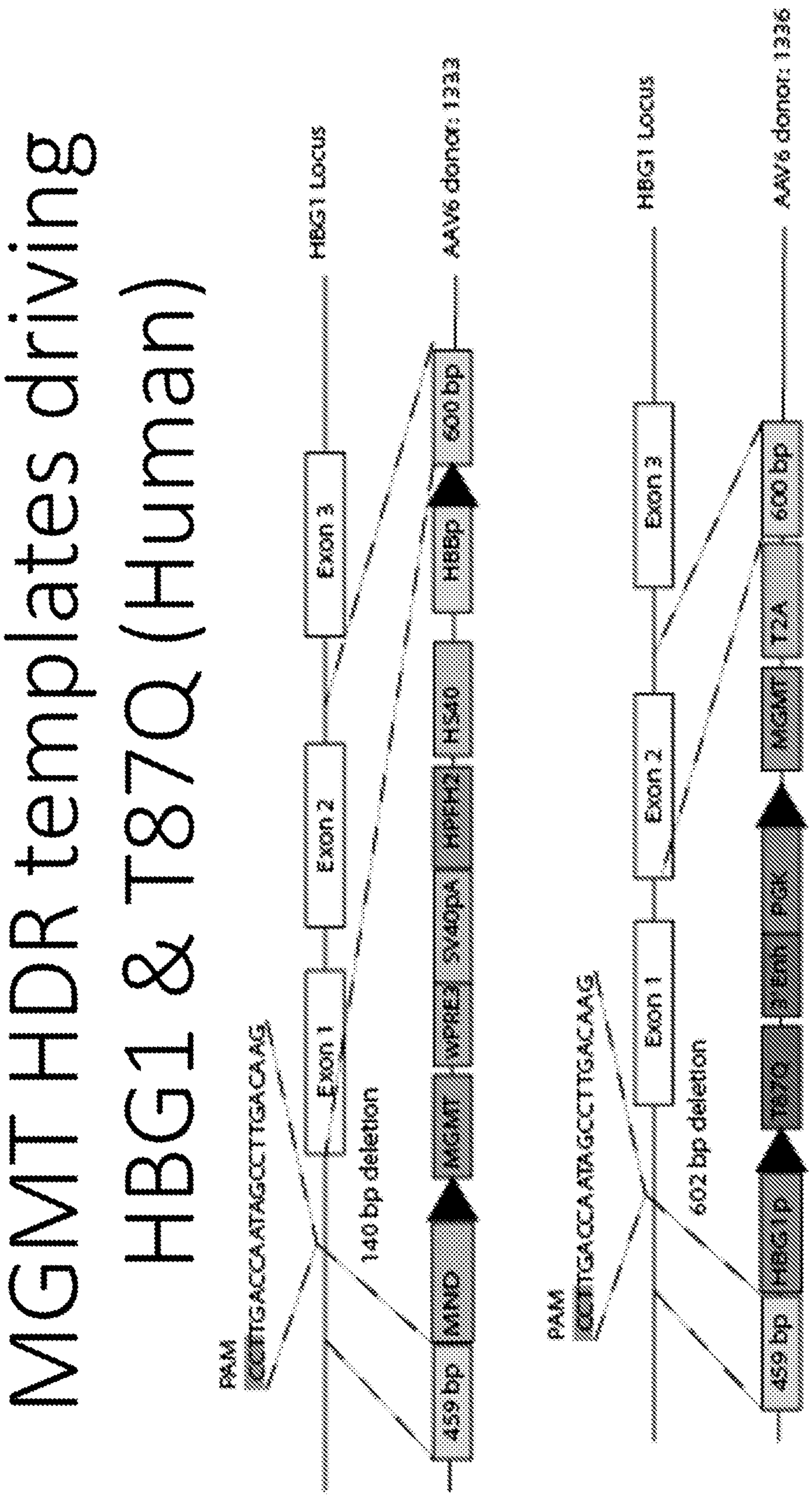
FIG. 29 demonstrates Construct 1333 is a rAAV construct that can drive homology-dependent repair into the human HBG1 locus. The donor template introduces a HBB promoter that drives Gamma globin expression and allows for chemo therapeutic selection, as it has a MND-promoter driving P140K MGMT expression. Construct 1336 is a rAAV construct that can drive homology-dependent repair into the human HBG1 locus. The donor template introduces a HBG1 d13 promoter that drives T87Q globin expression and allows for chemo therapeutic selection, as it has a PGK-promoter driving P140K MGMT expression.
Figure 31:
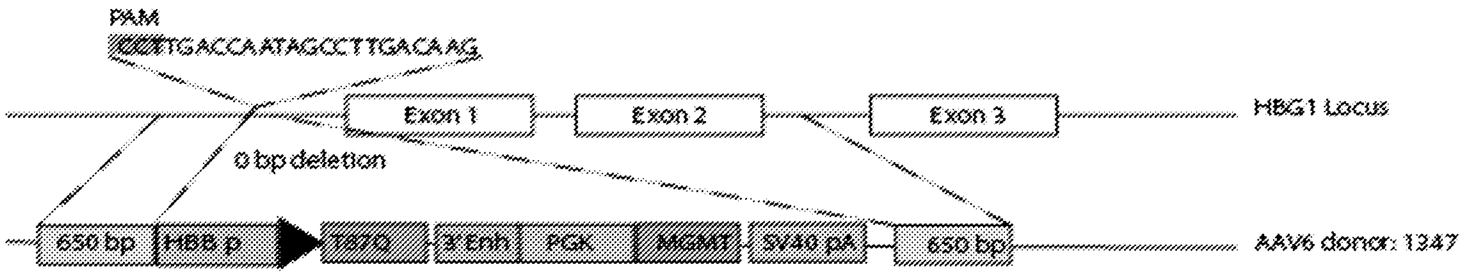
FIG. 31 demonstrates Construct 1347 is a rAAV construct that can drive homology-dependent repair into the human HBG1 locus. The donor template introduces a HBB promoter that drives T87Q globin expression and allows for chemo therapeutic selection, as it has a PGK-promoter driving P140K MGMT expression.
Figure 32:
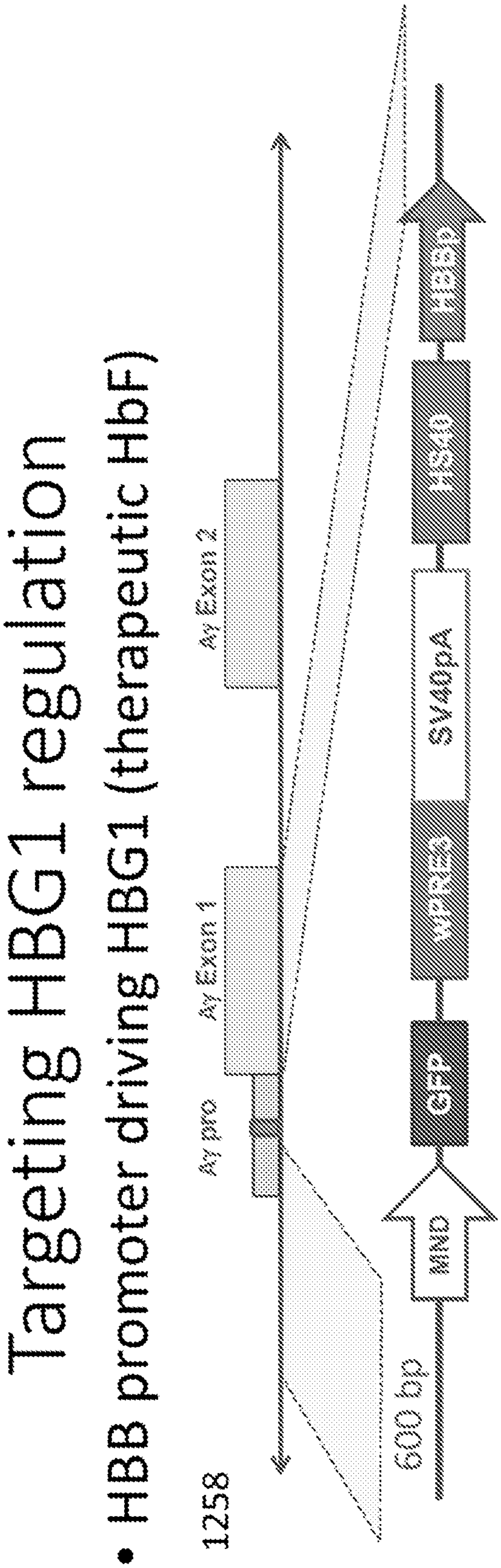
FIG. 32 provides an example of an HBB promoter driving HBG1 expression.
Figure 33:
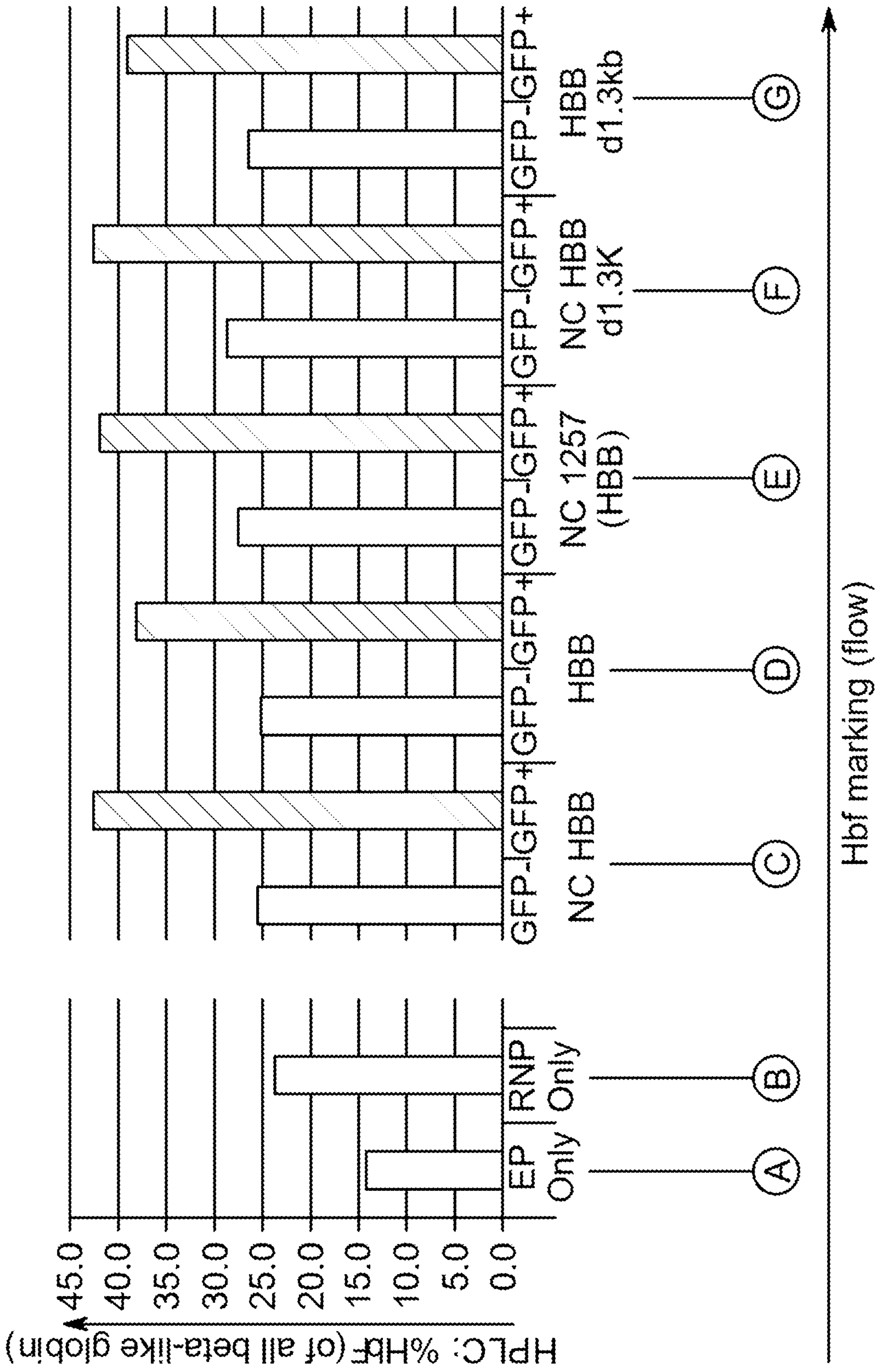
FIG. 33 demonstrates use of multiple HDR templates (numbers listed under flow plots) and TALEN co-delivery demonstrating increased HbF expression in GFP+ cells.
Figure 33:
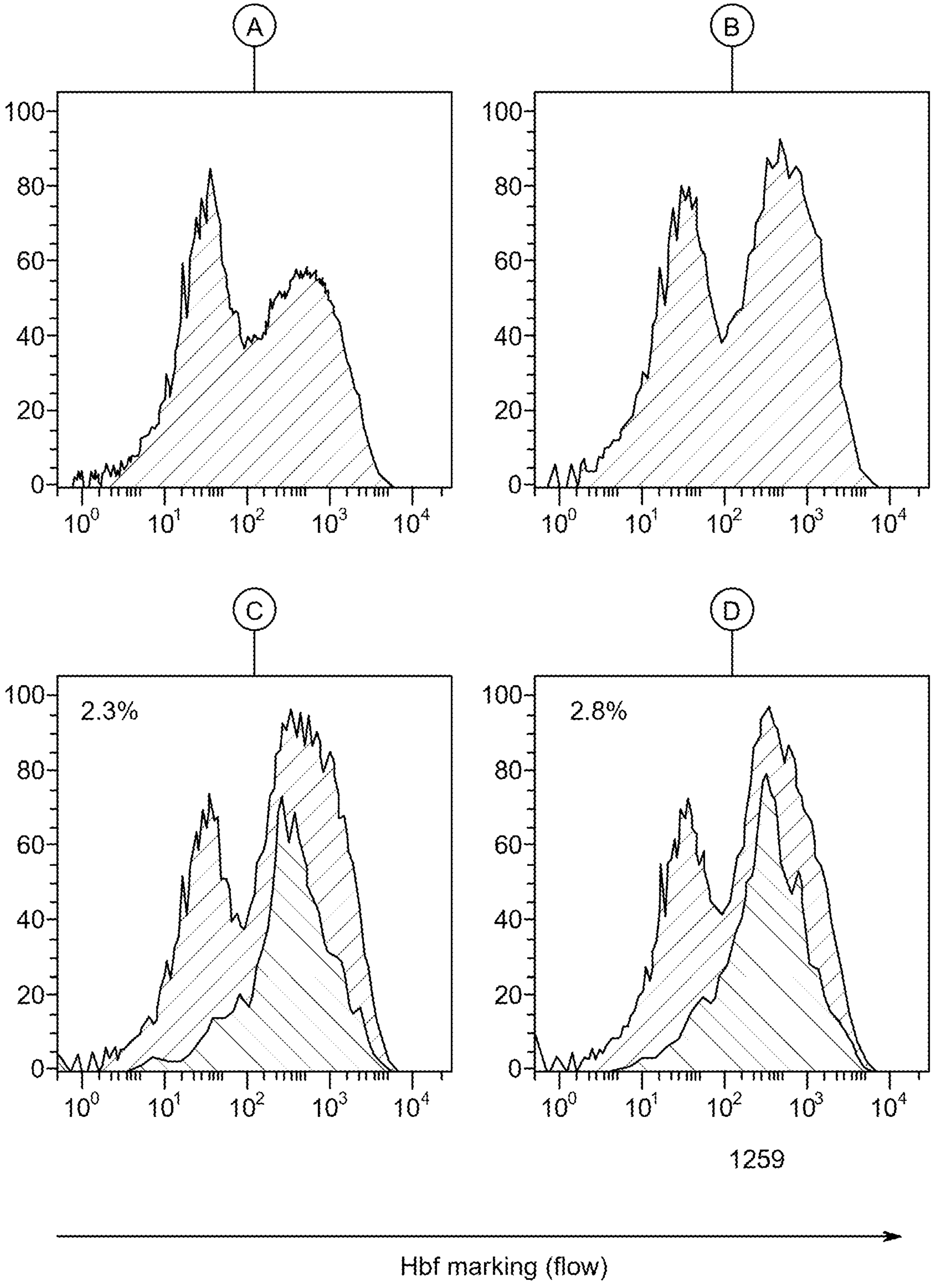
Figure 33:
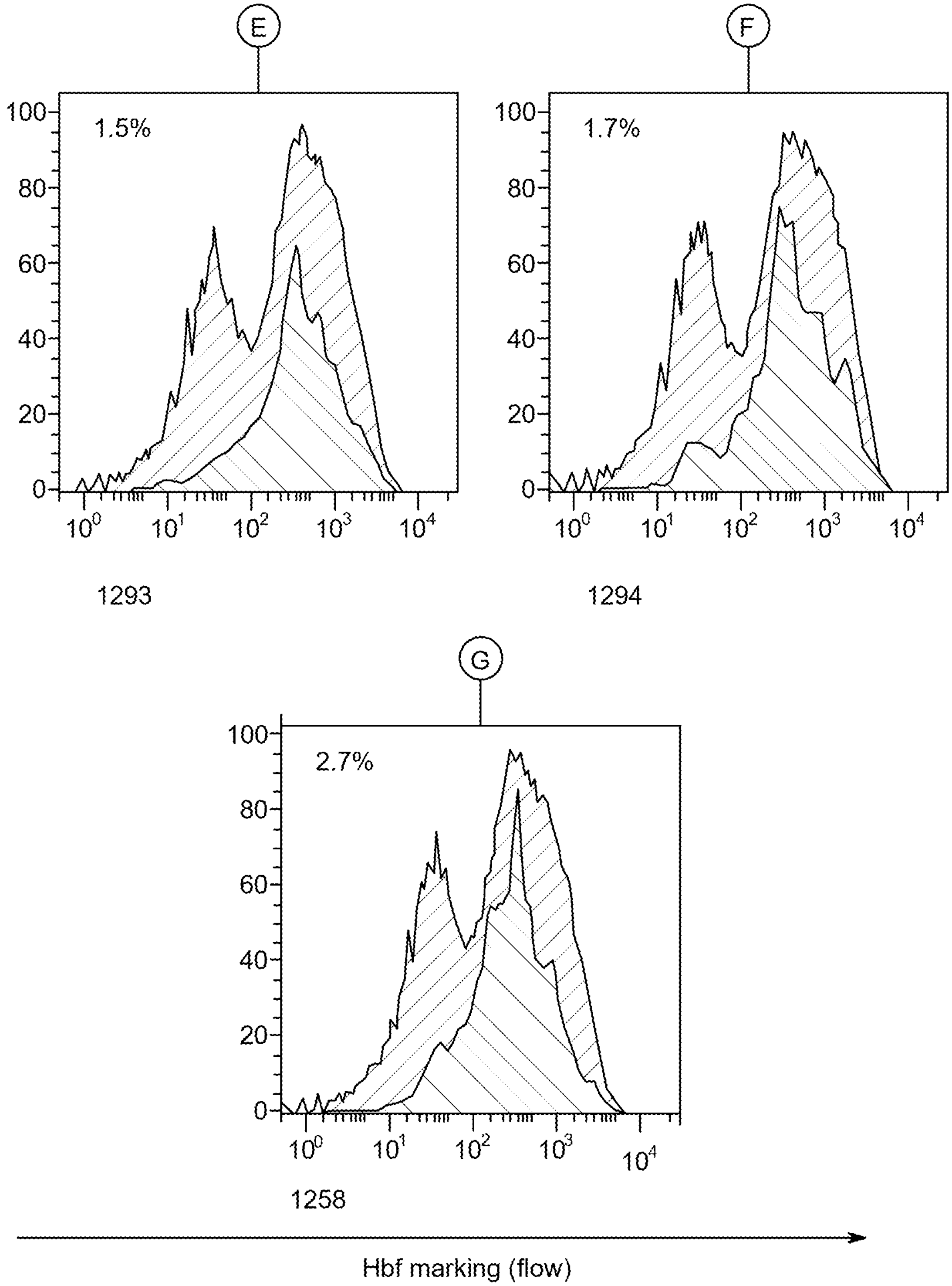
Figure 34:
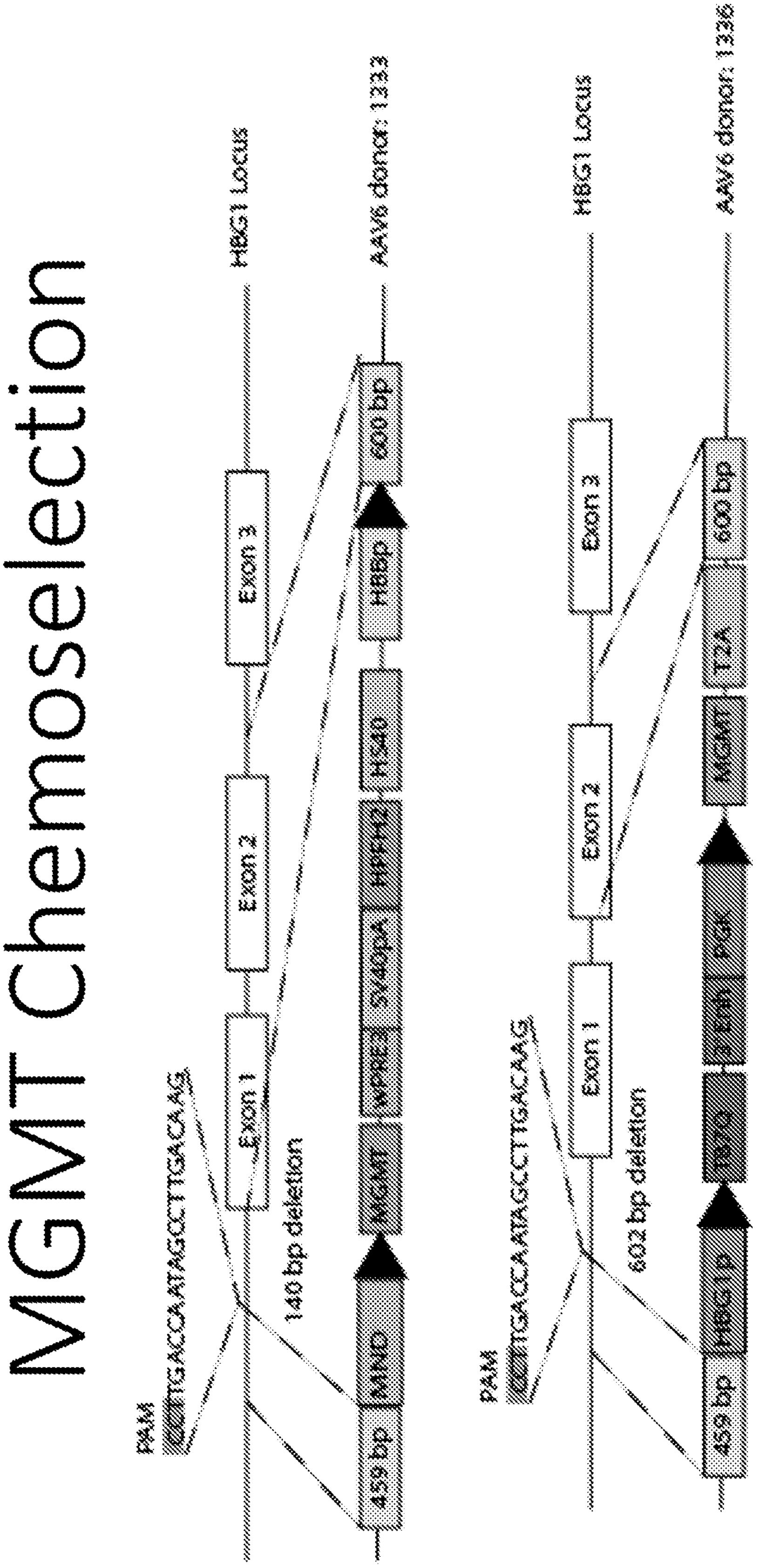
FIG. 34 demonstrates MGMT chemoselection HDR-cassettes (Constructs 1333, 1336) are designed to drive fetal hemoglobin expression as well as the ability to expand engrafted cells pre- or post-transplant via chemoselection.
Figure 35:
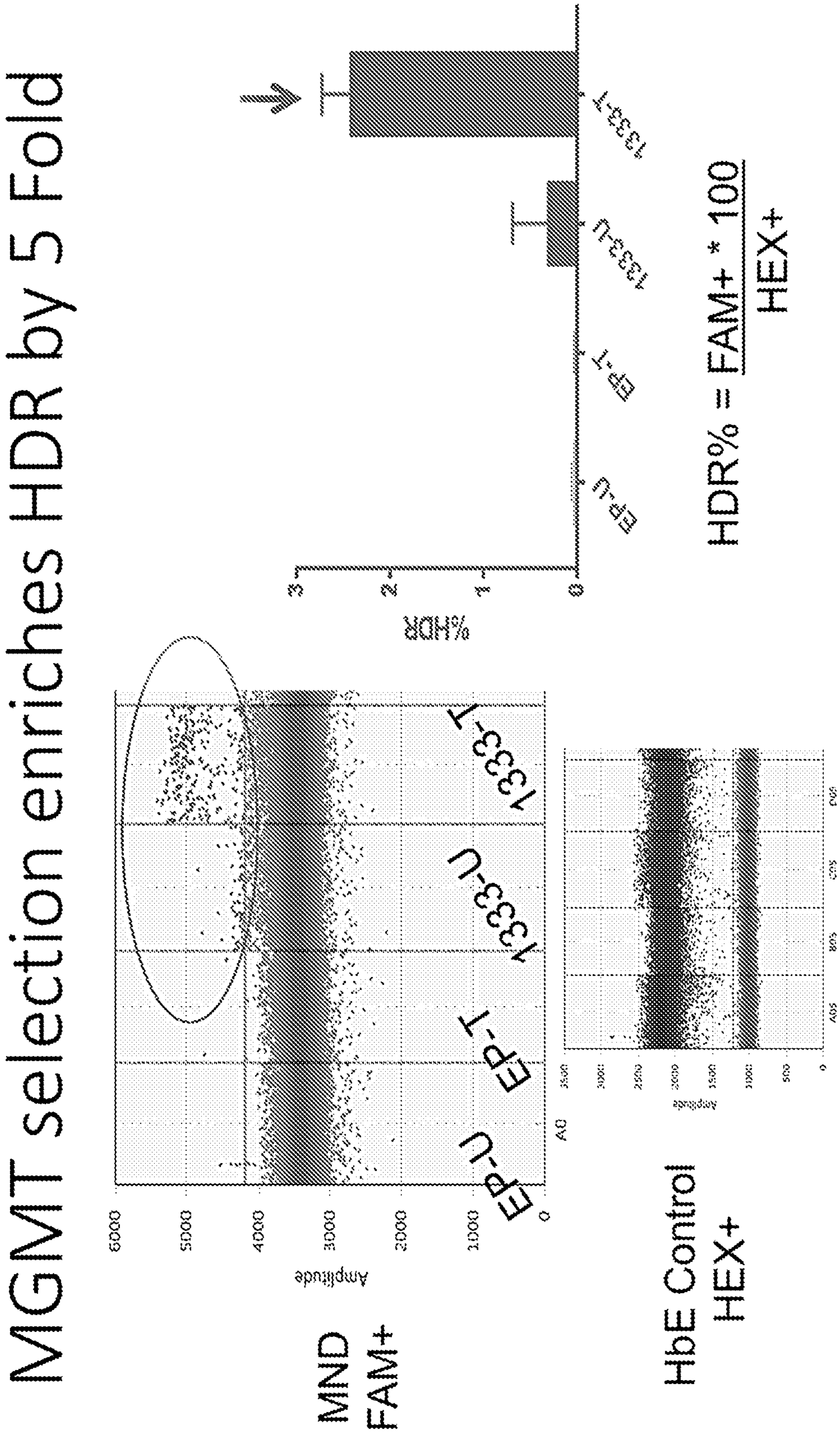
FIG. 35 demonstrates HDR editing and chemoselection using 1333 MGMT HDR donor cassette. Following HDR-editing of CD34+ HSC, chemoselection in vitro allows for 5-fold expansion of the edited population over non-edited cells. Edited cells are tracked using ddPCR based assay.
Figure 36:
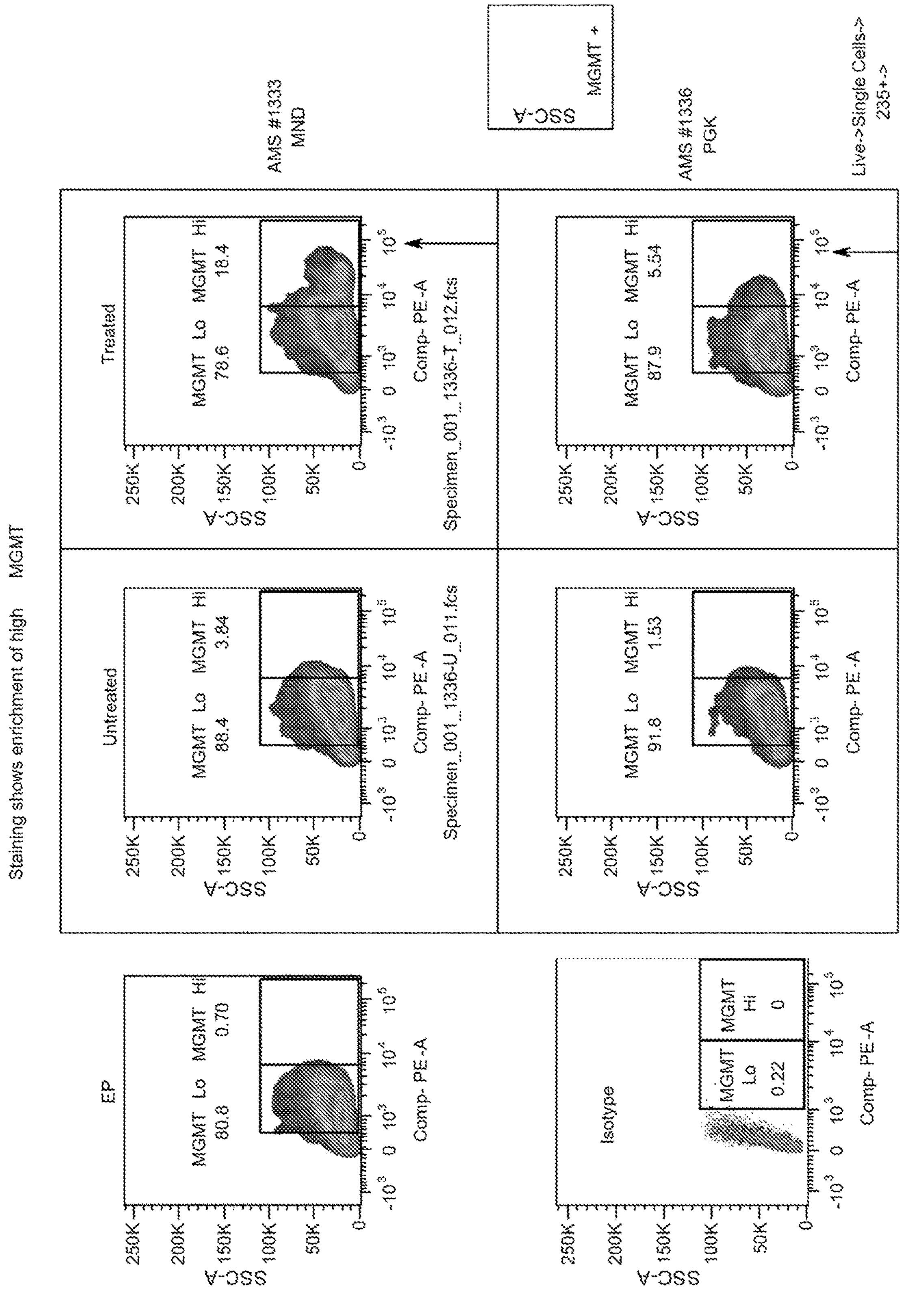
FIG. 36 demonstrates HDR editing and chemoselection using 1333 MGMT HDR donor cassette. Cells edited with an MGMT cassette are able to be chemoselected as shown here by flow cytometry expansion of MGMT Hi cells post selection.

3B. Homology-directed repair templates that integrate at the HBG1 locus and drive $\beta^{T87Q}$ expression. Constructs1345 (FIG. 27) is a donor template with optimized promoters (HBG1, HBB, PGK) and enhancers (HS-40, HPFH2), poly-A tail (SV-40) with varying homology arm lengths (400-1000 bp) that drive insertion at the HBG1 promoter region and drives HBB promoter-mediated induction of $\beta^{T87Q}$ globin (anti-sickling globin) at the HBG1 locus. (Rhesus version of this construct: 1348 is shown on FIG. 28). Data shown demonstrates results following co-delivery of these templates as AAV and RNP in mobilized primary human CD34+ HSC cells.

Strategy 4: Homology-Directed Repair Templates that Integrate at the HBG1 Locus and Drive HBG1 Expression or $\beta^{T87Q}$ Expression and have a P140K MGMT Cassette that Allows for Chemo-Therapeutic Selection of Edited Human or Non-Human Primate CD34+ Cells (FIGS. 28-31; 34-36).

4A. Homology-directed repair templates that integrate at the HBG1 locus and drive HBG1 expression and allows for chemo-selection. Construct 1333 is a donor template with optimized promoters (HBG1, HBB, PGK) and enhancers (HS-40, HPFH2), poly-A tail (SV-40) with varying homology arm lengths (400-1000 bp) and drive insertion at the HBG1 promoter region and induces HBG1 native promoter-mediated induction of G1 globin and has the P140K MGMT cassette that allows for enrichment of edited cells ex vivo before transplant or in vivo in the patient following infusion of edited cells.

4B. Homology-directed repair templates that integrate at the HBG1 locus and drive $\beta^{T87Q}$ expression. Constructs 1336, 1346, 1343, 1344: These are donor templates with optimized promoters (HBG1, HBB, PGK) and enhancers (HS-40, HPFH2), poly-A tail (SV-40) with varying homology arm lengths (400-1000 bp) that drive insertion at the HBG1 promoter region and drives HBB promoter-mediated induction of T87Q globin (anti-sickling globin) at the HBG1 locus. All constructs also have a P140K MGMT cassette that allows for enrichment of edited cells ex vivo before transplant or in vivo following infusion of edited cells. (Rhesus version: Construct 1348).

Conclusions

1. The data proves the idea that creating deletions using TALEN or RNP nuclease delivery in the promoter of gamma hemoglobin including re-creating the 13 bp deletion at the HBG1 and/or HBG2 loci drive fetal hemoglobin expression.
2. TALEN's as well as Crispr/Cas9 nucleases can create deletions in the promoter including re-creating the 13 bp deletion as well as a range of other useful deletions.
3. Edited mobilized human CD34+ HSC engraft and retain their multi-lineage engraftment potential in primary and secondary recipient mice.
4. Edits are sustained in the LT-HSC population and are able to re-populate the bone marrow in the scenario of a primary and secondary transplant and to continue to facilitate fetal hemoglobin production.
5. The HBG1 locus is amenable to HDR. Construct 1263 drives HDR rates of ~30% as assessed by GFP+ cells following co-delivery of TALEN and 1263 and confirms that the locus supports HDR.
6. Constructs 1324, 1325, and 1345 drive HDR following co-delivery of RNP+AAV donors. Construct 1345 produces 3.5% HDR in RNP+1345 treated cells.
7. AAV HDR-donor cassettes promote gamma globin or T87Q globin expression following HDR depending on the respective cassette.
8. MGMT donor templates are effective in permitting selection for HDR-edited cells. There is 5-fold enrichment of HDR edited cells when chemo-selection is used in vitro in CD34+ cells containing the MGMT cassettes.

The data confirms that the d13 deletion and related useful deletions can be used effectively as a therapeutic approach for treating sickle cell anemia and thalassemia. Most importantly, its shown that HDR cassettes can be delivered to HBG1 locus following nuclease cleavage at this site. The approach is useful and novel as both NHEJ and HDR outcomes will drive a functional response that is desirable. This combined strategy is unique as all edited cells (including HDR and NHEJ edited outcomes) have a therapeutic benefit and these combined events are more likely to provide a curative approach in sickle or β-thalassemia patients.

Example 3

Talen Mediated Therapeutic Gene Editing Strategy for β-Hemoglobinopathies

Hemoglobinopathies including sickle cell disease (SCD) and β-thalassemia are the most common single-gene disorders in the world and represent a major global public health concern. The unifying principle of this heterogeneous mix of gene mutations is the decreased production of wild type hemoglobin molecules either due to structural defects in the case of SCD or insufficient production of β-globin subunits.

Patients who carry both a mutation causing a hemoglobinopathy as well as increased expression of fetal hemoglobin (HPFH) tend to exhibit a milder phenotype. These mutations range from large deletions to single nucleotide polymorphisms. The focus of this Example is on a unique naturally occurring 13 bp deletion in the γ-hemoglobin promoter that has been shown to induce high levels of fetal hemoglobin expression.

The 13 bp deletion site offers a unique target for therapeutic gene editing in the treatment of hemoglobinopathies. The sequence specific introduction of double strand breaks using targeted nucleases, such as TALENs or RNPs, has the potential to generate a HPFH phenotype by NHEJ (via disruption of the distal CCAAT box) but also allows for the integration of therapeutic repair templates and selection elements via HDR.

Methods:

TALEN Design & Testing—Multiple TALEN pairs were designed, Golden Gate assembled into a novel expression vector with an encoded poly-A tail, mRNA was generated by CellScript IVT. mRNA was transfected into human mobilized peripheral blood CD34 cells using the Neon Transfection System.

Editing Efficiency—INDEL generation detected by T7 Assay following globin specific nested PCR. Colony sequencing and next generation sequencing were carried out to determine specific sequence variants. A globin specific ddPCR assay was developed to detect INDEL generation.

Erythroid Differentiation—Following TALEN editing, CD34 cells are moved to erythroid differentiation media and cultured for 7-10 days. HbF expression is assessed by flow and HPLC.

Murine Transplants—1e6 CD34 cells (Control & TALEN transfected) were injected by tail vein into W41 mice following minimal radiation (150 rad) 18 hours post electroporation. Marrow was harvested and sort/analyzed 24 weeks post transplant. Secondary animals were transplanted with 50% of the primary harvested cells and were subsequently harvested at 9 weeks.

HR Template Testing—HR Templates were designed and synthesized, packaged into AAV6 constructs and introduced to the CD34 cells at the time of TALEN transfection. Cells were differentiated and analyzed by flow and HPLC.

Results (In Vitro)

An experimental timeline (shown below) provided for neon transfection of human mobilized peripheral blood CD34 cells.

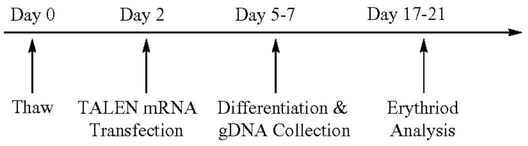

Figure 16:
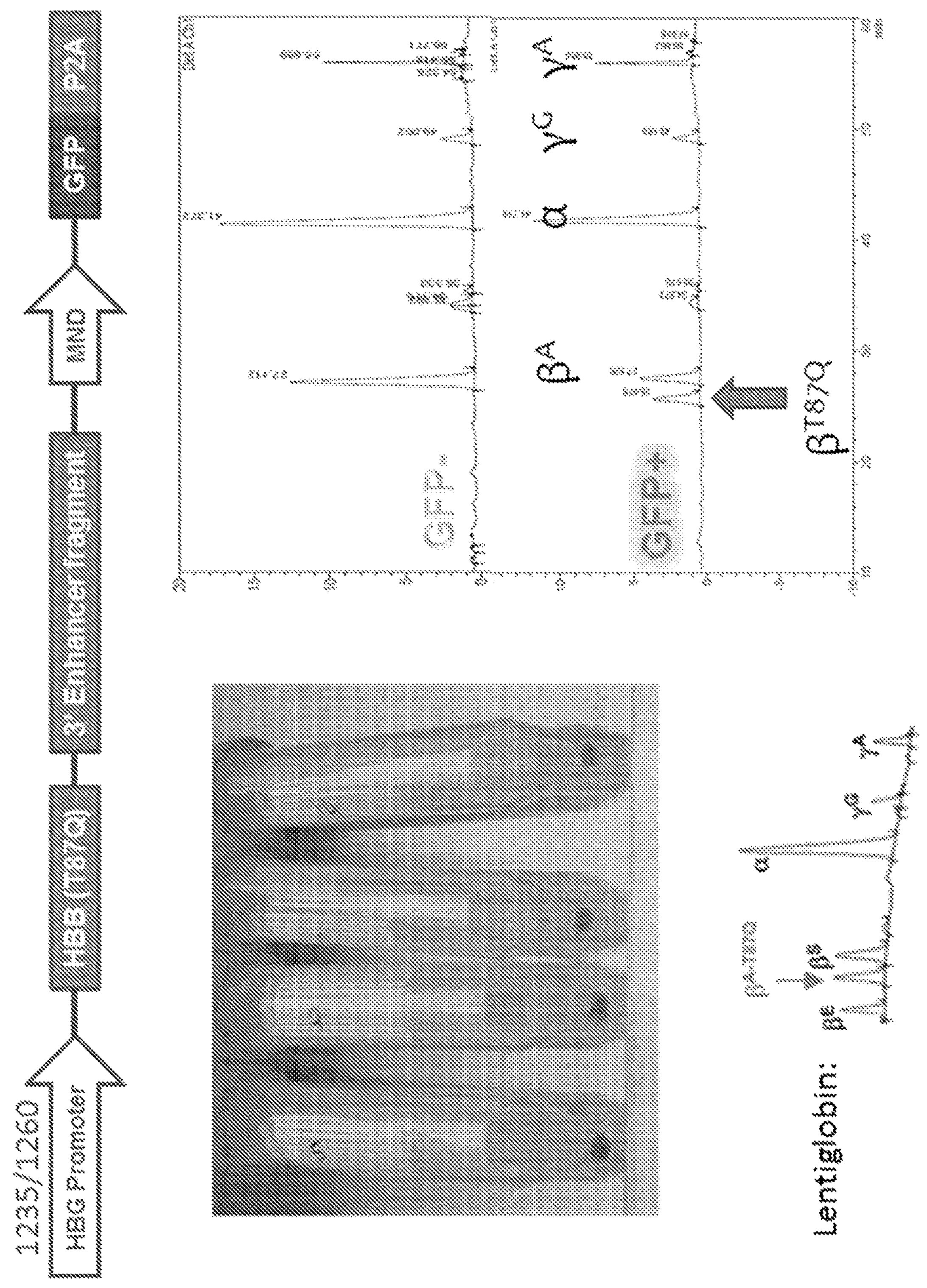
FIG. 16 demonstrates GFP Positive cells generated using construct 1235/60 also express T87Q as well as increased levels of HBF.
Figure 17:
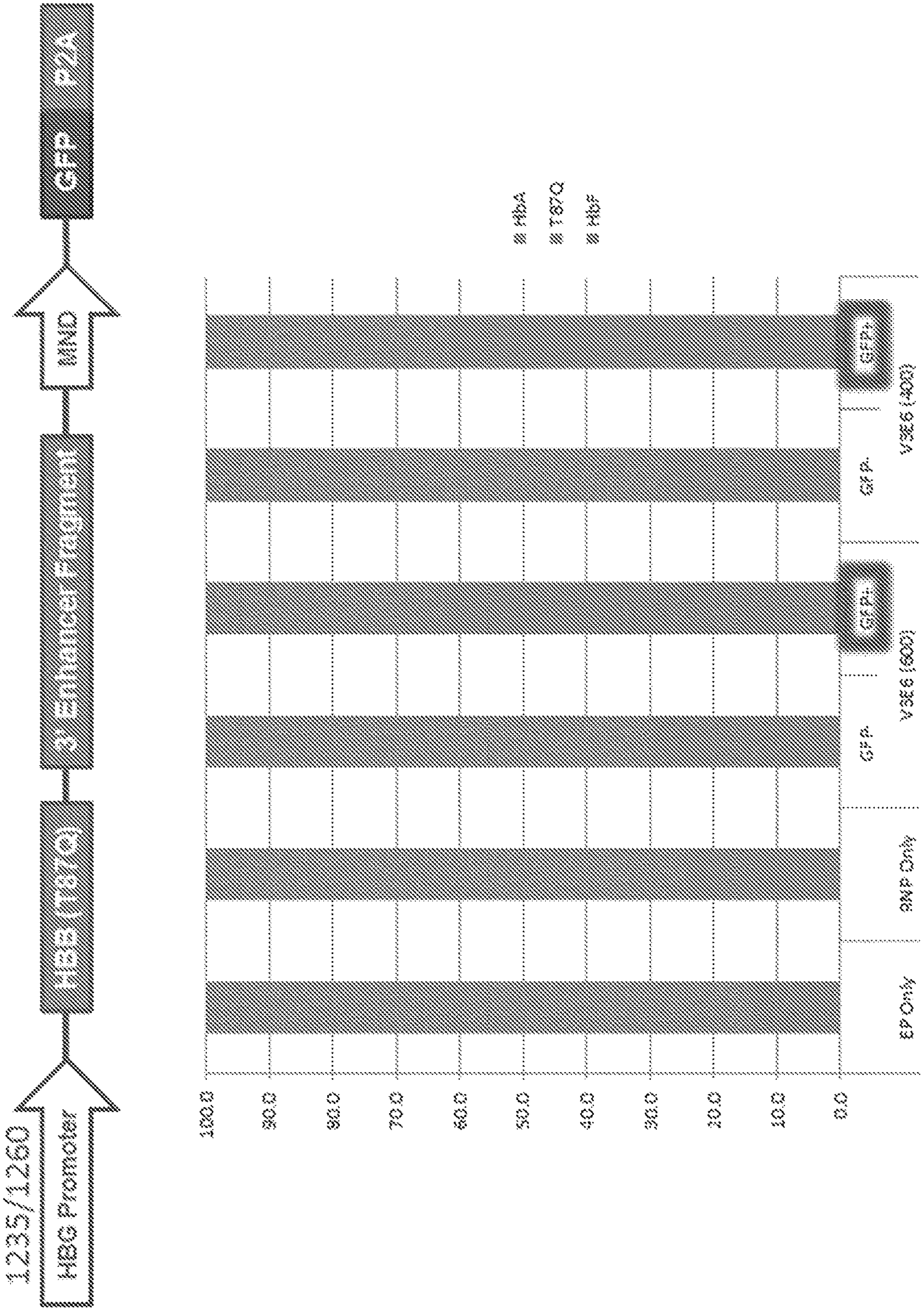
FIG. 17 demonstrates GFP Positive cells express both T87Q as well as increased levels of HBF FIG. 18 demonstrates the HDR templates V3E6 (with either 600 or 400 bp homology arms) are capable of expressing T87Q following HDR-editing. Fetal hemoglobin also increases in these cells likely due to NHEJ events in other alleles.
Figure 18:
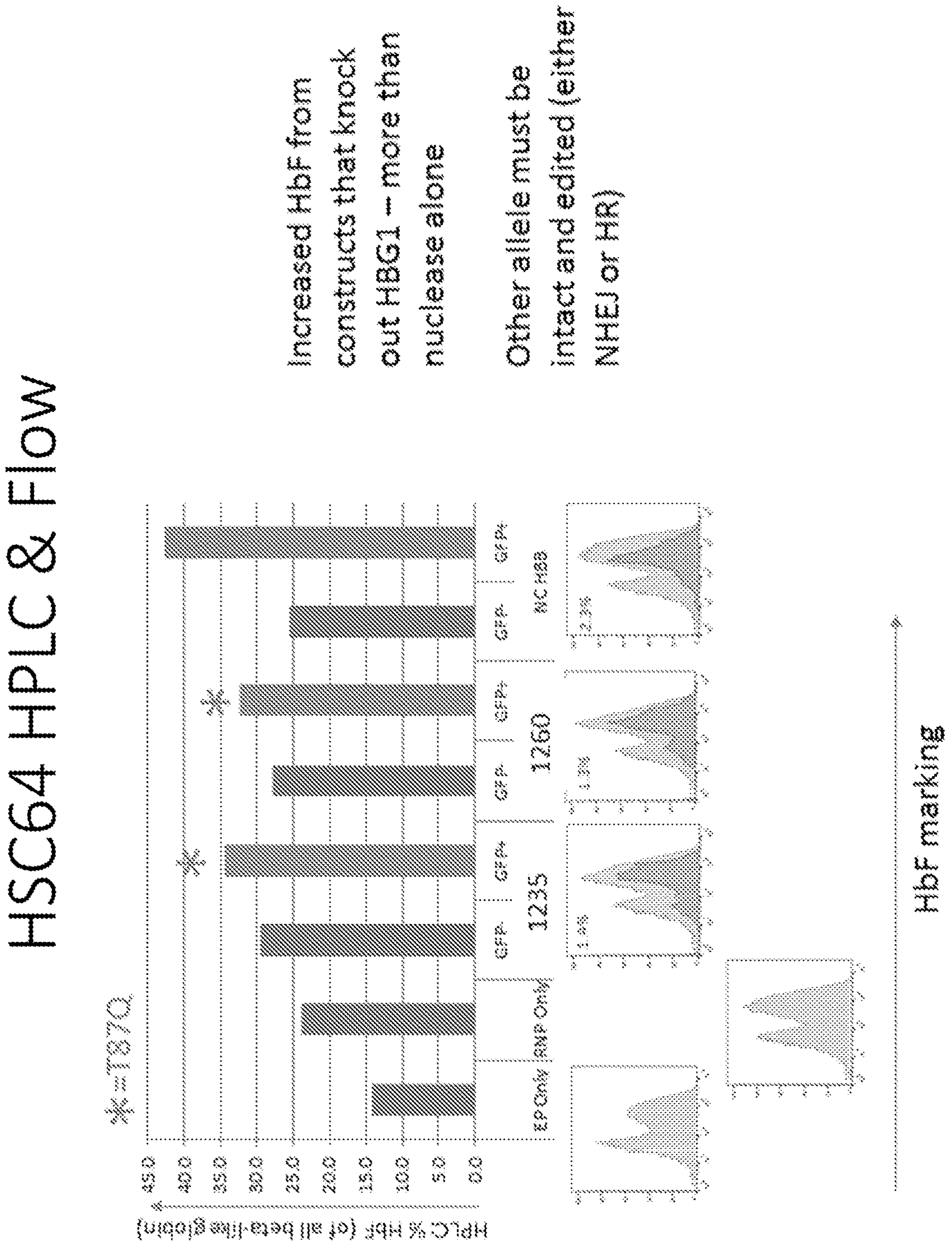
Figure 19:
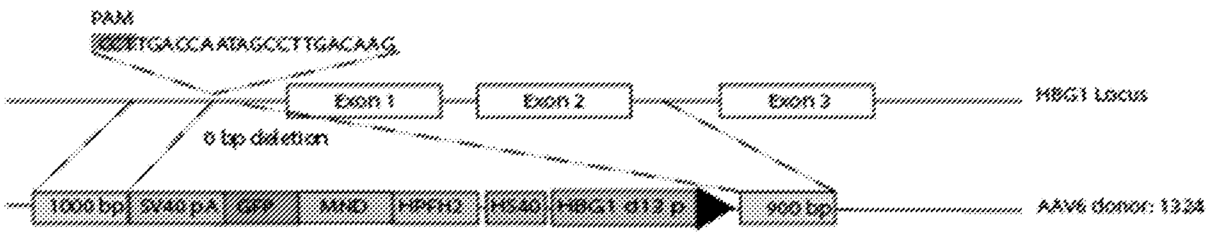
FIG. 19 demonstrates Construct 1324 is a rAAV construct that can drive homology-dependent repair into the HBG1 locus. The donor template introduces a d13 promoter that drives gamma-1 globin. MND-GFP is in the reverse orientation. It has an alternate HDR site due to incidental homology.
Figure 20:
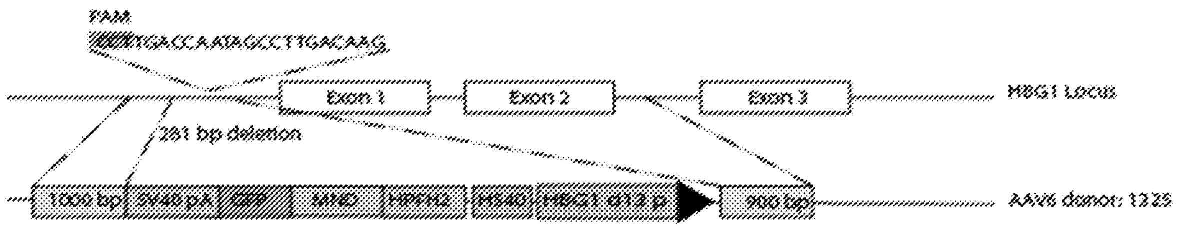
FIG. 20 demonstrates Construct 1325 is a rAAV construct that can drive homology-dependent repair into the HBG1 locus. The donor template introduces a d13 promoter that drives gamma-1 globin. This is a deletional construct that has a 240 bp deletion that may lower HDR rates. MND-GFP is in the reverse orientation.
Figure 21:
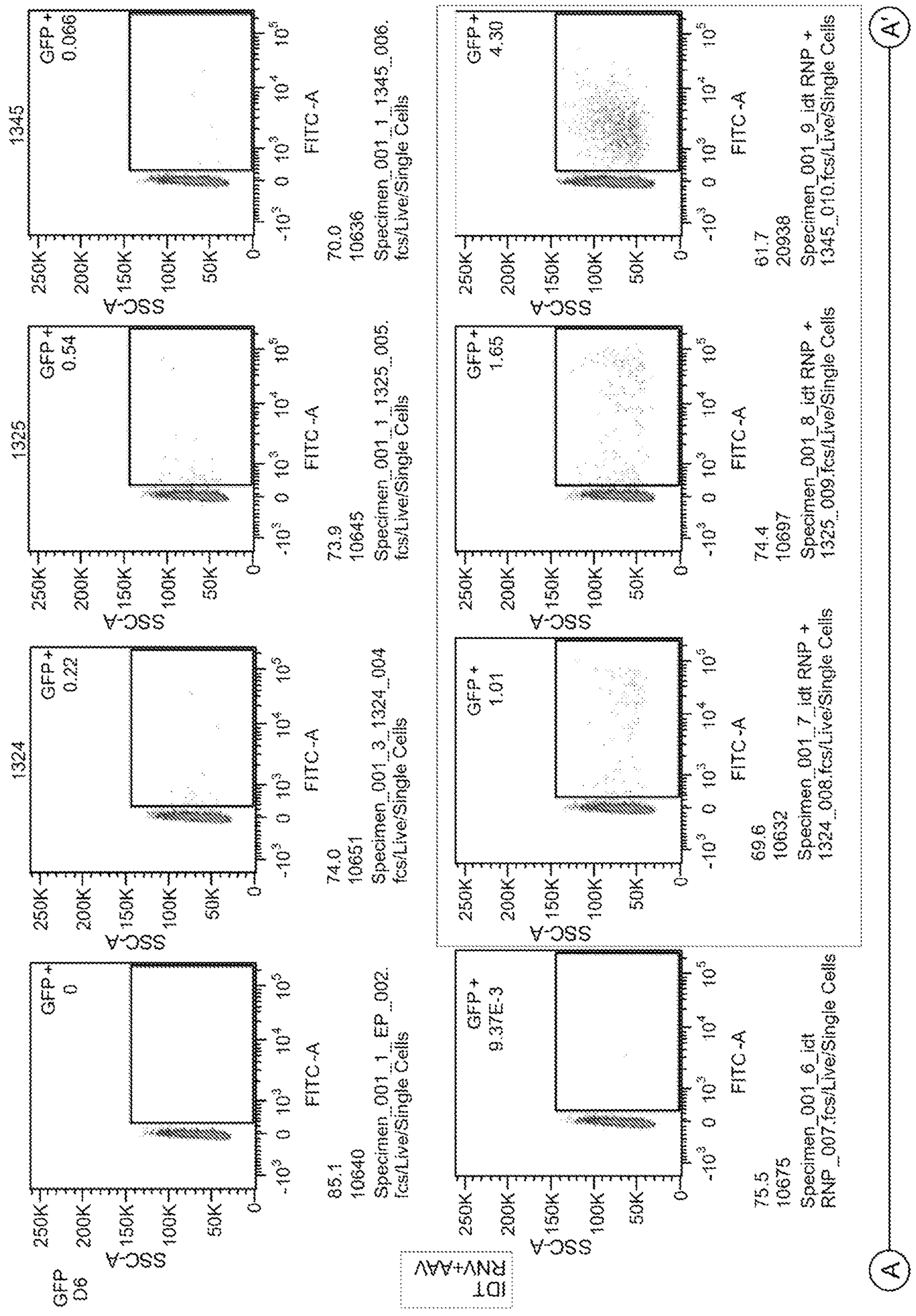
FIG. 21 shows that HDR occurs at HBG1 locus following with co-delivery of RNP and indicated AAV donor. The GFP+ population seen in the boxes are from day 6 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples. Construct 1345 is shown on FIG. 27.
Figure 21:
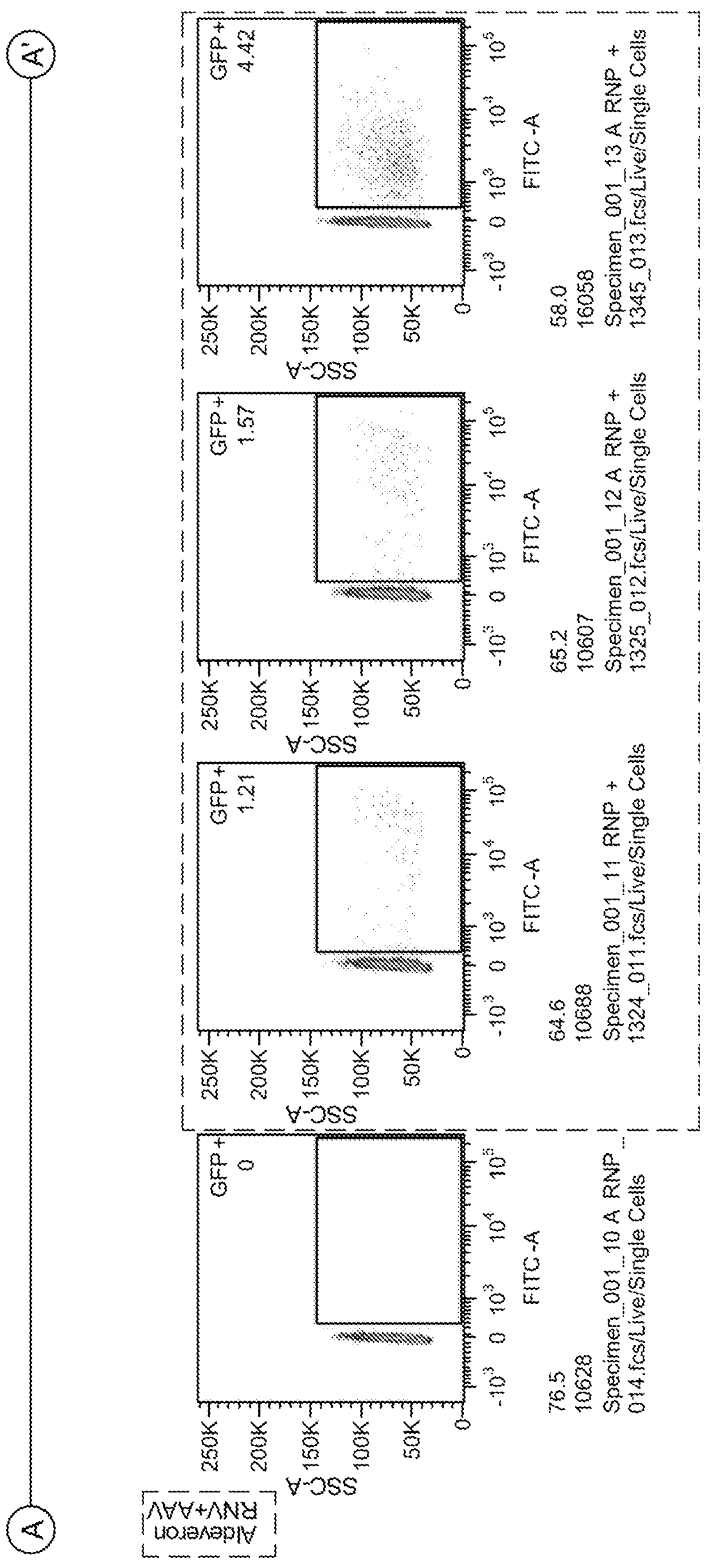
Figure 22:
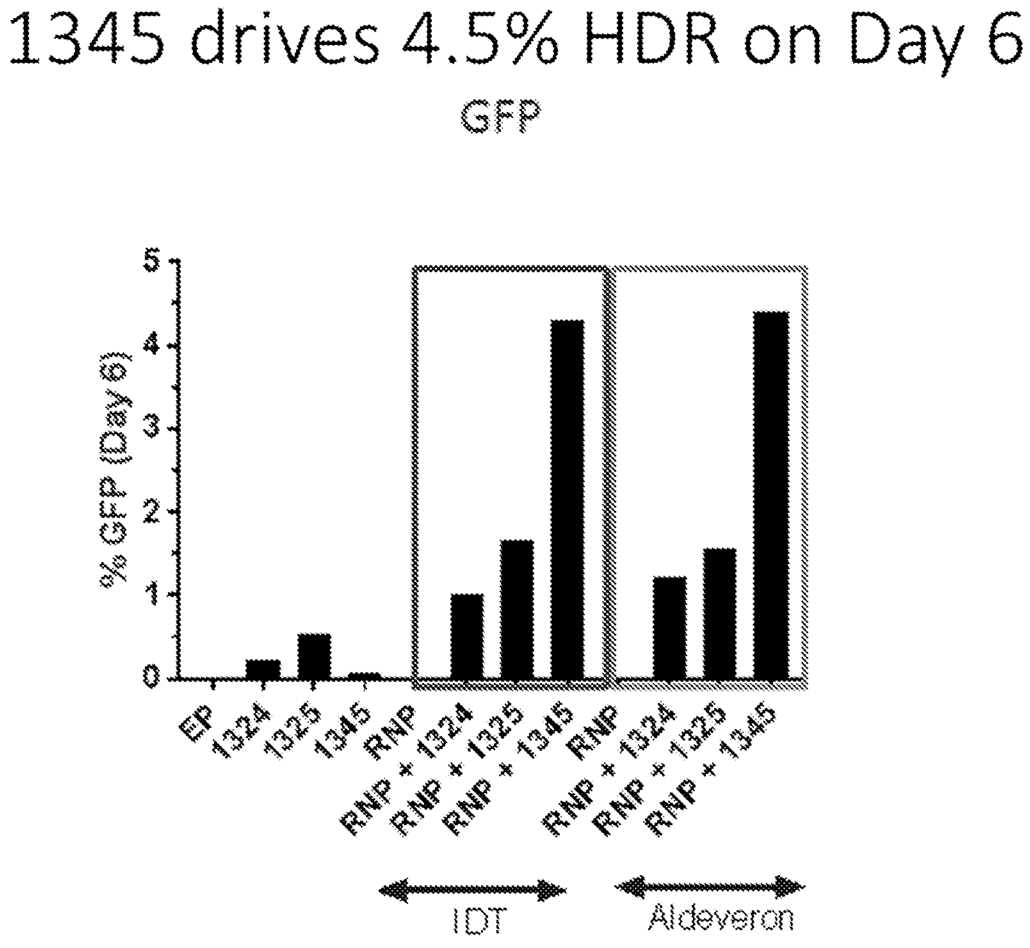
FIG. 22 shows that HDR occurs at HBG1 locus following with co-delivery of RNP and indicated AAV donor. The GFP+ population are from day 6 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples.
Figure 23:
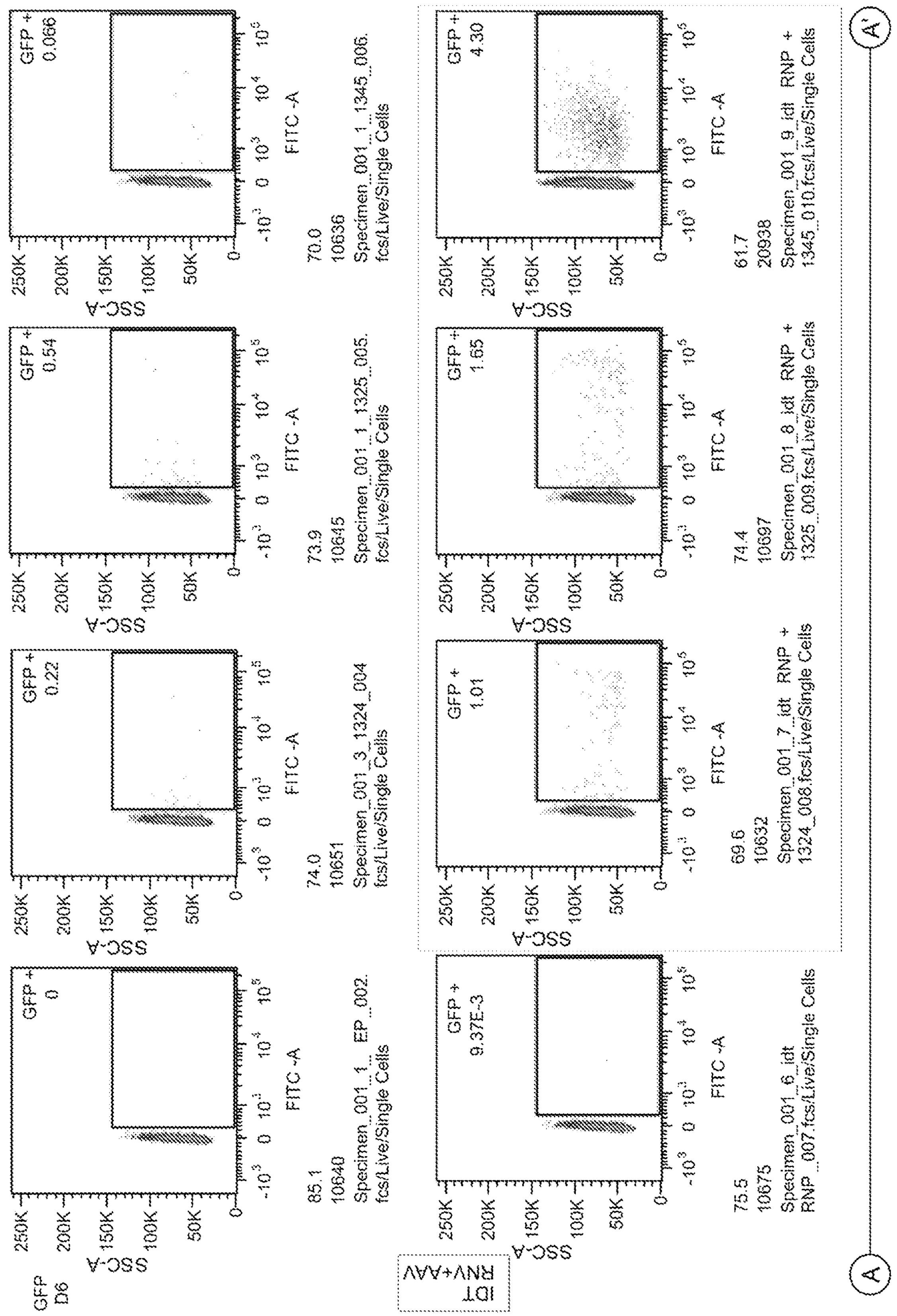
FIG. 23 shows that HDR occurs at HBG1 locus following with co-delivery of RNP and indicated AAV donor. The GFP+ population seen in the boxes are from day 13 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples.
Figure 23:
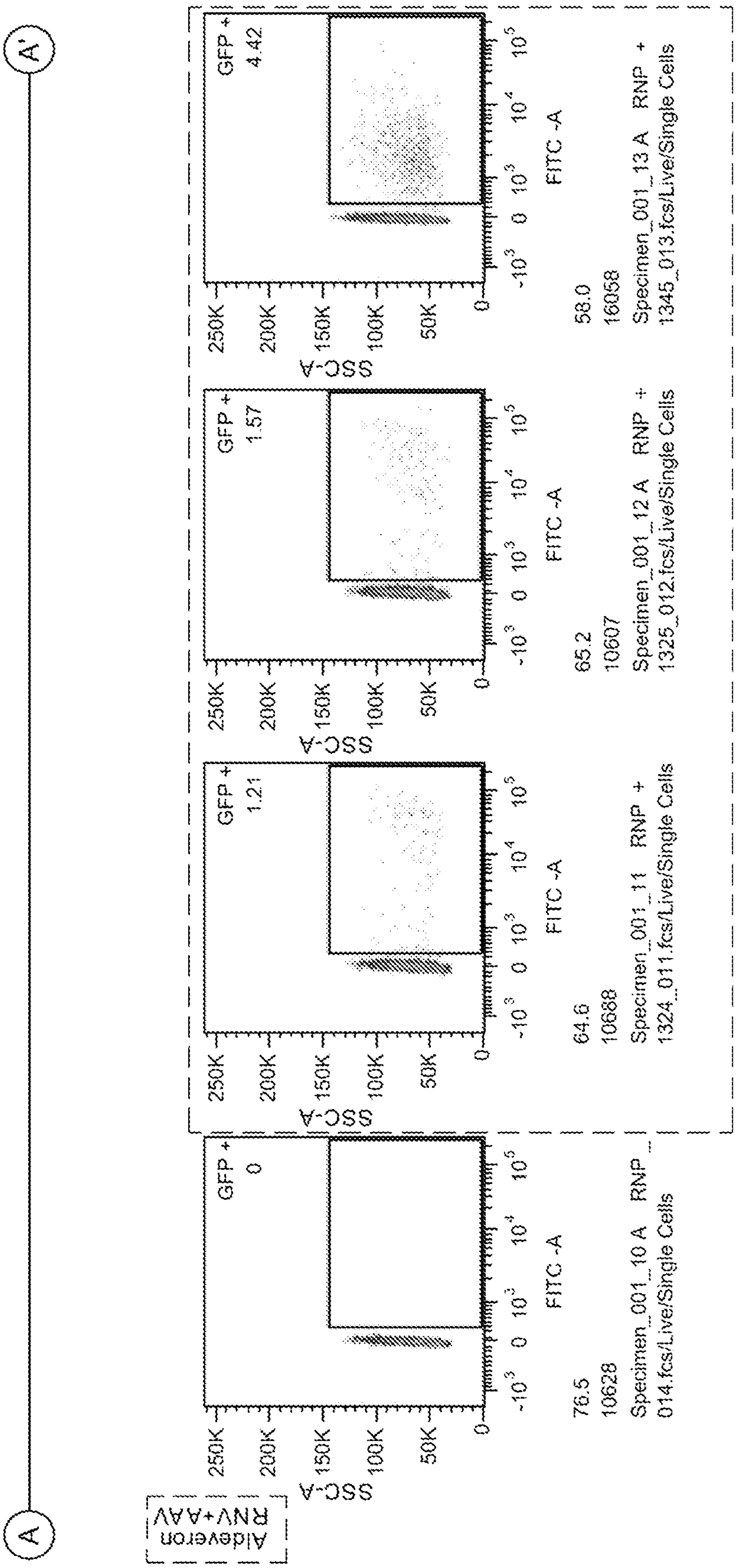
Figure 24:
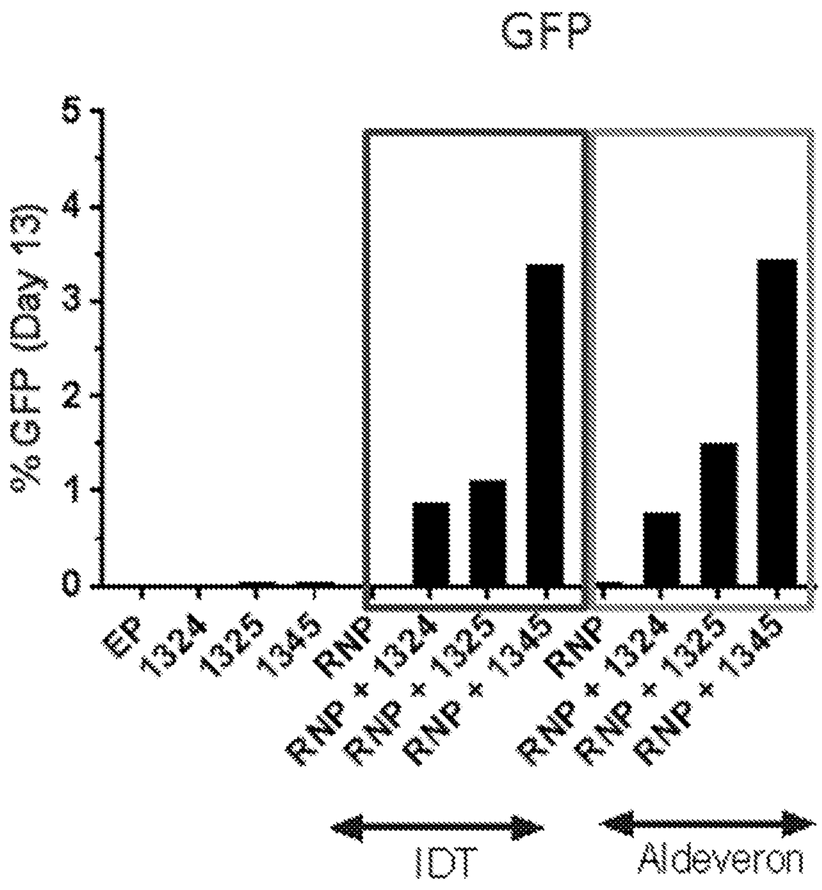
FIG. 24 shows that HDR occurs at HBG1 locus following with co-delivery of RNP and indicated AAV donor. The GFP+ population are from day 13 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples.
Figure 25:
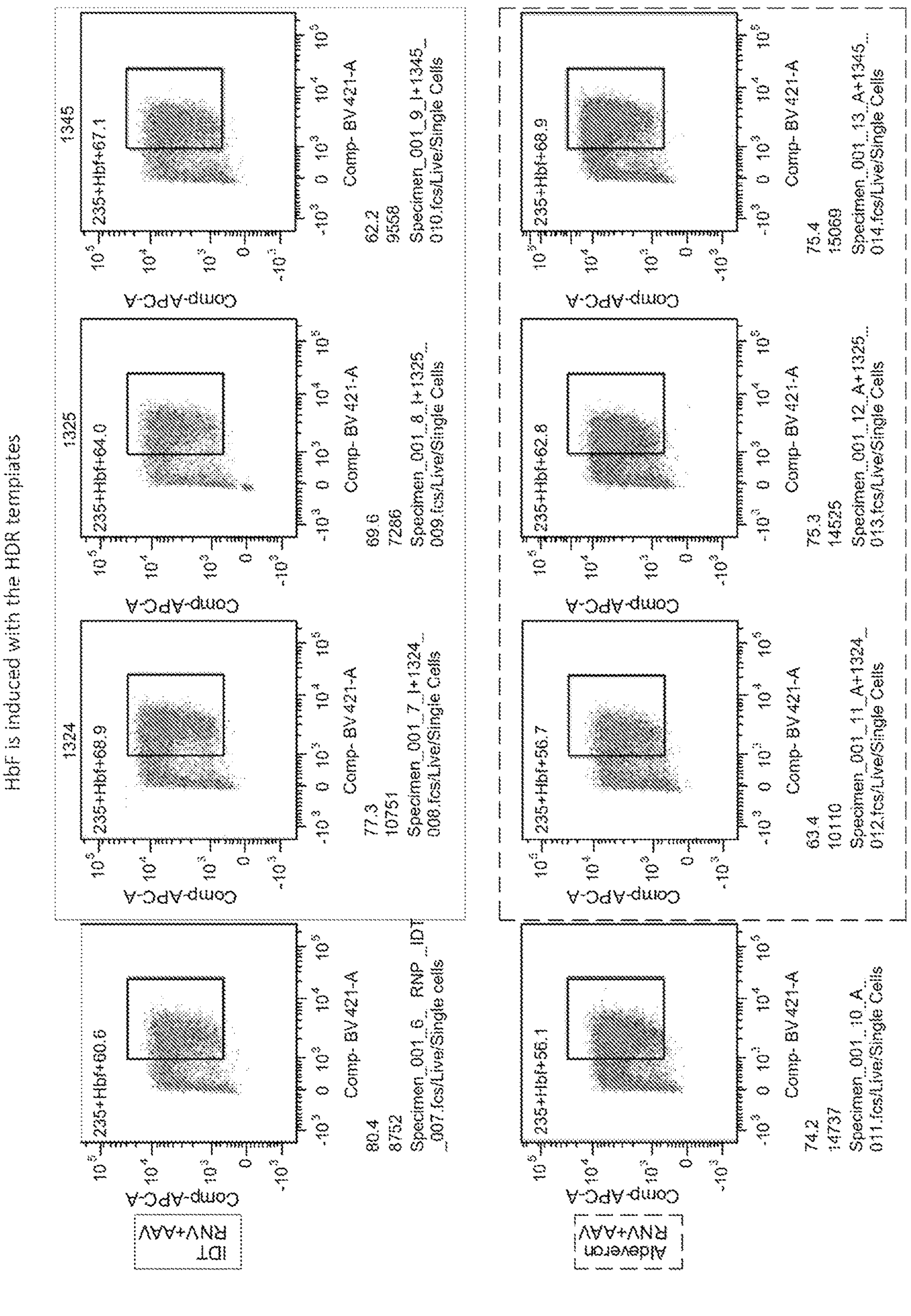
FIG. 25 shows that HDR drives increase in fetal hemoglobin induction in erythroid cells. All 3 AAV donors support HDR-based editing and lead to increased fetal hemoglobin induction following integration into the HBG1 locus in RNP+1324, RNP+1325, RNP+1345 samples. Irrespective of the Cas9 vendor used there is increased fetal hemoglobin induction with integration of AAV into the HBG1 locus in RNP+1324, RNP+1325, RNP+1345 samples.
Figure 26:
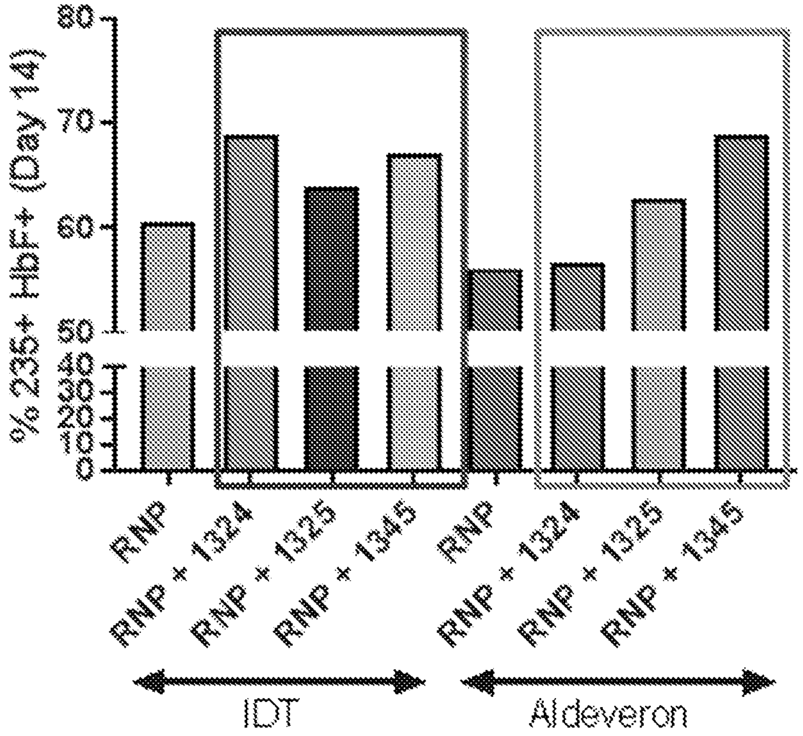
FIG. 26 shows that HDR drives increase in fetal hemoglobin induction in erythroid cells. All 3 AAV donors support HDR-based editing and lead to increased fetal hemoglobin induction following integration into the HBG1 locus in RNP+1324, RNP+1325, RNP+1345 samples. Irrespective of the Cas9 vendor used there is increased fetal hemoglobin induction with integration of AAV into the HBG1 locus in RNP+1324, RNP+1325, RNP+1345 samples.
Figure 27:
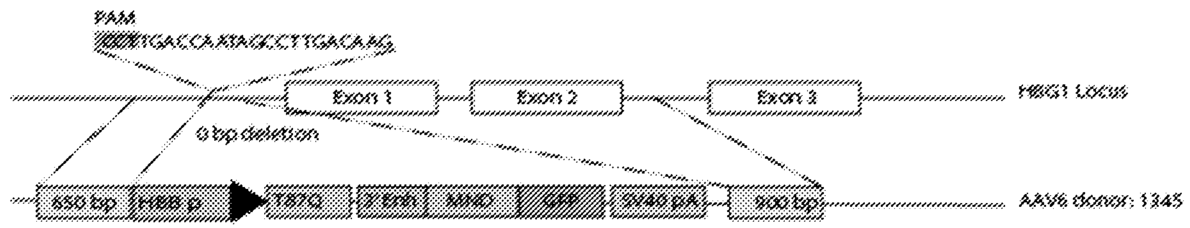
FIG. 27 demonstrates Construct 1345 is a rAAV construct that can drive homology-dependent repair into the HBG1 locus. The donor template introduces a HBB promoter that drives T87Q globin.
Figure 38:
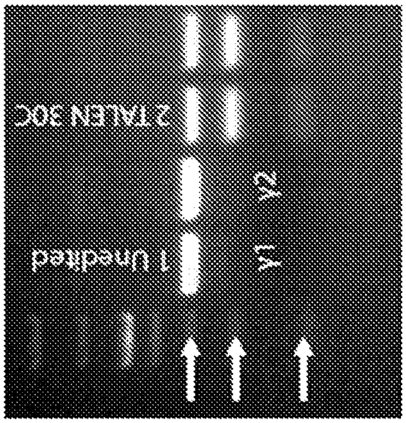
FIG. 38 provides a T7 analysis showing del13 TALEN pair transfection induces INDELs in human CD34 cells at both the γ1 (HBG1) and γ2 (HBG2) locus.
Figure 37:
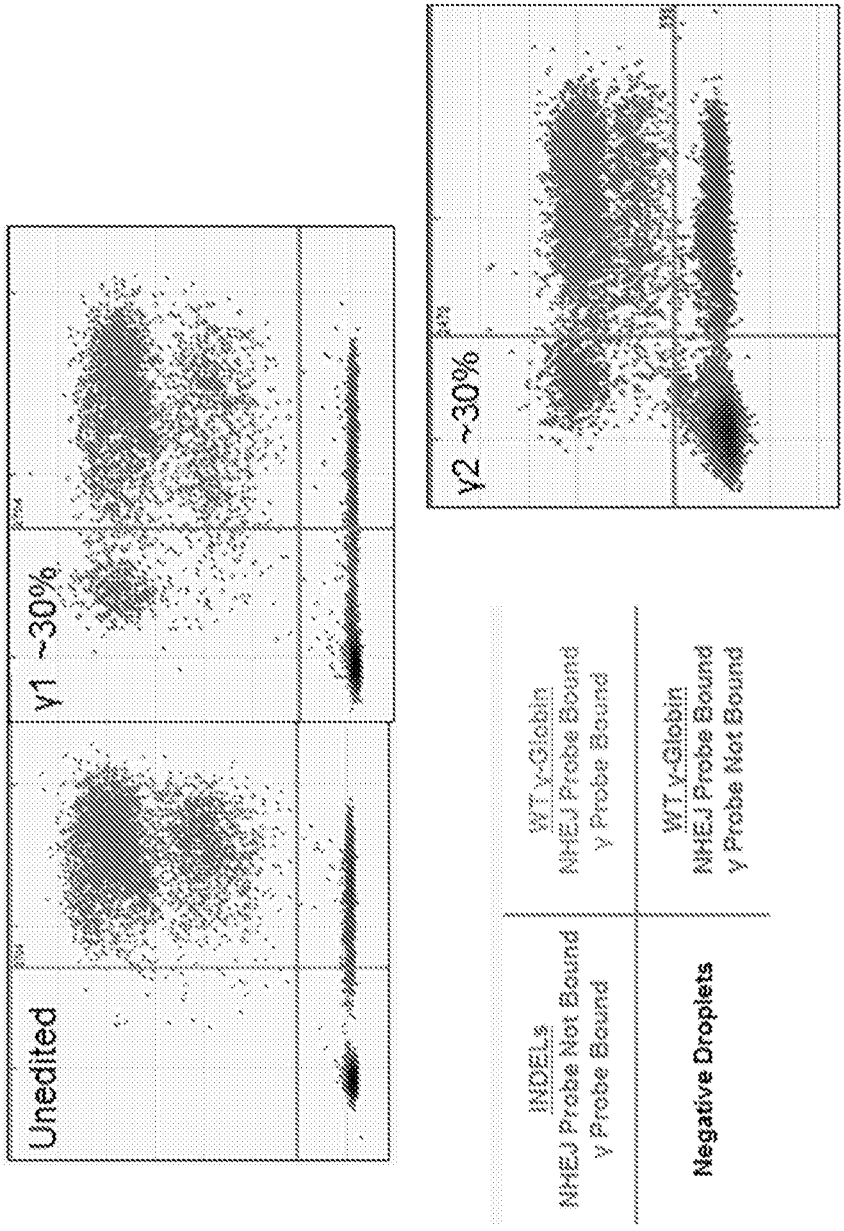
FIG. 37 demonstrates 20-30% INDEL rate at both loci using γ1 (HBG1) and γ2 (HBG2) specific probes with ddPCR. This increases to 50% with a 30C recovery step.
Figure 39:
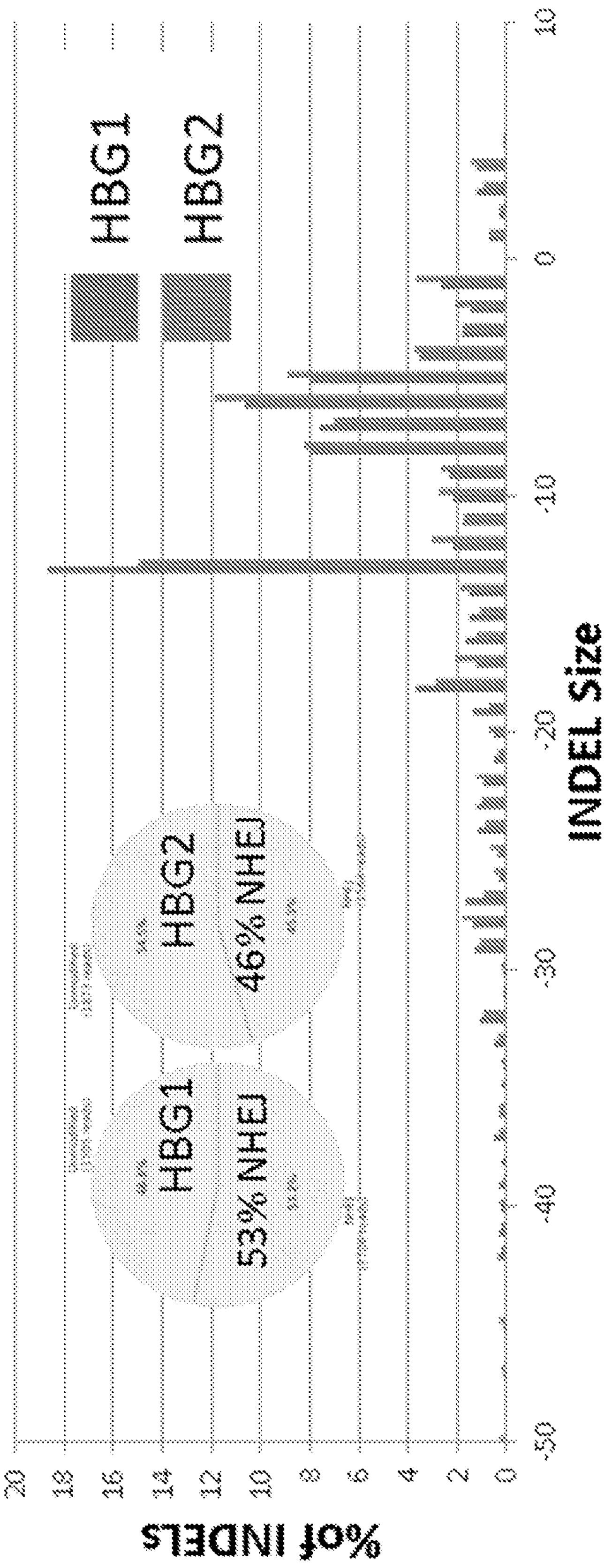
FIG. 39 shows confirmed editing rates (50% in this example) via Next Gen Sequencing. There is an overrepresentation of the 13 bp deletion likely the result of microhomology in the region.
Figure 40:
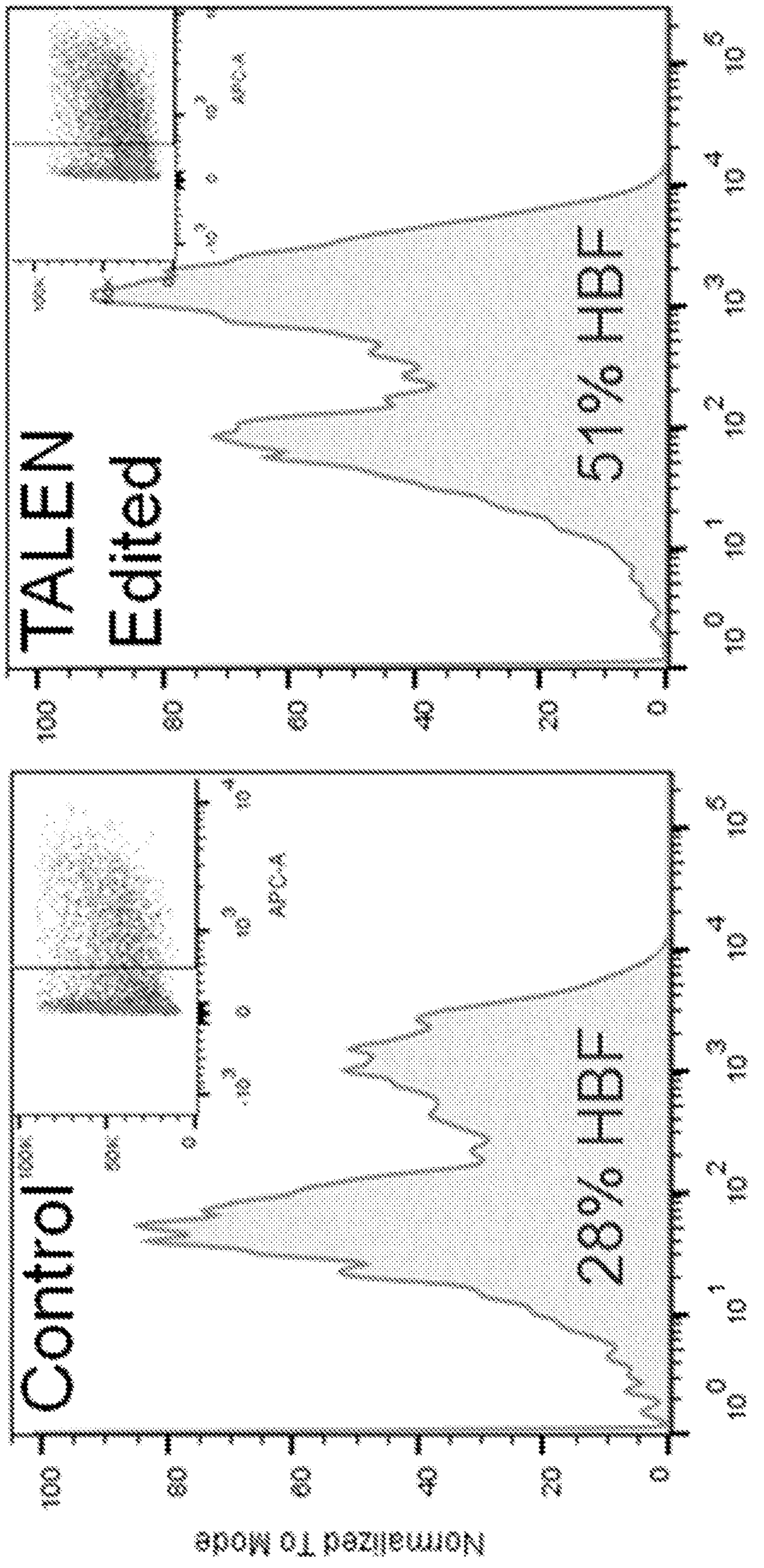
FIG. 40 shows results of HbF induction by flow cytometry. TALEN editing of peripheral blood CD34 cells followed by erythroid differentiation results in significantly increased number of F-cells.
Figure 41:
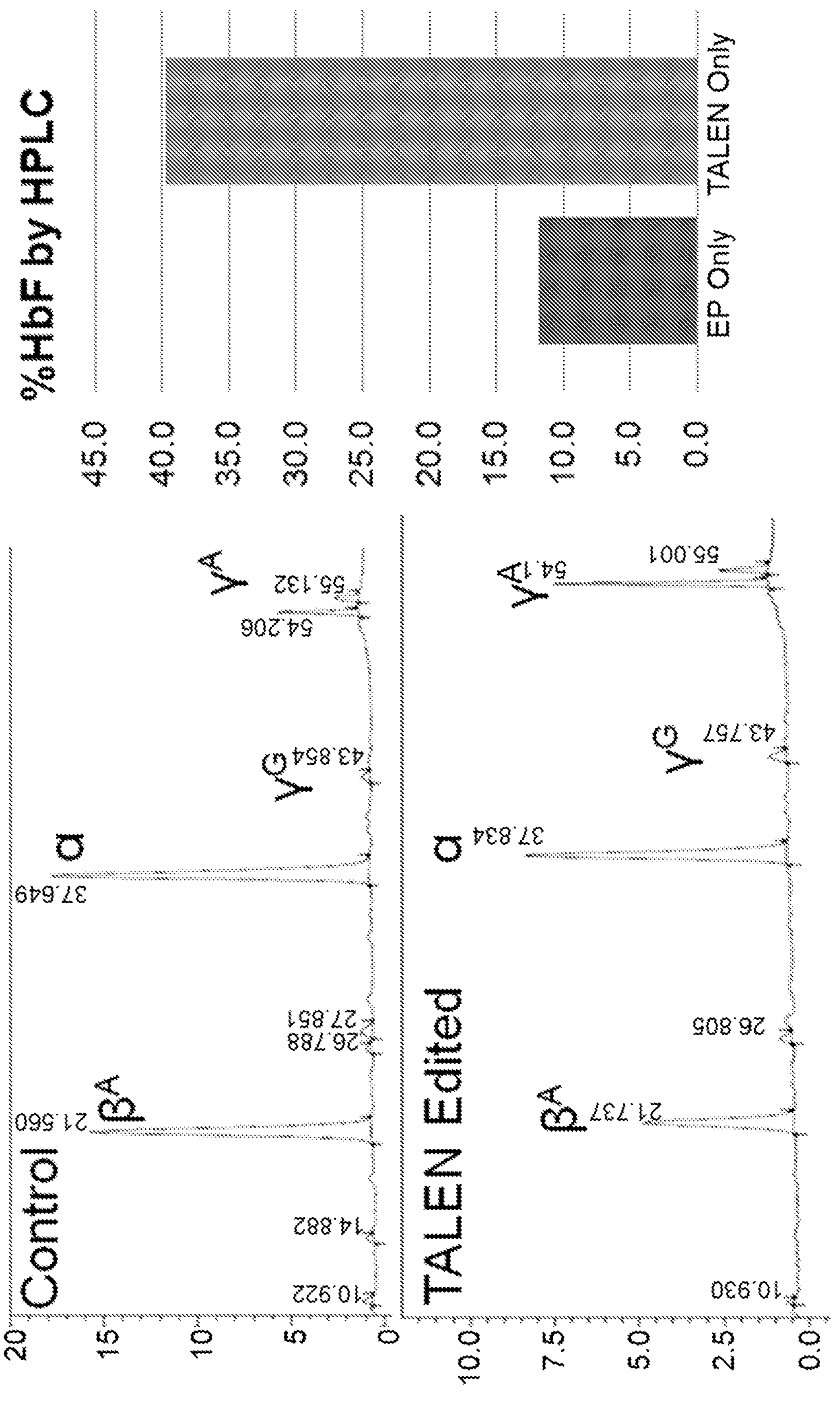
FIG. 41 shows results of HbF induction by HPLC. TALEN editing of peripheral blood CD34 cells followed by erythroid differentiation results in significantly increased HbF protein expression. The difference in protein expression is greater than the percent F-cells suggesting that the increased F-cells express higher levels of HbF than control F-cells.

T7 Analysis showed that del13 TALEN pair transfection induces INDELs in human CD34 cells at both the γ1(HBG1) and γ2(HBG2) locus (FIG. 38). ddPCR showed 20-30% INDEL rate at both loci using γ1(HBG1) and γ2(HBG2) specific probes. This increased to 50% with a 30C recovery step (FIG. 37). Next gen sequencing then provided confirmed editing rates (50% in this example). There was an overrepresentation of the 13 bp deletion, which was likely the result of microhomology in the region (FIG. 39). HbF induction by flow cytometry demonstrated TALEN editing of peripheral blood CD34 cells followed by erythroid differentiation, which resulted in significantly increased number of F-cells (FIG. 40). HbF induction by HPLC demonstrated TALEN editing of peripheral blood CD34 cells followed by erythroid differentiation, which resulted in significantly increased HbF protein expression (FIG. 41). The difference in protein expression was greater than the percent F-cells suggesting that the increased F-cells expressed higher levels of HbF than control F-cells. HR template integration yielded HbF induction and anti-sickling T87Q expression (FIGS. 16-17). Combined, over 60% of the globin expressed in edited cells is potentially clinically beneficial.

Results (In Vivo)

An experimental timeline (shown below) provided for neon transfected human CD34 cells transplanted by tail vein injection in W41 mice.

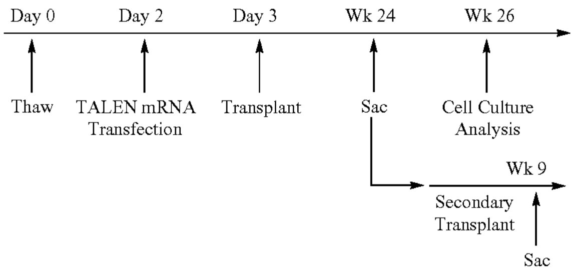

Figure 42:
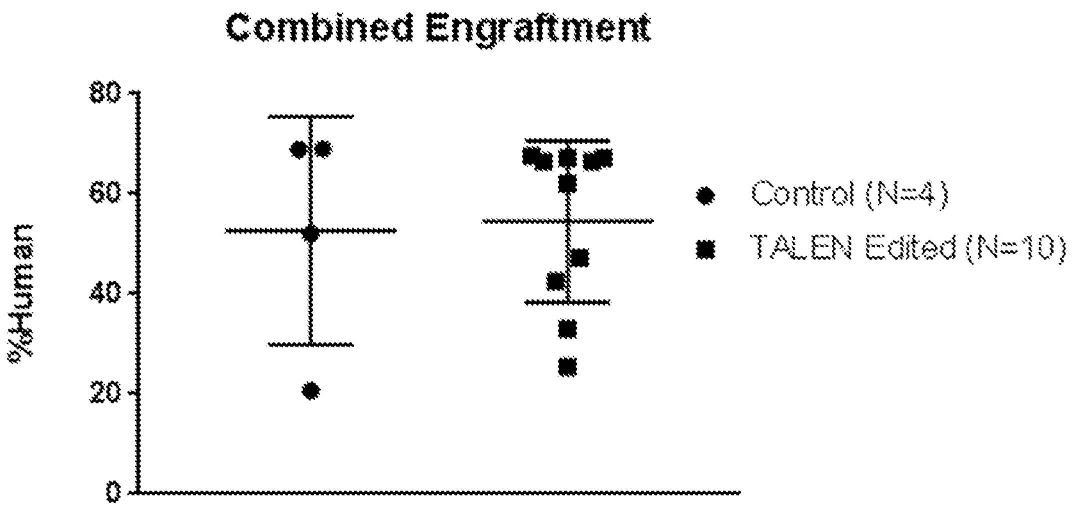
FIG. 42 shows results of human engraftment at week 24. No significant difference in percent human engraftment between control and edited cells is seen.
Figure 43:
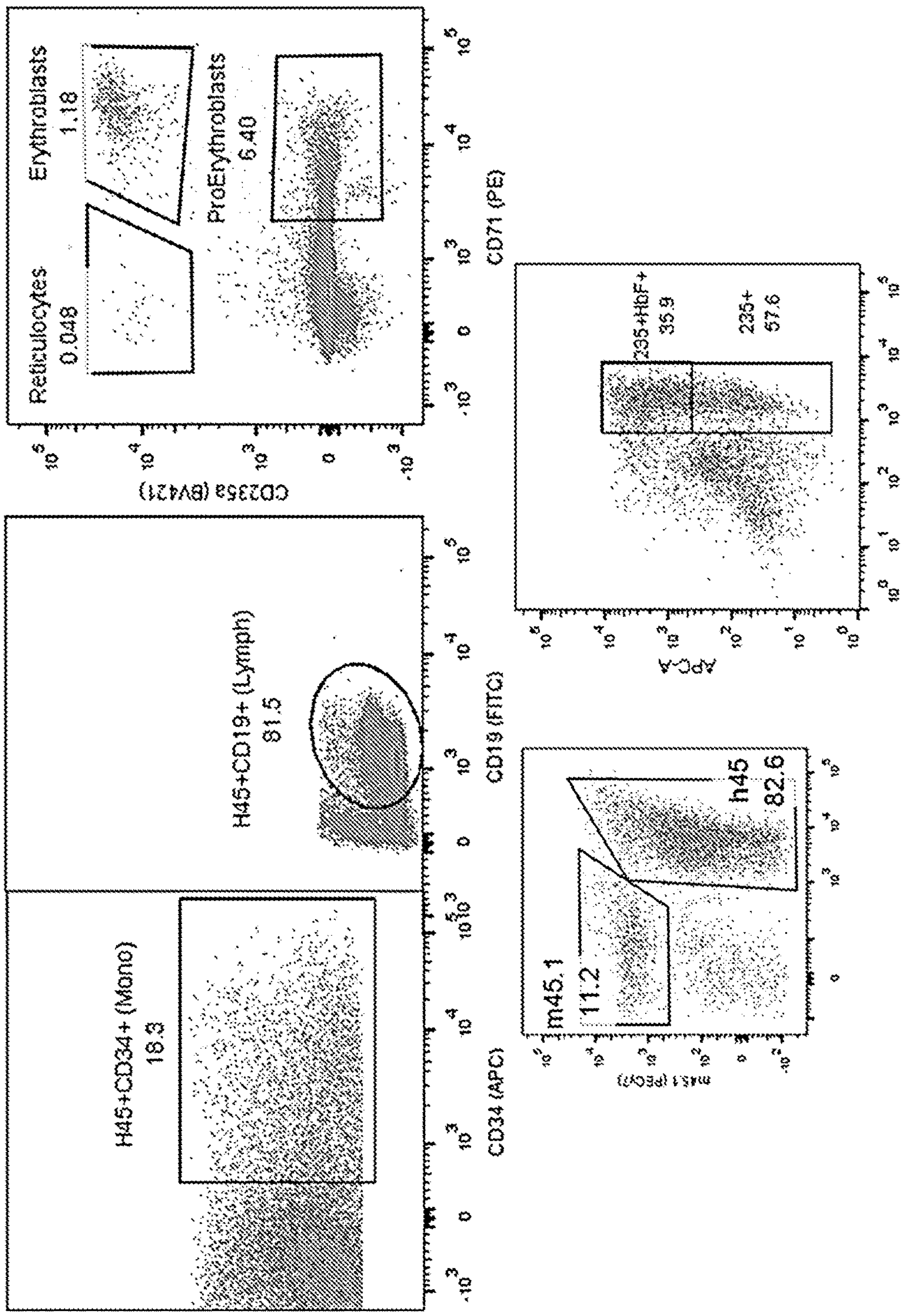
FIG. 43 shows engrafted edited CD34 cells generate all human hematopoietic lineages. Human erythroid, CD34+ Lymphoid and Myeloid, and CD19+ cells were all identified and sorted from harvested marrows following transplant (W24).
Figure 44:
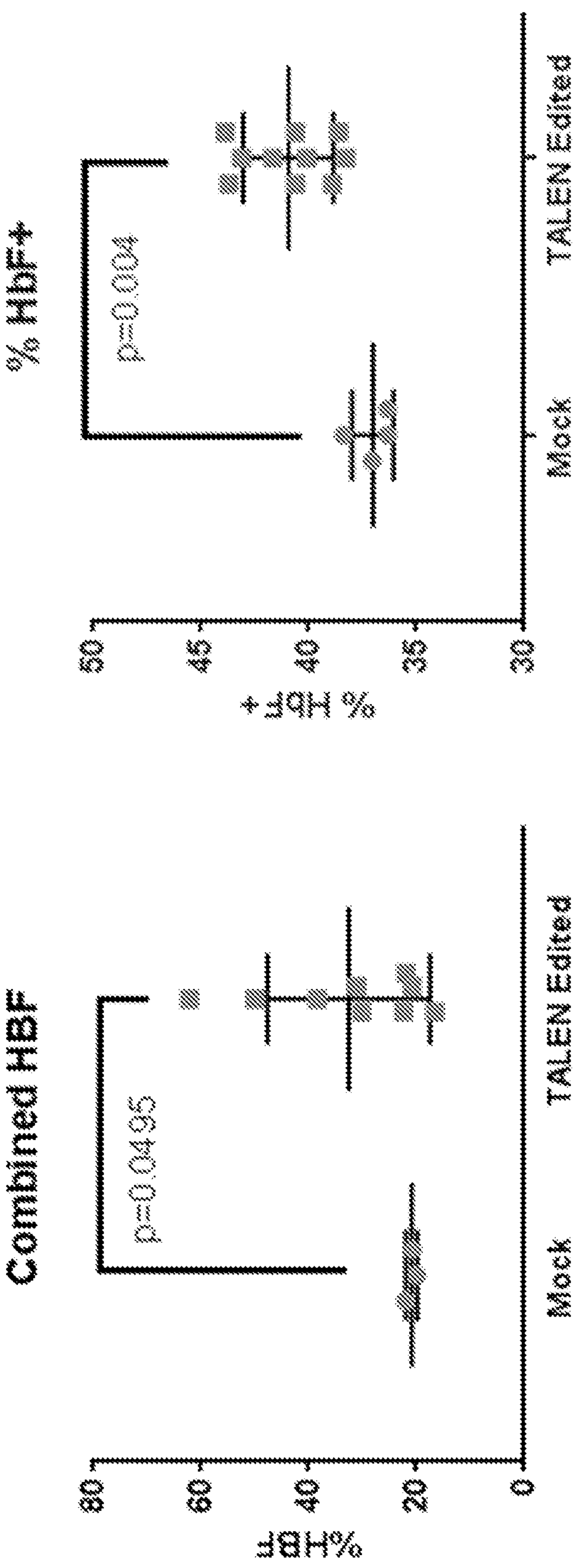
FIG. 44 shows TALEN edited CD34 cells produce more F-cells. At sac (A) there is a significantly higher rate of human F-Cells detected in the marrow. Differentiated CD34 cells from the marrow produce more F-Cells (B).
Figure 45:
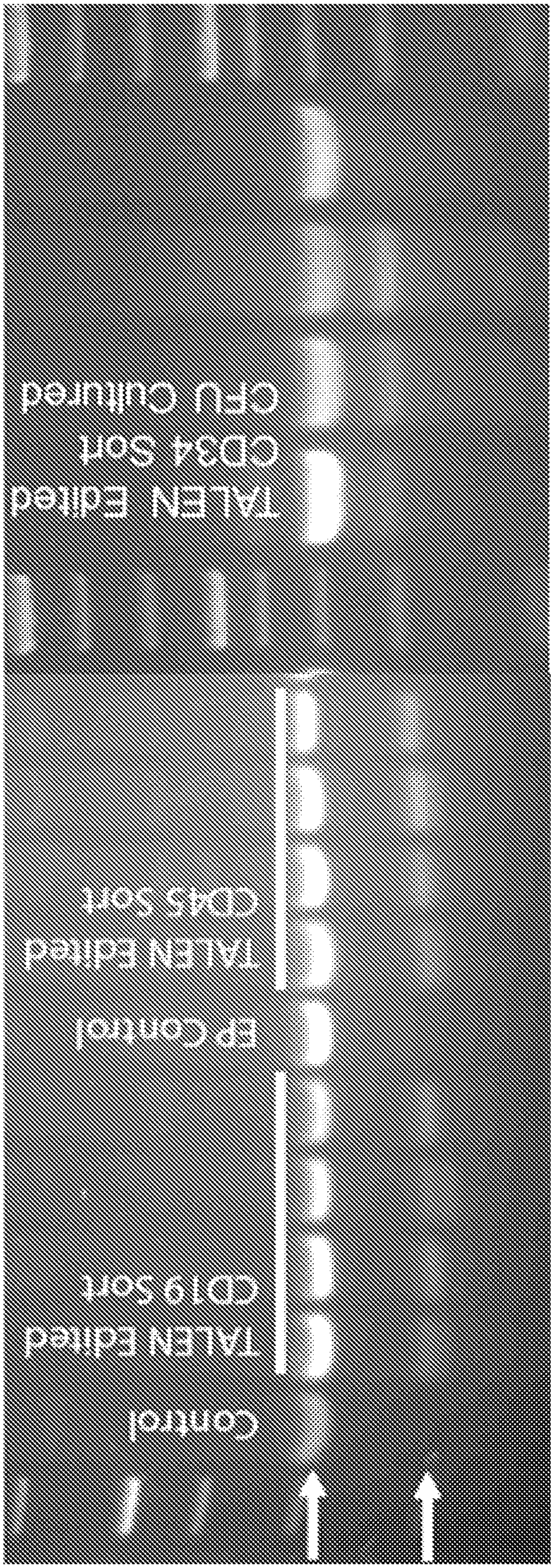
FIG. 45 shows sorted cells from all lineages retain INDELs from TALEN editing. T7 Analysis demonstrating INDELS are present in vitro.
Figure 47A:
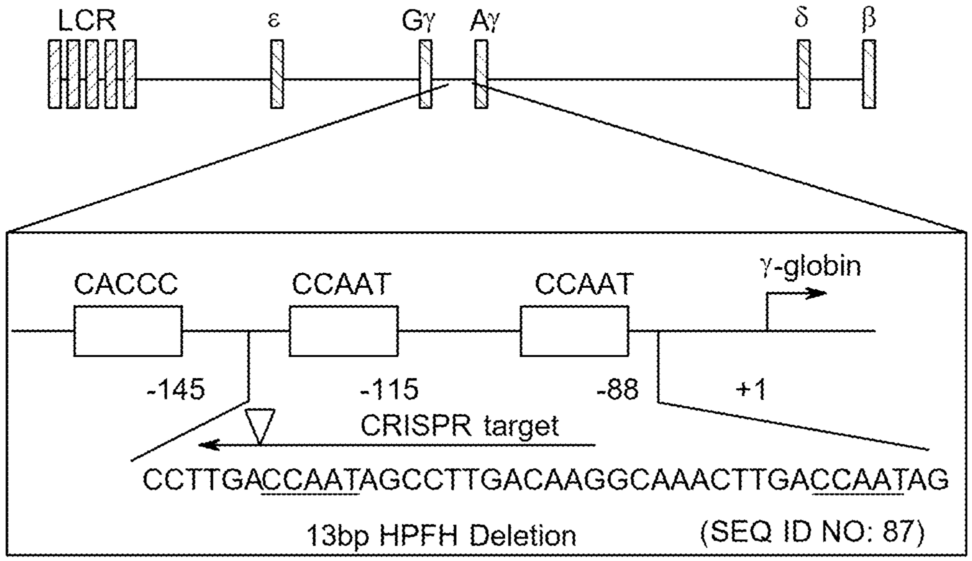
FIGS. 47A-47I show results of recapitulating the 13-nucleotide HPFH deletion by CRISPR/Cas9 gene editing.
Figure 47B:
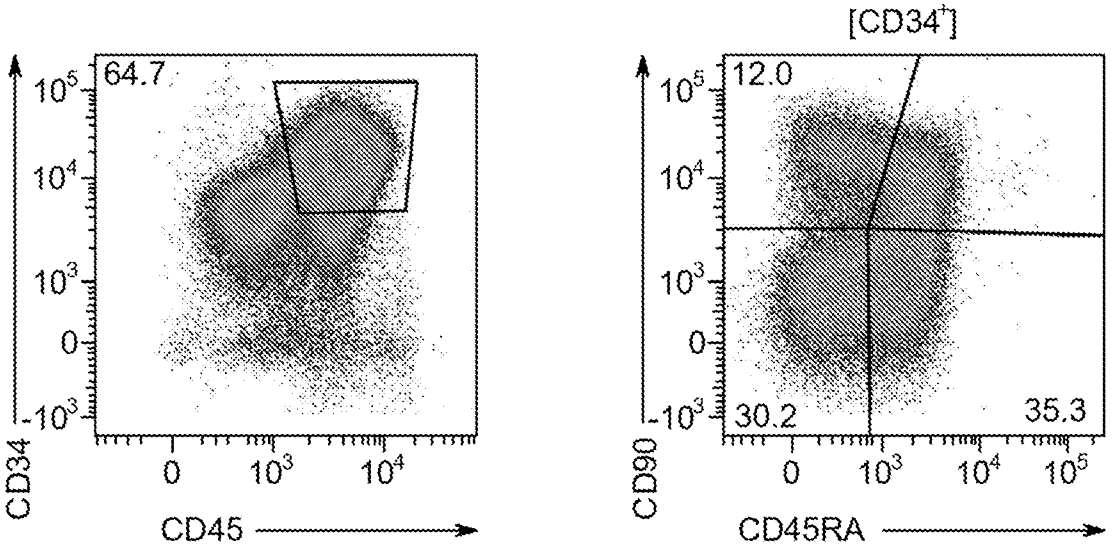
Figure 47C:
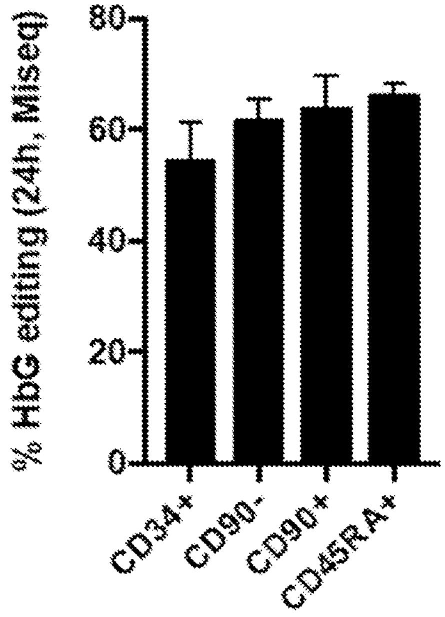
Figure 47D:
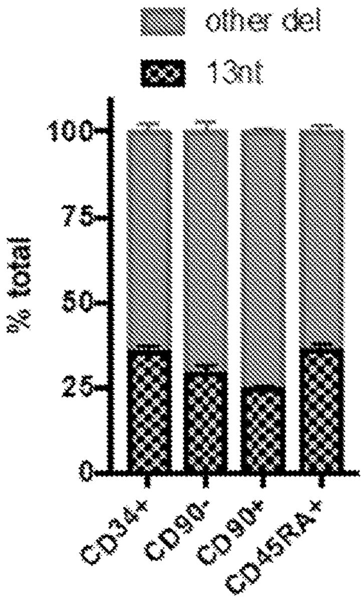
Figure 47E:
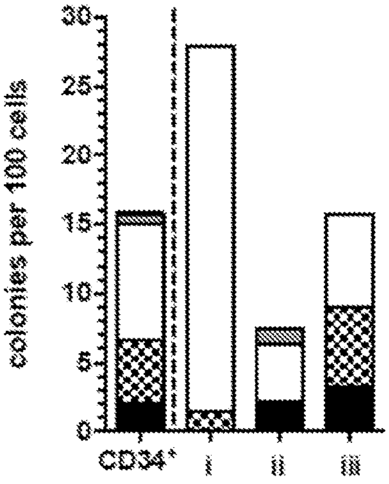
Figure 47F:
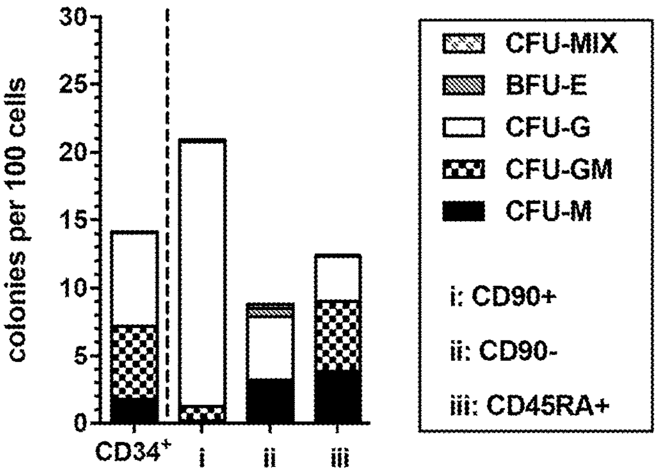
Figure 47G:
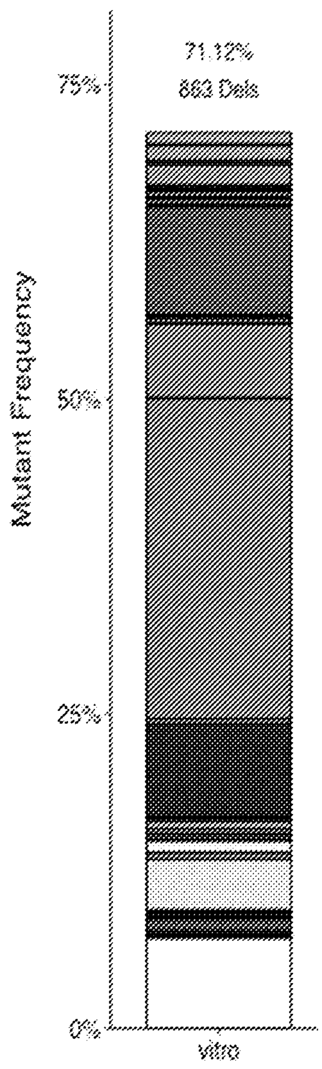
Figure 47H:
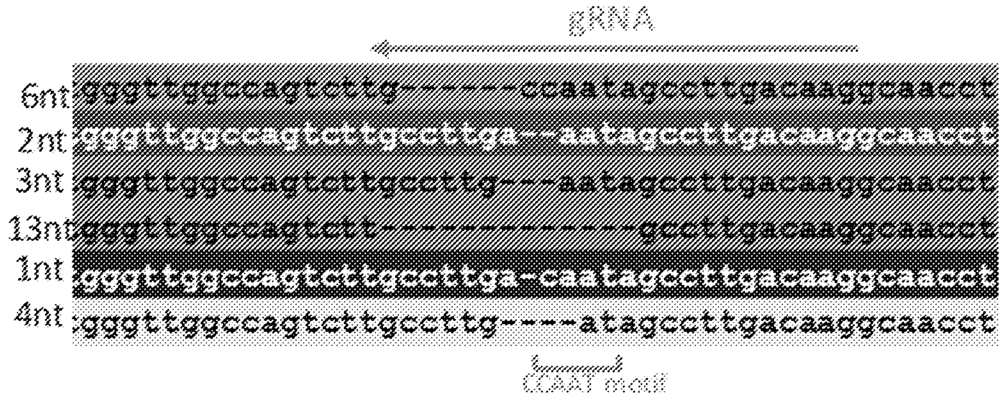
Figure 47I:
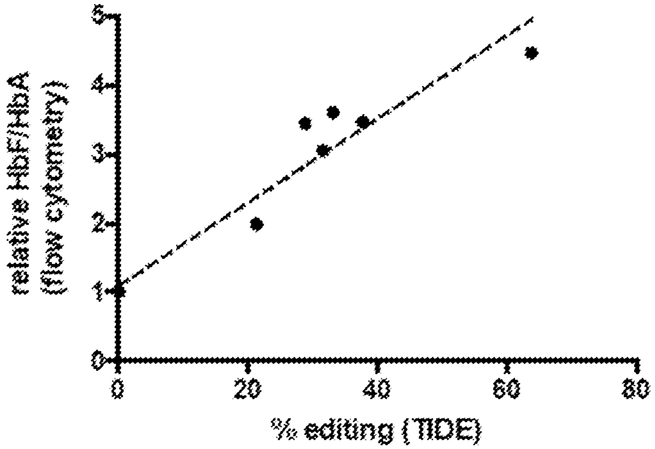
Figure 48B:
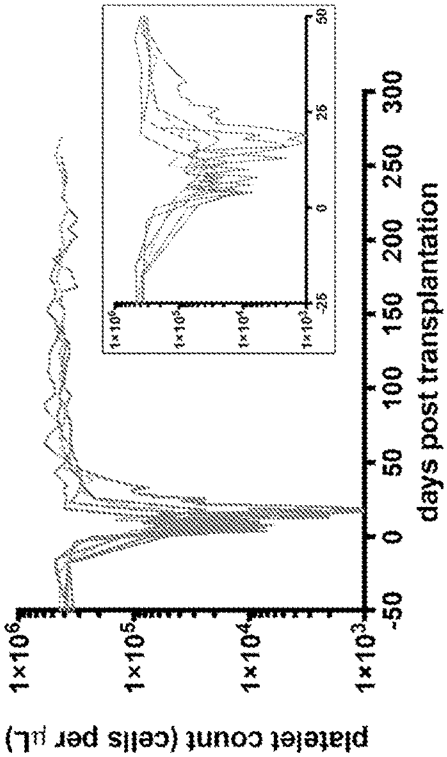
FIGS. 48A-48D show hematopoietic recovery in all transplanted animals by measuring neutrophil count (cells per μL) (FIG. 48A), platelet count (cells per μL) (FIG. 48B), lymphocyte count (cells per μL) (FIG. 48C), and monocyte count (cells per μL) (FIG. 48D) in view of days post transplantation.
Figure 48A:
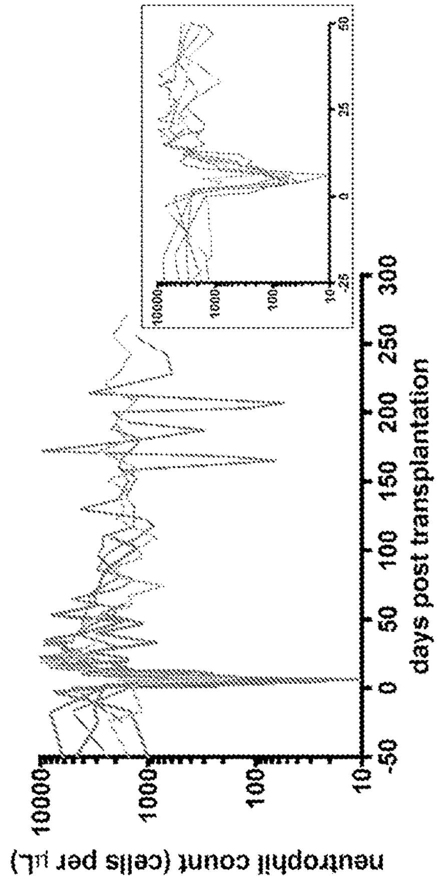
Figure 48D:
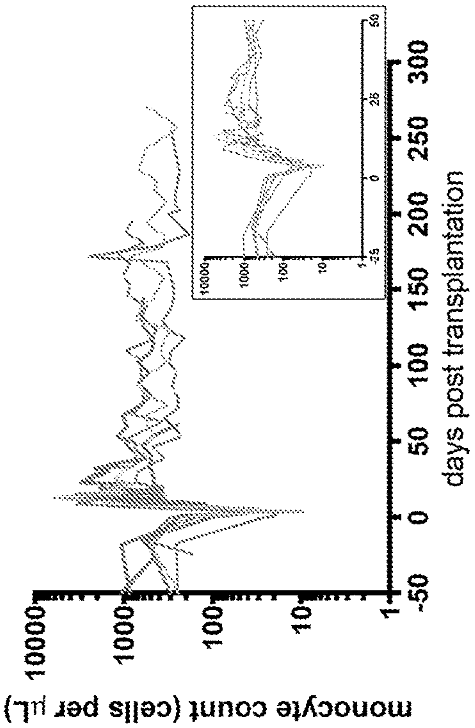
Figure 48C:
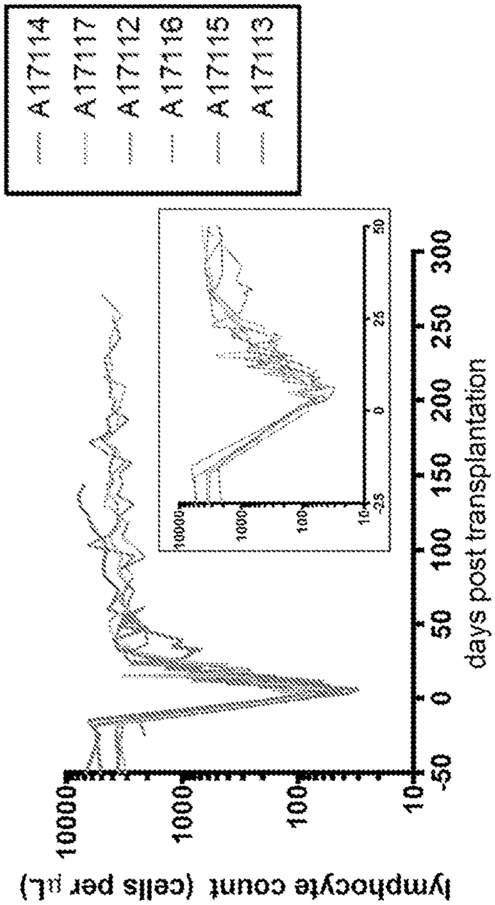
Figure 49A:
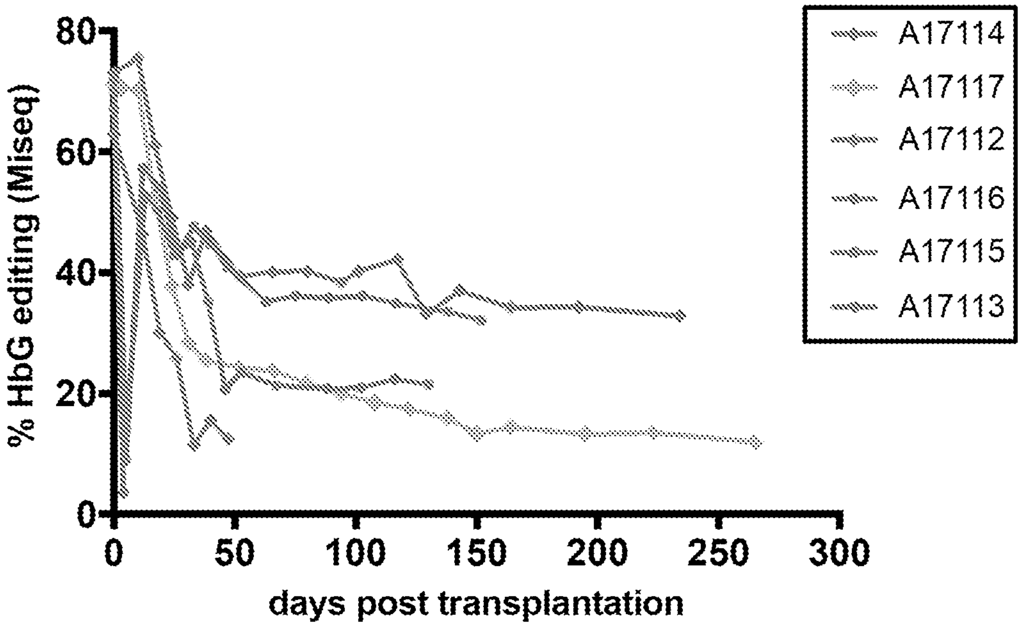
FIGS. 49A-49D show tracking of HbG editing in vivo in all transplanted animals.
Figure 49B:
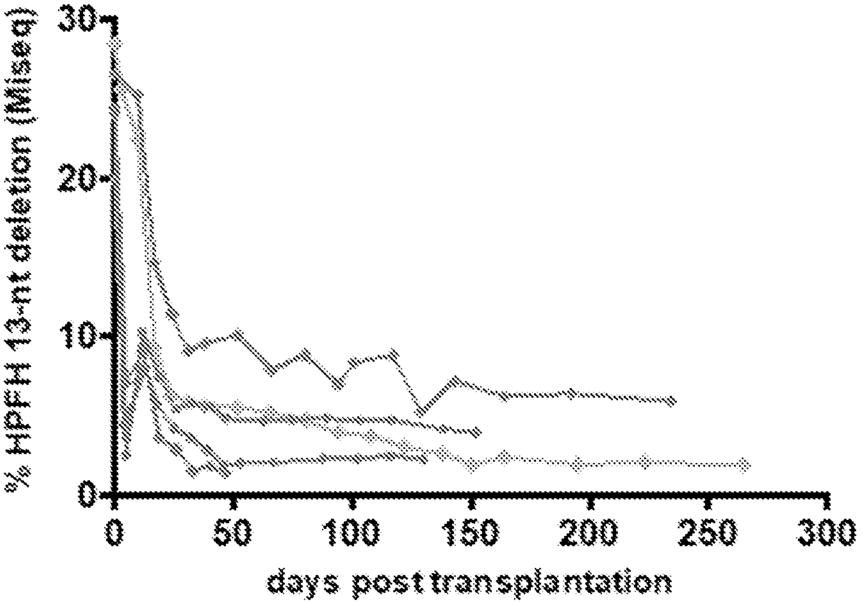
Figure 49C:
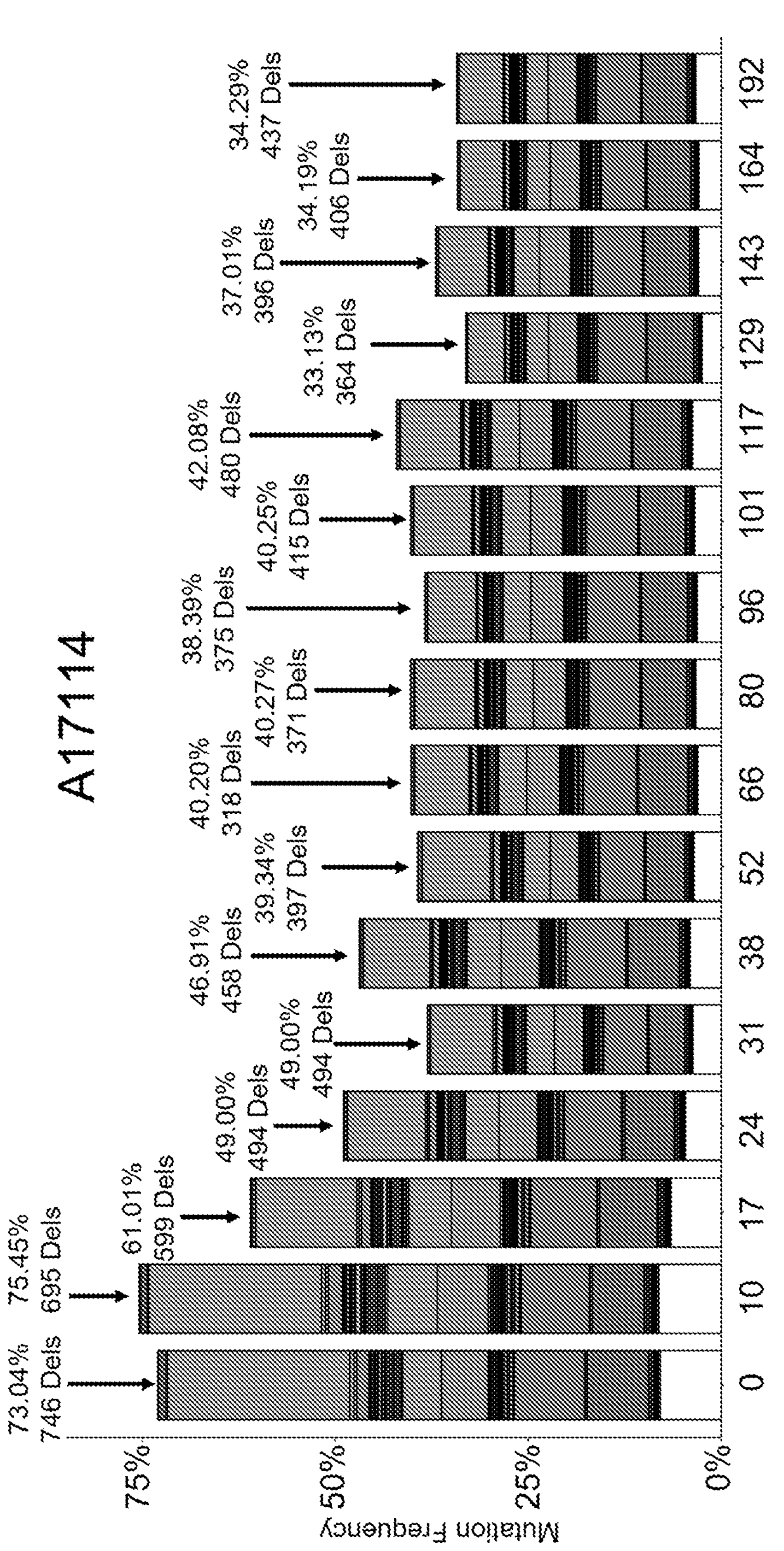
Figure 49D:
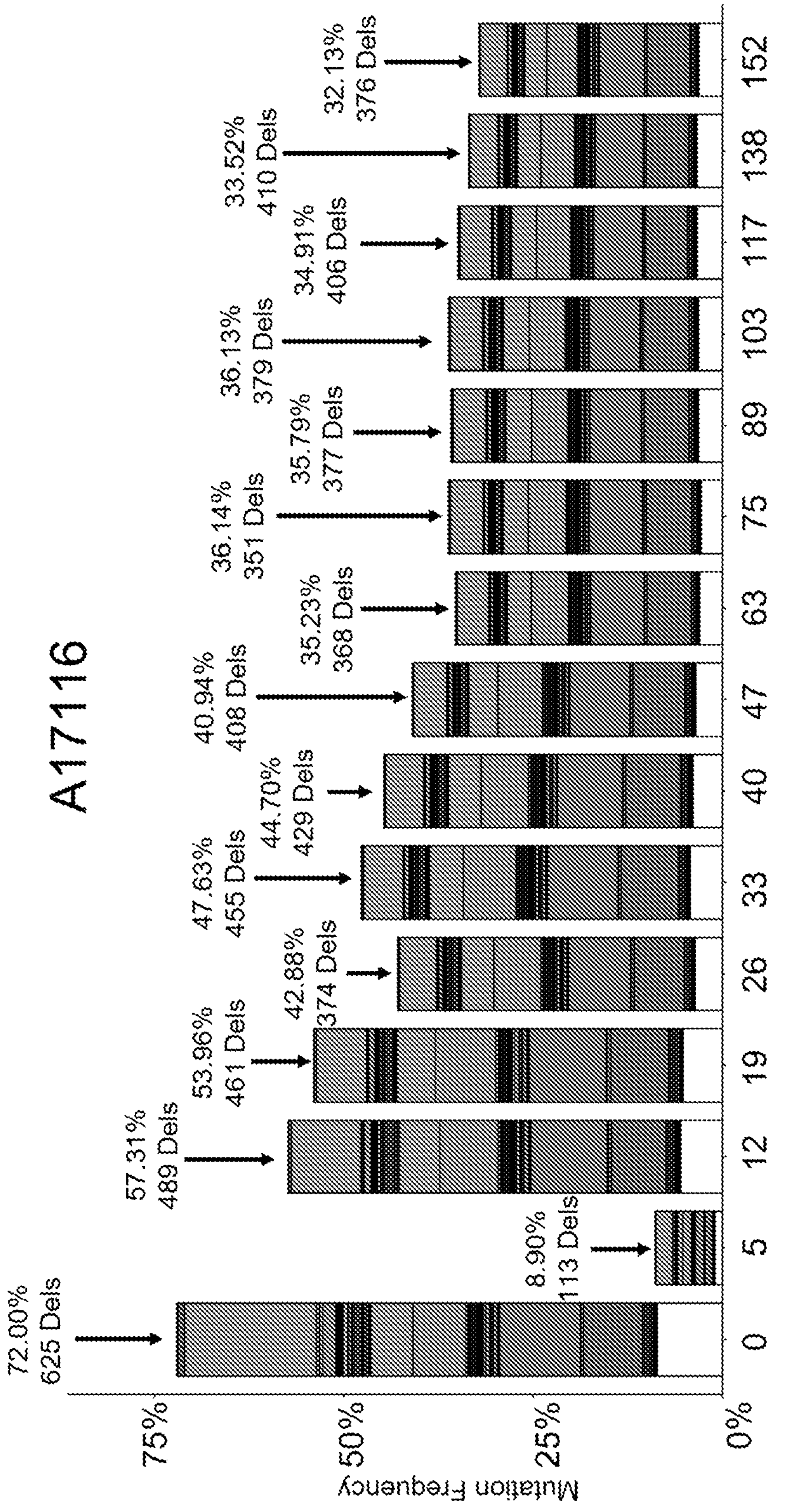
Figure 50B:
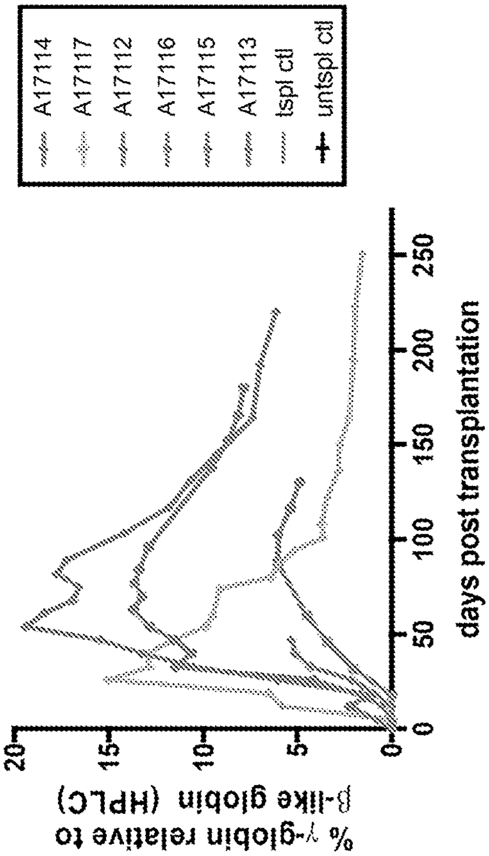
FIGS. 50A-50E show fetal hemoglobin production in all transplanted animals Percent F-cells (flow cytometry) (FIG. 50A) and percent γ-globin relative to β-like globin (HPLC) (FIG. 50B) was measured over days post transplantation for all transplanted animals. Percent F-cells (flow cytometry) was measured in view of percent γ-globin (HPLC) for four of the transplanted animals (FIG. 50B). Percent γ-globin and percent F-cells were then measured in view of HbG editing (measured by TIDE) (FIG. 50D). For four animal models the percent total of gamma-1, gamma-2, beta, alpha-2, and alpha-1 was measured over days post transplantation.
Figure 50D:
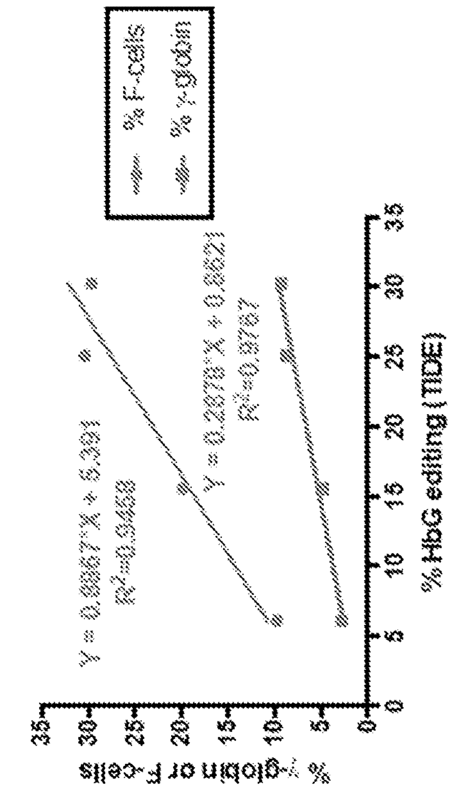
Figure 50A:
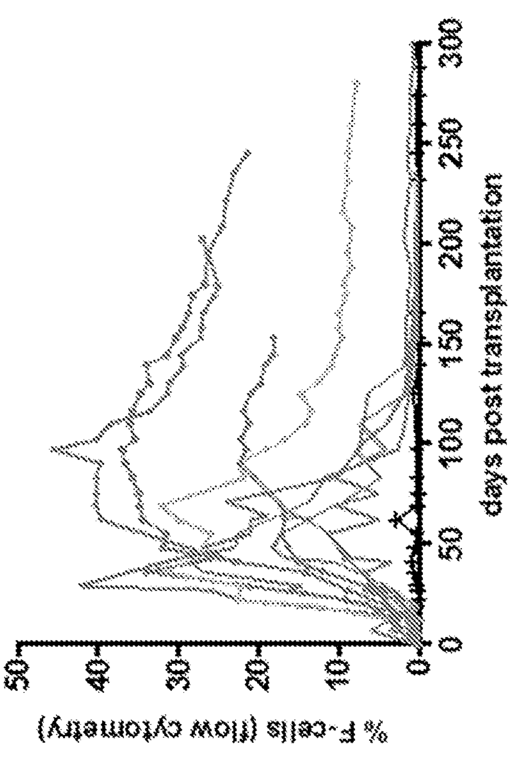
Figure 50C:
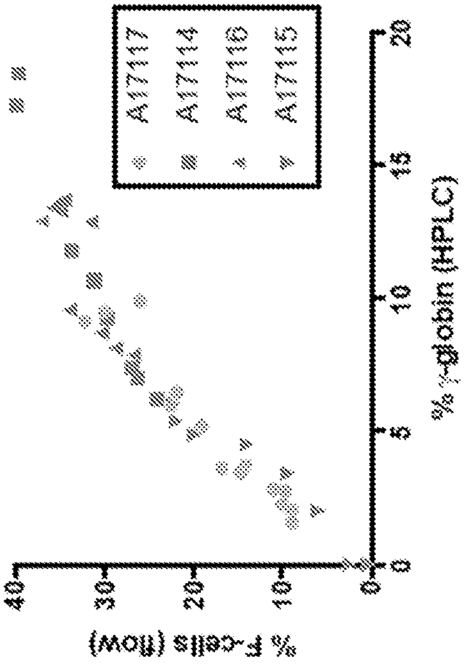
Figure 50E:
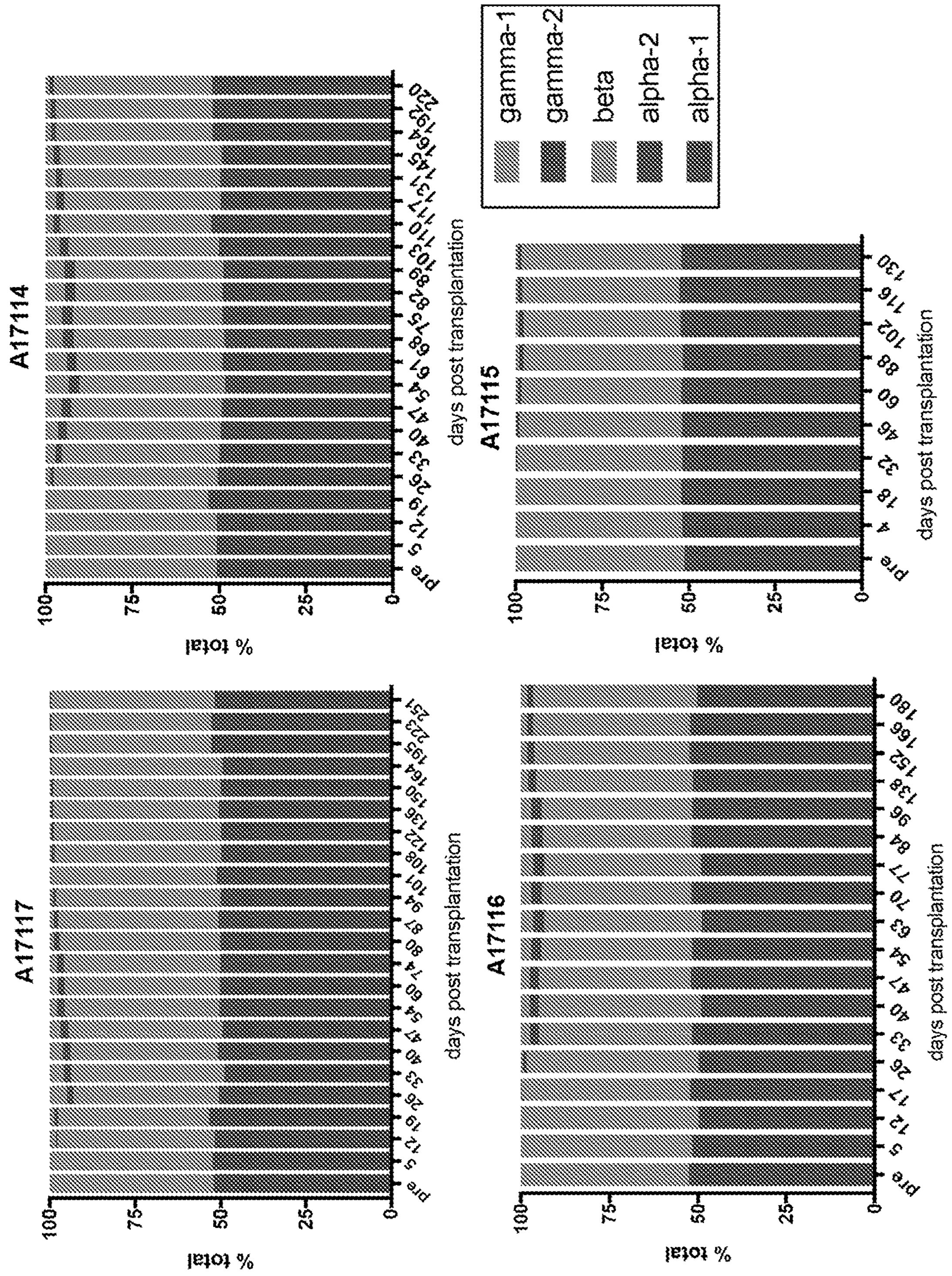
Figure 51A:
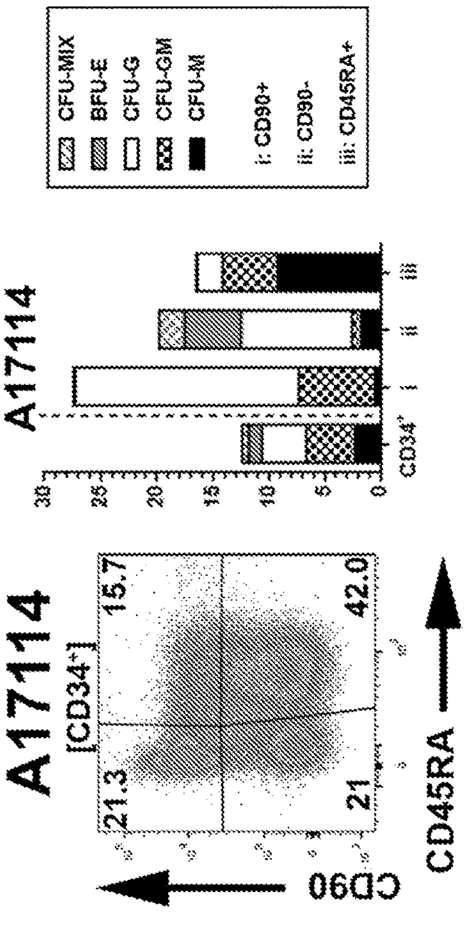
FIGS. 51A-51G shows multilineage engraftment of CRISPR/Cas9-edited HSPCs in bone marrow of transplanted animals at 6 months post infusion.
Figure 51B:
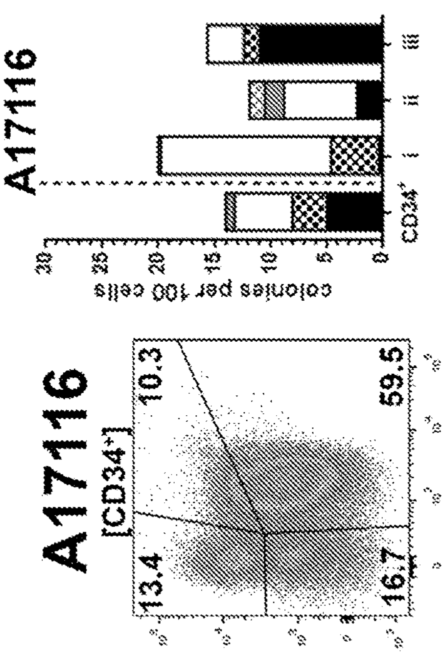
Figure 51C:
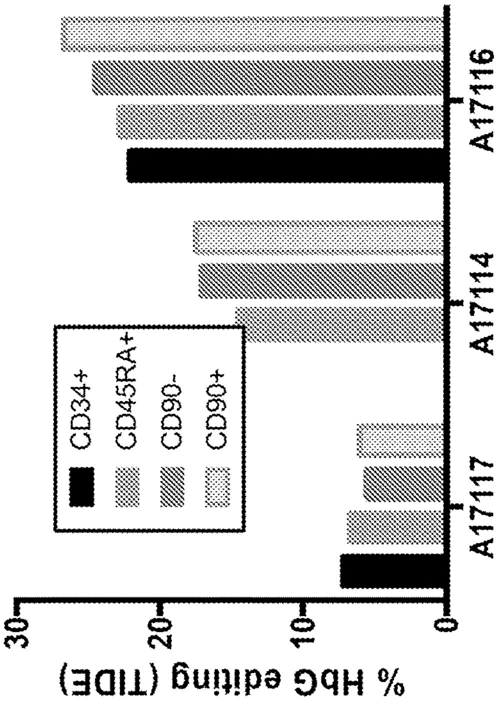
Figure 51D:
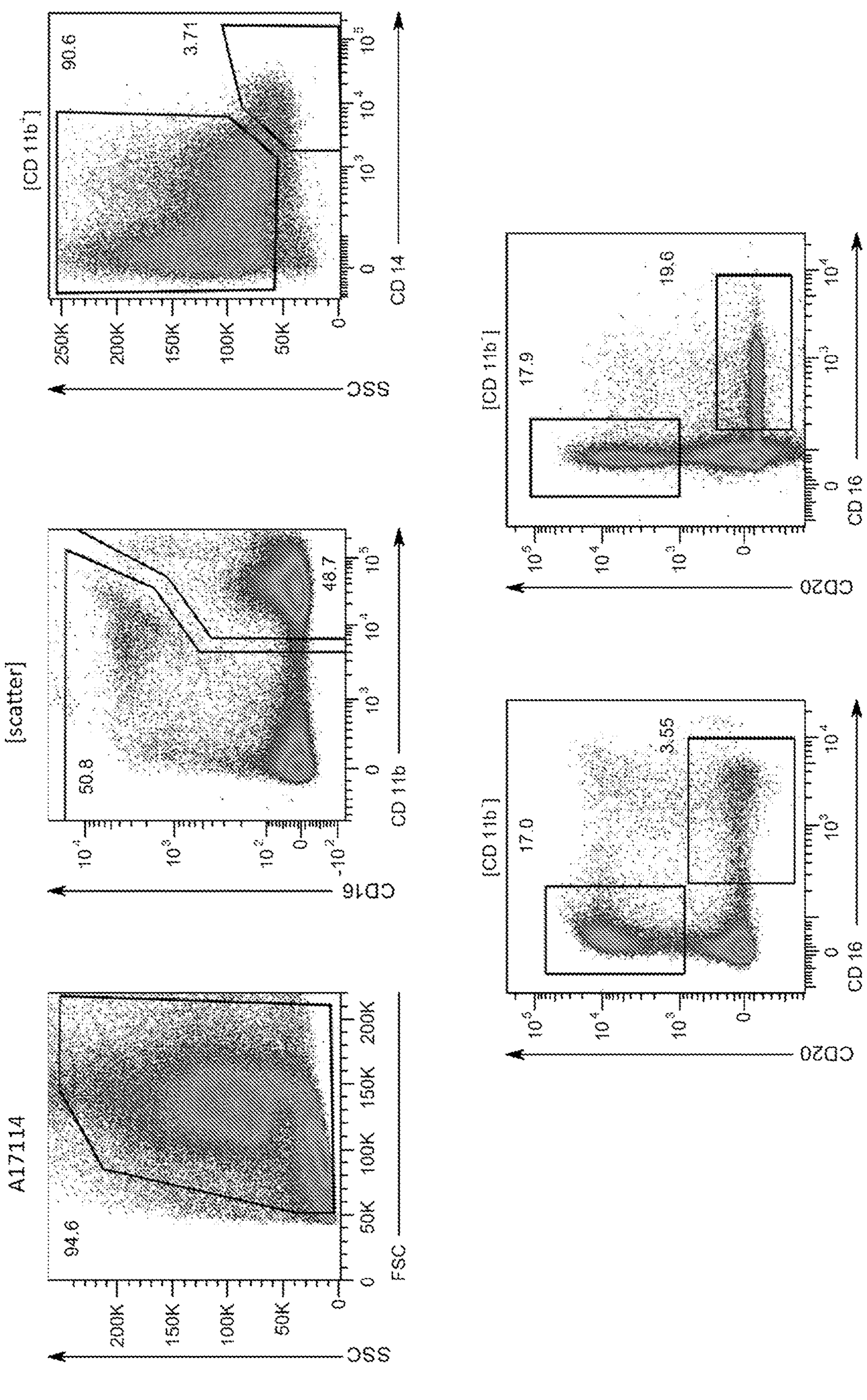
Figure 51E:
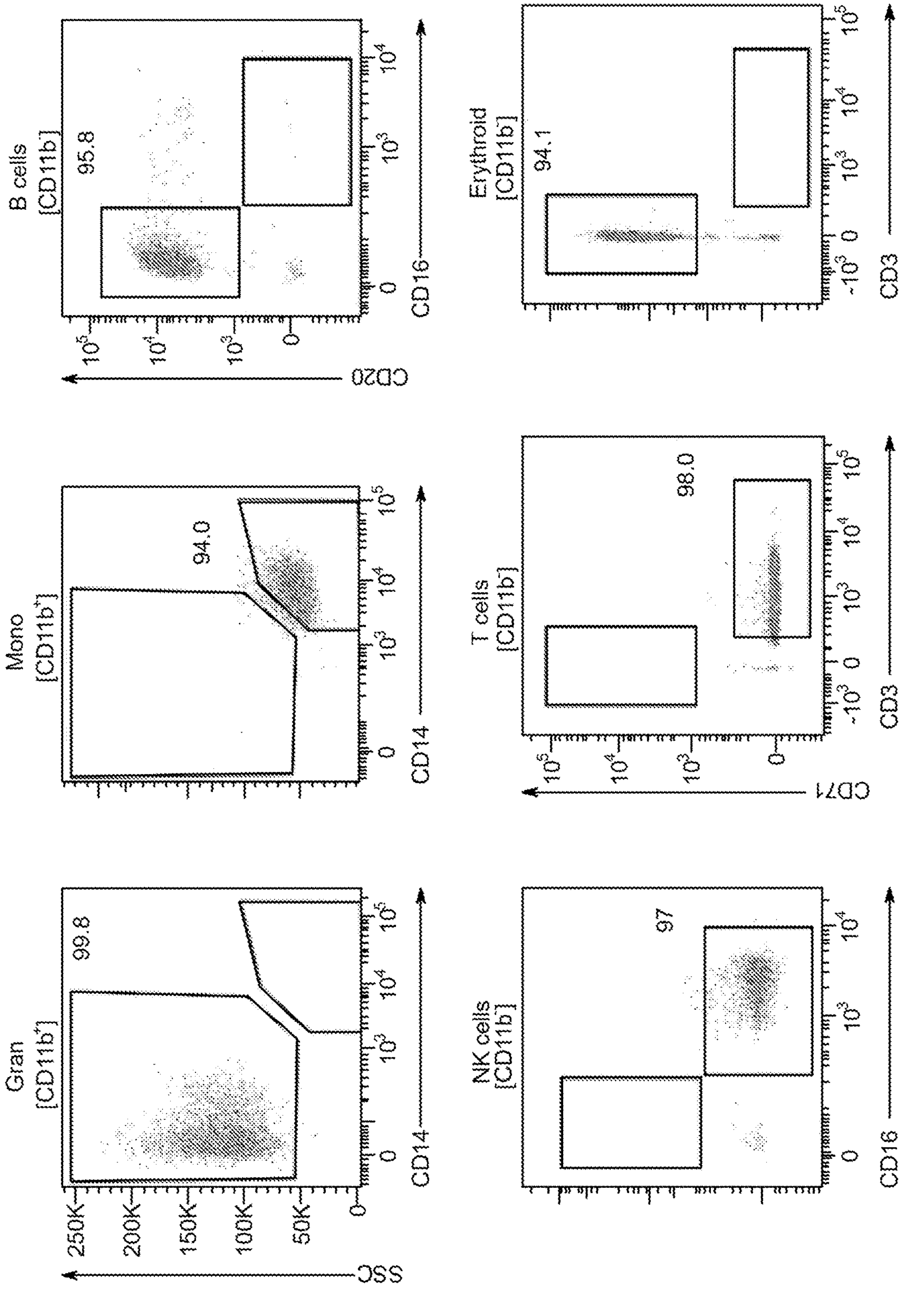
Figure 51F:
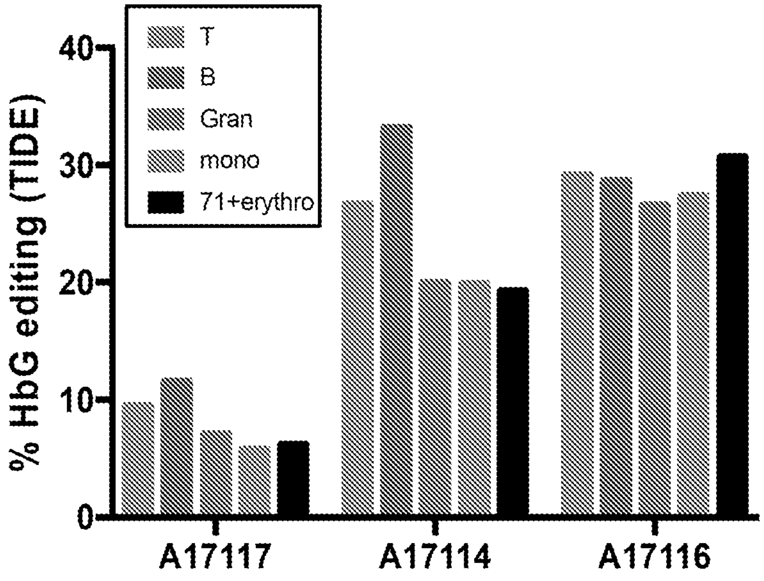
Figure 51G:
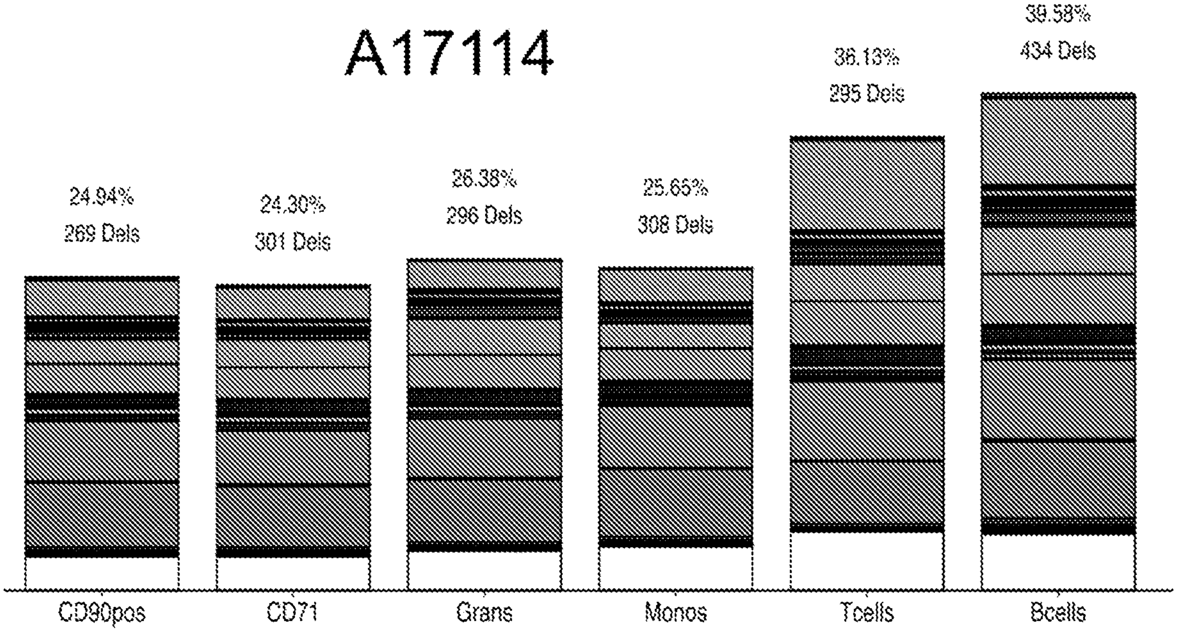
Figure 52:
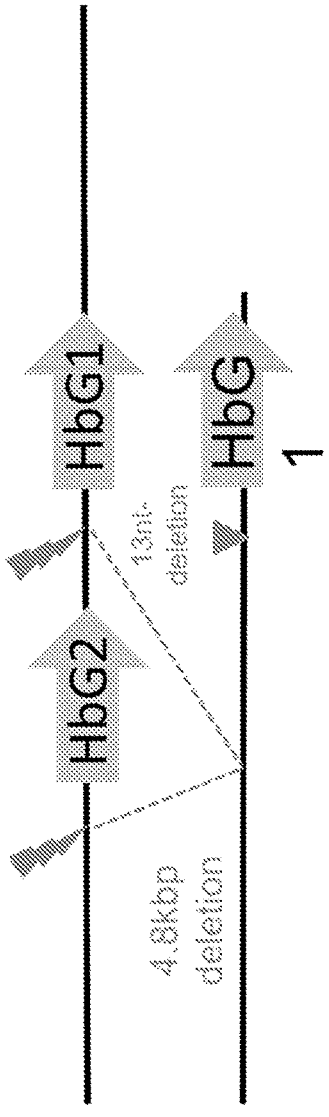
FIG. 52 provides quantification of large deletion events and off-target sites.
Figure 53A:
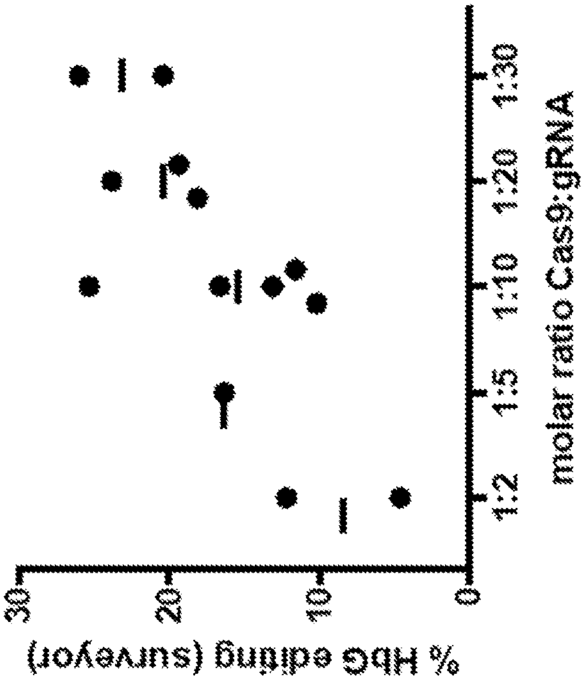
FIGS. 53A-53F show HbG editing efficiency in different HSPC subsets.
Figure 53B:
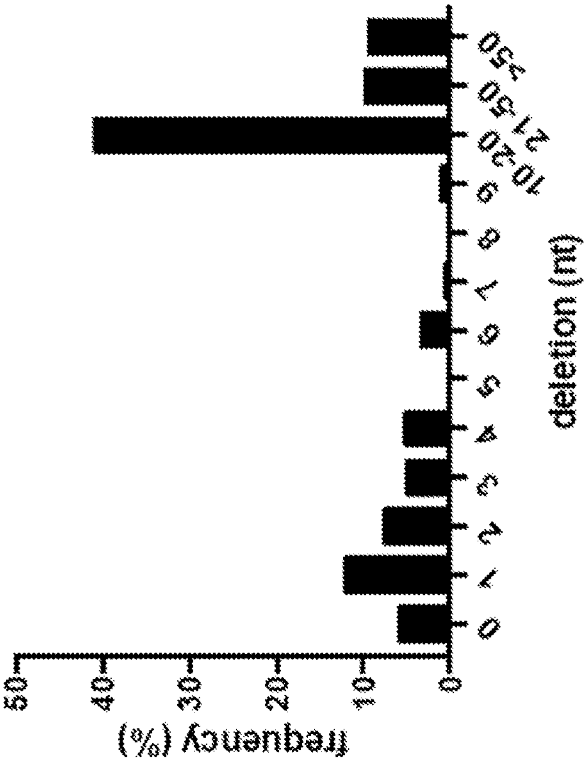
Figures 53C, 53D, 53E:
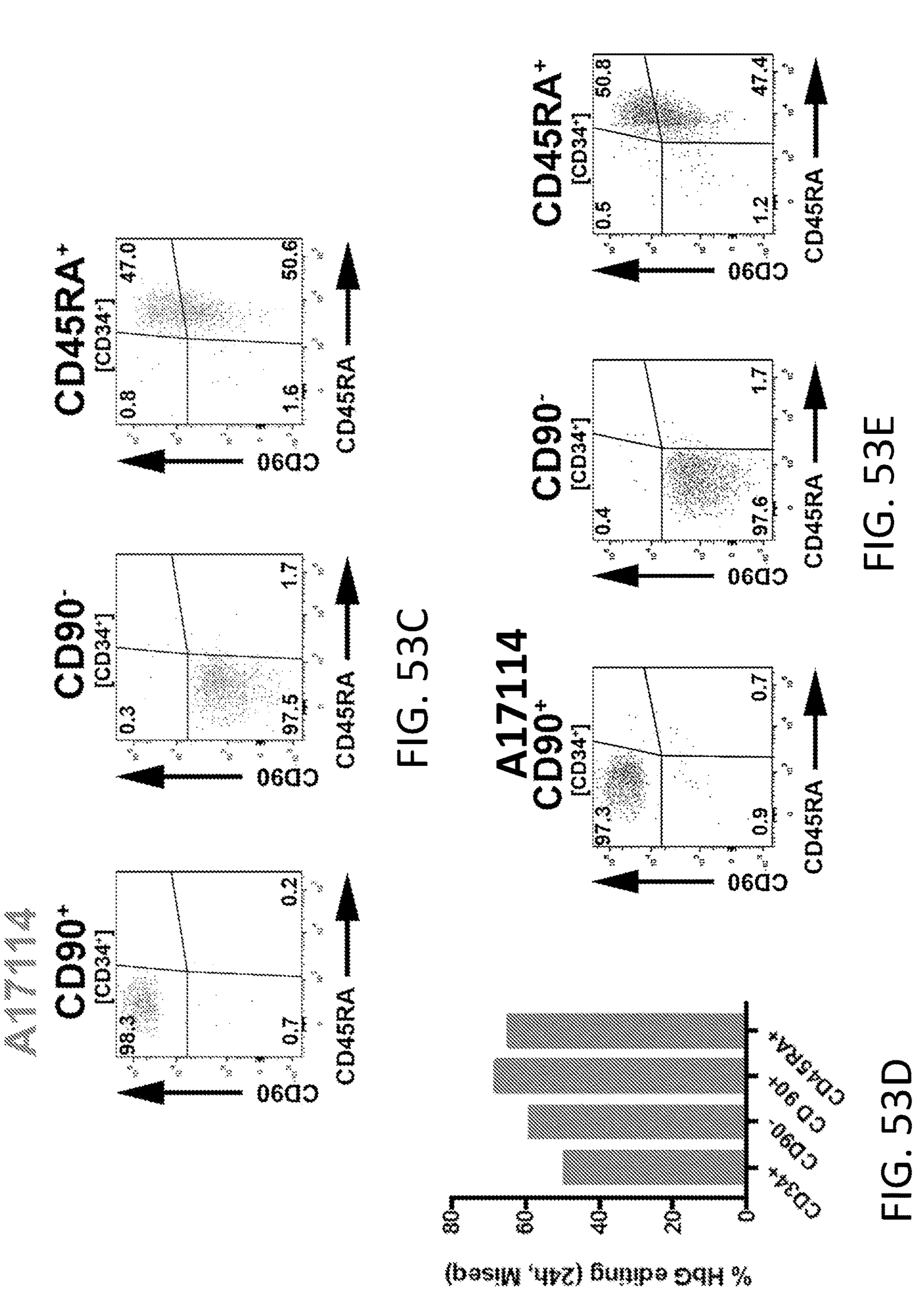
Figure 53F:
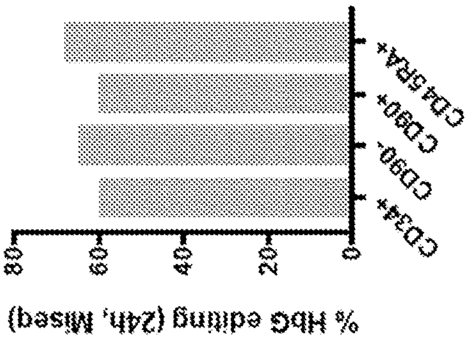
Figure 54A:
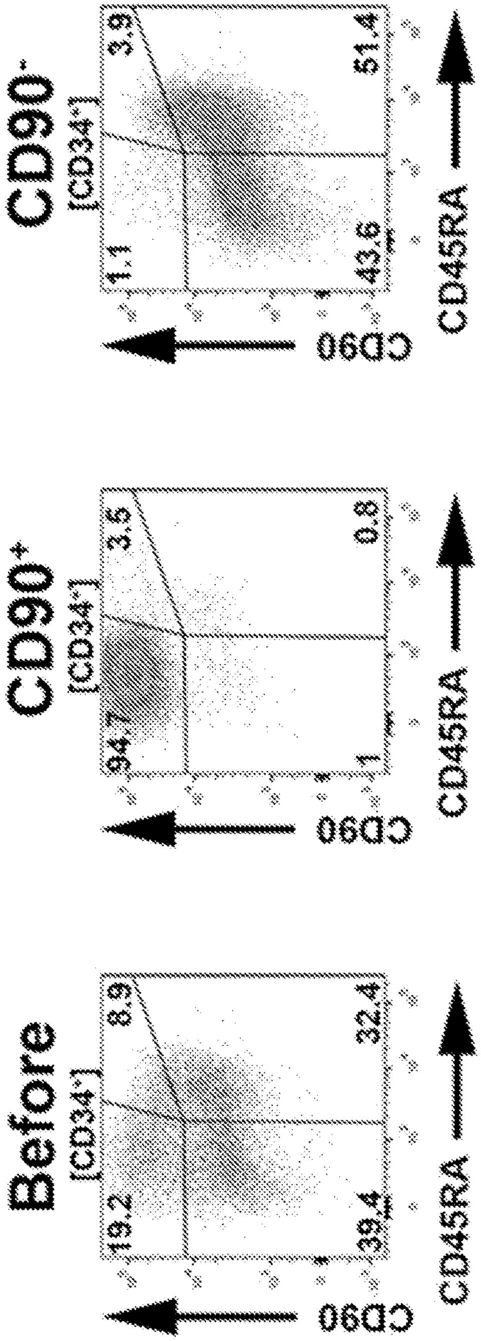
Figure 55A:
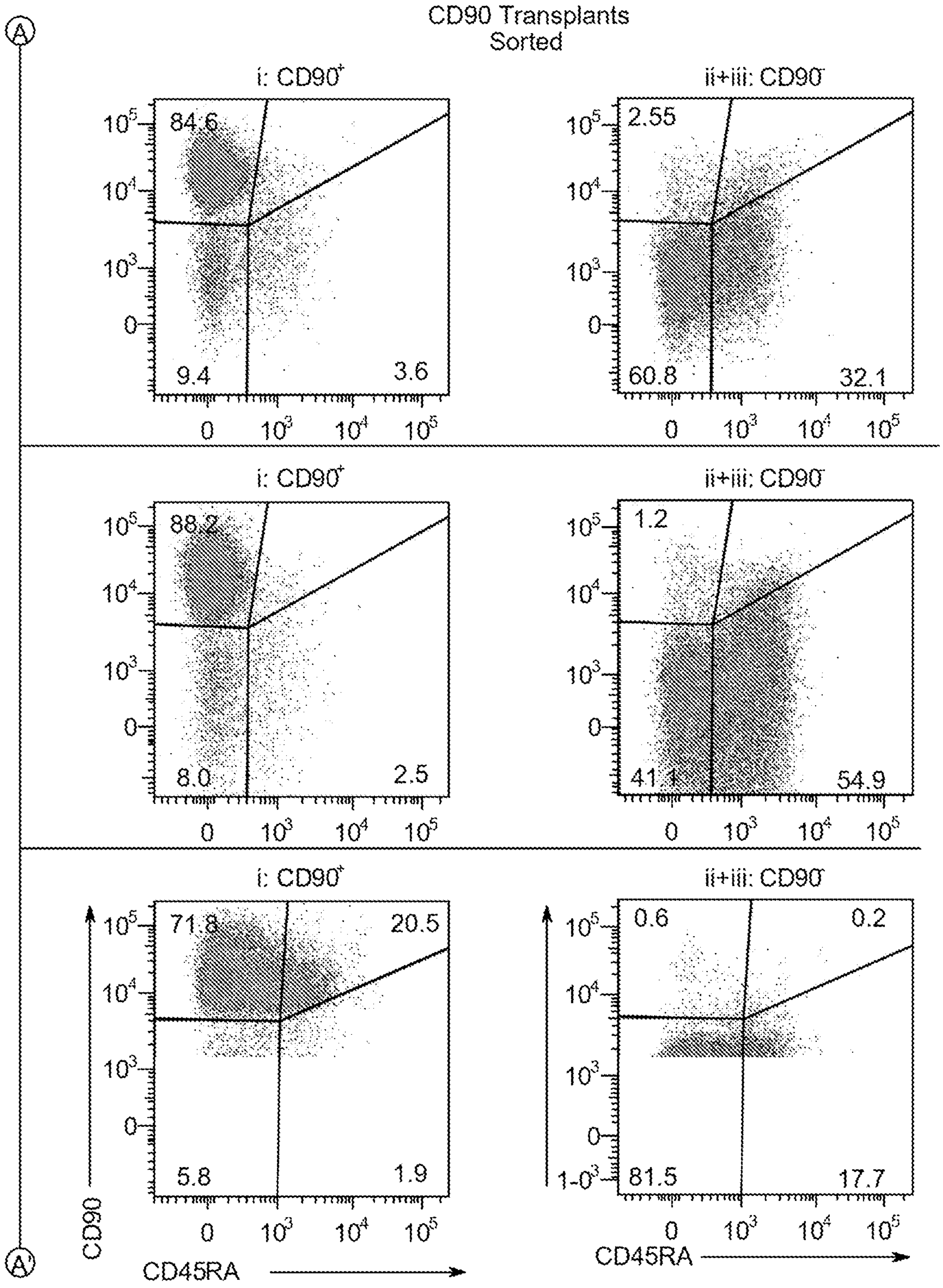
FIGS. 55A-55B provide flow cytometry analysis of infusion product pre- (FIG. 55A) and post- (FIG. 55B) CRISPR/Cas9 editing.
Figure 55A:
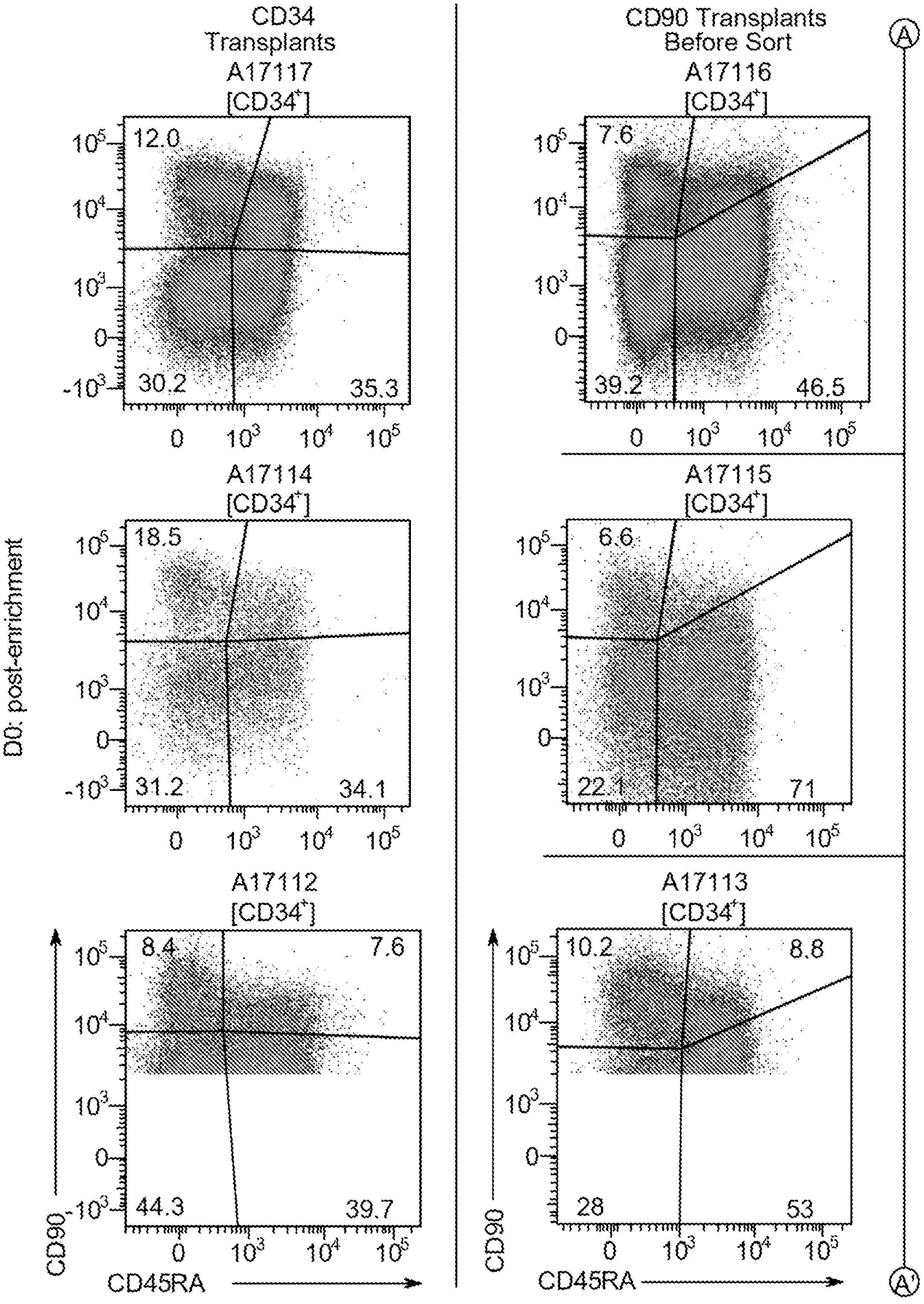
Figure 55B:
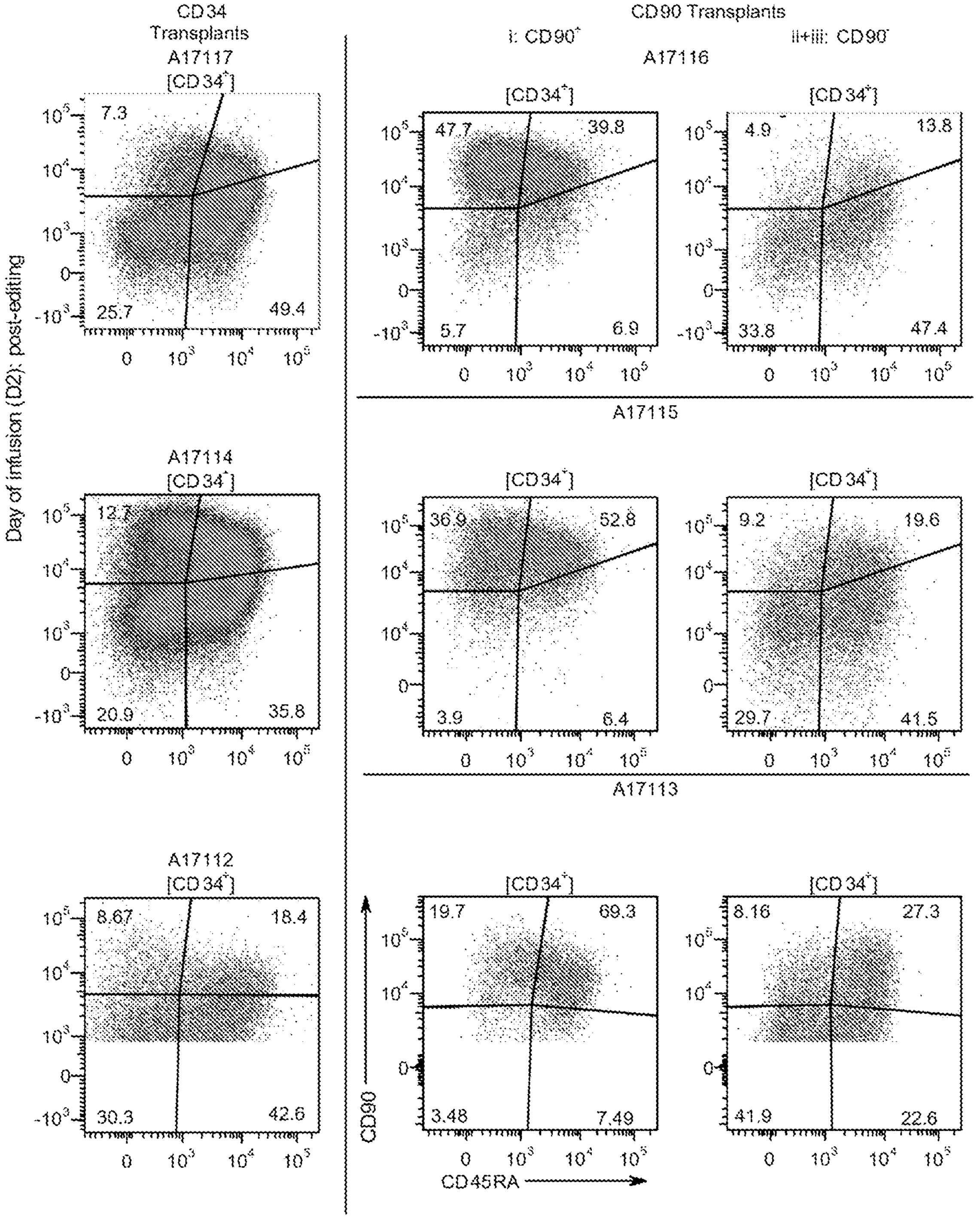
Figure 55B:
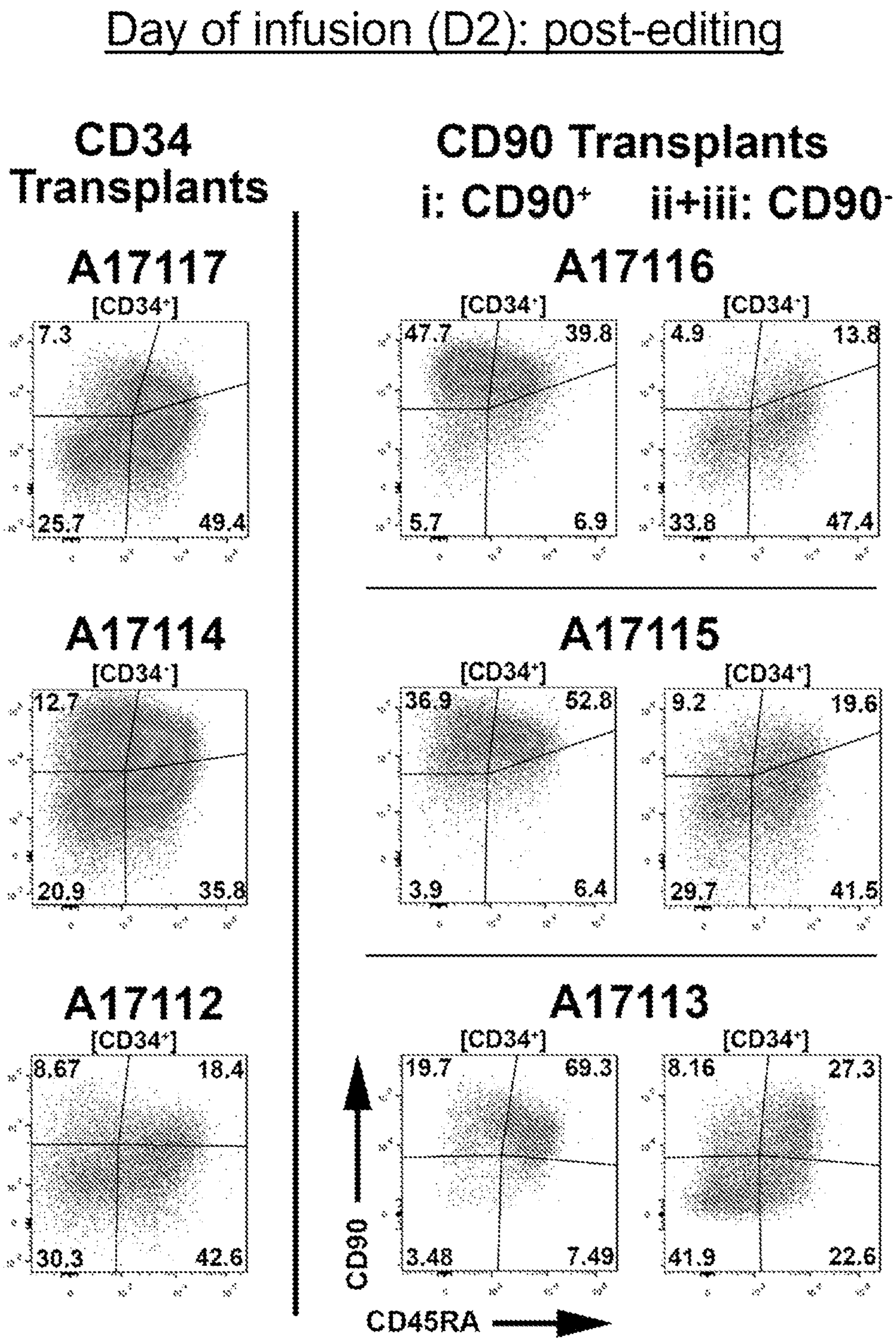
Figure 56A:
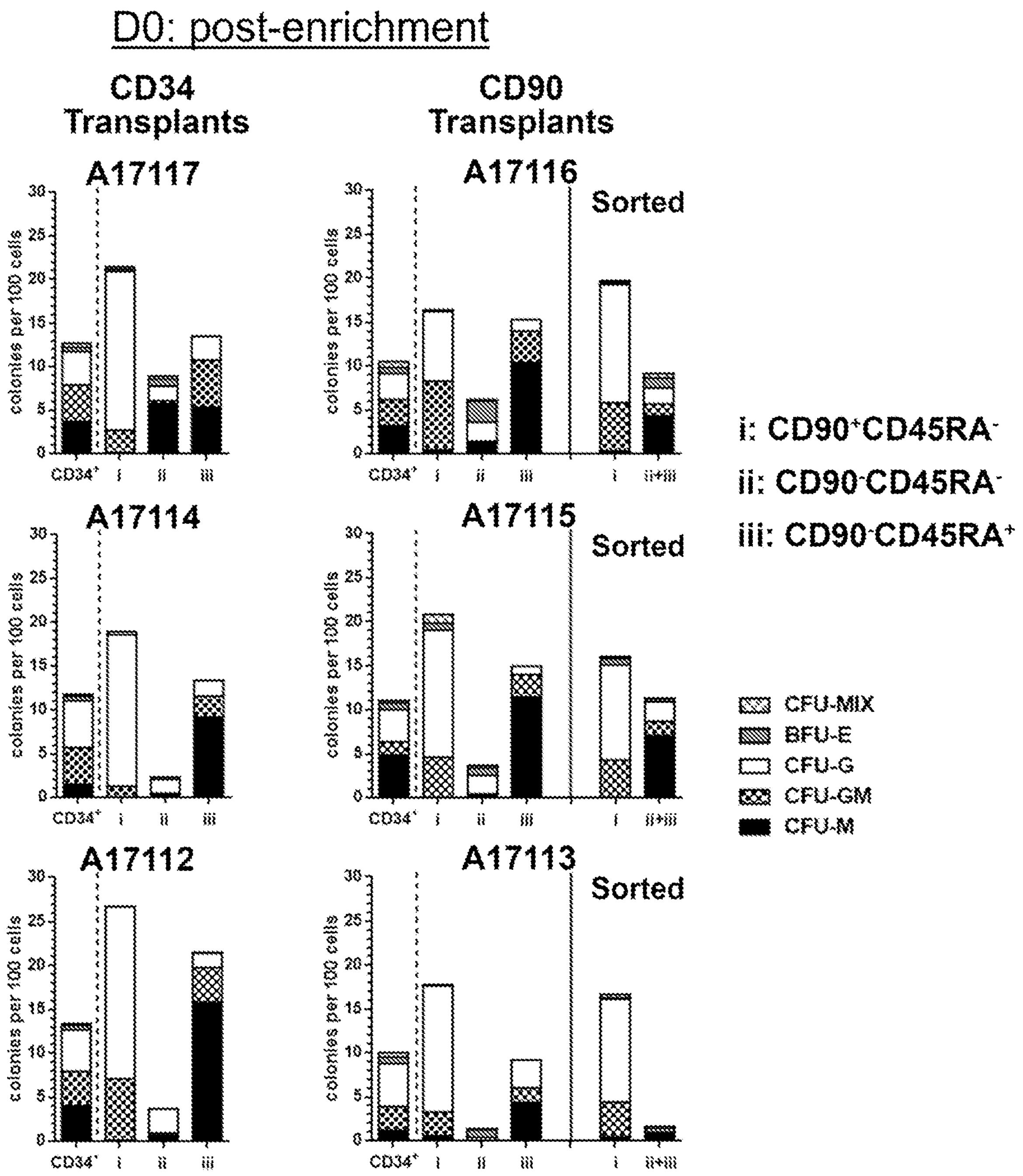
FIGS. 56A-56B provides colony-forming assays of infusion product pre- (FIG. 56A) and post- (FIG. 56B) editing.
Figure 56B:
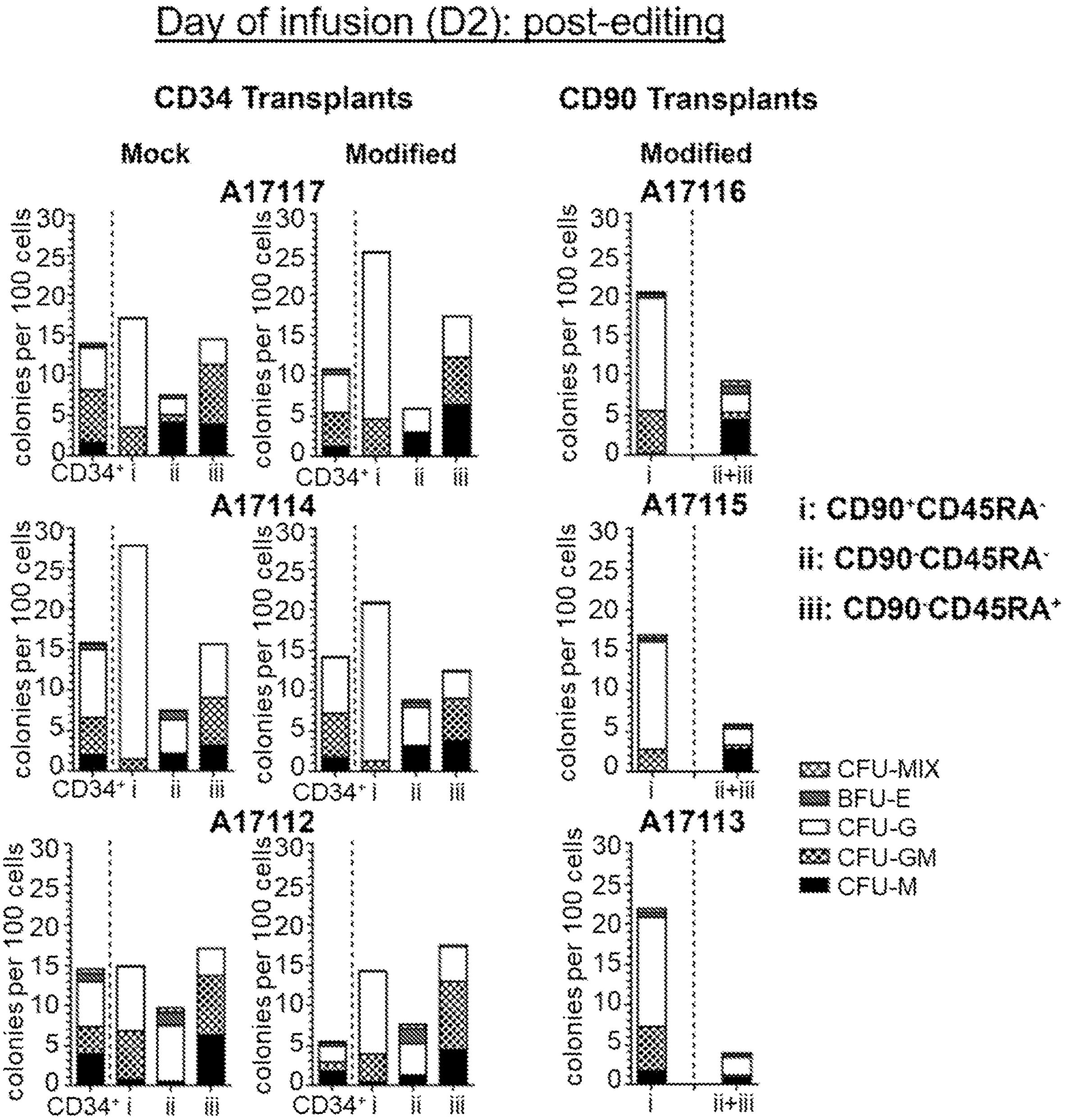
Figure 57:
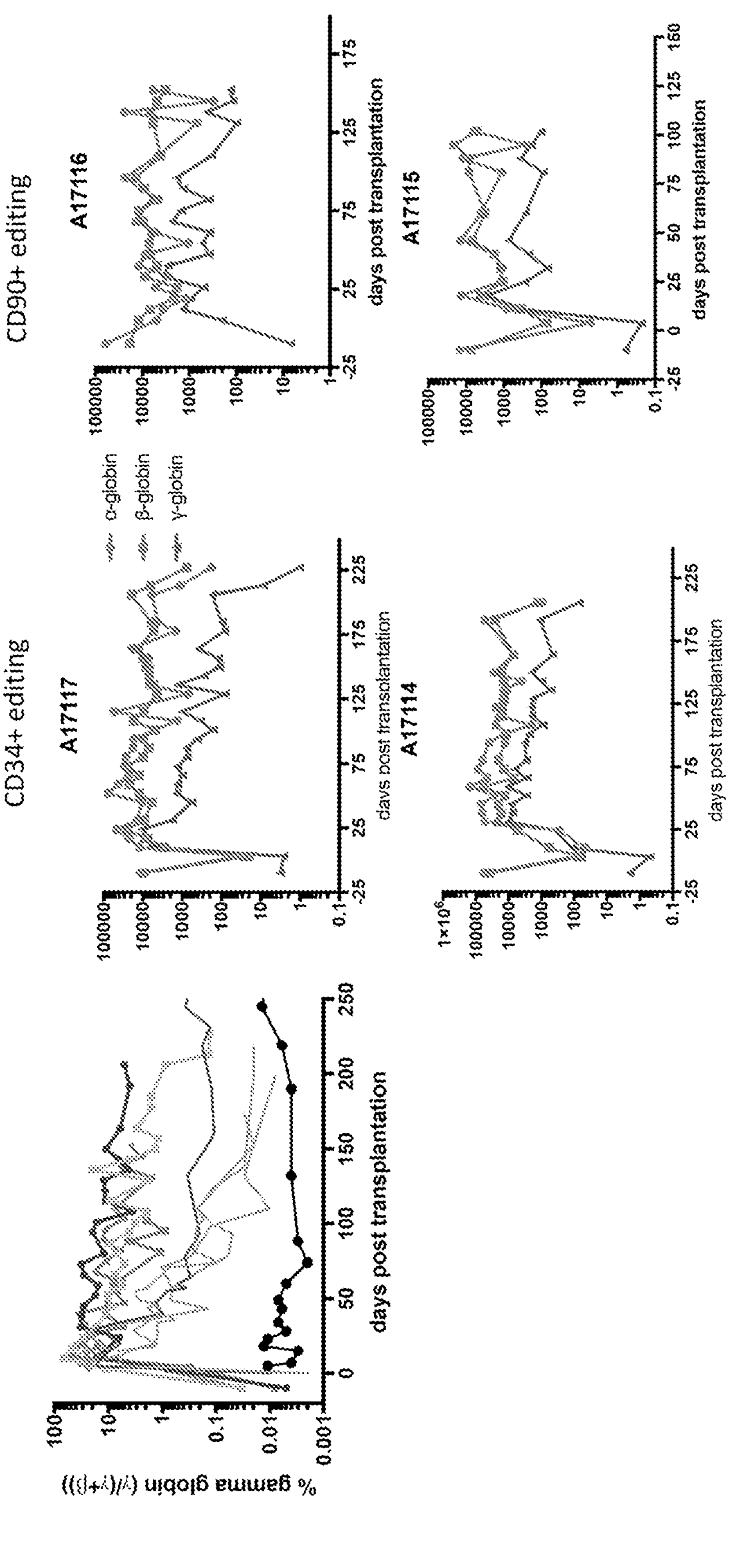
FIG. 57 shows quantitative PCR measurement of hemoglobin expression in peripheral blood of transplanted animals.
Figure 59:
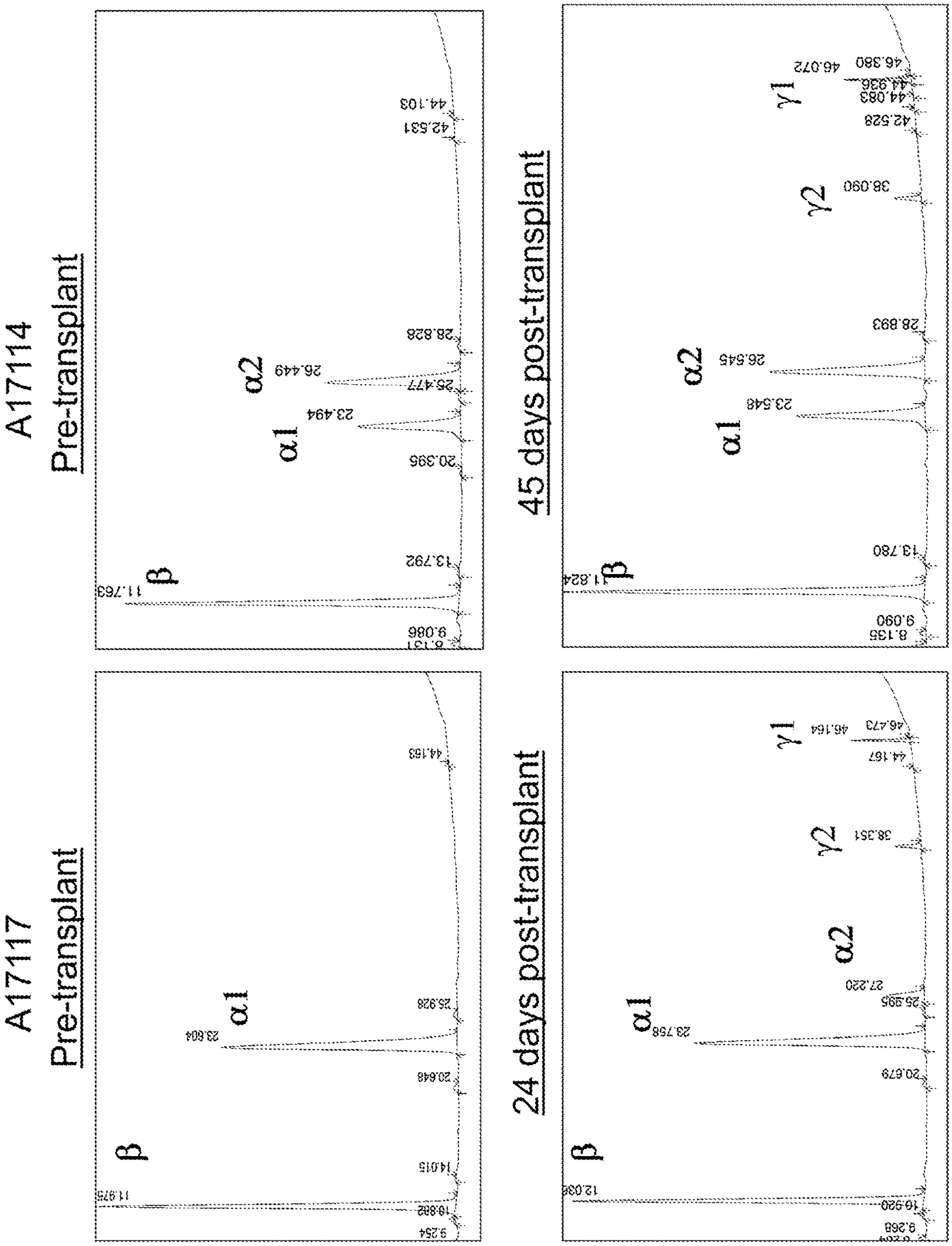
FIG. 59 shows representative HPLC profiles of peripheral blood from experimental animals pre- and post-transplant.
Figure 59:
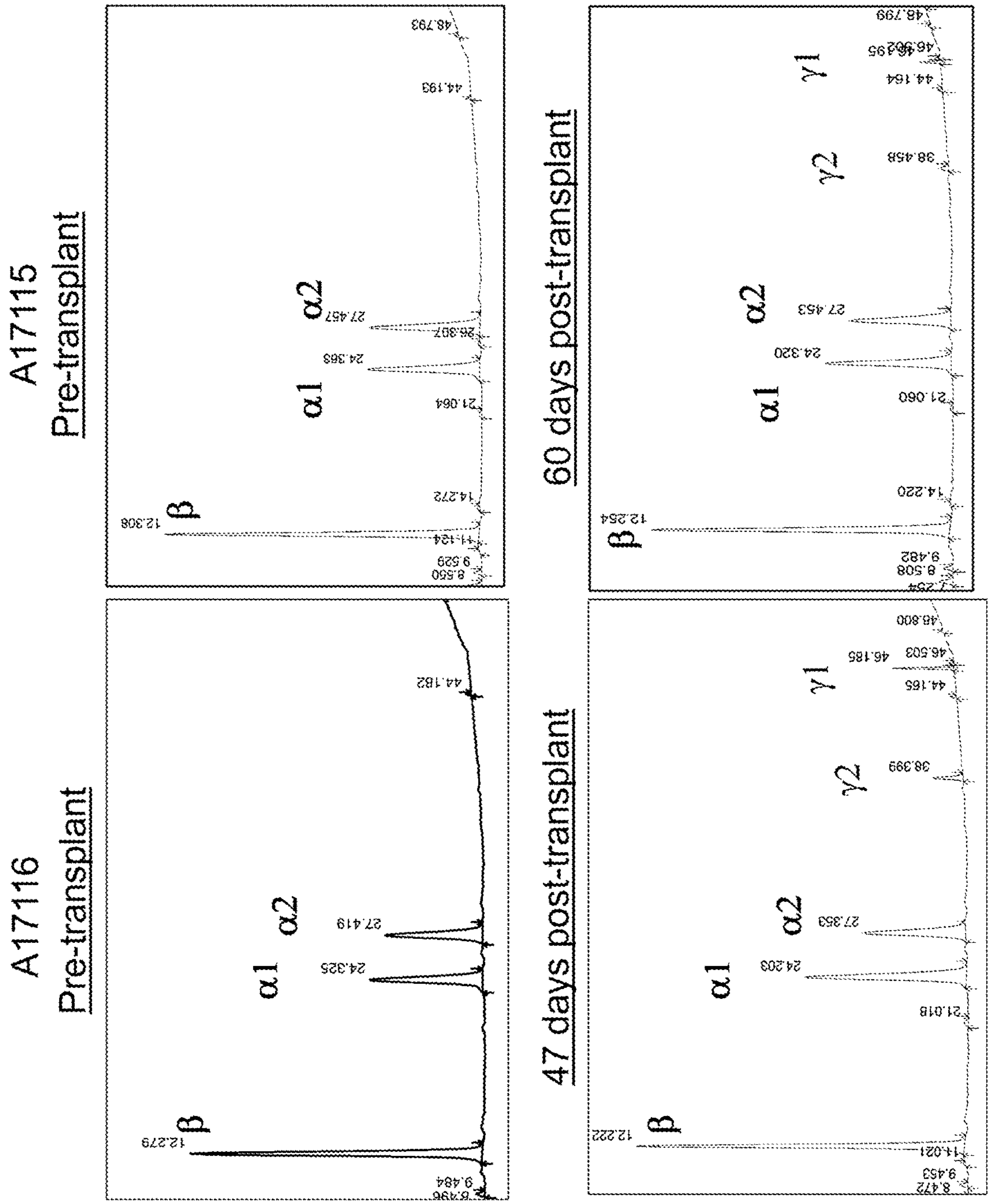

Week 24 human engraftment showed no significant differences in percent human engraftment between control and edited cells (FIG. 42). Engrafted edited CD34 cells generated all human hematopoietic lineages. Human erythroid, CD34+ Lymphoid and Myeloid, and CD19+ cells were all identified and sorted from harvested marrows following transplant (W24) (FIG. 43). The TALEN edited CD34 cells produced more F-Cells. At sac (A) there was a significantly higher rate of human F-Cells detected in the marrow, while differentiated CD34 cells from the marrow produced more F-Cells (B) (FIG. 44). Sorted cells from all lineages retained INDELs from TALEN editing. T7 Analysis demonstrated INDELS are present in vitro (FIG. 45). Secondary mice engraftments and marrow cells retained edits made; human engraftment at 9 weeks was low (<2%) but present and marrow cells retained edits at both loci.

Conclusions

It was demonstrated that TALEN mRNA mediated disruption of repressive elements in the promoters of the γ-hemoglobin genes HBG1 and HBG2 can result in the induction of fetal hemoglobin expression. These cells retain the ability to engraft in W41 mice and differentiate into multiple lineages while retaining the TALEN induced gene edits. The successful engraftment of hematopoietic cells in secondary mice suggests that at least a portion of the edited peripheral blood CD34 cells represent hematopoietic stem cells. A homologous repair template was successfully integrated at the cut site using the same TALEN mRNA to generate the double strand break resulting in the expression of both anti-sickling T87Q hemoglobin as well as increased levels of fetal hemoglobin. Additional repair templates allow for further exploration of controlling hemoglobin expression at this locus.

Example 4

CRISPR/Cas9-Edited Hematopoietic Stem and Progenitor Cells for the Reactivation of Fetal Hemoglobin A promising therapeutic strategy for hemoglobinopathies consists in the genome engineering of patients' hematopoietic stem and progenitor cells (HSPCs) to reactivate fetal hemoglobin (HbF) production, which can serve as substitute for defective or absent adult hemoglobin molecules. Here, the nonhuman primate (NHP) large animal transplantation model was used to address existing challenges for clinical translation of this approach to ensure efficient gene editing in scale-up conditions and optimize long-term engraftment of gene-edited cells.

Figure 61A:
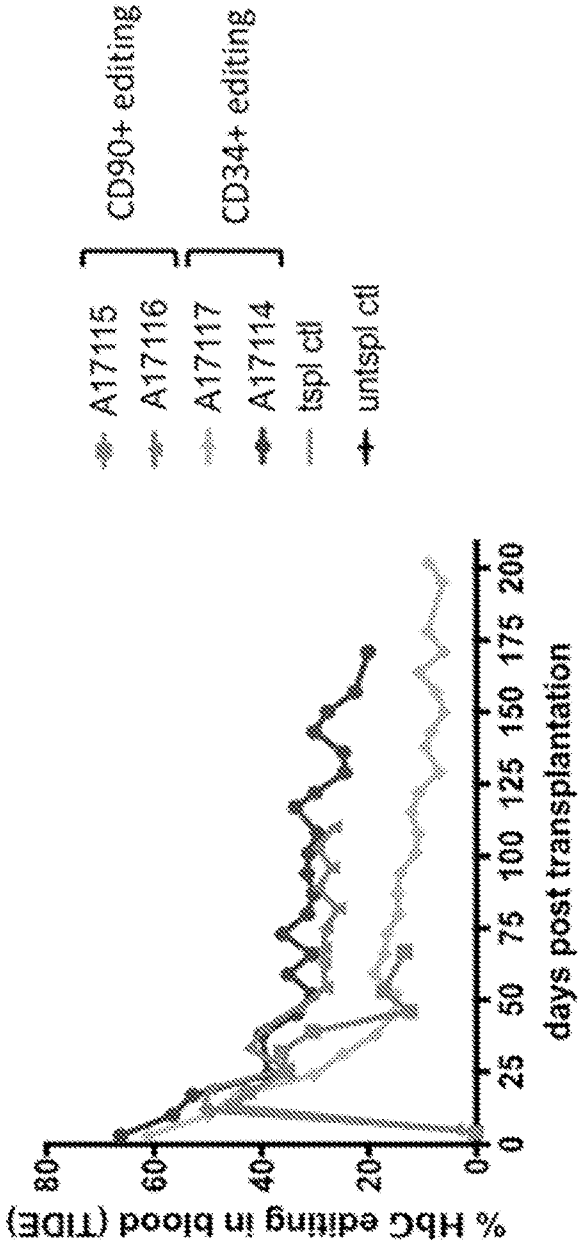
FIGS. 61A-61B shows.
Figure 61B:
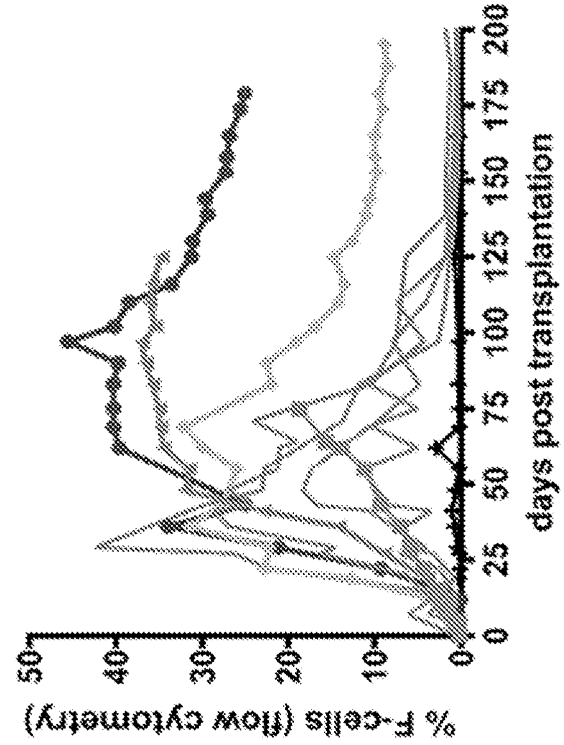
Figure 62A:
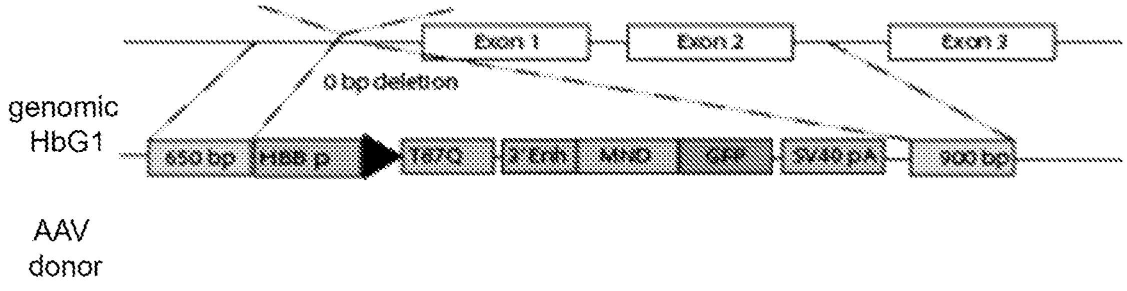
FIGS. 62A-62C demonstrate targeted integration of Globin T87Q/GFP donor cassette by HDR in Rhesus CD34+ HSPCs.
Figure 62B:
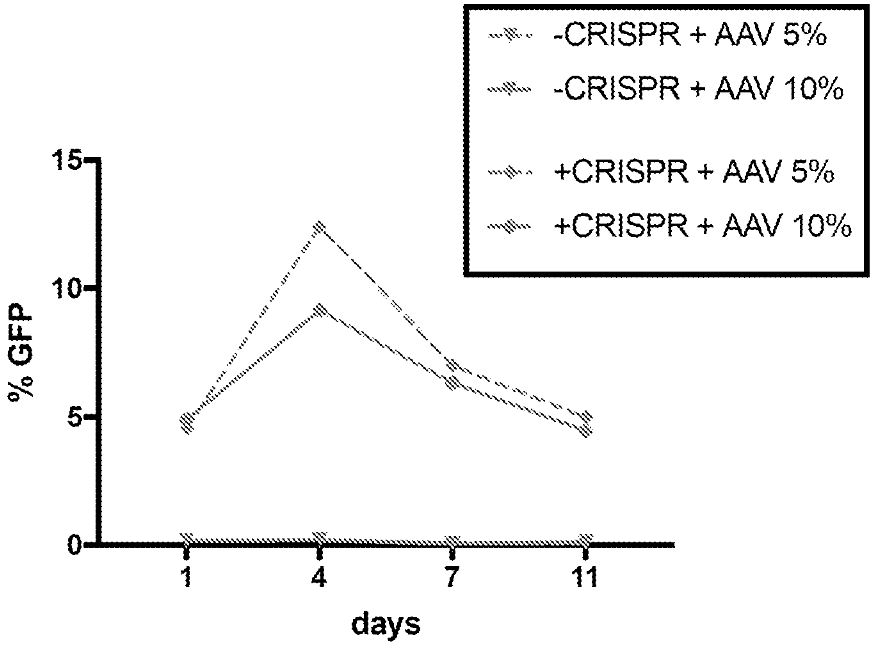
Figure 62C:
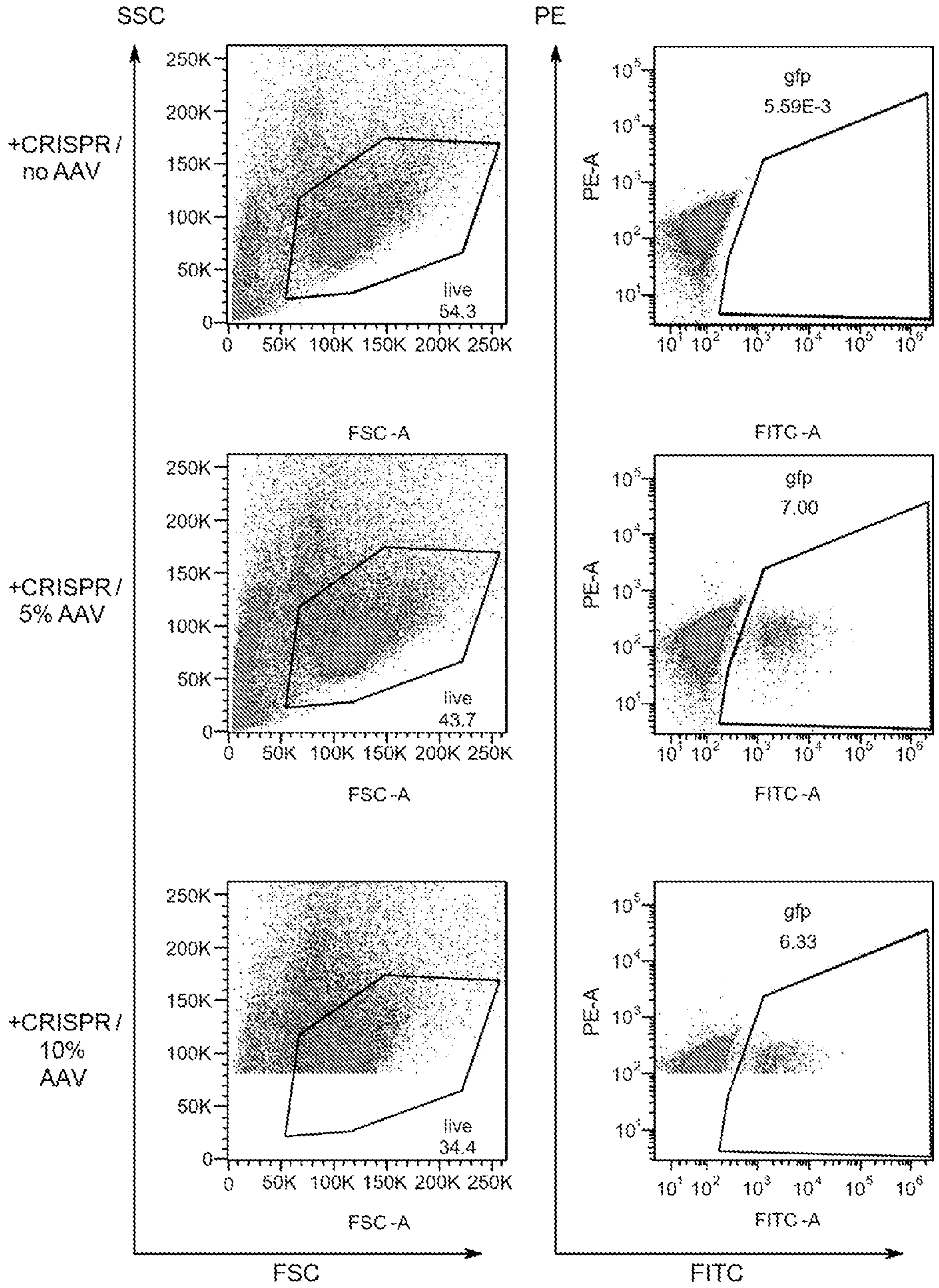

The CRISPR/Cas9 nuclease platform was employed to recapitulate a 13-nucleotide (nt) deletion in the gamma globin gene promoter identified in individuals with hereditary persistence of fetal hemoglobin (HPFH). Two rhesus macaques were transplanted with bone marrow-derived CD34+ cells edited ex vivo by CRISPR/Cas9 ribonucleoprotein electroporation. 70% editing efficiency was detected in the infusion product, with over 25% of cells containing the 13-nt deletion. Both animals showed rapid hematopoietic recovery and peripheral blood gene editing levels stabilized at 15% and 30%, respectively, at 6 months post transplantation (FIG. 61A). HbF production, as determined by peripheral blood F-cells staining (FIG. 61B) and quantitative PCR, was substantially increased in both animals as compared to controls and correlated with in vivo editing levels.

Figure 60A:
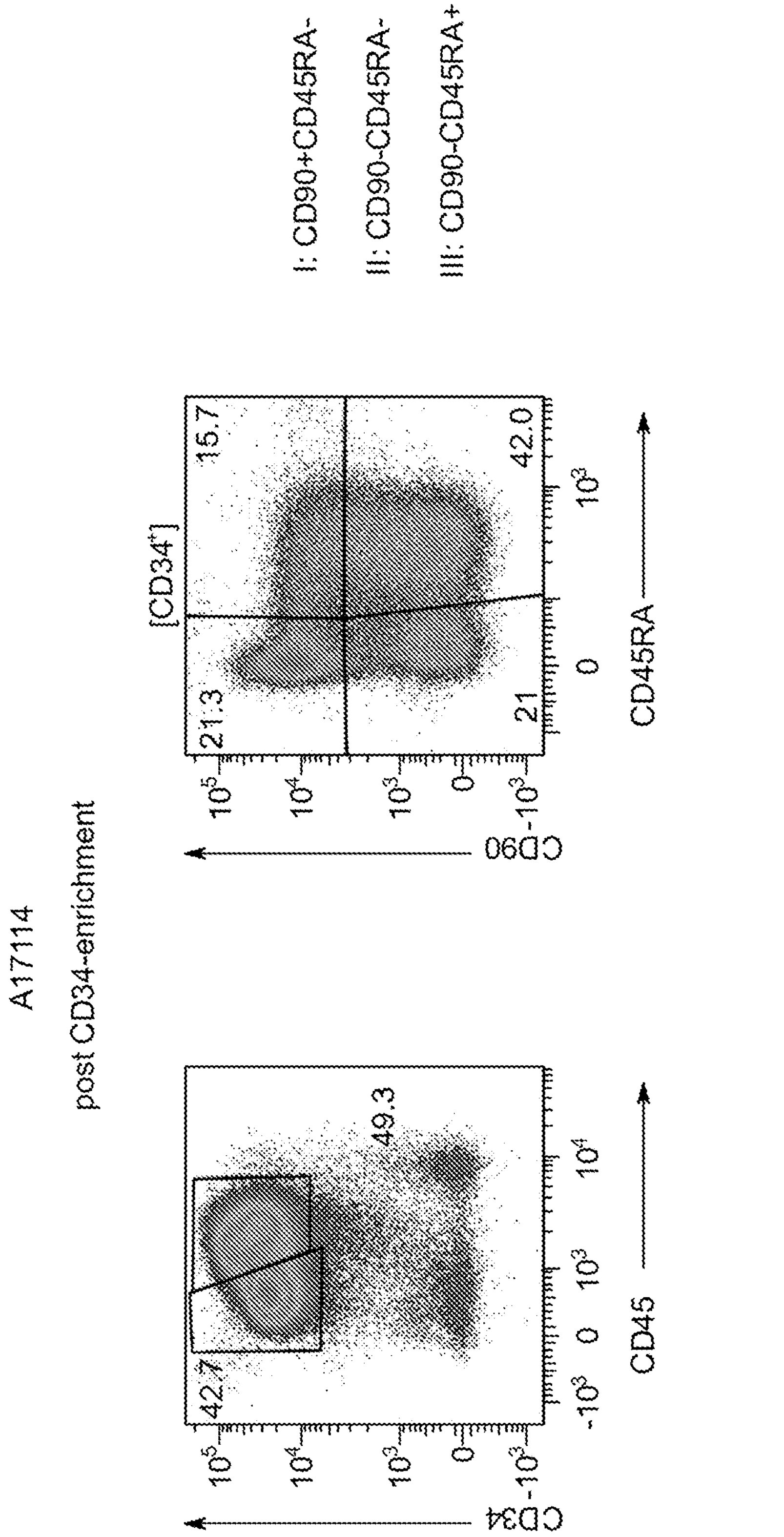
FIGS. 60A-F provides validation of sorting approach from bone marrow analysis of animal models A17114 and A17116.
Figure 60B:
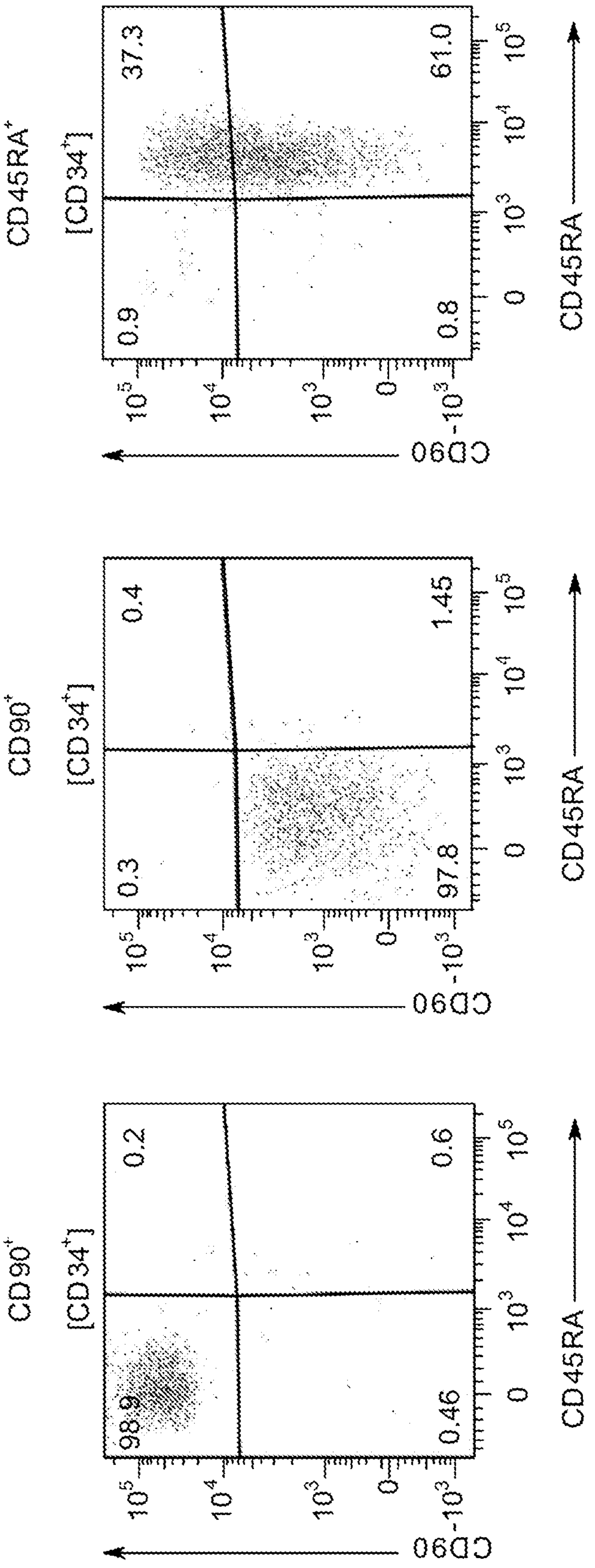
Figure 60C:
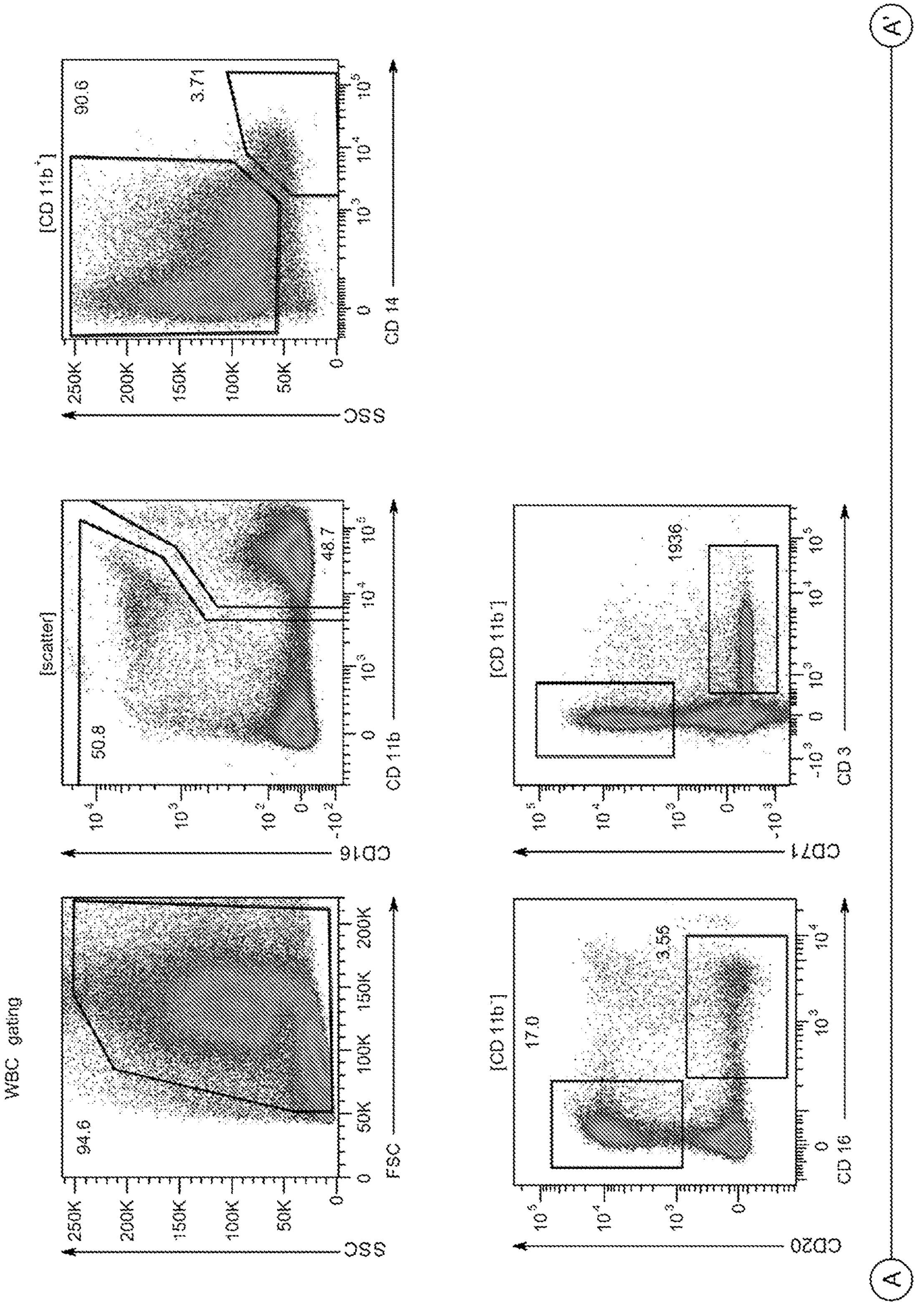
Figure 60C:
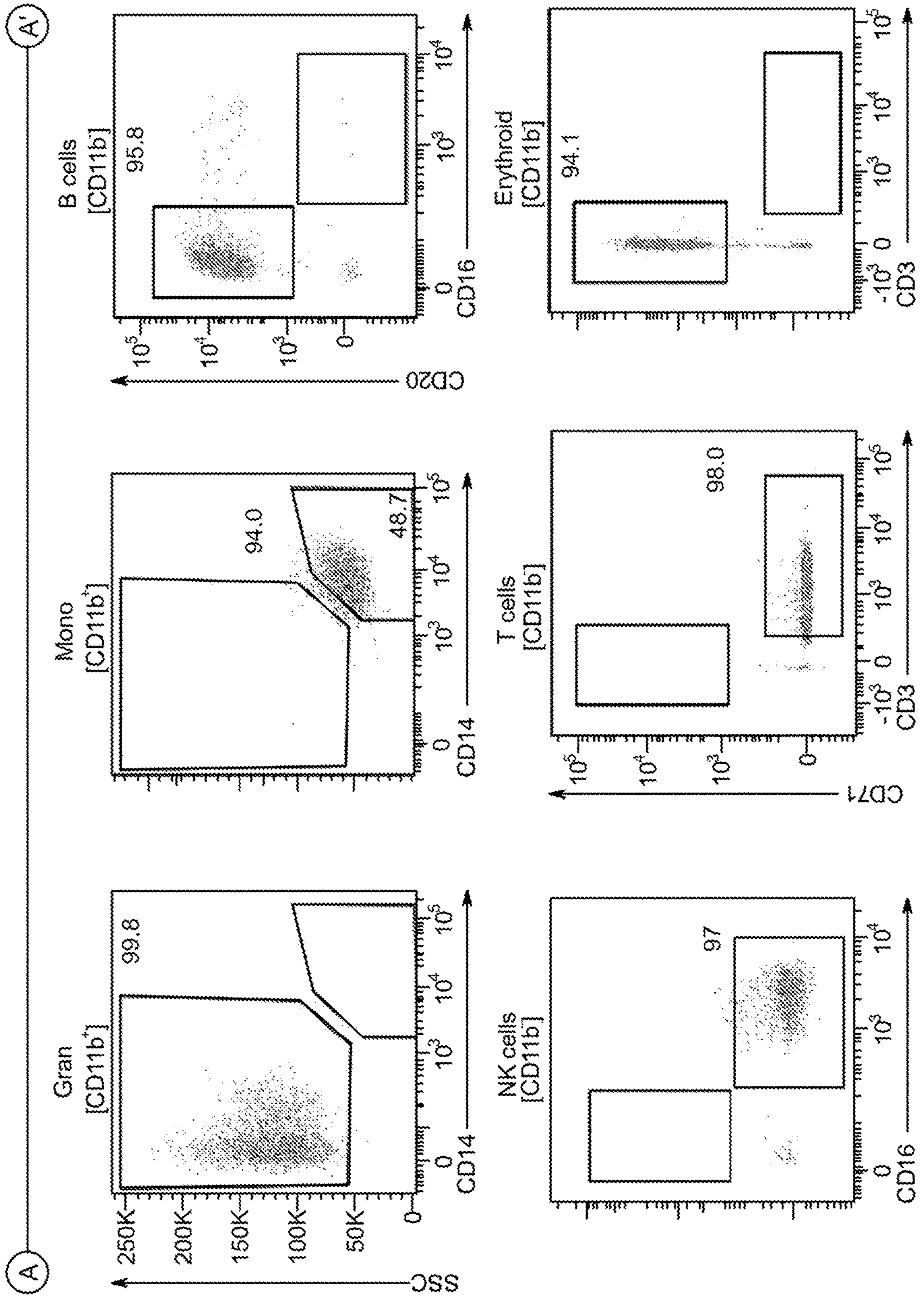
Figure 60D:
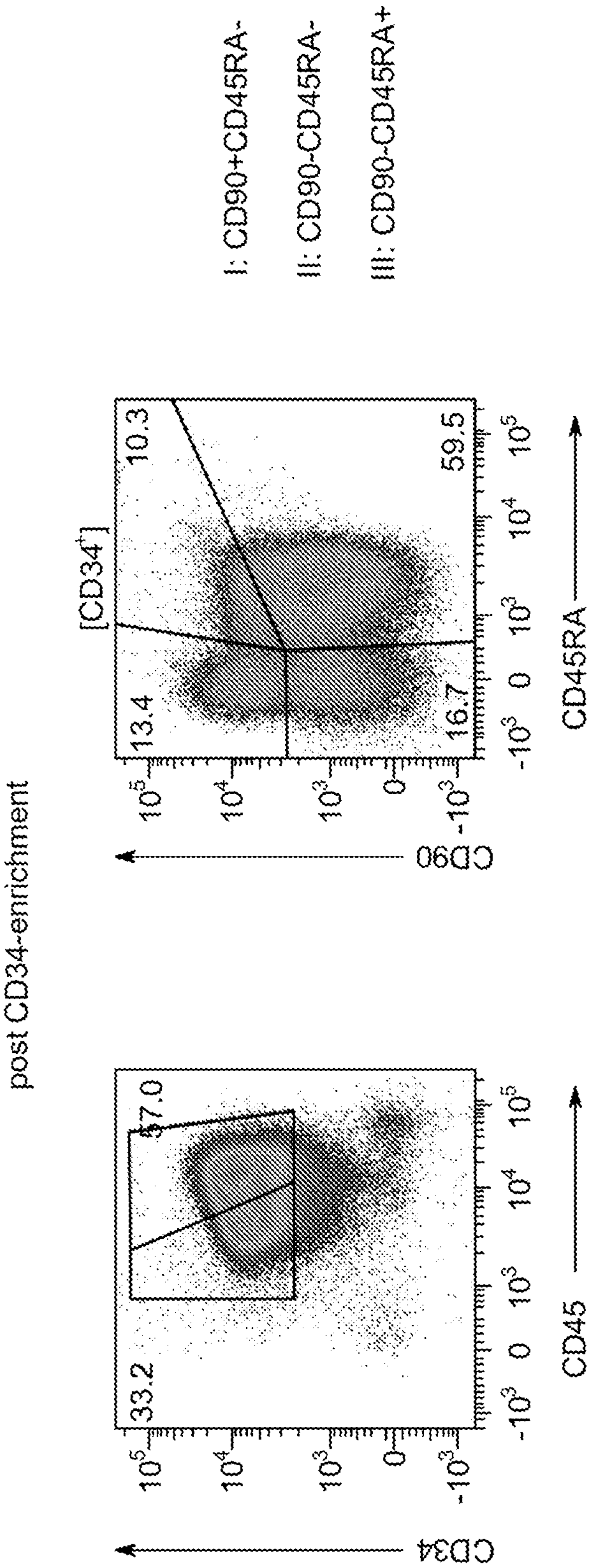
Figure 60E:
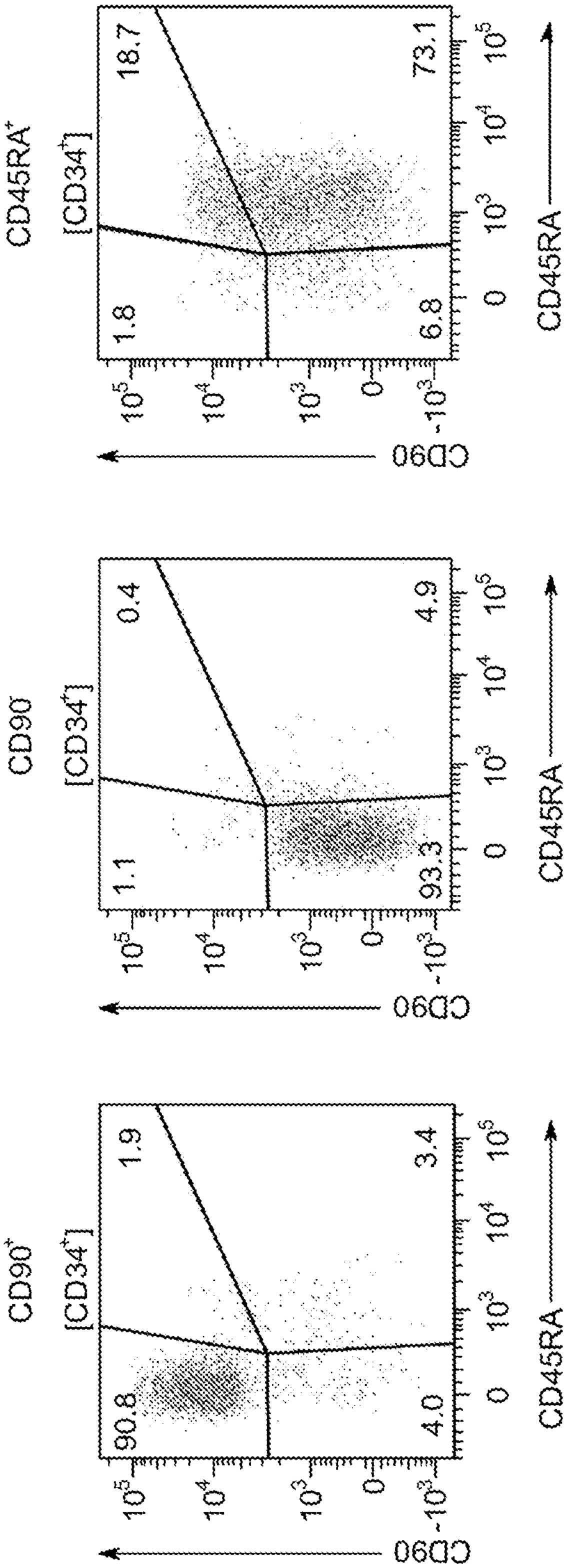
Figure 60F:
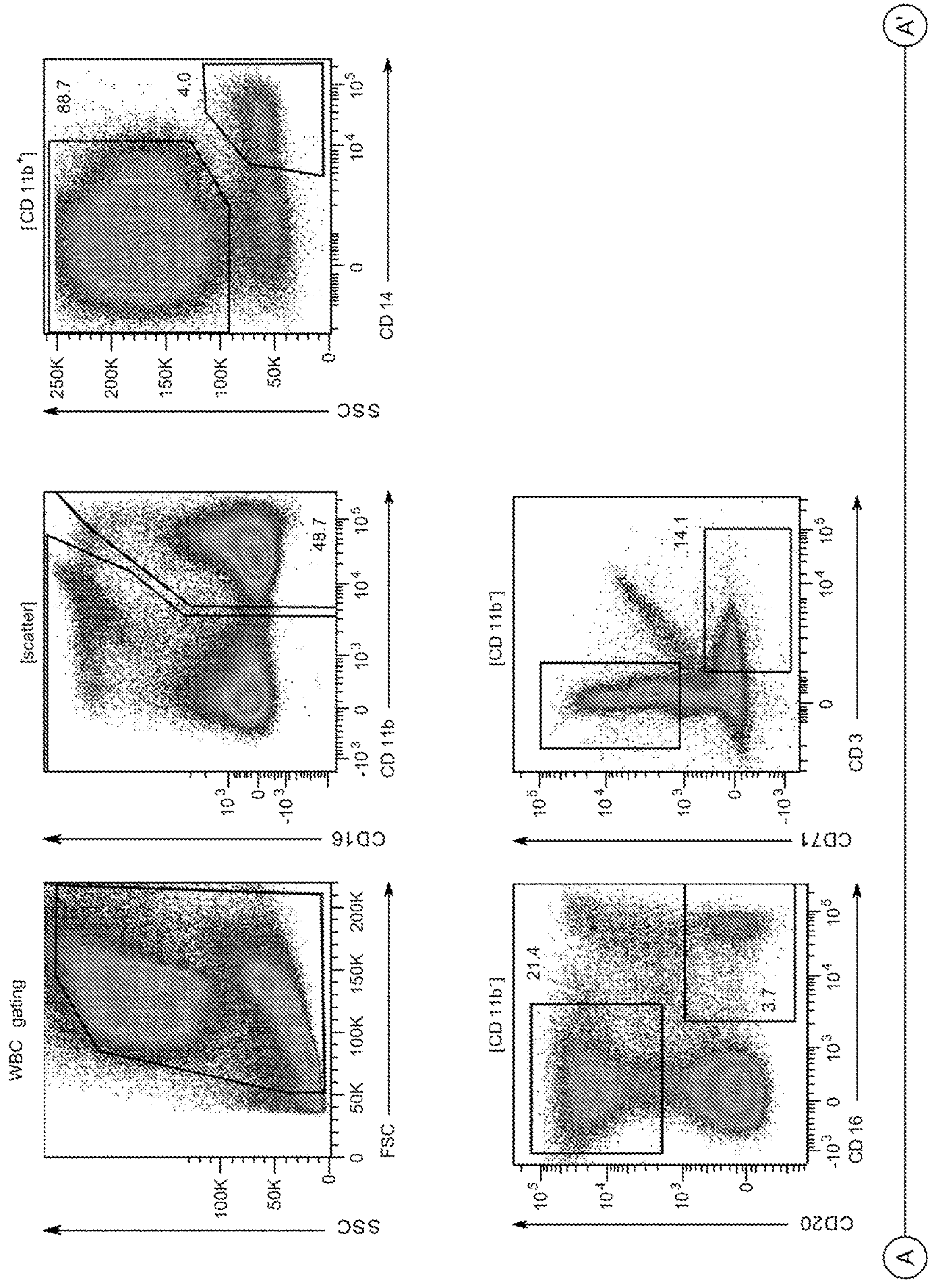
Figure 60F:
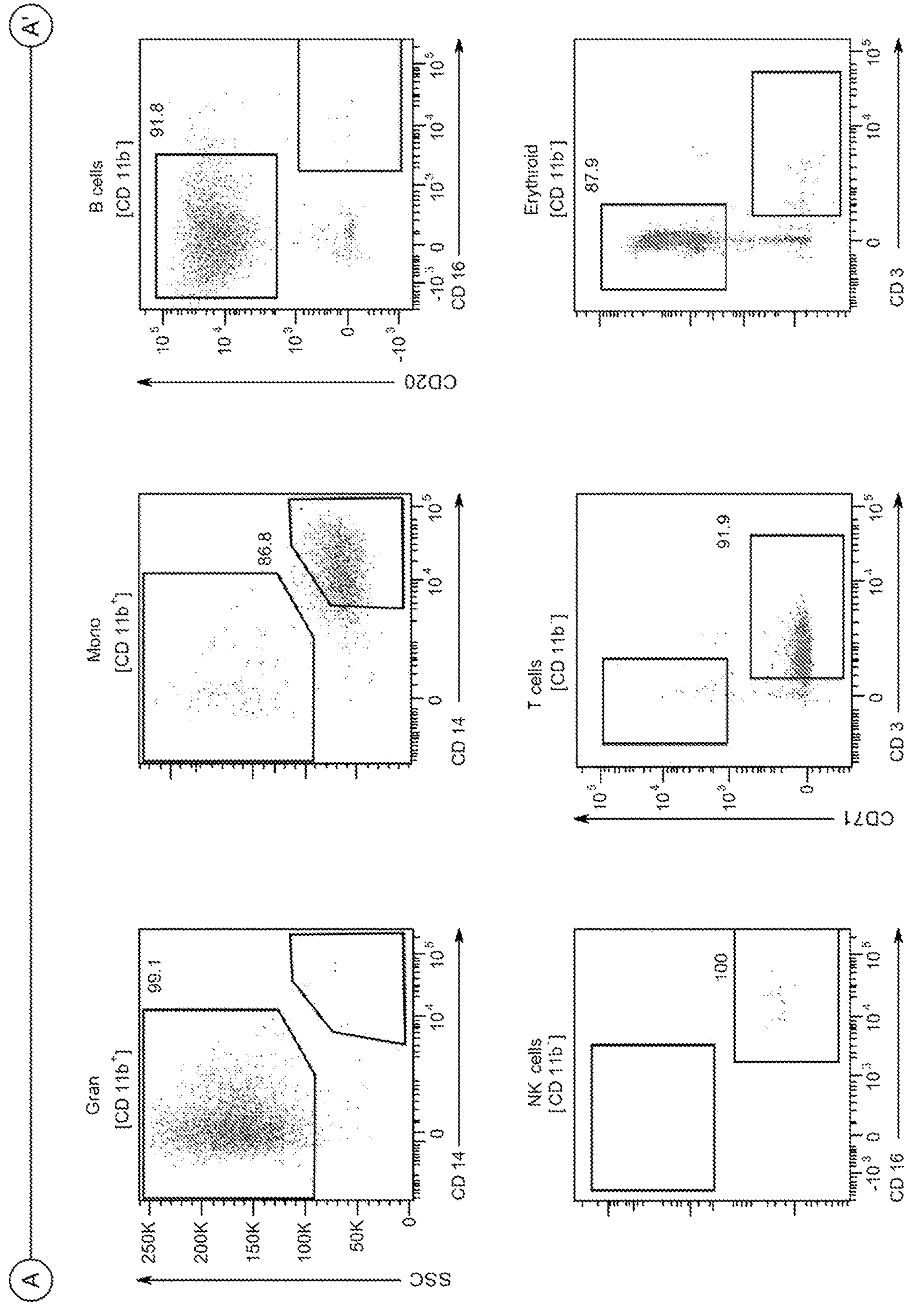

To circumvent challenges associated with scale up and cost of editing reagents, the transplantation protocol was further optimized by purifying a refined and more highly enriched target cell population ($CD34^+CD45RA^-CD90^+$) (described in PCT Application No. WO2017/218948, which is incorporated herein by reference in its entirety), and capable of both rapid short-term and as durable multilineage hematopoietic reconstitution. Two rhesus macaques were co-infused with this CRISPR/Cas9-edited subset (comprising only 5-7% of total CD34+ cells) along with the remaining un-edited cells. In vivo gene-editing levels started at less than 5% but rapidly increased to 50% within a week, and persisted at efficiencies comparable to animals receiving edited CD34+ cells, consistent with this refined cell subset as major contributor to hematopoietic recovery (FIG. 60A).

Taken together, these data demonstrate robust engraftment of CRISPR/Cas9-edited HSPCs following targeting of the 13nt-HPFH site in the NHP model leading to high levels of HbF production. In addition, efficient editing and engraftment of the CD90+ cell subset is shown, an approach that reduces the required amount of editing reagents by 95%, circumvents challenges associated with scale up, without compromising editing or engraftment efficiencies, and thereby facilitating clinical translation of gene editing for the treatment of hemoglobinopathies.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Sequence Information

| SEQ ID NO | NAME | SEQUENCE |
|---|---|---|
| 1 | HPFH sequence | CTTGACCAATAGCCTTGACAA |
| 2 | HPFH sequence | GACCAATAGCCTTGAC |
| 3 | HPFH sequence | CAATAGCCTTGAC |
| 4 | HPFH sequence | GACCAATAGC |
| 5 | HPFH sequence | CCAAT |
| 6 | HPFH sequence | CAAT |
| 7 | gamma globin target sequence | CTCAGGATCCACATGCAGCTTGTCACAGTGCAGTTCACTCAGCTGG<br>GCAAAGGTGCCCTTGAGATCATCCAGGTGCTTTGTGGCATCTCCCA<br>AGGAAGTCAGCACCTTCTTGCCATGTGCCTTGACTTTGGGGTTGCC<br>CATGATGGCAGAGGCAGAGGACAGGTTGCCAAAGCTGTCAAAGA<br>ACCTCTGGGTCCATGGGTAGACAACCAGGAGCCTGTGAGATTGAC<br>AAGAACAGTTTGACAGTCAGAAGGTGCCACAAATCCTGAGAAGCG<br>ACCTGGACTTTTGCCAGGCACAGGGTCCTTCCTTCCCTCCCTTGTC<br>CTGGTCACCAGAGCCTACCTTCCCAGGGTTTCTCCTCCAGCATCTT<br>CCACATTCACCTTGCCCCACAGGCTTGTGATAGTAGCCTTGTCCTC<br>CTCTGTGAAATGACCCATGGCGTCTGGACTAGGAGCTTATTGATA<br>ACCTCAGACGTTCCAGAAGCGAGTGTGTGGAACTGCTGAAGGGTG<br>CTTCCTTTTATTCTTCATCCCTAGCCAGCCGCCGGCCCCTGGCCTCA<br>CTGGATACTCTAAGACTATTGGTCAAGTTTGCCTTGTCAAGGCTAT<br>TGGTCAAGGCAAGGCTGGCCAACCCATGGGTGGAGTTTAGCCAGG<br>GACCGTTTCAGACAGATATTTGCATTGAGATAGTGTGGGGAAGGG<br>GCCCCCAAGAGGATACTGCTAATTTTTTTTATAGCCTTTGCCTTGTT<br>CCGATTCAGTCATTCCAGTTTTTCTCTAATTTATTCTTCCCTTTAGC<br>TAGTTTCCTTCTCCCATCATAGAGGATACCAGGACTTCTTTTGTCA<br>GCCGTTTTTTACCTTCTTGTCTCTAGCTCCAGTGAGGCCTGTAGTTT<br>AAAGCTAAAGCATGTACCAATTTTTGAAAAGTTCAGGGATTGTGA<br>AATGTGTTTTAGGCATAGGTCCAGGATTTTTGACGGGACAAATCTT<br>AGTCTCTTTCAGTTAGCAGTGGTTTCTAAGGAAAAAGTGCTATACT<br>TCTTTTTGAATATACTCTTTGTGACTTTTGCCATTATCTCTTAATTT<br>CTCAATAGTGCAGTGAAAACAATTTCTATAAAGCCACAGTTTCAG<br>CGCAGTAATAGATTAGTGTTACATAATATAAGACCTAATGCTTACC<br>TCAATATCTACTTATCCGTACCTATTTGAAATAAATCATGACTGTT<br>TCATCTTAGAAAAATATTTGATTCCATATTCAGGTATGTATGTATA<br>CACCAGATGATGTGTATTTACCACTGGATAAGTGTGTGTGCTGGCT<br>GATGACCCAGGGTTTTGGCGTAGCTCTTCTATGCTCAGTAAAGATG<br>ATGGTAGAATGTTCTTTGGCAGGTACTGTGGATTAGAATTAATTAT<br>CTTGTATAAATGCTAGGTTCACTTCTCAGGGAATCTTACTCTAAGA<br>CATAAGATGTGCGTGTACATGGAAAACAACTCTAAAGAGGCAAGG<br>GTTGTTTTTATTGACTAATAGTCCACACACTATTATAACTCGAATA<br>TTAGTGTACTTTAGACAGCTTTATTTCTAACACAGTGCTGTTTCTG |

-continued

| SEQ ID NO | NAME | SEQUENCE |
|---|---|---|
| | | ACATATTGGACCATTAACAGGGTAGGAAGTATTTATGGTGGTTTTT<br>TGGTTCTGTTTTGCTTTTGGTTAGTTTGTTTTTGTTTTTCTCTGAAAG<br>TGATCCATGATCTCTAACCTTGCTAGATTATAATGCCAGAAGCTCT<br>GGAATTCTGGCTTATCGGAGGCAAGCTGTATCTTCAAATTAGTTTA<br>TCCCCTAAGCTATCAGGTTGATTGAAATTATTATAATATTGGTGAA<br>ATTCTTTCATCCTTCATGATCCTGTGTAAAGCTTATATCTGCTCATT<br>GATACAGATGGCTAAAAGGCCAGAAAGACACACATTTACCCATGT<br>AACAAGCCTGCACATCCTGCACATGTACCTTCGAAATTAAAATGA<br>AATGAAATAAAATTAAAAGGAAAAAAATGCCATGGCAACATCAG<br>GAAGTTATCTTTTATGGTCTAAAAATGGGCAGCATAAATAATCTAC<br>CCCTTGTTTAGCATACTATTGAAAAATAACAATAAAAATCGGCAA<br>CCAGTAGCCCTTGCGTCTACTCTGCCTATGAAGTAGCCATTCATTT<br>ATTCCTTCAATTTTTTATAAACTTGTTTTACTAAAAAAAAAAAAGGA<br>CAAAGAAAGAAAGTGCGAATTGTGAAATGGTAGTGAGTGATGGC<br>ATTTGAAGTGGGTCCTTTATGATTTGATGGAGCCAGGCAGAAGAC<br>GTTTGGAGAAAGAAGTTCCTGAAAGTAGGAAGGGCATGTGGAAA<br>ACTCTGAGGCTGAGGAAAAAAAAGAAAGAAAGAAATATAAAGAA<br>AGAACTTGACATTTCACTGTATATAAACACATTACAAGCCTAAAG<br>TACGTTGAAGAAAAAATAGAATTCAAAGTTAGACAGAAGGGCTCA<br>GGCTTACTATTTGCATCTTACAGATGAGAGTAGTAGAGTTGGTATT<br>TTATTCTGAAACACAGAGGACAAGTGGAGATTTGTAAACCTGAGA<br>TAAACATGGTTTCTAATCCACTGAACACCGAAGCTTATTTTTTTCT<br>CTTTCTTCATCTGCCTTACTTAGTGCAAGGTGCTATAACAAAATAG<br>CATAGACTGGGTGACTTCAACAACAGGATTTTTTCTCACTTTTCTG<br>CTGGTTCCTGGTCAGGGCTCTCTTCCTGGGTTGCAGGTGGCTGACT<br>TCCCACTGTGTCCTCACCAGAAGGAAGAGAAATGGCTAATCTCTC<br>TGCTTCTGATGAGGAAAATAATTCTATGATGGGGATCTGCTCTCAT<br>GAGCTCCTCTAAACCTGATTACTTTTCCAAAGCCTCCCCCACAAAT<br>GG |
| 8 | gamma globin target sequence | CCATTTGTGGGGGAGGCTTTGGAAAAGTAATCAGGTTTAGAGGAG<br>CTCATGAGAGCAGATCCCCATCATAGAATTATTTTCCTCATCAGAA<br>GCAGAGAGATTAGCCATTTCTCTTCCTTCTGGTGAGGACACAGTGG<br>GAAGTCAGCCACCTGCAACCCAGGAAGAGAGCCCTGACCAGGAA<br>CCAGCAGAAAAGTGAGAAAAAATCCTGTTGTTGAAGTCACCCAGT<br>CTATGCTATTTTGTTATAGCACCTTGCACTAAGTAAGGCAGATGAA<br>GAAAGAGAAAAAAATAAGCTTCGGTGTTCAGTGGATTAGAAACCA<br>TGTTTATCTCAGGTTTACAAATCTCCACTTGTCCTCTGTGTTTCAGA<br>ATAAAATACCAACTCTACTACTCTCATCTGTAAGATGCAAATAGTA<br>AGCCTGAGCCCTTCTGTCTAACTTTGAATTCTATTTTTTCTTCAACG<br>TACTTTAGGCTTGTAATGTGTTTATATACAGTGAAATGTCAAGTTC<br>TTTCTTTATATTTCTTTCTTTCTTTTTTTTCCTCAGCCTCAGAGTTTT<br>CCACATGCCCTTCCTACTTTCAGGAACTTCTTTCTCCAAACGTCTTC<br>TGCCTGGCTCCATCAAATCATAAAGGACCCACTTCAAATGCCATC<br>ACTCACTACCATTTCACAATTCGCACTTTCTTTCTTTGTCCTTTTTTT<br>TTTTAGTAAAACAAGTTTATAAAAAATTGAAGGAATAAATGAATG<br>GCTACTTCATAGGCAGAGTAGACGCAAGGGCTACTGGTTGCCGAT<br>TTTTATTGTTATTTTTCAATAGTATGCTAAACAAGGGGTAGATTAT<br>TTATGCTGCCCATTTTTAGACCATAAAAGATAACTTCCTGATGTTG<br>CCATGGCATTTTTTTCCTTTTAATTTTATTTCATTTCATTTTAATTTC<br>GAAGGTACATGTGCAGGATGTGCAGGCTTGTTACATGGGTAAATG<br>TGTGTCTTTCTGGCCTTTTAGCCATCTGTATCAATGAGCAGATATA<br>AGCTTTACACAGGATCATGAAGGATGAAAGAATTTCACCAATATT<br>ATAATAATTTCAATCAACCTGATAGCTTAGGGGATAAACTAATTTG<br>AAGATACAGCTTGCCTCCGATAAGCCAGAATTCCAGAGCTTCTGG<br>CATTATAATCTAGCAAGGTTAGAGATCATGGATCACTTTCAGAGA<br>AAAACAAAAACAAACTAACCAAAAGCAAAACAGAACCAAAAAAC<br>CACCATAAATACTTCCTACCCTGTTAATGGTCCAATATGTCAGAAA<br>CAGCACTGTGTTAGAAATAAAGCTGTCTAAAGTACACTAATATTC<br>GAGTTATAATAGTGTGTGGACTATTAGTCAATAAAAACAACCCTT<br>GCCTCTTTAGAGTTGTTTTCCATGTACACGCACATCTTATGTCTTAG<br>AGTAAGATTCCCTGAGAAGTGAACCTAGCATTTATACAAGATAAT<br>TAATTCTAATCCACAGTACCTGCCAAAGAACATTCTACCATCATCT<br>TTACTGAGCATAGAAGAGCTACGCCAAAACCCTGGGTCATCAGCC<br>AGCACACACACTTATCCAGTGGTAAATACACATCATCTGGTGTAT<br>ACATACATACCTGAATATGGAATCAAATATTTTTCTAAGATGAAA<br>CAGTCATGATTTATTTCAAATAGGTACGGATAAGTAGATATTGAG<br>GTAAGCATTAGGTCTTATATTATGTAACACTAATCTATTACTGCGC<br>TGAAACTGTGGCTTTATAGAAATTGTTTTCACTGCACTATTGAGAA<br>ATTAAGAGATAATGGCAAAAGTCACAAAGAGTATATTCAAAAAG<br>AAGTATAGCACTTTTTCCTTAGAAACCACTGCTAACTGAAAGAGA<br>CTAAGATTTGTCCCGTCAAAAATCCTGGACCTATGCCTAAAACAC<br>ATTTCACAATCCCTGAACTTTTCAAAAATTGGTACATGCTTTAGCT<br>TTAAACTACAGGCCTCACTGGAGCTAGAGACAAGAAGGTAAAAA<br>ACGGCTGACAAAAGAAGTCCTGGTATCCTCTATGATGGGAGAAGG |

-continued

| SEQ ID NO | NAME | SEQUENCE |
|---|---|---|
| | | AAACTAGCTAAAGGGAAGAATAAATTAGAGAAAAACTGGAATGA<br>CTGAATCGGAACAAGGCAAAGGCTATAAAAAAAATTAGCAGTATC<br>CTCTTGGGGGCCCCTTCCCCACACTATCTCAATGCAAATATCTGTC<br>TGAAACGGTCCCTGGCTAAACTCCACCCATGGGTTGGCCAGCCTT<br>GCCTTGACCAATAGCCTTGACAAGGCAAACTTGACCAATAGTCTT<br>AGAGTATCCAGTGAGGCCAGGGGCCGGCGGCTGGCTAGGGATGA<br>AGAATAAAAGGAAGCACCCTTCAGCAGTTCCACACACTCGCTTCT<br>GGAACGTCTGAGGTTATCAATAAGCTCCTAGTCCAGACGCCATGG<br>GTCATTTCACAGAGGAGGACAAGGCTACTATCACAAGCCTGTGGG<br>GCAAGGTGAATGTGGAAGATGCTGGAGGAGAAACCCTGGGAAGG<br>TAGGCTCTGGTGACCAGGACAAGGGAGGGAAGGAAGGACCCTGT<br>GCCTGGCAAAAGTCCAGGTCGCTTCTCAGGATTTGTGGCACCTTCT<br>GACTGTCAAACTGTTCTTGTCAATCTCACAGGCTCCTGGTTGTCTA<br>CCCATGGACCCAGAGGTTCTTTGACAGCTTTGGCAACCTGTCCTCT<br>GCCTCTGCCATCATGGGCAACCCCAAAGTCAAGGCACATGGCAAG<br>AAGGTGCTGACTTCCTTGGGAGATGCCACAAAGCACCTGGATGAT<br>CTCAAGGGCACCTTTGCCCAGCTGAGTGAACTGCACTGTGACAAG<br>CTGCATGTGGATCCTGAG |
| 9 | 1 kb upstream of gamma globin transcriptional start site | GTCAATAAAAACAACCCTTGCCTCTTTAGAGTTGTTTTCCATGTAC<br>ACGCACATCTTATGTCTTAGAGTAAGATTCCCTGAGAAGTGAACCT<br>AGCATTTATACAAGATAATTAATTCTAATCCACAGTACCTGCCAAA<br>GAACATTCTACCATCATCTTTACTGAGCATAGAAGAGCTACGCCA<br>AAACCCTGGGTCATCAGCCAGCACACACACTTATCCAGTGGTAAA<br>TACACATCATCTGGTGTATACATACATACCTGAATATGGAATCAA<br>ATATTTTTCTAAGATGAAACAGTCATGATTTATTTCAAATAGGTAC<br>GGATAAGTAGATATTGAGGTAAGCATTAGGTCTTATATTATGTAA<br>CACTAATCTATTACTGCGCTGAAACTGTGGCTTTATAGAAATTGTT<br>TTCACTGCACTATTGAGAAATTAAGAGATAATGGCAAAAGTCACA<br>AAGAGTATATTCAAAAAGAAGTATAGCACTTTTTCCTTAGAAACC<br>ACTGCTAACTGAAAGAGACTAAGATTTGTCCCGTCAAAAATCCTG<br>GACCTATGCCTAAAACACATTTCACAATCCCTGAACTTTTCAAAAA<br>TTGGTACATGCTTTAGCTTTAAACTACAGGCCTCACTGGAGCTAGA<br>GACAAGAAGGTAAAAAACGGCTGACAAAAGAAGTCCTGGTATCC<br>TCTATGATGGGAGAAGGAAACTAGCTAAAGGGAAGAATAAATTA<br>GAGAAAAACTGGAATGACTGAATCGGAACAAGGCAAAGGCTATA<br>AAAAAAATTAGCAGTATCCTCTTGGGGGCCCCTTCCCCACACTATC<br>TCAATGCAAATATCTGTCTGAAACGGTCCCTGGCTAAACTCCACCC<br>ATGGGTTGGCCAGCCTTGCCTTGACCAATAGCCTTGACAAGGCAA<br>ACTTGACCAATAGTCTTAGAGTATCCAGTGAGGCCAGGGGCCGGC<br>GGCTGGCTAGGGATGAAGAATAAAAGGAAGCACCCTTCAGCAGTT<br>CCAC |
| 10 | Positive control: AMS# 1263 pAAV.HBG1(1 kb). MND.GFP.SV40pA | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTCATAA<br>ATACTTCCTACCCTGTTAATGGTCCAATATGTCAGAAACAGCACTG<br>TGTTAGAAATAAAGCTGTCTAAAGTACACTAATATTCGAGTTATA<br>ATAGTGTGTGGACTATTAGTCAATAAAAACAACCCTTGCCTCTTTA<br>GAGTTGTTTTCCATGTACACGCACATCTTATGTCTTAGAGTAAGAT<br>TCCCTGAGAAGTGAACCTAGCATTTATACAAGATAATTAATTCTAA<br>TCCACAGTACCTGCCAAAGAACATTCTACCATCATCTTTACTGAGC<br>ATAGAAGAGCTACGCCAAAACCCTGGGTCATCAGCCAGCACACAC<br>ACTTATCCAGTGGTAAATACACATCATCTGGTGTATACATACATAC<br>CTGAATATGGAATCAAATATTTTTCTAAGATGAAACAGTCATGATT<br>TATTTCAAATAGGTACGGATAAGTAGATATTGAGGTAAGCATTAG<br>GTCTTATATTATGTAACACTAATCTATTACTGCGCTGAAACTGTGG<br>CTTTATAGAAATTGTTTTCACTGCACTATTGAGAAATTAAGAGATA<br>ATGGCAAAAGTCACAAAGAGTATATTCAAAAAGAAGTATAGCACT<br>TTTTCCTTAGAAACCACTGCTAACTGAAAGAGACTAAGATTTGTCC<br>CGTCAAAAATCCTGGACCTATGCCTAAAACACATTTCACAATCCCT<br>GAACTTTTCAAAAATTGGTACATGCTTTAGCTTTAAACTACAGGCC<br>TCACTGGAGCTAGAGACAAGAAGGTAAAAAACGGCTGACAAAAG<br>AAGTCCTGGTATCCTCTATGATGGGAGAAGGAAACTAGCTAAAGG<br>GAAGAATAAATTAGAGAAAAACTGGAATGACTGAATCGGAACAA<br>GGCAAAGGCTATAAAAAAAATTAAGCAGCAGTATCCTCTTGGGGG<br>CCCCTTCCCCACACTATCTCAATGCAAATATCTGTCTGAAACGGTC<br>CCTGGCTAAACTCCACCCATGGGTTGGCCAGCCTTGCCTTGACGAA<br>CAGAGAAACAGGAGAATATGGGCCAAACAGGATATCTGTGGTAA<br>GCAGTTCCTGCCCCGGCTCAGGGCCAAGAACAGTTGGAACAGCAG<br>AATATGGGCCAAACAGGATATCTGTGGTAAGCAGTTCCTGCCCCG<br>GCTCAGGGCCAAGAACAGATGGTCCCCAGATGCGGTCCCGCCCTC<br>AGCAGTTTCTAGAGAACCATCAGATGTTTCCAGGGTGCCCCAAGG<br>ACCTGAAATGACCCTGTGCCTTATTTGAACTAACCAATCAGTTCGC |

-continued

| SEQ ID NO | NAME | SEQUENCE |
|---|---|---|
| | | TTCTCGCTTCTGTTCGCGCGCTTCTGCTCCCCGAGCTCTATATAAGC<br>AGAGCTCGTTTAGTGAACCGTCAGATCGCCTGGAGACGCCATCCA<br>CGCTGTTTTGACTTCCATAGAAGGATCTCGAGGCCACCATGGTGA<br>GCAAGGGCGAGGAGCTGTTCACCGGGGTGGTGCCCATCCTGGTCG<br>AGCTGGACGGCGACGTAAACGGCCACAAGTTCAGCGTGTCCGGCG<br>AGGGCGAGGGCGATGCCACCTACGGCAAGCTGACCCTGAAGTTCA<br>TCTGCACCACCGGCAAGCTGCCCGTGCCCTGGCCCACCCTCGTGAC<br>CACCCTGACCTACGGCGTGCAGTGCTTCAGCCGCTACCCCGACCA<br>CATGAAGCAGCACGACTTCTTCAAGTCCGCCATGCCCGAAGGCTA<br>CGTCCAGGAGCGCACCATCTTCTTCAAGGACGACGGCAACTACAA<br>GACCCGCGCCGAGGTGAAGTTCGAGGGCGACACCCTGGTGAACCG<br>CATCGAGCTGAAGGGCATCGACTTCAAGGAGGACGGCAACATCCT<br>GGGGCACAAGCTGGAGTACAACTACAACAGCCACAACGTCTATAT<br>CATGGCCGACAAGCAGAAGAACGGCATCAAGGTGAACTTCAAGA<br>TCCGCCACAACATCGAGGACGGCAGCGTGCAGCTCGCCGACCACT<br>ACCAGCAGAACACCCCCATCGGCGACGGCCCCGTGCTGCTGCCCG<br>ACAACCACTACCTGAGCACCCAGTCCGCCCTGAGCAAAGACCCCA<br>ACGAGAAGCGCGATCACATGGTCCTGCTGGAGTTCGTGACCGCCG<br>CCGGGATCACTCTCGGCATGGACGAGCTGTACAAGTAAACTAGTG<br>TCGACTGCTTTATTTGTGAAATTTGTGATGCTATTGCTTTATTTGTA<br>ACCATTATAAGCTGCAATAAACAAGTTAACAACAACAATTGCATT<br>CATTTTATGTTTCAGGTTCAGGGGGAGGTGTGGGAGGTTTTTTAAA<br>CAATAGCCTTGACAAGGCAAACTTGACCAATAGTCTTAGAGTATC<br>CAGTGAGGCCAGGGGCCGGCGGCTGGCTAGGGATGAAGAATAAA<br>AGGAAGCACCCTTCAGCAGTTCCACACACTCGCTTCTGGAACGTCT<br>GAGGTTATCAATAAGCTCCTAGTCCAGACGCCATGGGTCATTTCAC<br>AGAGGAGGACAAGGCTACTATCACAAGCCTGTGGGGCAAGGTGA<br>ATGTGGAAGATGCTGGAGGAGAAACCCTGGGAAGGTAGGCTCTG<br>GTGACCAGGACAAGGGAGGGAAGGAAGGACCCTGTGCCTGGCAA<br>AAGTCCAGGTCGCTTCTCAGGATTTGTGGCACCTTCTGACTGTCAA<br>ACTGTTCTTGTCAATCTCACAGGCTCCTGGTTGTCTACCCATGGAC<br>CCAGAGGTTCTTTGACAGCTTTGGCAACCTGTCCTCTGCCTCTGCC<br>ATCATGGGCAACCCCAAAGTCAAGGCACATGGCAAGAAGGTGCTG<br>ACTTCCTTGGGAGATGCCACAAAGCACCTGGATGATCTCAAGGGC<br>ACCTTTGCCCAGCTGAGTGAACTGCACTGTGACAAGCTGCATGTG<br>GATCCTGAGAACTTCAAGGTGAGTCCAGGAGATGTTTCAGCCCTG<br>TTGCCTTTAGTCTCGAGGCAACTTAGACAACTGAGTATTGATCTGA<br>GCACAGCAGGGTGTGAGCTGTTTGAAGATACTGGGGTTGGGGGTG<br>AAGAAACTGCAGAGGACTAACTGGGCTGAGACCCAGTGGTAATGT<br>TTTAGGGCCTAAGGAGCGCCTCTAAAAATCTAGATGGACAATTTT<br>GACTTTGAGAAAAGAGAGGTGGAAATGAGGAAAATGACTTTTCTT<br>TATTAGATTCCAGTAGAAAGAACTTTCATCTTTCCCTCATTTTTGTT<br>GTTTTAAAACATCTATCTGGAGGCAGGACAAGTATGGTCGTTAAA<br>AAGATGCAGGCAGAAGGCATATATTGGCTCAGTCAAAGTGGGGA<br>ACTTTGGGCTAGAGTAGATAAGTAGCATGGCGGGTTAATCATTAA<br>CTACAAGGAACCCCTAGTGATGGAGTTGGCCACTCCCTCTCTGCGC<br>GCTCGCTCGCTCACTGAGGCCGGGCGACCAAAGGTCGCCCGACGC<br>CCGGGCTTTGCCCGGGCGGCCTCAGTGAGCGAGCGAGCGCGCCAG<br>CTGGCGTAATAGCGAAGAGGCCCGCACCGATCGCCCTTCCCAACA<br>GTTGCGCAGCCTGAATGGCGAATGGCGATTCCGTTGCAATGGCTG<br>GCGGTAATATTGTTCTGGATATTACCAGCAAGGCCGATAGTTTGA<br>GTTCTTCTACTCAGGCAAGTGATGTTATTACTAATCAAAGAAGTAT<br>TGCGACAACGGTTAATTTGCGTGATGGACAGACTCTTTTACTCGGT<br>GGCCTCACTGATTATAAAAACACTTCTCAGGATTCTGGCGTACCGT<br>TCCTGTCTAAAATCCCTTTAATCGGCCTCCTGTTTAGCTCCCGCTCT<br>GATTCTAACGAGGAAAGCACGTTATACGTGCTCGTCAAAGCAACC<br>ATAGTACGCGCCCTGTAGCGGCGCATTAAGCGCGGCGGGTGTGGT<br>GGTTACGCGCAGCGTGACCGCTACACTTGCCAGCGCCCTAGCGCC<br>CGCTCCTTTCGCTTTCTTCCCTTCCTTTCTCGCCACGTTCGCCGGCT<br>TTCCCCGTCAAGCTCTAAATCGGGGGCTCCCTTTAGGGTTCCGATT<br>TAGTGCTTTACGGCACCTCGACCCCAAAAAACTTGATTAGGGTGA<br>TGGTTCACGTAGTGGGCCATCGCCCTGATAGACGGTTTTTCGCCCT<br>TTGACGTTGGAGTCCACGTTCTTTAATAGTGGACTCTTGTTCCAAA<br>CTGGAACAACACTCAACCCTATCTCGGTCTATTCTTTTGATTTATA<br>AGGGATTTTGCCGATTTCGGCCTATTGGTTAAAAAATGAGCTGATT<br>TAACAAAAATTTAACGCGAATTTTAACAAAATATTAACGTTTACA<br>ATTTAAATATTTGCTTATACAATCTTCCTGTTTTTGGGGCTTTTCTG<br>ATTATCAACCGGGGTACATATGATTGACATGCTAGTTTTACGATTA<br>CCGTTCATCGATTCTCTTGTTTGCTCCAGACTCTCAGGCAATGACC<br>TGATAGCCTTTGTAGAGACCTCTCAAAAATAGCTACCCTCTCCGGC<br>ATGAATTTATCAGCTAGAACGGTTGAATATCATATTGATGGTGATT<br>TGACTGTCTCCGGCCTTTCTCACCCGTTTGAATCTTTACCTACACAT<br>TACTCAGGCATTGCATTTAAAATATATGAGGGTTCTAAAAATTTTT<br>ATCCTTGCGTTGAAATAAAGGCTTCTCCCGCAAAAGTATTACAGG<br>GTCATAATGTTTTTGGTACAACCGATTTAGCTTTATGCTCTGAGGC |

-continued

| SEQ ID NO | NAME | SEQUENCE |
| --- | --- | --- |
| | | TTTATTGCTTAATTTTGCTAATTCTTTGCCTTGCCTGTATGATTTATT GGATGTTGGAATCGCCTGATGCGGTATTTTCTCCTTACGCATCTGT GCGGTATTTCACACCGCATATGGTGCACTCTCAGTACAATCTGCTC TGATGCCGCATAGTTAAGCCAGCCCCGACACCCGCCAACACCCGC TGACGCGCCCTGACGGGCTTGTCTGCTCCCGGCATCCGCTTACAGA CAAGCTGTGACCGTCTCCGGGAGCTGCATGTGTCAGAGGTTTTCAC CGTCATCACCGAAACGCGCGAGACGAAAGGGCCTCGTGATACGCC TATTTTTATAGGTTAATGTCATGATAATAATGGTTTCTTAGACGTC AGGTGGCACTTTTCGGGGAAATGTGCGCGGAACCCCTATTTGTTTA TTTTTCTAAATACATTCAAATATGTATCCGCTCATGAGACAATAAC CCTGATAAATGCTTCAATAATATTGAAAAAGGAAGAGTATGAGTA TTCAACATTTCCGTGTCGCCCTTATTCCCTTTTTTGCGGCATTTTGC CTTCCTGTTTTTGCTCACCCAGAAACGCTGGTGAAAGTAAAAGATG CTGAAGATCAGTTGGGTGCACGAGTGGGTTACATCGAACTGGATC TCAACAGCGGTAAGATCCTTGAGAGTTTTCGCCCCGAAGAACGTT TTCCAATGATGAGCACTTTTAAAGTTCTGCTATGTGGCGCGGTATT ATCCCGTATTGACGCCGGGCAAGAGCAACTCGGTCGCCGCATACA CTATTCTCAGAATGACTTGGTTGAGTACTCACCAGTCACAGAAAA GCATCTTACGGATGGCATGACAGTAAGAGAATTATGCAGTGCTGC CATAACCATGAGTGATAACACTGCGGCCAACTTACTTCTGACAAC GATCGGAGGACCGAAGGAGCTAACCGCTTTTTTGCACAACATGGG GGATCATGTAACTCGCCTTGATCGTTGGGAACCGGAGCTGAATGA AGCCATACCAAACGACGAGCGTGACACCACGATGCCTGTAGCAAT GGCAACAACGTTGCGCAAACTATTAACTGGCGAACTACTTACTCT AGCTTCCCGGCAACAATTAATAGACTGGATGGAGGCGGATAAAGT TGCAGGACCACTTCTGCGCTCGGCCCTTCCGGCTGGCTGGTTTATT GCTGATAAATCTGGAGCCGGTGAGCGTGGGTCTCGCGGTATCATT GCAGCACTGGGGCCAGATGGTAAGCCCTCCCGTATCGTAGTTATC TACACGACGGGGAGTCAGGCAACTATGGATGAACGAAATAGACA GATCGCTGAGATAGGTGCCTCACTGATTAAGCATTGGTAACTGTC AGACCAAGTTTACTCATATATACTTTAGATTGATTTAAAACTTCAT TTTTAATTTAAAAGGATCTAGGTGAAGATCCTTTTTGATAATCTCA TGACCAAAATCCCTTAACGTGAGTTTTCGTTCCACTGAGCGTCAGA CCCCGTAGAAAAGATCAAAGGATCTTCTTGAGATCCTTTTTTTCTG CGCGTAATCTGCTGCTTGCAAACAAAAAAACCACCGCTACCAGCG GTGGTTTGTTTGCCGGATCAAGAGCTACCAACTCTTTTTCCGAAGG TAACTGGCTTCAGCAGAGCGCAGATACCAAATACTGTCCTTCTAGT GTAGCCGTAGTTAGGCCACCACTTCAAGAACTCTGTAGCACCGCC TACATACCTCGCTCTGCTAATCCTGTTACCAGTGGCTGCTGCCAGT GGCGATAAGTCGTGTCTTACCGGGTTGGACTCAAGACGATAGTTA CCGGATAAGGCGCAGCGGTCGGGCTGAACGGGGGGTTCGTGCACA CAGCCCAGCTTGGAGCGAACGACCTACACCGAACTGAGATACCTA CAGCGTGAGCTATGAGAAAGCGCCACGCTTCCCGAAGGGAGAAA GGCGGACAGGTATCCGGTAAGCGGCAGGGTCGGAACAGGAGAGC GCACGAGGGAGCTTCCAGGGGGAAACGCCTGGTATCTTTATAGTC CTGTCGGGTTTCGCCACCTCTGACTTGAGCGTCGATTTTTGTGATG CTCGTCAGGGGGGCGGAGCCTATGGAAAAACGCCAGCAACGCGG CCTTTTTACGGTTCCTGGCCTTTTGCTGGCCTTTTGCTCACATGTTC TTTCCTGCGTTATCCCCTGATTCTGTGGATAACCGTATTACCGCCTT TGAGTGAGCTGATACCGCTCGCCGCAGCCGAACGACCGAGCGCAG CGAGTCAGTGAGCGAGGAAGCGGAAGAGCGCCCAATACGCAAAC CGCCTCTCCCCGCGCGTTGGCCGATTCATTAATG |
| 11 | Positive control: AMS# 1264 pAAV.HBG1.d59 5(1 kb).MND.GFP. SV40pA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGCATAAA TACTTCCTACCCTGTTAATGGTCCAATATGTCAGAAACAGCACTGT GTTAGAAATAAAGCTGTCTAAAGTACACTAATATTCGAGTTATAA TAGTGTGTGGACTATTAGTCAATAAAAACAACCCTTGCCTCTTTAG AGTTGTTTTCCATGTACACGCACATCTTATGTCTTAGAGTAAGATT CCCTGAGAAGTGAACCTAGCATTTATACAAGATAATTAATTCTAAT CCACAGTACCTGCCAAAGAACATTCTACCATCATCTTTACTGAGCA TAGAAGAGCTACGCCAAAACCCTGGGTCATCAGCCAGCACACACA CTTATCCAGTGGTAAATACACATCATCTGGTGTATACATACATACC TGAATATGGAATCAAATATTTTTCTAAGATGAAACAGTCATGATTT ATTTCAAATAGGTACGGATAAGTAGATATTGAGGTAAGCATTAGG TCTTATATTATGTAACACTAATCTATTACTGCGCTGAAACTGTGGC TTTATAGAAATTGTTTTCACTGCACTATTGAGAAATTAAGAGATAA TGGCAAAAGTCACAAAGAGTATATTCAAAAAGAAGTATAGCACTT TTTCCTTAGAAACCACTGCTAACTGAAAGAGACTAAGATTTGTCCC GTCAAAAATCCTGGACCTATGCCTAAAACACATTTCACAATCCCTG AACTTTTCAAAAATTGGTACATGCTTTAGCTTTAAACTACAGGCCT CACTGGAGCTAGAGACAAGAAGGTAAAAAACGGCTGACAAAAGA AGTCCTGGTATCCTCTATGATGGGAGAAGGAAACTAGCTAAAGGG |

-continued

| SEQ ID NO | NAME | SEQUENCE |
|---|---|---|
| | | AAGAATAAATTAGAGAAAAACTGGAATGACTGAATCGGAACAAG<br>GCAAAGGCTATAAAAAAAATTAAGCAGCAGTATCCTCTTGGGGGC<br>CCCTTCCCCACACTATCTCAATGCAAATATCTGTCTGAAACGGTCC<br>CTGGCTAAACTCCACCCATGGGTTGGCCAGCCTTGCCTTGACGAAC<br>AGAGAAACAGGAGAATATGGGCCAAACAGGATATCTGTGGTAAG<br>CAGTTCCTGCCCCGGCTCAGGGCCAAGAACAGTTGGAACAGCAGA<br>ATATGGGCCAAACAGGATATCTGTGGTAAGCAGTTCCTGCCCCGG<br>CTCAGGGCCAAGAACAGATGGTCCCCAGATGCGGTCCCGCCCTCA<br>GCAGTTTCTAGAGAACCATCAGATGTTTCCAGGGTGCCCCAAGGA<br>CCTGAAATGACCCTGTGCCTTATTTGAACTAACCAATCAGTTCGCT<br>TCTCGCTTCTGTTCGCGCGCTTCTGCTCCCCGAGCTCTATATAAGC<br>AGAGCTCGTTTAGTGAACCGTCAGATCGCCTGGAGACGCCATCCA<br>CGCTGTTTTGACTTCCATAGAAGGATCTCGAGGCCACCATGGTGA<br>GCAAGGGCGAGGAGCTGTTCACCGGGGTGGTGCCCATCCTGGTCG<br>AGCTGGACGGCGACGTAAACGGCCACAAGTTCAGCGTGTCCGGCG<br>AGGGCGAGGGCGATGCCACCTACGGCAAGCTGACCCTGAAGTTCA<br>TCTGCACCACCGGCAAGCTGCCCGTGCCCTGGCCCACCCTCGTGAC<br>CACCCTGACCTACGGCGTGCAGTGCTTCAGCCGCTACCCCGACCA<br>CATGAAGCAGCACGACTTCTTCAAGTCCGCCATGCCCGAAGGCTA<br>CGTCCAGGAGCGCACCATCTTCTTCAAGGACGACGGCAACTACAA<br>GACCCGCGCCGAGGTGAAGTTCGAGGGCGACACCCTGGTGAACCG<br>CATCGAGCTGAAGGGCATCGACTTCAAGGAGGACGGCAACATCCT<br>GGGGCACAAGCTGGAGTACAACTACAACAGCCACAACGTCTATAT<br>CATGGCCGACAAGCAGAAGAACGGCATCAAGGTGAACTTCAAGA<br>TCCGCCACAACATCGAGGACGGCAGCGTGCAGCTCGCCGACCACT<br>ACCAGCAGAACACCCCCATCGGCGACGGCCCCGTGCTGCTGCCCG<br>ACAACCACTACCTGAGCACCCAGTCCGCCCTGAGCAAAGACCCCA<br>ACGAGAAGCGCGATCACATGGTCCTGCTGGAGTTCGTGACCGCCG<br>CCGGGATCACTCTCGGCATGGACGAGCTGTACAAGTAAACTAGTG<br>TCGACTGCTTTATTTGTGAAATTTGTGATGCTATTGCTTTATTTGTA<br>ACCATTATAAGCTGCAATAAACAAGTTAACAACAACAATTGCATT<br>CATTTTATGTTTCAGGTTCAGGGGGAGGTGTGGGAGGTTTTTTAAA<br>AACTTCAAGGTGAGTCCAGGAGATGTTTCAGCCCTGTTGCCTTTAG<br>TCTCGAGGCAACTTAGACAACTGAGTATTGATCTGAGCACAGCAG<br>GGTGTGAGCTGTTTGAAGATACTGGGGTTGGGGGTGAAGAAACTG<br>CAGAGGACTAACTGGGCTGAGACCCAGTGGTAATGTTTTAGGGCC<br>TAAGGAGCGCCTCTAAAAATCTAGATGGACAATTTTGACTTTGAG<br>AAAAGAGAGGTGGAAATGAGGAAAATGACTTTTATTAGATTCCAG<br>TAGAAAGAACTTTCATCTTTCCCTCATTTTTGTTGTTTTAAAACATC<br>TATCTGGAGGCAGGACAAGTATGGTCGTTAAAAAGATGCAGGCAG<br>AAGGCATATATTGGCTCAGTCAAAGTGGGGAACTTTGGTGGCCAA<br>ACATACATTGCTAAGGCTATTCCTATATCAGCTGGACACATATAAA<br>ATGCTGCTAATGCTTCATTACAAACTTATATCCTTTAATTCCAGAT<br>GGGGGCAAAGTATGTCCAGGGGTGAGGAACAATTGAAACATTTGG<br>GCTGGAGTAGATTTTGAAAGTCAGCTCTGTGTGTGTGTGTGTGTGC<br>GCGCGCGCGTGTGTGTGTGTGTGTGTCAGCGTGTGTTTCTTTTAAC<br>GTCTTCAGCCTACAACATACAGGGTTCATGGTGGCAAGAAGATAG<br>CAAGATTTAAATTATGGCCAGTGACTAGTGCTTGAAGGGGAACAA<br>CTACCTGCATTTAATGGGAAGGCAAAATCTCAGGCTTTGAGGGAA<br>GTTAACATAGGCTTGATTCTGGGTAGAAGCTGGGTGTGTAGTTATC<br>TGGAGGCCAGGCTGGAGCTCTCAGCTCACTATGGGTTCATCTTTAT<br>TGTCTCCTTTCATCTCAACAGCTCCTGGGAAATGTGCTGGTGACCG<br>TTTTGGCAATCCATTTCGGCAAAGAATTCACCCCTGAGGTGCAGGC<br>TTCCTGGCAGAAGATGGTGACTGCAGTGGCCAGTGCCCTGCTAGA<br>GTAGATAAGTAGCATGGCGGGTTAATCATTAACTACAAGGAACCC<br>CTAGTGATGGAGTTGGCCACTCCCTCTCTGCGCGCTCGCTCGCTCA<br>CTGAGGCCGGGCGACCAAAGGTCGCCCGACGCCCGGGCTTTGCCC<br>GGGCGGCCTCAGTGAGCGAGCGAGCGCGCCAGCTGGCGTAATAGC<br>GAAGAGGCCCGCACCGATCGCCCTTCCCAACAGTTGCGCAGCCTG<br>AATGGCGAATGGCGATTCCGTTGCAATGGCTGGCGGTAATATTGT<br>TCTGGATATTACCAGCAAGGCCGATAGTTTGAGTTCTTCTACTCAG<br>GCAAGTGATGTTATTACTAATCAAAGAAGTATTGCGACAACGGTT<br>AATTTGCGTGATGGACAGACTCTTTTACTCGGTGGCCTCACTGATT<br>ATAAAAACACTTCTCAGGATTCTGGCGTACCGTTCCTGTCTAAAAT<br>CCCTTTAATCGGCCTCCTGTTTAGCTCCCGCTCTGATTCTAACGAG<br>GAAAGCACGTTATACGTGCTCGTCAAAGCAACCATAGTACGCGCC<br>CTGTAGCGGCGCATTAAGCGCGGCGGGTGTGGTGGTTACGCGCAG<br>CGTGACCGCTACACTTGCCAGCGCCCTAGCGCCCGCTCCTTTCGCT<br>TTCTTCCCTTCCTTTCTCGCCACGTTCGCCGGCTTTCCCCGTCAAGC<br>TCTAAATCGGGGGCTCCCTTTAGGGTTCCGATTTAGTGCTTTACGG<br>CACCTCGACCCCAAAAAACTTGATTAGGGTGATGGTTCACGTAGT<br>GGGCCATCGCCCTGATAGACGGTTTTTCGCCCTTTGACGTTGGAGT<br>CCACGTTCTTTAATAGTGGACTCTTGTTCCAAACTGGAACAACACT<br>CAACCCTATCTCGGTCTATTCTTTTGATTTATAAGGGATTTTGCCG<br>ATTTCGGCCTATTGGTTAAAAAATGAGCTGATTTAACAAAAATTTA |

-continued

| SEQ ID NO | NAME | SEQUENCE |
|---|---|---|
| | | ACGCGAATTTTAACAAAATATTAACGTTTACAATTTAAATATTTGC<br>TTATACAATCTTCCTGTTTTTGGGGCTTTTCTGATTATCAACCGGGG<br>TACATATGATTGACATGCTAGTTTTACGATTACCGTTCATCGATTC<br>TCTTGTTTGCTCCAGACTCTCAGGCAATGACCTGATAGCCTTTGTA<br>GAGACCTCTCAAAAATAGCTACCCTCTCCGGCATGAATTTATCAGC<br>TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA<br>AGGAGCTAACCGCTTTTTTGCACAACATGGGGGATCATGTAACTC<br>GCCTTGATCGTTGGGAACCGGAGCTGAATGAAGCCATACCAAACG<br>ACGAGCGTGACACCACGATGCCTGTAGCAATGGCAACAACGTTGC<br>GCAAACTATTAACTGGCGAACTACTTACTCTAGCTTCCCGGCAACA<br>ATTAATAGACTGGATGGAGGCGGATAAAGTTGCAGGACCACTTCT<br>GCGCTCGGCCCTTCCGGCTGGCTGGTTTATTGCTGATAAATCTGGA<br>GCCGGTGAGCGTGGGTCTCGCGGTATCATTGCAGCACTGGGGCCA<br>GATGGTAAGCCCTCCCGTATCGTAGTTATCTACACGACGGGGAGT<br>CAGGCAACTATGGATGAACGAAATAGACAGATCGCTGAGATAGGT<br>GCCTCACTGATTAAGCATTGGTAACTGTCAGACCAAGTTTACTCAT<br>ATATACTTTAGATTGATTTAAAACTTCATTTTTAATTTAAAAGGAT<br>CTAGGTGAAGATCCTTTTTGATAATCTCATGACCAAAATCCCTTAA<br>CGTGAGTTTTCGTTCCACTGAGCGTCAGACCCCGTAGAAAAGATC<br>AAAGGATCTTCTTGAGATCCTTTTTTTCTGCGCGTAATCTGCTGCTT<br>GCAAACAAAAAAACCACCGCTACCAGCGGTGGTTTGTTTGCCGGA<br>TCAAGAGCTACCAACTCTTTTTCCGAAGGTAACTGGCTTCAGCAGA<br>GCGCAGATACCAAATACTGTCCTTCTAGTGTAGCCGTAGTTAGGCC<br>ACCACTTCAAGAACTCTGTAGCACCGCCTACATACCTCGCTCTGCT<br>AATCCTGTTACCAGTGGCTGCTGCCAGTGGCGATAAGTCGTGTCTT<br>ACCGGGTTGGACTCAAGACGATAGTTACCGGATAAGGCGCAGCGG<br>TCGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACCT<br>CTGACTTGAGCGTCGATTTTTGTGATGCTCGTCAGGGGGGCGGAG<br>CCTATGGAAAAACGCCAGCAACGCGGCCTTTTTACGGTTCCTGGC<br>CTTTTGCTGGCCTTTTGCTCACATGTTCTTTCCTGCGTTATCCCCTG<br>ATTCTGTGGATAACCGTATTACCGCCTTTGAGTGAGCTGATACCGC<br>TCGCCGCAGCCGAACGACCGAGCGCAGCGAGTCAGTGAGCGAGG<br>AAGCGGAAGAGCGCCCAATACGCAAACCGCCTCTCCCCGCGCGTT<br>GGCCGATTCATTAATG |
| 12 | HBG1 constructs<br>Human:<br>AMS#1324<br>pAAV<br>HBG1(1k,900).<br>d13<br>[MND>GFP.SV40pA];<br>HPFH2.HS40.<br>HBG1d13p> | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC<br>GCGTAGATCTTACCCTGTTAATGGTCCAATATGTCAGAAACAGCA<br>CTGTGTTAGAAATAAAGCTGTCTAAAGTACACTAATATTCGAGTTA<br>TAATAGTGTGTGGACTATTAGTCAATAAAAACAACCCTTGCCTCTT<br>TAGAGTTGTTTTCCATGTACACGCACATCTTATGTCTTAGAGTAAG<br>ATTCCCTGAGAAGTGAACCTAGCATTTATACAAGATAATTAATTCT<br>AATCCACAGTACCTGCCAAAGAACATTCTACCATCATCTTTACTGA<br>GCATAGAAGAGCTACGCCAAAACCCTGGGTCATCAGCCAGCACAC<br>ACACTTATCCAGTGGTAAATACACATCATCTGGTGTATACATACAT<br>ACCTGAATATGGAATCAAATATTTTTCTAAGATGAAACAGTCATG |

-continued

| SEQ ID NO | NAME | SEQUENCE |
|---|---|---|
| | | ATTTATTTCAAATAGGTACGGATAAGTAGATATTGAGGTAAGCAT<br>TAGGTCTTATATTATGTAACACTAATCTATTACTGCGCTGAAACTG<br>TGGCTTTATAGAAATTGTTTTCACTGCACTATTGAGAAATTAAGAG<br>ATAATGGCAAAAGTCACAAAGAGTATATTCAAAAAGAAGTATAGC<br>ACTTTTTCCTTAGAAACCACTGCTAACTGAAAGAGACTAAGATTTG<br>TCCCGTCAAAAATCCTGGACCTATGCCTAAAACACATTTCACAATC<br>CCTGAACTTTTCAAAAATTGGTACATGCTTTAGCTTTAAACTACAG<br>GCCTCACTGGAGCTAGAGACAAGAAGGTAAAAAACGGCTGACAA<br>AAGAAGTCCTGGTATCCTCTATGATGGGAGAAGGAAACTAGCTAA<br>AGGGAAGAATAAATTAGAGAAAAACTGGAATGACTGAATCGGAA<br>CAAGGCAAAGGCTATAAAAAAAATTAGCAGTATCCTCTTGGGGGC<br>CCCTTCCCCACACTATCTCAATGCAAATATCTGTCTGAAACGGTCC<br>CTGGCTAAACTCCACCCATGGGTTGGCCAGCCTTGCCTTGACCAAT<br>AGCCTTGACGAATTCGCTTTAAAAAACCTCCCACATCTCCCCCTGA<br>ACCTGAAACATAAAATGAATGCAATTGTTGTTGTTAACTTGTTTAT<br>TGCAGCTTATAATGGTTACAAATAAAGCAATAGCATCACAAATTT<br>CACAAATAAAGCTTACTTGTACAGCTCGTCCATGCCGAGAGTGAT<br>CCCGGCGGCGGTCACGAACTCCAGCAGGACCATGTGATCGCGCTT<br>CTCGTTGGGGTCTTTGCTCAGGGCGGACTGGGTGCTCAGGTAGTG<br>GTTGTCGGGCAGCAGCACGGGGCCGTCGCCGATGGGGGTGTTCTG<br>CTGGTAGTGGTCGGCGAGCTGCACGCTGCCGTCCTCGATGTTGTGG<br>CGGATCTTGAAGTTCACCTTGATGCCGTTCTTCTGCTTGTCGGCCA<br>TGATATAGACGTTGTGGCTGTTGTAGTTGTACTCCAGCTTGTGCCC<br>CAGGATGTTGCCGTCCTCCTTGAAGTCGATGCCCTTCAGCTCGATG<br>CGGTTCACCAGGGTGTCGCCCTCGAACTTCACCTCGGCGCGGGTCT<br>TGTAGTTGCCGTCGTCCTTGAAGAAGATGGTGCGCTCCTGGACGTA<br>GCCTTCGGGCATGGCGGACTTGAAGAAGTCGTGCTGCTTCATGTG<br>GTCGGGGTAGCGGCTGAAGCACTGCACGCCGTAGGTCAGGGTGGT<br>CACGAGGGTGGGCCAGGGCACGGGCAGCTTGCCGGTGGTGCAGAT<br>GAACTTCAGGGTCAGCTTGCCGTAGGTGGCATCGCCCTCGCCCTCG<br>CCGGACACGCTGAACTTGTGGCCGTTTACGTCGCCGTCCAGCTCGA<br>CCAGGATGGGCACCACCCCGGTGAACAGCTCCTCGCCCTTGCTCA<br>CCATGGTGGCGGCGCGGCCGCGATCTGACGGTTCACTAAACGAGC<br>TCTGCTTATATAGAGCTCGGGGAGCAGAAGCGCGCGAACAGAAGC<br>GAGAAGCGAACTGATTGGTTAGTTCAAATAAGGCACAGGGTCATT<br>TCAGGTCCTTGGGGCACCCTGGAAACATCTGATGGTTCTCTAGAA<br>ACTGCTGAGGGCGGGACCGCATCTGGGGACCATCTGTTCTTGGCC<br>CTGAGCCGGGGCAGGAACTGCTTACCACAGATATCCTGTTTGGCC<br>CATATTCTGCTGTTCCAACTGTTCTTGGCCCTGAGCCGGGGCAGGA<br>ACTGCTTACCACAGATATCCTGTTTGGCCCATATTCTCCTGTTTCTC<br>TGTTCCCGCGGCGAGATCGAGACCATCCTGGCTAACACAGTGAAA<br>CCCCGTCTCTACTAAAAAAATACAAAAAATTAGCCGGGCTTGGTG<br>GCGGGTGCCTGTAGTCCCAGCTACTATGGAGGCTGAGGCGGGAGA<br>ATGGCGTGAACGCGGGGGGCGGAGCTTGCAGTGAGCAGAGATCA<br>GGGGCCACTGCACTCCAGCCTGGGCGACAGAGAGAGACTCTGTCT<br>CAAAAAAAAGAAAAAAAAAATTTAGTAGACTAGCTAAAAAAATC<br>CAGAGATAGTTATTGATGCATATGTAAAAGTCTTCCAATATTTACA<br>AGTACAATGAAAAAAAAATAACCTTGAATTAAGTGTAGAACTCAT<br>TGACAATGTTTCAAAGGATGTGAGGGATAAACTAAAATTTGGGCA<br>GTACATGCTGTTCCTGTGTACTTGGAACAGAGGGAGAAAATCTGG<br>GCTGGAAATATTGTTATAGGAGTTAGCACATGAAGGTGACAACTA<br>AATTATTTGGAGTAGATGGAGTCACCAGCACATGTGAATAGTTTT<br>AGAATGAAATGACCCAAGATAGAACTTTGGAGAGCCCCCAAATTT<br>AAATAAAATCAGTATAAGAGAAGAGGAAGAAACCAAATGGTATA<br>CTAGTCTAAATTGTTTCTTAGTGACAAAAGAATAACCTGAATATTA<br>GATTAGCTGCCTATATGCTCTCTGAATCAATTTCATTCAACATGCA<br>ACAGTTCTGGAACCTATCAGGGACCACAGTCAGCCAGGCAAGCAC<br>ATCTGCCCAAGCCAAGGGTGGAGGCATGCAGCTGTGGGGGTCTGT<br>GAAAACACTTGAGGGAGCAGATAACTGGGCCAACCATGACTCAGT<br>GCTTCTGGAGGCCAACAGGACTGCTGAGTCATCCTGTGGGGGTGG<br>AGGTGGGACAAGGGAAAGGGGTGAATGGTACTGCTGATTACAAC<br>CTCTGGTGCTGCCTCCCCCTCCTGTTTATCTGAGAGAGGCCTCACT<br>GGAGCTAGAGACAAGAAGGTAAAAAACGGCTGACAAAAGAAGTC<br>CTGGTATCCTCTATGATGGGAGAAGGAAACTAGCTAAAGGGAAGA<br>ATAAATTAGAGAAAAACTGGAATGACTGAATCGGAACAAGGCAA<br>AGGCTATAAAAAAAATTAGCAGTATCCTCTTGGGGGCCCCTTCCC<br>CACACTATCTCAATGCAAATATCTGTCTGAAACGGTCCCTGGCTAA<br>ACTCCACCCATGGGTTGGCCAGCCTTGCCTTGACAAGGCAAACTT<br>GACCAATAGTCTTAGAGTATCCAGTGAGGCCAGGGGCCGGCGGCT<br>GGCTAGGGATGAAGAATAAAAGGAAGCACCCTTCAGCAGTTCCAC<br>ACACTCGCTTCTGGAACGTCTGAGGTTATCAATAAGCTCCTAGTCC<br>AGACGCCATGGGTCATTTCACAGAGGAGGACAAGGCTACTATCAC<br>AAGCCTGTGGGGCAAGGTGAATGTGGAAGATGCTGGAGGAGAAA<br>CCCTGGGAAGGTAGGCTCTGGTGACCAGGACAAGGGAGGGAAGG<br>AAGGACCCTGTGCCTGGCAAAAGTCCAGGTCGCTTCTCAGGATTT |

-continued

| SEQ ID NO | NAME | SEQUENCE |
|---|---|---|
| | | GTGGCACCTTCTGACTGTCAAACTGTTCTTGTCAATCTCACAGGCT<br>CCTGGTTGTCTACCCATGGACCCAGAGGTTCTTTGACAGCTTTGGC<br>AACCTGTCCTCTGCCTCTGCCATCATGGGCAACCCCAAAGTCAAG<br>GCACATGGCAAGAAGGTGCTGACTTCCTTGGGAGATGCCACAAAG<br>CACCTGGATGATCTCAAGGGCACCTTTGCCCAGCTGAGTGAACTG<br>CACTGTGACAAGCTGCATGTGGATCCTGAGAACTTCAAGGTGAGT<br>CCAGGAGATGTTTCAGCCCTGTTGCCTTTAGTCTCGAGGCAACTTA<br>GACAACGGAGTATTGATCTGAGCACAGCAGGGTGTGAGCTGTTTG<br>AAGATACTGGGGTTGGGGGTGAAGAAACTGCAGAGGACTAACTG<br>GGCTGAGACCCAGTGGTAATGTTTTAGGGCCTAAGGAGTGCCTCT<br>AAAAATCTAGATGGACAATTTTGACTTTGAGAAAAGAGAGGTGGA<br>AATGAGGAAAATGACTTTTCTTTATTAGATTCCAGTAGAAAGAAC<br>TTTCATCTTTCCCTCATTTTTGTTGTTTTAAAAGTCGACAGGAACCCC<br>CTAGTGATGGAGTTGGCCACTCCCTCTCTGCGCGCTCGCTCGCTCA<br>CTGAGGCCGGGCGACCAAAGGTCGCCCGACGCCCGGGCTTTGCCC<br>GGGCGGCCTCAGTGAGCGAGCGAGCGCGCAGCTGGCGTAATAGC<br>GAAGAGGCCCGCACCGATCGCCCTTCCCAACAGTTGCGCAGCCTG<br>AATGGCGAATGGCGATTCCGTTGCAATGGCTGGCGGTAATATTGT<br>TCTGGATATTACCAGCAAGGCCGATAGTTTGAGTTCTTCTACTCAG<br>GCAAGTGATGTTATTACTAATCAAAGAAGTATTGCGACAACGGTT<br>AATTTGCGTGATGGACAGACTCTTTTACTCGGTGGCCTCACTGATT<br>ATAAAAACACTTCTCAGGATTCTGGCGTACCGTTCCTGTCTAAAAT<br>CCCTTTAATCGGCCTCCTGTTTAGCTCCCGCTCTGATTCTAACGAG<br>GAAAGCACGTTATACGTGCTCGTCAAAGCAACCATAGTACGCGCC<br>CTGTAGCGGCGCATTAAGCGCGGCGGGTGTGGTGGTTACGCGCAG<br>CGTGACCGCTACACTTGCCAGCGCCCTAGCGCCCGCTCCTTTCGCT<br>TTCTTCCCTTCCTTTCTCGCCACGTTCGCCGGCTTTCCCCGTCAAGC<br>TCTAAATCGGGGGCTCCCTTTAGGGTTCCGATTTAGTGCTTTACGG<br>CACCTCGACCCCAAAAAACTTGATTAGGGTGATGGTTCACGTAGT<br>GGGCCATCGCCCTGATAGACGGTTTTTCGCCCTTTGACGTTGGAGT<br>CCACGTTCTTTAATAGTGGACTCTTGTTCCAAACTGGAACAACACT<br>CAACCCTATCTCGGTCTATTCTTTTGATTTATAAGGGATTTTGCCG<br>ATTTCGGCCTATTGGTTAAAAAATGAGCTGATTTAACAAAAATTTA<br>ACGCGAATTTTAACAAAATATTAACGTTTACAATTTAAATATTTGC<br>TTATACAATCTTCCTGTTTTTGGGGCTTTTCTGATTATCAACCGGGG<br>TACATATGATTGACATGCTAGTTTTACGATTACCGTTCATCGATTC<br>TCTTGTTTGCTCCAGACTCTCAGGCAATGACCTGATAGCCTTTGTA<br>GAGACCTCTCAAAAATAGCTACCCTCTCCGGCATGAATTTATCAGC<br>TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA<br>AGGAGCTAACCGCTTTTTTGCACAACATGGGGGATCATGTAACTC<br>GCCTTGATCGTTGGGAACCGGAGCTGAATGAAGCCATACCAAACG<br>ACGAGCGTGACACCACGATGCCTGTAGCAATGGCAACAACGTTGC<br>GCAAACTATTAACTGGCGAACTACTTACTCTAGCTTCCCGGCAACA<br>ATTAATAGACTGGATGGAGGCGGATAAAGTTGCAGGACCACTTCT<br>GCGCTCGGCCCTTCCGGCTGGCTGGTTTATTGCTGATAAATCTGGA<br>GCCGGTGAGCGTGGGTCTCGCGGTATCATTGCAGCACTGGGGCCA<br>GATGGTAAGCCCTCCCGTATCGTAGTTATCTACACGACGGGGAGT<br>CAGGCAACTATGGATGAACGAAATAGACAGATCGCTGAGATAGGT<br>GCCTCACTGATTAAGCATTGGTAACTGTCAGACCAAGTTTACTCAT<br>ATATACTTTAGATTGATTTAAAACTTCATTTTTAATTTAAAAGGAT<br>CTAGGTGAAGATCCTTTTTGATAATCTCATGACCAAAATCCCTTAA |

-continued

| SEQ ID NO | NAME | SEQUENCE |
|---|---|---|
| | | CGTGAGTTTTCGTTCCACTGAGCGTCAGACCCCGTAGAAAAGATC<br>AAAGGATCTTCTTGAGATCCTTTTTTTCTGCGCGTAATCTGCTGCTT<br>GCAAACAAAAAAACCACCGCTACCAGCGGTGGTTTGTTTGCCGGA<br>TCAAGAGCTACCAACTCTTTTTCCGAAGGTAACTGGCTTCAGCAGA<br>GCGCAGATACCAAATACTGTCCTTCTAGTGTAGCCGTAGTTAGGCC<br>ACCACTTCAAGAACTCTGTAGCACCGCCTACATACCTCGCTCTGCT<br>AATCCTGTTACCAGTGGCTGCTGCCAGTGGCGATAAGTCGTGTCTT<br>ACCGGGTTGGACTCAAGACGATAGTTACCGGATAAGGCGCAGCGG<br>TCGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACCT<br>CTGACTTGAGCGTCGATTTTTGTGATGCTCGTCAGGGGGGCGGAG<br>CCTATGGAAAAACGCCAGCAACGCGGCCTTTTTACGGTTCCTGGC<br>CTTTTGCTGGCCTTTTGCTCACATGTTCTTTCCTGCGTTATCCCCTG<br>ATTCTGTGGATAACCGTATTACCGCCTTTGAGTGAGCTGATACCGC<br>TCGCCGCAGCCGAACGACCGAGCGCAGCGAGTCAGTGAGCGAGG<br>AAGCGGAAGAGCGCCCAATACGCAAACCGCCTCTCCCCGCGCGTT<br>GGCCGATTCATTAATG |
| 13 | HBG1 constructs<br>Human:<br>AMS#1325<br>pAAV<br>HBG1(7,900).d13<br>[MND>GFP.SV40pA];<br>HPFH2.HS40.<br>HBG1d13p> | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC<br>GCGTAGATCTTACCCTGTTAATGGTCCAATATGTCAGAAACAGCA<br>CTGTGTTAGAAATAAAGCTGTCTAAAGTACACTAATATTCGAGTTA<br>TAATAGTGTGTGGACTATTAGTCAATAAAAACAACCCTTGCCTCTT<br>TAGAGTTGTTTTCCATGTACACGCACATCTTATGTCTTAGAGTAAG<br>ATTCCCTGAGAAGTGAACCTAGCATTTATACAAGATAATTAATTCT<br>AATCCACAGTACCTGCCAAAGAACATTCTACCATCATCTTTACTGA<br>GCATAGAAGAGCTACGCCAAAACCCTGGGTCATCAGCCAGCACAC<br>ACACTTATCCAGTGGTAAATACACATCATCTGGTGTATACATACAT<br>ACCTGAATATGGAATCAAATATTTTTCTAAGATGAAACAGTCATG<br>ATTTATTTCAAATAGGTACGGATAAGTAGATATTGAGGTAAGCAT<br>TAGGTCTTATATTATGTAACACTAATCTATTACTGCGCTGAAACTG<br>TGGCTTTATAGAAATTGTTTTCACTGCACTATTGAGAAATTAAGAG<br>ATAATGGCAAAAGTCACAAAGAGTATATTCAAAAAGAAGTATAGC<br>ACTTTTTCCTTAGAAACCACTGCTAACTGAAAGAGACTAAGATTTG<br>TCCCGTCAAAAATCCTGGACCTATGCCTAAAACACATTTCACAATC<br>CCTGAACTTTTCAAAAATTGGTACATGCTTTAGCTTTAAACTACGA<br>ATTCGCTTTAAAAAACCTCCCACATCTCCCCCTGAACCTGAAACAT<br>AAAATGAATGCAATTGTTGTTGTTAACTTGTTTATTGCAGCTTATA<br>ATGGTTACAAATAAAGCAATAGCATCACAAATTTCACAAATAAAG<br>CTTACTTGTACAGCTCGTCCATGCCGAGAGTGATCCCGGCGGCGGT<br>CACGAACTCCAGCAGGACCATGTGATCGCGCTTCTCGTTGGGGTCT<br>TTGCTCAGGGCGGACTGGGTGCTCAGGTAGTGGTTGTCGGGCAGC<br>AGCACGGGGCCGTCGCCGATGGGGGTGTTCTGCTGGTAGTGGTCG<br>GCGAGCTGCACGCTGCCGTCCTCGATGTTGTGGCGGATCTTGAAGT<br>TCACCTTGATGCCGTTCTTCTGCTTGTCGGCCATGATATAGACGTT<br>GTGGCTGTTGTAGTTGTACTCCAGCTTGTGCCCCAGGATGTTGCCG<br>TCCTCCTTGAAGTCGATGCCCTTCAGCTCGATGCGGTTCACCAGGG<br>TGTCGCCCTCGAACTTCACCTCGGCGCGGGTCTTGTAGTTGCCGTC<br>GTCCTTGAAGAAGATGGTGCGCTCCTGGACGTAGCCTTCGGGCAT<br>GGCGGACTTGAAGAAGTCGTGCTGCTTCATGTGGTCGGGGTAGCG<br>GCTGAAGCACTGCACGCCGTAGGTCAGGGTGGTCACGAGGGTGGG<br>CCAGGGCACGGGCAGCTTGCCGGTGGTGCAGATGAACTTCAGGGT<br>CAGCTTGCCGTAGGTGGCATCGCCCTCGCCCTCGCCGGACACGCT<br>GAACTTGTGGCCGTTTACGTCGCCGTCCAGCTCGACCAGGATGGG<br>CACCACCCCGGTGAACAGCTCCTCGCCCTTGCTCACCATGGTGGCG<br>GCGCGGCCGCGATCTGACGGTTCACTAAACGAGCTCTGCTTATAT<br>AGAGCTCGGGGAGCAGAAGCGCGCGAACAGAAGCGAGAAGCGAA<br>CTGATTGGTTAGTTCAAATAAGGCACAGGGTCATTTCAGGTCCTTG<br>GGGCACCCTGGAAACATCTGATGGTTCTCTAGAAACTGCTGAGGG<br>CGGGACCGCATCTGGGGACCATCTGTTCTTGGCCCTGAGCCGGGG<br>CAGGAACTGCTTACCACAGATATCCTGTTTGGCCCATATTCTGCTG<br>TTCCAACTGTTCTTGGCCCTGAGCCGGGGCAGGAACTGCTTACCAC<br>AGATATCCTGTTTGGCCCATATTCTCCTGTTTCTCTGTTCCCGCGGC<br>GAGATCGAGACCATCCTGGCTAACACAGTGAAACCCCGTCTCTAC<br>TAAAAAAATACAAAAAATTAGCCGGGCTTGGTGGCGGGTGCCTGT<br>AGTCCCAGCTACTATGGAGGCTGAGGCGGGAGAATGGCGTGAACG<br>CGGGGGGCGGAGCTTGCAGTGAGCAGAGATCAGGGGCCACTGCA<br>CTCCAGCCTGGGCGACAGAGAGAGACTCTGTCTCAAAAAAAAGAA<br>AAAAAAAATTTAGTAGACTAGCTAAAAAAATCCAGAGATAGTTAT<br>TGATGCATATGTAAAAGTCTTCCAATATTTACAAGTACAATGAAA<br>AAAAAATAACCTTGAATTAAGTGTAGAACTCATTGACAATGTTTC |

-continued

| SEQ ID NO | NAME | SEQUENCE |
|---|---|---|
| | | AAAGGATGTGAGGGATAAACTAAAATTTGGGCAGTACATGCTGTT<br>CCTGTGTACTTGGAACAGAGGGAGAAAATCTGGGCTGGAAATATT<br>GTTATAGGAGTTAGCACATGAAGGTGACAACTAAATTATTTGGAG<br>TAGATGGAGTCACCAGCACATGTGAATAGTTTTAGAATGAAATGA<br>CCCAAGATAGAACTTTGGAGAGCCCCCAAATTTAAATAAAATCAG<br>TATAAGAGAAGAGGAAGAAACCAAATGGTATACTAGTCTAAATTG<br>TTTCTTAGTGACAAAAGAATAACCTGAATATTAGATTAGCTGCCTA<br>TATGCTCTCTGAATCAATTTCATTCAACATGCAACAGTTCTGGAAC<br>CTATCAGGGACCACAGTCAGCCAGGCAAGCACATCTGCCCAAGCC<br>AAGGGTGGAGGCATGCAGCTGTGGGGGTCTGTGAAAACACTTGAG<br>GGAGCAGATAACTGGGCCAACCATGACTCAGTGCTTCTGGAGGCC<br>AACAGGACTGCTGAGTCATCCTGTGGGGGTGGAGGTGGGACAAGG<br>GAAAGGGGTGAATGGTACTGCTGATTACAACCTCTGGTGCTGCCT<br>CCCCCTCCTGTTTATCTGAGAGAGGCCTCACTGGAGCTAGAGACA<br>AGAAGGTAAAAAACGGCTGACAAAAGAAGTCCTGGTATCCTCTAT<br>GATGGGAGAAGGAAACTAGCTAAAGGGAAGAATAAATTAGAGAA<br>AAACTGGAATGACTGAATCGGAACAAGGCAAAGGCTATAAAAAA<br>AATTAGCAGTATCCTCTTGGGGGCCCCTTCCCCACACTATCTCAAT<br>GCAAATATCTGTCTGAAACGGTCCCTGGCTAAACTCCACCCATGG<br>GTTGGCCAGCCTTGCCTTGACAAGGCAAACTTGACCAATAGTCTTA<br>GAGTATCCAGTGAGGCCAGGGGCCGGCGGCTGGCTAGGGATGAA<br>GAATAAAAGGAAGCACCCTTCAGCAGTTCCACACACTCGCTTCTG<br>GAACGTCTGAGGTTATCAATAAGCTCCTAGTCCAGACGCCATGGG<br>TCATTTCACAGAGGAGGACAAGGCTACTATCACAAGCCTGTGGGG<br>CAAGGTGAATGTGGAAGATGCTGGAGGAGAAACCCTGGGAAGGT<br>AGGCTCTGGTGACCAGGACAAGGGAGGGAAGGAAGGACCCTGTG<br>CCTGGCAAAAGTCCAGGTCGCTTCTCAGGATTTGTGGCACCTTCTG<br>ACTGTCAAACTGTTCTTGTCAATCTCACAGGCTCCTGGTTGTCTAC<br>CCATGGACCCAGAGGTTCTTTGACAGCTTTGGCAACCTGTCCTCTG<br>CCTCTGCCATCATGGGCAACCCCAAAGTCAAGGCACATGGCAAGA<br>AGGTGCTGACTTCCTTGGGAGATGCCACAAAGCACCTGGATGATC<br>TCAAGGGCACCTTTGCCCAGCTGAGTGAACTGCACTGTGACAAGC<br>TGCATGTGGATCCTGAGAACTTCAAGGTGAGTCCAGGAGATGTTT<br>CAGCCCTGTTGCCTTTAGTCTCGAGGCAACTTAGACAACGGAGTAT<br>TGATCTGAGCACAGCAGGGTGTGAGCTGTTTGAAGATACTGGGGT<br>TGGGGGTGAAGAAACTGCAGAGGACTAACTGGGCTGAGACCCAG<br>TGGTAATGTTTTAGGGCCTAAGGAGTGCCTCTAAAAATCTAGATG<br>GACAATTTTGACTTTGAGAAAAGAGAGGTGGAAATGAGGAAAAT<br>GACTTTTCTTTATTAGATTCCAGTAGAAAGAACTTTCATCTTTCCCT<br>CATTTTTGTTGTTTTAAAAGTCGACAGGAACCCCTAGTGATGGAGT<br>TGGCCACTCCCTCTCTGCGCGCTCGCTCGCTCACTGAGGCCGGGCG<br>ACCAAAGGTCGCCCGACGCCCGGGCTTTGCCCGGGCGGCCTCAGT<br>GAGCGAGCGAGCGCGCAGCTGGCGTAATAGCGAAGAGGCCCGCA<br>CCGATCGCCCTTCCCAACAGTTGCGCAGCCTGAATGGCGAATGGC<br>GATTCCGTTGCAATGGCTGGCGGTAATATTGTTCTGGATATTACCA<br>GCAAGGCCGATAGTTTGAGTTCTTCTACTCAGGCAAGTGATGTTAT<br>TACTAATCAAAGAAGTATTGCGACAACGGTTAATTTGCGTGATGG<br>ACAGACTCTTTTACTCGGTGGCCTCACTGATTATAAAAACACTTCT<br>CAGGATTCTGGCGTACCGTTCCTGTCTAAAATCCCTTTAATCGGCC<br>TCCTGTTTAGCTCCCGCTCTGATTCTAACGAGGAAAGCACGTTATA<br>CGTGCTCGTCAAAGCAACCATAGTACGCGCCCTGTAGCGGCGCAT<br>TAAGCGCGGCGGGTGTGGTGGTTACGCGCAGCGTGACCGCTACAC<br>TTGCCAGCGCCCTAGCGCCCGCTCCTTTCGCTTTCTTCCCTTCCTTT<br>CTCGCCACGTTCGCCGGCTTTCCCCGTCAAGCTCTAAATCGGGGGC<br>TCCCTTTAGGGTTCCGATTTAGTGCTTTACGGCACCTCGACCCCAA<br>AAAACTTGATTAGGGTGATGGTTCACGTAGTGGGCCATCGCCCTG<br>ATAGACGGTTTTTCGCCCTTTGACGTTGGAGTCCACGTTCTTTAAT<br>AGTGGACTCTTGTTCCAAACTGGAACAACACTCAACCCTATCTCGG<br>TCTATTCTTTTGATTTATAAGGGATTTTGCCGATTTCGGCCTATTGG<br>TTAAAAAATGAGCTGATTTAACAAAAATTTAACGCGAATTTTAAC<br>AAAATATTAACGTTTACAATTTAAATATTTGCTTATACAATCTTCC<br>TGTTTTTGGGGCTTTTCTGATTATCAACCGGGGTACATATGATTGA<br>CATGCTAGTTTTACGATTACCGTTCATCGATTCTCTTGTTTGCTCCA<br>GACTCTCAGGCAATGACCTGATAGCCTTTGTAGAGACCTCTCAAA<br>AATAGCTACCCTCTCCGGCATGAATTTATCAGCTAGAACGGTTGA<br>ATATCATATTGATGGTGATTTGACTGTCTCCGGCCTTTCTCACCCG<br>TTTGAATCTTTACCTACACATTACTCAGGCATTGCATTTAAAATAT<br>ATGAGGGTTCTAAAAATTTTTATCCTTGCGTTGAAATAAAGGCTTC<br>TCCCGCAAAAGTATTACAGGGTCATAATGTTTTTGGTACAACCGAT<br>TTAGCTTTATGCTCTGAGGCTTTATTGCTTAATTTTGCTAATTCTTT<br>GCCTTGCCTGTATGATTTATTGGATGTTGGAATCGCCTGATGCGGT<br>ATTTTCTCCTTACGCATCTGTGCGGTATTTCACACCGCATATGGTG<br>CACTCTCAGTACAATCTGCTCTGATGCCGCATAGTTAAGCCAGCCC<br>CGACACCCGCCAACACCCGCTGACGCGCCCTGACGGGCTTGTCTG<br>CTCCCGGCATCCGCTTACAGACAAGCTGTGACCGTCTCCGGGAGC |

-continued

| SEQ ID NO | NAME | SEQUENCE |
|---|---|---|
| | | TGCATGTGTCAGAGGTTTTCACCGTCATCACCGAAACGCGCGAGA |
| | | CGAAAGGGCCTCGTGATACGCCTATTTTTATAGGTTAATGTCATGA |
| | | TAATAATGGTTTCTTAGACGTCAGGTGGCACTTTTCGGGGAAATGT |
| | | GCGCGGAACCCCTATTTGTTTATTTTTCTAAATACATTCAAATATG |
| | | TATCCGCTCATGAGACAATAACCCTGATAAATGCTTCAATAATATT |
| | | GAAAAAGGAAGAGTATGAGTATTCAACATTTCCGTGTCGCCCTTA |
| | | TTCCCTTTTTTGCGGCATTTTGCCTTCCTGTTTTTGCTCACCCAGAA |
| | | ACGCTGGTGAAAGTAAAAGATGCTGAAGATCAGTTGGGTGCACGA |
| | | GTGGGTTACATCGAACTGGATCTCAACAGCGGTAAGATCCTTGAG |
| | | AGTTTTCGCCCCGAAGAACGTTTTCCAATGATGAGCACTTTTAAAG |
| | | TTCTGCTATGTGGCGCGGTATTATCCCGTATTGACGCCGGGCAAGA |
| | | GCAACTCGGTCGCCGCATACACTATTCTCAGAATGACTTGGTTGAG |
| | | TACTCACCAGTCACAGAAAAGCATCTTACGGATGGCATGACAGTA |
| | | AGAGAATTATGCAGTGCTGCCATAACCATGAGTGATAACACTGCG |
| | | GCCAACTTACTTCTGACAACGATCGGAGGACCGAAGGAGCTAACC |
| | | GCTTTTTTGCACAACATGGGGGATCATGTAACTCGCCTTGATCGTT |
| | | GGGAACCGGAGCTGAATGAAGCCATACCAAACGACGAGCGTGAC |
| | | ACCACGATGCCTGTAGCAATGGCAACAACGTTGCGCAAACTATTA |
| | | ACTGGCGAACTACTTACTCTAGCTTCCCGGCAACAATTAATAGACT |
| | | GGATGGAGGCGGATAAAGTTGCAGGACCACTTCTGCGCTCGGCCC |
| | | TTCCGGCTGGCTGGTTTATTGCTGATAAATCTGGAGCCGGTGAGCG |
| | | TGGGTCTCGCGGTATCATTGCAGCACTGGGGCCAGATGGTAAGCC |
| | | CTCCCGTATCGTAGTTATCTACACGACGGGGAGTCAGGCAACTAT |
| | | GGATGAACGAAATAGACAGATCGCTGAGATAGGTGCCTCACTGAT |
| | | TAAGCATTGGTAACTGTCAGACCAAGTTTACTCATATATACTTTAG |
| | | ATTGATTTAAAACTTCATTTTTAATTTAAAAGGATCTAGGTGAAGA |
| | | TCCTTTTTGATAATCTCATGACCAAAATCCCTTAACGTGAGTTTTC |
| | | GTTCCACTGAGCGTCAGACCCCGTAGAAAAGATCAAAGGATCTTC |
| | | TTGAGATCCTTTTTTTCTGCGCGTAATCTGCTGCTTGCAAACAAAA |
| | | AAACCACCGCTACCAGCGGTGGTTTGTTTGCCGGATCAAGAGCTA |
| | | CCAACTCTTTTTCCGAAGGTAACTGGCTTCAGCAGAGCGCAGATA |
| | | CCAAATACTGTCCTTCTAGTGTAGCCGTAGTTAGGCCACCACTTCA |
| | | AGAACTCTGTAGCACCGCCTACATACCTCGCTCTGCTAATCCTGTT |
| | | ACCAGTGGCTGCTGCCAGTGGCGATAAGTCGTGTCTTACCGGGTT |
| | | GGACTCAAGACGATAGTTACCGGATAAGGCGCAGCGGTCGGGCTG |
| | | AACGGGGGGTTCGTGCACACAGCCCAGCTTGGAGCGAACGACCTA |
| | | CACCGAACTGAGATACCTACAGCGTGAGCTATGAGAAAGCGCCAC |
| | | GCTTCCCGAAGGGAGAAAGGCGGACAGGTATCCGGTAAGCGGCA |
| | | GGGTCGGAACAGGAGAGCGCACGAGGGAGCTTCCAGGGGGAAAC |
| | | GCCTGGTATCTTTATAGTCCTGTCGGGTTTCGCCACCTCTGACTTG |
| | | AGCGTCGATTTTTGTGATGCTCGTCAGGGGGGCGGAGCCTATGGA |
| | | AAAACGCCAGCAACGCGGCCTTTTTACGGTTCCTGGCCTTTTGCTG |
| | | GCCTTTTGCTCACATGTTCTTTCCTGCGTTATCCCCTGATTCTGTGG |
| | | ATAACCGTATTACCGCCTTTGAGTGAGCTGATACCGCTCGCCGCAG |
| | | CCGAACGACCGAGCGCAGCGAGTCAGTGAGCGAGGAAGCGGAAG |
| | | AGCGCCCAATACGCAAACCGCCTCTCCCCGCGCGTTGGCCGATTC |
| | | ATTAATG |
| 14 | T87Q cassettes | CAGCTGCGCGCTCGCTCGCTCACTGAGGCCGCCCGGGCAAAGCCC |
| | Human: | GGGCGTCGGGCGACCTTTGGTCGCCCGGCCTCAGTGAGCGAGCGA |
| | AMS#1345 | GCGCGCAGAGAGGGAGTGGCCAACTCCATCACTAGGGGTTCCTAC |
| | pAAV | GCGTAGATCTGGTGTATACATACATACCTGAATATGGAATCAAAT |
| | HBG1(650).d0 | ATTTTTCTAAGATGAAACAGTCATGATTTATTTCAAATAGGTACGG |
| | HBBp>HBB(T87Q). | ATAAGTAGATATTGAGGTAAGCATTAGGTCTTATATTATGTAACAC |
| | core3'enh;MND> | TAATCTATTACTGCGCTGAAACTGTGGCTTTATAGAAATTGTTTTC |
| | GFP.SV40pA | ACTGCACTATTGAGAAATTAAGAGATAATGGCAAAAGTCACAAAG |
| | | AGTATATTCAAAAAGAAGTATAGCACTTTTTCCTTAGAAACCACTG |
| | | CTAACTGAAAGAGACTAAGATTTGTCCCGTCAAAAATCCTGGACC |
| | | TATGCCTAAAACACATTTCACAATCCCTGAACTTTTCAAAAATTGG |
| | | TACATGCTTTAGCTTTAAACTACAGGCCTCACTGGAGCTAGAGAC |
| | | AAGAAGGTAAAAAACGGCTGACAAAAGAAGTCCTGGTATCCTCTA |
| | | TGATGGGAGAAGGAAACTAGCTAAAGGGAAGAATAAATTAGAGA |
| | | AAAACTGGAATGACTGAATCGGAACAAGGCAAAGGCTATAAAAA |
| | | AAATTAAGCAGCAGTATCCTCTTGGGGGCCCCTTCCCCACACTATC |
| | | TCAATGCAAATATCTGTCTGAAACGGTCCCTGGCTAAACTCCACCC |
| | | ATGGGTTGGCCAGCCTTGCCTTGACGCTAGCGTAAATACACTTGCA |
| | | AAGGAGGATGTTTTTAGTAGCAATTTGTACTGATGGTATGGGGCC |
| | | AAGAGATATATCTTAGAGGGAGGGCTGAGGGTTTGAAGTCCAACT |
| | | CCTAAGCCAGTGCCAGAAGAGCCAAGGACAGGTACGGCTGTCATC |
| | | ACTTAGACCTCACCCTGTGGAGCCACACCCTAGGGTTGGCCAATCT |
| | | ACTCCCAGGAGCAGGGAGGGCAGGAGCCAGGGCTGGGCATAAAA |
| | | GTCAGGGCAGAGCCATCTATTGCTTACATTTGCTTCTGACACAACT |
| | | GTGTTCACTAGCAACCTCAAACAGACACCATGGTGCACCTGACTC |
| | | CTGAGGAGAAGTCTGCCGTTACTGCCCTGTGGGGCAAGGTGAACG |
| | | TGGATGAAGTTGGTGGTGAGGCCCTGGGCAGGTTGGTATCAAGGT |

-continued

| SEQ ID NO | NAME | SEQUENCE |
|---|---|---|
| | | TACAAGACAGGTTTAAGGAGACCAATAGAAACTGGGCATGTGGA<br>GACAGAGAAGACTCTTGGGTTTCTGATAGGCACTGACTCTCTCTGC<br>CTATTGGTCTATTTTCCCACCCTTAGGCTGCTGGTGGTCTACCCTTG<br>GACCCAGAGGTTCTTTGAGTCCTTTGGGGATCTGTCCACTCCTGAT<br>GCTGTTATGGGCAACCCTAAGGTGAAGGCTCATGGCAAGAAAGTG<br>CTCGGTGCCTTTAGTGATGGCCTGGCTCACCTGGACAACCTCAAGG<br>GCACCTTTGCCCAGCTGAGTGAGCTGCACTGTGACAAGCTGCACG<br>TGGATCCTGAGAACTTCAGGGTGAGTCTATGGGACCCTTGATGTTT<br>TCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGGAACAGAGAAACAGGAGAA<br>TATGGGCCAAACAGGATATCTGTGGTAAGCAGTTCCTGCCCCGGC<br>TCAGGGCCAAGAACAGTTGGAACAGCAGAATATGGGCCAAACAG<br>GATATCTGTGGTAAGCAGTTCCTGCCCCGGCTCAGGGCCAAGAAC<br>AGATGGTCCCCAGATGCGGTCCCGCCCTCAGCAGTTTCTAGAGAA<br>CCATCAGATGTTTCCAGGGTGCCCCAAGGACCTGAAATGACCCTG<br>TGCCTTATTTGAACTAACCAATCAGTTCGCTTCTCGCTTCTGTTCGC<br>GCGCTTCTGCTCCCCGAGCTCTATATAAGCAGAGCTCGTTTAGTGA<br>ACCGTCAGATCGCGGCCGCGCCGCCACCATGGTGAGCAAGGGCGA<br>GGAGCTGTTCACCGGGGTGGTGCCCATCCTGGTCGAGCTGGACGG<br>CGACGTAAACGGCCACAAGTTCAGCGTGTCCGGCGAGGGCGAGG<br>GCGATGCCACCTACGGCAAGCTGACCCTGAAGTTCATCTGCACCA<br>CCGGCAAGCTGCCCGTGCCCTGGCCCACCCTCGTGACCACCCTGA<br>CCTACGGCGTGCAGTGCTTCAGCCGCTACCCCGACCACATGAAGC<br>AGCACGACTTCTTCAAGTCCGCCATGCCCGAAGGCTACGTCCAGG<br>AGCGCACCATCTTCTTCAAGGACGACGGCAACTACAAGACCCGCG<br>CCGAGGTGAAGTTCGAGGGCGACACCCTGGTGAACCGCATCGAGC<br>TGAAGGGCATCGACTTCAAGGAGGACGGCAACATCCTGGGGCACA<br>AGCTGGAGTACAACTACAACAGCCACAACGTCTATATCATGGCCG<br>ACAAGCAGAAGAACGGCATCAAGGTGAACTTCAAGATCCGCCAC<br>AACATCGAGGACGGCAGCGTGCAGCTCGCCGACCACTACCAGCAG<br>AACACCCCCATCGGCGACGGCCCCGTGCTGCTGCCCGACAACCAC<br>TACCTGAGCACCCAGTCCGCCCTGAGCAAAGACCCCAACGAGAAG<br>CGCGATCACATGGTCCTGCTGGAGTTCGTGACCGCCGCCGGGATC<br>ACTCTCGGCATGGACGAGCTGTACAAGTAAGCTTTATTTGTGAAAT<br>TTGTGATGCTATTGCTTTATTTGTAACCATTATAAGCTGCAATAAA<br>CAAGTTAACAACAACAATTGCATTCATTTTATGTTTCAGGTTCAGG<br>GGGAGATGTGGGAGGTTTTTTAAAGCCCTGCAGGCAATAGCCTTG<br>ACAAGGCAAACTTGACCAATAGTCTTAGAGTATCCAGTGAGGCCA<br>GGGGCCGGCGGCTGGCTAGGGATGAAGAATAAAAGGAAGCACCC<br>TTCAGCAGTTCCACACACTCGCTTCTGGAACGTCTGAGGTTATCAA<br>TAAGCTCCTAGTCCAGACGCCATGGGTCATTTCACAGAGGAGGAC<br>AAGGCTACTATCACAAGCCTGTGGGGCAAGGTGAATGTGGAAGAT<br>GCTGGAGGAGAAACCCTGGGAAGGTAGGCTCTGGTGACCAGGAC<br>AAGGGAGGGAAGGAAGGACCCTGTGCCTGGCAAAAGTCCAGGTC<br>GCTTCTCAGGATTTGTGGCACCTTCTGACTGTCAAACTGTTCTTGT<br>CAATCTCACAGGCTCCTGGTTGTCTACCCATGGACCCAGAGGTTCT<br>TTGACAGCTTTGGCAACCTGTCCTCTGCCTCTGCCATCATGGGCAA<br>CCCCAAAGTCAAGGCACATGGCAAGAAGGTGCTGACTTCCTTGGG<br>AGATGCCACAAAGCACCTGGATGATCTCAAGGGCACCTTTGCCCA<br>GCTGAGTGAACTGCACTGTGACAAGCTGCATGTGGATCCTGAGAA<br>CTTCAAGGTGAGTCCAGGAGATGTTTCAGCCCTGTTGCCTTTAGTC<br>TCGAGGCGTCGACAGGAACCCCTAGTGATGGAGTTGGCCACTCCC<br>TCTCTGCGCGCTCGCTCGCTCACTGAGGCCGGGCGACCAAAGGTC<br>GCCCGACGCCCGGGCTTTGCCCGGGCGGCCTCAGTGAGCGAGCGA |

-continued

| SEQ ID NO | NAME | SEQUENCE |
|---|---|---|
| | | GCGCGCAGCTGGCGTAATAGCGAAGAGGCCCGCACCGATCGCCCT TCCCAACAGTTGCGCAGCCTGAATGGCGAATGGCGATTCCGTTGC AATGGCTGGCGGTAATATTGTTCTGGATATTACCAGCAAGGCCGA TAGTTTGAGTTCTTCTACTCAGGCAAGTGATGTTATTACTAATCAA AGAAGTATTGCGACAACGGTTAATTTGCGTGATGGACAGACTCTT TTACTCGGTGGCCTCACTGATTATAAAAACACTTCTCAGGATTCTG GCGTACCGTTCCTGTCTAAAATCCCTTTAATCGGCCTCCTGTTTAG CTCCCGCTCTGATTCTAACGAGGAAAGCACGTTATACGTGCTCGTC AAAGCAACCATAGTACGCGCCCTGTAGCGGCGCATTAAGCGCGGC GGGTGTGGTGGTTACGCGCAGCGTGACCGCTACACTTGCCAGCGC CCTAGCGCCCGCTCCTTTCGCTTTCTTCCCTTCCTTTCTCGCCACGT TCGCCGGCTTTCCCCGTCAAGCTCTAAATCGGGGGCTCCCTTTAGG GTTCCGATTTAGTGCTTTACGGCACCTCGACCCCAAAAAACTTGAT TAGGGTGATGGTTCACGTAGTGGGCCATCGCCCTGATAGACGGTT TTTCGCCCTTTGACGTTGGAGTCCACGTTCTTTAATAGTGGACTCTT GTTCCAAACTGGAACAACACTCAACCCTATCTCGGTCTATTCTTTT GATTTATAAGGGATTTTGCCGATTTCGGCCTATTGGTTAAAAAATG AGCTGATTTAACAAAAATTTAACGCGAATTTTAACAAAATATTAA CGTTTACAATTTAAATATTTGCTTATACAATCTTCCTGTTTTTGGGG CTTTTCTGATTATCAACCGGGGTACATATGATTGACATGCTAGTTT TACGATTACCGTTCATCGATTCTCTTGTTTGCTCCAGACTCTCAGG CAATGACCTGATAGCCTTTGTAGAGACCTCTCAAAAATAGCTACC CTCTCCGGCATGAATTTATCAGCTAGAACGGTTGAATATCATATTG ATGGTGATTTGACTGTCTCCGGCCTTTCTCACCCGTTTGAATCTTTA CCTACACATTACTCAGGCATTGCATTTAAAATATATGAGGGTTCTA AAAATTTTTATCCTTGCGTTGAAATAAAGGCTTCTCCCGCAAAAGT ATTACAGGGTCATAATGTTTTTGGTACAACCGATTTAGCTTTATGC TCTGAGGCTTTATTGCTTAATTTTGCTAATTCTTTGCCTTGCCTGTA TGATTTATTGGATGTTGGAATCGCCTGATGCGGTATTTTCTCCTTA CGCATCTGTGCGGTATTTCACACCGCATATGGTGCACTCTCAGTAC AATCTGCTCTGATGCCGCATAGTTAAGCCAGCCCCGACACCCGCC AACACCCGCTGACGCGCCCTGACGGGCTTGTCTGCTCCCGGCATCC GCTTACAGACAAGCTGTGACCGTCTCCGGGAGCTGCATGTGTCAG AGGTTTTCACCGTCATCACCGAAACGCGCGAGACGAAAGGGCCTC GTGATACGCCTATTTTTATAGGTTAATGTCATGATAATAATGGTTT CTTAGACGTCAGGTGGCACTTTTCGGGGAAATGTGCGCGGAACCC CTATTTGTTTATTTTTCTAAATACATTCAAATATGTATCCGCTCATG AGACAATAACCCTGATAAATGCTTCAATAATATTGAAAAAGGAAG AGTATGAGTATTCAACATTTCCGTGTCGCCCTTATTCCCTTTTTTGC GGCATTTTGCCTTCCTGTTTTTGCTCACCCAGAAACGCTGGTGAAA GTAAAAGATGCTGAAGATCAGTTGGGTGCACGAGTGGGTTACATC GAACTGGATCTCAACAGCGGTAAGATCCTTGAGAGTTTTCGCCCC GAAGAACGTTTTCCAATGATGAGCACTTTTAAAGTTCTGCTATGTG GCGCGGTATTATCCCGTATTGACGCCGGGCAAGAGCAACTCGGTC GCCGCATACACTATTCTCAGAATGACTTGGTTGAGTACTCACCAGT CACAGAAAAGCATCTTACGGATGGCATGACAGTAAGAGAATTATG CAGTGCTGCCATAACCATGAGTGATAACACTGCGGCCAACTTACT TCTGACAACGATCGGAGGACCGAAGGAGCTAACCGCTTTTTTGCA CAACATGGGGGATCATGTAACTCGCCTTGATCGTTGGGAACCGGA GCTGAATGAAGCCATACCAAACGACGAGCGTGACACCACGATGCC TGTAGCAATGGCAACAACGTTGCGCAAACTATTAACTGGCGAACT ACTTACTCTAGCTTCCCGGCAACAATTAATAGACTGGATGGAGGC GGATAAAGTTGCAGGACCACTTCTGCGCTCGGCCCTTCCGGCTGG CTGGTTTATTGCTGATAAATCTGGAGCCGGTGAGCGTGGGTCTCGC GGTATCATTGCAGCACTGGGGCCAGATGGTAAGCCCTCCCGTATC GTAGTTATCTACACGACGGGGAGTCAGGCAACTATGGATGAACGA AATAGACAGATCGCTGAGATAGGTGCCTCACTGATTAAGCATTGG TAACTGTCAGACCAAGTTTACTCATATATACTTTAGATTGATTTAA AACTTCATTTTTAATTTAAAAGGATCTAGGTGAAGATCCTTTTTGA TAATCTCATGACCAAAATCCCTTAACGTGAGTTTTCGTTCCACTGA GCGTCAGACCCCGTAGAAAAGATCAAAGGATCTTCTTGAGATCCT TTTTTTCTGCGCGTAATCTGCTGCTTGCAAACAAAAAAACCACCGC TACCAGCGGTGGTTTGTTTGCCGGATCAAGAGCTACCAACTCTTTT TCCGAAGGTAACTGGCTTCAGCAGAGCGCAGATACCAAATACTGT CCTTCTAGTGTAGCCGTAGTTAGGCCACCACTTCAAGAACTCTGTA GCACCGCCTACATACCTCGCTCTGCTAATCCTGTTACCAGTGGCTG CTGCCAGTGGCGATAAGTCGTGTCTTACCGGGTTGGACTCAAGAC GATAGTTACCGGATAAGGCGCAGCGGTCGGGCTGAACGGGGGGTT CGTGCACACAGCCCAGCTTGGAGCGAACGACCTACACCGAACTGA GATACCTACAGCGTGAGCTATGAGAAAGCGCCACGCTTCCCGAAG GGAGAAAGGCGGACAGGTATCCGGTAAGCGGCAGGGTCGGAACA GGAGAGCGCACGAGGGAGCTTCCAGGGGGAAACGCCTGGTATCTT TATAGTCCTGTCGGGTTTCGCCACCTCTGACTTGAGCGTCGATTTT TGTGATGCTCGTCAGGGGGGCGGAGCCTATGGAAAAACGCCAGCA ACGCGGCCTTTTTACGGTTCCTGGCCTTTTGCTGGCCTTTTGCTCAC |

-continued

| SEQ ID NO | NAME | SEQUENCE |
|---|---|---|
| | | ATGTTCTTTCCTGCGTTATCCCCTGATTCTGTGGATAACCGTATTAC CGCCTTTGAGTGAGCTGATACCGCTCGCCGCAGCCGAACGACCGA GCGCAGCGAGTCAGTGAGCGAGGAAGCGGAAGAGCGCCCAATAC GCAAACCGCCTCTCCCCGCGCGTTGGCCGATTCATTAATG |
| 15 | T87Q cassettes Rhesus: AMS#1348 Rhesus pAAV HBG1(650).d0 HBBp>HBB(T87Q). core3'enh;MND> GFP.SV40pA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTAC GCGTAGATCTGGTGCCTACATACATACCTGAATAAGAAAAAAAAA TACCTTTGCTGAGATGAAACACACATGATTTATTTCAAATAGGTAC AGAGAAGTAGATACTGAAGTAAGGATTAAGTATTATATTATATTA CATAACATTAATCTATTCCTGCACTGAAACCGTTGCTTTATATGAT TTTTTTTTCACTACACTAATGAGAACTTAAGAGATAATGGCCTAA AACCACAGAGAGTATTTTCAAAGATAAGTATAGCACAATGCTTAC TAAATGAGACTAAGACTTGTCCCATCGAAAATCCTGGACCTATGC CTAAAACACGTGTCACAATCCCCGAACTTTTCAAAAATTGGTACAT GCTTTAACTTTAATCTCCAGGCCTCACTGGAGCTAGAGACAAGAA GGTAAAAAAAGGCTGACAAAAGAAGTCCTGGTATCTTCTATGGTG GGAGAAGGAAACTAGCTAAAGGGAAGAATAAATTAGAGAAAAAT TGGAATGATTGAATCGGAACAAGGCAAAGGCTATAAAAAAATTA AGCAGCAGTATCCTCTTGGGGGCCCCTTCCCCACACTATCTCAATG CAAATATCTGTCTGAAACGGTCCCTGGCTAAACTCCACCCATGGGT TGGCCAGTCTTGCCTTGACGCTAGCGTAAATACACTTGCAAAGGA GGATGTTTTTAGTAGCAATTTGTACTGATGGTATGGGGCCAAGAG ATATATCTTAGAGGGAGGGCTGAGGGTTTGAAGTCCAACTCCTAA GCCAGTGCCAGAAGAGCCAAGGACAGGTACGGCTGTCATCACTTA GACCTCACCCTGTGGAGCCACACCCTAGGGTTGGCCAATCTACTCC CAGGAGCAGGGAGGGCAGGAGCCAGGGCTGGGCATAAAAGTCAG GGCAGAGCCATCTATTGCTTACATTTGCTTCTGACACAACTGTGTT CACTAGCAACCTCAAACAGACACCATGGTGCACCTGACTCCTGAG GAGAAGTCTGCCGTTACTGCCCTGTGGGGCAAGGTGAACGTGGAT GAAGTTGGTGGTGAGGCCCTGGGCAGGTTGGTATCAAGGTTACAA GACAGGTTTAAGGAGACCAATAGAAACTGGGCATGTGGAGACAG AGAAGACTCTTGGGTTTCTGATAGGCACTGACTCTCTCTGCCTATT GGTCTATTTTCCCACCCTTAGGCTGCTGGTGGTCTACCCTTGGACC CAGAGGTTCTTTGAGTCCTTTGGGGATCTGTCCACTCCTGATGCTG TTATGGGCAACCCTAAGGTGAAGGCTCATGGCAAGAAAGTGCTCG GTGCCTTTAGTGATGGCCTGGCTCACCTGGACAACCTCAAGGGCA CCTTTGCCCAGCTGAGTGAGCTGCACTGTGACAAGCTGCACGTGG ATCCTGAGAACTTCAGGGTGAGTCTATGGGACCCTTGATGTTTTCT TTCCCCTTCTTTTCTATGGTTAAGTTCATGTCATAGGAAGGGGAGA AGTAACAGGGTACACATATTGACCAAATCAGGGTAATTTTGCATT TGTAATTTTAAAAAATGCTTTCTTCTTTTAATATACTTTTTTGTTTA TCTTATTTCTAATACTTTCCCTAATCTCTTTCTTTCAGGGCAATAAT GATACAATGTATCATGCCTCTTTGCACCATTCTAAAGAATAACAGT GATAATTTCTGGGTTAAGGCAATAGCAATATTTCTGCATATAAATA TTTCTGCATATAAATTGTAACTGATGTAAGAGGTTTCATATTGCTA ATAGCAGCTACAATCCAGCTACCATTCTGCTTTTATTTTATGGTTG GGATAAGGCTGGATTATTCTGAGTCCAAGCTAGGCCCTTTTGCTAA TCATGTTCATACCTCTTATCTTCCTCCCACAGCTCCTGGGCAACGT GCTGGTCTGTGTGCTGGCCCATCACTTTGGCAAAGAATTCACCCCA CCAGTGCAGGCTGCCTATCAGAAAGTGGTGGCTGGTGTGGCTAAT GCCCTGGCCCACAAGTATCACTAAGCTCGCTTTCTTGCTGTCCAAT TTCTATTAAAGGTTCCTTTGTTCCCTAAGTCCAACTACTAAACTGG GGGATATTATGAAGGGCCTTGAGCATCTGGATTCTGCCTAATAAA AAACATTTATTTTCATTGCAATGATGTATTTAAATTATTTCTGAATA TTTTACTAAAAAGGGAATGTGGGAGGTTGCAGTGCTAGTCTCCCG GAACTATCACTCTTTCACAGTCTGCTTTGGAAGGACTGGGCTTAGT ATGAAAAGTTAGGACTGAGAAGAATTTGAAAGGGGGCTTTTTGTA GCTTGATATTCACTACTGTCTTATTACCCTATCATAGGCCCACCCC AAATGGAAGTCCCATTCTTCCTCAGGATGTTTAAGATTAGCATTCA GGAAGAGATCAGAGGTCTGCTGGCTCCCTTATCATGTCCCTTATGG TGCTTCTGGCTCTGCACCGCGGGAACAGAGAAACAGGAGAATATG GGCCAAACAGGATATCTGTGGTAAGCAGTTCCTGCCCCGGCTCAG GGCCAAGAACAGTTGGAACAGCAGAATATGGGCCAAACAGGATA TCTGTGGTAAGCAGTTCCTGCCCCGGCTCAGGGCCAAGAACAGAT GGTCCCCAGATGCGGTCCCGCCCTCAGCAGTTTCTAGAGAACCAT CAGATGTTTCCAGGGTGCCCCAAGGACCTGAAATGACCCTGTGCC TTATTTGAACTAACCAATCAGTTCGCTTCTCGCTTCTGTTCGCGCG CTTCTGCTCCCCGAGCTCTATATAAGCAGAGCTCGTTTAGTGAACC GTCAGATCGCGGCCGCGCCGCCACCATGGTGAGCAAGGGCGAGG AGCTGTTCACCGGGGTGGTGCCCATCCTGGTCGAGCTGGACGGCG ACGTAAACGGCCACAAGTTCAGCGTGTCCGGCGAGGGCGAGGGC GATGCCACCTACGGCAAGCTGACCCTGAAGTTCATCTGCACCACC GGCAAGCTGCCCGTGCCCTGGCCCACCCTCGTGACCACCCTGACCT |

-continued

| SEQ ID NO | NAME | SEQUENCE |
|---|---|---|
| | | ACGGCGTGCAGTGCTTCAGCCGCTACCCCGACCACATGAAGCAGC<br>ACGACTTCTTCAAGTCCGCCATGCCCGAAGGCTACGTCCAGGAGC<br>GCACCATCTTCTTCAAGGACGACGGCAACTACAAGACCCGCGCCG<br>AGGTGAAGTTCGAGGGCGACACCCTGGTGAACCGCATCGAGCTGA<br>AGGGCATCGACTTCAAGGAGGACGGCAACATCCTGGGGCACAAG<br>CTGGAGTACAACTACAACAGCCACAACGTCTATATCATGGCCGAC<br>AAGCAGAAGAACGGCATCAAGGTGAACTTCAAGATCCGCCACAA<br>CATCGAGGACGGCAGCGTGCAGCTCGCCGACCACTACCAGCAGAA<br>CACCCCCATCGGCGACGGCCCCGTGCTGCTGCCCGACAACCACTA<br>CCTGAGCACCCAGTCCGCCCTGAGCAAAGACCCCAACGAGAAGCG<br>CGATCACATGGTCCTGCTGGAGTTCGTGACCGCCGCCGGGATCAC<br>TCTCGGCATGGACGAGCTGTACAAGTAAGCTTTATTTGTGAAATTT<br>GTGATGCTATTGCTTTATTTGTAACCATTATAAGCTGCAATAAACA<br>AGTTAACAACAACAATTGCATTCATTTTATGTTTCAGGTTCAGGGG<br>GAGATGTGGGAGGTTTTTTAAAGCCCTGCAGGCAATAGCCTTGAC<br>AAGGCAACCTTGACCAATAGTCTTAGAGTATCAGGTGAGGCCAGG<br>GGCCGGCGGCTGGCTAGGGATGAAGAATAAAAGGAAGCACCCTC<br>CAGCAGTTCCACACACTCGCTTCTGGAACGGCTGAGATTATCAAT<br>AAGCTCCTAGTCCAGACGCCATGGGTCATTTCACAGAGGAGGACA<br>AGGCTACTATCACAAGCCTGTGGGGCAAGGTGAATGTGGAAGATG<br>CTGGAGGAGAAACCCTGGGAAGGTAGGCTCTGGTGACCAGGACA<br>AGGAAGGGAAGGAAGGACCCTGTGCCTGGCAAAAGTCCAGGCCA<br>CTTCTCAGGATTTGTGGCACTTTCTGACTGTCAAACTGCTCTTGTTC<br>AATCTCACAGGCTCCTGGTTGTCTACCCATGGACCCAGAGGTTCTT<br>TGACAGCTTTGGCAACCTGTCCTCTGCCTCTGCCATCATGGGCAAC<br>CCCAAGGTCAAGGCACACGGCAAGAAGGTGCTGACTTCCTTGGGA<br>GATGCCATAAAGAACCTGGATGATCTCAAGGGCACCTTTGCCCAG<br>CTGAGTGAGCTGCACTGTGACAAGCTGCATGTGGATCCTGAGAAC<br>TTCAGGGTGAGTCCAGGAGTTTCAGCAGTTTCAGAGTTCAGTCTCA<br>AGGCGTCGACAGGAACCCCTAGTGATGGAGTTGGCCACTCCCTCT<br>CTGCGCGCTCGCTCGCTCACTGAGGCCGGGCGACCAAAGGTCGCC<br>CGACGCCCGGGCTTTGCCCGGGCGGCCTCAGTGAGCGAGCGAGCG<br>CGCAGCTGGCGTAATAGCGAAGAGGCCCGCACCGATCGCCCTTCC<br>CAACAGTTGCGCAGCCTGAATGGCGAATGGCGATTCCGTTGCAAT<br>GGCTGGCGGTAATATTGTTCTGGATATTACCAGCAAGGCCGATAG<br>TTTGAGTTCTTCTACTCAGGCAAGTGATGTTATTACTAATCAAAGA<br>AGTATTGCGACAACGGTTAATTTGCGTGATGGACAGACTCTTTTAC<br>TCGGTGGCCTCACTGATTATAAAAACACTTCTCAGGATTCTGGCGT<br>ACCGTTCCTGTCTAAAATCCCTTTAATCGGCCTCCTGTTTAGCTCCC<br>GCTCTGATTCTAACGAGGAAAGCACGTTATACGTGCTCGTCAAAG<br>CAACCATAGTACGCGCCCTGTAGCGGCGCATTAAGCGCGGCGGGT<br>GTGGTGGTTACGCGCAGCGTGACCGCTACACTTGCCAGCGCCCTA<br>GCGCCCGCTCCTTTCGCTTTCTTCCCTTCCTTTCTCGCCACGTTCGC<br>CGGCTTTCCCCGTCAAGCTCTAAATCGGGGGCTCCCTTTAGGGTTC<br>CGATTTAGTGCTTTACGGCACCTCGACCCCAAAAAACTTGATTAGG<br>GTGATGGTTCACGTAGTGGGCCATCGCCCTGATAGACGGTTTTTCG<br>CCCTTTGACGTTGGAGTCCACGTTCTTTAATAGTGGACTCTTGTTC<br>CAAACTGGAACAACACTCAACCCTATCTCGGTCTATTCTTTTGATT<br>TATAAGGGATTTTGCCGATTTCGGCCTATTGGTTAAAAAATGAGCT<br>GATTTAACAAAAATTTAACGCGAATTTTAACAAAATATTAACGTTT<br>ACAATTTAAATATTTGCTTATACAATCTTCCTGTTTTTGGGGCTTTT<br>CTGATTATCAACCGGGGTACATATGATTGACATGCTAGTTTTACGA<br>TTACCGTTCATCGATTCTCTTGTTTGCTCCAGACTCTCAGGCAATG<br>ACCTGATAGCCTTTGTAGAGACCTCTCAAAAATAGCTACCCTCTCC<br>GGCATGAATTTATCAGCTAGAACGGTTGAATATCATATTGATGGT<br>GATTTGACTGTCTCCGGCCTTTCTCACCCGTTTGAATCTTTACCTAC<br>ACATTACTCAGGCATTGCATTTAAAATATATGAGGGTTCTAAAAAT<br>TTTTATCCTTGCGTTGAAATAAAGGCTTCTCCCGCAAAAGTATTAC<br>AGGGTCATAATGTTTTTGGTACAACCGATTTAGCTTTATGCTCTGA<br>GGCTTTATTGCTTAATTTTGCTAATTCTTTGCCTTGCCTGTATGATT<br>TATTGGATGTTGGAATCGCCTGATGCGGTATTTTCTCCTTACGCAT<br>CTGTGCGGTATTTCACACCGCATATGGTGCACTCTCAGTACAATCT<br>GCTCTGATGCCGCATAGTTAAGCCAGCCCCGACACCCGCCAACAC<br>CCGCTGACGCGCCCTGACGGGCTTGTCTGCTCCCGGCATCCGCTTA<br>CAGACAAGCTGTGACCGTCTCCGGGAGCTGCATGTGTCAGAGGTT<br>TTCACCGTCATCACCGAAACGCGCGAGACGAAAGGGCCTCGTGAT<br>ACGCCTATTTTTATAGGTTAATGTCATGATAATAATGGTTTCTTAG<br>ACGTCAGGTGGCACTTTTCGGGGAAATGTGCGCGGAACCCCTATT<br>TGTTTATTTTTCTAAATACATTCAAATATGTATCCGCTCATGAGAC<br>AATAACCCTGATAAATGCTTCAATAATATTGAAAAAGGAAGAGTA<br>TGAGTATTCAACATTTCCGTGTCGCCCTTATTCCCTTTTTTGCGGCA<br>TTTTGCCTTCCTGTTTTTGCTCACCCAGAAACGCTGGTGAAAGTAA<br>AAGATGCTGAAGATCAGTTGGGTGCACGAGTGGGTTACATCGAAC<br>TGGATCTCAACAGCGGTAAGATCCTTGAGAGTTTTCGCCCCGAAG<br>AACGTTTTCCAATGATGAGCACTTTTAAAGTTCTGCTATGTGGCGC |

-continued

| SEQ ID NO | NAME | SEQUENCE |
|---|---|---|
| | | GGTATTATCCCGTATTGACGCCGGGCAAGAGCAACTCGGTCGCCG CATACACTATTCTCAGAATGACTTGGTTGAGTACTCACCAGTCACA GAAAAGCATCTTACGGATGGCATGACAGTAAGAGAATTATGCAGT GCTGCCATAACCATGAGTGATAACACTGCGGCCAACTTACTTCTG ACAACGATCGGAGGACCGAAGGAGCTAACCGCTTTTTTGCACAAC ATGGGGGATCATGTAACTCGCCTTGATCGTTGGGAACCGGAGCTG AATGAAGCCATACCAAACGACGAGCGTGACACCACGATGCCTGTA GCAATGGCAACAACGTTGCGCAAACTATTAACTGGCGAACTACTT ACTCTAGCTTCCCGGCAACAATTAATAGACTGGATGGAGGCGGAT AAAGTTGCAGGACCACTTCTGCGCTCGGCCCTTCCGGCTGGCTGGT TTATTGCTGATAAATCTGGAGCCGGTGAGCGTGGGTCTCGCGGTAT CATTGCAGCACTGGGGCCAGATGGTAAGCCCTCCCGTATCGTAGT TATCTACACGACGGGGAGTCAGGCAACTATGGATGAACGAAATAG ACAGATCGCTGAGATAGGTGCCTCACTGATTAAGCATTGGTAACT GTCAGACCAAGTTTACTCATATATACTTTAGATTGATTTAAAACTT CATTTTTAATTTAAAAGGATCTAGGTGAAGATCCTTTTTGATAATC TCATGACCAAAATCCCTTAACGTGAGTTTTCGTTCCACTGAGCGTC AGACCCCGTAGAAAAGATCAAAGGATCTTCTTGAGATCCTTTTTTT CTGCGCGTAATCTGCTGCTTGCAAACAAAAAAACCACCGCTACCA GCGGTGGTTTGTTTGCCGGATCAAGAGCTACCAACTCTTTTTCCGA AGGTAACTGGCTTCAGCAGAGCGCAGATACCAAATACTGTCCTTC TAGTGTAGCCGTAGTTAGGCCACCACTTCAAGAACTCTGTAGCAC CGCCTACATACCTCGCTCTGCTAATCCTGTTACCAGTGGCTGCTGC CAGTGGCGATAAGTCGTGTCTTACCGGGTTGGACTCAAGACGATA GTTACCGGATAAGGCGCAGCGGTCGGGCTGAACGGGGGGTTCGTG CACACAGCCCAGCTTGGAGCGAACGACCTACACCGAACTGAGATA CCTACAGCGTGAGCTATGAGAAAGCGCCACGCTTCCCGAAGGGAG AAAGGCGGACAGGTATCCGGTAAGCGGCAGGGTCGGAACAGGAG AGCGCACGAGGGAGCTTCCAGGGGGAAACGCCTGGTATCTTTATA GTCCTGTCGGGTTTCGCCACCTCTGACTTGAGCGTCGATTTTTGTG ATGCTCGTCAGGGGGGCGGAGCCTATGGAAAAACGCCAGCAACG CGGCCTTTTTACGGTTCCTGGCCTTTTGCTGGCCTTTTGCTCACATG TTCTTTCCTGCGTTATCCCCTGATTCTGTGGATAACCGTATTACCGC CTTTGAGTGAGCTGATACCGCTCGCCGCAGCCGAACGACCGAGCG CAGCGAGTCAGTGAGCGAGGAAGCGGAAGAGCGCCCAATACGCA AACCGCCTCTCCCCGCGCGTTGGCCGATTCATTAATG |
| 16 | MGMT Cassettes Human: AMS#1244 pAAV HBB(400)>synTron. HBBopt(T87Q). wPRE3.USE- | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TAGTGCATCAACTTCTTATTTGTGTAATAAGAAAATTGGGAAAAC GATCTTCAATATGCTTACCAAGCTGTGATTCCAAATATTACGTAAA TACACTTGCAAAGGAGGATGTTTTTAGTAGCAATTTGTACTGATGG TATGGGGCCAAGAGATATATCTTAGAGGGAGGGCTGAGGGTTTGA AGTCCAACTCCTAAGCCAGTGCCAGAAGAGCCAAGGACAGGTACG GCTGTCATCACTTAGACCTCACCCTGTGGAGCCACACCCTAGGGTT GGCCAATCTACTCCCAGGAGCAGGGAGGGCAGGAGCCAGGGCTG GGCATAAAAGTCAGGGCAGAGCCATCTATTGCTTACATTTGCTTCT GACACAACTGTGTTCACTAGCAACCTCAAACAGACACCAGGTGAG TTAAACCCATGAGAGAGAATAACAGAACTGCGAGTGATGGGCCA GTTAAGCGTAGATGGCTAATTAGTTCAGACAAATGTAAAATGCCA ACACCGTCTGTAAAGAAACCTAACTGATCCTCTTCCTTTGTCCTGT CTTCTTCACAGGCCGCCACCATGGTCCATCTTACACCGGAGGAGA AGTCCGCTGTAACGGCACTGTGGGGGAAAGTTAATGTCGATGAAG TCGGCGGTGAAGCACTCGGCAGGTTGCTGGTAGTGTACCCGTGGA CACAACGATTCTTTGAAAGTTTCGGGGACCTGTCCACACCCGATGC TGTGATGGGTAATCCAAAAGTAAAAGCACACGGCAAGAAAGTCCT CGGCGCGTTTAGTGATGGTCTGGCCCATTTGGATAACTTGAAGGGT ACATTCGCGCAGCTTTCCGAACTCCACTGTGACAAGTTGCACGTAG ATCCAGAAAACTTCCGGCTTCTGGGCAATGTGCTTGTATGCGTTCT GGCTCACCATTTTGGGAAGGAGTTTACCCCACCCGTGCAAGCGGC TTACCAAAAAGTGGTCGCAGGAGTGGCTAATGCCCTTGCACATAA ATATCACTAAGGTACCGATAATCAACCTCTGGATTACAAAATTTGT GAAAGATTGACTGGTATTCTTAACTATGTTGCTCCTTTTACGCTAT GTGGATACGCTGCTTTAATGCCTTTGTATCATGCTATTGCTTCCCGT ATGGCTTTCATTTTCTCCTCCTTGTATAAATCCTGGTTAGTTCTTGC CACGGCGGAACTCATCGCCGCCTGCCTTGCCCGCTGCTGGACAGG GGCTCGGCTGTTGGGCACTGACAATTCCGTGGTGTTTATTTGTGAA ATTTGTGATGCTATTGCTTTATTTGTAACCATTCTAGCTTTATTTGT GAAATTTGTGATGCTATTGCTTTATTTGTAACCATTATAAGCTGCA ATAAACAAGTTAACAACAACAATTGCATTCATTTTATGTTTCAGGT TCAGGGGGAGATGTGGGAGGTTTTTTAAAGCTTAATTAACGAGAT CGAGACCATCCTGGCTAACACAGTGAAACCCCGTCTCTACTAAAA AAATACAAAAAATTAGCCGGGCTTGGTGGCGGGTGCCTGTAGTCC |

-continued

| SEQ ID NO | NAME | SEQUENCE |
|---|---|---|
| | | CAGCTACTATGGAGGCTGAGGCGGGAGAATGGCGTGAACGCGGG<br>GGGCGGAGCTTGCAGTGAGCAGAGATCAGGGGCCACTGCACTCCA<br>GCCTGGGCGACAGAGAGAGACTCTGTCTCAAAAAAAAGAAAAAA<br>AAAATTTAGTAGACTAGCTAAAAAAATCCAGAGATAGTTATTGAT<br>GCATATGTAAAAGTCTTCCAATATTTACAAGTACAATGAAAAAAA<br>AATAACCTTGAATTAAGTGTAGAACTCATTGACAATGTTTCAAAG<br>GATGTGAGGGATAAACTAAAATTTGGGCAGTACATGCTGTTCCTG<br>TGTACTTGGAACAGAGGGAGAAAATCTGGGCTGGAAATATTGTTA<br>TAGGAGTTAGCACATGAAGGTGACAACTAAATTATTTGGAGTAGA<br>TGGAGTCACCAGCACATGTGAATAGTTTTAGAATGAAATGACCCA<br>AGATAGAACTTTGGAGAGCCCCCAAATTTAAATAAAATCAGTATA<br>AGAGAAGAGGAAGAAACCAAATGGTATACTAGTCTAAATTGTTTC<br>TTAGTGACAAAAGAATAACCTGAATATTAGATTAGCTGCCTATAT<br>GCTCTCTGAATCAATTTCATTCAACATGCAACAGTCCGCGGGAAC<br>AGAGAAACAGGAGAATATGGGCCAAACAGGATATCTGTGGTAAG<br>CAGTTCCTGCCCCGGCTCAGGGCCAAGAACAGTTGGAACAGCAGA<br>ATATGGGCCAAACAGGATATCTGTGGTAAGCAGTTCCTGCCCCGG<br>CTCAGGGCCAAGAACAGATGGTCCCCAGATGCGGTCCCGCCCTCA<br>GCAGTTTCTAGAGAACCATCAGATGTTTCCAGGGTGCCCCAAGGA<br>CCTGAAATGACCCTGTGCCTTATTTGAACTAACCAATCAGTTCGCT<br>TCTCGCTTCTGTTCGCGCGCTTCTGCTCCCCGAGCTCTATATAAGC<br>AGAGCTCGTTTAGTGAACCGTCAGATCGCCTGGAGACGCCATCCA<br>CGCTGTTTTGACTTCCATAGAAGGCGGCCGCGCCGCCACCATGGT<br>GAGCAAGGGCGAGGAGCTGTTCACCGGGGTGGTGCCCATCCTGGT<br>CGAGCTGGACGGCGACGTAAACGGCCACAAGTTCAGCGTGTCCGG<br>CGAGGGCGAGGGCGATGCCACCTACGGCAAGCTGACCCTGAAGTT<br>CATCTGCACCACCGGCAAGCTGCCCGTGCCCTGGCCCACCCTCGTG<br>ACCACCCTGACCTACGGCGTGCAGTGCTTCAGCCGCTACCCCGAC<br>CACATGAAGCAGCACGACTTCTTCAAGTCCGCCATGCCCGAAGGC<br>TACGTCCAGGAGCGCACCATCTTCTTCAAGGACGACGGCAACTAC<br>AAGACCCGCGCCGAGGTGAAGTTCGAGGGCGACACCCTGGTGAAC<br>CGCATCGAGCTGAAGGGCATCGACTTCAAGGAGGACGGCAACATC<br>CTGGGGCACAAGCTGGAGTACAACTACAACAGCCACAACGTCTAT<br>ATCATGGCCGACAAGCAGAAGAACGGCATCAAGGTGAACTTCAA<br>GATCCGCCACAACATCGAGGACGGCAGCGTGCAGCTCGCCGACCA<br>CTACCAGCAGAACACCCCCATCGGCGACGGCCCCGTGCTGCTGCC<br>CGACAACCACTACCTGAGCACCCAGTCCGCCCTGAGCAAAGACCC<br>CAACGAGAAGCGCGATCACATGGTCCTGCTGGAGTTCGTGACCGC<br>CGCCGGGATCACTCTCGGCATGGACGAGCTGTACAAGGGAAGCGG<br>AGCTACTAACTTCAGCCTGCTGAAGCAGGCTGGAGACGTGGAGGA<br>GAACCCTGGACCTACCTGCAGGCCTGAGAACTTCAGGGTGAGTCT<br>ATGGGACGCTTGATGTTTTCTTTCCCCTTCTTTTCTATGGTTAAGTT<br>CATGTCATAGGAAGGGGATAAGTAACAGGGTACAGTTTAGAATGG<br>GAAACAGACGAATGATTGCATCAGTGTGGAAGTCTCAGGATCGTT<br>TTAGTTTCTTTTATTTGCTGTTCATAACAATTGTTTTCTTTTGTTTAA<br>TTCTTGCTTTCTTTTTTTTTCTTCTCCGCAATTTTTACTATTATACTT<br>AATGCCTTAACATTGTGTATAACAAAAGGAAATATCTCTGAGATA<br>CATTAAGTAACTTAAAAAAAAACTTTACACAGTCTGCCTAGTACA<br>TTACTATTTGGAATATATGTGTGCTTATTTGCATATTCATAATCTCC<br>CTACTTTGTCGACGTAGATAAGTAGCATGGCGGGTTAATCATTAAC<br>TACAAGGAACCCCTAGTGATGGAGTTGGCCACTCCCTCTCTGCGC<br>GCTCGCTCGCTCACTGAGGCCGGGCGACCAAAGGTCGCCCGACGC<br>CCGGGCTTTGCCCGGGCGGCCTCAGTGAGCGAGCGAGCGCGCCAG<br>CTGGCGTAATAGCGAAGAGGCCCGCACCGATCGCCCTTCCCAACA<br>GTTGCGCAGCCTGAATGGCGAATGGCGATTCCGTTGCAATGGCTG<br>GCGGTAATATTGTTCTGGATATTACCAGCAAGGCCGATAGTTTGA<br>GTTCTTCTACTCAGGCAAGTGATGTTATTACTAATCAAAGAAGTAT<br>TGCGACAACGGTTAATTTGCGTGATGGACAGACTCTTTTACTCGGT<br>GGCCTCACTGATTATAAAAACACTTCTCAGGATTCTGGCGTACCGT<br>TCCTGTCTAAAATCCCTTTAATCGGCCTCCTGTTTAGCTCCCGCTCT<br>GATTCTAACGAGGAAAGCACGTTATACGTGCTCGTCAAAGCAACC<br>ATAGTACGCGCCCTGTAGCGGCGCATTAAGCGCGGCGGGTGTGGT<br>GGTTACGCGCAGCGTGACCGCTACACTTGCCAGCGCCCTAGCGCC<br>CGCTCCTTTCGCTTTCTTCCCTTCCTTTCTCGCCACGTTCGCCGGCT<br>TTCCCCGTCAAGCTCTAAATCGGGGGCTCCCTTTAGGGTTCCGATT<br>TAGTGCTTTACGGCACCTCGACCCCAAAAAACTTGATTAGGGTGA<br>TGGTTCACGTAGTGGGCCATCGCCCTGATAGACGGTTTTTCGCCCT<br>TTGACGTTGGAGTCCACGTTCTTTAATAGTGGACTCTTGTTCCAAA<br>CTGGAACAACACTCAACCCTATCTCGGTCTATTCTTTTGATTTATA<br>AGGGATTTTGCCGATTTCGGCCTATTGGTTAAAAAATGAGCTGATT<br>TAACAAAAATTTAACGCGAATTTTAACAAAATATTAACGTTTACA<br>ATTTAAATATTTGCTTATACAATCTTCCTGTTTTTGGGGCTTTTCTG<br>ATTATCAACCGGGGTACATATGATTGACATGCTAGTTTTACGATTA<br>CCGTTCATCGATTCTCTTGTTTGCTCCAGACTCTCAGGCAATGACC<br>TGATAGCCTTTGTAGAGACCTCTCAAAAATAGCTACCCTCTCCGGC |

-continued

| SEQ ID NO | NAME | SEQUENCE |
|---|---|---|
| | | ATGAATTTATCAGCTAGAACGGTTGAATATCATATTGATGGTGATT<br>TGACTGTCTCCGGCCTTTCTCACCCGTTTGAATCTTTACCTACACAT<br>TACTCAGGCATTGCATTTAAAATATATGAGGGTTCTAAAAATTTTT<br>ATCCTTGCGTTGAAATAAAGGCTTCTCCCGCAAAAGTATTACAGG<br>GTCATAATGTTTTTGGTACAACCGATTTAGCTTTATGCTCTGAGGC<br>TTTATTGCTTAATTTTGCTAATTCTTTGCCTTGCCTGTATGATTTATT<br>GGATGTTGGAATCGCCTGATGCGGTATTTTCTCCTTACGCATCTGT<br>GCGGTATTTCACACCGCATATGGTGCACTCTCAGTACAATCTGCTC<br>TGATGCCGCATAGTTAAGCCAGCCCCGACACCCGCCAACACCCGC<br>TGACGCGCCCTGACGGGCTTGTCTGCTCCCGGCATCCGCTTACAGA<br>CAAGCTGTGACCGTCTCCGGGAGCTGCATGTGTCAGAGGTTTTCAC<br>CGTCATCACCGAAACGCGCGAGACGAAAGGGCCTCGTGATACGCC<br>TATTTTTATAGGTTAATGTCATGATAATAATGGTTTCTTAGACGTC<br>AGGTGGCACTTTTCGGGGAAATGTGCGCGGAACCCCTATTTGTTTA<br>TTTTTCTAAATACATTCAAATATGTATCCGCTCATGAGACAATAAC<br>CCTGATAAATGCTTCAATAATATTGAAAAAGGAAGAGTATGAGTA<br>TTCAACATTTCCGTGTCGCCCTTATTCCCTTTTTTGCGGCATTTTGC<br>CTTCCTGTTTTTGCTCACCCAGAAACGCTGGTGAAAGTAAAAGATG<br>CTGAAGATCAGTTGGGTGCACGAGTGGGTTACATCGAACTGGATC<br>TCAACAGCGGTAAGATCCTTGAGAGTTTTCGCCCCGAAGAACGTT<br>TTCCAATGATGAGCACTTTTAAAGTTCTGCTATGTGGCGCGGTATT<br>ATCCCGTATTGACGCCGGGCAAGAGCAACTCGGTCGCCGCATACA<br>CTATTCTCAGAATGACTTGGTTGAGTACTCACCAGTCACAGAAAA<br>GCATCTTACGGATGGCATGACAGTAAGAGAATTATGCAGTGCTGC<br>CATAACCATGAGTGATAACACTGCGGCCAACTTACTTCTGACAAC<br>GATCGGAGGACCGAAGGAGCTAACCGCTTTTTTGCACAACATGGG<br>GGATCATGTAACTCGCCTTGATCGTTGGGAACCGGAGCTGAATGA<br>AGCCATACCAAACGACGAGCGTGACACCACGATGCCTGTAGCAAT<br>GGCAACAACGTTGCGCAAACTATTAACTGGCGAACTACTTACTCT<br>AGCTTCCCGGCAACAATTAATAGACTGGATGGAGGCGGATAAAGT<br>TGCAGGACCACTTCTGCGCTCGGCCCTTCCGGCTGGCTGGTTTATT<br>GCTGATAAATCTGGAGCCGGTGAGCGTGGGTCTCGCGGTATCATT<br>GCAGCACTGGGGCCAGATGGTAAGCCCTCCCGTATCGTAGTTATC<br>TACACGACGGGGAGTCAGGCAACTATGGATGAACGAAATAGACA<br>GATCGCTGAGATAGGTGCCTCACTGATTAAGCATTGGTAACTGTC<br>AGACCAAGTTTACTCATATATACTTTAGATTGATTTAAAACTTCAT<br>TTTTAATTTAAAAGGATCTAGGTGAAGATCCTTTTTGATAATCTCA<br>TGACCAAAATCCCTTAACGTGAGTTTTCGTTCCACTGAGCGTCAGA<br>CCCCGTAGAAAAGATCAAAGGATCTTCTTGAGATCCTTTTTTTCTG<br>CGCGTAATCTGCTGCTTGCAAACAAAAAAACCACCGCTACCAGCG<br>GTGGTTTGTTTGCCGGATCAAGAGCTACCAACTCTTTTTCCGAAGG<br>TAACTGGCTTCAGCAGAGCGCAGATACCAAATACTGTCCTTCTAGT<br>GTAGCCGTAGTTAGGCCACCACTTCAAGAACTCTGTAGCACCGCC<br>TACATACCTCGCTCTGCTAATCCTGTTACCAGTGGCTGCTGCCAGT<br>GGCGATAAGTCGTGTCTTACCGGGTTGGACTCAAGACGATAGTTA<br>CCGGATAAGGCGCAGCGGTCGGGCTGAACGGGGGGTTCGTGCACA<br>CAGCCCAGCTTGGAGCGAACGACCTACACCGAACTGAGATACCTA<br>CAGCGTGAGCTATGAGAAAGCGCCACGCTTCCCGAAGGGAGAAA<br>GGCGGACAGGTATCCGGTAAGCGGCAGGGTCGGAACAGGAGAGC<br>GCACGAGGGAGCTTCCAGGGGGAAACGCCTGGTATCTTTATAGTC<br>CTGTCGGGTTTCGCCACCTCTGACTTGAGCGTCGATTTTTGTGATG<br>CTCGTCAGGGGGGCGGAGCCTATGGAAAAACGCCAGCAACGCGG<br>CCTTTTTACGGTTCCTGGCCTTTTGCTGGCCTTTTGCTCACATGTTC<br>TTTCCTGCGTTATCCCCTGATTCTGTGGATAACCGTATTACCGCCTT<br>TGAGTGAGCTGATACCGCTCGCCGCAGCCGAACGACCGAGCGCAG<br>CGAGTCAGTGAGCGAGGAAGCGGAAGAGCGCCCAATACGCAAAC<br>CGCCTCTCCCCGCGCGTTGGCCGATTCATTAATG |
| 17 | MGMT Cassettes<br>Human:<br>AMS#1343<br>pAAV<br>HBG1(650).d0<br>HBBp>HBB(T87Q).<br>core3'enh;PGK><br>MGMT(P140K).<br>SV40pA | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC<br>GCGTAGATCTGGTGTATACATACATACCTGAATATGGAATCAAAT<br>ATTTTTCTAAGATGAAACAGTCATGATTTATTTCAAATAGGTACGG<br>ATAAGTAGATATTGAGGTAAGCATTAGGTCTTATATTATGTAACAC<br>TAATCTATTACTGCGCTGAAACTGTGGCTTTATAGAAATTGTTTTC<br>ACTGCACTATTGAGAAATTAAGAGATAATGGCAAAAGTCACAAAG<br>AGTATATTCAAAAAGAAGTATAGCACTTTTTCCTTAGAAACCACTG<br>CTAACTGAAAGAGACTAAGATTTGTCCCGTCAAAAATCCTGGACC<br>TATGCCTAAAACACATTTCACAATCCCTGAACTTTTCAAAAATTGG<br>TACATGCTTTAGCTTTAAACTACAGGCCTCACTGGAGCTAGAGAC<br>AAGAAGGTAAAAAACGGCTGACAAAAGAAGTCCTGGTATCCTCTA<br>TGATGGGAGAAGGAAACTAGCTAAAGGGAAGAATAAATTAGAGA<br>AAAACTGGAATGACTGAATCGGAACAAGGCAAAGGCTATAAAAA<br>AAATTAAGCAGCAGTATCCTCTTGGGGGCCCCTTCCCCACACTATC<br>TCAATGCAAATATCTGTCTGAAACGGTCCCTGGCTAAACTCCACCC |

-continued

| SEQ ID NO | NAME | SEQUENCE |
|---|---|---|
| | | ATGGGTTGGCCAGCCTTGCCTTGACGCTAGCGTAAATACACTTGCA<br>AAGGAGGATGTTTTTAGTAGCAATTTGTACTGATGGTATGGGGCC<br>AAGAGATATATCTTAGAGGGAGGGCTGAGGGTTTGAAGTCCAACT<br>CCTAAGCCAGTGCCAGAAGAGCCAAGGACAGGTACGGCTGTCATC<br>ACTTAGACCTCACCCTGTGGAGCCACACCCTAGGGTTGGCCAATCT<br>ACTCCCAGGAGCAGGGAGGGCAGGAGCCAGGGCTGGGCATAAAA<br>GTCAGGGCAGAGCCATCTATTGCTTACATTTGCTTCTGACACAACT<br>GTGTTCACTAGCAACCTCAAACAGACACCATGGTGCACCTGACTC<br>CTGAGGAGAAGTCTGCCGTTACTGCCCTGTGGGGCAAGGTGAACG<br>TGGATGAAGTTGGTGGTGAGGCCCTGGGCAGGTTGGTATCAAGGT<br>TACAAGACAGGTTTAAGGAGACCAATAGAAACTGGGCATGTGGA<br>GACAGAGAAGACTCTTGGGTTTCTGATAGGCACTGACTCTCTCTGC<br>CTATTGGTCTATTTTCCCACCCTTAGGCTGCTGGTGGTCTACCCTTG<br>GACCCAGAGGTTCTTTGAGTCCTTTGGGGATCTGTCCACTCCTGAT<br>GCTGTTATGGGCAACCCTAAGGTGAAGGCTCATGGCAAGAAAGTG<br>CTCGGTGCCTTTAGTGATGGCCTGGCTCACCTGGACAACCTCAAGG<br>GCACCTTTGCCCAGCTGAGTGAGCTGCACTGTGACAAGCTGCACG<br>TGGATCCTGAGAACTTCAGGGTGAGTCTATGGGACCCTTGATGTTT<br>TCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGCCACGGGGTTGGGGTTGCG<br>CCTTTTCCAAGGCAGCCCTGGGTTTGCGCAGGGACGCGGCTGCTCT<br>GGGCGTGGTTCCGGGAAACGCAGCGGCGCCGACCCTGGGTCTCGC<br>ACATTCTTCACGTCCGTTCGCAGCGTCACCCGGATCTTCGCCGCTA<br>CCCTTGTGGGCCCCCCGGCGACGCTTCCTGCTCCGCCCCTAAGTCG<br>GGAAGGTTCCTTGCGGTTCGCGGCGTGCCGGACGTGACAAACGGA<br>AGCCGCACGTCTCACTAGTACCCTCGCAGACGGACAGCGCCAGGG<br>AGCAATGGCAGCGCGCCGACCGCGATGGGCTGTGGCCAATAGCGG<br>CTGCTCAGCGGGGCGCGCCGAGAGCAGCGGCCGGGAAGGGGCGG<br>TGCGGGAGGCGGGGTGTGGGGCGGTAGTGTGGGCCCTGTTCCTGC<br>CCGCGCGGTGTTCCGCATTCTGCAAGCCTCCGGAGCGCACGTCGG<br>CAGTCGGCTCCCTCGTTGACCGAATCACCGACCTCTCTCCCCAGCG<br>GCCGCGCCGCCACCATGGACAAGGATTGTGAAATGAAACGCACCA<br>CACTGGACAGCCCTTTGGGGAAGCTGGAGCTGTCTGGTTGTGAGC<br>AGGGTCTGCACGAAATAAAGCTCCTGGGCAAGGGGACGTCTGCAG<br>CTGATGCCGTGGAGGTCCCAGCCCCCGCTGCGGTTCTCGGAGGTC<br>CGGAGCCCCTGATGCAGTGCACAGCCTGGCTGAATGCCTATTTCC<br>ACCAGCCCGAGGCTATCGAAGAGTTCCCCGTGCCGGCTCTTCACC<br>ATCCCGTTTTCCAGCAAGAGTCGTTCACCAGACAGGTGTTATGGA<br>AGCTGCTGAAGGTTGTGAAATTCGGAGAAGTGATTTCTTACCAGC<br>AATTAGCAGCCCTGGCAGGCAACCCCAAAGCCGCGCGAGCAGTGG<br>GAGGAGCAATGAGAGGCAATCCTGTCAAAATCCTCATCCCGTGCC<br>ACAGAGTGGTCTGCAGCAGCGGAGCCGTGGGCAACTACTCCGGAG<br>GACTGGCCGTGAAGGAATGGCTTCTGGCCCATGAAGGCCACCGGT<br>TGGGGAAGCCAGGCTTGGGAGGGAGCTCAGGTCTGGCAGGGGCCT<br>GGCTCAAGGGAGCGGGAGCTACCTCGGGCTCCCCGCCTGCTGGCC<br>GAAACTAAGCTTTATTTGTGAAATTTGTGATGCTATTGCTTTATTTG<br>TAACCATTATAAGCTGCAATAAACAAGTTAACAACAACAATTGCA<br>TTCATTTTATGTTTCAGGTTCAGGGGGAGATGTGGGAGGTTTTTTA<br>AAGCCCTGCAGGCAATAGCCTTGACAAGGCAAACTTGACCAATAG<br>TCTTAGAGTATCCAGTGAGGCCAGGGGCCGGCGGCTGGCTAGGGA<br>TGAAGAATAAAAGGAAGCACCCTTCAGCAGTTCCACACACTCGCT<br>TCTGGAACGTCTGAGGTTATCAATAAGCTCCTAGTCCAGACGCCAT<br>GGGTCATTTCACAGAGGAGGACAAGGCTACTATCACAAGCCTGTG<br>GGGCAAGGTGAATGTGGAAGATGCTGGAGGAGAAACCCTGGGAA |

-continued

| SEQ ID NO | NAME | SEQUENCE |
|---|---|---|
| | | GGTAGGCTCTGGTGACCAGGACAAGGGAGGGAAGGAAGGACCCT |
| | | GTGCCTGGCAAAAGTCCAGGTCGCTTCTCAGGATTTGTGGCACCTT |
| | | CTGACTGTCAAACTGTTCTTGTCAATCTCACAGGCTCCTGGTTGTC |
| | | TACCCATGGACCCAGAGGTTCTTTGACAGCTTTGGCAACCTGTCCT |
| | | CTGCCTCTGCCATCATGGGCAACCCCAAAGTCAAGGCACATGGCA |
| | | AGAAGGTGCTGACTTCCTTGGGAGATGCCACAAAGCACCTGGATG |
| | | ATCTCAAGGGCACCTTTGCCCAGCTGAGTGAACTGCACTGTGACA |
| | | AGCTGCATGTGGATCCTGAGAACTTCAAGGTGAGTCCAGGAGATG |
| | | TTTCAGCCCTGTTGCCTTTAGTCTCGAGGCGTCGACAGGAACCCCT |
| | | AGTGATGGAGTTGGCCACTCCCTCTCTGCGCGCTCGCTCGCTCACT |
| | | GAGGCCGGGCGACCAAAGGTCGCCCGACGCCCGGGCTTTGCCCGG |
| | | GCGGCCTCAGTGAGCGAGCGAGCGCGCAGCTGGCGTAATAGCGA |
| | | AGAGGCCCGCACCGATCGCCCTTCCCAACAGTTGCGCAGCCTGAA |
| | | TGGCGAATGGCGATTCCGTTGCAATGGCTGGCGGTAATATTGTTCT |
| | | GGATATTACCAGCAAGGCCGATAGTTTGAGTTCTTCTACTCAGGCA |
| | | AGTGATGTTATTACTAATCAAAGAAGTATTGCGACAACGGTTAAT |
| | | TTGCGTGATGGACAGACTCTTTTACTCGGTGGCCTCACTGATTATA |
| | | AAAACACTTCTCAGGATTCTGGCGTACCGTTCCTGTCTAAAATCCC |
| | | TTTAATCGGCCTCCTGTTTAGCTCCCGCTCTGATTCTAACGAGGAA |
| | | AGCACGTTATACGTGCTCGTCAAAGCAACCATAGTACGCGCCCTG |
| | | TAGCGGCGCATTAAGCGCGGCGGGTGTGGTGGTTACGCGCAGCGT |
| | | GACCGCTACACTTGCCAGCGCCCTAGCGCCCGCTCCTTTCGCTTTC |
| | | TTCCCTTCCTTTCTCGCCACGTTCGCCGGCTTTCCCCGTCAAGCTCT |
| | | AAATCGGGGGCTCCCTTTAGGGTTCCGATTTAGTGCTTTACGGCAC |
| | | CTCGACCCCAAAAAACTTGATTAGGGTGATGGTTCACGTAGTGGG |
| | | CCATCGCCCTGATAGACGGTTTTTCGCCCTTTGACGTTGGAGTCCA |
| | | CGTTCTTTAATAGTGGACTCTTGTTCCAAACTGGAACAACACTCAA |
| | | CCCTATCTCGGTCTATTCTTTTGATTTATAAGGGATTTTGCCGATTT |
| | | CGGCCTATTGGTTAAAAAATGAGCTGATTTAACAAAAATTTAACG |
| | | CGAATTTTAACAAAATATTAACGTTTACAATTTAAATATTTGCTTA |
| | | TACAATCTTCCTGTTTTTGGGGCTTTTCTGATTATCAACCGGGGTA |
| | | CATATGATTGACATGCTAGTTTTACGATTACCGTTCATCGATTCTC |
| | | TTGTTTGCTCCAGACTCTCAGGCAATGACCTGATAGCCTTTGTAGA |
| | | GACCTCTCAAAAATAGCTACCCTCTCCGGCATGAATTTATCAGCTA |
| | | GAACGGTTGAATATCATATTGATGGTGATTTGACTGTCTCCGGCCT |
| | | TTCTCACCCGTTTGAATCTTTACCTACACATTACTCAGGCATTGCA |
| | | TTTAAAATATATGAGGGTTCTAAAAATTTTTATCCTTGCGTTGAAA |
| | | TAAAGGCTTCTCCCGCAAAAGTATTACAGGGTCATAATGTTTTTGG |
| | | TACAACCGATTTAGCTTTATGCTCTGAGGCTTTATTGCTTAATTTTG |
| | | CTAATTCTTTGCCTTGCCTGTATGATTTATTGGATGTTGGAATCGCC |
| | | TGATGCGGTATTTTCTCCTTACGCATCTGTGCGGTATTTCACACCG |
| | | CATATGGTGCACTCTCAGTACAATCTGCTCTGATGCCGCATAGTTA |
| | | AGCCAGCCCCGACACCCGCCAACACCCGCTGACGCGCCCTGACGG |
| | | GCTTGTCTGCTCCCGGCATCCGCTTACAGACAAGCTGTGACCGTCT |
| | | CCGGGAGCTGCATGTGTCAGAGGTTTTCACCGTCATCACCGAAAC |
| | | GCGCGAGACGAAAGGGCCTCGTGATACGCCTATTTTTATAGGTTA |
| | | ATGTCATGATAATAATGGTTTCTTAGACGTCAGGTGGCACTTTTCG |
| | | GGGAAATGTGCGCGGAACCCCTATTTGTTTATTTTTCTAAATACAT |
| | | TCAAATATGTATCCGCTCATGAGACAATAACCCTGATAAATGCTTC |
| | | AATAATATTGAAAAAGGAAGAGTATGAGTATTCAACATTTCCGTG |
| | | TCGCCCTTATTCCCTTTTTTGCGGCATTTTGCCTTCCTGTTTTTGCTC |
| | | ACCCAGAAACGCTGGTGAAAGTAAAAGATGCTGAAGATCAGTTGG |
| | | GTGCACGAGTGGGTTACATCGAACTGGATCTCAACAGCGGTAAGA |
| | | TCCTTGAGAGTTTTCGCCCCGAAGAACGTTTTCCAATGATGAGCAC |
| | | TTTTAAAGTTCTGCTATGTGGCGCGGTATTATCCCGTATTGACGCC |
| | | GGGCAAGAGCAACTCGGTCGCCGCATACACTATTCTCAGAATGAC |
| | | TTGGTTGAGTACTCACCAGTCACAGAAAAGCATCTTACGGATGGC |
| | | ATGACAGTAAGAGAATTATGCAGTGCTGCCATAACCATGAGTGAT |
| | | AACACTGCGGCCAACTTACTTCTGACAACGATCGGAGGACCGAAG |
| | | GAGCTAACCGCTTTTTTGCACAACATGGGGGATCATGTAACTCGCC |
| | | TTGATCGTTGGGAACCGGAGCTGAATGAAGCCATACCAAACGACG |
| | | AGCGTGACACCACGATGCCTGTAGCAATGGCAACAACGTTGCGCA |
| | | AACTATTAACTGGCGAACTACTTACTCTAGCTTCCCGGCAACAATT |
| | | AATAGACTGGATGGAGGCGGATAAAGTTGCAGGACCACTTCTGCG |
| | | CTCGGCCCTTCCGGCTGGCTGGTTTATTGCTGATAAATCTGGAGCC |
| | | GGTGAGCGTGGGTCTCGCGGTATCATTGCAGCACTGGGGCCAGAT |
| | | GGTAAGCCCTCCCGTATCGTAGTTATCTACACGACGGGGAGTCAG |
| | | GCAACTATGGATGAACGAAATAGACAGATCGCTGAGATAGGTGCC |
| | | TCACTGATTAAGCATTGGTAACTGTCAGACCAAGTTTACTCATATA |
| | | TACTTTAGATTGATTTAAAACTTCATTTTTAATTTAAAAGGATCTA |
| | | GGTGAAGATCCTTTTTGATAATCTCATGACCAAAATCCCTTAACGT |
| | | GAGTTTTCGTTCCACTGAGCGTCAGACCCCGTAGAAAAGATCAAA |
| | | GGATCTTCTTGAGATCCTTTTTTTCTGCGCGTAATCTGCTGCTTGCA |
| | | AACAAAAAAACCACCGCTACCAGCGGTGGTTTGTTTGCCGGATCA |
| | | AGAGCTACCAACTCTTTTTCCGAAGGTAACTGGCTTCAGCAGAGC |

-continued

| SEQ ID NO | NAME | SEQUENCE |
|---|---|---|
| | | GCAGATACCAAATACTGTCCTTCTAGTGTAGCCGTAGTTAGGCCAC |
| | | CACTTCAAGAACTCTGTAGCACCGCCTACATACCTCGCTCTGCTAA |
| | | TCCTGTTACCAGTGGCTGCTGCCAGTGGCGATAAGTCGTGTCTTAC |
| | | CGGGTTGGACTCAAGACGATAGTTACCGGATAAGGCGCAGCGGTC |
| | | GGGCTGAACGGGGGGTTCGTGCACACAGCCCAGCTTGGAGCGAAC |
| | | GACCTACACCGAACTGAGATACCTACAGCGTGAGCTATGAGAAAG |
| | | CGCCACGCTTCCCGAAGGGAGAAAGGCGGACAGGTATCCGGTAA |
| | | GCGGCAGGGTCGGAACAGGAGAGCGCACGAGGGAGCTTCCAGGG |
| | | GGAAACGCCTGGTATCTTTATAGTCCTGTCGGGTTTCGCCACCTCT |
| | | GACTTGAGCGTCGATTTTTGTGATGCTCGTCAGGGGGGCGGAGCC |
| | | TATGGAAAAACGCCAGCAACGCGGCCTTTTTACGGTTCCTGGCCTT |
| | | TTGCTGGCCTTTTGCTCACATGTTCTTTCCTGCGTTATCCCCTGATT |
| | | CTGTGGATAACCGTATTACCGCCTTTGAGTGAGCTGATACCGCTCG |
| | | CCGCAGCCGAACGACCGAGCGCAGCGAGTCAGTGAGCGAGGAAG |
| | | CGGAAGAGCGCCCAATACGCAAACCGCCTCTCCCCGCGCGTTGGC |
| | | CGATTCATTAATG |
| 18 | MGMT Cassettes | CAGCTGCGCGCTCGCTCGCTCACTGAGGCCGCCCGGGCAAAGCCC |
| | Human: | GGGCGTCGGGCGACCTTTGGTCGCCCGGCCTCAGTGAGCGAGCGA |
| | AMS#1346 | GCGCGCAGAGAGGGAGTGGCCAACTCCATCACTAGGGGTTCCTAC |
| | pAAV | GCGTAGATCTGGTGTATACATACATACCTGAATATGGAATCAAAT |
| | HBG1(650).d0 | ATTTTTCTAAGATGAAACAGTCATGATTTATTTCAAATAGGTACGG |
| | d13p>HBB(T87Q). | ATAAGTAGATATTGAGGTAAGCATTAGGTCTTATATTATGTAACAC |
| | core3'enh;PGK> | TAATCTATTACTGCGCTGAAACTGTGGCTTTATAGAAATTGTTTTC |
| | MGMT(P140K). | ACTGCACTATTGAGAAATTAAGAGATAATGGCAAAAGTCACAAAG |
| | SV40pA | AGTATATTCAAAAAGAAGTATAGCACTTTTTCCTTAGAAACCACTG |
| | | CTAACTGAAAGAGACTAAGATTTGTCCCGTCAAAAATCCTGGACC |
| | | TATGCCTAAAACACATTTCACAATCCCTGAACTTTTCAAAAATTGG |
| | | TACATGCTTTAGCTTTAAACTACAGGCCTCACTGGAGCTAGAGAC |
| | | AAGAAGGTAAAAAACGGCTGACAAAAGAAGTCCTGGTATCCTCTA |
| | | TGATGGGAGAAGGAAACTAGCTAAAGGGAAGAATAAATTAGAGA |
| | | AAAACTGGAATGACTGAATCGGAACAAGGCAAAGGCTATAAAAA |
| | | AAATTAAGCAGCAGTATCCTCTTGGGGGCCCCTTCCCCACACTATC |
| | | TCAATGCAAATATCTGTCTGAAACGGTCCCTGGCTAAACTCCACCC |
| | | ATGGGTTGGCCAGCCTTGCCTTGACAAGGCAAACTTGACCAATAG |
| | | TCTTAGAGTATCCAGTGAGGCCAGGGGCCGGCGGCTGGCTAGGGA |
| | | TGAAGAATAAAAGGAAGCACCCTTCAGCAGTTCCACACACTCGCT |
| | | TCTGGAACGTCTGAGGTTATCAATAAGCTCCTAGTCCAGACGCCAT |
| | | GGTGCACCTGACTCCTGAGGAGAAGTCTGCCGTTACTGCCCTGTG |
| | | GGGCAAGGTGAACGTGGATGAAGTTGGTGGTGAGGCCCTGGGCA |
| | | GGTTGGTATCAAGGTTACAAGACAGGTTTAAGGAGACCAATAGAA |
| | | ACTGGGCATGTGGAGACAGAGAAGACTCTTGGGTTTCTGATAGGC |
| | | ACTGACTCTCTCTGCCTATTGGTCTATTTTCCCACCCTTAGGCTGCT |
| | | GGTGGTCTACCCTTGGACCCAGAGGTTCTTTGAGTCCTTTGGGGAT |
| | | CTGTCCACTCCTGATGCTGTTATGGGCAACCCTAAGGTGAAGGCTC |
| | | ATGGCAAGAAAGTGCTCGGTGCCTTTAGTGATGGCCTGGCTCACC |
| | | TGGACAACCTCAAGGGCACCTTTGCCCAGCTGAGTGAGCTGCACT |
| | | GTGACAAGCTGCACGTGGATCCTGAGAACTTCAGGGTGAGTCTAT |
| | | GGGACCCTTGATGTTTTCTTTCCCCTTCTTTTCTATGGTTAAGTTCA |
| | | TGTCATAGGAAGGGGAGAAGTAACAGGGTACACATATTGACCAA |
| | | ATCAGGGTAATTTTGCATTTGTAATTTTAAAAAATGCTTTCTTCTTT |
| | | TAATATACTTTTTTGTTTATCTTATTTCTAATACTTTCCCTAATCTCT |
| | | TTCTTTCAGGGCAATAATGATACAATGTATCATGCCTCTTTGCACC |
| | | ATTCTAAAGAATAACAGTGATAATTTCTGGGTTAAGGCAATAGCA |
| | | ATATTTCTGCATATAAATATTTCTGCATATAAATTGTAACTGATGT |
| | | AAGAGGTTTCATATTGCTAATAGCAGCTACAATCCAGCTACCATTC |
| | | TGCTTTTATTTTATGGTTGGGATAAGGCTGGATTATTCTGAGTCCA |
| | | AGCTAGGCCCTTTTGCTAATCATGTTCATACCTCTTATCTTCCTCCC |
| | | ACAGCTCCTGGGCAACGTGCTGGTCTGTGTGCTGGCCCATCACTTT |
| | | GGCAAAGAATTCACCCCACCAGTGCAGGCTGCCTATCAGAAAGTG |
| | | GTGGCTGGTGTGGCTAATGCCCTGGCCCACAAGTATCACTAAGCT |
| | | CGCTTTCTTGCTGTCCAATTTCTATTAAAGGTTCCTTTGTTCCCTAA |
| | | GTCCAACTACTAAACTGGGGGATATTATGAAGGGCCTTGAGCATC |
| | | TGGATTCTGCCTAATAAAAAACATTTATTTTCATTGCAATGATGTA |
| | | TTTAAATTATTTCTGAATATTTTACTAAAAAGGGAATGTGGGAGGT |
| | | TGCAGTGCTAGTCTCCCGGAACTATCACTCTTTCACAGTCTGCTTT |
| | | GGAAGGACTGGGCTTAGTATGAAAAGTTAGGACTGAGAAGAATTT |
| | | GAAAGGGGGCTTTTTGTAGCTTGATATTCACTACTGTCTTATTACC |
| | | CTATCATAGGCCCACCCCAAATGGAAGTCCCATTCTTCCTCAGGAT |
| | | GTTTAAGATTAGCATTCAGGAAGAGATCAGAGGTCTGCTGGCTCC |
| | | CTTATCATGTCCCTTATGGTGCTTCTGGCTCTGCACCGCGGCCACG |
| | | GGGTTGGGGTTGCGCCTTTTCCAAGGCAGCCCTGGGTTTGCGCAG |
| | | GGACGCGGCTGCTCTGGGCGTGGTTCCGGGAAACGCAGCGGCGCC |
| | | GACCCTGGGTCTCGCACATTCTTCACGTCCGTTCGCAGCGTCACCC |
| | | GGATCTTCGCCGCTACCCTTGTGGGCCCCCCGGCGACGCTTCCTGC |

-continued

| SEQ ID NO | NAME | SEQUENCE |
|---|---|---|
| | | TCCGCCCCTAAGTCGGGAAGGTTCCTTGCGGTTCGCGGCGTGCCG |
| | | GACGTGACAAACGGAAGCCGCACGTCTCACTAGTACCCTCGCAGA |
| | | CGGACAGCGCCAGGGAGCAATGGCAGCGCGCCGACCGCGATGGG |
| | | CTGTGGCCAATAGCGGCTGCTCAGCGGGGCGCGCCGAGAGCAGCG |
| | | GCCGGGAAGGGGCGGTGCGGGAGGCGGGGTGTGGGGCGGTAGTG |
| | | TGGGCCCTGTTCCTGCCCGCGCGGTGTTCCGCATTCTGCAAGCCTC |
| | | CGGAGCGCACGTCGGCAGTCGGCTCCCTCGTTGACCGAATCACCG |
| | | ACCTCTCTCCCCAGCGGCCGCGCCGCCACCATGGACAAGGATTGT |
| | | GAAATGAAACGCACCACACTGGACAGCCCTTTGGGGAAGCTGGAG |
| | | CTGTCTGGTTGTGAGCAGGGTCTGCACGAAATAAAGCTCCTGGGC |
| | | AAGGGGACGTCTGCAGCTGATGCCGTGGAGGTCCCAGCCCCCGCT |
| | | GCGGTTCTCGGAGGTCCGGAGCCCCTGATGCAGTGCACAGCCTGG |
| | | CTGAATGCCTATTTCCACCAGCCCGAGGCTATCGAAGAGTTCCCCG |
| | | TGCCGGCTCTTCACCATCCCGTTTTCCAGCAAGAGTCGTTCACCAG |
| | | ACAGGTGTTATGGAAGCTGCTGAAGGTTGTGAAATTCGGAGAAGT |
| | | GATTTCTTACCAGCAATTAGCAGCCCTGGCAGGCAACCCCAAAGC |
| | | CGCGCGAGCAGTGGGAGGAGCAATGAGAGGCAATCCTGTCAAAA |
| | | TCCTCATCCCGTGCCACAGAGTGGTCTGCAGCAGCGGAGCCGTGG |
| | | GCAACTACTCCGGAGGACTGGCCGTGAAGGAATGGCTTCTGGCCC |
| | | ATGAAGGCCACCGGTTGGGGAAGCCAGGCTTGGGAGGGAGCTCA |
| | | GGTCTGGCAGGGGCCTGGCTCAAGGGAGCGGGAGCTACCTCGGGC |
| | | TCCCCGCCTGCTGGCCGAAACTAAGCTTTATTTGTGAAATTTGTGA |
| | | TGCTATTGCTTTATTTGTAACCATTATAAGCTGCAATAAACAAGTT |
| | | AACAACAACAATTGCATTCATTTTATGTTTCAGGTTCAGGGGGAG |
| | | ATGTGGGAGGTTTTTTAAAGCCCTGCAGGCAATAGCCTTGACAAG |
| | | GCAAACTTGACCAATAGTCTTAGAGTATCCAGTGAGGCCAGGGGC |
| | | CGGCGGCTGGCTAGGGATGAAGAATAAAAGGAAGCACCCTTCAG |
| | | CAGTTCCACACACTCGCTTCTGGAACGTCTGAGGTTATCAATAAGC |
| | | TCCTAGTCCAGACGCCATGGGTCATTTCACAGAGGAGGACAAGGC |
| | | TACTATCACAAGCCTGTGGGGCAAGGTGAATGTGGAAGATGCTGG |
| | | AGGAGAAACCCTGGGAAGGTAGGCTCTGGTGACCAGGACAAGGG |
| | | AGGGAAGGAAGGACCCTGTGCCTGGCAAAAGTCCAGGTCGCTTCT |
| | | CAGGATTTGTGGCACCTTCTGACTGTCAAACTGTTCTTGTCAATCT |
| | | CACAGGCTCCTGGTTGTCTACCCATGGACCCAGAGGTTCTTTGACA |
| | | GCTTTGGCAACCTGTCCTCTGCCTCTGCCATCATGGGCAACCCCAA |
| | | AGTCAAGGCACATGGCAAGAAGGTGCTGACTTCCTTGGGAGATGC |
| | | CACAAAGCACCTGGATGATCTCAAGGGCACCTTTGCCCAGCTGAG |
| | | TGAACTGCACTGTGACAAGCTGCATGTGGATCCTGAGAACTTCAA |
| | | GGTGAGTCCAGGAGATGTTTCAGCCCTGTTGCCTTTAGTCTCGAGG |
| | | CGTCGACAGGAACCCCTAGTGATGGAGTTGGCCACTCCCTCTCTGC |
| | | GCGCTCGCTCGCTCACTGAGGCCGGGCGACCAAAGGTCGCCCGAC |
| | | GCCCGGGCTTTGCCCGGGCGGCCTCAGTGAGCGAGCGAGCGCGCA |
| | | GCTGGCGTAATAGCGAAGAGGCCCGCACCGATCGCCCTTCCCAAC |
| | | AGTTGCGCAGCCTGAATGGCGAATGGCGATTCCGTTGCAATGGCT |
| | | GGCGGTAATATTGTTCTGGATATTACCAGCAAGGCCGATAGTTTG |
| | | AGTTCTTCTACTCAGGCAAGTGATGTTATTACTAATCAAAGAAGTA |
| | | TTGCGACAACGGTTAATTTGCGTGATGGACAGACTCTTTTACTCGG |
| | | TGGCCTCACTGATTATAAAAACACTTCTCAGGATTCTGGCGTACCG |
| | | TTCCTGTCTAAAATCCCTTTAATCGGCCTCCTGTTTAGCTCCCGCTC |
| | | TGATTCTAACGAGGAAAGCACGTTATACGTGCTCGTCAAAGCAAC |
| | | CATAGTACGCGCCCTGTAGCGGCGCATTAAGCGCGGCGGGTGTGG |
| | | TGGTTACGCGCAGCGTGACCGCTACACTTGCCAGCGCCCTAGCGC |
| | | CCGCTCCTTTCGCTTTCTTCCCTTCCTTTCTCGCCACGTTCGCCGGC |
| | | TTTCCCCGTCAAGCTCTAAATCGGGGGCTCCCTTTAGGGTTCCGAT |
| | | TTAGTGCTTTACGGCACCTCGACCCCAAAAAACTTGATTAGGGTG |
| | | ATGGTTCACGTAGTGGGCCATCGCCCTGATAGACGGTTTTTCGCCC |
| | | TTTGACGTTGGAGTCCACGTTCTTTAATAGTGGACTCTTGTTCCAA |
| | | ACTGGAACAACACTCAACCCTATCTCGGTCTATTCTTTTGATTTAT |
| | | AAGGGATTTTGCCGATTTCGGCCTATTGGTTAAAAAATGAGCTGAT |
| | | TTAACAAAAATTTAACGCGAATTTTAACAAAATATTAACGTTTACA |
| | | ATTTAAATATTTGCTTATACAATCTTCCTGTTTTTGGGGCTTTTCTG |
| | | ATTATCAACCGGGGTACATATGATTGACATGCTAGTTTTACGATTA |
| | | CCGTTCATCGATTCTCTTGTTTGCTCCAGACTCTCAGGCAATGACC |
| | | TGATAGCCTTTGTAGAGACCTCTCAAAAATAGCTACCCTCTCCGGC |
| | | ATGAATTTATCAGCTAGAACGGTTGAATATCATATTGATGGTGATT |
| | | TGACTGTCTCCGGCCTTTCTCACCCGTTTGAATCTTTACCTACACAT |
| | | TACTCAGGCATTGCATTTAAAATATATGAGGGTTCTAAAAATTTTT |
| | | ATCCTTGCGTTGAAATAAAGGCTTCTCCCGCAAAAGTATTACAGG |
| | | GTCATAATGTTTTTGGTACAACCGATTTAGCTTTATGCTCTGAGGC |
| | | TTTATTGCTTAATTTTGCTAATTCTTTGCCTTGCCTGTATGATTTATT |
| | | GGATGTTGGAATCGCCTGATGCGGTATTTTCTCCTTACGCATCTGT |
| | | GCGGTATTTCACACCGCATATGGTGCACTCTCAGTACAATCTGCTC |
| | | TGATGCCGCATAGTTAAGCCAGCCCCGACACCCGCCAACACCCGC |
| | | TGACGCGCCCTGACGGGCTTGTCTGCTCCCGGCATCCGCTTACAGA |
| | | CAAGCTGTGACCGTCTCCGGGAGCTGCATGTGTCAGAGGTTTTCAC |

-continued

| SEQ ID NO | NAME | SEQUENCE |
|---|---|---|
| | | CGTCATCACCGAAACGCGCGAGACGAAAGGGCCTCGTGATACGCC<br>TATTTTTATAGGTTAATGTCATGATAATAATGGTTTCTTAGACGTC<br>AGGTGGCACTTTTCGGGGAAATGTGCGCGGAACCCCTATTTGTTTA<br>TTTTTCTAAATACATTCAAATATGTATCCGCTCATGAGACAATAAC<br>CCTGATAAATGCTTCAATAATATTGAAAAAGGAAGAGTATGAGTA<br>TTCAACATTTCCGTGTCGCCCTTATTCCCTTTTTTGCGGCATTTTGC<br>CTTCCTGTTTTTGCTCACCCAGAAACGCTGGTGAAAGTAAAAGATG<br>CTGAAGATCAGTTGGGTGCACGAGTGGGTTACATCGAACTGGATC<br>TCAACAGCGGTAAGATCCTTGAGAGTTTTCGCCCCGAAGAACGTT<br>TTCCAATGATGAGCACTTTTAAAGTTCTGCTATGTGGCGCGGTATT<br>ATCCCGTATTGACGCCGGGCAAGAGCAACTCGGTCGCCGCATACA<br>CTATTCTCAGAATGACTTGGTTGAGTACTCACCAGTCACAGAAAA<br>GCATCTTACGGATGGCATGACAGTAAGAGAATTATGCAGTGCTGC<br>CATAACCATGAGTGATAACACTGCGGCCAACTTACTTCTGACAAC<br>GATCGGAGGACCGAAGGAGCTAACCGCTTTTTTGCACAACATGGG<br>GGATCATGTAACTCGCCTTGATCGTTGGGAACCGGAGCTGAATGA<br>AGCCATACCAAACGACGAGCGTGACACCACGATGCCTGTAGCAAT<br>GGCAACAACGTTGCGCAAACTATTAACTGGCGAACTACTTACTCT<br>AGCTTCCCGGCAACAATTAATAGACTGGATGGAGGCGGATAAAGT<br>TGCAGGACCACTTCTGCGCTCGGCCCTTCCGGCTGGCTGGTTTATT<br>GCTGATAAATCTGGAGCCGGTGAGCGTGGGTCTCGCGGTATCATT<br>GCAGCACTGGGGCCAGATGGTAAGCCCTCCCGTATCGTAGTTATC<br>TACACGACGGGGAGTCAGGCAACTATGGATGAACGAAATAGACA<br>GATCGCTGAGATAGGTGCCTCACTGATTAAGCATTGGTAACTGTC<br>AGACCAAGTTTACTCATATATACTTTAGATTGATTTAAAACTTCAT<br>TTTTAATTTAAAAGGATCTAGGTGAAGATCCTTTTTGATAATCTCA<br>TGACCAAAATCCCTTAACGTGAGTTTTCGTTCCACTGAGCGTCAGA<br>CCCCGTAGAAAAGATCAAAGGATCTTCTTGAGATCCTTTTTTTCTG<br>CGCGTAATCTGCTGCTTGCAAACAAAAAAACCACCGCTACCAGCG<br>GTGGTTTGTTTGCCGGATCAAGAGCTACCAACTCTTTTTCCGAAGG<br>TAACTGGCTTCAGCAGAGCGCAGATACCAAATACTGTCCTTCTAGT<br>GTAGCCGTAGTTAGGCCACCACTTCAAGAACTCTGTAGCACCGCC<br>TACATACCTCGCTCTGCTAATCCTGTTACCAGTGGCTGCTGCCAGT<br>GGCGATAAGTCGTGTCTTACCGGGTTGGACTCAAGACGATAGTTA<br>CCGGATAAGGCGCAGCGGTCGGGCTGAACGGGGGGTTCGTGCACA<br>CAGCCCAGCTTGGAGCGAACGACCTACACCGAACTGAGATACCTA<br>CAGCGTGAGCTATGAGAAAGCGCCACGCTTCCCGAAGGGAGAAA<br>GGCGGACAGGTATCCGGTAAGCGGCAGGGTCGGAACAGGAGAGC<br>GCACGAGGGAGCTTCCAGGGGGAAACGCCTGGTATCTTTATAGTC<br>CTGTCGGGTTTCGCCACCTCTGACTTGAGCGTCGATTTTTGTGATG<br>CTCGTCAGGGGGGCGGAGCCTATGGAAAAACGCCAGCAACGCGG<br>CCTTTTTACGGTTCCTGGCCTTTTGCTGGCCTTTTGCTCACATGTTC<br>TTTCCTGCGTTATCCCCTGATTCTGTGGATAACCGTATTACCGCCTT<br>TGAGTGAGCTGATACCGCTCGCCGCAGCCGAACGACCGAGCGCAG<br>CGAGTCAGTGAGCGAGGAAGCGGAAGAGCGCCCAATACGCAAAC<br>CGCCTCTCCCCGCGCGTTGGCCGATTCATTAATG |
| 19 | MGMT Cassettes Human: AMS#1336 pAAV HBG1(600).d-114,488 HBGd13-HBB(T87Q). core3'enh;PGK> MGMT.T2A.Ex2 | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTGAAACAGTCATGATTTATTTCAAATAGGTACGGATAAGTAGAT<br>ATTGAGGTAAGCATTAGGTCTTATATTATGTAACACTAATCTATTA<br>CTGCGCTGAAACTGTGGCTTTATAGAAATTGTTTTCACTGCACTAT<br>TGAGAAATTAAGAGATAATGGCAAAAGTCACAAAGAGTATATTCA<br>AAAAGAAGTATAGCACTTTTTCCTTAGAAACCACTGCTAACTGAA<br>AGAGACTAAGATTTGTCCCGTCAAAAATCCTGGACCTATGCCTAA<br>AACACATTTCACAATCCCTGAACTTTTCAAAAATTGGTACATGCTT<br>TAGCTTTAAACTACAGGCCTCACTGGAGCTAGAGACAAGAAGGTA<br>AAAAACGGCTGACAAAAGAAGTCCTGGTATCCTCTATGATGGGAG<br>AAGGAAACTAGCTAAAGGGAAGAATAAATTAGAGAAAAACTGGA<br>ATGACTGAATCGGAACAAGGCAAAGGCTATAAAAAAAAATTAGCA<br>GTATCCTCTTGGGGGCCCCTTCCCCACACTATCTCAATGCAAATAT<br>CTGTCTGAAACGGTCCCTGGCTAAACTCCACCCATGGGTTGGCCA<br>GCCTTGCCTTGACAAGGCAAACTTGACCAATAGTCTTAGAGTATCC<br>AGTGAGGCCAGGGGCCGGCGGCTGGCTAGGGATGAAGAATAAAA<br>GGAAGCACCCTTCAGCAGTTCCACACACTCGCTTCTGGAACGTCTG<br>AGGTTATCAATAAGCTCCTAGTCCAGACGCCATGGTGCACCTGAC<br>TCCTGAGGAGAAGTCTGCCGTTACTGCCCTGTGGGGCAAGGTGAA<br>CGTGGATGAAGTTGGTGGTGAGGCCCTGGGCAGGTTGGTATCAAG<br>GTTACAAGACAGGTTTAAGGAGACCAATAGAAACTGGGCATGTGG<br>AGACAGAGAAGACTCTTGGGTTTCTGATAGGCACTGACTCTCTCTG<br>CCTATTGGTCTATTTTCCCACCCTTAGGCTGCTGGTGGTCTACCCTT<br>GGACCCAGAGGTTCTTTGAGTCCTTTGGGGATCTGTCCACTCCTGA<br>TGCTGTTATGGGCAACCCTAAGGTGAAGGCTCATGGCAAGAAAGT |

-continued

| SEQ ID NO | NAME | SEQUENCE |
|---|---|---|
| | | GCTCGGTGCCTTTAGTGATGGCCTGGCTCACCTGGACAACCTCAAG<br>GGCACCTTTGCCCAGCTGAGTGAGCTGCACTGTGACAAGCTGCAC<br>GTGGATCCTGAGAACTTCAGGGTGAGTCTATGGGACCCTTGATGTT<br>TTCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGCCACGGGGTTGGGGTTGCG<br>CCTTTTCCAAGGCAGCCCTGGGTTTGCGCAGGGACGCGGCTGCTCT<br>GGGCGTGGTTCCGGGAAACGCAGCGGCGCCGACCCTGGGTCTCGC<br>ACATTCTTCACGTCCGTTCGCAGCGTCACCCGGATCTTCGCCGCTA<br>CCCTTGTGGGCCCCCCGGCGACGCTTCCTGCTCCGCCCCTAAGTCG<br>GGAAGGTTCCTTGCGGTTCGCGGCGTGCCGGACGTGACAAACGGA<br>AGCCGCACGTCTCACTAGTACCCTCGCAGACGGACAGCGCCAGGG<br>AGCAATGGCAGCGCGCCGACCGCGATGGGCTGTGGCCAATAGCGG<br>CTGCTCAGCGGGGCGCGCCGAGAGCAGCGGCCGGGAAGGGGCGG<br>TGCGGGAGGCGGGGTGTGGGGCGGTAGTGTGGGCCCTGTTCCTGC<br>CCGCGCGGTGTTCCGCATTCTGCAAGCCTCCGGAGCGCACGTCGG<br>CAGTCGGCTCCCTCGTTGACCGAATCACCGACCTCTCTCCCCAGCG<br>GCCGCGCCGCCACCATGGACAAGGATTGTGAAATGAAACGCACCA<br>CACTGGACAGCCCTTTGGGGAAGCTGGAGCTGTCTGGTTGTGAGC<br>AGGGTCTGCACGAAATAAAGCTCCTGGGCAAGGGGACGTCTGCAG<br>CTGATGCCGTGGAGGTCCCAGCCCCCGCTGCGGTTCTCGGAGGTC<br>CGGAGCCCCTGATGCAGTGCACAGCCTGGCTGAATGCCTATTTCC<br>ACCAGCCCGAGGCTATCGAAGAGTTCCCCGTGCCGGCTCTTCACC<br>ATCCCGTTTTCCAGCAAGAGTCGTTCACCAGACAGGTGTTATGGA<br>AGCTGCTGAAGGTTGTGAAATTCGGAGAAGTGATTTCTTACCAGC<br>AATTAGCAGCCCTGGCAGGCAACCCCAAAGCCGCGCGAGCAGTGG<br>GAGGAGCAATGAGAGGCAATCCTGTCAAAATCCTCATCCCGTGCC<br>ACAGAGTGGTCTGCAGCAGCGGAGCCGTGGGCAACTACTCCGGAG<br>GACTGGCCGTGAAGGAATGGCTTCTGGCCCATGAAGGCCACCGGT<br>TGGGGAAGCCAGGCTTGGGAGGGAGCTCAGGTCTGGCAGGGGCCT<br>GGCTCAAGGGAGCGGGAGCTACCTCGGGCTCCCCGCCTGCTGGCC<br>GAAACGAGGGCAGAGGAAGTCTTCTAACATGCGGTGACGTGGAG<br>GAGAATCCGGGCCCCCCTGCAGGAACTTCAAGGTGAGTCCAGGAG<br>ATGTTTCAGCCCTGTTGCCTTTAGTCTCGAGGCAACTTAGACAACG<br>GAGTATTGATCTGAGCACAGCAGGGTGTGAGCTGTTTGAAGATAC<br>TGGGGTTGGGGGTGAAGAAACTGCAGAGGACTAACTGGGCTGAG<br>ACCCAGTGGTAATGTTTTAGGGCCTAAGGAGTGCCTCTAAAAATC<br>TAGATGGACAATTTTGACTTTGAGAAAAGAGAGGTGGAAATGAGG<br>AAAATGACTTTTCTTTATTAGATTCCAGTAGAAAGAACTTTCATCT<br>TTCCCTCATTTTTGTTGTTTTAAAACATCTATCTGGAGGCAGGACA<br>AGTATGGTCGTTAAAAAGATGCAGGCAGAAGGCATATATTGGCTC<br>AGTCAAAGTGGGGAACTTTGGTGGCCAAACATACATTGCTAAGGC<br>TATTCCTATATCAGCTGGACACATATAAAATGCTGCTAATGCTTCA<br>TTACAAACTTATATCCTTTAATTCCAGATGGGGGCAAAGTATGTCC<br>AGGGGTGAGGAACAATTGAAACATTTGGGCTGGAGTAGATTTTGA<br>AAGTCAGCTCTGTGTGTGTGTGTGTGTGTGCGCGCGCGCGTGTCGA<br>CGTAGATAAGTAGCATGGCGGGTTAATCATTAACTACAAGGAACC<br>CCTAGTGATGGAGTTGGCCACTCCCTCTCTGCGCGCTCGCTCGCTC<br>ACTGAGGCCGGGCGACCAAAGGTCGCCCGACGCCCGGGCTTTGCC<br>CGGGCGGCCTCAGTGAGCGAGCGAGCGCGCCAGCTGGCGTAATAG<br>CGAAGAGGCCCGCACCGATCGCCCTTCCCAACAGTTGCGCAGCCT<br>GAATGGCGAATGGCGATTCCGTTGCAATGGCTGGCGGTAATATTG<br>TTCTGGATATTACCAGCAAGGCCGATAGTTTGAGTTCTTCTACTCA<br>GGCAAGTGATGTTATTACTAATCAAAGAAGTATTGCGACAACGGT<br>TAATTTGCGTGATGGACAGACTCTTTTACTCGGTGGCCTCACTGAT |

-continued

| SEQ ID NO | NAME | SEQUENCE |
|---|---|---|
| | | TATAAAAACACTTCTCAGGATTCTGGCGTACCGTTCCTGTCTAAAA<br>TCCCTTTAATCGGCCTCCTGTTTAGCTCCCGCTCTGATTCTAACGA<br>GGAAAGCACGTTATACGTGCTCGTCAAAGCAACCATAGTACGCGC<br>CCTGTAGCGGCGCATTAAGCGCGGCGGGTGTGGTGGTTACGCGCA<br>GCGTGACCGCTACACTTGCCAGCGCCCTAGCGCCCGCTCCTTTCGC<br>TTTCTTCCCTTCCTTTCTCGCCACGTTCGCCGGCTTTCCCCGTCAAG<br>CTCTAAATCGGGGGCTCCCTTTAGGGTTCCGATTTAGTGCTTTACG<br>GCACCTCGACCCCAAAAAACTTGATTAGGGTGATGGTTCACGTAG<br>TGGGCCATCGCCCTGATAGACGGTTTTTCGCCCTTTGACGTTGGAG<br>TCCACGTTCTTTAATAGTGGACTCTTGTTCCAAACTGGAACAACAC<br>TCAACCCTATCTCGGTCTATTCTTTTGATTTATAAGGGATTTTGCCG<br>ATTTCGGCCTATTGGTTAAAAAATGAGCTGATTTAACAAAAATTTA<br>ACGCGAATTTTAACAAAATATTAACGTTTACAATTTAAATATTTGC<br>TTATACAATCTTCCTGTTTTTGGGGCTTTTCTGATTATCAACCGGGG<br>TACATATGATTGACATGCTAGTTTTACGATTACCGTTCATCGATTC<br>TCTTGTTTGCTCCAGACTCTCAGGCAATGACCTGATAGCCTTTGTA<br>GAGACCTCTCAAAAATAGCTACCCTCTCCGGCATGAATTTATCAGC<br>TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA<br>AGGAGCTAACCGCTTTTTTGCACAACATGGGGGATCATGTAACTC<br>GCCTTGATCGTTGGGAACCGGAGCTGAATGAAGCCATACCAAACG<br>ACGAGCGTGACACCACGATGCCTGTAGCAATGGCAACAACGTTGC<br>GCAAACTATTAACTGGCGAACTACTTACTCTAGCTTCCCGGCAACA<br>ATTAATAGACTGGATGGAGGCGGATAAAGTTGCAGGACCACTTCT<br>GCGCTCGGCCCTTCCGGCTGGCTGGTTTATTGCTGATAAATCTGGA<br>GCCGGTGAGCGTGGGTCTCGCGGTATCATTGCAGCACTGGGGCCA<br>GATGGTAAGCCCTCCCGTATCGTAGTTATCTACACGACGGGGAGT<br>CAGGCAACTATGGATGAACGAAATAGACAGATCGCTGAGATAGGT<br>GCCTCACTGATTAAGCATTGGTAACTGTCAGACCAAGTTTACTCAT<br>ATATACTTTAGATTGATTTAAAACTTCATTTTTAATTTAAAAGGAT<br>CTAGGTGAAGATCCTTTTTGATAATCTCATGACCAAAATCCCTTAA<br>CGTGAGTTTTCGTTCCACTGAGCGTCAGACCCCGTAGAAAAGATC<br>AAAGGATCTTCTTGAGATCCTTTTTTTCTGCGCGTAATCTGCTGCTT<br>GCAAACAAAAAAACCACCGCTACCAGCGGTGGTTTGTTTGCCGGA<br>TCAAGAGCTACCAACTCTTTTTCCGAAGGTAACTGGCTTCAGCAGA<br>GCGCAGATACCAAATACTGTCCTTCTAGTGTAGCCGTAGTTAGGCC<br>ACCACTTCAAGAACTCTGTAGCACCGCCTACATACCTCGCTCTGCT<br>AATCCTGTTACCAGTGGCTGCTGCCAGTGGCGATAAGTCGTGTCTT<br>ACCGGGTTGGACTCAAGACGATAGTTACCGGATAAGGCGCAGCGG<br>TCGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACCT<br>CTGACTTGAGCGTCGATTTTTGTGATGCTCGTCAGGGGGGCGGAG<br>CCTATGGAAAAACGCCAGCAACGCGGCCTTTTTACGGTTCCTGGC<br>CTTTTGCTGGCCTTTTGCTCACATGTTCTTTCCTGCGTTATCCCCTG<br>ATTCTGTGGATAACCGTATTACCGCCTTTGAGTGAGCTGATACCGC<br>TCGCCGCAGCCGAACGACCGAGCGCAGCGAGTCAGTGAGCGAGG<br>AAGCGGAAGAGCGCCCAATACGCAAACCGCCTCTCCCCGCGCGTT<br>GGCCGATTCATTAATG |

-continued

| SEQ ID NO | NAME | SEQUENCE |
|---|---|---|
| 20 | MGMT Cassettes | CAGCTGCGCGCTCGCTCGCTCACTGAGGCCGCCCGGGCAAAGCCC |
| | Human: | GGGCGTCGGGCGACCTTTGGTCGCCCGGCCTCAGTGAGCGAGCGA |
| | AMS#1333 | GCGCGCAGAGAGGGAGTGGCCAACTCCATCACTAGGGGTTCCTTG |
| | pAAV HBG1d- | TAGTTAATGATTAACCCGCCATGCTACTTATCTACACGCGTAGATC |
| | 141,-1(459,600) | TAGAAATTGTTTTCACTGCACTATTGAGAAATTAAGAGATAATGG |
| | MND>MGMT.wPRE3. | CAAAAGTCACAAAGAGTATATTCAAAAAGAAGTATAGCACTTTTT |
| | SV40USE.pA; | CCTTAGAAACCACTGCTAACTGAAAGAGACTAAGATTTGTCCCGT |
| | HPFH- | CAAAAATCCTGGACCTATGCCTAAAACACATTTCACAATCCCTGA |
| | 2.HS40.HBBp> | ACTTTTCAAAAATTGGTACATGCTTTAGCTTTAAACTACAGGCCTC |
| | | ACTGGAGCTAGAGACAAGAAGGTAAAAAACGGCTGACAAAAGAA |
| | | GTCCTGGTATCCTCTATGATGGGAGAAGGAAACTAGCTAAAGGGA |
| | | AGAATAAATTAGAGAAAAACTGGAATGACTGAATCGGAACAAGG |
| | | CAAAGGCTATAAAAAAAAATTAGCAGTATCCTCTTGGGGGCCCCTT |
| | | CCCCACACTATCTCAATGCAAATATCTGTCTGAAACGGTCCCTGGC |
| | | TAAACTCCACCCGCGGGAACAGAGAAACAGGAGAATATGGGCCA |
| | | AACAGGATATCTGTGGTAAGCAGTTCCTGCCCCGGCTCAGGGCCA |
| | | AGAACAGTTGGAACAGCAGAATATGGGCCAAACAGGATATCTGTG |
| | | GTAAGCAGTTCCTGCCCCGGCTCAGGGCCAAGAACAGATGGTCCC |
| | | CAGATGCGGTCCCGCCCTCAGCAGTTTCTAGAGAACCATCAGATG |
| | | TTTCCAGGGTGCCCCAAGGACCTGAAATGACCCTGTGCCTTATTTG |
| | | AACTAACCAATCAGTTCGCTTCTCGCTTCTGTTCGCGCGCTTCTGC |
| | | TCCCCGAGCTCTATATAAGCAGAGCTCGTTTAGTGAACCGTCAGAT |
| | | CGCCTGGAGACGCCATCCACGCTGTTTTGACTTCCATAGAAGGCG |
| | | GCCGCGCCGCCACCATGGACAAGGATTGTGAAATGAAACGCACCA |
| | | CACTGGACAGCCCTTTGGGGAAGCTGGAGCTGTCTGGTTGTGAGC |
| | | AGGGTCTGCACGAAATAAAGCTCCTGGGCAAGGGGACGTCTGCAG |
| | | CTGATGCCGTGGAGGTCCCAGCCCCCGCTGCGGTTCTCGGAGGTC |
| | | CGGAGCCCCTGATGCAGTGCACAGCCTGGCTGAATGCCTATTTCC |
| | | ACCAGCCCGAGGCTATCGAAGAGTTCCCCGTGCCGGCTCTTCACC |
| | | ATCCCGTTTTCCAGCAAGAGTCGTTCACCAGACAGGTGTTATGGA |
| | | AGCTGCTGAAGGTTGTGAAATTCGGAGAAGTGATTTCTTACCAGC |
| | | AATTAGCAGCCCTGGCAGGCAACCCCAAAGCCGCGCGAGCAGTGG |
| | | GAGGAGCAATGAGAGGCAATCCTGTCAAAATCCTCATCCCGTGCC |
| | | ACAGAGTGGTCTGCAGCAGCGGAGCCGTGGGCAACTACTCCGGAG |
| | | GACTGGCCGTGAAGGAATGGCTTCTGGCCCATGAAGGCCACCGGT |
| | | TGGGGAAGCCAGGCTTGGGAGGGAGCTCAGGTCTGGCAGGGGCCT |
| | | GGCTCAAGGGAGCGGGAGCTACCTCGGGCTCCCCGCCTGCTGGCC |
| | | GAAACTAACCTGCAGGGATAATCAACCTCTGGATTACAAAATTTG |
| | | TGAAAGATTGACTGGTATTCTTAACTATGTTGCTCCTTTTACGCTA |
| | | TGTGGATACGCTGCTTTAATGCCTTTGTATCATGCTATTGCTTCCCG |
| | | TATGGCTTTCATTTTCTCCTCCTTGTATAAATCCTGGTTAGTTCTTG |
| | | CCACGGCGGAACTCATCGCCGCCTGCCTTGCCCGCTGCTGGACAG |
| | | GGGCTCGGCTGTTGGGCACTGACAATTCCGTGGTGTTTATTTGTGA |
| | | AATTTGTGATGCTATTGCTTTATTTGTAACCATTCTAGCTTTATTTG |
| | | TGAAATTTGTGATGCTATTGCTTTATTTGTAACCATTATAAGCTGC |
| | | AATAAACAAGTTAACAACAACAATTGCATTCATTTTATGTTTCAGG |
| | | TTCAGGGGGAGATGTGGGAGGTTTTTTAAAGCGAATTCCGAGATC |
| | | GAGACCATCCTGGCTAACACAGTGAAACCCCGTCTCTACTAAAAA |
| | | AATACAAAAAATTAGCCGGGCTTGGTGGCGGGTGCCTGTAGTCCC |
| | | AGCTACTATGGAGGCTGAGGCGGGAGAATGGCGTGAACGCGGGG |
| | | GGCGGAGCTTGCAGTGAGCAGAGATCAGGGGCCACTGCACTCCAG |
| | | CCTGGGCGACAGAGAGAGACTCTGTCTCAAAAAAAAGAAAAAAA |
| | | AAATTTAGTAGACTAGCTAAAAAAATCCAGAGATAGTTATTGATG |
| | | CATATGTAAAAGTCTTCCAATATTTACAAGTACAATGAAAAAAAA |
| | | ATAACCTTGAATTAAGTGTAGAACTCATTGACAATGTTTCAAAGG |
| | | ATGTGAGGGATAAACTAAAATTTGGGCAGTACATGCTGTTCCTGT |
| | | GTACTTGGAACAGAGGGAGAAAATCTGGGCTGGAAATATTGTTAT |
| | | AGGAGTTAGCACATGAAGGTGACAACTAAATTATTTGGAGTAGAT |
| | | GGAGTCACCAGCACATGTGAATAGTTTTAGAATGAAATGACCCAA |
| | | GATAGAACTTTGGAGAGCCCCCAAATTTAAATAAAATCAGTATAA |
| | | GAGAAGAGGAAGAAACCAAATGGTATACTAGTCTAAATTGTTTCT |
| | | TAGTGACAAAAGAATAACCTGAATATTAGATTAGCTGCCTATATG |
| | | CTCTCTGAATCAATTTCATTCAACATGCAACAGTTCTGGAACCTAT |
| | | CAGGGACCACAGTCAGCCAGGCAAGCACATCTGCCCAAGCCAAG |
| | | GGTGGAGGCATGCAGCTGTGGGGGTCTGTGAAAACACTTGAGGGA |
| | | GCAGATAACTGGGCCAACCATGACTCAGTGCTTCTGGAGGCCAAC |
| | | AGGACTGCTGAGTCATCCTGTGGGGGTGGAGGTGGGACAAGGGA |
| | | AAGGGGTGAATGGTACTGCTGATTACAACCTCTGGTGCTGCCTCCC |
| | | CCTCCTGTTTATCTGAGAGGCTAGCGTAAATACACTTGCAAAGGA |
| | | GGATGTTTTTAGTAGCAATTTGTACTGATGGTATGGGGCCAAGAG |
| | | ATATATCTTAGAGGGAGGGCTGAGGGTTTGAAGTCCAACTCCTAA |
| | | GCCAGTGCCAGAAGAGCCAAGGACAGGTACGGCTGTCATCACTTA |
| | | GACCTCACCCTGTGGAGCCACACCCTAGGGTTGGCCAATCTACTCC |
| | | CAGGAGCAGGGAGGGCAGGAGCCAGGGCTGGGCATAAAAGTCAG |
| | | GGCAGAGCCATCTATTGCTTACACTCGCTTCTGGAACGTCTGAGGT |

-continued

| SEQ ID NO | NAME | SEQUENCE |
|---|---|---|
| | | TATCAATAAGCTCCTAGTCCAGACGCCATGGGTCATTTCACAGAG |
| | | GAGGACAAGGCTACTATCACAAGCCTGTGGGGCAAGGTGAATGTG |
| | | GAAGATGCTGGAGGAGAAACCCTGGGAAGGTAGGCTCTGGTGAC |
| | | CAGGACAAGGGAGGGAAGGAAGGACCCTGTGCCTGGCAAAAGTC |
| | | CAGGTCGCTTCTCAGGATTTGTGGCACCTTCTGACTGTCAAACTGT |
| | | TCTTGTCAATCTCACAGGCTCCTGGTTGTCTACCCATGGACCCAGA |
| | | GGTTCTTTGACAGCTTTGGCAACCTGTCCTCTGCCTCTGCCATCAT |
| | | GGGCAACCCCAAAGTCAAGGCACATGGCAAGAAGGTGCTGACTTC |
| | | CTTGGGAGATGCCACAAAGCACCTGGATGATCTCAAGGGCACCTT |
| | | TGCCCAGCTGAGTGAACTGCACTGTGACAAGCTGCATGTGGATCC |
| | | TGAGAACTTCAAGGTGAGTCCAGGAGATGTTTCAGCCCTGTTGCCT |
| | | TTAGTCTCGAGGCAACTTAGACAACGGAGTATTGATCTGAGCACA |
| | | GCAGGGTGTGAGCTGTTTGAAGATACTGGGGTCTCGAGGTCGACG |
| | | TAGATAAGTAGCATGGCGGGTTAATCATTAACTACAAGGAACCCC |
| | | TAGTGATGGAGTTGGCCACTCCCTCTCTGCGCGCTCGCTCGCTCAC |
| | | TGAGGCCGGGCGACCAAAGGTCGCCCGACGCCCGGGCTTTGCCCG |
| | | GGCGGCCTCAGTGAGCGAGCGAGCGCGCCAGCTGGCGTAATAGCG |
| | | AAGAGGCCCGCACCGATCGCCCTTCCCAACAGTTGCGCAGCCTGA |
| | | ATGGCGAATGGCGATTCCGTTGCAATGGCTGGCGGTAATATTGTTC |
| | | TGGATATTACCAGCAAGGCCGATAGTTTGAGTTCTTCTACTCAGGC |
| | | AAGTGATGTTATTACTAATCAAAGAAGTATTGCGACAACGGTTAA |
| | | TTTGCGTGATGGACAGACTCTTTTACTCGGTGGCCTCACTGATTAT |
| | | AAAAACACTTCTCAGGATTCTGGCGTACCGTTCCTGTCTAAAATCC |
| | | CTTTAATCGGCCTCCTGTTTAGCTCCCGCTCTGATTCTAACGAGGA |
| | | AAGCACGTTATACGTGCTCGTCAAAGCAACCATAGTACGCGCCCT |
| | | GTAGCGGCGCATTAAGCGCGGCGGGTGTGGTGGTTACGCGCAGCG |
| | | TGACCGCTACACTTGCCAGCGCCCTAGCGCCCGCTCCTTTCGCTTT |
| | | CTTCCCTTCCTTTCTCGCCACGTTCGCCGGCTTTCCCCGTCAAGCTC |
| | | TAAATCGGGGGCTCCCTTTAGGGTTCCGATTTAGTGCTTTACGGCA |
| | | CCTCGACCCCAAAAAACTTGATTAGGGTGATGGTTCACGTAGTGG |
| | | GCCATCGCCCTGATAGACGGTTTTTCGCCCTTTGACGTTGGAGTCC |
| | | ACGTTCTTTAATAGTGGACTCTTGTTCCAAACTGGAACAACACTCA |
| | | ACCCTATCTCGGTCTATTCTTTTGATTTATAAGGGATTTTGCCGATT |
| | | TCGGCCTATTGGTTAAAAAATGAGCTGATTTAACAAAAATTTAAC |
| | | GCGAATTTTAACAAAATATTAACGTTTACAATTTAAATATTTGCTT |
| | | ATACAATCTTCCTGTTTTTGGGGCTTTTCTGATTATCAACCGGGGT |
| | | ACATATGATTGACATGCTAGTTTTACGATTACCGTTCATCGATTCT |
| | | CTTGTTTGCTCCAGACTCTCAGGCAATGACCTGATAGCCTTTGTAG |
| | | AGACCTCTCAAAAATAGCTACCCTCTCCGGCATGAATTTATCAGCT |
| | | AGAACGGTTGAATATCATATTGATGGTGATTTGACTGTCTCCGGCC |
| | | TTTCTCACCCGTTTGAATCTTTACCTACACATTACTCAGGCATTGC |
| | | ATTTAAAATATATGAGGGTTCTAAAAATTTTTATCCTTGCGTTGAA |
| | | ATAAAGGCTTCTCCCGCAAAAGTATTACAGGGTCATAATGTTTTTG |
| | | GTACAACCGATTTAGCTTTATGCTCTGAGGCTTTATTGCTTAATTTT |
| | | GCTAATTCTTTGCCTTGCCTGTATGATTTATTGGATGTTGGAATCG |
| | | CCTGATGCGGTATTTTCTCCTTACGCATCTGTGCGGTATTTCACAC |
| | | CGCATATGGTGCACTCTCAGTACAATCTGCTCTGATGCCGCATAGT |
| | | TAAGCCAGCCCCGACACCCGCCAACACCCGCTGACGCGCCCTGAC |
| | | GGGCTTGTCTGCTCCCGGCATCCGCTTACAGACAAGCTGTGACCGT |
| | | CTCCGGGAGCTGCATGTGTCAGAGGTTTTCACCGTCATCACCGAA |
| | | ACGCGCGAGACGAAAGGGCCTCGTGATACGCCTATTTTTATAGGT |
| | | TAATGTCATGATAATAATGGTTTCTTAGACGTCAGGTGGCACTTTT |
| | | CGGGGAAATGTGCGCGGAACCCCTATTTGTTTATTTTTCTAAATAC |
| | | ATTCAAATATGTATCCGCTCATGAGACAATAACCCTGATAAATGCT |
| | | TCAATAATATTGAAAAAGGAAGAGTATGAGTATTCAACATTTCCG |
| | | TGTCGCCCTTATTCCCTTTTTTGCGGCATTTTGCCTTCCTGTTTTTGC |
| | | TCACCCAGAAACGCTGGTGAAAGTAAAAGATGCTGAAGATCAGTT |
| | | GGGTGCACGAGTGGGTTACATCGAACTGGATCTCAACAGCGGTAA |
| | | GATCCTTGAGAGTTTTCGCCCCGAAGAACGTTTTCCAATGATGAGC |
| | | ACTTTTAAAGTTCTGCTATGTGGCGCGGTATTATCCCGTATTGACG |
| | | CCGGGCAAGAGCAACTCGGTCGCCGCATACACTATTCTCAGAATG |
| | | ACTTGGTTGAGTACTCACCAGTCACAGAAAAGCATCTTACGGATG |
| | | GCATGACAGTAAGAGAATTATGCAGTGCTGCCATAACCATGAGTG |
| | | ATAACACTGCGGCCAACTTACTTCTGACAACGATCGGAGGACCGA |
| | | AGGAGCTAACCGCTTTTTTGCACAACATGGGGGATCATGTAACTC |
| | | GCCTTGATCGTTGGGAACCGGAGCTGAATGAAGCCATACCAAACG |
| | | ACGAGCGTGACACCACGATGCCTGTAGCAATGGCAACAACGTTGC |
| | | GCAAACTATTAACTGGCGAACTACTTACTCTAGCTTCCCGGCAACA |
| | | ATTAATAGACTGGATGGAGGCGGATAAAGTTGCAGGACCACTTCT |
| | | GCGCTCGGCCCTTCCGGCTGGCTGGTTTATTGCTGATAAATCTGGA |
| | | GCCGGTGAGCGTGGGTCTCGCGGTATCATTGCAGCACTGGGGCCA |
| | | GATGGTAAGCCCTCCCGTATCGTAGTTATCTACACGACGGGGAGT |
| | | CAGGCAACTATGGATGAACGAAATAGACAGATCGCTGAGATAGGT |
| | | GCCTCACTGATTAAGCATTGGTAACTGTCAGACCAAGTTTACTCAT |
| | | ATATACTTTAGATTGATTTAAAACTTCATTTTTAATTTAAAAGGAT |

-continued

| SEQ ID NO | NAME | SEQUENCE |
|---|---|---|
| | | CTAGGTGAAGATCCTTTTTGATAATCTCATGACCAAAATCCCTTAA CGTGAGTTTTCGTTCCACTGAGCGTCAGACCCCGTAGAAAAGATC AAAGGATCTTCTTGAGATCCTTTTTTTCTGCGCGTAATCTGCTGCTT GCAAACAAAAAAACCACCGCTACCAGCGGTGGTTTGTTTGCCGGA TCAAGAGCTACCAACTCTTTTTCCGAAGGTAACTGGCTTCAGCAGA GCGCAGATACCAAATACTGTCCTTCTAGTGTAGCCGTAGTTAGGCC ACCACTTCAAGAACTCTGTAGCACCGCCTACATACCTCGCTCTGCT AATCCTGTTACCAGTGGCTGCTGCCAGTGGCGATAAGTCGTGTCTT ACCGGGTTGGACTCAAGACGATAGTTACCGGATAAGGCGCAGCGG TCGGGCTGAACGGGGGGTTCGTGCACACAGCCCAGCTTGGAGCGA ACGACCTACACCGAACTGAGATACCTACAGCGTGAGCTATGAGAA AGCGCCACGCTTCCCGAAGGGAGAAAGGCGGACAGGTATCCGGT AAGCGGCAGGGTCGGAACAGGAGAGCGCACGAGGGAGCTTCCAG GGGGAAACGCCTGGTATCTTTATAGTCCTGTCGGGTTTCGCCACCT CTGACTTGAGCGTCGATTTTTGTGATGCTCGTCAGGGGGGCGGAG CCTATGGAAAAACGCCAGCAACGCGGCCTTTTTACGGTTCCTGGC CTTTTGCTGGCCTTTTGCTCACATGTTCTTTCCTGCGTTATCCCCTG ATTCTGTGGATAACCGTATTACCGCCTTTGAGTGAGCTGATACCGC TCGCCGCAGCCGAACGACCGAGCGCAGCGAGTCAGTGAGCGAGG AAGCGGAAGAGCGCCCAATACGCAAACCGCCTCTCCCCGCGCGTT GGCCGATTCATTAATG |
| 21 | MGMT Cassettes Rhesus: AMS#1347 Rhesus pAAV HBG1(650).d0 HBBp>HBB(T87Q). core3'enh;PGK> MGMT(P140K). SV40pA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTAC GCGTAGATCTGGTGCCTACATACATACCTGAATAAGAAAAAAAAA TACCTTTGCTGAGATGAAACACACATGATTTATTTCAAATAGGTAC AGAGAAGTAGATACTGAAGTAAGGATTAAGTATTATATTATATTA CATAACATTAATCTATTCCTGCACTGAAACCGTTGCTTTATATGAT TTTTTTTTTCACTACACTAATGAGAACTTAAGAGATAATGGCCTAA AACCACAGAGAGTATTTTCAAAGATAAGTATAGCACAATGCTTAC TAAATGAGACTAAGACTTGTCCCATCGAAAATCCTGGACCTATGC CTAAAACACGTGTCACAATCCCCGAACTTTTCAAAAATTGGTACAT GCTTTAACTTTAATCTCCAGGCCTCACTGGAGCTAGAGACAAGAA GGTAAAAAAAGGCTGACAAAAGAAGTCCTGGTATCTTCTATGGTG GGAGAAGGAAACTAGCTAAAGGGAAGAATAAATTAGAGAAAAAT TGGAATGATTGAATCGGAACAAGGCAAAGGCTATAAAAAAATTA AGCAGCAGTATCCTCTTGGGGGCCCCTTCCCCACACTATCTCAATG CAAATATCTGTCTGAAACGGTCCCTGGCTAAACTCCACCCATGGGT TGGCCAGTCTTGCCTTGACGCTAGCGTAAATACACTTGCAAAGGA GGATGTTTTTAGTAGCAATTTGTACTGATGGTATGGGGCCAAGAG ATATATCTTAGAGGGAGGGCTGAGGGTTTGAAGTCCAACTCCTAA GCCAGTGCCAGAAGAGCCAAGGACAGGTACGGCTGTCATCACTTA GACCTCACCCTGTGGAGCCACACCCTAGGGTTGGCCAATCTACTCC CAGGAGCAGGGAGGGCAGGAGCCAGGGCTGGGCATAAAAGTCAG GGCAGAGCCATCTATTGCTTACATTTGCTTCTGACACAACTGTGTT CACTAGCAACCTCAAACAGACACCATGGTGCACCTGACTCCTGAG GAGAAGTCTGCCGTTACTGCCCTGTGGGGCAAGGTGAACGTGGAT GAAGTTGGTGGTGAGGCCCTGGGCAGGTTGGTATCAAGGTTACAA GACAGGTTTAAGGAGACCAATAGAAACTGGGCATGTGGAGACAG AGAAGACTCTTGGGTTTCTGATAGGCACTGACTCTCTCTGCCTATT GGTCTATTTTCCCACCCTTAGGCTGCTGGTGGTCTACCCTTGGACC CAGAGGTTCTTTGAGTCCTTTGGGGATCTGTCCACTCCTGATGCTG TTATGGGCAACCCTAAGGTGAAGGCTCATGGCAAGAAAGTGCTCG GTGCCTTTAGTGATGGCCTGGCTCACCTGGACAACCTCAAGGGCA CCTTTGCCCAGCTGAGTGAGCTGCACTGTGACAAGCTGCACGTGG ATCCTGAGAACTTCAGGGTGAGTCTATGGACCCTTGATGTTTTCT TTCCCCTTCTTTTCTATGGTTAAGTTCATGTCATAGGAAGGGGAGA AGTAACAGGGTACACATATTGACCAAATCAGGGTAATTTTGCATT TGTAATTTTAAAAAATGCTTTCTTCTTTTAATATACTTTTTTGTTTA TCTTATTTCTAATACTTTCCCTAATCTCTTTCTTTCAGGGCAATAAT GATACAATGTATCATGCCTCTTTGCACCATTCTAAAGAATAACAGT GATAATTTCTGGGTTAAGGCAATAGCAATATTTCTGCATATAAATA TTTCTGCATATAAATTGTAACTGATGTAAGAGGTTTCATATTGCTA ATAGCAGCTACAATCCAGCTACCATTCTGCTTTTATTTTATGGTTG GGATAAGGCTGGATTATTCTGAGTCCAAGCTAGGCCCTTTTGCTAA TCATGTTCATACCTCTTATCTTCCTCCCACAGCTCCTGGGCAACGT GCTGGTCTGTGTGCTGGCCCATCACTTTGGCAAAGAATTCACCCCA CCAGTGCAGGCTGCCTATCAGAAAGTGGTGGCTGGTGTGGCTAAT GCCCTGGCCCACAAGTATCACTAAGCTCGCTTTCTTGCTGTCCAAT TTCTATTAAAGGTTCCTTTGTTCCCTAAGTCCAACTACTAAACTGG GGGATATTATGAAGGGCCTTGAGCATCTGGATTCTGCCTAATAAA AAACATTTATTTTCATTGCAATGATGTATTTAAATTATTTCTGAATA TTTTACTAAAAAGGGAATGTGGAGGTTGCAGTGCTAGTCTCCCG GAACTATCACTCTTTCACAGTCTGCTTTGGAAGGACTGGGCTTAGT |

-continued

| SEQ ID NO | NAME | SEQUENCE |
|---|---|---|
| | | ATGAAAAGTTAGGACTGAGAAGAATTTGAAAGGGGGCTTTTTGTA<br>GCTTGATATTCACTACTGTCTTATTACCCTATCATAGGCCCACCCC<br>AAATGGAAGTCCCATTCTTCCTCAGGATGTTTAAGATTAGCATTCA<br>GGAAGAGATCAGAGGTCTGCTGGCTCCCTTATCATGTCCCTTATGG<br>TGCTTCTGGCTCTGCACCGCGGCCACGGGGTTGGGGTTGCGCCTTT<br>TCCAAGGCAGCCCTGGGTTTGCGCAGGGACGCGGCTGCTCTGGGC<br>GTGGTTCCGGGAAACGCAGCGGCGCCGACCCTGGGTCTCGCACAT<br>TCTTCACGTCCGTTCGCAGCGTCACCCGGATCTTCGCCGCTACCCT<br>TGTGGGCCCCCCGGCGACGCTTCCTGCTCCGCCCCTAAGTCGGGA<br>AGGTTCCTTGCGGTTCGCGGCGTGCCGGACGTGACAAACGGAAGC<br>CGCACGTCTCACTAGTACCCTCGCAGACGGACAGCGCCAGGGAGC<br>AATGGCAGCGCGCCGACCGCGATGGGCTGTGGCCAATAGCGGCTG<br>CTCAGCGGGGCGCGCCGAGAGCAGCGGCCGGGAAGGGGCGGTGC<br>GGGAGGCGGGGTGTGGGGCGGTAGTGTGGGCCCTGTTCCTGCCCG<br>CGCGGTGTTCCGCATTCTGCAAGCCTCCGGAGCGCACGTCGGCAG<br>TCGGCTCCCTCGTTGACCGAATCACCGACCTCTCTCCCCAGCGGCC<br>GCGCCGCCACCATGGACAAGGATTGTGAAATGAAACGCACCACAC<br>TGGACAGCCCTTTGGGGAAGCTGGAGCTGTCTGGTTGTGAGCAGG<br>GTCTGCACGAAATAAAGCTCCTGGGCAAGGGGACGTCTGCAGCTG<br>ATGCCGTGGAGGTCCCAGCCCCCGCTGCGGTTCTCGGAGGTCCGG<br>AGCCCCTGATGCAGTGCACAGCCTGGCTGAATGCCTATTTCCACCA<br>GCCCGAGGCTATCGAAGAGTTCCCCGTGCCGGCTCTTCACCATCCC<br>GTTTTCCAGCAAGAGTCGTTCACCAGACAGGTGTTATGGAAGCTG<br>CTGAAGGTTGTGAAATTCGGAGAAGTGATTTCTTACCAGCAATTA<br>GCAGCCCTGGCAGGCAACCCCAAAGCCGCGCGAGCAGTGGGAGG<br>AGCAATGAGAGGCAATCCTGTCAAAATCCTCATCCCGTGCCACAG<br>AGTGGTCTGCAGCAGCGGAGCCGTGGGCAACTACTCCGGAGGACT<br>GGCCGTGAAGGAATGGCTTCTGGCCCATGAAGGCCACCGGTTGGG<br>GAAGCCAGGCTTGGGAGGGAGCTCAGGTCTGGCAGGGGCCTGGCT<br>CAAGGGAGCGGGAGCTACCTCGGGCTCCCCGCCTGCTGGCCGAAA<br>CTAAGCTTTATTTGTGAAATTTGTGATGCTATTGCTTTATTTGTAAC<br>CATTATAAGCTGCAATAAACAAGTTAACAACAACAATTGCATTCA<br>TTTTATGTTTCAGGTTCAGGGGGAGATGTGGGAGGTTTTTTAAAGC<br>CCTGCAGGCAATAGCCTTGACAAGGCAACCTTGACCAATAGTCTT<br>AGAGTATCAGGTGAGGCCAGGGGCCGGCGGCTGGCTAGGGATGA<br>AGAATAAAAGGAAGCACCCTCCAGCAGTTCCACACACTCGCTTCT<br>GGAACGGCTGAGATTATCAATAAGCTCCTAGTCCAGACGCCATGG<br>GTCATTTCACAGAGGAGGACAAGGCTACTATCACAAGCCTGTGGG<br>GCAAGGTGAATGTGGAAGATGCTGGAGGAGAAACCCTGGGAAGG<br>TAGGCTCTGGTGACCAGGACAAGGAAGGGAAGGAAGGACCCTGT<br>GCCTGGCAAAAGTCCAGGCCACTTCTCAGGATTTGTGGCACTTTCT<br>GACTGTCAAACTGCTCTTGTTCAATCTCACAGGCTCCTGGTTGTCT<br>ACCCATGGACCCAGAGGTTCTTTGACAGCTTTGGCAACCTGTCCTC<br>TGCCTCTGCCATCATGGGCAACCCCAAGGTCAAGGCACACGGCAA<br>GAAGGTGCTGACTTCCTTGGGAGATGCCATAAAGAACCTGGATGA<br>TCTCAAGGGCACCTTTGCCCAGCTGAGTGAGCTGCACTGTGACAA<br>GCTGCATGTGGATCCTGAGAACTTCAGGGTGAGTCCAGGAGTTTC<br>AGCAGTTTCAGAGTTCAGTCTCAAGGCGTCGACAGGAACCCCTAG<br>TGATGGAGTTGGCCACTCCCTCTCTGCGCGCTCGCTCGCTCACTGA<br>GGCCGGGCGACCAAAGGTCGCCCGACGCCCGGGCTTTGCCCGGGC<br>GGCCTCAGTGAGCGAGCGAGCGCGCAGCTGGCGTAATAGCGAAG<br>AGGCCCGCACCGATCGCCCTTCCCAACAGTTGCGCAGCCTGAATG<br>GCGAATGGCGATTCCGTTGCAATGGCTGGCGGTAATATTGTTCTGG<br>ATATTACCAGCAAGGCCGATAGTTTGAGTTCTTCTACTCAGGCAAG<br>TGATGTTATTACTAATCAAAGAAGTATTGCGACAACGGTTAATTTG<br>CGTGATGGACAGACTCTTTTACTCGGTGGCCTCACTGATTATAAAA<br>ACACTTCTCAGGATTCTGGCGTACCGTTCCTGTCTAAAATCCCTTT<br>AATCGGCCTCCTGTTTAGCTCCCGCTCTGATTCTAACGAGGAAAGC<br>ACGTTATACGTGCTCGTCAAAGCAACCATAGTACGCGCCCTGTAG<br>CGGCGCATTAAGCGCGGCGGGTGTGGTGGTTACGCGCAGCGTGAC<br>CGCTACACTTGCCAGCGCCCTAGCGCCCGCTCCTTTCGCTTTCTTC<br>CCTTCCTTTCTCGCCACGTTCGCCGGCTTTCCCCGTCAAGCTCTAA<br>ATCGGGGGCTCCCTTTAGGGTTCCGATTTAGTGCTTTACGGCACCT<br>CGACCCCAAAAAACTTGATTAGGGTGATGGTTCACGTAGTGGGCC<br>ATCGCCCTGATAGACGGTTTTTCGCCCTTTGACGTTGGAGTCCACG<br>TTCTTTAATAGTGGACTCTTGTTCCAAACTGGAACAACACTCAACC<br>CTATCTCGGTCTATTCTTTTGATTTATAAGGGATTTTGCCGATTTCG<br>GCCTATTGGTTAAAAAATGAGCTGATTTAACAAAAATTTAACGCG<br>AATTTTAACAAAATATTAACGTTTACAATTTAAATATTTGCTTATA<br>CAATCTTCCTGTTTTTGGGGCTTTTCTGATTATCAACCGGGGTACA<br>TATGATTGACATGCTAGTTTTACGATTACCGTTCATCGATTCTCTTG<br>TTTGCTCCAGACTCTCAGGCAATGACCTGATAGCCTTTGTAGAGAC<br>CTCTCAAAAATAGCTACCCTCTCCGGCATGAATTTATCAGCTAGAA<br>CGGTTGAATATCATATTGATGGTGATTTGACTGTCTCCGGCCTTTC<br>TCACCCGTTTGAATCTTTACCTACACATTACTCAGGCATTGCATTT |

-continued

| SEQ ID NO | NAME | SEQUENCE |
|---|---|---|
| | | AAAATATATGAGGGTTCTAAAAATTTTTATCCTTGCGTTGAAATAA AGGCTTCTCCCGCAAAAGTATTACAGGGTCATAATGTTTTTGGTAC AACCGATTTAGCTTTATGCTCTGAGGCTTTATTGCTTAATTTTGCTA ATTCTTTGCCTTGCCTGTATGATTTATTGGATGTTGGAATCGCCTG ATGCGGTATTTTCTCCTTACGCATCTGTGCGGTATTTCACACCGCA TATGGTGCACTCTCAGTACAATCTGCTCTGATGCCGCATAGTTAAG CCAGCCCCGACACCCGCCAACACCCGCTGACGCGCCCTGACGGGC TTGTCTGCTCCCGGCATCCGCTTACAGACAAGCTGTGACCGTCTCC GGGAGCTGCATGTGTCAGAGGTTTTCACCGTCATCACCGAAACGC GCGAGACGAAAGGGCCTCGTGATACGCCTATTTTTATAGGTTAAT GTCATGATAATAATGGTTTCTTAGACGTCAGGTGGCACTTTTCGGG GAAATGTGCGCGGAACCCCTATTTGTTTATTTTTCTAAATACATTC AAATATGTATCCGCTCATGAGACAATAACCCTGATAAATGCTTCA ATAATATTGAAAAAGGAAGAGTATGAGTATTCAACATTTCCGTGT CGCCCTTATTCCCTTTTTTGCGGCATTTTGCCTTCCTGTTTTTGCTC ACCCAGAAACGCTGGTGAAAGTAAAAGATGCTGAAGATCAGTTGG GTGCACGAGTGGGTTACATCGAACTGGATCTCAACAGCGGTAAGA TCCTTGAGAGTTTTCGCCCCGAAGAACGTTTTCCAATGATGAGCAC TTTTAAAGTTCTGCTATGTGGCGCGGTATTATCCCGTATTGACGCC GGGCAAGAGCAACTCGGTCGCCGCATACACTATTCTCAGAATGAC TTGGTTGAGTACTCACCAGTCACAGAAAAGCATCTTACGGATGGC ATGACAGTAAGAGAATTATGCAGTGCTGCCATAACCATGAGTGAT AACACTGCGGCCAACTTACTTCTGACAACGATCGGAGGACCGAAG GAGCTAACCGCTTTTTTGCACAACATGGGGGATCATGTAACTCGCC TTGATCGTTGGGAACCGGAGCTGAATGAAGCCATACCAAACGACG AGCGTGACACCACGATGCCTGTAGCAATGGCAACAACGTTGCGCA AACTATTAACTGGCGAACTACTTACTCTAGCTTCCCGGCAACAATT AATAGACTGGATGGAGGCGGATAAAGTTGCAGGACCACTTCTGCG CTCGGCCCTTCCGGCTGGCTGGTTTATTGCTGATAAATCTGGAGCC GGTGAGCGTGGGTCTCGCGGTATCATTGCAGCACTGGGGCCAGAT GGTAAGCCCTCCCGTATCGTAGTTATCTACACGACGGGGAGTCAG GCAACTATGGATGAACGAAATAGACAGATCGCTGAGATAGGTGCC TCACTGATTAAGCATTGGTAACTGTCAGACCAAGTTTACTCATATA TACTTTAGATTGATTTAAAACTTCATTTTTAATTTAAAAGGATCTA GGTGAAGATCCTTTTTGATAATCTCATGACCAAAATCCCTTAACGT GAGTTTTCGTTCCACTGAGCGTCAGACCCCGTAGAAAAGATCAAA GGATCTTCTTGAGATCCTTTTTTTCTGCGCGTAATCTGCTGCTTGCA AACAAAAAAACCACCGCTACCAGCGGTGGTTTGTTTGCCGGATCA AGAGCTACCAACTCTTTTTCCGAAGGTAACTGGCTTCAGCAGAGC GCAGATACCAAATACTGTCCTTCTAGTGTAGCCGTAGTTAGGCCAC CACTTCAAGAACTCTGTAGCACCGCCTACATACCTCGCTCTGCTAA TCCTGTTACCAGTGGCTGCTGCCAGTGGCGATAAGTCGTGTCTTAC CGGGTTGGACTCAAGACGATAGTTACCGGATAAGGCGCAGCGGTC GGGCTGAACGGGGGGTTCGTGCACACAGCCCAGCTTGGAGCGAAC GACCTACACCGAACTGAGATACCTACAGCGTGAGCTATGAGAAAG CGCCACGCTTCCCGAAGGGAGAAAGGCGGACAGGTATCCGGTAA GCGGCAGGGTCGGAACAGGAGAGCGCACGAGGGAGCTTCCAGGG GGAAACGCCTGGTATCTTTATAGTCCTGTCGGGTTTCGCCACCTCT GACTTGAGCGTCGATTTTTGTGATGCTCGTCAGGGGGGCGGAGCC TATGGAAAAACGCCAGCAACGCGGCCTTTTTACGGTTCCTGGCCTT TTGCTGGCCTTTTGCTCACATGTTCTTTCCTGCGTTATCCCCTGATT CTGTGGATAACCGTATTACCGCCTTTGAGTGAGCTGATACCGCTCG CCGCAGCCGAACGACCGAGCGCAGCGAGTCAGTGAGCGAGGAAG CGGAAGAGCGCCCAATACGCAAACCGCCTCTCCCCGCGCGTTGGC CGATTCATTAATG |
| 22 | Deletion Vectors: AMS# 1240 pAAV d3.5 kb(600) MND>GFP.wPRE-O. BGHpA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TAGCCAGTGTTTACCATTGCAGAATGTACATGCGACTGAAAGGGT GAGGAAACCTGGGAAATGTCAGTTCCTCAAATACAGAGAACACTG AGGGAAGGATGAGAAATAAATGTGAAAGCAGACATGAATGGTAA TTGACAGAAGGAAACTAGGATGTGTCCAGTAAATGAATAATTACA GTGTGCAGTGATTATTGCAATGATTAATGTATGATAAGATAATATG AAAACACAGAATTCAAACAGCAGTGAACTGAGATTAGAATTGTGG AGAGCACTGGCATTTAAGAATGTCACACTTAGAATGTGTCTCTAG GCATTGTTCTGTGCATATATCATCTCAATATTCATTATCTGAAAAT TATGAATTAGGTACAAAGCTCAAATAATTTATTTTTTCAGGTTAGC AAGAACTTTTTTTTTTTTTTTCTGAGATAGAGCATTGCTATGGTTGC CCAGGCTGGAGTGCAATGGCATGATCCAGGCTCACTGCAACATCT GCCTCCCAGGTTCAAGCGATTCTCCTGCCTCAGCCTCCCAAGTAGC TGGCACTACAGGCATGTGCCACCACCATGCCTGGCTAATTTTCTAT TTTTAGTAGACCGCGGGAACAGAGAAACAGGAGAATATGGGCCA AACAGGATATCTGTGGTAAGCAGTTCCTGCCCCGGCTCAGGGCCA |

-continued

| SEQ ID NO | NAME | SEQUENCE |
|---|---|---|
| | | AGAACAGTTGGAACAGCAGAATATGGGCCAAACAGGATATCTGTG<br>GTAAGCAGTTCCTGCCCCGGCTCAGGGCCAAGAACAGATGGTCCC<br>CAGATGCGGTCCCGCCCTCAGCAGTTTCTAGAGAACCATCAGATG<br>TTTCCAGGGTGCCCCAAGGACCTGAAATGACCCTGTGCCTTATTTG<br>AACTAACCAATCAGTTCGCTTCTCGCTTCTGTTCGCGCGCTTCTGC<br>TCCCCGAGCTCTATATAAGCAGAGCTCGTTTAGTGAACCGTCAGAT<br>CGCCTGGAGACGCCATCCACGCTGTTTTGACTTCCATAGAAGGCG<br>GCCGCGCCGCCACCATGGTGAGCAAGGGCGAGGAGCTGTTCACCG<br>GGGTGGTGCCCATCCTGGTCGAGCTGGACGGCGACGTAAACGGCC<br>ACAAGTTCAGCGTGTCCGGCGAGGGCGAGGGCGATGCCACCTACG<br>GCAAGCTGACCCTGAAGTTCATCTGCACCACCGGCAAGCTGCCCG<br>TGCCCTGGCCCACCCTCGTGACCACCCTGACCTACGGCGTGCAGTG<br>CTTCAGCCGCTACCCCGACCACATGAAGCAGCACGACTTCTTCAA<br>GTCCGCCATGCCCGAAGGCTACGTCCAGGAGCGCACCATCTTCTTC<br>AAGGACGACGGCAACTACAAGACCCGCGCCGAGGTGAAGTTCGA<br>GGGCGACACCCTGGTGAACCGCATCGAGCTGAAGGGCATCGACTT<br>CAAGGAGGACGGCAACATCCTGGGGCACAAGCTGGAGTACAACT<br>ACAACAGCCACAACGTCTATATCATGGCCGACAAGCAGAAGAACG<br>GCATCAAGGTGAACTTCAAGATCCGCCACAACATCGAGGACGGCA<br>GCGTGCAGCTCGCCGACCACTACCAGCAGAACACCCCCATCGGCG<br>ACGGCCCCGTGCTGCTGCCCGACAACCACTACCTGAGCACCCAGT<br>CCGCCCTGAGCAAAGACCCCAACGAGAAGCGCGATCACATGGTCC<br>TGCTGGAGTTCGTGACCGCCGCCGGGATCACTCTCGGCATGGACG<br>AGCTGTACAAGTAACCTGCAGGGAGCATCTTACCGCCATTTATTCC<br>CATATTTGTTCTGTTTTTCTTGATTTGGGTATACATTTAAATGTTAA<br>TAAAACAAAATGGTGGGGCAATCATTTACATTTTTAGGGATATGT<br>AATTACTAGTTCAGGTGTATTGCCACAAGACAAACATGTTAAGAA<br>ACTTTCCCGTTATTTACGCTCTGTTCCTGTTAATCAACCTCTGGATT<br>ACAAAATTTGTGAAAGATTGACTGATATTCTTAACTATGTTGCTCC<br>TTTTACGCTGTGTGGATATGCTGCTTTATAGCCTCTGTATCTAGCTA<br>TTGCTTCCCGTACGGCTTTCGTTTTCTCCTCCTTGTATAAATCCTGG<br>TTGCTGTCTCTTTTAGAGGAGTTGTGGCCCGTTGTCCGTCAACGTG<br>GCGTGGTGTGCTCTGTGTTTGCTGACGCAACCCCCACTGGCTGGGG<br>CATTGCCACCACCTGTCAACTCCTTTCTGGGACTTTCGCTTTCCCCC<br>TCCCGATCGCCACGGCAGAACTCATCGCCGCCTGCCTTGCCCGCTG<br>CTGGACAGGGGCTAGGTTGCTGGGCACTGATAATTCCGTGGTGTT<br>GTCTGTGCCTTCTAGTTGCCAGCCATCTGTTGTTTGCCCCTCCCCCG<br>TGCCTTCCTTGACCCTGGAAGGTGCCACTCCCACTGTCCTTTCCTA<br>ATAAAATGAGGAAATTGCATCGCATTGTCTGAGTAGGTGTCATTCT<br>ATTCTGGGGGGTGGGGTGGGGCAGGACAGCAAGGGGGAGGATTG<br>GGAAGACAATAGCAGGCATGCTGGGGATGCGGTGGGCTCTATGGC<br>AGGGCAAGTTAAGGGAATAGTGGAATGAAGGTTCATTTTTCATTC<br>TCACAAACTAATGAAACCCTGCTTATCTTAAACCAACCTGCTCACT<br>GGAGCAGGGAGGACAGGACCAGCATAAAAGGCAGGGCAGAGTCG<br>ACTGTTGCTTACACTTTCTTCTGACATAACAGTGTTCACTAGCAAC<br>CTCAAACAGACACCATGGTGCATCTGACTCCTGAGGAGAAGACTG<br>CTGTCAATGCCCTGTGGGGCAAAGTGAACGTGGATGCAGTTGGTG<br>GTGAGGCCCTGGGCAGGTTGGTATCAAGGTTATAAGAGAGGCTCA<br>AGGAGGCAAATGGAAACTGGGCATGTGTAGACAGAGAAGACTCT<br>TGGGTTTCTGATAGGCACTGACTCTCTGTCCCTTGGGCTGTTTTCCT<br>ACCCTCAGATTACTGGTGGTCTACCCTTGGACCCAGAGGTTCTTTG<br>AGTCCTTTGGGGATCTGTCCTCTCCTGATGCTGTTATGGGCAACCC<br>TAAGGTGAAGGCTCATGGCAAGAAGGTGCTAGGTGCCTTTAGTGA<br>TGGCCTGGCTCACCTGGACAACCTCAAGGGCACTTTTTCTCAGCTG<br>AGTGAGCTGCCTCGAGGTCGACGTAGATAAGTAGCATGGCGGGTT<br>AATCATTAACTACAAGGAACCCCTAGTGATGGAGTTGGCCACTCC<br>CTCTCTGCGCGCTCGCTCGCTCACTGAGGCCGGGCGACCAAAGGT<br>CGCCCGACGCCCGGGCTTTGCCCGGGCGGCCTCAGTGAGCGAGCG<br>AGCGCGCCAGCTGGCGTAATAGCGAAGAGGCCCGCACCGATCGCC<br>CTTCCCAACAGTTGCGCAGCCTGAATGGCGAATGGCGATTCCGTT<br>GCAATGGCTGGCGGTAATATTGTTCTGGATATTACCAGCAAGGCC<br>GATAGTTTGAGTTCTTCTACTCAGGCAAGTGATGTTATTACTAATC<br>AAAGAAGTATTGCGACAACGGTTAATTTGCGTGATGGACAGACTC<br>TTTTACTCGGTGGCCTCACTGATTATAAAAACACTTCTCAGGATTC<br>TGGCGTACCGTTCCTGTCTAAAATCCCTTTAATCGGCCTCCTGTTT<br>AGCTCCCGCTCTGATTCTAACGAGGAAAGCACGTTATACGTGCTC<br>GTCAAAGCAACCATAGTACGCGCCCTGTAGCGGCGCATTAAGCGC<br>GGCGGGTGTGGTGGTTACGCGCAGCGTGACCGCTACACTTGCCAG<br>CGCCCTAGCGCCCGCTCCTTTCGCTTTCTTCCCTTCCTTTCTCGCCA<br>CGTTCGCCGGCTTTCCCCGTCAAGCTCTAAATCGGGGGCTCCCTTT<br>AGGGTTCCGATTTAGTGCTTTACGGCACCTCGACCCCAAAAAACTT<br>GATTAGGGTGATGGTTCACGTAGTGGGCCATCGCCCTGATAGACG<br>GTTTTTCGCCCTTTGACGTTGGAGTCCACGTTCTTTAATAGTGGAC<br>TCTTGTTCCAAACTGGAACAACACTCAACCCTATCTCGGTCTATTC<br>TTTTGATTTATAAGGGATTTTGCCGATTTCGGCCTATTGGTTAAAA |

-continued

| SEQ ID NO | NAME | SEQUENCE |
|---|---|---|
| | | AATGAGCTGATTTAACAAAAATTTAACGCGAATTTTAACAAAATA TTAACGTTTACAATTTAAATATTTGCTTATACAATCTTCCTGTTTTT GGGGCTTTTCTGATTATCAACCGGGGTACATATGATTGACATGCTA GTTTTACGATTACCGTTCATCGATTCTCTTGTTTGCTCCAGACTCTC AGGCAATGACCTGATAGCCTTTGTAGAGACCTCTCAAAAATAGCT ACCCTCTCCGGCATGAATTTATCAGCTAGAACGGTTGAATATCATA TTGATGGTGATTTGACTGTCTCCGGCCTTTCTCACCCGTTTGAATCT TTACCTACACATTACTCAGGCATTGCATTTAAAATATATGAGGGTT CTAAAAATTTTTATCCTTGCGTTGAAATAAAGGCTTCTCCCGCAAA AGTATTACAGGGTCATAATGTTTTTGGTACAACCGATTTAGCTTTA TGCTCTGAGGCTTTATTGCTTAATTTTGCTAATTCTTTGCCTTGCCT GTATGATTTATTGGATGTTGGAATCGCCTGATGCGGTATTTTCTCC TTACGCATCTGTGCGGTATTTCACACCGCATATGGTGCACTCTCAG TACAATCTGCTCTGATGCCGCATAGTTAAGCCAGCCCCGACACCC GCCAACACCCGCTGACGCGCCCTGACGGGCTTGTCTGCTCCCGGC ATCCGCTTACAGACAAGCTGTGACCGTCTCCGGGAGCTGCATGTG TCAGAGGTTTTCACCGTCATCACCGAAACGCGCGAGACGAAAGGG CCTCGTGATACGCCTATTTTTATAGGTTAATGTCATGATAATAATG GTTTCTTAGACGTCAGGTGGCACTTTTCGGGGAAATGTGCGCGGA ACCCCTATTTGTTTATTTTTCTAAATACATTCAAATATGTATCCGCT CATGAGACAATAACCCTGATAAATGCTTCAATAATATTGAAAAAG GAAGAGTATGAGTATTCAACATTTCCGTGTCGCCCTTATTCCCTTT TTTGCGGCATTTTGCCTTCCTGTTTTTGCTCACCCAGAAACGCTGGT GAAAGTAAAAGATGCTGAAGATCAGTTGGGTGCACGAGTGGGTTA CATCGAACTGGATCTCAACAGCGGTAAGATCCTTGAGAGTTTTCG CCCCGAAGAACGTTTTCCAATGATGAGCACTTTTAAAGTTCTGCTA TGTGGCGCGGTATTATCCCGTATTGACGCCGGGCAAGAGCAACTC GGTCGCCGCATACACTATTCTCAGAATGACTTGGTTGAGTACTCAC CAGTCACAGAAAAGCATCTTACGGATGGCATGACAGTAAGAGAAT TATGCAGTGCTGCCATAACCATGAGTGATAACACTGCGGCCAACT TACTTCTGACAACGATCGGAGGACCGAAGGAGCTAACCGCTTTTT TGCACAACATGGGGGATCATGTAACTCGCCTTGATCGTTGGGAAC CGGAGCTGAATGAAGCCATACCAAACGACGAGCGTGACACCACG ATGCCTGTAGCAATGGCAACAACGTTGCGCAAACTATTAACTGGC GAACTACTTACTCTAGCTTCCCGGCAACAATTAATAGACTGGATG GAGGCGGATAAAGTTGCAGGACCACTTCTGCGCTCGGCCCTTCCG GCTGGCTGGTTTATTGCTGATAAATCTGGAGCCGGTGAGCGTGGG TCTCGCGGTATCATTGCAGCACTGGGGCCAGATGGTAAGCCCTCC CGTATCGTAGTTATCTACACGACGGGGAGTCAGGCAACTATGGAT GAACGAAATAGACAGATCGCTGAGATAGGTGCCTCACTGATTAAG CATTGGTAACTGTCAGACCAAGTTTACTCATATATACTTTAGATTG ATTTAAAACTTCATTTTTAATTTAAAAGGATCTAGGTGAAGATCCT TTTTGATAATCTCATGACCAAAATCCCTTAACGTGAGTTTTCGTTC CACTGAGCGTCAGACCCCGTAGAAAAGATCAAAGGATCTTCTTGA GATCCTTTTTTTCTGCGCGTAATCTGCTGCTTGCAAACAAAAAAAC CACCGCTACCAGCGGTGGTTTGTTTGCCGGATCAAGAGCTACCAA CTCTTTTTCCGAAGGTAACTGGCTTCAGCAGAGCGCAGATACCAA ATACTGTCCTTCTAGTGTAGCCGTAGTTAGGCCACCACTTCAAGAA CTCTGTAGCACCGCCTACATACCTCGCTCTGCTAATCCTGTTACCA GTGGCTGCTGCCAGTGGCGATAAGTCGTGTCTTACCGGGTTGGACT CAAGACGATAGTTACCGGATAAGGCGCAGCGGTCGGGCTGAACG GGGGGTTCGTGCACACAGCCCAGCTTGGAGCGAACGACCTACACC GAACTGAGATACCTACAGCGTGAGCTATGAGAAAGCGCCACGCTT CCCGAAGGGAGAAAGGCGGACAGGTATCCGGTAAGCGGCAGGGT CGGAACAGGAGAGCGCACGAGGGAGCTTCCAGGGGGAAACGCCT GGTATCTTTATAGTCCTGTCGGGTTTCGCCACCTCTGACTTGAGCG TCGATTTTTGTGATGCTCGTCAGGGGGGCGGAGCCTATGGAAAAA CGCCAGCAACGCGGCCTTTTTACGGTTCCTGGCCTTTTGCTGGCCT TTTGCTCACATGTTCTTTCCTGCGTTATCCCCTGATTCTGTGGATAA CCGTATTACCGCCTTTGAGTGAGCTGATACCGCTCGCCGCAGCCGA ACGACCGAGCGCAGCGAGTCAGTGAGCGAGGAAGCGGAAGAGCG CCCAATACGCAAACCGCCTCTCCCCGCGCGTTGGCCGATTCATTAA TG |
| 23 | Deletion Vectors: AMS#1241 pAAV d3.5 kb(600) HPFH-2.MND>GFP. wPRE-O.BGHpA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TAGCCAGTGTTTACCATTGCAGAATGTACATGCGACTGAAAGGGT GAGGAAACCTGGGAAATGTCAGTTCCTCAAATACAGAGAACACTG AGGGAAGGATGAGAAATAAATGTGAAAGCAGACATGAATGGTAA TTGACAGAAGGAAACTAGGATGTGTCCAGTAAATGAATAATTACA GTGTGCAGTGATTATTGCAATGATTAATGTATGATAAGATAATATG AAAACACAGAATTCAAACAGCAGTGAACTGAGATTAGAATTGTGG AGAGCACTGGCATTTAAGAATGTCACACTTAGAATGTGTCTCTAG |

-continued

| SEQ ID NO | NAME | SEQUENCE |
|---|---|---|
| | | GCATTGTTCTGTGCATATATCATCTCAATATTCATTATCTGAAAAT<br>TATGAATTAGGTACAAAGCTCAAATAATTTATTTTTTCAGGTTAGC<br>AAGAACTTTTTTTTTTTTTTTCTGAGATAGAGCATTGCTATGGTTGC<br>CCAGGCTGGAGTGCAATGGCATGATCCAGGCTCACTGCAACATCT<br>GCCTCCCAGGTTCAAGCGATTCTCCTGCCTCAGCCTCCCAAGTAGC<br>TGGCACTACAGGCATGTGCCACCACCATGCCTGGCTAATTTTCTAT<br>TTTTAGTAGACGAGATCGAGACCATCCTGGCTAACACAGTGAAAC<br>CCCGTCTCTACTAAAAAAATACAAAAAATTAGCCGGGCTTGGTGG<br>CGGGTGCCTGTAGTCCCAGCTACTATGGAGGCTGAGGCGGGAGAA<br>TGGCGTGAACGCGGGGGGCGGAGCTTGCAGTGAGCAGAGATCAG<br>GGGCCACTGCACTCCAGCCTGGGCGACAGAGAGAGACTCTGTCTC<br>AAAAAAAAGAAAAAAAAAATTTAGTAGACTAGCTAAAAAAATCC<br>AGAGATAGTTATTGATGCATATGTAAAAGTCTTCCAATATTTACAA<br>GTACAATGAAAAAAAAATAACCTTGAATTAAGTGTAGAACTCATT<br>GACAATGTTTCAAAGGATGTGAGGGATAAACTAAAATTTGGGCAG<br>TACATGCTGTTCCTGTGTACTTGGAACAGAGGGAGAAAATCTGGG<br>CTGGAAATATTGTTATAGGAGTTAGCACATGAAGGTGACAACTAA<br>ATTATTTGGAGTAGATGGAGTCACCAGCACATGTGAATAGTTTTA<br>GAATGAAATGACCCAAGATAGAACTTTGGAGAGCCCCCAAATTTA<br>AATAAAATCAGTATAAGAGAAGAGGAAGAAACCAAATGGTATAC<br>TAGTCTAAATTGTTTCTTAGTGACAAAAGAATAACCTGAATATTAG<br>ATTAGCTGCCTATATGCTCTCTGAATCAATTTCATTCAACATGCAA<br>CAGTCCGCGGGAACAGAGAAACAGGAGAATATGGGCCAAACAGG<br>ATATCTGTGGTAAGCAGTTCCTGCCCCGGCTCAGGGCCAAGAACA<br>GTTGGAACAGCAGAATATGGGCCAAACAGGATATCTGTGGTAAGC<br>AGTTCCTGCCCCGGCTCAGGGCCAAGAACAGATGGTCCCCAGATG<br>CGGTCCCGCCCTCAGCAGTTTCTAGAGAACCATCAGATGTTTCCAG<br>GGTGCCCCAAGGACCTGAAATGACCCTGTGCCTTATTTGAACTAA<br>CCAATCAGTTCGCTTCTCGCTTCTGTTCGCGCGCTTCTGCTCCCCGA<br>GCTCTATATAAGCAGAGCTCGTTTAGTGAACCGTCAGATCGCCTG<br>GAGACGCCATCCACGCTGTTTTGACTTCCATAGAAGGCGGCCGCG<br>CCGCCACCATGGTGAGCAAGGGCGAGGAGCTGTTCACCGGGGTGG<br>TGCCCATCCTGGTCGAGCTGGACGGCGACGTAAACGGCCACAAGT<br>TCAGCGTGTCCGGCGAGGGCGAGGGCGATGCCACCTACGGCAAGC<br>TGACCCTGAAGTTCATCTGCACCACCGGCAAGCTGCCCGTGCCCTG<br>GCCCACCCTCGTGACCACCCTGACCTACGGCGTGCAGTGCTTCAGC<br>CGCTACCCCGACCACATGAAGCAGCACGACTTCTTCAAGTCCGCC<br>ATGCCCGAAGGCTACGTCCAGGAGCGCACCATCTTCTTCAAGGAC<br>GACGGCAACTACAAGACCCGCGCCGAGGTGAAGTTCGAGGGCGA<br>CACCCTGGTGAACCGCATCGAGCTGAAGGGCATCGACTTCAAGGA<br>GGACGGCAACATCCTGGGGCACAAGCTGGAGTACAACTACAACA<br>GCCACAACGTCTATATCATGGCCGACAAGCAGAAGAACGGCATCA<br>AGGTGAACTTCAAGATCCGCCACAACATCGAGGACGGCAGCGTGC<br>AGCTCGCCGACCACTACCAGCAGAACACCCCCATCGGCGACGGCC<br>CCGTGCTGCTGCCCGACAACCACTACCTGAGCACCCAGTCCGCCCT<br>GAGCAAAGACCCCAACGAGAAGCGCGATCACATGGTCCTGCTGGA<br>GTTCGTGACCGCCGCCGGGATCACTCTCGGCATGGACGAGCTGTA<br>CAAGTAACCTGCAGGGAGCATCTTACCGCCATTTATTCCCATATTT<br>GTTCTGTTTTTCTTGATTTGGGTATACATTTAAATGTTAATAAAACA<br>AAATGGTGGGGCAATCATTTACATTTTTAGGGATATGTAATTACTA<br>GTTCAGGTGTATTGCCACAAGACAAACATGTTAAGAAACTTTCCC<br>GTTATTTACGCTCTGTTCCTGTTAATCAACCTCTGGATTACAAAAT<br>TTGTGAAAGATTGACTGATATTCTTAACTATGTTGCTCCTTTTACG<br>CTGTGTGGATATGCTGCTTTATAGCCTCTGTATCTAGCTATTGCTTC<br>CCGTACGGCTTTCGTTTTCTCCTCCTTGTATAAATCCTGGTTGCTGT<br>CTCTTTTAGAGGAGTTGTGGCCCGTTGTCCGTCAACGTGGCGTGGT<br>GTGCTCTGTGTTTGCTGACGCAACCCCCACTGGCTGGGGCATTGCC<br>ACCACCTGTCAACTCCTTTCTGGGACTTTCGCTTTCCCCCTCCCGAT<br>CGCCACGGCAGAACTCATCGCCGCCTGCCTTGCCCGCTGCTGGAC<br>AGGGGCTAGGTTGCTGGGCACTGATAATTCCGTGGTGTTGTCTGTG<br>CCTTCTAGTTGCCAGCCATCTGTTGTTTGCCCCTCCCCCGTGCCTTC<br>CTTGACCCTGGAAGGTGCCACTCCCACTGTCCTTTCCTAATAAAAT<br>GAGGAAATTGCATCGCATTGTCTGAGTAGGTGTCATTCTATTCTGG<br>GGGGTGGGGTGGGGCAGGACAGCAAGGGGGAGGATTGGGAAGAC<br>AATAGCAGGCATGCTGGGGATGCGGTGGGCTCTATGGCAGGGCAA<br>GTTAAGGGAATAGTGGAATGAAGGTTCATTTTTCATTCTCACAAAC<br>TAATGAAACCCTGCTTATCTTAAACCAACCTGCTCACTGGAGCAG<br>GGAGGACAGGACCAGCATAAAAGGCAGGGCAGAGTCGACTGTTG<br>CTTACACTTTCTTCTGACATAACAGTGTTCACTAGCAACCTCAAAC<br>AGACACCATGGTGCATCTGACTCCTGAGGAGAAGACTGCTGTCAA<br>TGCCCTGTGGGGCAAAGTGAACGTGGATGCAGTTGGTGGTGAGGC<br>CCTGGGCAGGTTGGTATCAAGGTTATAAGAGAGGCTCAAGGAGGC<br>AAATGGAAACTGGGCATGTGTAGACAGAGAAGACTCTTGGGTTTC<br>TGATAGGCACTGACTCTCTGTCCCTTGGGCTGTTTTCCTACCCTCA<br>GATTACTGGTGGTCTACCCTTGGACCCAGAGGTTCTTTGAGTCCTT |

-continued

| SEQ ID NO | NAME | SEQUENCE |
|---|---|---|
| | | TGGGGATCTGTCCTCTCCTGATGCTGTTATGGGCAACCCTAAGGTG<br>AAGGCTCATGGCAAGAAGGTGCTAGGTGCCTTTAGTGATGGCCTG<br>GCTCACCTGGACAACCTCAAGGGCACTTTTTCTCAGCTGAGTGAGC<br>TGCCTCGAGGTCGACGTAGATAAGTAGCATGGCGGGTTAATCATT<br>AACTACAAGGAACCCCTAGTGATGGAGTTGGCCACTCCCTCTCTG<br>CGCGCTCGCTCGCTCACTGAGGCCGGGCGACCAAAGGTCGCCCGA<br>CGCCCGGGCTTTGCCCGGGCGGCCTCAGTGAGCGAGCGAGCGCGC<br>CAGCTGGCGTAATAGCGAAGAGGCCCGCACCGATCGCCCTTCCCA<br>ACAGTTGCGCAGCCTGAATGGCGAATGGCGATTCCGTTGCAATGG<br>CTGGCGGTAATATTGTTCTGGATATTACCAGCAAGGCCGATAGTTT<br>GAGTTCTTCTACTCAGGCAAGTGATGTTATTACTAATCAAAGAAGT<br>ATTGCGACAACGGTTAATTTGCGTGATGGACAGACTCTTTTACTCG<br>GTGGCCTCACTGATTATAAAAACACTTCTCAGGATTCTGGCGTACC<br>GTTCCTGTCTAAAATCCCTTTAATCGGCCTCCTGTTTAGCTCCCGCT<br>CTGATTCTAACGAGGAAAGCACGTTATACGTGCTCGTCAAAGCAA<br>CCATAGTACGCGCCCTGTAGCGGCGCATTAAGCGCGGCGGGTGTG<br>GTGGTTACGCGCAGCGTGACCGCTACACTTGCCAGCGCCCTAGCG<br>CCCGCTCCTTTCGCTTTCTTCCCTTCCTTTCTCGCCACGTTCGCCGG<br>CTTTCCCCGTCAAGCTCTAAATCGGGGGCTCCCTTTAGGGTTCCGA<br>TTTAGTGCTTTACGGCACCTCGACCCCAAAAAACTTGATTAGGGTG<br>ATGGTTCACGTAGTGGGCCATCGCCCTGATAGACGGTTTTTCGCCC<br>TTTGACGTTGGAGTCCACGTTCTTTAATAGTGGACTCTTGTTCCAA<br>ACTGGAACAACACTCAACCCTATCTCGGTCTATTCTTTTGATTTAT<br>AAGGGATTTTGCCGATTTCGGCCTATTGGTTAAAAAATGAGCTGAT<br>TTAACAAAAATTTAACGCGAATTTTAACAAAATATTAACGTTTACA<br>ATTTAAATATTTGCTTATACAATCTTCCTGTTTTTGGGGCTTTTCTG<br>ATTATCAACCGGGGTACATATGATTGACATGCTAGTTTTACGATTA<br>CCGTTCATCGATTCTCTTGTTTGCTCCAGACTCTCAGGCAATGACC<br>TGATAGCCTTTGTAGAGACCTCTCAAAAATAGCTACCCTCTCCGGC<br>ATGAATTTATCAGCTAGAACGGTTGAATATCATATTGATGGTGATT<br>TGACTGTCTCCGGCCTTTCTCACCCGTTTGAATCTTTACCTACACAT<br>TACTCAGGCATTGCATTTAAAATATATGAGGGTTCTAAAAATTTTT<br>ATCCTTGCGTTGAAATAAAGGCTTCTCCCGCAAAAGTATTACAGG<br>GTCATAATGTTTTTGGTACAACCGATTTAGCTTTATGCTCTGAGGC<br>TTTATTGCTTAATTTTGCTAATTCTTTGCCTTGCCTGTATGATTTATT<br>GGATGTTGGAATCGCCTGATGCGGTATTTTCTCCTTACGCATCTGT<br>GCGGTATTTCACACCGCATATGGTGCACTCTCAGTACAATCTGCTC<br>TGATGCCGCATAGTTAAGCCAGCCCCGACACCCGCCAACACCCGC<br>TGACGCGCCCTGACGGGCTTGTCTGCTCCCGGCATCCGCTTACAGA<br>CAAGCTGTGACCGTCTCCGGGAGCTGCATGTGTCAGAGGTTTTCAC<br>CGTCATCACCGAAACGCGCGAGACGAAAGGGCCTCGTGATACGCC<br>TATTTTTATAGGTTAATGTCATGATAATAATGGTTTCTTAGACGTC<br>AGGTGGCACTTTTCGGGGAAATGTGCGCGGAACCCCTATTTGTTTA<br>TTTTTCTAAATACATTCAAATATGTATCCGCTCATGAGACAATAAC<br>CCTGATAAATGCTTCAATAATATTGAAAAAGGAAGAGTATGAGTA<br>TTCAACATTTCCGTGTCGCCCTTATTCCCTTTTTTGCGGCATTTTGC<br>CTTCCTGTTTTTGCTCACCCAGAAACGCTGGTGAAAGTAAAAGATG<br>CTGAAGATCAGTTGGGTGCACGAGTGGGTTACATCGAACTGGATC<br>TCAACAGCGGTAAGATCCTTGAGAGTTTTCGCCCCGAAGAACGTT<br>TTCCAATGATGAGCACTTTTAAAGTTCTGCTATGTGGCGCGGTATT<br>ATCCCGTATTGACGCCGGGCAAGAGCAACTCGGTCGCCGCATACA<br>CTATTCTCAGAATGACTTGGTTGAGTACTCACCAGTCACAGAAAA<br>GCATCTTACGGATGGCATGACAGTAAGAGAATTATGCAGTGCTGC<br>CATAACCATGAGTGATAACACTGCGGCCAACTTACTTCTGACAAC<br>GATCGGAGGACCGAAGGAGCTAACCGCTTTTTTGCACAACATGGG<br>GGATCATGTAACTCGCCTTGATCGTTGGGAACCGGAGCTGAATGA<br>AGCCATACCAAACGACGAGCGTGACACCACGATGCCTGTAGCAAT<br>GGCAACAACGTTGCGCAAACTATTAACTGGCGAACTACTTACTCT<br>AGCTTCCCGGCAACAATTAATAGACTGGATGGAGGCGGATAAAGT<br>TGCAGGACCACTTCTGCGCTCGGCCCTTCCGGCTGGCTGGTTTATT<br>GCTGATAAATCTGGAGCCGGTGAGCGTGGGTCTCGCGGTATCATT<br>GCAGCACTGGGGCCAGATGGTAAGCCCTCCCGTATCGTAGTTATC<br>TACACGACGGGGAGTCAGGCAACTATGGATGAACGAAATAGACA<br>GATCGCTGAGATAGGTGCCTCACTGATTAAGCATTGGTAACTGTC<br>AGACCAAGTTTACTCATATATACTTTAGATTGATTTAAAACTTCAT<br>TTTTAATTTAAAAGGATCTAGGTGAAGATCCTTTTTGATAATCTCA<br>TGACCAAAATCCCTTAACGTGAGTTTTCGTTCCACTGAGCGTCAGA<br>CCCCGTAGAAAAGATCAAAGGATCTTCTTGAGATCCTTTTTTTCTG<br>CGCGTAATCTGCTGCTTGCAAACAAAAAAACCACCGCTACCAGCG<br>GTGGTTTGTTTGCCGGATCAAGAGCTACCAACTCTTTTTCCGAAGG<br>TAACTGGCTTCAGCAGAGCGCAGATACCAAATACTGTCCTTCTAGT<br>GTAGCCGTAGTTAGGCCACCACTTCAAGAACTCTGTAGCACCGCC<br>TACATACCTCGCTCTGCTAATCCTGTTACCAGTGGCTGCTGCCAGT<br>GGCGATAAGTCGTGTCTTACCGGGTTGGACTCAAGACGATAGTTA<br>CCGGATAAGGCGCAGCGGTCGGGCTGAACGGGGGGTTCGTGCACA |

-continued

| SEQ ID NO | NAME | SEQUENCE |
| --- | --- | --- |
| | | CAGCCCAGCTTGGAGCGAACGACCTACACCGAACTGAGATACCTA CAGCGTGAGCTATGAGAAAGCGCCACGCTTCCCGAAGGGAGAAA GGCGGACAGGTATCCGGTAAGCGGCAGGGTCGGAACAGGAGAGC GCACGAGGGAGCTTCCAGGGGGAAACGCCTGGTATCTTTATAGTC CTGTCGGGTTTCGCCACCTCTGACTTGAGCGTCGATTTTTGTGATG CTCGTCAGGGGGGCGGAGCCTATGGAAAAACGCCAGCAACGCGG CCTTTTTACGGTTCCTGGCCTTTTGCTGGCCTTTTGCTCACATGTTC TTTCCTGCGTTATCCCCTGATTCTGTGGATAACCGTATTACCGCCTT TGAGTGAGCTGATACCGCTCGCCGCAGCCGAACGACCGAGCGCAG CGAGTCAGTGAGCGAGGAAGCGGAAGAGCGCCCAATACGCAAAC CGCCTCTCCCCGCGCGTTGGCCGATTCATTAATG |
| 24 | Deletion Vectors: AMS#1255 pAAV HBG1d-1.3 kb,-382(600) MND>GFP.wPRE3. SV40USE.pA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TACGTACTTTAGGCTTGTAATGTGTTTATATACAGTGAAATGTCAA GTTCTTTCTTTATATTTCTTTCTTTCTTTTTTTTCCTCAGCCTCAGAG TTTTCCACATGCCCTTCCTACTTTCAGGAACTTCTTTCTCCAAACGT CTTCTGCCTGGCTCCATCAAATCATAAAGGACCCACTTCAAATGCC ATCACTCACTACCATTTCACAATTCGCACTTTCTTTCTTTGTCCTTT TTTTTTTTAGTAAAACAAGTTTATAAAAAATTGAAGGAATAAATGA ATGGCTACTTCATAGGCAGAGTAGACGCAAGGGCTACTGGTTGCC GATTTTTATTGTTATTTTTCAATAGTATGCTAAACAAGGGGTAGAT TATTTATGCTGCCCATTTTTAGACCATAAAAGATAACTTCCTGATG TTGCCATGGCATTTTTTTCCTTTTAATTTTATTTCATTTCATTTTAAT TTCGAAGGTACATGTGCAGGATGTGCAGGCTTGTTACATGGGTAA ATGTGTGTCTTTCTGGCCTTTTAGCCATCTGTATCAATGAGCAGAT ATAAGCTTTACACAGGATCATGAAGGATGAAAGAATTTCACCAAT CCGCGGGAACAGAGAAACAGGAGAATATGGGCCAAACAGGATAT CTGTGGTAAGCAGTTCCTGCCCCGGCTCAGGGCCAAGAACAGTTG GAACAGCAGAATATGGGCCAAACAGGATATCTGTGGTAAGCAGTT CCTGCCCCGGCTCAGGGCCAAGAACAGATGGTCCCCAGATGCGGT CCCGCCCTCAGCAGTTTCTAGAGAACCATCAGATGTTTCCAGGGTG CCCCAAGGACCTGAAATGACCCTGTGCCTTATTTGAACTAACCAAT CAGTTCGCTTCTCGCTTCTGTTCGCGCGCTTCTGCTCCCCGAGCTCT ATATAAGCAGAGCTCGTTTAGTGAACCGTCAGATCGCCTGGAGAC GCCATCCACGCTGTTTTGACTTCCATAGAAGGCGGCCGCGCCGCC ACCATGGTGAGCAAGGGCGAGGAGCTGTTCACCGGGGTGGTGCCC ATCCTGGTCGAGCTGGACGGCGACGTAAACGGCCACAAGTTCAGC GTGTCCGGCGAGGGCGAGGGCGATGCCACCTACGGCAAGCTGACC CTGAAGTTCATCTGCACCACCGGCAAGCTGCCCGTGCCCTGGCCC ACCCTCGTGACCACCCTGACCTACGGCGTGCAGTGCTTCAGCCGCT ACCCCGACCACATGAAGCAGCACGACTTCTTCAAGTCCGCCATGC CCGAAGGCTACGTCCAGGAGCGCACCATCTTCTTCAAGGACGACG GCAACTACAAGACCCGCGCCGAGGTGAAGTTCGAGGGCGACACCC TGGTGAACCGCATCGAGCTGAAGGGCATCGACTTCAAGGAGGACG GCAACATCCTGGGGCACAAGCTGGAGTACAACTACAACAGCCACA ACGTCTATATCATGGCCGACAAGCAGAAGAACGGCATCAAGGTGA ACTTCAAGATCCGCCACAACATCGAGGACGGCAGCGTGCAGCTCG CCGACCACTACCAGCAGAACACCCCCATCGGCGACGGCCCCGTGC TGCTGCCCGACAACCACTACCTGAGCACCCAGTCCGCCCTGAGCA AAGACCCCAACGAGAAGCGCGATCACATGGTCCTGCTGGAGTTCG TGACCGCCGCCGGGATCACTCTCGGCATGGACGAGCTGTACAAGT AACCTGCAGGGATAATCAACCTCTGGATTACAAAATTTGTGAAAG ATTGACTGGTATTCTTAACTATGTTGCTCCTTTTACGCTATGTGGAT ACGCTGCTTTAATGCCTTTGTATCATGCTATTGCTTCCCGTATGGCT TTCATTTTCTCCTCCTTGTATAAATCCTGGTTAGTTCTTGCCACGGC GGAACTCATCGCCGCCTGCCTTGCCCGCTGCTGGACAGGGGCTCG GCTGTTGGGCACTGACAATTCCGTGGTGTTTATTTGTGAAATTTGT GATGCTATTGCTTTATTTGTAACCATTCTAGCTTTATTTGTGAAATT TGTGATGCTATTGCTTTATTTGTAACCATTATAAGCTGCAATAAAC AAGTTAACAACAACAATTGCATTCATTTTATGTTTCAGGTTCAGGG GGAGATGTGGGAGGTTTTTTAAAGCGAATTCAGGCCTCACTGGAG CTAGAGACAAGAAGGTAAAAAACGGCTGACAAAAGAAGTCCTGG TATCCTCTATGATGGGAGAAGGAAACTAGCTAAAGGGAAGAATAA ATTAGAGAAAAACTGGAATGACTGAATCGGAACAAGGCAAAGGC TATAAAAAAAATTAGCAGTATCCTCTTGGGGGCCCCTTCCCCACAC TATCTCAATGCAAATATCTGTCTGAAACGGTCCCTGGCTAAACTCC ACCCATGGGTTGGCCAGCCTTGCCTTGACCAATAGCCTTGACAAG GCAAACTTGACCAATAGTCTTAGAGTATCCAGTGAGGCCAGGGGC CGGCGGCTGGCTAGGGATGAAGAATAAAAGGAAGCACCCTTCAG CAGTTCCACACACTCGCTTCTGGAACGTCTGAGGTTATCAATAAGC TCCTAGTCCAGACGCCATGGGTCATTTCACAGAGGAGGACAAGGC TACTATCACAAGCCTGTGGGGCAAGGTGAATGTGGAAGATGCTGG |

-continued

| SEQ ID NO | NAME | SEQUENCE |
|---|---|---|
| | | AGGAGAAACCCTGGGAAGGTAGGCTCTGGTGACCAGGACAAGGG<br>AGGGAAGGAAGGACCCTGTGCCTGGCAAAAGTCCAGGTCGCTTCT<br>CACTCGAGGTCGACGTAGATAAGTAGCATGGCGGGTTAATCATTA<br>ACTACAAGGAACCCCTAGTGATGGAGTTGGCCACTCCCTCTCTGC<br>GCGCTCGCTCGCTCACTGAGGCCGGGCGACCAAAGGTCGCCCGAC<br>GCCCGGGCTTTGCCCGGGCGGCCTCAGTGAGCGAGCGAGCGCGCC<br>AGCTGGCGTAATAGCGAAGAGGCCCGCACCGATCGCCCTTCCCAA<br>CAGTTGCGCAGCCTGAATGGCGAATGGCGATTCCGTTGCAATGGC<br>TGGCGGTAATATTGTTCTGGATATTACCAGCAAGGCCGATAGTTTG<br>AGTTCTTCTACTCAGGCAAGTGATGTTATTACTAATCAAAGAAGTA<br>TTGCGACAACGGTTAATTTGCGTGATGGACAGACTCTTTTACTCGG<br>TGGCCTCACTGATTATAAAAACACTTCTCAGGATTCTGGCGTACCG<br>TTCCTGTCTAAAATCCCTTTAATCGGCCTCCTGTTTAGCTCCCGCTC<br>TGATTCTAACGAGGAAAGCACGTTATACGTGCTCGTCAAAGCAAC<br>CATAGTACGCGCCCTGTAGCGGCGCATTAAGCGCGGCGGGTGTGG<br>TGGTTACGCGCAGCGTGACCGCTACACTTGCCAGCGCCCTAGCGC<br>CCGCTCCTTTCGCTTTCTTCCCTTCCTTTCTCGCCACGTTCGCCGGC<br>TTTCCCCGTCAAGCTCTAAATCGGGGGCTCCCTTTAGGGTTCCGAT<br>TTAGTGCTTTACGGCACCTCGACCCCAAAAAACTTGATTAGGGTG<br>ATGGTTCACGTAGTGGGCCATCGCCCTGATAGACGGTTTTTCGCCC<br>TTTGACGTTGGAGTCCACGTTCTTTAATAGTGGACTCTTGTTCCAA<br>ACTGGAACAACACTCAACCCTATCTCGGTCTATTCTTTTGATTTAT<br>AAGGGATTTTGCCGATTTCGGCCTATTGGTTAAAAAATGAGCTGAT<br>TTAACAAAAATTTAACGCGAATTTTAACAAAATATTAACGTTTACA<br>ATTTAAATATTTGCTTATACAATCTTCCTGTTTTTGGGGCTTTTCTG<br>ATTATCAACCGGGGTACATATGATTGACATGCTAGTTTTACGATTA<br>CCGTTCATCGATTCTCTTGTTTGCTCCAGACTCTCAGGCAATGACC<br>TGATAGCCTTTGTAGAGACCTCTCAAAAATAGCTACCCTCTCCGGC<br>ATGAATTTATCAGCTAGAACGGTTGAATATCATATTGATGGTGATT<br>TGACTGTCTCCGGCCTTTCTCACCCGTTTGAATCTTTACCTACACAT<br>TACTCAGGCATTGCATTTAAAATATATGAGGGTTCTAAAAATTTTT<br>ATCCTTGCGTTGAAATAAAGGCTTCTCCCGCAAAAGTATTACAGG<br>GTCATAATGTTTTTGGTACAACCGATTTAGCTTTATGCTCTGAGGC<br>TTTATTGCTTAATTTTGCTAATTCTTTGCCTTGCCTGTATGATTTATT<br>GGATGTTGGAATCGCCTGATGCGGTATTTTCTCCTTACGCATCTGT<br>GCGGTATTTCACACCGCATATGGTGCACTCTCAGTACAATCTGCTC<br>TGATGCCGCATAGTTAAGCCAGCCCCGACACCCGCCAACACCCGC<br>TGACGCGCCCTGACGGGCTTGTCTGCTCCCGGCATCCGCTTACAGA<br>CAAGCTGTGACCGTCTCCGGGAGCTGCATGTGTCAGAGGTTTTCAC<br>CGTCATCACCGAAACGCGCGAGACGAAAGGGCCTCGTGATACGCC<br>TATTTTTATAGGTTAATGTCATGATAATAATGGTTTCTTAGACGTC<br>AGGTGGCACTTTTCGGGGAAATGTGCGCGGAACCCCTATTTGTTTA<br>TTTTTCTAAATACATTCAAATATGTATCCGCTCATGAGACAATAAC<br>CCTGATAAATGCTTCAATAATATTGAAAAAGGAAGAGTATGAGTA<br>TTCAACATTTCCGTGTCGCCCTTATTCCCTTTTTTGCGGCATTTTGC<br>CTTCCTGTTTTTGCTCACCCAGAAACGCTGGTGAAAGTAAAAGATG<br>CTGAAGATCAGTTGGGTGCACGAGTGGGTTACATCGAACTGGATC<br>TCAACAGCGGTAAGATCCTTGAGAGTTTTCGCCCCGAAGAACGTT<br>TTCCAATGATGAGCACTTTTAAAGTTCTGCTATGTGGCGCGGTATT<br>ATCCCGTATTGACGCCGGGCAAGAGCAACTCGGTCGCCGCATACA<br>CTATTCTCAGAATGACTTGGTTGAGTACTCACCAGTCACAGAAAA<br>GCATCTTACGGATGGCATGACAGTAAGAGAATTATGCAGTGCTGC<br>CATAACCATGAGTGATAACACTGCGGCCAACTTACTTCTGACAAC<br>GATCGGAGGACCGAAGGAGCTAACCGCTTTTTTGCACAACATGGG<br>GGATCATGTAACTCGCCTTGATCGTTGGGAACCGGAGCTGAATGA<br>AGCCATACCAAACGACGAGCGTGACACCACGATGCCTGTAGCAAT<br>GGCAACAACGTTGCGCAAACTATTAACTGGCGAACTACTTACTCT<br>AGCTTCCCGGCAACAATTAATAGACTGGATGGAGGCGGATAAAGT<br>TGCAGGACCACTTCTGCGCTCGGCCCTTCCGGCTGGCTGGTTTATT<br>GCTGATAAATCTGGAGCCGGTGAGCGTGGGTCTCGCGGTATCATT<br>GCAGCACTGGGGCCAGATGGTAAGCCCTCCCGTATCGTAGTTATC<br>TACACGACGGGGAGTCAGGCAACTATGGATGAACGAAATAGACA<br>GATCGCTGAGATAGGTGCCTCACTGATTAAGCATTGGTAACTGTC<br>AGACCAAGTTTACTCATATATACTTTAGATTGATTTAAAACTTCAT<br>TTTTAATTTAAAAGGATCTAGGTGAAGATCCTTTTTGATAATCTCA<br>TGACCAAAATCCCTTAACGTGAGTTTTCGTTCCACTGAGCGTCAGA<br>CCCCGTAGAAAAGATCAAAGGATCTTCTTGAGATCCTTTTTTTCTG<br>CGCGTAATCTGCTGCTTGCAAACAAAAAAACCACCGCTACCAGCG<br>GTGGTTTGTTTGCCGGATCAAGAGCTACCAACTCTTTTTCCGAAGG<br>TAACTGGCTTCAGCAGAGCGCAGATACCAAATACTGTCCTTCTAGT<br>GTAGCCGTAGTTAGGCCACCACTTCAAGAACTCTGTAGCACCGCC<br>TACATACCTCGCTCTGCTAATCCTGTTACCAGTGGCTGCTGCCAGT<br>GGCGATAAGTCGTGTCTTACCGGGTTGGACTCAAGACGATAGTTA<br>CCGGATAAGGCGCAGCGGTCGGGCTGAACGGGGGGTTCGTGCACA<br>CAGCCCAGCTTGGAGCGAACGACCTACACCGAACTGAGATACCTA |

-continued

| SEQ ID NO | NAME | SEQUENCE |
|---|---|---|
| | | CAGCGTGAGCTATGAGAAAGCGCCACGCTTCCCGAAGGGAGAAA<br>GGCGGACAGGTATCCGGTAAGCGGCAGGGTCGGAACAGGAGAGC<br>GCACGAGGGAGCTTCCAGGGGGAAACGCCTGGTATCTTTATAGTC<br>CTGTCGGGTTTCGCCACCTCTGACTTGAGCGTCGATTTTTGTGATG<br>CTCGTCAGGGGGGCGGAGCCTATGGAAAAACGCCAGCAACGCGG<br>CCTTTTTACGGTTCCTGGCCTTTTGCTGGCCTTTTGCTCACATGTTC<br>TTTCCTGCGTTATCCCCTGATTCTGTGGATAACCGTATTACCGCCTT<br>TGAGTGAGCTGATACCGCTCGCCGCAGCCGAACGACCGAGCGCAG<br>CGAGTCAGTGAGCGAGGAAGCGGAAGAGCGCCCAATACGCAAAC<br>CGCCTCTCCCCGCGCGTTGGCCGATTCATTAATG |
| 25 | Deletion Vectors:<br>AMS#1256<br>pAAV HBG1d-<br>1.3 kb,-1(600)<br>MND>GFP.wPRE3.<br>SV40USE.pA;<br>HBBp> | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TACGTACTTTAGGCTTGTAATGTGTTTATATACAGTGAAATGTCAA<br>GTTCTTTCTTTATATTTCTTTCTTTCTTTTTTTTCCTCAGCCTCAGAG<br>TTTTCCACATGCCCTTCCTACTTTCAGGAACTTCTTTCTCCAAACGT<br>CTTCTGCCTGGCTCCATCAAATCATAAAGGACCCACTTCAAATGCC<br>ATCACTCACTACCATTTCACAATTCGCACTTTCTTTCTTTGTCCTTT<br>TTTTTTTTAGTAAAACAAGTTTATAAAAAATTGAAGGAATAAATGA<br>ATGGCTACTTCATAGGCAGAGTAGACGCAAGGGCTACTGGTTGCC<br>GATTTTTATTGTTATTTTTCAATAGTATGCTAAACAAGGGGTAGAT<br>TATTTATGCTGCCCATTTTTAGACCATAAAAGATAACTTCCTGATG<br>TTGCCATGGCATTTTTTTCCTTTTAATTTTATTTCATTTCATTTTAAT<br>TTCGAAGGTACATGTGCAGGATGTGCAGGCTTGTTACATGGGTAA<br>ATGTGTGTCTTTCTGGCCTTTTAGCCATCTGTATCAATGAGCAGAT<br>ATAAGCTTTACACAGGATCATGAAGGATGAAAGAATTTCACCAAT<br>CCGCGGGAACAGAGAAACAGGAGAATATGGGCCAAACAGGATAT<br>CTGTGGTAAGCAGTTCCTGCCCCGGCTCAGGGCCAAGAACAGTTG<br>GAACAGCAGAATATGGGCCAAACAGGATATCTGTGGTAAGCAGTT<br>CCTGCCCCGGCTCAGGGCCAAGAACAGATGGTCCCCAGATGCGGT<br>CCCGCCCTCAGCAGTTTCTAGAGAACCATCAGATGTTTCCAGGGTG<br>CCCCAAGGACCTGAAATGACCCTGTGCCTTATTTGAACTAACCAAT<br>CAGTTCGCTTCTCGCTTCTGTTCGCGCGCTTCTGCTCCCCGAGCTCT<br>ATATAAGCAGAGCTCGTTTAGTGAACCGTCAGATCGCCTGGAGAC<br>GCCATCCACGCTGTTTTGACTTCCATAGAAGGCGGCCGCGCCGCC<br>ACCATGGTGAGCAAGGGCGAGGAGCTGTTCACCGGGGTGGTGCCC<br>ATCCTGGTCGAGCTGGACGGCGACGTAAACGGCCACAAGTTCAGC<br>GTGTCCGGCGAGGGCGAGGGCGATGCCACCTACGGCAAGCTGACC<br>CTGAAGTTCATCTGCACCACCGGCAAGCTGCCCGTGCCCTGGCCC<br>ACCCTCGTGACCACCCTGACCTACGGCGTGCAGTGCTTCAGCCGCT<br>ACCCCGACCACATGAAGCAGCACGACTTCTTCAAGTCCGCCATGC<br>CCGAAGGCTACGTCCAGGAGCGCACCATCTTCTTCAAGGACGACG<br>GCAACTACAAGACCCGCGCCGAGGTGAAGTTCGAGGGCGACACCC<br>TGGTGAACCGCATCGAGCTGAAGGGCATCGACTTCAAGGAGGACG<br>GCAACATCCTGGGGCACAAGCTGGAGTACAACTACAACAGCCACA<br>ACGTCTATATCATGGCCGACAAGCAGAAGAACGGCATCAAGGTGA<br>ACTTCAAGATCCGCCACAACATCGAGGACGGCAGCGTGCAGCTCG<br>CCGACCACTACCAGCAGAACACCCCCATCGGCGACGGCCCCGTGC<br>TGCTGCCCGACAACCACTACCTGAGCACCCAGTCCGCCCTGAGCA<br>AAGACCCCAACGAGAAGCGCGATCACATGGTCCTGCTGGAGTTCG<br>TGACCGCCGCCGGGATCACTCTCGGCATGGACGAGCTGTACAAGT<br>AACCTGCAGGGATAATCAACCTCTGGATTACAAAATTTGTGAAAG<br>ATTGACTGGTATTCTTAACTATGTTGCTCCTTTTACGCTATGTGGAT<br>ACGCTGCTTTAATGCCTTTGTATCATGCTATTGCTTCCCGTATGGCT<br>TTCATTTTCTCCTCCTTGTATAAATCCTGGTTAGTTCTTGCCACGGC<br>GGAACTCATCGCCGCCTGCCTTGCCCGCTGCTGGACAGGGGCTCG<br>GCTGTTGGGCACTGACAATTCCGTGGTGTTTATTTGTGAAATTTGT<br>GATGCTATTGCTTTATTTGTAACCATTCTAGCTTTATTTGTGAAATT<br>TGTGATGCTATTGCTTTATTTGTAACCATTATAAGCTGCAATAAAC<br>AAGTTAACAACAACAATTGCATTCATTTTATGTTTCAGGTTCAGGG<br>GGAGATGTGGGAGGTTTTTTAAAGCGAATTCGTAAATACACTTGC<br>AAAGGAGGATGTTTTTAGTAGCAATTTGTACTGATGGTATGGGGC<br>CAAGAGATATATCTTAGAGGGAGGGCTGAGGGTTTGAAGTCCAAC<br>TCCTAAGCCAGTGCCAGAAGAGCCAAGGACAGGTACGGCTGTCAT<br>CACTTAGACCTCACCCTGTGGAGCCACACCCTAGGGTTGGCCAAT<br>CTACTCCCAGGAGCAGGGAGGGCAGGAGCCAGGGCTGGGCATAA<br>AAGTCAGGGCAGAGCCATCTATTGCTTACACTCGCTTCTGGAACGT<br>CTGAGGTTATCAATAAGCTCCTAGTCCAGACGCCATGGGTCATTTC<br>ACAGAGGAGGACAAGGCTACTATCACAAGCCTGTGGGGCAAGGT<br>GAATGTGGAAGATGCTGGAGGAGAAACCCTGGGAAGGTAGGCTC<br>TGGTGACCAGGACAAGGGAGGGAAGGAAGGACCCTGTGCCTGGC<br>AAAAGTCCAGGTCGCTTCTCAGGATTTGTGGCACCTTCTGACTGTC<br>AAACTGTTCTTGTCAATCTCACAGGCTCCTGGTTGTCTACCCATGG |

-continued

| SEQ ID NO | NAME | SEQUENCE |
|---|---|---|
| | | ACCCAGAGGTTCTTTGACAGCTTTGGCAACCTGTCCTCTGCCTCTG |
| | | CCATCATGGGCAACCCCAAAGTCAAGGCACATGGCAAGAAGGTGC |
| | | TGACTTCCTTGGGAGATGCCACAAAGCACCTGGATGATCTCAAGG |
| | | GCACCTTTGCCCAGCTGAGTGAACTGCACTGTGACAAGCTGCATG |
| | | TGGATCCTGAGAACTTCAAGGTGAGTCCAGGAGATGTTTCAGCCC |
| | | TGTTGCCTTTAGTCTCGAGGCAACTTAGACAACGGAGTATTGATCT |
| | | GAGCACAGCAGGGTGTGAGCTGTTTGAAGATACTGGGGTCTCGAG |
| | | GTCGACGTAGATAAGTAGCATGGCGGGTTAATCATTAACTACAAG |
| | | GAACCCCTAGTGATGGAGTTGGCCACTCCCTCTCTGCGCGCTCGCT |
| | | CGCTCACTGAGGCCGGGCGACCAAAGGTCGCCCGACGCCCGGGCT |
| | | TTGCCCGGGCGGCCTCAGTGAGCGAGCGAGCGCGCCAGCTGGCGT |
| | | AATAGCGAAGAGGCCCGCACCGATCGCCCTTCCCAACAGTTGCGC |
| | | AGCCTGAATGGCGAATGGCGATTCCGTTGCAATGGCTGGCGGTAA |
| | | TATTGTTCTGGATATTACCAGCAAGGCCGATAGTTTGAGTTCTTCT |
| | | ACTCAGGCAAGTGATGTTATTACTAATCAAAGAAGTATTGCGACA |
| | | ACGGTTAATTTGCGTGATGGACAGACTCTTTTACTCGGTGGCCTCA |
| | | CTGATTATAAAAACACTTCTCAGGATTCTGGCGTACCGTTCCTGTC |
| | | TAAAATCCCTTTAATCGGCCTCCTGTTTAGCTCCCGCTCTGATTCTA |
| | | ACGAGGAAAGCACGTTATACGTGCTCGTCAAAGCAACCATAGTAC |
| | | GCGCCCTGTAGCGGCGCATTAAGCGCGGCGGGTGTGGTGGTTACG |
| | | CGCAGCGTGACCGCTACACTTGCCAGCGCCCTAGCGCCCGCTCCTT |
| | | TCGCTTTCTTCCCTTCCTTTCTCGCCACGTTCGCCGGCTTTCCCCGT |
| | | CAAGCTCTAAATCGGGGGCTCCCTTTAGGGTTCCGATTTAGTGCTT |
| | | TACGGCACCTCGACCCCAAAAAACTTGATTAGGGTGATGGTTCAC |
| | | GTAGTGGGCCATCGCCCTGATAGACGGTTTTTCGCCCTTTGACGTT |
| | | GGAGTCCACGTTCTTTAATAGTGGACTCTTGTTCCAAACTGGAACA |
| | | ACACTCAACCCTATCTCGGTCTATTCTTTTGATTTATAAGGGATTTT |
| | | GCCGATTTCGGCCTATTGGTTAAAAAATGAGCTGATTTAACAAAA |
| | | ATTTAACGCGAATTTTAACAAAATATTAACGTTTACAATTTAAATA |
| | | TTTGCTTATACAATCTTCCTGTTTTTGGGGCTTTTCTGATTATCAAC |
| | | CGGGGTACATATGATTGACATGCTAGTTTTACGATTACCGTTCATC |
| | | GATTCTCTTGTTTGCTCCAGACTCTCAGGCAATGACCTGATAGCCT |
| | | TTGTAGAGACCTCTCAAAAATAGCTACCCTCTCCGGCATGAATTTA |
| | | TCAGCTAGAACGGTTGAATATCATATTGATGGTGATTTGACTGTCT |
| | | CCGGCCTTTCTCACCCGTTTGAATCTTTACCTACACATTACTCAGG |
| | | CATTGCATTTAAAATATATGAGGGTTCTAAAAATTTTTATCCTTGC |
| | | GTTGAAATAAAGGCTTCTCCCGCAAAAGTATTACAGGGTCATAAT |
| | | GTTTTTGGTACAACCGATTTAGCTTTATGCTCTGAGGCTTTATTGCT |
| | | TAATTTTGCTAATTCTTTGCCTTGCCTGTATGATTTATTGGATGTTG |
| | | GAATCGCCTGATGCGGTATTTTCTCCTTACGCATCTGTGCGGTATT |
| | | TCACACCGCATATGGTGCACTCTCAGTACAATCTGCTCTGATGCCG |
| | | CATAGTTAAGCCAGCCCCGACACCCGCCAACACCCGCTGACGCGC |
| | | CCTGACGGGCTTGTCTGCTCCCGGCATCCGCTTACAGACAAGCTGT |
| | | GACCGTCTCCGGGAGCTGCATGTGTCAGAGGTTTTCACCGTCATCA |
| | | CCGAAACGCGCGAGACGAAAGGGCCTCGTGATACGCCTATTTTTA |
| | | TAGGTTAATGTCATGATAATAATGGTTTCTTAGACGTCAGGTGGCA |
| | | CTTTTCGGGGAAATGTGCGCGGAACCCCTATTTGTTTATTTTTCTA |
| | | AATACATTCAAATATGTATCCGCTCATGAGACAATAACCCTGATA |
| | | AATGCTTCAATAATATTGAAAAAGGAAGAGTATGAGTATTCAACA |
| | | TTTCCGTGTCGCCCTTATTCCCTTTTTTGCGGCATTTTGCCTTCCTG |
| | | TTTTTGCTCACCCAGAAACGCTGGTGAAAGTAAAAGATGCTGAAG |
| | | ATCAGTTGGGTGCACGAGTGGGTTACATCGAACTGGATCTCAACA |
| | | GCGGTAAGATCCTTGAGAGTTTTCGCCCCGAAGAACGTTTTCCAAT |
| | | GATGAGCACTTTTAAAGTTCTGCTATGTGGCGCGGTATTATCCCGT |
| | | ATTGACGCCGGGCAAGAGCAACTCGGTCGCCGCATACACTATTCT |
| | | CAGAATGACTTGGTTGAGTACTCACCAGTCACAGAAAAGCATCTT |
| | | ACGGATGGCATGACAGTAAGAGAATTATGCAGTGCTGCCATAACC |
| | | ATGAGTGATAACACTGCGGCCAACTTACTTCTGACAACGATCGGA |
| | | GGACCGAAGGAGCTAACCGCTTTTTTGCACAACATGGGGGATCAT |
| | | GTAACTCGCCTTGATCGTTGGGAACCGGAGCTGAATGAAGCCATA |
| | | CCAAACGACGAGCGTGACACCACGATGCCTGTAGCAATGGCAACA |
| | | ACGTTGCGCAAACTATTAACTGGCGAACTACTTACTCTAGCTTCCC |
| | | GGCAACAATTAATAGACTGGATGGAGGCGGATAAAGTTGCAGGA |
| | | CCACTTCTGCGCTCGGCCCTTCCGGCTGGCTGGTTTATTGCTGATA |
| | | AATCTGGAGCCGGTGAGCGTGGGTCTCGCGGTATCATTGCAGCAC |
| | | TGGGGCCAGATGGTAAGCCCTCCCGTATCGTAGTTATCTACACGA |
| | | CGGGGAGTCAGGCAACTATGGATGAACGAAATAGACAGATCGCT |
| | | GAGATAGGTGCCTCACTGATTAAGCATTGGTAACTGTCAGACCAA |
| | | GTTTACTCATATATACTTTAGATTGATTTAAAACTTCATTTTTAATT |
| | | TAAAAGGATCTAGGTGAAGATCCTTTTTGATAATCTCATGACCAA |
| | | AATCCCTTAACGTGAGTTTTCGTTCCACTGAGCGTCAGACCCCGTA |
| | | GAAAAGATCAAAGGATCTTCTTGAGATCCTTTTTTTCTGCGCGTAA |
| | | TCTGCTGCTTGCAAACAAAAAAACCACCGCTACCAGCGGTGGTTT |
| | | GTTTGCCGGATCAAGAGCTACCAACTCTTTTTCCGAAGGTAACTGG |
| | | CTTCAGCAGAGCGCAGATACCAAATACTGTCCTTCTAGTGTAGCC |

-continued

| SEQ ID NO | NAME | SEQUENCE |
|---|---|---|
| | | GTAGTTAGGCCACCACTTCAAGAACTCTGTAGCACCGCCTACATA CCTCGCTCTGCTAATCCTGTTACCAGTGGCTGCTGCCAGTGGCGAT AAGTCGTGTCTTACCGGGTTGGACTCAAGACGATAGTTACCGGAT AAGGCGCAGCGGTCGGGCTGAACGGGGGGTTCGTGCACACAGCCC AGCTTGGAGCGAACGACCTACACCGAACTGAGATACCTACAGCGT GAGCTATGAGAAAGCGCCACGCTTCCCGAAGGGAGAAAGGCGGA CAGGTATCCGGTAAGCGGCAGGGTCGGAACAGGAGAGCGCACGA GGGAGCTTCCAGGGGGAAACGCCTGGTATCTTTATAGTCCTGTCG GGTTTCGCCACCTCTGACTTGAGCGTCGATTTTTGTGATGCTCGTC AGGGGGGCGGAGCCTATGGAAAAACGCCAGCAACGCGGCCTTTTT ACGGTTCCTGGCCTTTTGCTGGCCTTTTGCTCACATGTTCTTTCCTG CGTTATCCCCTGATTCTGTGGATAACCGTATTACCGCCTTTGAGTG AGCTGATACCGCTCGCCGCAGCCGAACGACCGAGCGCAGCGAGTC AGTGAGCGAGGAAGCGGAAGAGCGCCCAATACGCAAACCGCCTC TCCCCGCGCGTTGGCCGATTCATTAATG |
| 26 | HBG1 Round 1 & 2: V1E1 HBG1.d-667,-1(600) MND>GFP.wPREO. BGHpA;HBBp> (Upstream) | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACGTAGCCATGCT CTAGCGGCCTCGGCCTCTGCATAAATAAAAAAAATTAGTCAGCCA TGAGCTTGGACGCGTAGATCTCACTTTCAGAGAAAAACAAAAACA AACTAACCAAAAGCAAAACAGAACCAAAAAACCACCATAAATAC TTCCTACCCTGTTAATGGTCCAATATGTCAGAAACAGCACTGTGTT AGAAATAAAGCTGTCTAAAGTACACTAATATTCGAGTTATAATAG TGTGTGGACTATTAGTCAATAAAAACAACCCTTGCCTCTTTAGAGT TGTTTTCCATGTACACGCACATCTTATGTCTTAGAGTAAGATTCCC TGAGAAGTGAACCTAGCATTTATACAAGATAATTAATTCTAATCC ACAGTACCTGCCAAAGAACATTCTACCATCATCTTTACTGAGCATA GAAGAGCTACGCCAAAACCCTGGGTCATCAGCCAGCACACACACT TATCCAGTGGTAAATACACATCATCTGGTGTATACATACATACCTG AATATGGAATCAAATATTTTTCTAAGATGAAACAGTCATGATTTAT TTCAAATAGGTACGGATAAGTAGATATGAACAGAGAAACAGGAG AATATGGGCCAAACAGGATATCTGTGGTAAGCAGTTCCTGCCCCG GCTCAGGGCCAAGAACAGTTGGAACAGCAGAATATGGGCCAAAC AGGATATCTGTGGTAAGCAGTTCCTGCCCCGGCTCAGGGCCAAGA ACAGATGGTCCCCAGATGCGGTCCCGCCCTCAGCAGTTTCTAGAG AACCATCAGATGTTTCCAGGGTGCCCCAAGGACCTGAAATGACCC TGTGCCTTATTTGAACTAACCAATCAGTTCGCTTCTCGCTTCTGTTC GCGCGCTTCTGCTCCCCGAGCTCTATATAAGCAGAGCTCGTTTAGT GAACCGTCAGATCGCGGCCGCGCCGCCACCATGGTGAGCAAGGGC GAGGAGCTGTTCACCGGGGTGGTGCCCATCCTGGTCGAGCTGGAC GGCGACGTAAACGGCCACAAGTTCAGCGTGTCCGGCGAGGGCGA GGGCGATGCCACCTACGGCAAGCTGACCCTGAAGTTCATCTGCAC CACCGGCAAGCTGCCCGTGCCCTGGCCCACCCTCGTGACCACCCT GACCTACGGCGTGCAGTGCTTCAGCCGCTACCCCGACCACATGAA GCAGCACGACTTCTTCAAGTCCGCCATGCCCGAAGGCTACGTCCA GGAGCGCACCATCTTCTTCAAGGACGACGGCAACTACAAGACCCG CGCCGAGGTGAAGTTCGAGGGCGACACCCTGGTGAACCGCATCGA GCTGAAGGGCATCGACTTCAAGGAGGACGGCAACATCCTGGGGCA CAAGCTGGAGTACAACTACAACAGCCACAACGTCTATATCATGGC CGACAAGCAGAAGAACGGCATCAAGGTGAACTTCAAGATCCGCC ACAACATCGAGGACGGCAGCGTGCAGCTCGCCGACCACTACCAGC AGAACACCCCCATCGGCGACGGCCCCGTGCTGCTGCCCGACAACC ACTACCTGAGCACCCAGTCCGCCCTGAGCAAAGACCCCAACGAGA AGCGCGATCACATGGTCCTGCTGGAGTTCGTGACCGCCGCCGGGA TCACTCTCGGCATGGACGAGCTGTACAAGTAGGAGCATCTTACCG CCATTTATTCCCATATTTGTTCTGTTTTTCTTGATTTGGGTATACAT TTAAATGTTAATAAAACAAAATGGTGGGGCAATCATTTACATTTTT AGGGATATGTAATTACTAGTTCAGGTGTATTGCCACAAGACAAAC ATGTTAAGAAACTTTCCCGTTATTTACGCTCTGTTCCTGTTAATCA ACCTCTGGATTACAAAATTTGTGAAAGATTGACTGATATTCTTAAC TATGTTGCTCCTTTTACGCTGTGTGGATATGCTGCTTTATAGCCTCT GTATCTAGCTATTGCTTCCCGTACGGCTTTCGTTTTCTCCTCCTTGT ATAAATCCTGGTTGCTGTCTCTTTTAGAGGAGTTGTGGCCCGTTGT CCGTCAACGTGGCGTGGTGTGCTCTGTGTTTGCTGACGCAACCCCC ACTGGCTGGGGCATTGCCACCACCTGTCAACTCCTTTCTGGGACTT TCGCTTTCCCCCTCCCGATCGCCACGGCAGAACTCATCGCCGCCTG CCTTGCCCGCTGCTGGACAGGGGCTAGGTTGCTGGGCACTGATAA TTCCGTGGTGTTGTCTGTGCCTTCTAGTTGCCAGCCATCTGTTGTTT GCCCCTCCCCCGTGCCTTCCTTGACCCTGGAAGGTGCCACTCCCAC TGTCCTTTCCTAATAAAATGAGGAAATTGCATCGCATTGTCTGAGT AGGTGTCATTCTATTCTGGGGGGTGGGGTGGGGCAGGACAGCAAG GGGGAGGATTGGGAAGACAATAGCAGGCATGCTGGGGATGCGGT GGGCTCTATGGCTAGATGTCCCCAGTTAACCTCCTATTTGACACCA |

-continued

| SEQ ID NO | NAME | SEQUENCE |
|---|---|---|
| | | CTGATTACCCCATTGATAGTCACACTTTGGGTTGTAAGTGACTTTT<br>TATTTATTTGTATTTTTGACTGCATTAAGAGGTCTCTAGTTTTTTAT<br>CTCTTGTTTCCCAAAACCTAATAAGTAACTAATGCACAGAGCACAT<br>TGATTTGTATTTATTCTATTTTTAGACATAATTTATTAGCATGCATG<br>AGCAAATTAAGAAAAACAACAACAAATGAATGCATATATATGTAT<br>ATGTATGTGTGTATATATACACACATATATATATATATTTTTTCTTT<br>TCTTACCAGAAGGTTTTAATCCAAATAAGGAGAAGATATGCTTAG<br>AACCGAGGTAGAGTTTTCATCCATTCTGTCCTGTAAGTATTTTGCA<br>TATTCTGGAGACGCAGGAAGAGATCCATCTACATATCCCAAAGCT<br>GAATTATGGTAGACAAAACTCTTCCACTTTTAGTGCATCAACTTCT<br>TATTTGTGTAATAAGAAAATTGGGAAAACGATCTTCAATATGCTTA<br>CCAAGCTGTGATTCCAAATATTACGTAAATACACTTGCAAAGGAG<br>GATGTTTTTAGTAGCAATTTGTACTGATGGTATGGGGCCAAGAGAT<br>ATATCTTAGAGGGAGGGCTGAGGGTTTGAAGTCCAACTCCTAAGC<br>CAGTGCCAGAAGAGCCAAGGACAGGTACGGCTGTCATCACTTAGA<br>CCTCACCCTGTGGAGCCACACCCTAGGGTTGGCCAATCTACTCCCA<br>GGAGCAGGGAGGGCAGGAGCCAGGGCTGGGCATAAAAGTCAGGG<br>CAGAGCCATCTATTGCTTACACTCGCTTCTGGAACGTCTGAGGTTA<br>TCAATAAGCTCCTAGTCCAGACGCCATGGGTCATTTCACAGAGGA<br>GGACAAGGCTACTATCACAAGCCTGTGGGGCAAGGTGAATGTGGA<br>AGATGCTGGAGGAGAAACCCTGGGAAGGTAGGCTCTGGTGACCA<br>GGACAAGGGAGGGAAGGAAGGACCCTGTGCCTGGCAAAAGTCCA<br>GGTCGCTTCTCAGGATTTGTGGCACCTTCTGACTGTCAAACTGTTC<br>TTGTCAATCTCACAGGCTCCTGGTTGTCTACCCATGGACCCAGAGG<br>TTCTTTGACAGCTTTGGCAACCTGTCCTCTGCCTCTGCCATCATGG<br>GCAACCCCAAAGTCAAGGCACATGGCAAGAAGGTGCTGACTTCCT<br>TGGGAGATGCCACAAAGCACCTGGATGATCTCAAGGGCACCTTTG<br>CCCAGCTGAGTGAACTGCACTGTGACAAGCTGCATGTGGATCCTG<br>AGAACTTCAAGGTCGACGTAGATAAGTAGCATGGCGGGTTAATCA<br>TTAACTACAAGGAACCCCTAGTGATGGAGTTGGCCACTCCCTCTCT<br>GCGCGCTCGCTCGCTCACTGAGGCCGGGCGACCAAAGGTCGCCCG<br>ACGCCCGGGCTTTGCCCGGGCGGCCTCAGTGAGCGAGCGAGCGCG<br>CCAGCTGGCGTAATAGCGAAGAGGCCCGCACCGATCGCCCTTCCC<br>AACAGTTGCGCAGCCTGAATGGCGAATGGCGATTCCGTTGCAATG<br>GCTGGCGGTAATATTGTTCTGGATATTACCAGCAAGGCCGATAGTT<br>TGAGTTCTTCTACTCAGGCAAGTGATGTTATTACTAATCAAAGAAG<br>TATTGCGACAACGGTTAATTTGCGTGATGGACAGACTCTTTTACTC<br>GGTGGCCTCACTGATTATAAAAACACTTCTCAGGATTCTGGCGTAC<br>CGTTCCTGTCTAAAATCCCTTTAATCGGCCTCCTGTTTAGCTCCCGC<br>TCTGATTCTAACGAGGAAAGCACGTTATACGTGCTCGTCAAAGCA<br>ACCATAGTACGCGCCCTGTAGCGGCGCATTAAGCGCGGCGGGTGT<br>GGTGGTTACGCGCAGCGTGACCGCTACACTTGCCAGCGCCCTAGC<br>GCCCGCTCCTTTCGCTTTCTTCCCTTCCTTTCTCGCCACGTTCGCCG<br>GCTTTCCCCGTCAAGCTCTAAATCGGGGGCTCCCTTTAGGGTTCCG<br>ATTTAGTGCTTTACGGCACCTCGACCCCAAAAAACTTGATTAGGGT<br>GATGGTTCACGTAGTGGGCCATCGCCCTGATAGACGGTTTTTCGCC<br>CTTTGACGTTGGAGTCCACGTTCTTTAATAGTGGACTCTTGTTCCA<br>AACTGGAACAACACTCAACCCTATCTCGGTCTATTCTTTTGATTTA<br>TAAGGGATTTTGCCGATTTCGGCCTATTGGTTAAAAAATGAGCTGA<br>TTTAACAAAAATTTAACGCGAATTTTAACAAAATATTAACGTTTAC<br>AATTTAAATATTTGCTTATACAATCTTCCTGTTTTTGGGGCTTTTCT<br>GATTATCAACCGGGGTACATATGATTGACATGCTAGTTTTACGATT<br>ACCGTTCATCGATTCTCTTGTTTGCTCCAGACTCTCAGGCAATGAC<br>CTGATAGCCTTTGTAGAGACCTCTCAAAAATAGCTACCCTCTCCGG<br>CATGAATTTATCAGCTAGAACGGTTGAATATCATATTGATGGTGAT<br>TTGACTGTCTCCGGCCTTTCTCACCCGTTTGAATCTTTACCTACACA<br>TTACTCAGGCATTGCATTTAAAATATATGAGGGTTCTAAAAATTTT<br>TATCCTTGCGTTGAAATAAAGGCTTCTCCCGCAAAAGTATTACAGG<br>GTCATAATGTTTTTGGTACAACCGATTTAGCTTTATGCTCTGAGGC<br>TTTATTGCTTAATTTTGCTAATTCTTTGCCTTGCCTGTATGATTTATT<br>GGATGTTGGAATCGCCTGATGCGGTATTTTCTCCTTACGCATCTGT<br>GCGGTATTTCACACCGCATATGGTGCACTCTCAGTACAATCTGCTC<br>TGATGCCGCATAGTTAAGCCAGCCCCGACACCCGCCAACACCCGC<br>TGACGCGCCCTGACGGGCTTGTCTGCTCCCGGCATCCGCTTACAGA<br>CAAGCTGTGACCGTCTCCGGGAGCTGCATGTGTCAGAGGTTTTCAC<br>CGTCATCACCGAAACGCGCGAGACGAAAGGGCCTCGTGATACGCC<br>TATTTTTATAGGTTAATGTCATGATAATAATGGTTTCTTAGACGTC<br>AGGTGGCACTTTTCGGGGAAATGTGCGCGGAACCCCTATTTGTTTA<br>TTTTTCTAAATACATTCAAATATGTATCCGCTCATGAGACAATAAC<br>CCTGATAAATGCTTCAATAATATTGAAAAAGGAAGAGTATGAGTA<br>TTCAACATTTCCGTGTCGCCCTTATTCCCTTTTTTGCGGCATTTTGC<br>CTTCCTGTTTTTGCTCACCCAGAAACGCTGGTGAAAGTAAAAGATG<br>CTGAAGATCAGTTGGGTGCACGAGTGGGTTACATCGAACTGGATC<br>TCAACAGCGGTAAGATCCTTGAGAGTTTTCGCCCCGAAGAACGTT<br>TTCCAATGATGAGCACTTTTAAAGTTCTGCTATGTGGCGCGGTATT |

-continued

| SEQ ID NO | NAME | SEQUENCE |
|---|---|---|
| | | ATCCCGTATTGACGCCGGGCAAGAGCAACTCGGTCGCCGCATACA |
| | | CTATTCTCAGAATGACTTGGTTGAGTACTCACCAGTCACAGAAAA |
| | | GCATCTTACGGATGGCATGACAGTAAGAGAATTATGCAGTGCTGC |
| | | CATAACCATGAGTGATAACACTGCGGCCAACTTACTTCTGACAAC |
| | | GATCGGAGGACCGAAGGAGCTAACCGCTTTTTTGCACAACATGGG |
| | | GGATCATGTAACTCGCCTTGATCGTTGGGAACCGGAGCTGAATGA |
| | | AGCCATACCAAACGACGAGCGTGACACCACGATGCCTGTAGCAAT |
| | | GGCAACAACGTTGCGCAAACTATTAACTGGCGAACTACTTACTCT |
| | | AGCTTCCCGGCAACAATTAATAGACTGGATGGAGGCGGATAAAGT |
| | | TGCAGGACCACTTCTGCGCTCGGCCCTTCCGGCTGGCTGGTTTATT |
| | | GCTGATAAATCTGGAGCCGGTGAGCGTGGGTCTCGCGGTATCATT |
| | | GCAGCACTGGGGCCAGATGGTAAGCCCTCCCGTATCGTAGTTATC |
| | | TACACGACGGGGAGTCAGGCAACTATGGATGAACGAAATAGACA |
| | | GATCGCTGAGATAGGTGCCTCACTGATTAAGCATTGGTAACTGTC |
| | | AGACCAAGTTTACTCATATATACTTTAGATTGATTTAAAACTTCAT |
| | | TTTTAATTTAAAAGGATCTAGGTGAAGATCCTTTTTGATAATCTCA |
| | | TGACCAAAATCCCTTAACGTGAGTTTTCGTTCCACTGAGCGTCAGA |
| | | CCCCGTAGAAAAGATCAAAGGATCTTCTTGAGATCCTTTTTTTCTG |
| | | CGCGTAATCTGCTGCTTGCAAACAAAAAAACCACCGCTACCAGCG |
| | | GTGGTTTGTTTGCCGGATCAAGAGCTACCAACTCTTTTTCCGAAGG |
| | | TAACTGGCTTCAGCAGAGCGCAGATACCAAATACTGTCCTTCTAGT |
| | | GTAGCCGTAGTTAGGCCACCACTTCAAGAACTCTGTAGCACCGCC |
| | | TACATACCTCGCTCTGCTAATCCTGTTACCAGTGGCTGCTGCCAGT |
| | | GGCGATAAGTCGTGTCTTACCGGGTTGGACTCAAGACGATAGTTA |
| | | CCGGATAAGGCGCAGCGGTCGGGCTGAACGGGGGGTTCGTGCACA |
| | | CAGCCCAGCTTGGAGCGAACGACCTACACCGAACTGAGATACCTA |
| | | CAGCGTGAGCTATGAGAAAGCGCCACGCTTCCCGAAGGGAGAAA |
| | | GGCGGACAGGTATCCGGTAAGCGGCAGGGTCGGAACAGGAGAGC |
| | | GCACGAGGGAGCTTCCAGGGGGAAACGCCTGGTATCTTTATAGTC |
| | | CTGTCGGGTTTCGCCACCTCTGACTTGAGCGTCGATTTTTGTGATG |
| | | CTCGTCAGGGGGGCGGAGCCTATGGAAAAACGCCAGCAACGCGG |
| | | CCTTTTTACGGTTCCTGGCCTTTTGCTGGCCTTTTGCTCACATGTTC |
| | | TTTCCTGCGTTATCCCCTGATTCTGTGGATAACCGTATTACCGCCTT |
| | | TGAGTGAGCTGATACCGCTCGCCGCAGCCGAACGACCGAGCGCAG |
| | | CGAGTCAGTGAGCGAGGAAGCGGAAGAGCGCCCAATACGCAAAC |
| | | CGCCTCTCCCCGCGCGTTGGCCGATTCATTAATG |
| 27 | HBG1 Round 1 & 2: | CAGCTGCGCGCTCGCTCGCTCACTGAGGCCGCCCGGGCAAAGCCC |
| | V1E4 | GGGCGTCGGGCGACCTTTGGTCGCCCGGCCTCAGTGAGCGAGCGA |
| | HBG1(200-600). | GCGCGCAGAGAGGGAGTGGCCAACTCCATCACTAGGGGTTCCTTG |
| | d13&dATG,stop> | TAGTTAATGATTAACCCGCCATGCTACTTATCTACGTAGCCATGCT |
| | HBB(T87Q). | CTAGCGGCCTCGGCCTCTGCATAAATAAAAAAAATTAGTCAGCCA |
| | 3'enh;MND>GFP | TGAGCTTGGACGCGTAGATCTAGATGAAACAGTCATGATTTATTTC |
| | *200-600 bp HA | AAATAGGTACGGATAAGTAGATATTGAGGTAAGCATTAGGTCTTA |
| | | TATTATGTAACACTAATCTATTACTGCGCTGAAACTGTGGCTTTAT |
| | | AGAAATTGTTTTCACTGCACTATTGAGAAATTAAGAGATAATGGC |
| | | AAAAGTCACAAAGAGTATATTCAAAAAGAAGTATAGCACTTTTTC |
| | | CTTAGAAACCACTGCTAACTGAAAGAGACTAAGATTTGTCCCGTC |
| | | AAAAATCCTGGACCTATGCCTAAAACACATTTCACAATCCCTGAA |
| | | CTTTTCAAAAATTGGTACATGCTTTAGCTTTAAACTACAGGCCTCA |
| | | CTGGAGCTAGAGACAAGAAGGTAAAAAACGGCTGACAAAAGAAG |
| | | TCCTGGTATCCTCTATGATGGGAGAAGGAAACTAGCTAAAGGGAA |
| | | GAATAAATTAGAGAAAAACTGGAATGACTGAATCGGAACAAGGC |
| | | AAAGGCTATAAAAAAAAATTAGCAGTATCCTCTTGGGGGCCCCTTC |
| | | CCCACACTATCTCAATGCAAATATCTGTCTGAAACGGTCCCTGGCT |
| | | AAACTCCACCCATGGGTTGGCCAGCCTTGCCTTGACAAGGCAAAC |
| | | TTGACCAATAGTCTTAGAGTATCCAGTGAGGCCAGGGGCCGGCGG |
| | | CTGGCTAGGGATGAAGAATAAAAGGAAGCACCCTTCAGCAGTTCC |
| | | ACACACTCGCTTCTGGAACGTCTGAGGTTATCAATAAGCTCCTAGT |
| | | CCAGACGCCATGGTGCACCTGACTCCTGAGGAGAAGTCTGCCGTT |
| | | ACTGCCCTGTGGGGCAAGGTGAACGTGGATGAAGTTGGTGGTGAG |
| | | GCCCTGGGCAGGTTGGTATCAAGGTTACAAGACAGGTTTAAGGAG |
| | | ACCAATAGAAACTGGGCATGTGGAGACAGAGAAGACTCTTGGGTT |
| | | TCTGATAGGCACTGACTCTCTCTGCCTATTGGTCTATTTTCCCACCC |
| | | TTAGGCTGCTGGTGGTCTACCCTTGGACCCAGAGGTTCTTTGAGTC |
| | | CTTTGGGGATCTGTCCACTCCTGATGCTGTTATGGGCAACCCTAAG |
| | | GTGAAGGCTCATGGCAAGAAAGTGCTCGGTGCCTTTAGTGATGGC |
| | | CTGGCTCACCTGGACAACCTCAAGGGCACCTTTGCCCAGCTGAGT |
| | | GAGCTGCACTGTGACAAGCTGCACGTGGATCCTGAGAACTTCAGG |
| | | GTGAGTCTATGGGACCCTTGATGTTTTCTTTCCCCTTCTTTTCTATG |
| | | GTTAAGTTCATGTCATAGGAAGGGGAGAAGTAACAGGGTACACAT |
| | | ATTGACCAAATCAGGGTAATTTTGCATTTGTAATTTTAAAAAATGC |
| | | TTTCTTCTTTTAATATACTTTTTTGTTTATCTTATTTCTAATACTTTC |
| | | CCTAATCTCTTTCTTTCAGGGCAATAATGATACAATGTATCATGCC |
| | | TCTTTGCACCATTCTAAAGAATAACAGTGATAATTTCTGGGTTAAG |

-continued

| SEQ ID NO | NAME | SEQUENCE |
|---|---|---|
| | | GCAATAGCAATATTTCTGCATATAAATATTTCTGCATATAAATTGT<br>AACTGATGTAAGAGGTTTCATATTGCTAATAGCAGCTACAATCCA<br>GCTACCATTCTGCTTTTATTTTATGGTTGGGATAAGGCTGGATTAT<br>TCTGAGTCCAAGCTAGGCCCTTTTGCTAATCATGTTCATACCTCTT<br>ATCTTCCTCCCACAGCTCCTGGGCAACGTGCTGGTCTGTGTGCTGG<br>CCCATCACTTTGGCAAAGAATTCACCCCACCAGTGCAGGCTGCCT<br>ATCAGAAAGTGGTGGCTGGTGTGGCTAATGCCCTGGCCCACAAGT<br>ATCACTAAGCTCGCTTTCTTGCTGTCCAATTTCTATTAAAGGTTCCT<br>TTGTTCCCTAAGTCCAACTACTAAACTGGGGGATATTATGAAGGG<br>CCTTGAGCATCTGGATTCTGCCTAATAAAAAACATTTATTTTCATT<br>GCAATGATGTATTTAAATTATTTCTGAATATTTTACTAAAAAGGGA<br>ATGTGGGAGGTCAGTGCATTTAAAACATAAAGAAATGAAGAGCTA<br>GTTCAAACCTTGGGAAAATACACTATATCTTAAACTCCATGAAAG<br>AAGGTGAGGCTGCAAACAGCTAATGCACATTGGCAACAGCCCCTG<br>ATGCCTATGCCTTATTCATCCCTCAGAAAAGGATTCAAGTAGAGG<br>CTTGATTTGGAGGTTAAAGTTTTGCTATGCTGTATTTTACATTACTT<br>ATTGTTTTAGCTGTCCTCATGAATGTCTTTTCACTACCCATTTGCTT<br>ATCCTGCATCTCTCAGCCTTGACTCCACTCAGTTCTCTTGCTTAGA<br>GATACCACCTTTCCCCTGAAGTGTTCCTTCCATGTTTTACGGCGAG<br>ATGGTTTCTCCTCGCCTGGCCACTCAGCCTTAGTTGTCTCTGTTGTC<br>TTATAGAGGTCTACTTGAAGAAGGAAAAACAGGGGGCATGGTTTG<br>ACTGTCCTGTGAGCCCTTCTTCCCTGCCTCCCCCACTCACAGTGAC<br>CCGGAATCTGCAGTGCTAGTCTCCCGGAACTATCACTCTTTCACAG<br>TCTGCTTTGGAAGGACTGGGCTTAGTATGAAAAGTTAGGACTGAG<br>AAGAATTTGAAAGGGGGCTTTTTGTAGCTTGATATTCACTACTGTC<br>TTATTACCCTATCATAGGCCCACCCCAAATGGAAGTCCCATTCTTC<br>CTCAGGATGTTTAAGATTAGCATTCAGGAAGAGATCAGAGGTCTG<br>CTGGCTCCCTTATCATGTCCCTTATGGTGCTTCTGGCTCTGCAGTTA<br>TTAGCATAGTGTTACCATCAACCACCTTAACTTCATTTTTCTTATTC<br>AATACCTAGCCGCGGGAACAGAGAAACAGGAGAATATGGGCCAA<br>ACAGGATATCTGTGGTAAGCAGTTCCTGCCCCGGCTCAGGGCCAA<br>GAACAGTTGGAACAGCAGAATATGGGCCAAACAGGATATCTGTGG<br>TAAGCAGTTCCTGCCCCGGCTCAGGGCCAAGAACAGATGGTCCCC<br>AGATGCGGTCCCGCCCTCAGCAGTTTCTAGAGAACCATCAGATGT<br>TTCCAGGGTGCCCCAAGGACCTGAAATGACCCTGTGCCTTATTTGA<br>ACTAACCAATCAGTTCGCTTCTCGCTTCTGTTCGCGCGCTTCTGCTC<br>CCCGAGCTCTATATAAGCAGAGCTCGTTTAGTGAACCGTCAGATC<br>GCGGCCGCGCCGCCACCATGGTGAGCAAGGGCGAGGAGCTGTTCA<br>CCGGGGTGGTGCCCATCCTGGTCGAGCTGGACGGCGACGTAAACG<br>GCCACAAGTTCAGCGTGTCCGGCGAGGGCGAGGGCGATGCCACCT<br>ACGGCAAGCTGACCCTGAAGTTCATCTGCACCACCGGCAAGCTGC<br>CCGTGCCCTGGCCCACCCTCGTGACCACCCTGACCTACGGCGTGCA<br>GTGCTTCAGCCGCTACCCCGACCACATGAAGCAGCACGACTTCTTC<br>AAGTCCGCCATGCCCGAAGGCTACGTCCAGGAGCGCACCATCTTC<br>TTCAAGGACGACGGCAACTACAAGACCCGCGCCGAGGTGAAGTTC<br>GAGGGCGACACCCTGGTGAACCGCATCGAGCTGAAGGGCATCGAC<br>TTCAAGGAGGACGGCAACATCCTGGGGCACAAGCTGGAGTACAAC<br>TACAACAGCCACAACGTCTATATCATGGCCGACAAGCAGAAGAAC<br>GGCATCAAGGTGAACTTCAAGATCCGCCACAACATCGAGGACGGC<br>AGCGTGCAGCTCGCCGACCACTACCAGCAGAACACCCCCATCGGC<br>GACGGCCCCGTGCTGCTGCCCGACAACCACTACCTGAGCACCCAG<br>TCCGCCCTGAGCAAAGACCCCAACGAGAAGCGCGATCACATGGTC<br>CTGCTGGAGTTCGTGACCGCCGCCGGGATCACTCTCGGCATGGAC<br>GAGCTGTACAAGTAACCTGCAGGGCTCACTGCCCATGATTCAGAG<br>CTTTCAAGGATAGGCTTTATTCTGCAAGCAATACAAATAATAAATC<br>TATTCTGCTGAGAGATCACACATGATTTTCTTCAGCTCTTTTTTTTA<br>CATCTTTTTAAATATATGAGCCACAAAGGGTTTATATTGAGGGAA<br>GTGTGTATGTGTATTTCTGCATGCCTGTTTGTGTTTGTGGTGTGTGC<br>ATGCTCCTCATTTATTTTTATATGAGATGTGCATTTTGATGAGCAA<br>ATAAAAGCAGTAAAGACACTTGTACACGGGAGTTCTGCAAGTGGG<br>AGTAAATGGTGTAGGAGAAATCCGGTGGGAAGAAAGACCTCTATA<br>GGACAGGACTTCTCAGAAACAGATGTTTTGGAAGAGATGGGAAAA<br>GGTTCAGTGAAGACCTGGGGGCTGGATTGATTGCAGCTGAGTAGC<br>AAGGATGGTTCTTAAGGAAGGGAAAGTGTTCCAAGCTTTAGGAAT<br>TCAAGGTTTAGTCAGGTGTAGCAATTCTATTTTATTAGGAGGAATA<br>CTATTTCTAATGGCACTTAGCTTTTCACAGCCCTTGTGGATGCCTA<br>AGAAAGTGAAATTAATCCCATGCCCTCAAGTGTCGACGTAGATAA<br>GTAGCATGGCGGGTTAATCATTAACTACAAGGAACCCCTAGTGAT<br>GGAGTTGGCCACTCCCTCTCTGCGCGCTCGCTCGCTCACTGAGGCC<br>GGGCGACCAAAGGTCGCCCGACGCCCGGGCTTTGCCCGGGCGGCC<br>TCAGTGAGCGAGCGAGCGCGCCAGCTGGCGTAATAGCGAAGAGG<br>CCCGCACCGATCGCCCTTCCCAACAGTTGCGCAGCCTGAATGGCG<br>AATGGCGATTCCGTTGCAATGGCTGGCGGTAATATTGTTCTGGATA<br>TTACCAGCAAGGCCGATAGTTTGAGTTCTTCTACTCAGGCAAGTGA<br>TGTTATTACTAATCAAAGAAGTATTGCGACAACGGTTAATTTGCGT |

-continued

| SEQ ID NO | NAME | SEQUENCE |
|---|---|---|
| | | GATGGACAGACTCTTTTACTCGGTGGCCTCACTGATTATAAAAACA<br>CTTCTCAGGATTCTGGCGTACCGTTCCTGTCTAAAATCCCTTTAAT<br>CGGCCTCCTGTTTAGCTCCCGCTCTGATTCTAACGAGGAAAGCACG<br>TTATACGTGCTCGTCAAAGCAACCATAGTACGCGCCCTGTAGCGG<br>CGCATTAAGCGCGGCGGGTGTGGTGGTTACGCGCAGCGTGACCGC<br>TACACTTGCCAGCGCCCTAGCGCCCGCTCCTTTCGCTTTCTTCCCTT<br>CCTTTCTCGCCACGTTCGCCGGCTTTCCCCGTCAAGCTCTAAATCG<br>GGGGCTCCCTTTAGGGTTCCGATTTAGTGCTTTACGGCACCTCGAC<br>CCCAAAAAACTTGATTAGGGTGATGGTTCACGTAGTGGGCCATCG<br>CCCTGATAGACGGTTTTTCGCCCTTTGACGTTGGAGTCCACGTTCT<br>TTAATAGTGGACTCTTGTTCCAAACTGGAACAACACTCAACCCTAT<br>CTCGGTCTATTCTTTTGATTTATAAGGGATTTTGCCGATTTCGGCCT<br>ATTGGTTAAAAAATGAGCTGATTTAACAAAAATTTAACGCGAATT<br>TTAACAAAATATTAACGTTTACAATTTAAATATTTGCTTATACAAT<br>CTTCCTGTTTTTGGGGCTTTTCTGATTATCAACCGGGGTACATATG<br>ATTGACATGCTAGTTTTACGATTACCGTTCATCGATTCTCTTGTTTG<br>CTCCAGACTCTCAGGCAATGACCTGATAGCCTTTGTAGAGACCTCT<br>CAAAAATAGCTACCCTCTCCGGCATGAATTTATCAGCTAGAACGG<br>TTGAATATCATATTGATGGTGATTTGACTGTCTCCGGCCTTTCTCA<br>CCCGTTTGAATCTTTACCTACACATTACTCAGGCATTGCATTTAAA<br>ATATATGAGGGTTCTAAAAATTTTTATCCTTGCGTTGAAATAAAGG<br>CTTCTCCCGCAAAAGTATTACAGGGTCATAATGTTTTTGGTACAAC<br>CGATTTAGCTTTATGCTCTGAGGCTTTATTGCTTAATTTTGCTAATT<br>CTTTGCCTTGCCTGTATGATTTATTGGATGTTGGAATCGCCTGATG<br>CGGTATTTTCTCCTTACGCATCTGTGCGGTATTTCACACCGCATAT<br>GGTGCACTCTCAGTACAATCTGCTCTGATGCCGCATAGTTAAGCCA<br>GCCCCGACACCCGCCAACACCCGCTGACGCGCCCTGACGGGCTTG<br>TCTGCTCCCGGCATCCGCTTACAGACAAGCTGTGACCGTCTCCGGG<br>AGCTGCATGTGTCAGAGGTTTTCACCGTCATCACCGAAACGCGCG<br>AGACGAAAGGGCCTCGTGATACGCCTATTTTTATAGGTTAATGTCA<br>TGATAATAATGGTTTCTTAGACGTCAGGTGGCACTTTTCGGGGAAA<br>TGTGCGCGGAACCCCTATTTGTTTATTTTTCTAAATACATTCAAAT<br>ATGTATCCGCTCATGAGACAATAACCCTGATAAATGCTTCAATAAT<br>ATTGAAAAAGGAAGAGTATGAGTATTCAACATTTCCGTGTCGCCC<br>TTATTCCCTTTTTTGCGGCATTTTGCCTTCCTGTTTTTGCTCACCCA<br>GAAACGCTGGTGAAAGTAAAAGATGCTGAAGATCAGTTGGGTGCA<br>CGAGTGGGTTACATCGAACTGGATCTCAACAGCGGTAAGATCCTT<br>GAGAGTTTTCGCCCCGAAGAACGTTTTCCAATGATGAGCACTTTTA<br>AAGTTCTGCTATGTGGCGCGGTATTATCCCGTATTGACGCCGGGCA<br>AGAGCAACTCGGTCGCCGCATACACTATTCTCAGAATGACTTGGTT<br>GAGTACTCACCAGTCACAGAAAAGCATCTTACGGATGGCATGACA<br>GTAAGAGAATTATGCAGTGCTGCCATAACCATGAGTGATAACACT<br>GCGGCCAACTTACTTCTGACAACGATCGGAGGACCGAAGGAGCTA<br>ACCGCTTTTTTGCACAACATGGGGGATCATGTAACTCGCCTTGATC<br>GTTGGGAACCGGAGCTGAATGAAGCCATACCAAACGACGAGCGT<br>GACACCACGATGCCTGTAGCAATGGCAACAACGTTGCGCAAACTA<br>TTAACTGGCGAACTACTTACTCTAGCTTCCCGGCAACAATTAATAG<br>ACTGGATGGAGGCGGATAAAGTTGCAGGACCACTTCTGCGCTCGG<br>CCCTTCCGGCTGGCTGGTTTATTGCTGATAAATCTGGAGCCGGTGA<br>GCGTGGGTCTCGCGGTATCATTGCAGCACTGGGGCCAGATGGTAA<br>GCCCTCCCGTATCGTAGTTATCTACACGACGGGGAGTCAGGCAAC<br>TATGGATGAACGAAATAGACAGATCGCTGAGATAGGTGCCTCACT<br>GATTAAGCATTGGTAACTGTCAGACCAAGTTTACTCATATATACTT<br>TAGATTGATTTAAAACTTCATTTTTAATTTAAAAGGATCTAGGTGA<br>AGATCCTTTTTGATAATCTCATGACCAAAATCCCTTAACGTGAGTT<br>TTCGTTCCACTGAGCGTCAGACCCCGTAGAAAAGATCAAAGGATC<br>TTCTTGAGATCCTTTTTTTCTGCGCGTAATCTGCTGCTTGCAAACAA<br>AAAAACCACCGCTACCAGCGGTGGTTTGTTTGCCGGATCAAGAGC<br>TACCAACTCTTTTTCCGAAGGTAACTGGCTTCAGCAGAGCGCAGAT<br>ACCAAATACTGTCCTTCTAGTGTAGCCGTAGTTAGGCCACCACTTC<br>AAGAACTCTGTAGCACCGCCTACATACCTCGCTCTGCTAATCCTGT<br>TACCAGTGGCTGCTGCCAGTGGCGATAAGTCGTGTCTTACCGGGTT<br>GGACTCAAGACGATAGTTACCGGATAAGGCGCAGCGGTCGGGCTG<br>AACGGGGGGTTCGTGCACACAGCCCAGCTTGGAGCGAACGACCTA<br>CACCGAACTGAGATACCTACAGCGTGAGCTATGAGAAAGCGCCAC<br>GCTTCCCGAAGGGAGAAAGGCGGACAGGTATCCGGTAAGCGGCA<br>GGGTCGGAACAGGAGAGCGCACGAGGGAGCTTCCAGGGGGAAAC<br>GCCTGGTATCTTTATAGTCCTGTCGGGTTTCGCCACCTCTGACTTG<br>AGCGTCGATTTTTGTGATGCTCGTCAGGGGGGCGGAGCCTATGGA<br>AAAACGCCAGCAACGCGGCCTTTTTACGGTTCCTGGCCTTTTGCTG<br>GCCTTTTGCTCACATGTTCTTTCCTGCGTTATCCCCTGATTCTGTGG<br>ATAACCGTATTACCGCCTTTGAGTGAGCTGATACCGCTCGCCGCAG<br>CCGAACGACCGAGCGCAGCGAGTCAGTGAGCGAGGAAGCGGAAG<br>AGCGCCCAATACGCAAACCGCCTCTCCCCGCGCGTTGGCCGATTC<br>ATTAATG |

-continued

| SEQ ID NO | NAME | SEQUENCE |
|---|---|---|
| 28 | HBG1 Round 1 & 2:<br>AMS#1303<br>pAAV<br>HBG1(400).d13m<br>in>HBB(T87Q).<br>3'enh;MND>GFP.<br>SV40pA (V1E5) | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC<br>GCGTAGATCTTTTTTCCTTAGAAACCACTGCTAACTGAAAGAGACT<br>AAGATTTGTCCCGTCAAAAATCCTGGACCTATGCCTAAAACACATT<br>TCACAATCCCTGAACTTTTCAAAAATTGGTACATGCTTTAGCTTTA<br>AACTACAGGCCTCACTGGAGCTAGAGACAAGAAGGTAAAAAACG<br>GCTGACAAAAGAAGTCCTGGTATCCTCTATGATGGGAGAAGGAAA<br>CTAGCTAAAGGGAAGAATAAATTAGAGAAAAACTGGAATGACTG<br>AATCGGAACAAGGCAAAGGCTATAAAAAAAAATTAGCAGTATCCTC<br>TTGGGGGCCCCTTCCCCACACTATCTCAATGCAAATATCTGTCTGA<br>AACGGTCCCTGGCTAAACTCCACCCATGGGTTGGCCAGCCTTGCCT<br>TGACAAGGCAAACTTGACCAATAGTCTTAGAGTATCCAGTGAGGC<br>CAGGGGCCGGCGGCTGGCTAGGGATGAAGAATAAAAGGAAGCAC<br>CCTTCAGCAGTTCCACACACTCGCTTCTGGAACGTCTGAGGTTATC<br>AATAAGCTCCTAGTCCAGACGCCATGGTGCACCTGACTCCTGAGG<br>AGAAGTCTGCCGTTACTGCCCTGTGGGGCAAGGTGAACGTGGATG<br>AAGTTGGTGGTGAGGCCCTGGGCAGGTTGGTATCAAGGTTACAAG<br>ACAGGTTTAAGGAGACCAATAGAAACTGGGCATGTGGAGACAGA<br>GAAGACTCTTGGGTTTCTGATAGGCACTGACTCTCTCTGCCTATTG<br>GTCTATTTTCCCACCCTTAGGCTGCTGGTGGTCTACCCTTGGACCC<br>AGAGGTTCTTTGAGTCCTTTGGGGATCTGTCCACTCCTGATGCTGT<br>TATGGGCAACCCTAAGGTGAAGGCTCATGGCAAGAAAGTGCTCGG<br>TGCCTTTAGTGATGGCCTGGCTCACCTGGACAACCTCAAGGGCAC<br>CTTTGCCCAGCTGAGTGAGCTGCACTGTGACAAGCTGCACGTGGA<br>TCCTGAGAACTTCAGGGTGAGTCTATGGGACCCTTGATGTTTTCTT<br>TCCCCTTCTTTTCTATGGTTAAGTTCATGTCATAGGAAGGGGAGAA<br>GTAACAGGGTACACATATTGACCAAATCAGGGTAATTTTGCATTT<br>GTAATTTTAAAAAATGCTTTCTTCTTTTAATATACTTTTTTGTTTAT<br>CTTATTTCTAATACTTTCCCTAATCTCTTTCTTTCAGGGCAATAATG<br>ATACAATGTATCATGCCTCTTTGCACCATTCTAAAGAATAACAGTG<br>ATAATTTCTGGGTTAAGGCAATAGCAATATTTCTGCATATAAATAT<br>TTCTGCATATAAATTGTAACTGATGTAAGAGGTTTCATATTGCTAA<br>TAGCAGCTACAATCCAGCTACCATTCTGCTTTTATTTTATGGTTGG<br>GATAAGGCTGGATTATTCTGAGTCCAAGCTAGGCCCTTTTGCTAAT<br>CATGTTCATACCTCTTATCTTCCTCCCACAGCTCCTGGGCAACGTG<br>CTGGTCTGTGTGCTGGCCCATCACTTTGGCAAAGAATTCACCCCAC<br>CAGTGCAGGCTGCCTATCAGAAAGTGGTGGCTGGTGTGGCTAATG<br>CCCTGGCCCACAAGTATCACTAAGCTCGCTTTCTTGCTGTCCAATT<br>TCTATTAAAGGTTCCTTTGTTCCCTAAGTCCAACTACTAAACTGGG<br>GGATATTATGAAGGGCCTTGAGCATCTGGATTCTGCCTAATAAAA<br>AACATTTATTTTCATTGCAATGATGTATTTAAATTATTTCTGAATAT<br>TTTACTAAAAAGGGAATGTGGGAGGTCAGTGCATTTAAAACATAA<br>AGAAATGAAGAGCTAGTTCAAACCTTGGGAAAATACACTATATCT<br>TAAACTCCATGAAAGAAGGTGAGGCTGCAAACAGCTAATGCACAT<br>TGGCAACAGCCCCTGATGCCTATGCCTTATTCATCCCTCAGAAAAG<br>GATTCAAGTAGAGGCTTGATTTGGAGGTTAAAGTTTTGCTATGCTG<br>TATTTTACATTACTTATTGTTTTAGCTGTCCTCATGAATGTCTTTTC<br>ACTACCCATTTGCTTATCCTGCATCTCTCAGCCTTGACTCCACTCA<br>GTTCTCTTGCTTAGAGATACCACCTTTCCCCTGAAGTGTTCCTTCCA<br>TGTTTTACGGCGAGATGGTTTCTCCTCGCCTGGCCACTCAGCCTTA<br>GTTGTCTCTGTTGTCTTATAGAGGTCTACTTGAAGAAGGAAAAACA<br>GGGGGCATGGTTTGACTGTCCTGTGAGCCCTTCTTCCCTGCCTCCC<br>CCACTCACAGTGACCCGGAATCTGCAGTGCTAGTCTCCCGGAACT<br>ATCACTCTTTCACAGTCTGCTTTGGAAGGACTGGGCTTAGTATGAA<br>AAGTTAGGACTGAGAAGAATTTGAAAGGGGGCTTTTTGTAGCTTG<br>ATATTCACTACTGTCTTATTACCCTATCATAGGCCCACCCCAAATG<br>GAAGTCCCATTCTTCCTCAGGATGTTTAAGATTAGCATTCAGGAAG<br>AGATCAGAGGTCTGCTGGCTCCCTTATCATGTCCCTTATGGTGCTT<br>CTGGCTCTGCAGTTATTAGCATAGTGTTACCATCAACCACCTTAAC<br>TTCATTTTTCTTATTCAATACCTAGCCGCGGGAACAGAGAAACAGG<br>AGAATATGGGCCAAACAGGATATCTGTGGTAAGCAGTTCCTGCCC<br>CGGCTCAGGGCCAAGAACAGTTGGAACAGCAGAATATGGGCCAA<br>ACAGGATATCTGTGGTAAGCAGTTCCTGCCCCGGCTCAGGGCCAA<br>GAACAGATGGTCCCCAGATGCGGTCCCGCCCTCAGCAGTTTCTAG<br>AGAACCATCAGATGTTTCCAGGGTGCCCCAAGGACCTGAAATGAC<br>CCTGTGCCTTATTTGAACTAACCAATCAGTTCGCTTCTCGCTTCTGT<br>TCGCGCGCTTCTGCTCCCCGAGCTCTATATAAGCAGAGCTCGTTTA<br>GTGAACCGTCAGATCGCGGCCGCGCCGCCACCATGGTGAGCAAGG<br>GCGAGGAGCTGTTCACCGGGGTGGTGCCCATCCTGGTCGAGCTGG<br>ACGGCGACGTAAACGGCCACAAGTTCAGCGTGTCCGGCGAGGGCG<br>AGGGCGATGCCACCTACGGCAAGCTGACCCTGAAGTTCATCTGCA<br>CCACCGGCAAGCTGCCCGTGCCCTGGCCCACCCTCGTGACCACCCT<br>GACCTACGGCGTGCAGTGCTTCAGCCGCTACCCCGACCACATGAA |

-continued

| SEQ ID NO | NAME | SEQUENCE |
|---|---|---|
| | | GCAGCACGACTTCTTCAAGTCCGCCATGCCCGAAGGCTACGTCCA |
| | | GGAGCGCACCATCTTCTTCAAGGACGACGGCAACTACAAGACCCG |
| | | CGCCGAGGTGAAGTTCGAGGGCGACACCCTGGTGAACCGCATCGA |
| | | GCTGAAGGGCATCGACTTCAAGGAGGACGGCAACATCCTGGGGCA |
| | | CAAGCTGGAGTACAACTACAACAGCCACAACGTCTATATCATGGC |
| | | CGACAAGCAGAAGAACGGCATCAAGGTGAACTTCAAGATCCGCC |
| | | ACAACATCGAGGACGGCAGCGTGCAGCTCGCCGACCACTACCAGC |
| | | AGAACACCCCCATCGGCGACGGCCCCGTGCTGCTGCCCGACAACC |
| | | ACTACCTGAGCACCCAGTCCGCCCTGAGCAAAGACCCCAACGAGA |
| | | AGCGCGATCACATGGTCCTGCTGGAGTTCGTGACCGCCGCCGGGA |
| | | TCACTCTCGGCATGGACGAGCTGTACAAGTAAGCTTTATTTGTGAA |
| | | ATTTGTGATGCTATTGCTTTATTTGTAACCATTATAAGCTGCAATA |
| | | AACAAGTTAACAACAACAATTGCATTCATTTTATGTTTCAGGTTCA |
| | | GGGGGAGATGTGGGAGGTTTTTTAAAGCCCTGCAGGATGGGTCAT |
| | | TTCACAGAGGAGGACAAGGCTACTATCACAAGCCTGTGGGGCAAG |
| | | GTGAATGTGGAAGATGCTGGAGGAGAAACCCTGGGAAGGTAGGC |
| | | TCTGGTGACCAGGACAAGGGAGGGAAGGAAGGACCCTGTGCCTG |
| | | GCAAAAGTCCAGGTCGCTTCTCAGGATTTGTGGCACCTTCTGACTG |
| | | TCAAACTGTTCTTGTCAATCTCACAGGCTCCTGGTTGTCTACCCAT |
| | | GGACCCAGAGGTTCTTTGACAGCTTTGGCAACCTGTCCTCTGCCTC |
| | | TGCCATCATGGGCAACCCCAAAGTCAAGGCACATGGCAAGAAGGT |
| | | GCTGACTTCCTTGGGAGATGCCACAAAGCACCTGGATGATCTCAA |
| | | GGGCACCTTTGCCCAGCTGAGTGAACTGCAGTCGACAGGAACCCC |
| | | TAGTGATGGAGTTGGCCACTCCCTCTCTGCGCGCTCGCTCGCTCAC |
| | | TGAGGCCGGGCGACCAAAGGTCGCCCGACGCCCGGGCTTTGCCCG |
| | | GGCGGCCTCAGTGAGCGAGCGAGCGCGCAGCTGGCGTAATAGCG |
| | | AAGAGGCCCGCACCGATCGCCCTTCCCAACAGTTGCGCAGCCTGA |
| | | ATGGCGAATGGCGATTCCGTTGCAATGGCTGGCGGTAATATTGTTC |
| | | TGGATATTACCAGCAAGGCCGATAGTTTGAGTTCTTCTACTCAGGC |
| | | AAGTGATGTTATTACTAATCAAAGAAGTATTGCGACAACGGTTAA |
| | | TTTGCGTGATGGACAGACTCTTTTACTCGGTGGCCTCACTGATTAT |
| | | AAAAACACTTCTCAGGATTCTGGCGTACCGTTCCTGTCTAAAATCC |
| | | CTTTAATCGGCCTCCTGTTTAGCTCCCGCTCTGATTCTAACGAGGA |
| | | AAGCACGTTATACGTGCTCGTCAAAGCAACCATAGTACGCGCCCT |
| | | GTAGCGGCGCATTAAGCGCGGCGGGTGTGGTGGTTACGCGCAGCG |
| | | TGACCGCTACACTTGCCAGCGCCCTAGCGCCCGCTCCTTTCGCTTT |
| | | CTTCCCTTCCTTTCTCGCCACGTTCGCCGGCTTTCCCCGTCAAGCTC |
| | | TAAATCGGGGGCTCCCTTTAGGGTTCCGATTTAGTGCTTTACGGCA |
| | | CCTCGACCCCAAAAAACTTGATTAGGGTGATGGTTCACGTAGTGG |
| | | GCCATCGCCCTGATAGACGGTTTTTCGCCCTTTGACGTTGGAGTCC |
| | | ACGTTCTTTAATAGTGGACTCTTGTTCCAAACTGGAACAACACTCA |
| | | ACCCTATCTCGGTCTATTCTTTTGATTTATAAGGGATTTTGCCGATT |
| | | TCGGCCTATTGGTTAAAAAATGAGCTGATTTAACAAAAATTTAAC |
| | | GCGAATTTTAACAAAATATTAACGTTTACAATTTAAATATTTGCTT |
| | | ATACAATCTTCCTGTTTTTGGGGCTTTTCTGATTATCAACCGGGGT |
| | | ACATATGATTGACATGCTAGTTTTACGATTACCGTTCATCGATTCT |
| | | CTTGTTTGCTCCAGACTCTCAGGCAATGACCTGATAGCCTTTGTAG |
| | | AGACCTCTCAAAAATAGCTACCCTCTCCGGCATGAATTTATCAGCT |
| | | AGAACGGTTGAATATCATATTGATGGTGATTTGACTGTCTCCGGCC |
| | | TTTCTCACCCGTTTGAATCTTTACCTACACATTACTCAGGCATTGC |
| | | ATTTAAAATATATGAGGGTTCTAAAAATTTTTATCCTTGCGTTGAA |
| | | ATAAAGGCTTCTCCCGCAAAAGTATTACAGGGTCATAATGTTTTTG |
| | | GTACAACCGATTTAGCTTTATGCTCTGAGGCTTTATTGCTTAATTTT |
| | | GCTAATTCTTTGCCTTGCCTGTATGATTTATTGGATGTTGGAATCG |
| | | CCTGATGCGGTATTTTCTCCTTACGCATCTGTGCGGTATTTCACAC |
| | | CGCATATGGTGCACTCTCAGTACAATCTGCTCTGATGCCGCATAGT |
| | | TAAGCCAGCCCCGACACCCGCCAACACCCGCTGACGCGCCCTGAC |
| | | GGGCTTGTCTGCTCCCGGCATCCGCTTACAGACAAGCTGTGACCGT |
| | | CTCCGGGAGCTGCATGTGTCAGAGGTTTTCACCGTCATCACCGAA |
| | | ACGCGCGAGACGAAAGGGCCTCGTGATACGCCTATTTTTATAGGT |
| | | TAATGTCATGATAATAATGGTTTCTTAGACGTCAGGTGGCACTTTT |
| | | CGGGGAAATGTGCGCGGAACCCCTATTTGTTTATTTTTCTAAATAC |
| | | ATTCAAATATGTATCCGCTCATGAGACAATAACCCTGATAAATGCT |
| | | TCAATAATATTGAAAAAGGAAGAGTATGAGTATTCAACATTTCCG |
| | | TGTCGCCCTTATTCCCTTTTTTGCGGCATTTTGCCTTCCTGTTTTTGC |
| | | TCACCCAGAAACGCTGGTGAAAGTAAAAGATGCTGAAGATCAGTT |
| | | GGGTGCACGAGTGGGTTACATCGAACTGGATCTCAACAGCGGTAA |
| | | GATCCTTGAGAGTTTTCGCCCCGAAGAACGTTTTCCAATGATGAGC |
| | | ACTTTTAAAGTTCTGCTATGTGGCGCGGTATTATCCCGTATTGACG |
| | | CCGGGCAAGAGCAACTCGGTCGCCGCATACACTATTCTCAGAATG |
| | | ACTTGGTTGAGTACTCACCAGTCACAGAAAAGCATCTTACGGATG |
| | | GCATGACAGTAAGAGAATTATGCAGTGCTGCCATAACCATGAGTG |
| | | ATAACACTGCGGCCAACTTACTTCTGACAACGATCGGAGGACCGA |
| | | AGGAGCTAACCGCTTTTTTGCACAACATGGGGGATCATGTAACTC |
| | | GCCTTGATCGTTGGGAACCGGAGCTGAATGAAGCCATACCAAACG |

-continued

| SEQ ID NO | NAME | SEQUENCE |
|---|---|---|
| | | ACGAGCGTGACACCACGATGCCTGTAGCAATGGCAACAACGTTGC GCAAACTATTAACTGGCGAACTACTTACTCTAGCTTCCCGGCAACA ATTAATAGACTGGATGGAGGCGGATAAAGTTGCAGGACCACTTCT GCGCTCGGCCCTTCCGGCTGGCTGGTTTATTGCTGATAAATCTGGA GCCGGTGAGCGTGGGTCTCGCGGTATCATTGCAGCACTGGGGCCA GATGGTAAGCCCTCCCGTATCGTAGTTATCTACACGACGGGGAGT CAGGCAACTATGGATGAACGAAATAGACAGATCGCTGAGATAGGT GCCTCACTGATTAAGCATTGGTAACTGTCAGACCAAGTTTACTCAT ATATACTTTAGATTGATTTAAAACTTCATTTTTAATTTAAAAGGAT CTAGGTGAAGATCCTTTTTGATAATCTCATGACCAAAATCCCTTAA CGTGAGTTTTCGTTCCACTGAGCGTCAGACCCCGTAGAAAAGATC AAAGGATCTTCTTGAGATCCTTTTTTTCTGCGCGTAATCTGCTGCTT GCAAACAAAAAAACCACCGCTACCAGCGGTGGTTTGTTTGCCGGA TCAAGAGCTACCAACTCTTTTTCCGAAGGTAACTGGCTTCAGCAGA GCGCAGATACCAAATACTGTCCTTCTAGTGTAGCCGTAGTTAGGCC ACCACTTCAAGAACTCTGTAGCACCGCCTACATACCTCGCTCTGCT AATCCTGTTACCAGTGGCTGCTGCCAGTGGCGATAAGTCGTGTCTT ACCGGGTTGGACTCAAGACGATAGTTACCGGATAAGGCGCAGCGG TCGGGCTGAACGGGGGGTTCGTGCACACAGCCCAGCTTGGAGCGA ACGACCTACACCGAACTGAGATACCTACAGCGTGAGCTATGAGAA AGCGCCACGCTTCCCGAAGGGAGAAAGGCGGACAGGTATCCGGT AAGCGGCAGGGTCGGAACAGGAGAGCGCACGAGGGAGCTTCCAG GGGGAAACGCCTGGTATCTTTATAGTCCTGTCGGGTTTCGCCACCT CTGACTTGAGCGTCGATTTTTGTGATGCTCGTCAGGGGGGCGGAG CCTATGGAAAAACGCCAGCAACGCGGCCTTTTTACGGTTCCTGGC CTTTTGCTGGCCTTTTGCTCACATGTTCTTTCCTGCGTTATCCCCTG ATTCTGTGGATAACCGTATTACCGCCTTTGAGTGAGCTGATACCGC TCGCCGCAGCCGAACGACCGAGCGCAGCGAGTCAGTGAGCGAGG AAGCGGAAGAGCGCCCAATACGCAAACCGCCTCTCCCCGCGCGTT GGCCGATTCATTAATG |
| 29 | HBG1 Round 1 & 2: V3E5 HBG1(200-600). d13>HBB(T87Q). 3'enhCore;MND> GFP::T2A:: Ex2 *200-600 bp HA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACGTAGCCATGCT CTAGCGGCCTCGGCCTCTGCATAAATAAAAAAAATTAGTCAGCCA TGAGCTTGGACGCGTAGATCTTGAAACAGTCATGATTTATTTCAAA TAGGTACGGATAAGTAGATATTGAGGTAAGCATTAGGTCTTATAT TATGTAACACTAATCTATTACTGCGCTGAAACTGTGGCTTTATAGA AATTGTTTTCACTGCACTATTGAGAAATTAAGAGATAATGGCAAA AGTCACAAAGAGTATATTCAAAAAGAAGTATAGCACTTTTTCCTT AGAAACCACTGCTAACTGAAAGAGACTAAGATTTGTCCCGTCAAA AATCCTGGACCTATGCCTAAAACACATTTCACAATCCCTGAACTTT TCAAAAATTGGTACATGCTTTAGCTTTAAACTACAGGCCTCACTGG AGCTAGAGACAAGAAGGTAAAAAACGGCTGACAAAAGAAGTCCT GGTATCCTCTATGATGGGAGAAGGAAACTAGCTAAAGGGAAGAAT AAATTAGAGAAAAACTGGAATGACTGAATCGGAACAAGGCAAAG GCTATAAAAAAAATTAGCAGTATCCTCTTGGGGGCCCCTTCCCCAC ACTATCTCAATGCAAATATCTGTCTGAAACGGTCCCTGGCTAAACT CCACCCATGGGTTGGCCAGCCTTGCCTTGACAAGGCAAACTTGAC CAATAGTCTTAGAGTATCCAGTGAGGCCAGGGGCCGGCGGCTGGC TAGGGATGAAGAATAAAAGGAAGCACCCTTCAGCAGTTCCACACA CTCGCTTCTGGAACGTCTGAGGTTATCAATAAGCTCCTAGTCCAGA CGCCATGGTGCACCTGACTCCTGAGGAGAAGTCTGCCGTTACTGC CCTGTGGGGCAAGGTGAACGTGGATGAAGTTGGTGGTGAGGCCCT GGGCAGGTTGGTATCAAGGTTACAAGACAGGTTTAAGGAGACCAA TAGAAACTGGGCATGTGGAGACAGAGAAGACTCTTGGGTTTCTGA TAGGCACTGACTCTCTCTGCCTATTGGTCTATTTTCCCACCCTTAGG CTGCTGGTGGTCTACCCTTGGACCCAGAGGTTCTTTGAGTCCTTTG GGGATCTGTCCACTCCTGATGCTGTTATGGGCAACCCTAAGGTGA AGGCTCATGGCAAGAAAGTGCTCGGTGCCTTTAGTGATGGCCTGG CTCACCTGGACAACCTCAAGGGCACCTTTGCCCAGCTGAGTGAGC TGCACTGTGACAAGCTGCACGTGGATCCTGAGAACTTCAGGGTGA GTCTATGGGACCCTTGATGTTTTCTTTCCCCTTCTTTTCTATGGTTA AGTTCATGTCATAGGAAGGGGAGAAGTAACAGGGTACACATATTG ACCAAATCAGGGTAATTTTGCATTTGTAATTTTAAAAAATGCTTTC TTCTTTTAATATACTTTTTTGTTTATCTTATTTCTAATACTTTCCCTA ATCTCTTTCTTTCAGGGCAATAATGATACAATGTATCATGCCTCTT TGCACCATTCTAAAGAATAACAGTGATAATTTCTGGGTTAAGGCA ATAGCAATATTTCTGCATATAAATATTTCTGCATATAAATTGTAAC TGATGTAAGAGGTTTCATATTGCTAATAGCAGCTACAATCCAGCTA CCATTCTGCTTTTATTTTATGGTTGGGATAAGGCTGGATTATTCTG AGTCCAAGCTAGGCCCTTTTGCTAATCATGTTCATACCTCTTATCTT CCTCCCACAGCTCCTGGGCAACGTGCTGGTCTGTGTGCTGGCCCAT CACTTTGGCAAAGAATTCACCCCACCAGTGCAGGCTGCCTATCAG |

-continued

| SEQ ID NO | NAME | SEQUENCE |
|---|---|---|
| | | AAAGTGGTGGCTGGTGTGGCTAATGCCCTGGCCCACAAGTATCAC<br>TAAGCTCGCTTTCTTGCTGTCCAATTTCTATTAAAGGTTCCTTTGTT<br>CCCTAAGTCCAACTACTAAACTGGGGGATATTATGAAGGGCCTTG<br>AGCATCTGGATTCTGCCTAATAAAAAACATTTATTTTCATTGCTGC<br>AGTGCTAGTCTCCCGGAACTATCACTCTTTCACAGTCTGCTTTGGA<br>AGGACTGGGCTTAGTATGAAAAGTTAGGACTGAGAAGAATTTGAA<br>AGGGGGCTTTTTGTAGCTTGATATTCACTACTGTCTTATTACCCTAT<br>CATAGGCCCACCCCAAATGGAAGTCCCATTCTTCCTCAGGATGTTT<br>AAGATTAGCATTCAGGAAGAGATCAGAGGTCTGCTGGCTCCCTTA<br>TCATGTCCCTTATGGTGCTTCTGGCTCTGCACCGCGGGAACAGAGA<br>AACAGGAGAATATGGGCCAAACAGGATATCTGTGGTAAGCAGTTC<br>CTGCCCCGGCTCAGGGCCAAGAACAGTTGGAACAGCAGAATATGG<br>GCCAAACAGGATATCTGTGGTAAGCAGTTCCTGCCCCGGCTCAGG<br>GCCAAGAACAGATGGTCCCCAGATGCGGTCCCGCCCTCAGCAGTT<br>TCTAGAGAACCATCAGATGTTTCCAGGGTGCCCCAAGGACCTGAA<br>ATGACCCTGTGCCTTATTTGAACTAACCAATCAGTTCGCTTCTCGC<br>TTCTGTTCGCGCGCTTCTGCTCCCCGAGCTCTATATAAGCAGAGCT<br>CGTTTAGTGAACCGTCAGATCGCGGCCGCGCCGCCACCATGGTGA<br>GCAAGGGCGAGGAGCTGTTCACCGGGGTGGTGCCCATCCTGGTCG<br>AGCTGGACGGCGACGTAAACGGCCACAAGTTCAGCGTGTCCGGCG<br>AGGGCGAGGGCGATGCCACCTACGGCAAGCTGACCCTGAAGTTCA<br>TCTGCACCACCGGCAAGCTGCCCGTGCCCTGGCCCACCCTCGTGAC<br>CACCCTGACCTACGGCGTGCAGTGCTTCAGCCGCTACCCCGACCA<br>CATGAAGCAGCACGACTTCTTCAAGTCCGCCATGCCCGAAGGCTA<br>CGTCCAGGAGCGCACCATCTTCTTCAAGGACGACGGCAACTACAA<br>GACCCGCGCCGAGGTGAAGTTCGAGGGCGACACCCTGGTGAACCG<br>CATCGAGCTGAAGGGCATCGACTTCAAGGAGGACGGCAACATCCT<br>GGGGCACAAGCTGGAGTACAACTACAACAGCCACAACGTCTATAT<br>CATGGCCGACAAGCAGAAGAACGGCATCAAGGTGAACTTCAAGA<br>TCCGCCACAACATCGAGGACGGCAGCGTGCAGCTCGCCGACCACT<br>ACCAGCAGAACACCCCCATCGGCGACGGCCCCGTGCTGCTGCCCG<br>ACAACCACTACCTGAGCACCCAGTCCGCCCTGAGCAAAGACCCCA<br>ACGAGAAGCGCGATCACATGGTCCTGCTGGAGTTCGTGACCGCCG<br>CCGGGATCACTCTCGGCATGGACGAGCTGTACAAGGAGGGCAGAG<br>GAAGTCTTCTAACATGCGGTGACGTGGAGGAGAATCCGGGCCCCC<br>CTGCAGGAACTTCAAGGTGAGTCCAGGAGATGTTTCAGCCCTGTT<br>GCCTTTAGTCTCGAGGCAACTTAGACAACGGAGTATTGATCTGAG<br>CACAGCAGGGTGTGAGCTGTTTGAAGATACTGGGGTTGGGGGTGA<br>AGAAACTGCAGAGGACTAACTGGGCTGAGACCCAGTGGTAATGTT<br>TTAGGGCCTAAGGAGTGCCTCTAAAAATCTAGATGGACAATTTTG<br>ACTTTGAGAAAAGAGAGGTGGAAATGAGGAAAATGACTTTTCTTT<br>ATTAGATTCCAGTAGAAAGAACTTTCATCTTTCCCTCATTTTTGTTG<br>TTTTAAAACATCTATCTGGAGGCAGGACAAGTATGGTCGTTAAAA<br>AGATGCAGGCAGAAGGCATATATTGGCTCAGTCAAAGTGGGGAAC<br>TTTGGTGGCCAAACATACATTGCTAAGGCTATTCCTATATCAGCTG<br>GACACATATAAAATGCTGCTAATGCTTCATTACAAACTTATATCCT<br>TTAATTCCAGATGGGGGCAAAGTATGTCCAGGGGTGAGGAACAAT<br>TGAAACATTTGGGCTGGAGTAGATTTTGAAAGTCAGCTCTGTGTGT<br>GTGTGTGTGTGTGCGCGCGCGCGTGTCGACGTAGATAAGTAGCAT<br>GGCGGGTTAATCATTAACTACAAGGAACCCCTAGTGATGGAGTTG<br>GCCACTCCCTCTCTGCGCGCTCGCTCGCTCACTGAGGCCGGGCGAC<br>CAAAGGTCGCCCGACGCCCGGGCTTTGCCCGGGCGGCCTCAGTGA<br>GCGAGCGAGCGCGCCAGCTGGCGTAATAGCGAAGAGGCCCGCAC<br>CGATCGCCCTTCCCAACAGTTGCGCAGCCTGAATGGCGAATGGCG<br>ATTCCGTTGCAATGGCTGGCGGTAATATTGTTCTGGATATTACCAG<br>CAAGGCCGATAGTTTGAGTTCTTCTACTCAGGCAAGTGATGTTATT<br>ACTAATCAAAGAAGTATTGCGACAACGGTTAATTTGCGTGATGGA<br>CAGACTCTTTTACTCGGTGGCCTCACTGATTATAAAAACACTTCTC<br>AGGATTCTGGCGTACCGTTCCTGTCTAAAATCCCTTTAATCGGCCT<br>CCTGTTTAGCTCCCGCTCTGATTCTAACGAGGAAAGCACGTTATAC<br>GTGCTCGTCAAAGCAACCATAGTACGCGCCCTGTAGCGGCGCATT<br>AAGCGCGGCGGGTGTGGTGGTTACGCGCAGCGTGACCGCTACACT<br>TGCCAGCGCCCTAGCGCCCGCTCCTTTCGCTTTCTTCCCTTCCTTTC<br>TCGCCACGTTCGCCGGCTTTCCCCGTCAAGCTCTAAATCGGGGGCT<br>CCCTTTAGGGTTCCGATTTAGTGCTTTACGGCACCTCGACCCCAAA<br>AAACTTGATTAGGGTGATGGTTCACGTAGTGGGCCATCGCCCTGA<br>TAGACGGTTTTTCGCCCTTTGACGTTGGAGTCCACGTTCTTTAATA<br>GTGGACTCTTGTTCCAAACTGGAACAACACTCAACCCTATCTCGGT<br>CTATTCTTTTGATTTATAAGGGATTTTGCCGATTTCGGCCTATTGGT<br>TAAAAAATGAGCTGATTTAACAAAAATTTAACGCGAATTTTAACA<br>AAATATTAACGTTTACAATTTAAATATTTGCTTATACAATCTTCCT<br>GTTTTTGGGGCTTTTCTGATTATCAACCGGGGTACATATGATTGAC<br>ATGCTAGTTTTACGATTACCGTTCATCGATTCTCTTGTTTGCTCCAG<br>ACTCTCAGGCAATGACCTGATAGCCTTTGTAGAGACCTCTCAAAA<br>ATAGCTACCCTCTCCGGCATGAATTTATCAGCTAGAACGGTTGAAT |

-continued

| SEQ ID NO | NAME | SEQUENCE |
|---|---|---|
| | | ATCATATTGATGGTGATTTGACTGTCTCCGGCCTTTCTCACCCGTTT GAATCTTTACCTACACATTACTCAGGCATTGCATTTAAAATATATG AGGGTTCTAAAAATTTTTATCCTTGCGTTGAAATAAAGGCTTCTCC CGCAAAAGTATTACAGGGTCATAATGTTTTTGGTACAACCGATTTA GCTTTATGCTCTGAGGCTTTATTGCTTAATTTTGCTAATTCTTTGCC TTGCCTGTATGATTTATTGGATGTTGGAATCGCCTGATGCGGTATT TTCTCCTTACGCATCTGTGCGGTATTTCACACCGCATATGGTGCAC TCTCAGTACAATCTGCTCTGATGCCGCATAGTTAAGCCAGCCCCGA CACCCGCCAACACCCGCTGACGCGCCCTGACGGGCTTGTCTGCTCC CGGCATCCGCTTACAGACAAGCTGTGACCGTCTCCGGGAGCTGCA TGTGTCAGAGGTTTTCACCGTCATCACCGAAACGCGCGAGACGAA AGGGCCTCGTGATACGCCTATTTTTATAGGTTAATGTCATGATAAT AATGGTTTCTTAGACGTCAGGTGGCACTTTTCGGGGAAATGTGCGC GGAACCCCTATTTGTTTATTTTTCTAAATACATTCAAATATGTATCC GCTCATGAGACAATAACCCTGATAAATGCTTCAATAATATTGAAA AAGGAAGAGTATGAGTATTCAACATTTCCGTGTCGCCCTTATTCCC TTTTTTGCGGCATTTTGCCTTCCTGTTTTTGCTCACCCAGAAACGCT GGTGAAAGTAAAAGATGCTGAAGATCAGTTGGGTGCACGAGTGG GTTACATCGAACTGGATCTCAACAGCGGTAAGATCCTTGAGAGTT TTCGCCCCGAAGAACGTTTTCCAATGATGAGCACTTTTAAAGTTCT GCTATGTGGCGCGGTATTATCCCGTATTGACGCCGGGCAAGAGCA ACTCGGTCGCCGCATACACTATTCTCAGAATGACTTGGTTGAGTAC TCACCAGTCACAGAAAAGCATCTTACGGATGGCATGACAGTAAGA GAATTATGCAGTGCTGCCATAACCATGAGTGATAACACTGCGGCC AACTTACTTCTGACAACGATCGGAGGACCGAAGGAGCTAACCGCT TTTTTGCACAACATGGGGGATCATGTAACTCGCCTTGATCGTTGGG AACCGGAGCTGAATGAAGCCATACCAAACGACGAGCGTGACACC ACGATGCCTGTAGCAATGGCAACAACGTTGCGCAAACTATTAACT GGCGAACTACTTACTCTAGCTTCCCGGCAACAATTAATAGACTGG ATGGAGGCGGATAAAGTTGCAGGACCACTTCTGCGCTCGGCCCTT CCGGCTGGCTGGTTTATTGCTGATAAATCTGGAGCCGGTGAGCGT GGGTCTCGCGGTATCATTGCAGCACTGGGGCCAGATGGTAAGCCC TCCCGTATCGTAGTTATCTACACGACGGGGAGTCAGGCAACTATG GATGAACGAAATAGACAGATCGCTGAGATAGGTGCCTCACTGATT AAGCATTGGTAACTGTCAGACCAAGTTTACTCATATATACTTTAGA TTGATTTAAAACTTCATTTTTAATTTAAAAGGATCTAGGTGAAGAT CCTTTTTGATAATCTCATGACCAAAATCCCTTAACGTGAGTTTTCG TTCCACTGAGCGTCAGACCCCGTAGAAAAGATCAAAGGATCTTCT TGAGATCCTTTTTTTCTGCGCGTAATCTGCTGCTTGCAAACAAAAA AACCACCGCTACCAGCGGTGGTTTGTTTGCCGGATCAAGAGCTAC CAACTCTTTTTCCGAAGGTAACTGGCTTCAGCAGAGCGCAGATAC CAAATACTGTCCTTCTAGTGTAGCCGTAGTTAGGCCACCACTTCAA GAACTCTGTAGCACCGCCTACATACCTCGCTCTGCTAATCCTGTTA CCAGTGGCTGCTGCCAGTGGCGATAAGTCGTGTCTTACCGGGTTG GACTCAAGACGATAGTTACCGGATAAGGCGCAGCGGTCGGGCTGA ACGGGGGGTTCGTGCACACAGCCCAGCTTGGAGCGAACGACCTAC ACCGAACTGAGATACCTACAGCGTGAGCTATGAGAAAGCGCCACG CTTCCCGAAGGGAGAAAGGCGGACAGGTATCCGGTAAGCGGCAG GGTCGGAACAGGAGAGCGCACGAGGGAGCTTCCAGGGGGAAACG CCTGGTATCTTTATAGTCCTGTCGGGTTTCGCCACCTCTGACTTGA GCGTCGATTTTTGTGATGCTCGTCAGGGGGGCGGAGCCTATGGAA AAACGCCAGCAACGCGGCCTTTTTACGGTTCCTGGCCTTTTGCTGG CCTTTTGCTCACATGTTCTTTCCTGCGTTATCCCCTGATTCTGTGGA TAACCGTATTACCGCCTTTGAGTGAGCTGATACCGCTCGCCGCAGC CGAACGACCGAGCGCAGCGAGTCAGTGAGCGAGGAAGCGGAAGA GCGCCCAATACGCAAACCGCCTCTCCCCGCGCGTTGGCCGATTCAT TAATG |
| 30 | HBG1 Round 1 & 2: V3E6 HBG1(200-600). d13>HBB(T87Q). 3'enhCore; MND>GFP::T2A:: Ex2 *200-600 bp HA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TTCCTTAGAAACCACTGCTAACTGAAAGAGACTAAGATTTGTCCC GTCAAAAATCCTGGACCTATGCCTAAAACACATTTCACAATCCCTG AACTTTTCAAAAATTGGTACATGCTTTAGCTTTAAACTACAGGCCT CACTGGAGCTAGAGACAAGAAGGTAAAAAACGGCTGACAAAAGA AGTCCTGGTATCCTCTATGATGGGAGAAGGAAACTAGCTAAAGGG AAGAATAAATTAGAGAAAAACTGGAATGACTGAATCGGAACAAG GCAAAGGCTATAAAAAAAATTAGCAGTATCCTCTTGGGGGCCCCT TCCCCACACTATCTCAATGCAAATATCTGTCTGAAACGGTCCCTGG CTAAACTCCACCCATGGGTTGGCCAGCCTTGCCTTGACAAGGCAA ACTTGACCAATAGTCTTAGAGTATCCAGTGAGGCCAGGGGCCGGC GGCTGGCTAGGGATGAAGAATAAAAGGAAGCACCCTTCAGCAGTT CCACACACTCGCTTCTGGAACGTCTGAGGTTATCAATAAGCTCCTA GTCCAGACGCCATGGTGCACCTGACTCCTGAGGAGAAGTCTGCCG |

-continued

| SEQ ID NO | NAME | SEQUENCE |
|---|---|---|
| | | TTACTGCCCTGTGGGGCAAGGTGAACGTGGATGAAGTTGGTGGTG |
| | | AGGCCCTGGGCAGGTTGGTATCAAGGTTACAAGACAGGTTTAAGG |
| | | AGACCAATAGAAACTGGGCATGTGGAGACAGAGAAGACTCTTGG |
| | | GTTTCTGATAGGCACTGACTCTCTCTGCCTATTGGTCTATTTTCCCA |
| | | CCCTTAGGCTGCTGGTGGTCTACCCTTGGACCCAGAGGTTCTTTGA |
| | | GTCCTTTGGGGATCTGTCCACTCCTGATGCTGTTATGGGCAACCCT |
| | | AAGGTGAAGGCTCATGGCAAGAAAGTGCTCGGTGCCTTTAGTGAT |
| | | GGCCTGGCTCACCTGGACAACCTCAAGGGCACCTTTGCCCAGCTG |
| | | AGTGAGCTGCACTGTGACAAGCTGCACGTGGATCCTGAGAACTTC |
| | | AGGGTGAGTCTATGGGACCCTTGATGTTTTCTTTCCCCTTCTTTTCT |
| | | ATGGTTAAGTTCATGTCATAGGAAGGGGAGAAGTAACAGGGTACA |
| | | CATATTGACCAAATCAGGGTAATTTTGCATTTGTAATTTTAAAAAA |
| | | TGCTTTCTTCTTTTAATATACTTTTTTGTTTATCTTATTTCTAATACT |
| | | TTCCCTAATCTCTTTCTTTCAGGGCAATAATGATACAATGTATCAT |
| | | GCCTCTTTGCACCATTCTAAAGAATAACAGTGATAATTTCTGGGTT |
| | | AAGGCAATAGCAATATTTCTGCATATAAATATTTCTGCATATAAAT |
| | | TGTAACTGATGTAAGAGGTTTCATATTGCTAATAGCAGCTACAATC |
| | | CAGCTACCATTCTGCTTTTATTTTATGGTTGGGATAAGGCTGGATT |
| | | ATTCTGAGTCCAAGCTAGGCCCTTTTGCTAATCATGTTCATACCTC |
| | | TTATCTTCCTCCCACAGCTCCTGGGCAACGTGCTGGTCTGTGTGCT |
| | | GGCCCATCACTTTGGCAAAGAATTCACCCCACCAGTGCAGGCTGC |
| | | CTATCAGAAAGTGGTGGCTGGTGTGGCTAATGCCCTGGCCCACAA |
| | | GTATCACTAAGCTCGCTTTCTTGCTGTCCAATTTCTATTAAAGGTTC |
| | | CTTTGTTCCCTAAGTCCAACTACTAAACTGGGGGATATTATGAAGG |
| | | GCCTTGAGCATCTGGATTCTGCCTAATAAAAAACATTTATTTTCAT |
| | | TGCAATGATGTATTTAAATTATTTCTGAATATTTTACTAAAAAGGG |
| | | AATGTGGGAGGTTGCAGTGCTAGTCTCCCGGAACTATCACTCTTTC |
| | | ACAGTCTGCTTTGGAAGGACTGGGCTTAGTATGAAAAGTTAGGAC |
| | | TGAGAAGAATTTGAAAGGGGGCTTTTTGTAGCTTGATATTCACTAC |
| | | TGTCTTATTACCCTATCATAGGCCCACCCCAAATGGAAGTCCCATT |
| | | CTTCCTCAGGATGTTTAAGATTAGCATTCAGGAAGAGATCAGAGG |
| | | TCTGCTGGCTCCCTTATCATGTCCCTTATGGTGCTTCTGGCTCTGCA |
| | | CCGCGGGAACAGAGAAACAGGAGAATATGGGCCAAACAGGATAT |
| | | CTGTGGTAAGCAGTTCCTGCCCCGGCTCAGGGCCAAGAACAGTTG |
| | | GAACAGCAGAATATGGGCCAAACAGGATATCTGTGGTAAGCAGTT |
| | | CCTGCCCCGGCTCAGGGCCAAGAACAGATGGTCCCCAGATGCGGT |
| | | CCCGCCCTCAGCAGTTTCTAGAGAACCATCAGATGTTTCCAGGGTG |
| | | CCCCAAGGACCTGAAATGACCCTGTGCCTTATTTGAACTAACCAAT |
| | | CAGTTCGCTTCTCGCTTCTGTTCGCGCGCTTCTGCTCCCCGAGCTCT |
| | | ATATAAGCAGAGCTCGTTTAGTGAACCGTCAGATCGCGGCCGCGC |
| | | CGCCACCATGGTGAGCAAGGGCGAGGAGCTGTTCACCGGGGTGGT |
| | | GCCCATCCTGGTCGAGCTGGACGGCGACGTAAACGGCCACAAGTT |
| | | CAGCGTGTCCGGCGAGGGCGAGGGCGATGCCACCTACGGCAAGCT |
| | | GACCCTGAAGTTCATCTGCACCACCGGCAAGCTGCCCGTGCCCTG |
| | | GCCCACCCTCGTGACCACCCTGACCTACGGCGTGCAGTGCTTCAGC |
| | | CGCTACCCCGACCACATGAAGCAGCACGACTTCTTCAAGTCCGCC |
| | | ATGCCCGAAGGCTACGTCCAGGAGCGCACCATCTTCTTCAAGGAC |
| | | GACGGCAACTACAAGACCCGCGCCGAGGTGAAGTTCGAGGGCGA |
| | | CACCCTGGTGAACCGCATCGAGCTGAAGGGCATCGACTTCAAGGA |
| | | GGACGGCAACATCCTGGGGCACAAGCTGGAGTACAACTACAACA |
| | | GCCACAACGTCTATATCATGGCCGACAAGCAGAAGAACGGCATCA |
| | | AGGTGAACTTCAAGATCCGCCACAACATCGAGGACGGCAGCGTGC |
| | | AGCTCGCCGACCACTACCAGCAGAACACCCCCATCGGCGACGGCC |
| | | CCGTGCTGCTGCCCGACAACCACTACCTGAGCACCCAGTCCGCCCT |
| | | GAGCAAAGACCCCAACGAGAAGCGCGATCACATGGTCCTGCTGGA |
| | | GTTCGTGACCGCCGCCGGGATCACTCTCGGCATGGACGAGCTGTA |
| | | CAAGGAGGGCAGAGGAAGTCTTCTAACATGCGGTGACGTGGAGG |
| | | AGAATCCGGGCCCCCCTGCAGGAACTTCAAGGTGAGTCCAGGAGA |
| | | TGTTTCAGCCCTGTTGCCTTTAGTCTCGAGGCAACTTAGACAACGG |
| | | AGTATTGATCTGAGCACAGCAGGGTGTGAGCTGTTTGAAGATACT |
| | | GGGGTTGGGGGTGAAGAAACTGCAGAGGACTAACTGGGCTGAGA |
| | | CCCAGTGGTAATGTTTTAGGGCCTAAGGAGTGCCTCTAAAAATCT |
| | | AGATGGACAATTTTGACTTTGAGAAAAGAGAGGTGGAAATGAGG |
| | | AAAATGACTTTTCTTTATTAGATTCCAGTAGAAAGAACTTTCATCT |
| | | TTCCCTCATTTTTGTTGTTTTAAAACATCTATCTGGAGGCAGGACA |
| | | AGTATGGTCGTTAAAAAGATGCAGGCAGAAGGCATATATTGGCTC |
| | | AGTCAAAGTGGGGAACTTTGGTGGGTCGACGTAGATAAGTAGCAT |
| | | GGCGGGTTAATCATTAACTACAAGGAACCCCTAGTGATGGAGTTG |
| | | GCCACTCCCTCTCTGCGCGCTCGCTCGCTCACTGAGGCCGGGCGAC |
| | | CAAAGGTCGCCCGACGCCCGGGCTTTGCCCGGGCGGCCTCAGTGA |
| | | GCGAGCGAGCGCGCCAGCTGGCGTAATAGCGAAGAGGCCCGCAC |
| | | CGATCGCCCTTCCCAACAGTTGCGCAGCCTGAATGGCGAATGGCG |
| | | ATTCCGTTGCAATGGCTGGCGGTAATATTGTTCTGGATATTACCAG |
| | | CAAGGCCGATAGTTTGAGTTCTTCTACTCAGGCAAGTGATGTTATT |
| | | ACTAATCAAAGAAGTATTGCGACAACGGTTAATTTGCGTGATGGA |

-continued

| SEQ ID NO | NAME | SEQUENCE |
|---|---|---|
| | | CAGACTCTTTTACTCGGTGGCCTCACTGATTATAAAAACACTTCTC<br>AGGATTCTGGCGTACCGTTCCTGTCTAAAATCCCTTTAATCGGCCT<br>CCTGTTTAGCTCCCGCTCTGATTCTAACGAGGAAAGCACGTTATAC<br>GTGCTCGTCAAAGCAACCATAGTACGCGCCCTGTAGCGGCGCATT<br>AAGCGCGGCGGGTGTGGTGGTTACGCGCAGCGTGACCGCTACACT<br>TGCCAGCGCCCTAGCGCCCGCTCCTTTCGCTTTCTTCCCTTCCTTTC<br>TCGCCACGTTCGCCGGCTTTCCCCGTCAAGCTCTAAATCGGGGGCT<br>CCCTTTAGGGTTCCGATTTAGTGCTTTACGGCACCTCGACCCCAAA<br>AAACTTGATTAGGGTGATGGTTCACGTAGTGGGCCATCGCCCTGA<br>TAGACGGTTTTTCGCCCTTTGACGTTGGAGTCCACGTTCTTTAATA<br>GTGGACTCTTGTTCCAAACTGGAACAACACTCAACCCTATCTCGGT<br>CTATTCTTTTGATTTATAAGGGATTTTGCCGATTTCGGCCTATTGGT<br>TAAAAAATGAGCTGATTTAACAAAAATTTAACGCGAATTTTAACA<br>AAATATTAACGTTTACAATTTAAATATTTGCTTATACAATCTTCCT<br>GTTTTTGGGGCTTTTCTGATTATCAACCGGGGTACATATGATTGAC<br>ATGCTAGTTTTACGATTACCGTTCATCGATTCTCTTGTTTGCTCCAG<br>ACTCTCAGGCAATGACCTGATAGCCTTTGTAGAGACCTCTCAAAA<br>ATAGCTACCCTCTCCGGCATGAATTTATCAGCTAGAACGGTTGAAT<br>ATCATATTGATGGTGATTTGACTGTCTCCGGCCTTTCTCACCCGTTT<br>GAATCTTTACCTACACATTACTCAGGCATTGCATTTAAAATATATG<br>AGGGTTCTAAAAATTTTTATCCTTGCGTTGAAATAAAGGCTTCTCC<br>CGCAAAAGTATTACAGGGTCATAATGTTTTTGGTACAACCGATTTA<br>GCTTTATGCTCTGAGGCTTTATTGCTTAATTTTGCTAATTCTTTGCC<br>TTGCCTGTATGATTTATTGGATGTTGGAATCGCCTGATGCGGTATT<br>TTCTCCTTACGCATCTGTGCGGTATTTCACACCGCATATGGTGCAC<br>TCTCAGTACAATCTGCTCTGATGCCGCATAGTTAAGCCAGCCCCGA<br>CACCCGCCAACACCCGCTGACGCGCCCTGACGGGCTTGTCTGCTCC<br>CGGCATCCGCTTACAGACAAGCTGTGACCGTCTCCGGGAGCTGCA<br>TGTGTCAGAGGTTTTCACCGTCATCACCGAAACGCGCGAGACGAA<br>AGGGCCTCGTGATACGCCTATTTTTATAGGTTAATGTCATGATAAT<br>AATGGTTTCTTAGACGTCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGTGCACGAGTGG<br>GTTACATCGAACTGGATCTCAACAGCGGTAAGATCCTTGAGAGTT<br>TTCGCCCCGAAGAACGTTTTCCAATGATGAGCACTTTTAAAGTTCT<br>GCTATGTGGCGCGGTATTATCCCGTATTGACGCCGGGCAAGAGCA<br>ACTCGGTCGCCGCATACACTATTCTCAGAATGACTTGGTTGAGTAC<br>TCACCAGTCACAGAAAAGCATCTTACGGATGGCATGACAGTAAGA<br>GAATTATGCAGTGCTGCCATAACCATGAGTGATAACACTGCGGCC<br>AACTTACTTCTGACAACGATCGGAGGACCGAAGGAGCTAACCGCT<br>TTTTTGCACAACATGGGGGATCATGTAACTCGCCTTGATCGTTGGG<br>AACCGGAGCTGAATGAAGCCATACCAAACGACGAGCGTGACACC<br>ACGATGCCTGTAGCAATGGCAACAACGTTGCGCAAACTATTAACT<br>GGCGAACTACTTACTCTAGCTTCCCGGCAACAATTAATAGACTGG<br>ATGGAGGCGGATAAAGTTGCAGGACCACTTCTGCGCTCGGCCCTT<br>CCGGCTGGCTGGTTTATTGCTGATAAATCTGGAGCCGGTGAGCGT<br>GGGTCTCGCGGTATCATTGCAGCACTGGGGCCAGATGGTAAGCCC<br>TCCCGTATCGTAGTTATCTACACGACGGGGAGTCAGGCAACTATG<br>GATGAACGAAATAGACAGATCGCTGAGATAGGTGCCTCACTGATT<br>AAGCATTGGTAACTGTCAGACCAAGTTTACTCATATATACTTTAGA<br>TTGATTTAAAACTTCATTTTTAATTTAAAAGGATCTAGGTGAAGAT<br>CCTTTTTGATAATCTCATGACCAAAATCCCTTAACGTGAGTTTTCG<br>TTCCACTGAGCGTCAGACCCCGTAGAAAAGATCAAAGGATCTTCT<br>TGAGATCCTTTTTTTCTGCGCGTAATCTGCTGCTTGCAAACAAAAA<br>AACCACCGCTACCAGCGGTGGTTTGTTTGCCGGATCAAGAGCTAC<br>CAACTCTTTTTCCGAAGGTAACTGGCTTCAGCAGAGCGCAGATAC<br>CAAATACTGTCCTTCTAGTGTAGCCGTAGTTAGGCCACCACTTCAA<br>GAACTCTGTAGCACCGCCTACATACCTCGCTCTGCTAATCCTGTTA<br>CCAGTGGCTGCTGCCAGTGGCGATAAGTCGTGTCTTACCGGGTTG<br>GACTCAAGACGATAGTTACCGGATAAGGCGCAGCGGTCGGGCTGA<br>ACGGGGGGTTCGTGCACACAGCCCAGCTTGGAGCGAACGACCTAC<br>ACCGAACTGAGATACCTACAGCGTGAGCTATGAGAAAGCGCCACG<br>CTTCCCGAAGGGAGAAAGGCGGACAGGTATCCGGTAAGCGGCAG<br>GGTCGGAACAGGAGAGCGCACGAGGGAGCTTCCAGGGGGAAACG<br>CCTGGTATCTTTATAGTCCTGTCGGGTTTCGCCACCTCTGACTTGA<br>GCGTCGATTTTTGTGATGCTCGTCAGGGGGGCGGAGCCTATGGAA<br>AAACGCCAGCAACGCGGCCTTTTTACGGTTCCTGGCCTTTTGCTGG<br>CCTTTTGCTCACATGTTCTTTCCTGCGTTATCCCCTGATTCTGTGGA<br>TAACCGTATTACCGCCTTTGAGTGAGCTGATACCGCTCGCCGCAGC<br>CGAACGACCGAGCGCAGCGAGTCAGTGAGCGAGGAAGCGGAAGA<br>GCGCCCAATACGCAAACCGCCTCTCCCCGCGCGTTGGCCGATTCAT<br>TAATG |

-continued

| SEQ ID NO | NAME | SEQUENCE |
|---|---|---|
| 31 | HBG1 Round 1 & 2:<br>AMS#1292<br>pAAV<br>HBG1(600).d13min><br>HBB(T87Q).3'<br>enhCore;MND><br>GFP.SV40pA<br>(V3E7) | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTGAAACAGTCATGATTTATTTCAAATAGGTACGGATAAGTAGAT<br>ATTGAGGTAAGCATTAGGTCTTATATTATGTAACACTAATCTATTA<br>CTGCGCTGAAACTGTGGCTTTATAGAAATTGTTTTCACTGCACTAT<br>TGAGAAATTAAGAGATAATGGCAAAAGTCACAAAGAGTATATTCA<br>AAAAGAAGTATAGCACTTTTTCCTTAGAAACCACTGCTAACTGAA<br>AGAGACTAAGATTTGTCCCGTCAAAAATCCTGGACCTATGCCTAA<br>AACACATTTCACAATCCCTGAACTTTTCAAAAATTGGTACATGCTT<br>TAGCTTTAAACTACAGGCCTCACTGGAGCTAGAGACAAGAAGGTA<br>AAAAACGGCTGACAAAAGAAGTCCTGGTATCCTCTATGATGGGAG<br>AAGGAAACTAGCTAAAGGGAAGAATAAATTAGAGAAAAACTGGA<br>ATGACTGAATCGGAACAAGGCAAAGGCTATAAAAAAAATTAGCA<br>GTATCCTCTTGGGGGCCCCTTCCCCACACTATCTCAATGCAAATAT<br>CTGTCTGAAACGGTCCCTGGCTAAACTCCACCCATGGGTTGGCCA<br>GCCTTGCCTTGACAAGGCAAACTTGACCAATAGTCTTAGAGTATCC<br>AGTGAGGCCAGGGGCCGGCGGCTGGCTAGGGATGAAGAATAAAA<br>GGAAGCACCCTTCAGCAGTTCCACACACTCGCTTCTGGAACGTCTG<br>AGGTTATCAATAAGCTCCTAGTCCAGACGCCATGGTGCACCTGAC<br>TCCTGAGGAGAAGTCTGCCGTTACTGCCCTGTGGGGCAAGGTGAA<br>CGTGGATGAAGTTGGTGGTGAGGCCCTGGGCAGGTTGGTATCAAG<br>GTTACAAGACAGGTTTAAGGAGACCAATAGAAACTGGGCATGTGG<br>AGACAGAGAAGACTCTTGGGTTTCTGATAGGCACTGACTCTCTCTG<br>CCTATTGGTCTATTTTCCCACCCTTAGGCTGCTGGTGGTCTACCCTT<br>GGACCCAGAGGTTCTTTGAGTCCTTTGGGGATCTGTCCACTCCTGA<br>TGCTGTTATGGGCAACCCTAAGGTGAAGGCTCATGGCAAGAAAGT<br>GCTCGGTGCCTTTAGTGATGGCCTGGCTCACCTGGACAACCTCAAG<br>GGCACCTTTGCCCAGCTGAGTGAGCTGCACTGTGACAAGCTGCAC<br>GTGGATCCTGAGAACTTCAGGGTGAGTCTATGGGACCCTTGATGTT<br>TTCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGGAACAGAGAAACAGGAGAA<br>TATGGGCCAAACAGGATATCTGTGGTAAGCAGTTCCTGCCCCGGC<br>TCAGGGCCAAGAACAGTTGGAACAGCAGAATATGGGCCAAACAG<br>GATATCTGTGGTAAGCAGTTCCTGCCCCGGCTCAGGGCCAAGAAC<br>AGATGGTCCCCAGATGCGGTCCCGCCCTCAGCAGTTTCTAGAGAA<br>CCATCAGATGTTTCCAGGGTGCCCCAAGGACCTGAAATGACCCTG<br>TGCCTTATTTGAACTAACCAATCAGTTCGCTTCTCGCTTCTGTTCGC<br>GCGCTTCTGCTCCCCGAGCTCTATATAAGCAGAGCTCGTTTAGTGA<br>ACCGTCAGATCGCGGCCGCGCCGCCACCATGGTGAGCAAGGGCGA<br>GGAGCTGTTCACCGGGGTGGTGCCCATCCTGGTCGAGCTGGACGG<br>CGACGTAAACGGCCACAAGTTCAGCGTGTCCGGCGAGGGCGAGG<br>GCGATGCCACCTACGGCAAGCTGACCCTGAAGTTCATCTGCACCA<br>CCGGCAAGCTGCCCGTGCCCTGGCCCACCCTCGTGACCACCCTGA<br>CCTACGGCGTGCAGTGCTTCAGCCGCTACCCCGACCACATGAAGC<br>AGCACGACTTCTTCAAGTCCGCCATGCCCGAAGGCTACGTCCAGG<br>AGCGCACCATCTTCTTCAAGGACGACGGCAACTACAAGACCCGCG<br>CCGAGGTGAAGTTCGAGGGCGACACCCTGGTGAACCGCATCGAGC<br>TGAAGGGCATCGACTTCAAGGAGGACGGCAACATCCTGGGGCACA<br>AGCTGGAGTACAACTACAACAGCCACAACGTCTATATCATGGCCG<br>ACAAGCAGAAGAACGGCATCAAGGTGAACTTCAAGATCCGCCAC<br>AACATCGAGGACGGCAGCGTGCAGCTCGCCGACCACTACCAGCAG |

-continued

| SEQ ID NO | NAME | SEQUENCE |
|---|---|---|
| | | AACACCCCCATCGGCGACGGCCCCGTGCTGCTGCCCGACAACCAC<br>TACCTGAGCACCCAGTCCGCCCTGAGCAAAGACCCCAACGAGAAG<br>CGCGATCACATGGTCCTGCTGGAGTTCGTGACCGCCGCCGGGATC<br>ACTCTCGGCATGGACGAGCTGTACAAGTAAGCTTTATTTGTGAAAT<br>TTGTGATGCTATTGCTTTATTTGTAACCATTATAAGCTGCAATAAA<br>CAAGTTAACAACAACAATTGCATTCATTTTATGTTTCAGGTTCAGG<br>GGGAGATGTGGGAGGTTTTTTAAAGCCCTGCAGGATGGGTCATTT<br>CACAGAGGAGGACAAGGCTACTATCACAAGCCTGTGGGGCAAGG<br>TGAATGTGGAAGATGCTGGAGGAGAAACCCTGGGAAGGTAGGCT<br>CTGGTGACCAGGACAAGGGAGGGAAGGAAGGACCCTGTGCCTGG<br>CAAAAGTCCAGGTCGCTTCTCAGGATTTGTGGCACCTTCTGACTGT<br>CAAACTGTTCTTGTCAATCTCACAGGCTCCTGGTTGTCTACCCATG<br>GACCCAGAGGTTCTTTGACAGCTTTGGCAACCTGTCCTCTGCCTCT<br>GCCATCATGGGCAACCCCAAAGTCAAGGCACATGGCAAGAAGGT<br>GCTGACTTCCTTGGGAGATGCCACAAAGCACCTGGATGATCTCAA<br>GGGCACCTTTGCCCAGCTGAGTGAACTGCACTGTGACAAGCTGCA<br>TGTGGATCCTGAGAACTTCAAGGTGAGTCCAGGAGATGTTTCAGC<br>CCTGTTGCCTTTAGTCTCGAGGCAACTTAGACAACGGAGTATTGAT<br>CTGAGCACAGCAGGGTGTGAGCTGTTTGAAGATACTGGGGTTGGG<br>GGTGAAGAAACTGCAGAGGACTAACTGGGCTGAGACCCAGTGGT<br>AATGTGTCGACGTAGATAAGTAGCATGGCGGGTTAATCATTAACT<br>ACAAGGAACCCCTAGTGATGGAGTTGGCCACTCCCTCTCTGCGCG<br>CTCGCTCGCTCACTGAGGCCGGGCGACCAAAGGTCGCCCGACGCC<br>CGGGCTTTGCCCGGGCGGCCTCAGTGAGCGAGCGAGCGCGCCAGC<br>TGGCGTAATAGCGAAGAGGCCCGCACCGATCGCCCTTCCCAACAG<br>TTGCGCAGCCTGAATGGCGAATGGCGATTCCGTTGCAATGGCTGG<br>CGGTAATATTGTTCTGGATATTACCAGCAAGGCCGATAGTTTGAGT<br>TCTTCTACTCAGGCAAGTGATGTTATTACTAATCAAAGAAGTATTG<br>CGACAACGGTTAATTTGCGTGATGGACAGACTCTTTTACTCGGTGG<br>CCTCACTGATTATAAAAACACTTCTCAGGATTCTGGCGTACCGTTC<br>CTGTCTAAAATCCCTTTAATCGGCCTCCTGTTTAGCTCCCGCTCTG<br>ATTCTAACGAGGAAAGCACGTTATACGTGCTCGTCAAAGCAACCA<br>TAGTACGCGCCCTGTAGCGGCGCATTAAGCGCGGCGGGTGTGGTG<br>GTTACGCGCAGCGTGACCGCTACACTTGCCAGCGCCCTAGCGCCC<br>GCTCCTTTCGCTTTCTTCCCTTCCTTTCTCGCCACGTTCGCCGGCTT<br>TCCCCGTCAAGCTCTAAATCGGGGGCTCCCTTTAGGGTTCCGATTT<br>AGTGCTTTACGGCACCTCGACCCCAAAAAACTTGATTAGGGTGAT<br>GGTTCACGTAGTGGGCCATCGCCCTGATAGACGGTTTTTCGCCCTT<br>TGACGTTGGAGTCCACGTTCTTTAATAGTGGACTCTTGTTCCAAAC<br>TGGAACAACACTCAACCCTATCTCGGTCTATTCTTTTGATTTATAA<br>GGGATTTTGCCGATTTCGGCCTATTGGTTAAAAAATGAGCTGATTT<br>AACAAAAATTTAACGCGAATTTTAACAAAATATTAACGTTTACAA<br>TTTAAATATTTGCTTATACAATCTTCCTGTTTTTGGGGCTTTTCTGA<br>TTATCAACCGGGGTACATATGATTGACATGCTAGTTTTACGATTAC<br>CGTTCATCGATTCTCTTGTTTGCTCCAGACTCTCAGGCAATGACCT<br>GATAGCCTTTGTAGAGACCTCTCAAAAATAGCTACCCTCTCCGGCA<br>TGAATTTATCAGCTAGAACGGTTGAATATCATATTGATGGTGATTT<br>GACTGTCTCCGGCCTTTCTCACCCGTTTGAATCTTTACCTACACATT<br>ACTCAGGCATTGCATTTAAAATATATGAGGGTTCTAAAAATTTTTA<br>TCCTTGCGTTGAAATAAAGGCTTCTCCCGCAAAAGTATTACAGGGT<br>CATAATGTTTTTGGTACAACCGATTTAGCTTTATGCTCTGAGGCTT<br>TATTGCTTAATTTTGCTAATTCTTTGCCTTGCCTGTATGATTTATTG<br>GATGTTGGAATCGCCTGATGCGGTATTTTCTCCTTACGCATCTGTG<br>CGGTATTTCACACCGCATATGGTGCACTCTCAGTACAATCTGCTCT<br>GATGCCGCATAGTTAAGCCAGCCCCGACACCCGCCAACACCCGCT<br>GACGCGCCCTGACGGGCTTGTCTGCTCCCGGCATCCGCTTACAGAC<br>AAGCTGTGACCGTCTCCGGGAGCTGCATGTGTCAGAGGTTTTCACC<br>GTCATCACCGAAACGCGCGAGACGAAAGGGCCTCGTGATACGCCT<br>ATTTTTATAGGTTAATGTCATGATAATAATGGTTTCTTAGACGTCA<br>GGTGGCACTTTTCGGGGAAATGTGCGCGGAACCCCTATTTGTTTAT<br>TTTTCTAAATACATTCAAATATGTATCCGCTCATGAGACAATAACC<br>CTGATAAATGCTTCAATAATATTGAAAAAGGAAGAGTATGAGTAT<br>TCAACATTTCCGTGTCGCCCTTATTCCCTTTTTTGCGGCATTTTGCC<br>TTCCTGTTTTTGCTCACCCAGAAACGCTGGTGAAAGTAAAAGATGC<br>TGAAGATCAGTTGGGTGCACGAGTGGGTTACATCGAACTGGATCT<br>CAACAGCGGTAAGATCCTTGAGAGTTTTCGCCCCGAAGAACGTTT<br>TCCAATGATGAGCACTTTTAAAGTTCTGCTATGTGGCGCGGTATTA<br>TCCCGTATTGACGCCGGGCAAGAGCAACTCGGTCGCCGCATACAC<br>TATTCTCAGAATGACTTGGTTGAGTACTCACCAGTCACAGAAAAG<br>CATCTTACGGATGGCATGACAGTAAGAGAATTATGCAGTGCTGCC<br>ATAACCATGAGTGATAACACTGCGGCCAACTTACTTCTGACAACG<br>ATCGGAGGACCGAAGGAGCTAACCGCTTTTTTGCACAACATGGGG<br>GATCATGTAACTCGCCTTGATCGTTGGGAACCGGAGCTGAATGAA<br>GCCATACCAAACGACGAGCGTGACACCACGATGCCTGTAGCAATG<br>GCAACAACGTTGCGCAAACTATTAACTGGCGAACTACTTACTCTA |

-continued

| SEQ ID NO | NAME | SEQUENCE |
|---|---|---|
| | | GCTTCCCGGCAACAATTAATAGACTGGATGGAGGCGGATAAAGTT GCAGGACCACTTCTGCGCTCGGCCCTTCCGGCTGGCTGGTTTATTG CTGATAAATCTGGAGCCGGTGAGCGTGGGTCTCGCGGTATCATTG CAGCACTGGGGCCAGATGGTAAGCCCTCCCGTATCGTAGTTATCT ACACGACGGGGAGTCAGGCAACTATGGATGAACGAAATAGACAG ATCGCTGAGATAGGTGCCTCACTGATTAAGCATTGGTAACTGTCA GACCAAGTTTACTCATATATACTTTAGATTGATTTAAAACTTCATT TTTAATTTAAAAGGATCTAGGTGAAGATCCTTTTTGATAATCTCAT GACCAAAATCCCTTAACGTGAGTTTTCGTTCCACTGAGCGTCAGAC CCCGTAGAAAAGATCAAAGGATCTTCTTGAGATCCTTTTTTTCTGC GCGTAATCTGCTGCTTGCAAACAAAAAAACCACCGCTACCAGCGG TGGTTTGTTTGCCGGATCAAGAGCTACCAACTCTTTTTCCGAAGGT AACTGGCTTCAGCAGAGCGCAGATACCAAATACTGTCCTTCTAGT GTAGCCGTAGTTAGGCCACCACTTCAAGAACTCTGTAGCACCGCC TACATACCTCGCTCTGCTAATCCTGTTACCAGTGGCTGCTGCCAGT GGCGATAAGTCGTGTCTTACCGGGTTGGACTCAAGACGATAGTTA CCGGATAAGGCGCAGCGGTCGGGCTGAACGGGGGGTTCGTGCACA CAGCCCAGCTTGGAGCGAACGACCTACACCGAACTGAGATACCTA CAGCGTGAGCTATGAGAAAGCGCCACGCTTCCCGAAGGGAGAAA GGCGGACAGGTATCCGGTAAGCGGCAGGGTCGGAACAGGAGAGC GCACGAGGGAGCTTCCAGGGGGAAACGCCTGGTATCTTTATAGTC CTGTCGGGTTTCGCCACCTCTGACTTGAGCGTCGATTTTTGTGATG CTCGTCAGGGGGGCGGAGCCTATGGAAAAACGCCAGCAACGCGG CCTTTTTACGGTTCCTGGCCTTTTGCTGGCCTTTTGCTCACATGTTC TTTCCTGCGTTATCCCCTGATTCTGTGGATAACCGTATTACCGCCTT TGAGTGAGCTGATACCGCTCGCCGCAGCCGAACGACCGAGCGCAG CGAGTCAGTGAGCGAGGAAGCGGAAGAGCGCCCAATACGCAAAC CGCCTCTCCCCGCGCGTTGGCCGATTCATTAATG |
| 32 | HBG1 Round 1 & 2: V4E4 pAAV HBG1d-247 (200-600). HBBp>HBB (T87Q).3'enh; MND>MGMT::T2A:: Ex2 *200-600 bp HA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACGTAGCCATGCT CTAGCGGCCTCGGCCTCTGCATAAATAAAAAAAATTAGTCAGCCA TGAGCTTGGACGCGTAGATCTCATCTTTACTGAGCATAGAAGAGC TACGCCAAAACCCTGGGTCATCAGCCAGCACACACACACTTATCCAG TGGTAAATACACATCATCTGGTGTATACATACATACCTGAATATGG AATCAAATATTTTTCTAAGATGAAACAGTCATGATTTATTTCAAAT AGGTACGGATAAGTAGATATTGAGGTAAGCATTAGGTCTTATATT ATGTAACACTAATCTATTACTGCGCTGAAACTGTGGCTTTATAGAA ATTGTTTTCACTGCACTATTGAGAAATTAAGAGATAATGGCAAAA GTCACAAAGAGTATATTCAAAAAGAAGTATAGCACTTTTTCCTTA GAAACCACTGCTAACTGAAAGAGACTAAGATTTGTCCCGTCAAAA ATCCTGGACCTATGCCTAAAACACATTTCACAATCCCTGAACTTTT CAAAAATTGGTACATGCTTTAGCTTTAAACTACAGGCCTCACTGGA GCTAGAGACAAGAAGGTAAAAAACGGCTGACAAAAGAAGTCCTG GTATCCTCTATGATGGGAGAAGGAAACTAGCTAAAGGGAAGAATA AATTAGAGAAAAACTGGAATGACTGAATCGGAAGTAAATACACTT GCAAAGGAGGATGTTTTTAGTAGCAATTTGTACTGATGGTATGGG GCCAAGAGATATATCTTAGAGGGAGGGCTGAGGGTTTGAAGTCCA ACTCCTAAGCCAGTGCCAGAAGAGCCAAGGACAGGTACGGCTGTC ATCACTTAGACCTCACCCTGTGGAGCCACACCCTAGGGTTGGCCA ATCTACTCCCAGGAGCAGGGAGGGCAGGAGCCAGGGCTGGGCAT AAAAGTCAGGGCAGAGCCATCTATTGCTTATGGTGCACCTGACTC CTGAGGAGAAGTCTGCCGTTACTGCCCTGTGGGGCAAGGTGAACG TGGATGAAGTTGGTGGTGAGGCCCTGGGCAGGCTGCTGGTGGTCT ACCCTTGGACCCAGAGGTTCTTTGAGTCCTTTGGGGATCTGTCCAC TCCTGATGCTGTTATGGGCAACCCTAAGGTGAAGGCTCATGGCAA GAAAGTGCTCGGTGCCTTTAGTGATGGCCTGGCTCACCTGGACAA CCTCAAGGGCACCTTTGCCCAGCTGAGTGAGCTGCACTGTGACAA GCTGCACGTGGATCCTGAGAACTTCAGGGTGAGTCTATGGGACCC TTGATGTTTTCTTTCCCCTTCTTTTCTATGGTTAAGTTCATGTCATA GGAAGGGGAGAAGTAACAGGGTACACATATTGACCAAATCAGGG TAATTTTGCATTTGTAATTTTAAAAAATGCTTTCTTCTTTTAATATA CTTTTTTGTTTATCTTATTTCTAATACTTTCCCTAATCTCTTTCTTTC AGGGCAATAATGATACAATGTATCATGCCTCTTTGCACCATTCTAA AGAATAACAGTGATAATTTCTGGGTTAAGGCAATAGCAATATTTC TGCATATAAATATTTCTGCATATAAATTGTAACTGATGTAAGAGGT TTCATATTGCTAATAGCAGCTACAATCCAGCTACCATTCTGCTTTT ATTTTATGGTTGGGATAAGGCTGGATTATTCTGAGTCCAAGCTAGG CCCTTTTGCTAATCATGTTCATACCTCTTATCTTCCTCCCACAGCTC CTGGGCAACGTGCTGGTCTGTGTGCTGGCCCATCACTTTGGCAAAG AATTCACCCCACCAGTGCAGGCTGCCTATCAGAAAGTGGTGGCTG GTGTGGCTAATGCCCTGGCCCACAAGTATCACTAAGCTCGCTTTCT TGCTGTCCAATTTCTATTAAAGGTTCCTTTGTTCCCTAAGTCCAACT |

-continued

| SEQ ID NO | NAME | SEQUENCE |
|---|---|---|
| | | ACTAAACTGGGGGATATTATGAAGGGCCTTGAGCATCTGGATTCT<br>GCCTAATAAAAAACATTTATTTTCATTGCAATGATGTATTTAAATT<br>ATTTCTGAATATTTTACTAAAAAGGGAATGTGGGAGGTCAGTGCA<br>TTTAAAACATAAAGAAATGAAGAGCTAGTTCAAACCTTGGGAAAA<br>TACACTATATCTTAAACTCCATGAAAGAAGGTGAGGCTGCAAACA<br>GCTAATGCACATTGGCAACAGCCCCTGATGCCTATGCCTTATTCAT<br>CCCTCAGAAAAGGATTCAAGTAGAGGCTTGATTTGGAGGTTAAAG<br>TTTTGCTATGCTGTATTTTACATTACTTATTGTTTTAGCTGTCCTCA<br>TGAATGTCTTTTCACTACCCATTTGCTTATCCTGCATCTCTCAGCCT<br>TGACTCCACTCAGTTCTCTTGCTTAGAGATACCACCTTTCCCCTGA<br>AGTGTTCCTTCCATGTTTTACGGCGAGATGGTTTCTCCTCGCCTGG<br>CCACTCAGCCTTAGTTGTCTCTGTTGTCTTATAGAGGTCTACTTGA<br>AGAAGGAAAAACAGGGGGCATGGTTTGACTGTCCTGTGAGCCCTT<br>CTTCCCTGCCTCCCCCACTCACAGTGACCCGGAATCTGCAGTGCTA<br>GTCTCCCGGAACTATCACTCTTTCACAGTCTGCTTTGGAAGGACTG<br>GGCTTAGTATGAAAAGTTAGGACTGAGAAGAATTTGAAAGGGGGC<br>TTTTTGTAGCTTGATATTCACTACTGTCTTATTACCCTATCATAGGC<br>CCACCCCAAATGGAAGTCCCATTCTTCCTCAGGATGTTTAAGATTA<br>GCATTCAGGAAGAGATCAGAGGTCTGCTGGCTCCCTTATCATGTCC<br>CTTATGGTGCTTCTGGCTCTGCAGTTATTAGCATAGTGTTACCATC<br>AACCACCTTAACTTCATTTTTCTTATTCAATACCTAGCCGCGGGAA<br>CAGAGAAACAGGAGAATATGGGCCAAACAGGATATCTGTGGTAA<br>GCAGTTCCTGCCCCGGCTCAGGGCCAAGAACAGTTGGAACAGCAG<br>AATATGGGCCAAACAGGATATCTGTGGTAAGCAGTTCCTGCCCCG<br>GCTCAGGGCCAAGAACAGATGGTCCCCAGATGCGGTCCCGCCCTC<br>AGCAGTTTCTAGAGAACCATCAGATGTTTCCAGGGTGCCCCAAGG<br>ACCTGAAATGACCCTGTGCCTTATTTGAACTAACCAATCAGTTCGC<br>TTCTCGCTTCTGTTCGCGCGCTTCTGCTCCCCGAGCTCTATATAAGC<br>AGAGCTCGTTTAGTGAACCGTCAGATCGCGGCCGCGCCGCCACCA<br>TGGACAAGGATTGTGAAATGAAACGCACCACACTGGACAGCCCTT<br>TGGGGAAGCTGGAGCTGTCTGGTTGTGAGCAGGGTCTGCACGAAA<br>TAAAGCTCCTGGGCAAGGGGACGTCTGCAGCTGATGCCGTGGAGG<br>TCCCAGCCCCCGCTGCGGTTCTCGGAGGTCCGGAGCCCCTGATGC<br>AGTGCACAGCCTGGCTGAATGCCTATTTCCACCAGCCCGAGGCTA<br>TCGAAGAGTTCCCCGTGCCGGCTCTTCACCATCCCGTTTTCCAGCA<br>AGAGTCGTTCACCAGACAGGTGTTATGGAAGCTGCTGAAGGTTGT<br>GAAATTCGGAGAAGTGATTTCTTACCAGCAATTAGCAGCCCTGGC<br>AGGCAACCCCAAAGCCGCGCGAGCAGTGGGAGGAGCAATGAGAG<br>GCAATCCTGTCAAAATCCTCATCCCGTGCCACAGAGTGGTCTGCA<br>GCAGCGGAGCCGTGGGCAACTACTCCGGAGGACTGGCCGTGAAG<br>GAATGGCTTCTGGCCCATGAAGGCCACCGGTTGGGGAAGCCAGGC<br>TTGGGAGGGAGCTCAGGTCTGGCAGGGGCCTGGCTCAAGGGAGCG<br>GGAGCTACCTCGGGCTCCCCGCCTGCTGGCCGAAACGAGGGCAGA<br>GGAAGTCTTCTAACATGCGGTGACGTGGAGGAGAATCCGGGCCCC<br>CCTGCAGGAACTTCAAGGTGAGTCCAGGAGATGTTTCAGCCCTGT<br>TGCCTTTAGTCTCGAGGCAACTTAGACAACGGAGTATTGATCTGA<br>GCACAGCAGGGTGTGAGCTGTTTGAAGATACTGGGGTTGGGGGTG<br>AAGAAACTGCAGAGGACTAACTGGGCTGAGACCCAGTGGTAATGT<br>TTTAGGGCCTAAGGAGTGCCTCTAAAAATCTAGATGGACAATTTT<br>GACTTTGAGAAAAGAGAGGTGGAAATGAGGAAAATGACTTTTCTT<br>TATTAGATTCCAGTAGAAAGAACTTTCATCTTTCCCTCATTTTTGTT<br>GTTTTAAAACATCTATCTGGAGGCAGGACAAGTATGGTCGTTAAA<br>AAGATGCAGGCAGAAGGCATATATTGGCTCAGTCAAAGTGGGGA<br>ACTTTGGTGGCCAAACATACATTGCTAAGGCTATTCCTATATCAGC<br>TGGACACATATAAAATGCTGCTAATGCTTCATTACAAACTTATATC<br>CTTTAATTCCAGATGGGGGCAAAGTATGTCCAGGGGTGAGGAACA<br>ATTGAAACATTTGGGCTGGAGTAGATTTTGAAAGTCAGCTCTGTGT<br>GTGTGTGTGTGTGTGCGCGCGCGCGTGTCGACGTAGATAAGTAGC<br>ATGGCGGGTTAATCATTAACTACAAGGAACCCCTAGTGATGGAGT<br>TGGCCACTCCCTCTCTGCGCGCTCGCTCGCTCACTGAGGCCGGGCG<br>ACCAAAGGTCGCCCGACGCCCGGGCTTTGCCCGGGCGGCCTCAGT<br>GAGCGAGCGAGCGCGCCAGCTGGCGTAATAGCGAAGAGGCCCGC<br>ACCGATCGCCCTTCCCAACAGTTGCGCAGCCTGAATGGCGAATGG<br>CGATTCCGTTGCAATGGCTGGCGGTAATATTGTTCTGGATATTACC<br>AGCAAGGCCGATAGTTTGAGTTCTTCTACTCAGGCAAGTGATGTTA<br>TTACTAATCAAAGAAGTATTGCGACAACGGTTAATTTGCGTGATG<br>GACAGACTCTTTTACTCGGTGGCCTCACTGATTATAAAAACACTTC<br>TCAGGATTCTGGCGTACCGTTCCTGTCTAAAATCCCTTTAATCGGC<br>CTCCTGTTTAGCTCCCGCTCTGATTCTAACGAGGAAAGCACGTTAT<br>ACGTGCTCGTCAAAGCAACCATAGTACGCGCCCTGTAGCGGCGCA<br>TTAAGCGCGGCGGGTGTGGTGGTTACGCGCAGCGTGACCGCTACA<br>CTTGCCAGCGCCCTAGCGCCCGCTCCTTTCGCTTTCTTCCCTTCCTT<br>TCTCGCCACGTTCGCCGGCTTTCCCCGTCAAGCTCTAAATCGGGGG<br>CTCCCTTTAGGGTTCCGATTTAGTGCTTTACGGCACCTCGACCCCA<br>AAAAACTTGATTAGGGTGATGGTTCACGTAGTGGGCCATCGCCCT |

-continued

| SEQ ID NO | NAME | SEQUENCE |
|---|---|---|
| | | GATAGACGGTTTTTCGCCCTTTGACGTTGGAGTCCACGTTCTTTAA<br>TAGTGGACTCTTGTTCCAAACTGGAACAACACTCAACCCTATCTCG<br>GTCTATTCTTTTGATTTATAAGGGATTTTGCCGATTTCGGCCTATTG<br>GTTAAAAAATGAGCTGATTTAACAAAAATTTAACGCGAATTTTAA<br>CAAAATATTAACGTTTACAATTTAAATATTTGCTTATACAATCTTC<br>CTGTTTTTGGGGCTTTTCTGATTATCAACCGGGGTACATATGATTG<br>ACATGCTAGTTTTACGATTACCGTTCATCGATTCTCTTGTTTGCTCC<br>AGACTCTCAGGCAATGACCTGATAGCCTTTGTAGAGACCTCTCAA<br>AAATAGCTACCCTCTCCGGCATGAATTTATCAGCTAGAACGGTTG<br>AATATCATATTGATGGTGATTTGACTGTCTCCGGCCTTTCTCACCC<br>GTTTGAATCTTTACCTACACATTACTCAGGCATTGCATTTAAAATA<br>TATGAGGGTTCTAAAAATTTTTATCCTTGCGTTGAAATAAAGGCTT<br>CTCCCGCAAAAGTATTACAGGGTCATAATGTTTTTGGTACAACCGA<br>TTTAGCTTTATGCTCTGAGGCTTTATTGCTTAATTTTGCTAATTCTT<br>TGCCTTGCCTGTATGATTTATTGGATGTTGGAATCGCCTGATGCGG<br>TATTTTCTCCTTACGCATCTGTGCGGTATTTCACACCGCATATGGT<br>GCACTCTCAGTACAATCTGCTCTGATGCCGCATAGTTAAGCCAGCC<br>CCGACACCCGCCAACACCCGCTGACGCGCCCTGACGGGCTTGTCT<br>GCTCCCGGCATCCGCTTACAGACAAGCTGTGACCGTCTCCGGGAG<br>CTGCATGTGTCAGAGGTTTTCACCGTCATCACCGAAACGCGCGAG<br>ACGAAAGGGCCTCGTGATACGCCTATTTTTATAGGTTAATGTCATG<br>ATAATAATGGTTTCTTAGACGTCAGGTGGCACTTTTCGGGGAAATG<br>TGCGCGGAACCCCTATTTGTTTATTTTTCTAAATACATTCAAATAT<br>GTATCCGCTCATGAGACAATAACCCTGATAAATGCTTCAATAATAT<br>TGAAAAAGGAAGAGTATGAGTATTCAACATTTCCGTGTCGCCCTT<br>ATTCCCTTTTTTGCGGCATTTTGCCTTCCTGTTTTTGCTCACCCAGA<br>AACGCTGGTGAAAGTAAAAGATGCTGAAGATCAGTTGGGTGCACG<br>AGTGGGTTACATCGAACTGGATCTCAACAGCGGTAAGATCCTTGA<br>GAGTTTTCGCCCCGAAGAACGTTTTCCAATGATGAGCACTTTTAAA<br>GTTCTGCTATGTGGCGCGGTATTATCCCGTATTGACGCCGGGCAAG<br>AGCAACTCGGTCGCCGCATACACTATTCTCAGAATGACTTGGTTGA<br>GTACTCACCAGTCACAGAAAAGCATCTTACGGATGGCATGACAGT<br>AAGAGAATTATGCAGTGCTGCCATAACCATGAGTGATAACACTGC<br>GGCCAACTTACTTCTGACAACGATCGGAGGACCGAAGGAGCTAAC<br>CGCTTTTTTGCACAACATGGGGGATCATGTAACTCGCCTTGATCGT<br>TGGGAACCGGAGCTGAATGAAGCCATACCAAACGACGAGCGTGA<br>CACCACGATGCCTGTAGCAATGGCAACAACGTTGCGCAAACTATT<br>AACTGGCGAACTACTTACTCTAGCTTCCCGGCAACAATTAATAGA<br>CTGGATGGAGGCGGATAAAGTTGCAGGACCACTTCTGCGCTCGGC<br>CCTTCCGGCTGGCTGGTTTATTGCTGATAAATCTGGAGCCGGTGAG<br>CGTGGGTCTCGCGGTATCATTGCAGCACTGGGGCCAGATGGTAAG<br>CCCTCCCGTATCGTAGTTATCTACACGACGGGGAGTCAGGCAACT<br>ATGGATGAACGAAATAGACAGATCGCTGAGATAGGTGCCTCACTG<br>ATTAAGCATTGGTAACTGTCAGACCAAGTTTACTCATATATACTTT<br>AGATTGATTTAAAACTTCATTTTTAATTTAAAAGGATCTAGGTGAA<br>GATCCTTTTTGATAATCTCATGACCAAAATCCCTTAACGTGAGTTT<br>TCGTTCCACTGAGCGTCAGACCCCGTAGAAAAGATCAAAGGATCT<br>TCTTGAGATCCTTTTTTTCTGCGCGTAATCTGCTGCTTGCAAACAA<br>AAAAACCACCGCTACCAGCGGTGGTTTGTTTGCCGGATCAAGAGC<br>TACCAACTCTTTTTCCGAAGGTAACTGGCTTCAGCAGAGCGCAGAT<br>ACCAAATACTGTCCTTCTAGTGTAGCCGTAGTTAGGCCACCACTTC<br>AAGAACTCTGTAGCACCGCCTACATACCTCGCTCTGCTAATCCTGT<br>TACCAGTGGCTGCTGCCAGTGGCGATAAGTCGTGTCTTACCGGGTT<br>GGACTCAAGACGATAGTTACCGGATAAGGCGCAGCGGTCGGGCTG<br>AACGGGGGGTTCGTGCACACAGCCCAGCTTGGAGCGAACGACCTA<br>CACCGAACTGAGATACCTACAGCGTGAGCTATGAGAAAGCGCCAC<br>GCTTCCCGAAGGGAGAAAGGCGGACAGGTATCCGGTAAGCGGCA<br>GGGTCGGAACAGGAGAGCGCACGAGGGAGCTTCCAGGGGGAAAC<br>GCCTGGTATCTTTATAGTCCTGTCGGGTTTCGCCACCTCTGACTTG<br>AGCGTCGATTTTTGTGATGCTCGTCAGGGGGGCGGAGCCTATGGA<br>AAAACGCCAGCAACGCGGCCTTTTTACGGTTCCTGGCCTTTTGCTG<br>GCCTTTTGCTCACATGTTCTTTCCTGCGTTATCCCCTGATTCTGTGG<br>ATAACCGTATTACCGCCTTTGAGTGAGCTGATACCGCTCGCCGCAG<br>CCGAACGACCGAGCGCAGCGAGTCAGTGAGCGAGGAAGCGGAAG<br>AGCGCCCAATACGCAAACCGCCTCTCCCCGCGCGTTGGCCGATTC<br>ATTAATG |

-continued

| SEQ ID NO | NAME | SEQUENCE |
|---|---|---|
| 33 | HBG1 Round 1 & 2:<br>AMS#1304<br>pAAV<br>HBG1(400).d-<br>141,-1<br>HBBp>HBB(T87Q).<br>3'enh;MND><br>GFP.SV40pA<br>(V4E5) | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC<br>GCGTAGATCTTTTTTCCTTAGAAACCACTGCTAACTGAAAGAGACT<br>AAGATTTGTCCCGTCAAAAATCCTGGACCTATGCCTAAAACACATT<br>TCACAATCCCTGAACTTTTCAAAAATTGGTACATGCTTTAGCTTTA<br>AACTACAGGCCTCACTGGAGCTAGAGACAAGAAGGTAAAAAACG<br>GCTGACAAAAGAAGTCCTGGTATCCTCTATGATGGGAGAAGGAAA<br>CTAGCTAAAGGGAAGAATAAATTAGAGAAAAACTGGAATGACTG<br>AATCGGAACAAGGCAAAGGCTATAAAAAAAATTAGCAGTATCCTC<br>TTGGGGGCCCCTTCCCCACACTATCTCAATGCAAATATCTGTCTGA<br>AACGGTCCCTGGCTAAACTCCACGTAAATACACTTGCAAAGGAGG<br>ATGTTTTTAGTAGCAATTTGTACTGATGGTATGGGGCCAAGAGATA<br>TATCTTAGAGGGAGGGCTGAGGGTTTGAAGTCCAACTCCTAAGCC<br>AGTGCCAGAAGAGCCAAGGACAGGTACGGCTGTCATCACTTAGAC<br>CTCACCCTGTGGAGCCACACCCTAGGGTTGGCCAATCTACTCCCAG<br>GAGCAGGGAGGGCAGGAGCCAGGGCTGGGCATAAAAGTCAGGGC<br>AGAGCCATCTATTGCTTACATTTGCTTCTGACACAACTGTGTTCAC<br>TAGCAACCTCAAACAGACACCATGGTGCACCTGACTCCTGAGGAG<br>AAGTCTGCCGTTACTGCCCTGTGGGGCAAGGTGAACGTGGATGAA<br>GTTGGTGGTGAGGCCCTGGGCAGGTTGGTATCAAGGTTACAAGAC<br>AGGTTTAAGGAGACCAATAGAAACTGGGCATGTGGAGACAGAGA<br>AGACTCTTGGGTTTCTGATAGGCACTGACTCTCTCTGCCTATTGGT<br>CTATTTTCCCACCCTTAGGCTGCTGGTGGTCTACCCTTGGACCCAG<br>AGGTTCTTTGAGTCCTTTGGGGATCTGTCCACTCCTGATGCTGTTA<br>TGGGCAACCCTAAGGTGAAGGCTCATGGCAAGAAAGTGCTCGGTG<br>CCTTTAGTGATGGCCTGGCTCACCTGGACAACCTCAAGGGCACCTT<br>TGCCCAGCTGAGTGAGCTGCACTGTGACAAGCTGCACGTGGATCC<br>TGAGAACTTCAGGGTGAGTCTATGGGACCCTTGATGTTTTCTTTCC<br>CCTTCTTTTCTATGGTTAAGTTCATGTCATAGGAAGGGGAGAAGTA<br>ACAGGGTACACATATTGACCAAATCAGGGTAATTTTGCATTTGTA<br>ATTTTAAAAAATGCTTTCTTCTTTTAATATACTTTTTTGTTTATCTTA<br>TTTCTAATACTTTCCCTAATCTCTTTCTTTCAGGGCAATAATGATAC<br>AATGTATCATGCCTCTTTGCACCATTCTAAAGAATAACAGTGATAA<br>TTTCTGGGTTAAGGCAATAGCAATATTTCTGCATATAAATATTTCT<br>GCATATAAATTGTAACTGATGTAAGAGGTTTCATATTGCTAATAGC<br>AGCTACAATCCAGCTACCATTCTGCTTTTATTTTATGGTTGGGATA<br>AGGCTGGATTATTCTGAGTCCAAGCTAGGCCCTTTTGCTAATCATG<br>TTCATACCTCTTATCTTCCTCCCACAGCTCCTGGGCAACGTGCTGG<br>TCTGTGTGCTGGCCCATCACTTTGGCAAAGAATTCACCCCACCAGT<br>GCAGGCTGCCTATCAGAAAGTGGTGGCTGGTGTGGCTAATGCCCT<br>GGCCCACAAGTATCACTAAGCTCGCTTTCTTGCTGTCCAATTTCTA<br>TTAAAGGTTCCTTTGTTCCCTAAGTCCAACTACTAAACTGGGGGAT<br>ATTATGAAGGGCCTTGAGCATCTGGATTCTGCCTAATAAAAAACA<br>TTTATTTTCATTGCAATGATGTATTTAAATTATTTCTGAATATTTTA<br>CTAAAAAGGGAATGTGGGAGGTCAGTGCATTTAAAACATAAAGA<br>AATGAAGAGCTAGTTCAAACCTTGGGAAAATACACTATATCTTAA<br>ACTCCATGAAAGAAGGTGAGGCTGCAAACAGCTAATGCACATTGG<br>CAACAGCCCCTGATGCCTATGCCTTATTCATCCCTCAGAAAAGGAT<br>TCAAGTAGAGGCTTGATTTGGAGGTTAAAGTTTTGCTATGCTGTAT<br>TTTACATTACTTATTGTTTTAGCTGTCCTCATGAATGTCTTTTCACT<br>ACCCATTTGCTTATCCTGCATCTCTCAGCCTTGACTCCACTCAGTTC<br>TCTTGCTTAGAGATACCACCTTTCCCCTGAAGTGTTCCTTCCATGTT<br>TTACGGCGAGATGGTTTCTCCTCGCCTGGCCACTCAGCCTTAGTTG<br>TCTCTGTTGTCTTATAGAGGTCTACTTGAAGAAGGAAAAACAGGG<br>GGCATGGTTTGACTGTCCTGTGAGCCCTTCTTCCCTGCCTCCCCCA<br>CTCACAGTGACCCGGAATCTGCAGTGCTAGTCTCCCGGAACTATC<br>ACTCTTTCACAGTCTGCTTTGGAAGGACTGGGCTTAGTATGAAAAG<br>TTAGGACTGAGAAGAATTTGAAAGGGGGCTTTTTGTAGCTTGATA<br>TTCACTACTGTCTTATTACCCTATCATAGGCCCACCCCAAATGGAA<br>GTCCCATTCTTCCTCAGGATGTTTAAGATTAGCATTCAGGAAGAGA<br>TCAGAGGTCTGCTGGCTCCCTTATCATGTCCCTTATGGTGCTTCTG<br>GCTCTGCAGTTATTAGCATAGTGTTACCATCAACCACCTTAACTTC<br>ATTTTTCTTATTCAATACCTAGCCGCGGGAACAGAGAAACAGGAG<br>AATATGGGCCAAACAGGATATCTGTGGTAAGCAGTTCCTGCCCCG<br>GCTCAGGGCCAAGAACAGTTGGAACAGCAGAATATGGGCCAAAC<br>AGGATATCTGTGGTAAGCAGTTCCTGCCCCGGCTCAGGGCCAAGA<br>ACAGATGGTCCCCAGATGCGGTCCCGCCCTCAGCAGTTTCTAGAG<br>AACCATCAGATGTTTCCAGGGTGCCCCAAGGACCTGAAATGACCC<br>TGTGCCTTATTTGAACTAACCAATCAGTTCGCTTCTCGCTTCTGTTC<br>GCGCGCTTCTGCTCCCCGAGCTCTATATAAGCAGAGCTCGTTTAGT<br>GAACCGTCAGATCGCGGCCGCGCCGCCACCATGGTGAGCAAGGGC<br>GAGGAGCTGTTCACCGGGGTGGTGCCCATCCTGGTCGAGCTGGAC<br>GGCGACGTAAACGGCCACAAGTTCAGCGTGTCCGGCGAGGGCGA<br>GGGCGATGCCACCTACGGCAAGCTGACCCTGAAGTTCATCTGCAC |

-continued

| SEQ ID NO | NAME | SEQUENCE |
|---|---|---|
| | | CACCGGCAAGCTGCCCGTGCCCTGGCCCACCCTCGTGACCACCCT<br>GACCTACGGCGTGCAGTGCTTCAGCCGCTACCCCGACCACATGAA<br>GCAGCACGACTTCTTCAAGTCCGCCATGCCCGAAGGCTACGTCCA<br>GGAGCGCACCATCTTCTTCAAGGACGACGGCAACTACAAGACCCG<br>CGCCGAGGTGAAGTTCGAGGGCGACACCCTGGTGAACCGCATCGA<br>GCTGAAGGGCATCGACTTCAAGGAGGACGGCAACATCCTGGGGCA<br>CAAGCTGGAGTACAACTACAACAGCCACAACGTCTATATCATGGC<br>CGACAAGCAGAAGAACGGCATCAAGGTGAACTTCAAGATCCGCC<br>ACAACATCGAGGACGGCAGCGTGCAGCTCGCCGACCACTACCAGC<br>AGAACACCCCCATCGGCGACGGCCCCGTGCTGCTGCCCGACAACC<br>ACTACCTGAGCACCCAGTCCGCCCTGAGCAAAGACCCCAACGAGA<br>AGCGCGATCACATGGTCCTGCTGGAGTTCGTGACCGCCGCCGGGA<br>TCACTCTCGGCATGGACGAGCTGTACAAGTAAGCTTTATTTGTGAA<br>ATTTGTGATGCTATTGCTTTATTTGTAACCATTATAAGCTGCAATA<br>AACAAGTTAACAACAACAATTGCATTCATTTTATGTTTCAGGTTCA<br>GGGGGAGATGTGGGAGGTTTTTTAAAGCCCTGCAGGATGGGTCAT<br>TTCACAGAGGAGGACAAGGCTACTATCACAAGCCTGTGGGGCAAG<br>GTGAATGTGGAAGATGCTGGAGGAGAAACCCTGGGAAGGTAGGC<br>TCTGGTGACCAGGACAAGGGAGGGAAGGAAGGACCCTGTGCCTG<br>GCAAAAGTCCAGGTCGCTTCTCAGGATTTGTGGCACCTTCTGACTG<br>TCAAACTGTTCTTGTCAATCTCACAGGCTCCTGGTTGTCTACCCAT<br>GGACCCAGAGGTTCTTTGACAGCTTTGGCAACCTGTCCTCTGCCTC<br>TGCCATCATGGGCAACCCCAAAGTCAAGGCACATGGCAAGAAGGT<br>GCTGACTTCCTTGGGAGATGCCACAAAGCACCTGGATGATCTCAA<br>GGGCACCTTTGCCCAGCTGAGTGAACTGCAGTCGACAGGAACCCC<br>TAGTGATGGAGTTGGCCACTCCCTCTCTGCGCGCTCGCTCGCTCAC<br>TGAGGCCGGGCGACCAAAGGTCGCCCGACGCCCGGGCTTTGCCCG<br>GGCGGCCTCAGTGAGCGAGCGAGCGCGCAGCTGGCGTAATAGCG<br>AAGAGGCCCGCACCGATCGCCCTTCCCAACAGTTGCGCAGCCTGA<br>ATGGCGAATGGCGATTCCGTTGCAATGGCTGGCGGTAATATTGTTC<br>TGGATATTACCAGCAAGGCCGATAGTTTGAGTTCTTCTACTCAGGC<br>AAGTGATGTTATTACTAATCAAAGAAGTATTGCGACAACGGTTAA<br>TTTGCGTGATGGACAGACTCTTTTACTCGGTGGCCTCACTGATTAT<br>AAAAACACTTCTCAGGATTCTGGCGTACCGTTCCTGTCTAAAATCC<br>CTTTAATCGGCCTCCTGTTTAGCTCCCGCTCTGATTCTAACGAGGA<br>AAGCACGTTATACGTGCTCGTCAAAGCAACCATAGTACGCGCCCT<br>GTAGCGGCGCATTAAGCGCGGCGGGTGTGGTGGTTACGCGCAGCG<br>TGACCGCTACACTTGCCAGCGCCCTAGCGCCCGCTCCTTTCGCTTT<br>CTTCCCTTCCTTTCTCGCCACGTTCGCCGGCTTTCCCCGTCAAGCTC<br>TAAATCGGGGGCTCCCTTTAGGGTTCCGATTTAGTGCTTTACGGCA<br>CCTCGACCCCAAAAAACTTGATTAGGGTGATGGTTCACGTAGTGG<br>GCCATCGCCCTGATAGACGGTTTTTCGCCCTTTGACGTTGGAGTCC<br>ACGTTCTTTAATAGTGGACTCTTGTTCCAAACTGGAACAACACTCA<br>ACCCTATCTCGGTCTATTCTTTTGATTTATAAGGGATTTTGCCGATT<br>TCGGCCTATTGGTTAAAAAATGAGCTGATTTAACAAAAATTTAAC<br>GCGAATTTTAACAAAATATTAACGTTTACAATTTAAATATTTGCTT<br>ATACAATCTTCCTGTTTTTGGGGCTTTTCTGATTATCAACCGGGGT<br>ACATATGATTGACATGCTAGTTTTACGATTACCGTTCATCGATTCT<br>CTTGTTTGCTCCAGACTCTCAGGCAATGACCTGATAGCCTTTGTAG<br>AGACCTCTCAAAAATAGCTACCCTCTCCGGCATGAATTTATCAGCT<br>AGAACGGTTGAATATCATATTGATGGTGATTTGACTGTCTCCGGCC<br>TTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA |

-continued

| SEQ ID NO | NAME | SEQUENCE |
|---|---|---|
| | | AGGAGCTAACCGCTTTTTTGCACAACATGGGGGATCATGTAACTC |
| | | GCCTTGATCGTTGGGAACCGGAGCTGAATGAAGCCATACCAAACG |
| | | ACGAGCGTGACACCACGATGCCTGTAGCAATGGCAACAACGTTGC |
| | | GCAAACTATTAACTGGCGAACTACTTACTCTAGCTTCCCGGCAACA |
| | | ATTAATAGACTGGATGGAGGCGGATAAAGTTGCAGGACCACTTCT |
| | | GCGCTCGGCCCTTCCGGCTGGCTGGTTTATTGCTGATAAATCTGGA |
| | | GCCGGTGAGCGTGGGTCTCGCGGTATCATTGCAGCACTGGGGCCA |
| | | GATGGTAAGCCCTCCCGTATCGTAGTTATCTACACGACGGGGAGT |
| | | CAGGCAACTATGGATGAACGAAATAGACAGATCGCTGAGATAGGT |
| | | GCCTCACTGATTAAGCATTGGTAACTGTCAGACCAAGTTTACTCAT |
| | | ATATACTTTAGATTGATTTAAAACTTCATTTTTAATTTAAAAGGAT |
| | | CTAGGTGAAGATCCTTTTTGATAATCTCATGACCAAAATCCCTTAA |
| | | CGTGAGTTTTCGTTCCACTGAGCGTCAGACCCCGTAGAAAAGATC |
| | | AAAGGATCTTCTTGAGATCCTTTTTTTCTGCGCGTAATCTGCTGCTT |
| | | GCAAACAAAAAAACCACCGCTACCAGCGGTGGTTTGTTTGCCGGA |
| | | TCAAGAGCTACCAACTCTTTTTCCGAAGGTAACTGGCTTCAGCAGA |
| | | GCGCAGATACCAAATACTGTCCTTCTAGTGTAGCCGTAGTTAGGCC |
| | | ACCACTTCAAGAACTCTGTAGCACCGCCTACATACCTCGCTCTGCT |
| | | AATCCTGTTACCAGTGGCTGCTGCCAGTGGCGATAAGTCGTGTCTT |
| | | ACCGGGTTGGACTCAAGACGATAGTTACCGGATAAGGCGCAGCGG |
| | | TCGGGCTGAACGGGGGGTTCGTGCACACAGCCCAGCTTGGAGCGA |
| | | ACGACCTACACCGAACTGAGATACCTACAGCGTGAGCTATGAGAA |
| | | AGCGCCACGCTTCCCGAAGGGAGAAAGGCGGACAGGTATCCGGT |
| | | AAGCGGCAGGGTCGGAACAGGAGAGCGCACGAGGGAGCTTCCAG |
| | | GGGGAAACGCCTGGTATCTTTATAGTCCTGTCGGGTTTCGCCACCT |
| | | CTGACTTGAGCGTCGATTTTTGTGATGCTCGTCAGGGGGGCGGAG |
| | | CCTATGGAAAAACGCCAGCAACGCGGCCTTTTTACGGTTCCTGGC |
| | | CTTTTGCTGGCCTTTTGCTCACATGTTCTTTCCTGCGTTATCCCCTG |
| | | ATTCTGTGGATAACCGTATTACCGCCTTTGAGTGAGCTGATACCGC |
| | | TCGCCGCAGCCGAACGACCGAGCGCAGCGAGTCAGTGAGCGAGG |
| | | AAGCGGAAGAGCGCCCAATACGCAAACCGCCTCTCCCCGCGCGTT |
| | | GGCCGATTCATTAATG |
| 34 | HBG1 Round 1 & 2: | CAGCTGCGCGCTCGCTCGCTCACTGAGGCCGCCCGGGCAAAGCCC |
| | AMS#1238 | GGGCGTCGGGCGACCTTTGGTCGCCCGGCCTCAGTGAGCGAGCGA |
| | pAAV | GCGCGCAGAGAGGGAGTGGCCAACTCCATCACTAGGGGTTCCTTG |
| | HBG1(400).d13> | TAGTTAATGATTAACCCGCCATGCTACTTATCTACACGCGTAGATC |
| | HBBopt(T87Q). | TTTTTTCCTTAGAAACCACTGCTAACTGAAAGAGACTAAGATTTGT |
| | wPRE- | CCCGTCAAAAATCCTGGACCTATGCCTAAAACACATTTCACAATCC |
| | O.BGHpA;MND> | CTGAACTTTTCAAAAATTGGTACATGCTTTAGCTTTAAACTACAGG |
| | GFP::P2A:Ex2 | CCTCACTGGAGCTAGAGACAAGAAGGTAAAAAACGGCTGACAAA |
| | | AGAAGTCCTGGTATCCTCTATGATGGGAGAAGGAAACTAGCTAAA |
| | | GGGAAGAATAAATTAGAGAAAAACTGGAATGACTGAATCGGAAC |
| | | AAGGCAAAGGCTATAAAAAAAATTAGCAGTATCCTCTTGGGGGCC |
| | | CCTTCCCCACACTATCTCAATGCAAATATCTGTCTGAAACGGTCCC |
| | | TGGCTAAACTCCACCCATGGGTTGGCCAGCCTTGCCTTGACAAGG |
| | | CAAACTTGACCAATAGTCTTAGAGTATCCAGTGAGGCCAGGGGCC |
| | | GGCGGCTGGCTAGGGATGAAGAATAAAAGGAAGCACCCTTCAGC |
| | | AGTTCCACACACTCGCTTCTGGAACGTCTGAGGTTATCAATAAGCT |
| | | CCTAGTCCAGACGCCGCCGCCACCATGGTCCATCTTACACCGGAG |
| | | GAGAAGTCCGCTGTAACGGCACTGTGGGGGAAAGTTAATGTCGAT |
| | | GAAGTCGGCGGTGAAGCACTCGGCAGGTTGCTGGTAGTGTACCCG |
| | | TGGACACAACGATTCTTTGAAAGTTTCGGGGACCTGTCCACACCC |
| | | GATGCTGTGATGGGTAATCCAAAAGTAAAAGCACACGGCAAGAA |
| | | AGTCCTCGGCGCGTTTAGTGATGGTCTGGCCCATTTGGATAACTTG |
| | | AAGGGTACATTCGCGCAGCTTTCCGAACTCCACTGTGACAAGTTG |
| | | CACGTAGATCCAGAAAACTTCCGGCTTCTGGGCAATGTGCTTGTAT |
| | | GCGTTCTGGCTCACCATTTTGGGAAGGAGTTTACCCCACCCGTGCA |
| | | AGCGGCTTACCAAAAAGTGGTCGCAGGAGTGGCTAATGCCCTTGC |
| | | ACATAAATATCACTAAGGTACCGAGCATCTTACCGCCATTTATTCC |
| | | CATATTTGTTCTGTTTTTCTTGATTTGGGTATACATTTAAATGTTAA |
| | | TAAAACAAAATGGTGGGGCAATCATTTACATTTTTAGGGATATGT |
| | | AATTACTAGTTCAGGTGTATTGCCACAAGACAAACATGTTAAGAA |
| | | ACTTTCCCGTTATTTACGCTCTGTTCCTGTTAATCAACCTCTGGATT |
| | | ACAAAATTTGTGAAAGATTGACTGATATTCTTAACTATGTTGCTCC |
| | | TTTTACGCTGTGTGGATATGCTGCTTTATAGCCTCTGTATCTAGCTA |
| | | TTGCTTCCCGTACGGCTTTCGTTTTCTCCTCCTTGTATAAATCCTGG |
| | | TTGCTGTCTCTTTTAGAGGAGTTGTGGCCCGTTGTCCGTCAACGTG |
| | | GCGTGGTGTGCTCTGTGTTTGCTGACGCAACCCCCACTGGCTGGGG |
| | | CATTGCCACCACCTGTCAACTCCTTTCTGGGACTTTCGCTTTCCCCC |
| | | TCCCGATCGCCACGGCAGAACTCATCGCCGCCTGCCTTGCCCGCTG |
| | | CTGGACAGGGGCTAGGTTGCTGGGCACTGATAATTCCGTGGTGTT |
| | | GTCTGTGCCTTCTAGTTGCCAGCCATCTGTTGTTTGCCCCTCCCCCG |
| | | TGCCTTCCTTGACCCTGGAAGGTGCCACTCCCACTGTCCTTTCCTA |
| | | ATAAAATGAGGAAATTGCATCGCATTGTCTGAGTAGGTGTCATTCT |

-continued

| SEQ ID NO | NAME | SEQUENCE |
|---|---|---|
| | | ATTCTGGGGGGTGGGGTGGGGCAGGACAGCAAGGGGGAGGATTG<br>GGAAGACAATAGCAGGCATGCTGGGGATGCGGTGGGCTCTATGGC<br>CCGCGGGAACAGAGAAACAGGAGAATATGGGCCAAACAGGATAT<br>CTGTGGTAAGCAGTTCCTGCCCCGGCTCAGGGCCAAGAACAGTTG<br>GAACAGCAGAATATGGGCCAAACAGGATATCTGTGGTAAGCAGTT<br>CCTGCCCCGGCTCAGGGCCAAGAACAGATGGTCCCCAGATGCGGT<br>CCCGCCCTCAGCAGTTTCTAGAGAACCATCAGATGTTTCCAGGGTG<br>CCCCAAGGACCTGAAATGACCCTGTGCCTTATTTGAACTAACCAAT<br>CAGTTCGCTTCTCGCTTCTGTTCGCGCGCTTCTGCTCCCCGAGCTCT<br>ATATAAGCAGAGCTCGTTTAGTGAACCGTCAGATCGCCTGGAGAC<br>GCCATCCACGCTGTTTTGACTTCCATAGAAGGCGGCCGCGCCGCC<br>ACCATGGTGAGCAAGGGCGAGGAGCTGTTCACCGGGGTGGTGCCC<br>ATCCTGGTCGAGCTGGACGGCGACGTAAACGGCCACAAGTTCAGC<br>GTGTCCGGCGAGGGCGAGGGCGATGCCACCTACGGCAAGCTGACC<br>CTGAAGTTCATCTGCACCACCGGCAAGCTGCCCGTGCCCTGGCCC<br>ACCCTCGTGACCACCCTGACCTACGGCGTGCAGTGCTTCAGCCGCT<br>ACCCCGACCACATGAAGCAGCACGACTTCTTCAAGTCCGCCATGC<br>CCGAAGGCTACGTCCAGGAGCGCACCATCTTCTTCAAGGACGACG<br>GCAACTACAAGACCCGCGCCGAGGTGAAGTTCGAGGGCGACACCC<br>TGGTGAACCGCATCGAGCTGAAGGGCATCGACTTCAAGGAGGACG<br>GCAACATCCTGGGGCACAAGCTGGAGTACAACTACAACAGCCACA<br>ACGTCTATATCATGGCCGACAAGCAGAAGAACGGCATCAAGGTGA<br>ACTTCAAGATCCGCCACAACATCGAGGACGGCAGCGTGCAGCTCG<br>CCGACCACTACCAGCAGAACACCCCCATCGGCGACGGCCCCGTGC<br>TGCTGCCCGACAACCACTACCTGAGCACCCAGTCCGCCCTGAGCA<br>AAGACCCCAACGAGAAGCGCGATCACATGGTCCTGCTGGAGTTCG<br>TGACCGCCGCCGGGATCACTCTCGGCATGGACGAGCTGTACAAGG<br>GAAGCGGAGCTACTAACTTCAGCCTGCTGAAGCAGGCTGGAGACG<br>TGGAGGAGAACCCTGGACCTCCTGCAGGAACTTCAAGGTGAGTCC<br>AGGAGATGTTTCAGCCCTGTTGCCTTTAGTCTCGAGGCAACTTAGA<br>CAACGGAGTATTGATCTGAGCACAGCAGGGTGTGAGCTGTTTGAA<br>GATACTGGGGTTGGGGGTGAAGAAACTGCAGAGGACTAACTGGG<br>CTGAGACCCAGTGGTAATGTTTTAGGGCCTAAGGAGTGCCTCTAA<br>AAATCTAGATGGACAATTTTGACTTTGAGAAAAGAGAGGTGGAAA<br>TGAGGAAAATGACTTTTCTTTATTAGATTCCAGTAGAAAGAACTTT<br>CATCTTTCCCTCATTTTTGTTGTTTTAAAACATCTATCTGGAGGCAG<br>GACAAGTATGGTCGTTAAAAAGATGCAGGCAGAAGGCATATATTG<br>GCTCAGTCAAAGTGGGGAACTTTGGTGGGTCGACGTAGATAAGTA<br>GCATGGCGGGTTAATCATTAACTACAAGGAACCCCTAGTGATGGA<br>GTTGGCCACTCCCTCTCTGCGCGCTCGCTCGCTCACTGAGGCCGGG<br>CGACCAAAGGTCGCCCGACGCCCGGGCTTTGCCCGGGCGGCCTCA<br>GTGAGCGAGCGAGCGCGCCAGCTGGCGTAATAGCGAAGAGGCCC<br>GCACCGATCGCCCTTCCCAACAGTTGCGCAGCCTGAATGGCGAAT<br>GGCGATTCCGTTGCAATGGCTGGCGGTAATATTGTTCTGGATATTA<br>CCAGCAAGGCCGATAGTTTGAGTTCTTCTACTCAGGCAAGTGATGT<br>TATTACTAATCAAAGAAGTATTGCGACAACGGTTAATTTGCGTGAT<br>GGACAGACTCTTTTACTCGGTGGCCTCACTGATTATAAAAACACTT<br>CTCAGGATTCTGGCGTACCGTTCCTGTCTAAAATCCCTTTAATCGG<br>CCTCCTGTTTAGCTCCCGCTCTGATTCTAACGAGGAAAGCACGTTA<br>TACGTGCTCGTCAAAGCAACCATAGTACGCGCCCTGTAGCGGCGC<br>ATTAAGCGCGGCGGGTGTGGTGGTTACGCGCAGCGTGACCGCTAC<br>ACTTGCCAGCGCCCTAGCGCCCGCTCCTTTCGCTTTCTTCCCTTCCT<br>TTCTCGCCACGTTCGCCGGCTTTCCCCGTCAAGCTCTAAATCGGGG<br>GCTCCCTTTAGGGTTCCGATTTAGTGCTTTACGGCACCTCGACCCC<br>AAAAAACTTGATTAGGGTGATGGTTCACGTAGTGGGCCATCGCCC<br>TGATAGACGGTTTTTCGCCCTTTGACGTTGGAGTCCACGTTCTTTA<br>ATAGTGGACTCTTGTTCCAAACTGGAACAACACTCAACCCTATCTC<br>GGTCTATTCTTTTGATTTATAAGGGATTTTGCCGATTTCGGCCTATT<br>GGTTAAAAAATGAGCTGATTTAACAAAAATTTAACGCGAATTTTA<br>ACAAAATATTAACGTTTACAATTTAAATATTTGCTTATACAATCTT<br>CCTGTTTTTGGGGCTTTTCTGATTATCAACCGGGGTACATATGATT<br>GACATGCTAGTTTTACGATTACCGTTCATCGATTCTCTTGTTTGCTC<br>CAGACTCTCAGGCAATGACCTGATAGCCTTTGTAGAGACCTCTCA<br>AAAATAGCTACCCTCTCCGGCATGAATTTATCAGCTAGAACGGTT<br>GAATATCATATTGATGGTGATTTGACTGTCTCCGGCCTTTCTCACC<br>CGTTTGAATCTTTACCTACACATTACTCAGGCATTGCATTTAAAAT<br>ATATGAGGGTTCTAAAAATTTTTATCCTTGCGTTGAAATAAAGGCT<br>TCTCCCGCAAAAGTATTACAGGGTCATAATGTTTTTGGTACAACCG<br>ATTTAGCTTTATGCTCTGAGGCTTTATTGCTTAATTTTGCTAATTCT<br>TTGCCTTGCCTGTATGATTTATTGGATGTTGGAATCGCCTGATGCG<br>GTATTTTCTCCTTACGCATCTGTGCGGTATTTCACACCGCATATGG<br>TGCACTCTCAGTACAATCTGCTCTGATGCCGCATAGTTAAGCCAGC<br>CCCGACACCCGCCAACACCCGCTGACGCGCCCTGACGGGCTTGTC<br>TGCTCCCGGCATCCGCTTACAGACAAGCTGTGACCGTCTCCGGGA<br>GCTGCATGTGTCAGAGGTTTTCACCGTCATCACCGAAACGCGCGA |

-continued

| SEQ ID NO | NAME | SEQUENCE |
|---|---|---|
| | | GACGAAAGGGCCTCGTGATACGCCTATTTTTATAGGTTAATGTCAT<br>GATAATAATGGTTTCTTAGACGTCAGGTGGCACTTTTCGGGGAAAT<br>GTGCGCGGAACCCCTATTTGTTTATTTTTCTAAATACATTCAAATA<br>TGTATCCGCTCATGAGACAATAACCCTGATAAATGCTTCAATAATA<br>TTGAAAAAGGAAGAGTATGAGTATTCAACATTTCCGTGTCGCCCTT<br>ATTCCCTTTTTTGCGGCATTTTGCCTTCCTGTTTTTGCTCACCCAGA<br>AACGCTGGTGAAAGTAAAAGATGCTGAAGATCAGTTGGGTGCACG<br>AGTGGGTTACATCGAACTGGATCTCAACAGCGGTAAGATCCTTGA<br>GAGTTTTCGCCCCGAAGAACGTTTTCCAATGATGAGCACTTTTAAA<br>GTTCTGCTATGTGGCGCGGTATTATCCCGTATTGACGCCGGGCAAG<br>AGCAACTCGGTCGCCGCATACACTATTCTCAGAATGACTTGGTTGA<br>GTACTCACCAGTCACAGAAAAGCATCTTACGGATGGCATGACAGT<br>AAGAGAATTATGCAGTGCTGCCATAACCATGAGTGATAACACTGC<br>GGCCAACTTACTTCTGACAACGATCGGAGGACCGAAGGAGCTAAC<br>CGCTTTTTTGCACAACATGGGGGATCATGTAACTCGCCTTGATCGT<br>TGGGAACCGGAGCTGAATGAAGCCATACCAAACGACGAGCGTGA<br>CACCACGATGCCTGTAGCAATGGCAACAACGTTGCGCAAACTATT<br>AACTGGCGAACTACTTACTCTAGCTTCCCGGCAACAATTAATAGA<br>CTGGATGGAGGCGGATAAAGTTGCAGGACCACTTCTGCGCTCGGC<br>CCTTCCGGCTGGCTGGTTTATTGCTGATAAATCTGGAGCCGGTGAG<br>CGTGGGTCTCGCGGTATCATTGCAGCACTGGGGCCAGATGGTAAG<br>CCCTCCCGTATCGTAGTTATCTACACGACGGGGAGTCAGGCAACT<br>ATGGATGAACGAAATAGACAGATCGCTGAGATAGGTGCCTCACTG<br>ATTAAGCATTGGTAACTGTCAGACCAAGTTTACTCATATATACTTT<br>AGATTGATTTAAAACTTCATTTTTAATTTAAAAGGATCTAGGTGAA<br>GATCCTTTTTGATAATCTCATGACCAAAATCCCTTAACGTGAGTTT<br>TCGTTCCACTGAGCGTCAGACCCCGTAGAAAAGATCAAAGGATCT<br>TCTTGAGATCCTTTTTTTCTGCGCGTAATCTGCTGCTTGCAAACAA<br>AAAAACCACCGCTACCAGCGGTGGTTTGTTTGCCGGATCAAGAGC<br>TACCAACTCTTTTTCCGAAGGTAACTGGCTTCAGCAGAGCGCAGAT<br>ACCAAATACTGTCCTTCTAGTGTAGCCGTAGTTAGGCCACCACTTC<br>AAGAACTCTGTAGCACCGCCTACATACCTCGCTCTGCTAATCCTGT<br>TACCAGTGGCTGCTGCCAGTGGCGATAAGTCGTGTCTTACCGGGTT<br>GGACTCAAGACGATAGTTACCGGATAAGGCGCAGCGGTCGGGCTG<br>AACGGGGGGTTCGTGCACACAGCCCAGCTTGGAGCGAACGACCTA<br>CACCGAACTGAGATACCTACAGCGTGAGCTATGAGAAAGCGCCAC<br>GCTTCCCGAAGGGAGAAAGGCGGACAGGTATCCGGTAAGCGGCA<br>GGGTCGGAACAGGAGAGCGCACGAGGGAGCTTCCAGGGGGAAAC<br>GCCTGGTATCTTTATAGTCCTGTCGGGTTTCGCCACCTCTGACTTG<br>AGCGTCGATTTTTGTGATGCTCGTCAGGGGGGCGGAGCCTATGGA<br>AAAACGCCAGCAACGCGGCCTTTTTACGGTTCCTGGCCTTTTGCTG<br>GCCTTTTGCTCACATGTTCTTTCCTGCGTTATCCCCTGATTCTGTGG<br>ATAACCGTATTACCGCCTTTGAGTGAGCTGATACCGCTCGCCGCAG<br>CCGAACGACCGAGCGCAGCGAGTCAGTGAGCGAGGAAGCGGAAG<br>AGCGCCCAATACGCAAACCGCCTCTCCCCGCGCGTTGGCCGATTC<br>ATTAATG |
| 35 | HBG1 Round 1 & 2:<br>AMS#1239<br>pAAV<br>HBG1(400).d13><br>HBBopt(T87Q).<br>wPRE-<br>O.BGHpA;HPFH2.<br>MND>GFP::P2A:<br>Ex2 | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTTTTTCCTTAGAAACCACTGCTAACTGAAAGAGACTAAGATTTGT<br>CCCGTCAAAAATCCTGGACCTATGCCTAAAACACATTTCACAATCC<br>CTGAACTTTTCAAAAATTGGTACATGCTTTAGCTTTAAACTACAGG<br>CCTCACTGGAGCTAGAGACAAGAAGGTAAAAAACGGCTGACAAA<br>AGAAGTCCTGGTATCCTCTATGATGGGAGAAGGAAACTAGCTAAA<br>GGGAAGAATAAATTAGAGAAAAACTGGAATGACTGAATCGGAAC<br>AAGGCAAAGGCTATAAAAAAAAATTAGCAGTATCCTCTTGGGGGCC<br>CCTTCCCCACACTATCTCAATGCAAATATCTGTCTGAAACGGTCCC<br>TGGCTAAACTCCACCCATGGGTTGGCCAGCCTTGCCTTGACAAGG<br>CAAACTTGACCAATAGTCTTAGAGTATCCAGTGAGGCCAGGGGCC<br>GGCGGCTGGCTAGGGATGAAGAATAAAAGGAAGCACCCTTCAGC<br>AGTTCCACACACTCGCTTCTGGAACGTCTGAGGTTATCAATAAGCT<br>CCTAGTCCAGACGCCGCCGCCACCATGGTCCATCTTACACCGGAG<br>GAGAAGTCCGCTGTAACGGCACTGTGGGGAAAGTTAATGTCGAT<br>GAAGTCGGCGGTGAAGCACTCGGCAGGTTGCTGGTAGTGTACCCG<br>TGGACACAACGATTCTTTGAAAGTTTCGGGGACCTGTCCACACCC<br>GATGCTGTGATGGGTAATCCAAAAGTAAAAGCACACGGCAAGAA<br>AGTCCTCGGCGCGTTTAGTGATGGTCTGGCCCATTTGGATAACTTG<br>AAGGGTACATTCGCGCAGCTTTCCGAACTCCACTGTGACAAGTTG<br>CACGTAGATCCAGAAAACTTCCGGCTTCTGGGCAATGTGCTTGTAT<br>GCGTTCTGGCTCACCATTTTGGGAAGGAGTTTACCCCACCCGTGCA<br>AGCGGCTTACCAAAAAGTGGTCGCAGGAGTGGCTAATGCCCTTGC<br>ACATAAATATCACTAAGGTACCGAGCATCTTACCGCCATTTATTCC<br>CATATTTGTTCTGTTTTTCTTGATTTGGGTATACATTTAAATGTTAA |

-continued

| SEQ ID NO | NAME | SEQUENCE |
|---|---|---|
| | | TAAAACAAAATGGTGGGGCAATCATTTACATTTTTAGGGATATGT<br>AATTACTAGTTCAGGTGTATTGCCACAAGACAAACATGTTAAGAA<br>ACTTTCCCGTTATTTACGCTCTGTTCCTGTTAATCAACCTCTGGATT<br>ACAAAATTTGTGAAAGATTGACTGATATTCTTAACTATGTTGCTCC<br>TTTTACGCTGTGTGGATATGCTGCTTTATAGCCTCTGTATCTAGCTA<br>TTGCTTCCCGTACGGCTTTCGTTTTCTCCTCCTTGTATAAATCCTGG<br>TTGCTGTCTCTTTTAGAGGAGTTGTGGCCCGTTGTCCGTCAACGTG<br>GCGTGGTGTGCTCTGTGTTTGCTGACGCAACCCCCACTGGCTGGGG<br>CATTGCCACCACCTGTCAACTCCTTTCTGGGACTTTCGCTTTCCCCC<br>TCCCGATCGCCACGGCAGAACTCATCGCCGCCTGCCTTGCCCGCTG<br>CTGGACAGGGGCTAGGTTGCTGGGCACTGATAATTCCGTGGTGTT<br>GTCTGTGCCTTCTAGTTGCCAGCCATCTGTTGTTTGCCCCTCCCCCG<br>TGCCTTCCTTGACCCTGGAAGGTGCCACTCCCACTGTCCTTTCCTA<br>ATAAAATGAGGAAATTGCATCGCATTGTCTGAGTAGGTGTCATTCT<br>ATTCTGGGGGGTGGGGTGGGGCAGGACAGCAAGGGGGAGGATTG<br>GGAAGACAATAGCAGGCATGCTGGGGATGCGGTGGGCTCTATGGC<br>CGAGATCGAGACCATCCTGGCTAACACAGTGAAACCCCGTCTCTA<br>CTAAAAAAATACAAAAAATTAGCCGGGCTTGGTGGCGGGTGCCTG<br>TAGTCCCAGCTACTATGGAGGCTGAGGCGGGAGAATGGCGTGAAC<br>GCGGGGGGCGGAGCTTGCAGTGAGCAGAGATCAGGGGCCACTGC<br>ACTCCAGCCTGGGCGACAGAGAGAGACTCTGTCTCAAAAAAAAGA<br>AAAAAAAAATTTAGTAGACTAGCTAAAAAAATCCAGAGATAGTTA<br>TTGATGCATATGTAAAAGTCTTCCAATATTTACAAGTACAATGAAA<br>AAAAAATAACCTTGAATTAAGTGTAGAACTCATTGACAATGTTTC<br>AAAGGATGTGAGGGATAAACTAAAATTTGGGCAGTACATGCTGTT<br>CCTGTGTACTTGGAACAGAGGGAGAAAATCTGGGCTGGAAATATT<br>GTTATAGGAGTTAGCACATGAAGGTGACAACTAAATTATTTGGAG<br>TAGATGGAGTCACCAGCACATGTGAATAGTTTTAGAATGAAATGA<br>CCCAAGATAGAACTTTGGAGAGCCCCCAAATTTAAATAAAATCAG<br>TATAAGAGAAGAGGAAGAAACCAAATGGTATACTAGTCTAAATTG<br>TTTCTTAGTGACAAAAGAATAACCTGAATATTAGATTAGCTGCCTA<br>TATGCTCTCTGAATCAATTTCATTCAACATGCAACAGTCCGCGGGA<br>ACAGAGAAACAGGAGAATATGGGCCAAACAGGATATCTGTGGTA<br>AGCAGTTCCTGCCCCGGCTCAGGGCCAAGAACAGTTGGAACAGCA<br>GAATATGGGCCAAACAGGATATCTGTGGTAAGCAGTTCCTGCCCC<br>GGCTCAGGGCCAAGAACAGATGGTCCCCAGATGCGGTCCCGCCCT<br>CAGCAGTTTCTAGAGAACCATCAGATGTTTCCAGGGTGCCCCAAG<br>GACCTGAAATGACCCTGTGCCTTATTTGAACTAACCAATCAGTTCG<br>CTTCTCGCTTCTGTTCGCGCGCTTCTGCTCCCCGAGCTCTATATAAG<br>CAGAGCTCGTTTAGTGAACCGTCAGATCGCCTGGAGACGCCATCC<br>ACGCTGTTTTGACTTCCATAGAAGGCGGCCGCGCCGCCACCATGG<br>TGAGCAAGGGCGAGGAGCTGTTCACCGGGGTGGTGCCCATCCTGG<br>TCGAGCTGGACGGCGACGTAAACGGCCACAAGTTCAGCGTGTCCG<br>GCGAGGGCGAGGGCGATGCCACCTACGGCAAGCTGACCCTGAAGT<br>TCATCTGCACCACCGGCAAGCTGCCCGTGCCCTGGCCCACCCTCGT<br>GACCACCCTGACCTACGGCGTGCAGTGCTTCAGCCGCTACCCCGA<br>CCACATGAAGCAGCACGACTTCTTCAAGTCCGCCATGCCCGAAGG<br>CTACGTCCAGGAGCGCACCATCTTCTTCAAGGACGACGGCAACTA<br>CAAGACCCGCGCCGAGGTGAAGTTCGAGGGCGACACCCTGGTGAA<br>CCGCATCGAGCTGAAGGGCATCGACTTCAAGGAGGACGGCAACAT<br>CCTGGGGCACAAGCTGGAGTACAACTACAACAGCCACAACGTCTA<br>TATCATGGCCGACAAGCAGAAGAACGGCATCAAGGTGAACTTCAA<br>GATCCGCCACAACATCGAGGACGGCAGCGTGCAGCTCGCCGACCA<br>CTACCAGCAGAACACCCCCATCGGCGACGGCCCCGTGCTGCTGCC<br>CGACAACCACTACCTGAGCACCCAGTCCGCCCTGAGCAAAGACCC<br>CAACGAGAAGCGCGATCACATGGTCCTGCTGGAGTTCGTGACCGC<br>CGCCGGGATCACTCTCGGCATGGACGAGCTGTACAAGGGAAGCGG<br>AGCTACTAACTTCAGCCTGCTGAAGCAGGCTGGAGACGTGGAGGA<br>GAACCCTGGACCTCCTGCAGGAACTTCAAGGTGAGTCCAGGAGAT<br>GTTTCAGCCCTGTTGCCTTTAGTCTCGAGGCAACTTAGACAACGGA<br>GTATTGATCTGAGCACAGCAGGGTGTGAGCTGTTTGAAGATACTG<br>GGGTTGGGGGTGAAGAAACTGCAGAGGACTAACTGGGCTGAGAC<br>CCAGTGGTAATGTTTTAGGGCCTAAGGAGTGCCTCTAAAAATCTA<br>GATGGACAATTTTGACTTTGAGAAAAGAGAGGTGGAAATGAGGA<br>AAATGACTTTTCTTTATTAGATTCCAGTAGAAAGAACTTTCATCTT<br>TCCCTCATTTTTGTTGTTTTAAAACATCTATCTGGAGGCAGGACAA<br>GTATGGTCGTTAAAAAGATGCAGGCAGAAGGCATATATTGGCTCA<br>GTCAAAGTGGGGAACTTTGGTGGGTCGACGTAGATAAGTAGCATG<br>GCGGGTTAATCATTAACTACAAGGAACCCCTAGTGATGGAGTTGG<br>CCACTCCCTCTCTGCGCGCTCGCTCGCTCACTGAGGCCGGGCGACC<br>AAAGGTCGCCCGACGCCCGGGCTTTGCCCGGGCGGCCTCAGTGAG<br>CGAGCGAGCGCGCCAGCTGGCGTAATAGCGAAGAGGCCCGCACC<br>GATCGCCCTTCCCAACAGTTGCGCAGCCTGAATGGCGAATGGCGA<br>TTCCGTTGCAATGGCTGGCGGTAATATTGTTCTGGATATTACCAGC<br>AAGGCCGATAGTTTGAGTTCTTCTACTCAGGCAAGTGATGTTATTA |

-continued

| SEQ ID NO | NAME | SEQUENCE |
|---|---|---|
| | | CTAATCAAAGAAGTATTGCGACAACGGTTAATTTGCGTGATGGAC<br>AGACTCTTTTACTCGGTGGCCTCACTGATTATAAAAACACTTCTCA<br>GGATTCTGGCGTACCGTTCCTGTCTAAAATCCCTTTAATCGGCCTC<br>CTGTTTAGCTCCCGCTCTGATTCTAACGAGGAAAGCACGTTATACG<br>TGCTCGTCAAAGCAACCATAGTACGCGCCCTGTAGCGGCGCATTA<br>AGCGCGGCGGGTGTGGTGGTTACGCGCAGCGTGACCGCTACACTT<br>GCCAGCGCCCTAGCGCCCGCTCCTTTCGCTTTCTTCCCTTCCTTTCT<br>CGCCACGTTCGCCGGCTTTCCCCGTCAAGCTCTAAATCGGGGGCTC<br>CCTTTAGGGTTCCGATTTAGTGCTTTACGGCACCTCGACCCCAAAA<br>AACTTGATTAGGGTGATGGTTCACGTAGTGGGCCATCGCCCTGAT<br>AGACGGTTTTTCGCCCTTTGACGTTGGAGTCCACGTTCTTTAATAG<br>TGGACTCTTGTTCCAAACTGGAACAACACTCAACCCTATCTCGGTC<br>TATTCTTTTGATTTATAAGGGATTTTGCCGATTTCGGCCTATTGGTT<br>AAAAAATGAGCTGATTTAACAAAAATTTAACGCGAATTTTAACAA<br>AATATTAACGTTTACAATTTAAATATTTGCTTATACAATCTTCCTGT<br>TTTTGGGGCTTTTCTGATTATCAACCGGGGTACATATGATTGACAT<br>GCTAGTTTTACGATTACCGTTCATCGATTCTCTTGTTTGCTCCAGAC<br>TCTCAGGCAATGACCTGATAGCCTTTGTAGAGACCTCTCAAAAAT<br>AGCTACCCTCTCCGGCATGAATTTATCAGCTAGAACGGTTGAATAT<br>CATATTGATGGTGATTTGACTGTCTCCGGCCTTTCTCACCCGTTTG<br>AATCTTTACCTACACATTACTCAGGCATTGCATTTAAAATATATGA<br>GGGTTCTAAAAATTTTTATCCTTGCGTTGAAATAAAGGCTTCTCCC<br>GCAAAAGTATTACAGGGTCATAATGTTTTTGGTACAACCGATTTAG<br>CTTTATGCTCTGAGGCTTTATTGCTTAATTTTGCTAATTCTTTGCCT<br>TGCCTGTATGATTTATTGGATGTTGGAATCGCCTGATGCGGTATTT<br>TCTCCTTACGCATCTGTGCGGTATTTCACACCGCATATGGTGCACT<br>CTCAGTACAATCTGCTCTGATGCCGCATAGTTAAGCCAGCCCCGAC<br>ACCCGCCAACACCCGCTGACGCGCCCTGACGGGCTTGTCTGCTCCC<br>GGCATCCGCTTACAGACAAGCTGTGACCGTCTCCGGGAGCTGCAT<br>GTGTCAGAGGTTTTCACCGTCATCACCGAAACGCGCGAGACGAAA<br>GGGCCTCGTGATACGCCTATTTTTATAGGTTAATGTCATGATAATA<br>ATGGTTTCTTAGACGTCAGGTGGCACTTTTCGGGGAAATGTGCGCG<br>GAACCCCTATTTGTTTATTTTTCTAAATACATTCAAATATGTATCCG<br>CTCATGAGACAATAACCCTGATAAATGCTTCAATAATATTGAAAA<br>AGGAAGAGTATGAGTATTCAACATTTCCGTGTCGCCCTTATTCCCT<br>TTTTTGCGGCATTTTGCCTTCCTGTTTTTGCTCACCCAGAAACGCTG<br>GTGAAAGTAAAAGATGCTGAAGATCAGTTGGGTGCACGAGTGGGT<br>TACATCGAACTGGATCTCAACAGCGGTAAGATCCTTGAGAGTTTTC<br>GCCCCGAAGAACGTTTTCCAATGATGAGCACTTTTAAAGTTCTGCT<br>ATGTGGCGCGGTATTATCCCGTATTGACGCCGGGCAAGAGCAACT<br>CGGTCGCCGCATACACTATTCTCAGAATGACTTGGTTGAGTACTCA<br>CCAGTCACAGAAAAGCATCTTACGGATGGCATGACAGTAAGAGAA<br>TTATGCAGTGCTGCCATAACCATGAGTGATAACACTGCGGCCAAC<br>TTACTTCTGACAACGATCGGAGGACCGAAGGAGCTAACCGCTTTT<br>TTGCACAACATGGGGGATCATGTAACTCGCCTTGATCGTTGGGAA<br>CCGGAGCTGAATGAAGCCATACCAAACGACGAGCGTGACACCAC<br>GATGCCTGTAGCAATGGCAACAACGTTGCGCAAACTATTAACTGG<br>CGAACTACTTACTCTAGCTTCCCGGCAACAATTAATAGACTGGATG<br>GAGGCGGATAAAGTTGCAGGACCACTTCTGCGCTCGGCCCTTCCG<br>GCTGGCTGGTTTATTGCTGATAAATCTGGAGCCGGTGAGCGTGGG<br>TCTCGCGGTATCATTGCAGCACTGGGGCCAGATGGTAAGCCCTCC<br>CGTATCGTAGTTATCTACACGACGGGGAGTCAGGCAACTATGGAT<br>GAACGAAATAGACAGATCGCTGAGATAGGTGCCTCACTGATTAAG<br>CATTGGTAACTGTCAGACCAAGTTTACTCATATATACTTTAGATTG<br>ATTTAAAACTTCATTTTTAATTTAAAAGGATCTAGGTGAAGATCCT<br>TTTTGATAATCTCATGACCAAAATCCCTTAACGTGAGTTTTCGTTC<br>CACTGAGCGTCAGACCCCGTAGAAAAGATCAAAGGATCTTCTTGA<br>GATCCTTTTTTTCTGCGCGTAATCTGCTGCTTGCAAACAAAAAAAC<br>CACCGCTACCAGCGGTGGTTTGTTTGCCGGATCAAGAGCTACCAA<br>CTCTTTTTCCGAAGGTAACTGGCTTCAGCAGAGCGCAGATACCAA<br>ATACTGTCCTTCTAGTGTAGCCGTAGTTAGGCCACCACTTCAAGAA<br>CTCTGTAGCACCGCCTACATACCTCGCTCTGCTAATCCTGTTACCA<br>GTGGCTGCTGCCAGTGGCGATAAGTCGTGTCTTACCGGGTTGGACT<br>CAAGACGATAGTTACCGGATAAGGCGCAGCGGTCGGGCTGAACG<br>GGGGGTTCGTGCACACAGCCCAGCTTGGAGCGAACGACCTACACC<br>GAACTGAGATACCTACAGCGTGAGCTATGAGAAAGCGCCACGCTT<br>CCCGAAGGGAGAAAGGCGGACAGGTATCCGGTAAGCGGCAGGGT<br>CGGAACAGGAGAGCGCACGAGGGAGCTTCCAGGGGGAAACGCCT<br>GGTATCTTTATAGTCCTGTCGGGTTTCGCCACCTCTGACTTGAGCG |

-continued

| SEQ ID NO | NAME | SEQUENCE |
|---|---|---|
| | | TCGATTTTTGTGATGCTCGTCAGGGGGGCGGAGCCTATGGAAAAA<br>CGCCAGCAACGCGGCCTTTTTACGGTTCCTGGCCTTTTGCTGGCCT<br>TTTGCTCACATGTTCTTTCCTGCGTTATCCCCTGATTCTGTGGATAA<br>CCGTATTACCGCCTTTGAGTGAGCTGATACCGCTCGCCGCAGCCGA<br>ACGACCGAGCGCAGCGAGTCAGTGAGCGAGGAAGCGGAAGAGCG<br>CCCAATACGCAAACCGCCTCTCCCCGCGCGTTGGCCGATTCATTAA<br>TG |
| 36 | HBG1 Round 1 & 2:<br>AMS#1291<br>pAAV<br>HBG1(400).d13min><br>HBBopt(T87Q).<br>wPRE-<br>O.BGHpA;HPFH2.<br>MND>GFP.SV40Pa | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTTTTTCCTTAGAAACCACTGCTAACTGAAAGAGACTAAGATTTGT<br>CCCGTCAAAAATCCTGGACCTATGCCTAAAACACATTTCACAATCC<br>CTGAACTTTTCAAAAATTGGTACATGCTTTAGCTTTAAACTACAGG<br>CCTCACTGGAGCTAGAGACAAGAAGGTAAAAAACGGCTGACAAA<br>AGAAGTCCTGGTATCCTCTATGATGGGAGAAGGAAACTAGCTAAA<br>GGGAAGAATAAATTAGAGAAAAACTGGAATGACTGAATCGGAAC<br>AAGGCAAAGGCTATAAAAAAAAATTAGCAGTATCCTCTTGGGGGCC<br>CCTTCCCCACACTATCTCAATGCAAATATCTGTCTGAAACGGTCCC<br>TGGCTAAACTCCACCCATGGGTTGGCCAGCCTTGCCTTGACAAGG<br>CAAACTTGACCAATAGTCTTAGAGTATCCAGTGAGGCCAGGGGCC<br>GGCGGCTGGCTAGGGATGAAGAATAAAAGGAAGCACCCTTCAGC<br>AGTTCCACACACTCGCTTCTGGAACGTCTGAGGTTATCAATAAGCT<br>CCTAGTCCAGACGCCGCCGCCACCATGGTCCATCTTACACCGGAG<br>GAGAAGTCCGCTGTAACGGCACTGTGGGGGAAAGTTAATGTCGAT<br>GAAGTCGGCGGTGAAGCACTCGGCAGGTTGCTGGTAGTGTACCCG<br>TGGACACAACGATTCTTTGAAAGTTTCGGGGACCTGTCCACACCC<br>GATGCTGTGATGGGTAATCCAAAAGTAAAAGCACACGGCAAGAA<br>AGTCCTCGGCGCGTTTAGTGATGGTCTGGCCCATTTGGATAACTTG<br>AAGGGTACATTCGCGCAGCTTTCCGAACTCCACTGTGACAAGTTG<br>CACGTAGATCCAGAAAACTTCCGGCTTCTGGGCAATGTGCTTGTAT<br>GCGTTCTGGCTCACCATTTTGGGAAGGAGTTTACCCCACCCGTGCA<br>AGCGGCTTACCAAAAAGTGGTCGCAGGAGTGGCTAATGCCCTTGC<br>ACATAAATATCACTAAGGTACCGAGCATCTTACCGCCATTTATTCC<br>CATATTTGTTCTGTTTTTCTTGATTTGGGTATACATTTAAATGTTAA<br>TAAAACAAAATGGTGGGGCAATCATTTACATTTTTAGGGATATGT<br>AATTACTAGTTCAGGTGTATTGCCACAAGACAAACATGTTAAGAA<br>ACTTTCCCGTTATTTACGCTCTGTTCCTGTTAATCAACCTCTGGATT<br>ACAAAATTTGTGAAAGATTGACTGATATTCTTAACTATGTTGCTCC<br>TTTTACGCTGTGTGGATATGCTGCTTTATAGCCTCTGTATCTAGCTA<br>TTGCTTCCCGTACGGCTTTCGTTTTCTCCTCCTTGTATAAATCCTGG<br>TTGCTGTCTCTTTTAGAGGAGTTGTGGCCCGTTGTCCGTCAACGTG<br>GCGTGGTGTGCTCTGTGTTTGCTGACGCAACCCCCACTGGCTGGGG<br>CATTGCCACCACCTGTCAACTCCTTTCTGGGACTTTCGCTTTCCCCC<br>TCCCGATCGCCACGGCAGAACTCATCGCCGCCTGCCTTGCCCGCTG<br>CTGGACAGGGGCTAGGTTGCTGGGCACTGATAATTCCGTGGTGTT<br>GTCTGTGCCTTCTAGTTGCCAGCCATCTGTTGTTTGCCCCTCCCCCG<br>TGCCTTCCTTGACCCTGGAAGGTGCCACTCCCACTGTCCTTTCCTA<br>ATAAAATGAGGAAATTGCATCGCATTGTCTGAGTAGGTGTCATTCT<br>ATTCTGGGGGGTGGGGTGGGGCAGGACAGCAAGGGGGAGGATTG<br>GGAAGACAATAGCAGGCATGCTGGGGATGCGGTGGGCTCTATGGC<br>CGAGATCGAGACCATCCTGGCTAACACAGTGAAACCCCGTCTCTA<br>CTAAAAAAATACAAAAAATTAGCCGGGCTTGGTGGCGGGTGCCTG<br>TAGTCCCAGCTACTATGGAGGCTGAGGCGGGAGAATGGCGTGAAC<br>GCGGGGGGCGGAGCTTGCAGTGAGCAGAGATCAGGGGCCACTGC<br>ACTCCAGCCTGGGCGACAGAGAGAGACTCTGTCTCAAAAAAAAGA<br>AAAAAAAAATTTAGTAGACTAGCTAAAAAAATCCAGAGATAGTTA<br>TTGATGCATATGTAAAAGTCTTCCAATATTTACAAGTACAATGAAA<br>AAAAAATAACCTTGAATTAAGTGTAGAACTCATTGACAATGTTTC<br>AAAGGATGTGAGGGATAAACTAAAATTTGGGCAGTACATGCTGTT<br>CCTGTGTACTTGGAACAGAGGGAGAAAATCTGGGCTGGAAATATT<br>GTTATAGGAGTTAGCACATGAAGGTGACAACTAAATTATTTGGAG<br>TAGATGGAGTCACCAGCACATGTGAATAGTTTTAGAATGAAATGA<br>CCCAAGATAGAACTTTGGAGAGCCCCCAAATTTAAATAAAATCAG<br>TATAAGAGAAGAGGAAGAAACCAAATGGTATACTAGTCTAAATTG<br>TTTCTTAGTGACAAAAGAATAACCTGAATATTAGATTAGCTGCCTA<br>TATGCTCTCTGAATCAATTTCATTCAACATGCAACAGTCCGCGGGA<br>ACAGAGAAACAGGAGAATATGGGCCAAACAGGATATCTGTGGTA<br>AGCAGTTCCTGCCCCGGCTCAGGGCCAAGAACAGTTGGAACAGCA<br>GAATATGGGCCAAACAGGATATCTGTGGTAAGCAGTTCCTGCCCC<br>GGCTCAGGGCCAAGAACAGATGGTCCCCAGATGCGGTCCCGCCCT<br>CAGCAGTTTCTAGAGAACCATCAGATGTTTCCAGGGTGCCCCAAG<br>GACCTGAAATGACCCTGTGCCTTATTTGAACTAACCAATCAGTTCG<br>CTTCTCGCTTCTGTTCGCGCGCTTCTGCTCCCCGAGCTCTATATAAG |

-continued

| SEQ ID NO | NAME | SEQUENCE |
|---|---|---|
| | | CAGAGCTCGTTTAGTGAACCGTCAGATCGCCTGGAGACGCCATCC |
| | | ACGCTGTTTTGACTTCCATAGAAGGCGGCCGCGCCGCCACCATGG |
| | | TGAGCAAGGGCGAGGAGCTGTTCACCGGGGTGGTGCCCATCCTGG |
| | | TCGAGCTGGACGGCGACGTAAACGGCCACAAGTTCAGCGTGTCCG |
| | | GCGAGGGCGAGGGCGATGCCACCTACGGCAAGCTGACCCTGAAGT |
| | | TCATCTGCACCACCGGCAAGCTGCCCGTGCCCTGGCCCACCCTCGT |
| | | GACCACCCTGACCTACGGCGTGCAGTGCTTCAGCCGCTACCCCGA |
| | | CCACATGAAGCAGCACGACTTCTTCAAGTCCGCCATGCCCGAAGG |
| | | CTACGTCCAGGAGCGCACCATCTTCTTCAAGGACGACGGCAACTA |
| | | CAAGACCCGCGCCGAGGTGAAGTTCGAGGGCGACACCCTGGTGAA |
| | | CCGCATCGAGCTGAAGGGCATCGACTTCAAGGAGGACGGCAACAT |
| | | CCTGGGGCACAAGCTGGAGTACAACTACAACAGCCACAACGTCTA |
| | | TATCATGGCCGACAAGCAGAAGAACGGCATCAAGGTGAACTTCAA |
| | | GATCCGCCACAACATCGAGGACGGCAGCGTGCAGCTCGCCGACCA |
| | | CTACCAGCAGAACACCCCCATCGGCGACGGCCCCGTGCTGCTGCC |
| | | CGACAACCACTACCTGAGCACCCAGTCCGCCCTGAGCAAAGACCC |
| | | CAACGAGAAGCGCGATCACATGGTCCTGCTGGAGTTCGTGACCGC |
| | | CGCCGGGATCACTCTCGGCATGGACGAGCTGTACAAGTAAGCTTT |
| | | ATTTGTGAAATTTGTGATGCTATTGCTTTATTTGTAACCATTATAAG |
| | | CTGCAATAAACAAGTTAACAACAACAATTGCATTCATTTTATGTTT |
| | | CAGGTTCAGGGGGAGATGTGGGAGGTTTTTTAAAGCCCTGCAGGA |
| | | TGGGTCATTTCACAGAGGAGGACAAGGCTACTATCACAAGCCTGT |
| | | GGGGCAAGGTGAATGTGGAAGATGCTGGAGGAGAAACCCTGGGA |
| | | AGGTAGGCTCTGGTGACCAGGACAAGGGAGGGAAGGAAGGACCC |
| | | TGTGCCTGGCAAAAGTCCAGGTCGCTTCTCAGGATTTGTGGCACCT |
| | | TCTGACTGTCAAACTGTTCTTGTCAATCTCACAGGCTCCTGGTTGT |
| | | CTACCCATGGACCCAGAGGTTCTTTGACAGCTTTGGCAACCTGTCC |
| | | TCTGCCTCTGCCATCATGGGCAACCCCAAAGTCAAGGCACATGGC |
| | | AAGAAGGTGCTGACTTCCTTGGGAGATGCCACAAAGCACCTGGAT |
| | | GATCTCAAGGGCACCTTTGCCCAGCTGAGTGAACTGCAGTCGACG |
| | | TAGATAAGTAGCATGGCGGGTTAATCATTAACTACAAGGAACCCC |
| | | TAGTGATGGAGTTGGCCACTCCCTCTCTGCGCGCTCGCTCGCTCAC |
| | | TGAGGCCGGGCGACCAAAGGTCGCCCGACGCCCGGGCTTTGCCCG |
| | | GGCGGCCTCAGTGAGCGAGCGAGCGCGCCAGCTGGCGTAATAGCG |
| | | AAGAGGCCCGCACCGATCGCCCTTCCCAACAGTTGCGCAGCCTGA |
| | | ATGGCGAATGGCGATTCCGTTGCAATGGCTGGCGGTAATATTGTTC |
| | | TGGATATTACCAGCAAGGCCGATAGTTTGAGTTCTTCTACTCAGGC |
| | | AAGTGATGTTATTACTAATCAAAGAAGTATTGCGACAACGGTTAA |
| | | TTTGCGTGATGGACAGACTCTTTTACTCGGTGGCCTCACTGATTAT |
| | | AAAAACACTTCTCAGGATTCTGGCGTACCGTTCCTGTCTAAAATCC |
| | | CTTTAATCGGCCTCCTGTTTAGCTCCCGCTCTGATTCTAACGAGGA |
| | | AAGCACGTTATACGTGCTCGTCAAAGCAACCATAGTACGCGCCCT |
| | | GTAGCGGCGCATTAAGCGCGGCGGGTGTGGTGGTTACGCGCAGCG |
| | | TGACCGCTACACTTGCCAGCGCCCTAGCGCCCGCTCCTTTCGCTTT |
| | | CTTCCCTTCCTTTCTCGCCACGTTCGCCGGCTTTCCCCGTCAAGCTC |
| | | TAAATCGGGGGCTCCCTTTAGGGTTCCGATTTAGTGCTTTACGGCA |
| | | CCTCGACCCCAAAAAACTTGATTAGGGTGATGGTTCACGTAGTGG |
| | | GCCATCGCCCTGATAGACGGTTTTTCGCCCTTTGACGTTGGAGTCC |
| | | ACGTTCTTTAATAGTGGACTCTTGTTCCAAACTGGAACAACACTCA |
| | | ACCCTATCTCGGTCTATTCTTTTGATTTATAAGGGATTTTGCCGATT |
| | | TCGGCCTATTGGTTAAAAAATGAGCTGATTTAACAAAAATTTAAC |
| | | GCGAATTTTAACAAAATATTAACGTTTACAATTTAAATATTTGCTT |
| | | ATACAATCTTCCTGTTTTTGGGGCTTTTCTGATTATCAACCGGGGT |
| | | ACATATGATTGACATGCTAGTTTTACGATTACCGTTCATCGATTCT |
| | | CTTGTTTGCTCCAGACTCTCAGGCAATGACCTGATAGCCTTTGTAG |
| | | AGACCTCTCAAAAATAGCTACCCTCTCCGGCATGAATTTATCAGCT |
| | | AGAACGGTTGAATATCATATTGATGGTGATTTGACTGTCTCCGGCC |
| | | TTTCTCACCCGTTTGAATCTTTACCTACACATTACTCAGGCATTGC |
| | | ATTTAAAATATATGAGGGTTCTAAAAATTTTTATCCTTGCGTTGAA |
| | | ATAAAGGCTTCTCCCGCAAAAGTATTACAGGGTCATAATGTTTTTG |
| | | GTACAACCGATTTAGCTTTATGCTCTGAGGCTTTATTGCTTAATTTT |
| | | GCTAATTCTTTGCCTTGCCTGTATGATTTATTGGATGTTGGAATCG |
| | | CCTGATGCGGTATTTTCTCCTTACGCATCTGTGCGGTATTTCACAC |
| | | CGCATATGGTGCACTCTCAGTACAATCTGCTCTGATGCCGCATAGT |
| | | TAAGCCAGCCCCGACACCCGCCAACACCCGCTGACGCGCCCTGAC |
| | | GGGCTTGTCTGCTCCCGGCATCCGCTTACAGACAAGCTGTGACCGT |
| | | CTCCGGGAGCTGCATGTGTCAGAGGTTTTCACCGTCATCACCGAA |
| | | ACGCGCGAGACGAAAGGGCCTCGTGATACGCCTATTTTTATAGGT |
| | | TAATGTCATGATAATAATGGTTTCTTAGACGTCAGGTGGCACTTTT |
| | | CGGGGAAATGTGCGCGGAACCCCTATTTGTTTATTTTTCTAAATAC |
| | | ATTCAAATATGTATCCGCTCATGAGACAATAACCCTGATAAATGCT |
| | | TCAATAATATTGAAAAAGGAAGAGTATGAGTATTCAACATTTCCG |
| | | TGTCGCCCTTATTCCCTTTTTTGCGGCATTTTGCCTTCCTGTTTTTGC |
| | | TCACCCAGAAACGCTGGTGAAAGTAAAAGATGCTGAAGATCAGTT |
| | | GGGTGCACGAGTGGGTTACATCGAACTGGATCTCAACAGCGGTAA |

-continued

| SEQ ID NO | NAME | SEQUENCE |
|---|---|---|
| | | GATCCTTGAGAGTTTTCGCCCCGAAGAACGTTTTCCAATGATGAGC |
| | | ACTTTTAAAGTTCTGCTATGTGGCGCGGTATTATCCCGTATTGACG |
| | | CCGGGCAAGAGCAACTCGGTCGCCGCATACACTATTCTCAGAATG |
| | | ACTTGGTTGAGTACTCACCAGTCACAGAAAAGCATCTTACGGATG |
| | | GCATGACAGTAAGAGAATTATGCAGTGCTGCCATAACCATGAGTG |
| | | ATAACACTGCGGCCAACTTACTTCTGACAACGATCGGAGGACCGA |
| | | AGGAGCTAACCGCTTTTTTGCACAACATGGGGGATCATGTAACTC |
| | | GCCTTGATCGTTGGGAACCGGAGCTGAATGAAGCCATACCAAACG |
| | | ACGAGCGTGACACCACGATGCCTGTAGCAATGGCAACAACGTTGC |
| | | GCAAACTATTAACTGGCGAACTACTTACTCTAGCTTCCCGGCAACA |
| | | ATTAATAGACTGGATGGAGGCGGATAAAGTTGCAGGACCACTTCT |
| | | GCGCTCGGCCCTTCCGGCTGGCTGGTTTATTGCTGATAAATCTGGA |
| | | GCCGGTGAGCGTGGGTCTCGCGGTATCATTGCAGCACTGGGGCCA |
| | | GATGGTAAGCCCTCCCGTATCGTAGTTATCTACACGACGGGGAGT |
| | | CAGGCAACTATGGATGAACGAAATAGACAGATCGCTGAGATAGGT |
| | | GCCTCACTGATTAAGCATTGGTAACTGTCAGACCAAGTTTACTCAT |
| | | ATATACTTTAGATTGATTTAAAACTTCATTTTTAATTTAAAAGGAT |
| | | CTAGGTGAAGATCCTTTTTGATAATCTCATGACCAAAATCCCTTAA |
| | | CGTGAGTTTTCGTTCCACTGAGCGTCAGACCCCGTAGAAAAGATC |
| | | AAAGGATCTTCTTGAGATCCTTTTTTTCTGCGCGTAATCTGCTGCTT |
| | | GCAAACAAAAAAACCACCGCTACCAGCGGTGGTTTGTTTGCCGGA |
| | | TCAAGAGCTACCAACTCTTTTTCCGAAGGTAACTGGCTTCAGCAGA |
| | | GCGCAGATACCAAATACTGTCCTTCTAGTGTAGCCGTAGTTAGGCC |
| | | ACCACTTCAAGAACTCTGTAGCACCGCCTACATACCTCGCTCTGCT |
| | | AATCCTGTTACCAGTGGCTGCTGCCAGTGGCGATAAGTCGTGTCTT |
| | | ACCGGGTTGGACTCAAGACGATAGTTACCGGATAAGGCGCAGCGG |
| | | TCGGGCTGAACGGGGGGTTCGTGCACACAGCCCAGCTTGGAGCGA |
| | | ACGACCTACACCGAACTGAGATACCTACAGCGTGAGCTATGAGAA |
| | | AGCGCCACGCTTCCCGAAGGGAGAAAGGCGGACAGGTATCCGGT |
| | | AAGCGGCAGGGTCGGAACAGGAGAGCGCACGAGGGAGCTTCCAG |
| | | GGGGAAACGCCTGGTATCTTTATAGTCCTGTCGGGTTTCGCCACCT |
| | | CTGACTTGAGCGTCGATTTTTGTGATGCTCGTCAGGGGGGCGGAG |
| | | CCTATGGAAAAACGCCAGCAACGCGGCCTTTTTACGGTTCCTGGC |
| | | CTTTTGCTGGCCTTTTGCTCACATGTTCTTTCCTGCGTTATCCCCTG |
| | | ATTCTGTGGATAACCGTATTACCGCCTTTGAGTGAGCTGATACCGC |
| | | TCGCCGCAGCCGAACGACCGAGCGCAGCGAGTCAGTGAGCGAGG |
| | | AAGCGGAAGAGCGCCCAATACGCAAACCGCCTCTCCCCGCGCGTT |
| | | GGCCGATTCATTAATG |
| 37 | HBG1 Round 1 & 2: | CAGCTGCGCGCTCGCTCGCTCACTGAGGCCGCCCGGGCAAAGCCC |
| | AMS#1324 | GGGCGTCGGGCGACCTTTGGTCGCCCGGCCTCAGTGAGCGAGCGA |
| | pAAV | GCGCGCAGAGAGGGAGTGGCCAACTCCATCACTAGGGGTTCCTAC |
| | HBG1(11k,900).d13 | GCGTAGATCTTACCCTGTTAATGGTCCAATATGTCAGAAACAGCA |
| | [MND>GFP.SV40pA]; | CTGTGTTAGAAATAAAGCTGTCTAAAGTACACTAATATTCGAGTTA |
| | HPFH2.HS40. | TAATAGTGTGTGGACTATTAGTCAATAAAAACAACCCTTGCCTCTT |
| | HBG1d13p> | TAGAGTTGTTTTCCATGTACACGCACATCTTATGTCTTAGAGTAAG |
| | | ATTCCCTGAGAAGTGAACCTAGCATTTATACAAGATAATTAATTCT |
| | | AATCCACAGTACCTGCCAAAGAACATTCTACCATCATCTTTACTGA |
| | | GCATAGAAGAGCTACGCCAAAACCCTGGGTCATCAGCCAGCACAC |
| | | ACACTTATCCAGTGGTAAATACACATCATCTGGTGTATACATACAT |
| | | ACCTGAATATGGAATCAAATATTTTTCTAAGATGAAACAGTCATG |
| | | ATTTATTTCAAATAGGTACGGATAAGTAGATATTGAGGTAAGCAT |
| | | TAGGTCTTATATTATGTAACACTAATCTATTACTGCGCTGAAACTG |
| | | TGGCTTTATAGAAATTGTTTTCACTGCACTATTGAGAAATTAAGAG |
| | | ATAATGGCAAAAGTCACAAAGAGTATATTCAAAAAGAAGTATAGC |
| | | ACTTTTTCCTTAGAAACCACTGCTAACTGAAAGAGACTAAGATTTG |
| | | TCCCGTCAAAAATCCTGGACCTATGCCTAAAACACATTTCACAATC |
| | | CCTGAACTTTTCAAAAATTGGTACATGCTTTAGCTTTAAACTACAG |
| | | GCCTCACTGGAGCTAGAGACAAGAAGGTAAAAAACGGCTGACAA |
| | | AAGAAGTCCTGGTATCCTCTATGATGGGAGAAGGAAACTAGCTAA |
| | | AGGGAAGAATAAATTAGAGAAAAACTGGAATGACTGAATCGGAA |
| | | CAAGGCAAAGGCTATAAAAAAAATTAGCAGTATCCTCTTGGGGGC |
| | | CCCTTCCCCACACTATCTCAATGCAAATATCTGTCTGAAACGGTCC |
| | | CTGGCTAAACTCCACCCATGGGTTGGCCAGCCTTGCCTTGACCAAT |
| | | AGCCTTGACGAATTCGCTTTAAAAAACCTCCCACATCTCCCCCTGA |
| | | ACCTGAAACATAAAATGAATGCAATTGTTGTTGTTAACTTGTTTAT |
| | | TGCAGCTTATAATGGTTACAAATAAAGCAATAGCATCACAAATTT |
| | | CACAAATAAAGCTTACTTGTACAGCTCGTCCATGCCGAGAGTGAT |
| | | CCCGGCGGCGGTCACGAACTCCAGCAGGACCATGTGATCGCGCTT |
| | | CTCGTTGGGGTCTTTGCTCAGGGCGGACTGGGTGCTCAGGTAGTG |
| | | GTTGTCGGGCAGCAGCACGGGGCCGTCGCCGATGGGGGTGTTCTG |
| | | CTGGTAGTGGTCGGCGAGCTGCACGCTGCCGTCCTCGATGTTGTGG |
| | | CGGATCTTGAAGTTCACCTTGATGCCGTTCTTCTGCTTGTCGGCCA |
| | | TGATATAGACGTTGTGGCTGTTGTAGTTGTACTCCAGCTTGTGCCC |
| | | CAGGATGTTGCCGTCCTCCTTGAAGTCGATGCCCTTCAGCTCGATG |

-continued

| SEQ ID NO | NAME | SEQUENCE |
|---|---|---|
| | | CGGTTCACCAGGGTGTCGCCCTCGAACTTCACCTCGGCGCGGGTCT<br>TGTAGTTGCCGTCGTCCTTGAAGAAGATGGTGCGCTCCTGGACGTA<br>GCCTTCGGGCATGGCGGACTTGAAGAAGTCGTGCTGCTTCATGTG<br>GTCGGGGTAGCGGCTGAAGCACTGCACGCCGTAGGTCAGGGTGGT<br>CACGAGGGTGGGCCAGGGCACGGGCAGCTTGCCGGTGGTGCAGAT<br>GAACTTCAGGGTCAGCTTGCCGTAGGTGGCATCGCCCTCGCCCTCG<br>CCGGACACGCTGAACTTGTGGCCGTTTACGTCGCCGTCCAGCTCGA<br>CCAGGATGGGCACCACCCCGGTGAACAGCTCCTCGCCCTTGCTCA<br>CCATGGTGGCGGCGCGGCCGCGATCTGACGGTTCACTAAACGAGC<br>TCTGCTTATATAGAGCTCGGGGAGCAGAAGCGCGCGAACAGAAGC<br>GAGAAGCGAACTGATTGGTTAGTTCAAATAAGGCACAGGGTCATT<br>TCAGGTCCTTGGGGCACCCTGGAAACATCTGATGGTTCTCTAGAA<br>ACTGCTGAGGGCGGGACCGCATCTGGGGACCATCTGTTCTTGGCC<br>CTGAGCCGGGGCAGGAACTGCTTACCACAGATATCCTGTTTGGCC<br>CATATTCTGCTGTTCCAACTGTTCTTGGCCCTGAGCCGGGGCAGGA<br>ACTGCTTACCACAGATATCCTGTTTGGCCCATATTCTCCTGTTTCTC<br>TGTTCCCGCGGCGAGATCGAGACCATCCTGGCTAACACAGTGAAA<br>CCCCGTCTCTACTAAAAAAATACAAAAAATTAGCCGGGCTTGGTG<br>GCGGGTGCCTGTAGTCCCAGCTACTATGGAGGCTGAGGCGGGAGA<br>ATGGCGTGAACGCGGGGGGCGGAGCTTGCAGTGAGCAGAGATCA<br>GGGGCCACTGCACTCCAGCCTGGGCGACAGAGAGAGACTCTGTCT<br>CAAAAAAAAGAAAAAAAAAAATTTAGTAGACTAGCTAAAAAAATC<br>CAGAGATAGTTATTGATGCATATGTAAAAGTCTTCCAATATTTACA<br>AGTACAATGAAAAAAAAATAACCTTGAATTAAGTGTAGAACTCAT<br>TGACAATGTTTCAAAGGATGTGAGGGATAAACTAAAATTTGGGCA<br>GTACATGCTGTTCCTGTGTACTTGGAACAGAGGGAGAAAATCTGG<br>GCTGGAAATATTGTTATAGGAGTTAGCACATGAAGGTGACAACTA<br>AATTATTTGGAGTAGATGGAGTCACCAGCACATGTGAATAGTTTT<br>AGAATGAAATGACCCAAGATAGAACTTTGGAGAGCCCCCAAATTT<br>AAATAAAATCAGTATAAGAGAAGAGGAAGAAACCAAATGGTATA<br>CTAGTCTAAATTGTTTCTTAGTGACAAAAGAATAACCTGAATATTA<br>GATTAGCTGCCTATATGCTCTCTGAATCAATTTCATTCAACATGCA<br>ACAGTTCTGGAACCTATCAGGGACCACAGTCAGCCAGGCAAGCAC<br>ATCTGCCCAAGCCAAGGGTGGAGGCATGCAGCTGTGGGGGTCTGT<br>GAAAACACTTGAGGGAGCAGATAACTGGGCCAACCATGACTCAGT<br>GCTTCTGGAGGCCAACAGGACTGCTGAGTCATCCTGTGGGGGTGG<br>AGGTGGGACAAGGGAAAGGGGTGAATGGTACTGCTGATTACAAC<br>CTCTGGTGCTGCCTCCCCCTCCTGTTTATCTGAGAGAGGCCTCACT<br>GGAGCTAGAGACAAGAAGGTAAAAAACGGCTGACAAAAGAAGTC<br>CTGGTATCCTCTATGATGGGAGAAGGAAACTAGCTAAAGGGAAGA<br>ATAAATTAGAGAAAAACTGGAATGACTGAATCGGAACAAGGCAA<br>AGGCTATAAAAAAAATTAGCAGTATCCTCTTGGGGGCCCCTTCCC<br>CACACTATCTCAATGCAAATATCTGTCTGAAACGGTCCCTGGCTAA<br>ACTCCACCCATGGGTTGGCCAGCCTTGCCTTGACAAGGCAAACTT<br>GACCAATAGTCTTAGAGTATCCAGTGAGGCCAGGGGCCGGCGGCT<br>GGCTAGGGATGAAGAATAAAAGGAAGCACCCTTCAGCAGTTCCAC<br>ACACTCGCTTCTGGAACGTCTGAGGTTATCAATAAGCTCCTAGTCC<br>AGACGCCATGGGTCATTTCACAGAGGAGGACAAGGCTACTATCAC<br>AAGCCTGTGGGGCAAGGTGAATGTGGAAGATGCTGGAGGAGAAA<br>CCCTGGGAAGGTAGGCTCTGGTGACCAGGACAAGGGAGGGAAGG<br>AAGGACCCTGTGCCTGGCAAAAGTCCAGGTCGCTTCTCAGGATTT<br>GTGGCACCTTCTGACTGTCAAACTGTTCTTGTCAATCTCACAGGCT<br>CCTGGTTGTCTACCCATGGACCCAGAGGTTCTTTGACAGCTTTGGC<br>AACCTGTCCTCTGCCTCTGCCATCATGGGCAACCCCAAAGTCAAG<br>GCACATGGCAAGAAGGTGCTGACTTCCTTGGGAGATGCCACAAAG<br>CACCTGGATGATCTCAAGGGCACCTTTGCCCAGCTGAGTGAACTG<br>CACTGTGACAAGCTGCATGTGGATCCTGAGAACTTCAAGGTGAGT<br>CCAGGAGATGTTTCAGCCCTGTTGCCTTTAGTCTCGAGGCAACTTA<br>GACAACGGAGTATTGATCTGAGCACAGCAGGGTGTGAGCTGTTTG<br>AAGATACTGGGGTTGGGGGTGAAGAAACTGCAGAGGACTAACTG<br>GGCTGAGACCCAGTGGTAATGTTTTAGGGCCTAAGGAGTGCCTCT<br>AAAAATCTAGATGGACAATTTTGACTTTGAGAAAAGAGAGGTGGA<br>AATGAGGAAAATGACTTTTCTTTATTAGATTCCAGTAGAAAGAAC<br>TTTCATCTTTCCCTCATTTTTGTTGTTTTAAAAGTCGACAGGAACCC<br>CTAGTGATGGAGTTGGCCACTCCCTCTCTGCGCGCTCGCTCGCTCA<br>CTGAGGCCGGGCGACCAAAGGTCGCCCGACGCCCGGGCTTTGCCC<br>GGGCGGCCTCAGTGAGCGAGCGAGCGCGCAGCTGGCGTAATAGC<br>GAAGAGGCCCGCACCGATCGCCCTTCCCAACAGTTGCGCAGCCTG<br>AATGGCGAATGGCGATTCCGTTGCAATGGCTGGCGGTAATATTGT<br>TCTGGATATTACCAGCAAGGCCGATAGTTTGAGTTCTTCTACTCAG<br>GCAAGTGATGTTATTACTAATCAAAGAAGTATTGCGACAACGGTT<br>AATTTGCGTGATGGACAGACTCTTTTACTCGGTGGCCTCACTGATT<br>ATAAAAACACTTCTCAGGATTCTGGCGTACCGTTCCTGTCTAAAAT<br>CCCTTTAATCGGCCTCCTGTTTAGCTCCCGCTCTGATTCTAACGAG<br>GAAAGCACGTTATACGTGCTCGTCAAAGCAACCATAGTACGCGCC |

-continued

| SEQ ID NO | NAME | SEQUENCE |
|---|---|---|
| | | CTGTAGCGGCGCATTAAGCGCGGCGGGTGTGGTGGTTACGCGCAG<br>CGTGACCGCTACACTTGCCAGCGCCCTAGCGCCCGCTCCTTTCGCT<br>TTCTTCCCTTCCTTTCTCGCCACGTTCGCCGGCTTTCCCCGTCAAGC<br>TCTAAATCGGGGGCTCCCTTTAGGGTTCCGATTTAGTGCTTTACGG<br>CACCTCGACCCCAAAAAACTTGATTAGGGTGATGGTTCACGTAGT<br>GGGCCATCGCCCTGATAGACGGTTTTTCGCCCTTTGACGTTGGAGT<br>CCACGTTCTTTAATAGTGGACTCTTGTTCCAAACTGGAACAACACT<br>CAACCCTATCTCGGTCTATTCTTTTGATTTATAAGGGATTTTGCCG<br>ATTTCGGCCTATTGGTTAAAAAATGAGCTGATTTAACAAAAATTTA<br>ACGCGAATTTTAACAAAATATTAACGTTTACAATTTAAATATTTGC<br>TTATACAATCTTCCTGTTTTTGGGGCTTTTCTGATTATCAACCGGGG<br>TACATATGATTGACATGCTAGTTTTACGATTACCGTTCATCGATTC<br>TCTTGTTTGCTCCAGACTCTCAGGCAATGACCTGATAGCCTTTGTA<br>GAGACCTCTCAAAAATAGCTACCCTCTCCGGCATGAATTTATCAGC<br>TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA<br>AGGAGCTAACCGCTTTTTTGCACAACATGGGGGATCATGTAACTC<br>GCCTTGATCGTTGGGAACCGGAGCTGAATGAAGCCATACCAAACG<br>ACGAGCGTGACACCACGATGCCTGTAGCAATGGCAACAACGTTGC<br>GCAAACTATTAACTGGCGAACTACTTACTCTAGCTTCCCGGCAACA<br>ATTAATAGACTGGATGGAGGCGGATAAAGTTGCAGGACCACTTCT<br>GCGCTCGGCCCTTCCGGCTGGCTGGTTTATTGCTGATAAATCTGGA<br>GCCGGTGAGCGTGGGTCTCGCGGTATCATTGCAGCACTGGGGCCA<br>GATGGTAAGCCCTCCCGTATCGTAGTTATCTACACGACGGGGAGT<br>CAGGCAACTATGGATGAACGAAATAGACAGATCGCTGAGATAGGT<br>GCCTCACTGATTAAGCATTGGTAACTGTCAGACCAAGTTTACTCAT<br>ATATACTTTAGATTGATTTAAAACTTCATTTTTAATTTAAAAGGAT<br>CTAGGTGAAGATCCTTTTTGATAATCTCATGACCAAAATCCCTTAA<br>CGTGAGTTTTCGTTCCACTGAGCGTCAGACCCCGTAGAAAAGATC<br>AAAGGATCTTCTTGAGATCCTTTTTTTCTGCGCGTAATCTGCTGCTT<br>GCAAACAAAAAAACCACCGCTACCAGCGGTGGTTTGTTTGCCGGA<br>TCAAGAGCTACCAACTCTTTTTCCGAAGGTAACTGGCTTCAGCAGA<br>GCGCAGATACCAAATACTGTCCTTCTAGTGTAGCCGTAGTTAGGCC<br>ACCACTTCAAGAACTCTGTAGCACCGCCTACATACCTCGCTCTGCT<br>AATCCTGTTACCAGTGGCTGCTGCCAGTGGCGATAAGTCGTGTCTT<br>ACCGGGTTGGACTCAAGACGATAGTTACCGGATAAGGCGCAGCGG<br>TCGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACCT<br>CTGACTTGAGCGTCGATTTTTGTGATGCTCGTCAGGGGGGCGGAG<br>CCTATGGAAAAACGCCAGCAACGCGGCCTTTTTACGGTTCCTGGC<br>CTTTTGCTGGCCTTTTGCTCACATGTTCTTTCCTGCGTTATCCCCTG<br>ATTCTGTGGATAACCGTATTACCGCCTTTGAGTGAGCTGATACCGC<br>TCGCCGCAGCCGAACGACCGAGCGCAGCGAGTCAGTGAGCGAGG<br>AAGCGGAAGAGCGCCCAATACGCAAACCGCCTCTCCCCGCGCGTT<br>GGCCGATTCATTAATG |
| 38 | HBG1 Round 1 & 2:<br>AMS#1325<br>pAAV | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC |

-continued

| SEQ ID NO | NAME | SEQUENCE |
|---|---|---|
| | HBG1(7,900).d13<br>[MND>GFP.SV40pA];<br>HPFH2.HS40.<br>HBG1d13p> | GCGTAGATCTTACCCTGTTAATGGTCCAATATGTCAGAAACAGCA<br>CTGTGTTAGAAATAAAGCTGTCTAAAGTACACTAATATTCGAGTTA<br>TAATAGTGTGTGGACTATTAGTCAATAAAAACAACCCTTGCCTCTT<br>TAGAGTTGTTTTCCATGTACACGCACATCTTATGTCTTAGAGTAAG<br>ATTCCCTGAGAAGTGAACCTAGCATTTATACAAGATAATTAATTCT<br>AATCCACAGTACCTGCCAAAGAACATTCTACCATCATCTTTACTGA<br>GCATAGAAGAGCTACGCCAAAACCCTGGGTCATCAGCCAGCACAC<br>ACACTTATCCAGTGGTAAATACACATCATCTGGTGTATACATACAT<br>ACCTGAATATGGAATCAAATATTTTTCTAAGATGAAACAGTCATG<br>ATTTATTTCAAATAGGTACGGATAAGTAGATATTGAGGTAAGCAT<br>TAGGTCTTATATTATGTAACACTAATCTATTACTGCGCTGAAACTG<br>TGGCTTTATAGAAATTGTTTTCACTGCACTATTGAGAAATTAAGAG<br>ATAATGGCAAAAGTCACAAAGAGTATATTCAAAAAGAAGTATAGC<br>ACTTTTTCCTTAGAAACCACTGCTAACTGAAAGAGACTAAGATTTG<br>TCCCGTCAAAAATCCTGGACCTATGCCTAAAACACATTTCACAATC<br>CCTGAACTTTTCAAAAATTGGTACATGCTTTAGCTTTAAACTACGA<br>ATTCGCTTTAAAAAACCTCCCACATCTCCCCCTGAACCTGAAACAT<br>AAAATGAATGCAATTGTTGTTGTTAACTTGTTTATTGCAGCTTATA<br>ATGGTTACAAATAAAGCAATAGCATCACAAATTTCACAAATAAAG<br>CTTACTTGTACAGCTCGTCCATGCCGAGAGTGATCCCGGCGGCGGT<br>CACGAACTCCAGCAGGACCATGTGATCGCGCTTCTCGTTGGGGTCT<br>TTGCTCAGGGCGGACTGGGTGCTCAGGTAGTGGTTGTCGGGCAGC<br>AGCACGGGGCCGTCGCCGATGGGGGTGTTCTGCTGGTAGTGGTCG<br>GCGAGCTGCACGCTGCCGTCCTCGATGTTGTGGCGGATCTTGAAGT<br>TCACCTTGATGCCGTTCTTCTGCTTGTCGGCCATGATATAGACGTT<br>GTGGCTGTTGTAGTTGTACTCCAGCTTGTGCCCCAGGATGTTGCCG<br>TCCTCCTTGAAGTCGATGCCCTTCAGCTCGATGCGGTTCACCAGGG<br>TGTCGCCCTCGAACTTCACCTCGGCGCGGGTCTTGTAGTTGCCGTC<br>GTCCTTGAAGAAGATGGTGCGCTCCTGGACGTAGCCTTCGGGCAT<br>GGCGGACTTGAAGAAGTCGTGCTGCTTCATGTGGTCGGGGTAGCG<br>GCTGAAGCACTGCACGCCGTAGGTCAGGGTGGTCACGAGGGTGGG<br>CCAGGGCACGGGCAGCTTGCCGGTGGTGCAGATGAACTTCAGGGT<br>CAGCTTGCCGTAGGTGGCATCGCCCTCGCCCTCGCCGGACACGCT<br>GAACTTGTGGCCGTTTACGTCGCCGTCCAGCTCGACCAGGATGGG<br>CACCACCCCGGTGAACAGCTCCTCGCCCTTGCTCACCATGGTGGCG<br>GCGCGGCCGCGATCTGACGGTTCACTAAACGAGCTCTGCTTATAT<br>AGAGCTCGGGGAGCAGAAGCGCGCGAACAGAAGCGAGAAGCGAA<br>CTGATTGGTTAGTTCAAATAAGGCACAGGGTCATTTCAGGTCCTTG<br>GGGCACCCTGGAAACATCTGATGGTTCTCTAGAAACTGCTGAGGG<br>CGGGACCGCATCTGGGGACCATCTGTTCTTGGCCCTGAGCCGGGG<br>CAGGAACTGCTTACCACAGATATCCTGTTTGGCCCATATTCTGCTG<br>TTCCAACTGTTCTTGGCCCTGAGCCGGGGCAGGAACTGCTTACCAC<br>AGATATCCTGTTTGGCCCATATTCTCCTGTTTCTCTGTTCCCGCGGC<br>GAGATCGAGACCATCCTGGCTAACACAGTGAAACCCCGTCTCTAC<br>TAAAAAAATACAAAAAATTAGCCGGGCTTGGTGGCGGGTGCCTGT<br>AGTCCCAGCTACTATGGAGGCTGAGGCGGGAGAATGGCGTGAACG<br>CGGGGGGCGGAGCTTGCAGTGAGCAGAGATCAGGGGCCACTGCA<br>CTCCAGCCTGGGCGACAGAGAGAGACTCTGTCTCAAAAAAAAGAA<br>AAAAAAAATTTAGTAGACTAGCTAAAAAAATCCAGAGATAGTTAT<br>TGATGCATATGTAAAAGTCTTCCAATATTTACAAGTACAATGAAA<br>AAAAAATAACCTTGAATTAAGTGTAGAACTCATTGACAATGTTTC<br>AAAGGATGTGAGGGATAAACTAAAATTTGGGCAGTACATGCTGTT<br>CCTGTGTACTTGGAACAGAGGGAGAAAATCTGGGCTGGAAATATT<br>GTTATAGGAGTTAGCACATGAAGGTGACAACTAAATTATTTGGAG<br>TAGATGGAGTCACCAGCACATGTGAATAGTTTTAGAATGAAATGA<br>CCCAAGATAGAACTTTGGAGAGCCCCCAAATTTAAATAAAATCAG<br>TATAAGAGAAGAGGAAGAAACCAAATGGTATACTAGTCTAAATTG<br>TTTCTTAGTGACAAAAGAATAACCTGAATATTAGATTAGCTGCCTA<br>TATGCTCTCTGAATCAATTTCATTCAACATGCAACAGTTCTGGAAC<br>CTATCAGGGACCACAGTCAGCCAGGCAAGCACATCTGCCCAAGCC<br>AAGGGTGGAGGCATGCAGCTGTGGGGGTCTGTGAAAACACTTGAG<br>GGAGCAGATAACTGGGCCAACCATGACTCAGTGCTTCTGGAGGCC<br>AACAGGACTGCTGAGTCATCCTGTGGGGGTGGAGGTGGGACAAGG<br>GAAAGGGGTGAATGGTACTGCTGATTACAACCTCTGGTGCTGCCT<br>CCCCCTCCTGTTTATCTGAGAGAGGCCTCACTGGAGCTAGAGACA<br>AGAAGGTAAAAAACGGCTGACAAAAGAAGTCCTGGTATCCTCTAT<br>GATGGGAGAAGGAAACTAGCTAAAGGGAAGAATAAATTAGAGAA<br>AAACTGGAATGACTGAATCGGAACAAGGCAAAGGCTATAAAAAA<br>AATTAGCAGTATCCTCTTGGGGGCCCCTTCCCCACACTATCTCAAT<br>GCAAATATCTGTCTGAAACGGTCCCTGGCTAAACTCCACCCATGG<br>GTTGGCCAGCCTTGCCTTGACAAGGCAAACTTGACCAATAGTCTTA<br>GAGTATCCAGTGAGGCCAGGGGCCGGCGGCTGGCTAGGGATGAA<br>GAATAAAAGGAAGCACCCTTCAGCAGTTCCACACACTCGCTTCTG<br>GAACGTCTGAGGTTATCAATAAGCTCCTAGTCCAGACGCCATGGG<br>TCATTTCACAGAGGAGGACAAGGCTACTATCACAAGCCTGTGGGG |

-continued

| SEQ ID NO | NAME | SEQUENCE |
|---|---|---|
| | | CAAGGTGAATGTGGAAGATGCTGGAGGAGAAACCCTGGGAAGGT AGGCTCTGGTGACCAGGACAAGGGAGGGAAGGAAGGACCCTGTG CCTGGCAAAAGTCCAGGTCGCTTCTCAGGATTTGTGGCACCTTCTG ACTGTCAAACTGTTCTTGTCAATCTCACAGGCTCCTGGTTGTCTAC CCATGGACCCAGAGGTTCTTTGACAGCTTTGGCAACCTGTCCTCTG CCTCTGCCATCATGGGCAACCCCAAAGTCAAGGCACATGGCAAGA AGGTGCTGACTTCCTTGGGAGATGCCACAAAGCACCTGGATGATC TCAAGGGCACCTTTGCCCAGCTGAGTGAACTGCACTGTGACAAGC TGCATGTGGATCCTGAGAACTTCAAGGTGAGTCCAGGAGATGTTT CAGCCCTGTTGCCTTTAGTCTCGAGGCAACTTAGACAACGGAGTAT TGATCTGAGCACAGCAGGGTGTGAGCTGTTTGAAGATACTGGGGT TGGGGGTGAAGAAACTGCAGAGGACTAACTGGGCTGAGACCCAG TGGTAATGTTTTAGGGCCTAAGGAGTGCCTCTAAAAATCTAGATG GACAATTTTGACTTTGAGAAAAGAGAGGTGGAAATGAGGAAAAT GACTTTTCTTTATTAGATTCCAGTAGAAAGAACTTTCATCTTTCCCT CATTTTTGTTGTTTTAAAAGTCGACAGGAACCCCTAGTGATGGAGT TGGCCACTCCCTCTCTGCGCGCTCGCTCGCTCACTGAGGCCGGGCG ACCAAAGGTCGCCCGACGCCCGGGCTTTGCCCGGGCGGCCTCAGT GAGCGAGCGAGCGCGCAGCTGGCGTAATAGCGAAGAGGCCCGCA CCGATCGCCCTTCCCAACAGTTGCGCAGCCTGAATGGCGAATGGC GATTCCGTTGCAATGGCTGGCGGTAATATTGTTCTGGATATTACCA GCAAGGCCGATAGTTTGAGTTCTTCTACTCAGGCAAGTGATGTTAT TACTAATCAAAGAAGTATTGCGACAACGGTTAATTTGCGTGATGG ACAGACTCTTTTACTCGGTGGCCTCACTGATTATAAAAACACTTCT CAGGATTCTGGCGTACCGTTCCTGTCTAAAATCCCTTTAATCGGCC TCCTGTTTAGCTCCCGCTCTGATTCTAACGAGGAAAGCACGTTATA CGTGCTCGTCAAAGCAACCATAGTACGCGCCCTGTAGCGGCGCAT TAAGCGCGGCGGGTGTGGTGGTTACGCGCAGCGTGACCGCTACAC TTGCCAGCGCCCTAGCGCCCGCTCCTTTCGCTTTCTTCCCTTCCTTT CTCGCCACGTTCGCCGGCTTTCCCCGTCAAGCTCTAAATCGGGGGC TCCCTTTAGGGTTCCGATTTAGTGCTTTACGGCACCTCGACCCCAA AAAACTTGATTAGGGTGATGGTTCACGTAGTGGGCCATCGCCCTG ATAGACGGTTTTTCGCCCTTTGACGTTGGAGTCCACGTTCTTTAAT AGTGGACTCTTGTTCCAAACTGGAACAACACTCAACCCTATCTCGG TCTATTCTTTTGATTTATAAGGGATTTTGCCGATTTCGGCCTATTGG TTAAAAAATGAGCTGATTTAACAAAAATTTAACGCGAATTTTAAC AAAATATTAACGTTTACAATTTAAATATTTGCTTATACAATCTTCC TGTTTTTGGGGCTTTTCTGATTATCAACCGGGGTACATATGATTGA CATGCTAGTTTTACGATTACCGTTCATCGATTCTCTTGTTTGCTCCA GACTCTCAGGCAATGACCTGATAGCCTTTGTAGAGACCTCTCAAA AATAGCTACCCTCTCCGGCATGAATTTATCAGCTAGAACGGTTGA ATATCATATTGATGGTGATTTGACTGTCTCCGGCCTTTCTCACCCG TTTGAATCTTTACCTACACATTACTCAGGCATTGCATTTAAAATAT ATGAGGGTTCTAAAAATTTTTATCCTTGCGTTGAAATAAAGGCTTC TCCCGCAAAAGTATTACAGGGTCATAATGTTTTTGGTACAACCGAT TTAGCTTTATGCTCTGAGGCTTTATTGCTTAATTTTGCTAATTCTTT GCCTTGCCTGTATGATTTATTGGATGTTGGAATCGCCTGATGCGGT ATTTTCTCCTTACGCATCTGTGCGGTATTTCACACCGCATATGGTG CACTCTCAGTACAATCTGCTCTGATGCCGCATAGTTAAGCCAGCCC CGACACCCGCCAACACCCGCTGACGCGCCCTGACGGGCTTGTCTG CTCCCGGCATCCGCTTACAGACAAGCTGTGACCGTCTCCGGGAGC TGCATGTGTCAGAGGTTTTCACCGTCATCACCGAAACGCGCGAGA CGAAAGGGCCTCGTGATACGCCTATTTTTATAGGTTAATGTCATGA TAATAATGGTTTCTTAGACGTCAGGTGGCACTTTTCGGGGAAATGT GCGCGGAACCCCTATTTGTTTATTTTTCTAAATACATTCAAATATG TATCCGCTCATGAGACAATAACCCTGATAAATGCTTCAATAATATT GAAAAAGGAAGAGTATGAGTATTCAACATTTCCGTGTCGCCCTTA TTCCCTTTTTTGCGGCATTTTGCCTTCCTGTTTTTGCTCACCCAGAA ACGCTGGTGAAAGTAAAAGATGCTGAAGATCAGTTGGGTGCACGA GTGGGTTACATCGAACTGGATCTCAACAGCGGTAAGATCCTTGAG AGTTTTCGCCCCGAAGAACGTTTTCCAATGATGAGCACTTTTAAAG TTCTGCTATGTGGCGCGGTATTATCCCGTATTGACGCCGGGCAAGA GCAACTCGGTCGCCGCATACACTATTCTCAGAATGACTTGGTTGAG TACTCACCAGTCACAGAAAAGCATCTTACGGATGGCATGACAGTA AGAGAATTATGCAGTGCTGCCATAACCATGAGTGATAACACTGCG GCCAACTTACTTCTGACAACGATCGGAGGACCGAAGGAGCTAACC GCTTTTTTGCACAACATGGGGGATCATGTAACTCGCCTTGATCGTT GGGAACCGGAGCTGAATGAAGCCATACCAAACGACGAGCGTGAC ACCACGATGCCTGTAGCAATGGCAACAACGTTGCGCAAACTATTA ACTGGCGAACTACTTACTCTAGCTTCCCGGCAACAATTAATAGACT GGATGGAGGCGGATAAAGTTGCAGGACCACTTCTGCGCTCGGCCC TTCCGGCTGGCTGGTTTATTGCTGATAAATCTGGAGCCGGTGAGCG TGGGTCTCGCGGTATCATTGCAGCACTGGGGCCAGATGGTAAGCC CTCCCGTATCGTAGTTATCTACACGACGGGGAGTCAGGCAACTAT GGATGAACGAAATAGACAGATCGCTGAGATAGGTGCCTCACTGAT |

-continued

| SEQ ID NO | NAME | SEQUENCE |
|---|---|---|
| | | TAAGCATTGGTAACTGTCAGACCAAGTTTACTCATATATACTTTAG ATTGATTTAAAACTTCATTTTTAATTTAAAAGGATCTAGGTGAAGA TCCTTTTTGATAATCTCATGACCAAAATCCCTTAACGTGAGTTTTC GTTCCACTGAGCGTCAGACCCCGTAGAAAAGATCAAAGGATCTTC TTGAGATCCTTTTTTTCTGCGCGTAATCTGCTGCTTGCAAACAAAA AAACCACCGCTACCAGCGGTGGTTTGTTTGCCGGATCAAGAGCTA CCAACTCTTTTTCCGAAGGTAACTGGCTTCAGCAGAGCGCAGATA CCAAATACTGTCCTTCTAGTGTAGCCGTAGTTAGGCCACCACTTCA AGAACTCTGTAGCACCGCCTACATACCTCGCTCTGCTAATCCTGTT ACCAGTGGCTGCTGCCAGTGGCGATAAGTCGTGTCTTACCGGGTT GGACTCAAGACGATAGTTACCGGATAAGGCGCAGCGGTCGGGCTG AACGGGGGGTTCGTGCACACAGCCCAGCTTGGAGCGAACGACCTA CACCGAACTGAGATACCTACAGCGTGAGCTATGAGAAAGCGCCAC GCTTCCCGAAGGGAGAAAGGCGGACAGGTATCCGGTAAGCGGCA GGGTCGGAACAGGAGAGCGCACGAGGGAGCTTCCAGGGGGAAAC GCCTGGTATCTTTATAGTCCTGTCGGGTTTCGCCACCTCTGACTTG AGCGTCGATTTTTGTGATGCTCGTCAGGGGGGCGGAGCCTATGGA AAAACGCCAGCAACGCGGCCTTTTTACGGTTCCTGGCCTTTTGCTG GCCTTTTGCTCACATGTTCTTTCCTGCGTTATCCCCTGATTCTGTGG ATAACCGTATTACCGCCTTTGAGTGAGCTGATACCGCTCGCCGCAG CCGAACGACCGAGCGCAGCGAGTCAGTGAGCGAGGAAGCGGAAG AGCGCCCAATACGCAAACCGCCTCTCCCCGCGCGTTGGCCGATTC ATTAATG |
| 39 | HBG1 Round 1 & 2: AMS#1323 pAAV HBG1d-141,-1(459,600) [MND>GFP.wPRE3. SV40USE.pA]; HPFH-2.HS40.HBBp> | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TAGAAATTGTTTTCACTGCACTATTGAGAAATTAAGAGATAATGG CAAAAGTCACAAAGAGTATATTCAAAAAGAAGTATAGCACTTTTT CCTTAGAAACCACTGCTAACTGAAAGAGACTAAGATTTGTCCCGT CAAAAATCCTGGACCTATGCCTAAAACACATTTCACAATCCCTGA ACTTTTCAAAAATTGGTACATGCTTTAGCTTTAAACTACAGGCCTC ACTGGAGCTAGAGACAAGAAGGTAAAAAACGGCTGACAAAAGAA GTCCTGGTATCCTCTATGATGGGAGAAGGAAACTAGCTAAAGGGA AGAATAAATTAGAGAAAAACTGGAATGACTGAATCGGAACAAGG CAAAGGCTATAAAAAAAAATTAGCAGTATCCTCTTGGGGGCCCCTT CCCCACACTATCTCAATGCAAATATCTGTCTGAAACGGTCCCTGGC TAAACTCCACCCGCGGGCTTTAAAAAACCTCCCACATCTCCCCCTG AACCTGAAACATAAAATGAATGCAATTGTTGTTGTTAACTTGTTTA TTGCAGCTTATAATGGTTACAAATAAAGCAATAGCATCACAAATT TCACAAATAAAGCTAGAATGGTTACAAATAAAGCAATAGCATCAC AAATTTCACAAATAAACACCACGGAATTGTCAGTGCCCAACAGCC GAGCCCCTGTCCAGCAGCGGGCAAGGCAGGCGGCGATGAGTTCCG CCGTGGCAAGAACTAACCAGGATTTATACAAGGAGGAGAAAATG AAAGCCATACGGGAAGCAATAGCATGATACAAAGGCATTAAAGC AGCGTATCCACATAGCGTAAAAGGAGCAACATAGTTAAGAATACC AGTCAATCTTTCACAAATTTTGTAATCCAGAGGTTGATTATCCCTG CAGGTTACTTGTACAGCTCGTCCATGCCGAGAGTGATCCCGGCGG CGGTCACGAACTCCAGCAGGACCATGTGATCGCGCTTCTCGTTGG GGTCTTTGCTCAGGGCGGACTGGGTGCTCAGGTAGTGGTTGTCGG GCAGCAGCACGGGGCCGTCGCCGATGGGGGTGTTCTGCTGGTAGT GGTCGGCGAGCTGCACGCTGCCGTCCTCGATGTTGTGGCGGATCTT GAAGTTCACCTTGATGCCGTTCTTCTGCTTGTCGGCCATGATATAG ACGTTGTGGCTGTTGTAGTTGTACTCCAGCTTGTGCCCCAGGATGT TGCCGTCCTCCTTGAAGTCGATGCCCTTCAGCTCGATGCGGTTCAC CAGGGTGTCGCCCTCGAACTTCACCTCGGCGCGGGTCTTGTAGTTG CCGTCGTCCTTGAAGAAGATGGTGCGCTCCTGGACGTAGCCTTCG GGCATGGCGGACTTGAAGAAGTCGTGCTGCTTCATGTGGTCGGGG TAGCGGCTGAAGCACTGCACGCCGTAGGTCAGGGTGGTCACGAGG GTGGGCCAGGGCACGGGCAGCTTGCCGGTGGTGCAGATGAACTTC AGGGTCAGCTTGCCGTAGGTGGCATCGCCCTCGCCCTCGCCGGAC ACGCTGAACTTGTGGCCGTTTACGTCGCCGTCCAGCTCGACCAGG ATGGGCACCACCCCGGTGAACAGCTCCTCGCCCTTGCTCACCATG GTGGCGGCGCGGCCGCCTTCTATGGAAGTCAAAACAGCGTGGATG GCGTCTCCAGGCGATCTGACGGTTCACTAAACGAGCTCTGCTTATA TAGAGCTCGGGGAGCAGAAGCGCGCGAACAGAAGCGAGAAGCGA ACTGATTGGTTAGTTCAAATAAGGCACAGGGTCATTTCAGGTCCTT GGGGCACCCTGGAAACATCTGATGGTTCTCTAGAAACTGCTGAGG GCGGGACCGCATCTGGGGACCATCTGTTCTTGGCCCTGAGCCGGG GCAGGAACTGCTTACCACAGATATCCTGTTTGGCCCATATTCTGCT GTTCCAACTGTTCTTGGCCCTGAGCCGGGGCAGGAACTGCTTACCA CAGATATCCTGTTTGGCCCATATTCTCCTGTTTCTCTGTTCGAATTC CGAGATCGAGACCATCCTGGCTAACACAGTGAAACCCCGTCTCTA CTAAAAAAATACAAAAAATTAGCCGGGCTTGGTGGCGGGTGCCTG |

-continued

| SEQ ID NO | NAME | SEQUENCE |
|---|---|---|
| | | TAGTCCCAGCTACTATGGAGGCTGAGGCGGGAGAATGGCGTGAAC<br>GCGGGGGGCGGAGCTTGCAGTGAGCAGAGATCAGGGGCCACTGC<br>ACTCCAGCCTGGGCGACAGAGAGAGACTCTGTCTCAAAAAAAAGA<br>AAAAAAAAATTTAGTAGACTAGCTAAAAAAATCCAGAGATAGTTA<br>TTGATGCATATGTAAAGTCTTCCAATATTTACAAGTACAATGAAA<br>AAAAAATAACCTTGAATTAAGTGTAGAACTCATTGACAATGTTTC<br>AAAGGATGTGAGGGATAAACTAAAATTTGGGCAGTACATGCTGTT<br>CCTGTGTACTTGGAACAGAGGGAGAAAATCTGGGCTGGAAATATT<br>GTTATAGGAGTTAGCACATGAAGGTGACAACTAAATTATTTGGAG<br>TAGATGGAGTCACCAGCACATGTGAATAGTTTTAGAATGAAATGA<br>CCCAAGATAGAACTTTGGAGAGCCCCCAAATTTAAATAAAATCAG<br>TATAAGAGAAGAGGAAGAAACCAAATGGTATACTAGTCTAAATTG<br>TTTCTTAGTGACAAAAGAATAACCTGAATATTAGATTAGCTGCCTA<br>TATGCTCTCTGAATCAATTTCATTCAACATGCAACAGTTCTGGAAC<br>CTATCAGGGACCACAGTCAGCCAGGCAAGCACATCTGCCCAAGCC<br>AAGGGTGGAGGCATGCAGCTGTGGGGGTCTGTGAAAACACTTGAG<br>GGAGCAGATAACTGGGCCAACCATGACTCAGTGCTTCTGGAGGCC<br>AACAGGACTGCTGAGTCATCCTGTGGGGGTGGAGGTGGGACAAGG<br>GAAAGGGGTGAATGGTACTGCTGATTACAACCTCTGGTGCTGCCT<br>CCCCCTCCTGTTTATCTGAGAGGCTAGCGTAAATACACTTGCAAAG<br>GAGGATGTTTTTAGTAGCAATTTGTACTGATGGTATGGGGCCAAG<br>AGATATATCTTAGAGGGAGGGCTGAGGGTTTGAAGTCCAACTCCT<br>AAGCCAGTGCCAGAAGAGCCAAGGACAGGTACGGCTGTCATCACT<br>TAGACCTCACCCTGTGGAGCCACACCCTAGGGTTGGCCAATCTACT<br>CCCAGGAGCAGGGAGGGCAGGAGCCAGGGCTGGGCATAAAAGTC<br>AGGGCAGAGCCATCTATTGCTTACACTCGCTTCTGGAACGTCTGAG<br>GTTATCAATAAGCTCCTAGTCCAGACGCCATGGGTCATTTCACAGA<br>GGAGGACAAGGCTACTATCACAAGCCTGTGGGGCAAGGTGAATGT<br>GGAAGATGCTGGAGGAGAAACCCTGGGAAGGTAGGCTCTGGTGA<br>CCAGGACAAGGGAGGGAAGGAAGGACCCTGTGCCTGGCAAAAGT<br>CCAGGTCGCTTCTCAGGATTTGTGGCACCTTCTGACTGTCAAACTG<br>TTCTTGTCAATCTCACAGGCTCCTGGTTGTCTACCCATGGACCCAG<br>AGGTTCTTTGACAGCTTTGGCAACCTGTCCTCTGCCTCTGCCATCA<br>TGGGCAACCCCAAAGTCAAGGCACATGGCAAGAAGGTGCTGACTT<br>CCTTGGGAGATGCCACAAAGCACCTGGATGATCTCAAGGGCACCT<br>TTGCCCAGCTGAGTGAACTGCACTGTGACAAGCTGCATGTGGATC<br>CTGAGAACTTCAAGGTGAGTCCAGGAGATGTTTCAGCCCTGTTGC<br>CTTTAGTCTCGAGGCAACTTAGACAACGGAGTATTGATCTGAGCA<br>CAGCAGGGTGTGAGCTGTTTGAAGATACTGGGGTCTCGAGGTCGA<br>CGTAGATAAGTAGCATGGCGGGTTAATCATTAACTACAAGGAACC<br>CCTAGTGATGGAGTTGGCCACTCCCTCTCTGCGCGCTCGCTCGCTC<br>ACTGAGGCCGGGCGACCAAAGGTCGCCCGACGCCCGGGCTTTGCC<br>CGGGCGGCCTCAGTGAGCGAGCGAGCGCGCCAGCTGGCGTAATAG<br>CGAAGAGGCCCGCACCGATCGCCCTTCCCAACAGTTGCGCAGCCT<br>GAATGGCGAATGGCGATTCCGTTGCAATGGCTGGCGGTAATATTG<br>TTCTGGATATTACCAGCAAGGCCGATAGTTTGAGTTCTTCTACTCA<br>GGCAAGTGATGTTATTACTAATCAAAGAAGTATTGCGACAACGGT<br>TAATTTGCGTGATGGACAGACTCTTTTACTCGGTGGCCTCACTGAT<br>TATAAAAACACTTCTCAGGATTCTGGCGTACCGTTCCTGTCTAAAA<br>TCCCTTTAATCGGCCTCCTGTTTAGCTCCCGCTCTGATTCTAACGA<br>GGAAAGCACGTTATACGTGCTCGTCAAAGCAACCATAGTACGCGC<br>CCTGTAGCGGCGCATTAAGCGCGGCGGGTGTGGTGGTTACGCGCA<br>GCGTGACCGCTACACTTGCCAGCGCCCTAGCGCCCGCTCCTTTCGC<br>TTTCTTCCCTTCCTTTCTCGCCACGTTCGCCGGCTTTCCCCGTCAAG<br>CTCTAAATCGGGGGCTCCCTTTAGGGTTCCGATTTAGTGCTTTACG<br>GCACCTCGACCCCAAAAAACTTGATTAGGGTGATGGTTCACGTAG<br>TGGGCCATCGCCCTGATAGACGGTTTTTCGCCCTTTGACGTTGGAG<br>TCCACGTTCTTTAATAGTGGACTCTTGTTCCAAACTGGAACAACAC<br>TCAACCCTATCTCGGTCTATTCTTTTGATTTATAAGGGATTTTGCCG<br>ATTTCGGCCTATTGGTTAAAAAATGAGCTGATTTAACAAAAATTTA<br>ACGCGAATTTTAACAAAATATTAACGTTTACAATTTAAATATTTGC<br>TTATACAATCTTCCTGTTTTTGGGGCTTTTCTGATTATCAACCGGGG<br>TACATATGATTGACATGCTAGTTTTACGATTACCGTTCATCGATTC<br>TCTTGTTTGCTCCAGACTCTCAGGCAATGACCTGATAGCCTTTGTA<br>GAGACCTCTCAAAAATAGCTACCCTCTCCGGCATGAATTTATCAGC<br>TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT |

-continued

| SEQ ID NO | NAME | SEQUENCE |
|---|---|---|
| | | CTCCGGGAGCTGCATGTGTCAGAGGTTTTCACCGTCATCACCGAA |
| | | ACGCGCGAGACGAAAGGGCCTCGTGATACGCCTATTTTTATAGGT |
| | | TAATGTCATGATAATAATGGTTTCTTAGACGTCAGGTGGCACTTTT |
| | | CGGGGAAATGTGCGCGGAACCCCTATTTGTTTATTTTTCTAAATAC |
| | | ATTCAAATATGTATCCGCTCATGAGACAATAACCCTGATAAATGCT |
| | | TCAATAATATTGAAAAAGGAAGAGTATGAGTATTCAACATTTCCG |
| | | TGTCGCCCTTATTCCCTTTTTTGCGGCATTTTGCCTTCCTGTTTTTGC |
| | | TCACCCAGAAACGCTGGTGAAAGTAAAAGATGCTGAAGATCAGTT |
| | | GGGTGCACGAGTGGGTTACATCGAACTGGATCTCAACAGCGGTAA |
| | | GATCCTTGAGAGTTTTCGCCCCGAAGAACGTTTTCCAATGATGAGC |
| | | ACTTTTAAAGTTCTGCTATGTGGCGCGGTATTATCCCGTATTGACG |
| | | CCGGGCAAGAGCAACTCGGTCGCCGCATACACTATTCTCAGAATG |
| | | ACTTGGTTGAGTACTCACCAGTCACAGAAAAGCATCTTACGGATG |
| | | GCATGACAGTAAGAGAATTATGCAGTGCTGCCATAACCATGAGTG |
| | | ATAACACTGCGGCCAACTTACTTCTGACAACGATCGGAGGACCGA |
| | | AGGAGCTAACCGCTTTTTTGCACAACATGGGGGATCATGTAACTC |
| | | GCCTTGATCGTTGGGAACCGGAGCTGAATGAAGCCATACCAAACG |
| | | ACGAGCGTGACACCACGATGCCTGTAGCAATGGCAACAACGTTGC |
| | | GCAAACTATTAACTGGCGAACTACTTACTCTAGCTTCCCGGCAACA |
| | | ATTAATAGACTGGATGGAGGCGGATAAAGTTGCAGGACCACTTCT |
| | | GCGCTCGGCCCTTCCGGCTGGCTGGTTTATTGCTGATAAATCTGGA |
| | | GCCGGTGAGCGTGGGTCTCGCGGTATCATTGCAGCACTGGGGCCA |
| | | GATGGTAAGCCCTCCCGTATCGTAGTTATCTACACGACGGGGAGT |
| | | CAGGCAACTATGGATGAACGAAATAGACAGATCGCTGAGATAGGT |
| | | GCCTCACTGATTAAGCATTGGTAACTGTCAGACCAAGTTTACTCAT |
| | | ATATACTTTAGATTGATTTAAAACTTCATTTTTAATTTAAAAGGAT |
| | | CTAGGTGAAGATCCTTTTTGATAATCTCATGACCAAAATCCCTTAA |
| | | CGTGAGTTTTCGTTCCACTGAGCGTCAGACCCCGTAGAAAAGATC |
| | | AAAGGATCTTCTTGAGATCCTTTTTTTCTGCGCGTAATCTGCTGCTT |
| | | GCAAACAAAAAAACCACCGCTACCAGCGGTGGTTTGTTTGCCGGA |
| | | TCAAGAGCTACCAACTCTTTTTCCGAAGGTAACTGGCTTCAGCAGA |
| | | GCGCAGATACCAAATACTGTCCTTCTAGTGTAGCCGTAGTTAGGCC |
| | | ACCACTTCAAGAACTCTGTAGCACCGCCTACATACCTCGCTCTGCT |
| | | AATCCTGTTACCAGTGGCTGCTGCCAGTGGCGATAAGTCGTGTCTT |
| | | ACCGGGTTGGACTCAAGACGATAGTTACCGGATAAGGCGCAGCGG |
| | | TCGGGCTGAACGGGGGGTTCGTGCACACAGCCCAGCTTGGAGCGA |
| | | ACGACCTACACCGAACTGAGATACCTACAGCGTGAGCTATGAGAA |
| | | AGCGCCACGCTTCCCGAAGGGAGAAAGGCGGACAGGTATCCGGT |
| | | AAGCGGCAGGGTCGGAACAGGAGAGCGCACGAGGGAGCTTCCAG |
| | | GGGGAAACGCCTGGTATCTTTATAGTCCTGTCGGGTTTCGCCACCT |
| | | CTGACTTGAGCGTCGATTTTTGTGATGCTCGTCAGGGGGGCGGAG |
| | | CCTATGGAAAAACGCCAGCAACGCGGCCTTTTTACGGTTCCTGGC |
| | | CTTTTGCTGGCCTTTTGCTCACATGTTCTTTCCTGCGTTATCCCCTG |
| | | ATTCTGTGGATAACCGTATTACCGCCTTTGAGTGAGCTGATACCGC |
| | | TCGCCGCAGCCGAACGACCGAGCGCAGCGAGTCAGTGAGCGAGG |
| | | AAGCGGAAGAGCGCCCAATACGCAAACCGCCTCTCCCCGCGCGTT |
| | | GGCCGATTCATTAATG |
| 40 | HBG1 Round 1 & 2: | CAGCTGCGCGCTCGCTCGCTCACTGAGGCCGCCCGGGCAAAGCCC |
| | AMS#1333 | GGGCGTCGGGCGACCTTTGGTCGCCCGGCCTCAGTGAGCGAGCGA |
| | pAAV HBG1d- | GCGCGCAGAGAGGGAGTGGCCAACTCCATCACTAGGGGTTCCTTG |
| | 141,-1(459,600) | TAGTTAATGATTAACCCGCCATGCTACTTATCTACACGCGTAGATC |
| | MND>MGMT.wPRE3. | TAGAAATTGTTTTCACTGCACTATTGAGAAATTAAGAGATAATGG |
| | SV40USE.pA; | CAAAAGTCACAAAGAGTATATTCAAAAAGAAGTATAGCACTTTTT |
| | HPFH- | CCTTAGAAACCACTGCTAACTGAAAGAGACTAAGATTTGTCCCGT |
| | 2.HS40.HBBp> | CAAAAATCCTGGACCTATGCCTAAAACACATTTCACAATCCCTGA |
| | | ACTTTTCAAAAATTGGTACATGCTTTAGCTTTAAACTACAGGCCTC |
| | | ACTGGAGCTAGAGACAAGAAGGTAAAAAACGGCTGACAAAAGAA |
| | | GTCCTGGTATCCTCTATGATGGGAGAAGGAAACTAGCTAAAGGGA |
| | | AGAATAAATTAGAGAAAAACTGGAATGACTGAATCGGAACAAGG |
| | | CAAAGGCTATAAAAAAAAATTAGCAGTATCCTCTTGGGGGCCCCTT |
| | | CCCCACACTATCTCAATGCAAATATCTGTCTGAAACGGTCCCTGGC |
| | | TAAACTCCACCCGCGGGAACAGAGAAACAGGAGAATATGGGCCA |
| | | AACAGGATATCTGTGGTAAGCAGTTCCTGCCCCGGCTCAGGGCCA |
| | | AGAACAGTTGGAACAGCAGAATATGGGCCAAACAGGATATCTGTG |
| | | GTAAGCAGTTCCTGCCCCGGCTCAGGGCCAAGAACAGATGGTCCC |
| | | CAGATGCGGTCCCGCCCTCAGCAGTTTCTAGAGAACCATCAGATG |
| | | TTTCCAGGGTGCCCCAAGGACCTGAAATGACCCTGTGCCTTATTTG |
| | | AACTAACCAATCAGTTCGCTTCTCGCTTCTGTTCGCGCGCTTCTGC |
| | | TCCCCGAGCTCTATATAAGCAGAGCTCGTTTAGTGAACCGTCAGAT |
| | | CGCCTGGAGACGCCATCCACGCTGTTTTGACTTCCATAGAAGGCG |
| | | GCCGCGCCGCCACCATGGACAAGGATTGTGAAATGAAACGCACCA |
| | | CACTGGACAGCCCTTTGGGGAAGCTGGAGCTGTCTGGTTGTGAGC |
| | | AGGGTCTGCACGAAATAAAGCTCCTGGGCAAGGGGACGTCTGCAG |
| | | CTGATGCCGTGGAGGTCCCAGCCCCCGCTGCGGTTCTCGGAGGTC |

-continued

| SEQ ID NO | NAME | SEQUENCE |
|---|---|---|
| | | CGGAGCCCCTGATGCAGTGCACAGCCTGGCTGAATGCCTATTTCC<br>ACCAGCCCGAGGCTATCGAAGAGTTCCCCGTGCCGGCTCTTCACC<br>ATCCCGTTTTCCAGCAAGAGTCGTTCACCAGACAGGTGTTATGGA<br>AGCTGCTGAAGGTTGTGAAATTCGGAGAAGTGATTTCTTACCAGC<br>AATTAGCAGCCCTGGCAGGCAACCCCAAAGCCGCGCGAGCAGTGG<br>GAGGAGCAATGAGAGGCAATCCTGTCAAAATCCTCATCCCGTGCC<br>ACAGAGTGGTCTGCAGCAGCGGAGCCGTGGGCAACTACTCCGGAG<br>GACTGGCCGTGAAGGAATGGCTTCTGGCCCATGAAGGCCACCGGT<br>TGGGGAAGCCAGGCTTGGGAGGGAGCTCAGGTCTGGCAGGGGCCT<br>GGCTCAAGGGAGCGGGAGCTACCTCGGGCTCCCCGCCTGCTGGCC<br>GAAACTAACCTGCAGGGATAATCAACCTCTGGATTACAAAATTTG<br>TGAAAGATTGACTGGTATTCTTAACTATGTTGCTCCTTTTACGCTA<br>TGTGGATACGCTGCTTTAATGCCTTTGTATCATGCTATTGCTTCCCG<br>TATGGCTTTCATTTTCTCCTCCTTGTATAAATCCTGGTTAGTTCTTG<br>CCACGGCGGAACTCATCGCCGCCTGCCTTGCCCGCTGCTGGACAG<br>GGGCTCGGCTGTTGGGCACTGACAATTCCGTGGTGTTTATTTGTGA<br>AATTTGTGATGCTATTGCTTTATTTGTAACCATTCTAGCTTTATTTG<br>TGAAATTTGTGATGCTATTGCTTTATTTGTAACCATTATAAGCTGC<br>AATAAACAAGTTAACAACAACAATTGCATTCATTTTATGTTTCAGG<br>TTCAGGGGGAGATGTGGGAGGTTTTTTAAAGCGAATTCCGAGATC<br>GAGACCATCCTGGCTAACACAGTGAAACCCCGTCTCTACTAAAAA<br>AATACAAAAAATTAGCCGGGCTTGGTGGCGGGTGCCTGTAGTCCC<br>AGCTACTATGGAGGCTGAGGCGGGAGAATGGCGTGAACGCGGGG<br>GGCGGAGCTTGCAGTGAGCAGAGATCAGGGGCCACTGCACTCCAG<br>CCTGGGCGACAGAGAGAGACTCTGTCTCAAAAAAAAGAAAAAAA<br>AAATTTAGTAGACTAGCTAAAAAAATCCAGAGATAGTTATTGATG<br>CATATGTAAAAGTCTTCCAATATTTACAAGTACAATGAAAAAAAA<br>ATAACCTTGAATTAAGTGTAGAACTCATTGACAATGTTTCAAAGG<br>ATGTGAGGGATAAACTAAAATTTGGGCAGTACATGCTGTTCCTGT<br>GTACTTGGAACAGAGGGAGAAAATCTGGGCTGGAAATATTGTTAT<br>AGGAGTTAGCACATGAAGGTGACAACTAAATTATTTGGAGTAGAT<br>GGAGTCACCAGCACATGTGAATAGTTTTAGAATGAAATGACCCAA<br>GATAGAACTTTGGAGAGCCCCCAAATTTAAATAAAATCAGTATAA<br>GAGAAGAGGAAGAAACCAAATGGTATACTAGTCTAAATTGTTTCT<br>TAGTGACAAAAGAATAACCTGAATATTAGATTAGCTGCCTATATG<br>CTCTCTGAATCAATTTCATTCAACATGCAACAGTTCTGGAACCTAT<br>CAGGGACCACAGTCAGCCAGGCAAGCACATCTGCCCAAGCCAAG<br>GGTGGAGGCATGCAGCTGTGGGGGTCTGTGAAAACACTTGAGGGA<br>GCAGATAACTGGGCCAACCATGACTCAGTGCTTCTGGAGGCCAAC<br>AGGACTGCTGAGTCATCCTGTGGGGGTGGAGGTGGGACAAGGGA<br>AAGGGGTGAATGGTACTGCTGATTACAACCTCTGGTGCTGCCTCCC<br>CCTCCTGTTTATCTGAGAGGCTAGCGTAAATACACTTGCAAAGGA<br>GGATGTTTTTAGTAGCAATTTGTACTGATGGTATGGGGCCAAGAG<br>ATATATCTTAGAGGGAGGGCTGAGGGTTTGAAGTCCAACTCCTAA<br>GCCAGTGCCAGAAGAGCCAAGGACAGGTACGGCTGTCATCACTTA<br>GACCTCACCCTGTGGAGCCACACCCTAGGGTTGGCCAATCTACTCC<br>CAGGAGCAGGGAGGGCAGGAGCCAGGGCTGGGCATAAAAGTCAG<br>GGCAGAGCCATCTATTGCTTACACTCGCTTCTGGAACGTCTGAGGT<br>TATCAATAAGCTCCTAGTCCAGACGCCATGGGTCATTTCACAGAG<br>GAGGACAAGGCTACTATCACAAGCCTGTGGGGCAAGGTGAATGTG<br>GAAGATGCTGGAGGAGAAACCCTGGGAAGGTAGGCTCTGGTGAC<br>CAGGACAAGGGAGGGAAGGAAGGACCCTGTGCCTGGCAAAAGTC<br>CAGGTCGCTTCTCAGGATTTGTGGCACCTTCTGACTGTCAAACTGT<br>TCTTGTCAATCTCACAGGCTCCTGGTTGTCTACCCATGGACCCAGA<br>GGTTCTTTGACAGCTTTGGCAACCTGTCCTCTGCCTCTGCCATCAT<br>GGGCAACCCCAAAGTCAAGGCACATGGCAAGAAGGTGCTGACTTC<br>CTTGGGAGATGCCACAAAGCACCTGGATGATCTCAAGGGCACCTT<br>TGCCCAGCTGAGTGAACTGCACTGTGACAAGCTGCATGTGGATCC<br>TGAGAACTTCAAGGTGAGTCCAGGAGATGTTTCAGCCCTGTTGCCT<br>TTAGTCTCGAGGCAACTTAGACAACGGAGTATTGATCTGAGCACA<br>GCAGGGTGTGAGCTGTTTGAAGATACTGGGGTCTCGAGGTCGACG<br>TAGATAAGTAGCATGGCGGGTTAATCATTAACTACAAGGAACCCC<br>TAGTGATGGAGTTGGCCACTCCCTCTCTGCGCGCTCGCTCGCTCAC<br>TGAGGCCGGGCGACCAAAGGTCGCCCGACGCCCGGGCTTTGCCCG<br>GGCGGCCTCAGTGAGCGAGCGAGCGCGCCAGCTGGCGTAATAGCG<br>AAGAGGCCCGCACCGATCGCCCTTCCCAACAGTTGCGCAGCCTGA<br>ATGGCGAATGGCGATTCCGTTGCAATGGCTGGCGGTAATATTGTTC<br>TGGATATTACCAGCAAGGCCGATAGTTTGAGTTCTTCTACTCAGGC<br>AAGTGATGTTATTACTAATCAAAGAAGTATTGCGACAACGGTTAA<br>TTTGCGTGATGGACAGACTCTTTTACTCGGTGGCCTCACTGATTAT<br>AAAAACACTTCTCAGGATTCTGGCGTACCGTTCCTGTCTAAAATCC<br>CTTTAATCGGCCTCCTGTTTAGCTCCCGCTCTGATTCTAACGAGGA<br>AAGCACGTTATACGTGCTCGTCAAAGCAACCATAGTACGCGCCCT<br>GTAGCGGCGCATTAAGCGCGGCGGGTGTGGTGGTTACGCGCAGCG<br>TGACCGCTACACTTGCCAGCGCCCTAGCGCCCGCTCCTTTCGCTTT |

-continued

| SEQ ID NO | NAME | SEQUENCE |
|---|---|---|
| | | CTTCCCTTCCTTTCTCGCCACGTTCGCCGGCTTTCCCCGTCAAGCTC<br>TAAATCGGGGGCTCCCTTTAGGGTTCCGATTTAGTGCTTTACGGCA<br>CCTCGACCCCAAAAAACTTGATTAGGGTGATGGTTCACGTAGTGG<br>GCCATCGCCCTGATAGACGGTTTTTCGCCCTTTGACGTTGGAGTCC<br>ACGTTCTTTAATAGTGGACTCTTGTTCCAAACTGGAACAACACTCA<br>ACCCTATCTCGGTCTATTCTTTTGATTTATAAGGGATTTTGCCGATT<br>TCGGCCTATTGGTTAAAAAATGAGCTGATTTAACAAAAATTTAAC<br>GCGAATTTTAACAAAATATTAACGTTTACAATTTAAATATTTGCTT<br>ATACAATCTTCCTGTTTTTGGGGCTTTTCTGATTATCAACCGGGGT<br>ACATATGATTGACATGCTAGTTTTACGATTACCGTTCATCGATTCT<br>CTTGTTTGCTCCAGACTCTCAGGCAATGACCTGATAGCCTTTGTAG<br>AGACCTCTCAAAAATAGCTACCCTCTCCGGCATGAATTTATCAGCT<br>AGAACGGTTGAATATCATATTGATGGTGATTTGACTGTCTCCGGCC<br>TTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA<br>AGGAGCTAACCGCTTTTTTGCACAACATGGGGGATCATGTAACTC<br>GCCTTGATCGTTGGGAACCGGAGCTGAATGAAGCCATACCAAACG<br>ACGAGCGTGACACCACGATGCCTGTAGCAATGGCAACAACGTTGC<br>GCAAACTATTAACTGGCGAACTACTTACTCTAGCTTCCCGGCAACA<br>ATTAATAGACTGGATGGAGGCGGATAAAGTTGCAGGACCACTTCT<br>GCGCTCGGCCCTTCCGGCTGGCTGGTTTATTGCTGATAAATCTGGA<br>GCCGGTGAGCGTGGGTCTCGCGGTATCATTGCAGCACTGGGGCCA<br>GATGGTAAGCCCTCCCGTATCGTAGTTATCTACACGACGGGGAGT<br>CAGGCAACTATGGATGAACGAAATAGACAGATCGCTGAGATAGGT<br>GCCTCACTGATTAAGCATTGGTAACTGTCAGACCAAGTTTACTCAT<br>ATATACTTTAGATTGATTTAAAACTTCATTTTTAATTTAAAAGGAT<br>CTAGGTGAAGATCCTTTTTGATAATCTCATGACCAAAATCCCTTAA<br>CGTGAGTTTTCGTTCCACTGAGCGTCAGACCCCGTAGAAAAGATC<br>AAAGGATCTTCTTGAGATCCTTTTTTTCTGCGCGTAATCTGCTGCTT<br>GCAAACAAAAAAACCACCGCTACCAGCGGTGGTTTGTTTGCCGGA<br>TCAAGAGCTACCAACTCTTTTTCCGAAGGTAACTGGCTTCAGCAGA<br>GCGCAGATACCAAATACTGTCCTTCTAGTGTAGCCGTAGTTAGGCC<br>ACCACTTCAAGAACTCTGTAGCACCGCCTACATACCTCGCTCTGCT<br>AATCCTGTTACCAGTGGCTGCTGCCAGTGGCGATAAGTCGTGTCTT<br>ACCGGGTTGGACTCAAGACGATAGTTACCGGATAAGGCGCAGCGG<br>TCGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACCT<br>CTGACTTGAGCGTCGATTTTTGTGATGCTCGTCAGGGGGGCGGAG<br>CCTATGGAAAAACGCCAGCAACGCGGCCTTTTTACGGTTCCTGGC<br>CTTTTGCTGGCCTTTTGCTCACATGTTCTTTCCTGCGTTATCCCCTG<br>ATTCTGTGGATAACCGTATTACCGCCTTTGAGTGAGCTGATACCGC<br>TCGCCGCAGCCGAACGACCGAGCGCAGCGAGTCAGTGAGCGAGG<br>AAGCGGAAGAGCGCCCAATACGCAAACCGCCTCTCCCCGCGCGTT<br>GGCCGATTCATTAATG |
| 41 | HBG1 Round 1 & 2:<br>AMS#1334<br>pAAV HBG1d-<br>141,-1(459,600)<br>hPGK>MGMT.wPRE3. | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TAGAAATTGTTTTCACTGCACTATTGAGAAATTAAGAGATAATGG |

-continued

| SEQ ID NO | NAME | SEQUENCE |
|---|---|---|
| | SV40USE.pA; HPFH-2.HS40.HBBp> | CAAAAGTCACAAAGAGTATATTCAAAAAGAAGTATAGCACTTTTT CCTTAGAAACCACTGCTAACTGAAAGAGACTAAGATTTGTCCCGT CAAAAATCCTGGACCTATGCCTAAAACACATTTCACAATCCCTGA ACTTTTCAAAAATTGGTACATGCTTTAGCTTTAAACTACAGGCCTC ACTGGAGCTAGAGACAAGAAGGTAAAAAACGGCTGACAAAAGAA GTCCTGGTATCCTCTATGATGGGAGAAGGAAACTAGCTAAAGGGA AGAATAAATTAGAGAAAAACTGGAATGACTGAATCGGAACAAGG CAAAGGCTATAAAAAAAATTAGCAGTATCCTCTTGGGGGCCCCTT CCCCACACTATCTCAATGCAAATATCTGTCTGAAACGGTCCCTGGC TAAACTCCACCCGCGGCCACGGGGTTGGGGTTGCGCCTTTTCCAA GGCAGCCCTGGGTTTGCGCAGGGACGCGGCTGCTCTGGGCGTGGT TCCGGGAAACGCAGCGGCGCCGACCCTGGGTCTCGCACATTCTTC ACGTCCGTTCGCAGCGTCACCCGGATCTTCGCCGCTACCCTTGTGG GCCCCCCGGCGACGCTTCCTGCTCCGCCCCTAAGTCGGGAAGGTTC CTTGCGGTTCGCGGCGTGCCGGACGTGACAAACGGAAGCCGCACG TCTCACTAGTACCCTCGCAGACGGACAGCGCCAGGGAGCAATGGC AGCGCGCCGACCGCGATGGGCTGTGGCCAATAGCGGCTGCTCAGC GGGGCGCGCCGAGAGCAGCGGCCGGGAAGGGGCGGTGCGGGAGG CGGGGTGTGGGGCGGTAGTGTGGGCCCTGTTCCTGCCCGCGCGGT GTTCCGCATTCTGCAAGCCTCCGGAGCGCACGTCGGCAGTCGGCT CCCTCGTTGACCGAATCACCGACCTCTCTCCCCAGCGGCCGCGCCG CCACCATGGACAAGGATTGTGAAATGAAACGCACCACACTGGACA GCCCTTTGGGGAAGCTGGAGCTGTCTGGTTGTGAGCAGGGTCTGC ACGAAATAAAGCTCCTGGGCAAGGGGACGTCTGCAGCTGATGCCG TGGAGGTCCCAGCCCCCGCTGCGGTTCTCGGAGGTCCGGAGCCCC TGATGCAGTGCACAGCCTGGCTGAATGCCTATTTCCACCAGCCCG AGGCTATCGAAGAGTTCCCCGTGCCGGCTCTTCACCATCCCGTTTT CCAGCAAGAGTCGTTCACCAGACAGGTGTTATGGAAGCTGCTGAA GGTTGTGAAATTCGGAGAAGTGATTTCTTACCAGCAATTAGCAGC CCTGGCAGGCAACCCCAAAGCCGCGCGAGCAGTGGGAGGAGCAA TGAGAGGCAATCCTGTCAAAATCCTCATCCCGTGCCACAGAGTGG TCTGCAGCAGCGGAGCCGTGGGCAACTACTCCGGAGGACTGGCCG TGAAGGAATGGCTTCTGGCCCATGAAGGCCACCGGTTGGGGAAGC CAGGCTTGGGAGGGAGCTCAGGTCTGGCAGGGGCCTGGCTCAAGG GAGCGGGAGCTACCTCGGGCTCCCCGCCTGCTGGCCGAAACTAAC CTGCAGGGATAATCAACCTCTGGATTACAAAATTTGTGAAAGATT GACTGGTATTCTTAACTATGTTGCTCCTTTTACGCTATGTGGATAC GCTGCTTTAATGCCTTTGTATCATGCTATTGCTTCCCGTATGGCTTT CATTTTCTCCTCCTTGTATAAATCCTGGTTAGTTCTTGCCACGGCGG AACTCATCGCCGCCTGCCTTGCCCGCTGCTGGACAGGGGCTCGGCT GTTGGGCACTGACAATTCCGTGGTGTTTATTTGTGAAATTTGTGAT GCTATTGCTTTATTTGTAACCATTCTAGCTTTATTTGTGAAATTTGT GATGCTATTGCTTTATTTGTAACCATTATAAGCTGCAATAAACAAG TTAACAACAACAATTGCATTCATTTTATGTTTCAGGTTCAGGGGGA GATGTGGGAGGTTTTTTAAAGCGAATTCCGAGATCGAGACCATCC TGGCTAACACAGTGAAACCCCGTCTCTACTAAAAAAATACAAAAA ATTAGCCGGGCTTGGTGGCGGGTGCCTGTAGTCCCAGCTACTATG GAGGCTGAGGCGGGAGAATGGCGTGAACGCGGGGGGCGGAGCTT GCAGTGAGCAGAGATCAGGGGCCACTGCACTCCAGCCTGGGCGAC AGAGAGAGACTCTGTCTCAAAAAAAAGAAAAAAAAAAATTTAGTA GACTAGCTAAAAAAATCCAGAGATAGTTATTGATGCATATGTAAA AGTCTTCCAATATTTACAAGTACAATGAAAAAAAAATAACCTTGA ATTAAGTGTAGAACTCATTGACAATGTTTCAAAGGATGTGAGGGA TAAACTAAAATTTGGGCAGTACATGCTGTTCCTGTGTACTTGGAAC AGAGGGAGAAAATCTGGGCTGGAAATATTGTTATAGGAGTTAGCA CATGAAGGTGACAACTAAATTATTTGGAGTAGATGGAGTCACCAG CACATGTGAATAGTTTTAGAATGAAATGACCCAAGATAGAACTTT GGAGAGCCCCCAAATTTAAATAAAATCAGTATAAGAGAAGAGGA AGAAACCAAATGGTATACTAGTCTAAATTGTTTCTTAGTGACAAA AGAATAACCTGAATATTAGATTAGCTGCCTATATGCTCTCTGAATC AATTTCATTCAACATGCAACAGTTCTGGAACCTATCAGGGACCAC AGTCAGCCAGGCAAGCACATCTGCCCAAGCCAAGGGTGGAGGCAT GCAGCTGTGGGGGTCTGTGAAAACACTTGAGGGAGCAGATAACTG GGCCAACCATGACTCAGTGCTTCTGGAGGCCAACAGGACTGCTGA GTCATCCTGTGGGGGTGGAGGTGGGACAAGGGAAAGGGGTGAAT GGTACTGCTGATTACAACCTCTGGTGCTGCCTCCCCCTCCTGTTTA TCTGAGAGGCTAGCGTAAATACACTTGCAAAGGAGGATGTTTTTA GTAGCAATTTGTACTGATGGTATGGGGCCAAGAGATATATCTTAG AGGGAGGGCTGAGGGTTTGAAGTCCAACTCCTAAGCCAGTGCCAG AAGAGCCAAGGACAGGTACGGCTGTCATCACTTAGACCTCACCCT GTGGAGCCACACCCTAGGGTTGGCCAATCTACTCCCAGGAGCAGG GAGGGCAGGAGCCAGGGCTGGGCATAAAAGTCAGGGCAGAGCCA TCTATTGCTTACACTCGCTTCTGGAACGTCTGAGGTTATCAATAAG CTCCTAGTCCAGACGCCATGGGTCATTTCACAGAGGAGGACAAGG CTACTATCACAAGCCTGTGGGGCAAGGTGAATGTGGAAGATGCTG |

-continued

| SEQ ID NO | NAME | SEQUENCE |
|---|---|---|
| | | GAGGAGAAACCCTGGGAAGGTAGGCTCTGGTGACCAGGACAAGG<br>GAGGGAAGGAAGGACCCTGTGCCTGGCAAAAGTCCAGGTCGCTTC<br>TCAGGATTTGTGGCACCTTCTGACTGTCAAACTGTTCTTGTCAATC<br>TCACAGGCTCCTGGTTGTCTACCCATGGACCCAGAGGTTCTTTGAC<br>AGCTTTGGCAACCTGTCCTCTGCCTCTGCCATCATGGGCAACCCCA<br>AAGTCAAGGCACATGGCAAGAAGGTGCTGACTTCCTTGGGAGATG<br>CCACAAAGCACCTGGATGATCTCAAGGGCACCTTTGCCCAGCTGA<br>GTGAACTGCACTGTGACAAGCTGCATGTGGATCCTGAGAACTTCA<br>AGGTGAGTCCAGGAGATGTTTCAGCCCTGTTGCCTTTAGTCTCGAG<br>GCAACTTAGACAACGGAGTATTGATCTGAGCACAGCAGGGTGTGA<br>GCTGTTTGAAGATACTGGGGTCTCGAGGTCGACGTAGATAAGTAG<br>CATGGCGGGTTAATCATTAACTACAAGGAACCCCTAGTGATGGAG<br>TTGGCCACTCCCTCTCTGCGCGCTCGCTCGCTCACTGAGGCCGGGC<br>GACCAAAGGTCGCCCGACGCCCGGGCTTTGCCCGGGCGGCCTCAG<br>TGAGCGAGCGAGCGCGCCAGCTGGCGTAATAGCGAAGAGGCCCG<br>CACCGATCGCCCTTCCCAACAGTTGCGCAGCCTGAATGGCGAATG<br>GCGATTCCGTTGCAATGGCTGGCGGTAATATTGTTCTGGATATTAC<br>CAGCAAGGCCGATAGTTTGAGTTCTTCTACTCAGGCAAGTGATGTT<br>ATTACTAATCAAAGAAGTATTGCGACAACGGTTAATTTGCGTGAT<br>GGACAGACTCTTTTACTCGGTGGCCTCACTGATTATAAAAACACTT<br>CTCAGGATTCTGGCGTACCGTTCCTGTCTAAAATCCCTTTAATCGG<br>CCTCCTGTTTAGCTCCCGCTCTGATTCTAACGAGGAAAGCACGTTA<br>TACGTGCTCGTCAAAGCAACCATAGTACGCGCCCTGTAGCGGCGC<br>ATTAAGCGCGGCGGGTGTGGTGGTTACGCGCAGCGTGACCGCTAC<br>ACTTGCCAGCGCCCTAGCGCCCGCTCCTTTCGCTTTCTTCCCTTCCT<br>TTCTCGCCACGTTCGCCGGCTTTCCCCGTCAAGCTCTAAATCGGGG<br>GCTCCCTTTAGGGTTCCGATTTAGTGCTTTACGGCACCTCGACCCC<br>AAAAAACTTGATTAGGGTGATGGTTCACGTAGTGGGCCATCGCCC<br>TGATAGACGGTTTTTCGCCCTTTGACGTTGGAGTCCACGTTCTTTA<br>ATAGTGGACTCTTGTTCCAAACTGGAACAACACTCAACCCTATCTC<br>GGTCTATTCTTTTGATTTATAAGGGATTTTGCCGATTTCGGCCTATT<br>GGTTAAAAAATGAGCTGATTTAACAAAAATTTAACGCGAATTTTA<br>ACAAAATATTAACGTTTACAATTTAAATATTTGCTTATACAATCTT<br>CCTGTTTTTGGGGCTTTTCTGATTATCAACCGGGGTACATATGATT<br>GACATGCTAGTTTTACGATTACCGTTCATCGATTCTCTTGTTTGCTC<br>CAGACTCTCAGGCAATGACCTGATAGCCTTTGTAGAGACCTCTCA<br>AAAATAGCTACCCTCTCCGGCATGAATTTATCAGCTAGAACGGTT<br>GAATATCATATTGATGGTGATTTGACTGTCTCCGGCCTTTCTCACC<br>CGTTTGAATCTTTACCTACACATTACTCAGGCATTGCATTTAAAAT<br>ATATGAGGGTTCTAAAAATTTTTATCCTTGCGTTGAAATAAAGGCT<br>TCTCCCGCAAAAGTATTACAGGGTCATAATGTTTTTGGTACAACCG<br>ATTTAGCTTTATGCTCTGAGGCTTTATTGCTTAATTTTGCTAATTCT<br>TTGCCTTGCCTGTATGATTTATTGGATGTTGGAATCGCCTGATGCG<br>GTATTTTCTCCTTACGCATCTGTGCGGTATTTCACACCGCATATGG<br>TGCACTCTCAGTACAATCTGCTCTGATGCCGCATAGTTAAGCCAGC<br>CCCGACACCCGCCAACACCCGCTGACGCGCCCTGACGGGCTTGTC<br>TGCTCCCGGCATCCGCTTACAGACAAGCTGTGACCGTCTCCGGGA<br>GCTGCATGTGTCAGAGGTTTTCACCGTCATCACCGAAACGCGCGA<br>GACGAAAGGGCCTCGTGATACGCCTATTTTTATAGGTTAATGTCAT<br>GATAATAATGGTTTCTTAGACGTCAGGTGGCACTTTTCGGGGAAAT<br>GTGCGCGGAACCCCTATTTGTTTATTTTTCTAAATACATTCAAATA<br>TGTATCCGCTCATGAGACAATAACCCTGATAAATGCTTCAATAATA<br>TTGAAAAAGGAAGAGTATGAGTATTCAACATTTCCGTGTCGCCCTT<br>ATTCCCTTTTTTGCGGCATTTTGCCTTCCTGTTTTTGCTCACCCAGA<br>AACGCTGGTGAAAGTAAAAGATGCTGAAGATCAGTTGGGTGCACG<br>AGTGGGTTACATCGAACTGGATCTCAACAGCGGTAAGATCCTTGA<br>GAGTTTTCGCCCCGAAGAACGTTTTCCAATGATGAGCACTTTTAAA<br>GTTCTGCTATGTGGCGCGGTATTATCCCGTATTGACGCCGGGCAAG<br>AGCAACTCGGTCGCCGCATACACTATTCTCAGAATGACTTGGTTGA<br>GTACTCACCAGTCACAGAAAAGCATCTTACGGATGGCATGACAGT<br>AAGAGAATTATGCAGTGCTGCCATAACCATGAGTGATAACACTGC<br>GGCCAACTTACTTCTGACAACGATCGGAGGACCGAAGGAGCTAAC<br>CGCTTTTTTGCACAACATGGGGGATCATGTAACTCGCCTTGATCGT<br>TGGGAACCGGAGCTGAATGAAGCCATACCAAACGACGAGCGTGA<br>CACCACGATGCCTGTAGCAATGGCAACAACGTTGCGCAAACTATT<br>AACTGGCGAACTACTTACTCTAGCTTCCCGGCAACAATTAATAGA<br>CTGGATGGAGGCGGATAAAGTTGCAGGACCACTTCTGCGCTCGGC<br>CCTTCCGGCTGGCTGGTTTATTGCTGATAAATCTGGAGCCGGTGAG<br>CGTGGGTCTCGCGGTATCATTGCAGCACTGGGGCCAGATGGTAAG<br>CCCTCCCGTATCGTAGTTATCTACACGACGGGGAGTCAGGCAACT<br>ATGGATGAACGAAATAGACAGATCGCTGAGATAGGTGCCTCACTG<br>ATTAAGCATTGGTAACTGTCAGACCAAGTTTACTCATATATACTTT<br>AGATTGATTTAAAACTTCATTTTTAATTTAAAAGGATCTAGGTGAA<br>GATCCTTTTTGATAATCTCATGACCAAAATCCCTTAACGTGAGTTT<br>TCGTTCCACTGAGCGTCAGACCCCGTAGAAAAGATCAAAGGATCT |

-continued

| SEQ ID NO | NAME | SEQUENCE |
|---|---|---|
| | | TCTTGAGATCCTTTTTTTCTGCGCGTAATCTGCTGCTTGCAAACAA<br>AAAAACCACCGCTACCAGCGGTGGTTTGTTTGCCGGATCAAGAGC<br>TACCAACTCTTTTTCCGAAGGTAACTGGCTTCAGCAGAGCGCAGAT<br>ACCAAATACTGTCCTTCTAGTGTAGCCGTAGTTAGGCCACCACTTC<br>AAGAACTCTGTAGCACCGCCTACATACCTCGCTCTGCTAATCCTGT<br>TACCAGTGGCTGCTGCCAGTGGCGATAAGTCGTGTCTTACCGGGTT<br>GGACTCAAGACGATAGTTACCGGATAAGGCGCAGCGGTCGGGCTG<br>AACGGGGGGTTCGTGCACACAGCCCAGCTTGGAGCGAACGACCTA<br>CACCGAACTGAGATACCTACAGCGTGAGCTATGAGAAAGCGCCAC<br>GCTTCCCGAAGGGAGAAAGGCGGACAGGTATCCGGTAAGCGGCA<br>GGGTCGGAACAGGAGAGCGCACGAGGGAGCTTCCAGGGGGAAAC<br>GCCTGGTATCTTTATAGTCCTGTCGGGTTTCGCCACCTCTGACTTG<br>AGCGTCGATTTTTGTGATGCTCGTCAGGGGGGCGGAGCCTATGGA<br>AAAACGCCAGCAACGCGGCCTTTTTACGGTTCCTGGCCTTTTGCTG<br>GCCTTTTGCTCACATGTTCTTTCCTGCGTTATCCCCTGATTCTGTGG<br>ATAACCGTATTACCGCCTTTGAGTGAGCTGATACCGCTCGCCGCAG<br>CCGAACGACCGAGCGCAGCGAGTCAGTGAGCGAGGAAGCGGAAG<br>AGCGCCCAATACGCAAACCGCCTCTCCCCGCGCGTTGGCCGATTC<br>ATTAATG |
| 42 | HBG1 Round 1 & 2:<br>AMS#1336<br>pAAV<br>HBG1(600).d-<br>114,488 HBGd13-<br>HBB(T87Q).core3'<br>enh;PGK><br>MGMT.T2A.Ex2 | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTGAAACAGTCATGATTTATTTCAAATAGGTACGGATAAGTAGAT<br>ATTGAGGTAAGCATTAGGTCTTATATTATGTAACACTAATCTATTA<br>CTGCGCTGAAACTGTGGCTTTATAGAAATTGTTTTCACTGCACTAT<br>TGAGAAATTAAGAGATAATGGCAAAAGTCACAAAGAGTATATTCA<br>AAAAGAAGTATAGCACTTTTTCCTTAGAAACCACTGCTAACTGAA<br>AGAGACTAAGATTTGTCCCGTCAAAAATCCTGGACCTATGCCTAA<br>AACACATTTCACAATCCCTGAACTTTTCAAAAATTGGTACATGCTT<br>TAGCTTTAAACTACAGGCCTCACTGGAGCTAGAGACAAGAAGGTA<br>AAAAACGGCTGACAAAAGAAGTCCTGGTATCCTCTATGATGGGAG<br>AAGGAAACTAGCTAAAGGGAAGAATAAATTAGAGAAAAACTGGA<br>ATGACTGAATCGGAACAAGGCAAAGGCTATAAAAAAAATTAGCA<br>GTATCCTCTTGGGGGCCCCTTCCCCACACTATCTCAATGCAAATAT<br>CTGTCTGAAACGGTCCCTGGCTAAACTCCACCCATGGGTTGGCCA<br>GCCTTGCCTTGACAAGGCAAACTTGACCAATAGTCTTAGAGTATCC<br>AGTGAGGCCAGGGGCCGGCGGCTGGCTAGGGATGAAGAATAAAA<br>GGAAGCACCCTTCAGCAGTTCCACACACTCGCTTCTGGAACGTCTG<br>AGGTTATCAATAAGCTCCTAGTCCAGACGCCATGGTGCACCTGAC<br>TCCTGAGGAGAAGTCTGCCGTTACTGCCCTGTGGGGCAAGGTGAA<br>CGTGGATGAAGTTGGTGGTGAGGCCCTGGGCAGGTTGGTATCAAG<br>GTTACAAGACAGGTTTAAGGAGACCAATAGAAACTGGGCATGTGG<br>AGACAGAGAAGACTCTTGGGTTTCTGATAGGCACTGACTCTCTCTG<br>CCTATTGGTCTATTTTCCCACCCTTAGGCTGCTGGTGGTCTACCCTT<br>GGACCCAGAGGTTCTTTGAGTCCTTTGGGGATCTGTCCACTCCTGA<br>TGCTGTTATGGGCAACCCTAAGGTGAAGGCTCATGGCAAGAAAGT<br>GCTCGGTGCCTTTAGTGATGGCCTGGCTCACCTGGACAACCTCAAG<br>GGCACCTTTGCCCAGCTGAGTGAGCTGCACTGTGACAAGCTGCAC<br>GTGGATCCTGAGAACTTCAGGGTGAGTCTATGGGACCCTTGATGTT<br>TTCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGCCACGGGGTTGGGGTTGCG<br>CCTTTTCCAAGGCAGCCCTGGGTTTGCGCAGGGACGCGGCTGCTCT |

-continued

| SEQ ID NO | NAME | SEQUENCE |
|---|---|---|
| | | GGGCGTGGTTCCGGGAAACGCAGCGGCGCCGACCCTGGGTCTCGC<br>ACATTCTTCACGTCCGTTCGCAGCGTCACCCGGATCTTCGCCGCTA<br>CCCTTGTGGGCCCCCCGGCGACGCTTCCTGCTCCGCCCCTAAGTCG<br>GGAAGGTTCCTTGCGGTTCGCGGCGTGCCGGACGTGACAAACGGA<br>AGCCGCACGTCTCACTAGTACCCTCGCAGACGGACAGCGCCAGGG<br>AGCAATGGCAGCGCGCCGACCGCGATGGGCTGTGGCCAATAGCGG<br>CTGCTCAGCGGGGCGCGCCGAGAGCAGCGGCCGGGAAGGGGCGG<br>TGCGGGAGGCGGGGTGTGGGGCGGTAGTGTGGGCCCTGTTCCTGC<br>CCGCGCGGTGTTCCGCATTCTGCAAGCCTCCGGAGCGCACGTCGG<br>CAGTCGGCTCCCTCGTTGACCGAATCACCGACCTCTCTCCCCAGCG<br>GCCGCGCCGCCACCATGGACAAGGATTGTGAAATGAAACGCACCA<br>CACTGGACAGCCCTTTGGGGAAGCTGGAGCTGTCTGGTTGTGAGC<br>AGGGTCTGCACGAAATAAAGCTCCTGGGCAAGGGGACGTCTGCAG<br>CTGATGCCGTGGAGGTCCCAGCCCCCGCTGCGGTTCTCGGAGGTC<br>CGGAGCCCCTGATGCAGTGCACAGCCTGGCTGAATGCCTATTTCC<br>ACCAGCCCGAGGCTATCGAAGAGTTCCCCGTGCCGGCTCTTCACC<br>ATCCCGTTTTCCAGCAAGAGTCGTTCACCAGACAGGTGTTATGGA<br>AGCTGCTGAAGGTTGTGAAATTCGGAGAAGTGATTTCTTACCAGC<br>AATTAGCAGCCCTGGCAGGCAACCCCAAAGCCGCGCGAGCAGTGG<br>GAGGAGCAATGAGAGGCAATCCTGTCAAAATCCTCATCCCGTGCC<br>ACAGAGTGGTCTGCAGCAGCGGAGCCGTGGGCAACTACTCCGGAG<br>GACTGGCCGTGAAGGAATGGCTTCTGGCCCATGAAGGCCACCGGT<br>TGGGGAAGCCAGGCTTGGGAGGGAGCTCAGGTCTGGCAGGGGCCT<br>GGCTCAAGGGAGCGGAGCTACCTCGGGCTCCCCGCCTGCTGGCC<br>GAAACGAGGGCAGAGGAAGTCTTCTAACATGCGGTGACGTGGAG<br>GAGAATCCGGGCCCCCCTGCAGGAACTTCAAGGTGAGTCCAGGAG<br>ATGTTTCAGCCCTGTTGCCTTTAGTCTCGAGGCAACTTAGACAACG<br>GAGTATTGATCTGAGCACAGCAGGGTGTGAGCTGTTTGAAGATAC<br>TGGGGTTGGGGGTGAAGAAACTGCAGAGGACTAACTGGGCTGAG<br>ACCCAGTGGTAATGTTTTAGGGCCTAAGGAGTGCCTCTAAAAATC<br>TAGATGGACAATTTTGACTTTGAGAAAAGAGAGGTGGAAATGAGG<br>AAAATGACTTTTCTTTATTAGATTCCAGTAGAAAGAACTTTCATCT<br>TTCCCTCATTTTTGTTGTTTTAAAACATCTATCTGGAGGCAGGACA<br>AGTATGGTCGTTAAAAAGATGCAGGCAGAAGGCATATATTGGCTC<br>AGTCAAAGTGGGGAACTTTGGTGGCCAAACATACATTGCTAAGGC<br>TATTCCTATATCAGCTGGACACATATAAAATGCTGCTAATGCTTCA<br>TTACAAACTTATATCCTTTAATTCCAGATGGGGGCAAAGTATGTCC<br>AGGGGTGAGGAACAATTGAAACATTTGGGCTGGAGTAGATTTTGA<br>AAGTCAGCTCTGTGTGTGTGTGTGTGTGTGCGCGCGCGCGTGTCGA<br>CGTAGATAAGTAGCATGGCGGGTTAATCATTAACTACAAGGAACC<br>CCTAGTGATGGAGTTGGCCACTCCCTCTCTGCGCGCTCGCTCGCTC<br>ACTGAGGCCGGGCGACCAAAGGTCGCCCGACGCCCGGGCTTTGCC<br>CGGGCGGCCTCAGTGAGCGAGCGAGCGCGCCAGCTGGCGTAATAG<br>CGAAGAGGCCCGCACCGATCGCCCTTCCCAACAGTTGCGCAGCCT<br>GAATGGCGAATGGCGATTCCGTTGCAATGGCTGGCGGTAATATTG<br>TTCTGGATATTACCAGCAAGGCCGATAGTTTGAGTTCTTCTACTCA<br>GGCAAGTGATGTTATTACTAATCAAAGAAGTATTGCGACAACGGT<br>TAATTTGCGTGATGGACAGACTCTTTTACTCGGTGGCCTCACTGAT<br>TATAAAAACACTTCTCAGGATTCTGGCGTACCGTTCCTGTCTAAAA<br>TCCCTTTAATCGGCCTCCTGTTTAGCTCCCGCTCTGATTCTAACGA<br>GGAAAGCACGTTATACGTGCTCGTCAAAGCAACCATAGTACGCGC<br>CCTGTAGCGGCGCATTAAGCGCGGCGGGTGTGGTGGTTACGCGCA<br>GCGTGACCGCTACACTTGCCAGCGCCCTAGCGCCCGCTCCTTTCGC<br>TTTCTTCCCTTCCTTTCTCGCCACGTTCGCCGGCTTTCCCCGTCAAG<br>CTCTAAATCGGGGGCTCCCTTTAGGGTTCCGATTTAGTGCTTTACG<br>GCACCTCGACCCCAAAAAACTTGATTAGGGTGATGGTTCACGTAG<br>TGGGCCATCGCCCTGATAGACGGTTTTTCGCCCTTTGACGTTGGAG<br>TCCACGTTCTTTAATAGTGGACTCTTGTTCCAAACTGGAACAACAC<br>TCAACCCTATCTCGGTCTATTCTTTTGATTTATAAGGGATTTTGCCG<br>ATTTCGGCCTATTGGTTAAAAAATGAGCTGATTTAACAAAAATTTA<br>ACGCGAATTTTAACAAAATATTAACGTTTACAATTTAAATATTTGC<br>TTATACAATCTTCCTGTTTTTGGGGCTTTTCTGATTATCAACCGGGG<br>TACATATGATTGACATGCTAGTTTTACGATTACCGTTCATCGATTC<br>TCTTGTTTGCTCCAGACTCTCAGGCAATGACCTGATAGCCTTTGTA<br>GAGACCTCTCAAAAATAGCTACCCTCTCCGGCATGAATTTATCAGC<br>TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT |

-continued

| SEQ ID NO | NAME | SEQUENCE |
|---|---|---|
| | | CTCCGGGAGCTGCATGTGTCAGAGGTTTTCACCGTCATCACCGAA |
| | | ACGCGCGAGACGAAAGGGCCTCGTGATACGCCTATTTTTATAGGT |
| | | TAATGTCATGATAATAATGGTTTCTTAGACGTCAGGTGGCACTTTT |
| | | CGGGGAAATGTGCGCGGAACCCCTATTTGTTTATTTTTCTAAATAC |
| | | ATTCAAATATGTATCCGCTCATGAGACAATAACCCTGATAAATGCT |
| | | TCAATAATATTGAAAAAGGAAGAGTATGAGTATTCAACATTTCCG |
| | | TGTCGCCCTTATTCCCTTTTTTGCGGCATTTTGCCTTCCTGTTTTTGC |
| | | TCACCCAGAAACGCTGGTGAAAGTAAAAGATGCTGAAGATCAGTT |
| | | GGGTGCACGAGTGGGTTACATCGAACTGGATCTCAACAGCGGTAA |
| | | GATCCTTGAGAGTTTTCGCCCCGAAGAACGTTTTCCAATGATGAGC |
| | | ACTTTTAAAGTTCTGCTATGTGGCGCGGTATTATCCCGTATTGACG |
| | | CCGGGCAAGAGCAACTCGGTCGCCGCATACACTATTCTCAGAATG |
| | | ACTTGGTTGAGTACTCACCAGTCACAGAAAAGCATCTTACGGATG |
| | | GCATGACAGTAAGAGAATTATGCAGTGCTGCCATAACCATGAGTG |
| | | ATAACACTGCGGCCAACTTACTTCTGACAACGATCGGAGGACCGA |
| | | AGGAGCTAACCGCTTTTTTGCACAACATGGGGGATCATGTAACTC |
| | | GCCTTGATCGTTGGGAACCGGAGCTGAATGAAGCCATACCAAACG |
| | | ACGAGCGTGACACCACGATGCCTGTAGCAATGGCAACAACGTTGC |
| | | GCAAACTATTAACTGGCGAACTACTTACTCTAGCTTCCCGGCAACA |
| | | ATTAATAGACTGGATGGAGGCGGATAAAGTTGCAGGACCACTTCT |
| | | GCGCTCGGCCCTTCCGGCTGGCTGGTTTATTGCTGATAAATCTGGA |
| | | GCCGGTGAGCGTGGGTCTCGCGGTATCATTGCAGCACTGGGGCCA |
| | | GATGGTAAGCCCTCCCGTATCGTAGTTATCTACACGACGGGGAGT |
| | | CAGGCAACTATGGATGAACGAAATAGACAGATCGCTGAGATAGGT |
| | | GCCTCACTGATTAAGCATTGGTAACTGTCAGACCAAGTTTACTCAT |
| | | ATATACTTTAGATTGATTTAAAACTTCATTTTTAATTTAAAAGGAT |
| | | CTAGGTGAAGATCCTTTTTGATAATCTCATGACCAAAATCCCTTAA |
| | | CGTGAGTTTTCGTTCCACTGAGCGTCAGACCCCGTAGAAAAGATC |
| | | AAAGGATCTTCTTGAGATCCTTTTTTTCTGCGCGTAATCTGCTGCTT |
| | | GCAAACAAAAAAACCACCGCTACCAGCGGTGGTTTGTTTGCCGGA |
| | | TCAAGAGCTACCAACTCTTTTTCCGAAGGTAACTGGCTTCAGCAGA |
| | | GCGCAGATACCAAATACTGTCCTTCTAGTGTAGCCGTAGTTAGGCC |
| | | ACCACTTCAAGAACTCTGTAGCACCGCCTACATACCTCGCTCTGCT |
| | | AATCCTGTTACCAGTGGCTGCTGCCAGTGGCGATAAGTCGTGTCTT |
| | | ACCGGGTTGGACTCAAGACGATAGTTACCGGATAAGGCGCAGCGG |
| | | TCGGGCTGAACGGGGGGTTCGTGCACACAGCCCAGCTTGGAGCGA |
| | | ACGACCTACACCGAACTGAGATACCTACAGCGTGAGCTATGAGAA |
| | | AGCGCCACGCTTCCCGAAGGGAGAAAGGCGGACAGGTATCCGGT |
| | | AAGCGGCAGGGTCGGAACAGGAGAGCGCACGAGGGAGCTTCCAG |
| | | GGGGAAACGCCTGGTATCTTTATAGTCCTGTCGGGTTTCGCCACCT |
| | | CTGACTTGAGCGTCGATTTTTGTGATGCTCGTCAGGGGGGCGGAG |
| | | CCTATGGAAAAACGCCAGCAACGCGGCCTTTTTACGGTTCCTGGC |
| | | CTTTTGCTGGCCTTTTGCTCACATGTTCTTTCCTGCGTTATCCCCTG |
| | | ATTCTGTGGATAACCGTATTACCGCCTTTGAGTGAGCTGATACCGC |
| | | TCGCCGCAGCCGAACGACCGAGCGCAGCGAGTCAGTGAGCGAGG |
| | | AAGCGGAAGAGCGCCCAATACGCAAACCGCCTCTCCCCGCGCGTT |
| | | GGCCGATTCATTAATG |
| 43 | HBG1 Round 1 & 2: | CAGCTGCGCGCTCGCTCGCTCACTGAGGCCGCCCGGGCAAAGCCC |
| | AMS#1235 | GGGCGTCGGGCGACCTTTGGTCGCCCGGCCTCAGTGAGCGAGCGA |
| | HBG1(200-600). | GCGCGCAGAGAGGGAGTGGCCAACTCCATCACTAGGGGTTCCTTG |
| | d13>HBB(T87Q). | TAGTTAATGATTAACCCGCCATGCTACTTATCTACACGCGTAGATC |
| | 3′enhCore; | TTGAAACAGTCATGATTTATTTCAAATAGGTACGGATAAGTAGAT |
| | MND>GFP::T2A:: | ATTGAGGTAAGCATTAGGTCTTATATTATGTAACACTAATCTATTA |
| | Ex2 (corrected | CTGCGCTGAAACTGTGGCTTTATAGAAATTGTTTTCACTGCACTAT |
| | polyA) | TGAGAAATTAAGAGATAATGGCAAAAGTCACAAAGAGTATATTCA |
| | | AAAAGAAGTATAGCACTTTTTCCTTAGAAACCACTGCTAACTGAA |
| | | AGAGACTAAGATTTGTCCCGTCAAAAATCCTGGACCTATGCCTAA |
| | | AACACATTTCACAATCCCTGAACTTTTCAAAAATTGGTACATGCTT |
| | | TAGCTTTAAACTACAGGCCTCACTGGAGCTAGAGACAAGAAGGTA |
| | | AAAAACGGCTGACAAAAGAAGTCCTGGTATCCTCTATGATGGGAG |
| | | AAGGAAACTAGCTAAAGGGAAGAATAAATTAGAGAAAAACTGGA |
| | | ATGACTGAATCGGAACAAGGCAAAGGCTATAAAAAAAATTAGCA |
| | | GTATCCTCTTGGGGGCCCCTTCCCCACACTATCTCAATGCAAATAT |
| | | CTGTCTGAAACGGTCCCTGGCTAAACTCCACCCATGGGTTGGCCA |
| | | GCCTTGCCTTGACAAGGCAAACTTGACCAATAGTCTTAGAGTATCC |
| | | AGTGAGGCCAGGGGCCGGCGGCTGGCTAGGGATGAAGAATAAAA |
| | | GGAAGCACCCTTCAGCAGTTCCACACACTCGCTTCTGGAACGTCTG |
| | | AGGTTATCAATAAGCTCCTAGTCCAGACGCCATGGTGCACCTGAC |
| | | TCCTGAGGAGAAGTCTGCCGTTACTGCCCTGTGGGGCAAGGTGAA |
| | | CGTGGATGAAGTTGGTGGTGAGGCCCTGGGCAGGTTGGTATCAAG |
| | | GTTACAAGACAGGTTTAAGGAGACCAATAGAAACTGGGCATGTGG |
| | | AGACAGAGAAGACTCTTGGGTTTCTGATAGGCACTGACTCTCTCTG |
| | | CCTATTGGTCTATTTTCCCACCCTTAGGCTGCTGGTGGTCTACCCTT |
| | | GGACCCAGAGGTTCTTTGAGTCCTTTGGGGATCTGTCCACTCCTGA |

-continued

| SEQ ID NO | NAME | SEQUENCE |
|---|---|---|
| | | TGCTGTTATGGGCAACCCTAAGGTGAAGGCTCATGGCAAGAAAGT<br>GCTCGGTGCCTTTAGTGATGGCCTGGCTCACCTGGACAACCTCAAG<br>GGCACCTTTGCCCAGCTGAGTGAGCTGCACTGTGACAAGCTGCAC<br>GTGGATCCTGAGAACTTCAGGGTGAGTCTATGGGACCCTTGATGTT<br>TTCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGGAACAGAGAAACAGGAGAA<br>TATGGGCCAAACAGGATATCTGTGGTAAGCAGTTCCTGCCCCGGC<br>TCAGGGCCAAGAACAGTTGGAACAGCAGAATATGGGCCAAACAG<br>GATATCTGTGGTAAGCAGTTCCTGCCCCGGCTCAGGGCCAAGAAC<br>AGATGGTCCCCAGATGCGGTCCCGCCCTCAGCAGTTTCTAGAGAA<br>CCATCAGATGTTTCCAGGGTGCCCCAAGGACCTGAAATGACCCTG<br>TGCCTTATTTGAACTAACCAATCAGTTCGCTTCTCGCTTCTGTTCGC<br>GCGCTTCTGCTCCCCGAGCTCTATATAAGCAGAGCTCGTTTAGTGA<br>ACCGTCAGATCGCGGCCGCGCCGCCACCATGGTGAGCAAGGGCGA<br>GGAGCTGTTCACCGGGGTGGTGCCCATCCTGGTCGAGCTGGACGG<br>CGACGTAAACGGCCACAAGTTCAGCGTGTCCGGCGAGGGCGAGG<br>GCGATGCCACCTACGGCAAGCTGACCCTGAAGTTCATCTGCACCA<br>CCGGCAAGCTGCCCGTGCCCTGGCCCACCCTCGTGACCACCCTGA<br>CCTACGGCGTGCAGTGCTTCAGCCGCTACCCCGACCACATGAAGC<br>AGCACGACTTCTTCAAGTCCGCCATGCCCGAAGGCTACGTCCAGG<br>AGCGCACCATCTTCTTCAAGGACGACGGCAACTACAAGACCCGCG<br>CCGAGGTGAAGTTCGAGGGCGACACCCTGGTGAACCGCATCGAGC<br>TGAAGGGCATCGACTTCAAGGAGGACGGCAACATCCTGGGGCACA<br>AGCTGGAGTACAACTACAACAGCCACAACGTCTATATCATGGCCG<br>ACAAGCAGAAGAACGGCATCAAGGTGAACTTCAAGATCCGCCAC<br>AACATCGAGGACGGCAGCGTGCAGCTCGCCGACCACTACCAGCAG<br>AACACCCCCATCGGCGACGGCCCCGTGCTGCTGCCCGACAACCAC<br>TACCTGAGCACCCAGTCCGCCCTGAGCAAAGACCCCAACGAGAAG<br>CGCGATCACATGGTCCTGCTGGAGTTCGTGACCGCCGCCGGGATC<br>ACTCTCGGCATGGACGAGCTGTACAAGGAGGGCAGAGGAAGTCTT<br>CTAACATGCGGTGACGTGGAGGAGAATCCGGGCCCCCCTGCAGGA<br>ACTTCAAGGTGAGTCCAGGAGATGTTTCAGCCCTGTTGCCTTTAGT<br>CTCGAGGCAACTTAGACAACGGAGTATTGATCTGAGCACAGCAGG<br>GTGTGAGCTGTTTGAAGATACTGGGGTTGGGGGTGAAGAAACTGC<br>AGAGGACTAACTGGGCTGAGACCCAGTGGTAATGTTTTAGGGCCT<br>AAGGAGTGCCTCTAAAAATCTAGATGGACAATTTTGACTTTGAGA<br>AAAGAGAGGTGGAAATGAGGAAAATGACTTTTCTTTATTAGATTC<br>CAGTAGAAAGAACTTTCATCTTTCCCTCATTTTTGTTGTTTTAAAAC<br>ATCTATCTGGAGGCAGGACAAGTATGGTCGTTAAAAAGATGCAGG<br>CAGAAGGCATATATTGGCTCAGTCAAAGTGGGGAACTTTGGTGGC<br>CAAACATACATTGCTAAGGCTATTCCTATATCAGCTGGACACATAT<br>AAAATGCTGCTAATGCTTCATTACAAACTTATATCCTTTAATTCCA<br>GATGGGGGCAAAGTATGTCCAGGGGTGAGGAACAATTGAAACATT<br>TGGGCTGGAGTAGATTTTGAAAGTCAGCTCTGTGTGTGTGTGTGTG<br>TGTGCGCGCGCGCGTGTCGACGTAGATAAGTAGCATGGCGGGTTA<br>ATCATTAACTACAAGGAACCCCTAGTGATGGAGTTGGCCACTCCC<br>TCTCTGCGCGCTCGCTCGCTCACTGAGGCCGGGCGACCAAAGGTC<br>GCCCGACGCCCGGGCTTTGCCCGGGCGGCCTCAGTGAGCGAGCGA<br>GCGCGCCAGCTGGCGTAATAGCGAAGAGGCCCGCACCGATCGCCC<br>TTCCCAACAGTTGCGCAGCCTGAATGGCGAATGGCGATTCCGTTG<br>CAATGGCTGGCGGTAATATTGTTCTGGATATTACCAGCAAGGCCG<br>ATAGTTTGAGTTCTTCTACTCAGGCAAGTGATGTTATTACTAATCA<br>AAGAAGTATTGCGACAACGGTTAATTTGCGTGATGGACAGACTCT<br>TTTACTCGGTGGCCTCACTGATTATAAAAACACTTCTCAGGATTCT |

-continued

| SEQ ID NO | NAME | SEQUENCE |
|---|---|---|
| | | GGCGTACCGTTCCTGTCTAAAATCCCTTTAATCGGCCTCCTGTTTA |
| | | GCTCCCGCTCTGATTCTAACGAGGAAAGCACGTTATACGTGCTCGT |
| | | CAAAGCAACCATAGTACGCGCCCTGTAGCGGCGCATTAAGCGCGG |
| | | CGGGTGTGGTGGTTACGCGCAGCGTGACCGCTACACTTGCCAGCG |
| | | CCCTAGCGCCCGCTCCTTTCGCTTTCTTCCCTTCCTTTCTCGCCACG |
| | | TTCGCCGGCTTTCCCCGTCAAGCTCTAAATCGGGGGCTCCCTTTAG |
| | | GGTTCCGATTTAGTGCTTTACGGCACCTCGACCCCAAAAAACTTGA |
| | | TTAGGGTGATGGTTCACGTAGTGGGCCATCGCCCTGATAGACGGT |
| | | TTTTCGCCCTTTGACGTTGGAGTCCACGTTCTTTAATAGTGGACTCT |
| | | TGTTCCAAACTGGAACAACACTCAACCCTATCTCGGTCTATTCTTT |
| | | TGATTTATAAGGGATTTTGCCGATTTCGGCCTATTGGTTAAAAAAT |
| | | GAGCTGATTTAACAAAAATTTAACGCGAATTTTAACAAAATATTA |
| | | ACGTTTACAATTTAAATATTTGCTTATACAATCTTCCTGTTTTTGGG |
| | | GCTTTTCTGATTATCAACCGGGGTACATATGATTGACATGCTAGTT |
| | | TTACGATTACCGTTCATCGATTCTCTTGTTTGCTCCAGACTCTCAGG |
| | | CAATGACCTGATAGCCTTTGTAGAGACCTCTCAAAAATAGCTACC |
| | | CTCTCCGGCATGAATTTATCAGCTAGAACGGTTGAATATCATATTG |
| | | ATGGTGATTTGACTGTCTCCGGCCTTTCTCACCCGTTTGAATCTTTA |
| | | CCTACACATTACTCAGGCATTGCATTTAAAATATATGAGGGTTCTA |
| | | AAAATTTTTATCCTTGCGTTGAAATAAAGGCTTCTCCCGCAAAAGT |
| | | ATTACAGGGTCATAATGTTTTTGGTACAACCGATTTAGCTTTATGC |
| | | TCTGAGGCTTTATTGCTTAATTTTGCTAATTCTTTGCCTTGCCTGTA |
| | | TGATTTATTGGATGTTGGAATCGCCTGATGCGGTATTTTCTCCTTA |
| | | CGCATCTGTGCGGTATTTCACACCGCATATGGTGCACTCTCAGTAC |
| | | AATCTGCTCTGATGCCGCATAGTTAAGCCAGCCCCGACACCCGCC |
| | | AACACCCGCTGACGCGCCCTGACGGGCTTGTCTGCTCCCGGCATCC |
| | | GCTTACAGACAAGCTGTGACCGTCTCCGGGAGCTGCATGTGTCAG |
| | | AGGTTTTCACCGTCATCACCGAAACGCGCGAGACGAAAGGGCCTC |
| | | GTGATACGCCTATTTTTATAGGTTAATGTCATGATAATAATGGTTT |
| | | CTTAGACGTCAGGTGGCACTTTTCGGGGAAATGTGCGCGGAACCC |
| | | CTATTTGTTTATTTTTCTAAATACATTCAAATATGTATCCGCTCATG |
| | | AGACAATAACCCTGATAAATGCTTCAATAATATTGAAAAAGGAAG |
| | | AGTATGAGTATTCAACATTTCCGTGTCGCCCTTATTCCCTTTTTTGC |
| | | GGCATTTTGCCTTCCTGTTTTTGCTCACCCAGAAACGCTGGTGAAA |
| | | GTAAAAGATGCTGAAGATCAGTTGGGTGCACGAGTGGGTTACATC |
| | | GAACTGGATCTCAACAGCGGTAAGATCCTTGAGAGTTTTCGCCCC |
| | | GAAGAACGTTTTCCAATGATGAGCACTTTTAAAGTTCTGCTATGTG |
| | | GCGCGGTATTATCCCGTATTGACGCCGGGCAAGAGCAACTCGGTC |
| | | GCCGCATACACTATTCTCAGAATGACTTGGTTGAGTACTCACCAGT |
| | | CACAGAAAAGCATCTTACGGATGGCATGACAGTAAGAGAATTATG |
| | | CAGTGCTGCCATAACCATGAGTGATAACACTGCGGCCAACTTACT |
| | | TCTGACAACGATCGGAGGACCGAAGGAGCTAACCGCTTTTTTGCA |
| | | CAACATGGGGGATCATGTAACTCGCCTTGATCGTTGGGAACCGGA |
| | | GCTGAATGAAGCCATACCAAACGACGAGCGTGACACCACGATGCC |
| | | TGTAGCAATGGCAACAACGTTGCGCAAACTATTAACTGGCGAACT |
| | | ACTTACTCTAGCTTCCCGGCAACAATTAATAGACTGGATGGAGGC |
| | | GGATAAAGTTGCAGGACCACTTCTGCGCTCGGCCCTTCCGGCTGG |
| | | CTGGTTTATTGCTGATAAATCTGGAGCCGGTGAGCGTGGGTCTCGC |
| | | GGTATCATTGCAGCACTGGGGCCAGATGGTAAGCCCTCCCGTATC |
| | | GTAGTTATCTACACGACGGGGAGTCAGGCAACTATGGATGAACGA |
| | | AATAGACAGATCGCTGAGATAGGTGCCTCACTGATTAAGCATTGG |
| | | TAACTGTCAGACCAAGTTTACTCATATATACTTTAGATTGATTTAA |
| | | AACTTCATTTTTAATTTAAAAGGATCTAGGTGAAGATCCTTTTTGA |
| | | TAATCTCATGACCAAAATCCCTTAACGTGAGTTTTCGTTCCACTGA |
| | | GCGTCAGACCCCGTAGAAAAGATCAAAGGATCTTCTTGAGATCCT |
| | | TTTTTTCTGCGCGTAATCTGCTGCTTGCAAACAAAAAAACCACCGC |
| | | TACCAGCGGTGGTTTGTTTGCCGGATCAAGAGCTACCAACTCTTTT |
| | | TCCGAAGGTAACTGGCTTCAGCAGAGCGCAGATACCAAATACTGT |
| | | CCTTCTAGTGTAGCCGTAGTTAGGCCACCACTTCAAGAACTCTGTA |
| | | GCACCGCCTACATACCTCGCTCTGCTAATCCTGTTACCAGTGGCTG |
| | | CTGCCAGTGGCGATAAGTCGTGTCTTACCGGGTTGGACTCAAGAC |
| | | GATAGTTACCGGATAAGGCGCAGCGGTCGGGCTGAACGGGGGGTT |
| | | CGTGCACACAGCCCAGCTTGGAGCGAACGACCTACACCGAACTGA |
| | | GATACCTACAGCGTGAGCTATGAGAAAGCGCCACGCTTCCCGAAG |
| | | GGAGAAAGGCGGACAGGTATCCGGTAAGCGGCAGGGTCGGAACA |
| | | GGAGAGCGCACGAGGGAGCTTCCAGGGGGAAACGCCTGGTATCTT |
| | | TATAGTCCTGTCGGGTTTCGCCACCTCTGACTTGAGCGTCGATTTT |
| | | TGTGATGCTCGTCAGGGGGGCGGAGCCTATGGAAAAACGCCAGCA |
| | | ACGCGGCCTTTTTACGGTTCCTGGCCTTTTGCTGGCCTTTTGCTCAC |
| | | ATGTTCTTTCCTGCGTTATCCCCTGATTCTGTGGATAACCGTATTAC |
| | | CGCCTTTGAGTGAGCTGATACCGCTCGCCGCAGCCGAACGACCGA |
| | | GCGCAGCGAGTCAGTGAGCGAGGAAGCGGAAGAGCGCCCAATAC |
| | | GCAAACCGCCTCTCCCCGCGCGTTGGCCGATTCATTAATG |

-continued

| SEQ ID NO | NAME | SEQUENCE |
|---|---|---|
| 44 | HBG1 Round 1 & 2:<br>AMS#1260<br>HBG1(200-600).<br>d13>HBB(T87Q).<br>3′enhCore;<br>MND>GFP::T2A::<br>Ex2 (corrected<br>polyA) | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTCCTTAGAAACCACTGCTAACTGAAAGAGACTAAGATTTGTCCC<br>GTCAAAAATCCTGGACCTATGCCTAAAACACATTTCACAATCCCTG<br>AACTTTTCAAAAATTGGTACATGCTTTAGCTTTAAACTACAGGCCT<br>CACTGGAGCTAGAGACAAGAAGGTAAAAAACGGCTGACAAAAGA<br>AGTCCTGGTATCCTCTATGATGGGAGAAGGAAACTAGCTAAAGGG<br>AAGAATAAATTAGAGAAAAACTGGAATGACTGAATCGGAACAAG<br>GCAAAGGCTATAAAAAAAATTAGCAGTATCCTCTTGGGGGCCCCT<br>TCCCCACACTATCTCAATGCAAATATCTGTCTGAAACGGTCCCTGG<br>CTAAACTCCACCCATGGGTTGGCCAGCCTTGCCTTGACAAGGCAA<br>ACTTGACCAATAGTCTTAGAGTATCCAGTGAGGCCAGGGGCCGGC<br>GGCTGGCTAGGGATGAAGAATAAAAGGAAGCACCCTTCAGCAGTT<br>CCACACACTCGCTTCTGGAACGTCTGAGGTTATCAATAAGCTCCTA<br>GTCCAGACGCCATGGTGCACCTGACTCCTGAGGAGAAGTCTGCCG<br>TTACTGCCCTGTGGGGCAAGGTGAACGTGGATGAAGTTGGTGGTG<br>AGGCCCTGGGCAGGTTGGTATCAAGGTTACAAGACAGGTTTAAGG<br>AGACCAATAGAAACTGGGCATGTGGAGACAGAGAAGACTCTTGG<br>GTTTCTGATAGGCACTGACTCTCTCTGCCTATTGGTCTATTTTCCCA<br>CCCTTAGGCTGCTGGTGGTCTACCCTTGGACCCAGAGGTTCTTTGA<br>GTCCTTTGGGGATCTGTCCACTCCTGATGCTGTTATGGGCAACCCT<br>AAGGTGAAGGCTCATGGCAAGAAAGTGCTCGGTGCCTTTAGTGAT<br>GGCCTGGCTCACCTGGACAACCTCAAGGGCACCTTTGCCCAGCTG<br>AGTGAGCTGCACTGTGACAAGCTGCACGTGGATCCTGAGAACTTC<br>AGGGTGAGTCTATGGGACCCTTGATGTTTTCTTTCCCCTTCTTTTCT<br>ATGGTTAAGTTCATGTCATAGGAAGGGGAGAAGTAACAGGGTACA<br>CATATTGACCAAATCAGGGTAATTTTGCATTTGTAATTTTAAAAAA<br>TGCTTTCTTCTTTTAATATACTTTTTTGTTTATCTTATTTCTAATACT<br>TTCCCTAATCTCTTTCTTTCAGGGCAATAATGATACAATGTATCAT<br>GCCTCTTTGCACCATTCTAAAGAATAACAGTGATAATTTCTGGGTT<br>AAGGCAATAGCAATATTTCTGCATATAAATATTTCTGCATATAAAT<br>TGTAACTGATGTAAGAGGTTTCATATTGCTAATAGCAGCTACAATC<br>CAGCTACCATTCTGCTTTTATTTTATGGTTGGGATAAGGCTGGATT<br>ATTCTGAGTCCAAGCTAGGCCCTTTTGCTAATCATGTTCATACCTC<br>TTATCTTCCTCCCACAGCTCCTGGGCAACGTGCTGGTCTGTGTGCT<br>GGCCCATCACTTTGGCAAAGAATTCACCCCACCAGTGCAGGCTGC<br>CTATCAGAAAGTGGTGGCTGGTGTGGCTAATGCCCTGGCCCACAA<br>GTATCACTAAGCTCGCTTTCTTGCTGTCCAATTTCTATTAAAGGTTC<br>CTTTGTTCCCTAAGTCCAACTACTAAACTGGGGGATATTATGAAGG<br>GCCTTGAGCATCTGGATTCTGCCTAATAAAAAACATTTATTTTCAT<br>TGCAATGATGTATTTAAATTATTTCTGAATATTTTACTAAAAAGGG<br>AATGTGGGAGGTTGCAGTGCTAGTCTCCCGGAACTATCACTCTTTC<br>ACAGTCTGCTTTGGAAGGACTGGGCTTAGTATGAAAAGTTAGGAC<br>TGAGAAGAATTTGAAAGGGGGCTTTTTGTAGCTTGATATTCACTAC<br>TGTCTTATTACCCTATCATAGGCCCACCCCAAATGGAAGTCCCATT<br>CTTCCTCAGGATGTTTAAGATTAGCATTCAGGAAGAGATCAGAGG<br>TCTGCTGGCTCCCTTATCATGTCCCTTATGGTGCTTCTGGCTCTGCA<br>CCGCGGGAACAGAGAAACAGGAGAATATGGGCCAAACAGGATAT<br>CTGTGGTAAGCAGTTCCTGCCCCGGCTCAGGGCCAAGAACAGTTG<br>GAACAGCAGAATATGGGCCAAACAGGATATCTGTGGTAAGCAGTT<br>CCTGCCCCGGCTCAGGGCCAAGAACAGATGGTCCCCAGATGCGGT<br>CCCGCCCTCAGCAGTTTCTAGAGAACCATCAGATGTTTCCAGGGTG<br>CCCCAAGGACCTGAAATGACCCTGTGCCTTATTTGAACTAACCAAT<br>CAGTTCGCTTCTCGCTTCTGTTCGCGCGCTTCTGCTCCCCGAGCTCT<br>ATATAAGCAGAGCTCGTTTAGTGAACCGTCAGATCGCGGCCGCGC<br>CGCCACCATGGTGAGCAAGGGCGAGGAGCTGTTCACCGGGGTGGT<br>GCCCATCCTGGTCGAGCTGGACGGCGACGTAAACGGCCACAAGTT<br>CAGCGTGTCCGGCGAGGGCGAGGGCGATGCCACCTACGGCAAGCT<br>GACCCTGAAGTTCATCTGCACCACCGGCAAGCTGCCCGTGCCCTG<br>GCCCACCCTCGTGACCACCCTGACCTACGGCGTGCAGTGCTTCAGC<br>CGCTACCCCGACCACATGAAGCAGCACGACTTCTTCAAGTCCGCC<br>ATGCCCGAAGGCTACGTCCAGGAGCGCACCATCTTCTTCAAGGAC<br>GACGGCAACTACAAGACCCGCGCCGAGGTGAAGTTCGAGGGCGA<br>CACCCTGGTGAACCGCATCGAGCTGAAGGGCATCGACTTCAAGGA<br>GGACGGCAACATCCTGGGGCACAAGCTGGAGTACAACTACAACA<br>GCCACAACGTCTATATCATGGCCGACAAGCAGAAGAACGGCATCA<br>AGGTGAACTTCAAGATCCGCCACAACATCGAGGACGGCAGCGTGC<br>AGCTCGCCGACCACTACCAGCAGAACACCCCCATCGGCGACGGCC<br>CCGTGCTGCTGCCCGACAACCACTACCTGAGCACCCAGTCCGCCCT<br>GAGCAAAGACCCCAACGAGAAGCGCGATCACATGGTCCTGCTGGA<br>GTTCGTGACCGCCGCCGGGATCACTCTCGGCATGGACGAGCTGTA<br>CAAGGAGGGCAGAGGAAGTCTTCTAACATGCGGTGACGTGGAGG<br>AGAATCCGGGCCCCCCTGCAGGAACTTCAAGGTGAGTCCAGGAGA |

-continued

| SEQ ID NO | NAME | SEQUENCE |
|---|---|---|
| | | TGTTTCAGCCCTGTTGCCTTTAGTCTCGAGGCAACTTAGACAACGG AGTATTGATCTGAGCACAGCAGGGTGTGAGCTGTTTGAAGATACT GGGGTTGGGGGTGAAGAAACTGCAGAGGACTAACTGGGCTGAGA CCCAGTGGTAATGTTTTAGGGCCTAAGGAGTGCCTCTAAAAATCT AGATGGACAATTTTGACTTTGAGAAAAGAGAGGTGGAAATGAGG AAAATGACTTTTCTTTATTAGATTCCAGTAGAAAGAACTTTCATCT TTCCCTCATTTTTGTTGTTTTAAAACATCTATCTGGAGGCAGGACA AGTATGGTCGTTAAAAAGATGCAGGCAGAAGGCATATATTGGCTC AGTCAAAGTGGGGAACTTTGGTGGGTCGACGTAGATAAGTAGCAT GGCGGGTTAATCATTAACTACAAGGAACCCCTAGTGATGGAGTTG GCCACTCCCTCTCTGCGCGCTCGCTCGCTCACTGAGGCCGGGCGAC CAAAGGTCGCCCGACGCCCGGGCTTTGCCCGGGCGGCCTCAGTGA GCGAGCGAGCGCGCCAGCTGGCGTAATAGCGAAGAGGCCCGCAC CGATCGCCCTTCCCAACAGTTGCGCAGCCTGAATGGCGAATGGCG ATTCCGTTGCAATGGCTGGCGGTAATATTGTTCTGGATATTACCAG CAAGGCCGATAGTTTGAGTTCTTCTACTCAGGCAAGTGATGTTATT ACTAATCAAAGAAGTATTGCGACAACGGTTAATTTGCGTGATGGA CAGACTCTTTTACTCGGTGGCCTCACTGATTATAAAAACACTTCTC AGGATTCTGGCGTACCGTTCCTGTCTAAAATCCCTTTAATCGGCCT CCTGTTTAGCTCCCGCTCTGATTCTAACGAGGAAAGCACGTTATAC GTGCTCGTCAAAGCAACCATAGTACGCGCCCTGTAGCGGCGCATT AAGCGCGGCGGGTGTGGTGGTTACGCGCAGCGTGACCGCTACACT TGCCAGCGCCCTAGCGCCCGCTCCTTTCGCTTTCTTCCCTTCCTTTC TCGCCACGTTCGCCGGCTTTCCCCGTCAAGCTCTAAATCGGGGGCT CCCTTTAGGGTTCCGATTTAGTGCTTTACGGCACCTCGACCCCAAA AAACTTGATTAGGGTGATGGTTCACGTAGTGGGCCATCGCCCTGA TAGACGGTTTTTCGCCCTTTGACGTTGGAGTCCACGTTCTTTAATA GTGGACTCTTGTTCCAAACTGGAACAACACTCAACCCTATCTCGGT CTATTCTTTTGATTTATAAGGGATTTTGCCGATTTCGGCCTATTGGT TAAAAAATGAGCTGATTTAACAAAAATTTAACGCGAATTTTAACA AAATATTAACGTTTACAATTTAAATATTTGCTTATACAATCTTCCT GTTTTTGGGGCTTTTCTGATTATCAACCGGGGTACATATGATTGAC ATGCTAGTTTTACGATTACCGTTCATCGATTCTCTTGTTTGCTCCAG ACTCTCAGGCAATGACCTGATAGCCTTTGTAGAGACCTCTCAAAA ATAGCTACCCTCTCCGGCATGAATTTATCAGCTAGAACGGTTGAAT ATCATATTGATGGTGATTTGACTGTCTCCGGCCTTTCTCACCCGTTT GAATCTTTACCTACACATTACTCAGGCATTGCATTTAAAATATATG AGGGTTCTAAAAATTTTTATCCTTGCGTTGAAATAAAGGCTTCTCC CGCAAAAGTATTACAGGGTCATAATGTTTTTGGTACAACCGATTTA GCTTTATGCTCTGAGGCTTTATTGCTTAATTTTGCTAATTCTTTGCC TTGCCTGTATGATTTATTGGATGTTGGAATCGCCTGATGCGGTATT TTCTCCTTACGCATCTGTGCGGTATTTCACACCGCATATGGTGCAC TCTCAGTACAATCTGCTCTGATGCCGCATAGTTAAGCCAGCCCCGA CACCCGCCAACACCCGCTGACGCGCCCTGACGGGCTTGTCTGCTCC CGGCATCCGCTTACAGACAAGCTGTGACCGTCTCCGGGAGCTGCA TGTGTCAGAGGTTTTCACCGTCATCACCGAAACGCGCGAGACGAA AGGGCCTCGTGATACGCCTATTTTTATAGGTTAATGTCATGATAAT AATGGTTTCTTAGACGTCAGGTGGCACTTTTCGGGGAAATGTGCGC GGAACCCCTATTTGTTTATTTTTCTAAATACATTCAAATATGTATCC GCTCATGAGACAATAACCCTGATAAATGCTTCAATAATATTGAAA AAGGAAGAGTATGAGTATTCAACATTTCCGTGTCGCCCTTATTCCC TTTTTTGCGGCATTTTGCCTTCCTGTTTTTGCTCACCCAGAAACGCT GGTGAAAGTAAAAGATGCTGAAGATCAGTTGGGTGCACGAGTGG GTTACATCGAACTGGATCTCAACAGCGGTAAGATCCTTGAGAGTT TTCGCCCCGAAGAACGTTTTCCAATGATGAGCACTTTTAAAGTTCT GCTATGTGGCGCGGTATTATCCCGTATTGACGCCGGGCAAGAGCA ACTCGGTCGCCGCATACACTATTCTCAGAATGACTTGGTTGAGTAC TCACCAGTCACAGAAAAGCATCTTACGGATGGCATGACAGTAAGA GAATTATGCAGTGCTGCCATAACCATGAGTGATAACACTGCGGCC AACTTACTTCTGACAACGATCGGAGGACCGAAGGAGCTAACCGCT TTTTTGCACAACATGGGGGATCATGTAACTCGCCTTGATCGTTGGG AACCGGAGCTGAATGAAGCCATACCAAACGACGAGCGTGACACC ACGATGCCTGTAGCAATGGCAACAACGTTGCGCAAACTATTAACT GGCGAACTACTTACTCTAGCTTCCCGGCAACAATTAATAGACTGG ATGGAGGCGGATAAAGTTGCAGGACCACTTCTGCGCTCGGCCCTT CCGGCTGGCTGGTTTATTGCTGATAAATCTGGAGCCGGTGAGCGT GGGTCTCGCGGTATCATTGCAGCACTGGGGCCAGATGGTAAGCCC TCCCGTATCGTAGTTATCTACACGACGGGGAGTCAGGCAACTATG GATGAACGAAATAGACAGATCGCTGAGATAGGTGCCTCACTGATT AAGCATTGGTAACTGTCAGACCAAGTTTACTCATATATACTTTAGA TTGATTTAAAACTTCATTTTTAATTTAAAAGGATCTAGGTGAAGAT CCTTTTTGATAATCTCATGACCAAAATCCCTTAACGTGAGTTTTCG TTCCACTGAGCGTCAGACCCCGTAGAAAAGATCAAAGGATCTTCT TGAGATCCTTTTTTTCTGCGCGTAATCTGCTGCTTGCAAACAAAAA AACCACCGCTACCAGCGGTGGTTTGTTTGCCGGATCAAGAGCTAC |

-continued

| SEQ ID NO | NAME | SEQUENCE |
|---|---|---|
| | | CAACTCTTTTTCCGAAGGTAACTGGCTTCAGCAGAGCGCAGATAC CAAATACTGTCCTTCTAGTGTAGCCGTAGTTAGGCCACCACTTCAA GAACTCTGTAGCACCGCCTACATACCTCGCTCTGCTAATCCTGTTA CCAGTGGCTGCTGCCAGTGGCGATAAGTCGTGTCTTACCGGGTTG GACTCAAGACGATAGTTACCGGATAAGGCGCAGCGGTCGGGCTGA ACGGGGGGTTCGTGCACACAGCCCAGCTTGGAGCGAACGACCTAC ACCGAACTGAGATACCTACAGCGTGAGCTATGAGAAAGCGCCACG CTTCCCGAAGGGAGAAAGGCGGACAGGTATCCGGTAAGCGGCAG GGTCGGAACAGGAGAGCGCACGAGGGAGCTTCCAGGGGGAAACG CCTGGTATCTTTATAGTCCTGTCGGGTTTCGCCACCTCTGACTTGA GCGTCGATTTTTGTGATGCTCGTCAGGGGGGCGGAGCCTATGGAA AAACGCCAGCAACGCGGCCTTTTTACGGTTCCTGGCCTTTTGCTGG CCTTTTGCTCACATGTTCTTTCCTGCGTTATCCCCTGATTCTGTGGA TAACCGTATTACCGCCTTTGAGTGAGCTGATACCGCTCGCCGCAGC CGAACGACCGAGCGCAGCGAGTCAGTGAGCGAGGAAGCGGAAGA GCGCCCAATACGCAAACCGCCTCTCCCCGCGCGTTGGCCGATTCAT TAATG |
| 45 | HBG1 Round 1 & 2: AMS#1258 pAAVHBG1-1(600) MND>GFP.wPRE3. SV40USE.pA; HS40.HBBp> | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TAGAAATTGTTTTCACTGCACTATTGAGAAATTAAGAGATAATGG CAAAAGTCACAAAGAGTATATTCAAAAAGAAGTATAGCACTTTTT CCTTAGAAACCACTGCTAACTGAAAGAGACTAAGATTTGTCCCGT CAAAAATCCTGGACCTATGCCTAAAACACATTTCACAATCCCTGA ACTTTTCAAAAATTGGTACATGCTTTAGCTTTAAACTACAGGCCTC ACTGGAGCTAGAGACAAGAAGGTAAAAAACGGCTGACAAAAGAA GTCCTGGTATCCTCTATGATGGGAGAAGGAAACTAGCTAAAGGGA AGAATAAATTAGAGAAAAACTGGAATGACTGAATCGGAACAAGG CAAAGGCTATAAAAAAAATTAGCAGTATCCTCTTGGGGGCCCCTT CCCCACACTATCTCAATGCAAATATCTGTCTGAAACGGTCCCTGGC TAAACTCCACCCATGGGTTGGCCAGCCTTGCCTTGACCAATAGCCT TGACAAGGCAAACTTGACCAATAGTCTTAGAGTATCCAGTGAGGC CAGGGGCCGGCGGCTGGCTAGGGATGAAGAATAAAAGGAAGCAC CCTTCAGCAGTTCCACCCGCGGGAACAGAGAAACAGGAGAATATG GGCCAAACAGGATATCTGTGGTAAGCAGTTCCTGCCCCGGCTCAG GGCCAAGAACAGTTGGAACAGCAGAATATGGGCCAAACAGGATA TCTGTGGTAAGCAGTTCCTGCCCCGGCTCAGGGCCAAGAACAGAT GGTCCCCAGATGCGGTCCCGCCCTCAGCAGTTTCTAGAGAACCAT CAGATGTTTCCAGGGTGCCCCAAGGACCTGAAATGACCCTGTGCC TTATTTGAACTAACCAATCAGTTCGCTTCTCGCTTCTGTTCGCGCG CTTCTGCTCCCCGAGCTCTATATAAGCAGAGCTCGTTTAGTGAACC GTCAGATCGCCTGGAGACGCCATCCACGCTGTTTTGACTTCCATAG AAGGCGGCCGCGCCGCCACCATGGTGAGCAAGGGCGAGGAGCTG TTCACCGGGGTGGTGCCCATCCTGGTCGAGCTGGACGGCGACGTA AACGGCCACAAGTTCAGCGTGTCCGGCGAGGGCGAGGGCGATGCC ACCTACGGCAAGCTGACCCTGAAGTTCATCTGCACCACCGGCAAG CTGCCCGTGCCCTGGCCCACCCTCGTGACCACCCTGACCTACGGCG TGCAGTGCTTCAGCCGCTACCCCGACCACATGAAGCAGCACGACT TCTTCAAGTCCGCCATGCCCGAAGGCTACGTCCAGGAGCGCACCA TCTTCTTCAAGGACGACGGCAACTACAAGACCCGCGCCGAGGTGA AGTTCGAGGGCGACACCCTGGTGAACCGCATCGAGCTGAAGGGCA TCGACTTCAAGGAGGACGGCAACATCCTGGGGCACAAGCTGGAGT ACAACTACAACAGCCACAACGTCTATATCATGGCCGACAAGCAGA AGAACGGCATCAAGGTGAACTTCAAGATCCGCCACAACATCGAGG ACGGCAGCGTGCAGCTCGCCGACCACTACCAGCAGAACACCCCCA TCGGCGACGGCCCCGTGCTGCTGCCCGACAACCACTACCTGAGCA CCCAGTCCGCCCTGAGCAAAGACCCCAACGAGAAGCGCGATCACA TGGTCCTGCTGGAGTTCGTGACCGCCGCCGGGATCACTCTCGGCAT GGACGAGCTGTACAAGTAACCTGCAGGGATAATCAACCTCTGGAT TACAAAATTTGTGAAAGATTGACTGGTATTCTTAACTATGTTGCTC CTTTTACGCTATGTGGATACGCTGCTTTAATGCCTTTGTATCATGCT ATTGCTTCCCGTATGGCTTTCATTTTCTCCTCCTTGTATAAATCCTG GTTAGTTCTTGCCACGGCGGAACTCATCGCCGCCTGCCTTGCCCGC TGCTGGACAGGGGCTCGGCTGTTGGGCACTGACAATTCCGTGGTG TTTATTTGTGAAATTTGTGATGCTATTGCTTTATTTGTAACCATTCT AGCTTTATTTGTGAAATTTGTGATGCTATTGCTTTATTTGTAACCAT TATAAGCTGCAATAAACAAGTTAACAACAACAATTGCATTCATTTT ATGTTTCAGGTTCAGGGGGAGATGTGGGAGGTTTTTTAAAGCGAA TTCTCTGGAACCTATCAGGGACCACAGTCAGCCAGGCAAGCACAT CTGCCCAAGCCAAGGGTGGAGGCATGCAGCTGTGGGGGTCTGTGA AAACACTTGAGGGAGCAGATAACTGGGCCAACCATGACTCAGTGC TTCTGGAGGCCAACAGGACTGCTGAGTCATCCTGTGGGGGTGGAG GTGGGACAAGGGAAAGGGGTGAATGGTACTGCTGATTACAACCTC |

-continued

| SEQ ID NO | NAME | SEQUENCE |
|---|---|---|
| | | TGGTGCTGCCTCCCCCTCCTGTTTATCTGAGAGGCTAGCGTAAATA<br>CACTTGCAAAGGAGGATGTTTTTAGTAGCAATTTGTACTGATGGTA<br>TGGGGCCAAGAGATATATCTTAGAGGGAGGGCTGAGGGTTTGAAG<br>TCCAACTCCTAAGCCAGTGCCAGAAGAGCCAAGGACAGGTACGGC<br>TGTCATCACTTAGACCTCACCCTGTGGAGCCACACCCTAGGGTTGG<br>CCAATCTACTCCCAGGAGCAGGGAGGGCAGGAGCCAGGGCTGGG<br>CATAAAAGTCAGGGCAGAGCCATCTATTGCTTACACTCGCTTCTGG<br>AACGTCTGAGGTTATCAATAAGCTCCTAGTCCAGACGCCATGGGT<br>CATTTCACAGAGGAGGACAAGGCTACTATCACAAGCCTGTGGGGC<br>AAGGTGAATGTGGAAGATGCTGGAGGAGAAACCCTGGGAAGGTA<br>GGCTCTGGTGACCAGGACAAGGGAGGGAAGGAAGGACCCTGTGC<br>CTGGCAAAAGTCCAGGTCGCTTCTCAGGATTTGTGGCACCTTCTGA<br>CTGTCAAACTGTTCTTGTCAATCTCACAGGCTCCTGGTTGTCTACC<br>CATGGACCCAGAGGTTCTTTGACAGCTTTGGCAACCTGTCCTCTGC<br>CTCTGCCATCATGGGCAACCCCAAAGTCAAGGCACATGGCAAGAA<br>GGTGCTGACTTCCTTGGGAGATGCCACAAAGCACCTGGATGATCT<br>CAAGGGCACCTTTGCCCAGCTGAGTGAACTGCACTGTGACAAGCT<br>GCATGTGGATCCTGAGAACTTCAAGGTGAGTCCAGGAGATGTTTC<br>AGCCCTGTTGCCTTTAGTCTCGAGGCAACTTAGACAACGGAGTATT<br>GATCTGAGCACAGCAGGGTGTGAGCTGTTTGAAGATACTGGGGTC<br>TCGAGGTCGACGTAGATAAGTAGCATGGCGGGTTAATCATTAACT<br>ACAAGGAACCCCTAGTGATGGAGTTGGCCACTCCCTCTCTGCGCG<br>CTCGCTCGCTCACTGAGGCCGGGCGACCAAAGGTCGCCCGACGCC<br>CGGGCTTTGCCCGGGCGGCCTCAGTGAGCGAGCGAGCGCGCCAGC<br>TGGCGTAATAGCGAAGAGGCCCGCACCGATCGCCCTTCCCAACAG<br>TTGCGCAGCCTGAATGGCGAATGGCGATTCCGTTGCAATGGCTGG<br>CGGTAATATTGTTCTGGATATTACCAGCAAGGCCGATAGTTTGAGT<br>TCTTCTACTCAGGCAAGTGATGTTATTACTAATCAAAGAAGTATTG<br>CGACAACGGTTAATTTGCGTGATGGACAGACTCTTTTACTCGGTGG<br>CCTCACTGATTATAAAAACACTTCTCAGGATTCTGGCGTACCGTTC<br>CTGTCTAAAATCCCTTTAATCGGCCTCCTGTTTAGCTCCCGCTCTG<br>ATTCTAACGAGGAAAGCACGTTATACGTGCTCGTCAAAGCAACCA<br>TAGTACGCGCCCTGTAGCGGCGCATTAAGCGCGGCGGGTGTGGTG<br>GTTACGCGCAGCGTGACCGCTACACTTGCCAGCGCCCTAGCGCCC<br>GCTCCTTTCGCTTTCTTCCCTTCCTTTCTCGCCACGTTCGCCGGCTT<br>TCCCCGTCAAGCTCTAAATCGGGGGCTCCCTTTAGGGTTCCGATTT<br>AGTGCTTTACGGCACCTCGACCCCAAAAAACTTGATTAGGGTGAT<br>GGTTCACGTAGTGGGCCATCGCCCTGATAGACGGTTTTTCGCCCTT<br>TGACGTTGGAGTCCACGTTCTTTAATAGTGGACTCTTGTTCCAAAC<br>TGGAACAACACTCAACCCTATCTCGGTCTATTCTTTTGATTTATAA<br>GGGATTTTGCCGATTTCGGCCTATTGGTTAAAAAATGAGCTGATTT<br>AACAAAAATTTAACGCGAATTTTAACAAAATATTAACGTTTACAA<br>TTTAAATATTTGCTTATACAATCTTCCTGTTTTTGGGGCTTTTCTGA<br>TTATCAACCGGGGTACATATGATTGACATGCTAGTTTTACGATTAC<br>CGTTCATCGATTCTCTTGTTTGCTCCAGACTCTCAGGCAATGACCT<br>GATAGCCTTTGTAGAGACCTCTCAAAAATAGCTACCCTCTCCGGCA<br>TGAATTTATCAGCTAGAACGGTTGAATATCATATTGATGGTGATTT<br>GACTGTCTCCGGCCTTTCTCACCCGTTTGAATCTTTACCTACACATT<br>ACTCAGGCATTGCATTTAAAATATATGAGGGTTCTAAAAATTTTTA<br>TCCTTGCGTTGAAATAAAGGCTTCTCCCGCAAAAGTATTACAGGGT<br>CATAATGTTTTTGGTACAACCGATTTAGCTTTATGCTCTGAGGCTT<br>TATTGCTTAATTTTGCTAATTCTTTGCCTTGCCTGTATGATTTATTG<br>GATGTTGGAATCGCCTGATGCGGTATTTTCTCCTTACGCATCTGTG<br>CGGTATTTCACACCGCATATGGTGCACTCTCAGTACAATCTGCTCT<br>GATGCCGCATAGTTAAGCCAGCCCCGACACCCGCCAACACCCGCT<br>GACGCGCCCTGACGGGCTTGTCTGCTCCCGGCATCCGCTTACAGAC<br>AAGCTGTGACCGTCTCCGGGAGCTGCATGTGTCAGAGGTTTTCACC<br>GTCATCACCGAAACGCGCGAGACGAAAGGGCCTCGTGATACGCCT<br>ATTTTTATAGGTTAATGTCATGATAATAATGGTTTCTTAGACGTCA<br>GGTGGCACTTTTCGGGGAAATGTGCGCGGAACCCCTATTTGTTTAT<br>TTTTCTAAATACATTCAAATATGTATCCGCTCATGAGACAATAACC<br>CTGATAAATGCTTCAATAATATTGAAAAAGGAAGAGTATGAGTAT<br>TCAACATTTCCGTGTCGCCCTTATTCCCTTTTTTGCGGCATTTTGCC<br>TTCCTGTTTTTGCTCACCCAGAAACGCTGGTGAAAGTAAAAGATGC<br>TGAAGATCAGTTGGGTGCACGAGTGGGTTACATCGAACTGGATCT<br>CAACAGCGGTAAGATCCTTGAGAGTTTTCGCCCCGAAGAACGTTT<br>TCCAATGATGAGCACTTTTAAAGTTCTGCTATGTGGCGCGGTATTA<br>TCCCGTATTGACGCCGGGCAAGAGCAACTCGGTCGCCGCATACAC<br>TATTCTCAGAATGACTTGGTTGAGTACTCACCAGTCACAGAAAAG<br>CATCTTACGGATGGCATGACAGTAAGAGAATTATGCAGTGCTGCC<br>ATAACCATGAGTGATAACACTGCGGCCAACTTACTTCTGACAACG<br>ATCGGAGGACCGAAGGAGCTAACCGCTTTTTTGCACAACATGGGG<br>GATCATGTAACTCGCCTTGATCGTTGGGAACCGGAGCTGAATGAA<br>GCCATACCAAACGACGAGCGTGACACCACGATGCCTGTAGCAATG<br>GCAACAACGTTGCGCAAACTATTAACTGGCGAACTACTTACTCTA |

-continued

| SEQ ID NO | NAME | SEQUENCE |
|---|---|---|
| | | GCTTCCCGGCAACAATTAATAGACTGGATGGAGGCGGATAAAGTT GCAGGACCACTTCTGCGCTCGGCCCTTCCGGCTGGCTGGTTTATTG CTGATAAATCTGGAGCCGGTGAGCGTGGGTCTCGCGGTATCATTG CAGCACTGGGGCCAGATGGTAAGCCCTCCCGTATCGTAGTTATCT ACACGACGGGGAGTCAGGCAACTATGGATGAACGAAATAGACAG ATCGCTGAGATAGGTGCCTCACTGATTAAGCATTGGTAACTGTCA GACCAAGTTTACTCATATATACTTTAGATTGATTTAAAACTTCATT TTTAATTTAAAAGGATCTAGGTGAAGATCCTTTTTGATAATCTCAT GACCAAAATCCCTTAACGTGAGTTTTCGTTCCACTGAGCGTCAGAC CCCGTAGAAAAGATCAAAGGATCTTCTTGAGATCCTTTTTTTCTGC GCGTAATCTGCTGCTTGCAAACAAAAAAACCACCGCTACCAGCGG TGGTTTGTTTGCCGGATCAAGAGCTACCAACTCTTTTTCCGAAGGT AACTGGCTTCAGCAGAGCGCAGATACCAAATACTGTCCTTCTAGT GTAGCCGTAGTTAGGCCACCACTTCAAGAACTCTGTAGCACCGCC TACATACCTCGCTCTGCTAATCCTGTTACCAGTGGCTGCTGCCAGT GGCGATAAGTCGTGTCTTACCGGGTTGGACTCAAGACGATAGTTA CCGGATAAGGCGCAGCGGTCGGGCTGAACGGGGGGTTCGTGCACA CAGCCCAGCTTGGAGCGAACGACCTACACCGAACTGAGATACCTA CAGCGTGAGCTATGAGAAAGCGCCACGCTTCCCGAAGGGAGAAA GGCGGACAGGTATCCGGTAAGCGGCAGGGTCGGAACAGGAGAGC GCACGAGGGAGCTTCCAGGGGGAAACGCCTGGTATCTTTATAGTC CTGTCGGGTTTCGCCACCTCTGACTTGAGCGTCGATTTTTGTGATG CTCGTCAGGGGGGCGGAGCCTATGGAAAAACGCCAGCAACGCGG CCTTTTTACGGTTCCTGGCCTTTTGCTGGCCTTTTGCTCACATGTTC TTTCCTGCGTTATCCCCTGATTCTGTGGATAACCGTATTACCGCCTT TGAGTGAGCTGATACCGCTCGCCGCAGCCGAACGACCGAGCGCAG CGAGTCAGTGAGCGAGGAAGCGGAAGAGCGCCCAATACGCAAAC CGCCTCTCCCCGCGCGTTGGCCGATTCATTAATG |
| 46 | HBG1 Round 1 & 2: AMS#1259 pAAVHBG1-1(600) MND>GFP.wPRE3. SV40USE.pA; HBBp> | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTTG TAGTTAATGATTAACCCGCCATGCTACTTATCTACACGCGTAGATC TAGAAATTGTTTTCACTGCACTATTGAGAAATTAAGAGATAATGG CAAAAGTCACAAAGAGTATATTCAAAAAGAAGTATAGCACTTTTT CCTTAGAAACCACTGCTAACTGAAAGAGACTAAGATTTGTCCCGT CAAAAATCCTGGACCTATGCCTAAAACACATTTCACAATCCCTGA ACTTTTCAAAAATTGGTACATGCTTTAGCTTTAAACTACAGGCCTC ACTGGAGCTAGAGACAAGAAGGTAAAAAACGGCTGACAAAAGAA GTCCTGGTATCCTCTATGATGGGAGAAGGAAACTAGCTAAAGGGA AGAATAAATTAGAGAAAAACTGGAATGACTGAATCGGAACAAGG CAAAGGCTATAAAAAAAATTAGCAGTATCCTCTTGGGGGCCCCTT CCCCACACTATCTCAATGCAAATATCTGTCTGAAACGGTCCCTGGC TAAACTCCACCCATGGGTTGGCCAGCCTTGCCTTGACCAATAGCCT TGACAAGGCAAACTTGACCAATAGTCTTAGAGTATCCAGTGAGGC CAGGGGCCGGCGGCTGGCTAGGGATGAAGAATAAAAGGAAGCAC CCTTCAGCAGTTCCACCCGCGGGAACAGAGAAACAGGAGAATATG GGCCAAACAGGATATCTGTGGTAAGCAGTTCCTGCCCCGGCTCAG GGCCAAGAACAGTTGGAACAGCAGAATATGGGCCAAACAGGATA TCTGTGGTAAGCAGTTCCTGCCCCGGCTCAGGGCCAAGAACAGAT GGTCCCCAGATGCGGTCCCGCCCTCAGCAGTTTCTAGAGAACCAT CAGATGTTTCCAGGGTGCCCCAAGGACCTGAAATGACCCTGTGCC TTATTTGAACTAACCAATCAGTTCGCTTCTCGCTTCTGTTCGCGCG CTTCTGCTCCCCGAGCTCTATATAAGCAGAGCTCGTTTAGTGAACC GTCAGATCGCCTGGAGACGCCATCCACGCTGTTTTGACTTCCATAG AAGGCGGCCGCGCCGCCACCATGGTGAGCAAGGGCGAGGAGCTG TTCACCGGGGTGGTGCCCATCCTGGTCGAGCTGGACGGCGACGTA AACGGCCACAAGTTCAGCGTGTCCGGCGAGGGCGAGGGCGATGCC ACCTACGGCAAGCTGACCCTGAAGTTCATCTGCACCACCGGCAAG CTGCCCGTGCCCTGGCCCACCCTCGTGACCACCCTGACCTACGGCG TGCAGTGCTTCAGCCGCTACCCCGACCACATGAAGCAGCACGACT TCTTCAAGTCCGCCATGCCCGAAGGCTACGTCCAGGAGCGCACCA TCTTCTTCAAGGACGACGGCAACTACAAGACCCGCGCCGAGGTGA AGTTCGAGGGCGACACCCTGGTGAACCGCATCGAGCTGAAGGGCA TCGACTTCAAGGAGGACGGCAACATCCTGGGGCACAAGCTGGAGT ACAACTACAACAGCCACAACGTCTATATCATGGCCGACAAGCAGA AGAACGGCATCAAGGTGAACTTCAAGATCCGCCACAACATCGAGG ACGGCAGCGTGCAGCTCGCCGACCACTACCAGCAGAACACCCCCA TCGGCGACGGCCCCGTGCTGCTGCCCGACAACCACTACCTGAGCA CCCAGTCCGCCCTGAGCAAAGACCCCAACGAGAAGCGCGATCACA TGGTCCTGCTGGAGTTCGTGACCGCCGCCGGGATCACTCTCGGCAT GGACGAGCTGTACAAGTAACCTGCAGGGATAATCAACCTCTGGAT TACAAAATTTGTGAAAGATTGACTGGTATTCTTAACTATGTTGCTC CTTTTACGCTATGTGGATACGCTGCTTTAATGCCTTTGTATCATGCT ATTGCTTCCCGTATGGCTTTCATTTTCTCCTCCTTGTATAAATCCTG |

-continued

| SEQ ID NO | NAME | SEQUENCE |
|---|---|---|
| | | GTTAGTTCTTGCCACGGCGGAACTCATCGCCGCCTGCCTTGCCCGC<br>TGCTGGACAGGGGCTCGGCTGTTGGGCACTGACAATTCCGTGGTG<br>TTTATTTGTGAAATTTGTGATGCTATTGCTTTATTTGTAACCATTCT<br>AGCTTTATTTGTGAAATTTGTGATGCTATTGCTTTATTTGTAACCAT<br>TATAAGCTGCAATAAACAAGTTAACAACAACAATTGCATTCATTTT<br>ATGTTTCAGGTTCAGGGGGAGATGTGGGAGGTTTTTTAAAGCGAA<br>TTCGTAAATACACTTGCAAAGGAGGATGTTTTTAGTAGCAATTTGT<br>ACTGATGGTATGGGGCCAAGAGATATATCTTAGAGGGAGGGCTGA<br>GGGTTTGAAGTCCAACTCCTAAGCCAGTGCCAGAAGAGCCAAGGA<br>CAGGTACGGCTGTCATCACTTAGACCTCACCCTGTGGAGCCACAC<br>CCTAGGGTTGGCCAATCTACTCCCAGGAGCAGGGAGGGCAGGAGC<br>CAGGGCTGGGCATAAAAGTCAGGGCAGAGCCATCTATTGCTTACA<br>CTCGCTTCTGGAACGTCTGAGGTTATCAATAAGCTCCTAGTCCAGA<br>CGCCATGGGTCATTTCACAGAGGAGGACAAGGCTACTATCACAAG<br>CCTGTGGGGCAAGGTGAATGTGGAAGATGCTGGAGGAGAAACCCT<br>GGGAAGGTAGGCTCTGGTGACCAGGACAAGGGAGGGAAGGAAGG<br>ACCCTGTGCCTGGCAAAAGTCCAGGTCGCTTCTCAGGATTTGTGGC<br>ACCTTCTGACTGTCAAACTGTTCTTGTCAATCTCACAGGCTCCTGG<br>TTGTCTACCCATGGACCCAGAGGTTCTTTGACAGCTTTGGCAACCT<br>GTCCTCTGCCTCTGCCATCATGGGCAACCCCAAAGTCAAGGCACA<br>TGGCAAGAAGGTGCTGACTTCCTTGGGAGATGCCACAAAGCACCT<br>GGATGATCTCAAGGGCACCTTTGCCCAGCTGAGTGAACTGCACTG<br>TGACAAGCTGCATGTGGATCCTGAGAACTTCAAGGTGAGTCCAGG<br>AGATGTTTCAGCCCTGTTGCCTTTAGTCTCGAGGCAACTTAGACAA<br>CGGAGTATTGATCTGAGCACAGCAGGGTGTGAGCTGTTTGAAGAT<br>ACTGGGGTCTCGAGGTCGACGTAGATAAGTAGCATGGCGGGTTAA<br>TCATTAACTACAAGGAACCCCTAGTGATGGAGTTGGCCACTCCCTC<br>TCTGCGCGCTCGCTCGCTCACTGAGGCCGGGCGACCAAAGGTCGC<br>CCGACGCCCGGGCTTTGCCCGGGCGGCCTCAGTGAGCGAGCGAGC<br>GCGCCAGCTGGCGTAATAGCGAAGAGGCCCGCACCGATCGCCCTT<br>CCCAACAGTTGCGCAGCCTGAATGGCGAATGGCGATTCCGTTGCA<br>ATGGCTGGCGGTAATATTGTTCTGGATATTACCAGCAAGGCCGAT<br>AGTTTGAGTTCTTCTACTCAGGCAAGTGATGTTATTACTAATCAAA<br>GAAGTATTGCGACAACGGTTAATTTGCGTGATGGACAGACTCTTTT<br>ACTCGGTGGCCTCACTGATTATAAAAACACTTCTCAGGATTCTGGC<br>GTACCGTTCCTGTCTAAAATCCCTTTAATCGGCCTCCTGTTTAGCTC<br>CCGCTCTGATTCTAACGAGGAAAGCACGTTATACGTGCTCGTCAA<br>AGCAACCATAGTACGCGCCCTGTAGCGGCGCATTAAGCGCGGCGG<br>GTGTGGTGGTTACGCGCAGCGTGACCGCTACACTTGCCAGCGCCC<br>TAGCGCCCGCTCCTTTCGCTTTCTTCCCTTCCTTTCTCGCCACGTTC<br>GCCGGCTTTCCCCGTCAAGCTCTAAATCGGGGGCTCCCTTTAGGGT<br>TCCGATTTAGTGCTTTACGGCACCTCGACCCCAAAAAACTTGATTA<br>GGGTGATGGTTCACGTAGTGGGCCATCGCCCTGATAGACGGTTTTT<br>CGCCCTTTGACGTTGGAGTCCACGTTCTTTAATAGTGGACTCTTGT<br>TCCAAACTGGAACAACACTCAACCCTATCTCGGTCTATTCTTTTGA<br>TTTATAAGGGATTTTGCCGATTTCGGCCTATTGGTTAAAAAATGAG<br>CTGATTTAACAAAAATTTAACGCGAATTTTAACAAAATATTAACGT<br>TTACAATTTAAATATTTGCTTATACAATCTTCCTGTTTTTGGGGCTT<br>TTCTGATTATCAACCGGGGTACATATGATTGACATGCTAGTTTTAC<br>GATTACCGTTCATCGATTCTCTTGTTTGCTCCAGACTCTCAGGCAA<br>TGACCTGATAGCCTTTGTAGAGACCTCTCAAAAATAGCTACCCTCT<br>CCGGCATGAATTTATCAGCTAGAACGGTTGAATATCATATTGATG<br>GTGATTTGACTGTCTCCGGCCTTTCTCACCCGTTTGAATCTTTACCT<br>ACACATTACTCAGGCATTGCATTTAAAATATATGAGGGTTCTAAA<br>AATTTTTATCCTTGCGTTGAAATAAAGGCTTCTCCCGCAAAAGTAT<br>TACAGGGTCATAATGTTTTTGGTACAACCGATTTAGCTTTATGCTC<br>TGAGGCTTTATTGCTTAATTTTGCTAATTCTTTGCCTTGCCTGTATG<br>ATTTATTGGATGTTGGAATCGCCTGATGCGGTATTTTCTCCTTACG<br>CATCTGTGCGGTATTTCACACCGCATATGGTGCACTCTCAGTACAA<br>TCTGCTCTGATGCCGCATAGTTAAGCCAGCCCCGACACCCGCCAA<br>CACCCGCTGACGCGCCCTGACGGGCTTGTCTGCTCCCGGCATCCGC<br>TTACAGACAAGCTGTGACCGTCTCCGGGAGCTGCATGTGTCAGAG<br>GTTTTCACCGTCATCACCGAAACGCGCGAGACGAAAGGGCCTCGT<br>GATACGCCTATTTTTATAGGTTAATGTCATGATAATAATGGTTTCT<br>TAGACGTCAGGTGGCACTTTTCGGGGAAATGTGCGCGGAACCCCT<br>ATTTGTTTATTTTTCTAAATACATTCAAATATGTATCCGCTCATGAG<br>ACAATAACCCTGATAAATGCTTCAATAATATTGAAAAAGGAAGAG<br>TATGAGTATTCAACATTTCCGTGTCGCCCTTATTCCCTTTTTTGCGG<br>CATTTTGCCTTCCTGTTTTTGCTCACCCAGAAACGCTGGTGAAAGT<br>AAAAGATGCTGAAGATCAGTTGGGTGCACGAGTGGGTTACATCGA<br>ACTGGATCTCAACAGCGGTAAGATCCTTGAGAGTTTTCGCCCCGA<br>AGAACGTTTTCCAATGATGAGCACTTTTAAAGTTCTGCTATGTGGC<br>GCGGTATTATCCCGTATTGACGCCGGGCAAGAGCAACTCGGTCGC<br>CGCATACACTATTCTCAGAATGACTTGGTTGAGTACTCACCAGTCA<br>CAGAAAAGCATCTTACGGATGGCATGACAGTAAGAGAATTATGCA |

-continued

| SEQ ID NO | NAME | SEQUENCE |
|---|---|---|
| | | GTGCTGCCATAACCATGAGTGATAACACTGCGGCCAACTTACTTCT |
| | | GACAACGATCGGAGGACCGAAGGAGCTAACCGCTTTTTTGCACAA |
| | | CATGGGGGATCATGTAACTCGCCTTGATCGTTGGGAACCGGAGCT |
| | | GAATGAAGCCATACCAAACGACGAGCGTGACACCACGATGCCTGT |
| | | AGCAATGGCAACAACGTTGCGCAAACTATTAACTGGCGAACTACT |
| | | TACTCTAGCTTCCCGGCAACAATTAATAGACTGGATGGAGGCGGA |
| | | TAAAGTTGCAGGACCACTTCTGCGCTCGGCCCTTCCGGCTGGCTGG |
| | | TTTATTGCTGATAAATCTGGAGCCGGTGAGCGTGGGTCTCGCGGTA |
| | | TCATTGCAGCACTGGGGCCAGATGGTAAGCCCTCCCGTATCGTAG |
| | | TTATCTACACGACGGGGAGTCAGGCAACTATGGATGAACGAAATA |
| | | GACAGATCGCTGAGATAGGTGCCTCACTGATTAAGCATTGGTAAC |
| | | TGTCAGACCAAGTTTACTCATATATACTTTAGATTGATTTAAAACT |
| | | TCATTTTTAATTTAAAAGGATCTAGGTGAAGATCCTTTTTGATAAT |
| | | CTCATGACCAAAATCCCTTAACGTGAGTTTTCGTTCCACTGAGCGT |
| | | CAGACCCCGTAGAAAAGATCAAAGGATCTTCTTGAGATCCTTTTTT |
| | | TCTGCGCGTAATCTGCTGCTTGCAAACAAAAAAACCACCGCTACC |
| | | AGCGGTGGTTTGTTTGCCGGATCAAGAGCTACCAACTCTTTTTCCG |
| | | AAGGTAACTGGCTTCAGCAGAGCGCAGATACCAAATACTGTCCTT |
| | | CTAGTGTAGCCGTAGTTAGGCCACCACTTCAAGAACTCTGTAGCA |
| | | CCGCCTACATACCTCGCTCTGCTAATCCTGTTACCAGTGGCTGCTG |
| | | CCAGTGGCGATAAGTCGTGTCTTACCGGGTTGGACTCAAGACGAT |
| | | AGTTACCGGATAAGGCGCAGCGGTCGGGCTGAACGGGGGGTTCGT |
| | | GCACACAGCCCAGCTTGGAGCGAACGACCTACACCGAACTGAGAT |
| | | ACCTACAGCGTGAGCTATGAGAAAGCGCCACGCTTCCCGAAGGGA |
| | | GAAAGGCGGACAGGTATCCGGTAAGCGGCAGGGTCGGAACAGGA |
| | | GAGCGCACGAGGGAGCTTCCAGGGGGAAACGCCTGGTATCTTTAT |
| | | AGTCCTGTCGGGTTTCGCCACCTCTGACTTGAGCGTCGATTTTTGT |
| | | GATGCTCGTCAGGGGGGCGGAGCCTATGGAAAAACGCCAGCAAC |
| | | GCGGCCTTTTTACGGTTCCTGGCCTTTTGCTGGCCTTTTGCTCACAT |
| | | GTTCTTTCCTGCGTTATCCCCTGATTCTGTGGATAACCGTATTACCG |
| | | CCTTTGAGTGAGCTGATACCGCTCGCCGCAGCCGAACGACCGAGC |
| | | GCAGCGAGTCAGTGAGCGAGGAAGCGGAAGAGCGCCCAATACGC |
| | | AAACCGCCTCTCCCCGCGCGTTGGCCGATTCATTAATG |
| 47 | HBG1 Round 1 & 2: | CAGCTGCGCGCTCGCTCGCTCACTGAGGCCGCCCGGGCAAAGCCC |
| | AMS#1293 | GGGCGTCGGGCGACCTTTGGTCGCCCGGCCTCAGTGAGCGAGCGA |
| | pAAV HBG1d- | GCGCGCAGAGAGGGAGTGGCCAACTCCATCACTAGGGGTTCCTTG |
| | 141,-1(459,600) | TAGTTAATGATTAACCCGCCATGCTACTTATCTACACGCGTAGATC |
| | MND>GFP.wPRE3. | TAGAAATTGTTTTCACTGCACTATTGAGAAATTAAGAGATAATGG |
| | SV40USE.pA; | CAAAAGTCACAAAGAGTATATTCAAAAAGAAGTATAGCACTTTTT |
| | HPFH- | CCTTAGAAACCACTGCTAACTGAAAGAGACTAAGATTTGTCCCGT |
| | 2.HS40.HBBp> | CAAAAATCCTGGACCTATGCCTAAAACACATTTCACAATCCCTGA |
| | | ACTTTTCAAAAATTGGTACATGCTTTAGCTTTAAACTACAGGCCTC |
| | | ACTGGAGCTAGAGACAAGAAGGTAAAAAACGGCTGACAAAAGAA |
| | | GTCCTGGTATCCTCTATGATGGGAGAAGGAAACTAGCTAAAGGGA |
| | | AGAATAAATTAGAGAAAAACTGGAATGACTGAATCGGAACAAGG |
| | | CAAAGGCTATAAAAAAAATTAGCAGTATCCTCTTGGGGGCCCCTT |
| | | CCCCACACTATCTCAATGCAAATATCTGTCTGAAACGGTCCCTGGC |
| | | TAAACTCCACCCGCGGGAACAGAGAAACAGGAGAATATGGGCCA |
| | | AACAGGATATCTGTGGTAAGCAGTTCCTGCCCCGGCTCAGGGCCA |
| | | AGAACAGTTGGAACAGCAGAATATGGGCCAAACAGGATATCTGTG |
| | | GTAAGCAGTTCCTGCCCCGGCTCAGGGCCAAGAACAGATGGTCCC |
| | | CAGATGCGGTCCCGCCCTCAGCAGTTTCTAGAGAACCATCAGATG |
| | | TTTCCAGGGTGCCCCAAGGACCTGAAATGACCCTGTGCCTTATTTG |
| | | AACTAACCAATCAGTTCGCTTCTCGCTTCTGTTCGCGCGCTTCTGC |
| | | TCCCCGAGCTCTATATAAGCAGAGCTCGTTTAGTGAACCGTCAGAT |
| | | CGCCTGGAGACGCCATCCACGCTGTTTTGACTTCCATAGAAGGCG |
| | | GCCGCGCCGCCACCATGGTGAGCAAGGGCGAGGAGCTGTTCACCG |
| | | GGGTGGTGCCCATCCTGGTCGAGCTGGACGGCGACGTAAACGGCC |
| | | ACAAGTTCAGCGTGTCCGGCGAGGGCGAGGGCGATGCCACCTACG |
| | | GCAAGCTGACCCTGAAGTTCATCTGCACCACCGGCAAGCTGCCCG |
| | | TGCCCTGGCCCACCCTCGTGACCACCCTGACCTACGGCGTGCAGTG |
| | | CTTCAGCCGCTACCCCGACCACATGAAGCAGCACGACTTCTTCAA |
| | | GTCCGCCATGCCCGAAGGCTACGTCCAGGAGCGCACCATCTTCTTC |
| | | AAGGACGACGGCAACTACAAGACCCGCGCCGAGGTGAAGTTCGA |
| | | GGGCGACACCCTGGTGAACCGCATCGAGCTGAAGGGCATCGACTT |
| | | CAAGGAGGACGGCAACATCCTGGGGCACAAGCTGGAGTACAACT |
| | | ACAACAGCCACAACGTCTATATCATGGCCGACAAGCAGAAGAACG |
| | | GCATCAAGGTGAACTTCAAGATCCGCCACAACATCGAGGACGGCA |
| | | GCGTGCAGCTCGCCGACCACTACCAGCAGAACACCCCCATCGGCG |
| | | ACGGCCCCGTGCTGCTGCCCGACAACCACTACCTGAGCACCCAGT |
| | | CCGCCCTGAGCAAAGACCCCAACGAGAAGCGCGATCACATGGTCC |
| | | TGCTGGAGTTCGTGACCGCCGCCGGGATCACTCTCGGCATGGACG |
| | | AGCTGTACAAGTAACCTGCAGGGATAATCAACCTCTGGATTACAA |
| | | AATTTGTGAAAGATTGACTGGTATTCTTAACTATGTTGCTCCTTTT |

-continued

| SEQ ID NO | NAME | SEQUENCE |
|---|---|---|
| | | ACGCTATGTGGATACGCTGCTTTAATGCCTTTGTATCATGCTATTG CTTCCCGTATGGCTTTCATTTTCTCCTCCTTGTATAAATCCTGGTTA GTTCTTGCCACGGCGGAACTCATCGCCGCCTGCCTTGCCCGCTGCT GGACAGGGGCTCGGCTGTTGGGCACTGACAATTCCGTGGTGTTTA TTTGTGAAATTTGTGATGCTATTGCTTTATTTGTAACCATTCTAGCT TTATTTGTGAAATTTGTGATGCTATTGCTTTATTTGTAACCATTATA AGCTGCAATAAACAAGTTAACAACAACAATTGCATTCATTTTATGT TTCAGGTTCAGGGGGAGATGTGGGAGGTTTTTTAAAGCGAATTCC GAGATCGAGACCATCCTGGCTAACACAGTGAAACCCCGTCTCTAC TAAAAAAATACAAAAAATTAGCCGGGCTTGGTGGCGGGTGCCTGT AGTCCCAGCTACTATGGAGGCTGAGGCGGGAGAATGGCGTGAACG CGGGGGGCGGAGCTTGCAGTGAGCAGAGATCAGGGGCCACTGCA CTCCAGCCTGGGCGACAGAGAGAGACTCTGTCTCAAAAAAAAGAA AAAAAAAATTTAGTAGACTAGCTAAAAAAATCCAGAGATAGTTAT TGATGCATATGTAAAAGTCTTCCAATATTTACAAGTACAATGAAA AAAAAATAACCTTGAATTAAGTGTAGAACTCATTGACAATGTTTC AAAGGATGTGAGGGATAAACTAAAATTTGGGCAGTACATGCTGTT CCTGTGTACTTGGAACAGAGGGAGAAAATCTGGGCTGGAAATATT GTTATAGGAGTTAGCACATGAAGGTGACAACTAAATTATTTGGAG TAGATGGAGTCACCAGCACATGTGAATAGTTTTAGAATGAAATGA CCCAAGATAGAACTTTGGAGAGCCCCCAAATTTAAATAAAATCAG TATAAGAGAAGAGGAAGAAACCAAATGGTATACTAGTCTAAATTG TTTCTTAGTGACAAAAGAATAACCTGAATATTAGATTAGCTGCCTA TATGCTCTCTGAATCAATTTCATTCAACATGCAACAGTTCTGGAAC CTATCAGGGACCACAGTCAGCCAGGCAAGCACATCTGCCCAAGCC AAGGGTGGAGGCATGCAGCTGTGGGGGTCTGTGAAAACACTTGAG GGAGCAGATAACTGGGCCAACCATGACTCAGTGCTTCTGGAGGCC AACAGGACTGCTGAGTCATCCTGTGGGGGTGGAGGTGGGACAAGG GAAAGGGGTGAATGGTACTGCTGATTACAACCTCTGGTGCTGCCT CCCCCTCCTGTTTATCTGAGAGGCTAGCGTAAATACACTTGCAAAG GAGGATGTTTTTAGTAGCAATTTGTACTGATGGTATGGGGCCAAG AGATATATCTTAGAGGGAGGGCTGAGGGTTTGAAGTCCAACTCCT AAGCCAGTGCCAGAAGAGCCAAGGACAGGTACGGCTGTCATCACT TAGACCTCACCCTGTGGAGCCACACCCTAGGGTTGGCCAATCTACT CCCAGGAGCAGGGAGGGCAGGAGCCAGGGCTGGGCATAAAAGTC AGGGCAGAGCCATCTATTGCTTACACTCGCTTCTGGAACGTCTGAG GTTATCAATAAGCTCCTAGTCCAGACGCCATGGGTCATTTCACAGA GGAGGACAAGGCTACTATCACAAGCCTGTGGGGCAAGGTGAATGT GGAAGATGCTGGAGGAGAAACCCTGGGAAGGTAGGCTCTGGTGA CCAGGACAAGGGAGGGAAGGAAGGACCCTGTGCCTGGCAAAAGT CCAGGTCGCTTCTCAGGATTTGTGGCACCTTCTGACTGTCAAACTG TTCTTGTCAATCTCACAGGCTCCTGGTTGTCTACCCATGGACCCAG AGGTTCTTTGACAGCTTTGGCAACCTGTCCTCTGCCTCTGCCATCA TGGGCAACCCCAAAGTCAAGGCACATGGCAAGAAGGTGCTGACTT CCTTGGGAGATGCCACAAAGCACCTGGATGATCTCAAGGGCACCT TTGCCCAGCTGAGTGAACTGCACTGTGACAAGCTGCATGTGGATC CTGAGAACTTCAAGGTGAGTCCAGGAGATGTTTCAGCCCTGTTGC CTTTAGTCTCGAGGCAACTTAGACAACGGAGTATTGATCTGAGCA CAGCAGGGTGTGAGCTGTTTGAAGATACTGGGGTCTCGAGGTCGA CGTAGATAAGTAGCATGGCGGGTTAATCATTAACTACAAGGAACC CCTAGTGATGGAGTTGGCCACTCCCTCTCTGCGCGCTCGCTCGCTC ACTGAGGCCGGGCGACCAAAGGTCGCCCGACGCCCGGGCTTTGCC CGGGCGGCCTCAGTGAGCGAGCGAGCGCGCCAGCTGGCGTAATAG CGAAGAGGCCCGCACCGATCGCCCTTCCCAACAGTTGCGCAGCCT GAATGGCGAATGGCGATTCCGTTGCAATGGCTGGCGGTAATATTG TTCTGGATATTACCAGCAAGGCCGATAGTTTGAGTTCTTCTACTCA GGCAAGTGATGTTATTACTAATCAAAGAAGTATTGCGACAACGGT TAATTTGCGTGATGGACAGACTCTTTTACTCGGTGGCCTCACTGAT TATAAAAACACTTCTCAGGATTCTGGCGTACCGTTCCTGTCTAAAA TCCCTTTAATCGGCCTCCTGTTTAGCTCCCGCTCTGATTCTAACGA GGAAAGCACGTTATACGTGCTCGTCAAAGCAACCATAGTACGCGC CCTGTAGCGGCGCATTAAGCGCGGCGGGTGTGGTGGTTACGCGCA GCGTGACCGCTACACTTGCCAGCGCCCTAGCGCCCGCTCCTTTCGC TTTCTTCCCTTCCTTTCTCGCCACGTTCGCCGGCTTTCCCCGTCAAG CTCTAAATCGGGGGCTCCCTTTAGGGTTCCGATTTAGTGCTTTACG GCACCTCGACCCCAAAAAACTTGATTAGGGTGATGGTTCACGTAG TGGGCCATCGCCCTGATAGACGGTTTTTCGCCCTTTGACGTTGGAG TCCACGTTCTTTAATAGTGGACTCTTGTTCCAAACTGGAACAACAC TCAACCCTATCTCGGTCTATTCTTTTGATTTATAAGGGATTTTGCCG ATTTCGGCCTATTGGTTAAAAAATGAGCTGATTTAACAAAAATTTA ACGCGAATTTTAACAAAATATTAACGTTTACAATTTAAATATTTGC TTATACAATCTTCCTGTTTTTGGGGCTTTTCTGATTATCAACCGGGG TACATATGATTGACATGCTAGTTTTACGATTACCGTTCATCGATTC TCTTGTTTGCTCCAGACTCTCAGGCAATGACCTGATAGCCTTTGTA GAGACCTCTCAAAAATAGCTACCCTCTCCGGCATGAATTTATCAGC |

-continued

| SEQ ID NO | NAME | SEQUENCE |
|---|---|---|
| | | TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA<br>AGGAGCTAACCGCTTTTTTGCACAACATGGGGGATCATGTAACTC<br>GCCTTGATCGTTGGGAACCGGAGCTGAATGAAGCCATACCAAACG<br>ACGAGCGTGACACCACGATGCCTGTAGCAATGGCAACAACGTTGC<br>GCAAACTATTAACTGGCGAACTACTTACTCTAGCTTCCCGGCAACA<br>ATTAATAGACTGGATGGAGGCGGATAAAGTTGCAGGACCACTTCT<br>GCGCTCGGCCCTTCCGGCTGGCTGGTTTATTGCTGATAAATCTGGA<br>GCCGGTGAGCGTGGGTCTCGCGGTATCATTGCAGCACTGGGGCCA<br>GATGGTAAGCCCTCCCGTATCGTAGTTATCTACACGACGGGGAGT<br>CAGGCAACTATGGATGAACGAAATAGACAGATCGCTGAGATAGGT<br>GCCTCACTGATTAAGCATTGGTAACTGTCAGACCAAGTTTACTCAT<br>ATATACTTTAGATTGATTTAAAACTTCATTTTTAATTTAAAAGGAT<br>CTAGGTGAAGATCCTTTTTGATAATCTCATGACCAAAATCCCTTAA<br>CGTGAGTTTTCGTTCCACTGAGCGTCAGACCCCGTAGAAAAGATC<br>AAAGGATCTTCTTGAGATCCTTTTTTTCTGCGCGTAATCTGCTGCTT<br>GCAAACAAAAAAACCACCGCTACCAGCGGTGGTTTGTTTGCCGGA<br>TCAAGAGCTACCAACTCTTTTTCCGAAGGTAACTGGCTTCAGCAGA<br>GCGCAGATACCAAATACTGTCCTTCTAGTGTAGCCGTAGTTAGGCC<br>ACCACTTCAAGAACTCTGTAGCACCGCCTACATACCTCGCTCTGCT<br>AATCCTGTTACCAGTGGCTGCTGCCAGTGGCGATAAGTCGTGTCTT<br>ACCGGGTTGGACTCAAGACGATAGTTACCGGATAAGGCGCAGCGG<br>TCGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACCT<br>CTGACTTGAGCGTCGATTTTTGTGATGCTCGTCAGGGGGGCGGAG<br>CCTATGGAAAAACGCCAGCAACGCGGCCTTTTTACGGTTCCTGGC<br>CTTTTGCTGGCCTTTTGCTCACATGTTCTTTCCTGCGTTATCCCCTG<br>ATTCTGTGGATAACCGTATTACCGCCTTTGAGTGAGCTGATACCGC<br>TCGCCGCAGCCGAACGACCGAGCGCAGCGAGTCAGTGAGCGAGG<br>AAGCGGAAGAGCGCCCAATACGCAAACCGCCTCTCCCCGCGCGTT<br>GGCCGATTCATTAATG |
| 48 | HBG1 Round 1 & 2:<br>AMS#1294<br>pAAV HBG1d-<br>141,-1(459,600)<br>MND>GFP.wPRE3.<br>SV40USE.pA;<br>HS40.HBBp> | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TAGAAATTGTTTTCACTGCACTATTGAGAAATTAAGAGATAATGG<br>CAAAAGTCACAAAGAGTATATTCAAAAAGAAGTATAGCACTTTTT<br>CCTTAGAAACCACTGCTAACTGAAAGAGACTAAGATTTGTCCCGT<br>CAAAAATCCTGGACCTATGCCTAAAACACATTTCACAATCCCTGA<br>ACTTTTCAAAAATTGGTACATGCTTTAGCTTTAAACTACAGGCCTC<br>ACTGGAGCTAGAGACAAGAAGGTAAAAAACGGCTGACAAAAGAA<br>GTCCTGGTATCCTCTATGATGGGAGAAGGAAACTAGCTAAAGGGA<br>AGAATAAATTAGAGAAAAACTGGAATGACTGAATCGGAACAAGG<br>CAAAGGCTATAAAAAAAAATTAGCAGTATCCTCTTGGGGGCCCCTT<br>CCCCACACTATCTCAATGCAAATATCTGTCTGAAACGGTCCCTGGC<br>TAAACTCCACCCGCGGGAACAGAGAAACAGGAGAATATGGGCCA<br>AACAGGATATCTGTGGTAAGCAGTTCCTGCCCCGGCTCAGGGCCA<br>AGAACAGTTGGAACAGCAGAATATGGGCCAAACAGGATATCTGTG |

-continued

| SEQ ID NO | NAME | SEQUENCE |
|---|---|---|
| | | GTAAGCAGTTCCTGCCCCGGCTCAGGGCCAAGAACAGATGGTCCC<br>CAGATGCGGTCCCGCCCTCAGCAGTTTCTAGAGAACCATCAGATG<br>TTTCCAGGGTGCCCCAAGGACCTGAAATGACCCTGTGCCTTATTTG<br>AACTAACCAATCAGTTCGCTTCTCGCTTCTGTTCGCGCGCTTCTGC<br>TCCCCGAGCTCTATATAAGCAGAGCTCGTTTAGTGAACCGTCAGAT<br>CGCCTGGAGACGCCATCCACGCTGTTTTGACTTCCATAGAAGGCG<br>GCCGCGCCGCCACCATGGTGAGCAAGGGCGAGGAGCTGTTCACCG<br>GGGTGGTGCCCATCCTGGTCGAGCTGGACGGCGACGTAAACGGCC<br>ACAAGTTCAGCGTGTCCGGCGAGGGCGAGGGCGATGCCACCTACG<br>GCAAGCTGACCCTGAAGTTCATCTGCACCACCGGCAAGCTGCCCG<br>TGCCCTGGCCCACCCTCGTGACCACCCTGACCTACGGCGTGCAGTG<br>CTTCAGCCGCTACCCCGACCACATGAAGCAGCACGACTTCTTCAA<br>GTCCGCCATGCCCGAAGGCTACGTCCAGGAGCGCACCATCTTCTTC<br>AAGGACGACGGCAACTACAAGACCCGCGCCGAGGTGAAGTTCGA<br>GGGCGACACCCTGGTGAACCGCATCGAGCTGAAGGGCATCGACTT<br>CAAGGAGGACGGCAACATCCTGGGGCACAAGCTGGAGTACAACT<br>ACAACAGCCACAACGTCTATATCATGGCCGACAAGCAGAAGAACG<br>GCATCAAGGTGAACTTCAAGATCCGCCACAACATCGAGGACGGCA<br>GCGTGCAGCTCGCCGACCACTACCAGCAGAACACCCCCATCGGCG<br>ACGGCCCCGTGCTGCTGCCCGACAACCACTACCTGAGCACCCAGT<br>CCGCCCTGAGCAAAGACCCCAACGAGAAGCGCGATCACATGGTCC<br>TGCTGGAGTTCGTGACCGCCGCCGGGATCACTCTCGGCATGGACG<br>AGCTGTACAAGTAACCTGCAGGGATAATCAACCTCTGGATTACAA<br>AATTTGTGAAAGATTGACTGGTATTCTTAACTATGTTGCTCCTTTT<br>ACGCTATGTGGATACGCTGCTTTAATGCCTTTGTATCATGCTATTG<br>CTTCCCGTATGGCTTTCATTTTCTCCTCCTTGTATAAATCCTGGTTA<br>GTTCTTGCCACGGCGGAACTCATCGCCGCCTGCCTTGCCCGCTGCT<br>GGACAGGGGCTCGGCTGTTGGGCACTGACAATTCCGTGGTGTTTA<br>TTTGTGAAATTTGTGATGCTATTGCTTTATTTGTAACCATTCTAGCT<br>TTATTTGTGAAATTTGTGATGCTATTGCTTTATTTGTAACCATTATA<br>AGCTGCAATAAACAAGTTAACAACAACAATTGCATTCATTTTATGT<br>TTCAGGTTCAGGGGGAGATGTGGGAGGTTTTTTAAAGCGAATTCT<br>CTGGAACCTATCAGGGACCACAGTCAGCCAGGCAAGCACATCTGC<br>CCAAGCCAAGGGTGGAGGCATGCAGCTGTGGGGGTCTGTGAAAAC<br>ACTTGAGGGAGCAGATAACTGGGCCAACCATGACTCAGTGCTTCT<br>GGAGGCCAACAGGACTGCTGAGTCATCCTGTGGGGGTGGAGGTGG<br>GACAAGGGAAAGGGGTGAATGGTACTGCTGATTACAACCTCTGGT<br>GCTGCCTCCCCCTCCTGTTTATCTGAGAGGCTAGCGTAAATACACT<br>TGCAAAGGAGGATGTTTTTAGTAGCAATTTGTACTGATGGTATGG<br>GGCCAAGAGATATATCTTAGAGGGAGGGCTGAGGGTTTGAAGTCC<br>AACTCCTAAGCCAGTGCCAGAAGAGCCAAGGACAGGTACGGCTGT<br>CATCACTTAGACCTCACCCTGTGGAGCCACACCCTAGGGTTGGCC<br>AATCTACTCCCAGGAGCAGGGAGGGCAGGAGCCAGGGCTGGGCA<br>TAAAAGTCAGGGCAGAGCCATCTATTGCTTACACTCGCTTCTGGA<br>ACGTCTGAGGTTATCAATAAGCTCCTAGTCCAGACGCCATGGGTC<br>ATTTCACAGAGGAGGACAAGGCTACTATCACAAGCCTGTGGGGCA<br>AGGTGAATGTGGAAGATGCTGGAGGAGAAACCCTGGGAAGGTAG<br>GCTCTGGTGACCAGGACAAGGGAGGGAAGGAAGGACCCTGTGCC<br>TGGCAAAAGTCCAGGTCGCTTCTCAGGATTTGTGGCACCTTCTGAC<br>TGTCAAACTGTTCTTGTCAATCTCACAGGCTCCTGGTTGTCTACCC<br>ATGGACCCAGAGGTTCTTTGACAGCTTTGGCAACCTGTCCTCTGCC<br>TCTGCCATCATGGGCAACCCCAAAGTCAAGGCACATGGCAAGAAG<br>GTGCTGACTTCCTTGGGAGATGCCACAAAGCACCTGGATGATCTC<br>AAGGGCACCTTTGCCCAGCTGAGTGAACTGCACTGTGACAAGCTG<br>CATGTGGATCCTGAGAACTTCAAGGTGAGTCCAGGAGATGTTTCA<br>GCCCTGTTGCCTTTAGTCTCGAGGCAACTTAGACAACGGAGTATTG<br>ATCTGAGCACAGCAGGGTGTGAGCTGTTTGAAGATACTGGGGTCT<br>CGAGGTCGACGTAGATAAGTAGCATGGCGGGTTAATCATTAACTA<br>CAAGGAACCCCTAGTGATGGAGTTGGCCACTCCCTCTCTGCGCGCT<br>CGCTCGCTCACTGAGGCCGGGCGACCAAAGGTCGCCCGACGCCCG<br>GGCTTTGCCCGGGCGGCCTCAGTGAGCGAGCGAGCGCGCCAGCTG<br>GCGTAATAGCGAAGAGGCCCGCACCGATCGCCCTTCCCAACAGTT<br>GCGCAGCCTGAATGGCGAATGGCGATTCCGTTGCAATGGCTGGCG<br>GTAATATTGTTCTGGATATTACCAGCAAGGCCGATAGTTTGAGTTC<br>TTCTACTCAGGCAAGTGATGTTATTACTAATCAAAGAAGTATTGCG<br>ACAACGGTTAATTTGCGTGATGGACAGACTCTTTTACTCGGTGGCC<br>TCACTGATTATAAAAACACTTCTCAGGATTCTGGCGTACCGTTCCT<br>GTCTAAAATCCCTTTAATCGGCCTCCTGTTTAGCTCCCGCTCTGATT<br>CTAACGAGGAAAGCACGTTATACGTGCTCGTCAAAGCAACCATAG<br>TACGCGCCCTGTAGCGGCGCATTAAGCGCGGCGGGTGTGGTGGTT<br>ACGCGCAGCGTGACCGCTACACTTGCCAGCGCCCTAGCGCCCGCT<br>CCTTTCGCTTTCTTCCCTTCCTTTCTCGCCACGTTCGCCGGCTTTCC<br>CCGTCAAGCTCTAAATCGGGGGCTCCCTTTAGGGTTCCGATTTAGT<br>GCTTTACGGCACCTCGACCCCAAAAAACTTGATTAGGGTGATGGT<br>TCACGTAGTGGGCCATCGCCCTGATAGACGGTTTTTCGCCCTTTGA |

-continued

| SEQ ID NO | NAME | SEQUENCE |
|---|---|---|
| | | CGTTGGAGTCCACGTTCTTTAATAGTGGACTCTTGTTCCAAACTGG AACAACACTCAACCCTATCTCGGTCTATTCTTTTGATTTATAAGGG ATTTTGCCGATTTCGGCCTATTGGTTAAAAAATGAGCTGATTTAAC AAAAATTTAACGCGAATTTTAACAAAATATTAACGTTTACAATTTA AATATTTGCTTATACAATCTTCCTGTTTTTGGGGCTTTTCTGATTAT CAACCGGGGTACATATGATTGACATGCTAGTTTTACGATTACCGTT CATCGATTCTCTTGTTTGCTCCAGACTCTCAGGCAATGACCTGATA GCCTTTGTAGAGACCTCTCAAAAATAGCTACCCTCTCCGGCATGAA TTTATCAGCTAGAACGGTTGAATATCATATTGATGGTGATTTGACT GTCTCCGGCCTTTCTCACCCGTTTGAATCTTTACCTACACATTACTC AGGCATTGCATTTAAAATATATGAGGGTTCTAAAAATTTTTATCCT TGCGTTGAAATAAAGGCTTCTCCCGCAAAAGTATTACAGGGTCAT AATGTTTTTGGTACAACCGATTTAGCTTTATGCTCTGAGGCTTTATT GCTTAATTTTGCTAATTCTTTGCCTTGCCTGTATGATTTATTGGATG TTGGAATCGCCTGATGCGGTATTTTCTCCTTACGCATCTGTGCGGT ATTTCACACCGCATATGGTGCACTCTCAGTACAATCTGCTCTGATG CCGCATAGTTAAGCCAGCCCCGACACCCGCCAACACCCGCTGACG CGCCCTGACGGGCTTGTCTGCTCCCGGCATCCGCTTACAGACAAGC TGTGACCGTCTCCGGGAGCTGCATGTGTCAGAGGTTTTCACCGTCA TCACCGAAACGCGCGAGACGAAAGGGCCTCGTGATACGCCTATTT TTATAGGTTAATGTCATGATAATAATGGTTTCTTAGACGTCAGGTG GCACTTTTCGGGGAAATGTGCGCGGAACCCCTATTTGTTTATTTTT CTAAATACATTCAAATATGTATCCGCTCATGAGACAATAACCCTG ATAAATGCTTCAATAATATTGAAAAAGGAAGAGTATGAGTATTCA ACATTTCCGTGTCGCCCTTATTCCCTTTTTTGCGGCATTTTGCCTTC CTGTTTTTGCTCACCCAGAAACGCTGGTGAAAGTAAAAGATGCTG AAGATCAGTTGGGTGCACGAGTGGGTTACATCGAACTGGATCTCA ACAGCGGTAAGATCCTTGAGAGTTTTCGCCCCGAAGAACGTTTTCC AATGATGAGCACTTTTAAAGTTCTGCTATGTGGCGCGGTATTATCC CGTATTGACGCCGGGCAAGAGCAACTCGGTCGCCGCATACACTAT TCTCAGAATGACTTGGTTGAGTACTCACCAGTCACAGAAAAGCAT CTTACGGATGGCATGACAGTAAGAGAATTATGCAGTGCTGCCATA ACCATGAGTGATAACACTGCGGCCAACTTACTTCTGACAACGATC GGAGGACCGAAGGAGCTAACCGCTTTTTTGCACAACATGGGGGAT CATGTAACTCGCCTTGATCGTTGGGAACCGGAGCTGAATGAAGCC ATACCAAACGACGAGCGTGACACCACGATGCCTGTAGCAATGGCA ACAACGTTGCGCAAACTATTAACTGGCGAACTACTTACTCTAGCTT CCCGGCAACAATTAATAGACTGGATGGAGGCGGATAAAGTTGCAG GACCACTTCTGCGCTCGGCCCTTCCGGCTGGCTGGTTTATTGCTGA TAAATCTGGAGCCGGTGAGCGTGGGTCTCGCGGTATCATTGCAGC ACTGGGGCCAGATGGTAAGCCCTCCCGTATCGTAGTTATCTACAC GACGGGGAGTCAGGCAACTATGGATGAACGAAATAGACAGATCG CTGAGATAGGTGCCTCACTGATTAAGCATTGGTAACTGTCAGACC AAGTTTACTCATATATACTTTAGATTGATTTAAAACTTCATTTTTAA TTTAAAAGGATCTAGGTGAAGATCCTTTTTGATAATCTCATGACCA AAATCCCTTAACGTGAGTTTTCGTTCCACTGAGCGTCAGACCCCGT AGAAAAGATCAAAGGATCTTCTTGAGATCCTTTTTTTCTGCGCGTA ATCTGCTGCTTGCAAACAAAAAAACCACCGCTACCAGCGGTGGTT TGTTTGCCGGATCAAGAGCTACCAACTCTTTTTCCGAAGGTAACTG GCTTCAGCAGAGCGCAGATACCAAATACTGTCCTTCTAGTGTAGC CGTAGTTAGGCCACCACTTCAAGAACTCTGTAGCACCGCCTACAT ACCTCGCTCTGCTAATCCTGTTACCAGTGGCTGCTGCCAGTGGCGA TAAGTCGTGTCTTACCGGGTTGGACTCAAGACGATAGTTACCGGA TAAGGCGCAGCGGTCGGGCTGAACGGGGGGTTCGTGCACACAGCC CAGCTTGGAGCGAACGACCTACACCGAACTGAGATACCTACAGCG TGAGCTATGAGAAAGCGCCACGCTTCCCGAAGGGAGAAAGGCGG ACAGGTATCCGGTAAGCGGCAGGGTCGGAACAGGAGAGCGCACG AGGGAGCTTCCAGGGGGAAACGCCTGGTATCTTTATAGTCCTGTC GGGTTTCGCCACCTCTGACTTGAGCGTCGATTTTTGTGATGCTCGT CAGGGGGGCGGAGCCTATGGAAAAACGCCAGCAACGCGGCCTTTT TACGGTTCCTGGCCTTTTGCTGGCCTTTTGCTCACATGTTCTTTCCT GCGTTATCCCCTGATTCTGTGGATAACCGTATTACCGCCTTTGAGT GAGCTGATACCGCTCGCCGCAGCCGAACGACCGAGCGCAGCGAGT CAGTGAGCGAGGAAGCGGAAGAGCGCCCAATACGCAAACCGCCT CTCCCCGCGCGTTGGCCGATTCATTAATG |
| 49 | HBG1 Round 3: AMS#1343 pAAV HBG1(650).d0 HBBp>HBB(T87Q). core3'enh;PGK >MGMT(P140K). SV40pA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTAC GCGTAGATCTGGTGTATACATACATACCTGAATATGGAATCAAAT ATTTTTCTAAGATGAAACAGTCATGATTTATTTCAAATAGGTACGG ATAAGTAGATATTGAGGTAAGCATTAGGTCTTATATTATGTAACAC TAATCTATTACTGCGCTGAAACTGTGGCTTTATAGAAATTGTTTTC ACTGCACTATTGAGAAATTAAGAGATAATGGCAAAAGTCACAAAG AGTATATTCAAAAAGAAGTATAGCACTTTTTCCTTAGAAACCACTG |

-continued

| SEQ ID NO | NAME | SEQUENCE |
|---|---|---|
| | | CTAACTGAAAGAGACTAAGATTTGTCCCGTCAAAAATCCTGGACC<br>TATGCCTAAAACACATTTCACAATCCCTGAACTTTTCAAAAATTGG<br>TACATGCTTTAGCTTTAAACTACAGGCCTCACTGGAGCTAGAGAC<br>AAGAAGGTAAAAAACGGCTGACAAAAGAAGTCCTGGTATCCTCTA<br>TGATGGGAGAAGGAAACTAGCTAAAGGGAAGAATAAATTAGAGA<br>AAAACTGGAATGACTGAATCGGAACAAGGCAAAGGCTATAAAAA<br>AAATTAAGCAGCAGTATCCTCTTGGGGGCCCCTTCCCCACACTATC<br>TCAATGCAAATATCTGTCTGAAACGGTCCCTGGCTAAACTCCACCC<br>ATGGGTTGGCCAGCCTTGCCTTGACGCTAGCGTAAATACACTTGCA<br>AAGGAGGATGTTTTTAGTAGCAATTTGTACTGATGGTATGGGGCC<br>AAGAGATATATCTTAGAGGGAGGGCTGAGGGTTTGAAGTCCAACT<br>CCTAAGCCAGTGCCAGAAGAGCCAAGGACAGGTACGGCTGTCATC<br>ACTTAGACCTCACCCTGTGGAGCCACACCCTAGGGTTGGCCAATCT<br>ACTCCCAGGAGCAGGGAGGGCAGGAGCCAGGGCTGGGCATAAAA<br>GTCAGGGCAGAGCCATCTATTGCTTACATTTGCTTCTGACACAACT<br>GTGTTCACTAGCAACCTCAAACAGACACCATGGTGCACCTGACTC<br>CTGAGGAGAAGTCTGCCGTTACTGCCCTGTGGGGCAAGGTGAACG<br>TGGATGAAGTTGGTGGTGAGGCCCTGGGCAGGTTGGTATCAAGGT<br>TACAAGACAGGTTTAAGGAGACCAATAGAAACTGGGCATGTGGA<br>GACAGAGAAGACTCTTGGGTTTCTGATAGGCACTGACTCTCTCTGC<br>CTATTGGTCTATTTTCCCACCCTTAGGCTGCTGGTGGTCTACCCTTG<br>GACCCAGAGGTTCTTTGAGTCCTTTGGGGATCTGTCCACTCCTGAT<br>GCTGTTATGGGCAACCCTAAGGTGAAGGCTCATGGCAAGAAAGTG<br>CTCGGTGCCTTTAGTGATGGCCTGGCTCACCTGGACAACCTCAAGG<br>GCACCTTTGCCCAGCTGAGTGAGCTGCACTGTGACAAGCTGCACG<br>TGGATCCTGAGAACTTCAGGGTGAGTCTATGGGACCCTTGATGTTT<br>TCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGCCACGGGGTTGGGGTTGCG<br>CCTTTTCCAAGGCAGCCCTGGGTTTGCGCAGGGACGCGGCTGCTCT<br>GGGCGTGGTTCCGGGAAACGCAGCGGCGCCGACCCTGGGTCTCGC<br>ACATTCTTCACGTCCGTTCGCAGCGTCACCCGGATCTTCGCCGCTA<br>CCCTTGTGGGCCCCCCGGCGACGCTTCCTGCTCCGCCCCTAAGTCG<br>GGAAGGTTCCTTGCGGTTCGCGGCGTGCCGGACGTGACAAACGGA<br>AGCCGCACGTCTCACTAGTACCCTCGCAGACGGACAGCGCCAGGG<br>AGCAATGGCAGCGCGCCGACCGCGATGGGCTGTGGCCAATAGCGG<br>CTGCTCAGCGGGGCGCGCCGAGAGCAGCGGCCGGGAAGGGGCGG<br>TGCGGGAGGCGGGGTGTGGGGCGGTAGTGTGGGCCCTGTTCCTGC<br>CCGCGCGGTGTTCCGCATTCTGCAAGCCTCCGGAGCGCACGTCGG<br>CAGTCGGCTCCCTCGTTGACCGAATCACCGACCTCTCTCCCCAGCG<br>GCCGCGCCGCCACCATGGACAAGGATTGTGAAATGAAACGCACCA<br>CACTGGACAGCCCTTTGGGGAAGCTGGAGCTGTCTGGTTGTGAGC<br>AGGGTCTGCACGAAATAAAGCTCCTGGGCAAGGGGACGTCTGCAG<br>CTGATGCCGTGGAGGTCCCAGCCCCCGCTGCGGTTCTCGGAGGTC<br>CGGAGCCCCTGATGCAGTGCACAGCCTGGCTGAATGCCTATTTCC<br>ACCAGCCCGAGGCTATCGAAGAGTTCCCCGTGCCGGCTCTTCACC<br>ATCCCGTTTTCCAGCAAGAGTCGTTCACCAGACAGGTGTTATGGA<br>AGCTGCTGAAGGTTGTGAAATTCGGAGAAGTGATTTCTTACCAGC<br>AATTAGCAGCCCTGGCAGGCAACCCCAAAGCCGCGCGAGCAGTGG<br>GAGGAGCAATGAGAGGCAATCCTGTCAAAATCCTCATCCCGTGCC<br>ACAGAGTGGTCTGCAGCAGCGGAGCCGTGGGCAACTACTCCGGAG<br>GACTGGCCGTGAAGGAATGGCTTCTGGCCCATGAAGGCCACCGGT<br>TGGGGAAGCCAGGCTTGGGAGGGAGCTCAGGTCTGGCAGGGGCCT<br>GGCTCAAGGGAGCGGGAGCTACCTCGGGCTCCCCGCCTGCTGGCC<br>GAAACTAAGCTTTATTTGTGAAATTTGTGATGCTATTGCTTTATTTG |

-continued

| SEQ ID NO | NAME | SEQUENCE |
|---|---|---|
| | | TAACCATTATAAGCTGCAATAAACAAGTTAACAACAACAATTGCA<br>TTCATTTTATGTTTCAGGTTCAGGGGGAGATGTGGGAGGTTTTTTA<br>AAGCCCTGCAGGCAATAGCCTTGACAAGGCAAACTTGACCAATAG<br>TCTTAGAGTATCCAGTGAGGCCAGGGGCCGGCGGCTGGCTAGGGA<br>TGAAGAATAAAAGGAAGCACCCTTCAGCAGTTCCACACACTCGCT<br>TCTGGAACGTCTGAGGTTATCAATAAGCTCCTAGTCCAGACGCCAT<br>GGGTCATTTCACAGAGGAGGACAAGGCTACTATCACAAGCCTGTG<br>GGGCAAGGTGAATGTGGAAGATGCTGGAGGAGAAACCCTGGGAA<br>GGTAGGCTCTGGTGACCAGGACAAGGGAGGGAAGGAAGGACCCT<br>GTGCCTGGCAAAAGTCCAGGTCGCTTCTCAGGATTTGTGGCACCTT<br>CTGACTGTCAAACTGTTCTTGTCAATCTCACAGGCTCCTGGTTGTC<br>TACCCATGGACCCAGAGGTTCTTTGACAGCTTTGGCAACCTGTCCT<br>CTGCCTCTGCCATCATGGGCAACCCCAAAGTCAAGGCACATGGCA<br>AGAAGGTGCTGACTTCCTTGGGAGATGCCACAAAGCACCTGGATG<br>ATCTCAAGGGCACCTTTGCCCAGCTGAGTGAACTGCACTGTGACA<br>AGCTGCATGTGGATCCTGAGAACTTCAAGGTGAGTCCAGGAGATG<br>TTTCAGCCCTGTTGCCTTTAGTCTCGAGGCGTCGACAGGAACCCCT<br>AGTGATGGAGTTGGCCACTCCCTCTCTGCGCGCTCGCTCGCTCACT<br>GAGGCCGGGCGACCAAAGGTCGCCCGACGCCCGGGCTTTGCCCGG<br>GCGGCCTCAGTGAGCGAGCGAGCGCGCAGCTGGCGTAATAGCGA<br>AGAGGCCCGCACCGATCGCCCTTCCCAACAGTTGCGCAGCCTGAA<br>TGGCGAATGGCGATTCCGTTGCAATGGCTGGCGGTAATATTGTTCT<br>GGATATTACCAGCAAGGCCGATAGTTTGAGTTCTTCTACTCAGGCA<br>AGTGATGTTATTACTAATCAAAGAAGTATTGCGACAACGGTTAAT<br>TTGCGTGATGGACAGACTCTTTTACTCGGTGGCCTCACTGATTATA<br>AAAACACTTCTCAGGATTCTGGCGTACCGTTCCTGTCTAAAATCCC<br>TTTAATCGGCCTCCTGTTTAGCTCCCGCTCTGATTCTAACGAGGAA<br>AGCACGTTATACGTGCTCGTCAAAGCAACCATAGTACGCGCCCTG<br>TAGCGGCGCATTAAGCGCGGCGGGTGTGGTGGTTACGCGCAGCGT<br>GACCGCTACACTTGCCAGCGCCCTAGCGCCCGCTCCTTTCGCTTTC<br>TTCCCTTCCTTTCTCGCCACGTTCGCCGGCTTTCCCCGTCAAGCTCT<br>AAATCGGGGGCTCCCTTTAGGGTTCCGATTTAGTGCTTTACGGCAC<br>CTCGACCCCAAAAAACTTGATTAGGGTGATGGTTCACGTAGTGGG<br>CCATCGCCCTGATAGACGGTTTTTCGCCCTTTGACGTTGGAGTCCA<br>CGTTCTTTAATAGTGGACTCTTGTTCCAAACTGGAACAACACTCAA<br>CCCTATCTCGGTCTATTCTTTTGATTTATAAGGGATTTTGCCGATTT<br>CGGCCTATTGGTTAAAAAATGAGCTGATTTAACAAAAATTTAACG<br>CGAATTTTAACAAAATATTAACGTTTACAATTTAAATATTTGCTTA<br>TACAATCTTCCTGTTTTTGGGGCTTTTCTGATTATCAACCGGGGTA<br>CATATGATTGACATGCTAGTTTTACGATTACCGTTCATCGATTCTC<br>TTGTTTGCTCCAGACTCTCAGGCAATGACCTGATAGCCTTTGTAGA<br>GACCTCTCAAAAATAGCTACCCTCTCCGGCATGAATTTATCAGCTA<br>GAACGGTTGAATATCATATTGATGGTGATTTGACTGTCTCCGGCCT<br>TTCTCACCCGTTTGAATCTTTACCTACACATTACTCAGGCATTGCA<br>TTTAAAATATATGAGGGTTCTAAAAATTTTTATCCTTGCGTTGAAA<br>TAAAGGCTTCTCCCGCAAAAGTATTACAGGGTCATAATGTTTTTGG<br>TACAACCGATTTAGCTTTATGCTCTGAGGCTTTATTGCTTAATTTTG<br>CTAATTCTTTGCCTTGCCTGTATGATTTATTGGATGTTGGAATCGCC<br>TGATGCGGTATTTTCTCCTTACGCATCTGTGCGGTATTTCACACCG<br>CATATGGTGCACTCTCAGTACAATCTGCTCTGATGCCGCATAGTTA<br>AGCCAGCCCCGACACCCGCCAACACCCGCTGACGCGCCCTGACGG<br>GCTTGTCTGCTCCCGGCATCCGCTTACAGACAAGCTGTGACCGTCT<br>CCGGGAGCTGCATGTGTCAGAGGTTTTCACCGTCATCACCGAAAC<br>GCGCGAGACGAAAGGGCCTCGTGATACGCCTATTTTTATAGGTTA<br>ATGTCATGATAATAATGGTTTCTTAGACGTCAGGTGGCACTTTTCG<br>GGGAAATGTGCGCGGAACCCCTATTTGTTTATTTTTCTAAATACAT<br>TCAAATATGTATCCGCTCATGAGACAATAACCCTGATAAATGCTTC<br>AATAATATTGAAAAAGGAAGAGTATGAGTATTCAACATTTCCGTG<br>TCGCCCTTATTCCCTTTTTTGCGGCATTTTGCCTTCCTGTTTTTGCTC<br>ACCCAGAAACGCTGGTGAAAGTAAAAGATGCTGAAGATCAGTTGG<br>GTGCACGAGTGGGTTACATCGAACTGGATCTCAACAGCGGTAAGA<br>TCCTTGAGAGTTTTCGCCCCGAAGAACGTTTTCCAATGATGAGCAC<br>TTTTAAAGTTCTGCTATGTGGCGCGGTATTATCCCGTATTGACGCC<br>GGGCAAGAGCAACTCGGTCGCCGCATACACTATTCTCAGAATGAC<br>TTGGTTGAGTACTCACCAGTCACAGAAAAGCATCTTACGGATGGC<br>ATGACAGTAAGAGAATTATGCAGTGCTGCCATAACCATGAGTGAT<br>AACACTGCGGCCAACTTACTTCTGACAACGATCGGAGGACCGAAG<br>GAGCTAACCGCTTTTTTGCACAACATGGGGGATCATGTAACTCGCC<br>TTGATCGTTGGGAACCGGAGCTGAATGAAGCCATACCAAACGACG<br>AGCGTGACACCACGATGCCTGTAGCAATGGCAACAACGTTGCGCA<br>AACTATTAACTGGCGAACTACTTACTCTAGCTTCCCGGCAACAATT<br>AATAGACTGGATGGAGGCGGATAAAGTTGCAGGACCACTTCTGCG<br>CTCGGCCCTTCCGGCTGGCTGGTTTATTGCTGATAAATCTGGAGCC<br>GGTGAGCGTGGGTCTCGCGGTATCATTGCAGCACTGGGGCCAGAT<br>GGTAAGCCCTCCCGTATCGTAGTTATCTACACGACGGGGAGTCAG |

-continued

| SEQ ID NO | NAME | SEQUENCE |
|---|---|---|
| | | GCAACTATGGATGAACGAAATAGACAGATCGCTGAGATAGGTGCC |
| | | TCACTGATTAAGCATTGGTAACTGTCAGACCAAGTTTACTCATATA |
| | | TACTTTAGATTGATTTAAAACTTCATTTTTAATTTAAAAGGATCTA |
| | | GGTGAAGATCCTTTTTGATAATCTCATGACCAAAATCCCTTAACGT |
| | | GAGTTTTCGTTCCACTGAGCGTCAGACCCCGTAGAAAAGATCAAA |
| | | GGATCTTCTTGAGATCCTTTTTTTCTGCGCGTAATCTGCTGCTTGCA |
| | | AACAAAAAAACCACCGCTACCAGCGGTGGTTTGTTTGCCGGATCA |
| | | AGAGCTACCAACTCTTTTTCCGAAGGTAACTGGCTTCAGCAGAGC |
| | | GCAGATACCAAATACTGTCCTTCTAGTGTAGCCGTAGTTAGGCCAC |
| | | CACTTCAAGAACTCTGTAGCACCGCCTACATACCTCGCTCTGCTAA |
| | | TCCTGTTACCAGTGGCTGCTGCCAGTGGCGATAAGTCGTGTCTTAC |
| | | CGGGTTGGACTCAAGACGATAGTTACCGGATAAGGCGCAGCGGTC |
| | | GGGCTGAACGGGGGGTTCGTGCACACAGCCCAGCTTGGAGCGAAC |
| | | GACCTACACCGAACTGAGATACCTACAGCGTGAGCTATGAGAAAG |
| | | CGCCACGCTTCCCGAAGGGAGAAAGGCGGACAGGTATCCGGTAA |
| | | GCGGCAGGGTCGGAACAGGAGAGCGCACGAGGGAGCTTCCAGGG |
| | | GGAAACGCCTGGTATCTTTATAGTCCTGTCGGGTTTCGCCACCTCT |
| | | GACTTGAGCGTCGATTTTTGTGATGCTCGTCAGGGGGGCGGAGCC |
| | | TATGGAAAAACGCCAGCAACGCGGCCTTTTTACGGTTCCTGGCCTT |
| | | TTGCTGGCCTTTTGCTCACATGTTCTTTCCTGCGTTATCCCCTGATT |
| | | CTGTGGATAACCGTATTACCGCCTTTGAGTGAGCTGATACCGCTCG |
| | | CCGCAGCCGAACGACCGAGCGCAGCGAGTCAGTGAGCGAGGAAG |
| | | CGGAAGAGCGCCCAATACGCAAACCGCCTCTCCCCGCGCGTTGGC |
| | | CGATTCATTAATG |
| 50 | HBG1 Round 3: | CAGCTGCGCGCTCGCTCGCTCACTGAGGCCGCCCGGGCAAAGCCC |
| | AMS#1344 | GGGCGTCGGGCGACCTTTGGTCGCCCGGCCTCAGTGAGCGAGCGA |
| | pAAV | GCGCGCAGAGAGGGAGTGGCCAACTCCATCACTAGGGGTTCCTAC |
| | HBG1(500).d0 | GCGTAGATCTGTGGCTTTATAGAAATTGTTTTCACTGCACTATTGA |
| | HBBp>HBB(T87Q). | GAAATTAAGAGATAATGGCAAAAGTCACAAAGAGTATATTCAAA |
| | core3'enh;PGK> | AAGAAGTATAGCACTTTTTCCTTAGAAACCACTGCTAACTGAAAG |
| | MGMT(P140K). | AGACTAAGATTTGTCCCGTCAAAAATCCTGGACCTATGCCTAAAA |
| | wPRE3.SV40pA | CACATTTCACAATCCCTGAACTTTTCAAAAATTGGTACATGCTTTA |
| | | GCTTTAAACTACAGGCCTCACTGGAGCTAGAGACAAGAAGGTAAA |
| | | AAACGGCTGACAAAAGAAGTCCTGGTATCCTCTATGATGGGAGAA |
| | | GGAAACTAGCTAAAGGGAAGAATAAATTAGAGAAAAACTGGAAT |
| | | GACTGAATCGGAACAAGGCAAAGGCTATAAAAAAAAATTAAGCAG |
| | | CAGTATCCTCTTGGGGGCCCCTTCCCCACACTATCTCAATGCAAAT |
| | | ATCTGTCTGAAACGGTCCCTGGCTAAACTCCACCCATGGGTTGGCC |
| | | AGCCTTGCCTTGACGCTAGCGTAAATACACTTGCAAAGGAGGATG |
| | | TTTTTAGTAGCAATTTGTACTGATGGTATGGGGCCAAGAGATATAT |
| | | CTTAGAGGGAGGGCTGAGGGTTTGAAGTCCAACTCCTAAGCCAGT |
| | | GCCAGAAGAGCCAAGGACAGGTACGGCTGTCATCACTTAGACCTC |
| | | ACCCTGTGGAGCCACACCCTAGGGTTGGCCAATCTACTCCCAGGA |
| | | GCAGGGAGGGCAGGAGCCAGGGCTGGGCATAAAAGTCAGGGCAG |
| | | AGCCATCTATTGCTTACATTTGCTTCTGACACAACTGTGTTCACTA |
| | | GCAACCTCAAACAGACACCATGGTGCACCTGACTCCTGAGGAGAA |
| | | GTCTGCCGTTACTGCCCTGTGGGGCAAGGTGAACGTGGATGAAGT |
| | | TGGTGGTGAGGCCCTGGGCAGGTTGGTATCAAGGTTACAAGACAG |
| | | GTTTAAGGAGACCAATAGAAACTGGGCATGTGGAGACAGAGAAG |
| | | ACTCTTGGGTTTCTGATAGGCACTGACTCTCTCTGCCTATTGGTCT |
| | | ATTTTCCCACCCTTAGGCTGCTGGTGGTCTACCCTTGGACCCAGAG |
| | | GTTCTTTGAGTCCTTTGGGGATCTGTCCACTCCTGATGCTGTTATG |
| | | GGCAACCCTAAGGTGAAGGCTCATGGCAAGAAAGTGCTCGGTGCC |
| | | TTTAGTGATGGCCTGGCTCACCTGGACAACCTCAAGGGCACCTTTG |
| | | CCCAGCTGAGTGAGCTGCACTGTGACAAGCTGCACGTGGATCCTG |
| | | AGAACTTCAGGGTGAGTCTATGGGACCCTTGATGTTTTCTTTCCCC |
| | | TTCTTTTCTATGGTTAAGTTCATGTCATAGGAAGGGGAGAAGTAAC |
| | | AGGGTACACATATTGACCAAATCAGGGTAATTTTGCATTTGTAATT |
| | | TTAAAAAATGCTTTCTTCTTTTAATATACTTTTTTGTTTATCTTATTT |
| | | CTAATACTTTCCCTAATCTCTTTCTTTCAGGGCAATAATGATACAA |
| | | TGTATCATGCCTCTTTGCACCATTCTAAAGAATAACAGTGATAATT |
| | | TCTGGGTTAAGGCAATAGCAATATTTCTGCATATAAATATTTCTGC |
| | | ATATAAATTGTAACTGATGTAAGAGGTTTCATATTGCTAATAGCAG |
| | | CTACAATCCAGCTACCATTCTGCTTTTATTTTATGGTTGGGATAAG |
| | | GCTGGATTATTCTGAGTCCAAGCTAGGCCCTTTTGCTAATCATGTT |
| | | CATACCTCTTATCTTCCTCCCACAGCTCCTGGGCAACGTGCTGGTC |
| | | TGTGTGCTGGCCCATCACTTTGGCAAAGAATTCACCCCACCAGTGC |
| | | AGGCTGCCTATCAGAAAGTGGTGGCTGGTGTGGCTAATGCCCTGG |
| | | CCCACAAGTATCACTAAGCTCGCTTTCTTGCTGTCCAATTTCTATT |
| | | AAAGGTTCCTTTGTTCCCTAAGTCCAACTACTAAACTGGGGGATAT |
| | | TATGAAGGGCCTTGAGCATCTGGATTCTGCCTAATAAAAAACATTT |
| | | ATTTTCATTGCAATGATGTATTTAAATTATTTCTGAATATTTTACTA |
| | | AAAAGGGAATGTGGGAGGTTGCAGTGCTAGTCTCCCGGAACTATC |
| | | ACTCTTTCACAGTCTGCTTTGGAAGGACTGGGCTTAGTATGAAAAG |

-continued

| SEQ ID NO | NAME | SEQUENCE |
|---|---|---|
| | | TTAGGACTGAGAAGAATTTGAAAGGGGGCTTTTTGTAGCTTGATA |
| | | TTCACTACTGTCTTATTACCCTATCATAGGCCCACCCCAAATGGAA |
| | | GTCCCATTCTTCCTCAGGATGTTTAAGATTAGCATTCAGGAAGAGA |
| | | TCAGAGGTCTGCTGGCTCCCTTATCATGTCCCTTATGGTGCTTCTG |
| | | GCTCTGCACCGCGGCCACGGGGTTGGGGTTGCGCCTTTTCCAAGG |
| | | CAGCCCTGGGTTTGCGCAGGGACGCGGCTGCTCTGGGCGTGGTTC |
| | | CGGGAAACGCAGCGGCGCCGACCCTGGGTCTCGCACATTCTTCAC |
| | | GTCCGTTCGCAGCGTCACCCGGATCTTCGCCGCTACCCTTGTGGGC |
| | | CCCCCGGCGACGCTTCCTGCTCCGCCCCTAAGTCGGGAAGGTTCCT |
| | | TGCGGTTCGCGGCGTGCCGGACGTGACAAACGGAAGCCGCACGTC |
| | | TCACTAGTACCCTCGCAGACGGACAGCGCCAGGGAGCAATGGCAG |
| | | CGCGCCGACCGCGATGGGCTGTGGCCAATAGCGGCTGCTCAGCGG |
| | | GGCGCGCCGAGAGCAGCGGCCGGGAAGGGGCGGTGCGGGAGGCG |
| | | GGGTGTGGGGCGGTAGTGTGGGCCCTGTTCCTGCCCGCGCGGTGT |
| | | TCCGCATTCTGCAAGCCTCCGGAGCGCACGTCGGCAGTCGGCTCC |
| | | CTCGTTGACCGAATCACCGACCTCTCTCCCCAGCGGCCGCGCCGCC |
| | | ACCATGGACAAGGATTGTGAAATGAAACGCACCACACTGGACAGC |
| | | CCTTTGGGGAAGCTGGAGCTGTCTGGTTGTGAGCAGGGTCTGCAC |
| | | GAAATAAAGCTCCTGGGCAAGGGGACGTCTGCAGCTGATGCCGTG |
| | | GAGGTCCCAGCCCCCGCTGCGGTTCTCGGAGGTCCGGAGCCCCTG |
| | | ATGCAGTGCACAGCCTGGCTGAATGCCTATTTCCACCAGCCCGAG |
| | | GCTATCGAAGAGTTCCCCGTGCCGGCTCTTCACCATCCCGTTTTCC |
| | | AGCAAGAGTCGTTCACCAGACAGGTGTTATGGAAGCTGCTGAAGG |
| | | TTGTGAAATTCGGAGAAGTGATTTCTTACCAGCAATTAGCAGCCCT |
| | | GGCAGGCAACCCCAAAGCCGCGCGAGCAGTGGGAGGAGCAATGA |
| | | GAGGCAATCCTGTCAAAATCCTCATCCCGTGCCACAGAGTGGTCT |
| | | GCAGCAGCGGAGCCGTGGGCAACTACTCCGGAGGACTGGCCGTGA |
| | | AGGAATGGCTTCTGGCCCATGAAGGCCACCGGTTGGGGAAGCCAG |
| | | GCTTGGGAGGGAGCTCAGGTCTGGCAGGGGCCTGGCTCAAGGGAG |
| | | CGGGAGCTACCTCGGGCTCCCCGCCTGCTGGCCGAAACTAAGATA |
| | | ATCAACCTCTGGATTACAAAATTTGTGAAAGATTGACTGGTATTCT |
| | | TAACTATGTTGCTCCTTTTACGCTATGTGGATACGCTGCTTTAATG |
| | | CCTTTGTATCATGCTATTGCTTCCCGTATGGCTTTCATTTTCTCCTC |
| | | CTTGTATAAATCCTGGTTAGTTCTTGCCACGGCGGAACTCATCGCC |
| | | GCCTGCCTTGCCCGCTGCTGGACAGGGGCTCGGCTGTTGGGCACT |
| | | GACAATTCCGTGGTGTTTATTTGTGAAATTTGTGATGCTATTGCTTT |
| | | ATTTGTAACCATTCTAGCTTTATTTGTGAAATTTGTGATGCTATTGC |
| | | TTTATTTGTAACCATTATAAGCTGCAATAAACAAGTTAACAACAAC |
| | | AATTGCATTCATTTTATGTTTCAGGTTCAGGGGGAGATGTGGGAGG |
| | | TTTTTTAAAGCCCTGCAGGCAATAGCCTTGACAAGGCAAACTTGA |
| | | CCAATAGTCTTAGAGTATCCAGTGAGGCCAGGGGCCGGCGGCTGG |
| | | CTAGGGATGAAGAATAAAAGGAAGCACCCTTCAGCAGTTCCACAC |
| | | ACTCGCTTCTGGAACGTCTGAGGTTATCAATAAGCTCCTAGTCCAG |
| | | ACGCCATGGGTCATTTCACAGAGGAGGACAAGGCTACTATCACAA |
| | | GCCTGTGGGGCAAGGTGAATGTGGAAGATGCTGGAGGAGAAACC |
| | | CTGGGAAGGTAGGCTCTGGTGACCAGGACAAGGGAGGGAAGGAA |
| | | GGACCCTGTGCCTGGCAAAAGTCCAGGTCGCTTCTCAGGATTTGTG |
| | | GCACCTTCTGACTGTCAAACTGTTCTTGTCAATCTCACAGGCTCCT |
| | | GGTTGTCTACCCATGGACCCAGAGGTTCTTTGACAGCTTTGGCAAC |
| | | CTGTCCTCTGCCTCTGCCATCATGGGCAACCCCAAAGTCAAGGCAC |
| | | ATGGCAAGAAGGTGCTGACTTGTCGACAGGAACCCCTAGTGATGG |
| | | AGTTGGCCACTCCCTCTCTGCGCGCTCGCTCGCTCACTGAGGCCGG |
| | | GCGACCAAAGGTCGCCCGACGCCCGGGCTTTGCCCGGGCGGCCTC |
| | | AGTGAGCGAGCGAGCGCGCAGCTGGCGTAATAGCGAAGAGGCCC |
| | | GCACCGATCGCCCTTCCCAACAGTTGCGCAGCCTGAATGGCGAAT |
| | | GGCGATTCCGTTGCAATGGCTGGCGGTAATATTGTTCTGGATATTA |
| | | CCAGCAAGGCCGATAGTTTGAGTTCTTCTACTCAGGCAAGTGATGT |
| | | TATTACTAATCAAAGAAGTATTGCGACAACGGTTAATTTGCGTGAT |
| | | GGACAGACTCTTTTACTCGGTGGCCTCACTGATTATAAAAACACTT |
| | | CTCAGGATTCTGGCGTACCGTTCCTGTCTAAAATCCCTTTAATCGG |
| | | CCTCCTGTTTAGCTCCCGCTCTGATTCTAACGAGGAAAGCACGTTA |
| | | TACGTGCTCGTCAAAGCAACCATAGTACGCGCCCTGTAGCGGCGC |
| | | ATTAAGCGCGGCGGGTGTGGTGGTTACGCGCAGCGTGACCGCTAC |
| | | ACTTGCCAGCGCCCTAGCGCCCGCTCCTTTCGCTTTCTTCCCTTCCT |
| | | TTCTCGCCACGTTCGCCGGCTTTCCCCGTCAAGCTCTAAATCGGGG |
| | | GCTCCCTTTAGGGTTCCGATTTAGTGCTTTACGGCACCTCGACCCC |
| | | AAAAAACTTGATTAGGGTGATGGTTCACGTAGTGGGCCATCGCCC |
| | | TGATAGACGGTTTTTCGCCCTTTGACGTTGGAGTCCACGTTCTTTA |
| | | ATAGTGGACTCTTGTTCCAAACTGGAACAACACTCAACCCTATCTC |
| | | GGTCTATTCTTTTGATTTATAAGGGATTTTGCCGATTTCGGCCTATT |
| | | GGTTAAAAAATGAGCTGATTTAACAAAAATTTAACGCGAATTTTA |
| | | ACAAAATATTAACGTTTACAATTTAAATATTTGCTTATACAATCTT |
| | | CCTGTTTTTGGGGCTTTTCTGATTATCAACCGGGGTACATATGATT |
| | | GACATGCTAGTTTTACGATTACCGTTCATCGATTCTCTTGTTTGCTC |
| | | CAGACTCTCAGGCAATGACCTGATAGCCTTTGTAGAGACCTCTCA |

-continued

| SEQ ID NO | NAME | SEQUENCE |
|---|---|---|
| | | AAAATAGCTACCCTCTCCGGCATGAATTTATCAGCTAGAACGGTT<br>GAATATCATATTGATGGTGATTTGACTGTCTCCGGCCTTTCTCACC<br>CGTTTGAATCTTTACCTACACATTACTCAGGCATTGCATTTAAAAT<br>ATATGAGGGTTCTAAAAATTTTTATCCTTGCGTTGAAATAAAGGCT<br>TCTCCCGCAAAAGTATTACAGGGTCATAATGTTTTTGGTACAACCG<br>ATTTAGCTTTATGCTCTGAGGCTTTATTGCTTAATTTTGCTAATTCT<br>TTGCCTTGCCTGTATGATTTATTGGATGTTGGAATCGCCTGATGCG<br>GTATTTTCTCCTTACGCATCTGTGCGGTATTTCACACCGCATATGG<br>TGCACTCTCAGTACAATCTGCTCTGATGCCGCATAGTTAAGCCAGC<br>CCCGACACCCGCCAACACCCGCTGACGCGCCCTGACGGGCTTGTC<br>TGCTCCCGGCATCCGCTTACAGACAAGCTGTGACCGTCTCCGGGA<br>GCTGCATGTGTCAGAGGTTTTCACCGTCATCACCGAAACGCGCGA<br>GACGAAAGGGCCTCGTGATACGCCTATTTTTATAGGTTAATGTCAT<br>GATAATAATGGTTTCTTAGACGTCAGGTGGCACTTTTCGGGGAAAT<br>GTGCGCGGAACCCCTATTTGTTTATTTTTCTAAATACATTCAAATA<br>TGTATCCGCTCATGAGACAATAACCCTGATAAATGCTTCAATAATA<br>TTGAAAAAGGAAGAGTATGAGTATTCAACATTTCCGTGTCGCCCTT<br>ATTCCCTTTTTTGCGGCATTTTGCCTTCCTGTTTTTGCTCACCCAGA<br>AACGCTGGTGAAAGTAAAAGATGCTGAAGATCAGTTGGGTGCACG<br>AGTGGGTTACATCGAACTGGATCTCAACAGCGGTAAGATCCTTGA<br>GAGTTTTCGCCCCGAAGAACGTTTTCCAATGATGAGCACTTTTAAA<br>GTTCTGCTATGTGGCGCGGTATTATCCCGTATTGACGCCGGGCAAG<br>AGCAACTCGGTCGCCGCATACACTATTCTCAGAATGACTTGGTTGA<br>GTACTCACCAGTCACAGAAAAGCATCTTACGGATGGCATGACAGT<br>AAGAGAATTATGCAGTGCTGCCATAACCATGAGTGATAACACTGC<br>GGCCAACTTACTTCTGACAACGATCGGAGGACCGAAGGAGCTAAC<br>CGCTTTTTTGCACAACATGGGGGATCATGTAACTCGCCTTGATCGT<br>TGGGAACCGGAGCTGAATGAAGCCATACCAAACGACGAGCGTGA<br>CACCACGATGCCTGTAGCAATGGCAACAACGTTGCGCAAACTATT<br>AACTGGCGAACTACTTACTCTAGCTTCCCGGCAACAATTAATAGA<br>CTGGATGGAGGCGGATAAAGTTGCAGGACCACTTCTGCGCTCGGC<br>CCTTCCGGCTGGCTGGTTTATTGCTGATAAATCTGGAGCCGGTGAG<br>CGTGGGTCTCGCGGTATCATTGCAGCACTGGGGCCAGATGGTAAG<br>CCCTCCCGTATCGTAGTTATCTACACGACGGGGAGTCAGGCAACT<br>ATGGATGAACGAAATAGACAGATCGCTGAGATAGGTGCCTCACTG<br>ATTAAGCATTGGTAACTGTCAGACCAAGTTTACTCATATATACTTT<br>AGATTGATTTAAAACTTCATTTTTAATTTAAAAGGATCTAGGTGAA<br>GATCCTTTTTGATAATCTCATGACCAAAATCCCTTAACGTGAGTTT<br>TCGTTCCACTGAGCGTCAGACCCCGTAGAAAAGATCAAAGGATCT<br>TCTTGAGATCCTTTTTTTCTGCGCGTAATCTGCTGCTTGCAAACAA<br>AAAAACCACCGCTACCAGCGGTGGTTTGTTTGCCGGATCAAGAGC<br>TACCAACTCTTTTTCCGAAGGTAACTGGCTTCAGCAGAGCGCAGAT<br>ACCAAATACTGTCCTTCTAGTGTAGCCGTAGTTAGGCCACCACTTC<br>AAGAACTCTGTAGCACCGCCTACATACCTCGCTCTGCTAATCCTGT<br>TACCAGTGGCTGCTGCCAGTGGCGATAAGTCGTGTCTTACCGGGTT<br>GGACTCAAGACGATAGTTACCGGATAAGGCGCAGCGGTCGGGCTG<br>AACGGGGGGTTCGTGCACACAGCCCAGCTTGGAGCGAACGACCTA<br>CACCGAACTGAGATACCTACAGCGTGAGCTATGAGAAAGCGCCAC<br>GCTTCCCGAAGGGAGAAAGGCGGACAGGTATCCGGTAAGCGGCA<br>GGGTCGGAACAGGAGAGCGCACGAGGGAGCTTCCAGGGGGAAAC<br>GCCTGGTATCTTTATAGTCCTGTCGGGTTTCGCCACCTCTGACTTG<br>AGCGTCGATTTTTGTGATGCTCGTCAGGGGGGCGGAGCCTATGGA<br>AAAACGCCAGCAACGCGGCCTTTTTACGGTTCCTGGCCTTTTGCTG<br>GCCTTTTGCTCACATGTTCTTTCCTGCGTTATCCCCTGATTCTGTGG<br>ATAACCGTATTACCGCCTTTGAGTGAGCTGATACCGCTCGCCGCAG<br>CCGAACGACCGAGCGCAGCGAGTCAGTGAGCGAGGAAGCGGAAG<br>AGCGCCCAATACGCAAACCGCCTCTCCCCGCGCGTTGGCCGATTC<br>ATTAATG |
| 51 | HBG1 Round 3:<br>AMS#1345<br>pAAV<br>HBG1(650).d0<br>HBBp>HBB(T87Q).<br>core3'enh;<br>MND>GFP.SV40pA | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC<br>GCGTAGATCTGGTGTATACATACATACCTGAATATGGAATCAAAT<br>ATTTTTCTAAGATGAAACAGTCATGATTTATTTCAAATAGGTACGG<br>ATAAGTAGATATTGAGGTAAGCATTAGGTCTTATATTATGTAACAC<br>TAATCTATTACTGCGCTGAAACTGTGGCTTTATAGAAATTGTTTTC<br>ACTGCACTATTGAGAAATTAAGAGATAATGGCAAAAGTCACAAAG<br>AGTATATTCAAAAAGAAGTATAGCACTTTTTCCTTAGAAACCACTG<br>CTAACTGAAAGAGACTAAGATTTGTCCCGTCAAAAATCCTGGACC<br>TATGCCTAAAACACATTTCACAATCCCTGAACTTTTCAAAAATTGG<br>TACATGCTTTAGCTTTAAACTACAGGCCTCACTGGAGCTAGAGAC<br>AAGAAGGTAAAAAACGGCTGACAAAAGAAGTCCTGGTATCCTCTA<br>TGATGGGAGAAGGAAACTAGCTAAAGGGAAGAATAAATTAGAGA<br>AAAACTGGAATGACTGAATCGGAACAAGGCAAAGGCTATAAAAA<br>AAATTAAGCAGCAGTATCCTCTTGGGGGCCCCTTCCCCACACTATC |

-continued

| SEQ ID NO | NAME | SEQUENCE |
|---|---|---|
| | | TCAATGCAAATATCTGTCTGAAACGGTCCCTGGCTAAACTCCACCC<br>ATGGGTTGGCCAGCCTTGCCTTGACGCTAGCGTAAATACACTTGCA<br>AAGGAGGATGTTTTTAGTAGCAATTTGTACTGATGGTATGGGGCC<br>AAGAGATATATCTTAGAGGGAGGGCTGAGGGTTTGAAGTCCAACT<br>CCTAAGCCAGTGCCAGAAGAGCCAAGGACAGGTACGGCTGTCATC<br>ACTTAGACCTCACCCTGTGGAGCCACACCCTAGGGTTGGCCAATCT<br>ACTCCCAGGAGCAGGGAGGGCAGGAGCCAGGGCTGGGCATAAAA<br>GTCAGGGCAGAGCCATCTATTGCTTACATTTGCTTCTGACACAACT<br>GTGTTCACTAGCAACCTCAAACAGACACCATGGTGCACCTGACTC<br>CTGAGGAGAAGTCTGCCGTTACTGCCCTGTGGGGCAAGGTGAACG<br>TGGATGAAGTTGGTGGTGAGGCCCTGGGCAGGTTGGTATCAAGGT<br>TACAAGACAGGTTTAAGGAGACCAATAGAAACTGGGCATGTGGA<br>GACAGAGAAGACTCTTGGGTTTCTGATAGGCACTGACTCTCTCTGC<br>CTATTGGTCTATTTTCCCACCCTTAGGCTGCTGGTGGTCTACCCTTG<br>GACCCAGAGGTTCTTTGAGTCCTTTGGGGATCTGTCCACTCCTGAT<br>GCTGTTATGGGCAACCCTAAGGTGAAGGCTCATGGCAAGAAAGTG<br>CTCGGTGCCTTTAGTGATGGCCTGGCTCACCTGGACAACCTCAAGG<br>GCACCTTTGCCCAGCTGAGTGAGCTGCACTGTGACAAGCTGCACG<br>TGGATCCTGAGAACTTCAGGGTGAGTCTATGGGACCCTTGATGTTT<br>TCTTTCCCCTTCTTTTCTATGGTTAAGTTCATGTCATAGGAAGGGG<br>AGAAGTAACAGGGTACACATATTGACCAAATCAGGGTAATTTTGC<br>ATTTGTAATTTTAAAAAATGCTTTCTTCTTTTAATATACTTTTTTGT<br>TTATCTTATTTCTAATACTTTCCCTAATCTCTTTCTTTCAGGGCAAT<br>AATGATACAATGTATCATGCCTCTTTGCACCATTCTAAAGAATAAC<br>AGTGATAATTTCTGGGTTAAGGCAATAGCAATATTTCTGCATATAA<br>ATATTTCTGCATATAAATTGTAACTGATGTAAGAGGTTTCATATTG<br>CTAATAGCAGCTACAATCCAGCTACCATTCTGCTTTTATTTTATGG<br>TTGGGATAAGGCTGGATTATTCTGAGTCCAAGCTAGGCCCTTTTGC<br>TAATCATGTTCATACCTCTTATCTTCCTCCCACAGCTCCTGGGCAA<br>CGTGCTGGTCTGTGTGCTGGCCCATCACTTTGGCAAAGAATTCACC<br>CCACCAGTGCAGGCTGCCTATCAGAAAGTGGTGGCTGGTGTGGCT<br>AATGCCCTGGCCCACAAGTATCACTAAGCTCGCTTTCTTGCTGTCC<br>AATTTCTATTAAAGGTTCCTTTGTTCCCTAAGTCCAACTACTAAAC<br>TGGGGGATATTATGAAGGGCCTTGAGCATCTGGATTCTGCCTAAT<br>AAAAAACATTTATTTTCATTGCAATGATGTATTTAAATTATTTCTG<br>AATATTTTACTAAAAAGGGAATGTGGGAGGTTGCAGTGCTAGTCT<br>CCCGGAACTATCACTCTTTCACAGTCTGCTTTGGAAGGACTGGGCT<br>TAGTATGAAAAGTTAGGACTGAGAAGAATTTGAAAGGGGGCTTTT<br>TGTAGCTTGATATTCACTACTGTCTTATTACCCTATCATAGGCCCA<br>CCCCAAATGGAAGTCCCATTCTTCCTCAGGATGTTTAAGATTAGCA<br>TTCAGGAAGAGATCAGAGGTCTGCTGGCTCCCTTATCATGTCCCTT<br>ATGGTGCTTCTGGCTCTGCACCGCGGGAACAGAGAAACAGGAGAA<br>TATGGGCCAAACAGGATATCTGTGGTAAGCAGTTCCTGCCCCGGC<br>TCAGGGCCAAGAACAGTTGGAACAGCAGAATATGGGCCAAACAG<br>GATATCTGTGGTAAGCAGTTCCTGCCCCGGCTCAGGGCCAAGAAC<br>AGATGGTCCCCAGATGCGGTCCCGCCCTCAGCAGTTTCTAGAGAA<br>CCATCAGATGTTTCCAGGGTGCCCCAAGGACCTGAAATGACCCTG<br>TGCCTTATTTGAACTAACCAATCAGTTCGCTTCTCGCTTCTGTTCGC<br>GCGCTTCTGCTCCCCGAGCTCTATATAAGCAGAGCTCGTTTAGTGA<br>ACCGTCAGATCGCGGCCGCGCCGCCACCATGGTGAGCAAGGGCGA<br>GGAGCTGTTCACCGGGGTGGTGCCCATCCTGGTCGAGCTGGACGG<br>CGACGTAAACGGCCACAAGTTCAGCGTGTCCGGCGAGGGCGAGG<br>GCGATGCCACCTACGGCAAGCTGACCCTGAAGTTCATCTGCACCA<br>CCGGCAAGCTGCCCGTGCCCTGGCCCACCCTCGTGACCACCCTGA<br>CCTACGGCGTGCAGTGCTTCAGCCGCTACCCCGACCACATGAAGC<br>AGCACGACTTCTTCAAGTCCGCCATGCCCGAAGGCTACGTCCAGG<br>AGCGCACCATCTTCTTCAAGGACGACGGCAACTACAAGACCCGCG<br>CCGAGGTGAAGTTCGAGGGCGACACCCTGGTGAACCGCATCGAGC<br>TGAAGGGCATCGACTTCAAGGAGGACGGCAACATCCTGGGGCACA<br>AGCTGGAGTACAACTACAACAGCCACAACGTCTATATCATGGCCG<br>ACAAGCAGAAGAACGGCATCAAGGTGAACTTCAAGATCCGCCAC<br>AACATCGAGGACGGCAGCGTGCAGCTCGCCGACCACTACCAGCAG<br>AACACCCCCATCGGCGACGGCCCCGTGCTGCTGCCCGACAACCAC<br>TACCTGAGCACCCAGTCCGCCCTGAGCAAAGACCCCAACGAGAAG<br>CGCGATCACATGGTCCTGCTGGAGTTCGTGACCGCCGCCGGGATC<br>ACTCTCGGCATGGACGAGCTGTACAAGTAAGCTTTATTTGTGAAAT<br>TTGTGATGCTATTGCTTTATTTGTAACCATTATAAGCTGCAATAAA<br>CAAGTTAACAACAACAATTGCATTCATTTTATGTTTCAGGTTCAGG<br>GGGAGATGTGGGAGGTTTTTTAAAGCCCTGCAGGCAATAGCCTTG<br>ACAAGGCAAACTTGACCAATAGTCTTAGAGTATCCAGTGAGGCCA<br>GGGGCCGGCGGCTGGCTAGGGATGAAGAATAAAAGGAAGCACCC<br>TTCAGCAGTTCCACACACTCGCTTCTGGAACGTCTGAGGTTATCAA<br>TAAGCTCCTAGTCCAGACGCCATGGGTCATTTCACAGAGGAGGAC<br>AAGGCTACTATCACAAGCCTGTGGGGCAAGGTGAATGTGGAAGAT<br>GCTGGAGGAGAAACCCTGGGAAGGTAGGCTCTGGTGACCAGGAC |

-continued

| SEQ ID NO | NAME | SEQUENCE |
|---|---|---|
| | | AAGGGAGGGAAGGAAGGACCCTGTGCCTGGCAAAAGTCCAGGTC |
| | | GCTTCTCAGGATTTGTGGCACCTTCTGACTGTCAAACTGTTCTTGT |
| | | CAATCTCACAGGCTCCTGGTTGTCTACCCATGGACCCAGAGGTTCT |
| | | TTGACAGCTTTGGCAACCTGTCCTCTGCCTCTGCCATCATGGGCAA |
| | | CCCCAAAGTCAAGGCACATGGCAAGAAGGTGCTGACTTCCTTGGG |
| | | AGATGCCACAAAGCACCTGGATGATCTCAAGGGCACCTTTGCCCA |
| | | GCTGAGTGAACTGCACTGTGACAAGCTGCATGTGGATCCTGAGAA |
| | | CTTCAAGGTGAGTCCAGGAGATGTTTCAGCCCTGTTGCCTTTAGTC |
| | | TCGAGGCGTCGACAGGAACCCCTAGTGATGGAGTTGGCCACTCCC |
| | | TCTCTGCGCGCTCGCTCGCTCACTGAGGCCGGGCGACCAAAGGTC |
| | | GCCCGACGCCCGGGCTTTGCCCGGGCGGCCTCAGTGAGCGAGCGA |
| | | GCGCGCAGCTGGCGTAATAGCGAAGAGGCCCGCACCGATCGCCCT |
| | | TCCCAACAGTTGCGCAGCCTGAATGGCGAATGGCGATTCCGTTGC |
| | | AATGGCTGGCGGTAATATTGTTCTGGATATTACCAGCAAGGCCGA |
| | | TAGTTTGAGTTCTTCTACTCAGGCAAGTGATGTTATTACTAATCAA |
| | | AGAAGTATTGCGACAACGGTTAATTTGCGTGATGGACAGACTCTT |
| | | TTACTCGGTGGCCTCACTGATTATAAAAACACTTCTCAGGATTCTG |
| | | GCGTACCGTTCCTGTCTAAAATCCCTTTAATCGGCCTCCTGTTTAG |
| | | CTCCCGCTCTGATTCTAACGAGGAAAGCACGTTATACGTGCTCGTC |
| | | AAAGCAACCATAGTACGCGCCCTGTAGCGGCGCATTAAGCGCGGC |
| | | GGGTGTGGTGGTTACGCGCAGCGTGACCGCTACACTTGCCAGCGC |
| | | CCTAGCGCCCGCTCCTTTCGCTTTCTTCCCTTCCTTTCTCGCCACGT |
| | | TCGCCGGCTTTCCCCGTCAAGCTCTAAATCGGGGGCTCCCTTTAGG |
| | | GTTCCGATTTAGTGCTTTACGGCACCTCGACCCCAAAAAACTTGAT |
| | | TAGGGTGATGGTTCACGTAGTGGGCCATCGCCCTGATAGACGGTT |
| | | TTTCGCCCTTTGACGTTGGAGTCCACGTTCTTTAATAGTGGACTCTT |
| | | GTTCCAAACTGGAACAACACTCAACCCTATCTCGGTCTATTCTTTT |
| | | GATTTATAAGGGATTTTGCCGATTTCGGCCTATTGGTTAAAAAATG |
| | | AGCTGATTTAACAAAAATTTAACGCGAATTTTAACAAAATATTAA |
| | | CGTTTACAATTTAAATATTTGCTTATACAATCTTCCTGTTTTTGGGG |
| | | CTTTTCTGATTATCAACCGGGGTACATATGATTGACATGCTAGTTT |
| | | TACGATTACCGTTCATCGATTCTCTTGTTTGCTCCAGACTCTCAGG |
| | | CAATGACCTGATAGCCTTTGTAGAGACCTCTCAAAAATAGCTACC |
| | | CTCTCCGGCATGAATTTATCAGCTAGAACGGTTGAATATCATATTG |
| | | ATGGTGATTTGACTGTCTCCGGCCTTTCTCACCCGTTTGAATCTTTA |
| | | CCTACACATTACTCAGGCATTGCATTTAAAATATATGAGGGTTCTA |
| | | AAAATTTTTATCCTTGCGTTGAAATAAAGGCTTCTCCCGCAAAAGT |
| | | ATTACAGGGTCATAATGTTTTTGGTACAACCGATTTAGCTTTATGC |
| | | TCTGAGGCTTTATTGCTTAATTTTGCTAATTCTTTGCCTTGCCTGTA |
| | | TGATTTATTGGATGTTGGAATCGCCTGATGCGGTATTTTCTCCTTA |
| | | CGCATCTGTGCGGTATTTCACACCGCATATGGTGCACTCTCAGTAC |
| | | AATCTGCTCTGATGCCGCATAGTTAAGCCAGCCCCGACACCCGCC |
| | | AACACCCGCTGACGCGCCCTGACGGGCTTGTCTGCTCCCGGCATCC |
| | | GCTTACAGACAAGCTGTGACCGTCTCCGGGAGCTGCATGTGTCAG |
| | | AGGTTTTCACCGTCATCACCGAAACGCGCGAGACGAAAGGGCCTC |
| | | GTGATACGCCTATTTTTATAGGTTAATGTCATGATAATAATGGTTT |
| | | CTTAGACGTCAGGTGGCACTTTTCGGGGAAATGTGCGCGGAACCC |
| | | CTATTTGTTTATTTTTCTAAATACATTCAAATATGTATCCGCTCATG |
| | | AGACAATAACCCTGATAAATGCTTCAATAATATTGAAAAAGGAAG |
| | | AGTATGAGTATTCAACATTTCCGTGTCGCCCTTATTCCCTTTTTTGC |
| | | GGCATTTTGCCTTCCTGTTTTTGCTCACCCAGAAACGCTGGTGAAA |
| | | GTAAAAGATGCTGAAGATCAGTTGGGTGCACGAGTGGGTTACATC |
| | | GAACTGGATCTCAACAGCGGTAAGATCCTTGAGAGTTTTCGCCCC |
| | | GAAGAACGTTTTCCAATGATGAGCACTTTTAAAGTTCTGCTATGTG |
| | | GCGCGGTATTATCCCGTATTGACGCCGGGCAAGAGCAACTCGGTC |
| | | GCCGCATACACTATTCTCAGAATGACTTGGTTGAGTACTCACCAGT |
| | | CACAGAAAAGCATCTTACGGATGGCATGACAGTAAGAGAATTATG |
| | | CAGTGCTGCCATAACCATGAGTGATAACACTGCGGCCAACTTACT |
| | | TCTGACAACGATCGGAGGACCGAAGGAGCTAACCGCTTTTTTGCA |
| | | CAACATGGGGGATCATGTAACTCGCCTTGATCGTTGGGAACCGGA |
| | | GCTGAATGAAGCCATACCAAACGACGAGCGTGACACCACGATGCC |
| | | TGTAGCAATGGCAACAACGTTGCGCAAACTATTAACTGGCGAACT |
| | | ACTTACTCTAGCTTCCCGGCAACAATTAATAGACTGGATGGAGGC |
| | | GGATAAAGTTGCAGGACCACTTCTGCGCTCGGCCCTTCCGGCTGG |
| | | CTGGTTTATTGCTGATAAATCTGGAGCCGGTGAGCGTGGGTCTCGC |
| | | GGTATCATTGCAGCACTGGGGCCAGATGGTAAGCCCTCCCGTATC |
| | | GTAGTTATCTACACGACGGGGAGTCAGGCAACTATGGATGAACGA |
| | | AATAGACAGATCGCTGAGATAGGTGCCTCACTGATTAAGCATTGG |
| | | TAACTGTCAGACCAAGTTTACTCATATATACTTTAGATTGATTTAA |
| | | AACTTCATTTTTAATTTAAAAGGATCTAGGTGAAGATCCTTTTTGA |
| | | TAATCTCATGACCAAAATCCCTTAACGTGAGTTTTCGTTCCACTGA |
| | | GCGTCAGACCCCGTAGAAAAGATCAAAGGATCTTCTTGAGATCCT |
| | | TTTTTCTGCGCGTAATCTGCTGCTTGCAAACAAAAAAACCACCGC |
| | | TACCAGCGGTGGTTTGTTTGCCGGATCAAGAGCTACCAACTCTTTT |
| | | TCCGAAGGTAACTGGCTTCAGCAGAGCGCAGATACCAAATACTGT |

-continued

| SEQ ID NO | NAME | SEQUENCE |
|---|---|---|
| | | CCTTCTAGTGTAGCCGTAGTTAGGCCACCACTTCAAGAACTCTGTA GCACCGCCTACATACCTCGCTCTGCTAATCCTGTTACCAGTGGCTG CTGCCAGTGGCGATAAGTCGTGTCTTACCGGGTTGGACTCAAGAC GATAGTTACCGGATAAGGCGCAGCGGTCGGGCTGAACGGGGGGTT CGTGCACACAGCCCAGCTTGGAGCGAACGACCTACACCGAACTGA GATACCTACAGCGTGAGCTATGAGAAAGCGCCACGCTTCCCGAAG GGAGAAAGGCGGACAGGTATCCGGTAAGCGGCAGGGTCGGAACA GGAGAGCGCACGAGGGAGCTTCCAGGGGGAAACGCCTGGTATCTT TATAGTCCTGTCGGGTTTCGCCACCTCTGACTTGAGCGTCGATTTT TGTGATGCTCGTCAGGGGGGCGGAGCCTATGGAAAAACGCCAGCA ACGCGGCCTTTTTACGGTTCCTGGCCTTTTGCTGGCCTTTTGCTCAC ATGTTCTTTCCTGCGTTATCCCCTGATTCTGTGGATAACCGTATTAC CGCCTTTGAGTGAGCTGATACCGCTCGCCGCAGCCGAACGACCGA GCGCAGCGAGTCAGTGAGCGAGGAAGCGGAAGAGCGCCCAATAC GCAAACCGCCTCTCCCCGCGCGTTGGCCGATTCATTAATG |
| 52 | HBG1 Round 3: AMS#1346 pAAV HBG1(650).d0 d13p>HBB(T87Q). core3'enh;PGK> MGMT(P140K). SV40pA | CAGCTGCGCGCTCGCTCGCTCACTGAGGCCGCCCGGGCAAAGCCC GGGCGTCGGGCGACCTTTGGTCGCCCGGCCTCAGTGAGCGAGCGA GCGCGCAGAGAGGGAGTGGCCAACTCCATCACTAGGGGTTCCTAC GCGTAGATCTGGTGTATACATACATACCTGAATATGGAATCAAAT ATTTTTCTAAGATGAAACAGTCATGATTTATTTCAAATAGGTACGG ATAAGTAGATATTGAGGTAAGCATTAGGTCTTATATTATGTAACAC TAATCTATTACTGCGCTGAAACTGTGGCTTTATAGAAATTGTTTTC ACTGCACTATTGAGAAATTAAGAGATAATGGCAAAAGTCACAAAG AGTATATTCAAAAAGAAGTATAGCACTTTTTCCTTAGAAACCACTG CTAACTGAAAGAGACTAAGATTTGTCCCGTCAAAAATCCTGGACC TATGCCTAAAACACATTTCACAATCCCTGAACTTTTCAAAAATTGG TACATGCTTTAGCTTTAAACTACAGGCCTCACTGGAGCTAGAGAC AAGAAGGTAAAAAACGGCTGACAAAAGAAGTCCTGGTATCCTCTA TGATGGGAGAAGGAAACTAGCTAAAGGGAAGAATAAATTAGAGA AAAACTGGAATGACTGAATCGGAACAAGGCAAAGGCTATAAAAA AAATTAAGCAGCAGTATCCTCTTGGGGGCCCCTTCCCCACACTATC TCAATGCAAATATCTGTCTGAAACGGTCCCTGGCTAAACTCCACCC ATGGGTTGGCCAGCCTTGCCTTGACAAGGCAAACTTGACCAATAG TCTTAGAGTATCCAGTGAGGCCAGGGGCCGGCGGCTGGCTAGGGA TGAAGAATAAAAGGAAGCACCCTTCAGCAGTTCCACACACTCGCT TCTGGAACGTCTGAGGTTATCAATAAGCTCCTAGTCCAGACGCCAT GGTGCACCTGACTCCTGAGGAGAAGTCTGCCGTTACTGCCCTGTG GGGCAAGGTGAACGTGGATGAAGTTGGTGGTGAGGCCCTGGGCA GGTTGGTATCAAGGTTACAAGACAGGTTTAAGGAGACCAATAGAA ACTGGGCATGTGGAGACAGAGAAGACTCTTGGGTTTCTGATAGGC ACTGACTCTCTCTGCCTATTGGTCTATTTTCCCACCCTTAGGCTGCT GGTGGTCTACCCTTGGACCCAGAGGTTCTTTGAGTCCTTTGGGGAT CTGTCCACTCCTGATGCTGTTATGGGCAACCCTAAGGTGAAGGCTC ATGGCAAGAAAGTGCTCGGTGCCTTTAGTGATGGCCTGGCTCACC TGGACAACCTCAAGGGCACCTTTGCCCAGCTGAGTGAGCTGCACT GTGACAAGCTGCACGTGGATCCTGAGAACTTCAGGGTGAGTCTAT GGGACCCTTGATGTTTTCTTTCCCCTTCTTTTCTATGGTTAAGTTCA TGTCATAGGAAGGGGAGAAGTAACAGGGTACACATATTGACCAA ATCAGGGTAATTTTGCATTTGTAATTTTAAAAAATGCTTTCTTCTTT TAATATACTTTTTTGTTTATCTTATTTCTAATACTTTCCCTAATCTCT TTCTTTCAGGGCAATAATGATACAATGTATCATGCCTCTTTGCACC ATTCTAAAGAATAACAGTGATAATTTCTGGGTTAAGGCAATAGCA ATATTTCTGCATATAAATATTTCTGCATATAAATTGTAACTGATGT AAGAGGTTTCATATTGCTAATAGCAGCTACAATCCAGCTACCATTC TGCTTTTATTTTATGGTTGGGATAAGGCTGGATTATTCTGAGTCCA AGCTAGGCCCTTTTGCTAATCATGTTCATACCTCTTATCTTCCTCCC ACAGCTCCTGGGCAACGTGCTGGTCTGTGTGCTGGCCCATCACTTT GGCAAAGAATTCACCCCACCAGTGCAGGCTGCCTATCAGAAAGTG GTGGCTGGTGTGGCTAATGCCCTGGCCCACAAGTATCACTAAGCT CGCTTTCTTGCTGTCCAATTTCTATTAAAGGTTCCTTTGTTCCCTAA GTCCAACTACTAAACTGGGGGATATTATGAAGGGCCTTGAGCATC TGGATTCTGCCTAATAAAAAACATTTATTTTCATTGCAATGATGTA TTTAAATTATTTCTGAATATTTTACTAAAAAGGGAATGTGGGAGGT TGCAGTGCTAGTCTCCCGGAACTATCACTCTTTCACAGTCTGCTTT GGAAGGACTGGGCTTAGTATGAAAAGTTAGGACTGAGAAGAATTT GAAAGGGGGCTTTTTGTAGCTTGATATTCACTACTGTCTTATTACC CTATCATAGGCCCACCCCAAATGGAAGTCCCATTCTTCCTCAGGAT GTTTAAGATTAGCATTCAGGAAGAGATCAGAGGTCTGCTGGCTCC CTTATCATGTCCCTTATGGTGCTTCTGGCTCTGCACCGCGGCCACG GGGTTGGGGTTGCGCCTTTTCCAAGGCAGCCCTGGGTTTGCGCAG GGACGCGGCTGCTCTGGGCGTGGTTCCGGGAAACGCAGCGGCGCC GACCCTGGGTCTCGCACATTCTTCACGTCCGTTCGCAGCGTCACCC GGATCTTCGCCGCTACCCTTGTGGGCCCCCCGGCGACGCTTCCTGC TCCGCCCCTAAGTCGGGAAGGTTCCTTGCGGTTCGCGGCGTGCCG |

-continued

| SEQ ID NO | NAME | SEQUENCE |
|---|---|---|
| | | GACGTGACAAACGGAAGCCGCACGTCTCACTAGTACCCTCGCAGA |
| | | CGGACAGCGCCAGGGAGCAATGGCAGCGCGCCGACCGCGATGGG |
| | | CTGTGGCCAATAGCGGCTGCTCAGCGGGGCGCGCCGAGAGCAGCG |
| | | GCCGGGAAGGGGCGGTGCGGGAGGCGGGGTGTGGGGCGGTAGTG |
| | | TGGGCCCTGTTCCTGCCCGCGCGGTGTTCCGCATTCTGCAAGCCTC |
| | | CGGAGCGCACGTCGGCAGTCGGCTCCCTCGTTGACCGAATCACCG |
| | | ACCTCTCTCCCCAGCGGCCGCGCCGCCACCATGGACAAGGATTGT |
| | | GAAATGAAACGCACCACACTGGACAGCCCTTTGGGGAAGCTGGAG |
| | | CTGTCTGGTTGTGAGCAGGGTCTGCACGAAATAAAGCTCCTGGGC |
| | | AAGGGGACGTCTGCAGCTGATGCCGTGGAGGTCCCAGCCCCCGCT |
| | | GCGGTTCTCGGAGGTCCGGAGCCCCTGATGCAGTGCACAGCCTGG |
| | | CTGAATGCCTATTTCCACCAGCCCGAGGCTATCGAAGAGTTCCCCG |
| | | TGCCGGCTCTTCACCATCCCGTTTTCCAGCAAGAGTCGTTCACCAG |
| | | ACAGGTGTTATGGAAGCTGCTGAAGGTTGTGAAATTCGGAGAAGT |
| | | GATTTCTTACCAGCAATTAGCAGCCCTGGCAGGCAACCCCAAAGC |
| | | CGCGCGAGCAGTGGGAGGAGCAATGAGAGGCAATCCTGTCAAAA |
| | | TCCTCATCCCGTGCCACAGAGTGGTCTGCAGCAGCGGAGCCGTGG |
| | | GCAACTACTCCGGAGGACTGGCCGTGAAGGAATGGCTTCTGGCCC |
| | | ATGAAGGCCACCGGTTGGGGAAGCCAGGCTTGGGAGGGAGCTCA |
| | | GGTCTGGCAGGGGCCTGGCTCAAGGGAGCGGGAGCTACCTCGGGC |
| | | TCCCCGCCTGCTGGCCGAAACTAAGCTTTATTTGTGAAATTTGTGA |
| | | TGCTATTGCTTTATTTGTAACCATTATAAGCTGCAATAAACAAGTT |
| | | AACAACAACAATTGCATTCATTTTATGTTTCAGGTTCAGGGGGAG |
| | | ATGTGGGAGGTTTTTTAAAGCCCTGCAGGCAATAGCCTTGACAAG |
| | | GCAAACTTGACCAATAGTCTTAGAGTATCCAGTGAGGCCAGGGGC |
| | | CGGCGGCTGGCTAGGGATGAAGAATAAAAGGAAGCACCCTTCAG |
| | | CAGTTCCACACACTCGCTTCTGGAACGTCTGAGGTTATCAATAAGC |
| | | TCCTAGTCCAGACGCCATGGGTCATTTCACAGAGGAGGACAAGGC |
| | | TACTATCACAAGCCTGTGGGGCAAGGTGAATGTGGAAGATGCTGG |
| | | AGGAGAAACCCTGGGAAGGTAGGCTCTGGTGACCAGGACAAGGG |
| | | AGGGAAGGAAGGACCCTGTGCCTGGCAAAAGTCCAGGTCGCTTCT |
| | | CAGGATTTGTGGCACCTTCTGACTGTCAAACTGTTCTTGTCAATCT |
| | | CACAGGCTCCTGGTTGTCTACCCATGGACCCAGAGGTTCTTTGACA |
| | | GCTTTGGCAACCTGTCCTCTGCCTCTGCCATCATGGGCAACCCCAA |
| | | AGTCAAGGCACATGGCAAGAAGGTGCTGACTTCCTTGGGAGATGC |
| | | CACAAAGCACCTGGATGATCTCAAGGGCACCTTTGCCCAGCTGAG |
| | | TGAACTGCACTGTGACAAGCTGCATGTGGATCCTGAGAACTTCAA |
| | | GGTGAGTCCAGGAGATGTTTCAGCCCTGTTGCCTTTAGTCTCGAGG |
| | | CGTCGACAGGAACCCCTAGTGATGGAGTTGGCCACTCCCTCTCTGC |
| | | GCGCTCGCTCGCTCACTGAGGCCGGGCGACCAAAGGTCGCCCGAC |
| | | GCCCGGGCTTTGCCCGGGCGGCCTCAGTGAGCGAGCGAGCGCGCA |
| | | GCTGGCGTAATAGCGAAGAGGCCCGCACCGATCGCCCTTCCCAAC |
| | | AGTTGCGCAGCCTGAATGGCGAATGGCGATTCCGTTGCAATGGCT |
| | | GGCGGTAATATTGTTCTGGATATTACCAGCAAGGCCGATAGTTTG |
| | | AGTTCTTCTACTCAGGCAAGTGATGTTATTACTAATCAAAGAAGTA |
| | | TTGCGACAACGGTTAATTTGCGTGATGGACAGACTCTTTTACTCGG |
| | | TGGCCTCACTGATTATAAAAACACTTCTCAGGATTCTGGCGTACCG |
| | | TTCCTGTCTAAAATCCCTTTAATCGGCCTCCTGTTTAGCTCCCGCTC |
| | | TGATTCTAACGAGGAAAGCACGTTATACGTGCTCGTCAAAGCAAC |
| | | CATAGTACGCGCCCTGTAGCGGCGCATTAAGCGCGGCGGGTGTGG |
| | | TGGTTACGCGCAGCGTGACCGCTACACTTGCCAGCGCCCTAGCGC |
| | | CCGCTCCTTTCGCTTTCTTCCCTTCCTTTCTCGCCACGTTCGCCGGC |
| | | TTTCCCCGTCAAGCTCTAAATCGGGGGCTCCCTTTAGGGTTCCGAT |
| | | TTAGTGCTTTACGGCACCTCGACCCCAAAAAACTTGATTAGGGTG |
| | | ATGGTTCACGTAGTGGGCCATCGCCCTGATAGACGGTTTTTCGCCC |
| | | TTTGACGTTGGAGTCCACGTTCTTTAATAGTGGACTCTTGTTCCAA |
| | | ACTGGAACAACACTCAACCCTATCTCGGTCTATTCTTTTGATTTAT |
| | | AAGGGATTTTGCCGATTTCGGCCTATTGGTTAAAAAATGAGCTGAT |
| | | TTAACAAAAATTTAACGCGAATTTTAACAAAATATTAACGTTTACA |
| | | ATTTAAATATTTGCTTATACAATCTTCCTGTTTTTGGGGCTTTTCTG |
| | | ATTATCAACCGGGGTACATATGATTGACATGCTAGTTTTACGATTA |
| | | CCGTTCATCGATTCTCTTGTTTGCTCCAGACTCTCAGGCAATGACC |
| | | TGATAGCCTTTGTAGAGACCTCTCAAAAATAGCTACCCTCTCCGGC |
| | | ATGAATTTATCAGCTAGAACGGTTGAATATCATATTGATGGTGATT |
| | | TGACTGTCTCCGGCCTTTCTCACCCGTTTGAATCTTTACCTACACAT |
| | | TACTCAGGCATTGCATTTAAAATATATGAGGGTTCTAAAAATTTTT |
| | | ATCCTTGCGTTGAAATAAAGGCTTCTCCCGCAAAAGTATTACAGG |
| | | GTCATAATGTTTTTGGTACAACCGATTTAGCTTTATGCTCTGAGGC |
| | | TTTATTGCTTAATTTTGCTAATTCTTTGCCTTGCCTGTATGATTTATT |
| | | GGATGTTGGAATCGCCTGATGCGGTATTTTCTCCTTACGCATCTGT |
| | | GCGGTATTTCACACCGCATATGGTGCACTCTCAGTACAATCTGCTC |
| | | TGATGCCGCATAGTTAAGCCAGCCCCGACACCCGCCAACACCCGC |
| | | TGACGCGCCCTGACGGGCTTGTCTGCTCCCGGCATCCGCTTACAGA |
| | | CAAGCTGTGACCGTCTCCGGGAGCTGCATGTGTCAGAGGTTTTCAC |
| | | CGTCATCACCGAAACGCGCGAGACGAAAGGGCCTCGTGATACGCC |

-continued

| SEQ ID NO | NAME | SEQUENCE |
|---|---|---|
| | | TATTTTTATAGGTTAATGTCATGATAATAATGGTTTCTTAGACGTC<br>AGGTGGCACTTTTCGGGGAAATGTGCGCGGAACCCCTATTTGTTTA<br>TTTTTCTAAATACATTCAAATATGTATCCGCTCATGAGACAATAAC<br>CCTGATAAATGCTTCAATAATATTGAAAAAGGAAGAGTATGAGTA<br>TTCAACATTTCCGTGTCGCCCTTATTCCCTTTTTTGCGGCATTTTGC<br>CTTCCTGTTTTTGCTCACCCAGAAACGCTGGTGAAAGTAAAAGATG<br>CTGAAGATCAGTTGGGTGCACGAGTGGGTTACATCGAACTGGATC<br>TCAACAGCGGTAAGATCCTTGAGAGTTTTCGCCCCGAAGAACGTT<br>TTCCAATGATGAGCACTTTTAAAGTTCTGCTATGTGGCGCGGTATT<br>ATCCCGTATTGACGCCGGGCAAGAGCAACTCGGTCGCCGCATACA<br>CTATTCTCAGAATGACTTGGTTGAGTACTCACCAGTCACAGAAAA<br>GCATCTTACGGATGGCATGACAGTAAGAGAATTATGCAGTGCTGC<br>CATAACCATGAGTGATAACACTGCGGCCAACTTACTTCTGACAAC<br>GATCGGAGGACCGAAGGAGCTAACCGCTTTTTTGCACAACATGGG<br>GGATCATGTAACTCGCCTTGATCGTTGGGAACCGGAGCTGAATGA<br>AGCCATACCAAACGACGAGCGTGACACCACGATGCCTGTAGCAAT<br>GGCAACAACGTTGCGCAAACTATTAACTGGCGAACTACTTACTCT<br>AGCTTCCCGGCAACAATTAATAGACTGGATGGAGGCGGATAAAGT<br>TGCAGGACCACTTCTGCGCTCGGCCCTTCCGGCTGGCTGGTTTATT<br>GCTGATAAATCTGGAGCCGGTGAGCGTGGGTCTCGCGGTATCATT<br>GCAGCACTGGGGCCAGATGGTAAGCCCTCCCGTATCGTAGTTATC<br>TACACGACGGGGAGTCAGGCAACTATGGATGAACGAAATAGACA<br>GATCGCTGAGATAGGTGCCTCACTGATTAAGCATTGGTAACTGTC<br>AGACCAAGTTTACTCATATATACTTTAGATTGATTTAAAACTTCAT<br>TTTTAATTTAAAAGGATCTAGGTGAAGATCCTTTTTGATAATCTCA<br>TGACCAAAATCCCTTAACGTGAGTTTTCGTTCCACTGAGCGTCAGA<br>CCCCGTAGAAAAGATCAAAGGATCTTCTTGAGATCCTTTTTTTCTG<br>CGCGTAATCTGCTGCTTGCAAACAAAAAAACCACCGCTACCAGCG<br>GTGGTTTGTTTGCCGGATCAAGAGCTACCAACTCTTTTTCCGAAGG<br>TAACTGGCTTCAGCAGAGCGCAGATACCAAATACTGTCCTTCTAGT<br>GTAGCCGTAGTTAGGCCACCACTTCAAGAACTCTGTAGCACCGCC<br>TACATACCTCGCTCTGCTAATCCTGTTACCAGTGGCTGCTGCCAGT<br>GGCGATAAGTCGTGTCTTACCGGGTTGGACTCAAGACGATAGTTA<br>CCGGATAAGGCGCAGCGGTCGGGCTGAACGGGGGGTTCGTGCACA<br>CAGCCCAGCTTGGAGCGAACGACCTACACCGAACTGAGATACCTA<br>CAGCGTGAGCTATGAGAAAGCGCCACGCTTCCCGAAGGGAGAAA<br>GGCGGACAGGTATCCGGTAAGCGGCAGGGTCGGAACAGGAGAGC<br>GCACGAGGGAGCTTCCAGGGGGAAACGCCTGGTATCTTTATAGTC<br>CTGTCGGGTTTCGCCACCTCTGACTTGAGCGTCGATTTTTGTGATG<br>CTCGTCAGGGGGGCGGAGCCTATGGAAAAACGCCAGCAACGCGG<br>CCTTTTTACGGTTCCTGGCCTTTTGCTGGCCTTTTGCTCACATGTTC<br>TTTCCTGCGTTATCCCCTGATTCTGTGGATAACCGTATTACCGCCTT<br>TGAGTGAGCTGATACCGCTCGCCGCAGCCGAACGACCGAGCGCAG<br>CGAGTCAGTGAGCGAGGAAGCGGAAGAGCGCCCAATACGCAAAC<br>CGCCTCTCCCCGCGCGTTGGCCGATTCATTAATG |
| 53 | d13 Repair Only:<br>AMS#1315<br>pAAV<br>HBG1(2.1 kb).<br>13bp.deletion | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTGC<br>GGCCGCGATGTGAGGACACAGTGGGAAGTCAGCCACCTGCAACCC<br>AGGAAGAGAGCCCTGACCAGGAACCAGCAGAAAAGTGAGAAAAA<br>ATCCTGTTGTTGAAGTCACCCAGTCTATGCTATTTTGTTATAGCAC<br>CTTGCACTAAGTAAGGCAGATGAAGAAAGAGAAAAAAATAAGCT<br>TCGGTGTTCAGTGGATTAGAAACCATGTTTATCTCAGGTTTACAAA<br>TCTCCACTTGTCCTCTGTGTTTCAGAATAAAATACCAACTCTACTA<br>CTCTCATCTGTAAGATGCAAATAGTAAGCCTGAGCCCTTCTGTCTA<br>ACTTTGAATTCTATTTTTTCTTCAACGTACTTTAGGCTTGTAATGTG<br>TTTATATACAGTGAAATGTCAAGTTCTTTCTTTATATTTCTTTCTTT<br>CTTTTTTTTCCTCAGCCTCAGAGTTTTCCACATGCCCTTCCTACTTT<br>CAGGAACTTCTTTCTCCAAACGTCTTCTGCCTGGCTCCATCAAATC<br>ATAAAGGACCCACTTCAAATGCCATCACTCACTACCATTTCACAAT<br>TCGCACTTTCTTTCTTTGTCCTTTTTTTTTTTAGTAAAACAAGTTTAT<br>AAAAAATTGAAGGAATAAATGAATGGCTACTTCATAGGCAGAGTA<br>GACGCAAGGGCTACTGGTTGCCGATTTTTATTGTTATTTTTCAATA<br>GTATGCTAAACAAGGGGTAGATTATTTATGCTGCCCATTTTTAGAC<br>CATAAAAGATAACTTCCTGATGTTGCCATGGCATTTTTTTCCTTTTA<br>ATTTTATTTCATTTCATTTTAATTTCGAAGGTACATGTGCAGGATGT<br>GCAGGCTTGTTACATGGGTAAATGTGTGTCTTTCTGGCCTTTTAGC<br>CATCTGTATCAATGAGCAGATATAAGCTTTACACAGGATCATGAA<br>GGATGAAAGAATTTCACCAATATTATAATAATTTCAATCAACCTG<br>ATAGCTTAGGGGATAAACTAATTTGAAGATACAGCTTGCCTCCGA<br>TAAGCCAGAATTCCAGAGCTTCTGGCATTATAATCTAGCAAGGTT<br>AGAGATCATGGATCACTTTCAGAGAAAAACAAAAACAAACTAACC<br>AAAAGCAAAACAGAACCAAAAACCACCATAAATACTTCCTACCC<br>TGTTAATGGTCCAATATGTCAGAAACAGCACTGTGTTAGAAATAA |

-continued

| SEQ ID NO | NAME | SEQUENCE |
|---|---|---|
| | | AGCTGTCTAAAGTACACTAATATTCGAGTTATAATAGTGTGTGGAC<br>TATTAGTCAATAAAAACAACCCTTGCCTCTTTAGAGTTGTTTTCCA<br>TGTACACGCACATCTTATGTCTTAGAGTAAGATTCCCTGAGAAGTG<br>AACCTAGCATTTATACAAGATAATTAATTCTAATCCACAGTACCTG<br>CCAAAGAACATTCTACCATCATCTTTACTGAGCATAGAAGAGCTA<br>CGCCAAAACCCTGGGTCATCAGCCAGCACACACACTTATCCAGTG<br>GTAAATACACATCATCTGGTGTATACATACATACCTGAATATGGA<br>ATCAAATATTTTTCTAAGATGAAACAGTCATGATTTATTTCAAATA<br>GGTACGGATAAGTAGATATTGAGGTAAGCATTAGGTCTTATATTA<br>TGTAACACTAATCTATTACTGCGCTGAAACTGTGGCTTTATAGAAA<br>TTGTTTTCACTGCACTATTGAGAAATTAAGAGATAATGGCAAAAG<br>TCACAAAGAGTATATTCAAAAAGAAGTATAGCACTTTTTCCTTAG<br>AAACCACTGCTAACTGAAAGAGACTAAGATTTGTCCCGTCAAAAA<br>TCCTGGACCTATGCCTAAAACACATTTCACAATCCCTGAACTTTTC<br>AAAAATTGGTACATGCTTTAGCTTTAAACTACAGGCCTCACTGGA<br>GCTAGAGACAAGAAGGTAAAAAACGGCTGACAAAAGAAGTCCTG<br>GTATCCTCTATGATGGGAGAAGGAAACTAGCTAAAGGGAAGAATA<br>AATTAGAGAAAAACTGGAATGACTGAATCGGAACAAGGCAAAGG<br>CTATAAAAAAAATTAGCAGTATCCTCTTGGGGGCCCCTTCCCCACA<br>CTATCTCAATGCAAATATCTGTCTGAAACGGTCCCTGGCTAAACTC<br>CACCCATGGGTTGGCCAGCCTTGCCTTGACAAGGCAAACTTGACC<br>AATAGTCTTAGAGTATCCAGTGAGGCCAGGGGCCGGCGGCTGGCT<br>AGGGATGAAGAATAAAAGGAAGCACCCTTCAGCAGTTCCACACAC<br>TCGCTTCTGGAACGTCTGAGGTTATCAATAAGCTCCTAGTCCAGAC<br>GCCATGGGTCATTTCACAGAGGAGGACAAGGCTACTATCACAAGC<br>CTGTGGGGCAAGGTGAATGTGGAAGATGCTGGAGGAGAAACCCT<br>GGGAAGGTAGGCTCTGGTGACCAGGACAAGGGAGGGAAGGAAGG<br>ACCCTGTGCCTGGCAAAAGTCCAGGTCGCTTCTCAGGATTTGTGGC<br>ACCTTCTGACTGTCAAACTGTTCTTGTCAATCTCACAGGCTCCTGG<br>TTGTCTACCCATGGACCCAGAGGTTCTTTGACAGCTTTGGCAACCT<br>GTCCTCTGCCTCTGCCATCATGGGCAACCCCAAAGTCAAGGCACA<br>TGGCAAGAAGGTGCTGACTTCCTTGGGAGATGCCACAAAGCACCT<br>GGATGATCTCAAGGGCACCTTTGCCCAGCTGAGTGAACTGCACTG<br>TGACAAGCTGCATGTGGATCCTGAGAACTTCAAGGTGAGTCCAGG<br>AGATGTTTCAGCCCTGTTGCCTTTAGTCTCGAGGCAACTTAGACAA<br>CGGAGTATTGATCTGAGCACAGCAGGGTGTGAGCTGTTTGAAGAT<br>ACTGGGGTTGGGGGTGAAGAAACTGCAGAGGACTAACTGGGCTG<br>AGACCCAGTGGTAATGTTTTAGGGCCTAAGGAGTGCCTCTAAAAA<br>TCTAGATGGACAATTTTGACTTTGAGAAAAGAGAGGTGGAAATGA<br>GGAAAATGACTTTTCTTTATTAGATTCCAGTAGAAAGAACTTTCAT<br>CTTTCCCTCATTTTTGTTGTTTTAAAACATCTATCTGGAGGCAGGA<br>CAAGTATGGTCGTTAAAAAGATGCAGGCAGAAGGCATATATTGGC<br>TCAGTCAAAGTGGGGAACTTTGGTGGCCAAACATACATTGCTAAG<br>GCTATTCCTATATCAGCTGGACACATATAAAATGCTGCTAATGCTT<br>CATTACAAACTTATATCCTTTAATTCCAGATGGGGGCAAAGTATGT<br>CCAGGGGTGAGGAACAATTGAAACATTTGGGCTGGAGTAGATTTT<br>GAAAGTCAGCTCTGTGTGTGTGTGTGTGTGTGCGCGCGCGCGTGTG<br>TGTGTGTGTGTCAGCGTGTGTTTCTTTTAACGTCTTCAGCCTACAA<br>CATACAGGGTTCATGGTGGCAAGAAGATAGCAAGATTTAAATTAT<br>GGCCAGTGACTAGTGCTTGAAGGGGAACAACTACCTGCATTTAAT<br>GGGAAGGCAAAATCTCAGGCTTTGAGGGAAGTTAACATAGGCTTG<br>ATTCTGGGTGGAAGCTTGGTGTGTAGTTATCTGGAGGCCAGGCTG<br>GAGCTCTCAGCTCACTATGGGTTCATCTTTATTGTCTCCTTTCATCT<br>CAACAGCTCCTGGGAAATGTGCTGGTGACCGTTTTGGCAATCCATT<br>TCGGCAAAGAATTCACCCCTGAGGTGCAGGCTTCCTGGCAGAAGA<br>TGGTGACTGCAGTGGCCAGTGCCCTGTCCTCCAGATACCACTGAG<br>CTCACTGCCCATGATTCAGAGCTTTCAAGGATAGGCTTTATTCTGC<br>AAGCAATACAAATAATAAATCTATTCTGCTGAGAGATCACACATG<br>ATTTTCTTCAGCTCTTTTTTTTACATCTTTTTAAATATATGAGCCAC<br>AAAGGGTTTATATTGAGGGAAGTGTGTATGTGTATTTCTGCATGCC<br>TGTTTGTGTTTGTGGTGTGTGCATGCTCCTCATTTATTTTTATATGA<br>GATGTGCATTTTGATGAGCAAATAAAAGCAGTAAAGACACTTGTA<br>CACGGGAGTTCTGCAAGTGGGAGTAAATGGTGTAGGAGAAATCCG<br>GTGGGAAGAAAGACCTCTATAGGACAGGACTTCTCAGAAACAGAT<br>GTTTTGGAAGAGATGGGAAAAGGTTCAGTGAAGACCTGGGGGCTG<br>GATTGATTGCAGCTGAGTAGCAAGGATGGTTCTTAAGGAAGGGAA<br>AGTGTTCCAAGCTTTAGGAATTCAAGGTTTAGTCAGGTGTAGCAAT<br>TCTATTTTATTAGGAGGAATACTATTTCTAATGGCACTTAGCTTTTC<br>ACAGCCCTTGTGGATGCCTAAATCGGATCCCCTGCAGGAGGAACC<br>CCTAGTGATGGAGTTGGCCACTCCCTCTCTGCGCGCTCGCTCGCTC<br>ACTGAGGCCGGGCGACCAAAGGTCGCCCGACGCCCGGGCTTTGCC<br>CGGGCGGCCTCAGTGAGCGAGCGAGCGCGCAGCTGGCGTAATAGC<br>GAAGAGGCCCGCACCGATCGCCCTTCCCAACAGTTGCGCAGCCTG<br>AATGGCGAATGGCGATTCCGTTGCAATGGCTGGCGGTAATATTGT<br>TCTGGATATTACCAGCAAGGCCGATAGTTTGAGTTCTTCTACTCAG |

-continued

| SEQ ID NO | NAME | SEQUENCE |
|---|---|---|
| | | GCAAGTGATGTTATTACTAATCAAAGAAGTATTGCGACAACGGTT<br>AATTTGCGTGATGGACAGACTCTTTTACTCGGTGGCCTCACTGATT<br>ATAAAAACACTTCTCAGGATTCTGGCGTACCGTTCCTGTCTAAAAT<br>CCCTTTAATCGGCCTCCTGTTTAGCTCCCGCTCTGATTCTAACGAG<br>GAAAGCACGTTATACGTGCTCGTCAAAGCAACCATAGTACGCGCC<br>CTGTAGCGGCGCATTAAGCGCGGCGGGTGTGGTGGTTACGCGCAG<br>CGTGACCGCTACACTTGCCAGCGCCCTAGCGCCCGCTCCTTTCGCT<br>TTCTTCCCTTCCTTTCTCGCCACGTTCGCCGGCTTTCCCCGTCAAGC<br>TCTAAATCGGGGGCTCCCTTTAGGGTTCCGATTTAGTGCTTTACGG<br>CACCTCGACCCCAAAAAACTTGATTAGGGTGATGGTTCACGTAGT<br>GGGCCATCGCCCTGATAGACGGTTTTTCGCCCTTTGACGTTGGAGT<br>CCACGTTCTTTAATAGTGGACTCTTGTTCCAAACTGGAACAACACT<br>CAACCCTATCTCGGTCTATTCTTTTGATTTATAAGGGATTTTGCCG<br>ATTTCGGCCTATTGGTTAAAAAATGAGCTGATTTAACAAAAATTTA<br>ACGCGAATTTTAACAAAATATTAACGTTTACAATTTAAATATTTGC<br>TTATACAATCTTCCTGTTTTTGGGGCTTTTCTGATTATCAACCGGGG<br>TACATATGATTGACATGCTAGTTTTACGATTACCGTTCATCGATTC<br>TCTTGTTTGCTCCAGACTCTCAGGCAATGACCTGATAGCCTTTGTA<br>GAGACCTCTCAAAAATAGCTACCCTCTCCGGCATGAATTTATCAGC<br>TAGAACGGTTGAATATCATATTGATGGTGATTTGACTGTCTCCGGC<br>CTTTCTCACCCGTTTGAATCTTTACCTACACATTACTCAGGCATTGC<br>ATTTAAAATATATGAGGGTTCTAAAAATTTTTATCCTTGCGTTGAA<br>ATAAAGGCTTCTCCCGCAAAAGTATTACAGGGTCATAATGTTTTTG<br>GTACAACCGATTTAGCTTTATGCTCTGAGGCTTTATTGCTTAATTTT<br>GCTAATTCTTTGCCTTGCCTGTATGATTTATTGGATGTTGGAATCG<br>CCTGATGCGGTATTTTCTCCTTACGCATCTGTGCGGTATTTCACAC<br>CGCATATGGTGCACTCTCAGTACAATCTGCTCTGATGCCGCATAGT<br>TAAGCCAGCCCCGACACCCGCCAACACCCGCTGACGCGCCCTGAC<br>GGGCTTGTCTGCTCCCGGCATCCGCTTACAGACAAGCTGTGACCGT<br>CTCCGGGAGCTGCATGTGTCAGAGGTTTTCACCGTCATCACCGAA<br>ACGCGCGAGACGAAAGGGCCTCGTGATACGCCTATTTTTATAGGT<br>TAATGTCATGATAATAATGGTTTCTTAGACGTCAGGTGGCACTTTT<br>CGGGGAAATGTGCGCGGAACCCCTATTTGTTTATTTTTCTAAATAC<br>ATTCAAATATGTATCCGCTCATGAGACAATAACCCTGATAAATGCT<br>TCAATAATATTGAAAAAGGAAGAGTATGAGTATTCAACATTTCCG<br>TGTCGCCCTTATTCCCTTTTTTGCGGCATTTTGCCTTCCTGTTTTTGC<br>TCACCCAGAAACGCTGGTGAAAGTAAAAGATGCTGAAGATCAGTT<br>GGGTGCACGAGTGGGTTACATCGAACTGGATCTCAACAGCGGTAA<br>GATCCTTGAGAGTTTTCGCCCCGAAGAACGTTTTCCAATGATGAGC<br>ACTTTTAAAGTTCTGCTATGTGGCGCGGTATTATCCCGTATTGACG<br>CCGGGCAAGAGCAACTCGGTCGCCGCATACACTATTCTCAGAATG<br>ACTTGGTTGAGTACTCACCAGTCACAGAAAAGCATCTTACGGATG<br>GCATGACAGTAAGAGAATTATGCAGTGCTGCCATAACCATGAGTG<br>ATAACACTGCGGCCAACTTACTTCTGACAACGATCGGAGGACCGA<br>AGGAGCTAACCGCTTTTTTGCACAACATGGGGGATCATGTAACTC<br>GCCTTGATCGTTGGGAACCGGAGCTGAATGAAGCCATACCAAACG<br>ACGAGCGTGACACCACGATGCCTGTAGCAATGGCAACAACGTTGC<br>GCAAACTATTAACTGGCGAACTACTTACTCTAGCTTCCCGGCAACA<br>ATTAATAGACTGGATGGAGGCGGATAAAGTTGCAGGACCACTTCT<br>GCGCTCGGCCCTTCCGGCTGGCTGGTTTATTGCTGATAAATCTGGA<br>GCCGGTGAGCGTGGGTCTCGCGGTATCATTGCAGCACTGGGGCCA<br>GATGGTAAGCCCTCCCGTATCGTAGTTATCTACACGACGGGGAGT<br>CAGGCAACTATGGATGAACGAAATAGACAGATCGCTGAGATAGGT<br>GCCTCACTGATTAAGCATTGGTAACTGTCAGACCAAGTTTACTCAT<br>ATATACTTTAGATTGATTTAAAACTTCATTTTTAATTTAAAAGGAT<br>CTAGGTGAAGATCCTTTTTGATAATCTCATGACCAAAATCCCTTAA<br>CGTGAGTTTTCGTTCCACTGAGCGTCAGACCCCGTAGAAAAGATC<br>AAAGGATCTTCTTGAGATCCTTTTTTTCTGCGCGTAATCTGCTGCTT<br>GCAAACAAAAAAACCACCGCTACCAGCGGTGGTTTGTTTGCCGGA<br>TCAAGAGCTACCAACTCTTTTTCCGAAGGTAACTGGCTTCAGCAGA<br>GCGCAGATACCAAATACTGTCCTTCTAGTGTAGCCGTAGTTAGGCC<br>ACCACTTCAAGAACTCTGTAGCACCGCCTACATACCTCGCTCTGCT<br>AATCCTGTTACCAGTGGCTGCTGCCAGTGGCGATAAGTCGTGTCTT<br>ACCGGGTTGGACTCAAGACGATAGTTACCGGATAAGGCGCAGCGG<br>TCGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACCT<br>CTGACTTGAGCGTCGATTTTTGTGATGCTCGTCAGGGGGGCGGAG |

-continued

| SEQ ID NO | NAME | SEQUENCE |
|---|---|---|
| | | CCTATGGAAAAACGCCAGCAACGCGGCCTTTTTACGGTTCCTGGC<br>CTTTTGCTGGCCTTTTGCTCACATGTTCTTTCCTGCGTTATCCCCTG<br>ATTCTGTGGATAACCGTATTACCGCCTTTGAGTGAGCTGATACCGC<br>TCGCCGCAGCCGAACGACCGAGCGCAGCGAGTCAGTGAGCGAGG<br>AAGCGGAAGAGCGCCCAATACGCAAACCGCCTCTCCCCGCGCGTT<br>GGCCGATTCATTAATG |
| 54 | Rhesus: AMS#1268 Rhesus Gilman V3E6(400) HBG1(200-600). d13>HBB(T87Q). 3'enhCore; MND>GFP::T2A:: Ex2 | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTAAGTATAGCACAATGCTTACTAAATGAGACTAAGACTTGTCCC<br>ATCGAAAATCCTGGACCTATGCCTAAAACACGTGTCACAATCCCC<br>GAACTTTTCAAAAATTGGTACATGCTTTAACTTTAATCTCCAGGCC<br>TCACTGGAGCTAGAGACAAGAAGGTAAAAAAAGGCTGACAAAAG<br>AAGTCCTGGTATCTTCTATGGTGGGAGAAGGAAACTAGCTAAAGG<br>GAAGAATAAATTAGAGAAAAATTGGAATGATTGAATCGGAACAA<br>GGCAAAGGCTATAAAAAAATTAAGCAGCAGTATCCTCTTGGGGGC<br>CCCTTCCCCACACTATCTCAATGCAAATATCTGTCTGAAACGGTCC<br>CTGGCTAAACTCCACCCATGGGTTGGCCAGTCTTGCCTTGACAAGG<br>CAACCTTGACCAATAGTCTTAGAGTATCAGGTGAGGCCAGGGGCC<br>GGCGGCTGGCTAGGGATGAAGAATAAAAGGAAGCACCCTCCAGC<br>AGTTCCACACACTCGCTTCTGGAACGGCTGAGATTATCAATAAGCT<br>CCTAGTCCAGACGCCATGGTGCACCTGACTCCTGAGGAGAAGTCT<br>GCCGTTACTGCCCTGTGGGGCAAGGTGAACGTGGATGAAGTTGGT<br>GGTGAGGCCCTGGGCAGGTTGGTATCAAGGTTACAAGACAGGTTT<br>AAGGAGACCAATAGAAACTGGGCATGTGGAGACAGAGAAGACTC<br>TTGGGTTTCTGATAGGCACTGACTCTCTCTGCCTATTGGTCTATTTT<br>CCCACCCTTAGGCTGCTGGTGGTCTACCCTTGGACCCAGAGGTTCT<br>TTGAGTCCTTTGGGGATCTGTCCACTCCTGATGCTGTTATGGGCAA<br>CCCTAAGGTGAAGGCTCATGGCAAGAAAGTGCTCGGTGCCTTTAG<br>TGATGGCCTGGCTCACCTGGACAACCTCAAGGGCACCTTTGCCCA<br>GCTGAGTGAGCTGCACTGTGACAAGCTGCACGTGGATCCTGAGAA<br>CTTCAGGGTGAGTCTATGGGACCCTTGATGTTTTCTTTCCCCTTCTT<br>TTCTATGGTTAAGTTCATGTCATAGGAAGGGGAGAAGTAACAGGG<br>TACACATATTGACCAAATCAGGGTAATTTTGCATTTGTAATTTTAA<br>AAAATGCTTTCTTCTTTTAATATACTTTTTTGTTTATCTTATTTCTAA<br>TACTTTCCCTAATCTCTTTCTTTCAGGGCAATAATGATACAATGTA<br>TCATGCCTCTTTGCACCATTCTAAAGAATAACAGTGATAATTTCTG<br>GGTTAAGGCAATAGCAATATTTCTGCATATAAATATTTCTGCATAT<br>AAATTGTAACTGATGTAAGAGGTTTCATATTGCTAATAGCAGCTAC<br>AATCCAGCTACCATTCTGCTTTTATTTTATGGTTGGGATAAGGCTG<br>GATTATTCTGAGTCCAAGCTAGGCCCTTTTGCTAATCATGTTCATA<br>CCTCTTATCTTCCTCCCACAGCTCCTGGGCAACGTGCTGGTCTGTG<br>TGCTGGCCCATCACTTTGGCAAAGAATTCACCCCACCAGTGCAGG<br>CTGCCTATCAGAAAGTGGTGGCTGGTGTGGCTAATGCCCTGGCCC<br>ACAAGTATCACTAAGCTCGCTTTCTTGCTGTCCAATTTCTATTAAA<br>GGTTCCTTTGTTCCCTAAGTCCAACTACTAAACTGGGGGATATTAT<br>GAAGGGCCTTGAGCATCTGGATTCTGCCTAATAAAAAACATTTATT<br>TTCATTGCAATGATGTATTTAAATTATTTCTGAATATTTTACTAAAA<br>AGGGAATGTGGGAGGTTGCAGTGCTAGTCTCCCGGAACTATCACT<br>CTTTCACAGTCTGCTTTGGAAGGACTGGGCTTAGTATGAAAAGTTA<br>GGACTGAGAAGAATTTGAAAGGGGGCTTTTTGTAGCTTGATATTC<br>ACTACTGTCTTATTACCCTATCATAGGCCCACCCCAAATGGAAGTC<br>CCATTCTTCCTCAGGATGTTTAAGATTAGCATTCAGGAAGAGATCA<br>GAGGTCTGCTGGCTCCCTTATCATGTCCCTTATGGTGCTTCTGGCT<br>CTGCACCGCGGGAACAGAGAAACAGGAGAATATGGGCCAAACAG<br>GATATCTGTGGTAAGCAGTTCCTGCCCCGGCTCAGGGCCAAGAAC<br>AGTTGGAACAGCAGAATATGGGCCAAACAGGATATCTGTGGTAAG<br>CAGTTCCTGCCCCGGCTCAGGGCCAAGAACAGATGGTCCCCAGAT<br>GCGGTCCCGCCCTCAGCAGTTTCTAGAGAACCATCAGATGTTTCCA<br>GGGTGCCCCAAGGACCTGAAATGACCCTGTGCCTTATTTGAACTA<br>ACCAATCAGTTCGCTTCTCGCTTCTGTTCGCGCGCTTCTGCTCCCCG<br>AGCTCTATATAAGCAGAGCTCGTTTAGTGAACCGTCAGATCGCGG<br>CCGCGCCGCCACCATGGTGAGCAAGGGCGAGGAGCTGTTCACCGG<br>GGTGGTGCCCATCCTGGTCGAGCTGGACGGCGACGTAAACGGCCA<br>CAAGTTCAGCGTGTCCGGCGAGGGCGAGGGCGATGCCACCTACGG<br>CAAGCTGACCCTGAAGTTCATCTGCACCACCGGCAAGCTGCCCGT<br>GCCCTGGCCCACCCTCGTGACCACCCTGACCTACGGCGTGCAGTG<br>CTTCAGCCGCTACCCCGACCACATGAAGCAGCACGACTTCTTCAA<br>GTCCGCCATGCCCGAAGGCTACGTCCAGGAGCGCACCATCTTCTTC<br>AAGGACGACGGCAACTACAAGACCCGCGCCGAGGTGAAGTTCGA<br>GGGCGACACCCTGGTGAACCGCATCGAGCTGAAGGGCATCGACTT<br>CAAGGAGGACGGCAACATCCTGGGGCACAAGCTGGAGTACAACT<br>ACAACAGCCACAACGTCTATATCATGGCCGACAAGCAGAAGAACG |

-continued

| SEQ ID NO | NAME | SEQUENCE |
|---|---|---|
| | | GCATCAAGGTGAACTTCAAGATCCGCCACAACATCGAGGACGGCA GCGTGCAGCTCGCCGACCACTACCAGCAGAACACCCCCATCGGCG ACGGCCCCGTGCTGCTGCCCGACAACCACTACCTGAGCACCCAGT CCGCCCTGAGCAAAGACCCCAACGAGAAGCGCGATCACATGGTCC TGCTGGAGTTCGTGACCGCCGCCGGGATCACTCTCGGCATGGACG AGCTGTACAAGGAGGGCAGAGGAAGTCTTCTAACATGCGGTGACG TGGAGGAGAATCCGGGCCCCCCTGCAGGAACTTCAGGGTGAGTCC AGGAGTTTCAGCAGTTTCAGAGTTCAGTCTCAAGGCAACTTAGAC AACTGAGTATTGATCTGAGGACAGTCGAATCTACCTGCTGGGTGT GAGCTATTTGAAGATACTGGGGTTGGGAGTGAAGAAACTGCAGAG GACTAACTGGGCTGAGACCGAATGGTAATGTTTTAGGGCCTAAGG AGTGCCTCTAAAAATCTAGACGGACAATTTTGACATTGACAAAAG AGAGGTGGAAATGAGGAAAATGACTTTTCTTTATTAGATTCCGGT AGAAAGAACTTTCATCTTTCCCTCATTTTTGTTATTTGTTTTAAAAC ATCTATCTGGAGGCAGGACAAGTATGGTCATTAAAAAGATGCAGG CAGAAGGCATATATTGGCCCAGTCAAAGTGTCGACGTAGATAAGT AGCATGGCGGGTTAATCATTAACTACAAGGAACCCCTAGTGATGG AGTTGGCCACTCCCTCTCTGCGCGCTCGCTCGCTCACTGAGGCCGG GCGACCAAAGGTCGCCCGACGCCCGGGCTTTGCCCGGGCGGCCTC AGTGAGCGAGCGAGCGCGCCAGCTGGCGTAATAGCGAAGAGGCC CGCACCGATCGCCCTTCCCAACAGTTGCGCAGCCTGAATGGCGAA TGGCGATTCCGTTGCAATGGCTGGCGGTAATATTGTTCTGGATATT ACCAGCAAGGCCGATAGTTTGAGTTCTTCTACTCAGGCAAGTGAT GTTATTACTAATCAAAGAAGTATTGCGACAACGGTTAATTTGCGTG ATGGACAGACTCTTTTACTCGGTGGCCTCACTGATTATAAAAACAC TTCTCAGGATTCTGGCGTACCGTTCCTGTCTAAAATCCCTTTAATC GGCCTCCTGTTTAGCTCCCGCTCTGATTCTAACGAGGAAAGCACGT TATACGTGCTCGTCAAAGCAACCATAGTACGCGCCCTGTAGCGGC GCATTAAGCGCGGCGGGTGTGGTGGTTACGCGCAGCGTGACCGCT ACACTTGCCAGCGCCCTAGCGCCCGCTCCTTTCGCTTTCTTCCCTTC CTTTCTCGCCACGTTCGCCGGCTTTCCCCGTCAAGCTCTAAATCGG GGGCTCCCTTTAGGGTTCCGATTTAGTGCTTTACGGCACCTCGACC CCAAAAAACTTGATTAGGGTGATGGTTCACGTAGTGGGCCATCGC CCTGATAGACGGTTTTTCGCCCTTTGACGTTGGAGTCCACGTTCTT TAATAGTGGACTCTTGTTCCAAACTGGAACAACACTCAACCCTATC TCGGTCTATTCTTTTGATTTATAAGGGATTTTGCCGATTTCGGCCTA TTGGTTAAAAAATGAGCTGATTTAACAAAAATTTAACGCGAATTTT AACAAAATATTAACGTTTACAATTTAAATATTTGCTTATACAATCT TCCTGTTTTTGGGGCTTTTCTGATTATCAACCGGGGTACATATGAT TGACATGCTAGTTTTACGATTACCGTTCATCGATTCTCTTGTTTGCT CCAGACTCTCAGGCAATGACCTGATAGCCTTTGTAGAGACCTCTCA AAAATAGCTACCCTCTCCGGCATGAATTTATCAGCTAGAACGGTT GAATATCATATTGATGGTGATTTGACTGTCTCCGGCCTTTCTCACC CGTTTGAATCTTTACCTACACATTACTCAGGCATTGCATTTAAAAT ATATGAGGGTTCTAAAAATTTTTATCCTTGCGTTGAAATAAAGGCT TCTCCCGCAAAAGTATTACAGGGTCATAATGTTTTTGGTACAACCG ATTTAGCTTTATGCTCTGAGGCTTTATTGCTTAATTTTGCTAATTCT TTGCCTTGCCTGTATGATTTATTGGATGTTGGAATCGCCTGATGCG GTATTTTCTCCTTACGCATCTGTGCGGTATTTCACACCGCATATGG TGCACTCTCAGTACAATCTGCTCTGATGCCGCATAGTTAAGCCAGC CCCGACACCCGCCAACACCCGCTGACGCGCCCTGACGGGCTTGTC TGCTCCCGGCATCCGCTTACAGACAAGCTGTGACCGTCTCCGGGA GCTGCATGTGTCAGAGGTTTTCACCGTCATCACCGAAACGCGCGA GACGAAAGGGCCTCGTGATACGCCTATTTTTATAGGTTAATGTCAT GATAATAATGGTTTCTTAGACGTCAGGTGGCACTTTTCGGGGAAAT GTGCGCGGAACCCCTATTTGTTTATTTTTCTAAATACATTCAAATA TGTATCCGCTCATGAGACAATAACCCTGATAAATGCTTCAATAATA TTGAAAAAGGAAGAGTATGAGTATTCAACATTTCCGTGTCGCCCTT ATTCCCTTTTTTGCGGCATTTTGCCTTCCTGTTTTTGCTCACCCAGA AACGCTGGTGAAAGTAAAAGATGCTGAAGATCAGTTGGGTGCACG AGTGGGTTACATCGAACTGGATCTCAACAGCGGTAAGATCCTTGA GAGTTTTCGCCCCGAAGAACGTTTTCCAATGATGAGCACTTTTAAA GTTCTGCTATGTGGCGCGGTATTATCCCGTATTGACGCCGGGCAAG AGCAACTCGGTCGCCGCATACACTATTCTCAGAATGACTTGGTTGA GTACTCACCAGTCACAGAAAAGCATCTTACGGATGGCATGACAGT AAGAGAATTATGCAGTGCTGCCATAACCATGAGTGATAACACTGC GGCCAACTTACTTCTGACAACGATCGGAGGACCGAAGGAGCTAAC CGCTTTTTTGCACAACATGGGGGATCATGTAACTCGCCTTGATCGT TGGGAACCGGAGCTGAATGAAGCCATACCAAACGACGAGCGTGA CACCACGATGCCTGTAGCAATGGCAACAACGTTGCGCAAACTATT AACTGGCGAACTACTTACTCTAGCTTCCCGGCAACAATTAATAGA CTGGATGGAGGCGGATAAAGTTGCAGGACCACTTCTGCGCTCGGC CCTTCCGGCTGGCTGGTTTATTGCTGATAAATCTGGAGCCGGTGAG CGTGGGTCTCGCGGTATCATTGCAGCACTGGGGCCAGATGGTAAG CCCTCCCGTATCGTAGTTATCTACACGACGGGGAGTCAGGCAACT |

-continued

| SEQ ID NO | NAME | SEQUENCE |
|---|---|---|
| | | ATGGATGAACGAAATAGACAGATCGCTGAGATAGGTGCCTCACTG<br>ATTAAGCATTGGTAACTGTCAGACCAAGTTTACTCATATATACTTT<br>AGATTGATTTAAAACTTCATTTTTAATTTAAAAGGATCTAGGTGAA<br>GATCCTTTTTGATAATCTCATGACCAAAATCCCTTAACGTGAGTTT<br>TCGTTCCACTGAGCGTCAGACCCCGTAGAAAAGATCAAAGGATCT<br>TCTTGAGATCCTTTTTTTCTGCGCGTAATCTGCTGCTTGCAAACAA<br>AAAAACCACCGCTACCAGCGGTGGTTTGTTTGCCGGATCAAGAGC<br>TACCAACTCTTTTTCCGAAGGTAACTGGCTTCAGCAGAGCGCAGAT<br>ACCAAATACTGTCCTTCTAGTGTAGCCGTAGTTAGGCCACCACTTC<br>AAGAACTCTGTAGCACCGCCTACATACCTCGCTCTGCTAATCCTGT<br>TACCAGTGGCTGCTGCCAGTGGCGATAAGTCGTGTCTTACCGGGTT<br>GGACTCAAGACGATAGTTACCGGATAAGGCGCAGCGGTCGGGCTG<br>AACGGGGGGTTCGTGCACACAGCCCAGCTTGGAGCGAACGACCTA<br>CACCGAACTGAGATACCTACAGCGTGAGCTATGAGAAAGCGCCAC<br>GCTTCCCGAAGGGAGAAAGGCGGACAGGTATCCGGTAAGCGGCA<br>GGGTCGGAACAGGAGAGCGCACGAGGGAGCTTCCAGGGGGAAAC<br>GCCTGGTATCTTTATAGTCCTGTCGGGTTTCGCCACCTCTGACTTG<br>AGCGTCGATTTTTGTGATGCTCGTCAGGGGGGCGGAGCCTATGGA<br>AAAACGCCAGCAACGCGGCCTTTTTACGGTTCCTGGCCTTTTGCTG<br>GCCTTTTGCTCACATGTTCTTTCCTGCGTTATCCCCTGATTCTGTGG<br>ATAACCGTATTACCGCCTTTGAGTGAGCTGATACCGCTCGCCGCAG<br>CCGAACGACCGAGCGCAGCGAGTCAGTGAGCGAGGAAGCGGAAG<br>AGCGCCCAATACGCAAACCGCCTCTCCCCGCGCGTTGGCCGATTC<br>ATTAATG |
| 55 | Rhesus:<br>AMS#1308<br>pAAV Rhesus<br>HBG1d-141,-<br>1(885,959)<br>MND>GFP.wPRE3.<br>SV40USE.pA;<br>HBBp> | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTTG<br>TAGTTAATGATTAACCCGCCATGCTACTTATCTACACGCGTAGATC<br>TTCCCAACTGTCACAGTGTGTGGCCTATTAGTCAATTAAAGCAGTC<br>CCTGCCTCTTTAGAGTTGTTTTCCATGCAATTACATGTCTTATGTCT<br>TAGAATAAGATTCCCTGAGAACTGAACCTAGCATTTATACAAGAT<br>AATTAATTCTAAGCCATAGTACCTGCCAAAGAACATTCTACTATCA<br>TCTTTACTGAACACAGAAGAGCTACACCAAAAACCTGGGTCATCA<br>GCCAGCACACACACTTATCCAGTGATAAATACACATCATCGGGTG<br>CCTACATACATACCTGAATAAGAAAAAAAAATACCTTTGCTGAGA<br>TGAAACACACATGATTTATTTCAAATAGGTACAGAGAAGTAGATA<br>CTGAAGTAAGGATTAAGTATTATATTATATTACATAACATTAATCT<br>ATTCCTGCACTGAAACCGTTGCTTTATATGATTTTTTTTTCACTAC<br>ACTAATGAGAACTTAAGAGATAATGGCCTAAAACCACAGAGAGTA<br>TTTTCAAAGATAAGTATAGCACAATGCTTACTAAATGAGACTAAG<br>ACTTGTCCCATCGAAAATCCTGGACCTATGCCTAAAACACGTGTCA<br>CAATCCCCGAACTTTTCAAAAATTGGTACATGCTTTAACTTTAATC<br>TCCAGGCCTCACTGGAGCTAGAGACAAGAAGGTAAAAAAAGGCT<br>GACAAAAGAAGTCCTGGTATCTTCTATGGTGGGAGAAGGAAACTA<br>GCTAAAGGGAAGAATAAATTAGAGAAAAATTGGAATGATTGAAT<br>CGGAACAAGGCAAAGGCTATAAAAAAATTAAGCAGCAGTATCCTC<br>TTGGGGGCCCCTTCCCCACACTATCTCAATGCAAATATCTGTCTGA<br>AACGGTCCCTGGCTAAACTCCACCCGCGGGAACAGAGAAACAGG<br>AGAATATGGGCCAAACAGGATATCTGTGGTAAGCAGTTCCTGCCC<br>CGGCTCAGGGCCAAGAACAGTTGGAACAGCAGAATATGGGCCAA<br>ACAGGATATCTGTGGTAAGCAGTTCCTGCCCCGGCTCAGGGCCAA<br>GAACAGATGGTCCCCAGATGCGGTCCCGCCCTCAGCAGTTTCTAG<br>AGAACCATCAGATGTTTCCAGGGTGCCCCAAGGACCTGAAATGAC<br>CCTGTGCCTTATTTGAACTAACCAATCAGTTCGCTTCTCGCTTCTGT<br>TCGCGCGCTTCTGCTCCCCGAGCTCTATATAAGCAGAGCTCGTTTA<br>GTGAACCGTCAGATCGCCTGGAGACGCCATCCACGCTGTTTTGACT<br>TCCATAGAAGGCGGCCGCGCCGCCACCATGGTGAGCAAGGGCGA<br>GGAGCTGTTCACCGGGGTGGTGCCCATCCTGGTCGAGCTGGACGG<br>CGACGTAAACGGCCACAAGTTCAGCGTGTCCGGCGAGGGCGAGG<br>GCGATGCCACCTACGGCAAGCTGACCCTGAAGTTCATCTGCACCA<br>CCGGCAAGCTGCCCGTGCCCTGGCCCACCCTCGTGACCACCCTGA<br>CCTACGGCGTGCAGTGCTTCAGCCGCTACCCCGACCACATGAAGC<br>AGCACGACTTCTTCAAGTCCGCCATGCCCGAAGGCTACGTCCAGG<br>AGCGCACCATCTTCTTCAAGGACGACGGCAACTACAAGACCCGCG<br>CCGAGGTGAAGTTCGAGGGCGACACCCTGGTGAACCGCATCGAGC<br>TGAAGGGCATCGACTTCAAGGAGGACGGCAACATCCTGGGGCACA<br>AGCTGGAGTACAACTACAACAGCCACAACGTCTATATCATGGCCG<br>ACAAGCAGAAGAACGGCATCAAGGTGAACTTCAAGATCCGCCAC<br>AACATCGAGGACGGCAGCGTGCAGCTCGCCGACCACTACCAGCAG<br>AACACCCCCATCGGCGACGGCCCCGTGCTGCTGCCCGACAACCAC<br>TACCTGAGCACCCAGTCCGCCCTGAGCAAAGACCCCAACGAGAAG<br>CGCGATCACATGGTCCTGCTGGAGTTCGTGACCGCCGCCGGGATC<br>ACTCTCGGCATGGACGAGCTGTACAAGTAACCTGCAGGATAATC<br>AACCTCTGGATTACAAAATTTGTGAAAGATTGACTGGTATTCTTAA |

-continued

| SEQ ID NO | NAME | SEQUENCE |
|---|---|---|
| | | CTATGTTGCTCCTTTTACGCTATGTGGATACGCTGCTTTAATGCCTT<br>TGTATCATGCTATTGCTTCCCGTATGGCTTTCATTTTCTCCTCCTTG<br>TATAAATCCTGGTTAGTTCTTGCCACGGCGGAACTCATCGCCGCCT<br>GCCTTGCCCGCTGCTGGACAGGGGCTCGGCTGTTGGGCACTGACA<br>ATTCCGTGGTGTTTATTTGTGAAATTTGTGATGCTATTGCTTTATTT<br>GTAACCATTCTAGCTTTATTTGTGAAATTTGTGATGCTATTGCTTTA<br>TTTGTAACCATTATAAGCTGCAATAAACAAGTTAACAACAACAAT<br>TGCATTCATTTTATGTTTCAGGTTCAGGGGGAGATGTGGGAGGTTT<br>TTTAAAGCGAATTCGTAAATACACTTGCAAAGGAGGATGTTTTTA<br>GTAGCAATTTGTACTGATGGTATGGGGCCAAGAGATATATCTTAG<br>AGGGAGGGCTGAGGGTTTGAAGTCCAACTCCTAAGCCAGTGCCAG<br>AAGAGCCAAGGACAGGTACGGCTGTCATCACTTAGACCTCACCCT<br>GTGGAGCCACACCCTAGGGTTGGCCAATCTACTCCCAGGAGCAGG<br>GAGGGCAGGAGCCAGGGCTGGGCATAAAAGTCAGGGCAGAGCCA<br>TCTATTGCTTACACTCGCTTCTGGAACGGCTGAGATTATCAATAAG<br>CTCCTAGTCCAGACGCCATGGGTCATTTCACAGAGGAGGACAAGG<br>CTACTATCACAAGCCTGTGGGGCAAGGTGAATGTGGAAGATGCTG<br>GAGGAGAAACCCTGGGAAGGTAGGCTCTGGTGACCAGGACAAGG<br>AAGGGAAGGAAGGACCCTGTGCCTGGCAAAAGTCCAGGCCACTTC<br>TCAGGATTTGTGGCACTTTCTGACTGTCAAACTGCTCTTGTTCAAT<br>CTCACAGGCTCCTGGTTGTCTACCCATGGACCCAGAGGTTCTTTGA<br>CAGCTTTGGCAACCTGTCCTCTGCCTCTGCCATCATGGGCAACCCC<br>AAGGTCAAGGCACACGGCAAGAAGGTGCTGACTTCCTTGGGAGAT<br>GCCATAAAGAACCTGGATGATCTCAAGGGCACCTTTGCCCAGCTG<br>AGTGAGCTGCACTGTGACAAGCTGCATGTGGATCCTGAGAACTTC<br>AGGGTGAGTCCAGGAGTTTCAGCAGTTTCAGAGTTCAGTCTCAAG<br>GCAACTTAGACAACTGAGTATTGATCTGAGGACAGTCGAATCTAC<br>CTGCTGGGTGTGAGCTATTTGAAGATACTGGGGTTGGGAGTGAAG<br>AAACTGCAGAGGACTAACTGGGCTGAGACCGAATGGTAATGTTTT<br>AGGGCCTAAGGAGTGCCTCTAAAAATCTAGACGGACAATTTTGAC<br>ATTGACAAAAGAGAGGTGGAAATGAGGAAAATGACTTTTCTTTAT<br>TAGATTCCGGTAGAAAGAACTTTCATCTTTCCCTCATTTTTGTTATT<br>TGTTTTAAAACATCTATCTGGAGGCAGGACAAGTATGGTCATTAA<br>AAAGATGCAGGCAGAAGGCATATATTGGCCCAGTCAAAGTGGGG<br>AACTCTGGTGACCAAACAGAGTCTGAGGCTATTCCTATATCAGCT<br>GGACACATACAAAATGCCGCCTCGAGGTCGACGTAGATAAGTAGC<br>ATGGCGGGTTAATCATTAACTACAAGGAACCCCTAGTGATGGAGT<br>TGGCCACTCCCTCTCTGCGCGCTCGCTCGCTCACTGAGGCCGGGCG<br>ACCAAAGGTCGCCCGACGCCCGGGCTTTGCCCGGGCGGCCTCAGT<br>GAGCGAGCGAGCGCGCCAGCTGGCGTAATAGCGAAGAGGCCCGC<br>ACCGATCGCCCTTCCCAACAGTTGCGCAGCCTGAATGGCGAATGG<br>CGATTCCGTTGCAATGGCTGGCGGTAATATTGTTCTGGATATTACC<br>AGCAAGGCCGATAGTTTGAGTTCTTCTACTCAGGCAAGTGATGTTA<br>TTACTAATCAAAGAAGTATTGCGACAACGGTTAATTTGCGTGATG<br>GACAGACTCTTTTACTCGGTGGCCTCACTGATTATAAAAACACTTC<br>TCAGGATTCTGGCGTACCGTTCCTGTCTAAAATCCCTTTAATCGGC<br>CTCCTGTTTAGCTCCCGCTCTGATTCTAACGAGGAAAGCACGTTAT<br>ACGTGCTCGTCAAAGCAACCATAGTACGCGCCCTGTAGCGGCGCA<br>TTAAGCGCGGCGGGTGTGGTGGTTACGCGCAGCGTGACCGCTACA<br>CTTGCCAGCGCCCTAGCGCCCGCTCCTTTCGCTTTCTTCCCTTCCTT<br>TCTCGCCACGTTCGCCGGCTTTCCCCGTCAAGCTCTAAATCGGGGG<br>CTCCCTTTAGGGTTCCGATTTAGTGCTTTACGGCACCTCGACCCCA<br>AAAAACTTGATTAGGGTGATGGTTCACGTAGTGGGCCATCGCCCT<br>GATAGACGGTTTTTCGCCCTTTGACGTTGGAGTCCACGTTCTTTAA<br>TAGTGGACTCTTGTTCCAAACTGGAACAACACTCAACCCTATCTCG<br>GTCTATTCTTTTGATTTATAAGGGATTTTGCCGATTTCGGCCTATTG<br>GTTAAAAAATGAGCTGATTTAACAAAAATTTAACGCGAATTTTAA<br>CAAAATATTAACGTTTACAATTTAAATATTTGCTTATACAATCTTC<br>CTGTTTTTGGGGCTTTTCTGATTATCAACCGGGGTACATATGATTG<br>ACATGCTAGTTTTACGATTACCGTTCATCGATTCTCTTGTTTGCTCC<br>AGACTCTCAGGCAATGACCTGATAGCCTTTGTAGAGACCTCTCAA<br>AAATAGCTACCCTCTCCGGCATGAATTTATCAGCTAGAACGGTTG<br>AATATCATATTGATGGTGATTTGACTGTCTCCGGCCTTTCTCACCC<br>GTTTGAATCTTTACCTACACATTACTCAGGCATTGCATTTAAAATA<br>TATGAGGGTTCTAAAAATTTTTATCCTTGCGTTGAAATAAAGGCTT<br>CTCCCGCAAAAGTATTACAGGGTCATAATGTTTTTGGTACAACCGA<br>TTTAGCTTTATGCTCTGAGGCTTTATTGCTTAATTTTGCTAATTCTT<br>TGCCTTGCCTGTATGATTTATTGGATGTTGGAATCGCCTGATGCGG<br>TATTTTCTCCTTACGCATCTGTGCGGTATTTCACACCGCATATGGT<br>GCACTCTCAGTACAATCTGCTCTGATGCCGCATAGTTAAGCCAGCC<br>CCGACACCCGCCAACACCCGCTGACGCGCCCTGACGGGCTTGTCT<br>GCTCCCGGCATCCGCTTACAGACAAGCTGTGACCGTCTCCGGGAG<br>CTGCATGTGTCAGAGGTTTTCACCGTCATCACCGAAACGCGCGAG<br>ACGAAAGGGCCTCGTGATACGCCTATTTTTATAGGTTAATGTCATG<br>ATAATAATGGTTTCTTAGACGTCAGGTGGCACTTTTCGGGGAAATG |

-continued

| SEQ ID NO | NAME | SEQUENCE |
|---|---|---|
| | | TGCGCGGAACCCCTATTTGTTTATTTTTCTAAATACATTCAAATAT<br>GTATCCGCTCATGAGACAATAACCCTGATAAATGCTTCAATAATAT<br>TGAAAAAGGAAGAGTATGAGTATTCAACATTTCCGTGTCGCCCTT<br>ATTCCCTTTTTTGCGGCATTTTGCCTTCCTGTTTTTGCTCACCCAGA<br>AACGCTGGTGAAAGTAAAAGATGCTGAAGATCAGTTGGGTGCACG<br>AGTGGGTTACATCGAACTGGATCTCAACAGCGGTAAGATCCTTGA<br>GAGTTTTCGCCCCGAAGAACGTTTTCCAATGATGAGCACTTTTAAA<br>GTTCTGCTATGTGGCGCGGTATTATCCCGTATTGACGCCGGGCAAG<br>AGCAACTCGGTCGCCGCATACACTATTCTCAGAATGACTTGGTTGA<br>GTACTCACCAGTCACAGAAAAGCATCTTACGGATGGCATGACAGT<br>AAGAGAATTATGCAGTGCTGCCATAACCATGAGTGATAACACTGC<br>GGCCAACTTACTTCTGACAACGATCGGAGGACCGAAGGAGCTAAC<br>CGCTTTTTTGCACAACATGGGGGATCATGTAACTCGCCTTGATCGT<br>TGGGAACCGGAGCTGAATGAAGCCATACCAAACGACGAGCGTGA<br>CACCACGATGCCTGTAGCAATGGCAACAACGTTGCGCAAACTATT<br>AACTGGCGAACTACTTACTCTAGCTTCCCGGCAACAATTAATAGA<br>CTGGATGGAGGCGGATAAAGTTGCAGGACCACTTCTGCGCTCGGC<br>CCTTCCGGCTGGCTGGTTTATTGCTGATAAATCTGGAGCCGGTGAG<br>CGTGGGTCTCGCGGTATCATTGCAGCACTGGGGCCAGATGGTAAG<br>CCCTCCCGTATCGTAGTTATCTACACGACGGGGAGTCAGGCAACT<br>ATGGATGAACGAAATAGACAGATCGCTGAGATAGGTGCCTCACTG<br>ATTAAGCATTGGTAACTGTCAGACCAAGTTTACTCATATATACTTT<br>AGATTGATTTAAAACTTCATTTTTAATTTAAAAGGATCTAGGTGAA<br>GATCCTTTTTGATAATCTCATGACCAAAATCCCTTAACGTGAGTTT<br>TCGTTCCACTGAGCGTCAGACCCCGTAGAAAAGATCAAAGGATCT<br>TCTTGAGATCCTTTTTTTCTGCGCGTAATCTGCTGCTTGCAAACAA<br>AAAAACCACCGCTACCAGCGGTGGTTTGTTTGCCGGATCAAGAGC<br>TACCAACTCTTTTTCCGAAGGTAACTGGCTTCAGCAGAGCGCAGAT<br>ACCAAATACTGTCCTTCTAGTGTAGCCGTAGTTAGGCCACCACTTC<br>AAGAACTCTGTAGCACCGCCTACATACCTCGCTCTGCTAATCCTGT<br>TACCAGTGGCTGCTGCCAGTGGCGATAAGTCGTGTCTTACCGGGTT<br>GGACTCAAGACGATAGTTACCGGATAAGGCGCAGCGGTCGGGCTG<br>AACGGGGGGTTCGTGCACACAGCCCAGCTTGGAGCGAACGACCTA<br>CACCGAACTGAGATACCTACAGCGTGAGCTATGAGAAAGCGCCAC<br>GCTTCCCGAAGGGAGAAAGGCGGACAGGTATCCGGTAAGCGGCA<br>GGGTCGGAACAGGAGAGCGCACGAGGGAGCTTCCAGGGGGAAAC<br>GCCTGGTATCTTTATAGTCCTGTCGGGTTTCGCCACCTCTGACTTG<br>AGCGTCGATTTTTGTGATGCTCGTCAGGGGGGCGGAGCCTATGGA<br>AAAACGCCAGCAACGCGGCCTTTTTACGGTTCCTGGCCTTTTGCTG<br>GCCTTTTGCTCACATGTTCTTTCCTGCGTTATCCCCTGATTCTGTGG<br>ATAACCGTATTACCGCCTTTGAGTGAGCTGATACCGCTCGCCGCAG<br>CCGAACGACCGAGCGCAGCGAGTCAGTGAGCGAGGAAGCGGAAG<br>AGCGCCCAATACGCAAACCGCCTCTCCCCGCGCGTTGGCCGATTC<br>ATTAATG |
| 56 | Rhesus:<br>AMS#1347<br>Rhesus pAAV<br>HBG1(650).d0<br>HBBp>HBB(T87Q).<br>core3'enh;PGK<br>>MGMT(P140K).<br>SV40pA | CAGCTGCGCGCTCGCTCGCTCACTGAGGCCGCCCGGGCAAAGCCC<br>GGGCGTCGGGCGACCTTTGGTCGCCCGGCCTCAGTGAGCGAGCGA<br>GCGCGCAGAGAGGGAGTGGCCAACTCCATCACTAGGGGTTCCTAC<br>GCGTAGATCTGGTGCCTACATACATACCTGAATAAGAAAAAAAAA<br>TACCTTTGCTGAGATGAAACACACATGATTTATTTCAAATAGGTAC<br>AGAGAAGTAGATACTGAAGTAAGGATTAAGTATTATATTATATTA<br>CATAACATTAATCTATTCCTGCACTGAAACCGTTGCTTTATATGAT<br>TTTTTTTTTCACTACACTAATGAGAACTTAAGAGATAATGGCCTAA<br>AACCACAGAGAGTATTTTCAAAGATAAGTATAGCACAATGCTTAC<br>TAAATGAGACTAAGACTTGTCCCATCGAAAATCCTGGACCTATGC<br>CTAAAACACGTGTCACAATCCCCGAACTTTTCAAAAATTGGTACAT<br>GCTTTAACTTTAATCTCCAGGCCTCACTGGAGCTAGAGACAAGAA<br>GGTAAAAAAAGGCTGACAAAAGAAGTCCTGGTATCTTCTATGGTG<br>GGAGAAGGAAACTAGCTAAAGGGAAGAATAAATTAGAGAAAAAT<br>TGGAATGATTGAATCGGAACAAGGCAAAGGCTATAAAAAAAATTA<br>AGCAGCAGTATCCTCTTGGGGGCCCCTTCCCCACACTATCTCAATG<br>CAAATATCTGTCTGAAACGGTCCCTGGCTAAACTCCACCCATGGGT<br>TGGCCAGTCTTGCCTTGACGCTAGCGTAAATACACTTGCAAAGGA<br>GGATGTTTTTAGTAGCAATTTGTACTGATGGTATGGGGCCAAGAG<br>ATATATCTTAGAGGGAGGGCTGAGGGTTTGAAGTCCAACTCCTAA<br>GCCAGTGCCAGAAGAGCCAAGGACAGGTACGGCTGTCATCACTTA<br>GACCTCACCCTGTGGAGCCACACCCTAGGGTTGGCCAATCTACTCC<br>CAGGAGCAGGGAGGGCAGGAGCCAGGGCTGGGCATAAAAGTCAG<br>GGCAGAGCCATCTATTGCTTACATTTGCTTCTGACACAACTGTGTT<br>CACTAGCAACCTCAAACAGACACCATGGTGCACCTGACTCCTGAG<br>GAGAAGTCTGCCGTTACTGCCCTGTGGGGCAAGGTGAACGTGGAT<br>GAAGTTGGTGGTGAGGCCCTGGGCAGGTTGGTATCAAGGTTACAA<br>GACAGGTTTAAGGAGACCAATAGAAACTGGGCATGTGGAGACAG<br>AGAAGACTCTTGGGTTTCTGATAGGCACTGACTCTCTCTGCCTATT<br>GGTCTATTTTCCCACCCTTAGGCTGCTGGTGGTCTACCCTTGGACC |

-continued

| SEQ ID NO | NAME | SEQUENCE |
|---|---|---|
| | | CAGAGGTTCTTTGAGTCCTTTGGGGATCTGTCCACTCCTGATGCTG |
| | | TTATGGGCAACCCTAAGGTGAAGGCTCATGGCAAGAAAGTGCTCG |
| | | GTGCCTTTAGTGATGGCCTGGCTCACCTGGACAACCTCAAGGGCA |
| | | CCTTTGCCCAGCTGAGTGAGCTGCACTGTGACAAGCTGCACGTGG |
| | | ATCCTGAGAACTTCAGGGTGAGTCTATGGGACCCTTGATGTTTTCT |
| | | TTCCCCTTCTTTTCTATGGTTAAGTTCATGTCATAGGAAGGGGAGA |
| | | AGTAACAGGGTACACATATTGACCAAATCAGGGTAATTTTGCATT |
| | | TGTAATTTTAAAAAATGCTTTCTTCTTTTAATATACTTTTTTGTTTA |
| | | TCTTATTTCTAATACTTTCCCTAATCTCTTTCTTTCAGGGCAATAAT |
| | | GATACAATGTATCATGCCTCTTTGCACCATTCTAAAGAATAACAGT |
| | | GATAATTTCTGGGTTAAGGCAATAGCAATATTTCTGCATATAAATA |
| | | TTTCTGCATATAAATTGTAACTGATGTAAGAGGTTTCATATTGCTA |
| | | ATAGCAGCTACAATCCAGCTACCATTCTGCTTTTATTTTATGGTTG |
| | | GGATAAGGCTGGATTATTCTGAGTCCAAGCTAGGCCCTTTTGCTAA |
| | | TCATGTTCATACCTCTTATCTTCCTCCCACAGCTCCTGGGCAACGT |
| | | GCTGGTCTGTGTGCTGGCCCATCACTTTGGCAAAGAATTCACCCCA |
| | | CCAGTGCAGGCTGCCTATCAGAAAGTGGTGGCTGGTGTGGCTAAT |
| | | GCCCTGGCCCACAAGTATCACTAAGCTCGCTTTCTTGCTGTCCAAT |
| | | TTCTATTAAAGGTTCCTTTGTTCCCTAAGTCCAACTACTAAACTGG |
| | | GGGATATTATGAAGGGCCTTGAGCATCTGGATTCTGCCTAATAAA |
| | | AAACATTTATTTTCATTGCAATGATGTATTTAAATTATTTCTGAATA |
| | | TTTTACTAAAAAGGGAATGTGGGAGGTTGCAGTGCTAGTCTCCCG |
| | | GAACTATCACTCTTTCACAGTCTGCTTTGGAAGGACTGGGCTTAGT |
| | | ATGAAAAGTTAGGACTGAGAAGAATTTGAAAGGGGGCTTTTTGTA |
| | | GCTTGATATTCACTACTGTCTTATTACCCTATCATAGGCCCACCCC |
| | | AAATGGAAGTCCCATTCTTCCTCAGGATGTTTAAGATTAGCATTCA |
| | | GGAAGAGATCAGAGGTCTGCTGGCTCCCTTATCATGTCCCTTATGG |
| | | TGCTTCTGGCTCTGCACCGCGGCCACGGGGTTGGGGTTGCGCCTTT |
| | | TCCAAGGCAGCCCTGGGTTTGCGCAGGGACGCGGCTGCTCTGGGC |
| | | GTGGTTCCGGGAAACGCAGCGGCGCCGACCCTGGGTCTCGCACAT |
| | | TCTTCACGTCCGTTCGCAGCGTCACCCGGATCTTCGCCGCTACCCT |
| | | TGTGGGCCCCCCGGCGACGCTTCCTGCTCCGCCCCTAAGTCGGGA |
| | | AGGTTCCTTGCGGTTCGCGGCGTGCCGGACGTGACAAACGGAAGC |
| | | CGCACGTCTCACTAGTACCCTCGCAGACGGACAGCGCCAGGGAGC |
| | | AATGGCAGCGCGCCGACCGCGATGGGCTGTGGCCAATAGCGGCTG |
| | | CTCAGCGGGGCGCGCCGAGAGCAGCGGCCGGGAAGGGGCGGTGC |
| | | GGGAGGCGGGGTGTGGGGCGGTAGTGTGGGCCCTGTTCCTGCCCG |
| | | CGCGGTGTTCCGCATTCTGCAAGCCTCCGGAGCGCACGTCGGCAG |
| | | TCGGCTCCCTCGTTGACCGAATCACCGACCTCTCTCCCCAGCGGCC |
| | | GCGCCGCCACCATGGACAAGGATTGTGAAATGAAACGCACCACAC |
| | | TGGACAGCCCTTTGGGGAAGCTGGAGCTGTCTGGTTGTGAGCAGG |
| | | GTCTGCACGAAATAAAGCTCCTGGGCAAGGGGACGTCTGCAGCTG |
| | | ATGCCGTGGAGGTCCCAGCCCCCGCTGCGGTTCTCGGAGGTCCGG |
| | | AGCCCCTGATGCAGTGCACAGCCTGGCTGAATGCCTATTTCCACCA |
| | | GCCCGAGGCTATCGAAGAGTTCCCCGTGCCGGCTCTTCACCATCCC |
| | | GTTTTCCAGCAAGAGTCGTTCACCAGACAGGTGTTATGGAAGCTG |
| | | CTGAAGGTTGTGAAATTCGGAGAAGTGATTTCTTACCAGCAATTA |
| | | GCAGCCCTGGCAGGCAACCCCAAAGCCGCGCGAGCAGTGGGAGG |
| | | AGCAATGAGAGGCAATCCTGTCAAAATCCTCATCCCGTGCCACAG |
| | | AGTGGTCTGCAGCAGCGGAGCCGTGGGCAACTACTCCGGAGGACT |
| | | GGCCGTGAAGGAATGGCTTCTGGCCCATGAAGGCCACCGGTTGGG |
| | | GAAGCCAGGCTTGGGAGGGAGCTCAGGTCTGGCAGGGGCCTGGCT |
| | | CAAGGGAGCGGGAGCTACCTCGGGCTCCCCGCCTGCTGGCCGAAA |
| | | CTAAGCTTTATTTGTGAAATTTGTGATGCTATTGCTTTATTTGTAAC |
| | | CATTATAAGCTGCAATAAACAAGTTAACAACAACAATTGCATTCA |
| | | TTTTATGTTTCAGGTTCAGGGGGAGATGTGGGAGGTTTTTTAAAGC |
| | | CCTGCAGGCAATAGCCTTGACAAGGCAACCTTGACCAATAGTCTT |
| | | AGAGTATCAGGTGAGGCCAGGGGCCGGCGGCTGGCTAGGGATGA |
| | | AGAATAAAAGGAAGCACCCTCCAGCAGTTCCACACACTCGCTTCT |
| | | GGAACGGCTGAGATTATCAATAAGCTCCTAGTCCAGACGCCATGG |
| | | GTCATTTCACAGAGGAGGACAAGGCTACTATCACAAGCCTGTGGG |
| | | GCAAGGTGAATGTGGAAGATGCTGGAGGAGAAACCCTGGGAAGG |
| | | TAGGCTCTGGTGACCAGGACAAGGAAGGGAAGGAAGGACCCTGT |
| | | GCCTGGCAAAAGTCCAGGCCACTTCTCAGGATTTGTGGCACTTTCT |
| | | GACTGTCAAACTGCTCTTGTTCAATCTCACAGGCTCCTGGTTGTCT |
| | | ACCCATGGACCCAGAGGTTCTTTGACAGCTTTGGCAACCTGTCCTC |
| | | TGCCTCTGCCATCATGGGCAACCCCAAGGTCAAGGCACACGGCAA |
| | | GAAGGTGCTGACTTCCTTGGGAGATGCCATAAAGAACCTGGATGA |
| | | TCTCAAGGGCACCTTTGCCCAGCTGAGTGAGCTGCACTGTGACAA |
| | | GCTGCATGTGGATCCTGAGAACTTCAGGGTGAGTCCAGGAGTTTC |
| | | AGCAGTTTCAGAGTTCAGTCTCAAGGCGTCGACAGGAACCCCTAG |
| | | TGATGGAGTTGGCCACTCCCTCTCTGCGCGCTCGCTCGCTCACTGA |
| | | GGCCGGGCGACCAAAGGTCGCCCGACGCCCGGGCTTTGCCCGGGC |
| | | GGCCTCAGTGAGCGAGCGAGCGCGCAGCTGGCGTAATAGCGAAG |
| | | AGGCCCGCACCGATCGCCCTTCCCAACAGTTGCGCAGCCTGAATG |

-continued

| SEQ ID NO | NAME | SEQUENCE |
|---|---|---|
| | | GCGAATGGCGATTCCGTTGCAATGGCTGGCGGTAATATTGTTCTGG<br>ATATTACCAGCAAGGCCGATAGTTTGAGTTCTTCTACTCAGGCAAG<br>TGATGTTATTACTAATCAAAGAAGTATTGCGACAACGGTTAATTTG<br>CGTGATGGACAGACTCTTTTACTCGGTGGCCTCACTGATTATAAAA<br>ACACTTCTCAGGATTCTGGCGTACCGTTCCTGTCTAAAATCCCTTT<br>AATCGGCCTCCTGTTTAGCTCCCGCTCTGATTCTAACGAGGAAAGC<br>ACGTTATACGTGCTCGTCAAAGCAACCATAGTACGCGCCCTGTAG<br>CGGCGCATTAAGCGCGGCGGGTGTGGTGGTTACGCGCAGCGTGAC<br>CGCTACACTTGCCAGCGCCCTAGCGCCCGCTCCTTTCGCTTTCTTC<br>CCTTCCTTTCTCGCCACGTTCGCCGGCTTTCCCCGTCAAGCTCTAA<br>ATCGGGGGCTCCCTTTAGGGTTCCGATTTAGTGCTTTACGGCACCT<br>CGACCCCAAAAAACTTGATTAGGGTGATGGTTCACGTAGTGGGCC<br>ATCGCCCTGATAGACGGTTTTTCGCCCTTTGACGTTGGAGTCCACG<br>TTCTTTAATAGTGGACTCTTGTTCCAAACTGGAACAACACTCAACC<br>CTATCTCGGTCTATTCTTTTGATTTATAAGGGATTTTGCCGATTTCG<br>GCCTATTGGTTAAAAAATGAGCTGATTTAACAAAAATTTAACGCG<br>AATTTTAACAAAATATTAACGTTTACAATTTAAATATTTGCTTATA<br>CAATCTTCCTGTTTTTGGGGCTTTTCTGATTATCAACCGGGGTACA<br>TATGATTGACATGCTAGTTTTACGATTACCGTTCATCGATTCTCTTG<br>TTTGCTCCAGACTCTCAGGCAATGACCTGATAGCCTTTGTAGAGAC<br>CTCTCAAAAATAGCTACCCTCTCCGGCATGAATTTATCAGCTAGAA<br>CGGTTGAATATCATATTGATGGTGATTTGACTGTCTCCGGCCTTTC<br>TCACCCGTTTGAATCTTTACCTACACATTACTCAGGCATTGCATTT<br>AAAATATATGAGGGTTCTAAAAATTTTTATCCTTGCGTTGAAATAA<br>AGGCTTCTCCCGCAAAAGTATTACAGGGTCATAATGTTTTTGGTAC<br>AACCGATTTAGCTTTATGCTCTGAGGCTTTATTGCTTAATTTTGCTA<br>ATTCTTTGCCTTGCCTGTATGATTTATTGGATGTTGGAATCGCCTG<br>ATGCGGTATTTTCTCCTTACGCATCTGTGCGGTATTTCACACCGCA<br>TATGGTGCACTCTCAGTACAATCTGCTCTGATGCCGCATAGTTAAG<br>CCAGCCCCGACACCCGCCAACACCCGCTGACGCGCCCTGACGGGC<br>TTGTCTGCTCCCGGCATCCGCTTACAGACAAGCTGTGACCGTCTCC<br>GGGAGCTGCATGTGTCAGAGGTTTTCACCGTCATCACCGAAACGC<br>GCGAGACGAAAGGGCCTCGTGATACGCCTATTTTTATAGGTTAAT<br>GTCATGATAATAATGGTTTCTTAGACGTCAGGTGGCACTTTTCGGG<br>GAAATGTGCGCGGAACCCCTATTTGTTTATTTTTCTAAATACATTC<br>AAATATGTATCCGCTCATGAGACAATAACCCTGATAAATGCTTCA<br>ATAATATTGAAAAAGGAAGAGTATGAGTATTCAACATTTCCGTGT<br>CGCCCTTATTCCCTTTTTTGCGGCATTTTGCCTTCCTGTTTTTGCTC<br>ACCCAGAAACGCTGGTGAAAGTAAAAGATGCTGAAGATCAGTTGG<br>GTGCACGAGTGGGTTACATCGAACTGGATCTCAACAGCGGTAAGA<br>TCCTTGAGAGTTTTCGCCCCGAAGAACGTTTTCCAATGATGAGCAC<br>TTTTAAAGTTCTGCTATGTGGCGCGGTATTATCCCGTATTGACGCC<br>GGGCAAGAGCAACTCGGTCGCCGCATACACTATTCTCAGAATGAC<br>TTGGTTGAGTACTCACCAGTCACAGAAAAGCATCTTACGGATGGC<br>ATGACAGTAAGAGAATTATGCAGTGCTGCCATAACCATGAGTGAT<br>AACACTGCGGCCAACTTACTTCTGACAACGATCGGAGGACCGAAG<br>GAGCTAACCGCTTTTTTGCACAACATGGGGGATCATGTAACTCGCC<br>TTGATCGTTGGGAACCGGAGCTGAATGAAGCCATACCAAACGACG<br>AGCGTGACACCACGATGCCTGTAGCAATGGCAACAACGTTGCGCA<br>AACTATTAACTGGCGAACTACTTACTCTAGCTTCCCGGCAACAATT<br>AATAGACTGGATGGAGGCGGATAAAGTTGCAGGACCACTTCTGCG<br>CTCGGCCCTTCCGGCTGGCTGGTTTATTGCTGATAAATCTGGAGCC<br>GGTGAGCGTGGGTCTCGCGGTATCATTGCAGCACTGGGGCCAGAT<br>GGTAAGCCCTCCCGTATCGTAGTTATCTACACGACGGGGAGTCAG<br>GCAACTATGGATGAACGAAATAGACAGATCGCTGAGATAGGTGCC<br>TCACTGATTAAGCATTGGTAACTGTCAGACCAAGTTTACTCATATA<br>TACTTTAGATTGATTTAAAACTTCATTTTTAATTTAAAAGGATCTA<br>GGTGAAGATCCTTTTTGATAATCTCATGACCAAAATCCCTTAACGT<br>GAGTTTTCGTTCCACTGAGCGTCAGACCCCGTAGAAAAGATCAAA<br>GGATCTTCTTGAGATCCTTTTTTTCTGCGCGTAATCTGCTGCTTGCA<br>AACAAAAAAACCACCGCTACCAGCGGTGGTTTGTTTGCCGGATCA<br>AGAGCTACCAACTCTTTTTCCGAAGGTAACTGGCTTCAGCAGAGC<br>GCAGATACCAAATACTGTCCTTCTAGTGTAGCCGTAGTTAGGCCAC<br>CACTTCAAGAACTCTGTAGCACCGCCTACATACCTCGCTCTGCTAA<br>TCCTGTTACCAGTGGCTGCTGCCAGTGGCGATAAGTCGTGTCTTAC<br>CGGGTTGGACTCAAGACGATAGTTACCGGATAAGGCGCAGCGGTC<br>GGGCTGAACGGGGGGTTCGTGCACACAGCCCAGCTTGGAGCGAAC<br>GACCTACACCGAACTGAGATACCTACAGCGTGAGCTATGAGAAAG<br>CGCCACGCTTCCCGAAGGGAGAAAGGCGGACAGGTATCCGGTAA<br>GCGGCAGGGTCGGAACAGGAGAGCGCACGAGGGAGCTTCCAGGG<br>GGAAACGCCTGGTATCTTTATAGTCCTGTCGGGTTTCGCCACCTCT<br>GACTTGAGCGTCGATTTTTGTGATGCTCGTCAGGGGGGCGGAGCC<br>TATGGAAAAACGCCAGCAACGCGGCCTTTTTACGGTTCCTGGCCTT<br>TTGCTGGCCTTTTGCTCACATGTTCTTTCCTGCGTTATCCCCTGATT<br>CTGTGGATAACCGTATTACCGCCTTTGAGTGAGCTGATACCGCTCG |

-continued

| SEQ ID NO | NAME | SEQUENCE |
|---|---|---|
| | | CCGCAGCCGAACGACCGAGCGCAGCGAGTCAGTGAGCGAGGAAG |
| | | CGGAAGAGCGCCCAATACGCAAACCGCCTCTCCCCGCGCGTTGGC |
| | | CGATTCATTAATG |
| 57 | Rhesus: | CAGCTGCGCGCTCGCTCGCTCACTGAGGCCGCCCGGGCAAAGCCC |
| | AMS#1348 | GGGCGTCGGGCGACCTTTGGTCGCCCGGCCTCAGTGAGCGAGCGA |
| | Rhesus pAAV | GCGCGCAGAGAGGGAGTGGCCAACTCCATCACTAGGGGTTCCTAC |
| | HBG1(650).d0 | GCGTAGATCTGGTGCCTACATACATACCTGAATAAGAAAAAAAAA |
| | HBBp>HBB(T87Q). | TACCTTTGCTGAGATGAAACACACATGATTTATTTCAAATAGGTAC |
| | core3'enh; | AGAGAAGTAGATACTGAAGTAAGGATTAAGTATTATATTATATTA |
| | MND>GFP.SV40pA | CATAACATTAATCTATTCCTGCACTGAAACCGTTGCTTTATATGAT |
| | | TTTTTTTTTCACTACACTAATGAGAACTTAAGAGATAATGGCCTAA |
| | | AACCACAGAGAGTATTTTCAAAGATAAGTATAGCACAATGCTTAC |
| | | TAAATGAGACTAAGACTTGTCCCATCGAAAATCCTGGACCTATGC |
| | | CTAAAACACGTGTCACAATCCCCGAACTTTTCAAAATTGGTACAT |
| | | GCTTTAACTTTAATCTCCAGGCCTCACTGGAGCTAGAGACAAGAA |
| | | GGTAAAAAAAGGCTGACAAAAGAAGTCCTGGTATCTTCTATGGTG |
| | | GGAGAAGGAAACTAGCTAAAGGGAAGAATAAATTAGAGAAAAAT |
| | | TGGAATGATTGAATCGGAACAAGGCAAAGGCTATAAAAAAATTA |
| | | AGCAGCAGTATCCTCTTGGGGGCCCCTTCCCCACACTATCTCAATG |
| | | CAAATATCTGTCTGAAACGGTCCCTGGCTAAACTCCACCCATGGGT |
| | | TGGCCAGTCTTGCCTTGACGCTAGCGTAAATACACTTGCAAAGGA |
| | | GGATGTTTTTAGTAGCAATTTGTACTGATGGTATGGGGCCAAGAG |
| | | ATATATCTTAGAGGGAGGGCTGAGGGTTTGAAGTCCAACTCCTAA |
| | | GCCAGTGCCAGAAGAGCCAAGGACAGGTACGGCTGTCATCACTTA |
| | | GACCTCACCCTGTGGAGCCACACCCTAGGGTTGGCCAATCTACTCC |
| | | CAGGAGCAGGGAGGGCAGGAGCCAGGGCTGGGCATAAAAGTCAG |
| | | GGCAGAGCCATCTATTGCTTACATTTGCTTCTGACACAACTGTGTT |
| | | CACTAGCAACCTCAAACAGACACCATGGTGCACCTGACTCCTGAG |
| | | GAGAAGTCTGCCGTTACTGCCCTGTGGGGCAAGGTGAACGTGGAT |
| | | GAAGTTGGTGGTGAGGCCCTGGGCAGGTTGGTATCAAGGTTACAA |
| | | GACAGGTTTAAGGAGACCAATAGAAACTGGGCATGTGGAGACAG |
| | | AGAAGACTCTTGGGTTTCTGATAGGCACTGACTCTCTCTGCCTATT |
| | | GGTCTATTTTCCCACCCTTAGGCTGCTGGTGGTCTACCCTTGGACC |
| | | CAGAGGTTCTTTGAGTCCTTTGGGGATCTGTCCACTCCTGATGCTG |
| | | TTATGGGCAACCCTAAGGTGAAGGCTCATGGCAAGAAAGTGCTCG |
| | | GTGCCTTTAGTGATGGCCTGGCTCACCTGGACAACCTCAAGGGCA |
| | | CCTTTGCCCAGCTGAGTGAGCTGCACTGTGACAAGCTGCACGTGG |
| | | ATCCTGAGAACTTCAGGGTGAGTCTATGGGACCCTTGATGTTTTCT |
| | | TTCCCCTTCTTTTCTATGGTTAAGTTCATGTCATAGGAAGGGGAGA |
| | | AGTAACAGGGTACACATATTGACCAAATCAGGGTAATTTTGCATT |
| | | TGTAATTTTAAAAAATGCTTTCTTCTTTTAATATACTTTTTTGTTTA |
| | | TCTTATTTCTAATACTTTCCCTAATCTCTTTCTTTCAGGGCAATAAT |
| | | GATACAATGTATCATGCCTCTTTGCACCATTCTAAAGAATAACAGT |
| | | GATAATTTCTGGGTTAAGGCAATAGCAATATTTCTGCATATAAATA |
| | | TTTCTGCATATAAATTGTAACTGATGTAAGAGGTTTCATATTGCTA |
| | | ATAGCAGCTACAATCCAGCTACCATTCTGCTTTTATTTTATGGTTG |
| | | GGATAAGGCTGGATTATTCTGAGTCCAAGCTAGGCCCTTTTGCTAA |
| | | TCATGTTCATACCTCTTATCTTCCTCCCACAGCTCCTGGGCAACGT |
| | | GCTGGTCTGTGTGCTGGCCCATCACTTTGGCAAAGAATTCACCCCA |
| | | CCAGTGCAGGCTGCCTATCAGAAAGTGGTGGCTGGTGTGGCTAAT |
| | | GCCCTGGCCCACAAGTATCACTAAGCTCGCTTTCTTGCTGTCCAAT |
| | | TTCTATTAAAGGTTCCTTTGTTCCCTAAGTCCAACTACTAAACTGG |
| | | GGGATATTATGAAGGGCCTTGAGCATCTGGATTCTGCCTAATAAA |
| | | AAACATTTATTTTCATTGCAATGATGTATTTAAATTATTTCTGAATA |
| | | TTTTACTAAAAAGGGAATGTGGGAGGTTGCAGTGCTAGTCTCCCG |
| | | GAACTATCACTCTTTCACAGTCTGCTTTGGAAGGACTGGGCTTAGT |
| | | ATGAAAAGTTAGGACTGAGAAGAATTTGAAAGGGGGCTTTTTGTA |
| | | GCTTGATATTCACTACTGTCTTATTACCCTATCATAGGCCCACCCC |
| | | AAATGGAAGTCCCATTCTTCCTCAGGATGTTTAAGATTAGCATTCA |
| | | GGAAGAGATCAGAGGTCTGCTGGCTCCCTTATCATGTCCCTTATGG |
| | | TGCTTCTGGCTCTGCACCGCGGGAACAGAGAAACAGGAGAATATG |
| | | GGCCAAACAGGATATCTGTGGTAAGCAGTTCCTGCCCCGGCTCAG |
| | | GGCCAAGAACAGTTGGAACAGCAGAATATGGGCCAAACAGGATA |
| | | TCTGTGGTAAGCAGTTCCTGCCCCGGCTCAGGGCCAAGAACAGAT |
| | | GGTCCCCAGATGCGGTCCCGCCCTCAGCAGTTTCTAGAGAACCAT |
| | | CAGATGTTTCCAGGGTGCCCCAAGGACCTGAAATGACCCTGTGCC |
| | | TTATTTGAACTAACCAATCAGTTCGCTTCTCGCTTCTGTTCGCGCG |
| | | CTTCTGCTCCCCGAGCTCTATATAAGCAGAGCTCGTTTAGTGAACC |
| | | GTCAGATCGCGGCCGCGCCGCCACCATGGTGAGCAAGGGCGAGG |
| | | AGCTGTTCACCGGGGTGGTGCCCATCCTGGTCGAGCTGGACGGCG |
| | | ACGTAAACGGCCACAAGTTCAGCGTGTCCGGCGAGGGCGAGGGC |
| | | GATGCCACCTACGGCAAGCTGACCCTGAAGTTCATCTGCACCACC |
| | | GGCAAGCTGCCCGTGCCCTGGCCCACCCTCGTGACCACCCTGACCT |
| | | ACGGCGTGCAGTGCTTCAGCCGCTACCCCGACCACATGAAGCAGC |

-continued

| SEQ ID NO | NAME | SEQUENCE |
|---|---|---|
| | | ACGACTTCTTCAAGTCCGCCATGCCCGAAGGCTACGTCCAGGAGC |
| | | GCACCATCTTCTTCAAGGACGACGGCAACTACAAGACCCGCGCCG |
| | | AGGTGAAGTTCGAGGGCGACACCCTGGTGAACCGCATCGAGCTGA |
| | | AGGGCATCGACTTCAAGGAGGACGGCAACATCCTGGGGCACAAG |
| | | CTGGAGTACAACTACAACAGCCACAACGTCTATATCATGGCCGAC |
| | | AAGCAGAAGAACGGCATCAAGGTGAACTTCAAGATCCGCCACAA |
| | | CATCGAGGACGGCAGCGTGCAGCTCGCCGACCACTACCAGCAGAA |
| | | CACCCCCATCGGCGACGGCCCCGTGCTGCTGCCCGACAACCACTA |
| | | CCTGAGCACCCAGTCCGCCCTGAGCAAAGACCCCAACGAGAAGCG |
| | | CGATCACATGGTCCTGCTGGAGTTCGTGACCGCCGCCGGGATCAC |
| | | TCTCGGCATGGACGAGCTGTACAAGTAAGCTTTATTTGTGAAATTT |
| | | GTGATGCTATTGCTTTATTTGTAACCATTATAAGCTGCAATAAACA |
| | | AGTTAACAACAACAATTGCATTCATTTTATGTTTCAGGTTCAGGGG |
| | | GAGATGTGGGAGGTTTTTTAAAGCCCTGCAGGCAATAGCCTTGAC |
| | | AAGGCAACCTTGACCAATAGTCTTAGAGTATCAGGTGAGGCCAGG |
| | | GGCCGGCGGCTGGCTAGGGATGAAGAATAAAAGGAAGCACCCTC |
| | | CAGCAGTTCCACACACTCGCTTCTGGAACGGCTGAGATTATCAAT |
| | | AAGCTCCTAGTCCAGACGCCATGGGTCATTTCACAGAGGAGGACA |
| | | AGGCTACTATCACAAGCCTGTGGGGCAAGGTGAATGTGGAAGATG |
| | | CTGGAGGAGAAACCCTGGGAAGGTAGGCTCTGGTGACCAGGACA |
| | | AGGAAGGGAAGGAAGGACCCTGTGCCTGGCAAAAGTCCAGGCCA |
| | | CTTCTCAGGATTTGTGGCACTTTCTGACTGTCAAACTGCTCTTGTTC |
| | | AATCTCACAGGCTCCTGGTTGTCTACCCATGGACCCAGAGGTTCTT |
| | | TGACAGCTTTGGCAACCTGTCCTCTGCCTCTGCCATCATGGGCAAC |
| | | CCCAAGGTCAAGGCACACGGCAAGAAGGTGCTGACTTCCTTGGGA |
| | | GATGCCATAAAGAACCTGGATGATCTCAAGGGCACCTTTGCCCAG |
| | | CTGAGTGAGCTGCACTGTGACAAGCTGCATGTGGATCCTGAGAAC |
| | | TTCAGGGTGAGTCCAGGAGTTTCAGCAGTTTCAGAGTTCAGTCTCA |
| | | AGGCGTCGACAGGAACCCCTAGTGATGGAGTTGGCCACTCCCTCT |
| | | CTGCGCGCTCGCTCGCTCACTGAGGCCGGGCGACCAAAGGTCGCC |
| | | CGACGCCCGGGCTTTGCCCGGGCGGCCTCAGTGAGCGAGCGAGCG |
| | | CGCAGCTGGCGTAATAGCGAAGAGGCCCGCACCGATCGCCCTTCC |
| | | CAACAGTTGCGCAGCCTGAATGGCGAATGGCGATTCCGTTGCAAT |
| | | GGCTGGCGGTAATATTGTTCTGGATATTACCAGCAAGGCCGATAG |
| | | TTTGAGTTCTTCTACTCAGGCAAGTGATGTTATTACTAATCAAAGA |
| | | AGTATTGCGACAACGGTTAATTTGCGTGATGGACAGACTCTTTTAC |
| | | TCGGTGGCCTCACTGATTATAAAAACACTTCTCAGGATTCTGGCGT |
| | | ACCGTTCCTGTCTAAAATCCCTTTAATCGGCCTCCTGTTTAGCTCCC |
| | | GCTCTGATTCTAACGAGGAAAGCACGTTATACGTGCTCGTCAAAG |
| | | CAACCATAGTACGCGCCCTGTAGCGGCGCATTAAGCGCGGCGGGT |
| | | GTGGTGGTTACGCGCAGCGTGACCGCTACACTTGCCAGCGCCCTA |
| | | GCGCCCGCTCCTTTCGCTTTCTTCCCTTCCTTTCTCGCCACGTTCGC |
| | | CGGCTTTCCCCGTCAAGCTCTAAATCGGGGGCTCCCTTTAGGGTTC |
| | | CGATTTAGTGCTTTACGGCACCTCGACCCCAAAAAACTTGATTAGG |
| | | GTGATGGTTCACGTAGTGGGCCATCGCCCTGATAGACGGTTTTTCG |
| | | CCCTTTGACGTTGGAGTCCACGTTCTTTAATAGTGGACTCTTGTTC |
| | | CAAACTGGAACAACACTCAACCCTATCTCGGTCTATTCTTTTGATT |
| | | TATAAGGGATTTTGCCGATTTCGGCCTATTGGTTAAAAAATGAGCT |
| | | GATTTAACAAAAATTTAACGCGAATTTTAACAAAATATTAACGTTT |
| | | ACAATTTAAATATTTGCTTATACAATCTTCCTGTTTTTGGGGCTTTT |
| | | CTGATTATCAACCGGGGTACATATGATTGACATGCTAGTTTTACGA |
| | | TTACCGTTCATCGATTCTCTTGTTTGCTCCAGACTCTCAGGCAATG |
| | | ACCTGATAGCCTTTGTAGAGACCTCTCAAAAATAGCTACCCTCTCC |
| | | GGCATGAATTTATCAGCTAGAACGGTTGAATATCATATTGATGGT |
| | | GATTTGACTGTCTCCGGCCTTTCTCACCCGTTTGAATCTTTACCTAC |
| | | ACATTACTCAGGCATTGCATTTAAAATATATGAGGGTTCTAAAAAT |
| | | TTTTATCCTTGCGTTGAAATAAAGGCTTCTCCCGCAAAAGTATTAC |
| | | AGGGTCATAATGTTTTTGGTACAACCGATTTAGCTTTATGCTCTGA |
| | | GGCTTTATTGCTTAATTTTGCTAATTCTTTGCCTTGCCTGTATGATT |
| | | TATTGGATGTTGGAATCGCCTGATGCGGTATTTTCTCCTTACGCAT |
| | | CTGTGCGGTATTTCACACCGCATATGGTGCACTCTCAGTACAATCT |
| | | GCTCTGATGCCGCATAGTTAAGCCAGCCCCGACACCCGCCAACAC |
| | | CCGCTGACGCGCCCTGACGGGCTTGTCTGCTCCCGGCATCCGCTTA |
| | | CAGACAAGCTGTGACCGTCTCCGGGAGCTGCATGTGTCAGAGGTT |
| | | TTCACCGTCATCACCGAAACGCGCGAGACGAAAGGGCCTCGTGAT |
| | | ACGCCTATTTTTATAGGTTAATGTCATGATAATAATGGTTTCTTAG |
| | | ACGTCAGGTGGCACTTTTCGGGGAAATGTGCGCGGAACCCCTATT |
| | | TGTTTATTTTTCTAAATACATTCAAATATGTATCCGCTCATGAGAC |
| | | AATAACCCTGATAAATGCTTCAATAATATTGAAAAAGGAAGAGTA |
| | | TGAGTATTCAACATTTCCGTGTCGCCCTTATTCCCTTTTTTGCGGCA |
| | | TTTTGCCTTCCTGTTTTTGCTCACCCAGAAACGCTGGTGAAAGTAA |
| | | AAGATGCTGAAGATCAGTTGGGTGCACGAGTGGGTTACATCGAAC |
| | | TGGATCTCAACAGCGGTAAGATCCTTGAGAGTTTTCGCCCCGAAG |
| | | AACGTTTTCCAATGATGAGCACTTTTAAAGTTCTGCTATGTGGCGC |
| | | GGTATTATCCCGTATTGACGCCGGGCAAGAGCAACTCGGTCGCCG |

-continued

| SEQ ID NO | NAME | SEQUENCE |
|---|---|---|
| | | CATACACTATTCTCAGAATGACTTGGTTGAGTACTCACCAGTCACA<br>GAAAAGCATCTTACGGATGGCATGACAGTAAGAGAATTATGCAGT<br>GCTGCCATAACCATGAGTGATAACACTGCGGCCAACTTACTTCTG<br>ACAACGATCGGAGGACCGAAGGAGCTAACCGCTTTTTTGCACAAC<br>ATGGGGGATCATGTAACTCGCCTTGATCGTTGGGAACCGGAGCTG<br>AATGAAGCCATACCAAACGACGAGCGTGACACCACGATGCCTGTA<br>GCAATGGCAACAACGTTGCGCAAACTATTAACTGGCGAACTACTT<br>ACTCTAGCTTCCCGGCAACAATTAATAGACTGGATGGAGGCGGAT<br>AAAGTTGCAGGACCACTTCTGCGCTCGGCCCTTCCGGCTGGCTGGT<br>TTATTGCTGATAAATCTGGAGCCGGTGAGCGTGGGTCTCGCGGTAT<br>CATTGCAGCACTGGGGCCAGATGGTAAGCCCTCCCGTATCGTAGT<br>TATCTACACGACGGGGAGTCAGGCAACTATGGATGAACGAAATAG<br>ACAGATCGCTGAGATAGGTGCCTCACTGATTAAGCATTGGTAACT<br>GTCAGACCAAGTTTACTCATATATACTTTAGATTGATTTAAAACTT<br>CATTTTTAATTTAAAAGGATCTAGGTGAAGATCCTTTTTGATAATC<br>TCATGACCAAAATCCCTTAACGTGAGTTTTCGTTCCACTGAGCGTC<br>AGACCCCGTAGAAAAGATCAAAGGATCTTCTTGAGATCCTTTTTTT<br>CTGCGCGTAATCTGCTGCTTGCAAACAAAAAAACCACCGCTACCA<br>GCGGTGGTTTGTTTGCCGGATCAAGAGCTACCAACTCTTTTTCCGA<br>AGGTAACTGGCTTCAGCAGAGCGCAGATACCAAATACTGTCCTTC<br>TAGTGTAGCCGTAGTTAGGCCACCACTTCAAGAACTCTGTAGCAC<br>CGCCTACATACCTCGCTCTGCTAATCCTGTTACCAGTGGCTGCTGC<br>CAGTGGCGATAAGTCGTGTCTTACCGGGTTGGACTCAAGACGATA<br>GTTACCGGATAAGGCGCAGCGGTCGGGCTGAACGGGGGGTTCGTG<br>CACACAGCCCAGCTTGGAGCGAACGACCTACACCGAACTGAGATA<br>CCTACAGCGTGAGCTATGAGAAAGCGCCACGCTTCCCGAAGGGAG<br>AAAGGCGGACAGGTATCCGGTAAGCGGCAGGGTCGGAACAGGAG<br>AGCGCACGAGGGAGCTTCCAGGGGGAAACGCCTGGTATCTTTATA<br>GTCCTGTCGGGTTTCGCCACCTCTGACTTGAGCGTCGATTTTTGTG<br>ATGCTCGTCAGGGGGGCGGAGCCTATGGAAAAACGCCAGCAACG<br>CGGCCTTTTTACGGTTCCTGGCCTTTTGCTGGCCTTTTGCTCACATG<br>TTCTTTCCTGCGTTATCCCCTGATTCTGTGGATAACCGTATTACCGC<br>CTTTGAGTGAGCTGATACCGCTCGCCGCAGCCGAACGACCGAGCG<br>CAGCGAGTCAGTGAGCGAGGAAGCGGAAGAGCGCCCAATACGCA<br>AACCGCCTCTCCCCGCGCGTTGGCCGATTCATTAATG |
| 58 | TALEN Plasmid: Tal5-1 (Plasmid 1288)<br>RVDs: H, NH, NH, NH, NG, NH, NH, HD, HD, NI, NH, HD, HD, NG, NG, NH | GCGTATAATGGACTATTGTGTGCTGATAAGGAGAACATAAGCGCA<br>GAACAATATGTATCTATTCCGGTGTTGTGTTCCTTTGTTATTCTGCT<br>ATTATGTTCTCTTATAGTGTGACGAAAGCAGCATAATTAATCGCCA<br>CTTGTTCTTTGATTGTGTTACGATATCCAGAGACTTAGAAACGGGG<br>GAACCGGGATGAGCAAGGTAAAAATCGGTGAGTTGATCAACACG<br>CTTGTGAATGAGGTAGAGGCAATTGATGCCTCAGACCGCCCACAA<br>GGCGACAAAACGAAGAGAATTAAAGCCGCAGCCGCACGGTATAA<br>GAACGCGTTATTTAATGATAAAAGAAAGTTCCGTGGGAAAGGATT<br>GCAGAAAAGAATAACCGCGAATACTTTTAACGCCTATATGAGCAG<br>GGCAAGAAAGCGGTTTGATGATAAATTACATCATAGCTTTGATAA<br>AAATATTAATAAATTATCGGAAAAGTATCCTCTTTACAGCGAAGA<br>ATTATCTTCATGGCTTTCTATGCCTACGGCTAATATTCGCCAGCAC<br>ATGTCATCGTTACAATCTAAATTGAAAGAAATAATGCCGCTTGCC<br>GAAGAGTTATCAAATGTAAGAATAGGCTCTAAAGGCAGTGATGCA<br>AAAATAGCAAGACTAATAAAAAAATATCCAGATTGGAGTTTTGCT<br>CTTAGTGATTTAAACAGTGATGATTGGAAGGAGCGCCGTGACTAT<br>CTTTATAAGTTATTCCAACAAGGCTCTGCGTTGTTAGAAGAACTAC<br>ACCAGCTCAAGGTCAACCATGAGGTTCTGTACCATCTGCAGCTAA<br>GCCCTGCGGAGCGTACATCTATACAGCAACGATGGGCCGATGTTC<br>TGCGCGAGAAGAAGCGTAATGTTGTGGTTATTGACTACCCAACAT<br>ACATGCAGTCTATCTATGATATTTTGAATAATCCTGCGACTTTATT<br>TAGTTTAAACACTCGTTCTGGAATGGCACCTTTGGCCTTTGCTCTG<br>GCTGCGGTATCAGGGCGAAGAATGATTGAGATAATGTTTCAGGGT<br>GAATTTGCCGTTTCAGGAAAGTATACGGTTAATTTCTCAGGGCAA<br>GCTAAAAAACGCTCTGAAGATAAAAGCGTAACCAGAACGATTTAT<br>ACTTTATGCGAAGCAAAATTATTCGTTGAATTATTAACAGAATTGC<br>GTTCTTGCTCTGCTGCATCTGATTTCGATGAGGTTGTTAAAGGATA<br>TGGAAAGGATGATACAAGGTCTGAGAACGGCAGGATAAATGCTAT<br>TTTAGCAAAAGCATTTAACCCTTGGGTTAAATCATTTTTCGGCGAT<br>GACCGTCGTGTTTATAAAGATAGCCGCGCTATTTACGCTCGCATCG<br>CTTATGAGATGTTCTTCCGCGTCGATCCACGGTGGAAAAACGTCG<br>ACGAGGATGTGTTCTTCATGGAGATTCTCGGACACGACGATGAGA<br>ACACCCAGCTGCACTATAAGCAGTTCAAGCTGGCCAACTTCTCCA<br>GAACCTGGCGACCTGAAGTTGGGGATGAAAACACCAGGCTGGTGG<br>CTCTGCAGAAACTGGACGATGAAATGCCAGGCTTTGCCAGAGGTG<br>ACGCTGGCGTCCGTCTGCATGAAACCGTTAAGCAGCTGGTGGAGC<br>AGGACCCATCAGCAAAAATAACCAACAGCACTCTCCGGGCCTTTA<br>AATTTAGCCCGACGATGATTAGCCGGTACCTGGAGTTTGCCGCTG<br>ATGCATTGGGGCAGTTCGTTGGCGAGAACGGGCAGTGGCAGCTGA |

-continued

| SEQ ID NO | NAME | SEQUENCE |
|---|---|---|
| | | AGATAGAGACACCTGCAATCGTCCTGCCTGATGAAGAATCCGTTG<br>AAACCATCGACGAACCGGATGATGAGTCCCAAGACGACGAGCTG<br>GATGAAGATGAAATTGAGCTCGACGAGGGTGGCGGCGATGAACC<br>AACCGAAGAGGAAGGGCCAGAAGAACATCAGCCAACTGCTCTAA<br>AACCCGTCTTCAAGCCTGCAAAAAATAACGGGGACGGAACGTACA<br>AGATAGAGTTTGAATACGATGGAAAGCATTATGCCTGGTCCGGCC<br>CCGCCGATAGCCCTATGGCCGCAATGCGATCCGCATGGGAAACGT<br>ACTACAGCTAAAAGAAAAGCCACCGGTGTTAATCGGTGGCTTTTT<br>TATTGAGGCCTGTCCCTACCCATCCCCTGCAAGGGACGGAAGGAT<br>TAGGCGGAAACTGCAGCTGCAACTACGGACATCGCCGTCCCGACT<br>GCAGGGACTTCCCCGCGTAAAGCGGGGCTTAAATTCGGGCTGGCC<br>AACCCTATTTTTCTGCAATCGCTGGCGATGTTAGTTTCGTGGATAG<br>CGTTTCCAGCTTTTCAATGGCCAGCTCAAAATGTGCTGGCAGCACC<br>TTCTCCAGTTCCGTATCAATATCGGTGATCGGCAGCTCTCCACAAG<br>ACATACTCCGGCGACCGCCACGAACTACATCGCGCAGCAGCTCCC<br>GTTCGTAGACACGCATGTTGCCCAGAGCCGTTTCTGCAGCCGTTAA<br>TATCCGGCGCAGCTCGGCGATGATTGCCGGGAGATCATCCACGGT<br>TATTGGGTTCGGTGATGGGTTCCTGCAGGCGCGGCGGAGAGCCAT<br>CCAGACGCCGCTAACCCATGCGTTACGGTACTGAAAACTTTGTGCT<br>ATGTCGTTTATCAGGCCCCGAAGTTCTTCTTTCTGCCGCCAGTCCA<br>GTGGTTCACCGGCGTTCTTAGGCTCAGGCTCGACAAAAGCATACT<br>CGCCGTTTTTCCGGATAGCTGGCAGAACCTCGTTCGTCACCCACTT<br>GCGGAACCGCCAGGCTGTCGTCCCCTGTTTCACCGCGTCGCGGCA<br>GCGGAGGATTATGGTGTAGAGGCCAGATTCCGATACCACATTTAC<br>TTCCCTGGCCATCCGATCAAGTTTTTGTGCCTCGGTTAAACCGAGG<br>GTCAATTTTTCATCATGATCCAGCTTACGCAATGCATCAGAAGGGT<br>TGGCTATATTCAATGCAGCACAGATATCCAGCGCCACAAACCACG<br>GGTCACCACCGACAAGAACCACCCGTATAGGGTGGCTTTCCTGAA<br>ATGAAAAGACGGAGAGAGCCTTCATTGCGCCTCCCCGGATTTCAG<br>CTGCTCAGAAAGGGACAGGGAGCAGCCGCGAGCTTCCTGCGTGAG<br>TTCGCGCGCGACCTGCAGAAGTTCCGCAGCTTCCTGCAAATACAG<br>CGTGGCCTCATAACTGGAGATAGTGCGGTGAGCAGAGCCCACAAG<br>CGCTTCAACCTGCAGCAGGCGTTCCTCAATCGTCTTCAGCAGGCCC<br>TGGGCGTTTAACTGAATCTGGTTCATGCGATCACCTCGCTGACCGG<br>GATACGGGCTGACAGAACGAGGACAAAACGGCTGGCGAACTGGC<br>GACGAGCTTCTCGCTCGGATGATGCAGTGGTGGAAAGGCGGTGGA<br>TATGGGATTTTTTGTCCGTGCGGACGACAGCTGCAAATTTGAATTT<br>GAACATGGTATGCATTCCTATCTTGTATAGGGTGCTACCACCAGAG<br>TTGAGAATCTCTATAGGGGTGGTAGCCCAGACAGGGTTCTCAACA<br>CCGGTACAAGAAGAAACCGGCCCAACCGAAGTTGGCCCCATCTGA<br>GCCACCATAATTCAGGTATGCGCAGATTTAACACACAAAAAAACA<br>CGCTGGCGCGTGTTGTGCGCTTCTTGTCATTCGGGGTTGAGAGGCC<br>CGGCTGCAGATTTTGCTGCAGCGGGGTAACTCTACCGCCAAAGCA<br>GAACGCACGTCAATAATTTAGGTGGATATTTTACCCCGTGACCAGT<br>CACGTGCACAGGTGTTTTTATAGTTTGCTTTACTGACTGATCAGAA<br>CCTGATCAGTTATTGGAGTCCGGTAATCTTATTGATGACCGCAGCC<br>ACCTTAGATGTTGTCTCAAACCCCATACGGCCACGAATGAGCCAC<br>TGGAACGGAATAGTCAGCAGGTACAGCGGAACGAACCACAAACG<br>GTTCAGACGCTGCCAGAACGTCGCATCACGACGTTCCATCCATTCG<br>GTATTGTCGACGACCTGGTAAGCGTATTGTCCTGGCGTTTTTGCTG<br>CTTCCGAGTAGCAATCCTCTTCACCACAAAGAAAGTTACTTATCTG<br>CTTCCAGTTTTCGAACCCTTCTTCTTTGAGCCGCTTTTCCAGCTCAT<br>TCCTCCACAAAACAGGCACCCATCCTCTGCGATAAATCATGATTAT<br>TTGTCCTTTAAATAAGGCTGTAGAACTGCAAAATCGCTCTCGTTCA<br>CATGCTGTACGTAGATGCGTAGCAAATTGCCGTTCCATCCCTGTAA<br>TCCACCTTCTTTGGAAAGATCGTCCTTGACCTCACGAAGAACTTTA<br>TCCAATAGCCCTGCGGCACAAGAAATTGCCTGCTCTGGATCAGCA<br>AATTCATATTGATTAATAGGTGATTGCCACACACCAAAAACAGGA<br>ATCATCTTTTCGGCTAAACGCCTCTCCTGTTCTTTCTTAATCTCAAG<br>TTGTAAGCGGACCAGCTCACCATCCATCATTTTTTGTAGATCATGC<br>GCCACTATTCACCCCCACTGGCCATCAGCAAATAAAGCTTCATACT<br>CGGACACCGGCAGGCGGCTTCCACGGATTGAAAGGTCAAGCCAAC<br>CACGTCCAGATGGGTCAGCCTTATCCGATTCTTCCCACCGTTCTGC<br>AGCTGTAGCAACCAGGCATTCTACCGCCTTCATGTAGTCTTCTGTA<br>CGGAACCAGCCGTAGTTAATGCCACCATCAGTAACTGCCCAGGCC<br>ATCTTTTTCTCTTCGGCCTCAATAGCCCGGATGCGGTTATCGCACA<br>GCTCGCGACAGTACTTCAGCTGTTCGTAATCCAGTTGCTTCAGGAA<br>CTCTGGTGTCGACGTCATAGTGGCTTCACCTTATAGGCTTTTAGAA<br>GCGCCCTGGCTTCGTCTGTGTGGTCTTCCATGCTCTTATCGCTGGC<br>AATGCAGCAATAAACTCCCTCACTATCTGAGAACCCGTTCATCCG<br>AATGATCGTGAATGGAAGTTCCCGGCCAGTTTTATAATCGCTATAG<br>CTTGTCGCGTCGTGGCTGACCTTGACCACATAAGGGTCGTAGCCCT<br>CCACGATGACAAGGCATTCCCGTTGTTTTCCCATTACCCCTCCGGT<br>TATATCGCCACGGCTTGCCGCTGGCTTAGAAACGCTTTCAGCAGCC<br>TTATTTCGCGTACTGATAGCAGGTCCATAAATTCGGTCATGTACAG |

-continued

| SEQ ID NO | NAME | SEQUENCE |
|---|---|---|
| | | CGAGGCGAACGTTCTCGCGATGCTGGCCACTGGCCACAGGCGTAC |
| | | CGCCTCCATTTCGGTTGCTGGCAACGCGTTCTCCGCCCACGCCTCC |
| | | GGTACCGCCACCGGGATAGCCTCCAGTGCCTGGATAATTACTGAT |
| | | TGTGGGGCGTCCGGAACGTGCTCTGTTTTGGATCGAGGGTTACCAT |
| | | GTATATCTATATTTAGATCCAAATCGCGATCCACTTCGATGGTGGT |
| | | TTTTTCCACCTTACGTGCGTGAATTGATAAACCGGCCTCGCGGCGC |
| | | TTCTCCACGATATTCATGAGGAACTCGACCGAGTCCGGGTCAATG |
| | | GAACGCATCGTGGGGCGTGCATCGCCATCTCTGGCGCGTCTGGTCT |
| | | TACTGGATAGCCCCATAGACTCCAGGATGCCTATGCAGAGGTCTG |
| | | CAGGCGCTTTCTTCTTGCCTTTCTCTGTGTTGAAGCCGCCGATGCG |
| | | TAAAACGTTGTTTAGCAGATCGCGCCGTTCCGGCGTGAGCAGGTT |
| | | ATCTCTGGCGCGTTTGAGGGCGTCCATGTCTGCTTCACCTTCCAGG |
| | | GTTTTTGGATCGATACCGCAGTCGCGGAAGTACTGCTGCAGCGTC |
| | | GCCGATTTGAGGGTGTAGAAACCACGCATGCCTATCTCAACAGCA |
| | | GGGGTCGATTTCACTCGGTAATCGGTTATGGCCGGGAATTTAGCCT |
| | | GGAACTCTGCGTCGGCCTGTTCCCGCGTCATGGCCGTAGTGACGA |
| | | ACTGCTGCCATCTTCCGGCAACGCGATAAGCGTAGGTAAAGTGAA |
| | | TCAACGCTTCTTCACGGTCAAGGCGACGGGCGGTTATCTCATCCAG |
| | | CTGCATGGTTTCAAACAGGCGCACTTTTTTCAGGCCGCCGTCGAAA |
| | | TAGAATTTTAACGCCACCTCGTCGACATCCAGCTGCAGCTCCTTTT |
| | | CGATGTCCCAGCGGACCAGCTGGGCCTGCTCATCCAGGGACAGGG |
| | | TGCGTTTTTTTATCAACTCATCGTGTTCGGCCTGGTCAGGAGTATC |
| | | GACACTCAGGTGGCGCTCCATAAGCTGCTCAAAGACCAGTTCACG |
| | | GGCTTCTTTACGTAAATCCTTACCGATGCTGTTTGCAAGCGCGTCG |
| | | GTGGCCATAGGCGCGACCTGATAGCCATCATCATGCATGATGCAA |
| | | ATCATGTTGCTGGCATAATCATTTCTGGCCGATGCCTCGAGCGCGG |
| | | CGGCTTTAATTTTGAGCTGCATGAATGAAGAGTTAGCCACGCCGA |
| | | GTGAAATTCGGTCACCGTCAAAGACAACGTCTGTCAGCAGCCCGG |
| | | AGTGGCCAGCCGTTTCGAGCAAGGCCTGCGCGTAGGCGCGTTTGA |
| | | TTTTTTCCGGATCGGTTTCACGTTTACCGCGAAGCTTGTCGAAACC |
| | | GATAATGTATTCCTGAGCTGTACGGTCGCGGCGCAGCATCTGGAT |
| | | GGCGTCGCTGGGGACCACTTCGCCGCAGAACATGCCGAAATGGCG |
| | | GTGGAAGTGTTTCTCCTCAATCGATACACCTGAAGATATCGACGG |
| | | GCTGTAGATGAGGCCGTCATATTTTTTCACCATCACTTTAGGCTGG |
| | | TTGGTGAAATCGTCGACTTCCTTCTCCTGTTTGTTTTTCTGGTTAAC |
| | | GCAGAGAAACTTTTTGTCAGGGAACTGTAGTCTCAGCTGCATGGT |
| | | AACGTCTTCGGCGAACGTCGAACTGTCGGTGGCCAGCATGATTCG |
| | | TTCGCCGCGTTGCACTGCAGCGATAACCTCGGTCATGATCCGATTT |
| | | TTCTCGGTATAAAATACGCGGATAGGCTTGTTGGTTTCGCGGTTGC |
| | | GAACGTCGACCGGGAGTTCAATCACGTGAATTTGCAGCCAGGCAG |
| | | GTAGGCCCAGCTCCTCGCGTCGCTTCATCGCCAGTTCAGCCAGGTC |
| | | AACAAGCAGATCGTTGGCATCGGCATCCACCATAATGGCATGCTC |
| | | TTCAGTACGCGCCAGCGCGTCGATAAGCGTGTTGAATACGCCTAC |
| | | CGGGTTTTCCATCGCACGCCCGGCCAGAATGGCACGCAGGCCCTG |
| | | TGTTGCTTCATCGAAGCCGAAGAAGTCATGCTGGCGCATCAGCGG |
| | | TTGCCAGCAGCCTTTAAGTATGGAGTTGATGCAAATAGTCAGCTTG |
| | | TTGGCATATGGCGCCATTTCCTGATAGCCGGGATCCTGATAATGCA |
| | | GAATGTCGGCTTTCGCGCCTTTCCCTTCGGTCATCATTTCATGCAG |
| | | GCCGCCTATCAGGGATACGCGGTGCGCGACGGAAACGCCACGCGT |
| | | GGACTGCAGCATCAGTGGACGCAGGAGGCCTGTCGATTTACCCGA |
| | | CCCCATCCCGGCGCGGACAATAACGATGCCCTGCAGCTGTGCGGC |
| | | GTATGTCATCACCTCATCGGTCATCCTGGAGGTTTCAAACCGTTTG |
| | | TAAGTGATGTGTGACGGGCGAAGGTTCGGGTTGGTGATGCGTTCA |
| | | CTGAACGAACGTGATGTTTGCGCGGCACGGCATTTGCGATTCAAC |
| | | CGGCGCGTAATGTGATCTTTAACGGTACCGTTATAAATTTCTGCGA |
| | | TACCCATATCCCGCAGCGTGCTGCTGAAAAGGCGCATAAGTTCTTT |
| | | CGGGCTGTTTGGTACCGGGCATGTCAGCATGCCAATATCAACGGC |
| | | GCGAAGCAGTTCTTTGGCAAAAGTGCGTCTGTTCAGACGCGGGAG |
| | | AGTACGCAGCTTATTCAGCGTGATCGACAACAGATCGGTTGCACG |
| | | GCTCAGATGATTTCTCGTTAACTGGCGAGCGACTTCCTTCAGCCCT |
| | | CTCAGGCTGTGCAGGTCGTTAAAATCGCTGCATTCCAGCTCAGGGT |
| | | CATCCTCAAAAGTTGGGTAAACACATTTGACGCCGGAAAACTTCT |
| | | CCATGATGTCGAATCCGGTGCGGAGGCCTGTGTTGCCTTTTCCTTC |
| | | AGCTGAGGATTTGCGGTCGTTATCGAGAGCGCAAGTGATTTGCGC |
| | | AGCCGGGTACATGTTCACCAGCTGCTCGACAACGTGAATCATGTT |
| | | GTTAGCGGAAACCGCAATGACTACCGCGTCAAAGCGTTTTTTCGG |
| | | GTCGTTTCTGGTCGCCAGCCAGATGGATGCCCCGGTGGCGAAACC |
| | | CTCTGCAGTCGCAATTTTTTGCGCCCCCTGCAGGTCGCCAATAACA |
| | | AAGCATGCACCGACGAAATCACCGTTAGTGATGGCGCTGGTCTGG |
| | | AACTTGCCACCATTCAGATCGATACGTTGCCAGCCAACAATCCGC |
| | | CCGTCTTTTCTTCCGTCCAGGTGGGACAGAGGTATCGCCATGTAAG |
| | | TTGTTGGTCCACGGCTCCATTTCGCACTGTCGTGACTGGTCACGCG |
| | | ACGTATATCACAAGCGCCAAATACGTCACGAATTCCCTTTTTTACC |
| | | GCATAAGGCCAGGAGCCATCTTCAGCTGGCGAATGTTCCCAGGCG |
| | | CGATGGAAAGCCAACCATCCAAGCAGGCGTTCCTGCTCCATCTGA |

-continued

| SEQ ID NO | NAME | SEQUENCE |
|---|---|---|
| | | TTGTTTTTTAAATCATTAACGCGTTGTTGTTCAGCTCGGAGGCGGC<br>GTGCTTCAGCCTGGCGCTCCATGCGTGCACGTTCTTCTTCCGGCTG<br>AGCGACCACGGTCGCACCATTCCGTTGCTGTTCACGGCGATACTCC<br>GAAAACAGGAATGAAAAGCCACTCCAGGAGCCAGCGTCATGCGC<br>TTTTTCAACGAAGTTAACGAAAGGATAACTGATGCCATCCTTGCTC<br>TGCTCAAGGCGTGAATAGATTTCCACACGGCCTTTAAGGCTCTTCT<br>GCAGAGCTTCCGGGGAGGAATTATTGTAGGTGGTATAGCGCTCTA<br>CACCACCGCGCGGATTGAGCTGAATCTTATCAGCACACGCAGGCC<br>AGTTGATACCGGCCATCTTCGCCAGCTCAGTCAGCTCATCACGTGC<br>CGCGTCAAGCAGTGAAAACGGATCGCTGCCAAAGCGCTCCGCGTA<br>GAATTCTTGTAAGGTCATTTTTTAGCCTTTCCATGCGAATTAGCAT<br>TTTTTCGGGTTGAAAAAATCCGCAGGAGCAGCCACAATAAACGCA<br>CTATCTTTCTGAAGGACGTATCTGCGTTATCGTGGCTACTTCCTGA<br>AAAAGGCCCGAGTTTGCCGACTCGGTTTTTTTTCGTCTTTTTTCGG<br>CTGCTACGGTCTGGTTCAACCCCGACAAAGTATAGATCGGATTAA<br>ACCAGAATTATAGTCAGCAATAAACCCTGTTATTGTATCATCTACC<br>CTCAACCATGAACGATTTGATCGTACCGACTACTTGGTGCACAAAT<br>TGAAGATCACTTTTATCATGGATAACCCGTTGAGAGTTAGCACTAT<br>CAAGGTAGTAATGCTGCTCGTCATAACGGGCTAATCGTTGAATTGT<br>GATCTCGCCGTTATTATCACAAACCAGTACATCCTCACCCGGTACA<br>AGCGTAAGTGAAGAATCGACCAGGATAACATCTCCCGGCTGGTAG<br>TTTCGCTGAATCTGGTTCCCGACCGTCAGTGCGTAAACGGTGTTCC<br>GTTGACTCACGAACGGCAGGAATCGCTCTGTGTTGGCAGGTTCTCC<br>AGGCTGCCAGTCTCTATCCGGTCCTGTCTCTGTCGTACCAATAACA<br>GGAACGCGGTCTGGATCAGATTCAGTGCCATACAGTATCCATTGC<br>ACGGGCTTACGCAGGCATTTTGCCAGCGATAGCCCGATCTCCAGC<br>GACGGCATCACGTCGCCACGTTCTAAGTTTTGGACGCCCGGAAGA<br>GAGATTCCTACAGCTTCTGCCACTTGCTTCAGCGTCAGTTTCAGCT<br>CTAAACGGCGTGCTTTCAGTCGTTCGCCTCGTGTTTTCATACCCTT<br>AATCATAAATGATCTCTTTATAGCTGGCTATAATTTTTATAAATTA<br>TACCTAGCTTTAATTTTCACTTATTGATTATAATAATCCCCATGAA<br>ACCCGAAGAACTTGTGCGCCATTTCGGCGATGTGGAAAAAGCAGC<br>GGTTGGCGTGGGCGTGACACCCGGCGCAGTCTATCAATGGCTGCA<br>AGCTGGGGAGATTCCACCTCTACGACAAAGCGATATAGAGGTCCG<br>TACCGCGTACAAATTAAAGAGTGATTTCACCTCTCAGCGCATGGG<br>TAAGGAAGGGCATAACAAGGGGATCCTCTAGACGCAGAAAGGCC<br>CACCCGAAGGTGAGCCAGTGTGATTACATTTGCGGCCTAACTGTG<br>GCCAGTCCAGTTACGCTGGAGTCACTAGTGCGGCCGCGACAACTT<br>GTCTAGGGCCCAATGGCCCATACACTTAGTGTAATACGACTCACT<br>ATAGGGAGAGCGGCCGCTTTTTCAGCAAGATTAAGCCGCCACCAT<br>GGCGCCGCGGCCTCCTAAGAAGAAGCGGAAAGTCGAATTCGTGGA<br>TCTGCGAACACTGGGCTATAGCCAGCAGCAGCAGGAGAAGATCAA<br>ACCCAAGGTGAGGTCCACAGTCGCACAGCACCATGAAGCCCTGGT<br>GGGCCACGGGTTCACTCACGCTCATATTGTCGCACTGTCTCAGCAT<br>CCAGCCGCTCTGGGAACCGTGGCAGTCACATACCAGCACATCATT<br>ACTGCCCTGCCCGAGGCTACCCATGAAGACATCGTGGGAGTCGGC<br>AAACAGTGGAGCGGCGCACGGGCCCTGGAGGCTCTGCTGACCGAC<br>GCAGGGGAACTGAGAGGACCCCCTCTGCAGCTGGATACAGGGCA<br>GCTGGTGAAGATTGCTAAGAGGGGAGGGGTGACAGCAATGGAAG<br>CCGTCCACGCAAGCAGGAACGCACTGACAGGGGCCCCCCTGAACC<br>TGACCCCGGACCAAGTGGTGGCTATCGCCAGCAATCACGGCGGCA<br>AGCAAGCGCTCGAAACGGTGCAGCGGCTGTTGCCGGTGCTGTGCC<br>AGGACCATGGCCTGACCCCGGACCAAGTGGTGGCTATCGCCAGCA<br>ATCACGGCGGCAAGCAAGCGCTCGAAACGGTGCAGCGGCTGTTGC<br>CGGTGCTGTGCCAGGACCATGGCCTGACCCCGGACCAAGTGGTGG<br>CTATCGCCAGCAATCACGGCGGCAAGCAAGCGCTCGAAACGGTGC<br>AGCGGCTGTTGCCGGTGCTGTGCCAGGACCATGGCCTGACCCCGG<br>ACCAAGTGGTGGCTATCGCCAGCAACGGTGGCGGCAAGCAAGCGC<br>TCGAAACGGTGCAGCGGCTGTTGCCGGTGCTGTGCCAGGACCATG<br>GCCTGACCCCGGACCAAGTGGTGGCTATCGCCAGCAACGGTGGCG<br>GCAAGCAAGCGCTCGAAACGGTGCAGCGGCTGTTGCCGGTGCTGT<br>GCCAGGACCATGGCCTGACCCCGGACCAAGTGGTGGCTATCGCCA<br>GCAATCACGGTGGAAAACAGGCCCTTGAAACGGTGCAGCGGCTGT<br>TGCCGGTGCTGTGCCAGGACCATGGCCTGACCCCGGACCAAGTGG<br>TGGCTATCGCCAGCAATCACGGCGGCAAGCAAGCGCTCGAAACGG<br>TGCAGCGGCTGTTGCCGGTGCTGTGCCAGGACCATGGCCTGACTC<br>CGGACCAAGTGGTGGCTATCGCCAGCCACGATGGCGGCAAGCAAG<br>CGCTCGAAACGGTGCAGCGGCTGTTGCCGGTGCTGTGCCAGGACC<br>ATGGCCTGACTCCGGACCAAGTGGTGGCTATCGCCAGCCACGATG<br>GCGGCAAGCAAGCGCTCGAAACGGTGCAGCGGCTGTTGCCGGTGC<br>TGTGCCAGGACCATGGCCTGACCCCGGACCAAGTGGTGGCTATCG<br>CCAGCAACATTGGCGGCAAGCAAGCGCTCGAAACGGTGCAGCGG<br>CTGTTGCCGGTGCTGTGCCAGGACCATGGCCTGACCCCGGACCAA<br>GTGGTGGCTATCGCCAGCAATCACGGCGGCAAGCAAGCGCTCGAA<br>ACGGTGCAGCGGCTGTTGCCGGTGCTGTGCCAGGACCATGGCCTG |

-continued

| SEQ ID NO | NAME | SEQUENCE |
|---|---|---|
| | | ACTCCGGACCAAGTGGTGGCTATCGCCAGCCACGATGGCGGCAAG<br>CAAGCGCTCGAAACGGTGCAGCGGCTGTTGCCGGTGCTGTGCCAG<br>GACCATGGCCTGACTCCGGACCAAGTGGTGGCTATCGCCAGCCAC<br>GATGGCGGCAAGCAAGCGCTCGAAACGGTGCAGCGGCTGTTGCCG<br>GTGCTGTGCCAGGACCATGGCCTGACCCCGGACCAAGTGGTGGCT<br>ATCGCCAGCAACGGTGGCGGCAAGCAAGCGCTCGAAACGGTGCA<br>GCGGCTGTTGCCGGTGCTGTGCCAGGACCATGGCCTGACCCCGGA<br>CCAAGTGGTGGCTATCGCCAGCAACGGTGGCGGCAAGCAAGCGCT<br>CGAAACGGTGCAGCGGCTGTTGCCGGTGCTGTGCCAGGACCATGG<br>CCTGACCCCGGACCAAGTGGTGGCTATCGCCAGCAATCACGGCGG<br>CAAGCAAGCGCTCGAAAGCATTGTGGCCCAGCTGAGCCGGCCTGA<br>TCCGGCGTTGGCCGCGTTGACCAACGACCACCTGGTCGCTCTGGCT<br>TGCCTGGGAGGACGCCCTGCTATGGACGCTGTGAAGAAAGGACTG<br>CCCCACGCACCCGAACTGATTAGACGGGTGAACCGGAGAATCGGC<br>GAGAGAACATCCCATAGGGTGGCAATCTCTAGAACTCAGCTGGTC<br>AAGAGTGAACTGGAGGAAAAGAAATCAGAGCTGCGCCACAAGCT<br>GAAATACGTGCCTCATGAGTATATCGAACTGATCGAGATTGCTCG<br>CAATTCAACCCAGGACCGGATCCTGGAAATGAAAGTGATGGAGTT<br>CTTTATGAAAGTCTACGGATATCGGGGGAAACACCTGGGAGGGAG<br>CAGAAAGCCAGATGGGGCCATCTACACAGTGGGATCCCCCATCGA<br>CTATGGCGTGATTGTCGATACTAAAGCCTACAGCGGAGGCTATAA<br>CCTGCCTATCGGCCAGGCTGACGAGATGCAGAGATACGTGGAGGA<br>AAACCAGACCCGCAATAAGCATATTAACCCCAATGAATGGTGGAA<br>AGTGTATCCTAGCTCCGTCACAGAGTTCAAGTTTCTGTTCGTGAGC<br>GGACACTTTAAGGGCAACTACAAAGCACAGCTGACTAGGCTGAAT<br>CATATCACCAACTGCAATGGAGCCGTGCTGTCTGTCGAGGAACTG<br>CTGATCGGGGGAGAGATGATTAAGGCTGGCACACTGACTCTGGAG<br>GAAGTGAGGCGCAAGTTCAACAATGGGGAAATCAACTTCTAACCT<br>GCAGGATGATAAGCTAGCCCCGGGCGTACGGAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAACGAGACCTTAGGGCCATTAGACTTGAAGTCAAG<br>CGGCCGCTTACAACTGGACCTTGCTGGTACATAGAACTGATTAACT<br>GACCATTTAAATCATACCAACATGGTCAAATAAAACGAAAGGCTC<br>AGTCGAAAGACTGGGCCTTTCGTTTTAATCTGATCGGCACGTAAG<br>AGGTTCCAACTTTCACCATAATGAAATAAGATCACTACCGGGCGT<br>ATTTTGAGTTATCGAGATTTTCAGGAGCTAAGGAAGCTAAAATGA<br>GCCATATTCAACGGGAAACGTCTTGCTCGAGGCCGCGATTAAATT<br>CCAACATGGATGCTGATTTATATGGGTATAAATGGGCTCGCGATA<br>ATGTCGGGCAATCAGGTGCGACAATCTATCGATTGTATGGGAAGC<br>CCGATGCGCCAGAGTTGTTTCTGAAACATGGCAAAGGTAGCGTTG<br>CCAATGATGTTACAGATGAGATGGTCAGGCTAAACTGGCTGACGG<br>AATTTATGCCTCTTCCGACCATCAAGCATTTTATCCGTACTCCTGA<br>TGATGCATGGTTACTCACCACTGCGATCCCAGGGAAAACAGCATT<br>CCAGGTATTAGAAGAATATCCTGATTCAGGTGAAAATATTGTTGA<br>TGCGCTGGCAGTGTTCCTGCGCCGGTTGCATTCGATTCCTGTTTGT<br>AATTGTCCTTTTAACGGCGATCGCGTATTTCGTCTGGCTCAGGCGC<br>AATCACGAATGAATAACGGTTTGGTTGGTGCGAGTGATTTTGATG<br>ACGAGCGTAATGGCTGGCCTGTTGAACAAGTCTGGAAAGAAATGC<br>ATAAACTTTTGCCATTCTCACCGGATTCAGTCGTCACTCATGGTGA<br>TTTCTCACTTGATAACCTTATTTTTGACGAGGGGAAATTAATAGGT<br>TGTATTGATGTTGGACGAGTCGGAATCGCAGACCGATACCAGGAT<br>CTTGCCATCCTATGGAACTGCCTCGGTGAGTTTTCTCCTTCATTAC<br>AGAAACGGCTTTTTCAAAAATATGGTATTGATAATCCTGATATGA<br>ATAAATTGCAGTTTCACTTGATGCTCGATGAGTTTTTCTAACCTAG<br>GTGACAGAAGTCAAAAGCCTCCGGTCGGAGGCTTTTGACTTTCTG<br>CTAGATCTGTTTCAATGCGGTGAAGGGCCAGGCAGCTGGGGATTA<br>TGTCCAGACCCGGCCAGCATGTTGGTTTTATCGCATATTCAGCGTT<br>GTCGCGTTTACCCAGGTAAAATGGAAGCAGTGTATCGTCTGCGTG<br>AATGTGCAAATCAGGAACGTAACCGTGGTACATAGATGCAGTCCC<br>TTGCGGGTCGTTCCCTTCAACGAGTAGGACGCGGTGCCCTTGCAA<br>GGCTAACCATTGCGCCTGGTGTACTGCAGATGAGGTTTTATAAACC<br>CCTCCCTTGTGTGACATAACGGAAAGTACAACCGGGTTTTTATCGT<br>CAGGTCTTTGGTTTGGGTTACCAAACACACTCCGCATATGGCTAAT<br>TTGGTCAATTGTGTAGCCAGCGCGACGTTCTACTCGGCCCCTCATC<br>TCAAAATCAGGAGCCGGTAGACGACCAGCTTTTTCCGCATCTCTG<br>ATAGCCTGCGGTGTTACGCCGATCAGGTCTGCAACTTCTGTTATAC<br>CCCAGCGGCGAGTAATACGACGCGCTTCCGGGCTGTCATCGCCGA<br>ACTGTGCGATGGCAATAGCGCGCGTCATTTCCTGACCGCGATTGAT<br>ACAGTCTTTCAGCAAATTAATTAACGACATCCTGTTTCCTCTCAAA |

-continued

| SEQ ID NO | NAME | SEQUENCE |
|---|---|---|
| | | CATGCCCTTATCTTTGTGTTTTTCATCATACTTTACGTTTTTAAAGC |
| | | AAAGCAACATAAAAAAAGCAAAGTGACTTAGAAAACGCAAAGTT |
| | | AAGGTTCAAATCAATTTTTTGATGCGCTACAGAAGCTATTTAGCTT |
| | | CATCTAAGCGCAACGGTATTACTTACGTTGGTATATTTAAAACCTA |
| | | ACTTAATGATTTTAAATGATAATAAATCATACCAATTGCTATCAAA |
| | | AGTTAAGCGAACATGCTGATTTTCACGCTGTTTATACACTTTGAGG |
| | | CATCTCTATCTCTTCTGTCTCTATATTGAAACACAATCAAAGAACA |
| | | TCAATCCATGTGACATCCCCCACTATCTAAGAACACCATAACAGA |
| | | ACACAACATAGGAATGCAACATTAATGTATCAATAATTCGGAACA |
| | | TATGCACTATATCATATCTCAATTACGGAACATATCAGCACACAAT |
| | | TGCCCATTATACGC |
| 59 | TALEN Plasmid: | GCGTATAATGGACTATTGTGTGCTGATAAGGAGAACATAAGCGCA |
| | Tal5-2 (Plasmid | GAACAATATGTATCTATTCCGGTGTTGTGTTCCTTTGTTATTCTGCT |
| | 1287) | ATTATGTTCTCTTATAGTGTGACGAAAGCAGCATAATTAATCGCCA |
| | RVDs: NH, NH, | CTTGTTCTTTGATTGTGTTACGATATCCAGAGACTTAGAAACGGGG |
| | NG, HD, NI, NI, | GAACCGGGATGAGCAAGGTAAAAATCGGTGAGTTGATCAACACG |
| | NH, NG, NG, NG, | CTTGTGAATGAGGTAGAGGCAATTGATGCCTCAGACCGCCCACAA |
| | NH, HD, HD, NG, | GGCGACAAAACGAAGAGAATTAAAGCCGCAGCCGCACGGTATAA |
| | NG, NH, NG, HD | GAACGCGTTATTTAATGATAAAAGAAAGTTCCGTGGGAAAGGATT |
| | | GCAGAAAAGAATAACCGCGAATACTTTTAACGCCTATATGAGCAG |
| | | GGCAAGAAAGCGGTTTGATGATAAATTACATCATAGCTTTGATAA |
| | | AAATATTAATAAATTATCGGAAAAGTATCCTCTTTACAGCGAAGA |
| | | ATTATCTTCATGGCTTTCTATGCCTACGGCTAATATTCGCCAGCAC |
| | | ATGTCATCGTTACAATCTAAATTGAAAGAAATAATGCCGCTTGCC |
| | | GAAGAGTTATCAAATGTAAGAATAGGCTCTAAAGGCAGTGATGCA |
| | | AAAATAGCAAGACTAATAAAAAAATATCCAGATTGGAGTTTTGCT |
| | | CTTAGTGATTTAAACAGTGATGATTGGAAGGAGCGCCGTGACTAT |
| | | CTTTATAAGTTATTCCAACAAGGCTCTGCGTTGTTAGAAGAACTAC |
| | | ACCAGCTCAAGGTCAACCATGAGGTTCTGTACCATCTGCAGCTAA |
| | | GCCCTGCGGAGCGTACATCTATACAGCAACGATGGGCCGATGTTC |
| | | TGCGCGAGAAGAAGCGTAATGTTGTGGTTATTGACTACCCAACAT |
| | | ACATGCAGTCTATCTATGATATTTTGAATAATCCTGCGACTTTATT |
| | | TAGTTTAAACACTCGTTCTGGAATGGCACCTTTGGCCTTTGCTCTG |
| | | GCTGCGGTATCAGGGCGAAGAATGATTGAGATAATGTTTCAGGGT |
| | | GAATTTGCCGTTTCAGGAAAGTATACGGTTAATTTCTCAGGGCAA |
| | | GCTAAAAAACGCTCTGAAGATAAAAGCGTAACCAGAACGATTTAT |
| | | ACTTTATGCGAAGCAAAATTATTCGTTGAATTATTAACAGAATTGC |
| | | GTTCTTGCTCTGCTGCATCTGATTTCGATGAGGTTGTTAAAGGATA |
| | | TGGAAAGGATGATACAAGGTCTGAGAACGGCAGGATAAATGCTAT |
| | | TTTAGCAAAAGCATTTAACCCTTGGGTTAAATCATTTTTCGGCGAT |
| | | GACCGTCGTGTTTATAAAGATAGCCGCGCTATTTACGCTCGCATCG |
| | | CTTATGAGATGTTCTTCCGCGTCGATCCACGGTGGAAAAACGTCG |
| | | ACGAGGATGTGTTCTTCATGGAGATTCTCGGACACGACGATGAGA |
| | | ACACCCAGCTGCACTATAAGCAGTTCAAGCTGGCCAACTTCTCCA |
| | | GAACCTGGCGACCTGAAGTTGGGGATGAAAACACCAGGCTGGTGG |
| | | CTCTGCAGAAACTGGACGATGAAATGCCAGGCTTTGCCAGAGGTG |
| | | ACGCTGGCGTCCGTCTGCATGAAACCGTTAAGCAGCTGGTGGAGC |
| | | AGGACCCATCAGCAAAAATAACCAACAGCACTCTCCGGGCCTTTA |
| | | AATTTAGCCCGACGATGATTAGCCGGTACCTGGAGTTTGCCGCTG |
| | | ATGCATTGGGGCAGTTCGTTGGCGAGAACGGGCAGTGGCAGCTGA |
| | | AGATAGAGACACCTGCAATCGTCCTGCCTGATGAAGAATCCGTTG |
| | | AAACCATCGACGAACCGGATGATGAGTCCCAAGACGACGAGCTG |
| | | GATGAAGATGAAATTGAGCTCGACGAGGGTGGCGGCGATGAACC |
| | | AACCGAAGAGGAAGGGCCAGAAGAACATCAGCCAACTGCTCTAA |
| | | AACCCGTCTTCAAGCCTGCAAAAAATAACGGGGACGGAACGTACA |
| | | AGATAGAGTTTGAATACGATGGAAAGCATTATGCCTGGTCCGGCC |
| | | CCGCCGATAGCCCTATGGCCGCAATGCGATCCGCATGGGAAACGT |
| | | ACTACAGCTAAAAGAAAAGCCACCGGTGTTAATCGGTGGCTTTTT |
| | | TATTGAGGCCTGTCCCTACCCATCCCCTGCAAGGGACGGAAGGAT |
| | | TAGGCGGAAACTGCAGCTGCAACTACGGACATCGCCGTCCCGACT |
| | | GCAGGGACTTCCCCGCGTAAAGCGGGGCTTAAATTCGGGCTGGCC |
| | | AACCCTATTTTTCTGCAATCGCTGGCGATGTTAGTTTCGTGGATAG |
| | | CGTTTCCAGCTTTTCAATGGCCAGCTCAAAATGTGCTGGCAGCACC |
| | | TTCTCCAGTTCCGTATCAATATCGGTGATCGGCAGCTCTCCACAAG |
| | | ACATACTCCGGCGACCGCCACGAACTACATCGCGCAGCAGCTCCC |
| | | GTTCGTAGACACGCATGTTGCCCAGAGCCGTTTCTGCAGCCGTTAA |
| | | TATCCGGCGCAGCTCGGCGATGATTGCCGGGAGATCATCCACGGT |
| | | TATTGGGTTCGGTGATGGGTTCCTGCAGGCGCGGCGGAGAGCCAT |
| | | CCAGACGCCGCTAACCCATGCGTTACGGTACTGAAAACTTTGTGCT |
| | | ATGTCGTTTATCAGGCCCCGAAGTTCTTCTTTCTGCCGCCAGTCCA |
| | | GTGGTTCACCGGCGTTCTTAGGCTCAGGCTCGACAAAAGCATACT |
| | | CGCCGTTTTTCCGGATAGCTGGCAGAACCTCGTTCGTCACCCACTT |
| | | GCGGAACCGCCAGGCTGTCGTCCCCTGTTTCACCGCGTCGCGGCA |
| | | GCGGAGGATTATGGTGTAGAGGCCAGATTCCGATACCACATTTAC |

-continued

| SEQ ID NO | NAME | SEQUENCE |
| --- | --- | --- |
| | | TTCCCTGGCCATCCGATCAAGTTTTGTGCCTCGGTTAAACCGAGG<br>GTCAATTTTTCATCATGATCCAGCTTACGCAATGCATCAGAAGGGT<br>TGGCTATATTCAATGCAGCACAGATATCCAGCGCCACAAACCACG<br>GGTCACCACCGACAAGAACCACCCGTATAGGGTGGCTTTCCTGAA<br>ATGAAAAGACGGAGAGAGCCTTCATTGCGCCTCCCCGGATTTCAG<br>CTGCTCAGAAAGGGACAGGGAGCAGCCGCGAGCTTCCTGCGTGAG<br>TTCGCGCGCGACCTGCAGAAGTTCCGCAGCTTCCTGCAAATACAG<br>CGTGGCCTCATAACTGGAGATAGTGCGGTGAGCAGAGCCCACAAG<br>CGCTTCAACCTGCAGCAGGCGTTCCTCAATCGTCTTCAGCAGGCCC<br>TGGGCGTTTAACTGAATCTGGTTCATGCGATCACCTCGCTGACCGG<br>GATACGGGCTGACAGAACGAGGACAAAACGGCTGGCGAACTGGC<br>GACGAGCTTCTCGCTCGGATGATGCAGTGGTGGAAAGGCGGTGGA<br>TATGGGATTTTTTGTCCGTGCGGACGACAGCTGCAAATTTGAATTT<br>GAACATGGTATGCATTCCTATCTTGTATAGGGTGCTACCACCAGAG<br>TTGAGAATCTCTATAGGGGTGGTAGCCCAGACAGGGTTCTCAACA<br>CCGGTACAAGAAGAAACCGGCCCAACCGAAGTTGGCCCCATCTGA<br>GCCACCATAATTCAGGTATGCGCAGATTTAACACACAAAAAAACA<br>CGCTGGCGCGTGTTGTGCGCTTCTTGTCATTCGGGGTTGAGAGGCC<br>CGGCTGCAGATTTTGCTGCAGCGGGGTAACTCTACCGCCAAAGCA<br>GAACGCACGTCAATAATTTAGGTGGATATTTTACCCCGTGACCAGT<br>CACGTGCACAGGTGTTTTTATAGTTTGCTTTACTGACTGATCAGAA<br>CCTGATCAGTTATTGGAGTCCGGTAATCTTATTGATGACCGCAGCC<br>ACCTTAGATGTTGTCTCAAACCCCATACGGCCACGAATGAGCCAC<br>TGGAACGGAATAGTCAGCAGGTACAGCGGAACGAACCACAAACG<br>GTTCAGACGCTGCCAGAACGTCGCATCACGACGTTCCATCCATTCG<br>GTATTGTCGACGACCTGGTAAGCGTATTGTCCTGGCGTTTTTGCTG<br>CTTCCGAGTAGCAATCCTCTTCACCACAAAGAAAGTTACTTATCTG<br>CTTCCAGTTTTCGAACCCTTCTTCTTTGAGCCGCTTTTCCAGCTCAT<br>TCCTCCACAAAACAGGCACCCATCCTCTGCGATAAATCATGATTAT<br>TTGTCCTTTAAATAAGGCTGTAGAACTGCAAAATCGCTCTCGTTCA<br>CATGCTGTACGTAGATGCGTAGCAAATTGCCGTTCCATCCCTGTAA<br>TCCACCTTCTTTGGAAAGATCGTCCTTGACCTCACGAAGAACTTTA<br>TCCAATAGCCCTGCGGCACAAGAAATTGCCTGCTCTGGATCAGCA<br>AATTCATATTGATTAATAGGTGATTGCCACACACCAAAAACAGGA<br>ATCATCTTTTCGGCTAAACGCCTCTCCTGTTCTTTCTTAATCTCAAG<br>TTGTAAGCGGACCAGCTCACCATCCATCATTTTTTGTAGATCATGC<br>GCCACTATTCACCCCCACTGGCCATCAGCAAATAAAGCTTCATACT<br>CGGACACCGGCAGGCGGCTTCCACGGATTGAAAGGTCAAGCCAAC<br>CACGTCCAGATGGGTCAGCCTTATCCGATTCTTCCCACCGTTCTGC<br>AGCTGTAGCAACCAGGCATTCTACCGCCTTCATGTAGTCTTCTGTA<br>CGGAACCAGCCGTAGTTAATGCCACCATCAGTAACTGCCCAGGCC<br>ATCTTTTTCTCTTCGGCCTCAATAGCCCGGATGCGGTTATCGCACA<br>GCTCGCGACAGTACTTCAGCTGTTCGTAATCCAGTTGCTTCAGGAA<br>CTCTGGTGTCGACGTCATAGTGGCTTCACCTTATAGGCTTTTAGAA<br>GCGCCCTGGCTTCGTCTGTGTGGTCTTCCATGCTCTTATCGCTGGC<br>AATGCAGCAATAAACTCCCTCACTATCTGAGAACCCGTTCATCCG<br>AATGATCGTGAATGGAAGTTCCCGGCCAGTTTTATAATCGCTATAG<br>CTTGTCGCGTCGTGGCTGACCTTGACCACATAAGGGTCGTAGCCCT<br>CCACGATGACAAGGCATTCCCGTTGTTTTCCCATTACCCCTCCGGT<br>TATATCGCCACGGCTTGCCGCTGGCTTAGAAACGCTTTCAGCAGCC<br>TTATTTCGCGTACTGATAGCAGGTCCATAAATTCGGTCATGTACAG<br>CGAGGCGAACGTTCTCGCGATGCTGGCCACTGGCCACAGGCGTAC<br>CGCCTCCATTTCGGTTGCTGGCAACGCGTTCTCCGCCCACGCCTCC<br>GGTACCGCCACCGGGATAGCCTCCAGTGCCTGGATAATTACTGAT<br>TGTGGGGCGTCCGGAACGTGCTCTGTTTTGGATCGAGGGTTACCAT<br>GTATATCTATATTTAGATCCAAATCGCGATCCACTTCGATGGTGGT<br>TTTTTCCACCTTACGTGCGTGAATTGATAAACCGGCCTCGCGGCGC<br>TTCTCCACGATATTCATGAGGAACTCGACCGAGTCCGGGTCAATG<br>GAACGCATCGTGGGGCGTGCATCGCCATCTCTGGCGCGTCTGGTCT<br>TACTGGATAGCCCCATAGACTCCAGGATGCCTATGCAGAGGTCTG<br>CAGGCGCTTTCTTCTTGCCTTTCTCTGTGTTGAAGCCGCCGATGCG<br>TAAAACGTTGTTTAGCAGATCGCGCCGTTCCGGCGTGAGCAGGTT<br>ATCTCTGGCGCGTTTGAGGGCGTCCATGTCTGCTTCACCTTCCAGG<br>GTTTTTGGATCGATACCGCAGTCGCGGAAGTACTGCTGCAGCGTC<br>GCCGATTTGAGGGTGTAGAAACCACGCATGCCTATCTCAACAGCA<br>GGGGTCGATTTCACTCGGTAATCGGTTATGGCCGGGAATTTAGCCT<br>GGAACTCTGCGTCGGCCTGTTCCCGCGTCATGGCCGTAGTGACGA<br>ACTGCTGCCATCTTCCGGCAACGCGATAAGCGTAGGTAAAGTGAA<br>TCAACGCTTCTTCACGGTCAAGGCGACGGGCGGTTATCTCATCCAG<br>CTGCATGGTTTCAAACAGGCGCACTTTTTTCAGGCCGCCGTCGAAA<br>TAGAATTTTAACGCCACCTCGTCGACATCCAGCTGCAGCTCCTTTT<br>CGATGTCCCAGCGGACCAGCTGGGCCTGCTCATCCAGGGACAGGG<br>TGCGTTTTTTTATCAACTCATCGTGTTCGGCCTGGTCAGGAGTATC<br>GACACTCAGGTGGCGCTCCATAAGCTGCTCAAAGACCAGTTCACG<br>GGCTTCTTTACGTAAATCCTTACCGATGCTGTTTGCAAGCGCGTCG |

-continued

| SEQ ID NO | NAME | SEQUENCE |
|---|---|---|
| | | GTGGCCATAGGCGCGACCTGATAGCCATCATCATGCATGATGCAA |
| | | ATCATGTTGCTGGCATAATCATTTCTGGCCGATGCCTCGAGCGCGG |
| | | CGGCTTTAATTTTGAGCTGCATGAATGAAGAGTTAGCCACGCCGA |
| | | GTGAAATTCGGTCACCGTCAAAGACAACGTCTGTCAGCAGCCCGG |
| | | AGTGGCCAGCCGTTTCGAGCAAGGCCTGCGCGTAGGCGCGTTTGA |
| | | TTTTTTCCGGATCGGTTTCACGTTTACCGCGAAGCTTGTCGAAACC |
| | | GATAATGTATTCCTGAGCTGTACGGTCGCGGCGCAGCATCTGGAT |
| | | GGCGTCGCTGGGGACCACTTCGCCGCAGAACATGCCGAAATGGCG |
| | | GTGGAAGTGTTTCTCCTCAATCGATACACCTGAAGATATCGACGG |
| | | GCTGTAGATGAGGCCGTCATATTTTTTCACCATCACTTTAGGCTGG |
| | | TTGGTGAAATCGTCGACTTCCTTCTCCTGTTTGTTTTTCTGGTTAAC |
| | | GCAGAGAAACTTTTTGTCAGGGAACTGTAGTCTCAGCTGCATGGT |
| | | AACGTCTTCGGCGAACGTCGAACTGTCGGTGGCCAGCATGATTCG |
| | | TTCGCCGCGTTGCACTGCAGCGATAACCTCGGTCATGATCCGATTT |
| | | TTCTCGGTATAAAATACGCGGATAGGCTTGTTGGTTTCGCGGTTGC |
| | | GAACGTCGACCGGGAGTTCAATCACGTGAATTTGCAGCCAGGCAG |
| | | GTAGGCCCAGCTCCTCGCGTCGCTTCATCGCCAGTTCAGCCAGGTC |
| | | AACAAGCAGATCGTTGGCATCGGCATCCACCATAATGGCATGCTC |
| | | TTCAGTACGCGCCAGCGCGTCGATAAGCGTGTTGAATACGCCTAC |
| | | CGGGTTTTCCATCGCACGCCCGGCCAGAATGGCACGCAGGCCCTG |
| | | TGTTGCTTCATCGAAGCCGAAGAAGTCATGCTGGCGCATCAGCGG |
| | | TTGCCAGCAGCCTTTAAGTATGGAGTTGATGCAAATAGTCAGCTTG |
| | | TTGGCATATGGCGCCATTTCCTGATAGCCGGGATCCTGATAATGCA |
| | | GAATGTCGGCTTTCGCGCCTTTCCCTTCGGTCATCATTTCATGCAG |
| | | GCCGCCTATCAGGGATACGCGGTGCGCGACGGAAACGCCACGCGT |
| | | GGACTGCAGCATCAGTGGACGCAGGAGGCCTGTCGATTTACCCGA |
| | | CCCCATCCCGGCGCGGACAATAACGATGCCCTGCAGCTGTGCGGC |
| | | GTATGTCATCACCTCATCGGTCATCCTGGAGGTTTCAAACCGTTTG |
| | | TAAGTGATGTGTGACGGGCGAAGGTTCGGGTTGGTGATGCGTTCA |
| | | CTGAACGAACGTGATGTTTGCGCGGCACGGCATTTGCGATTCAAC |
| | | CGGCGCGTAATGTGATCTTTAACGGTACCGTTATAAATTTCTGCGA |
| | | TACCCATATCCCGCAGCGTGCTGCTGAAAAGGCGCATAAGTTCTTT |
| | | CGGGCTGTTTGGTACCGGGCATGTCAGCATGCCAATATCAACGGC |
| | | GCGAAGCAGTTCTTTGGCAAAAGTGCGTCTGTTCAGACGCGGGAG |
| | | AGTACGCAGCTTATTCAGCGTGATCGACAACAGATCGGTTGCACG |
| | | GCTCAGATGATTTCTCGTTAACTGGCGAGCGACTTCCTTCAGCCCT |
| | | CTCAGGCTGTGCAGGTCGTTAAAATCGCTGCATTCCAGCTCAGGGT |
| | | CATCCTCAAAAGTTGGGTAAACACATTTGACGCCGGAAAACTTCT |
| | | CCATGATGTCGAATCCGGTGCGGAGGCCTGTGTTGCCTTTTCCTTC |
| | | AGCTGAGGATTTGCGGTCGTTATCGAGAGCGCAAGTGATTTGCGC |
| | | AGCCGGGTACATGTTCACCAGCTGCTCGACAACGTGAATCATGTT |
| | | GTTAGCGGAAACCGCAATGACTACCGCGTCAAAGCGTTTTTTCGG |
| | | GTCGTTTCTGGTCGCCAGCCAGATGGATGCCCCGGTGGCGAAACC |
| | | CTCTGCAGTCGCAATTTTTTGCGCCCCCTGCAGGTCGCCAATAACA |
| | | AAGCATGCACCGACGAAATCACCGTTAGTGATGGCGCTGGTCTGG |
| | | AACTTGCCACCATTCAGATCGATACGTTGCCAGCCAACAATCCGC |
| | | CCGTCTTTTCTTCCGTCCAGGTGGGACAGAGGTATCGCCATGTAAG |
| | | TTGTTGGTCCACGGCTCCATTTCGCACTGTCGTGACTGGTCACGCG |
| | | ACGTATATCACAAGCGCCAAATACGTCACGAATTCCCTTTTTTACC |
| | | GCATAAGGCCAGGAGCCATCTTCAGCTGGCGAATGTTCCCAGGCG |
| | | CGATGGAAAGCCAACCATCCAAGCAGGCGTTCCTGCTCCATCTGA |
| | | TTGTTTTTTAAATCATTAACGCGTTGTTGTTCAGCTCGGAGGCGGC |
| | | GTGCTTCAGCCTGGCGCTCCATGCGTGCACGTTCTTCTTCCGGCTG |
| | | AGCGACCACGGTCGCACCATTCCGTTGCTGTTCACGGCGATACTCC |
| | | GAAAACAGGAATGAAAAGCCACTCCAGGAGCCAGCGTCATGCGC |
| | | TTTTTCAACGAAGTTAACGAAAGGATAACTGATGCCATCCTTGCTC |
| | | TGCTCAAGGCGTGAATAGATTTCCACACGGCCTTTAAGGCTCTTCT |
| | | GCAGAGCTTCCGGGGAGGAATTATTGTAGGTGGTATAGCGCTCTA |
| | | CACCACCGCGCGGATTGAGCTGAATCTTATCAGCACACGCAGGCC |
| | | AGTTGATACCGGCCATCTTCGCCAGCTCAGTCAGCTCATCACGTGC |
| | | CGCGTCAAGCAGTGAAAACGGATCGCTGCCAAAGCGCTCCGCGTA |
| | | GAATTCTTGTAAGGTCATTTTTTAGCCTTTCCATGCGAATTAGCAT |
| | | TTTTTCGGGTTGAAAAAATCCGCAGGAGCAGCCACAATAAACGCA |
| | | CTATCTTTCTGAAGGACGTATCTGCGTTATCGTGGCTACTTCCTGA |
| | | AAAAGGCCCGAGTTTGCCGACTCGGTTTTTTTTTCGTCTTTTTTCGG |
| | | CTGCTACGGTCTGGTTCAACCCCGACAAAGTATAGATCGGATTAA |
| | | ACCAGAATTATAGTCAGCAATAAACCCTGTTATTGTATCATCTACC |
| | | CTCAACCATGAACGATTTGATCGTACCGACTACTTGGTGCACAAAT |
| | | TGAAGATCACTTTTATCATGGATAACCCGTTGAGAGTTAGCACTAT |
| | | CAAGGTAGTAATGCTGCTCGTCATAACGGGCTAATCGTTGAATTGT |
| | | GATCTCGCCGTTATTATCACAAACCAGTACATCCTCACCCGGTACA |
| | | AGCGTAAGTGAAGAATCGACCAGGATAACATCTCCCGGCTGGTAG |
| | | TTTCGCTGAATCTGGTTCCCGACCGTCAGTGCGTAAACGGTGTTCC |
| | | GTTGACTCACGAACGGCAGGAATCGCTCTGTGTTGGCAGGTTCTCC |
| | | AGGCTGCCAGTCTCTATCCGGTCCTGTCTCTGTCGTACCAATAACA |

-continued

| SEQ ID NO | NAME | SEQUENCE |
|---|---|---|
| | | GGAACGCGGTCTGGATCAGATTCAGTGCCATACAGTATCCATTGC<br>ACGGGCTTACGCAGGCATTTTGCCAGCGATAGCCCGATCTCCAGC<br>GACGGCATCACGTCGCCACGTTCTAAGTTTTGGACGCCCGGAAGA<br>GAGATTCCTACAGCTTCTGCCACTTGCTTCAGCGTCAGTTTCAGCT<br>CTAAACGGCGTGCTTTCAGTCGTTCGCCTCGTGTTTTCATACCCTT<br>AATCATAAATGATCTCTTTATAGCTGGCTATAATTTTTATAAATTA<br>TACCTAGCTTTAATTTTCACTTATTGATTATAATAATCCCCATGAA<br>ACCCGAAGAACTTGTGCGCCATTTCGGCGATGTGGAAAAAGCAGC<br>GGTTGGCGTGGGCGTGACACCCGGCGCAGTCTATCAATGGCTGCA<br>AGCTGGGGAGATTCCACCTCTACGACAAAGCGATATAGAGGTCCG<br>TACCGCGTACAAATTAAAGAGTGATTTCACCTCTCAGCGCATGGG<br>TAAGGAAGGGCATAACAAGGGGATCCTCTAGACGCAGAAAGGCC<br>CACCCGAAGGTGAGCCAGTGTGATTACATTTGCGGCCTAACTGTG<br>GCCAGTCCAGTTACGCTGGAGTCACTAGTGCGGCCGCGACAACTT<br>GTCTAGGGCCCAATGGCCCATACACTTAGTGTAATACGACTCACT<br>ATAGGGAGAGCGGCCGCTTTTTCAGCAAGATTAAGCCGCCACCAT<br>GGCGCCGCGGCCTCCTAAGAAGAAGCGGAAAGTCGAATTCGTGGA<br>TCTGCGAACACTGGGCTATAGCCAGCAGCAGCAGGAGAAGATCAA<br>ACCCAAGGTGAGGTCCACAGTCGCACAGCACCATGAAGCCCTGGT<br>GGGCCACGGGTTCACTCACGCTCATATTGTCGCACTGTCTCAGCAT<br>CCAGCCGCTCTGGGAACCGTGGCAGTCACATACCAGCACATCATT<br>ACTGCCCTGCCCGAGGCTACCCATGAAGACATCGTGGGAGTCGGC<br>AAACAGTGGAGCGGCGCACGGGCCCTGGAGGCTCTGCTGACCGAC<br>GCAGGGGAACTGAGAGGACCCCCTCTGCAGCTGGATACAGGGCA<br>GCTGGTGAAGATTGCTAAGAGGGGAGGGGTGACAGCAATGGAAG<br>CCGTCCACGCAAGCAGGAACGCACTGACAGGGGCCCCCCTGAACC<br>TGACCCCGGACCAAGTGGTGGCTATCGCCAGCAATCACGGCGGCA<br>AGCAAGCGCTCGAAACGGTGCAGCGGCTGTTGCCGGTGCTGTGCC<br>AGGACCATGGCCTGACCCCGGACCAAGTGGTGGCTATCGCCAGCA<br>ATCACGGCGGCAAGCAAGCGCTCGAAACGGTGCAGCGGCTGTTGC<br>CGGTGCTGTGCCAGGACCATGGCCTGACCCCGGACCAAGTGGTGG<br>CTATCGCCAGCAACGGTGGCGGCAAGCAAGCGCTCGAAACGGTGC<br>AGCGGCTGTTGCCGGTGCTGTGCCAGGACCATGGCCTGACTCCGG<br>ACCAAGTGGTGGCTATCGCCAGCCACGATGGCGGCAAGCAAGCGC<br>TCGAAACGGTGCAGCGGCTGTTGCCGGTGCTGTGCCAGGACCATG<br>GCCTGACCCCGGACCAAGTGGTGGCTATCGCCAGCAACATTGGCG<br>GCAAGCAAGCGCTCGAAACGGTGCAGCGGCTGTTGCCGGTGCTGT<br>GCCAGGACCATGGCCTGACCCCGGACCAAGTGGTGGCTATCGCCA<br>GCAACATTGGTGGAAAACAGGCCCTTGAAACGGTGCAGCGGCTGT<br>TGCCGGTGCTGTGCCAGGACCATGGCCTGACCCCGGACCAAGTGG<br>TGGCTATCGCCAGCAATCACGGCGGCAAGCAAGCGCTCGAAACGG<br>TGCAGCGGCTGTTGCCGGTGCTGTGCCAGGACCATGGCCTGACCC<br>CGGACCAAGTGGTGGCTATCGCCAGCAACGGTGGCGGCAAGCAA<br>GCGCTCGAAACGGTGCAGCGGCTGTTGCCGGTGCTGTGCCAGGAC<br>CATGGCCTGACCCCGGACCAAGTGGTGGCTATCGCCAGCAACGGT<br>GGCGGCAAGCAAGCGCTCGAAACGGTGCAGCGGCTGTTGCCGGTG<br>CTGTGCCAGGACCATGGCCTGACCCCGGACCAAGTGGTGGCTATC<br>GCCAGCAACGGTGGCGGCAAGCAAGCGCTCGAAACGGTGCAGCG<br>GCTGTTGCCGGTGCTGTGCCAGGACCATGGCCTGACCCCGGACCA<br>AGTGGTGGCTATCGCCAGCAATCACGGCGGCAAGCAAGCGCTCGA<br>AACGGTGCAGCGGCTGTTGCCGGTGCTGTGCCAGGACCATGGCCT<br>GACTCCGGACCAAGTGGTGGCTATCGCCAGCCACGATGGCGGCAA<br>GCAAGCGCTCGAAACGGTGCAGCGGCTGTTGCCGGTGCTGTGCCA<br>GGACCATGGCCTGACTCCGGACCAAGTGGTGGCTATCGCCAGCCA<br>CGATGGCGGCAAGCAAGCGCTCGAAACGGTGCAGCGGCTGTTGCC<br>GGTGCTGTGCCAGGACCATGGCCTGACCCCGGACCAAGTGGTGGC<br>TATCGCCAGCAACGGTGGCGGCAAGCAAGCGCTCGAAACGGTGCA<br>GCGGCTGTTGCCGGTGCTGTGCCAGGACCATGGCCTGACCCCGGA<br>CCAAGTGGTGGCTATCGCCAGCAACGGTGGCGGCAAGCAAGCGCT<br>CGAAACGGTGCAGCGGCTGTTGCCGGTGCTGTGCCAGGACCATGG<br>CCTGACCCCGGACCAAGTGGTGGCTATCGCCAGCAATCACGGCGG<br>CAAGCAAGCGCTCGAAACGGTGCAGCGGCTGTTGCCGGTGCTGTG<br>CCAGGACCATGGCCTGACCCCGGACCAAGTGGTGGCTATCGCCAG<br>CAACGGTGGCGGCAAGCAAGCGCTCGAAACGGTGCAGCGGCTGTT<br>GCCGGTGCTGTGCCAGGACCATGGCCTGACCCCGGACCAAGTGGT<br>GGCTATCGCCAGCCACGATGGCGGCAAGCAAGCGCTCGAAAGCAT<br>TGTGGCCCAGCTGAGCCGGCCTGATCCGGCGTTGGCCGCGTTGAC<br>CAACGACCACCTGGTCGCTCTGGCTTGCCTGGGAGGACGCCCTGC<br>TATGGACGCTGTGAAGAAAGGACTGCCCCACGCACCCGAACTGAT<br>TAGACGGGTGAACCGGAGAATCGGCGAGAGAACATCCCATAGGG<br>TGGCAATCTCTAGAACTCAGCTGGTCAAGAGTGAACTGGAGGAAA<br>AGAAATCAGAGCTGCGCCACAAGCTGAAATACGTGCCTCATGAGT<br>ATATCGAACTGATCGAGATTGCTCGCAATTCAACCCAGGACCGGA<br>TCCTGGAAATGAAAGTGATGGAGTTCTTTATGAAAGTCTACGGAT<br>ATCGGGGGAAACACCTGGGAGGGAGCAGAAAGCCAGATGGGGCC |

-continued

| SEQ ID NO | NAME | SEQUENCE |
|---|---|---|
| | | ATCTACACAGTGGGATCCCCCATCGACTATGGCGTGATTGTCGATA<br>CTAAAGCCTACAGCGGAGGCTATAACCTGCCTATCGGCCAGGCTG<br>ACGAGATGCAGAGATACGTGGAGGAAAACCAGACCCGCAATAAG<br>CATATTAACCCCAATGAATGGTGGAAAGTGTATCCTAGCTCCGTC<br>ACAGAGTTCAAGTTTCTGTTCGTGAGCGGACACTTTAAGGGCAAC<br>TACAAAGCACAGCTGACTAGGCTGAATCATATCACCAACTGCAAT<br>GGAGCCGTGCTGTCTGTCGAGGAACTGCTGATCGGGGGAGAGATG<br>ATTAAGGCTGGCACACTGACTCTGGAGGAAGTGAGGCGCAAGTTC<br>AACAATGGGGAAATCAACTTCTAACCTGCAGGATGATAAGCTAGC<br>CCCGGGCGTACGGAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAACGAGAC<br>CTTAGGGCCATTAGACTTGAAGTCAAGCGGCCGCTTACAACTGGA<br>CCTTGCTGGTACATAGAACTGATTAACTGACCATTTAAATCATACC<br>AACATGGTCAAATAAAACGAAAGGCTCAGTCGAAAGACTGGGCCT<br>TTCGTTTTAATCTGATCGGCACGTAAGAGGTTCCAACTTTCACCAT<br>AATGAAATAAGATCACTACCGGGCGTATTTTGAGTTATCGAGATTT<br>TCAGGAGCTAAGGAAGCTAAAATGAGCCATATTCAACGGGAAAC<br>GTCTTGCTCGAGGCCGCGATTAAATTCCAACATGGATGCTGATTTA<br>TATGGGTATAAATGGGCTCGCGATAATGTCGGGCAATCAGGTGCG<br>ACAATCTATCGATTGTATGGGAAGCCCGATGCGCCAGAGTTGTTTC<br>TGAAACATGGCAAAGGTAGCGTTGCCAATGATGTTACAGATGAGA<br>TGGTCAGGCTAAACTGGCTGACGGAATTTATGCCTCTTCCGACCAT<br>CAAGCATTTTATCCGTACTCCTGATGATGCATGGTTACTCACCACT<br>GCGATCCCAGGGAAAACAGCATTCCAGGTATTAGAAGAATATCCT<br>GATTCAGGTGAAAATATTGTTGATGCGCTGGCAGTGTTCCTGCGCC<br>GGTTGCATTCGATTCCTGTTTGTAATTGTCCTTTTAACGGCGATCG<br>CGTATTTCGTCTGGCTCAGGCGCAATCACGAATGAATAACGGTTTG<br>GTTGGTGCGAGTGATTTTGATGACGAGCGTAATGGCTGGCCTGTTG<br>AACAAGTCTGGAAAGAAATGCATAAACTTTTGCCATTCTCACCGG<br>ATTCAGTCGTCACTCATGGTGATTTCTCACTTGATAACCTTATTTTT<br>GACGAGGGGAAATTAATAGGTTGTATTGATGTTGGACGAGTCGGA<br>ATCGCAGACCGATACCAGGATCTTGCCATCCTATGGAACTGCCTC<br>GGTGAGTTTTCTCCTTCATTACAGAAACGGCTTTTTCAAAAATATG<br>GTATTGATAATCCTGATATGAATAAATTGCAGTTTCACTTGATGCT<br>CGATGAGTTTTTCTAACCTAGGTGACAGAAGTCAAAAGCCTCCGG<br>TCGGAGGCTTTTGACTTTCTGCTAGATCTGTTTCAATGCGGTGAAG<br>GGCCAGGCAGCTGGGGATTATGTCCAGACCCGGCCAGCATGTTGG<br>TTTTATCGCATATTCAGCGTTGTCGCGTTTACCCAGGTAAAATGGA<br>AGCAGTGTATCGTCTGCGTGAATGTGCAAATCAGGAACGTAACCG<br>TGGTACATAGATGCAGTCCCTTGCGGGTCGTTCCCTTCAACGAGTA<br>GGACGCGGTGCCCTTGCAAGGCTAACCATTGCGCCTGGTGTACTG<br>CAGATGAGGTTTTATAAACCCCTCCCTTGTGTGACATAACGGAAA<br>GTACAACCGGGTTTTTATCGTCAGGTCTTTGGTTTGGGTTACCAAA<br>CACACTCCGCATATGGCTAATTTGGTCAATTGTGTAGCCAGCGCGA<br>CGTTCTACTCGGCCCCTCATCTCAAAATCAGGAGCCGGTAGACGA<br>CCAGCTTTTTCCGCATCTCTGATAGCCTGCGGTGTTACGCCGATCA<br>GGTCTGCAACTTCTGTTATACCCCAGCGGCGAGTAATACGACGCG<br>CTTCCGGGCTGTCATCGCCGAACTGTGCGATGGCAATAGCGCGCG<br>TCATTTCCTGACCGCGATTGATACAGTCTTTCAGCAAATTAATTAA<br>CGACATCCTGTTTCCTCTCAAACATGCCCTTATCTTTGTGTTTTTCA<br>TCATACTTTACGTTTTTAAAGCAAAGCAACATAAAAAAAGCAAAG<br>TGACTTAGAAAACGCAAAGTTAAGGTTCAAATCAATTTTTTGATGC<br>GCTACAGAAGCTATTTAGCTTCATCTAAGCGCAACGGTATTACTTA<br>CGTTGGTATATTTAAAACCTAACTTAATGATTTTAAATGATAATAA<br>ATCATACCAATTGCTATCAAAAGTTAAGCGAACATGCTGATTTTCA<br>CGCTGTTTATACACTTTGAGGCATCTCTATCTCTTCTGTCTCTATAT<br>TGAAACACAATCAAAGAACATCAATCCATGTGACATCCCCCACTA<br>TCTAAGAACACCATAACAGAACACAACATAGGAATGCAACATTAA<br>TGTATCAATAATTCGGAACATATGCACTATATCATATCTCAATTAC<br>GGAACATATCAGCACACAATTGCCCATTATACGC |

What is claimed is:

1. A method for increasing gamma globin expression in a hematopoietic stem or progenitor cell comprising introducing into the cell one or more engineered nucleases that cleave a target site set forth in SEQ ID NO: 9 and a DNA donor repair template having the sequence as set forth in SEQ ID NOs: 17, 18, 19, 20, or 21, whereby the DNA donor repair template is inserted into the cell genome by homology directed repair at a double strand break introduced by the one or more engineered nucleases.

2. The method of claim 1, wherein the DNA donor repair template has the sequence as set forth in SEQ ID NO: 17.

3. The method of claim 1, wherein the DNA donor repair template has the sequence as set forth in SEQ ID NO: 18.

4. The method of claim 1, wherein the DNA donor repair template has the sequence as set forth in SEQ ID NO: 19.

5. The method of claim 1, wherein the DNA donor repair template has the sequence as set forth in SEQ ID NO: 20.

6. The method of claim 1, wherein the DNA donor repair template has the sequence as set forth in SEQ ID NO: 21.

7. A method for increasing gamma globin expression in a hematopoietic stem or progenitor cell comprising introducing into the cell one or more engineered nucleases that cleave a target site set forth in SEQ ID NO: 9 and a DNA donor repair template having at least 99% sequence identity to the sequence as set forth in SEQ ID NOs: 17, 18, 19, 20, or 21, whereby the DNA donor repair template is inserted into the cell genome by homology directed repair at a double strand break introduced by the one or more engineered nucleases.

8. The method of claim 7, wherein the DNA donor repair template has the sequence having at least 99% sequence identity to the sequence as set forth in SEQ ID NO: 17.

9. The method of claim 7, wherein the DNA donor repair template has the sequence having at least 99% sequence identity to the sequence as set forth in SEQ ID NO: 18.

10. The method of claim 7, wherein the DNA donor repair template has the sequence having at least 99% sequence identity to the sequence as set forth in SEQ ID NO: 19.

11. The method of claim 7, wherein the DNA donor repair template has the sequence having at least 99% sequence identity to the sequence as set forth in SEQ ID NO: 20.

12. The method of claim 7, wherein the DNA donor repair template has the sequence having at least 99% sequence identity to the sequence as set forth in SEQ ID NO: 21.

13. A method for increasing gamma globin expression in a hematopoietic stem or progenitor cell comprising introducing into the cell one or more engineered nucleases that cleave a target site set forth in SEQ ID NO: 9 and a DNA donor repair template having at least 98% sequence identity to the sequence as set forth in SEQ ID NOs: 17, 18, 19, 20, or 21, whereby the DNA donor repair template is inserted into the cell genome by homology directed repair at a double strand break introduced by the one or more engineered nucleases.

14. The method of claim 13, wherein the DNA donor repair template has the sequence having at least 98% sequence identity to the sequence as set forth in SEQ ID NO: 17.

15. The method of claim 13, wherein the DNA donor repair template has the sequence having at least 98% sequence identity to the sequence as set forth in SEQ ID NO: 18.

16. The method of claim 13, wherein the DNA donor repair template has the sequence having at least 98% sequence identity to the sequence as set forth in SEQ ID NO: 19.

17. The method of claim 13, wherein the DNA donor repair template has the sequence having at least 98% sequence identity to the sequence as set forth in SEQ ID NO: 20.

18. The method of claim 13, wherein the DNA donor repair template has the sequence having at least 98% sequence identity to the sequence as set forth in SEQ ID NO: 21.

* * * * *

SEQUENCE LISTING

<160> NUMBER OF SEQ ID NOS: 93

<210> SEQ ID NO 1
<211> LENGTH: 21
<212> TYPE: DNA
<213> ORGANISM: Homo sapiens

<400> SEQUENCE: 1
cttgaccaat agccttgaca a 21

<210> SEQ ID NO 2
<211> LENGTH: 16
<212> TYPE: DNA
<213> ORGANISM: Homo sapiens

<400> SEQUENCE: 2
gaccaatagc cttgac 16

<210> SEQ ID NO 3
<211> LENGTH: 13
<212> TYPE: DNA
<213> ORGANISM: Homo sapiens

<400> SEQUENCE: 3
caatagcctt gac 13

<210> SEQ ID NO 4
<211> LENGTH: 10
<212> TYPE: DNA
<213> ORGANISM: Homo sapiens

<400> SEQUENCE: 4
gaccaatagc 10

<210> SEQ ID NO 5
<211> LENGTH: 5
<212> TYPE: DNA
<213> ORGANISM: Homo sapiens

<400> SEQUENCE: 5 ccaat 5

<210> SEQ ID NO 6
<211> LENGTH: 4
<212> TYPE: DNA
<213> ORGANISM: Homo sapiens

<400> SEQUENCE: 6 caat 4

<210> SEQ ID NO 7
<211> LENGTH: 2835
<212> TYPE: DNA
<213> ORGANISM: Homo sapiens

<400> SEQUENCE: 7
ctcaggatcc acatgcagct tgtcacagtg cagttcactc agctgggcaa aggtgccctt 60
gagatcatcc aggtgctttg tggcatctcc caaggaagtc agcaccttct tgccatgtgc 120
cttgactttg gggttgccca tgatggcaga ggcagaggac aggttgccaa agctgtcaaa 180
gaacctctgg gtccatgggt agacaaccag gagcctgtga gattgacaag aacagtttga 240
cagtcagaag gtgccacaaa tcctgagaag cgacctggac ttttgccagg cacagggtcc 300

-continued

```
ttccttccct cccttgtcct ggtcaccaga gcctaccttc ccagggtttc tcctccagca    360
tcttccacat tcaccttgcc ccacaggctt gtgatagtag ccttgtcctc ctctgtgaaa    420
tgacccatgg cgtctggact aggagcttat tgataacctc agacgttcca gaagcgagtg    480
tgtggaactg ctgaagggtg cttcctttta ttcttcatcc ctagccagcc gccggcccct    540
ggcctcactg gatactctaa gactattggt caagtttgcc ttgtcaaggc tattggtcaa    600
ggcaaggctg gccaacccat gggtggagtt tagccaggga ccgtttcaga cagatatttg    660
cattgagata gtgtggggaa ggggccccca agaggatact gctaattttt tttatagcct    720
ttgccttgtt ccgattcagt cattccagtt tttctctaat ttattcttcc ctttagctag    780
tttccttctc ccatcataga ggataccagg acttcttttg tcagccgttt tttaccttct    840
tgtctctagc tccagtgagg cctgtagttt aaagctaaag catgtaccaa tttttgaaaa    900
gttcagggat tgtgaaatgt gttttaggca taggtccagg atttttgacg ggacaaatct    960
tagtctcttt cagttagcag tggtttctaa ggaaaaagtg ctatacttct ttttgaatat   1020
actctttgtg acttttgcca ttatctctta atttctcaat agtgcagtga aaacaatttc   1080
tataaagcca cagtttcagc gcagtaatag attagtgtta cataatataa gacctaatgc   1140
ttacctcaat atctacttat ccgtacctat ttgaaataaa tcatgactgt ttcatcttag   1200
aaaaatattt gattccatat tcaggtatgt atgtatacac cagatgatgt gtatttacca   1260
ctggataagt gtgtgtgctg gctgatgacc cagggttttg gcgtagctct tctatgctca   1320
gtaaagatga tggtagaatg ttctttggca ggtactgtgg attagaatta attatcttgt   1380
ataaatgcta ggttcacttc tcagggaatc ttactctaag acataagatg tgcgtgtaca   1440
tggaaaacaa ctctaaagag gcaagggttg tttttattga ctaatagtcc acacactatt   1500
ataactcgaa tattagtgta ctttagacag ctttatttct aacacagtgc tgtttctgac   1560
atattggacc attaacaggg taggaagtat ttatggtggt tttttggttc tgttttgctt   1620
ttggttagtt tgtttttgtt tttctctgaa agtgatccat gatctctaac cttgctagat   1680
tataatgcca gaagctctgg aattctggct tatcggaggc aagctgtatc ttcaaattag   1740
tttatcccct aagctatcag gttgattgaa attattataa tattggtgaa attctttcat   1800
ccttcatgat cctgtgtaaa gcttatatct gctcattgat acagatggct aaaaggccag   1860
aaagacacac atttacccat gtaacaagcc tgcacatcct gcacatgtac cttcgaaatt   1920
aaaatgaaat gaaataaaat taaaaggaaa aaaatgccat ggcaacatca ggaagttatc   1980
ttttatggtc taaaaatggg cagcataaat aatctacccc ttgtttagca tactattgaa   2040
aaataacaat aaaaatcggc aaccagtagc ccttgcgtct actctgccta tgaagtagcc   2100
attcatttat tccttcaatt ttttataaac ttgttttact aaaaaaaaaa aggacaaaga   2160
aagaaagtgc gaattgtgaa atggtagtga gtgatggcat ttgaagtggg tcctttatga   2220
tttgatggag ccaggcagaa gacgtttgga gaaagaagtt cctgaaagta ggaagggcat   2280
gtggaaaact ctgaggctga ggaaaaaaaa gaaagaaaga aatataaaga aagaacttga   2340
catttcactg tatataaaca cattacaagc ctaaagtacg ttgaagaaaa aatagaattc   2400
aaagttagac agaagggctc aggcttacta tttgcatctt acagatgaga gtagtagagt   2460
tggtatttta ttctgaaaca cagaggacaa gtggagattt gtaaacctga gataaacatg   2520
gtttctaatc cactgaacac cgaagcttat tttttctct ttcttcatct gccttactta    2580
gtgcaaggtg ctataacaaa atagcataga ctgggtgact tcaacaacag gatttttct    2640
```

```
cacttttctg ctggttcctg gtcagggctc tcttcctggg ttgcaggtgg ctgacttccc   2700

actgtgtcct caccagaagg aagagaaatg gctaatctct ctgcttctga tgaggaaaat   2760

aattctatga tggggatctg ctctcatgag ctcctctaaa cctgattact tttccaaagc   2820

ctcccccaca aatgg                                                    2835
```

<210> SEQ ID NO 8
<211> LENGTH: 2835
<212> TYPE: DNA
<213> ORGANISM: Homo sapiens

<400> SEQUENCE: 8

```
ccatttgtgg gggaggcttt ggaaaagtaa tcaggtttag aggagctcat gagagcagat     60

ccccatcata gaattatttt cctcatcaga agcagagaga ttagccattt ctcttccttc    120

tggtgaggac acagtgggaa gtcagccacc tgcaacccag gaagagagcc ctgaccagga    180

accagcagaa aagtgagaaa aaatcctgtt gttgaagtca cccagtctat gctattttgt    240

tatagcacct tgcactaagt aaggcagatg aagaaagaga aaaaaataag cttcggtgtt    300

cagtggatta gaaaccatgt ttatctcagg tttacaaatc tccacttgtc ctctgtgttt    360

cagaataaaa taccaactct actactctca tctgtaagat gcaaatagta agcctgagcc    420

cttctgtcta actttgaatt ctatttttc ttcaacgtac tttaggcttg taatgtgttt    480

atatacagtg aaatgtcaag ttctttcttt atatttcttt ctttcttttt tttcctcagc    540

ctcagagttt tccacatgcc cttcctactt tcaggaactt ctttctccaa acgtcttctg    600

cctggctcca tcaaatcata aaggacccac ttcaaatgcc atcactcact accatttcac    660

aattcgcact ttctttcttt gtcctttttt tttttagtaa aacaagttta taaaaaattg    720

aaggaataaa tgaatggcta cttcataggc agagtagacg caagggctac tggttgccga    780

tttttattgt tatttttcaa tagtatgcta aacaaggggt agattattta tgctgcccat    840

ttttagacca taaaagataa cttcctgatg ttgccatggc atttttttcc ttttaatttt    900

atttcatttc attttaattt cgaaggtaca tgtgcaggat gtgcaggctt gttacatggg    960

taaatgtgtg tctttctggc cttttagcca tctgtatcaa tgagcagata taagctttac   1020

acaggatcat gaaggatgaa agaatttcac caatattata ataatttcaa tcaacctgat   1080

agcttagggg ataaactaat ttgaagatac agcttgcctc cgataagcca gaattccaga   1140

gcttctggca ttataatcta gcaaggttag agatcatgga tcactttcag agaaaaacaa   1200

aaacaaacta accaaaagca aaacagaacc aaaaaaccac cataaatact tcctaccctg   1260

ttaatggtcc aatatgtcag aaacagcact gtgttagaaa taaagctgtc taaagtacac   1320

taatattcga gttataatag tgtgtggact attagtcaat aaaaacaacc cttgcctctt   1380

tagagttgtt ttccatgtac acgcacatct tatgtcttag agtaagattc cctgagaagt   1440

gaacctagca tttatacaag ataattaatt ctaatccaca gtacctgcca aagaacattc   1500

taccatcatc tttactgagc atagaagagc tacgccaaaa ccctgggtca tcagccagca   1560

cacacactta tccagtggta aatacacatc atctggtgta tacatacata cctgaatatg   1620

gaatcaaata tttttctaag atgaaacagt catgatttat ttcaaatagg tacggataag   1680

tagatattga ggtaagcatt aggtcttata ttatgtaaca ctaatctatt actgcgctga   1740

aactgtggct ttatagaaat tgttttcact gcactattga gaaattaaga gataatggca   1800

aaagtcacaa agagtatatt caaaaagaag tatagcactt tttccttaga aaccactgct   1860

aactgaaaga gactaagatt tgtcccgtca aaaatcctgg acctatgcct aaaacacatt   1920
```

-continued

```
tcacaatccc tgaacttttc aaaaattggt acatgcttta gctttaaact acaggcctca   1980
ctggagctag agacaagaag gtaaaaaacg gctgacaaaa gaagtcctgg tatcctctat   2040
gatgggagaa ggaaactagc taaagggaag aataaattag agaaaaactg gaatgactga   2100
atcggaacaa ggcaaaggct ataaaaaaaa ttagcagtat cctcttgggg gccccttccc   2160
cacactatct caatgcaaat atctgtctga aacggtccct ggctaaactc cacccatggg   2220
ttggccagcc ttgccttgac caatagcctt gacaaggcaa acttgaccaa tagtcttaga   2280
gtatccagtg aggccagggg ccggcggctg gctagggatg aagaataaaa ggaagcaccc   2340
ttcagcagtt ccacacactc gcttctggaa cgtctgaggt tatcaataag ctcctagtcc   2400
agacgccatg ggtcatttca cagaggagga caaggctact atcacaagcc tgtggggcaa   2460
ggtgaatgtg gaagatgctg gaggagaaac cctgggaagg taggctctgg tgaccaggac   2520
aagggaggga aggaaggacc ctgtgcctgg caaaagtcca ggtcgcttct caggatttgt   2580
ggcaccttct gactgtcaaa ctgttcttgt caatctcaca ggctcctggt tgtctaccca   2640
tggacccaga ggttctttga cagctttggc aacctgtcct ctgcctctgc catcatgggc   2700
aaccccaaag tcaaggcaca tggcaagaag gtgctgactt ccttgggaga tgccacaaag   2760
cacctggatg atctcaaggg cacctttgcc cagctgagtg aactgcactg tgacaagctg   2820
catgtggatc ctgag                                                    2835
```

```
<210> SEQ ID NO 9
<211> LENGTH: 1000
<212> TYPE: DNA
<213> ORGANISM: Homo sapiens

<400> SEQUENCE: 9

gtcaataaaa acaacccttg cctctttaga gttgttttcc atgtacacgc acatcttatg     60
tcttagagta agattccctg agaagtgaac ctagcattta tacaagataa ttaattctaa    120
tccacagtac ctgccaaaga acattctacc atcatcttta ctgagcatag aagagctacg    180
ccaaaaccct gggtcatcag ccagcacaca cacttatcca gtggtaaata cacatcatct    240
ggtgtataca tacatacctg aatatggaat caaatatttt tctaagatga aacagtcatg    300
atttatttca aataggtacg gataagtaga tattgaggta agcattaggt cttatattat    360
gtaacactaa tctattactg cgctgaaact gtggctttat agaaattgtt ttcactgcac    420
tattgagaaa ttaagagata atggcaaaag tcacaaagag tatattcaaa aagaagtata    480
gcactttttc cttagaaacc actgctaact gaaagagact aagatttgtc ccgtcaaaaa    540
tcctggacct atgcctaaaa cacatttcac aatccctgaa cttttcaaaa attggtacat    600
gctttagctt taaactacag gcctcactgg agctagagac aagaaggtaa aaaacggctg    660
acaaaagaag tcctggtatc ctctatgatg ggagaaggaa actagctaaa gggaagaata    720
aattagagaa aaactggaat gactgaatcg gaacaaggca aaggctataa aaaaaattag    780
cagtatcctc ttgggggccc cttccccaca ctatctcaat gcaaatatct gtctgaaacg    840
gtccctggct aaactccacc catgggttgg ccagccttgc cttgaccaat agccttgaca    900
aggcaaactt gaccaatagt cttagagtat ccagtgaggc caggggccgg cggctggcta    960
gggatgaaga ataaaaggaa gcacccttca gcagttccac                         1000

<210> SEQ ID NO 10
<211> LENGTH: 7210
<212> TYPE: DNA
```

<213> ORGANISM: Artificial
<220> FEATURE:
<223> OTHER INFORMATION: AAV donor template

<400> SEQUENCE: 10
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtcata 180
aatacttcct accctgttaa tggtccaata tgtcagaaac agcactgtgt tagaaataaa 240
gctgtctaaa gtacactaat attcgagtta taatagtgtg tggactatta gtcaataaaa 300
acaacccttg cctctttaga gttgttttcc atgtacacgc acatcttatg tcttagagta 360
agattccctg agaagtgaac ctagcattta tacaagataa ttaattctaa tccacagtac 420
ctgccaaaga acattctacc atcatcttta ctgagcatag aagagctacg ccaaaaccct 480
gggtcatcag ccagcacaca cacttatcca gtggtaaata cacatcatct ggtgtataca 540
tacatacctg aatatggaat caaatatttt tctaagatga aacagtcatg atttatttca 600
aataggtacg gataagtaga tattgaggta agcattaggt cttatattat gtaacactaa 660
tctattactg cgctgaaact gtggctttat agaaattgtt ttcactgcac tattgagaaa 720
ttaagagata atggcaaaag tcacaaagag tatattcaaa aagaagtata gcactttttc 780
cttagaaacc actgctaact gaaagagact aagatttgtc ccgtcaaaaa tcctggacct 840
atgcctaaaa cacatttcac aatccctgaa cttttcaaaa attggtacat gctttagctt 900
taaactacag gcctcactgg agctagagac aagaaggtaa aaaacggctg acaaaagaag 960
tcctggtatc ctctatgatg ggagaaggaa actagctaaa gggaagaata aattagagaa 1020
aaactggaat gactgaatcg gaacaaggca aaggctataa aaaaaattaa gcagcagtat 1080
cctcttgggg gccccttccc cacactatct caatgcaaat atctgtctga aacggtccct 1140
ggctaaactc cacccatggg ttggccagcc ttgccttgac gaacagagaa acaggagaat 1200
atgggccaaa caggatatct gtggtaagca gttcctgccc cggctcaggg ccaagaacag 1260
ttggaacagc agaatatggg ccaaacagga tatctgtggt aagcagttcc tgccccggct 1320
cagggccaag aacagatggt ccccagatgc ggtcccgccc tcagcagttt ctagagaacc 1380
atcagatgtt tccagggtgc cccaaggacc tgaaatgacc ctgtgcctta tttgaactaa 1440
ccaatcagtt cgcttctcgc ttctgttcgc gcgcttctgc tccccgagct ctatataagc 1500
agagctcgtt tagtgaaccg tcagatcgcc tggagacgcc atccacgctg ttttgacttc 1560
catagaagga tctcgaggcc accatggtga gcaagggcga ggagctgttc accggggtgg 1620
tgcccatcct ggtcgagctg gacggcgacg taaacggcca caagttcagc gtgtccggcg 1680
agggcgaggg cgatgccacc tacggcaagc tgaccctgaa gttcatctgc accaccggca 1740
agctgcccgt gccctggccc accctcgtga ccaccctgac ctacggcgtg cagtgcttca 1800
gccgctaccc cgaccacatg aagcagcacg acttcttcaa gtccgccatg cccgaaggct 1860
acgtccagga gcgcaccatc ttcttcaagg acgacggcaa ctacaagacc cgcgccgagg 1920
tgaagttcga gggcgacacc ctggtgaacc gcatcgagct gaagggcatc gacttcaagg 1980
aggacggcaa catcctgggg cacaagctgg agtacaacta caacagccac aacgtctata 2040
tcatggccga caagcagaag aacggcatca aggtgaactt caagatccgc cacaacatcg 2100
aggacggcag cgtgcagctc gccgaccact accagcagaa cacccccatc ggcgacggcc 2160
ccgtgctgct gcccgacaac cactacctga gcacccagtc cgccctgagc aaagacccca 2220

```
acgagaagcg cgatcacatg gtcctgctgg agttcgtgac cgccgccggg atcactctcg   2280
gcatggacga gctgtacaag taaactagtg tcgactgctt tatttgtgaa atttgtgatg   2340
ctattgcttt atttgtaacc attataagct gcaataaaca agttaacaac aacaattgca   2400
ttcattttat gtttcaggtt cagggggagg tgtgggaggt tttttaaaca atagccttga   2460
caaggcaaac ttgaccaata gtcttagagt atccagtgag gccaggggcc ggcggctggc   2520
tagggatgaa gaataaaagg aagcaccctt cagcagttcc acacactcgc ttctggaacg   2580
tctgaggtta tcaataagct cctagtccag acgccatggg tcatttcaca gaggaggaca   2640
aggctactat cacaagcctg tggggcaagg tgaatgtgga agatgctgga ggagaaaccc   2700
tgggaaggta ggctctggtg accaggacaa gggagggaag gaaggaccct gtgcctggca   2760
aaagtccagg tcgcttctca ggatttgtgg caccttctga ctgtcaaact gttcttgtca   2820
atctcacagg ctcctggttg tctacccatg gacccagagg ttctttgaca gctttggcaa   2880
cctgtcctct gcctctgcca tcatgggcaa ccccaaagtc aaggcacatg gcaagaaggt   2940
gctgacttcc ttgggagatg ccacaaagca cctggatgat ctcaagggca cctttgccca   3000
gctgagtgaa ctgcactgtg acaagctgca tgtggatcct gagaacttca aggtgagtcc   3060
aggagatgtt tcagccctgt tgcctttagt ctcgaggcaa cttagacaac tgagtattga   3120
tctgagcaca gcagggtgtg agctgtttga agatactggg gttgggggtg aagaaactgc   3180
agaggactaa ctgggctgag acccagtggt aatgttttag ggcctaagga gcgcctctaa   3240
aaatctagat ggacaatttt gactttgaga aaagagaggt ggaaatgagg aaaatgactt   3300
ttctttatta gattccagta gaaagaactt tcatctttcc ctcatttttg ttgttttaaa   3360
acatctatct ggaggcagga caagtatggt cgttaaaaag atgcaggcag aaggcatata   3420
ttggctcagt caaagtgggg aactttgggc tagagtagat aagtagcatg gcgggttaat   3480
cattaactac aaggaacccc tagtgatgga gttggccact ccctctctgc gcgctcgctc   3540
gctcactgag gccgggcgac caaaggtcgc ccgacgcccg ggctttgccc gggcggcctc   3600
agtgagcgag cgagcgcgcc agctggcgta atagcgaaga ggcccgcacc gatcgccctt   3660
cccaacagtt gcgcagcctg aatggcgaat ggcgattccg ttgcaatggc tggcggtaat   3720
attgttctgg atattaccag caaggccgat agtttgagtt cttctactca ggcaagtgat   3780
gttattacta atcaaagaag tattgcgaca acggttaatt tgcgtgatgg acagactctt   3840
ttactcggtg gcctcactga ttataaaaac acttctcagg attctggcgt accgttcctg   3900
tctaaaatcc ctttaatcgg cctcctgttt agctcccgct ctgattctaa cgaggaaagc   3960
acgttatacg tgctcgtcaa agcaaccata gtacgcgccc tgtagcggcg cattaagcgc   4020
ggcgggtgtg gtggttacgc gcagcgtgac cgctacactt gccagcgccc tagcgcccgc   4080
tcctttcgct ttcttccctt cctttctcgc cacgttcgcc ggctttcccc gtcaagctct   4140
aaatcggggg ctccctttag ggttccgatt tagtgcttta cggcacctcg accccaaaaa   4200
acttgattag ggtgatggtt cacgtagtgg gccatcgccc tgatagacgg tttttcgccc   4260
tttgacgttg gagtccacgt tctttaatag tggactcttg ttccaaactg gaacaacact   4320
caaccctatc tcggtctatt cttttgattt ataagggatt ttgccgattt cggcctattg   4380
gttaaaaaat gagctgattt aacaaaaatt taacgcgaat tttaacaaaa tattaacgtt   4440
tacaatttaa atatttgctt atacaatctt cctgtttttg gggcttttct gattatcaac   4500
cggggtacat atgattgaca tgctagtttt acgattaccg ttcatcgatt ctcttgtttg   4560
```

-continued

```
ctccagactc tcaggcaatg acctgatagc ctttgtagag acctctcaaa aatagctacc   4620
ctctccggca tgaatttatc agctagaacg gttgaatatc atattgatgg tgatttgact   4680
gtctccggcc tttctcaccc gtttgaatct ttacctacac attactcagg cattgcattt   4740
aaaatatatg agggttctaa aaatttttat ccttgcgttg aaataaaggc ttctcccgca   4800
aaagtattac agggtcataa tgtttttggt acaaccgatt tagctttatg ctctgaggct   4860
ttattgctta attttgctaa ttctttgcct tgcctgtatg atttattgga tgttggaatc   4920
gcctgatgcg gtattttctc cttacgcatc tgtgcggtat ttcacaccgc atatggtgca   4980
ctctcagtac aatctgctct gatgccgcat agttaagcca gccccgacac ccgccaacac   5040
ccgctgacgc gccctgacgg gcttgtctgc tcccggcatc cgcttacaga caagctgtga   5100
ccgtctccgg gagctgcatg tgtcagaggt tttcaccgtc atcaccgaaa cgcgcgagac   5160
gaaagggcct cgtgatacgc ctatttttat aggttaatgt catgataata atggtttctt   5220
agacgtcagg tggcactttt cggggaaatg tgcgcggaac ccctatttgt ttatttttct   5280
aaatacattc aaatatgtat ccgctcatga gacaataacc ctgataaatg cttcaataat   5340
attgaaaaag gaagagtatg agtattcaac atttccgtgt cgcccttatt cccttttttg   5400
cggcattttg ccttcctgtt tttgctcacc cagaaacgct ggtgaaagta aaagatgctg   5460
aagatcagtt gggtgcacga gtgggttaca tcgaactgga tctcaacagc ggtaagatcc   5520
ttgagagttt tcgccccgaa gaacgttttc caatgatgag cacttttaaa gttctgctat   5580
gtggcgcggt attatcccgt attgacgccg ggcaagagca actcggtcgc cgcatacact   5640
attctcagaa tgacttggtt gagtactcac cagtcacaga aaagcatctt acggatggca   5700
tgacagtaag agaattatgc agtgctgcca taaccatgag tgataacact gcggccaact   5760
tacttctgac aacgatcgga ggaccgaagg agctaaccgc ttttttgcac aacatggggg   5820
atcatgtaac tcgccttgat cgttgggaac cggagctgaa tgaagccata ccaaacgacg   5880
agcgtgacac cacgatgcct gtagcaatgg caacaacgtt gcgcaaacta ttaactggcg   5940
aactacttac tctagcttcc cggcaacaat taatagactg gatggaggcg gataaagttg   6000
caggaccact tctgcgctcg gcccttccgg ctggctggtt tattgctgat aaatctggag   6060
ccggtgagcg tgggtctcgc ggtatcattg cagcactggg gccagatggt aagccctccc   6120
gtatcgtagt tatctacacg acggggagtc aggcaactat ggatgaacga aatagacaga   6180
tcgctgagat aggtgcctca ctgattaagc attggtaact gtcagaccaa gtttactcat   6240
atatacttta gattgattta aaacttcatt tttaatttaa aaggatctag gtgaagatcc   6300
tttttgataa tctcatgacc aaaatccctt aacgtgagtt ttcgttccac tgagcgtcag   6360
accccgtaga aaagatcaaa ggatcttctt gagatccttt ttttctgcgc gtaatctgct   6420
gcttgcaaac aaaaaaacca ccgctaccag cggtggtttg tttgccggat caagagctac   6480
caactctttt tccgaaggta actggcttca gcagagcgca gataccaaat actgtccttc   6540
tagtgtagcc gtagttaggc caccacttca agaactctgt agcaccgcct acatacctcg   6600
ctctgctaat cctgttacca gtggctgctg ccagtggcga taagtcgtgt cttaccgggt   6660
tggactcaag acgatagtta ccggataagg cgcagcggtc gggctgaacg gggggttcgt   6720
gcacacagcc cagcttggag cgaacgacct acaccgaact gagataccta cagcgtgagc   6780
tatgagaaag cgccacgctt cccgaaggga gaaaggcgga caggtatccg gtaagcggca   6840
gggtcggaac aggagagcgc acgagggagc ttccaggggg aaacgcctgg tatctttata   6900
gtcctgtcgg gtttcgccac ctctgacttg agcgtcgatt tttgtgatgc tcgtcagggg   6960
```

-continued

```
ggcggagcct atggaaaaac gccagcaacg cggccttttt acggttcctg gccttttgct   7020

ggccttttgc tcacatgttc tttcctgcgt tatcccctga ttctgtggat aaccgtatta   7080

ccgcctttga gtgagctgat accgctcgcc gcagccgaac gaccgagcgc agcgagtcag   7140

tgagcgagga agcggaagag cgcccaatac gcaaaccgcc tctccccgcg cgttggccga   7200

ttcattaatg                                                          7210
```

<210> SEQ ID NO 11
<211> LENGTH: 7204
<212> TYPE: DNA
<213> ORGANISM: Artificial
<220> FEATURE:
<223> OTHER INFORMATION: AAV donor template

<400> SEQUENCE: 11

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac acgcgcataa    180

atacttccta ccctgttaat ggtccaatat gtcagaaaca gcactgtgtt agaaataaag    240

ctgtctaaag tacactaata ttcgagttat aatagtgtgt ggactattag tcaataaaaa    300

caacccttgc ctctttagag ttgttttcca tgtacacgca catcttatgt cttagagtaa    360

gattccctga gaagtgaacc tagcatttat acaagataat taattctaat ccacagtacc    420

tgccaaagaa cattctacca tcatctttac tgagcataga agagctacgc caaaaccctg    480

ggtcatcagc cagcacacac acttatccag tggtaaatac acatcatctg gtgtatacat    540

acatacctga atatggaatc aaatattttt ctaagatgaa acagtcatga tttatttcaa    600

ataggtacgg ataagtagat attgaggtaa gcattaggtc ttatattatg taacactaat    660

ctattactgc gctgaaactg tggctttata gaaattgttt tcactgcact attgagaaat    720

taagagataa tggcaaaagt cacaaagagt atattcaaaa agaagtatag cacttttttcc    780

ttagaaacca ctgctaactg aaagagacta agatttgtcc cgtcaaaaat cctggaccta    840

tgcctaaaac acatttcaca atccctgaac ttttcaaaaa ttggtacatg ctttagcttt    900

aaactacagg cctcactgga gctagagaca agaaggtaaa aaacggctga caaaagaagt    960

cctggtatcc tctatgatgg gagaaggaaa ctagctaaag ggaagaataa attagagaaa   1020

aactggaatg actgaatcgg aacaaggcaa aggctataaa aaaaattaag cagcagtatc   1080

ctcttggggg ccccttcccc acactatctc aatgcaaata tctgtctgaa acggtccctg   1140

gctaaactcc acccatgggt tggccagcct tgccttgacg aacagagaaa caggagaata   1200

tgggccaaac aggatatctg tggtaagcag ttcctgcccc ggctcagggc caagaacagt   1260

tggaacagca gaatatgggc caaacaggat atctgtggta agcagttcct gccccggctc   1320

agggccaaga acagatggtc cccagatgcg gtcccgccct cagcagtttc tagagaacca   1380

tcagatgttt ccagggtgcc ccaaggacct gaaatgaccc tgtgccttat ttgaactaac   1440

caatcagttc gcttctcgct tctgttcgcg cgcttctgct ccccgagctc tatataagca   1500

gagctcgttt agtgaaccgt cagatcgcct ggagacgcca tccacgctgt tttgacttcc   1560

atagaaggat ctcgaggcca ccatggtgag caagggcgag gagctgttca ccggggtggt   1620

gcccatcctg gtcgagctgg acggcgacgt aaacggccac aagttcagcg tgtccggcga   1680

gggcgagggc gatgccacct acggcaagct gaccctgaag ttcatctgca ccaccggcaa   1740
```

-continued

```
gctgcccgtg ccctggccca ccctcgtgac caccctgacc tacggcgtgc agtgcttcag   1800
ccgctacccc gaccacatga agcagcacga cttcttcaag tccgccatgc ccgaaggcta   1860
cgtccaggag cgcaccatct tcttcaagga cgacggcaac tacaagaccc gcgccgaggt   1920
gaagttcgag ggcgacaccc tggtgaaccg catcgagctg aagggcatcg acttcaagga   1980
ggacggcaac atcctggggc acaagctgga gtacaactac aacagccaca acgtctatat   2040
catggccgac aagcagaaga acggcatcaa ggtgaacttc aagatccgcc acaacatcga   2100
ggacggcagc gtgcagctcg ccgaccacta ccagcagaac acccccatcg gcgacggccc   2160
cgtgctgctg cccgacaacc actacctgag cacccagtcc gccctgagca aagaccccaa   2220
cgagaagcgc gatcacatgg tcctgctgga gttcgtgacc gccgccggga tcactctcgg   2280
catggacgag ctgtacaagt aaactagtgt cgactgcttt atttgtgaaa tttgtgatgc   2340
tattgcttta tttgtaacca ttataagctg caataaacaa gttaacaaca acaattgcat   2400
tcattttatg tttcaggttc agggggaggt gtgggaggtt ttttaaaaac ttcaaggtga   2460
gtccaggaga tgtttcagcc ctgttgcctt tagtctcgag gcaacttaga caactgagta   2520
ttgatctgag cacagcaggg tgtgagctgt ttgaagatac tggggttggg ggtgaagaaa   2580
ctgcagagga ctaactgggc tgagacccag tggtaatgtt ttagggccta aggagcgcct   2640
ctaaaaatct agatggacaa ttttgacttt gagaaaagag aggtggaaat gaggaaaatg   2700
acttttatta gattccagta gaaagaactt tcatctttcc ctcatttttg ttgttttaaa   2760
acatctatct ggaggcagga caagtatggt cgttaaaaag atgcaggcag aaggcatata   2820
ttggctcagt caaagtgggg aactttggtg gccaaacata cattgctaag gctattccta   2880
tatcagctgg acacatataa aatgctgcta atgcttcatt acaaacttat atcctttaat   2940
tccagatggg ggcaaagtat gtccaggggt gaggaacaat tgaaacattt gggctggagt   3000
agattttgaa agtcagctct gtgtgtgtgt gtgtgtgcgc gcgcgcgtgt gtgtgtgtgt   3060
gtgtcagcgt gtgtttcttt taacgtcttc agcctacaac atacagggtt catggtggca   3120
agaagatagc aagatttaaa ttatggccag tgactagtgc ttgaagggga acaactacct   3180
gcatttaatg ggaaggcaaa atctcaggct ttgagggaag ttaacatagg cttgattctg   3240
ggtagaagct gggtgtgtag ttatctggag gccaggctgg agctctcagc tcactatggg   3300
ttcatcttta ttgtctcctt tcatctcaac agctcctggg aaatgtgctg gtgaccgttt   3360
tggcaatcca tttcggcaaa gaattcaccc ctgaggtgca ggcttcctgg cagaagatgg   3420
tgactgcagt ggccagtgcc ctgctagagt agataagtag catggcgggt taatcattaa   3480
ctacaaggaa cccctagtga tggagttggc cactccctct ctgcgcgctc gctcgctcac   3540
tgaggccggg cgaccaaagg tcgcccgacg cccgggcttt gcccgggcgg cctcagtgag   3600
cgagcgagcg cgccagctgg cgtaatagcg aagaggcccg caccgatcgc ccttcccaac   3660
agttgcgcag cctgaatggc gaatggcgat tccgttgcaa tggctggcgg taatattgtt   3720
ctggatatta ccagcaaggc cgatagtttg agttcttcta ctcaggcaag tgatgttatt   3780
actaatcaaa gaagtattgc gacaacggtt aatttgcgtg atggacagac tcttttactc   3840
ggtggcctca ctgattataa aaacacttct caggattctg gcgtaccgtt cctgtctaaa   3900
atccctttaa tcggcctcct gtttagctcc cgctctgatt ctaacgagga aagcacgtta   3960
tacgtgctcg tcaaagcaac catagtacgc gccctgtagc ggcgcattaa gcgcggcggg   4020
tgtggtggtt acgcgcagcg tgaccgctac acttgccagc gccctagcgc ccgctccttt   4080
cgctttcttc ccttcctttc tcgccacgtt cgccggcttt ccccgtcaag ctctaaatcg   4140
```

ggggctccct ttagggttcc gatttagtgc tttacggcac ctcgacccca aaaaacttga 4200
ttagggtgat ggttcacgta gtgggccatc gccctgatag acggtttttc gccctttgac 4260
gttggagtcc acgttcttta atagtggact cttgttccaa actggaacaa cactcaaccc 4320
tatctcggtc tattcttttg atttataagg gattttgccg atttcggcct attggttaaa 4380
aaatgagctg atttaacaaa aatttaacgc gaattttaac aaaatattaa cgtttacaat 4440
ttaaatattt gcttatacaa tcttcctgtt tttggggctt ttctgattat caaccggggt 4500
acatatgatt gacatgctag ttttacgatt accgttcatc gattctcttg tttgctccag 4560
actctcaggc aatgacctga tagcctttgt agagacctct caaaaatagc taccctctcc 4620
ggcatgaatt tatcagctag aacggttgaa tatcatattg atggtgattt gactgtctcc 4680
ggcctttctc acccgtttga atctttacct acacattact caggcattgc atttaaaata 4740
tatgagggtt ctaaaaattt ttatccttgc gttgaaataa aggcttctcc cgcaaaagta 4800
ttacagggtc ataatgtttt tggtacaacc gatttagctt tatgctctga ggctttattg 4860
cttaattttg ctaattcttt gccttgcctg tatgatttat tggatgttgg aatcgcctga 4920
tgcggtattt tctccttacg catctgtgcg gtatttcaca ccgcatatgg tgcactctca 4980
gtacaatctg ctctgatgcc gcatagttaa gccagccccg acacccgcca acacccgctg 5040
acgcgccctg acgggcttgt ctgctcccgg catccgctta cagacaagct gtgaccgtct 5100
ccgggagctg catgtgtcag aggttttcac cgtcatcacc gaaacgcgcg agacgaaagg 5160
gcctcgtgat acgcctattt ttataggtta atgtcatgat aataatggtt tcttagacgt 5220
caggtggcac ttttcgggga aatgtgcgcg gaacccctat ttgtttattt ttctaaatac 5280
attcaaatat gtatccgctc atgagacaat aaccctgata aatgcttcaa taatattgaa 5340
aaaggaagag tatgagtatt caacatttcc gtgtcgccct tattcccttt tttgcggcat 5400
tttgccttcc tgtttttgct cacccagaaa cgctggtgaa agtaaaagat gctgaagatc 5460
agttgggtgc acgagtgggt tacatcgaac tggatctcaa cagcggtaag atccttgaga 5520
gttttcgccc cgaagaacgt tttccaatga tgagcacttt taaagttctg ctatgtggcg 5580
cggtattatc ccgtattgac gccgggcaag agcaactcgg tcgccgcata cactattctc 5640
agaatgactt ggttgagtac tcaccagtca cagaaaagca tcttacggat ggcatgacag 5700
taagagaatt atgcagtgct gccataacca tgagtgataa cactgcggcc aacttacttc 5760
tgacaacgat cggaggaccg aaggagctaa ccgctttttt gcacaacatg ggggatcatg 5820
taactcgcct tgatcgttgg gaaccggagc tgaatgaagc cataccaaac gacgagcgtg 5880
acaccacgat gcctgtagca atggcaacaa cgttgcgcaa actattaact ggcgaactac 5940
ttactctagc ttcccggcaa caattaatag actggatgga ggcggataaa gttgcaggac 6000
cacttctgcg ctcggccctt ccggctggct ggtttattgc tgataaatct ggagccggtg 6060
agcgtgggtc tcgcggtatc attgcagcac tggggccaga tggtaagccc tcccgtatcg 6120
tagttatcta cacgacgggg agtcaggcaa ctatggatga acgaaataga cagatcgctg 6180
agataggtgc ctcactgatt aagcattggt aactgtcaga ccaagtttac tcatatatac 6240
tttagattga tttaaaactt catttttaat ttaaaaggat ctaggtgaag atcctttttg 6300
ataatctcat gaccaaaatc ccttaacgtg agttttcgtt ccactgagcg tcagaccccg 6360
tagaaaagat caaaggatct tcttgagatc ctttttttct gcgcgtaatc tgctgcttgc 6420
aaacaaaaaa accaccgcta ccagcggtgg tttgtttgcc ggatcaagag ctaccaactc 6480

-continued

```
tttttccgaa ggtaactggc ttcagcagag cgcagatacc aaatactgtc cttctagtgt   6540

agccgtagtt aggccaccac ttcaagaact ctgtagcacc gcctacatac ctcgctctgc   6600

taatcctgtt accagtggct gctgccagtg gcgataagtc gtgtcttacc gggttggact   6660

caagacgata gttaccggat aaggcgcagc ggtcgggctg aacggggggt tcgtgcacac   6720

agcccagctt ggagcgaacg acctacaccg aactgagata cctacagcgt gagctatgag   6780

aaagcgccac gcttcccgaa gggagaaagg cggacaggta tccggtaagc ggcagggtcg   6840

gaacaggaga gcgcacgagg gagcttccag ggggaaacgc ctggtatctt tatagtcctg   6900

tcgggtttcg ccacctctga cttgagcgtc gatttttgtg atgctcgtca ggggggcgga   6960

gcctatggaa aaacgccagc aacgcggcct ttttacggtt cctggccttt tgctggcctt   7020

ttgctcacat gttctttcct gcgttatccc ctgattctgt ggataaccgt attaccgcct   7080

ttgagtgagc tgataccgct cgccgcagcc gaacgaccga gcgcagcgag tcagtgagcg   7140

aggaagcgga agagcgccca atacgcaaac cgcctctccc cgcgcgttgg ccgattcatt   7200

aatg                                                                7204
```

<210> SEQ ID NO 12
<211> LENGTH: 8236
<212> TYPE: DNA
<213> ORGANISM: Artificial
<220> FEATURE:
<223> OTHER INFORMATION: AAV donor template

<400> SEQUENCE: 12

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt cctacgcgta gatcttaccc tgttaatggt ccaatatgtc agaaacagca    180

ctgtgttaga aataaagctg tctaaagtac actaatattc gagttataat agtgtgtgga    240

ctattagtca ataaaaacaa ccccttgcctc tttagagttg ttttccatgt acacgcacat    300

cttatgtctt agagtaagat tccctgagaa gtgaacctag catttataca agataattaa    360

ttctaatcca cagtacctgc caaagaacat tctaccatca tctttactga gcatagaaga    420

gctacgccaa aaccctgggt catcagccag cacacacact tatccagtgg taaatacaca    480

tcatctggtg tatacataca tacctgaata tggaatcaaa tatttttcta agatgaaaca    540

gtcatgattt atttcaaata ggtacggata agtagatatt gaggtaagca ttaggtctta    600

tattatgtaa cactaatcta ttactgcgct gaaactgtgg ctttatagaa attgttttca    660

ctgcactatt gagaaattaa gagataatgg caaaagtcac aaagagtata ttcaaaaaga    720

agtatagcac tttttcctta gaaaccactg ctaactgaaa gagactaaga tttgtcccgt    780

caaaaatcct ggacctatgc ctaaaacaca tttcacaatc cctgaacttt tcaaaaattg    840

gtacatgctt tagctttaaa ctacaggcct cactggagct agagacaaga aggtaaaaaa    900

cggctgacaa aagaagtcct ggtatcctct atgatgggag aaggaaacta gctaaaggga    960

agaataaatt agagaaaaac tggaatgact gaatcggaac aaggcaaagg ctataaaaaa   1020

aattagcagt atcctcttgg gggccccttc cccacactat ctcaatgcaa atatctgtct   1080

gaaacggtcc ctggctaaac tccacccatg ggttggccag ccttgccttg accaatagcc   1140

ttgacgaatt cgctttaaaa aacctcccac atctccccct gaacctgaaa cataaaatga   1200

atgcaattgt tgttgttaac ttgtttattg cagcttataa tggttacaaa taaagcaata   1260

gcatcacaaa tttcacaaat aaagcttact tgtacagctc gtccatgccg agagtgatcc   1320
```

-continued

```
cggcggcggt cacgaactcc agcaggacca tgtgatcgcg cttctcgttg gggtctttgc   1380
tcagggcgga ctgggtgctc aggtagtggt tgtcgggcag cagcacgggg ccgtcgccga   1440
tgggggtgtt ctgctggtag tggtcggcga gctgcacgct gccgtcctcg atgttgtggc   1500
ggatcttgaa gttcaccttg atgccgttct tctgcttgtc ggccatgata tagacgttgt   1560
ggctgttgta gttgtactcc agcttgtgcc ccaggatgtt gccgtcctcc ttgaagtcga   1620
tgcccttcag ctcgatgcgg ttcaccaggg tgtcgccctc gaacttcacc tcggcgcggg   1680
tcttgtagtt gccgtcgtcc ttgaagaaga tggtgcgctc ctggacgtag ccttcgggca   1740
tggcggactt gaagaagtcg tgctgcttca tgtggtcggg gtagcggctg aagcactgca   1800
cgccgtaggt cagggtggtc acgagggtgg gccagggcac gggcagcttg ccggtggtgc   1860
agatgaactt cagggtcagc ttgccgtagg tggcatcgcc ctcgccctcg ccggacacgc   1920
tgaacttgtg gccgtttacg tcgccgtcca gctcgaccag gatgggcacc accccggtga   1980
acagctcctc gcccttgctc accatggtgg cggcgcggcc gcgatctgac ggttcactaa   2040
acgagctctg cttatataga gctcggggag cagaagcgcg cgaacagaag cgagaagcga   2100
actgattggt tagttcaaat aaggcacagg gtcatttcag gtccttgggg caccctggaa   2160
acatctgatg gttctctaga aactgctgag ggcgggaccg catctgggga ccatctgttc   2220
ttggccctga gccggggcag gaactgctta ccacagatat cctgtttggc ccatattctg   2280
ctgttccaac tgttcttggc cctgagccgg ggcaggaact gcttaccaca gatatcctgt   2340
ttggcccata ttctcctgtt tctctgttcc cgcggcgaga tcgagaccat cctggctaac   2400
acagtgaaac cccgtctcta ctaaaaaaat acaaaaaatt agccgggctt ggtggcgggt   2460
gcctgtagtc ccagctacta tggaggctga ggcgggagaa tggcgtgaac gcgggggggcg   2520
gagcttgcag tgagcagaga tcaggggcca ctgcactcca gcctgggcga cagagagaga   2580
ctctgtctca aaaaaaagaa aaaaaaaatt tagtagacta gctaaaaaaa tccagagata   2640
gttattgatg catatgtaaa agtcttccaa tatttacaag tacaatgaaa aaaaaataac   2700
cttgaattaa gtgtagaact cattgacaat gtttcaaagg atgtgaggga taaactaaaa   2760
tttgggcagt acatgctgtt cctgtgtact tggaacagag ggagaaaatc tgggctggaa   2820
atattgttat aggagttagc acatgaaggt gacaactaaa ttatttggag tagatggagt   2880
caccagcaca tgtgaatagt tttagaatga aatgacccaa gatagaactt tggagagccc   2940
ccaaatttaa ataaaatcag tataagagaa gaggaagaaa ccaaatggta tactagtcta   3000
aattgtttct tagtgacaaa agaataacct gaatattaga ttagctgcct atatgctctc   3060
tgaatcaatt tcattcaaca tgcaacagtt ctggaaccta tcagggacca cagtcagcca   3120
ggcaagcaca tctgcccaag ccaagggtgg aggcatgcag ctgtgggggt ctgtgaaaac   3180
acttgaggga gcagataact gggccaacca tgactcagtg cttctggagg ccaacaggac   3240
tgctgagtca tcctgtgggg gtggaggtgg gacaagggaa aggggtgaat ggtactgctg   3300
attacaacct ctggtgctgc ctccccctcc tgtttatctg agagaggcct cactggagct   3360
agagacaaga aggtaaaaaa cggctgacaa aagaagtcct ggtatcctct atgatgggag   3420
aaggaaacta gctaaaggga agaataaatt agagaaaaac tggaatgact gaatcggaac   3480
aaggcaaagg ctataaaaaa aattagcagt atcctcttgg gggccccttc cccacactat   3540
ctcaatgcaa atatctgtct gaaacggtcc ctggctaaac tccacccatg ggttggccag   3600
ccttgccttg acaaggcaaa cttgaccaat agtcttagag tatccagtga ggccaggggc   3660
```

-continued

```
cggcggctgg ctagggatga agaataaaag gaagcaccct tcagcagttc cacacactcg   3720
cttctggaac gtctgaggtt atcaataagc tcctagtcca gacgccatgg gtcatttcac   3780
agaggaggac aaggctacta tcacaagcct gtggggcaag gtgaatgtgg aagatgctgg   3840
aggagaaacc ctgggaaggt aggctctggt gaccaggaca agggagggaa ggaaggaccc   3900
tgtgcctggc aaaagtccag gtcgcttctc aggatttgtg gcaccttctg actgtcaaac   3960
tgttcttgtc aatctcacag gctcctggtt gtctacccat ggacccagag gttctttgac   4020
agctttggca acctgtcctc tgcctctgcc atcatgggca accccaaagt caaggcacat   4080
ggcaagaagg tgctgacttc cttgggagat gccacaaagc acctggatga tctcaagggc   4140
acctttgccc agctgagtga actgcactgt gacaagctgc atgtggatcc tgagaacttc   4200
aaggtgagtc caggagatgt ttcagccctg ttgcctttag tctcgaggca acttagacaa   4260
cggagtattg atctgagcac agcagggtgt gagctgtttg aagatactgg ggttgggggt   4320
gaagaaactg cagaggacta actgggctga gacccagtgg taatgtttta gggcctaagg   4380
agtgcctcta aaaatctaga tggacaattt tgactttgag aaaagagagg tggaaatgag   4440
gaaaatgact tttctttatt agattccagt agaaagaact ttcatctttc cctcattttt   4500
gttgttttaa aagtcgacag gaacccctag tgatggagtt ggccactccc tctctgcgcg   4560
ctcgctcgct cactgaggcc gggcgaccaa aggtcgcccg acgcccgggc tttgcccggg   4620
cggcctcagt gagcgagcga gcgcgcagct ggcgtaatag cgaagaggcc cgcaccgatc   4680
gcccttccca acagttgcgc agcctgaatg gcgaatggcg attccgttgc aatggctggc   4740
ggtaatattg ttctggatat taccagcaag gccgatagtt tgagttcttc tactcaggca   4800
agtgatgtta ttactaatca aagaagtatt gcgacaacgg ttaatttgcg tgatggacag   4860
actcttttac tcggtggcct cactgattat aaaaacactt ctcaggattc tggcgtaccg   4920
ttcctgtcta aaatcccttt aatcggcctc ctgtttagct cccgctctga ttctaacgag   4980
gaaagcacgt tatacgtgct cgtcaaagca accatagtac gcgccctgta gcggcgcatt   5040
aagcgcggcg ggtgtggtgg ttacgcgcag cgtgaccgct acacttgcca gcgccctagc   5100
gcccgctcct ttcgctttct tcccttcctt tctcgccacg ttcgccggct ttccccgtca   5160
agctctaaat cgggggctcc ctttagggtt ccgatttagt gctttacggc acctcgaccc   5220
caaaaaactt gattagggtg atggttcacg tagtgggcca tcgccctgat agacggtttt   5280
tcgccctttg acgttggagt ccacgttctt taatagtgga ctcttgttcc aaactggaac   5340
aacactcaac cctatctcgg tctattcttt tgatttataa gggattttgc cgatttcggc   5400
ctattggtta aaaaatgagc tgatttaaca aaaatttaac gcgaatttta acaaaatatt   5460
aacgtttaca atttaaatat ttgcttatac aatcttcctg tttttggggc ttttctgatt   5520
atcaaccggg gtacatatga ttgacatgct agttttacga ttaccgttca tcgattctct   5580
tgtttgctcc agactctcag gcaatgacct gatagccttt gtagagacct ctcaaaaata   5640
gctaccctct ccggcatgaa tttatcagct agaacggttg aatatcatat tgatggtgat   5700
ttgactgtct ccggcctttc tcacccgttt gaatctttac ctacacatta ctcaggcatt   5760
gcatttaaaa tatatgaggg ttctaaaaat ttttatcctt gcgttgaaat aaaggcttct   5820
cccgcaaaag tattacaggg tcataatgtt tttggtacaa ccgatttagc tttatgctct   5880
gaggctttat tgcttaattt tgctaattct ttgccttgcc tgtatgattt attggatgtt   5940
ggaatcgcct gatgcggtat tttctcctta cgcatctgtg cggtatttca caccgcatat   6000
ggtgcactct cagtacaatc tgctctgatg ccgcatagtt aagccagccc cgacacccgc   6060
```

```
caacacccgc tgacgcgccc tgacgggctt gtctgctccc ggcatccgct tacagacaag   6120
ctgtgaccgt ctccgggagc tgcatgtgtc agaggttttc accgtcatca ccgaaacgcg   6180
cgagacgaaa gggcctcgtg atacgcctat ttttataggt taatgtcatg ataataatgg   6240
tttcttagac gtcaggtggc acttttcggg gaaatgtgcg cggaacccct atttgtttat   6300
ttttctaaat acattcaaat atgtatccgc tcatgagaca ataaccctga taaatgcttc   6360
aataatattg aaaaaggaag agtatgagta ttcaacattt ccgtgtcgcc cttattccct   6420
tttttgcggc attttgcctt cctgtttttg ctcacccaga aacgctggtg aaagtaaaag   6480
atgctgaaga tcagttgggt gcacgagtgg gttacatcga actggatctc aacagcggta   6540
agatccttga gagttttcgc cccgaagaac gttttccaat gatgagcact tttaaagttc   6600
tgctatgtgg cgcggtatta tcccgtattg acgccgggca agagcaactc ggtcgccgca   6660
tacactattc tcagaatgac ttggttgagt actcaccagt cacagaaaag catcttacgg   6720
atggcatgac agtaagagaa ttatgcagtg ctgccataac catgagtgat aacactgcgg   6780
ccaacttact tctgacaacg atcggaggac cgaaggagct aaccgctttt ttgcacaaca   6840
tgggggatca tgtaactcgc cttgatcgtt gggaaccgga gctgaatgaa gccataccaa   6900
acgacgagcg tgacaccacg atgcctgtag caatggcaac aacgttgcgc aaactattaa   6960
ctggcgaact acttactcta gcttcccggc aacaattaat agactggatg gaggcggata   7020
aagttgcagg accacttctg cgctcggccc ttccggctgg ctggtttatt gctgataaat   7080
ctggagccgg tgagcgtggg tctcgcggta tcattgcagc actggggcca gatggtaagc   7140
cctcccgtat cgtagttatc tacacgacgg ggagtcaggc aactatggat gaacgaaata   7200
gacagatcgc tgagataggt gcctcactga ttaagcattg gtaactgtca gaccaagttt   7260
actcatatat actttagatt gatttaaaac ttcattttta atttaaaagg atctaggtga   7320
agatcctttt tgataatctc atgaccaaaa tcccttaacg tgagttttcg ttccactgag   7380
cgtcagaccc cgtagaaaag atcaaaggat cttcttgaga tccttttttt ctgcgcgtaa   7440
tctgctgctt gcaaacaaaa aaaccaccgc taccagcggt ggtttgtttg ccggatcaag   7500
agctaccaac tctttttccg aaggtaactg gcttcagcag agcgcagata ccaaatactg   7560
tccttctagt gtagccgtag ttaggccacc acttcaagaa ctctgtagca ccgcctacat   7620
acctcgctct gctaatcctg ttaccagtgg ctgctgccag tggcgataag tcgtgtctta   7680
ccgggttgga ctcaagacga tagttaccgg ataaggcgca gcggtcgggc tgaacggggg   7740
gttcgtgcac acagcccagc ttggagcgaa cgacctacac cgaactgaga tacctacagc   7800
gtgagctatg agaaagcgcc acgcttcccg aagggagaaa ggcggacagg tatccggtaa   7860
gcggcagggt cggaacagga gagcgcacga gggagcttcc agggggaaac gcctggtatc   7920
tttatagtcc tgtcgggttt cgccacctct gacttgagcg tcgatttttg tgatgctcgt   7980
caggggggcg gagcctatgg aaaaacgcca gcaacgcggc ctttttacgg ttcctggcct   8040
tttgctggcc ttttgctcac atgttctttc ctgcgttatc ccctgattct gtggataacc   8100
gtattaccgc ctttgagtga gctgataccg ctcgccgcag ccgaacgacc gagcgcagcg   8160
agtcagtgag cgaggaagcg gaagagcgcc caatacgcaa accgcctctc cccgcgcgtt   8220
ggccgattca ttaatg                                                   8236
```

<210> SEQ ID NO 13
<211> LENGTH: 7955
<212> TYPE: DNA

<213> ORGANISM: Artificial
<220> FEATURE:
<223> OTHER INFORMATION: AAV donor template

<400> SEQUENCE: 13
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatcttaccc tgttaatggt ccaatatgtc agaaacagca 180
ctgtgttaga aataaagctg tctaaagtac actaatattc gagttataat agtgtgtgga 240
ctattagtca ataaaaacaa cccttgcctc tttagagttg ttttccatgt acacgcacat 300
cttatgtctt agagtaagat tccctgagaa gtgaacctag catttataca agataattaa 360
ttctaatcca cagtacctgc caaagaacat tctaccatca tctttactga gcatagaaga 420
gctacgccaa aaccctgggt catcagccag cacacacact tatccagtgg taaatacaca 480
tcatctggtg tatacataca tacctgaata tggaatcaaa tatttttcta agatgaaaca 540
gtcatgattt atttcaaata ggtacggata agtagatatt gaggtaagca ttaggtctta 600
tattatgtaa cactaatcta ttactgcgct gaaactgtgg ctttatagaa attgttttca 660
ctgcactatt gagaaattaa gagataatgg caaaagtcac aaagagtata ttcaaaaaga 720
agtatagcac tttttcctta gaaaccactg ctaactgaaa gagactaaga tttgtcccgt 780
caaaaatcct ggacctatgc ctaaaacaca tttcacaatc cctgaacttt tcaaaaattg 840
gtacatgctt tagctttaaa ctacgaattc gctttaaaaa acctcccaca tctcccccctg 900 aacctgaaac ataaaatgaa tgcaattgtt gttgttaact tgtttattgc agcttataat 960
ggttacaaat aaagcaatag catcacaaat ttcacaaata aagcttactt gtacagctcg 1020
tccatgccga gagtgatccc ggcggcggtc acgaactcca gcaggaccat gtgatcgcgc 1080
ttctcgttgg ggtctttgct cagggcggac tgggtgctca ggtagtggtt gtcgggcagc 1140
agcacggggc cgtcgccgat gggggtgttc tgctggtagt ggtcggcgag ctgcacgctg 1200
ccgtcctcga tgttgtggcg gatcttgaag ttcaccttga tgccgttctt ctgcttgtcg 1260
gccatgatat agacgttgtg gctgttgtag ttgtactcca gcttgtgccc caggatgttg 1320
ccgtcctcct tgaagtcgat gcccttcagc tcgatgcggt tcaccagggt gtcgccctcg 1380
aacttcacct cggcgcgggt cttgtagttg ccgtcgtcct tgaagaagat ggtgcgctcc 1440
tggacgtagc cttcgggcat ggcggacttg aagaagtcgt gctgcttcat gtggtcgggg 1500
tagcggctga agcactgcac gccgtaggtc agggtggtca cgagggtggg ccagggcacg 1560
ggcagcttgc cggtggtgca gatgaacttc agggtcagct tgccgtaggt ggcatcgccc 1620
tcgccctcgc cggacacgct gaacttgtgg ccgtttacgt cgccgtccag ctcgaccagg 1680
atgggcacca ccccggtgaa cagctcctcg cccttgctca ccatggtggc ggcgcggccg 1740
cgatctgacg gttcactaaa cgagctctgc ttatatagag ctcggggagc agaagcgcgc 1800
gaacagaagc gagaagcgaa ctgattggtt agttcaaata aggcacaggg tcatttcagg 1860
tccttggggc accctggaaa catctgatgg ttctctagaa actgctgagg gcgggaccgc 1920
atctggggac catctgttct tggccctgag ccggggcagg aactgcttac cacagatatc 1980
ctgtttggcc catattctgc tgttccaact gttcttggcc ctgagccggg gcaggaactg 2040
cttaccacag atatcctgtt tggcccatat tctcctgttt ctctgttccc gcggcgagat 2100
cgagaccatc ctggctaaca cagtgaaacc ccgtctctac taaaaaaata caaaaaatta 2160
gccgggcttg gtggcgggtg cctgtagtcc cagctactat ggaggctgag gcgggagaat 2220
ggcgtgaacg cgggggggcgg agcttgcagt gagcagagat caggggccac tgcactccag 2280
cctgggcgac agagagagac tctgtctcaa aaaaaagaaa aaaaaaattt agtagactag 2340
ctaaaaaaat ccagagatag ttattgatgc atatgtaaaa gtcttccaat atttacaagt 2400
acaatgaaaa aaaaataacc ttgaattaag tgtagaactc attgacaatg tttcaaagga 2460
tgtgagggat aaactaaaat ttgggcagta catgctgttc ctgtgtactt ggaacagagg 2520
gagaaaatct gggctggaaa tattgttata ggagttagca catgaaggtg acaactaaat 2580
tatttggagt agatggagtc accagcacat gtgaatagtt ttagaatgaa atgacccaag 2640
atagaacttt ggagagcccc caaatttaaa taaaatcagt ataagagaag aggaagaaac 2700
caaatggtat actagtctaa attgtttctt agtgacaaaa gaataacctg aatattagat 2760
tagctgccta tatgctctct gaatcaattt cattcaacat gcaacagttc tggaacctat 2820
cagggaccac agtcagccag gcaagcacat ctgcccaagc caagggtgga ggcatgcagc 2880
tgtgggggtc tgtgaaaaca cttgagggag cagataactg ggccaaccat gactcagtgc 2940
ttctggaggc caacaggact gctgagtcat cctgtggggg tggaggtggg acaagggaaa 3000
ggggtgaatg gtactgctga ttacaacctc tggtgctgcc tccccctcct gtttatctga 3060
gagaggcctc actggagcta gagacaagaa ggtaaaaaac ggctgacaaa agaagtcctg 3120
gtatcctcta tgatgggaga aggaaactag ctaaagggaa gaataaatta gagaaaaact 3180
ggaatgactg aatcggaaca aggcaaaggc tataaaaaaa attagcagta tcctcttggg 3240
ggccccttcc ccacactatc tcaatgcaaa tatctgtctg aaacggtccc tggctaaact 3300
ccacccatgg gttggccagc cttgccttga caaggcaaac ttgaccaata gtcttagagt 3360
atccagtgag gccaggggcc ggcggctggc tagggatgaa gaataaaagg aagcacccctt 3420 cagcagttcc acacactcgc ttctggaacg tctgaggtta tcaataagct cctagtccag 3480
acgccatggg tcatttcaca gaggaggaca aggctactat cacaagcctg tggggcaagg 3540
tgaatgtgga agatgctgga ggagaaaccc tgggaaggta ggctctggtg accaggacaa 3600
gggagggaag gaaggaccct gtgcctggca aaagtccagg tcgcttctca ggatttgtgg 3660
caccttctga ctgtcaaact gttcttgtca atctcacagg ctcctggttg tctacccatg 3720
gacccagagg ttctttgaca gctttggcaa cctgtcctct gcctctgcca tcatgggcaa 3780
ccccaaagtc aaggcacatg gcaagaaggt gctgacttcc ttgggagatg ccacaaagca 3840
cctggatgat ctcaagggca cctttgccca gctgagtgaa ctgcactgtg acaagctgca 3900
tgtggatcct gagaacttca aggtgagtcc aggagatgtt tcagccctgt tgcctttagt 3960
ctcgaggcaa cttagacaac ggagtattga tctgagcaca gcagggtgtg agctgtttga 4020
agatactggg gttgggggtg aagaaactgc agaggactaa ctgggctgag acccagtggt 4080
aatgttttag ggcctaagga gtgcctctaa aaatctagat ggacaatttt gactttgaga 4140
aaagagaggt ggaaatgagg aaaatgactt ttctttatta gattccagta gaaagaactt 4200
tcatctttcc ctcatttttg ttgttttaaa agtcgacagg aacccctagt gatggagttg 4260
gccactccct ctctgcgcgc tcgctcgctc actgaggccg ggcgaccaaa ggtcgcccga 4320
cgcccgggct ttgcccgggc ggcctcagtg agcgagcgag cgcgcagctg gcgtaatagc 4380
gaagaggccc gcaccgatcg cccttcccaa cagttgcgca gcctgaatgg cgaatggcga 4440
ttccgttgca atggctggcg gtaatattgt tctggatatt accagcaagg ccgatagttt 4500
gagttcttct actcaggcaa gtgatgttat tactaatcaa agaagtattg cgacaacggt 4560

-continued

```
taatttgcgt gatggacaga ctcttttact cggtggcctc actgattata aaaacacttc   4620
tcaggattct ggcgtaccgt tcctgtctaa aatcccttta atcggcctcc tgtttagctc   4680
ccgctctgat tctaacgagg aaagcacgtt atacgtgctc gtcaaagcaa ccatagtacg   4740
cgccctgtag cggcgcatta agcgcggcgg gtgtggtggt tacgcgcagc gtgaccgcta   4800
cacttgccag cgccctagcg cccgctcctt tcgctttctt cccttccttt ctcgccacgt   4860
tcgccggctt tccccgtcaa gctctaaatc gggggctccc tttagggttc cgatttagtg   4920
ctttacggca cctcgacccc aaaaaacttg attagggtga tggttcacgt agtgggccat   4980
cgccctgata gacggttttt cgccctttga cgttggagtc cacgttcttt aatagtggac   5040
tcttgttcca aactggaaca acactcaacc ctatctcggt ctattctttt gatttataag   5100
ggattttgcc gatttcggcc tattggttaa aaaatgagct gatttaacaa aaatttaacg   5160
cgaattttaa caaaatatta acgtttacaa tttaaatatt tgcttataca atcttcctgt   5220
ttttggggct tttctgatta tcaaccgggg tacatatgat tgacatgcta gttttacgat   5280
taccgttcat cgattctctt gtttgctcca gactctcagg caatgacctg atagcctttg   5340
tagagacctc tcaaaaatag ctaccctctc cggcatgaat ttatcagcta gaacggttga   5400
atatcatatt gatggtgatt tgactgtctc cggcctttct cacccgtttg aatctttacc   5460
tacacattac tcaggcattg catttaaaat atatgagggt tctaaaaatt tttatccttg   5520
cgttgaaata aaggcttctc ccgcaaaagt attacagggt cataatgttt ttggtacaac   5580
cgatttagct ttatgctctg aggctttatt gcttaatttt gctaattctt tgccttgcct   5640
gtatgattta ttggatgttg gaatcgcctg atgcggtatt ttctccttac gcatctgtgc   5700
ggtatttcac accgcatatg gtgcactctc agtacaatct gctctgatgc cgcatagtta   5760
agccagcccc gacacccgcc aacacccgct gacgcgccct gacgggcttg tctgctcccg   5820
gcatccgctt acagacaagc tgtgaccgtc tccgggagct gcatgtgtca gaggttttca   5880
ccgtcatcac cgaaacgcgc gagacgaaag ggcctcgtga tacgcctatt tttataggtt   5940
aatgtcatga taataatggt ttcttagacg tcaggtggca cttttcgggg aaatgtgcgc   6000
ggaaccccta tttgtttatt tttctaaata cattcaaata tgtatccgct catgagacaa   6060
taaccctgat aaatgcttca ataatattga aaaaggaaga gtatgagtat tcaacatttc   6120
cgtgtcgccc ttattccctt ttttgcggca ttttgccttc ctgtttttgc tcacccagaa   6180
acgctggtga aagtaaaaga tgctgaagat cagttgggtg cacgagtggg ttacatcgaa   6240
ctggatctca acagcggtaa gatccttgag agttttcgcc ccgaagaacg ttttccaatg   6300
atgagcactt ttaaagttct gctatgtggc gcggtattat cccgtattga cgccgggcaa   6360
gagcaactcg gtcgccgcat acactattct cagaatgact tggttgagta ctcaccagtc   6420
acagaaaagc atcttacgga tggcatgaca gtaagagaat tatgcagtgc tgccataacc   6480
atgagtgata acactgcggc caacttactt ctgacaacga tcggaggacc gaaggagcta   6540
accgcttttt tgcacaacat gggggatcat gtaactcgcc ttgatcgttg ggaaccggag   6600
ctgaatgaag ccataccaaa cgacgagcgt gacaccacga tgcctgtagc aatggcaaca   6660
acgttgcgca aactattaac tggcgaacta cttactctag cttcccggca acaattaata   6720
gactggatgg aggcggataa agttgcagga ccacttctgc gctcggccct tccggctggc   6780
tggtttattg ctgataaatc tggagccggt gagcgtgggt ctcgcggtat cattgcagca   6840
ctggggccag atggtaagcc ctcccgtatc gtagttatct acacgacggg gagtcaggca   6900
actatggatg aacgaaatag acagatcgct gagataggtg cctcactgat taagcattgg   6960
```

taactgtcag accaagttta ctcatatata ctttagattg atttaaaact tcatttttaa 7020
tttaaaagga tctaggtgaa gatccttttt gataatctca tgaccaaaat cccttaacgt 7080
gagttttcgt tccactgagc gtcagacccc gtagaaaaga tcaaaggatc ttcttgagat 7140
cctttttttc tgcgcgtaat ctgctgcttg caaacaaaaa aaccaccgct accagcggtg 7200
gtttgtttgc cggatcaaga gctaccaact ctttttccga aggtaactgg cttcagcaga 7260
gcgcagatac caaatactgt ccttctagtg tagccgtagt taggccacca cttcaagaac 7320
tctgtagcac cgcctacata cctcgctctg ctaatcctgt taccagtggc tgctgccagt 7380
ggcgataagt cgtgtcttac cgggttggac tcaagacgat agttaccgga taaggcgcag 7440
cggtcgggct gaacgggggg ttcgtgcaca cagcccagct tggagcgaac gacctacacc 7500
gaactgagat acctacagcg tgagctatga gaaagcgcca cgcttcccga agggagaaag 7560
gcggacaggt atccggtaag cggcagggtc ggaacaggag agcgcacgag ggagcttcca 7620
gggggaaacg cctggtatct ttatagtcct gtcgggtttc gccacctctg acttgagcgt 7680
cgatttttgt gatgctcgtc aggggggcgg agcctatgga aaaacgccag caacgcggcc 7740
tttttacggt tcctggcctt ttgctggcct tttgctcaca tgttctttcc tgcgttatcc 7800
cctgattctg tggataaccg tattaccgcc tttgagtgag ctgataccgc tcgccgcagc 7860
cgaacgaccg agcgcagcga gtcagtgagc gaggaagcgg aagagcgccc aatacgcaaa 7920
ccgcctctcc ccgcgcgttg gccgattcat taatg 7955

<210> SEQ ID NO 14
<211> LENGTH: 8222
<212> TYPE: DNA
<213> ORGANISM: Artificial
<220> FEATURE:
<223> OTHER INFORMATION: AAV donor template

<400> SEQUENCE: 14
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgt atacatacat acctgaatat ggaatcaaat 180
atttttctaa gatgaaacag tcatgattta tttcaaatag gtacggataa gtagatattg 240
aggtaagcat taggtcttat attatgtaac actaatctat tactgcgctg aaactgtggc 300
tttatagaaa ttgttttcac tgcactattg agaaattaag agataatggc aaaagtcaca 360
aagagtatat tcaaaaagaa gtatagcact ttttccttag aaaccactgc taactgaaag 420
agactaagat ttgtcccgtc aaaaatcctg gacctatgcc taaaacacat ttcacaatcc 480
ctgaactttt caaaaattgg tacatgcttt agctttaaac tacaggcctc actggagcta 540
gagacaagaa ggtaaaaaac ggctgacaaa agaagtcctg gtatcctcta tgatgggaga 600
aggaaactag ctaaagggaa gaataaatta gagaaaaact ggaatgactg aatcggaaca 660
aggcaaaggc tataaaaaaa attaagcagc agtatcctct tgggggcccc ttccccacac 720
tatctcaatg caaatatctg tctgaaacgg tccctggcta aactccaccc atgggttggc 780
cagccttgcc ttgacgctag cgtaaataca cttgcaaagg aggatgtttt tagtagcaat 840
ttgtactgat ggtatggggc caagagatat atcttagagg gagggctgag ggtttgaagt 900
ccaactccta agccagtgcc agaagagcca aggacaggta cggctgtcat cacttagacc 960
tcaccctgtg gagccacacc ctagggttgg ccaatctact cccaggagca gggagggcag 1020
gagccagggc tgggcataaa agtcagggca gagccatcta ttgcttacat ttgcttctga 1080
cacaactgtg ttcactagca acctcaaaca gacaccatgg tgcacctgac tcctgaggag 1140
aagtctgccg ttactgccct gtggggcaag gtgaacgtgg atgaagttgg tggtgaggcc 1200
ctgggcaggt tggtatcaag gttacaagac aggtttaagg agaccaatag aaactgggca 1260
tgtggagaca gagaagactc ttgggtttct gataggcact gactctctct gcctattggt 1320
ctattttccc acccttaggc tgctggtggt ctacccttgg acccagaggt tctttgagtc 1380
ctttggggat ctgtccactc ctgatgctgt tatgggcaac cctaaggtga aggctcatgg 1440
caagaaagtg ctcggtgcct ttagtgatgg cctggctcac ctggacaacc tcaagggcac 1500
ctttgcccag ctgagtgagc tgcactgtga caagctgcac gtggatcctg agaacttcag 1560
ggtgagtcta tgggaccctt gatgttttct ttccccttct tttctatggt taagttcatg 1620
tcataggaag gggagaagta acagggtaca catattgacc aaatcagggt aattttgcat 1680
ttgtaatttt aaaaaatgct ttcttctttt aatatacttt tttgtttatc ttatttctaa 1740
tactttccct aatctctttc tttcagggca ataatgatac aatgtatcat gcctctttgc 1800
accattctaa agaataacag tgataatttc tgggttaagg caatagcaat atttctgcat 1860
ataaatattt ctgcatataa attgtaactg atgtaagagg tttcatattg ctaatagcag 1920
ctacaatcca gctaccattc tgcttttatt ttatggttgg gataaggctg gattattctg 1980
agtccaagct aggccctttt gctaatcatg ttcatacctc ttatcttcct cccacagctc 2040
ctgggcaacg tgctggtctg tgtgctggcc catcactttg gcaaagaatt caccccacca 2100
gtgcaggctg cctatcagaa agtggtggct ggtgtggcta atgccctggc ccacaagtat 2160
cactaagctc gctttcttgc tgtccaattt ctattaaagg ttcctttgtt ccctaagtcc 2220
aactactaaa ctgggggata ttatgaaggg ccttgagcat ctggattctg cctaataaaa 2280
aacatttatt ttcattgcaa tgatgtattt aaattatttc tgaatatttt actaaaaagg 2340
gaatgtggga ggttgcagtg ctagtctccc ggaactatca ctctttcaca gtctgctttg 2400
gaaggactgg gcttagtatg aaaagttagg actgagaaga atttgaaagg gggctttttg 2460
tagcttgata ttcactactg tcttattacc ctatcatagg cccacccaa atggaagtcc 2520 cattcttcct caggatgttt aagattagca ttcaggaaga gatcagaggt ctgctggctc 2580
ccttatcatg tcccttatgg tgcttctggc tctgcaccgc gggaacagag aaacaggaga 2640
atatgggcca aacaggatat ctgtggtaag cagttcctgc cccggctcag ggccaagaac 2700
agttggaaca gcagaatatg ggccaaacag gatatctgtg gtaagcagtt cctgccccgg 2760
ctcagggcca agaacagatg gtccccagat gcggtcccgc cctcagcagt ttctagagaa 2820
ccatcagatg tttccagggt gccccaagga cctgaaatga ccctgtgcct tatttgaact 2880
aaccaatcag ttcgcttctc gcttctgttc gcgcgcttct gctccccgag ctctatataa 2940
gcagagctcg tttagtgaac cgtcagatcg cggccgcgcc gccaccatgg tgagcaaggg 3000
cgaggagctg ttcaccgggg tggtgcccat cctggtcgag ctggacggcg acgtaaacgg 3060
ccacaagttc agcgtgtccg gcgagggcga gggcgatgcc acctacggca agctgaccct 3120
gaagttcatc tgcaccaccg gcaagctgcc cgtgccctgg cccaccctcg tgaccaccct 3180
gacctacggc gtgcagtgct tcagccgcta ccccgaccac atgaagcagc acgacttctt 3240
caagtccgcc atgcccgaag gctacgtcca ggagcgcacc atcttcttca aggacgacgg 3300
caactacaag acccgcgccg aggtgaagtt cgagggcgac accctggtga accgcatcga 3360
gctgaagggc atcgacttca aggaggacgg caacatcctg gggcacaagc tggagtacaa 3420

-continued ctacaacagc cacaacgtct atatcatggc cgacaagcag aagaacggca tcaaggtgaa 3480
cttcaagatc cgccacaaca tcgaggacgg cagcgtgcag ctcgccgacc actaccagca 3540
gaacaccccc atcggcgacg gccccgtgct gctgcccgac aaccactacc tgagcaccca 3600
gtccgccctg agcaaagacc ccaacgagaa gcgcgatcac atggtcctgc tggagttcgt 3660
gaccgccgcc gggatcactc tcggcatgga cgagctgtac aagtaagctt tatttgtgaa 3720
atttgtgatg ctattgcttt atttgtaacc attataagct gcaataaaca agttaacaac 3780
aacaattgca ttcattttat gtttcaggtt cagggggaga tgtgggaggt tttttaaagc 3840
cctgcaggca atagccttga caaggcaaac ttgaccaata gtcttagagt atccagtgag 3900
gccaggggcc ggcggctggc tagggatgaa gaataaaagg aagcaccctt cagcagttcc 3960
acacactcgc ttctggaacg tctgaggtta tcaataagct cctagtccag acgccatggg 4020
tcatttcaca gaggaggaca aggctactat cacaagcctg tggggcaagg tgaatgtgga 4080
agatgctgga ggagaaaccc tgggaaggta ggctctggtg accaggacaa gggagggaag 4140
gaaggaccct gtgcctggca aaagtccagg tcgcttctca ggatttgtgg caccttctga 4200
ctgtcaaact gttcttgtca atctcacagg ctcctggttg tctacccatg gacccagagg 4260
ttctttgaca gctttggcaa cctgtcctct gcctctgcca tcatgggcaa ccccaaagtc 4320
aaggcacatg gcaagaaggt gctgacttcc ttgggagatg ccacaaagca cctggatgat 4380
ctcaagggca cctttgccca gctgagtgaa ctgcactgtg acaagctgca tgtggatcct 4440
gagaacttca aggtgagtcc aggagatgtt tcagccctgt tgcctttagt ctcgaggcgt 4500
cgacaggaac ccctagtgat ggagttggcc actccctctc tgcgcgctcg ctcgctcact 4560
gaggccgggc gaccaaaggt cgcccgacgc ccgggctttg cccgggcggc ctcagtgagc 4620
gagcgagcgc gcagctggcg taatagcgaa gaggcccgca ccgatcgccc ttcccaacag 4680
ttgcgcagcc tgaatggcga atggcgattc cgttgcaatg gctggcggta atattgttct 4740
ggatattacc agcaaggccg atagtttgag ttcttctact caggcaagtg atgttattac 4800
taatcaaaga agtattgcga caacggttaa tttgcgtgat ggacagactc ttttactcgg 4860
tggcctcact gattataaaa acacttctca ggattctggc gtaccgttcc tgtctaaaat 4920
ccctttaatc ggcctcctgt ttagctcccg ctctgattct aacgaggaaa gcacgttata 4980
cgtgctcgtc aaagcaacca tagtacgcgc cctgtagcgg cgcattaagc gcggcgggtg 5040
tggtggttac gcgcagcgtg accgctacac ttgccagcgc cctagcgccc gctcctttcg 5100
ctttcttccc ttcctttctc gccacgttcg ccggctttcc ccgtcaagct ctaaatcggg 5160
ggctcccttt agggttccga tttagtgctt tacggcacct cgaccccaaa aaacttgatt 5220
agggtgatgg ttcacgtagt gggccatcgc cctgatagac ggtttttcgc cctttgacgt 5280
tggagtccac gttctttaat agtggactct tgttccaaac tggaacaaca ctcaacccta 5340
tctcggtcta ttcttttgat ttataaggga ttttgccgat ttcggcctat tggttaaaaa 5400
atgagctgat ttaacaaaaa tttaacgcga attttaacaa aatattaacg tttacaattt 5460
aaatatttgc ttatacaatc ttcctgtttt tggggctttt ctgattatca accggggtac 5520
atatgattga catgctagtt ttacgattac cgttcatcga ttctcttgtt tgctccagac 5580
tctcaggcaa tgacctgata gcctttgtag agacctctca aaaatagcta ccctctccgg 5640
catgaattta tcagctagaa cggttgaata tcatattgat ggtgatttga ctgtctccgg 5700
cctttctcac ccgtttgaat ctttacctac acattactca ggcattgcat ttaaaatata 5760

-continued tgagggttct aaaaattttt atccttgcgt tgaaataaag gcttctcccg caaaagtatt 5820
acagggtcat aatgtttttg gtacaaccga tttagcttta tgctctgagg ctttattgct 5880
taattttgct aattctttgc cttgcctgta tgatttattg gatgttggaa tcgcctgatg 5940
cggtattttc tccttacgca tctgtgcggt atttcacacc gcatatggtg cactctcagt 6000
acaatctgct ctgatgccgc atagttaagc cagccccgac acccgccaac acccgctgac 6060
gcgccctgac gggcttgtct gctcccggca tccgcttaca gacaagctgt gaccgtctcc 6120
gggagctgca tgtgtcagag gttttcaccg tcatcaccga aacgcgcgag acgaaagggc 6180
ctcgtgatac gcctattttt ataggttaat gtcatgataa taatggtttc ttagacgtca 6240
ggtggcactt ttcggggaaa tgtgcgcgga acccctattt gtttattttt ctaaatacat 6300
tcaaatatgt atccgctcat gagacaataa ccctgataaa tgcttcaata atattgaaaa 6360
aggaagagta tgagtattca acatttccgt gtcgccctta ttcccttttt tgcggcattt 6420
tgccttcctg tttttgctca cccagaaacg ctggtgaaag taaaagatgc tgaagatcag 6480
ttgggtgcac gagtgggtta catcgaactg gatctcaaca gcggtaagat ccttgagagt 6540
tttcgccccg aagaacgttt tccaatgatg agcactttta aagttctgct atgtggcgcg 6600
gtattatccc gtattgacgc cgggcaagag caactcggtc gccgcataca ctattctcag 6660
aatgacttgg ttgagtactc accagtcaca gaaaagcatc ttacggatgg catgacagta 6720
agagaattat gcagtgctgc cataaccatg agtgataaca ctgcggccaa cttacttctg 6780
acaacgatcg gaggaccgaa ggagctaacc gcttttttgc acaacatggg ggatcatgta 6840
actcgccttg atcgttggga accggagctg aatgaagcca taccaaacga cgagcgtgac 6900
accacgatgc ctgtagcaat ggcaacaacg ttgcgcaaac tattaactgg cgaactactt 6960
actctagctt cccggcaaca attaatagac tggatggagg cggataaagt tgcaggacca 7020
cttctgcgct cggcccttcc ggctggctgg tttattgctg ataaatctgg agccggtgag 7080
cgtgggtctc gcggtatcat tgcagcactg gggccagatg gtaagccctc ccgtatcgta 7140
gttatctaca cgacggggag tcaggcaact atggatgaac gaaatagaca gatcgctgag 7200
ataggtgcct cactgattaa gcattggtaa ctgtcagacc aagtttactc atatatactt 7260
tagattgatt taaaacttca tttttaattt aaaaggatct aggtgaagat cctttttgat 7320
aatctcatga ccaaaatccc ttaacgtgag ttttcgttcc actgagcgtc agaccccgta 7380
gaaaagatca aaggatcttc ttgagatcct ttttttctgc gcgtaatctg ctgcttgcaa 7440
acaaaaaaac caccgctacc agcggtggtt tgtttgccgg atcaagagct accaactctt 7500
tttccgaagg taactggctt cagcagagcg cagataccaa atactgtcct tctagtgtag 7560
ccgtagttag gccaccactt caagaactct gtagcaccgc ctacatacct cgctctgcta 7620
atcctgttac cagtggctgc tgccagtggc gataagtcgt gtcttaccgg gttggactca 7680
agacgatagt taccggataa ggcgcagcgg tcgggctgaa cggggggttc gtgcacacag 7740
cccagcttgg agcgaacgac ctacaccgaa ctgagatacc tacagcgtga gctatgagaa 7800
agcgccacgc ttcccgaagg gagaaaggcg gacaggtatc cggtaagcgg cagggtcgga 7860
acaggagagc gcacgaggga gcttccaggg ggaaacgcct ggtatcttta tagtcctgtc 7920
gggtttcgcc acctctgact tgagcgtcga tttttgtgat gctcgtcagg ggggcggagc 7980
ctatggaaaa acgccagcaa cgcggccttt ttacggttcc tggccttttg ctggcctttt 8040
gctcacatgt tctttcctgc gttatcccct gattctgtgg ataaccgtat taccgccttt 8100
gagtgagctg ataccgctcg ccgcagccga acgaccgagc gcagcgagtc agtgagcgag 8160
gaagcggaag agcgcccaat acgcaaaccg cctctccccg cgcgttggcc gattcattaa 8220
tg 8222

<210> SEQ ID NO 15
<211> LENGTH: 8214
<212> TYPE: DNA
<213> ORGANISM: Artificial
<220> FEATURE:
<223> OTHER INFORMATION: AAV donor template

<400> SEQUENCE: 15
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgc ctacatacat acctgaataa gaaaaaaaaa 180
tacctttgct gagatgaaac acacatgatt tatttcaaat aggtacagag aagtagatac 240
tgaagtaagg attaagtatt atattatatt acataacatt aatctattcc tgcactgaaa 300
ccgttgcttt atatgatttt ttttttcact acactaatga gaacttaaga gataatggcc 360
taaaaccaca gagagtattt tcaaagataa gtatagcaca atgcttacta aatgagacta 420
agacttgtcc catcgaaaat cctggaccta tgcctaaaac acgtgtcaca atccccgaac 480
ttttcaaaaa ttggtacatg ctttaacttt aatctccagg cctcactgga gctagagaca 540
agaaggtaaa aaaaggctga caaaagaagt cctggtatct tctatggtgg gagaaggaaa 600
ctagctaaag ggaagaataa attagagaaa aattggaatg attgaatcgg aacaaggcaa 660
aggctataaa aaaattaagc agcagtatcc tcttgggggc cccttcccca cactatctca 720
atgcaaatat ctgtctgaaa cggtccctgg ctaaactcca cccatgggtt ggccagtctt 780
gccttgacgc tagcgtaaat acacttgcaa aggaggatgt ttttagtagc aatttgtact 840
gatggtatgg ggccaagaga tatatcttag agggagggct gagggtttga agtccaactc 900
ctaagccagt gccagaagag ccaaggacag gtacggctgt catcacttag acctcaccct 960
gtggagccac accctagggt tggccaatct actcccagga gcagggaggg caggagccag 1020
ggctgggcat aaaagtcagg gcagagccat ctattgctta catttgcttc tgacacaact 1080
gtgttcacta gcaacctcaa acagacacca tggtgcacct gactcctgag gagaagtctg 1140
ccgttactgc cctgtggggc aaggtgaacg tggatgaagt tggtggtgag gccctgggca 1200
ggttggtatc aaggttacaa gacaggttta aggagaccaa tagaaactgg gcatgtggag 1260
acagagaaga ctcttgggtt tctgataggc actgactctc tctgcctatt ggtctatttt 1320
cccaccctta ggctgctggt ggtctaccct tggacccaga ggttctttga gtcctttggg 1380
gatctgtcca ctcctgatgc tgttatgggc aaccctaagg tgaaggctca tggcaagaaa 1440
gtgctcggtg cctttagtga tggcctggct cacctggaca acctcaaggg cacctttgcc 1500
cagctgagtg agctgcactg tgacaagctg cacgtggatc ctgagaactt cagggtgagt 1560
ctatgggacc cttgatgttt tctttcccct tcttttctat ggttaagttc atgtcatagg 1620
aaggggagaa gtaacagggt acacatattg accaaatcag ggtaattttg catttgtaat 1680
tttaaaaaat gctttcttct tttaatatac ttttttgttt atcttatttc taatactttc 1740
cctaatctct ttctttcagg gcaataatga tacaatgtat catgcctctt tgcaccattc 1800
taaagaataa cagtgataat ttctgggtta aggcaatagc aatatttctg catataaata 1860
tttctgcata taaattgtaa ctgatgtaag aggtttcata ttgctaatag cagctacaat 1920

-continued

```
ccagctacca ttctgctttt attttatggt tgggataagg ctggattatt ctgagtccaa   1980
gctaggccct tttgctaatc atgttcatac ctcttatctt cctcccacag ctcctgggca   2040
acgtgctggt ctgtgtgctg gcccatcact ttggcaaaga attcacccca ccagtgcagg   2100
ctgcctatca gaaagtggtg gctggtgtgg ctaatgccct ggcccacaag tatcactaag   2160
ctcgctttct tgctgtccaa tttctattaa aggttccttt gttccctaag tccaactact   2220
aaactggggg atattatgaa gggccttgag catctggatt ctgcctaata aaaaacattt   2280
attttcattg caatgatgta tttaaattat ttctgaatat tttactaaaa agggaatgtg   2340
ggaggttgca gtgctagtct cccggaacta tcactctttc acagtctgct ttggaaggac   2400
tgggcttagt atgaaaagtt aggactgaga agaatttgaa agggggcttt ttgtagcttg   2460
atattcacta ctgtcttatt accctatcat aggcccaccc caaatggaag tcccattctt   2520
cctcaggatg tttaagatta gcattcagga agagatcaga ggtctgctgg ctcccttatc   2580
atgtccctta tggtgcttct ggctctgcac cgcgggaaca gagaaacagg agaatatggg   2640
ccaaacagga tatctgtggt aagcagttcc tgccccggct cagggccaag aacagttgga   2700
acagcagaat atgggccaaa caggatatct gtggtaagca gttcctgccc cggctcaggg   2760
ccaagaacag atggtcccca gatgcggtcc cgccctcagc agtttctaga gaaccatcag   2820
atgtttccag ggtgccccaa ggacctgaaa tgaccctgtg ccttatttga actaaccaat   2880
cagttcgctt ctcgcttctg ttcgcgcgct tctgctcccc gagctctata taagcagagc   2940
tcgtttagtg aaccgtcaga tcgcggccgc gccgccacca tggtgagcaa gggcgaggag   3000
ctgttcaccg gggtggtgcc catcctggtc gagctggacg gcgacgtaaa cggccacaag   3060
ttcagcgtgt ccggcgaggg cgagggcgat gccacctacg gcaagctgac cctgaagttc   3120
atctgcacca ccggcaagct gcccgtgccc tggcccaccc tcgtgaccac cctgacctac   3180
ggcgtgcagt gcttcagccg ctaccccgac cacatgaagc agcacgactt cttcaagtcc   3240
gccatgcccg aaggctacgt ccaggagcgc accatcttct tcaaggacga cggcaactac   3300
aagacccgcg ccgaggtgaa gttcgagggc gacaccctgg tgaaccgcat cgagctgaag   3360
ggcatcgact tcaaggagga cggcaacatc ctggggcaca agctggagta caactacaac   3420
agccacaacg tctatatcat ggccgacaag cagaagaacg gcatcaaggt gaacttcaag   3480
atccgccaca acatcgagga cggcagcgtg cagctcgccg accactacca gcagaacacc   3540
cccatcggcg acggccccgt gctgctgccc gacaaccact acctgagcac ccagtccgcc   3600
ctgagcaaag accccaacga gaagcgcgat cacatggtcc tgctggagtt cgtgaccgcc   3660
gccgggatca ctctcggcat ggacgagctg tacaagtaag ctttatttgt gaaatttgtg   3720
atgctattgc tttatttgta accattataa gctgcaataa acaagttaac aacaacaatt   3780
gcattcattt tatgtttcag gttcaggggg agatgtggga ggtttttaa agccctgcag   3840
gcaatagcct tgacaaggca accttgacca atagtcttag agtatcaggt gaggccaggg   3900
gccggcggct ggctagggat gaagaataaa aggaagcacc ctccagcagt tccacacact   3960
cgcttctgga acggctgaga ttatcaataa gctcctagtc cagacgccat gggtcatttc   4020
acagaggagg acaaggctac tatcacaagc ctgtggggca aggtgaatgt ggaagatgct   4080
ggaggagaaa ccctgggaag gtaggctctg gtgaccagga caaggaaggg aaggaaggac   4140
cctgtgcctg gcaaaagtcc aggccacttc tcaggatttg tggcactttc tgactgtcaa   4200
actgctcttg ttcaatctca caggctcctg gttgtctacc catggaccca gaggttcttt   4260
gacagctttg gcaacctgtc ctctgcctct gccatcatgg gcaaccccaa ggtcaaggca   4320
```

-continued cacggcaaga aggtgctgac ttccttggga gatgccataa agaacctgga tgatctcaag 4380
ggcacctttg cccagctgag tgagctgcac tgtgacaagc tgcatgtgga tcctgagaac 4440
ttcagggtga gtccaggagt ttcagcagtt tcagagttca gtctcaaggc gtcgacagga 4500
acccctagtg atggagttgg ccactccctc tctgcgcgct cgctcgctca ctgaggccgg 4560
gcgaccaaag gtcgcccgac gcccgggctt tgcccgggcg gcctcagtga gcgagcgagc 4620
gcgcagctgg cgtaatagcg aagaggcccg caccgatcgc ccttcccaac agttgcgcag 4680
cctgaatggc gaatggcgat tccgttgcaa tggctggcgg taatattgtt ctggatatta 4740
ccagcaaggc cgatagtttg agttcttcta ctcaggcaag tgatgttatt actaatcaaa 4800
gaagtattgc gacaacggtt aatttgcgtg atggacagac tcttttactc ggtggcctca 4860
ctgattataa aaacacttct caggattctg gcgtaccgtt cctgtctaaa atccctttaa 4920
tcggcctcct gtttagctcc cgctctgatt ctaacgagga aagcacgtta tacgtgctcg 4980
tcaaagcaac catagtacgc gccctgtagc ggcgcattaa gcgcggcggg tgtggtggtt 5040
acgcgcagcg tgaccgctac acttgccagc gccctagcgc ccgctccttt cgctttcttc 5100
ccttcctttc tcgccacgtt cgccggcttt ccccgtcaag ctctaaatcg ggggctccct 5160
ttagggttcc gatttagtgc tttacggcac ctcgacccca aaaaacttga ttagggtgat 5220
ggttcacgta gtgggccatc gccctgatag acggtttttc gccctttgac gttggagtcc 5280
acgttcttta atagtggact cttgttccaa actggaacaa cactcaaccc tatctcggtc 5340
tattcttttg atttataagg gattttgccg atttcggcct attggttaaa aaatgagctg 5400
atttaacaaa aatttaacgc gaattttaac aaaatattaa cgtttacaat ttaaatattt 5460
gcttatacaa tcttcctgtt tttggggctt ttctgattat caaccggggt acatatgatt 5520
gacatgctag ttttacgatt accgttcatc gattctcttg tttgctccag actctcaggc 5580
aatgacctga tagcctttgt agagacctct caaaaatagc taccctctcc ggcatgaatt 5640
tatcagctag aacggttgaa tatcatattg atggtgattt gactgtctcc ggcctttctc 5700
acccgtttga atctttacct acacattact caggcattgc atttaaaata tatgagggtt 5760
ctaaaaattt ttatccttgc gttgaaataa aggcttctcc cgcaaaagta ttacagggtc 5820
ataatgtttt tggtacaacc gatttagctt tatgctctga ggctttattg cttaattttg 5880
ctaattcttt gccttgcctg tatgatttat tggatgttgg aatcgcctga tgcggtattt 5940
tctccttacg catctgtgcg gtatttcaca ccgcatatgg tgcactctca gtacaatctg 6000
ctctgatgcc gcatagttaa gccagccccg acacccgcca acacccgctg acgcgccctg 6060
acgggcttgt ctgctcccgg catccgctta cagacaagct gtgaccgtct ccgggagctg 6120
catgtgtcag aggttttcac cgtcatcacc gaaacgcgcg agacgaaagg gcctcgtgat 6180
acgcctattt ttataggtta atgtcatgat aataatggtt tcttagacgt caggtggcac 6240
ttttcgggga aatgtgcgcg gaacccctat ttgtttattt ttctaaatac attcaaatat 6300
gtatccgctc atgagacaat aaccctgata aatgcttcaa taatattgaa aaaggaagag 6360
tatgagtatt caacatttcc gtgtcgccct tattcccttt tttgcggcat tttgccttcc 6420
tgtttttgct cacccagaaa cgctggtgaa agtaaaagat gctgaagatc agttgggtgc 6480
acgagtgggt tacatcgaac tggatctcaa cagcggtaag atccttgaga gttttcgccc 6540
cgaagaacgt tttccaatga tgagcacttt taaagttctg ctatgtggcg cggtattatc 6600
ccgtattgac gccgggcaag agcaactcgg tcgccgcata cactattctc agaatgactt 6660

```
ggttgagtac tcaccagtca cagaaaagca tcttacggat ggcatgacag taagagaatt   6720

atgcagtgct gccataacca tgagtgataa cactgcggcc aacttacttc tgacaacgat   6780

cggaggaccg aaggagctaa ccgctttttt gcacaacatg ggggatcatg taactcgcct   6840

tgatcgttgg gaaccggagc tgaatgaagc cataccaaac gacgagcgtg acaccacgat   6900

gcctgtagca atggcaacaa cgttgcgcaa actattaact ggcgaactac ttactctagc   6960

ttcccggcaa caattaatag actggatgga ggcggataaa gttgcaggac cacttctgcg   7020

ctcggccctt ccggctggct ggtttattgc tgataaatct ggagccggtg agcgtgggtc   7080

tcgcggtatc attgcagcac tggggccaga tggtaagccc tcccgtatcg tagttatcta   7140

cacgacgggg agtcaggcaa ctatggatga acgaaataga cagatcgctg agataggtgc   7200

ctcactgatt aagcattggt aactgtcaga ccaagtttac tcatatatac tttagattga   7260

tttaaaactt catttttaat ttaaaaggat ctaggtgaag atcctttttg ataatctcat   7320

gaccaaaatc ccttaacgtg agttttcgtt ccactgagcg tcagaccccg tagaaaagat   7380

caaaggatct tcttgagatc ctttttttct gcgcgtaatc tgctgcttgc aaacaaaaaa   7440

accaccgcta ccagcggtgg tttgtttgcc ggatcaagag ctaccaactc tttttccgaa   7500

ggtaactggc ttcagcagag cgcagatacc aaatactgtc cttctagtgt agccgtagtt   7560

aggccaccac ttcaagaact ctgtagcacc gcctacatac ctcgctctgc taatcctgtt   7620

accagtggct gctgccagtg gcgataagtc gtgtcttacc gggttggact caagacgata   7680

gttaccggat aaggcgcagc ggtcgggctg aacggggggt tcgtgcacac agcccagctt   7740

ggagcgaacg acctacaccg aactgagata cctacagcgt gagctatgag aaagcgccac   7800

gcttcccgaa gggagaaagg cggacaggta tccggtaagc ggcagggtcg gaacaggaga   7860

gcgcacgagg gagcttccag ggggaaacgc ctggtatctt tatagtcctg tcgggtttcg   7920

ccacctctga cttgagcgtc gatttttgtg atgctcgtca ggggggcgga gcctatggaa   7980

aaacgccagc aacgcggcct ttttacggtt cctggccttt tgctggcctt ttgctcacat   8040

gttctttcct gcgttatccc ctgattctgt ggataaccgt attaccgcct ttgagtgagc   8100

tgataccgct cgccgcagcc gaacgaccga gcgcagcgag tcagtgagcg aggaagcgga   8160

agagcgccca atacgcaaac cgcctctccc cgcgcgttgg ccgattcatt aatg         8214
```

<210> SEQ ID NO 16
<211> LENGTH: 7712
<212> TYPE: DNA
<213> ORGANISM: Artificial
<220> FEATURE:
<223> OTHER INFORMATION: AAV donor template

<400> SEQUENCE: 16

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac acgcgtagat    180

ctagtgcatc aacttcttat ttgtgtaata agaaaattgg gaaaacgatc ttcaatatgc    240

ttaccaagct gtgattccaa atattacgta aatacacttg caaaggagga tgtttttagt    300

agcaatttgt actgatggta tggggccaag agatatatct tagagggagg gctgagggtt    360

tgaagtccaa ctcctaagcc agtgccagaa gagccaagga caggtacggc tgtcatcact    420

tagacctcac cctgtggagc cacaccctag ggttggccaa tctactccca ggagcaggga    480

gggcaggagc cagggctggg cataaaagtc agggcagagc catctattgc ttacatttgc    540
```

-continued

```
ttctgacaca actgtgttca ctagcaacct caaacagaca ccaggtgagt taaacccatg    600
agagagaata acagaactgc gagtgatggg ccagttaagc gtagatggct aattagttca    660
gacaaatgta aaatgccaac accgtctgta aagaaaccta actgatcctc ttcctttgtc    720
ctgtcttctt cacaggccgc caccatggtc catcttacac cggaggagaa gtccgctgta    780
acggcactgt gggggaaagt taatgtcgat gaagtcggcg gtgaagcact cggcaggttg    840
ctggtagtgt acccgtggac acaacgattc tttgaaagtt tcggggacct gtccacaccc    900
gatgctgtga tgggtaatcc aaaagtaaaa gcacacggca agaaagtcct cggcgcgttt    960
agtgatggtc tggcccattt ggataacttg aagggtacat tcgcgcagct ttccgaactc   1020
cactgtgaca agttgcacgt agatccagaa aacttccggc ttctgggcaa tgtgcttgta   1080
tgcgttctgg ctcaccattt tgggaaggag tttaccccac ccgtgcaagc ggcttaccaa   1140
aaagtggtcg caggagtggc taatgccctt gcacataaat atcactaagg taccgataat   1200
caacctctgg attacaaaat ttgtgaaaga ttgactggta ttcttaacta tgttgctcct   1260
tttacgctat gtggatacgc tgctttaatg cctttgtatc atgctattgc ttcccgtatg   1320
gctttcattt tctcctcctt gtataaatcc tggttagttc ttgccacggc ggaactcatc   1380
gccgcctgcc ttgcccgctg ctggacaggg gctcggctgt tgggcactga caattccgtg   1440
gtgtttattt gtgaaatttg tgatgctatt gctttatttg taaccattct agctttattt   1500
gtgaaatttg tgatgctatt gctttatttg taaccattat aagctgcaat aaacaagtta   1560
acaacaacaa ttgcattcat tttatgtttc aggttcaggg ggagatgtgg gaggtttttt   1620
aaagcttaat taacgagatc gagaccatcc tggctaacac agtgaaaccc cgtctctact   1680
aaaaaaatac aaaaaattag ccgggcttgg tggcgggtgc ctgtagtccc agctactatg   1740
gaggctgagg cgggagaatg gcgtgaacgc gggggcggga gcttgcagtg agcagagatc   1800
aggggccact gcactccagc ctgggcgaca gagagagact ctgtctcaaa aaaaagaaaa   1860
aaaaaattta gtagactagc taaaaaaatc cagagatagt tattgatgca tatgtaaaag   1920
tcttccaata tttacaagta caatgaaaaa aaaataacct tgaattaagt gtagaactca   1980
ttgacaatgt ttcaaaggat gtgagggata aactaaaatt tgggcagtac atgctgttcc   2040
tgtgtacttg gaacagaggg agaaaatctg ggctggaaat attgttatag gagttagcac   2100
atgaaggtga caactaaatt atttggagta gatggagtca ccagcacatg tgaatagttt   2160
tagaatgaaa tgacccaaga tagaactttg gagagccccc aaatttaaat aaaatcagta   2220
taagagaaga ggaagaaacc aaatggtata ctagtctaaa ttgtttctta gtgacaaaag   2280
aataacctga atattagatt agctgcctat atgctctctg aatcaatttc attcaacatg   2340
caacagtccg cgggaacaga gaaacaggag aatatgggcc aaacaggata tctgtggtaa   2400
gcagttcctg ccccggctca gggccaagaa cagttggaac agcagaatat gggccaaaca   2460
ggatatctgt ggtaagcagt tcctgccccg gctcagggcc aagaacagat ggtccccaga   2520
tgcggtcccg ccctcagcag tttctagaga accatcagat gtttccaggg tgccccaagg   2580
acctgaaatg accctgtgcc ttatttgaac taaccaatca gttcgcttct cgcttctgtt   2640
cgcgcgcttc tgctccccga gctctatata agcagagctc gtttagtgaa ccgtcagatc   2700
gcctggagac gccatccacg ctgttttgac ttccatagaa ggcggccgcg ccgccaccat   2760
ggtgagcaag ggcgaggagc tgttcaccgg ggtggtgccc atcctggtcg agctggacgg   2820
cgacgtaaac ggccacaagt tcagcgtgtc cggcgagggc gagggcgatg ccacctacgg   2880
```

caagctgacc ctgaagttca tctgcaccac cggcaagctg cccgtgccct ggcccaccct 2940
cgtgaccacc ctgacctacg gcgtgcagtg cttcagccgc taccccgacc acatgaagca 3000
gcacgacttc ttcaagtccg ccatgcccga aggctacgtc caggagcgca ccatcttctt 3060
caaggacgac ggcaactaca agacccgcgc cgaggtgaag ttcgagggcg acaccctggt 3120
gaaccgcatc gagctgaagg gcatcgactt caaggaggac ggcaacatcc tggggcacaa 3180
gctggagtac aactacaaca gccacaacgt ctatatcatg gccgacaagc agaagaacgg 3240
catcaaggtg aacttcaaga tccgccacaa catcgaggac ggcagcgtgc agctcgccga 3300
ccactaccag cagaacaccc ccatcggcga cggccccgtg ctgctgcccg acaaccacta 3360
cctgagcacc cagtccgccc tgagcaaaga ccccaacgag aagcgcgatc acatggtcct 3420
gctggagttc gtgaccgccg ccgggatcac tctcggcatg gacgagctgt acaagggaag 3480
cggagctact aacttcagcc tgctgaagca ggctggagac gtggaggaga accctggacc 3540
tacctgcagg cctgagaact tcagggtgag tctatgggac gcttgatgtt ttctttcccc 3600
ttcttttcta tggttaagtt catgtcatag gaaggggata agtaacaggg tacagtttag 3660
aatgggaaac agacgaatga ttgcatcagt gtggaagtct caggatcgtt ttagtttctt 3720
ttatttgctg ttcataacaa ttgttttctt ttgtttaatt cttgctttct ttttttttct 3780
tctccgcaat ttttactatt atacttaatg ccttaacatt gtgtataaca aaaggaaata 3840
tctctgagat acattaagta acttaaaaaa aaactttaca cagtctgcct agtacattac 3900
tatttggaat atatgtgtgc ttatttgcat attcataatc tccctacttt gtcgacgtag 3960
ataagtagca tggcgggtta atcattaact acaaggaacc cctagtgatg gagttggcca 4020
ctccctctct gcgcgctcgc tcgctcactg aggccgggcg accaaaggtc gcccgacgcc 4080
cgggctttgc ccgggcggcc tcagtgagcg agcgagcgcg ccagctggcg taatagcgaa 4140
gaggcccgca ccgatcgccc ttcccaacag ttgcgcagcc tgaatggcga atggcgattc 4200
cgttgcaatg gctggcggta atattgttct ggatattacc agcaaggccg atagtttgag 4260
ttcttctact caggcaagtg atgttattac taatcaaaga agtattgcga caacggttaa 4320
tttgcgtgat ggacagactc ttttactcgg tggcctcact gattataaaa acacttctca 4380
ggattctggc gtaccgttcc tgtctaaaat ccctttaatc ggcctcctgt ttagctcccg 4440
ctctgattct aacgaggaaa gcacgttata cgtgctcgtc aaagcaacca tagtacgcgc 4500
cctgtagcgg cgcattaagc gcggcgggtg tggtggttac gcgcagcgtg accgctacac 4560
ttgccagcgc cctagcgccc gctcctttcg ctttcttccc ttcctttctc gccacgttcg 4620
ccggctttcc ccgtcaagct ctaaatcggg ggctcccttt agggttccga tttagtgctt 4680
tacggcacct cgaccccaaa aaacttgatt agggtgatgg ttcacgtagt gggccatcgc 4740
cctgatagac ggtttttcgc cctttgacgt tggagtccac gttctttaat agtggactct 4800
tgttccaaac tggaacaaca ctcaacccta tctcggtcta ttcttttgat ttataaggga 4860
ttttgccgat ttcggcctat tggttaaaaa atgagctgat ttaacaaaaa tttaacgcga 4920
attttaacaa aatattaacg tttacaattt aaatatttgc ttatacaatc ttcctgtttt 4980
tggggctttt ctgattatca accggggtac atatgattga catgctagtt ttacgattac 5040
cgttcatcga ttctcttgtt tgctccagac tctcaggcaa tgacctgata gcctttgtag 5100
agacctctca aaaatagcta ccctctccgg catgaattta tcagctagaa cggttgaata 5160
tcatattgat ggtgatttga ctgtctccgg cctttctcac ccgtttgaat ctttacctac 5220
acattactca ggcattgcat ttaaaatata tgagggttct aaaaattttt atccttgcgt 5280

-continued

```
tgaaataaag gcttctcccg caaaagtatt acagggtcat aatgtttttg gtacaaccga   5340
tttagcttta tgctctgagg ctttattgct taattttgct aattctttgc cttgcctgta   5400
tgatttattg gatgttggaa tcgcctgatg cggtattttc tccttacgca tctgtgcggt   5460
atttcacacc gcatatggtg cactctcagt acaatctgct ctgatgccgc atagttaagc   5520
cagccccgac acccgccaac acccgctgac gcgccctgac gggcttgtct gctcccggca   5580
tccgcttaca gacaagctgt gaccgtctcc gggagctgca tgtgtcagag gttttcaccg   5640
tcatcaccga aacgcgcgag acgaaagggc ctcgtgatac gcctattttt ataggttaat   5700
gtcatgataa taatggtttc ttagacgtca ggtggcactt ttcggggaaa tgtgcgcgga   5760
acccctattt gtttattttt ctaaatacat tcaaatatgt atccgctcat gagacaataa   5820
ccctgataaa tgcttcaata atattgaaaa aggaagagta tgagtattca acatttccgt   5880
gtcgccctta ttcccttttt tgcggcattt tgccttcctg tttttgctca cccagaaacg   5940
ctggtgaaag taaaagatgc tgaagatcag ttgggtgcac gagtgggtta catcgaactg   6000
gatctcaaca gcggtaagat ccttgagagt tttcgccccg aagaacgttt tccaatgatg   6060
agcactttta aagttctgct atgtggcgcg gtattatccc gtattgacgc cgggcaagag   6120
caactcggtc gccgcataca ctattctcag aatgacttgg ttgagtactc accagtcaca   6180
gaaaagcatc ttacggatgg catgacagta agagaattat gcagtgctgc cataaccatg   6240
agtgataaca ctgcggccaa cttacttctg acaacgatcg gaggaccgaa ggagctaacc   6300
gcttttttgc acaacatggg ggatcatgta actcgccttg atcgttggga accggagctg   6360
aatgaagcca taccaaacga cgagcgtgac accacgatgc ctgtagcaat ggcaacaacg   6420
ttgcgcaaac tattaactgg cgaactactt actctagctt cccggcaaca attaatagac   6480
tggatggagg cggataaagt tgcaggacca cttctgcgct cggcccttcc ggctggctgg   6540
tttattgctg ataaatctgg agccggtgag cgtgggtctc gcggtatcat tgcagcactg   6600
gggccagatg gtaagccctc ccgtatcgta gttatctaca cgacggggag tcaggcaact   6660
atggatgaac gaaatagaca gatcgctgag ataggtgcct cactgattaa gcattggtaa   6720
ctgtcagacc aagtttactc atatatactt tagattgatt taaaacttca tttttaattt   6780
aaaaggatct aggtgaagat cctttttgat aatctcatga ccaaaatccc ttaacgtgag   6840
ttttcgttcc actgagcgtc agaccccgta gaaaagatca aaggatcttc ttgagatcct   6900
ttttttctgc gcgtaatctg ctgcttgcaa acaaaaaaac caccgctacc agcggtggtt   6960
tgtttgccgg atcaagagct accaactctt tttccgaagg taactggctt cagcagagcg   7020
cagataccaa atactgtcct tctagtgtag ccgtagttag gccaccactt caagaactct   7080
gtagcaccgc ctacatacct cgctctgcta atcctgttac cagtggctgc tgccagtggc   7140
gataagtcgt gtcttaccgg gttggactca agacgatagt taccggataa ggcgcagcgg   7200
tcgggctgaa cggggggttc gtgcacacag cccagcttgg agcgaacgac ctacaccgaa   7260
ctgagatacc tacagcgtga gctatgagaa agcgccacgc ttcccgaagg gagaaaggcg   7320
gacaggtatc cggtaagcgg cagggtcgga acaggagagc gcacgaggga gcttccaggg   7380
ggaaacgcct ggtatcttta tagtcctgtc gggtttcgcc acctctgact tgagcgtcga   7440
tttttgtgat gctcgtcagg ggggcggagc ctatggaaaa acgccagcaa cgcggccttt   7500
ttacggttcc tggccttttg ctggcctttt gctcacatgt tctttcctgc gttatcccct   7560
gattctgtgg ataaccgtat taccgccttt gagtgagctg ataccgctcg ccgcagccga   7620
```

acgaccgagc gcagcgagtc agtgagcgag gaagcggaag agcgcccaat acgcaaaccg 7680
cctctccccg cgcgttggcc gattcattaa tg 7712

<210> SEQ ID NO 17
<211> LENGTH: 8293
<212> TYPE: DNA
<213> ORGANISM: Artificial
<220> FEATURE:
<223> OTHER INFORMATION: AAV donor template

<400> SEQUENCE: 17
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgt atacatacat acctgaatat ggaatcaaat 180
atttttctaa gatgaaacag tcatgattta tttcaaatag gtacggataa gtagatattg 240
aggtaagcat taggtcttat attatgtaac actaatctat tactgcgctg aaactgtggc 300
tttatagaaa ttgttttcac tgcactattg agaaattaag agataatggc aaaagtcaca 360
aagagtatat tcaaaaagaa gtatagcact tttccttag aaaccactgc taactgaaag 420
agactaagat ttgtcccgtc aaaaatcctg gacctatgcc taaaacacat ttcacaatcc 480
ctgaactttt caaaaattgg tacatgcttt agctttaaac tacaggcctc actggagcta 540
gagacaagaa ggtaaaaaac ggctgacaaa agaagtcctg gtatcctcta tgatgggaga 600
aggaaactag ctaaagggaa gaataaatta gagaaaaact ggaatgactg aatcggaaca 660
aggcaaaggc tataaaaaaa attaagcagc agtatcctct tgggggcccc ttccccacac 720
tatctcaatg caaatatctg tctgaaacgg tccctggcta aactccaccc atgggttggc 780
cagccttgcc ttgacgctag cgtaaataca cttgcaaagg aggatgtttt tagtagcaat 840
ttgtactgat ggtatggggc caagagatat atcttagagg gagggctgag ggtttgaagt 900
ccaactccta agccagtgcc agaagagcca aggacaggta cggctgtcat cacttagacc 960
tcaccctgtg gagccacacc ctagggttgg ccaatctact cccaggagca gggagggcag 1020
gagccagggc tgggcataaa agtcagggca gagccatcta ttgcttacat ttgcttctga 1080
cacaactgtg ttcactagca acctcaaaca gacaccatgg tgcacctgac tcctgaggag 1140
aagtctgccg ttactgccct gtggggcaag gtgaacgtgg atgaagttgg tggtgaggcc 1200
ctgggcaggt tggtatcaag gttacaagac aggtttaagg agaccaatag aaactgggca 1260
tgtggagaca gagaagactc ttgggtttct gataggcact gactctctct gcctattggt 1320
ctattttccc acccttaggc tgctggtggt ctacccttgg acccagaggt tctttgagtc 1380
ctttggggat ctgtccactc ctgatgctgt tatgggcaac cctaaggtga aggctcatgg 1440
caagaaagtg ctcggtgcct ttagtgatgg cctggctcac ctggacaacc tcaagggcac 1500
ctttgcccag ctgagtgagc tgcactgtga caagctgcac gtggatcctg agaacttcag 1560
ggtgagtcta tgggaccctt gatgttttct ttccccttct tttctatggt taagttcatg 1620
tcataggaag gggagaagta acagggtaca catattgacc aaatcagggt aatttttgcat 1680 ttgtaatttt aaaaaatgct ttcttctttt aatatacttt tttgtttatc ttatttctaa 1740
tactttccct aatctctttc tttcagggca ataatgatac aatgtatcat gcctctttgc 1800
accattctaa agaataacag tgataatttc tgggttaagg caatagcaat atttctgcat 1860
ataaatattt ctgcatataa attgtaactg atgtaagagg tttcatattg ctaatagcag 1920
ctacaatcca gctaccattc tgcttttatt ttatggttgg gataaggctg gattattctg 1980

-continued

```
agtccaagct aggccctttt gctaatcatg ttcatacctc ttatcttcct cccacagctc   2040
ctgggcaacg tgctggtctg tgtgctggcc catcactttg gcaaagaatt caccccacca   2100
gtgcaggctg cctatcagaa agtggtggct ggtgtggcta atgccctggc ccacaagtat   2160
cactaagctc gctttcttgc tgtccaattt ctattaaagg ttcctttgtt ccctaagtcc   2220
aactactaaa ctgggggata ttatgaaggg ccttgagcat ctggattctg cctaataaaa   2280
aacatttatt ttcattgcaa tgatgtattt aaattatttc tgaatatttt actaaaaagg   2340
gaatgtggga ggttgcagtg ctagtctccc ggaactatca ctctttcaca gtctgctttg   2400
gaaggactgg gcttagtatg aaaagttagg actgagaaga atttgaaagg gggctttttg   2460
tagcttgata ttcactactg tcttattacc ctatcatagg cccaccccaa atggaagtcc   2520
cattcttcct caggatgttt aagattagca ttcaggaaga gatcagaggt ctgctggctc   2580
ccttatcatg tcccttatgg tgcttctggc tctgcaccgc ggccacgggg ttggggttgc   2640
gccttttcca aggcagccct gggtttgcgc agggacgcgg ctgctctggg cgtggttccg   2700
ggaaacgcag cggcgccgac cctgggtctc gcacattctt cacgtccgtt cgcagcgtca   2760
cccggatctt cgccgctacc cttgtgggcc ccccggcgac gcttcctgct ccgcccctaa   2820
gtcgggaagg ttccttgcgg ttcgcggcgt gccggacgtg acaaacggaa gccgcacgtc   2880
tcactagtac cctcgcagac ggacagcgcc agggagcaat ggcagcgcgc cgaccgcgat   2940
gggctgtggc caatagcggc tgctcagcgg ggcgcgccga gagcagcggc cgggaagggg   3000
cggtgcggga ggcggggtgt ggggcggtag tgtgggccct gttcctgccc gcgcggtgtt   3060
ccgcattctg caagcctccg gagcgcacgt cggcagtcgg ctccctcgtt gaccgaatca   3120
ccgacctctc tccccagcgg ccgcgccgcc accatggaca aggattgtga aatgaaacgc   3180
accacactgg acagcccttt ggggaagctg gagctgtctg gttgtgagca gggtctgcac   3240
gaaataaagc tcctgggcaa ggggacgtct gcagctgatg ccgtggaggt cccagccccc   3300
gctgcggttc tcggaggtcc ggagcccctg atgcagtgca cagcctggct gaatgcctat   3360
ttccaccagc ccgaggctat cgaagagttc cccgtgccgg ctcttcacca tcccgttttc   3420
cagcaagagt cgttcaccag acaggtgtta tggaagctgc tgaaggttgt gaaattcgga   3480
gaagtgattt cttaccagca attagcagcc ctggcaggca accccaaagc cgcgcgagca   3540
gtgggaggag caatgagagg caatcctgtc aaaatcctca tcccgtgcca cagagtggtc   3600
tgcagcagcg gagccgtggg caactactcc ggaggactgg ccgtgaagga atggcttctg   3660
gcccatgaag gccaccggtt ggggaagcca ggcttgggag ggagctcagg tctggcaggg   3720
gcctggctca agggagcggg agctacctcg ggctccccgc ctgctggccg aaactaagct   3780
ttatttgtga aatttgtgat gctattgctt tatttgtaac cattataagc tgcaataaac   3840
aagttaacaa caacaattgc attcatttta tgtttcaggt tcagggggag atgtgggagg   3900
tttttaaag ccctgcaggc aatagccttg acaaggcaaa cttgaccaat agtcttagag   3960
tatccagtga ggccaggggc cggcggctgg ctagggatga agaataaaag gaagcaccct   4020
tcagcagttc cacacactcg cttctggaac gtctgaggtt atcaataagc tcctagtcca   4080
gacgccatgg gtcatttcac agaggaggac aaggctacta tcacaagcct gtggggcaag   4140
gtgaatgtgg aagatgctgg aggagaaacc ctgggaaggt aggctctggt gaccaggaca   4200
agggagggaa ggaaggaccc tgtgcctggc aaaagtccag gtcgcttctc aggatttgtg   4260
gcaccttctg actgtcaaac tgttcttgtc aatctcacag gctcctggtt gtctacccat   4320
```

-continued

```
ggacccagag gttctttgac agctttggca acctgtcctc tgcctctgcc atcatgggca   4380
accccaaagt caaggcacat ggcaagaagg tgctgacttc cttgggagat gccacaaagc   4440
acctggatga tctcaagggc acctttgccc agctgagtga actgcactgt gacaagctgc   4500
atgtggatcc tgagaacttc aaggtgagtc caggagatgt ttcagccctg ttgcctttag   4560
tctcgaggcg tcgacaggaa cccctagtga tggagttggc cactccctct ctgcgcgctc   4620
gctcgctcac tgaggccggg cgaccaaagg tcgcccgacg cccgggcttt gcccgggcgg   4680
cctcagtgag cgagcgagcg cgcagctggc gtaatagcga agaggcccgc accgatcgcc   4740
cttcccaaca gttgcgcagc ctgaatggcg aatggcgatt ccgttgcaat ggctggcggt   4800
aatattgttc tggatattac cagcaaggcc gatagtttga gttcttctac tcaggcaagt   4860
gatgttatta ctaatcaaag aagtattgcg acaacggtta atttgcgtga tggacagact   4920
cttttactcg gtggcctcac tgattataaa aacacttctc aggattctgg cgtaccgttc   4980
ctgtctaaaa tccctttaat cggcctcctg tttagctccc gctctgattc taacgaggaa   5040
agcacgttat acgtgctcgt caaagcaacc atagtacgcg ccctgtagcg gcgcattaag   5100
cgcggcgggt gtggtggtta cgcgcagcgt gaccgctaca cttgccagcg ccctagcgcc   5160
cgctcctttc gctttcttcc cttcctttct cgccacgttc gccggctttc cccgtcaagc   5220
tctaaatcgg gggctccctt tagggttccg atttagtgct ttacggcacc tcgaccccaa   5280
aaaacttgat tagggtgatg gttcacgtag tgggccatcg ccctgataga cggtttttcg   5340
ccctttgacg ttggagtcca cgttctttaa tagtggactc ttgttccaaa ctggaacaac   5400
actcaaccct atctcggtct attcttttga tttataaggg attttgccga tttcggccta   5460
ttggttaaaa aatgagctga tttaacaaaa atttaacgcg aattttaaca aaatattaac   5520
gtttacaatt taaatatttg cttatacaat cttcctgttt ttggggcttt tctgattatc   5580
aaccggggta catatgattg acatgctagt tttacgatta ccgttcatcg attctcttgt   5640
ttgctccaga ctctcaggca atgacctgat agcctttgta gagacctctc aaaaatagct   5700
accctctccg gcatgaattt atcagctaga acggttgaat atcatattga tggtgatttg   5760
actgtctccg gcctttctca cccgtttgaa tctttaccta cacattactc aggcattgca   5820
tttaaaatat atgagggttc taaaaatttt tatccttgcg ttgaaataaa ggcttctccc   5880
gcaaaagtat tacagggtca taatgttttt ggtacaaccg atttagcttt atgctctgag   5940
gctttattgc ttaattttgc taattctttg ccttgcctgt atgatttatt ggatgttgga   6000
atcgcctgat gcggtatttt ctccttacgc atctgtgcgg tatttcacac cgcatatggt   6060
gcactctcag tacaatctgc tctgatgccg catagttaag ccagccccga cacccgccaa   6120
cacccgctga cgcgccctga cgggcttgtc tgctcccggc atccgcttac agacaagctg   6180
tgaccgtctc cgggagctgc atgtgtcaga ggttttcacc gtcatcaccg aaacgcgcga   6240
gacgaaaggg cctcgtgata cgcctatttt tataggttaa tgtcatgata ataatggttt   6300
cttagacgtc aggtggcact tttcggggaa atgtgcgcgg aacccctatt tgtttatttt   6360
tctaaataca ttcaaatatg tatccgctca tgagacaata accctgataa atgcttcaat   6420
aatattgaaa aaggaagagt atgagtattc aacatttccg tgtcgccctt attccctttt   6480
ttgcggcatt ttgccttcct gtttttgctc acccagaaac gctggtgaaa gtaaaagatg   6540
ctgaagatca gttgggtgca cgagtgggtt acatcgaact ggatctcaac agcggtaaga   6600
tccttgagag ttttcgcccc gaagaacgtt ttccaatgat gagcactttt aaagttctgc   6660
tatgtggcgc ggtattatcc cgtattgacg ccgggcaaga gcaactcggt cgccgcatac   6720
```

actattctca gaatgacttg gttgagtact caccagtcac agaaaagcat cttacggatg 6780
gcatgacagt aagagaatta tgcagtgctg ccataaccat gagtgataac actgcggcca 6840
acttacttct gacaacgatc ggaggaccga aggagctaac cgcttttttg cacaacatgg 6900
gggatcatgt aactcgcctt gatcgttggg aaccggagct gaatgaagcc ataccaaacg 6960
acgagcgtga caccacgatg cctgtagcaa tggcaacaac gttgcgcaaa ctattaactg 7020
gcgaactact tactctagct tcccggcaac aattaataga ctggatggag gcggataaag 7080
ttgcaggacc acttctgcgc tcggcccttc cggctggctg gtttattgct gataaatctg 7140
gagccggtga gcgtgggtct cgcggtatca ttgcagcact ggggccagat ggtaagccct 7200
cccgtatcgt agttatctac acgacgggga gtcaggcaac tatggatgaa cgaaatagac 7260
agatcgctga gataggtgcc tcactgatta agcattggta actgtcagac caagtttact 7320
catatatact ttagattgat ttaaaacttc atttttaatt taaaaggatc taggtgaaga 7380
tcctttttga taatctcatg accaaaatcc cttaacgtga gttttcgttc cactgagcgt 7440
cagaccccgt agaaaagatc aaaggatctt cttgagatcc tttttttctg cgcgtaatct 7500
gctgcttgca aacaaaaaaa ccaccgctac cagcggtggt ttgtttgccg gatcaagagc 7560
taccaactct ttttccgaag gtaactggct tcagcagagc gcagatacca aatactgtcc 7620
ttctagtgta gccgtagtta ggccaccact tcaagaactc tgtagcaccg cctacatacc 7680
tcgctctgct aatcctgtta ccagtggctg ctgccagtgg cgataagtcg tgtcttaccg 7740
ggttggactc aagacgatag ttaccggata aggcgcagcg gtcgggctga acggggggtt 7800
cgtgcacaca gcccagcttg gagcgaacga cctacaccga actgagatac ctacagcgtg 7860
agctatgaga aagcgccacg cttcccgaag ggagaaaggc ggacaggtat ccggtaagcg 7920
gcagggtcgg aacaggagag cgcacgaggg agcttccagg gggaaacgcc tggtatcttt 7980
atagtcctgt cgggtttcgc cacctctgac ttgagcgtcg atttttgtga tgctcgtcag 8040
gggggcggag cctatggaaa aacgccagca acgcggcctt tttacggttc ctggcctttt 8100
gctggccttt tgctcacatg ttctttcctg cgttatcccc tgattctgtg gataaccgta 8160
ttaccgcctt tgagtgagct gataccgctc gccgcagccg aacgaccgag cgcagcgagt 8220
cagtgagcga ggaagcggaa gagcgcccaa tacgcaaacc gcctctcccc gcgcgttggc 8280
cgattcatta atg 8293

<210> SEQ ID NO 18
<211> LENGTH: 8126
<212> TYPE: DNA
<213> ORGANISM: Artificial
<220> FEATURE:
<223> OTHER INFORMATION: AAV donor template

<400> SEQUENCE: 18
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgt atacatacat acctgaatat ggaatcaaat 180
atttttctaa gatgaaacag tcatgattta tttcaaatag gtacggataa gtagatattg 240
aggtaagcat taggtcttat attatgtaac actaatctat tactgcgctg aaactgtggc 300
tttatagaaa ttgttttcac tgcactattg agaaattaag agataatggc aaaagtcaca 360
aagagtatat tcaaaaagaa gtatagcact ttttccttag aaaccactgc taactgaaag 420

-continued

```
agactaagat ttgtcccgtc aaaaatcctg gacctatgcc taaaacacat ttcacaatcc    480
ctgaactttt caaaaattgg tacatgcttt agctttaaac tacaggcctc actggagcta    540
gagacaagaa ggtaaaaaac ggctgacaaa agaagtcctg gtatcctcta tgatgggaga    600
aggaaactag ctaaagggaa gaataaatta gagaaaaact ggaatgactg aatcggaaca    660
aggcaaaggc tataaaaaaa attaagcagc agtatcctct tgggggcccc ttccccacac    720
tatctcaatg caaatatctg tctgaaacgg tccctggcta aactccaccc atgggttggc    780
cagccttgcc ttgacaaggc aaacttgacc aatagtctta gagtatccag tgaggccagg    840
ggccggcggc tggctaggga tgaagaataa aaggaagcac ccttcagcag ttccacacac    900
tcgcttctgg aacgtctgag gttatcaata agctcctagt ccagacgcca tggtgcacct    960
gactcctgag gagaagtctg ccgttactgc cctgtggggc aaggtgaacg tggatgaagt   1020
tggtggtgag gccctgggca ggttggtatc aaggttacaa gacaggttta aggagaccaa   1080
tagaaactgg gcatgtggag acagagaaga ctcttgggtt tctgataggc actgactctc   1140
tctgcctatt ggtctatttt cccaccctta ggctgctggt ggtctaccct tggacccaga   1200
ggttctttga gtcctttggg gatctgtcca ctcctgatgc tgttatgggc aaccctaagg   1260
tgaaggctca tggcaagaaa gtgctcggtg cctttagtga tggcctggct cacctggaca   1320
acctcaaggg cacctttgcc cagctgagtg agctgcactg tgacaagctg cacgtggatc   1380
ctgagaactt cagggtgagt ctatgggacc cttgatgttt tctttcccct tcttttctat   1440
ggttaagttc atgtcatagg aaggggagaa gtaacagggt acacatattg accaaatcag   1500
ggtaattttg catttgtaat tttaaaaaat gctttcttct tttaatatac ttttttgttt   1560
atcttatttc taatactttc cctaatctct ttctttcagg gcaataatga tacaatgtat   1620
catgcctctt tgcaccattc taaagaataa cagtgataat ttctgggtta aggcaatagc   1680
aatatttctg catataaata tttctgcata taaattgtaa ctgatgtaag aggtttcata   1740
ttgctaatag cagctacaat ccagctacca ttctgctttt attttatggt tgggataagg   1800
ctggattatt ctgagtccaa gctaggccct tttgctaatc atgttcatac ctcttatctt   1860
cctcccacag ctcctgggca acgtgctggt ctgtgtgctg gcccatcact ttggcaaaga   1920
attcacccca ccagtgcagg ctgcctatca gaaagtggtg gctggtgtgg ctaatgccct   1980
ggcccacaag tatcactaag ctcgctttct tgctgtccaa tttctattaa aggttccttt   2040
gttccctaag tccaactact aaactggggg atattatgaa gggccttgag catctggatt   2100
ctgcctaata aaaaacattt attttcattg caatgatgta tttaaattat ttctgaatat   2160
tttactaaaa agggaatgtg ggaggttgca gtgctagtct cccggaacta tcactctttc   2220
acagtctgct ttggaaggac tgggcttagt atgaaaagtt aggactgaga agaatttgaa   2280
agggggcttt ttgtagcttg atattcacta ctgtcttatt accctatcat aggcccaccc   2340
caaatggaag tcccattctt cctcaggatg tttaagatta gcattcagga agagatcaga   2400
ggtctgctgg ctcccttatc atgtccctta tggtgcttct ggctctgcac cgcggccacg   2460
gggttggggt tgcgcctttt ccaaggcagc cctgggtttg cgcagggacg cggctgctct   2520
gggcgtggtt ccgggaaacg cagcggcgcc gaccctgggt ctcgcacatt cttcacgtcc   2580
gttcgcagcg tcacccggat cttcgccgct acccttgtgg gccccccggc gacgcttcct   2640
gctccgcccc taagtcggga aggttccttg cggttcgcgg cgtgccggac gtgacaaacg   2700
gaagccgcac gtctcactag taccctcgca gacggacagc gccagggagc aatggcagcg   2760
cgccgaccgc gatgggctgt ggccaatagc ggctgctcag cggggcgcgc cgagagcagc   2820
```

ggccgggaag gggcggtgcg ggaggcgggg tgtggggcgg tagtgtgggc cctgttcctg 2880
cccgcgcggt gttccgcatt ctgcaagcct ccggagcgca cgtcggcagt cggctccctc 2940
gttgaccgaa tcaccgacct ctctccccag cggccgcgcc gccaccatgg acaaggattg 3000
tgaaatgaaa cgcaccacac tggacagccc tttggggaag ctggagctgt ctggttgtga 3060
gcagggtctg cacgaaataa agctcctggg caaggggacg tctgcagctg atgccgtgga 3120
ggtcccagcc cccgctgcgg ttctcggagg tccggagccc ctgatgcagt gcacagcctg 3180
gctgaatgcc tatttccacc agcccgaggc tatcgaagag ttccccgtgc cggctcttca 3240
ccatcccgtt ttccagcaag agtcgttcac cagacaggtg ttatggaagc tgctgaaggt 3300
tgtgaaattc ggagaagtga tttcttacca gcaattagca gccctggcag gcaaccccaa 3360
agccgcgcga gcagtgggag gagcaatgag aggcaatcct gtcaaaatcc tcatcccgtg 3420
ccacagagtg gtctgcagca gcggagccgt gggcaactac tccggaggac tggccgtgaa 3480
ggaatggctt ctggcccatg aaggccaccg gttggggaag ccaggcttgg gagggagctc 3540
aggtctggca ggggcctggc tcaagggagc gggagctacc tcgggctccc cgcctgctgg 3600
ccgaaactaa gctttatttg tgaaatttgt gatgctattg ctttatttgt aaccattata 3660
agctgcaata aacaagttaa caacaacaat tgcattcatt ttatgtttca ggttcagggg 3720
gagatgtggg aggtttttta aagccctgca ggcaatagcc ttgacaaggc aaacttgacc 3780
aatagtctta gagtatccag tgaggccagg ggccggcggc tggctaggga tgaagaataa 3840
aaggaagcac ccttcagcag ttccacacac tcgcttctgg aacgtctgag gttatcaata 3900
agctcctagt ccagacgcca tggtcattt cacagaggag gacaaggcta ctatcacaag 3960
cctgtggggc aaggtgaatg tggaagatgc tggaggagaa accctgggaa ggtaggctct 4020
ggtgaccagg acaagggagg gaaggaagga ccctgtgcct ggcaaaagtc caggtcgctt 4080
ctcaggattt gtggcacctt ctgactgtca aactgttctt gtcaatctca caggctcctg 4140
gttgtctacc catggaccca gaggttcttt gacagctttg gcaacctgtc ctctgcctct 4200
gccatcatgg gcaaccccaa agtcaaggca catggcaaga aggtgctgac ttccttggga 4260
gatgccacaa agcacctgga tgatctcaag ggcacctttg cccagctgag tgaactgcac 4320
tgtgacaagc tgcatgtgga tcctgagaac ttcaaggtga gtccaggaga tgtttcagcc 4380
ctgttgcctt tagtctcgag gcgtcgacag gaacccctag tgatggagtt ggccactccc 4440
tctctgcgcg ctcgctcgct cactgaggcc gggcgaccaa aggtcgcccg acgcccgggc 4500
tttgcccggg cggcctcagt gagcgagcga gcgcgcagct ggcgtaatag cgaagaggcc 4560
cgcaccgatc gcccttccca acagttgcgc agcctgaatg gcgaatggcg attccgttgc 4620
aatggctggc ggtaatattg ttctggatat taccagcaag gccgatagtt tgagttcttc 4680
tactcaggca agtgatgtta ttactaatca aagaagtatt gcgacaacgg ttaatttgcg 4740
tgatggacag actcttttac tcggtggcct cactgattat aaaaacactt ctcaggattc 4800
tggcgtaccg ttcctgtcta aaatcccttt aatcggcctc ctgtttagct cccgctctga 4860
ttctaacgag gaaagcacgt tatacgtgct cgtcaaagca accatagtac gcgccctgta 4920
gcggcgcatt aagcgcggcg ggtgtggtgg ttacgcgcag cgtgaccgct acacttgcca 4980
gcgccctagc gcccgctcct ttcgctttct tcccttcctt tctcgccacg ttcgccggct 5040
ttccccgtca agctctaaat cgggggctcc ctttagggtt ccgatttagt gctttacggc 5100
acctcgaccc caaaaaactt gattagggtg atggttcacg tagtgggcca tcgccctgat 5160

```
agacggtttt tcgccctttg acgttggagt ccacgttctt taatagtgga ctcttgttcc   5220
aaactggaac aacactcaac cctatctcgg tctattcttt tgatttataa gggattttgc   5280
cgatttcggc ctattggtta aaaaatgagc tgatttaaca aaaatttaac gcgaatttta   5340
acaaaatatt aacgtttaca atttaaatat ttgcttatac aatcttcctg tttttggggc   5400
ttttctgatt atcaaccggg gtacatatga ttgacatgct agttttacga ttaccgttca   5460
tcgattctct tgtttgctcc agactctcag gcaatgacct gatagccttt gtagagacct   5520
ctcaaaaata gctaccctct ccggcatgaa tttatcagct agaacggttg aatatcatat   5580
tgatggtgat ttgactgtct ccggcctttc tcacccgttt gaatctttac ctacacatta   5640
ctcaggcatt gcatttaaaa tatatgaggg ttctaaaaat ttttatcctt gcgttgaaat   5700
aaaggcttct cccgcaaaag tattacaggg tcataatgtt tttggtacaa ccgatttagc   5760
tttatgctct gaggctttat tgcttaattt tgctaattct ttgccttgcc tgtatgattt   5820
attggatgtt ggaatcgcct gatgcggtat tttctcctta cgcatctgtg cggtatttca   5880
caccgcatat ggtgcactct cagtacaatc tgctctgatg ccgcatagtt aagccagccc   5940
cgacacccgc caacacccgc tgacgcgccc tgacgggctt gtctgctccc ggcatccgct   6000
tacagacaag ctgtgaccgt ctccgggagc tgcatgtgtc agaggttttc accgtcatca   6060
ccgaaacgcg cgagacgaaa gggcctcgtg atacgcctat ttttataggt taatgtcatg   6120
ataataatgg tttcttagac gtcaggtggc acttttcggg gaaatgtgcg cggaacccct   6180
atttgtttat ttttctaaat acattcaaat atgtatccgc tcatgagaca ataaccctga   6240
taaatgcttc aataatattg aaaaaggaag agtatgagta ttcaacattt ccgtgtcgcc   6300
cttattccct tttttgcggc attttgcctt cctgtttttg ctcacccaga aacgctggtg   6360
aaagtaaaag atgctgaaga tcagttgggt gcacgagtgg gttacatcga actggatctc   6420
aacagcggta agatccttga gagttttcgc cccgaagaac gttttccaat gatgagcact   6480
tttaaagttc tgctatgtgg cgcggtatta tcccgtattg acgccgggca agagcaactc   6540
ggtcgccgca tacactattc tcagaatgac ttggttgagt actcaccagt cacagaaaag   6600
catcttacgg atggcatgac agtaagagaa ttatgcagtg ctgccataac catgagtgat   6660
aacactgcgg ccaacttact tctgacaacg atcggaggac cgaaggagct aaccgctttt   6720
ttgcacaaca tgggggatca tgtaactcgc cttgatcgtt gggaaccgga gctgaatgaa   6780
gccataccaa acgacgagcg tgacaccacg atgcctgtag caatggcaac aacgttgcgc   6840
aaactattaa ctggcgaact acttactcta gcttcccggc aacaattaat agactggatg   6900
gaggcggata aagttgcagg accacttctg cgctcggccc ttccggctgg ctggtttatt   6960
gctgataaat ctggagccgg tgagcgtggg tctcgcggta tcattgcagc actggggcca   7020
gatggtaagc cctcccgtat cgtagttatc tacacgacgg ggagtcaggc aactatggat   7080
gaacgaaata gacagatcgc tgagataggt gcctcactga ttaagcattg gtaactgtca   7140
gaccaagttt actcatatat actttagatt gatttaaaac ttcattttta atttaaaagg   7200
atctaggtga agatcctttt tgataatctc atgaccaaaa tcccttaacg tgagttttcg   7260
ttccactgag cgtcagaccc cgtagaaaag atcaaaggat cttcttgaga tccttttttt   7320
ctgcgcgtaa tctgctgctt gcaaacaaaa aaaccaccgc taccagcggt ggtttgtttg   7380
ccggatcaag agctaccaac tctttttccg aaggtaactg gcttcagcag agcgcagata   7440
ccaaatactg tccttctagt gtagccgtag ttaggccacc acttcaagaa ctctgtagca   7500
ccgcctacat acctcgctct gctaatcctg ttaccagtgg ctgctgccag tggcgataag   7560
```

tcgtgtctta ccgggttgga ctcaagacga tagttaccgg ataaggcgca gcggtcgggc 7620
tgaacggggg gttcgtgcac acagcccagc ttggagcgaa cgacctacac cgaactgaga 7680
tacctacagc gtgagctatg agaaagcgcc acgcttcccg aagggagaaa ggcggacagg 7740
tatccggtaa gcggcagggt cggaacagga gagcgcacga gggagcttcc agggggaaac 7800
gcctggtatc tttatagtcc tgtcgggttt cgccacctct gacttgagcg tcgatttttg 7860
tgatgctcgt caggggggcg gagcctatgg aaaaacgcca gcaacgcggc ctttttacgg 7920
ttcctggcct tttgctggcc ttttgctcac atgttctttc ctgcgttatc ccctgattct 7980
gtggataacc gtattaccgc ctttgagtga gctgataccg ctcgccgcag ccgaacgacc 8040
gagcgcagcg agtcagtgag cgaggaagcg gaagagcgcc caatacgcaa accgcctctc 8100
cccgcgcgtt ggccgattca ttaatg 8126

<210> SEQ ID NO 19
<211> LENGTH: 8024
<212> TYPE: DNA
<213> ORGANISM: Artificial
<220> FEATURE:
<223> OTHER INFORMATION: AAV donor template

<400> SEQUENCE: 19
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
cttgaaacag tcatgattta tttcaaatag gtacggataa gtagatattg aggtaagcat 240
taggtcttat attatgtaac actaatctat tactgcgctg aaactgtggc tttatagaaa 300
ttgttttcac tgcactattg agaaattaag agataatggc aaaagtcaca aagagtatat 360
tcaaaaagaa gtatagcact tttccttag aaaccactgc taactgaaag agactaagat 420
ttgtcccgtc aaaaatcctg gacctatgcc taaaacacat ttcacaatcc ctgaactttt 480
caaaaattgg tacatgcttt agctttaaac tacaggcctc actggagcta gagacaagaa 540
ggtaaaaaac ggctgacaaa agaagtcctg gtatcctcta tgatgggaga aggaaactag 600
ctaaagggaa gaataaatta gagaaaaact ggaatgactg aatcggaaca aggcaaaggc 660
tataaaaaaa attagcagta tcctcttggg ggccccttcc ccacactatc tcaatgcaaa 720
tatctgtctg aaacggtccc tggctaaact ccacccatgg gttggccagc cttgccttga 780
caaggcaaac ttgaccaata gtcttagagt atccagtgag gccaggggcc ggcggctggc 840
tagggatgaa gaataaaagg aagcaccctt cagcagttcc acacactcgc ttctggaacg 900
tctgaggtta tcaataagct cctagtccag acgccatggt gcacctgact cctgaggaga 960
agtctgccgt tactgccctg tggggcaagg tgaacgtgga tgaagttggt ggtgaggccc 1020
tgggcaggtt ggtatcaagg ttacaagaca ggtttaagga gaccaataga aactgggcat 1080
gtggagacag agaagactct tgggtttctg ataggcactg actctctctg cctattggtc 1140
tattttccca cccttaggct gctggtggtc taccettgga cccagaggtt ctttgagtcc 1200
tttggggatc tgtccactcc tgatgctgtt atgggcaacc ctaaggtgaa ggctcatggc 1260
aagaaagtgc tcggtgcctt tagtgatggc ctggctcacc tggacaacct caagggcacc 1320
tttgcccagc tgagtgagct gcactgtgac aagctgcacg tggatcctga gaacttcagg 1380
gtgagtctat gggacccttg atgttttctt tccccttctt ttctatggtt aagttcatgt 1440

-continued cataggaagg ggagaagtaa cagggtacac atattgacca aatcagggta attttgcatt 1500
tgtaatttta aaaaatgctt tcttctttta atatactttt ttgtttatct tatttctaat 1560
actttcccta atctctttct ttcagggcaa taatgataca atgtatcatg cctctttgca 1620
ccattctaaa gaataacagt gataatttct gggttaaggc aatagcaata tttctgcata 1680
taaatatttc tgcatataaa ttgtaactga tgtaagaggt ttcatattgc taatagcagc 1740
tacaatccag ctaccattct gcttttattt tatggttggg ataaggctgg attattctga 1800
gtccaagcta ggccctttttg ctaatcatgt tcatacctct tatcttcctc ccacagctcc 1860
tgggcaacgt gctggtctgt gtgctggccc atcactttgg caaagaattc accccaccag 1920
tgcaggctgc ctatcagaaa gtggtggctg gtgtggctaa tgccctggcc cacaagtatc 1980
actaagctcg ctttcttgct gtccaatttc tattaaaggt tcctttgttc cctaagtcca 2040
actactaaac tgggggatat tatgaagggc cttgagcatc tggattctgc ctaataaaaa 2100
acatttattt tcattgcaat gatgtattta aattatttct gaatatttta ctaaaaaggg 2160
aatgtgggag gttgcagtgc tagtctcccg gaactatcac tctttcacag tctgctttgg 2220
aaggactggg cttagtatga aaagttagga ctgagaagaa tttgaaaggg ggctttttgt 2280
agcttgatat tcactactgt cttattaccc tatcataggc ccaccccaaa tggaagtccc 2340
attcttcctc aggatgttta agattagcat tcaggaagag atcagaggtc tgctggctcc 2400
cttatcatgt cccttatggt gcttctggct ctgcaccgcg gccacggggt tggggttgcg 2460
ccttttccaa ggcagccctg ggtttgcgca gggacgcggc tgctctgggc gtggttccgg 2520
gaaacgcagc ggcgccgacc ctgggtctcg cacattcttc acgtccgttc gcagcgtcac 2580
ccggatcttc gccgctaccc ttgtgggccc cccggcgacg cttcctgctc cgcccctaag 2640
tcgggaaggt tccttgcggt tcgcggcgtg ccggacgtga caaacggaag ccgcacgtct 2700
cactagtacc ctcgcagacg gacagcgcca gggagcaatg gcagcgcgcc gaccgcgatg 2760
ggctgtggcc aatagcggct gctcagcggg gcgcgccgag agcagcggcc gggaaggggc 2820
ggtgcgggag gcggggtgtg gggcggtagt gtgggccctg ttcctgcccg cgcggtgttc 2880
cgcattctgc aagcctccgg agcgcacgtc ggcagtcggc tccctcgttg accgaatcac 2940
cgacctctct ccccagcggc cgcgccgcca ccatggacaa ggattgtgaa atgaaacgca 3000
ccacactgga cagccctttg ggaagctgg agctgtctgg ttgtgagcag ggtctgcacg 3060
aaataaagct cctgggcaag gggacgtctg cagctgatgc cgtggaggtc ccagcccccg 3120
ctgcggttct cggaggtccg gagcccctga tgcagtgcac agcctggctg aatgcctatt 3180
tccaccagcc cgaggctatc gaagagttcc ccgtgccggc tcttcaccat cccgttttcc 3240
agcaagagtc gttcaccaga caggtgttat ggaagctgct gaaggttgtg aaattcggag 3300
aagtgatttc ttaccagcaa ttagcagccc tggcaggcaa ccccaaagcc gcgcgagcag 3360
tgggaggagc aatgagaggc aatcctgtca aaatcctcat cccgtgccac agagtggtct 3420
gcagcagcgg agccgtgggc aactactccg gaggactggc cgtgaaggaa tggcttctgg 3480
cccatgaagg ccaccggttg gggaagccag gcttgggagg gagctcaggt ctggcagggg 3540
cctggctcaa gggagcggga gctacctcgg gctccccgcc tgctggccga aacgagggca 3600
gaggaagtct tctaacatgc ggtgacgtgg aggagaatcc gggccccccct gcaggaactt 3660 caaggtgagt ccaggagatg tttcagccct gttgccttta gtctcgaggc aacttagaca 3720
acggagtatt gatctgagca cagcagggtg tgagctgttt gaagatactg ggttggggg 3780 tgaagaaact gcagaggact aactgggctg agacccagtg gtaatgtttt agggcctaag 3840
gagtgcctct aaaaatctag atggacaatt ttgactttga gaaaagagag gtggaaatga 3900
ggaaaatgac ttttctttat tagattccag tagaaagaac tttcatcttt ccctcatttt 3960
tgttgtttta aaacatctat ctggaggcag gacaagtatg gtcgttaaaa agatgcaggc 4020
agaaggcata tattggctca gtcaaagtgg ggaactttgg tggccaaaca tacattgcta 4080
aggctattcc tatatcagct ggacacatat aaaatgctgc taatgcttca ttacaaactt 4140
atatccttta attccagatg ggggcaaagt atgtccaggg gtgaggaaca attgaaacat 4200
ttgggctgga gtagattttg aaagtcagct ctgtgtgtgt gtgtgtgtgt gcgcgcgcgc 4260
gtgtcgacgt agataagtag catggcgggt taatcattaa ctacaaggaa cccctagtga 4320
tggagttggc cactccctct ctgcgcgctc gctcgctcac tgaggccggg cgaccaaagg 4380
tcgcccgacg cccgggcttt gcccgggcgg cctcagtgag cgagcgagcg cgccagctgg 4440
cgtaatagcg aagaggcccg caccgatcgc ccttcccaac agttgcgcag cctgaatggc 4500
gaatggcgat tccgttgcaa tggctggcgg taatattgtt ctggatatta ccagcaaggc 4560
cgatagtttg agttcttcta ctcaggcaag tgatgttatt actaatcaaa gaagtattgc 4620
gacaacggtt aatttgcgtg atggacagac tcttttactc ggtggcctca ctgattataa 4680
aaacacttct caggattctg gcgtaccgtt cctgtctaaa atccctttaa tcggcctcct 4740
gtttagctcc cgctctgatt ctaacgagga aagcacgtta tacgtgctcg tcaaagcaac 4800
catagtacgc gccctgtagc ggcgcattaa gcgcggcggg tgtggtggtt acgcgcagcg 4860
tgaccgctac acttgccagc gccctagcgc ccgctccttt cgctttcttc ccttcctttc 4920
tcgccacgtt cgccggcttt ccccgtcaag ctctaaatcg ggggctccct ttagggttcc 4980
gatttagtgc tttacggcac ctcgacccca aaaaacttga ttagggtgat ggttcacgta 5040
gtgggccatc gccctgatag acggtttttc gccctttgac gttggagtcc acgttcttta 5100
atagtggact cttgttccaa actggaacaa cactcaaccc tatctcggtc tattcttttg 5160
atttataagg gattttgccg atttcggcct attggttaaa aaatgagctg atttaacaaa 5220
aatttaacgc gaattttaac aaaatattaa cgtttacaat ttaaatattt gcttatacaa 5280
tcttcctgtt tttggggctt ttctgattat caaccggggt acatatgatt gacatgctag 5340
ttttacgatt accgttcatc gattctcttg tttgctccag actctcaggc aatgacctga 5400
tagcctttgt agagacctct caaaaatagc taccctctcc ggcatgaatt tatcagctag 5460
aacggttgaa tatcatattg atggtgattt gactgtctcc ggcctttctc acccgtttga 5520
atctttacct acacattact caggcattgc atttaaaata tatgagggtt ctaaaaattt 5580
ttatccttgc gttgaaataa aggcttctcc cgcaaaagta ttacagggtc ataatgtttt 5640
tggtacaacc gatttagctt tatgctctga ggctttattg cttaattttg ctaattcttt 5700
gccttgcctg tatgatttat tggatgttgg aatcgcctga tgcggtattt tctccttacg 5760
catctgtgcg gtatttcaca ccgcatatgg tgcactctca gtacaatctg ctctgatgcc 5820
gcatagttaa gccagccccg acacccgcca acacccgctg acgcgccctg acgggcttgt 5880
ctgctcccgg catccgctta cagacaagct gtgaccgtct ccgggagctg catgtgtcag 5940
aggttttcac cgtcatcacc gaaacgcgcg agacgaaagg gcctcgtgat acgcctattt 6000
ttataggtta atgtcatgat aataatggtt tcttagacgt caggtggcac ttttcgggga 6060
aatgtgcgcg gaacccctat ttgtttattt ttctaaatac attcaaatat gtatccgctc 6120
atgagacaat aaccctgata aatgcttcaa taatattgaa aaaggaagag tatgagtatt 6180
caacatttcc gtgtcgccct tattcccttt tttgcggcat tttgccttcc tgtttttgct 6240
cacccagaaa cgctggtgaa agtaaaagat gctgaagatc agttgggtgc acgagtgggt 6300
tacatcgaac tggatctcaa cagcggtaag atccttgaga gttttcgccc cgaagaacgt 6360
tttccaatga tgagcacttt taaagttctg ctatgtggcg cggtattatc ccgtattgac 6420
gccgggcaag agcaactcgg tcgccgcata cactattctc agaatgactt ggttgagtac 6480
tcaccagtca cagaaaagca tcttacggat ggcatgacag taagagaatt atgcagtgct 6540
gccataacca tgagtgataa cactgcggcc aacttacttc tgacaacgat cggaggaccg 6600
aaggagctaa ccgctttttt gcacaacatg ggggatcatg taactcgcct tgatcgttgg 6660
gaaccggagc tgaatgaagc cataccaaac gacgagcgtg acaccacgat gcctgtagca 6720
atggcaacaa cgttgcgcaa actattaact ggcgaactac ttactctagc ttcccggcaa 6780
caattaatag actggatgga ggcggataaa gttgcaggac cacttctgcg ctcggccctt 6840
ccggctggct ggtttattgc tgataaatct ggagccggtg agcgtgggtc tcgcggtatc 6900
attgcagcac tggggccaga tggtaagccc tcccgtatcg tagttatcta cacgacgggg 6960
agtcaggcaa ctatggatga acgaaataga cagatcgctg agataggtgc ctcactgatt 7020
aagcattggt aactgtcaga ccaagtttac tcatatatac tttagattga tttaaaactt 7080
catttttaat ttaaaaggat ctaggtgaag atcctttttg ataatctcat gaccaaaatc 7140
ccttaacgtg agttttcgtt ccactgagcg tcagaccccg tagaaaagat caaaggatct 7200
tcttgagatc cttttttctt gcgcgtaatc tgctgcttgc aaacaaaaaa accaccgcta 7260
ccagcggtgg tttgtttgcc ggatcaagag ctaccaactc tttttccgaa ggtaactggc 7320
ttcagcagag cgcagatacc aaatactgtc cttctagtgt agccgtagtt aggccaccac 7380
ttcaagaact ctgtagcacc gcctacatac ctcgctctgc taatcctgtt accagtggct 7440
gctgccagtg gcgataagtc gtgtcttacc gggttggact caagacgata gttaccggat 7500
aaggcgcagc ggtcgggctg aacggggggt tcgtgcacac agcccagctt ggagcgaacg 7560
acctacaccg aactgagata cctacagcgt gagctatgag aaagcgccac gcttcccgaa 7620
gggagaaagg cggacaggta tccggtaagc ggcagggtcg gaacaggaga gcgcacgagg 7680
gagcttccag ggggaaacgc ctggtatctt tatagtcctg tcgggtttcg ccacctctga 7740
cttgagcgtc gatttttgtg atgctcgtca ggggggcgga gcctatggaa aaacgccagc 7800
aacgcggcct ttttacggtt cctggccttt tgctggcctt ttgctcacat gttctttcct 7860
gcgttatccc ctgattctgt ggataaccgt attaccgcct ttgagtgagc tgataccgct 7920
cgccgcagcc gaacgaccga gcgcagcgag tcagtgagcg aggaagcgga agagcgccca 7980
atacgcaaac cgcctctccc cgcgcgttgg ccgattcatt aatg 8024

<210> SEQ ID NO 20
<211> LENGTH: 7729
<212> TYPE: DNA
<213> ORGANISM: Artificial
<220> FEATURE:
<223> OTHER INFORMATION: AAV donor template

<400> SEQUENCE: 20
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctagaaattg ttttcactgc actattgaga aattaagaga taatggcaaa agtcacaaag 240
agtatattca aaaagaagta tagcactttt tccttagaaa ccactgctaa ctgaaagaga 300
ctaagatttg tcccgtcaaa aatcctggac ctatgcctaa aacacatttc acaatccctg 360
aacttttcaa aaattggtac atgctttagc tttaaactac aggcctcact ggagctagag 420
acaagaaggt aaaaaacggc tgacaaaaga agtcctggta tcctctatga tgggagaagg 480
aaactagcta aagggaagaa taaattagag aaaaactgga atgactgaat cggaacaagg 540
caaaggctat aaaaaaaatt agcagtatcc tcttgggggc cccttcccca cactatctca 600
atgcaaatat ctgtctgaaa cggtccctgg ctaaactcca cccgcgggaa cagagaaaca 660
ggagaatatg ggccaaacag gatatctgtg gtaagcagtt cctgccccgg ctcagggcca 720
agaacagttg gaacagcaga atatgggcca aacaggatat ctgtggtaag cagttcctgc 780
cccggctcag ggccaagaac agatggtccc cagatgcggt cccgccctca gcagtttcta 840
gagaaccatc agatgtttcc agggtgcccc aaggacctga aatgaccctg tgccttattt 900
gaactaacca atcagttcgc ttctcgcttc tgttcgcgcg cttctgctcc ccgagctcta 960
tataagcaga gctcgtttag tgaaccgtca gatcgcctgg agacgccatc cacgctgttt 1020
tgacttccat agaaggcggc cgcgccgcca ccatggacaa ggattgtgaa atgaaacgca 1080
ccacactgga cagccctttg ggaagctgg agctgtctgg ttgtgagcag ggtctgcacg 1140
aaataaagct cctgggcaag ggacgtctg cagctgatgc cgtggaggtc ccagcccccg 1200
ctgcggttct cggaggtccg gagcccctga tgcagtgcac agcctggctg aatgcctatt 1260
tccaccagcc cgaggctatc gaagagttcc ccgtgccggc tcttcaccat cccgttttcc 1320
agcaagagtc gttcaccaga caggtgttat ggaagctgct gaaggttgtg aaattcggag 1380
aagtgatttc ttaccagcaa ttagcagccc tggcaggcaa ccccaaagcc gcgcgagcag 1440
tgggaggagc aatgagaggc aatcctgtca aaatcctcat cccgtgccac agagtggtct 1500
gcagcagcgg agccgtgggc aactactccg gaggactggc cgtgaaggaa tggcttctgg 1560
cccatgaagg ccaccggttg ggaagccag gcttgggagg gagctcaggt ctggcagggg 1620
cctggctcaa gggagcggga gctacctcgg gctccccgcc tgctggccga aactaacctg 1680
cagggataat caacctctgg attacaaaat ttgtgaaaga ttgactggta ttcttaacta 1740
tgttgctcct tttacgctat gtggatacgc tgctttaatg cctttgtatc atgctattgc 1800
ttcccgtatg gctttcattt tctcctcctt gtataaatcc tggttagttc ttgccacggc 1860
ggaactcatc gccgcctgcc ttgcccgctg ctggacaggg gctcggctgt tgggcactga 1920
caattccgtg gtgtttattt gtgaaatttg tgatgctatt gctttatttg taaccattct 1980
agctttattt gtgaaatttg tgatgctatt gctttatttg taaccattat aagctgcaat 2040
aaacaagtta acaacaacaa ttgcattcat tttatgtttc aggttcaggg ggagatgtgg 2100
gaggtttttt aaagcgaatt ccgagatcga gaccatcctg gctaacacag tgaaaccccg 2160
tctctactaa aaaaatacaa aaaattagcc gggcttggtg gcgggtgcct gtagtcccag 2220
ctactatgga ggctgaggcg ggagaatggc gtgaacgcgg ggggcggagc ttgcagtgag 2280
cagagatcag gggccactgc actccagcct gggcgacaga gagagactct gtctcaaaaa 2340
aaagaaaaaa aaaatttagt agactagcta aaaaaatcca gagatagtta ttgatgcata 2400
tgtaaaagtc ttccaatatt tacaagtaca atgaaaaaaa aataaccttg aattaagtgt 2460
agaactcatt gacaatgttt caaaggatgt gagggataaa ctaaaatttg ggcagtacat 2520
gctgttcctg tgtacttgga acagagggag aaaatctggg ctggaaatat tgttatagga 2580
gttagcacat gaaggtgaca actaaattat ttggagtaga tggagtcacc agcacatgtg 2640
aatagtttta gaatgaaatg acccaagata gaactttgga gagcccccaa atttaaataa 2700
aatcagtata agagaagagg aagaaaccaa atggtatact agtctaaatt gtttcttagt 2760
gacaaaagaa taacctgaat attagattag ctgcctatat gctctctgaa tcaatttcat 2820
tcaacatgca acagttctgg aacctatcag ggaccacagt cagccaggca agcacatctg 2880
cccaagccaa gggtggaggc atgcagctgt gggggtctgt gaaaacactt gagggagcag 2940
ataactgggc caaccatgac tcagtgcttc tggaggccaa caggactgct gagtcatcct 3000
gtgggggtgg aggtgggaca agggaaaggg gtgaatggta ctgctgatta caacctctgg 3060
tgctgcctcc ccctcctgtt tatctgagag gctagcgtaa atacacttgc aaaggaggat 3120
gtttttagta gcaatttgta ctgatggtat ggggccaaga gatatatctt agagggaggg 3180
ctgagggttt gaagtccaac tcctaagcca gtgccagaag agccaaggac aggtacggct 3240
gtcatcactt agacctcacc ctgtggagcc acaccctagg gttggccaat ctactcccag 3300
gagcagggag ggcaggagcc agggctgggc ataaaagtca gggcagagcc atctattgct 3360
tacactcgct tctggaacgt ctgaggttat caataagctc ctagtccaga cgccatgggt 3420
catttcacag aggaggacaa ggctactatc acaagcctgt ggggcaaggt gaatgtggaa 3480
gatgctggag gagaaaccct gggaaggtag gctctggtga ccaggacaag ggagggaagg 3540
aaggaccctg tgcctggcaa aagtccaggt cgcttctcag gatttgtggc accttctgac 3600
tgtcaaactg ttcttgtcaa tctcacaggc tcctggttgt ctacccatgg acccagaggt 3660
tctttgacag ctttggcaac ctgtcctctg cctctgccat catgggcaac cccaaagtca 3720
aggcacatgg caagaaggtg ctgacttcct tgggagatgc cacaaagcac ctggatgatc 3780
tcaagggcac ctttgcccag ctgagtgaac tgcactgtga caagctgcat gtggatcctg 3840
agaacttcaa ggtgagtcca ggagatgttt cagccctgtt gcctttagtc tcgaggcaac 3900
ttagacaacg gagtattgat ctgagcacag cagggtgtga gctgtttgaa gatactgggg 3960
tctcgaggtc gacgtagata agtagcatgg cgggttaatc attaactaca aggaacccct 4020
agtgatggag ttggccactc cctctctgcg cgctcgctcg ctcactgagg ccgggcgacc 4080
aaaggtcgcc cgacgcccgg gctttgcccg ggcggcctca gtgagcgagc gagcgcgcca 4140
gctggcgtaa tagcgaagag gcccgcaccg atcgcccttc ccaacagttg cgcagcctga 4200
atggcgaatg gcgattccgt tgcaatggct ggcggtaata ttgttctgga tattaccagc 4260
aaggccgata gtttgagttc ttctactcag gcaagtgatg ttattactaa tcaaagaagt 4320
attgcgacaa cggttaattt gcgtgatgga cagactcttt tactcggtgg cctcactgat 4380
tataaaaaca cttctcagga ttctggcgta ccgttcctgt ctaaaatccc tttaatcggc 4440
ctcctgttta gctcccgctc tgattctaac gaggaaagca cgttatacgt gctcgtcaaa 4500
gcaaccatag tacgcgccct gtagcggcgc attaagcgcg gcgggtgtgg tggttacgcg 4560
cagcgtgacc gctacacttg ccagcgccct agcgcccgct cctttcgctt tcttcccttc 4620
ctttctcgcc acgttcgccg gctttccccg tcaagctcta aatcgggggc tccctttagg 4680
gttccgattt agtgctttac ggcacctcga ccccaaaaaa cttgattagg gtgatggttc 4740
acgtagtggg ccatcgccct gatagacggt ttttcgccct ttgacgttgg agtccacgtt 4800
ctttaatagt ggactcttgt tccaaactgg aacaacactc aaccctatct cggtctattc 4860
ttttgattta taagggattt tgccgatttc ggcctattgg ttaaaaaatg agctgattta 4920
acaaaaattt aacgcgaatt ttaacaaaat attaacgttt acaatttaaa tatttgctta 4980

-continued

```
tacaatcttc ctgtttttgg ggcttttctg attatcaacc ggggtacata tgattgacat   5040
gctagtttta cgattaccgt tcatcgattc tcttgtttgc tccagactct caggcaatga   5100
cctgatagcc tttgtagaga cctctcaaaa atagctaccc tctccggcat gaatttatca   5160
gctagaacgg ttgaatatca tattgatggt gatttgactg tctccggcct ttctcacccg   5220
tttgaatctt tacctacaca ttactcaggc attgcattta aaatatatga gggttctaaa   5280
aatttttatc cttgcgttga aataaaggct tctcccgcaa aagtattaca gggtcataat   5340
gtttttggta caaccgattt agctttatgc tctgaggctt tattgcttaa ttttgctaat   5400
tctttgcctt gcctgtatga tttattggat gttggaatcg cctgatgcgg tattttctcc   5460
ttacgcatct gtgcggtatt tcacaccgca tatggtgcac tctcagtaca atctgctctg   5520
atgccgcata gttaagccag ccccgacacc cgccaacacc cgctgacgcg ccctgacggg   5580
cttgtctgct cccggcatcc gcttacagac aagctgtgac cgtctccggg agctgcatgt   5640
gtcagaggtt ttcaccgtca tcaccgaaac gcgcgagacg aaagggcctc gtgatacgcc   5700
tatttttata ggttaatgtc atgataataa tggtttctta gacgtcaggt ggcacttttc   5760
ggggaaatgt gcgcggaacc cctatttgtt tatttttcta aatacattca aatatgtatc   5820
cgctcatgag acaataaccc tgataaatgc ttcaataata ttgaaaaagg aagagtatga   5880
gtattcaaca tttccgtgtc gcccttattc cctttttttgc ggcattttgc cttcctgttt   5940
ttgctcaccc agaaacgctg gtgaaagtaa aagatgctga agatcagttg ggtgcacgag   6000
tgggttacat cgaactggat ctcaacagcg gtaagatcct tgagagtttt cgccccgaag   6060
aacgttttcc aatgatgagc acttttaaag ttctgctatg tggcgcggta ttatcccgta   6120
ttgacgccgg gcaagagcaa ctcggtcgcc gcatacacta ttctcagaat gacttggttg   6180
agtactcacc agtcacagaa aagcatctta cggatggcat gacagtaaga gaattatgca   6240
gtgctgccat aaccatgagt gataacactg cggccaactt acttctgaca acgatcggag   6300
gaccgaagga gctaaccgct tttttgcaca acatggggga tcatgtaact cgccttgatc   6360
gttgggaacc ggagctgaat gaagccatac caaacgacga gcgtgacacc acgatgcctg   6420
tagcaatggc aacaacgttg cgcaaactat taactggcga actacttact ctagcttccc   6480
ggcaacaatt aatagactgg atggaggcgg ataaagttgc aggaccactt ctgcgctcgg   6540
cccttccggc tggctggttt attgctgata aatctggagc cggtgagcgt gggtctcgcg   6600
gtatcattgc agcactgggg ccagatggta agccctcccg tatcgtagtt atctacacga   6660
cggggagtca ggcaactatg gatgaacgaa atagacagat cgctgagata ggtgcctcac   6720
tgattaagca ttggtaactg tcagaccaag tttactcata tatactttag attgatttaa   6780
aacttcattt ttaatttaaa aggatctagg tgaagatcct ttttgataat ctcatgacca   6840
aaatccctta acgtgagttt tcgttccact gagcgtcaga ccccgtagaa aagatcaaag   6900
gatcttcttg agatcctttt tttctgcgcg taatctgctg cttgcaaaca aaaaaaccac   6960
cgctaccagc ggtggtttgt ttgccggatc aagagctacc aactcttttt ccgaaggtaa   7020
ctggcttcag cagagcgcag ataccaaata ctgtccttct agtgtagccg tagttaggcc   7080
accacttcaa gaactctgta gcaccgccta catacctcgc tctgctaatc ctgttaccag   7140
tggctgctgc cagtggcgat aagtcgtgtc ttaccgggtt ggactcaaga cgatagttac   7200
cggataaggc gcagcggtcg ggctgaacgg ggggttcgtg cacacagccc agcttggagc   7260
gaacgaccta caccgaactg agatacctac agcgtgagct atgagaaagc gccacgcttc   7320
```

ccgaagggag aaaggcggac aggtatccgg taagcggcag ggtcggaaca ggagagcgca 7380
cgagggagct tccaggggga aacgcctggt atctttatag tcctgtcggg tttcgccacc 7440
tctgacttga gcgtcgattt ttgtgatgct cgtcaggggg gcggagccta tggaaaaacg 7500
ccagcaacgc ggccttttta cggttcctgg ccttttgctg gccttttgct cacatgttct 7560
ttcctgcgtt atcccctgat tctgtggata accgtattac cgcctttgag tgagctgata 7620
ccgctcgccg cagccgaacg accgagcgca gcgagtcagt gagcgaggaa gcggaagagc 7680
gcccaatacg caaaccgcct ctccccgcgc gttggccgat tcattaatg 7729

<210> SEQ ID NO 21
<211> LENGTH: 8285
<212> TYPE: DNA
<213> ORGANISM: Artificial
<220> FEATURE:
<223> OTHER INFORMATION: AAV donor template

<400> SEQUENCE: 21
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgc ctacatacat acctgaataa gaaaaaaaaa 180
tacctttgct gagatgaaac acacatgatt tatttcaaat aggtacagag aagtagatac 240
tgaagtaagg attaagtatt atattatatt acataacatt aatctattcc tgcactgaaa 300
ccgttgcttt atatgatttt ttttttcact acactaatga gaacttaaga gataatggcc 360
taaaaccaca gagagtattt tcaaagataa gtatagcaca atgcttacta aatgagacta 420
agacttgtcc catcgaaaat cctggaccta tgcctaaaac acgtgtcaca atccccgaac 480
ttttcaaaaa ttggtacatg ctttaacttt aatctccagg cctcactgga gctagagaca 540
agaaggtaaa aaaaggctga caaaagaagt cctggtatct tctatggtgg gagaaggaaa 600
ctagctaaag ggaagaataa attagagaaa aattggaatg attgaatcgg aacaaggcaa 660
aggctataaa aaaattaagc agcagtatcc tcttgggggc cccttcccca cactatctca 720
atgcaaatat ctgtctgaaa cggtccctgg ctaaactcca cccatgggtt ggccagtctt 780
gccttgacgc tagcgtaaat acacttgcaa aggaggatgt ttttagtagc aatttgtact 840
gatggtatgg ggccaagaga tatatcttag agggagggct gagggtttga agtccaactc 900
ctaagccagt gccagaagag ccaaggacag gtacggctgt catcacttag acctcaccct 960
gtggagccac accctagggt tggccaatct actcccagga gcagggaggg caggagccag 1020
ggctgggcat aaaagtcagg gcagagccat ctattgctta catttgcttc tgacacaact 1080
gtgttcacta gcaacctcaa acagacacca tggtgcacct gactcctgag gagaagtctg 1140
ccgttactgc cctgtggggc aaggtgaacg tggatgaagt tggtggtgag gccctgggca 1200
ggttggtatc aaggttacaa gacaggttta aggagaccaa tagaaactgg gcatgtggag 1260
acagagaaga ctcttgggtt tctgataggc actgactctc tctgcctatt ggtctatttt 1320
cccaccctta ggctgctggt ggtctaccct tggacccaga ggttctttga gtcctttggg 1380
gatctgtcca ctcctgatgc tgttatgggc aaccctaagg tgaaggctca tggcaagaaa 1440
gtgctcggtg cctttagtga tggcctggct cacctggaca acctcaaggg cacctttgcc 1500
cagctgagtg agctgcactg tgacaagctg cacgtggatc ctgagaactt cagggtgagt 1560
ctatgggacc cttgatgttt tctttcccct tcttttctat ggttaagttc atgtcatagg 1620
aaggggagaa gtaacagggt acacatattg accaaatcag ggtaattttg catttgtaat 1680
tttaaaaaat gctttcttct tttaatatac ttttttgttt atcttatttc taatactttc 1740
cctaatctct ttctttcagg gcaataatga tacaatgtat catgcctctt tgcaccattc 1800
taaagaataa cagtgataat ttctgggtta aggcaatagc aatatttctg catataaata 1860
tttctgcata taaattgtaa ctgatgtaag aggtttcata ttgctaatag cagctacaat 1920
ccagctacca ttctgctttt attttatggt tgggataagg ctggattatt ctgagtccaa 1980
gctaggccct tttgctaatc atgttcatac ctcttatctt cctcccacag ctcctgggca 2040
acgtgctggt ctgtgtgctg gcccatcact ttggcaaaga attcacccca ccagtgcagg 2100
ctgcctatca gaaagtggtg gctggtgtgg ctaatgccct ggcccacaag tatcactaag 2160
ctcgctttct tgctgtccaa tttctattaa aggttccttt gttccctaag tccaactact 2220
aaactggggg atattatgaa gggccttgag catctggatt ctgcctaata aaaaacattt 2280
attttcattg caatgatgta tttaaattat ttctgaatat tttactaaaa agggaatgtg 2340
ggaggttgca gtgctagtct cccggaacta tcactctttc acagtctgct ttggaaggac 2400
tgggcttagt atgaaaagtt aggactgaga agaatttgaa agggggcttt ttgtagcttg 2460
atattcacta ctgtcttatt accctatcat aggcccaccc caaatggaag tcccattctt 2520
cctcaggatg tttaagatta gcattcagga agagatcaga ggtctgctgg ctcccttatc 2580
atgtccctta tggtgcttct ggctctgcac cgcggccacg gggttggggt tgcgcctttt 2640
ccaaggcagc cctgggtttg cgcagggacg cggctgctct gggcgtggtt ccgggaaacg 2700
cagcggcgcc gaccctgggt ctcgcacatt cttcacgtcc gttcgcagcg tcacccggat 2760
cttcgccgct acccttgtgg gccccccggc gacgcttcct gctccgcccc taagtcggga 2820
aggttccttg cggttcgcgg cgtgccggac gtgacaaacg gaagccgcac gtctcactag 2880
taccctcgca gacggacagc gccagggagc aatggcagcg cgccgaccgc gatgggctgt 2940
ggccaatagc ggctgctcag cggggcgcgc cgagagcagc ggccgggaag gggcggtgcg 3000
ggaggcgggg tgtggggcgg tagtgtgggc cctgttcctg cccgcgcggt gttccgcatt 3060
ctgcaagcct ccggagcgca cgtcggcagt cggctccctc gttgaccgaa tcaccgacct 3120
ctctccccag cggccgcgcc gccaccatgg acaaggattg tgaaatgaaa cgcaccacac 3180
tggacagccc tttggggaag ctggagctgt ctggttgtga gcagggtctg cacgaaataa 3240
agctcctggg caaggggacg tctgcagctg atgccgtgga ggtcccagcc cccgctgcgg 3300
ttctcggagg tccggagccc ctgatgcagt gcacagcctg gctgaatgcc tatttccacc 3360
agcccgaggc tatcgaagag ttccccgtgc cggctcttca ccatcccgtt ttccagcaag 3420
agtcgttcac cagacaggtg ttatggaagc tgctgaaggt tgtgaaattc ggagaagtga 3480
tttcttacca gcaattagca gccctggcag gcaaccccaa agccgcgcga gcagtgggag 3540
gagcaatgag aggcaatcct gtcaaaatcc tcatcccgtg ccacagagtg gtctgcagca 3600
gcggagccgt gggcaactac tccggaggac tggccgtgaa ggaatggctt ctggcccatg 3660
aaggccaccg gttggggaag ccaggcttgg gagggagctc aggtctggca ggggcctggc 3720
tcaagggagc gggagctacc tcgggctccc cgcctgctgg ccgaaactaa gctttatttg 3780
tgaaatttgt gatgctattg ctttatttgt aaccattata agctgcaata aacaagttaa 3840
caacaacaat tgcattcatt ttatgtttca ggttcagggg gagatgtggg aggtttttta 3900
aagccctgca ggcaatagcc ttgacaaggc aaccttgacc aatagtctta gagtatcagg 3960
tgaggccagg ggccggcggc tggctaggga tgaagaataa aaggaagcac cctccagcag 4020

-continued ttccacacac tcgcttctgg aacggctgag attatcaata agctcctagt ccagacgcca 4080
tgggtcattt cacagaggag gacaaggcta ctatcacaag cctgtggggc aaggtgaatg 4140
tggaagatgc tggaggagaa accctgggaa ggtaggctct ggtgaccagg acaaggaagg 4200
gaaggaagga ccctgtgcct ggcaaaagtc caggccactt ctcaggattt gtggcacttt 4260
ctgactgtca aactgctctt gttcaatctc acaggctcct ggttgtctac ccatggaccc 4320
agaggttctt tgacagcttt ggcaacctgt cctctgcctc tgccatcatg ggcaacccca 4380
aggtcaaggc acacggcaag aaggtgctga cttccttggg agatgccata aagaacctgg 4440
atgatctcaa gggcaccttt gcccagctga gtgagctgca ctgtgacaag ctgcatgtgg 4500
atcctgagaa cttcagggtg agtccaggag tttcagcagt ttcagagttc agtctcaagg 4560
cgtcgacagg aacccctagt gatggagttg gccactccct ctctgcgcgc tcgctcgctc 4620
actgaggccg ggcgaccaaa ggtcgcccga cgcccgggct ttgcccgggc ggcctcagtg 4680
agcgagcgag cgcgcagctg gcgtaatagc gaagaggccc gcaccgatcg cccttcccaa 4740
cagttgcgca gcctgaatgg cgaatggcga ttccgttgca atggctggcg gtaatattgt 4800
tctggatatt accagcaagg ccgatagttt gagttcttct actcaggcaa gtgatgttat 4860
tactaatcaa agaagtattg cgacaacggt taatttgcgt gatggacaga ctcttttact 4920
cggtggcctc actgattata aaaacacttc tcaggattct ggcgtaccgt tcctgtctaa 4980
aatcccttta atcggcctcc tgtttagctc ccgctctgat tctaacgagg aaagcacgtt 5040
atacgtgctc gtcaaagcaa ccatagtacg cgccctgtag cggcgcatta agcgcggcgg 5100
gtgtggtggt tacgcgcagc gtgaccgcta cacttgccag cgccctagcg cccgctcctt 5160
tcgctttctt cccttccttt ctcgccacgt tcgccggctt tccccgtcaa gctctaaatc 5220
gggggctccc tttagggttc cgatttagtg ctttacggca cctcgacccc aaaaaacttg 5280
attagggtga tggttcacgt agtgggccat cgccctgata gacggttttt cgccctttga 5340
cgttggagtc cacgttcttt aatagtggac tcttgttcca aactggaaca acactcaacc 5400
ctatctcggt ctattctttt gatttataag ggattttgcc gatttcggcc tattggttaa 5460
aaaatgagct gatttaacaa aaatttaacg cgaattttaa caaaatatta acgtttacaa 5520
tttaaatatt tgcttataca atcttcctgt ttttggggct tttctgatta tcaaccgggg 5580
tacatatgat tgacatgcta gttttacgat taccgttcat cgattctctt gtttgctcca 5640
gactctcagg caatgacctg atagcctttg tagagacctc tcaaaaatag ctaccctctc 5700
cggcatgaat ttatcagcta gaacggttga atatcatatt gatggtgatt tgactgtctc 5760
cggcctttct cacccgtttg aatctttacc tacacattac tcaggcattg catttaaaat 5820
atatgagggt tctaaaaatt tttatccttg cgttgaaata aaggcttctc ccgcaaaagt 5880
attacagggt cataatgttt ttggtacaac cgatttagct ttatgctctg aggctttatt 5940
gcttaatttt gctaattctt tgccttgcct gtatgattta ttggatgttg gaatcgcctg 6000
atgcggtatt ttctccttac gcatctgtgc ggtatttcac accgcatatg gtgcactctc 6060
agtacaatct gctctgatgc cgcatagtta agccagcccc gacacccgcc aacacccgct 6120
gacgcgccct gacgggcttg tctgctcccg gcatccgctt acagacaagc tgtgaccgtc 6180
tccgggagct gcatgtgtca gaggttttca ccgtcatcac cgaaacgcgc gagacgaaag 6240
ggcctcgtga tacgcctatt tttataggtt aatgtcatga taataatggt ttcttagacg 6300
tcaggtggca cttttcgggg aaatgtgcgc ggaaccccta tttgtttatt tttctaaata 6360
cattcaaata tgtatccgct catgagacaa taaccctgat aaatgcttca ataatattga 6420
aaaaggaaga gtatgagtat tcaacatttc cgtgtcgccc ttattccctt ttttgcggca 6480
ttttgccttc ctgtttttgc tcacccagaa acgctggtga aagtaaaaga tgctgaagat 6540
cagttgggtg cacgagtggg ttacatcgaa ctggatctca acagcggtaa gatccttgag 6600
agttttcgcc ccgaagaacg ttttccaatg atgagcactt ttaaagttct gctatgtggc 6660
gcggtattat cccgtattga cgccgggcaa gagcaactcg gtcgccgcat acactattct 6720
cagaatgact tggttgagta ctcaccagtc acagaaaagc atcttacgga tggcatgaca 6780
gtaagagaat tatgcagtgc tgccataacc atgagtgata acactgcggc caacttactt 6840
ctgacaacga tcggaggacc gaaggagcta accgcttttt tgcacaacat gggggatcat 6900
gtaactcgcc ttgatcgttg ggaaccggag ctgaatgaag ccataccaaa cgacgagcgt 6960
gacaccacga tgcctgtagc aatggcaaca acgttgcgca aactattaac tggcgaacta 7020
cttactctag cttcccggca acaattaata gactggatgg aggcggataa agttgcagga 7080
ccacttctgc gctcggccct tccggctggc tggtttattg ctgataaatc tggagccggt 7140
gagcgtgggt ctcgcggtat cattgcagca ctggggccag atggtaagcc ctcccgtatc 7200
gtagttatct acacgacggg gagtcaggca actatggatg aacgaaatag acagatcgct 7260
gagataggtg cctcactgat taagcattgg taactgtcag accaagttta ctcatatata 7320
ctttagattg atttaaaact tcatttttaa tttaaaagga tctaggtgaa gatccttttt 7380
gataatctca tgaccaaaat cccttaacgt gagttttcgt tccactgagc gtcagacccc 7440
gtagaaaaga tcaaaggatc ttcttgagat cctttttttc tgcgcgtaat ctgctgcttg 7500
caaacaaaaa aaccaccgct accagcggtg gtttgtttgc cggatcaaga gctaccaact 7560
ctttttccga aggtaactgg cttcagcaga gcgcagatac caaatactgt ccttctagtg 7620
tagccgtagt taggccacca cttcaagaac tctgtagcac cgcctacata cctcgctctg 7680
ctaatcctgt taccagtggc tgctgccagt ggcgataagt cgtgtcttac cgggttggac 7740
tcaagacgat agttaccgga taaggcgcag cggtcgggct gaacgggggg ttcgtgcaca 7800
cagcccagct tggagcgaac gacctacacc gaactgagat acctacagcg tgagctatga 7860
gaaagcgcca cgcttcccga agggagaaag gcggacaggt atccggtaag cggcagggtc 7920
ggaacaggag agcgcacgag ggagcttcca gggggaaacg cctggtatct ttatagtcct 7980
gtcgggtttc gccacctctg acttgagcgt cgatttttgt gatgctcgtc aggggggcgg 8040
agcctatgga aaaacgccag caacgcggcc tttttacggt tcctggcctt ttgctggcct 8100
tttgctcaca tgttctttcc tgcgttatcc cctgattctg tggataaccg tattaccgcc 8160
tttgagtgag ctgataccgc tcgccgcagc cgaacgaccg agcgcagcga gtcagtgagc 8220
gaggaagcgg aagagcgccc aatacgcaaa ccgcctctcc ccgcgcgttg gccgattcat 8280
taatg 8285

<210> SEQ ID NO 22
<211> LENGTH: 7095
<212> TYPE: DNA
<213> ORGANISM: Artificial
<220> FEATURE:
<223> OTHER INFORMATION: AAV donor template

<400> SEQUENCE: 22
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120

-continued

```
actaggggtt ccttgtagtt aatgattaac ccgccatgct acttatctac acgcgtagat    180
ctagccagtg tttaccattg cagaatgtac atgcgactga aagggtgagg aaacctggga    240
aatgtcagtt cctcaaatac agagaacact gagggaagga tgagaaataa atgtgaaagc    300
agacatgaat ggtaattgac agaaggaaac taggatgtgt ccagtaaatg aataattaca    360
gtgtgcagtg attattgcaa tgattaatgt atgataagat aatatgaaaa cacagaattc    420
aaacagcagt gaactgagat tagaattgtg gagagcactg gcatttaaga atgtcacact    480
tagaatgtgt ctctaggcat tgttctgtgc atatatcatc tcaatattca ttatctgaaa    540
attatgaatt aggtacaaag ctcaaataat ttatttttc aggttagcaa gaactttttt    600
ttttttttc tgagatagag cattgctatg gttgcccagg ctggagtgca atggcatgat    660
ccaggctcac tgcaacatct gcctcccagg ttcaagcgat tctcctgcct cagcctccca    720
agtagctggc actacaggca tgtgccacca ccatgcctgg ctaattttct atttttagta    780
gaccgcggga acagagaaac aggagaatat gggccaaaca ggatatctgt ggtaagcagt    840
tcctgccccg gctcagggcc aagaacagtt ggaacagcag aatatgggcc aaacaggata    900
tctgtggtaa gcagttcctg ccccggctca gggccaagaa cagatggtcc ccagatgcgg    960
tcccgccctc agcagtttct agagaaccat cagatgtttc cagggtgccc caaggacctg   1020
aaatgaccct gtgccttatt tgaactaacc aatcagttcg cttctcgctt ctgttcgcgc   1080
gcttctgctc cccgagctct atataagcag agctcgttta gtgaaccgtc agatcgcctg   1140
gagacgccat ccacgctgtt ttgacttcca tagaaggcgg ccgcgccgcc accatggtga   1200
gcaagggcga ggagctgttc accggggtgg tgcccatcct ggtcgagctg gacggcgacg   1260
taaacggcca caagttcagc gtgtccggcg agggcgaggg cgatgccacc tacggcaagc   1320
tgaccctgaa gttcatctgc accaccggca agctgcccgt gccctggccc accctcgtga   1380
ccaccctgac ctacggcgtg cagtgcttca gccgctaccc cgaccacatg aagcagcacg   1440
acttcttcaa gtccgccatg cccgaaggct acgtccagga gcgcaccatc ttcttcaagg   1500
acgacggcaa ctacaagacc cgcgccgagg tgaagttcga gggcgacacc ctggtgaacc   1560
gcatcgagct gaagggcatc gacttcaagg aggacggcaa catcctgggg cacaagctgg   1620
agtacaacta caacagccac aacgtctata tcatggccga caagcagaag aacggcatca   1680
aggtgaactt caagatccgc cacaacatcg aggacggcag cgtgcagctc gccgaccact   1740
accagcagaa cacccccatc ggcgacggcc ccgtgctgct gcccgacaac cactacctga   1800
gcacccagtc cgccctgagc aaagacccca acgagaagcg cgatcacatg gtcctgctgg   1860
agttcgtgac cgccgccggg atcactctcg gcatggacga gctgtacaag taacctgcag   1920
ggagcatctt accgccattt attcccatat ttgttctgtt tttcttgatt tgggtataca   1980
tttaaatgtt aataaaacaa aatggtgggg caatcattta catttttagg gatatgtaat   2040
tactagttca ggtgtattgc cacaagacaa acatgttaag aaactttccc gttatttacg   2100
ctctgttcct gttaatcaac ctctggatta caaaatttgt gaaagattga ctgatattct   2160
taactatgtt gctcctttta cgctgtgtgg atatgctgct ttatagcctc tgtatctagc   2220
tattgcttcc cgtacggctt tcgttttctc ctccttgtat aaatcctggt tgctgtctct   2280
tttagaggag ttgtggcccg ttgtccgtca acgtggcgtg gtgtgctctg tgtttgctga   2340
cgcaaccccc actggctggg gcattgccac cacctgtcaa ctcctttctg ggactttcgc   2400
tttccccctc ccgatcgcca cggcagaact catcgccgcc tgccttgccc gctgctggac   2460
aggggctagg ttgctgggca ctgataattc cgtggtgttg tctgtgcctt ctagttgcca   2520
```

-continued

```
gccatctgtt gtttgcccct cccccgtgcc ttccttgacc ctggaaggtg ccactcccac   2580
tgtcctttcc taataaaatg aggaaattgc atcgcattgt ctgagtaggt gtcattctat   2640
tctggggggt ggggtggggc aggacagcaa gggggaggat tgggaagaca atagcaggca   2700
tgctggggat gcggtgggct ctatggcagg gcaagttaag ggaatagtgg aatgaaggtt   2760
catttttcat tctcacaaac taatgaaacc ctgcttatct taaaccaacc tgctcactgg   2820
agcagggagg acaggaccag cataaaaggc agggcagagt cgactgttgc ttacactttc   2880
ttctgacata acagtgttca ctagcaacct caaacagaca ccatggtgca tctgactcct   2940
gaggagaaga ctgctgtcaa tgccctgtgg ggcaaagtga acgtggatgc agttggtggt   3000
gaggccctgg gcaggttggt atcaaggtta taagagaggc tcaaggaggc aaatggaaac   3060
tgggcatgtg tagacagaga agactcttgg gtttctgata ggcactgact ctctgtccct   3120
tgggctgttt tcctaccctc agattactgg tggtctaccc ttggacccag aggttctttg   3180
agtcctttgg ggatctgtcc tctcctgatg ctgttatggg caaccctaag gtgaaggctc   3240
atggcaagaa ggtgctaggt gcctttagtg atggcctggc tcacctggac aacctcaagg   3300
gcactttttc tcagctgagt gagctgcctc gaggtcgacg tagataagta gcatggcggg   3360
ttaatcatta actacaagga acccctagtg atggagttgg ccactccctc tctgcgcgct   3420
cgctcgctca ctgaggccgg gcgaccaaag gtcgcccgac gcccgggctt tgcccgggcg   3480
gcctcagtga gcgagcgagc gcgccagctg gcgtaatagc gaagaggccc gcaccgatcg   3540
cccttcccaa cagttgcgca gcctgaatgg cgaatggcga ttccgttgca atggctggcg   3600
gtaatattgt tctggatatt accagcaagg ccgatagttt gagttcttct actcaggcaa   3660
gtgatgttat tactaatcaa agaagtattg cgacaacggt taatttgcgt gatggacaga   3720
ctcttttact cggtggcctc actgattata aaaacacttc tcaggattct ggcgtaccgt   3780
tcctgtctaa aatcccttta atcggcctcc tgtttagctc ccgctctgat tctaacgagg   3840
aaagcacgtt atacgtgctc gtcaaagcaa ccatagtacg cgccctgtag cggcgcatta   3900
agcgcggcgg gtgtggtggt tacgcgcagc gtgaccgcta cacttgccag cgccctagcg   3960
cccgctcctt tcgctttctt cccttccttt ctcgccacgt tcgccggctt tccccgtcaa   4020
gctctaaatc gggggctccc tttagggttc cgatttagtg ctttacggca cctcgacccc   4080
aaaaaacttg attagggtga tggttcacgt agtgggccat cgccctgata gacggttttt   4140
cgccctttga cgttggagtc cacgttcttt aatagtggac tcttgttcca aactggaaca   4200
acactcaacc ctatctcggt ctattctttt gatttataag ggattttgcc gatttcggcc   4260
tattggttaa aaaatgagct gatttaacaa aaatttaacg cgaattttaa caaaatatta   4320
acgtttacaa tttaaatatt tgcttataca atcttcctgt ttttggggct tttctgatta   4380
tcaaccgggg tacatatgat tgacatgcta gttttacgat taccgttcat cgattctctt   4440
gtttgctcca gactctcagg caatgacctg atagcctttg tagagacctc tcaaaaatag   4500
ctaccctctc cggcatgaat ttatcagcta gaacggttga atatcatatt gatggtgatt   4560
tgactgtctc cggcctttct cacccgtttg aatctttacc tacacattac tcaggcattg   4620
catttaaaat atatgagggt tctaaaaatt tttatccttg cgttgaaata aaggcttctc   4680
ccgcaaaagt attacagggt cataatgttt ttggtacaac cgatttagct ttatgctctg   4740
aggctttatt gcttaatttt gctaattctt tgccttgcct gtatgattta ttggatgttg   4800
gaatcgcctg atgcggtatt ttctccttac gcatctgtgc ggtatttcac accgcatatg   4860
```

-continued

```
gtgcactctc agtacaatct gctctgatgc cgcatagtta agccagcccc gacacccgcc   4920
aacacccgct gacgcgccct gacgggcttg tctgctcccg gcatccgctt acagacaagc   4980
tgtgaccgtc tccgggagct gcatgtgtca gaggttttca ccgtcatcac cgaaacgcgc   5040
gagacgaaag ggcctcgtga tacgcctatt tttataggtt aatgtcatga taataatggt   5100
ttcttagacg tcaggtggca cttttcgggg aaatgtgcgc ggaaccccta tttgtttatt   5160
tttctaaata cattcaaata tgtatccgct catgagacaa taaccctgat aaatgcttca   5220
ataatattga aaaaggaaga gtatgagtat tcaacatttc cgtgtcgccc ttattccctt   5280
ttttgcggca ttttgccttc ctgtttttgc tcacccagaa acgctggtga aagtaaaaga   5340
tgctgaagat cagttgggtg cacgagtggg ttacatcgaa ctggatctca acagcggtaa   5400
gatccttgag agttttcgcc ccgaagaacg ttttccaatg atgagcactt ttaaagttct   5460
gctatgtggc gcggtattat cccgtattga cgccgggcaa gagcaactcg gtcgccgcat   5520
acactattct cagaatgact tggttgagta ctcaccagtc acagaaaagc atcttacgga   5580
tggcatgaca gtaagagaat tatgcagtgc tgccataacc atgagtgata acactgcggc   5640
caacttactt ctgacaacga tcggaggacc gaaggagcta accgcttttt tgcacaacat   5700
gggggatcat gtaactcgcc ttgatcgttg ggaaccggag ctgaatgaag ccataccaaa   5760
cgacgagcgt gacaccacga tgcctgtagc aatggcaaca acgttgcgca aactattaac   5820
tggcgaacta cttactctag cttcccggca acaattaata gactggatgg aggcggataa   5880
agttgcagga ccacttctgc gctcggccct tccggctggc tggtttattg ctgataaatc   5940
tggagccggt gagcgtgggt ctcgcggtat cattgcagca ctggggccag atggtaagcc   6000
ctcccgtatc gtagttatct acacgacggg gagtcaggca actatggatg aacgaaatag   6060
acagatcgct gagataggtg cctcactgat taagcattgg taactgtcag accaagttta   6120
ctcatatata ctttagattg atttaaaact tcatttttaa tttaaaagga tctaggtgaa   6180
gatccttttt gataatctca tgaccaaaat cccttaacgt gagttttcgt tccactgagc   6240
gtcagacccc gtagaaaaga tcaaaggatc ttcttgagat cctttttttc tgcgcgtaat   6300
ctgctgcttg caaacaaaaa aaccaccgct accagcggtg gtttgtttgc cggatcaaga   6360
gctaccaact ctttttccga aggtaactgg cttcagcaga gcgcagatac caaatactgt   6420
ccttctagtg tagccgtagt taggccacca cttcaagaac tctgtagcac cgcctacata   6480
cctcgctctg ctaatcctgt taccagtggc tgctgccagt ggcgataagt cgtgtcttac   6540
cgggttggac tcaagacgat agttaccgga taaggcgcag cggtcgggct gaacgggggg   6600
ttcgtgcaca cagcccagct tggagcgaac gacctacacc gaactgagat acctacagcg   6660
tgagctatga gaaagcgcca cgcttcccga agggagaaag gcggacaggt atccggtaag   6720
cggcagggtc ggaacaggag agcgcacgag ggagcttcca gggggaaacg cctggtatct   6780
ttatagtcct gtcgggtttc gccacctctg acttgagcgt cgatttttgt gatgctcgtc   6840
aggggggcgg agcctatgga aaaacgccag caacgcggcc tttttacggt tcctggcctt   6900
ttgctggcct tttgctcaca tgttctttcc tgcgttatcc cctgattctg tggataaccg   6960
tattaccgcc tttgagtgag ctgataccgc tcgccgcagc cgaacgaccg agcgcagcga   7020
gtcagtgagc gaggaagcgg aagagcgccc aatacgcaaa ccgcctctcc ccgcgcgttg   7080
gccgattcat taatg                                                    7095
```

<210> SEQ ID NO 23
<211> LENGTH: 7809

<212> TYPE: DNA
<213> ORGANISM: Artificial
<220> FEATURE:
<223> OTHER INFORMATION: AAV donor template

<400> SEQUENCE: 23
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctagccagtg tttaccattg cagaatgtac atgcgactga aagggtgagg aaacctggga 240
aatgtcagtt cctcaaatac agagaacact gagggaagga tgagaaataa atgtgaaagc 300
agacatgaat ggtaattgac agaaggaaac taggatgtgt ccagtaaatg aataattaca 360
gtgtgcagtg attattgcaa tgattaatgt atgataagat aatatgaaaa cacagaattc 420
aaacagcagt gaactgagat tagaattgtg gagagcactg gcatttaaga atgtcacact 480
tagaatgtgt ctctaggcat tgttctgtgc atatatcatc tcaatattca ttatctgaaa 540
attatgaatt aggtacaaag ctcaaataat ttattttttc aggttagcaa gaactttttt 600
tttttttttc tgagatagag cattgctatg gttgcccagg ctggagtgca atggcatgat 660
ccaggctcac tgcaacatct gcctcccagg ttcaagcgat tctcctgcct cagcctccca 720
agtagctggc actacaggca tgtgccacca ccatgcctgg ctaattttct atttttagta 780
gacgagatcg agaccatcct ggctaacaca gtgaaacccc gtctctacta aaaaaataca 840
aaaaattagc cgggcttggt ggcgggtgcc tgtagtccca gctactatgg aggctgaggc 900
gggagaatgg cgtgaacgcg gggggcggag cttgcagtga gcagagatca ggggccactg 960
cactccagcc tgggcgacag agagagactc tgtctcaaaa aaaagaaaaa aaaaatttag 1020
tagactagct aaaaaaatcc agagatagtt attgatgcat atgtaaaagt cttccaatat 1080
ttacaagtac aatgaaaaaa aaataacctt gaattaagtg tagaactcat tgacaatgtt 1140
tcaaaggatg tgagggataa actaaaattt gggcagtaca tgctgttcct gtgtacttgg 1200
aacagaggga gaaaatctgg gctggaaata ttgttatagg agttagcaca tgaaggtgac 1260
aactaaatta tttggagtag atggagtcac cagcacatgt gaatagtttt agaatgaaat 1320
gacccaagat agaactttgg agagccccca aatttaaata aaatcagtat aagagaagag 1380
gaagaaacca aatggtatac tagtctaaat tgtttcttag tgacaaaaga ataacctgaa 1440
tattagatta gctgcctata tgctctctga atcaatttca ttcaacatgc aacagtccgc 1500
gggaacagag aaacaggaga atatgggcca aacaggatat ctgtggtaag cagttcctgc 1560
cccggctcag ggccaagaac agttggaaca gcagaatatg ggccaaacag gatatctgtg 1620
gtaagcagtt cctgccccgg ctcagggcca agaacagatg gtccccagat gcggtcccgc 1680
cctcagcagt ttctagagaa ccatcagatg tttccagggt gccccaagga cctgaaatga 1740
ccctgtgcct tatttgaact aaccaatcag ttcgcttctc gcttctgttc gcgcgcttct 1800
gctccccgag ctctatataa gcagagctcg tttagtgaac cgtcagatcg cctggagacg 1860
ccatccacgc tgttttgact tccatagaag gcggccgcgc cgccaccatg gtgagcaagg 1920
gcgaggagct gttcaccggg gtggtgccca tcctggtcga gctggacggc gacgtaaacg 1980
gccacaagtt cagcgtgtcc ggcgagggcg agggcgatgc cacctacggc aagctgaccc 2040
tgaagttcat ctgcaccacc ggcaagctgc ccgtgccctg gcccaccctc gtgaccaccc 2100
tgacctacgg cgtgcagtgc ttcagccgct accccgacca catgaagcag cacgacttct 2160
tcaagtccgc catgcccgaa ggctacgtcc aggagcgcac catcttcttc aaggacgacg 2220
gcaactacaa gacccgcgcc gaggtgaagt tcgagggcga caccctggtg aaccgcatcg 2280
agctgaaggg catcgacttc aaggaggacg gcaacatcct ggggcacaag ctggagtaca 2340
actacaacag ccacaacgtc tatatcatgg ccgacaagca gaagaacggc atcaaggtga 2400
acttcaagat ccgccacaac atcgaggacg gcagcgtgca gctcgccgac cactaccagc 2460
agaacacccc catcggcgac ggccccgtgc tgctgcccga caaccactac ctgagcaccc 2520
agtccgccct gagcaaagac cccaacgaga agcgcgatca catggtcctg ctggagttcg 2580
tgaccgccgc cgggatcact ctcggcatgg acgagctgta caagtaacct gcagggagca 2640
tcttaccgcc atttattccc atatttgttc tgtttttctt gatttgggta tacatttaaa 2700
tgttaataaa acaaaatggt ggggcaatca tttacatttt tagggatatg taattactag 2760
ttcaggtgta ttgccacaag acaaacatgt taagaaactt tcccgttatt tacgctctgt 2820
tcctgttaat caacctctgg attacaaaat ttgtgaaaga ttgactgata ttcttaacta 2880
tgttgctcct tttacgctgt gtggatatgc tgctttatag cctctgtatc tagctattgc 2940
ttcccgtacg gctttcgttt tctcctcctt gtataaatcc tggttgctgt ctcttttaga 3000
ggagttgtgg cccgttgtcc gtcaacgtgg cgtggtgtgc tctgtgtttg ctgacgcaac 3060
ccccactggc tggggcattg ccaccacctg tcaactcctt tctgggactt tcgctttccc 3120
cctcccgatc gccacggcag aactcatcgc cgcctgcctt gcccgctgct ggacaggggc 3180
taggttgctg ggcactgata attccgtggt gttgtctgtg ccttctagtt gccagccatc 3240
tgttgtttgc ccctcccccg tgccttcctt gaccctggaa ggtgccactc ccactgtcct 3300
ttcctaataa aatgaggaaa ttgcatcgca ttgtctgagt aggtgtcatt ctattctggg 3360
gggtggggtg gggcaggaca gcaaggggga ggattgggaa gacaatagca ggcatgctgg 3420
ggatgcggtg ggctctatgg cagggcaagt taagggaata gtggaatgaa ggttcatttt 3480
tcattctcac aaactaatga aaccctgctt atcttaaacc aacctgctca ctggagcagg 3540
gaggacagga ccagcataaa aggcagggca gagtcgactg ttgcttacac tttcttctga 3600
cataacagtg ttcactagca acctcaaaca gacaccatgg tgcatctgac tcctgaggag 3660
aagactgctg tcaatgccct gtggggcaaa gtgaacgtgg atgcagttgg tggtgaggcc 3720
ctgggcaggt tggtatcaag gttataagag aggctcaagg aggcaaatgg aaactgggca 3780
tgtgtagaca gagaagactc ttgggtttct gataggcact gactctctgt cccttgggct 3840
gttttcctac cctcagatta ctggtggtct acccttggac ccagaggttc tttgagtcct 3900
ttggggatct gtcctctcct gatgctgtta tgggcaaccc taaggtgaag gctcatggca 3960
agaaggtgct aggtgccttt agtgatggcc tggctcacct ggacaacctc aagggcactt 4020
tttctcagct gagtgagctg cctcgaggtc gacgtagata agtagcatgg cgggttaatc 4080
attaactaca aggaacccct agtgatggag ttggccactc cctctctgcg cgctcgctcg 4140
ctcactgagg ccgggcgacc aaaggtcgcc cgacgcccgg gctttgcccg ggcggcctca 4200
gtgagcgagc gagcgcgcca gctggcgtaa tagcgaagag gcccgcaccg atcgcccttc 4260
ccaacagttg cgcagcctga atggcgaatg gcgattccgt tgcaatggct ggcggtaata 4320
ttgttctgga tattaccagc aaggccgata gtttgagttc ttctactcag gcaagtgatg 4380
ttattactaa tcaaagaagt attgcgacaa cggttaattt gcgtgatgga cagactcttt 4440
tactcggtgg cctcactgat tataaaaaca cttctcagga ttctggcgta ccgttcctgt 4500
ctaaaatccc tttaatcggc ctcctgttta gctcccgctc tgattctaac gaggaaagca 4560

```
cgttatacgt gctcgtcaaa gcaaccatag tacgcgccct gtagcggcgc attaagcgcg   4620
gcgggtgtgg tggttacgcg cagcgtgacc gctacacttg ccagcgccct agcgcccgct   4680
cctttcgctt tcttcccttc ctttctcgcc acgttcgccg gctttccccg tcaagctcta   4740
aatcgggggc tccctttagg gttccgattt agtgctttac ggcacctcga ccccaaaaaa   4800
cttgattagg gtgatggttc acgtagtggg ccatcgccct gatagacggt ttttcgccct   4860
ttgacgttgg agtccacgtt ctttaatagt ggactcttgt tccaaactgg aacaacactc   4920
aaccctatct cggtctattc ttttgattta taagggattt tgccgatttc ggcctattgg   4980
ttaaaaaatg agctgattta acaaaaattt aacgcgaatt ttaacaaaat attaacgttt   5040
acaatttaaa tatttgctta tacaatcttc ctgtttttgg ggcttttctg attatcaacc   5100
ggggtacata tgattgacat gctagtttta cgattaccgt tcatcgattc tcttgtttgc   5160
tccagactct caggcaatga cctgatagcc tttgtagaga cctctcaaaa atagctaccc   5220
tctccggcat gaatttatca gctagaacgg ttgaatatca tattgatggt gatttgactg   5280
tctccggcct ttctcacccg tttgaatctt tacctacaca ttactcaggc attgcattta   5340
aaatatatga gggttctaaa aatttttatc cttgcgttga aataaaggct tctcccgcaa   5400
aagtattaca gggtcataat gtttttggta caaccgattt agctttatgc tctgaggctt   5460
tattgcttaa ttttgctaat tctttgcctt gcctgtatga tttattggat gttggaatcg   5520
cctgatgcgg tattttctcc ttacgcatct gtgcggtatt tcacaccgca tatggtgcac   5580
tctcagtaca atctgctctg atgccgcata gttaagccag ccccgacacc cgccaacacc   5640
cgctgacgcg ccctgacggg cttgtctgct cccggcatcc gcttacagac aagctgtgac   5700
cgtctccggg agctgcatgt gtcagaggtt ttcaccgtca tcaccgaaac gcgcgagacg   5760
aaagggcctc gtgatacgcc tatttttata ggttaatgtc atgataataa tggtttctta   5820
gacgtcaggt ggcacttttc ggggaaatgt gcgcggaacc cctatttgtt tatttttcta   5880
aatacattca aatatgtatc cgctcatgag acaataaccc tgataaatgc ttcaataata   5940
ttgaaaaagg aagagtatga gtattcaaca tttccgtgtc gcccttattc ccttttttgc   6000
ggcattttgc cttcctgttt ttgctcaccc agaaacgctg gtgaaagtaa aagatgctga   6060
agatcagttg ggtgcacgag tgggttacat cgaactggat ctcaacagcg gtaagatcct   6120
tgagagtttt cgccccgaag aacgttttcc aatgatgagc acttttaaag ttctgctatg   6180
tggcgcggta ttatcccgta ttgacgccgg gcaagagcaa ctcggtcgcc gcatacacta   6240
ttctcagaat gacttggttg agtactcacc agtcacagaa aagcatctta cggatggcat   6300
gacagtaaga gaattatgca gtgctgccat aaccatgagt gataacactg cggccaactt   6360
acttctgaca acgatcggag gaccgaagga gctaaccgct tttttgcaca acatggggga   6420
tcatgtaact cgccttgatc gttgggaacc ggagctgaat gaagccatac caaacgacga   6480
gcgtgacacc acgatgcctg tagcaatggc aacaacgttg cgcaaactat taactggcga   6540
actacttact ctagcttccc ggcaacaatt aatagactgg atggaggcgg ataaagttgc   6600
aggaccactt ctgcgctcgg cccttccggc tggctggttt attgctgata aatctggagc   6660
cggtgagcgt gggtctcgcg gtatcattgc agcactgggg ccagatggta agccctcccg   6720
tatcgtagtt atctacacga cggggagtca ggcaactatg gatgaacgaa atagacagat   6780
cgctgagata ggtgcctcac tgattaagca ttggtaactg tcagaccaag tttactcata   6840
tatactttag attgatttaa aacttcattt ttaatttaaa aggatctagg tgaagatcct   6900
```

-continued

```
ttttgataat ctcatgacca aaatccctta acgtgagttt tcgttccact gagcgtcaga   6960
ccccgtagaa aagatcaaag gatcttcttg agatcctttt tttctgcgcg taatctgctg   7020
cttgcaaaca aaaaaaccac cgctaccagc ggtggtttgt ttgccggatc aagagctacc   7080
aactcttttt ccgaaggtaa ctggcttcag cagagcgcag ataccaaata ctgtccttct   7140
agtgtagccg tagttaggcc accacttcaa gaactctgta gcaccgccta catacctcgc   7200
tctgctaatc ctgttaccag tggctgctgc cagtggcgat aagtcgtgtc ttaccgggtt   7260
ggactcaaga cgatagttac cggataaggc gcagcggtcg ggctgaacgg ggggttcgtg   7320
cacacagccc agcttggagc gaacgaccta caccgaactg agatacctac agcgtgagct   7380
atgagaaagc gccacgcttc ccgaagggag aaaggcggac aggtatccgg taagcggcag   7440
ggtcggaaca ggagagcgca cgagggagct tccaggggga aacgcctggt atctttatag   7500
tcctgtcggg tttcgccacc tctgacttga gcgtcgattt ttgtgatgct cgtcaggggg   7560
gcggagccta tggaaaaacg ccagcaacgc ggccttttta cggttcctgg ccttttgctg   7620
gccttttgct cacatgttct ttcctgcgtt atcccctgat tctgtggata accgtattac   7680
cgcctttgag tgagctgata ccgctcgccg cagccgaacg accgagcgca gcgagtcagt   7740
gagcgaggaa gcggaagagc gcccaatacg caaaccgcct ctccccgcgc gttggccgat   7800
tcattaatg                                                           7809
```

<210> SEQ ID NO 24
<211> LENGTH: 6726
<212> TYPE: DNA
<213> ORGANISM: Artificial
<220> FEATURE:
<223> OTHER INFORMATION: AAV donor template

<400> SEQUENCE: 24

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtagat    180
ctacgtactt taggcttgta atgtgtttat atacagtgaa atgtcaagtt ctttctttat    240
atttctttct ttcttttttt tcctcagcct cagagttttc cacatgccct tcctactttc    300
aggaacttct ttctccaaac gtcttctgcc tggctccatc aaatcataaa ggacccactt    360
caaatgccat cactcactac catttcacaa ttcgcacttt ctttctttgt cctttttttt    420
tttagtaaaa caagtttata aaaaattgaa ggaataaatg aatggctact tcataggcag    480
agtagacgca agggctactg gttgccgatt tttattgtta tttttcaata gtatgctaaa    540
caaggggtag attatttatg ctgcccattt ttagaccata aaagataact tcctgatgtt    600
gccatggcat ttttttcctt ttaattttat ttcatttcat tttaatttcg aaggtacatg    660
tgcaggatgt gcaggcttgt tacatgggta aatgtgtgtc tttctggcct tttagccatc    720
tgtatcaatg agcagatata agctttacac aggatcatga aggatgaaag aatttcacca    780
atccgcggga acagagaaac aggagaatat gggccaaaca ggatatctgt ggtaagcagt    840
tcctgccccg gctcagggcc aagaacagtt ggaacagcag aatatgggcc aaacaggata    900
tctgtggtaa gcagttcctg ccccggctca gggccaagaa cagatggtcc ccagatgcgg    960
tcccgccctc agcagtttct agagaaccat cagatgtttc cagggtgccc caaggacctg   1020
aaatgaccct gtgccttatt tgaactaacc aatcagttcg cttctcgctt ctgttcgcgc   1080
gcttctgctc cccgagctct atataagcag agctcgttta gtgaaccgtc agatcgcctg   1140
```

```
gagacgccat ccacgctgtt ttgacttcca tagaaggcgg ccgcgccgcc accatggtga   1200
gcaagggcga ggagctgttc accggggtgg tgcccatcct ggtcgagctg gacggcgacg   1260
taaacggcca caagttcagc gtgtccggcg agggcgaggg cgatgccacc tacggcaagc   1320
tgaccctgaa gttcatctgc accaccggca agctgcccgt gccctggccc accctcgtga   1380
ccaccctgac ctacggcgtg cagtgcttca gccgctaccc cgaccacatg aagcagcacg   1440
acttcttcaa gtccgccatg cccgaaggct acgtccagga gcgcaccatc ttcttcaagg   1500
acgacggcaa ctacaagacc cgcgccgagg tgaagttcga gggcgacacc ctggtgaacc   1560
gcatcgagct gaagggcatc gacttcaagg aggacggcaa catcctgggg cacaagctgg   1620
agtacaacta caacagccac aacgtctata tcatggccga caagcagaag aacggcatca   1680
aggtgaactt caagatccgc cacaacatcg aggacggcag cgtgcagctc gccgaccact   1740
accagcagaa cacccccatc ggcgacggcc ccgtgctgct gcccgacaac cactacctga   1800
gcacccagtc cgccctgagc aaagacccca acgagaagcg cgatcacatg gtcctgctgg   1860
agttcgtgac cgccgccggg atcactctcg gcatggacga gctgtacaag taacctgcag   1920
ggataatcaa cctctggatt acaaaatttg tgaaagattg actggtattc ttaactatgt   1980
tgctcctttt acgctatgtg gatacgctgc tttaatgcct ttgtatcatg ctattgcttc   2040
ccgtatggct ttcattttct cctccttgta taaatcctgg ttagttcttg ccacggcgga   2100
actcatcgcc gcctgccttg cccgctgctg gacaggggct cggctgttgg gcactgacaa   2160
ttccgtggtg tttatttgtg aaatttgtga tgctattgct ttatttgtaa ccattctagc   2220
tttatttgtg aaatttgtga tgctattgct ttatttgtaa ccattataag ctgcaataaa   2280
caagttaaca acaacaattg cattcatttt atgtttcagg ttcaggggga gatgtgggag   2340
gtttttttaaa gcgaattcag gcctcactgg agctagagac aagaaggtaa aaaacggctg   2400
acaaaagaag tcctggtatc ctctatgatg ggagaaggaa actagctaaa gggaagaata   2460
aattagagaa aaactggaat gactgaatcg gaacaaggca aaggctataa aaaaaattag   2520
cagtatcctc ttgggggccc cttccccaca ctatctcaat gcaaatatct gtctgaaacg   2580
gtccctggct aaactccacc catgggttgg ccagccttgc cttgaccaat agccttgaca   2640
aggcaaactt gaccaatagt cttagagtat ccagtgaggc caggggccgg cggctggcta   2700
gggatgaaga ataaaaggaa gcacccttca gcagttccac acactcgctt ctggaacgtc   2760
tgaggttatc aataagctcc tagtccagac gccatgggtc atttcacaga ggaggacaag   2820
gctactatca caagcctgtg gggcaaggtg aatgtggaag atgctggagg agaaaccctg   2880
ggaaggtagg ctctggtgac caggacaagg gagggaagga aggaccctgt gcctggcaaa   2940
agtccaggtc gcttctcact cgaggtcgac gtagataagt agcatggcgg gttaatcatt   3000
aactacaagg aacccctagt gatggagttg gccactccct ctctgcgcgc tcgctcgctc   3060
actgaggccg ggcgaccaaa ggtcgcccga cgcccgggct ttgcccgggc ggcctcagtg   3120
agcgagcgag cgcgccagct ggcgtaatag cgaagaggcc cgcaccgatc gcccttccca   3180
acagttgcgc agcctgaatg gcgaatggcg attccgttgc aatggctggc ggtaatattg   3240
ttctggatat taccagcaag gccgatagtt tgagttcttc tactcaggca agtgatgtta   3300
ttactaatca aagaagtatt gcgacaacgg ttaatttgcg tgatggacag actcttttac   3360
tcggtggcct cactgattat aaaaacactt ctcaggattc tggcgtaccg ttcctgtcta   3420
aaatcccttt aatcggcctc ctgtttagct cccgctctga ttctaacgag gaaagcacgt   3480
```

tatacgtgct cgtcaaagca accatagtac gcgccctgta gcggcgcatt aagcgcggcg 3540
ggtgtggtgg ttacgcgcag cgtgaccgct acacttgcca gcgccctagc gcccgctcct 3600
ttcgctttct tcccttcctt tctcgccacg ttcgccggct ttccccgtca agctctaaat 3660
cgggggctcc ctttagggtt ccgatttagt gctttacggc acctcgaccc caaaaaactt 3720
gattagggtg atggttcacg tagtgggcca tcgccctgat agacggtttt tcgccctttg 3780
acgttggagt ccacgttctt taatagtgga ctcttgttcc aaactggaac aacactcaac 3840
cctatctcgg tctattcttt tgatttataa gggattttgc cgatttcggc ctattggtta 3900
aaaaatgagc tgatttaaca aaaatttaac gcgaatttta acaaaatatt aacgtttaca 3960
atttaaatat ttgcttatac aatcttcctg tttttggggc ttttctgatt atcaaccggg 4020
gtacatatga ttgacatgct agttttacga ttaccgttca tcgattctct tgtttgctcc 4080
agactctcag gcaatgacct gatagccttt gtagagacct ctcaaaaata gctaccctct 4140
ccggcatgaa tttatcagct agaacggttg aatatcatat tgatggtgat ttgactgtct 4200
ccggcctttc tcacccgttt gaatctttac ctacacatta ctcaggcatt gcatttaaaa 4260
tatatgaggg ttctaaaaat ttttatcctt gcgttgaaat aaaggcttct cccgcaaaag 4320
tattacaggg tcataatgtt tttggtacaa ccgatttagc tttatgctct gaggctttat 4380
tgcttaattt tgctaattct ttgccttgcc tgtatgattt attggatgtt ggaatcgcct 4440
gatgcggtat tttctcctta cgcatctgtg cggtatttca caccgcatat ggtgcactct 4500
cagtacaatc tgctctgatg ccgcatagtt aagccagccc cgacacccgc caacacccgc 4560
tgacgcgccc tgacgggctt gtctgctccc ggcatccgct tacagacaag ctgtgaccgt 4620
ctccgggagc tgcatgtgtc agaggttttc accgtcatca ccgaaacgcg cgagacgaaa 4680
gggcctcgtg atacgcctat ttttataggt taatgtcatg ataataatgg tttcttagac 4740
gtcaggtggc acttttcggg gaaatgtgcg cggaacccct atttgtttat ttttctaaat 4800
acattcaaat atgtatccgc tcatgagaca ataaccctga taaatgcttc aataatattg 4860
aaaaaggaag agtatgagta ttcaacattt ccgtgtcgcc cttattccct tttttgcggc 4920
attttgcctt cctgtttttg ctcacccaga aacgctggtg aaagtaaaag atgctgaaga 4980
tcagttgggt gcacgagtgg gttacatcga actggatctc aacagcggta agatccttga 5040
gagttttcgc cccgaagaac gttttccaat gatgagcact tttaaagttc tgctatgtgg 5100
cgcggtatta tcccgtattg acgccgggca agagcaactc ggtcgccgca tacactattc 5160
tcagaatgac ttggttgagt actcaccagt cacagaaaag catcttacgg atggcatgac 5220
agtaagagaa ttatgcagtg ctgccataac catgagtgat aacactgcgg ccaacttact 5280
tctgacaacg atcggaggac cgaaggagct aaccgctttt ttgcacaaca tgggggatca 5340
tgtaactcgc cttgatcgtt gggaaccgga gctgaatgaa gccataccaa acgacgagcg 5400
tgacaccacg atgcctgtag caatggcaac aacgttgcgc aaactattaa ctggcgaact 5460
acttactcta gcttcccggc aacaattaat agactggatg gaggcggata aagttgcagg 5520
accacttctg cgctcggccc ttccggctgg ctggtttatt gctgataaat ctggagccgg 5580
tgagcgtggg tctcgcggta tcattgcagc actggggcca gatggtaagc cctcccgtat 5640
cgtagttatc tacacgacgg ggagtcaggc aactatggat gaacgaaata gacagatcgc 5700
tgagataggt gcctcactga ttaagcattg gtaactgtca gaccaagttt actcatatat 5760
actttagatt gatttaaaac ttcattttta atttaaaagg atctaggtga agatcctttt 5820
tgataatctc atgaccaaaa tcccttaacg tgagttttcg ttccactgag cgtcagaccc 5880
cgtagaaaag atcaaaggat cttcttgaga tcctttttt ctgcgcgtaa tctgctgctt 5940
gcaaacaaaa aaaccaccgc taccagcggt ggtttgtttg ccggatcaag agctaccaac 6000
tctttttccg aaggtaactg gcttcagcag agcgcagata ccaaatactg tccttctagt 6060
gtagccgtag ttaggccacc acttcaagaa ctctgtagca ccgcctacat acctcgctct 6120
gctaatcctg ttaccagtgg ctgctgccag tggcgataag tcgtgtctta ccgggttgga 6180
ctcaagacga tagttaccgg ataaggcgca gcggtcgggc tgaacggggg gttcgtgcac 6240
acagcccagc ttggagcgaa cgacctacac cgaactgaga tacctacagc gtgagctatg 6300
agaaagcgcc acgcttcccg aagggagaaa ggcggacagg tatccggtaa gcggcagggt 6360
cggaacagga gagcgcacga gggagcttcc agggggaaac gcctggtatc tttatagtcc 6420
tgtcgggttt cgccacctct gacttgagcg tcgatttttg tgatgctcgt caggggggcg 6480
gagcctatgg aaaaacgcca gcaacgcggc ctttttacgg ttcctggcct tttgctggcc 6540
ttttgctcac atgttctttc ctgcgttatc ccctgattct gtggataacc gtattaccgc 6600
ctttgagtga gctgataccg ctcgccgcag ccgaacgacc gagcgcagcg agtcagtgag 6660
cgaggaagcg gaagagcgcc caatacgcaa accgcctctc cccgcgcgtt ggccgattca 6720
ttaatg 6726

<210> SEQ ID NO 25
<211> LENGTH: 6991
<212> TYPE: DNA
<213> ORGANISM: Artificial
<220> FEATURE:
<223> OTHER INFORMATION: AAV donor template

<400> SEQUENCE: 25
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctacgtactt taggcttgta atgtgtttat atacagtgaa atgtcaagtt ctttctttat 240
atttctttct ttcttttttt tcctcagcct cagagttttc cacatgccct tcctactttc 300
aggaacttct ttctccaaac gtcttctgcc tggctccatc aaatcataaa ggacccactt 360
caaatgccat cactcactac catttcacaa ttcgcacttt ctttctttgt cctttttttt 420
tttagtaaaa caagtttata aaaaattgaa ggaataaatg aatggctact tcataggcag 480
agtagacgca agggctactg gttgccgatt tttattgtta tttttcaata gtatgctaaa 540
caaggggtag attatttatg ctgcccattt ttagaccata aaagataact tcctgatgtt 600
gccatggcat ttttttcctt ttaattttat ttcatttcat tttaatttcg aaggtacatg 660
tgcaggatgt gcaggcttgt tacatgggta aatgtgtgtc tttctggcct tttagccatc 720
tgtatcaatg agcagatata agctttacac aggatcatga aggatgaaag aatttcacca 780
atccgcggga acagagaaac aggagaatat gggccaaaca ggatatctgt ggtaagcagt 840
tcctgccccg gctcagggcc aagaacagtt ggaacagcag aatatgggcc aaacaggata 900
tctgtggtaa gcagttcctg ccccggctca gggccaagaa cagatggtcc ccagatgcgg 960
tcccgccctc agcagtttct agagaaccat cagatgtttc cagggtgccc caaggacctg 1020
aaatgaccct gtgccttatt tgaactaacc aatcagttcg cttctcgctt ctgttcgcgc 1080
gcttctgctc cccgagctct atataagcag agctcgttta gtgaaccgtc agatcgcctg 1140
gagacgccat ccacgctgtt ttgacttcca tagaaggcgg ccgcgccgcc accatggtga 1200
gcaagggcga ggagctgttc accggggtgg tgcccatcct ggtcgagctg gacggcgacg 1260
taaacggcca caagttcagc gtgtccggcg agggcgaggg cgatgccacc tacggcaagc 1320
tgaccctgaa gttcatctgc accaccggca agctgcccgt gccctggccc accctcgtga 1380
ccaccctgac ctacggcgtg cagtgcttca gccgctaccc cgaccacatg aagcagcacg 1440
acttcttcaa gtccgccatg cccgaaggct acgtccagga gcgcaccatc ttcttcaagg 1500
acgacggcaa ctacaagacc cgcgccgagg tgaagttcga gggcgacacc ctggtgaacc 1560
gcatcgagct gaagggcatc gacttcaagg aggacggcaa catcctgggg cacaagctgg 1620
agtacaacta caacagccac aacgtctata tcatggccga caagcagaag aacggcatca 1680
aggtgaactt caagatccgc cacaacatcg aggacggcag cgtgcagctc gccgaccact 1740
accagcagaa cacccccatc ggcgacggcc ccgtgctgct gcccgacaac cactacctga 1800
gcacccagtc cgccctgagc aaagacccca acgagaagcg cgatcacatg gtcctgctgg 1860
agttcgtgac cgccgccggg atcactctcg gcatggacga gctgtacaag taacctgcag 1920
ggataatcaa cctctggatt acaaaatttg tgaaagattg actggtattc ttaactatgt 1980
tgctcctttt acgctatgtg gatacgctgc tttaatgcct ttgtatcatg ctattgcttc 2040
ccgtatggct ttcattttct cctccttgta taaatcctgg ttagttcttg ccacggcgga 2100
actcatcgcc gcctgccttg cccgctgctg gacaggggct cggctgttgg gcactgacaa 2160
ttccgtggtg tttatttgtg aaatttgtga tgctattgct ttatttgtaa ccattctagc 2220
tttatttgtg aaatttgtga tgctattgct ttatttgtaa ccattataag ctgcaataaa 2280
caagttaaca acaacaattg cattcatttt atgtttcagg ttcaggggga gatgtgggag 2340 gtttttttaaa gcgaattcgt aaatacactt gcaaaggagg atgtttttag tagcaatttg 2400
tactgatggt atggggccaa gagatatatc ttagagggag ggctgagggt ttgaagtcca 2460
actcctaagc cagtgccaga agagccaagg acaggtacgg ctgtcatcac ttagacctca 2520
ccctgtggag ccacacccta gggttggcca atctactccc aggagcaggg agggcaggag 2580
ccagggctgg gcataaaagt cagggcagag ccatctattg cttacactcg cttctggaac 2640
gtctgaggtt atcaataagc tcctagtcca gacgccatgg gtcatttcac agaggaggac 2700
aaggctacta tcacaagcct gtggggcaag gtgaatgtgg aagatgctgg aggagaaacc 2760
ctgggaaggt aggctctggt gaccaggaca agggagggaa ggaaggaccc tgtgcctggc 2820
aaaagtccag gtcgcttctc aggatttgtg gcaccttctg actgtcaaac tgttcttgtc 2880
aatctcacag gctcctggtt gtctacccat ggacccagag gttctttgac agctttggca 2940
acctgtcctc tgcctctgcc atcatgggca accccaaagt caaggcacat ggcaagaagg 3000
tgctgacttc cttgggagat gccacaaagc acctggatga tctcaagggc acctttgccc 3060
agctgagtga actgcactgt gacaagctgc atgtggatcc tgagaacttc aaggtgagtc 3120
caggagatgt ttcagccctg ttgcctttag tctcgaggca acttagacaa cggagtattg 3180
atctgagcac agcagggtgt gagctgtttg aagatactgg ggtctcgagg tcgacgtaga 3240
taagtagcat ggcgggttaa tcattaacta caaggaaccc ctagtgatgg agttggccac 3300
tccctctctg cgcgctcgct cgctcactga ggccgggcga ccaaaggtcg cccgacgccc 3360
gggctttgcc cgggcggcct cagtgagcga gcgagcgcgc cagctggcgt aatagcgaag 3420
aggcccgcac cgatcgccct tcccaacagt tgcgcagcct gaatggcgaa tggcgattcc 3480
gttgcaatgg ctggcggtaa tattgttctg gatattacca gcaaggccga tagtttgagt 3540

-continued tcttctactc aggcaagtga tgttattact aatcaaagaa gtattgcgac aacggttaat 3600
ttgcgtgatg gacagactct tttactcggt ggcctcactg attataaaaa cacttctcag 3660
gattctggcg taccgttcct gtctaaaatc cctttaatcg gcctcctgtt tagctcccgc 3720
tctgattcta acgaggaaag cacgttatac gtgctcgtca aagcaaccat agtacgcgcc 3780
ctgtagcggc gcattaagcg cggcgggtgt ggtggttacg cgcagcgtga ccgctacact 3840
tgccagcgcc ctagcgcccg ctcctttcgc tttcttccct tcctttctcg ccacgttcgc 3900
cggctttccc cgtcaagctc taaatcgggg gctcccttta gggttccgat ttagtgcttt 3960
acggcacctc gaccccaaaa aacttgatta gggtgatggt tcacgtagtg ggccatcgcc 4020
ctgatagacg gtttttcgcc ctttgacgtt ggagtccacg ttctttaata gtggactctt 4080
gttccaaact ggaacaacac tcaaccctat ctcggtctat tcttttgatt tataagggat 4140
tttgccgatt tcggcctatt ggttaaaaaa tgagctgatt taacaaaaat ttaacgcgaa 4200
ttttaacaaa atattaacgt ttacaattta aatatttgct tatacaatct tcctgttttt 4260
ggggcttttc tgattatcaa ccggggtaca tatgattgac atgctagttt tacgattacc 4320
gttcatcgat tctcttgttt gctccagact ctcaggcaat gacctgatag cctttgtaga 4380
gacctctcaa aaatagctac cctctccggc atgaatttat cagctagaac ggttgaatat 4440
catattgatg gtgatttgac tgtctccggc ctttctcacc cgtttgaatc tttacctaca 4500
cattactcag gcattgcatt taaaatatat gagggttcta aaaattttta tccttgcgtt 4560
gaaataaagg cttctcccgc aaaagtatta cagggtcata atgtttttgg tacaaccgat 4620
ttagctttat gctctgaggc tttattgctt aattttgcta attctttgcc ttgcctgtat 4680
gatttattgg atgttggaat cgcctgatgc ggtattttct ccttacgcat ctgtgcggta 4740
tttcacaccg catatggtgc actctcagta caatctgctc tgatgccgca tagttaagcc 4800
agccccgaca cccgccaaca cccgctgacg cgccctgacg ggcttgtctg ctcccggcat 4860
ccgcttacag acaagctgtg accgtctccg ggagctgcat gtgtcagagg ttttcaccgt 4920
catcaccgaa acgcgcgaga cgaaagggcc tcgtgatacg cctattttta taggttaatg 4980
tcatgataat aatggtttct tagacgtcag gtggcacttt tcggggaaat gtgcgcggaa 5040
cccctatttg tttatttttc taaatacatt caaatatgta tccgctcatg agacaataac 5100
cctgataaat gcttcaataa tattgaaaaa ggaagagtat gagtattcaa catttccgtg 5160
tcgcccttat tccctttttt gcggcatttt gccttcctgt ttttgctcac ccagaaacgc 5220
tggtgaaagt aaaagatgct gaagatcagt tgggtgcacg agtgggttac atcgaactgg 5280
atctcaacag cggtaagatc cttgagagtt ttcgccccga agaacgtttt ccaatgatga 5340
gcacttttaa agttctgcta tgtggcgcgg tattatcccg tattgacgcc gggcaagagc 5400
aactcggtcg ccgcatacac tattctcaga atgacttggt tgagtactca ccagtcacag 5460
aaaagcatct tacggatggc atgacagtaa gagaattatg cagtgctgcc ataaccatga 5520
gtgataacac tgcggccaac ttacttctga caacgatcgg aggaccgaag gagctaaccg 5580
cttttttgca caacatgggg gatcatgtaa ctcgccttga tcgttgggaa ccggagctga 5640
atgaagccat accaaacgac gagcgtgaca ccacgatgcc tgtagcaatg gcaacaacgt 5700
tgcgcaaact attaactggc gaactactta ctctagcttc ccggcaacaa ttaatagact 5760
ggatggaggc ggataaagtt gcaggaccac ttctgcgctc ggcccttccg gctggctggt 5820
ttattgctga taaatctgga gccggtgagc gtgggtctcg cggtatcatt gcagcactgg 5880
ggccagatgg taagccctcc cgtatcgtag ttatctacac gacggggagt caggcaacta 5940
tggatgaacg aaatagacag atcgctgaga taggtgcctc actgattaag cattggtaac 6000
tgtcagacca agtttactca tatatacttt agattgattt aaaacttcat ttttaattta 6060
aaaggatcta ggtgaagatc ctttttgata atctcatgac caaaatccct taacgtgagt 6120
tttcgttcca ctgagcgtca gaccccgtag aaaagatcaa aggatcttct tgagatcctt 6180
tttttctgcg cgtaatctgc tgcttgcaaa caaaaaaacc accgctacca gcggtggttt 6240
gtttgccgga tcaagagcta ccaactcttt ttccgaaggt aactggcttc agcagagcgc 6300
agataccaaa tactgtcctt ctagtgtagc cgtagttagg ccaccacttc aagaactctg 6360
tagcaccgcc tacatacctc gctctgctaa tcctgttacc agtggctgct gccagtggcg 6420
ataagtcgtg tcttaccggg ttggactcaa gacgatagtt accggataag gcgcagcggt 6480
cgggctgaac ggggggttcg tgcacacagc ccagcttgga gcgaacgacc tacaccgaac 6540
tgagatacct acagcgtgag ctatgagaaa gcgccacgct tcccgaaggg agaaaggcgg 6600
acaggtatcc ggtaagcggc agggtcggaa caggagagcg cacgagggag cttccagggg 6660
gaaacgcctg gtatctttat agtcctgtcg ggtttcgcca cctctgactt gagcgtcgat 6720
ttttgtgatg ctcgtcaggg gggcggagcc tatggaaaaa cgccagcaac gcggcctttt 6780
tacggttcct ggccttttgc tggccttttg ctcacatgtt ctttcctgcg ttatcccctg 6840
attctgtgga taaccgtatt accgcctttg agtgagctga taccgctcgc cgcagccgaa 6900
cgaccgagcg cagcgagtca gtgagcgagg aagcggaaga gcgcccaata cgcaaaccgc 6960
ctctccccgc gcgttggccg attcattaat g 6991

<210> SEQ ID NO 26
<211> LENGTH: 7724
<212> TYPE: DNA
<213> ORGANISM: Artificial
<220> FEATURE:
<223> OTHER INFORMATION: AAV donor template

<400> SEQUENCE: 26
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtagccatgc 180
tctagcggcc tcggcctctg cataaataaa aaaaattagt cagccatgag cttggacgcg 240
tagatctcac tttcagagaa aaacaaaaac aaactaacca aaagcaaaac agaaccaaaa 300
aaccaccata aatacttcct accctgttaa tggtccaata tgtcagaaac agcactgtgt 360
tagaaataaa gctgtctaaa gtacactaat attcgagtta taatagtgtg tggactatta 420
gtcaataaaa acaacccttg cctctttaga gttgttttcc atgtacacgc acatcttatg 480
tcttagagta agattccctg agaagtgaac ctagcattta tacaagataa ttaattctaa 540
tccacagtac ctgccaaaga acattctacc atcatcttta ctgagcatag aagagctacg 600
ccaaaaccct gggtcatcag ccagcacaca cacttatcca gtggtaaata cacatcatct 660
ggtgtataca tacatacctg aatatggaat caaatatttt tctaagatga aacagtcatg 720
atttatttca aataggtacg gataagtaga tatgaacaga gaaacaggag aatatgggcc 780
aaacaggata tctgtggtaa gcagttcctg ccccggctca gggccaagaa cagttggaac 840
agcagaatat gggccaaaca ggatatctgt ggtaagcagt tcctgccccg gctcagggcc 900
aagaacagat ggtccccaga tgcggtcccg ccctcagcag tttctagaga accatcagat 960

```
gtttccaggg tgccccaagg acctgaaatg accctgtgcc ttatttgaac taaccaatca   1020
gttcgcttct cgcttctgtt cgcgcgcttc tgctccccga gctctatata agcagagctc   1080
gtttagtgaa ccgtcagatc gcggccgcgc cgccaccatg gtgagcaagg gcgaggagct   1140
gttcaccggg gtggtgccca tcctggtcga gctggacggc gacgtaaacg gccacaagtt   1200
cagcgtgtcc ggcgagggcg agggcgatgc cacctacggc aagctgaccc tgaagttcat   1260
ctgcaccacc ggcaagctgc ccgtgccctg gcccaccctc gtgaccaccc tgacctacgg   1320
cgtgcagtgc ttcagccgct accccgacca catgaagcag cacgacttct tcaagtccgc   1380
catgcccgaa ggctacgtcc aggagcgcac catcttcttc aaggacgacg gcaactacaa   1440
gacccgcgcc gaggtgaagt tcgagggcga caccctggtg aaccgcatcg agctgaaggg   1500
catcgacttc aaggaggacg gcaacatcct ggggcacaag ctggagtaca actacaacag   1560
ccacaacgtc tatatcatgg ccgacaagca gaagaacggc atcaaggtga acttcaagat   1620
ccgccacaac atcgaggacg gcagcgtgca gctcgccgac cactaccagc agaacacccc   1680
catcggcgac ggccccgtgc tgctgcccga caaccactac ctgagcaccc agtccgccct   1740
gagcaaagac cccaacgaga agcgcgatca catggtcctg ctggagttcg tgaccgccgc   1800
cgggatcact ctcggcatgg acgagctgta caagtaggag catcttaccg ccatttattc   1860
ccatatttgt tctgtttttc ttgatttggg tatacattta aatgttaata aaacaaaatg   1920
gtggggcaat catttacatt tttagggata tgtaattact agttcaggtg tattgccaca   1980
agacaaacat gttaagaaac tttcccgtta tttacgctct gttcctgtta atcaacctct   2040
ggattacaaa atttgtgaaa gattgactga tattcttaac tatgttgctc cttttacgct   2100
gtgtggatat gctgctttat agcctctgta tctagctatt gcttcccgta cggctttcgt   2160
tttctcctcc ttgtataaat cctggttgct gtctctttta gaggagttgt ggcccgttgt   2220
ccgtcaacgt ggcgtggtgt gctctgtgtt tgctgacgca acccccactg gctggggcat   2280
tgccaccacc tgtcaactcc tttctgggac tttcgctttc cccctcccga tcgccacggc   2340
agaactcatc gccgcctgcc ttgcccgctg ctggacaggg gctaggttgc tgggcactga   2400
taattccgtg gtgttgtctg tgccttctag ttgccagcca tctgttgttt gcccctcccc   2460
cgtgccttcc ttgaccctgg aaggtgccac tcccactgtc ctttcctaat aaaatgagga   2520
aattgcatcg cattgtctga gtaggtgtca ttctattctg gggggtgggg tggggcagga   2580
cagcaagggg gaggattggg aagacaatag caggcatgct ggggatgcgg tgggctctat   2640
ggctagatgt ccccagttaa cctcctattt gacaccactg attaccccat tgatagtcac   2700
actttgggtt gtaagtgact ttttatttat ttgtattttt gactgcatta agaggtctct   2760
agtttttat ctcttgtttc ccaaaaccta ataagtaact aatgcacaga gcacattgat   2820
ttgtatttat tctattttta gacataattt attagcatgc atgagcaaat taagaaaaac   2880
aacaacaaat gaatgcatat atatgtatat gtatgtgtgt atatatacac acatatatat   2940
atatattttt tcttttctta ccagaaggtt ttaatccaaa taaggagaag atatgcttag   3000
aaccgaggta gagttttcat ccattctgtc ctgtaagtat tttgcatatt ctggagacgc   3060
aggaagagat ccatctacat atcccaaagc tgaattatgg tagacaaaac tcttccactt   3120
ttagtgcatc aacttcttat ttgtgtaata agaaaattgg gaaaacgatc ttcaatatgc   3180
ttaccaagct gtgattccaa atattacgta aatacacttg caaaggagga tgtttttagt   3240
agcaatttgt actgatggta tggggccaag agatatatct tagagggagg gctgagggtt   3300
```

```
tgaagtccaa ctcctaagcc agtgccagaa gagccaagga caggtacggc tgtcatcact   3360
tagacctcac cctgtggagc cacaccctag ggttggccaa tctactccca ggagcaggga   3420
gggcaggagc cagggctggg cataaaagtc agggcagagc catctattgc ttacactcgc   3480
ttctggaacg tctgaggtta tcaataagct cctagtccag acgccatggg tcatttcaca   3540
gaggaggaca aggctactat cacaagcctg tggggcaagg tgaatgtgga agatgctgga   3600
ggagaaaccc tgggaaggta ggctctggtg accaggacaa gggagggaag gaaggaccct   3660
gtgcctggca aaagtccagg tcgcttctca ggatttgtgg caccttctga ctgtcaaact   3720
gttcttgtca atctcacagg ctcctggttg tctacccatg gacccagagg ttctttgaca   3780
gctttggcaa cctgtcctct gcctctgcca tcatgggcaa ccccaaagtc aaggcacatg   3840
gcaagaaggt gctgacttcc ttgggagatg ccacaaagca cctggatgat ctcaagggca   3900
cctttgccca gctgagtgaa ctgcactgtg acaagctgca tgtggatcct gagaacttca   3960
aggtcgacgt agataagtag catggcgggt taatcattaa ctacaaggaa cccctagtga   4020
tggagttggc cactccctct ctgcgcgctc gctcgctcac tgaggccggg cgaccaaagg   4080
tcgcccgacg cccgggcttt gcccgggcgg cctcagtgag cgagcgagcg cgccagctgg   4140
cgtaatagcg aagaggcccg caccgatcgc ccttcccaac agttgcgcag cctgaatggc   4200
gaatggcgat tccgttgcaa tggctggcgg taatattgtt ctggatatta ccagcaaggc   4260
cgatagtttg agttcttcta ctcaggcaag tgatgttatt actaatcaaa gaagtattgc   4320
gacaacggtt aatttgcgtg atggacagac tcttttactc ggtggcctca ctgattataa   4380
aaacacttct caggattctg gcgtaccgtt cctgtctaaa atccctttaa tcggcctcct   4440
gtttagctcc cgctctgatt ctaacgagga aagcacgtta tacgtgctcg tcaaagcaac   4500
catagtacgc gccctgtagc ggcgcattaa gcgcggcggg tgtggtggtt acgcgcagcg   4560
tgaccgctac acttgccagc gccctagcgc ccgctccttt cgctttcttc ccttcctttc   4620
tcgccacgtt cgccggcttt ccccgtcaag ctctaaatcg ggggctccct ttagggttcc   4680
gatttagtgc tttacggcac ctcgacccca aaaaacttga ttagggtgat ggttcacgta   4740
gtgggccatc gccctgatag acggtttttc gccctttgac gttggagtcc acgttcttta   4800
atagtggact cttgttccaa actggaacaa cactcaaccc tatctcggtc tattcttttg   4860
atttataagg gattttgccg atttcggcct attggttaaa aaatgagctg atttaacaaa   4920
aatttaacgc gaattttaac aaaatattaa cgtttacaat ttaaatattt gcttatacaa   4980
tcttcctgtt tttggggctt ttctgattat caaccggggt acatatgatt gacatgctag   5040
ttttacgatt accgttcatc gattctcttg tttgctccag actctcaggc aatgacctga   5100
tagcctttgt agagacctct caaaaatagc taccctctcc ggcatgaatt tatcagctag   5160
aacggttgaa tatcatattg atggtgattt gactgtctcc ggcctttctc acccgtttga   5220
atctttacct acacattact caggcattgc atttaaaata tatgagggtt ctaaaaattt   5280
ttatccttgc gttgaaataa aggcttctcc cgcaaaagta ttacagggtc ataatgtttt   5340
tggtacaacc gatttagctt tatgctctga ggctttattg cttaattttg ctaattcttt   5400
gccttgcctg tatgatttat tggatgttgg aatcgcctga tgcggtattt tctccttacg   5460
catctgtgcg gtatttcaca ccgcatatgg tgcactctca gtacaatctg ctctgatgcc   5520
gcatagttaa gccagccccg acacccgcca acacccgctg acgcgccctg acgggcttgt   5580
ctgctcccgg catccgctta cagacaagct gtgaccgtct ccgggagctg catgtgtcag   5640
aggttttcac cgtcatcacc gaaacgcgcg agacgaaagg gcctcgtgat acgcctattt   5700
```

-continued ttataggtta atgtcatgat aataatggtt tcttagacgt caggtggcac ttttcgggga 5760
aatgtgcgcg gaacccctat ttgtttattt ttctaaatac attcaaatat gtatccgctc 5820
atgagacaat aaccctgata aatgcttcaa taatattgaa aaaggaagag tatgagtatt 5880
caacatttcc gtgtcgccct tattcccttt tttgcggcat tttgccttcc tgtttttgct 5940
cacccagaaa cgctggtgaa agtaaaagat gctgaagatc agttgggtgc acgagtgggt 6000
tacatcgaac tggatctcaa cagcggtaag atccttgaga gttttcgccc cgaagaacgt 6060
tttccaatga tgagcacttt taaagttctg ctatgtggcg cggtattatc ccgtattgac 6120
gccgggcaag agcaactcgg tcgccgcata cactattctc agaatgactt ggttgagtac 6180
tcaccagtca cagaaaagca tcttacggat ggcatgacag taagagaatt atgcagtgct 6240
gccataacca tgagtgataa cactgcggcc aacttacttc tgacaacgat cggaggaccg 6300
aaggagctaa ccgctttttt gcacaacatg ggggatcatg taactcgcct tgatcgttgg 6360
gaaccggagc tgaatgaagc cataccaaac gacgagcgtg acaccacgat gcctgtagca 6420
atggcaacaa cgttgcgcaa actattaact ggcgaactac ttactctagc ttcccggcaa 6480
caattaatag actggatgga ggcggataaa gttgcaggac cacttctgcg ctcggccctt 6540
ccggctggct ggtttattgc tgataaatct ggagccggtg agcgtgggtc tcgcggtatc 6600
attgcagcac tggggccaga tggtaagccc tcccgtatcg tagttatcta cacgacgggg 6660
agtcaggcaa ctatggatga acgaaataga cagatcgctg agataggtgc ctcactgatt 6720
aagcattggt aactgtcaga ccaagtttac tcatatatac tttagattga tttaaaactt 6780
catttttaat ttaaaaggat ctaggtgaag atcctttttg ataatctcat gaccaaaatc 6840
ccttaacgtg agttttcgtt ccactgagcg tcagaccccg tagaaaagat caaaggatct 6900
tcttgagatc ctttttttct gcgcgtaatc tgctgcttgc aaacaaaaaa accaccgcta 6960
ccagcggtgg tttgtttgcc ggatcaagag ctaccaactc tttttccgaa ggtaactggc 7020
ttcagcagag cgcagatacc aaatactgtc cttctagtgt agccgtagtt aggccaccac 7080
ttcaagaact ctgtagcacc gcctacatac ctcgctctgc taatcctgtt accagtggct 7140
gctgccagtg gcgataagtc gtgtcttacc gggttggact caagacgata gttaccggat 7200
aaggcgcagc ggtcgggctg aacggggggt tcgtgcacac agcccagctt ggagcgaacg 7260
acctacaccg aactgagata cctacagcgt gagctatgag aaagcgccac gcttcccgaa 7320
gggagaaagg cggacaggta tccggtaagc ggcagggtcg gaacaggaga gcgcacgagg 7380
gagcttccag ggggaaacgc ctggtatctt tatagtcctg tcgggtttcg ccacctctga 7440
cttgagcgtc gatttttgtg atgctcgtca ggggggcgga gcctatggaa aaacgccagc 7500
aacgcggcct ttttacggtt cctggccttt tgctggcctt ttgctcacat gttctttcct 7560
gcgttatccc ctgattctgt ggataaccgt attaccgcct ttgagtgagc tgataccgct 7620
cgccgcagcc gaacgaccga gcgcagcgag tcagtgagcg aggaagcgga agagcgccca 7680
atacgcaaac cgcctctccc cgcgcgttgg ccgattcatt aatg 7724

<210> SEQ ID NO 27
<211> LENGTH: 8525
<212> TYPE: DNA
<213> ORGANISM: Artificial
<220> FEATURE:
<223> OTHER INFORMATION: AAV donor template

<400> SEQUENCE: 27

-continued

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctagcggcc tcggcctctg cataaataaa aaaaattagt cagccatgag cttggacgcg    240
tagatctaga tgaaacagtc atgatttatt tcaaataggt acggataagt agatattgag    300
gtaagcatta ggtcttatat tatgtaacac taatctatta ctgcgctgaa actgtggctt    360
tatagaaatt gttttcactg cactattgag aaattaagag ataatggcaa aagtcacaaa    420
gagtatattc aaaaagaagt atagcacttt ttccttagaa accactgcta actgaaagag    480
actaagattt gtcccgtcaa aaatcctgga cctatgccta aaacacattt cacaatccct    540
gaacttttca aaaattggta catgctttag ctttaaacta caggcctcac tggagctaga    600
gacaagaagg taaaaaacgg ctgacaaaag aagtcctggt atcctctatg atgggagaag    660
gaaactagct aaagggaaga ataaattaga gaaaaactgg aatgactgaa tcggaacaag    720
gcaaaggcta taaaaaaaat tagcagtatc ctcttggggg ccccttcccc acactatctc    780
aatgcaaata tctgtctgaa acggtccctg gctaaactcc acccatgggt tggccagcct    840
tgccttgaca aggcaaactt gaccaatagt cttagagtat ccagtgaggc caggggccgg    900
cggctggcta gggatgaaga ataaaaggaa gcacccttca gcagttccac acactcgctt    960
ctggaacgtc tgaggttatc aataagctcc tagtccagac gccatggtgc acctgactcc   1020
tgaggagaag tctgccgtta ctgccctgtg gggcaaggtg aacgtggatg aagttggtgg   1080
tgaggccctg ggcaggttgg tatcaaggtt acaagacagg tttaaggaga ccaatagaaa   1140
ctgggcatgt ggagacagag aagactcttg ggtttctgat aggcactgac tctctctgcc   1200
tattggtcta ttttcccacc cttaggctgc tggtggtcta cccttggacc cagaggttct   1260
ttgagtcctt tggggatctg tccactcctg atgctgttat gggcaaccct aaggtgaagg   1320
ctcatggcaa gaaagtgctc ggtgccttta gtgatggcct ggctcacctg gacaacctca   1380
agggcacctt tgcccagctg agtgagctgc actgtgacaa gctgcacgtg gatcctgaga   1440
acttcagggt gagtctatgg gacccttgat gttttctttc cccttctttt ctatggttaa   1500
gttcatgtca taggaagggg agaagtaaca gggtacacat attgaccaaa tcagggtaat   1560
tttgcatttg taattttaaa aaatgctttc ttcttttaat atactttttt gtttatctta   1620
tttctaatac tttccctaat ctctttcttt cagggcaata atgatacaat gtatcatgcc   1680
tctttgcacc attctaaaga ataacagtga taatttctgg gttaaggcaa tagcaatatt   1740
tctgcatata aatatttctg catataaatt gtaactgatg taagaggttt catattgcta   1800
atagcagcta caatccagct accattctgc ttttatttta tggttgggat aaggctggat   1860
tattctgagt ccaagctagg cccttttgct aatcatgttc atacctctta tcttcctccc   1920
acagctcctg ggcaacgtgc tggtctgtgt gctggcccat cactttggca aagaattcac   1980
cccaccagtg caggctgcct atcagaaagt ggtggctggt gtggctaatg ccctggccca   2040
caagtatcac taagctcgct ttcttgctgt ccaatttcta ttaaaggttc ctttgttccc   2100
taagtccaac tactaaactg ggggatatta tgaagggcct tgagcatctg gattctgcct   2160
aataaaaaac atttattttc attgcaatga tgtatttaaa ttatttctga atattttact   2220
aaaaagggaa tgtgggaggt cagtgcattt aaaacataaa gaaatgaaga gctagttcaa   2280
accttgggaa aatacactat atcttaaact ccatgaaaga aggtgaggct gcaaacagct   2340
aatgcacatt ggcaacagcc cctgatgcct atgccttatt catccctcag aaaaggattc   2400
```

-continued aagtagaggc ttgatttgga ggttaaagtt ttgctatgct gtattttaca ttacttattg 2460
ttttagctgt cctcatgaat gtcttttcac tacccatttg cttatcctgc atctctcagc 2520
cttgactcca ctcagttctc ttgcttagag ataccacctt tcccctgaag tgttccttcc 2580
atgttttacg gcgagatggt ttctcctcgc ctggccactc agccttagtt gtctctgttg 2640
tcttatagag gtctacttga agaaggaaaa acagggggca tggtttgact gtcctgtgag 2700
cccttcttcc ctgcctcccc cactcacagt gacccggaat ctgcagtgct agtctcccgg 2760
aactatcact ctttcacagt ctgctttgga aggactgggc ttagtatgaa aagttaggac 2820
tgagaagaat ttgaaagggg gctttttgta gcttgatatt cactactgtc ttattaccct 2880
atcataggcc caccccaaat ggaagtccca ttcttcctca ggatgtttaa gattagcatt 2940
caggaagaga tcagaggtct gctggctccc ttatcatgtc ccttatggtg cttctggctc 3000
tgcagttatt agcatagtgt taccatcaac caccttaact tcatttttct tattcaatac 3060
ctagccgcgg gaacagagaa acaggagaat atgggccaaa caggatatct gtggtaagca 3120
gttcctgccc cggctcaggg ccaagaacag ttggaacagc agaatatggg ccaaacagga 3180
tatctgtggt aagcagttcc tgccccggct cagggccaag aacagatggt ccccagatgc 3240
ggtcccgccc tcagcagttt ctagagaacc atcagatgtt tccagggtgc cccaaggacc 3300
tgaaatgacc ctgtgcctta tttgaactaa ccaatcagtt cgcttctcgc ttctgttcgc 3360
gcgcttctgc tccccgagct ctatataagc agagctcgtt tagtgaaccg tcagatcgcg 3420
gccgcgccgc caccatggtg agcaagggcg aggagctgtt caccggggtg gtgcccatcc 3480
tggtcgagct ggacggcgac gtaaacggcc acaagttcag cgtgtccggc gagggcgagg 3540
gcgatgccac ctacggcaag ctgaccctga agttcatctg caccaccggc aagctgcccg 3600
tgccctggcc caccctcgtg accaccctga cctacggcgt gcagtgcttc agccgctacc 3660
ccgaccacat gaagcagcac gacttcttca agtccgccat gcccgaaggc tacgtccagg 3720
agcgcaccat cttcttcaag gacgacggca actacaagac ccgcgccgag gtgaagttcg 3780
agggcgacac cctggtgaac cgcatcgagc tgaagggcat cgacttcaag gaggacggca 3840
acatcctggg gcacaagctg gagtacaact acaacagcca caacgtctat atcatggccg 3900
acaagcagaa gaacggcatc aaggtgaact tcaagatccg ccacaacatc gaggacggca 3960
gcgtgcagct cgccgaccac taccagcaga acacccccat cggcgacggc cccgtgctgc 4020
tgcccgacaa ccactacctg agcacccagt ccgccctgag caaagacccc aacgagaagc 4080
gcgatcacat ggtcctgctg gagttcgtga ccgccgccgg gatcactctc ggcatggacg 4140
agctgtacaa gtaacctgca gggctcactg cccatgattc agagctttca aggataggct 4200
ttattctgca agcaatacaa ataataaatc tattctgctg agagatcaca catgattttc 4260
ttcagctctt ttttttacat ctttttaaat atatgagcca caaagggttt atattgaggg 4320
aagtgtgtat gtgtatttct gcatgcctgt ttgtgtttgt ggtgtgtgca tgctcctcat 4380
ttatttttat atgagatgtg cattttgatg agcaaataaa agcagtaaag acacttgtac 4440
acgggagttc tgcaagtggg agtaaatggt gtaggagaaa tccggtggga agaaagacct 4500
ctataggaca ggacttctca gaaacagatg ttttggaaga gatgggaaaa ggttcagtga 4560
agacctgggg gctggattga ttgcagctga gtagcaagga tggttcttaa ggaagggaaa 4620
gtgttccaag ctttaggaat tcaaggttta gtcaggtgta gcaattctat tttattagga 4680
ggaatactat ttctaatggc acttagcttt tcacagccct tgtggatgcc taagaaagtg 4740
aaattaatcc catgccctca agtgtcgacg tagataagta gcatggcggg ttaatcatta 4800
actacaagga acccctagtg atggagttgg ccactccctc tctgcgcgct cgctcgctca 4860
ctgaggccgg gcgaccaaag gtcgcccgac gcccgggctt tgcccgggcg gcctcagtga 4920
gcgagcgagc gcgccagctg gcgtaatagc gaagaggccc gcaccgatcg cccttcccaa 4980
cagttgcgca gcctgaatgg cgaatggcga ttccgttgca atggctggcg gtaatattgt 5040
tctggatatt accagcaagg ccgatagttt gagttcttct actcaggcaa gtgatgttat 5100
tactaatcaa agaagtattg cgacaacggt taatttgcgt gatggacaga ctcttttact 5160
cggtggcctc actgattata aaaacacttc tcaggattct ggcgtaccgt tcctgtctaa 5220
aatcccttta atcggcctcc tgtttagctc ccgctctgat tctaacgagg aaagcacgtt 5280
atacgtgctc gtcaaagcaa ccatagtacg cgccctgtag cggcgcatta agcgcggcgg 5340
gtgtggtggt tacgcgcagc gtgaccgcta cacttgccag cgccctagcg cccgctcctt 5400
tcgctttctt cccttccttt ctcgccacgt tcgccggctt tccccgtcaa gctctaaatc 5460
gggggctccc tttagggttc cgatttagtg ctttacggca cctcgacccc aaaaaacttg 5520
attagggtga tggttcacgt agtgggccat cgccctgata gacggttttt cgccctttga 5580
cgttggagtc cacgttcttt aatagtggac tcttgttcca aactggaaca acactcaacc 5640
ctatctcggt ctattctttt gatttataag ggattttgcc gatttcggcc tattggttaa 5700
aaaatgagct gatttaacaa aaatttaacg cgaattttaa caaaatatta acgtttacaa 5760
tttaaatatt tgcttataca atcttcctgt ttttggggct tttctgatta tcaaccgggg 5820
tacatatgat tgacatgcta gttttacgat taccgttcat cgattctctt gtttgctcca 5880
gactctcagg caatgacctg atagcctttg tagagacctc tcaaaaatag ctaccctctc 5940
cggcatgaat ttatcagcta gaacggttga atatcatatt gatggtgatt tgactgtctc 6000
cggcctttct cacccgtttg aatctttacc tacacattac tcaggcattg catttaaaat 6060
atatgagggt tctaaaaatt tttatccttg cgttgaaata aaggcttctc ccgcaaaagt 6120
attacagggt cataatgttt ttggtacaac cgatttagct ttatgctctg aggctttatt 6180
gcttaatttt gctaattctt tgccttgcct gtatgattta ttggatgttg gaatcgcctg 6240
atgcggtatt ttctccttac gcatctgtgc ggtatttcac accgcatatg gtgcactctc 6300
agtacaatct gctctgatgc cgcatagtta agccagcccc gacacccgcc aacacccgct 6360
gacgcgccct gacgggcttg tctgctcccg gcatccgctt acagacaagc tgtgaccgtc 6420
tccgggagct gcatgtgtca gaggttttca ccgtcatcac cgaaacgcgc gagacgaaag 6480
ggcctcgtga tacgcctatt tttataggtt aatgtcatga taataatggt ttcttagacg 6540
tcaggtggca cttttcgggg aaatgtgcgc ggaaccccta tttgtttatt tttctaaata 6600
cattcaaata tgtatccgct catgagacaa taaccctgat aaatgcttca ataatattga 6660
aaaaggaaga gtatgagtat tcaacatttc cgtgtcgccc ttattccctt ttttgcggca 6720
ttttgccttc ctgtttttgc tcacccagaa acgctggtga aagtaaaaga tgctgaagat 6780
cagttgggtg cacgagtggg ttacatcgaa ctggatctca acagcggtaa gatccttgag 6840
agttttcgcc ccgaagaacg ttttccaatg atgagcactt ttaaagttct gctatgtggc 6900
gcggtattat cccgtattga cgccgggcaa gagcaactcg gtcgccgcat acactattct 6960
cagaatgact tggttgagta ctcaccagtc acagaaaagc atcttacgga tggcatgaca 7020
gtaagagaat tatgcagtgc tgccataacc atgagtgata acactgcggc caacttactt 7080
ctgacaacga tcggaggacc gaaggagcta accgcttttt tgcacaacat gggggatcat 7140

-continued gtaactcgcc ttgatcgttg ggaaccggag ctgaatgaag ccataccaaa cgacgagcgt 7200
gacaccacga tgcctgtagc aatggcaaca acgttgcgca aactattaac tggcgaacta 7260
cttactctag cttcccggca acaattaata gactggatgg aggcggataa agttgcagga 7320
ccacttctgc gctcggccct tccggctggc tggtttattg ctgataaatc tggagccggt 7380
gagcgtgggt ctcgcggtat cattgcagca ctggggccag atggtaagcc ctcccgtatc 7440
gtagttatct acacgacggg gagtcaggca actatggatg aacgaaatag acagatcgct 7500
gagataggtg cctcactgat taagcattgg taactgtcag accaagttta ctcatatata 7560
ctttagattg atttaaaact tcatttttaa tttaaaagga tctaggtgaa gatccttttt 7620
gataatctca tgaccaaaat cccttaacgt gagttttcgt tccactgagc gtcagacccc 7680
gtagaaaaga tcaaaggatc ttcttgagat cctttttttc tgcgcgtaat ctgctgcttg 7740
caaacaaaaa aaccaccgct accagcggtg gtttgtttgc cggatcaaga gctaccaact 7800
ctttttccga aggtaactgg cttcagcaga gcgcagatac caaatactgt ccttctagtg 7860
tagccgtagt taggccacca cttcaagaac tctgtagcac cgcctacata cctcgctctg 7920
ctaatcctgt taccagtggc tgctgccagt ggcgataagt cgtgtcttac cgggttggac 7980
tcaagacgat agttaccgga taaggcgcag cggtcgggct gaacgggggg ttcgtgcaca 8040
cagcccagct tggagcgaac gacctacacc gaactgagat acctacagcg tgagctatga 8100
gaaagcgcca cgcttcccga agggagaaag gcggacaggt atccggtaag cggcagggtc 8160
ggaacaggag agcgcacgag ggagcttcca gggggaaacg cctggtatct ttatagtcct 8220
gtcgggtttc gccacctctg acttgagcgt cgatttttgt gatgctcgtc aggggggcgg 8280
agcctatgga aaaacgccag caacgcggcc tttttacggt tcctggcctt ttgctggcct 8340
tttgctcaca tgttctttcc tgcgttatcc cctgattctg tggataaccg tattaccgcc 8400
tttgagtgag ctgataccgc tcgccgcagc cgaacgaccg agcgcagcga gtcagtgagc 8460
gaggaagcgg aagagcgccc aatacgcaaa ccgcctctcc ccgcgcgttg gccgattcat 8520
taatg 8525

<210> SEQ ID NO 28
<211> LENGTH: 8118
<212> TYPE: DNA
<213> ORGANISM: Artificial
<220> FEATURE:
<223> OTHER INFORMATION: AAV donor template

<400> SEQUENCE: 28
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctttttt ccttagaaac cactgctaac tgaaagagac 180
taagatttgt cccgtcaaaa atcctggacc tatgcctaaa acacatttca caatccctga 240
acttttcaaa aattggtaca tgctttagct ttaaactaca ggcctcactg gagctagaga 300
caagaaggta aaaaacggct gacaaaagaa gtcctggtat cctctatgat gggagaagga 360
aactagctaa agggaagaat aaattagaga aaaactggaa tgactgaatc ggaacaaggc 420
aaaggctata aaaaaaatta gcagtatcct cttgggggcc ccttccccac actatctcaa 480
tgcaaatatc tgtctgaaac ggtccctggc taaactccac ccatgggttg gccagccttg 540
ccttgacaag gcaaacttga ccaatagtct tagagtatcc agtgaggcca ggggccggcg 600

-continued

```
gctggctagg gatgaagaat aaaaggaagc acccttcagc agttccacac actcgcttct    660
ggaacgtctg aggttatcaa taagctccta gtccagacgc catggtgcac ctgactcctg    720
aggagaagtc tgccgttact gccctgtggg gcaaggtgaa cgtggatgaa gttggtggtg    780
aggccctggg caggttggta tcaaggttac aagacaggtt taaggagacc aatagaaact    840
gggcatgtgg agacagagaa gactcttggg tttctgatag gcactgactc tctctgccta    900
ttggtctatt ttcccaccct taggctgctg gtggtctacc cttggaccca gaggttcttt    960
gagtcctttg gggatctgtc cactcctgat gctgttatgg gcaaccctaa ggtgaaggct   1020
catggcaaga aagtgctcgg tgcctttagt gatggcctgg ctcacctgga caacctcaag   1080
ggcacctttg cccagctgag tgagctgcac tgtgacaagc tgcacgtgga tcctgagaac   1140
ttcagggtga gtctatggga cccttgatgt tttctttccc cttcttttct atggttaagt   1200
tcatgtcata ggaaggggag aagtaacagg gtacacatat tgaccaaatc agggtaattt   1260
tgcatttgta attttaaaaa atgctttctt cttttaatat actttttgt ttatcttatt   1320
tctaatactt tccctaatct ctttctttca gggcaataat gatacaatgt atcatgcctc   1380
tttgcaccat tctaaagaat aacagtgata atttctgggt taaggcaata gcaatatttc   1440
tgcatataaa tatttctgca tataaattgt aactgatgta agaggtttca tattgctaat   1500
agcagctaca atccagctac cattctgctt ttattttatg gttgggataa ggctggatta   1560
ttctgagtcc aagctaggcc cttttgctaa tcatgttcat acctcttatc ttcctcccac   1620
agctcctggg caacgtgctg gtctgtgtgc tggcccatca ctttggcaaa gaattcaccc   1680
caccagtgca ggctgcctat cagaaagtgg tggctggtgt ggctaatgcc ctggcccaca   1740
agtatcacta agctcgcttt cttgctgtcc aatttctatt aaaggttcct ttgttcccta   1800
agtccaacta ctaaactggg ggatattatg aagggccttg agcatctgga ttctgcctaa   1860
taaaaaacat ttattttcat tgcaatgatg tatttaaatt atttctgaat attttactaa   1920
aaagggaatg tgggaggtca gtgcatttaa aacataaaga aatgaagagc tagttcaaac   1980
cttgggaaaa tacactatat cttaaactcc atgaaagaag gtgaggctgc aaacagctaa   2040
tgcacattgg caacagcccc tgatgcctat gccttattca tccctcagaa aaggattcaa   2100
gtagaggctt gatttggagg ttaaagtttt gctatgctgt attttacatt acttattgtt   2160
ttagctgtcc tcatgaatgt cttttcacta cccatttgct tatcctgcat ctctcagcct   2220
tgactccact cagttctctt gcttagagat accacctttc ccctgaagtg ttccttccat   2280
gttttacggc gagatggttt ctcctcgcct ggccactcag ccttagttgt ctctgttgtc   2340
ttatagaggt ctacttgaag aaggaaaaac agggggcatg gtttgactgt cctgtgagcc   2400
cttcttccct gcctccccca ctcacagtga cccggaatct gcagtgctag tctcccggaa   2460
ctatcactct ttcacagtct gctttggaag gactgggctt agtatgaaaa gttaggactg   2520
agaagaattt gaaagggggc tttttgtagc ttgatattca ctactgtctt attaccctat   2580
cataggccca ccccaaatgg aagtcccatt cttcctcagg atgtttaaga ttagcattca   2640
ggaagagatc agaggtctgc tggctccctt atcatgtccc ttatggtgct tctggctctg   2700
cagttattag catagtgtta ccatcaacca ccttaacttc atttttctta ttcaatacct   2760
agccgcggga acagagaaac aggagaatat gggccaaaca ggatatctgt ggtaagcagt   2820
tcctgccccg gctcagggcc aagaacagtt ggaacagcag aatatgggcc aaacaggata   2880
tctgtggtaa gcagttcctg ccccggctca gggccaagaa cagatggtcc ccagatgcgg   2940
tcccgccctc agcagtttct agagaaccat cagatgtttc cagggtgccc caaggacctg   3000
```

-continued

```
aaatgaccct gtgccttatt tgaactaacc aatcagttcg cttctcgctt ctgttcgcgc   3060
gcttctgctc cccgagctct atataagcag agctcgttta gtgaaccgtc agatcgcggc   3120
cgcgccgcca ccatggtgag caagggcgag gagctgttca ccggggtggt gcccatcctg   3180
gtcgagctgg acggcgacgt aaacggccac aagttcagcg tgtccggcga gggcgagggc   3240
gatgccacct acggcaagct gaccctgaag ttcatctgca ccaccggcaa gctgcccgtg   3300
ccctggccca ccctcgtgac caccctgacc tacggcgtgc agtgcttcag ccgctacccc   3360
gaccacatga agcagcacga cttcttcaag tccgccatgc ccgaaggcta cgtccaggag   3420
cgcaccatct tcttcaagga cgacggcaac tacaagaccc gcgccgaggt gaagttcgag   3480
ggcgacaccc tggtgaaccg catcgagctg aagggcatcg acttcaagga ggacggcaac   3540
atcctggggc acaagctgga gtacaactac aacagccaca acgtctatat catggccgac   3600
aagcagaaga acggcatcaa ggtgaacttc aagatccgcc acaacatcga ggacggcagc   3660
gtgcagctcg ccgaccacta ccagcagaac acccccatcg gcgacggccc cgtgctgctg   3720
cccgacaacc actacctgag cacccagtcc gccctgagca aagaccccaa cgagaagcgc   3780
gatcacatgg tcctgctgga gttcgtgacc gccgccggga tcactctcgg catggacgag   3840
ctgtacaagt aagctttatt tgtgaaattt gtgatgctat tgctttattt gtaaccatta   3900
taagctgcaa taaacaagtt aacaacaaca attgcattca ttttatgttt caggttcagg   3960
gggagatgtg ggaggttttt taaagccctg caggatgggt catttcacag aggaggacaa   4020
ggctactatc acaagcctgt ggggcaaggt gaatgtggaa gatgctggag gagaaaccct   4080
gggaaggtag gctctggtga ccaggacaag ggagggaagg aaggaccctg tgcctggcaa   4140
aagtccaggt cgcttctcag gatttgtggc accttctgac tgtcaaactg ttcttgtcaa   4200
tctcacaggc tcctggttgt ctacccatgg acccagaggt tctttgacag ctttggcaac   4260
ctgtcctctg cctctgccat catgggcaac cccaaagtca aggcacatgg caagaaggtg   4320
ctgacttcct tgggagatgc cacaaagcac ctggatgatc tcaagggcac ctttgcccag   4380
ctgagtgaac tgcagtcgac aggaacccct agtgatggag ttggccactc cctctctgcg   4440
cgctcgctcg ctcactgagg ccgggcgacc aaaggtcgcc cgacgcccgg gctttgcccg   4500
ggcggcctca gtgagcgagc gagcgcgcag ctggcgtaat agcgaagagg cccgcaccga   4560
tcgcccttcc caacagttgc gcagcctgaa tggcgaatgg cgattccgtt gcaatggctg   4620
gcggtaatat tgttctggat attaccagca aggccgatag tttgagttct tctactcagg   4680
caagtgatgt tattactaat caaagaagta ttgcgacaac ggttaatttg cgtgatggac   4740
agactctttt actcggtggc ctcactgatt ataaaaacac ttctcaggat tctggcgtac   4800
cgttcctgtc taaaatccct ttaatcggcc tcctgtttag ctcccgctct gattctaacg   4860
aggaaagcac gttatacgtg ctcgtcaaag caaccatagt acgcgccctg tagcggcgca   4920
ttaagcgcgg cgggtgtggt ggttacgcgc agcgtgaccg ctacacttgc cagcgcccta   4980
gcgcccgctc ctttcgcttt cttcccttcc tttctcgcca cgttcgccgg ctttccccgt   5040
caagctctaa atcgggggct ccctttaggg ttccgattta gtgctttacg gcacctcgac   5100
cccaaaaaac ttgattaggg tgatggttca cgtagtgggc catcgccctg atagacggtt   5160
tttcgccctt tgacgttgga gtccacgttc tttaatagtg gactcttgtt ccaaactgga   5220
acaacactca accctatctc ggtctattct tttgatttat aagggatttt gccgatttcg   5280
gcctattggt taaaaaatga gctgatttaa caaaaattta acgcgaattt taacaaaata   5340
```

-continued ttaacgttta caatttaaat atttgcttat acaatcttcc tgtttttggg gcttttctga 5400
ttatcaaccg gggtacatat gattgacatg ctagttttac gattaccgtt catcgattct 5460
cttgtttgct ccagactctc aggcaatgac ctgatagcct ttgtagagac ctctcaaaaa 5520
tagctaccct ctccggcatg aatttatcag ctagaacggt tgaatatcat attgatggtg 5580
atttgactgt ctccggcctt tctcacccgt ttgaatcttt acctacacat tactcaggca 5640
ttgcatttaa aatatatgag ggttctaaaa atttttatcc ttgcgttgaa ataaaggctt 5700
ctcccgcaaa agtattacag ggtcataatg tttttggtac aaccgattta gctttatgct 5760
ctgaggcttt attgcttaat tttgctaatt ctttgccttg cctgtatgat ttattggatg 5820
ttggaatcgc ctgatgcggt attttctcct tacgcatctg tgcggtattt cacaccgcat 5880
atggtgcact ctcagtacaa tctgctctga tgccgcatag ttaagccagc cccgacaccc 5940
gccaacaccc gctgacgcgc cctgacgggc ttgtctgctc ccggcatccg cttacagaca 6000
agctgtgacc gtctccggga gctgcatgtg tcagaggttt tcaccgtcat caccgaaacg 6060
cgcgagacga aagggcctcg tgatacgcct atttttatag gttaatgtca tgataataat 6120
ggtttcttag acgtcaggtg gcacttttcg gggaaatgtg cgcggaaccc ctatttgttt 6180
atttttctaa atacattcaa atatgtatcc gctcatgaga caataaccct gataaatgct 6240
tcaataatat tgaaaaagga agagtatgag tattcaacat ttccgtgtcg cccttattcc 6300
cttttttgcg gcattttgcc ttcctgtttt tgctcaccca gaaacgctgg tgaaagtaaa 6360
agatgctgaa gatcagttgg gtgcacgagt gggttacatc gaactggatc tcaacagcgg 6420
taagatcctt gagagttttc gccccgaaga acgttttcca atgatgagca cttttaaagt 6480
tctgctatgt ggcgcggtat tatcccgtat tgacgccggg caagagcaac tcggtcgccg 6540
catacactat tctcagaatg acttggttga gtactcacca gtcacagaaa agcatcttac 6600
ggatggcatg acagtaagag aattatgcag tgctgccata accatgagtg ataacactgc 6660
ggccaactta cttctgacaa cgatcggagg accgaaggag ctaaccgctt ttttgcacaa 6720
catgggggat catgtaactc gccttgatcg ttgggaaccg gagctgaatg aagccatacc 6780
aaacgacgag cgtgacacca cgatgcctgt agcaatggca acaacgttgc gcaaactatt 6840
aactggcgaa ctacttactc tagcttcccg gcaacaatta atagactgga tggaggcgga 6900
taaagttgca ggaccacttc tgcgctcggc ccttccggct ggctggttta ttgctgataa 6960
atctggagcc ggtgagcgtg ggtctcgcgg tatcattgca gcactggggc cagatggtaa 7020
gccctcccgt atcgtagtta tctacacgac ggggagtcag gcaactatgg atgaacgaaa 7080
tagacagatc gctgagatag gtgcctcact gattaagcat tggtaactgt cagaccaagt 7140
ttactcatat atactttaga ttgatttaaa acttcatttt taatttaaaa ggatctaggt 7200
gaagatcctt tttgataatc tcatgaccaa aatcccttaa cgtgagtttt cgttccactg 7260
agcgtcagac cccgtagaaa agatcaaagg atcttcttga gatccttttt ttctgcgcgt 7320
aatctgctgc ttgcaaacaa aaaaaccacc gctaccagcg gtggtttgtt tgccggatca 7380
agagctacca actctttttc cgaaggtaac tggcttcagc agagcgcaga taccaaatac 7440
tgtccttcta gtgtagccgt agttaggcca ccacttcaag aactctgtag caccgcctac 7500
atacctcgct ctgctaatcc tgttaccagt ggctgctgcc agtggcgata agtcgtgtct 7560
taccgggttg gactcaagac gatagttacc ggataaggcg cagcggtcgg gctgaacggg 7620
gggttcgtgc acacagccca gcttggagcg aacgacctac accgaactga gatacctaca 7680
gcgtgagcta tgagaaagcg ccacgcttcc cgaagggaga aaggcggaca ggtatccggt 7740
aagcggcagg gtcggaacag gagagcgcac gagggagctt ccagggggaa acgcctggta 7800
tctttatagt cctgtcgggt ttcgccacct ctgacttgag cgtcgatttt tgtgatgctc 7860
gtcagggggg cggagcctat ggaaaaacgc cagcaacgcg gcctttttac ggttcctggc 7920
cttttgctgg ccttttgctc acatgttctt tcctgcgtta tcccctgatt ctgtggataa 7980
ccgtattacc gcctttgagt gagctgatac cgctcgccgc agccgaacga ccgagcgcag 8040
cgagtcagtg agcgaggaag cggaagagcg cccaatacgc aaaccgcctc tccccgcgcg 8100
ttggccgatt cattaatg 8118

<210> SEQ ID NO 29
<211> LENGTH: 7963
<212> TYPE: DNA
<213> ORGANISM: Artificial
<220> FEATURE:
<223> OTHER INFORMATION: AAV donor template

<400> SEQUENCE: 29
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtagccatgc 180
tctagcggcc tcggcctctg cataaataaa aaaaattagt cagccatgag cttggacgcg 240
tagatcttga aacagtcatg atttatttca aataggtacg gataagtaga tattgaggta 300
agcattaggt cttatattat gtaacactaa tctattactg cgctgaaact gtggctttat 360
agaaattgtt ttcactgcac tattgagaaa ttaagagata atggcaaaag tcacaaagag 420
tatattcaaa aagaagtata gcactttttc cttagaaacc actgctaact gaaagagact 480
aagatttgtc ccgtcaaaaa tcctggacct atgcctaaaa cacatttcac aatccctgaa 540
cttttcaaaa attggtacat gctttagctt taaactacag gcctcactgg agctagagac 600
aagaaggtaa aaaacggctg acaaaagaag tcctggtatc ctctatgatg ggagaaggaa 660
actagctaaa gggaagaata aattagagaa aaactggaat gactgaatcg gaacaaggca 720
aaggctataa aaaaaattag cagtatcctc ttgggggccc cttccccaca ctatctcaat 780
gcaaatatct gtctgaaacg gtccctggct aaactccacc catgggttgg ccagccttgc 840
cttgacaagg caaacttgac caatagtctt agagtatcca gtgaggccag gggccggcgg 900
ctggctaggg atgaagaata aaaggaagca cccttcagca gttccacaca ctcgcttctg 960
gaacgtctga ggttatcaat aagctcctag tccagacgcc atggtgcacc tgactcctga 1020
ggagaagtct gccgttactg ccctgtgggg caaggtgaac gtggatgaag ttggtggtga 1080
ggccctgggc aggttggtat caaggttaca agacaggttt aaggagacca atagaaactg 1140
ggcatgtgga gacagagaag actcttgggt ttctgatagg cactgactct ctctgcctat 1200
tggtctattt tcccaccctt aggctgctgg tggtctaccc ttggacccag aggttctttg 1260
agtcctttgg ggatctgtcc actcctgatg ctgttatggg caaccctaag gtgaaggctc 1320
atggcaagaa agtgctcggt gcctttagtg atggcctggc tcacctggac aacctcaagg 1380
gcacctttgc ccagctgagt gagctgcact gtgacaagct gcacgtggat cctgagaact 1440
tcagggtgag tctatgggac ccttgatgtt ttctttcccc ttcttttcta tggttaagtt 1500
catgtcatag gaaggggaga agtaacaggg tacacatatt gaccaaatca gggtaatttt 1560
gcatttgtaa ttttaaaaaa tgctttcttc ttttaatata cttttttgtt tatcttattt 1620

```
ctaatacttt ccctaatctc tttctttcag ggcaataatg atacaatgta tcatgcctct   1680
ttgcaccatt ctaaagaata acagtgataa tttctgggtt aaggcaatag caatatttct   1740
gcatataaat atttctgcat ataaattgta actgatgtaa gaggtttcat attgctaata   1800
gcagctacaa tccagctacc attctgcttt tattttatgg ttgggataag gctggattat   1860
tctgagtcca agctaggccc ttttgctaat catgttcata cctcttatct tcctcccaca   1920
gctcctgggc aacgtgctgg tctgtgtgct ggcccatcac tttggcaaag aattcacccc   1980
accagtgcag gctgcctatc agaaagtggt ggctggtgtg gctaatgccc tggcccacaa   2040
gtatcactaa gctcgctttc ttgctgtcca atttctatta aaggttcctt tgttccctaa   2100
gtccaactac taaactgggg gatattatga agggccttga gcatctggat tctgcctaat   2160
aaaaaacatt tattttcatt gctgcagtgc tagtctcccg gaactatcac tctttcacag   2220
tctgctttgg aaggactggg cttagtatga aaagttagga ctgagaagaa tttgaaaggg   2280
ggctttttgt agcttgatat tcactactgt cttattaccc tatcataggc ccaccccaaa   2340
tggaagtccc attcttcctc aggatgttta agattagcat tcaggaagag atcagaggtc   2400
tgctggctcc cttatcatgt cccttatggt gcttctggct ctgcaccgcg ggaacagaga   2460
aacaggagaa tatgggccaa acaggatatc tgtggtaagc agttcctgcc ccggctcagg   2520
gccaagaaca gttggaacag cagaatatgg gccaaacagg atatctgtgg taagcagttc   2580
ctgccccggc tcagggccaa gaacagatgg tccccagatg cggtcccgcc ctcagcagtt   2640
tctagagaac catcagatgt ttccagggtg ccccaaggac ctgaaatgac cctgtgcctt   2700
atttgaacta accaatcagt tcgcttctcg cttctgttcg cgcgcttctg ctccccgagc   2760
tctatataag cagagctcgt ttagtgaacc gtcagatcgc ggccgcgccg ccaccatggt   2820
gagcaagggc gaggagctgt tcaccggggt ggtgcccatc ctggtcgagc tggacggcga   2880
cgtaaacggc cacaagttca gcgtgtccgg cgagggcgag ggcgatgcca cctacggcaa   2940
gctgaccctg aagttcatct gcaccaccgg caagctgccc gtgccctggc ccaccctcgt   3000
gaccaccctg acctacggcg tgcagtgctt cagccgctac cccgaccaca tgaagcagca   3060
cgacttcttc aagtccgcca tgcccgaagg ctacgtccag gagcgcacca tcttcttcaa   3120
ggacgacggc aactacaaga cccgcgccga ggtgaagttc gagggcgaca ccctggtgaa   3180
ccgcatcgag ctgaagggca tcgacttcaa ggaggacggc aacatcctgg ggcacaagct   3240
ggagtacaac tacaacagcc acaacgtcta tatcatggcc gacaagcaga agaacggcat   3300
caaggtgaac ttcaagatcc gccacaacat cgaggacggc agcgtgcagc tcgccgacca   3360
ctaccagcag aacaccccca tcggcgacgg ccccgtgctg ctgcccgaca accactacct   3420
gagcacccag tccgccctga gcaaagaccc caacgagaag cgcgatcaca tggtcctgct   3480
ggagttcgtg accgccgccg ggatcactct cggcatggac gagctgtaca aggagggcag   3540
aggaagtctt ctaacatgcg gtgacgtgga ggagaatccg ggcccccctg caggaacttc   3600
aaggtgagtc caggagatgt ttcagccctg ttgcctttag tctcgaggca acttagacaa   3660
cggagtattg atctgagcac agcagggtgt gagctgtttg aagatactgg ggttgggggt   3720
gaagaaactg cagaggacta actgggctga gacccagtgg taatgtttta gggcctaagg   3780
agtgcctcta aaaatctaga tggacaattt tgactttgag aaaagagagg tggaaatgag   3840
gaaaatgact tttctttatt agattccagt agaaagaact ttcatctttc cctcattttt   3900
gttgttttaa aacatctatc tggaggcagg acaagtatgg tcgttaaaaa gatgcaggca   3960
gaaggcatat attggctcag tcaaagtggg gaactttggt ggccaaacat acattgctaa   4020
```

```
ggctattcct atatcagctg gacacatata aaatgctgct aatgcttcat tacaaactta   4080
tatcctttaa ttccagatgg gggcaaagta tgtccagggg tgaggaacaa ttgaaacatt   4140
tgggctggag tagattttga aagtcagctc tgtgtgtgtg tgtgtgtgtg cgcgcgcgcg   4200
tgtcgacgta gataagtagc atggcgggtt aatcattaac tacaaggaac ccctagtgat   4260
ggagttggcc actccctctc tgcgcgctcg ctcgctcact gaggccgggc gaccaaaggt   4320
cgcccgacgc ccgggctttg cccgggcggc ctcagtgagc gagcgagcgc gccagctggc   4380
gtaatagcga agaggcccgc accgatcgcc cttcccaaca gttgcgcagc ctgaatggcg   4440
aatggcgatt ccgttgcaat ggctggcggt aatattgttc tggatattac cagcaaggcc   4500
gatagtttga gttcttctac tcaggcaagt gatgttatta ctaatcaaag aagtattgcg   4560
acaacggtta atttgcgtga tggacagact cttttactcg gtggcctcac tgattataaa   4620
aacacttctc aggattctgg cgtaccgttc ctgtctaaaa tccctttaat cggcctcctg   4680
tttagctccc gctctgattc taacgaggaa agcacgttat acgtgctcgt caaagcaacc   4740
atagtacgcg ccctgtagcg gcgcattaag cgcggcgggt gtggtggtta cgcgcagcgt   4800
gaccgctaca cttgccagcg ccctagcgcc cgctcctttc gctttcttcc cttcctttct   4860
cgccacgttc gccggctttc cccgtcaagc tctaaatcgg gggctccctt tagggttccg   4920
atttagtgct ttacggcacc tcgaccccaa aaaacttgat tagggtgatg gttcacgtag   4980
tgggccatcg ccctgataga cggtttttcg ccctttgacg ttggagtcca cgttctttaa   5040
tagtggactc ttgttccaaa ctggaacaac actcaaccct atctcggtct attcttttga   5100
tttataaggg attttgccga tttcggccta ttggttaaaa aatgagctga tttaacaaaa   5160
atttaacgcg aattttaaca aaatattaac gtttacaatt taaatatttg cttatacaat   5220
cttcctgttt ttggggcttt tctgattatc aaccggggta catatgattg acatgctagt   5280
tttacgatta ccgttcatcg attctcttgt ttgctccaga ctctcaggca atgacctgat   5340
agcctttgta gagacctctc aaaaatagct accctctccg gcatgaattt atcagctaga   5400
acggttgaat atcatattga tggtgatttg actgtctccg gcctttctca cccgtttgaa   5460
tctttaccta cacattactc aggcattgca tttaaaatat atgagggttc taaaaatttt   5520
tatccttgcg ttgaaataaa ggcttctccc gcaaaagtat tacagggtca taatgttttt   5580
ggtacaaccg atttagcttt atgctctgag gctttattgc ttaattttgc taattctttg   5640
ccttgcctgt atgatttatt ggatgttgga atcgcctgat gcggtatttt ctccttacgc   5700
atctgtgcgg tatttcacac cgcatatggt gcactctcag tacaatctgc tctgatgccg   5760
catagttaag ccagccccga cacccgccaa cacccgctga cgcgccctga cgggcttgtc   5820
tgctcccggc atccgcttac agacaagctg tgaccgtctc cgggagctgc atgtgtcaga   5880
ggttttcacc gtcatcaccg aaacgcgcga gacgaaaggg cctcgtgata cgcctatttt   5940
tataggttaa tgtcatgata ataatggttt cttagacgtc aggtggcact tttcggggaa   6000
atgtgcgcgg aacccctatt tgtttatttt tctaaataca ttcaaatatg tatccgctca   6060
tgagacaata accctgataa atgcttcaat aatattgaaa aaggaagagt atgagtattc   6120
aacatttccg tgtcgccctt attccctttt ttgcggcatt ttgccttcct gtttttgctc   6180
acccagaaac gctggtgaaa gtaaaagatg ctgaagatca gttgggtgca cgagtgggtt   6240
acatcgaact ggatctcaac agcggtaaga tccttgagag ttttcgcccc gaagaacgtt   6300
ttccaatgat gagcactttt aaagttctgc tatgtggcgc ggtattatcc cgtattgacg   6360
```

-continued ccgggcaaga gcaactcggt cgccgcatac actattctca gaatgacttg gttgagtact 6420
caccagtcac agaaaagcat cttacggatg gcatgacagt aagagaatta tgcagtgctg 6480
ccataaccat gagtgataac actgcggcca acttacttct gacaacgatc ggaggaccga 6540
aggagctaac cgcttttttg cacaacatgg gggatcatgt aactcgcctt gatcgttggg 6600
aaccggagct gaatgaagcc ataccaaacg acgagcgtga caccacgatg cctgtagcaa 6660
tggcaacaac gttgcgcaaa ctattaactg gcgaactact tactctagct tcccggcaac 6720
aattaataga ctggatggag gcggataaag ttgcaggacc acttctgcgc tcggcccttc 6780
cggctggctg gtttattgct gataaatctg gagccggtga gcgtgggtct cgcggtatca 6840
ttgcagcact ggggccagat ggtaagccct cccgtatcgt agttatctac acgacgggga 6900
gtcaggcaac tatggatgaa cgaaatagac agatcgctga gataggtgcc tcactgatta 6960
agcattggta actgtcagac caagtttact catatatact ttagattgat ttaaaacttc 7020
atttttaatt taaaaggatc taggtgaaga tcctttttga taatctcatg accaaaatcc 7080
cttaacgtga gttttcgttc cactgagcgt cagaccccgt agaaaagatc aaaggatctt 7140
cttgagatcc tttttttctg cgcgtaatct gctgcttgca aacaaaaaaa ccaccgctac 7200
cagcggtggt ttgtttgccg gatcaagagc taccaactct ttttccgaag gtaactggct 7260
tcagcagagc gcagatacca aatactgtcc ttctagtgta gccgtagtta ggccaccact 7320
tcaagaactc tgtagcaccg cctacatacc tcgctctgct aatcctgtta ccagtggctg 7380
ctgccagtgg cgataagtcg tgtcttaccg ggttggactc aagacgatag ttaccggata 7440
aggcgcagcg gtcgggctga acggggggtt cgtgcacaca gcccagcttg gagcgaacga 7500
cctacaccga actgagatac ctacagcgtg agctatgaga aagcgccacg cttcccgaag 7560
ggagaaaggc ggacaggtat ccggtaagcg gcagggtcgg aacaggagag cgcacgaggg 7620
agcttccagg gggaaacgcc tggtatcttt atagtcctgt cgggtttcgc cacctctgac 7680
ttgagcgtcg atttttgtga tgctcgtcag gggggcggag cctatggaaa aacgccagca 7740
acgcggcctt tttacggttc ctggcctttt gctggccttt tgctcacatg ttctttcctg 7800
cgttatcccc tgattctgtg gataaccgta ttaccgcctt tgagtgagct gataccgctc 7860
gccgcagccg aacgaccgag cgcagcgagt cagtgagcga ggaagcggaa gagcgcccaa 7920
tacgcaaacc gcctctcccc gcgcgttggc cgattcatta atg 7963

<210> SEQ ID NO 30
<211> LENGTH: 7553
<212> TYPE: DNA
<213> ORGANISM: Artificial
<220> FEATURE:
<223> OTHER INFORMATION: AAV donor template

<400> SEQUENCE: 30
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
cttccttaga aaccactgct aactgaaaga gactaagatt tgtcccgtca aaaatcctgg 240
acctatgcct aaaacacatt tcacaatccc tgaacttttc aaaaattggt acatgcttta 300
gctttaaact acaggcctca ctggagctag agacaagaag gtaaaaaacg gctgacaaaa 360
gaagtcctgg tatcctctat gatgggagaa ggaaactagc taaagggaag aataaattag 420
agaaaaactg gaatgactga atcggaacaa ggcaaaggct ataaaaaaaa ttagcagtat 480
cctcttgggg gccccttccc cacactatct caatgcaaat atctgtctga aacggtccct 540
ggctaaactc cacccatggg ttggccagcc ttgccttgac aaggcaaact tgaccaatag 600
tcttagagta tccagtgagg ccaggggccg gcggctggct agggatgaag aataaaagga 660
agcacccttc agcagttcca cacactcgct tctggaacgt ctgaggttat caataagctc 720
ctagtccaga cgccatggtg cacctgactc ctgaggagaa gtctgccgtt actgccctgt 780
ggggcaaggt gaacgtggat gaagttggtg gtgaggccct gggcaggttg gtatcaaggt 840
tacaagacag gtttaaggag accaatagaa actgggcatg tggagacaga gaagactctt 900
gggtttctga taggcactga ctctctctgc ctattggtct attttcccac ccttaggctg 960
ctggtggtct acccttggac ccagaggttc tttgagtcct ttggggatct gtccactcct 1020
gatgctgtta tgggcaaccc taaggtgaag gctcatggca agaaagtgct cggtgccttt 1080
agtgatggcc tggctcacct ggacaacctc aagggcacct ttgcccagct gagtgagctg 1140
cactgtgaca agctgcacgt ggatcctgag aacttcaggg tgagtctatg ggacccttga 1200
tgttttcttt ccccttcttt tctatggtta agttcatgtc ataggaaggg gagaagtaac 1260
agggtacaca tattgaccaa atcagggtaa ttttgcattt gtaattttaa aaaatgcttt 1320
cttcttttaa tatacttttt tgtttatctt atttctaata ctttccctaa tctctttctt 1380
tcagggcaat aatgatacaa tgtatcatgc ctctttgcac cattctaaag aataacagtg 1440
ataatttctg ggttaaggca atagcaatat ttctgcatat aaatatttct gcatataaat 1500
tgtaactgat gtaagaggtt tcatattgct aatagcagct acaatccagc taccattctg 1560
cttttatttt atggttggga taaggctgga ttattctgag tccaagctag gccctttttgc 1620
taatcatgtt catacctctt atcttcctcc cacagctcct gggcaacgtg ctggtctgtg 1680
tgctggccca tcactttggc aaagaattca ccccaccagt gcaggctgcc tatcagaaag 1740
tggtggctgg tgtggctaat gccctggccc acaagtatca ctaagctcgc tttcttgctg 1800
tccaatttct attaaaggtt cctttgttcc ctaagtccaa ctactaaact gggggatatt 1860
atgaagggcc ttgagcatct ggattctgcc taataaaaaa catttatttt cattgcaatg 1920
atgtatttaa attatttctg aatattttac taaaaaggga atgtgggagg ttgcagtgct 1980
agtctcccgg aactatcact ctttcacagt ctgctttgga aggactgggc ttagtatgaa 2040
aagttaggac tgagaagaat ttgaaagggg gctttttgta gcttgatatt cactactgtc 2100
ttattaccct atcataggcc caccccaaat ggaagtccca ttcttcctca ggatgtttaa 2160
gattagcatt caggaagaga tcagaggtct gctggctccc ttatcatgtc ccttatggtg 2220
cttctggctc tgcaccgcgg gaacagagaa acaggagaat atgggccaaa caggatatct 2280
gtggtaagca gttcctgccc cggctcaggg ccaagaacag ttggaacagc agaatatggg 2340
ccaaacagga tatctgtggt aagcagttcc tgccccggct cagggccaag aacagatggt 2400
ccccagatgc ggtcccgccc tcagcagttt ctagagaacc atcagatgtt tccagggtgc 2460
cccaaggacc tgaaatgacc ctgtgcctta tttgaactaa ccaatcagtt cgcttctcgc 2520
ttctgttcgc gcgcttctgc tccccgagct ctatataagc agagctcgtt tagtgaaccg 2580
tcagatcgcg gccgcgccgc caccatggtg agcaagggcg aggagctgtt caccggggtg 2640
gtgcccatcc tggtcgagct ggacggcgac gtaaacggcc acaagttcag cgtgtccggc 2700
gagggcgagg gcgatgccac ctacggcaag ctgaccctga agttcatctg caccaccggc 2760
aagctgcccg tgccctggcc caccctcgtg accaccctga cctacggcgt gcagtgcttc 2820

-continued agccgctacc ccgaccacat gaagcagcac gacttcttca agtccgccat gcccgaaggc 2880
tacgtccagg agcgcaccat cttcttcaag gacgacggca actacaagac ccgcgccgag 2940
gtgaagttcg agggcgacac cctggtgaac cgcatcgagc tgaagggcat cgacttcaag 3000
gaggacggca acatcctggg gcacaagctg gagtacaact acaacagcca caacgtctat 3060
atcatggccg acaagcagaa gaacggcatc aaggtgaact tcaagatccg ccacaacatc 3120
gaggacggca gcgtgcagct cgccgaccac taccagcaga acacccccat cggcgacggc 3180
cccgtgctgc tgcccgacaa ccactacctg agcacccagt ccgccctgag caaagacccc 3240
aacgagaagc gcgatcacat ggtcctgctg gagttcgtga ccgccgccgg gatcactctc 3300
ggcatggacg agctgtacaa ggagggcaga ggaagtcttc taacatgcgg tgacgtggag 3360
gagaatccgg gcccccctgc aggaacttca aggtgagtcc aggagatgtt tcagccctgt 3420
tgcctttagt ctcgaggcaa cttagacaac ggagtattga tctgagcaca gcagggtgtg 3480
agctgtttga agatactggg gttgggggtg aagaaactgc agaggactaa ctgggctgag 3540
acccagtggt aatgttttag ggcctaagga gtgcctctaa aaatctagat ggacaatttt 3600
gactttgaga aaagagaggt ggaaatgagg aaaatgactt ttctttatta gattccagta 3660
gaaagaactt tcatctttcc ctcatttttg ttgttttaaa acatctatct ggaggcagga 3720
caagtatggt cgttaaaaag atgcaggcag aaggcatata ttggctcagt caaagtgggg 3780
aactttggtg ggtcgacgta gataagtagc atggcgggtt aatcattaac tacaaggaac 3840
ccctagtgat ggagttggcc actccctctc tgcgcgctcg ctcgctcact gaggccgggc 3900
gaccaaaggt cgcccgacgc ccgggctttg cccgggcggc ctcagtgagc gagcgagcgc 3960
gccagctggc gtaatagcga agaggcccgc accgatcgcc cttcccaaca gttgcgcagc 4020
ctgaatggcg aatggcgatt ccgttgcaat ggctggcggt aatattgttc tggatattac 4080
cagcaaggcc gatagtttga gttcttctac tcaggcaagt gatgttatta ctaatcaaag 4140
aagtattgcg acaacggtta atttgcgtga tggacagact cttttactcg gtggcctcac 4200
tgattataaa aacacttctc aggattctgg cgtaccgttc ctgtctaaaa tccctttaat 4260
cggcctcctg tttagctccc gctctgattc taacgaggaa agcacgttat acgtgctcgt 4320
caaagcaacc atagtacgcg ccctgtagcg gcgcattaag cgcggcgggt gtggtggtta 4380
cgcgcagcgt gaccgctaca cttgccagcg ccctagcgcc cgctcctttc gctttcttcc 4440
cttcctttct cgccacgttc gccggctttc cccgtcaagc tctaaatcgg gggctccctt 4500
tagggttccg atttagtgct ttacggcacc tcgaccccaa aaaacttgat tagggtgatg 4560
gttcacgtag tgggccatcg ccctgataga cggtttttcg ccctttgacg ttggagtcca 4620
cgttctttaa tagtggactc ttgttccaaa ctggaacaac actcaaccct atctcggtct 4680
attcttttga tttataaggg attttgccga tttcggccta ttggttaaaa aatgagctga 4740
tttaacaaaa atttaacgcg aattttaaca aaatattaac gtttacaatt taaatatttg 4800
cttatacaat cttcctgttt ttggggcttt tctgattatc aaccggggta catatgattg 4860
acatgctagt tttacgatta ccgttcatcg attctcttgt ttgctccaga ctctcaggca 4920
atgacctgat agcctttgta gagacctctc aaaaatagct accctctccg gcatgaattt 4980
atcagctaga acggttgaat atcatattga tggtgatttg actgtctccg gcctttctca 5040
cccgtttgaa tctttaccta cacattactc aggcattgca tttaaaatat atgagggttc 5100
taaaaatttt tatccttgcg ttgaaataaa ggcttctccc gcaaaagtat tacagggtca 5160
taatgttttt ggtacaaccg atttagcttt atgctctgag gctttattgc ttaattttgc 5220
taattctttg ccttgcctgt atgatttatt ggatgttgga atcgcctgat gcggtatttt 5280
ctccttacgc atctgtgcgg tatttcacac cgcatatggt gcactctcag tacaatctgc 5340
tctgatgccg catagttaag ccagccccga cacccgccaa cacccgctga cgcgccctga 5400
cgggcttgtc tgctcccggc atccgcttac agacaagctg tgaccgtctc cgggagctgc 5460
atgtgtcaga ggttttcacc gtcatcaccg aaacgcgcga gacgaaaggg cctcgtgata 5520
cgcctatttt tataggttaa tgtcatgata ataatggttt cttagacgtc aggtggcact 5580
tttcggggaa atgtgcgcgg aacccctatt tgtttatttt tctaaataca ttcaaatatg 5640
tatccgctca tgagacaata accctgataa atgcttcaat aatattgaaa aaggaagagt 5700
atgagtattc aacatttccg tgtcgccctt attccctttt ttgcggcatt ttgccttcct 5760
gtttttgctc acccagaaac gctggtgaaa gtaaaagatg ctgaagatca gttgggtgca 5820
cgagtgggtt acatcgaact ggatctcaac agcggtaaga tccttgagag ttttcgcccc 5880
gaagaacgtt ttccaatgat gagcactttt aaagttctgc tatgtggcgc ggtattatcc 5940
cgtattgacg ccgggcaaga gcaactcggt cgccgcatac actattctca gaatgacttg 6000
gttgagtact caccagtcac agaaaagcat cttacggatg gcatgacagt aagagaatta 6060
tgcagtgctg ccataaccat gagtgataac actgcggcca acttacttct gacaacgatc 6120
ggaggaccga aggagctaac cgcttttttg cacaacatgg gggatcatgt aactcgcctt 6180
gatcgttggg aaccggagct gaatgaagcc ataccaaacg acgagcgtga caccacgatg 6240
cctgtagcaa tggcaacaac gttgcgcaaa ctattaactg gcgaactact tactctagct 6300
tcccggcaac aattaataga ctggatggag gcggataaag ttgcaggacc acttctgcgc 6360
tcggcccttc cggctggctg gtttattgct gataaatctg gagccggtga gcgtgggtct 6420
cgcggtatca ttgcagcact ggggccagat ggtaagccct cccgtatcgt agttatctac 6480
acgacgggga gtcaggcaac tatggatgaa cgaaatagac agatcgctga gataggtgcc 6540
tcactgatta agcattggta actgtcagac caagtttact catatatact ttagattgat 6600
ttaaaacttc atttttaatt taaaaggatc taggtgaaga tcctttttga taatctcatg 6660
accaaaatcc cttaacgtga gttttcgttc cactgagcgt cagaccccgt agaaaagatc 6720
aaaggatctt cttgagatcc tttttttctg cgcgtaatct gctgcttgca aacaaaaaaa 6780
ccaccgctac cagcggtggt ttgtttgccg gatcaagagc taccaactct ttttccgaag 6840
gtaactggct tcagcagagc gcagatacca aatactgtcc ttctagtgta gccgtagtta 6900
ggccaccact tcaagaactc tgtagcaccg cctacatacc tcgctctgct aatcctgtta 6960
ccagtggctg ctgccagtgg cgataagtcg tgtcttaccg ggttggactc aagacgatag 7020
ttaccggata aggcgcagcg gtcgggctga acggggggtt cgtgcacaca gcccagcttg 7080
gagcgaacga cctacaccga actgagatac ctacagcgtg agctatgaga aagcgccacg 7140
cttcccgaag ggagaaaggc ggacaggtat ccggtaagcg gcagggtcgg aacaggagag 7200
cgcacgaggg agcttccagg gggaaacgcc tggtatcttt atagtcctgt cgggtttcgc 7260
cacctctgac ttgagcgtcg atttttgtga tgctcgtcag gggggcggag cctatggaaa 7320
aacgccagca acgcggcctt tttacggttc ctggcctttt gctggccttt tgctcacatg 7380
ttctttcctg cgttatcccc tgattctgtg gataaccgta ttaccgcctt tgagtgagct 7440
gataccgctc gccgcagccg aacgaccgag cgcagcgagt cagtgagcga ggaagcggaa 7500
gagcgcccaa tacgcaaacc gcctctcccc gcgcgttggc cgattcatta atg 7553

<210> SEQ ID NO 31
<211> LENGTH: 8029
<212> TYPE: DNA
<213> ORGANISM: Artificial
<220> FEATURE:
<223> OTHER INFORMATION: AAV donor template

<400> SEQUENCE: 31
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
cttgaaacag tcatgattta tttcaaatag gtacggataa gtagatattg aggtaagcat 240
taggtcttat attatgtaac actaatctat tactgcgctg aaactgtggc tttatagaaa 300
ttgttttcac tgcactattg agaaattaag agataatggc aaaagtcaca aagagtatat 360
tcaaaaagaa gtatagcact tttttcttag aaaccactgc taactgaaag agactaagat 420
ttgtcccgtc aaaaatcctg gacctatgcc taaaacacat ttcacaatcc ctgaactttt 480
caaaaattgg tacatgcttt agctttaaac tacaggcctc actggagcta gagacaagaa 540
ggtaaaaaac ggctgacaaa agaagtcctg gtatcctcta tgatgggaga aggaaactag 600
ctaaagggaa gaataaatta gagaaaaact ggaatgactg aatcggaaca aggcaaaggc 660
tataaaaaaa attagcagta tcctcttggg ggccccttcc ccacactatc tcaatgcaaa 720
tatctgtctg aaacggtccc tggctaaact ccacccatgg gttggccagc cttgccttga 780
caaggcaaac ttgaccaata gtcttagagt atccagtgag gccaggggcc ggcggctggc 840
tagggatgaa gaataaaagg aagcaccctt cagcagttcc acacactcgc ttctggaacg 900
tctgaggtta tcaataagct cctagtccag acgccatggt gcacctgact cctgaggaga 960
agtctgccgt tactgccctg tggggcaagg tgaacgtgga tgaagttggt ggtgaggccc 1020
tgggcaggtt ggtatcaagg ttacaagaca ggtttaagga gaccaataga aactgggcat 1080
gtggagacag agaagactct tgggtttctg ataggcactg actctctctg cctattggtc 1140
tattttccca cccttaggct gctggtggtc tacccttgga cccagaggtt ctttgagtcc 1200
tttggggatc tgtccactcc tgatgctgtt atgggcaacc ctaaggtgaa ggctcatggc 1260
aagaaagtgc tcggtgcctt tagtgatggc ctggctcacc tggacaacct caagggcacc 1320
tttgcccagc tgagtgagct gcactgtgac aagctgcacg tggatcctga gaacttcagg 1380
gtgagtctat gggacccttg atgttttctt tccccttctt ttctatggtt aagttcatgt 1440
cataggaagg ggagaagtaa cagggtacac atattgacca aatcagggta attttgcatt 1500
tgtaatttta aaaaatgctt tcttctttta atatactttt ttgtttatct tatttctaat 1560
actttcccta atctctttct ttcagggcaa taatgataca atgtatcatg cctctttgca 1620
ccattctaaa gaataacagt gataatttct gggttaaggc aatagcaata tttctgcata 1680
taaatatttc tgcatataaa ttgtaactga tgtaagaggt ttcatattgc taatagcagc 1740
tacaatccag ctaccattct gcttttattt tatggttggg ataaggctgg attattctga 1800
gtccaagcta ggcccttttg ctaatcatgt tcatacctct tatcttcctc ccacagctcc 1860
tgggcaacgt gctggtctgt gtgctggccc atcactttgg caaagaattc accccaccag 1920
tgcaggctgc ctatcagaaa gtggtggctg gtgtggctaa tgccctggcc cacaagtatc 1980
actaagctcg ctttcttgct gtccaatttc tattaaaggt tcctttgttc cctaagtcca 2040
actactaaac tgggggatat tatgaagggc cttgagcatc tggattctgc ctaataaaaa 2100
acatttattt tcattgcaat gatgtattta aattatttct gaatatttta ctaaaaaggg 2160
aatgtgggag gttgcagtgc tagtctcccg gaactatcac tctttcacag tctgctttgg 2220
aaggactggg cttagtatga aaagttagga ctgagaagaa tttgaaaggg ggctttttgt 2280
agcttgatat tcactactgt cttattaccc tatcataggc ccaccccaaa tggaagtccc 2340
attcttcctc aggatgttta agattagcat tcaggaagag atcagaggtc tgctggctcc 2400
cttatcatgt cccttatggt gcttctggct ctgcaccgcg ggaacagaga aacaggagaa 2460
tatgggccaa acaggatatc tgtggtaagc agttcctgcc ccggctcagg gccaagaaca 2520
gttggaacag cagaatatgg gccaaacagg atatctgtgg taagcagttc ctgccccggc 2580
tcagggccaa gaacagatgg tccccagatg cggtcccgcc ctcagcagtt tctagagaac 2640
catcagatgt ttccagggtg ccccaaggac ctgaaatgac cctgtgcctt atttgaacta 2700
accaatcagt tcgcttctcg cttctgttcg cgcgcttctg ctccccgagc tctatataag 2760
cagagctcgt ttagtgaacc gtcagatcgc ggccgcgccg ccaccatggt gagcaagggc 2820
gaggagctgt tcaccggggt ggtgcccatc ctggtcgagc tggacggcga cgtaaacggc 2880
cacaagttca gcgtgtccgg cgagggcgag ggcgatgcca cctacggcaa gctgaccctg 2940
aagttcatct gcaccaccgg caagctgccc gtgccctggc ccaccctcgt gaccaccctg 3000
acctacggcg tgcagtgctt cagccgctac cccgaccaca tgaagcagca cgacttcttc 3060
aagtccgcca tgcccgaagg ctacgtccag gagcgcacca tcttcttcaa ggacgacggc 3120
aactacaaga cccgcgccga ggtgaagttc gagggcgaca ccctggtgaa ccgcatcgag 3180
ctgaagggca tcgacttcaa ggaggacggc aacatcctgg ggcacaagct ggagtacaac 3240
tacaacagcc acaacgtcta tatcatggcc gacaagcaga agaacggcat caaggtgaac 3300
ttcaagatcc gccacaacat cgaggacggc agcgtgcagc tcgccgacca ctaccagcag 3360
aacaccccca tcggcgacgg ccccgtgctg ctgcccgaca accactacct gagcacccag 3420
tccgccctga gcaaagaccc caacgagaag cgcgatcaca tggtcctgct ggagttcgtg 3480
accgccgccg ggatcactct cggcatggac gagctgtaca agtaagcttt atttgtgaaa 3540
tttgtgatgc tattgcttta tttgtaacca ttataagctg caataaacaa gttaacaaca 3600
acaattgcat tcattttatg tttcaggttc agggggagat gtgggaggtt ttttaaagcc 3660
ctgcaggatg ggtcatttca cagaggagga caaggctact atcacaagcc tgtggggcaa 3720
ggtgaatgtg gaagatgctg gaggagaaac cctgggaagg taggctctgg tgaccaggac 3780
aagggaggga aggaaggacc ctgtgcctgg caaaagtcca ggtcgcttct caggatttgt 3840
ggcaccttct gactgtcaaa ctgttcttgt caatctcaca ggctcctggt tgtctaccca 3900
tggacccaga ggttctttga cagctttggc aacctgtcct ctgcctctgc catcatgggc 3960
aaccccaaag tcaaggcaca tggcaagaag gtgctgactt ccttgggaga tgccacaaag 4020
cacctggatg atctcaaggg cacctttgcc cagctgagtg aactgcactg tgacaagctg 4080
catgtggatc ctgagaactt caaggtgagt ccaggagatg tttcagccct gttgccttta 4140
gtctcgaggc aacttagaca acggagtatt gatctgagca cagcagggtg tgagctgttt 4200
gaagatactg gggttggggg tgaagaaact gcagaggact aactgggctg agacccagtg 4260
gtaatgtgtc gacgtagata agtagcatgg cgggttaatc attaactaca aggaacccct 4320
agtgatggag ttggccactc cctctctgcg cgctcgctcg ctcactgagg ccgggcgacc 4380
aaaggtcgcc cgacgcccgg gctttgcccg ggcggcctca gtgagcgagc gagcgcgcca 4440
gctggcgtaa tagcgaagag gcccgcaccg atcgcccttc ccaacagttg cgcagcctga 4500
atggcgaatg gcgattccgt tgcaatggct ggcggtaata ttgttctgga tattaccagc 4560
aaggccgata gtttgagttc ttctactcag gcaagtgatg ttattactaa tcaaagaagt 4620
attgcgacaa cggttaattt gcgtgatgga cagactcttt tactcggtgg cctcactgat 4680
tataaaaaca cttctcagga ttctggcgta ccgttcctgt ctaaaatccc tttaatcggc 4740
ctcctgttta gctcccgctc tgattctaac gaggaaagca cgttatacgt gctcgtcaaa 4800
gcaaccatag tacgcgccct gtagcggcgc attaagcgcg gcgggtgtgg tggttacgcg 4860
cagcgtgacc gctacacttg ccagcgccct agcgcccgct cctttcgctt tcttcccttc 4920
ctttctcgcc acgttcgccg gctttccccg tcaagctcta aatcgggggc tccctttagg 4980
gttccgattt agtgctttac ggcacctcga ccccaaaaaa cttgattagg gtgatggttc 5040
acgtagtggg ccatcgccct gatagacggt ttttcgccct ttgacgttgg agtccacgtt 5100
ctttaatagt ggactcttgt tccaaactgg aacaacactc aaccctatct cggtctattc 5160
ttttgattta taagggattt tgccgatttc ggcctattgg ttaaaaaatg agctgattta 5220
acaaaaattt aacgcgaatt ttaacaaaat attaacgttt acaatttaaa tatttgctta 5280
tacaatcttc ctgtttttgg ggcttttctg attatcaacc ggggtacata tgattgacat 5340
gctagtttta cgattaccgt tcatcgattc tcttgtttgc tccagactct caggcaatga 5400
cctgatagcc tttgtagaga cctctcaaaa atagctaccc tctccggcat gaatttatca 5460
gctagaacgg ttgaatatca tattgatggt gatttgactg tctccggcct ttctcacccg 5520
tttgaatctt tacctacaca ttactcaggc attgcattta aaatatatga gggttctaaa 5580
aatttttatc cttgcgttga aataaaggct tctcccgcaa aagtattaca gggtcataat 5640
gtttttggta caaccgattt agctttatgc tctgaggctt tattgcttaa ttttgctaat 5700
tctttgcctt gcctgtatga tttattggat gttggaatcg cctgatgcgg tattttctcc 5760
ttacgcatct gtgcggtatt tcacaccgca tatggtgcac tctcagtaca atctgctctg 5820
atgccgcata gttaagccag ccccgacacc cgccaacacc cgctgacgcg ccctgacggg 5880
cttgtctgct cccggcatcc gcttacagac aagctgtgac cgtctccggg agctgcatgt 5940
gtcagaggtt ttcaccgtca tcaccgaaac gcgcgagacg aaagggcctc gtgatacgcc 6000
tatttttata ggttaatgtc atgataataa tggtttctta gacgtcaggt ggcacttttc 6060
ggggaaatgt gcgcggaacc cctatttgtt tatttttcta aatacattca aatatgtatc 6120
cgctcatgag acaataaccc tgataaatgc ttcaataata ttgaaaaagg aagagtatga 6180
gtattcaaca tttccgtgtc gcccttattc ccttttttgc ggcattttgc cttcctgttt 6240
ttgctcaccc agaaacgctg gtgaaagtaa aagatgctga agatcagttg ggtgcacgag 6300
tgggttacat cgaactggat ctcaacagcg gtaagatcct tgagagtttt cgccccgaag 6360
aacgttttcc aatgatgagc acttttaaag ttctgctatg tggcgcggta ttatcccgta 6420
ttgacgccgg gcaagagcaa ctcggtcgcc gcatacacta ttctcagaat gacttggttg 6480
agtactcacc agtcacagaa aagcatctta cggatggcat gacagtaaga gaattatgca 6540
gtgctgccat aaccatgagt gataacactg cggccaactt acttctgaca acgatcggag 6600
gaccgaagga gctaaccgct tttttgcaca acatggggga tcatgtaact cgccttgatc 6660
gttgggaacc ggagctgaat gaagccatac caaacgacga gcgtgacacc acgatgcctg 6720
tagcaatggc aacaacgttg cgcaaactat taactggcga actacttact ctagcttccc 6780
ggcaacaatt aatagactgg atggaggcgg ataaagttgc aggaccactt ctgcgctcgg 6840
cccttccggc tggctggttt attgctgata aatctggagc cggtgagcgt gggtctcgcg 6900
gtatcattgc agcactgggg ccagatggta agccctcccg tatcgtagtt atctacacga 6960
cggggagtca ggcaactatg gatgaacgaa atagacagat cgctgagata ggtgcctcac 7020
tgattaagca ttggtaactg tcagaccaag tttactcata tatactttag attgatttaa 7080
aacttcattt ttaatttaaa aggatctagg tgaagatcct ttttgataat ctcatgacca 7140
aaatccctta acgtgagttt tcgttccact gagcgtcaga ccccgtagaa aagatcaaag 7200
gatcttcttg agatcctttt tttctgcgcg taatctgctg cttgcaaaca aaaaaaccac 7260
cgctaccagc ggtggtttgt ttgccggatc aagagctacc aactcttttt ccgaaggtaa 7320
ctggcttcag cagagcgcag ataccaaata ctgtccttct agtgtagccg tagttaggcc 7380
accacttcaa gaactctgta gcaccgccta catacctcgc tctgctaatc ctgttaccag 7440
tggctgctgc cagtggcgat aagtcgtgtc ttaccgggtt ggactcaaga cgatagttac 7500
cggataaggc gcagcggtcg ggctgaacgg ggggttcgtg cacacagccc agcttggagc 7560
gaacgaccta caccgaactg agatacctac agcgtgagct atgagaaagc gccacgcttc 7620
ccgaagggag aaaggcggac aggtatccgg taagcggcag ggtcggaaca ggagagcgca 7680
cgagggagct tccaggggga aacgcctggt atctttatag tcctgtcggg tttcgccacc 7740
tctgacttga gcgtcgattt ttgtgatgct cgtcaggggg gcggagccta tggaaaaacg 7800
ccagcaacgc ggccttttta cggttcctgg ccttttgctg gccttttgct cacatgttct 7860
ttcctgcgtt atcccctgat tctgtggata accgtattac cgcctttgag tgagctgata 7920
ccgctcgccg cagccgaacg accgagcgca gcgagtcagt gagcgaggaa gcggaagagc 7980
gcccaatacg caaaccgcct ctccccgcgc gttggccgat tcattaatg 8029

<210> SEQ ID NO 32
<211> LENGTH: 8466
<212> TYPE: DNA
<213> ORGANISM: Artificial
<220> FEATURE:
<223> OTHER INFORMATION: AAV donor template

<400> SEQUENCE: 32
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtagccatgc 180
tctagcggcc tcggcctctg cataaataaa aaaaattagt cagccatgag cttggacgcg 240
tagatctcat ctttactgag catagaagag ctacgccaaa accctgggtc atcagccagc 300
acacacactt atccagtggt aaatacacat catctggtgt atacatacat acctgaatat 360
ggaatcaaat atttttctaa gatgaaacag tcatgattta tttcaaatag gtacggataa 420
gtagatattg aggtaagcat taggtcttat attatgtaac actaatctat tactgcgctg 480
aaactgtggc tttatagaaa ttgttttcac tgcactattg agaaattaag agataatggc 540
aaaagtcaca aagagtatat tcaaaaagaa gtatagcact tttccttag aaaccactgc 600 taactgaaag agactaagat ttgtcccgtc aaaaatcctg gacctatgcc taaaacacat 660
ttcacaatcc ctgaactttt caaaaattgg tacatgcttt agctttaaac tacaggcctc 720
actggagcta gagacaagaa ggtaaaaaac ggctgacaaa agaagtcctg gtatcctcta 780
tgatgggaga aggaaactag ctaaagggaa gaataaatta gagaaaaact ggaatgactg 840

-continued

```
aatcggaagt aaatacactt gcaaaggagg atgtttttag tagcaatttg tactgatggt    900
atggggccaa gagatatatc ttagagggag ggctgagggt ttgaagtcca actcctaagc    960
cagtgccaga agagccaagg acaggtacgg ctgtcatcac ttagacctca ccctgtggag   1020
ccacacccta gggttggcca atctactccc aggagcaggg agggcaggag ccagggctgg   1080
gcataaaagt cagggcagag ccatctattg cttatggtgc acctgactcc tgaggagaag   1140
tctgccgtta ctgccctgtg gggcaaggtg aacgtggatg aagttggtgg tgaggccctg   1200
ggcaggctgc tggtggtcta cccttggacc cagaggttct ttgagtcctt tggggatctg   1260
tccactcctg atgctgttat gggcaaccct aaggtgaagg ctcatggcaa gaaagtgctc   1320
ggtgccttta gtgatggcct ggctcacctg gacaacctca agggcacctt tgcccagctg   1380
agtgagctgc actgtgacaa gctgcacgtg gatcctgaga acttcagggt gagtctatgg   1440
gacccttgat gttttctttc cccttctttt ctatggttaa gttcatgtca taggaagggg   1500
agaagtaaca gggtacacat attgaccaaa tcagggtaat tttgcatttg taattttaaa   1560
aaatgctttc ttcttttaat atactttttt gtttatctta tttctaatac tttccctaat   1620
ctctttcttt cagggcaata atgatacaat gtatcatgcc tctttgcacc attctaaaga   1680
ataacagtga taatttctgg gttaaggcaa tagcaatatt tctgcatata aatatttctg   1740
catataaatt gtaactgatg taagaggttt catattgcta atagcagcta caatccagct   1800
accattctgc ttttatttta tggttgggat aaggctggat tattctgagt ccaagctagg   1860
cccttttgct aatcatgttc atacctctta tcttcctccc acagctcctg ggcaacgtgc   1920
tggtctgtgt gctggcccat cactttggca aagaattcac cccaccagtg caggctgcct   1980
atcagaaagt ggtggctggt gtggctaatg ccctggccca caagtatcac taagctcgct   2040
ttcttgctgt ccaatttcta ttaaaggttc ctttgttccc taagtccaac tactaaactg   2100
ggggatatta tgaagggcct tgagcatctg gattctgcct aataaaaaac atttattttc   2160
attgcaatga tgtatttaaa ttatttctga atattttact aaaaagggaa tgtgggaggt   2220
cagtgcattt aaaacataaa gaaatgaaga gctagttcaa accttgggaa aatacactat   2280
atcttaaact ccatgaaaga aggtgaggct gcaaacagct aatgcacatt ggcaacagcc   2340
cctgatgcct atgccttatt catccctcag aaaaggattc aagtagaggc ttgatttgga   2400
ggttaaagtt ttgctatgct gtattttaca ttacttattg ttttagctgt cctcatgaat   2460
gtcttttcac tacccatttg cttatcctgc atctctcagc cttgactcca ctcagttctc   2520
ttgcttagag ataccacctt tcccctgaag tgttccttcc atgttttacg gcgagatggt   2580
ttctcctcgc ctggccactc agccttagtt gtctctgttg tcttatagag gtctacttga   2640
agaaggaaaa acagggggca tggtttgact gtcctgtgag cccttcttcc ctgcctcccc   2700
cactcacagt gacccggaat ctgcagtgct agtctcccgg aactatcact ctttcacagt   2760
ctgctttgga aggactgggc ttagtatgaa aagttaggac tgagaagaat ttgaaagggg   2820
gctttttgta gcttgatatt cactactgtc ttattaccct atcataggcc caccccaaat   2880
ggaagtccca ttcttcctca ggatgtttaa gattagcatt caggaagaga tcagaggtct   2940
gctggctccc ttatcatgtc ccttatggtg cttctggctc tgcagttatt agcatagtgt   3000
taccatcaac caccttaact tcatttttct tattcaatac ctagccgcgg gaacagagaa   3060
acaggagaat atgggccaaa caggatatct gtggtaagca gttcctgccc cggctcaggg   3120
ccaagaacag ttggaacagc agaatatggg ccaaacagga tatctgtggt aagcagttcc   3180
tgccccggct cagggccaag aacagatggt ccccagatgc ggtcccgccc tcagcagttt   3240
```

-continued

```
ctagagaacc atcagatgtt tccagggtgc cccaaggacc tgaaatgacc ctgtgcctta   3300
tttgaactaa ccaatcagtt cgcttctcgc ttctgttcgc gcgcttctgc tccccgagct   3360
ctatataagc agagctcgtt tagtgaaccg tcagatcgcg gccgcgccgc caccatggac   3420
aaggattgtg aaatgaaacg caccacactg gacagccctt tggggaagct ggagctgtct   3480
ggttgtgagc agggtctgca cgaaataaag ctcctgggca aggggacgtc tgcagctgat   3540
gccgtggagg tcccagcccc cgctgcggtt ctcggaggtc cggagcccct gatgcagtgc   3600
acagcctggc tgaatgccta tttccaccag cccgaggcta tcgaagagtt ccccgtgccg   3660
gctcttcacc atcccgtttt ccagcaagag tcgttcacca gacaggtgtt atggaagctg   3720
ctgaaggttg tgaaattcgg agaagtgatt tcttaccagc aattagcagc cctggcaggc   3780
aaccccaaag ccgcgcgagc agtgggagga gcaatgagag gcaatcctgt caaaatcctc   3840
atcccgtgcc acagagtggt ctgcagcagc ggagccgtgg gcaactactc cggaggactg   3900
gccgtgaagg aatggcttct ggcccatgaa ggccaccggt tggggaagcc aggcttggga   3960
gggagctcag gtctggcagg ggcctggctc aagggagcgg gagctacctc gggctccccg   4020
cctgctggcc gaaacgaggg cagaggaagt cttctaacat gcggtgacgt ggaggagaat   4080
ccgggccccc ctgcaggaac ttcaaggtga gtccaggaga tgtttcagcc ctgttgcctt   4140
tagtctcgag gcaacttaga caacggagta ttgatctgag cacagcaggg tgtgagctgt   4200
ttgaagatac tggggttggg ggtgaagaaa ctgcagagga ctaactgggc tgagacccag   4260
tggtaatgtt ttagggccta aggagtgcct ctaaaaatct agatggacaa ttttgacttt   4320
gagaaaagag aggtggaaat gaggaaaatg acttttcttt attagattcc agtagaaaga   4380
actttcatct ttccctcatt tttgttgttt taaaacatct atctggaggc aggacaagta   4440
tggtcgttaa aaagatgcag gcagaaggca tatattggct cagtcaaagt ggggaacttt   4500
ggtggccaaa catacattgc taaggctatt cctatatcag ctggacacat ataaaatgct   4560
gctaatgctt cattacaaac ttatatcctt taattccaga tgggggcaaa gtatgtccag   4620
gggtgaggaa caattgaaac atttgggctg gagtagattt tgaaagtcag ctctgtgtgt   4680
gtgtgtgtgt gtgcgcgcgc gcgtgtcgac gtagataagt agcatggcgg gttaatcatt   4740
aactacaagg aacccctagt gatggagttg gccactccct ctctgcgcgc tcgctcgctc   4800
actgaggccg ggcgaccaaa ggtcgcccga cgcccgggct ttgcccgggc ggcctcagtg   4860
agcgagcgag cgcgccagct ggcgtaatag cgaagaggcc cgcaccgatc gcccttccca   4920
acagttgcgc agcctgaatg gcgaatggcg attccgttgc aatggctggc ggtaatattg   4980
ttctggatat taccagcaag gccgatagtt tgagttcttc tactcaggca agtgatgtta   5040
ttactaatca aagaagtatt gcgacaacgg ttaatttgcg tgatggacag actcttttac   5100
tcggtggcct cactgattat aaaaacactt ctcaggattc tggcgtaccg ttcctgtcta   5160
aaatcccttt aatcggcctc ctgtttagct cccgctctga ttctaacgag gaaagcacgt   5220
tatacgtgct cgtcaaagca accatagtac gcgccctgta gcggcgcatt aagcgcggcg   5280
ggtgtggtgg ttacgcgcag cgtgaccgct acacttgcca gcgccctagc gcccgctcct   5340
ttcgctttct tcccttcctt tctcgccacg ttcgccggct ttccccgtca agctctaaat   5400
cgggggctcc ctttagggtt ccgatttagt gctttacggc acctcgaccc caaaaaactt   5460
gattagggtg atggttcacg tagtgggcca tcgccctgat agacggtttt tcgccctttg   5520
acgttggagt ccacgttctt taatagtgga ctcttgttcc aaactggaac aacactcaac   5580
```

-continued

```
cctatctcgg tctattcttt tgatttataa gggattttgc cgatttcggc ctattggtta   5640
aaaaatgagc tgatttaaca aaaatttaac gcgaatttta acaaaatatt aacgtttaca   5700
atttaaatat ttgcttatac aatcttcctg tttttggggc ttttctgatt atcaaccggg   5760
gtacatatga ttgacatgct agttttacga ttaccgttca tcgattctct tgtttgctcc   5820
agactctcag gcaatgacct gatagccttt gtagagacct ctcaaaaata gctaccctct   5880
ccggcatgaa tttatcagct agaacggttg aatatcatat tgatggtgat ttgactgtct   5940
ccggcctttc tcacccgttt gaatctttac ctacacatta ctcaggcatt gcatttaaaa   6000
tatatgaggg ttctaaaaat ttttatcctt gcgttgaaat aaaggcttct cccgcaaaag   6060
tattacaggg tcataatgtt tttggtacaa ccgatttagc tttatgctct gaggctttat   6120
tgcttaattt tgctaattct ttgccttgcc tgtatgattt attggatgtt ggaatcgcct   6180
gatgcggtat tttctcctta cgcatctgtg cggtatttca caccgcatat ggtgcactct   6240
cagtacaatc tgctctgatg ccgcatagtt aagccagccc cgacacccgc caacacccgc   6300
tgacgcgccc tgacgggctt gtctgctccc ggcatccgct tacagacaag ctgtgaccgt   6360
ctccgggagc tgcatgtgtc agaggttttc accgtcatca ccgaaacgcg cgagacgaaa   6420
gggcctcgtg atacgcctat ttttataggt taatgtcatg ataataatgg tttcttagac   6480
gtcaggtggc acttttcggg gaaatgtgcg cggaacccct atttgtttat ttttctaaat   6540
acattcaaat atgtatccgc tcatgagaca ataaccctga taaatgcttc aataatattg   6600
aaaaaggaag agtatgagta ttcaacattt ccgtgtcgcc cttattccct tttttgcggc   6660
attttgcctt cctgtttttg ctcacccaga aacgctggtg aaagtaaaag atgctgaaga   6720
tcagttgggt gcacgagtgg gttacatcga actggatctc aacagcggta agatccttga   6780
gagttttcgc cccgaagaac gttttccaat gatgagcact tttaaagttc tgctatgtgg   6840
cgcggtatta tcccgtattg acgccgggca agagcaactc ggtcgccgca tacactattc   6900
tcagaatgac ttggttgagt actcaccagt cacagaaaag catcttacgg atggcatgac   6960
agtaagagaa ttatgcagtg ctgccataac catgagtgat aacactgcgg ccaacttact   7020
tctgacaacg atcggaggac cgaaggagct aaccgctttt ttgcacaaca tgggggatca   7080
tgtaactcgc cttgatcgtt gggaaccgga gctgaatgaa gccataccaa acgacgagcg   7140
tgacaccacg atgcctgtag caatggcaac aacgttgcgc aaactattaa ctggcgaact   7200
acttactcta gcttcccggc aacaattaat agactggatg gaggcggata aagttgcagg   7260
accacttctg cgctcggccc ttccggctgg ctggtttatt gctgataaat ctggagccgg   7320
tgagcgtggg tctcgcggta tcattgcagc actggggcca gatggtaagc cctcccgtat   7380
cgtagttatc tacacgacgg ggagtcaggc aactatggat gaacgaaata gacagatcgc   7440
tgagataggt gcctcactga ttaagcattg gtaactgtca gaccaagttt actcatatat   7500
actttagatt gatttaaaac ttcattttta atttaaaagg atctaggtga agatcctttt   7560
tgataatctc atgaccaaaa tcccttaacg tgagttttcg ttccactgag cgtcagaccc   7620
cgtagaaaag atcaaaggat cttcttgaga tccttttttt ctgcgcgtaa tctgctgctt   7680
gcaaacaaaa aaaccaccgc taccagcggt ggtttgtttg ccggatcaag agctaccaac   7740
tctttttccg aaggtaactg gcttcagcag agcgcagata ccaaatactg tccttctagt   7800
gtagccgtag ttaggccacc acttcaagaa ctctgtagca ccgcctacat acctcgctct   7860
gctaatcctg ttaccagtgg ctgctgccag tggcgataag tcgtgtctta ccgggttgga   7920
ctcaagacga tagttaccgg ataaggcgca gcggtcgggc tgaacggggg gttcgtgcac   7980
```

acagcccagc ttggagcgaa cgacctacac cgaactgaga tacctacagc gtgagctatg 8040
agaaagcgcc acgcttcccg aagggagaaa ggcggacagg tatccggtaa gcggcagggt 8100
cggaacagga gagcgcacga gggagcttcc agggggaaac gcctggtatc tttatagtcc 8160
tgtcgggttt cgccacctct gacttgagcg tcgatttttg tgatgctcgt caggggggcg 8220
gagcctatgg aaaaacgcca gcaacgcggc ctttttacgg ttcctggcct tttgctggcc 8280
ttttgctcac atgttctttc ctgcgttatc ccctgattct gtggataacc gtattaccgc 8340
ctttgagtga gctgataccg ctcgccgcag ccgaacgacc gagcgcagcg agtcagtgag 8400
cgaggaagcg gaagagcgcc caatacgcaa accgcctctc cccgcgcgtt ggccgattca 8460
ttaatg 8466

<210> SEQ ID NO 33
<211> LENGTH: 8252
<212> TYPE: DNA
<213> ORGANISM: Artificial
<220> FEATURE:
<223> OTHER INFORMATION: AAV donor template

<400> SEQUENCE: 33
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctttttt ccttagaaac cactgctaac tgaaagagac 180
taagatttgt cccgtcaaaa atcctggacc tatgcctaaa acacatttca caatccctga 240
acttttcaaa aattggtaca tgctttagct ttaaactaca ggcctcactg gagctagaga 300
caagaaggta aaaaacggct gacaaaagaa gtcctggtat cctctatgat gggagaagga 360
aactagctaa agggaagaat aaattagaga aaaactggaa tgactgaatc ggaacaaggc 420
aaaggctata aaaaaaatta gcagtatcct cttgggggcc ccttccccac actatctcaa 480
tgcaaatatc tgtctgaaac ggtccctggc taaactccac gtaaatacac ttgcaaagga 540
ggatgttttt agtagcaatt tgtactgatg gtatggggcc aagagatata tcttagaggg 600
agggctgagg gtttgaagtc caactcctaa gccagtgcca gaagagccaa ggacaggtac 660
ggctgtcatc acttagacct caccctgtgg agccacaccc tagggttggc caatctactc 720
ccaggagcag ggagggcagg agccagggct gggcataaaa gtcagggcag agccatctat 780
tgcttacatt tgcttctgac acaactgtgt tcactagcaa cctcaaacag acaccatggt 840
gcacctgact cctgaggaga agtctgccgt tactgccctg tggggcaagg tgaacgtgga 900
tgaagttggt ggtgaggccc tgggcaggtt ggtatcaagg ttacaagaca ggtttaagga 960
gaccaataga aactgggcat gtggagacag agaagactct tgggtttctg ataggcactg 1020
actctctctg cctattggtc tattttccca cccttaggct gctggtggtc tacccttgga 1080
cccagaggtt ctttgagtcc tttggggatc tgtccactcc tgatgctgtt atgggcaacc 1140
ctaaggtgaa ggctcatggc aagaaagtgc tcggtgcctt tagtgatggc ctggctcacc 1200
tggacaacct caagggcacc tttgcccagc tgagtgagct gcactgtgac aagctgcacg 1260
tggatcctga gaacttcagg gtgagtctat gggacccttg atgttttctt tccccttctt 1320
ttctatggtt aagttcatgt cataggaagg ggagaagtaa cagggtacac atattgacca 1380
aatcagggta attttgcatt tgtaatttta aaaaatgctt tcttctttta atatactttt 1440
ttgtttatct tatttctaat actttcccta atctctttct ttcagggcaa taatgataca 1500

-continued atgtatcatg cctctttgca ccattctaaa gaataacagt gataatttct gggttaaggc 1560
aatagcaata tttctgcata taaatatttc tgcatataaa ttgtaactga tgtaagaggt 1620
ttcatattgc taatagcagc tacaatccag ctaccattct gcttttattt tatggttggg 1680
ataaggctgg attattctga gtccaagcta ggcccttttg ctaatcatgt tcatacctct 1740
tatcttcctc ccacagctcc tgggcaacgt gctggtctgt gtgctggccc atcactttgg 1800
caaagaattc accccaccag tgcaggctgc ctatcagaaa gtggtggctg gtgtggctaa 1860
tgccctggcc cacaagtatc actaagctcg ctttcttgct gtccaatttc tattaaaggt 1920
tcctttgttc cctaagtcca actactaaac tgggggatat tatgaagggc cttgagcatc 1980
tggattctgc ctaataaaaa acatttattt tcattgcaat gatgtattta aattatttct 2040
gaatatttta ctaaaaaggg aatgtgggag gtcagtgcat ttaaaacata aagaaatgaa 2100
gagctagttc aaaccttggg aaaatacact atatcttaaa ctccatgaaa gaaggtgagg 2160
ctgcaaacag ctaatgcaca ttggcaacag cccctgatgc ctatgcctta ttcatccctc 2220
agaaaaggat tcaagtagag gcttgatttg gaggttaaag ttttgctatg ctgtatttta 2280
cattacttat tgttttagct gtcctcatga atgtcttttc actacccatt tgcttatcct 2340
gcatctctca gccttgactc cactcagttc tcttgcttag agataccacc tttcccctga 2400
agtgttcctt ccatgtttta cggcgagatg gtttctcctc gcctggccac tcagccttag 2460
ttgtctctgt tgtcttatag aggtctactt gaagaaggaa aaacaggggg catggtttga 2520
ctgtcctgtg agcccttctt ccctgcctcc cccactcaca gtgacccgga atctgcagtg 2580
ctagtctccc ggaactatca ctctttcaca gtctgctttg gaaggactgg gcttagtatg 2640
aaaagttagg actgagaaga atttgaaagg gggctttttg tagcttgata ttcactactg 2700
tcttattacc ctatcatagg cccaccccaa atggaagtcc cattcttcct caggatgttt 2760
aagattagca ttcaggaaga gatcagaggt ctgctggctc ccttatcatg tcccttatgg 2820
tgcttctggc tctgcagtta ttagcatagt gttaccatca accaccttaa cttcattttt 2880
cttattcaat acctagccgc gggaacagag aaacaggaga atatgggcca aacaggatat 2940
ctgtggtaag cagttcctgc cccggctcag ggccaagaac agttggaaca gcagaatatg 3000
ggccaaacag gatatctgtg gtaagcagtt cctgccccgg ctcagggcca agaacagatg 3060
gtccccagat gcggtcccgc cctcagcagt ttctagagaa ccatcagatg tttccagggt 3120
gccccaagga cctgaaatga ccctgtgcct tatttgaact aaccaatcag ttcgcttctc 3180
gcttctgttc gcgcgcttct gctccccgag ctctatataa gcagagctcg tttagtgaac 3240
cgtcagatcg cggccgcgcc gccaccatgg tgagcaaggg cgaggagctg ttcaccgggg 3300
tggtgcccat cctggtcgag ctggacggcg acgtaaacgg ccacaagttc agcgtgtccg 3360
gcgagggcga gggcgatgcc acctacggca agctgaccct gaagttcatc tgcaccaccg 3420
gcaagctgcc cgtgccctgg cccaccctcg tgaccaccct gacctacggc gtgcagtgct 3480
tcagccgcta ccccgaccac atgaagcagc acgacttctt caagtccgcc atgcccgaag 3540
gctacgtcca ggagcgcacc atcttcttca aggacgacgg caactacaag acccgcgccg 3600
aggtgaagtt cgagggcgac accctggtga accgcatcga gctgaagggc atcgacttca 3660
aggaggacgg caacatcctg gggcacaagc tggagtacaa ctacaacagc cacaacgtct 3720
atatcatggc cgacaagcag aagaacggca tcaaggtgaa cttcaagatc cgccacaaca 3780
tcgaggacgg cagcgtgcag ctcgccgacc actaccagca gaacaccccc atcggcgacg 3840
gccccgtgct gctgcccgac aaccactacc tgagcaccca gtccgccctg agcaaagacc 3900

-continued ccaacgagaa gcgcgatcac atggtcctgc tggagttcgt gaccgccgcc gggatcactc 3960
tcggcatgga cgagctgtac aagtaagctt tatttgtgaa atttgtgatg ctattgcttt 4020
atttgtaacc attataagct gcaataaaca agttaacaac aacaattgca ttcattttat 4080
gtttcaggtt cagggggaga tgtgggaggt tttttaaagc cctgcaggat gggtcatttc 4140
acagaggagg acaaggctac tatcacaagc ctgtggggca aggtgaatgt ggaagatgct 4200
ggaggagaaa ccctgggaag gtaggctctg gtgaccagga caagggaggg aaggaaggac 4260
cctgtgcctg gcaaaagtcc aggtcgcttc tcaggatttg tggcaccttc tgactgtcaa 4320
actgttcttg tcaatctcac aggctcctgg ttgtctaccc atggacccag aggttctttg 4380
acagctttgg caacctgtcc tctgcctctg ccatcatggg caaccccaaa gtcaaggcac 4440
atggcaagaa ggtgctgact tccttgggag atgccacaaa gcacctggat gatctcaagg 4500
gcacctttgc ccagctgagt gaactgcagt cgacaggaac ccctagtgat ggagttggcc 4560
actccctctc tgcgcgctcg ctcgctcact gaggccgggc gaccaaaggt cgcccgacgc 4620
ccgggctttg cccgggcggc ctcagtgagc gagcgagcgc gcagctggcg taatagcgaa 4680
gaggcccgca ccgatcgccc ttcccaacag ttgcgcagcc tgaatggcga atggcgattc 4740
cgttgcaatg gctggcggta atattgttct ggatattacc agcaaggccg atagtttgag 4800
ttcttctact caggcaagtg atgttattac taatcaaaga agtattgcga caacggttaa 4860
tttgcgtgat ggacagactc ttttactcgg tggcctcact gattataaaa acacttctca 4920
ggattctggc gtaccgttcc tgtctaaaat ccctttaatc ggcctcctgt ttagctcccg 4980
ctctgattct aacgaggaaa gcacgttata cgtgctcgtc aaagcaacca tagtacgcgc 5040
cctgtagcgg cgcattaagc gcggcgggtg tggtggttac gcgcagcgtg accgctacac 5100
ttgccagcgc cctagcgccc gctcctttcg ctttcttccc ttcctttctc gccacgttcg 5160
ccggctttcc ccgtcaagct ctaaatcggg ggctcccttt agggttccga tttagtgctt 5220
tacggcacct cgaccccaaa aaacttgatt agggtgatgg ttcacgtagt gggccatcgc 5280
cctgatagac ggtttttcgc cctttgacgt tggagtccac gttctttaat agtggactct 5340
tgttccaaac tggaacaaca ctcaacccta tctcggtcta ttcttttgat ttataaggga 5400
ttttgccgat ttcggcctat tggttaaaaa atgagctgat ttaacaaaaa tttaacgcga 5460
attttaacaa aatattaacg tttacaattt aaatatttgc ttatacaatc ttcctgtttt 5520
tggggctttt ctgattatca accggggtac atatgattga catgctagtt ttacgattac 5580
cgttcatcga ttctcttgtt tgctccagac tctcaggcaa tgacctgata gcctttgtag 5640
agacctctca aaaatagcta ccctctccgg catgaattta tcagctagaa cggttgaata 5700
tcatattgat ggtgatttga ctgtctccgg cctttctcac ccgtttgaat ctttacctac 5760
acattactca ggcattgcat ttaaaatata tgagggttct aaaaattttt atccttgcgt 5820
tgaaataaag gcttctcccg caaaagtatt acagggtcat aatgtttttg gtacaaccga 5880
tttagcttta tgctctgagg ctttattgct taattttgct aattctttgc cttgcctgta 5940
tgatttattg gatgttggaa tcgcctgatg cggtattttc tccttacgca tctgtgcggt 6000
atttcacacc gcatatggtg cactctcagt acaatctgct ctgatgccgc atagttaagc 6060
cagccccgac acccgccaac acccgctgac gcgccctgac gggcttgtct gctcccggca 6120
tccgcttaca gacaagctgt gaccgtctcc gggagctgca tgtgtcagag gttttcaccg 6180
tcatcaccga aacgcgcgag acgaaagggc ctcgtgatac gcctattttt ataggttaat 6240
gtcatgataa taatggtttc ttagacgtca ggtggcactt ttcggggaaa tgtgcgcgga 6300
acccctattt gtttattttt ctaaatacat tcaaatatgt atccgctcat gagacaataa 6360
ccctgataaa tgcttcaata atattgaaaa aggaagagta tgagtattca acatttccgt 6420
gtcgccctta ttcccttttt tgcggcattt tgccttcctg tttttgctca cccagaaacg 6480
ctggtgaaag taaaagatgc tgaagatcag ttgggtgcac gagtgggtta catcgaactg 6540
gatctcaaca gcggtaagat ccttgagagt tttcgccccg aagaacgttt tccaatgatg 6600
agcactttta aagttctgct atgtggcgcg gtattatccc gtattgacgc cgggcaagag 6660
caactcggtc gccgcataca ctattctcag aatgacttgg ttgagtactc accagtcaca 6720
gaaaagcatc ttacggatgg catgacagta agagaattat gcagtgctgc cataaccatg 6780
agtgataaca ctgcggccaa cttacttctg acaacgatcg gaggaccgaa ggagctaacc 6840
gcttttttgc acaacatggg ggatcatgta actcgccttg atcgttggga accggagctg 6900
aatgaagcca taccaaacga cgagcgtgac accacgatgc ctgtagcaat ggcaacaacg 6960
ttgcgcaaac tattaactgg cgaactactt actctagctt cccggcaaca attaatagac 7020
tggatggagg cggataaagt tgcaggacca cttctgcgct cggcccttcc ggctggctgg 7080
tttattgctg ataaatctgg agccggtgag cgtgggtctc gcggtatcat tgcagcactg 7140
gggccagatg gtaagccctc ccgtatcgta gttatctaca cgacggggag tcaggcaact 7200
atggatgaac gaaatagaca gatcgctgag ataggtgcct cactgattaa gcattggtaa 7260
ctgtcagacc aagtttactc atatatactt tagattgatt taaaacttca tttttaattt 7320
aaaaggatct aggtgaagat cctttttgat aatctcatga ccaaaatccc ttaacgtgag 7380
ttttcgttcc actgagcgtc agaccccgta gaaaagatca aaggatcttc ttgagatcct 7440 tttttctgc gcgtaatctg ctgcttgcaa acaaaaaaac caccgctacc agcggtggtt 7500
tgtttgccgg atcaagagct accaactctt tttccgaagg taactggctt cagcagagcg 7560
cagataccaa atactgtcct tctagtgtag ccgtagttag gccaccactt caagaactct 7620
gtagcaccgc ctacatacct cgctctgcta atcctgttac cagtggctgc tgccagtggc 7680
gataagtcgt gtcttaccgg gttggactca agacgatagt taccggataa ggcgcagcgg 7740
tcgggctgaa cggggggttc gtgcacacag cccagcttgg agcgaacgac ctacaccgaa 7800
ctgagatacc tacagcgtga gctatgagaa agcgccacgc ttcccgaagg gagaaaggcg 7860
gacaggtatc cggtaagcgg cagggtcgga acaggagagc gcacgaggga gcttccaggg 7920
ggaaacgcct ggtatcttta tagtcctgtc gggtttcgcc acctctgact tgagcgtcga 7980
tttttgtgat gctcgtcagg ggggcggagc ctatggaaaa acgccagcaa cgcggccttt 8040
ttacggttcc tggccttttg ctggcctttt gctcacatgt tctttcctgc gttatcccct 8100
gattctgtgg ataaccgtat taccgccttt gagtgagctg ataccgctcg ccgcagccga 8160
acgaccgagc gcagcgagtc agtgagcgag gaagcggaag agcgcccaat acgcaaaccg 8220
cctctccccg cgcgttggcc gattcattaa tg 8252

<210> SEQ ID NO 34
<211> LENGTH: 7375
<212> TYPE: DNA
<213> ORGANISM: Artificial
<220> FEATURE:
<223> OTHER INFORMATION: AAV donor template

<400> SEQUENCE: 34
cagctgcgcg ctcgctcgct cactgaggcc gcccgggcaa agcccgggcg tcgggcgacc 60

-continued

```
tttggtcgcc cggcctcagt gagcgagcga gcgcgcagag agggagtggc caactccatc    120
actaggggtt ccttgtagtt aatgattaac ccgccatgct acttatctac acgcgtagat    180
ctttttttcct tagaaaccac tgctaactga aagagactaa gatttgtccc gtcaaaaatc   240
ctggacctat gcctaaaaca catttcacaa tccctgaact tttcaaaaat tggtacatgc    300
tttagcttta aactacaggc ctcactggag ctagagacaa gaaggtaaaa aacggctgac    360
aaaagaagtc ctggtatcct ctatgatggg agaaggaaac tagctaaagg gaagaataaa    420
ttagagaaaa actggaatga ctgaatcgga acaaggcaaa ggctataaaa aaaattagca    480
gtatcctctt gggggcccct tccccacact atctcaatgc aaatatctgt ctgaaacggt    540
ccctggctaa actccaccca tgggttggcc agccttgcct tgacaaggca aacttgacca    600
atagtcttag agtatccagt gaggccaggg gccggcggct ggctagggat gaagaataaa    660
aggaagcacc cttcagcagt tccacacact cgcttctgga acgtctgagg ttatcaataa    720
gctcctagtc cagacgccgc cgccaccatg gtccatctta caccggagga gaagtccgct    780
gtaacggcac tgtgggggaa agttaatgtc gatgaagtcg gcggtgaagc actcggcagg    840
ttgctggtag tgtacccgtg gacacaacga ttctttgaaa gtttcgggga cctgtccaca    900
cccgatgctg tgatgggtaa tccaaaagta aaagcacacg gcaagaaagt cctcggcgcg    960
tttagtgatg gtctggccca tttggataac ttgaagggta cattcgcgca gctttccgaa   1020
ctccactgtg acaagttgca cgtagatcca gaaaacttcc ggcttctggg caatgtgctt   1080
gtatgcgttc tggctcacca ttttgggaag gagtttaccc cacccgtgca agcggcttac   1140
caaaaagtgg tcgcaggagt ggctaatgcc cttgcacata aatatcacta aggtaccgag   1200
catcttaccg ccatttattc ccatatttgt tctgtttttc ttgatttggg tatacattta   1260
aatgttaata aaacaaaatg gtggggcaat catttacatt tttagggata tgtaattact   1320
agttcaggtg tattgccaca agacaaacat gttaagaaac tttcccgtta tttacgctct   1380
gttcctgtta atcaacctct ggattacaaa atttgtgaaa gattgactga tattcttaac   1440
tatgttgctc cttttacgct gtgtggatat gctgctttat agcctctgta tctagctatt   1500
gcttcccgta cggctttcgt tttctcctcc ttgtataaat cctggttgct gtctctttta   1560
gaggagttgt ggcccgttgt ccgtcaacgt ggcgtggtgt gctctgtgtt tgctgacgca   1620
acccccactg gctggggcat tgccaccacc tgtcaactcc tttctgggac tttcgctttc   1680
cccctcccga tcgccacggc agaactcatc gccgcctgcc ttgcccgctg ctggacaggg   1740
gctaggttgc tgggcactga taattccgtg gtgttgtctg tgccttctag ttgccagcca   1800
tctgttgttt gcccctcccc cgtgccttcc ttgaccctgg aaggtgccac tcccactgtc   1860
ctttcctaat aaaatgagga aattgcatcg cattgtctga gtaggtgtca ttctattctg   1920
gggggtgggg tggggcagga cagcaagggg gaggattggg aagacaatag caggcatgct   1980
ggggatgcgg tgggctctat ggcccgcggg aacagagaaa caggagaata tgggccaaac   2040
aggatatctg tggtaagcag ttcctgcccc ggctcagggc caagaacagt tggaacagca   2100
gaatatgggc caaacaggat atctgtggta agcagttcct gccccggctc agggccaaga   2160
acagatggtc cccagatgcg gtcccgccct cagcagtttc tagagaacca tcagatgttt   2220
ccagggtgcc ccaaggacct gaaatgaccc tgtgccttat ttgaactaac caatcagttc   2280
gcttctcgct tctgttcgcg cgcttctgct ccccgagctc tatataagca gagctcgttt   2340
agtgaaccgt cagatcgcct ggagacgcca tccacgctgt tttgacttcc atagaaggcg   2400
```

-continued

```
gccgcgccgc caccatggtg agcaagggcg aggagctgtt caccggggtg gtgcccatcc   2460
tggtcgagct ggacggcgac gtaaacggcc acaagttcag cgtgtccggc gagggcgagg   2520
gcgatgccac ctacggcaag ctgaccctga agttcatctg caccaccggc aagctgcccg   2580
tgccctggcc caccctcgtg accaccctga cctacggcgt gcagtgcttc agccgctacc   2640
ccgaccacat gaagcagcac gacttcttca agtccgccat gcccgaaggc tacgtccagg   2700
agcgcaccat cttcttcaag gacgacggca actacaagac ccgcgccgag gtgaagttcg   2760
agggcgacac cctggtgaac cgcatcgagc tgaagggcat cgacttcaag gaggacggca   2820
acatcctggg gcacaagctg gagtacaact acaacagcca caacgtctat atcatggccg   2880
acaagcagaa gaacggcatc aaggtgaact tcaagatccg ccacaacatc gaggacggca   2940
gcgtgcagct cgccgaccac taccagcaga acacccccat cggcgacggc cccgtgctgc   3000
tgcccgacaa ccactacctg agcacccagt ccgccctgag caaagacccc aacgagaagc   3060
gcgatcacat ggtcctgctg gagttcgtga ccgccgccgg gatcactctc ggcatggacg   3120
agctgtacaa gggaagcgga gctactaact tcagcctgct gaagcaggct ggagacgtgg   3180
aggagaaccc tggacctcct gcaggaactt caaggtgagt ccaggagatg tttcagccct   3240
gttgccttta gtctcgaggc aacttagaca acggagtatt gatctgagca cagcagggtg   3300
tgagctgttt gaagatactg gggttggggg tgaagaaact gcagaggact aactgggctg   3360
agacccagtg gtaatgtttt agggcctaag gagtgcctct aaaaatctag atggacaatt   3420
ttgactttga gaaaagagag gtggaaatga ggaaaatgac ttttctttat tagattccag   3480
tagaaagaac tttcatcttt ccctcatttt tgttgtttta aaacatctat ctggaggcag   3540
gacaagtatg gtcgttaaaa agatgcaggc agaaggcata tattggctca gtcaaagtgg   3600
ggaactttgg tgggtcgacg tagataagta gcatggcggg ttaatcatta actacaagga   3660
acccctagtg atggagttgg ccactccctc tctgcgcgct cgctcgctca ctgaggccgg   3720
gcgaccaaag gtcgcccgac gcccgggctt tgcccgggcg gcctcagtga gcgagcgagc   3780
gcgccagctg gcgtaatagc gaagaggccc gcaccgatcg cccttcccaa cagttgcgca   3840
gcctgaatgg cgaatggcga ttccgttgca atggctggcg gtaatattgt tctggatatt   3900
accagcaagg ccgatagttt gagttcttct actcaggcaa gtgatgttat tactaatcaa   3960
agaagtattg cgacaacggt taatttgcgt gatggacaga ctcttttact cggtggcctc   4020
actgattata aaaacacttc tcaggattct ggcgtaccgt tcctgtctaa aatcccttta   4080
atcggcctcc tgtttagctc ccgctctgat tctaacgagg aaagcacgtt atacgtgctc   4140
gtcaaagcaa ccatagtacg cgccctgtag cggcgcatta agcgcggcgg gtgtggtggt   4200
tacgcgcagc gtgaccgcta cacttgccag cgccctagcg cccgctcctt tcgctttctt   4260
cccttccttt ctcgccacgt tcgccggctt tccccgtcaa gctctaaatc gggggctccc   4320
tttagggttc cgatttagtg ctttacggca cctcgacccc aaaaaacttg attagggtga   4380
tggttcacgt agtgggccat cgccctgata gacggttttt cgccctttga cgttggagtc   4440
cacgttcttt aatagtggac tcttgttcca aactggaaca acactcaacc ctatctcggt   4500
ctattctttt gatttataag ggattttgcc gatttcggcc tattggttaa aaaatgagct   4560
gatttaacaa aaatttaacg cgaattttaa caaaatatta acgtttacaa tttaaatatt   4620
tgcttataca atcttcctgt ttttggggct tttctgatta tcaaccgggg tacatatgat   4680
tgacatgcta gttttacgat taccgttcat cgattctctt gtttgctcca gactctcagg   4740
caatgacctg atagcctttg tagagacctc tcaaaaatag ctaccctctc cggcatgaat   4800
```

```
ttatcagcta gaacggttga atatcatatt gatggtgatt tgactgtctc cggcctttct   4860
cacccgtttg aatctttacc tacacattac tcaggcattg catttaaaat atatgagggt   4920
tctaaaaatt tttatccttg cgttgaaata aaggcttctc ccgcaaaagt attacagggt   4980
cataatgttt ttggtacaac cgatttagct ttatgctctg aggctttatt gcttaatttt   5040
gctaattctt tgccttgcct gtatgattta ttggatgttg gaatcgcctg atgcggtatt   5100
ttctccttac gcatctgtgc ggtatttcac accgcatatg gtgcactctc agtacaatct   5160
gctctgatgc cgcatagtta agccagcccc gacacccgcc aacacccgct gacgcgccct   5220
gacgggcttg tctgctcccg gcatccgctt acagacaagc tgtgaccgtc tccgggagct   5280
gcatgtgtca gaggttttca ccgtcatcac cgaaacgcgc gagacgaaag ggcctcgtga   5340
tacgcctatt tttataggtt aatgtcatga taataatggt ttcttagacg tcaggtggca   5400
cttttcgggg aaatgtgcgc ggaaccccta tttgtttatt tttctaaata cattcaaata   5460
tgtatccgct catgagacaa taaccctgat aaatgcttca ataatattga aaaaggaaga   5520
gtatgagtat tcaacatttc cgtgtcgccc ttattccctt ttttgcggca ttttgccttc   5580
ctgtttttgc tcacccagaa acgctggtga aagtaaaaga tgctgaagat cagttgggtg   5640
cacgagtggg ttacatcgaa ctggatctca acagcggtaa gatccttgag agttttcgcc   5700
ccgaagaacg ttttccaatg atgagcactt ttaaagttct gctatgtggc gcggtattat   5760
cccgtattga cgccgggcaa gagcaactcg gtcgccgcat acactattct cagaatgact   5820
tggttgagta ctcaccagtc acagaaaagc atcttacgga tggcatgaca gtaagagaat   5880
tatgcagtgc tgccataacc atgagtgata acactgcggc caacttactt ctgacaacga   5940
tcggaggacc gaaggagcta accgcttttt tgcacaacat gggggatcat gtaactcgcc   6000
ttgatcgttg ggaaccggag ctgaatgaag ccataccaaa cgacgagcgt gacaccacga   6060
tgcctgtagc aatggcaaca acgttgcgca aactattaac tggcgaacta cttactctag   6120
cttcccggca acaattaata gactggatgg aggcggataa agttgcagga ccacttctgc   6180
gctcggccct tccggctggc tggtttattg ctgataaatc tggagccggt gagcgtgggt   6240
ctcgcggtat cattgcagca ctggggccag atggtaagcc ctcccgtatc gtagttatct   6300
acacgacggg gagtcaggca actatggatg aacgaaatag acagatcgct gagataggtg   6360
cctcactgat taagcattgg taactgtcag accaagttta ctcatatata ctttagattg   6420
atttaaaact tcatttttaa tttaaaagga tctaggtgaa gatccttttt gataatctca   6480
tgaccaaaat cccttaacgt gagttttcgt tccactgagc gtcagacccc gtagaaaaga   6540
tcaaaggatc ttcttgagat cctttttttc tgcgcgtaat ctgctgcttg caaacaaaaa   6600
aaccaccgct accagcggtg gtttgtttgc cggatcaaga gctaccaact ctttttccga   6660
aggtaactgg cttcagcaga gcgcagatac caaatactgt ccttctagtg tagccgtagt   6720
taggccacca cttcaagaac tctgtagcac cgcctacata cctcgctctg ctaatcctgt   6780
taccagtggc tgctgccagt ggcgataagt cgtgtcttac cgggttggac tcaagacgat   6840
agttaccgga taaggcgcag cggtcgggct gaacgggggg ttcgtgcaca cagcccagct   6900
tggagcgaac gacctacacc gaactgagat acctacagcg tgagctatga gaaagcgcca   6960
cgcttcccga agggagaaag gcggacaggt atccggtaag cggcagggtc ggaacaggag   7020
agcgcacgag ggagcttcca gggggaaacg cctggtatct ttatagtcct gtcgggtttc   7080
gccacctctg acttgagcgt cgatttttgt gatgctcgtc aggggggcgg agcctatgga   7140
```

-continued aaaacgccag caacgcggcc tttttacggt tcctggcctt ttgctggcct tttgctcaca 7200
tgttctttcc tgcgttatcc cctgattctg tggataaccg tattaccgcc tttgagtgag 7260
ctgataccgc tcgccgcagc cgaacgaccg agcgcagcga gtcagtgagc gaggaagcgg 7320
aagagcgccc aatacgcaaa ccgcctctcc ccgcgcgttg gccgattcat taatg 7375

<210> SEQ ID NO 35
<211> LENGTH: 8089
<212> TYPE: DNA
<213> ORGANISM: Artificial
<220> FEATURE:
<223> OTHER INFORMATION: AAV donor template

<400> SEQUENCE: 35
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180 ctttttcct tagaaaccac tgctaactga aagagactaa gatttgtccc gtcaaaaatc 240
ctggacctat gcctaaaaca catttcacaa tccctgaact tttcaaaaat tggtacatgc 300
tttagcttta aactacaggc ctcactggag ctagagacaa gaaggtaaaa aacggctgac 360
aaaagaagtc ctggtatcct ctatgatggg agaaggaaac tagctaaagg gaagaataaa 420
ttagagaaaa actggaatga ctgaatcgga acaaggcaaa ggctataaaa aaaattagca 480
gtatcctctt gggggcccct tccccacact atctcaatgc aaatatctgt ctgaaacggt 540
ccctggctaa actccaccca tgggttggcc agccttgcct tgacaaggca aacttgacca 600
atagtcttag agtatccagt gaggccaggg gccggcggct ggctagggat gaagaataaa 660
aggaagcacc cttcagcagt tccacacact cgcttctgga acgtctgagg ttatcaataa 720
gctcctagtc cagacgccgc cgccaccatg gtccatctta caccggagga gaagtccgct 780
gtaacggcac tgtgggggaa agttaatgtc gatgaagtcg gcggtgaagc actcggcagg 840
ttgctggtag tgtacccgtg gacacaacga ttctttgaaa gtttcgggga cctgtccaca 900
cccgatgctg tgatgggtaa tccaaaagta aaagcacacg gcaagaaagt cctcggcgcg 960
tttagtgatg gtctggccca tttggataac ttgaagggta cattcgcgca gctttccgaa 1020
ctccactgtg acaagttgca cgtagatcca gaaaacttcc ggcttctggg caatgtgctt 1080
gtatgcgttc tggctcacca ttttgggaag gagtttaccc cacccgtgca agcggcttac 1140
caaaaagtgg tcgcaggagt ggctaatgcc cttgcacata aatatcacta aggtaccgag 1200
catcttaccg ccatttattc ccatatttgt tctgtttttc ttgatttggg tatacattta 1260
aatgttaata aaacaaaatg gtggggcaat catttacatt tttagggata tgtaattact 1320
agttcaggtg tattgccaca agacaaacat gttaagaaac tttcccgtta tttacgctct 1380
gttcctgtta atcaacctct ggattacaaa atttgtgaaa gattgactga tattcttaac 1440
tatgttgctc cttttacgct gtgtggatat gctgctttat agcctctgta tctagctatt 1500
gcttcccgta cggctttcgt tttctcctcc ttgtataaat cctggttgct gtctctttta 1560
gaggagttgt ggcccgttgt ccgtcaacgt ggcgtggtgt gctctgtgtt tgctgacgca 1620
acccccactg gctggggcat tgccaccacc tgtcaactcc tttctgggac tttcgctttc 1680
cccctcccga tcgccacggc agaactcatc gccgcctgcc ttgcccgctg ctggacaggg 1740
gctaggttgc tgggcactga taattccgtg gtgttgtctg tgccttctag ttgccagcca 1800
tctgttgttt gcccctcccc cgtgccttcc ttgaccctgg aaggtgccac tcccactgtc 1860

```
ctttcctaat aaaatgagga aattgcatcg cattgtctga gtaggtgtca ttctattctg   1920
gggggtgggg tggggcagga cagcaagggg gaggattggg aagacaatag caggcatgct   1980
ggggatgcgg tgggctctat ggccgagatc gagaccatcc tggctaacac agtgaaaccc   2040
cgtctctact aaaaaaatac aaaaaattag ccgggcttgg tggcgggtgc ctgtagtccc   2100
agctactatg gaggctgagg cgggagaatg gcgtgaacgc ggggggcgga gcttgcagtg   2160
agcagagatc aggggccact gcactccagc ctgggcgaca gagagagact ctgtctcaaa   2220
aaaaagaaaa aaaaaattta gtagactagc taaaaaaatc cagagatagt tattgatgca   2280
tatgtaaaag tcttccaata tttacaagta caatgaaaaa aaaataacct tgaattaagt   2340
gtagaactca ttgacaatgt ttcaaaggat gtgagggata aactaaaatt tgggcagtac   2400
atgctgttcc tgtgtacttg gaacagaggg agaaaatctg ggctggaaat attgttatag   2460
gagttagcac atgaaggtga caactaaatt atttggagta gatggagtca ccagcacatg   2520
tgaatagttt tagaatgaaa tgacccaaga tagaactttg gagagccccc aaatttaaat   2580
aaaatcagta taagagaaga ggaagaaacc aaatggtata ctagtctaaa ttgtttctta   2640
gtgacaaaag aataacctga atattagatt agctgcctat atgctctctg aatcaatttc   2700
attcaacatg caacagtccg cgggaacaga gaaacaggag aatatgggcc aaacaggata   2760
tctgtggtaa gcagttcctg ccccggctca gggccaagaa cagttggaac agcagaatat   2820
gggccaaaca ggatatctgt ggtaagcagt tcctgccccg gctcagggcc aagaacagat   2880
ggtccccaga tgcggtcccg ccctcagcag tttctagaga accatcagat gtttccaggg   2940
tgccccaagg acctgaaatg accctgtgcc ttatttgaac taaccaatca gttcgcttct   3000
cgcttctgtt cgcgcgcttc tgctccccga gctctatata agcagagctc gtttagtgaa   3060
ccgtcagatc gcctggagac gccatccacg ctgttttgac ttccatagaa ggcggccgcg   3120
ccgccaccat ggtgagcaag ggcgaggagc tgttcaccgg ggtggtgccc atcctggtcg   3180
agctggacgg cgacgtaaac ggccacaagt tcagcgtgtc cggcgagggc gagggcgatg   3240
ccacctacgg caagctgacc ctgaagttca tctgcaccac cggcaagctg cccgtgccct   3300
ggcccaccct cgtgaccacc ctgacctacg gcgtgcagtg cttcagccgc taccccgacc   3360
acatgaagca gcacgacttc ttcaagtccg ccatgcccga aggctacgtc caggagcgca   3420
ccatcttctt caaggacgac ggcaactaca agacccgcgc cgaggtgaag ttcgagggcg   3480
acaccctggt gaaccgcatc gagctgaagg gcatcgactt caaggaggac ggcaacatcc   3540
tggggcacaa gctggagtac aactacaaca gccacaacgt ctatatcatg gccgacaagc   3600
agaagaacgg catcaaggtg aacttcaaga tccgccacaa catcgaggac ggcagcgtgc   3660
agctcgccga ccactaccag cagaacaccc ccatcggcga cggccccgtg ctgctgcccg   3720
acaaccacta cctgagcacc cagtccgccc tgagcaaaga ccccaacgag aagcgcgatc   3780
acatggtcct gctggagttc gtgaccgccg ccgggatcac tctcggcatg gacgagctgt   3840
acaagggaag cggagctact aacttcagcc tgctgaagca ggctggagac gtggaggaga   3900
accctggacc tcctgcagga acttcaaggt gagtccagga gatgtttcag ccctgttgcc   3960
tttagtctcg aggcaactta gacaacggag tattgatctg agcacagcag ggtgtgagct   4020
gtttgaagat actggggttg gggggtgaaga aactgcagag gactaactgg gctgagaccc   4080
agtggtaatg ttttagggcc taaggagtgc ctctaaaaat ctagatggac aattttgact   4140
ttgagaaaag agaggtggaa atgaggaaaa tgacttttct ttattagatt ccagtagaaa   4200
```

-continued

```
gaactttcat ctttccctca tttttgttgt tttaaaacat ctatctggag gcaggacaag   4260
tatggtcgtt aaaaagatgc aggcagaagg catatattgg ctcagtcaaa gtggggaact   4320
ttggtgggtc gacgtagata agtagcatgg cgggttaatc attaactaca aggaacccct   4380
agtgatggag ttggccactc cctctctgcg cgctcgctcg ctcactgagg ccgggcgacc   4440
aaaggtcgcc cgacgcccgg gctttgcccg ggcggcctca gtgagcgagc gagcgcgcca   4500
gctggcgtaa tagcgaagag gcccgcaccg atcgcccttc ccaacagttg cgcagcctga   4560
atggcgaatg gcgattccgt tgcaatggct ggcggtaata ttgttctgga tattaccagc   4620
aaggccgata gtttgagttc ttctactcag gcaagtgatg ttattactaa tcaaagaagt   4680
attgcgacaa cggttaattt gcgtgatgga cagactcttt tactcggtgg cctcactgat   4740
tataaaaaca cttctcagga ttctggcgta ccgttcctgt ctaaaatccc tttaatcggc   4800
ctcctgttta gctcccgctc tgattctaac gaggaaagca cgttatacgt gctcgtcaaa   4860
gcaaccatag tacgcgccct gtagcggcgc attaagcgcg gcgggtgtgg tggttacgcg   4920
cagcgtgacc gctacacttg ccagcgccct agcgcccgct cctttcgctt tcttcccttc   4980
ctttctcgcc acgttcgccg gctttccccg tcaagctcta aatcgggggc tccctttagg   5040
gttccgattt agtgctttac ggcacctcga ccccaaaaaa cttgattagg gtgatggttc   5100
acgtagtggg ccatcgccct gatagacggt ttttcgccct ttgacgttgg agtccacgtt   5160
ctttaatagt ggactcttgt tccaaactgg aacaacactc aaccctatct cggtctattc   5220
ttttgattta taagggattt tgccgatttc ggcctattgg ttaaaaaatg agctgattta   5280
acaaaaattt aacgcgaatt ttaacaaaat attaacgttt acaatttaaa tatttgctta   5340
tacaatcttc ctgtttttgg ggcttttctg attatcaacc ggggtacata tgattgacat   5400
gctagtttta cgattaccgt tcatcgattc tcttgtttgc tccagactct caggcaatga   5460
cctgatagcc tttgtagaga cctctcaaaa atagctaccc tctccggcat gaatttatca   5520
gctagaacgg ttgaatatca tattgatggt gatttgactg tctccggcct ttctcacccg   5580
tttgaatctt tacctacaca ttactcaggc attgcattta aaatatatga gggttctaaa   5640
aatttttatc cttgcgttga aataaaggct tctcccgcaa aagtattaca gggtcataat   5700
gtttttggta caaccgattt agctttatgc tctgaggctt tattgcttaa ttttgctaat   5760
tctttgcctt gcctgtatga tttattggat gttggaatcg cctgatgcgg tattttctcc   5820
ttacgcatct gtgcggtatt tcacaccgca tatggtgcac tctcagtaca atctgctctg   5880
atgccgcata gttaagccag ccccgacacc cgccaacacc cgctgacgcg ccctgacggg   5940
cttgtctgct cccggcatcc gcttacagac aagctgtgac cgtctccggg agctgcatgt   6000
gtcagaggtt ttcaccgtca tcaccgaaac gcgcgagacg aaagggcctc gtgatacgcc   6060
tatttttata ggttaatgtc atgataataa tggtttctta gacgtcaggt ggcacttttc   6120
ggggaaatgt gcgcggaacc cctatttgtt tatttttcta aatacattca aatatgtatc   6180
cgctcatgag acaataaccc tgataaatgc ttcaataata ttgaaaaagg aagagtatga   6240
gtattcaaca tttccgtgtc gcccttattc ccttttttgc ggcattttgc cttcctgttt   6300
ttgctcaccc agaaacgctg gtgaaagtaa aagatgctga agatcagttg ggtgcacgag   6360
tgggttacat cgaactggat ctcaacagcg gtaagatcct tgagagtttt cgccccgaag   6420
aacgttttcc aatgatgagc acttttaaag ttctgctatg tggcgcggta ttatcccgta   6480
ttgacgccgg gcaagagcaa ctcggtcgcc gcatacacta ttctcagaat gacttggttg   6540
agtactcacc agtcacagaa aagcatctta cggatggcat gacagtaaga gaattatgca   6600
```

```
gtgctgccat aaccatgagt gataacactg cggccaactt acttctgaca acgatcggag   6660
gaccgaagga gctaaccgct tttttgcaca acatggggga tcatgtaact cgccttgatc   6720
gttgggaacc ggagctgaat gaagccatac caaacgacga gcgtgacacc acgatgcctg   6780
tagcaatggc aacaacgttg cgcaaactat taactggcga actacttact ctagcttccc   6840
ggcaacaatt aatagactgg atggaggcgg ataaagttgc aggaccactt ctgcgctcgg   6900
cccttccggc tggctggttt attgctgata aatctggagc cggtgagcgt gggtctcgcg   6960
gtatcattgc agcactgggg ccagatggta agccctcccg tatcgtagtt atctacacga   7020
cggggagtca ggcaactatg gatgaacgaa atagacagat cgctgagata ggtgcctcac   7080
tgattaagca ttggtaactg tcagaccaag tttactcata tatactttag attgatttaa   7140
aacttcattt ttaatttaaa aggatctagg tgaagatcct ttttgataat ctcatgacca   7200
aaatccctta acgtgagttt tcgttccact gagcgtcaga ccccgtagaa aagatcaaag   7260
gatcttcttg agatcctttt tttctgcgcg taatctgctg cttgcaaaca aaaaaaccac   7320
cgctaccagc ggtggtttgt ttgccggatc aagagctacc aactcttttt ccgaaggtaa   7380
ctggcttcag cagagcgcag ataccaaata ctgtccttct agtgtagccg tagttaggcc   7440
accacttcaa gaactctgta gcaccgccta catacctcgc tctgctaatc ctgttaccag   7500
tggctgctgc cagtggcgat aagtcgtgtc ttaccgggtt ggactcaaga cgatagttac   7560
cggataaggc gcagcggtcg ggctgaacgg ggggttcgtg cacacagccc agcttggagc   7620
gaacgaccta caccgaactg agatacctac agcgtgagct atgagaaagc gccacgcttc   7680
ccgaagggag aaaggcggac aggtatccgg taagcggcag ggtcggaaca ggagagcgca   7740
cgagggagct tccaggggga aacgcctggt atctttatag tcctgtcggg tttcgccacc   7800
tctgacttga gcgtcgattt ttgtgatgct cgtcaggggg gcggagccta tggaaaaacg   7860
ccagcaacgc ggccttttta cggttcctgg ccttttgctg gccttttgct cacatgttct   7920
ttcctgcgtt atcccctgat tctgtggata accgtattac cgcctttgag tgagctgata   7980
ccgctcgccg cagccgaacg accgagcgca gcgagtcagt gagcgaggaa gcggaagagc   8040
gcccaatacg caaaccgcct ctccccgcgc gttggccgat tcattaatg              8089
```

```
<210> SEQ ID NO 36
<211> LENGTH: 8152
<212> TYPE: DNA
<213> ORGANISM: Artificial
<220> FEATURE:
<223> OTHER INFORMATION: AAV donor template

<400> SEQUENCE: 36
```

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtagat    180
ctttttttcct tagaaaccac tgctaactga aagagactaa gatttgtccc gtcaaaaatc   240
ctggacctat gcctaaaaca catttcacaa tccctgaact tttcaaaaat tggtacatgc    300
tttagcttta aactacaggc ctcactggag ctagagacaa gaaggtaaaa aacggctgac    360
aaaagaagtc ctggtatcct ctatgatggg agaaggaaac tagctaaagg gaagaataaa    420
ttagagaaaa actggaatga ctgaatcgga acaaggcaaa ggctataaaa aaaattagca    480
gtatcctctt gggggcccct tccccacact atctcaatgc aaatatctgt ctgaaacggt    540
```

-continued

```
ccctggctaa actccaccca tgggttggcc agccttgcct tgacaaggca aacttgacca    600
atagtcttag agtatccagt gaggccaggg gccggcggct ggctagggat gaagaataaa    660
aggaagcacc cttcagcagt tccacacact cgcttctgga acgtctgagg ttatcaataa    720
gctcctagtc cagacgccgc cgccaccatg gtccatctta caccggagga gaagtccgct    780
gtaacggcac tgtgggggaa agttaatgtc gatgaagtcg gcggtgaagc actcggcagg    840
ttgctggtag tgtacccgtg gacacaacga ttctttgaaa gtttcgggga cctgtccaca    900
cccgatgctg tgatgggtaa tccaaaagta aaagcacacg gcaagaaagt cctcggcgcg    960
tttagtgatg gtctggccca tttggataac ttgaagggta cattcgcgca gctttccgaa   1020
ctccactgtg acaagttgca cgtagatcca gaaaacttcc ggcttctggg caatgtgctt   1080
gtatgcgttc tggctcacca ttttgggaag gagtttaccc cacccgtgca agcggcttac   1140
caaaaagtgg tcgcaggagt ggctaatgcc cttgcacata aatatcacta aggtaccgag   1200
catcttaccg ccatttattc ccatatttgt tctgtttttc ttgatttggg tatacattta   1260
aatgttaata aaacaaaatg gtggggcaat catttacatt tttagggata tgtaattact   1320
agttcaggtg tattgccaca agacaaacat gttaagaaac tttcccgtta tttacgctct   1380
gttcctgtta atcaacctct ggattacaaa atttgtgaaa gattgactga tattcttaac   1440
tatgttgctc cttttacgct gtgtggatat gctgctttat agcctctgta tctagctatt   1500
gcttcccgta cggctttcgt tttctcctcc ttgtataaat cctggttgct gtctctttta   1560
gaggagttgt ggcccgttgt ccgtcaacgt ggcgtggtgt gctctgtgtt tgctgacgca   1620
acccccactg gctggggcat tgccaccacc tgtcaactcc tttctgggac tttcgctttc   1680
cccctcccga tcgccacggc agaactcatc gccgcctgcc ttgcccgctg ctggacaggg   1740
gctaggttgc tgggcactga taattccgtg gtgttgtctg tgccttctag ttgccagcca   1800
tctgttgttt gcccctcccc cgtgccttcc ttgaccctgg aaggtgccac tcccactgtc   1860
ctttcctaat aaaatgagga aattgcatcg cattgtctga gtaggtgtca ttctattctg   1920
gggggtgggg tggggcagga cagcaagggg gaggattggg aagacaatag caggcatgct   1980
ggggatgcgg tgggctctat ggccgagatc gagaccatcc tggctaacac agtgaaaccc   2040
cgtctctact aaaaaaatac aaaaaattag ccgggcttgg tggcgggtgc ctgtagtccc   2100
agctactatg gaggctgagg cgggagaatg gcgtgaacgc ggggggcgga gcttgcagtg   2160
agcagagatc aggggccact gcactccagc ctgggcgaca gagagagact ctgtctcaaa   2220
aaaaagaaaa aaaaaattta gtagactagc taaaaaaatc cagagatagt tattgatgca   2280
tatgtaaaag tcttccaata tttacaagta caatgaaaaa aaaataacct tgaattaagt   2340
gtagaactca ttgacaatgt ttcaaaggat gtgagggata aactaaaatt tgggcagtac   2400
atgctgttcc tgtgtacttg gaacagaggg agaaaatctg ggctggaaat attgttatag   2460
gagttagcac atgaaggtga caactaaatt atttggagta gatggagtca ccagcacatg   2520
tgaatagttt tagaatgaaa tgacccaaga tagaactttg gagagccccc aaatttaaat   2580
aaaatcagta taagagaaga ggaagaaacc aaatggtata ctagtctaaa ttgtttctta   2640
gtgacaaaag aataacctga atattagatt agctgcctat atgctctctg aatcaatttc   2700
attcaacatg caacagtccg cgggaacaga gaaacaggag aatatgggcc aaacaggata   2760
tctgtggtaa gcagttcctg ccccggctca gggccaagaa cagttggaac agcagaatat   2820
gggccaaaca ggatatctgt ggtaagcagt tcctgccccg gctcagggcc aagaacagat   2880
ggtccccaga tgcggtcccg ccctcagcag tttctagaga accatcagat gtttccaggg   2940
```

tgccccaagg acctgaaatg accctgtgcc ttatttgaac taaccaatca gttcgcttct 3000
cgcttctgtt cgcgcgcttc tgctccccga gctctatata agcagagctc gtttagtgaa 3060
ccgtcagatc gcctggagac gccatccacg ctgttttgac ttccatagaa ggcggccgcg 3120
ccgccaccat ggtgagcaag ggcgaggagc tgttcaccgg ggtggtgccc atcctggtcg 3180
agctggacgg cgacgtaaac ggccacaagt tcagcgtgtc cggcgagggc gagggcgatg 3240
ccacctacgg caagctgacc ctgaagttca tctgcaccac cggcaagctg cccgtgccct 3300
ggcccaccct cgtgaccacc ctgacctacg gcgtgcagtg cttcagccgc taccccgacc 3360
acatgaagca gcacgacttc ttcaagtccg ccatgcccga aggctacgtc caggagcgca 3420
ccatcttctt caaggacgac ggcaactaca agacccgcgc cgaggtgaag ttcgagggcg 3480
acaccctggt gaaccgcatc gagctgaagg gcatcgactt caaggaggac ggcaacatcc 3540
tggggcacaa gctggagtac aactacaaca gccacaacgt ctatatcatg gccgacaagc 3600
agaagaacgg catcaaggtg aacttcaaga tccgccacaa catcgaggac ggcagcgtgc 3660
agctcgccga ccactaccag cagaacaccc ccatcggcga cggccccgtg ctgctgcccg 3720
acaaccacta cctgagcacc cagtccgccc tgagcaaaga ccccaacgag aagcgcgatc 3780
acatggtcct gctggagttc gtgaccgccg ccgggatcac tctcggcatg gacgagctgt 3840
acaagtaagc tttatttgtg aaatttgtga tgctattgct ttatttgtaa ccattataag 3900
ctgcaataaa caagttaaca acaacaattg cattcatttt atgtttcagg ttcaggggga 3960
gatgtgggag gtttttaaa gccctgcagg atgggtcatt tcacagagga ggacaaggct 4020
actatcacaa gcctgtgggg caaggtgaat gtggaagatg ctggaggaga aaccctggga 4080
aggtaggctc tggtgaccag gacaagggag ggaaggaagg accctgtgcc tggcaaaagt 4140
ccaggtcgct tctcaggatt tgtggcacct tctgactgtc aaactgttct tgtcaatctc 4200
acaggctcct ggttgtctac ccatggaccc agaggttctt tgacagcttt ggcaacctgt 4260
cctctgcctc tgccatcatg ggcaacccca aagtcaaggc acatggcaag aaggtgctga 4320
cttccttggg agatgccaca aagcacctgg atgatctcaa gggcaccttt gcccagctga 4380
gtgaactgca gtcgacgtag ataagtagca tggcgggtta atcattaact acaaggaacc 4440
cctagtgatg gagttggcca ctccctctct gcgcgctcgc tcgctcactg aggccgggcg 4500
accaaaggtc gcccgacgcc cgggctttgc ccgggcggcc tcagtgagcg agcgagcgcg 4560
ccagctggcg taatagcgaa gaggcccgca ccgatcgccc ttcccaacag ttgcgcagcc 4620
tgaatggcga atggcgattc cgttgcaatg gctggcggta atattgttct ggatattacc 4680
agcaaggccg atagtttgag ttcttctact caggcaagtg atgttattac taatcaaaga 4740
agtattgcga caacggttaa tttgcgtgat ggacagactc ttttactcgg tggcctcact 4800
gattataaaa acacttctca ggattctggc gtaccgttcc tgtctaaaat ccctttaatc 4860
ggcctcctgt ttagctcccg ctctgattct aacgaggaaa gcacgttata cgtgctcgtc 4920
aaagcaacca tagtacgcgc cctgtagcgg cgcattaagc gcggcgggtg tggtggttac 4980
gcgcagcgtg accgctacac ttgccagcgc cctagcgccc gctcctttcg ctttcttccc 5040
ttcctttctc gccacgttcg ccggctttcc ccgtcaagct ctaaatcggg ggctcccttt 5100
agggttccga tttagtgctt tacggcacct cgaccccaaa aaacttgatt agggtgatgg 5160
ttcacgtagt gggccatcgc cctgatagac ggtttttcgc cctttgacgt tggagtccac 5220
gttctttaat agtggactct tgttccaaac tggaacaaca ctcaacccta tctcggtcta 5280

-continued ttcttttgat ttataaggga ttttgccgat ttcggcctat tggttaaaaa atgagctgat 5340
ttaacaaaaa tttaacgcga attttaacaa aatattaacg tttacaattt aaatatttgc 5400
ttatacaatc ttcctgtttt tggggctttt ctgattatca accggggtac atatgattga 5460
catgctagtt ttacgattac cgttcatcga ttctcttgtt tgctccagac tctcaggcaa 5520
tgacctgata gcctttgtag agacctctca aaaatagcta ccctctccgg catgaattta 5580
tcagctagaa cggttgaata tcatattgat ggtgatttga ctgtctccgg cctttctcac 5640
ccgtttgaat ctttacctac acattactca ggcattgcat ttaaaatata tgagggttct 5700
aaaaattttt atccttgcgt tgaaataaag gcttctcccg caaaagtatt acagggtcat 5760
aatgtttttg gtacaaccga tttagcttta tgctctgagg ctttattgct taattttgct 5820
aattctttgc cttgcctgta tgatttattg gatgttggaa tcgcctgatg cggtattttc 5880
tccttacgca tctgtgcggt atttcacacc gcatatggtg cactctcagt acaatctgct 5940
ctgatgccgc atagttaagc cagccccgac acccgccaac acccgctgac gcgccctgac 6000
gggcttgtct gctcccggca tccgcttaca gacaagctgt gaccgtctcc gggagctgca 6060
tgtgtcagag gttttcaccg tcatcaccga aacgcgcgag acgaaagggc ctcgtgatac 6120
gcctattttt ataggttaat gtcatgataa taatggtttc ttagacgtca ggtggcactt 6180
ttcggggaaa tgtgcgcgga acccctattt gtttattttt ctaaatacat tcaaatatgt 6240
atccgctcat gagacaataa ccctgataaa tgcttcaata atattgaaaa aggaagagta 6300
tgagtattca acatttccgt gtcgccctta ttcccttttt tgcggcattt tgccttcctg 6360
tttttgctca cccagaaacg ctggtgaaag taaaagatgc tgaagatcag ttgggtgcac 6420
gagtgggtta catcgaactg gatctcaaca gcggtaagat ccttgagagt tttcgccccg 6480
aagaacgttt tccaatgatg agcactttta aagttctgct atgtggcgcg gtattatccc 6540
gtattgacgc cgggcaagag caactcggtc gccgcataca ctattctcag aatgacttgg 6600
ttgagtactc accagtcaca gaaaagcatc ttacggatgg catgacagta agagaattat 6660
gcagtgctgc cataaccatg agtgataaca ctgcggccaa cttacttctg acaacgatcg 6720
gaggaccgaa ggagctaacc gcttttttgc acaacatggg ggatcatgta actcgccttg 6780
atcgttggga accggagctg aatgaagcca taccaaacga cgagcgtgac accacgatgc 6840
ctgtagcaat ggcaacaacg ttgcgcaaac tattaactgg cgaactactt actctagctt 6900
cccggcaaca attaatagac tggatggagg cggataaagt tgcaggacca cttctgcgct 6960
cggcccttcc ggctggctgg tttattgctg ataaatctgg agccggtgag cgtgggtctc 7020
gcggtatcat tgcagcactg gggccagatg gtaagccctc ccgtatcgta gttatctaca 7080
cgacggggag tcaggcaact atggatgaac gaaatagaca gatcgctgag ataggtgcct 7140
cactgattaa gcattggtaa ctgtcagacc aagtttactc atatatactt tagattgatt 7200
taaaacttca tttttaattt aaaaggatct aggtgaagat cctttttgat aatctcatga 7260
ccaaaatccc ttaacgtgag ttttcgttcc actgagcgtc agaccccgta gaaaagatca 7320
aaggatcttc ttgagatcct ttttttctgc gcgtaatctg ctgcttgcaa acaaaaaaac 7380
caccgctacc agcggtggtt tgtttgccgg atcaagagct accaactctt tttccgaagg 7440
taactggctt cagcagagcg cagataccaa atactgtcct tctagtgtag ccgtagttag 7500
gccaccactt caagaactct gtagcaccgc ctacatacct cgctctgcta atcctgttac 7560
cagtggctgc tgccagtggc gataagtcgt gtcttaccgg gttggactca agacgatagt 7620
taccggataa ggcgcagcgg tcgggctgaa cggggggttc gtgcacacag cccagcttgg 7680
agcgaacgac ctacaccgaa ctgagatacc tacagcgtga gctatgagaa agcgccacgc 7740
ttcccgaagg gagaaaggcg gacaggtatc cggtaagcgg cagggtcgga acaggagagc 7800
gcacgaggga gcttccaggg ggaaacgcct ggtatcttta tagtcctgtc gggtttcgcc 7860
acctctgact tgagcgtcga tttttgtgat gctcgtcagg ggggcggagc ctatggaaaa 7920
acgccagcaa cgcggccttt ttacggttcc tggccttttg ctggcctttt gctcacatgt 7980
tctttcctgc gttatcccct gattctgtgg ataaccgtat taccgccttt gagtgagctg 8040
ataccgctcg ccgcagccga acgaccgagc gcagcgagtc agtgagcgag gaagcggaag 8100
agcgcccaat acgcaaaccg cctctccccg cgcgttggcc gattcattaa tg 8152

<210> SEQ ID NO 37
<211> LENGTH: 8236
<212> TYPE: DNA
<213> ORGANISM: Artificial
<220> FEATURE:
<223> OTHER INFORMATION: AAV donor template

<400> SEQUENCE: 37
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatcttaccc tgttaatggt ccaatatgtc agaaacagca 180
ctgtgttaga aataaagctg tctaaagtac actaatattc gagttataat agtgtgtgga 240
ctattagtca ataaaaacaa cccttgcctc tttagagttg ttttccatgt acacgcacat 300
cttatgtctt agagtaagat tccctgagaa gtgaacctag catttataca agataattaa 360
ttctaatcca cagtacctgc caaagaacat tctaccatca tctttactga gcatagaaga 420
gctacgccaa aaccctgggt catcagccag cacacacact tatccagtgg taaatacaca 480
tcatctggtg tatacataca tacctgaata tggaatcaaa tatttttcta agatgaaaca 540
gtcatgattt atttcaaata ggtacggata agtagatatt gaggtaagca ttaggtctta 600
tattatgtaa cactaatcta ttactgcgct gaaactgtgg ctttatagaa attgttttca 660
ctgcactatt gagaaattaa gagataatgg caaaagtcac aaagagtata ttcaaaaaga 720
agtatagcac tttttcctta gaaaccactg ctaactgaaa gagactaaga tttgtcccgt 780
caaaaatcct ggacctatgc ctaaaacaca tttcacaatc cctgaacttt tcaaaaattg 840
gtacatgctt tagctttaaa ctacaggcct cactggagct agagacaaga aggtaaaaaa 900
cggctgacaa aagaagtcct ggtatcctct atgatgggag aaggaaacta gctaaaggga 960
agaataaatt agagaaaaac tggaatgact gaatcggaac aaggcaaagg ctataaaaaa 1020
aattagcagt atcctcttgg gggcccccttc cccacactat ctcaatgcaa atatctgtct 1080
gaaacggtcc ctggctaaac tccacccatg ggttggccag ccttgccttg accaatagcc 1140
ttgacgaatt cgctttaaaa aacctcccac atctccccct gaacctgaaa cataaaatga 1200
atgcaattgt tgttgttaac ttgtttattg cagcttataa tggttacaaa taaagcaata 1260
gcatcacaaa tttcacaaat aaagcttact tgtacagctc gtccatgccg agagtgatcc 1320
cggcggcggt cacgaactcc agcaggacca tgtgatcgcg cttctcgttg gggtctttgc 1380
tcagggcgga ctgggtgctc aggtagtggt tgtcgggcag cagcacgggg ccgtcgccga 1440
tgggggtgtt ctgctggtag tggtcggcga gctgcacgct gccgtcctcg atgttgtggc 1500
ggatcttgaa gttcaccttg atgccgttct tctgcttgtc ggccatgata tagacgttgt 1560

-continued

```
ggctgttgta gttgtactcc agcttgtgcc ccaggatgtt gccgtcctcc ttgaagtcga   1620
tgcccttcag ctcgatgcgg ttcaccaggg tgtcgccctc gaacttcacc tcggcgcggg   1680
tcttgtagtt gccgtcgtcc ttgaagaaga tggtgcgctc ctggacgtag ccttcgggca   1740
tggcggactt gaagaagtcg tgctgcttca tgtggtcggg gtagcggctg aagcactgca   1800
cgccgtaggt cagggtggtc acgagggtgg gccagggcac gggcagcttg ccggtggtgc   1860
agatgaactt cagggtcagc ttgccgtagg tggcatcgcc ctcgccctcg ccggacacgc   1920
tgaacttgtg gccgtttacg tcgccgtcca gctcgaccag gatgggcacc accccggtga   1980
acagctcctc gcccttgctc accatggtgg cggcgcggcc gcgatctgac ggttcactaa   2040
acgagctctg cttatataga gctcggggag cagaagcgcg cgaacagaag cgagaagcga   2100
actgattggt tagttcaaat aaggcacagg gtcatttcag gtccttgggg caccctggaa   2160
acatctgatg gttctctaga aactgctgag ggcgggaccg catctgggga ccatctgttc   2220
ttggccctga gccggggcag gaactgctta ccacagatat cctgtttggc ccatattctg   2280
ctgttccaac tgttcttggc cctgagccgg ggcaggaact gcttaccaca gatatcctgt   2340
ttggcccata ttctcctgtt tctctgttcc cgcggcgaga tcgagaccat cctggctaac   2400
acagtgaaac cccgtctcta ctaaaaaaat acaaaaaatt agccgggctt ggtggcgggt   2460
gcctgtagtc ccagctacta tggaggctga ggcgggagaa tggcgtgaac gcgggggcg   2520
gagcttgcag tgagcagaga tcaggggcca ctgcactcca gcctgggcga cagagagaga   2580
ctctgtctca aaaaaaagaa aaaaaaaatt tagtagacta gctaaaaaaa tccagagata   2640
gttattgatg catatgtaaa agtcttccaa tatttacaag tacaatgaaa aaaaaataac   2700
cttgaattaa gtgtagaact cattgacaat gtttcaaagg atgtgaggga taaactaaaa   2760
tttgggcagt acatgctgtt cctgtgtact tggaacagag ggagaaaatc tgggctggaa   2820
atattgttat aggagttagc acatgaaggt gacaactaaa ttatttggag tagatggagt   2880
caccagcaca tgtgaatagt tttagaatga aatgacccaa gatagaactt tggagagccc   2940
ccaaatttaa ataaaatcag tataagagaa gaggaagaaa ccaaatggta tactagtcta   3000
aattgtttct tagtgacaaa agaataacct gaatattaga ttagctgcct atatgctctc   3060
tgaatcaatt tcattcaaca tgcaacagtt ctggaaccta tcagggacca cagtcagcca   3120
ggcaagcaca tctgcccaag ccaagggtgg aggcatgcag ctgtggggt ctgtgaaaac   3180
acttgaggga gcagataact gggccaacca tgactcagtg cttctggagg ccaacaggac   3240
tgctgagtca tcctgtgggg gtggaggtgg gacaagggaa aggggtgaat ggtactgctg   3300
attacaacct ctggtgctgc ctccccctcc tgtttatctg agagaggcct cactggagct   3360
agagacaaga aggtaaaaaa cggctgacaa aagaagtcct ggtatcctct atgatgggag   3420
aaggaaacta gctaaaggga agaataaatt agagaaaaac tggaatgact gaatcggaac   3480
aaggcaaagg ctataaaaaa aattagcagt atcctcttgg gggccccttc cccacactat   3540
ctcaatgcaa atatctgtct gaaacggtcc ctggctaaac tccacccatg ggttggccag   3600
ccttgccttg acaaggcaaa cttgaccaat agtcttagag tatccagtga ggccaggggc   3660
cggcggctgg ctagggatga agaataaaag gaagcaccct tcagcagttc cacacactcg   3720
cttctggaac gtctgaggtt atcaataagc tcctagtcca gacgccatgg gtcatttcac   3780
agaggaggac aaggctacta tcacaagcct gtggggcaag gtgaatgtgg aagatgctgg   3840
aggagaaacc ctgggaaggt aggctctggt gaccaggaca agggagggaa ggaaggaccc   3900
tgtgcctggc aaaagtccag gtcgcttctc aggatttgtg gcaccttctg actgtcaaac   3960
```

-continued tgttcttgtc aatctcacag gctcctggtt gtctacccat ggacccagag gttctttgac 4020
agctttggca acctgtcctc tgcctctgcc atcatgggca accccaaagt caaggcacat 4080
ggcaagaagg tgctgacttc cttgggagat gccacaaagc acctggatga tctcaagggc 4140
acctttgccc agctgagtga actgcactgt gacaagctgc atgtggatcc tgagaacttc 4200
aaggtgagtc caggagatgt ttcagccctg ttgcctttag tctcgaggca acttagacaa 4260
cggagtattg atctgagcac agcagggtgt gagctgtttg aagatactgg ggttgggggt 4320
gaagaaactg cagaggacta actgggctga gacccagtgg taatgtttta gggcctaagg 4380
agtgcctcta aaaatctaga tggacaattt tgactttgag aaaagagagg tggaaatgag 4440
gaaaatgact tttctttatt agattccagt agaaagaact ttcatctttc cctcattttt 4500
gttgttttaa aagtcgacag gaacccctag tgatggagtt ggccactccc tctctgcgcg 4560
ctcgctcgct cactgaggcc gggcgaccaa aggtcgcccg acgcccgggc tttgcccggg 4620
cggcctcagt gagcgagcga gcgcgcagct ggcgtaatag cgaagaggcc cgcaccgatc 4680
gcccttccca acagttgcgc agcctgaatg gcgaatggcg attccgttgc aatggctggc 4740
ggtaatattg ttctggatat taccagcaag gccgatagtt tgagttcttc tactcaggca 4800
agtgatgtta ttactaatca aagaagtatt gcgacaacgg ttaatttgcg tgatggacag 4860
actcttttac tcggtggcct cactgattat aaaaacactt ctcaggattc tggcgtaccg 4920
ttcctgtcta aaatcccttt aatcggcctc ctgtttagct cccgctctga ttctaacgag 4980
gaaagcacgt tatacgtgct cgtcaaagca accatagtac gcgccctgta gcggcgcatt 5040
aagcgcggcg ggtgtggtgg ttacgcgcag cgtgaccgct acacttgcca gcgccctagc 5100
gcccgctcct ttcgctttct tcccttcctt tctcgccacg ttcgccggct ttccccgtca 5160
agctctaaat cgggggctcc ctttagggtt ccgatttagt gctttacggc acctcgaccc 5220
caaaaaactt gattagggtg atggttcacg tagtgggcca tcgccctgat agacggtttt 5280
tcgccctttg acgttggagt ccacgttctt taatagtgga ctcttgttcc aaactggaac 5340
aacactcaac cctatctcgg tctattcttt tgatttataa gggattttgc cgatttcggc 5400
ctattggtta aaaaatgagc tgatttaaca aaaatttaac gcgaatttta acaaaatatt 5460
aacgtttaca atttaaatat ttgcttatac aatcttcctg tttttggggc ttttctgatt 5520
atcaaccggg gtacatatga ttgacatgct agttttacga ttaccgttca tcgattctct 5580
tgtttgctcc agactctcag gcaatgacct gatagccttt gtagagacct ctcaaaaata 5640
gctaccctct ccggcatgaa tttatcagct agaacggttg aatatcatat tgatggtgat 5700
ttgactgtct ccggcctttc tcacccgttt gaatctttac ctacacatta ctcaggcatt 5760
gcatttaaaa tatatgaggg ttctaaaaat ttttatcctt gcgttgaaat aaaggcttct 5820
cccgcaaaag tattacaggg tcataatgtt tttggtacaa ccgatttagc tttatgctct 5880
gaggctttat tgcttaattt tgctaattct ttgccttgcc tgtatgattt attggatgtt 5940
ggaatcgcct gatgcggtat tttctcctta cgcatctgtg cggtatttca caccgcatat 6000
ggtgcactct cagtacaatc tgctctgatg ccgcatagtt aagccagccc cgacacccgc 6060
caacacccgc tgacgcgccc tgacgggctt gtctgctccc ggcatccgct tacagacaag 6120
ctgtgaccgt ctccgggagc tgcatgtgtc agaggttttc accgtcatca ccgaaacgcg 6180
cgagacgaaa gggcctcgtg atacgcctat ttttataggt taatgtcatg ataataatgg 6240
tttcttagac gtcaggtggc acttttcggg gaaatgtgcg cggaacccct atttgtttat 6300

-continued

```
ttttctaaat acattcaaat atgtatccgc tcatgagaca ataaccctga taaatgcttc   6360

aataatattg aaaaaggaag agtatgagta ttcaacattt ccgtgtcgcc cttattccct   6420

tttttgcggc attttgcctt cctgtttttg ctcacccaga aacgctggtg aaagtaaaag   6480

atgctgaaga tcagttgggt gcacgagtgg gttacatcga actggatctc aacagcggta   6540

agatccttga gagttttcgc cccgaagaac gttttccaat gatgagcact tttaaagttc   6600

tgctatgtgg cgcggtatta tcccgtattg acgccgggca agagcaactc ggtcgccgca   6660

tacactattc tcagaatgac ttggttgagt actcaccagt cacagaaaag catcttacgg   6720

atggcatgac agtaagagaa ttatgcagtg ctgccataac catgagtgat aacactgcgg   6780

ccaacttact tctgacaacg atcggaggac cgaaggagct aaccgctttt ttgcacaaca   6840

tgggggatca tgtaactcgc cttgatcgtt gggaaccgga gctgaatgaa gccataccaa   6900

acgacgagcg tgacaccacg atgcctgtag caatggcaac aacgttgcgc aaactattaa   6960

ctggcgaact acttactcta gcttcccggc aacaattaat agactggatg gaggcggata   7020

aagttgcagg accacttctg cgctcggccc ttccggctgg ctggtttatt gctgataaat   7080

ctggagccgg tgagcgtggg tctcgcggta tcattgcagc actggggcca gatggtaagc   7140

cctcccgtat cgtagttatc tacacgacgg ggagtcaggc aactatggat gaacgaaata   7200

gacagatcgc tgagataggt gcctcactga ttaagcattg gtaactgtca gaccaagttt   7260

actcatatat actttagatt gatttaaaac ttcattttta atttaaaagg atctaggtga   7320

agatcctttt tgataatctc atgaccaaaa tcccttaacg tgagttttcg ttccactgag   7380

cgtcagaccc cgtagaaaag atcaaaggat cttcttgaga tccttttttt ctgcgcgtaa   7440

tctgctgctt gcaaacaaaa aaaccaccgc taccagcggt ggtttgtttg ccggatcaag   7500

agctaccaac tctttttccg aaggtaactg gcttcagcag agcgcagata ccaaatactg   7560

tccttctagt gtagccgtag ttaggccacc acttcaagaa ctctgtagca ccgcctacat   7620

acctcgctct gctaatcctg ttaccagtgg ctgctgccag tggcgataag tcgtgtctta   7680

ccgggttgga ctcaagacga tagttaccgg ataaggcgca gcggtcgggc tgaacggggg   7740

gttcgtgcac acagcccagc ttggagcgaa cgacctacac cgaactgaga tacctacagc   7800

gtgagctatg agaaagcgcc acgcttcccg aagggagaaa ggcggacagg tatccggtaa   7860

gcggcagggt cggaacagga gagcgcacga gggagcttcc agggggaaac gcctggtatc   7920

tttatagtcc tgtcgggttt cgccacctct gacttgagcg tcgatttttg tgatgctcgt   7980

caggggggcg gagcctatgg aaaaacgcca gcaacgcggc ctttttacgg ttcctggcct   8040

tttgctggcc ttttgctcac atgttctttc ctgcgttatc ccctgattct gtggataacc   8100

gtattaccgc ctttgagtga gctgataccg ctcgccgcag ccgaacgacc gagcgcagcg   8160

agtcagtgag cgaggaagcg gaagagcgcc caatacgcaa accgcctctc cccgcgcgtt   8220

ggccgattca ttaatg                                                   8236


<210> SEQ ID NO 38
<211> LENGTH: 7955
<212> TYPE: DNA
<213> ORGANISM: Artificial
<220> FEATURE:
<223> OTHER INFORMATION: AAV donor template

<400> SEQUENCE: 38

cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120
```

-continued

```
actaggggtt cctacgcgta gatcttaccc tgttaatggt ccaatatgtc agaaacagca    180
ctgtgttaga aataaagctg tctaaagtac actaatattc gagttataat agtgtgtgga    240
ctattagtca ataaaaacaa cccttgcctc tttagagttg ttttccatgt acacgcacat    300
cttatgtctt agagtaagat tccctgagaa gtgaacctag catttataca agataattaa    360
ttctaatcca cagtacctgc caaagaacat tctaccatca tctttactga gcatagaaga    420
gctacgccaa aaccctgggt catcagccag cacacacact tatccagtgg taaatacaca    480
tcatctggtg tatacataca tacctgaata tggaatcaaa tatttttcta agatgaaaca    540
gtcatgattt atttcaaata ggtacggata agtagatatt gaggtaagca ttaggtctta    600
tattatgtaa cactaatcta ttactgcgct gaaactgtgg ctttatagaa attgttttca    660
ctgcactatt gagaaattaa gagataatgg caaaagtcac aaagagtata ttcaaaaaga    720
agtatagcac tttttcctta gaaaccactg ctaactgaaa gagactaaga tttgtcccgt    780
caaaaatcct ggacctatgc ctaaaacaca tttcacaatc cctgaacttt tcaaaaattg    840
gtacatgctt tagctttaaa ctacgaattc gctttaaaaa acctcccaca tctccccctg    900
aacctgaaac ataaaatgaa tgcaattgtt gttgttaact tgtttattgc agcttataat    960
ggttacaaat aaagcaatag catcacaaat ttcacaaata aagcttactt gtacagctcg   1020
tccatgccga gagtgatccc ggcggcggtc acgaactcca gcaggaccat gtgatcgcgc   1080
ttctcgttgg ggtctttgct cagggcggac tgggtgctca ggtagtggtt gtcgggcagc   1140
agcacggggc cgtcgccgat gggggtgttc tgctggtagt ggtcggcgag ctgcacgctg   1200
ccgtcctcga tgttgtggcg gatcttgaag ttcaccttga tgccgttctt ctgcttgtcg   1260
gccatgatat agacgttgtg gctgttgtag ttgtactcca gcttgtgccc caggatgttg   1320
ccgtcctcct tgaagtcgat gcccttcagc tcgatgcggt tcaccagggt gtcgccctcg   1380
aacttcacct cggcgcgggt cttgtagttg ccgtcgtcct tgaagaagat ggtgcgctcc   1440
tggacgtagc cttcgggcat ggcggacttg aagaagtcgt gctgcttcat gtggtcgggg   1500
tagcggctga agcactgcac gccgtaggtc agggtggtca cgagggtggg ccagggcacg   1560
ggcagcttgc cggtggtgca gatgaacttc agggtcagct tgccgtaggt ggcatcgccc   1620
tcgccctcgc cggacacgct gaacttgtgg ccgtttacgt cgccgtccag ctcgaccagg   1680
atgggcacca ccccggtgaa cagctcctcg cccttgctca ccatggtggc ggcgcggccg   1740
cgatctgacg gttcactaaa cgagctctgc ttatatagag ctcggggagc agaagcgcgc   1800
gaacagaagc gagaagcgaa ctgattggtt agttcaaata aggcacaggg tcatttcagg   1860
tccttggggc accctggaaa catctgatgg ttctctagaa actgctgagg gcgggaccgc   1920
atctggggac catctgttct tggccctgag ccggggcagg aactgcttac cacagatatc   1980
ctgtttggcc catattctgc tgttccaact gttcttggcc ctgagccggg gcaggaactg   2040
cttaccacag atatcctgtt tggcccatat tctcctgttt ctctgttccc gcggcgagat   2100
cgagaccatc ctggctaaca cagtgaaacc ccgtctctac taaaaaaata caaaaaatta   2160
gccgggcttg gtggcgggtg cctgtagtcc cagctactat ggaggctgag gcgggagaat   2220
ggcgtgaacg cggggggcgg agcttgcagt gagcagagat caggggccac tgcactccag   2280
cctgggcgac agagagagac tctgtctcaa aaaaaagaaa aaaaaaattt agtagactag   2340
ctaaaaaaat ccagagatag ttattgatgc atatgtaaaa gtcttccaat atttacaagt   2400
acaatgaaaa aaaaataacc ttgaattaag tgtagaactc attgacaatg tttcaaagga   2460
```

-continued

```
tgtgagggat aaactaaaat ttgggcagta catgctgttc ctgtgtactt ggaacagagg   2520
gagaaaatct gggctggaaa tattgttata ggagttagca catgaaggtg acaactaaat   2580
tatttggagt agatggagtc accagcacat gtgaatagtt ttagaatgaa atgacccaag   2640
atagaacttt ggagagcccc caaatttaaa taaaatcagt ataagagaag aggaagaaac   2700
caaatggtat actagtctaa attgtttctt agtgacaaaa gaataacctg aatattagat   2760
tagctgccta tatgctctct gaatcaattt cattcaacat gcaacagttc tggaacctat   2820
cagggaccac agtcagccag gcaagcacat ctgcccaagc caagggtgga ggcatgcagc   2880
tgtgggggtc tgtgaaaaca cttgagggag cagataactg ggccaaccat gactcagtgc   2940
ttctggaggc caacaggact gctgagtcat cctgtggggg tggaggtggg acaagggaaa   3000
ggggtgaatg gtactgctga ttacaacctc tggtgctgcc tccccctcct gtttatctga   3060
gagaggcctc actggagcta gagacaagaa ggtaaaaaac ggctgacaaa agaagtcctg   3120
gtatcctcta tgatgggaga aggaaactag ctaaagggaa gaataaatta gagaaaaact   3180
ggaatgactg aatcggaaca aggcaaaggc tataaaaaaa attagcagta tcctcttggg   3240
ggccccttcc ccacactatc tcaatgcaaa tatctgtctg aaacggtccc tggctaaact   3300
ccacccatgg gttggccagc cttgccttga caaggcaaac ttgaccaata gtcttagagt   3360
atccagtgag gccaggggcc ggcggctggc tagggatgaa gaataaaagg aagcaccctt   3420
cagcagttcc acacactcgc ttctggaacg tctgaggtta tcaataagct cctagtccag   3480
acgccatggg tcatttcaca gaggaggaca aggctactat cacaagcctg tggggcaagg   3540
tgaatgtgga agatgctgga ggagaaaccc tgggaaggta ggctctggtg accaggacaa   3600
gggagggaag gaaggaccct gtgcctggca aaagtccagg tcgcttctca ggatttgtgg   3660
caccttctga ctgtcaaact gttcttgtca atctcacagg ctcctggttg tctacccatg   3720
gacccagagg ttctttgaca gctttggcaa cctgtcctct gcctctgcca tcatgggcaa   3780
ccccaaagtc aaggcacatg gcaagaaggt gctgacttcc ttgggagatg ccacaaagca   3840
cctggatgat ctcaagggca cctttgccca gctgagtgaa ctgcactgtg acaagctgca   3900
tgtggatcct gagaacttca aggtgagtcc aggagatgtt tcagccctgt tgcctttagt   3960
ctcgaggcaa cttagacaac ggagtattga tctgagcaca gcagggtgtg agctgtttga   4020
agatactggg gttgggggtg aagaaactgc agaggactaa ctgggctgag acccagtggt   4080
aatgttttag ggcctaagga gtgcctctaa aaatctagat ggacaatttt gactttgaga   4140
aaagagaggt ggaaatgagg aaaatgactt ttctttatta gattccagta gaaagaactt   4200
tcatctttcc ctcatttttg ttgttttaaa agtcgacagg aacccctagt gatggagttg   4260
gccactccct ctctgcgcgc tcgctcgctc actgaggccg ggcgaccaaa ggtcgcccga   4320
cgcccgggct ttgcccgggc ggcctcagtg agcgagcgag cgcgcagctg gcgtaatagc   4380
gaagaggccc gcaccgatcg cccttcccaa cagttgcgca gcctgaatgg cgaatggcga   4440
ttccgttgca atggctggcg gtaatattgt tctggatatt accagcaagg ccgatagttt   4500
gagttcttct actcaggcaa gtgatgttat tactaatcaa agaagtattg cgacaacggt   4560
taatttgcgt gatggacaga ctcttttact cggtggcctc actgattata aaaacacttc   4620
tcaggattct ggcgtaccgt tcctgtctaa aatcccttta atcggcctcc tgtttagctc   4680
ccgctctgat tctaacgagg aaagcacgtt atacgtgctc gtcaaagcaa ccatagtacg   4740
cgccctgtag cggcgcatta agcgcggcgg gtgtggtggt tacgcgcagc gtgaccgcta   4800
cacttgccag cgccctagcg cccgctcctt tcgctttctt cccttccttt ctcgccacgt   4860
```

-continued tcgccggctt tccccgtcaa gctctaaatc gggggctccc tttagggttc cgatttagtg 4920
ctttacggca cctcgacccc aaaaaacttg attagggtga tggttcacgt agtgggccat 4980
cgccctgata gacggttttt cgccctttga cgttggagtc cacgttcttt aatagtggac 5040
tcttgttcca aactggaaca acactcaacc ctatctcggt ctattctttt gatttataag 5100
ggattttgcc gatttcggcc tattggttaa aaaatgagct gatttaacaa aaatttaacg 5160
cgaattttaa caaaatatta acgtttacaa tttaaatatt tgcttataca atcttcctgt 5220
ttttggggct tttctgatta tcaaccgggg tacatatgat tgacatgcta gttttacgat 5280
taccgttcat cgattctctt gtttgctcca gactctcagg caatgacctg atagcctttg 5340
tagagacctc tcaaaaatag ctaccctctc cggcatgaat ttatcagcta gaacggttga 5400
atatcatatt gatggtgatt tgactgtctc cggcctttct cacccgtttg aatctttacc 5460
tacacattac tcaggcattg catttaaaat atatgagggt tctaaaaatt tttatccttg 5520
cgttgaaata aaggcttctc ccgcaaaagt attacagggt cataatgttt ttggtacaac 5580
cgatttagct ttatgctctg aggctttatt gcttaatttt gctaattctt tgccttgcct 5640
gtatgattta ttggatgttg gaatcgcctg atgcggtatt ttctccttac gcatctgtgc 5700
ggtatttcac accgcatatg gtgcactctc agtacaatct gctctgatgc cgcatagtta 5760
agccagcccc gacacccgcc aacacccgct gacgcgccct gacgggcttg tctgctcccg 5820
gcatccgctt acagacaagc tgtgaccgtc tccgggagct gcatgtgtca gaggttttca 5880
ccgtcatcac cgaaacgcgc gagacgaaag ggcctcgtga tacgcctatt tttataggtt 5940
aatgtcatga taataatggt ttcttagacg tcaggtggca cttttcgggg aaatgtgcgc 6000
ggaaccccta tttgtttatt tttctaaata cattcaaata tgtatccgct catgagacaa 6060
taaccctgat aaatgcttca ataatattga aaaaggaaga gtatgagtat tcaacatttc 6120
cgtgtcgccc ttattccctt ttttgcggca ttttgccttc ctgtttttgc tcacccagaa 6180
acgctggtga aagtaaaaga tgctgaagat cagttgggtg cacgagtggg ttacatcgaa 6240
ctggatctca acagcggtaa gatccttgag agttttcgcc ccgaagaacg ttttccaatg 6300
atgagcactt ttaaagttct gctatgtggc gcggtattat cccgtattga cgccgggcaa 6360
gagcaactcg gtcgccgcat acactattct cagaatgact tggttgagta ctcaccagtc 6420
acagaaaagc atcttacgga tggcatgaca gtaagagaat tatgcagtgc tgccataacc 6480
atgagtgata acactgcggc caacttactt ctgacaacga tcggaggacc gaaggagcta 6540
accgcttttt tgcacaacat gggggatcat gtaactcgcc ttgatcgttg ggaaccggag 6600
ctgaatgaag ccataccaaa cgacgagcgt gacaccacga tgcctgtagc aatggcaaca 6660
acgttgcgca aactattaac tggcgaacta cttactctag cttcccggca acaattaata 6720
gactggatgg aggcggataa agttgcagga ccacttctgc gctcggccct tccggctggc 6780
tggtttattg ctgataaatc tggagccggt gagcgtgggt ctcgcggtat cattgcagca 6840
ctggggccag atggtaagcc ctcccgtatc gtagttatct acacgacggg gagtcaggca 6900
actatggatg aacgaaatag acagatcgct gagataggtg cctcactgat taagcattgg 6960
taactgtcag accaagttta ctcatatata ctttagattg atttaaaact tcatttttaa 7020
tttaaaagga tctaggtgaa gatccttttt gataatctca tgaccaaaat cccttaacgt 7080
gagttttcgt tccactgagc gtcagacccc gtagaaaaga tcaaaggatc ttcttgagat 7140
cctttttttc tgcgcgtaat ctgctgcttg caaacaaaaa aaccaccgct accagcggtg 7200
gtttgtttgc cggatcaaga gctaccaact ctttttccga aggtaactgg cttcagcaga 7260
gcgcagatac caaatactgt ccttctagtg tagccgtagt taggccacca cttcaagaac 7320
tctgtagcac cgcctacata cctcgctctg ctaatcctgt taccagtggc tgctgccagt 7380
ggcgataagt cgtgtcttac cgggttggac tcaagacgat agttaccgga taaggcgcag 7440
cggtcgggct gaacgggggg ttcgtgcaca cagcccagct tggagcgaac gacctacacc 7500
gaactgagat acctacagcg tgagctatga gaaagcgcca cgcttcccga agggagaaag 7560
gcggacaggt atccggtaag cggcagggtc ggaacaggag agcgcacgag ggagcttcca 7620
gggggaaacg cctggtatct ttatagtcct gtcgggtttc gccacctctg acttgagcgt 7680
cgatttttgt gatgctcgtc aggggggcgg agcctatgga aaaacgccag caacgcggcc 7740
tttttacggt tcctggcctt ttgctggcct tttgctcaca tgttctttcc tgcgttatcc 7800
cctgattctg tggataaccg tattaccgcc tttgagtgag ctgataccgc tcgccgcagc 7860
cgaacgaccg agcgcagcga gtcagtgagc gaggaagcgg aagagcgccc aatacgcaaa 7920
ccgcctctcc ccgcgcgttg gccgattcat taatg 7955

<210> SEQ ID NO 39
<211> LENGTH: 7825
<212> TYPE: DNA
<213> ORGANISM: Artificial
<220> FEATURE:
<223> OTHER INFORMATION: AAV donor template

<400> SEQUENCE: 39
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctagaaattg ttttcactgc actattgaga aattaagaga taatggcaaa agtcacaaag 240
agtatattca aaaagaagta tagcactttt tccttagaaa ccactgctaa ctgaaagaga 300
ctaagatttg tcccgtcaaa aatcctggac ctatgcctaa aacacatttc acaatccctg 360
aacttttcaa aaattggtac atgctttagc tttaaactac aggcctcact ggagctagag 420
acaagaaggt aaaaaacggc tgacaaaaga agtcctggta tcctctatga tgggagaagg 480
aaactagcta aagggaagaa taaattagag aaaaactgga atgactgaat cggaacaagg 540
caaaggctat aaaaaaaatt agcagtatcc tcttgggggc cccttcccca cactatctca 600
atgcaaatat ctgtctgaaa cggtccctgg ctaaactcca cccgcgggct ttaaaaaacc 660
tcccacatct ccccctgaac ctgaaacata aaatgaatgc aattgttgtt gttaacttgt 720
ttattgcagc ttataatggt tacaaataaa gcaatagcat cacaaatttc acaaataaag 780
ctagaatggt tacaaataaa gcaatagcat cacaaatttc acaaataaac accacggaat 840
tgtcagtgcc caacagccga gcccctgtcc agcagcgggc aaggcaggcg gcgatgagtt 900
ccgccgtggc aagaactaac caggatttat acaaggagga gaaaatgaaa gccatacggg 960
aagcaatagc atgatacaaa ggcattaaag cagcgtatcc acatagcgta aaaggagcaa 1020
catagttaag aataccagtc aatctttcac aaattttgta atccagaggt tgattatccc 1080
tgcaggttac ttgtacagct cgtccatgcc gagagtgatc ccggcggcgg tcacgaactc 1140
cagcaggacc atgtgatcgc gcttctcgtt ggggtctttg ctcagggcgg actgggtgct 1200
caggtagtgg ttgtcgggca gcagcacggg gccgtcgccg atgggggtgt tctgctggta 1260
gtggtcggcg agctgcacgc tgccgtcctc gatgttgtgg cggatcttga agttcacctt 1320

-continued

```
gatgccgttc ttctgcttgt cggccatgat atagacgttg tggctgttgt agttgtactc   1380
cagcttgtgc cccaggatgt tgccgtcctc cttgaagtcg atgcccttca gctcgatgcg   1440
gttcaccagg gtgtcgccct cgaacttcac ctcggcgcgg gtcttgtagt tgccgtcgtc   1500
cttgaagaag atggtgcgct cctggacgta gccttcgggc atggcggact tgaagaagtc   1560
gtgctgcttc atgtggtcgg ggtagcggct gaagcactgc acgccgtagg tcagggtggt   1620
cacgagggtg ggccagggca cgggcagctt gccggtggtg cagatgaact tcagggtcag   1680
cttgccgtag gtggcatcgc cctcgccctc gccggacacg ctgaacttgt ggccgtttac   1740
gtcgccgtcc agctcgacca ggatgggcac caccccggtg aacagctcct cgcccttgct   1800
caccatggtg gcggcgcggc cgccttctat ggaagtcaaa acagcgtgga tggcgtctcc   1860
aggcgatctg acggttcact aaacgagctc tgcttatata gagctcgggg agcagaagcg   1920
cgcgaacaga agcgagaagc gaactgattg gttagttcaa ataaggcaca gggtcatttc   1980
aggtccttgg ggcaccctgg aaacatctga tggttctcta gaaactgctg agggcgggac   2040
cgcatctggg gaccatctgt tcttggccct gagccggggc aggaactgct taccacagat   2100
atcctgtttg gcccatattc tgctgttcca actgttcttg gccctgagcc ggggcaggaa   2160
ctgcttacca cagatatcct gtttggccca tattctcctg tttctctgtt cgaattccga   2220
gatcgagacc atcctggcta acacagtgaa accccgtctc tactaaaaaa atacaaaaaa   2280
ttagccgggc ttggtggcgg gtgcctgtag tcccagctac tatggaggct gaggcgggag   2340
aatggcgtga acgcgggggg cggagcttgc agtgagcaga gatcaggggc cactgcactc   2400
cagcctgggc gacagagaga gactctgtct caaaaaaaag aaaaaaaaaa tttagtagac   2460
tagctaaaaa aatccagaga tagttattga tgcatatgta aaagtcttcc aatatttaca   2520
agtacaatga aaaaaaaata accttgaatt aagtgtagaa ctcattgaca atgtttcaaa   2580
ggatgtgagg gataaactaa aatttgggca gtacatgctg ttcctgtgta cttggaacag   2640
agggagaaaa tctgggctgg aaatattgtt ataggagtta gcacatgaag gtgacaacta   2700
aattatttgg agtagatgga gtcaccagca catgtgaata gttttagaat gaaatgaccc   2760
aagatagaac tttggagagc ccccaaattt aaataaaatc agtataagag aagaggaaga   2820
aaccaaatgg tatactagtc taaattgttt cttagtgaca aaagaataac ctgaatatta   2880
gattagctgc ctatatgctc tctgaatcaa tttcattcaa catgcaacag ttctggaacc   2940
tatcagggac cacagtcagc caggcaagca catctgccca agccaagggt ggaggcatgc   3000
agctgtgggg gtctgtgaaa acacttgagg gagcagataa ctgggccaac catgactcag   3060
tgcttctgga ggccaacagg actgctgagt catcctgtgg gggtggaggt gggacaaggg   3120
aaaggggtga atggtactgc tgattacaac ctctggtgct gcctcccccct cctgtttatc   3180
tgagaggcta gcgtaaatac acttgcaaag gaggatgttt ttagtagcaa tttgtactga   3240
tggtatgggg ccaagagata tatcttagag ggagggctga gggtttgaag tccaactcct   3300
aagccagtgc cagaagagcc aaggacaggt acggctgtca tcacttagac ctcaccctgt   3360
ggagccacac cctagggttg gccaatctac tcccaggagc agggagggca ggagccaggg   3420
ctgggcataa aagtcagggc agagccatct attgcttaca ctcgcttctg gaacgtctga   3480
ggttatcaat aagctcctag tccagacgcc atgggtcatt tcacagagga ggacaaggct   3540
actatcacaa gcctgtgggg caaggtgaat gtggaagatg ctggaggaga aaccctggga   3600
aggtaggctc tggtgaccag gacaagggag ggaaggaagg accctgtgcc tggcaaaagt   3660
```

-continued

```
ccaggtcgct tctcaggatt tgtggcacct tctgactgtc aaactgttct tgtcaatctc   3720
acaggctcct ggttgtctac ccatggaccc agaggttctt tgacagcttt ggcaacctgt   3780
cctctgcctc tgccatcatg ggcaacccca aagtcaaggc acatggcaag aaggtgctga   3840
cttccttggg agatgccaca aagcacctgg atgatctcaa gggcaccttt gcccagctga   3900
gtgaactgca ctgtgacaag ctgcatgtgg atcctgagaa cttcaaggtg agtccaggag   3960
atgtttcagc cctgttgcct ttagtctcga ggcaacttag acaacggagt attgatctga   4020
gcacagcagg gtgtgagctg tttgaagata ctggggtctc gaggtcgacg tagataagta   4080
gcatggcggg ttaatcatta actacaagga acccctagtg atggagttgg ccactccctc   4140
tctgcgcgct cgctcgctca ctgaggccgg gcgaccaaag gtcgcccgac gcccgggctt   4200
tgcccgggcg gcctcagtga gcgagcgagc gcgccagctg gcgtaatagc gaagaggccc   4260
gcaccgatcg cccttcccaa cagttgcgca gcctgaatgg cgaatggcga ttccgttgca   4320
atggctggcg gtaatattgt tctggatatt accagcaagg ccgatagttt gagttcttct   4380
actcaggcaa gtgatgttat tactaatcaa agaagtattg cgacaacggt taatttgcgt   4440
gatggacaga ctcttttact cggtggcctc actgattata aaaacacttc tcaggattct   4500
ggcgtaccgt tcctgtctaa aatcccttta atcggcctcc tgtttagctc ccgctctgat   4560
tctaacgagg aaagcacgtt atacgtgctc gtcaaagcaa ccatagtacg cgccctgtag   4620
cggcgcatta agcgcggcgg gtgtggtggt tacgcgcagc gtgaccgcta cacttgccag   4680
cgccctagcg cccgctcctt tcgctttctt cccttccttt ctcgccacgt tcgccggctt   4740
tccccgtcaa gctctaaatc gggggctccc tttagggttc cgatttagtg ctttacggca   4800
cctcgacccc aaaaaacttg attagggtga tggttcacgt agtgggccat cgccctgata   4860
gacggttttt cgccctttga cgttggagtc cacgttcttt aatagtggac tcttgttcca   4920
aactggaaca acactcaacc ctatctcggt ctattctttt gatttataag ggattttgcc   4980
gatttcggcc tattggttaa aaaatgagct gatttaacaa aaatttaacg cgaattttaa   5040
caaaatatta acgtttacaa tttaaatatt tgcttataca atcttcctgt ttttggggct   5100
tttctgatta tcaaccgggg tacatatgat tgacatgcta gttttacgat taccgttcat   5160
cgattctctt gtttgctcca gactctcagg caatgacctg atagcctttg tagagacctc   5220
tcaaaaatag ctaccctctc cggcatgaat ttatcagcta gaacggttga atatcatatt   5280
gatggtgatt tgactgtctc cggcctttct cacccgtttg aatctttacc tacacattac   5340
tcaggcattg catttaaaat atatgagggt tctaaaaatt tttatccttg cgttgaaata   5400
aaggcttctc ccgcaaaagt attacagggt cataatgttt ttggtacaac cgatttagct   5460
ttatgctctg aggctttatt gcttaatttt gctaattctt tgccttgcct gtatgattta   5520
ttggatgttg gaatcgcctg atgcggtatt ttctccttac gcatctgtgc ggtatttcac   5580
accgcatatg gtgcactctc agtacaatct gctctgatgc cgcatagtta agccagcccc   5640
gacacccgcc aacacccgct gacgcgccct gacgggcttg tctgctcccg gcatccgctt   5700
acagacaagc tgtgaccgtc tccgggagct gcatgtgtca gaggttttca ccgtcatcac   5760
cgaaacgcgc gagacgaaag ggcctcgtga tacgcctatt tttataggtt aatgtcatga   5820
taataatggt ttcttagacg tcaggtggca cttttcgggg aaatgtgcgc ggaaccccta   5880
tttgtttatt tttctaaata cattcaaata tgtatccgct catgagacaa taaccctgat   5940
aaatgcttca ataatattga aaaaggaaga gtatgagtat tcaacatttc cgtgtcgccc   6000
ttattccctt ttttgcggca ttttgccttc ctgtttttgc tcacccagaa acgctggtga   6060
```

aagtaaaaga tgctgaagat cagttgggtg cacgagtggg ttacatcgaa ctggatctca 6120
acagcggtaa gatccttgag agttttcgcc ccgaagaacg ttttccaatg atgagcactt 6180
ttaaagttct gctatgtggc gcggtattat cccgtattga cgccgggcaa gagcaactcg 6240
gtcgccgcat acactattct cagaatgact tggttgagta ctcaccagtc acagaaaagc 6300
atcttacgga tggcatgaca gtaagagaat tatgcagtgc tgccataacc atgagtgata 6360
acactgcggc caacttactt ctgacaacga tcggaggacc gaaggagcta accgcttttt 6420
tgcacaacat gggggatcat gtaactcgcc ttgatcgttg ggaaccggag ctgaatgaag 6480
ccataccaaa cgacgagcgt gacaccacga tgcctgtagc aatggcaaca acgttgcgca 6540
aactattaac tggcgaacta cttactctag cttcccggca acaattaata gactggatgg 6600
aggcggataa agttgcagga ccacttctgc gctcggccct tccggctggc tggtttattg 6660
ctgataaatc tggagccggt gagcgtgggt ctcgcggtat cattgcagca ctggggccag 6720
atggtaagcc ctcccgtatc gtagttatct acacgacggg gagtcaggca actatggatg 6780
aacgaaatag acagatcgct gagataggtg cctcactgat taagcattgg taactgtcag 6840
accaagttta ctcatatata ctttagattg atttaaaact tcatttttaa tttaaaagga 6900
tctaggtgaa gatccttttt gataatctca tgaccaaaat cccttaacgt gagttttcgt 6960
tccactgagc gtcagacccc gtagaaaaga tcaaaggatc ttcttgagat cctttttttc 7020
tgcgcgtaat ctgctgcttg caaacaaaaa aaccaccgct accagcggtg gtttgtttgc 7080
cggatcaaga gctaccaact ctttttccga aggtaactgg cttcagcaga gcgcagatac 7140
caaatactgt ccttctagtg tagccgtagt taggccacca cttcaagaac tctgtagcac 7200
cgcctacata cctcgctctg ctaatcctgt taccagtggc tgctgccagt ggcgataagt 7260
cgtgtcttac cgggttggac tcaagacgat agttaccgga taaggcgcag cggtcgggct 7320
gaacgggggg ttcgtgcaca cagcccagct tggagcgaac gacctacacc gaactgagat 7380
acctacagcg tgagctatga gaaagcgcca cgcttcccga agggagaaag gcggacaggt 7440
atccggtaag cggcagggtc ggaacaggag agcgcacgag ggagcttcca gggggaaacg 7500
cctggtatct ttatagtcct gtcgggtttc gccacctctg acttgagcgt cgatttttgt 7560
gatgctcgtc aggggggcgg agcctatgga aaaacgccag caacgcggcc tttttacggt 7620
tcctggcctt ttgctggcct tttgctcaca tgttctttcc tgcgttatcc cctgattctg 7680
tggataaccg tattaccgcc tttgagtgag ctgataccgc tcgccgcagc cgaacgaccg 7740
agcgcagcga gtcagtgagc gaggaagcgg aagagcgccc aatacgcaaa ccgcctctcc 7800
ccgcgcgttg gccgattcat taatg 7825

<210> SEQ ID NO 40
<211> LENGTH: 7729
<212> TYPE: DNA
<213> ORGANISM: Artificial
<220> FEATURE:
<223> OTHER INFORMATION: AAV donor template

<400> SEQUENCE: 40
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctagaaattg ttttcactgc actattgaga aattaagaga taatggcaaa agtcacaaag 240

-continued

```
agtatattca aaaagaagta tagcactttt tccttagaaa ccactgctaa ctgaaagaga    300
ctaagatttg tcccgtcaaa aatcctggac ctatgcctaa aacacatttc acaatccctg    360
aacttttcaa aaattggtac atgctttagc tttaaactac aggcctcact ggagctagag    420
acaagaaggt aaaaaacggc tgacaaaaga agtcctggta tcctctatga tgggagaagg    480
aaactagcta aagggaagaa taaattagag aaaaactgga atgactgaat cggaacaagg    540
caaaggctat aaaaaaaatt agcagtatcc tcttgggggc cccttcccca cactatctca    600
atgcaaatat ctgtctgaaa cggtccctgg ctaaactcca cccgcgggaa cagagaaaca    660
ggagaatatg ggccaaacag gatatctgtg gtaagcagtt cctgccccgg ctcagggcca    720
agaacagttg gaacagcaga atatgggcca aacaggatat ctgtggtaag cagttcctgc    780
cccggctcag ggccaagaac agatggtccc cagatgcggt cccgccctca gcagtttcta    840
gagaaccatc agatgtttcc agggtgcccc aaggacctga aatgaccctg tgccttattt    900
gaactaacca atcagttcgc ttctcgcttc tgttcgcgcg cttctgctcc ccgagctcta    960
tataagcaga gctcgtttag tgaaccgtca gatcgcctgg agacgccatc cacgctgttt   1020
tgacttccat agaaggcggc cgcgccgcca ccatggacaa ggattgtgaa atgaaacgca   1080
ccacactgga cagccctttg ggaagctgg agctgtctgg ttgtgagcag ggtctgcacg   1140
aaataaagct cctgggcaag ggacgtctg cagctgatgc cgtggaggtc ccagcccccg   1200
ctgcggttct cggaggtccg gagcccctga tgcagtgcac agcctggctg aatgcctatt   1260
tccaccagcc cgaggctatc gaagagttcc ccgtgccggc tcttcaccat cccgttttcc   1320
agcaagagtc gttcaccaga caggtgttat ggaagctgct gaaggttgtg aaattcggag   1380
aagtgatttc ttaccagcaa ttagcagccc tggcaggcaa ccccaaagcc gcgcgagcag   1440
tgggaggagc aatgagaggc aatcctgtca aaatcctcat cccgtgccac agagtggtct   1500
gcagcagcgg agccgtgggc aactactccg gaggactggc cgtgaaggaa tggcttctgg   1560
cccatgaagg ccaccggttg gggaagccag gcttgggagg gagctcaggt ctggcagggg   1620
cctggctcaa gggagcggga gctacctcgg gctccccgcc tgctggccga aactaacctg   1680
cagggataat caacctctgg attacaaaat ttgtgaaaga ttgactggta ttcttaacta   1740
tgttgctcct tttacgctat gtggatacgc tgctttaatg cctttgtatc atgctattgc   1800
ttcccgtatg gctttcattt tctcctcctt gtataaatcc tggttagttc ttgccacggc   1860
ggaactcatc gccgcctgcc ttgcccgctg ctggacaggg gctcggctgt tgggcactga   1920
caattccgtg gtgtttattt gtgaaatttg tgatgctatt gctttatttg taaccattct   1980
agctttattt gtgaaatttg tgatgctatt gctttatttg taaccattat aagctgcaat   2040
aaacaagtta acaacaacaa ttgcattcat tttatgtttc aggttcaggg ggagatgtgg   2100
gaggtttttt aaagcgaatt ccgagatcga gaccatcctg gctaacacag tgaaaccccg   2160
tctctactaa aaaaatacaa aaaattagcc gggcttggtg gcgggtgcct gtagtcccag   2220
ctactatgga ggctgaggcg ggagaatggc gtgaacgcgg ggggcggagc ttgcagtgag   2280
cagagatcag ggccactgc actccagcct gggcgacaga gagagactct gtctcaaaaa   2340
aaagaaaaaa aaaatttagt agactagcta aaaaaatcca gagatagtta ttgatgcata   2400
tgtaaaagtc ttccaatatt tacaagtaca atgaaaaaaa aataaccttg aattaagtgt   2460
agaactcatt gacaatgttt caaaggatgt gagggataaa ctaaaatttg ggcagtacat   2520
gctgttcctg tgtacttgga acagagggag aaaatctggg ctggaaatat tgttatagga   2580
gttagcacat gaaggtgaca actaaattat ttggagtaga tggagtcacc agcacatgtg   2640
```

-continued aatagtttta gaatgaaatg acccaagata gaactttgga gagcccccaa atttaaataa 2700
aatcagtata agagaagagg aagaaaccaa atggtatact agtctaaatt gtttcttagt 2760
gacaaaagaa taacctgaat attagattag ctgcctatat gctctctgaa tcaatttcat 2820
tcaacatgca acagttctgg aacctatcag ggaccacagt cagccaggca agcacatctg 2880
cccaagccaa gggtggaggc atgcagctgt gggggtctgt gaaaacactt gagggagcag 2940
ataactgggc caaccatgac tcagtgcttc tggaggccaa caggactgct gagtcatcct 3000
gtgggggtgg aggtgggaca agggaaaggg gtgaatggta ctgctgatta caacctctgg 3060
tgctgcctcc ccctcctgtt tatctgagag gctagcgtaa atacacttgc aaaggaggat 3120
gtttttagta gcaatttgta ctgatggtat ggggccaaga gatatatctt agagggaggg 3180
ctgagggttt gaagtccaac tcctaagcca gtgccagaag agccaaggac aggtacggct 3240
gtcatcactt agacctcacc ctgtggagcc acaccctagg gttggccaat ctactcccag 3300
gagcagggag ggcaggagcc agggctgggc ataaaagtca gggcagagcc atctattgct 3360
tacactcgct tctggaacgt ctgaggttat caataagctc ctagtccaga cgccatgggt 3420
catttcacag aggaggacaa ggctactatc acaagcctgt ggggcaaggt gaatgtggaa 3480
gatgctggag gagaaaccct gggaaggtag gctctggtga ccaggacaag ggagggaagg 3540
aaggaccctg tgcctggcaa aagtccaggt cgcttctcag gatttgtggc accttctgac 3600
tgtcaaactg ttcttgtcaa tctcacaggc tcctggttgt ctacccatgg acccagaggt 3660
tctttgacag ctttggcaac ctgtcctctg cctctgccat catgggcaac cccaaagtca 3720
aggcacatgg caagaaggtg ctgacttcct tgggagatgc cacaaagcac ctggatgatc 3780
tcaagggcac ctttgcccag ctgagtgaac tgcactgtga caagctgcat gtggatcctg 3840
agaacttcaa ggtgagtcca ggagatgttt cagccctgtt gcctttagtc tcgaggcaac 3900
ttagacaacg gagtattgat ctgagcacag cagggtgtga gctgtttgaa gatactgggg 3960
tctcgaggtc gacgtagata agtagcatgg cgggttaatc attaactaca aggaacccct 4020
agtgatggag ttggccactc cctctctgcg cgctcgctcg ctcactgagg ccgggcgacc 4080
aaaggtcgcc cgacgcccgg gctttgcccg ggcggcctca gtgagcgagc gagcgcgcca 4140
gctggcgtaa tagcgaagag gcccgcaccg atcgcccttc ccaacagttg cgcagcctga 4200
atggcgaatg gcgattccgt tgcaatggct ggcggtaata ttgttctgga tattaccagc 4260
aaggccgata gtttgagttc ttctactcag gcaagtgatg ttattactaa tcaaagaagt 4320
attgcgacaa cggttaattt gcgtgatgga cagactcttt tactcggtgg cctcactgat 4380
tataaaaaca cttctcagga ttctggcgta ccgttcctgt ctaaaatccc tttaatcggc 4440
ctcctgttta gctcccgctc tgattctaac gaggaaagca cgttatacgt gctcgtcaaa 4500
gcaaccatag tacgcgccct gtagcggcgc attaagcgcg gcgggtgtgg tggttacgcg 4560
cagcgtgacc gctacacttg ccagcgccct agcgcccgct cctttcgctt tcttcccttc 4620
ctttctcgcc acgttcgccg gctttccccg tcaagctcta aatcgggggc tccctttagg 4680
gttccgattt agtgctttac ggcacctcga ccccaaaaaa cttgattagg gtgatggttc 4740
acgtagtggg ccatcgccct gatagacggt ttttcgccct ttgacgttgg agtccacgtt 4800
ctttaatagt ggactcttgt tccaaactgg aacaacactc aaccctatct cggtctattc 4860
ttttgattta taagggattt tgccgatttc ggcctattgg ttaaaaaatg agctgattta 4920
acaaaaattt aacgcgaatt ttaacaaaat attaacgttt acaatttaaa tatttgctta 4980

-continued

```
tacaatcttc ctgtttttgg ggcttttctg attatcaacc ggggtacata tgattgacat   5040
gctagtttta cgattaccgt tcatcgattc tcttgtttgc tccagactct caggcaatga   5100
cctgatagcc tttgtagaga cctctcaaaa atagctaccc tctccggcat gaatttatca   5160
gctagaacgg ttgaatatca tattgatggt gatttgactg tctccggcct ttctcacccg   5220
tttgaatctt tacctacaca ttactcaggc attgcattta aaatatatga gggttctaaa   5280
aatttttatc cttgcgttga aataaaggct tctcccgcaa aagtattaca gggtcataat   5340
gtttttggta caaccgattt agctttatgc tctgaggctt tattgcttaa ttttgctaat   5400
tctttgcctt gcctgtatga tttattggat gttggaatcg cctgatgcgg tattttctcc   5460
ttacgcatct gtgcggtatt tcacaccgca tatggtgcac tctcagtaca atctgctctg   5520
atgccgcata gttaagccag ccccgacacc cgccaacacc cgctgacgcg ccctgacggg   5580
cttgtctgct cccggcatcc gcttacagac aagctgtgac cgtctccggg agctgcatgt   5640
gtcagaggtt ttcaccgtca tcaccgaaac gcgcgagacg aaagggcctc gtgatacgcc   5700
tatttttata ggttaatgtc atgataataa tggtttctta gacgtcaggt ggcacttttc   5760
ggggaaatgt gcgcggaacc cctatttgtt tatttttcta aatacattca aatatgtatc   5820
cgctcatgag acaataaccc tgataaatgc ttcaataata ttgaaaaagg aagagtatga   5880
gtattcaaca tttccgtgtc gcccttattc cctttttttgc ggcattttgc cttcctgttt   5940
ttgctcaccc agaaacgctg gtgaaagtaa aagatgctga agatcagttg ggtgcacgag   6000
tgggttacat cgaactggat ctcaacagcg gtaagatcct tgagagtttt cgccccgaag   6060
aacgttttcc aatgatgagc acttttaaag ttctgctatg tggcgcggta ttatcccgta   6120
ttgacgccgg gcaagagcaa ctcggtcgcc gcatacacta ttctcagaat gacttggttg   6180
agtactcacc agtcacagaa aagcatctta cggatggcat gacagtaaga gaattatgca   6240
gtgctgccat aaccatgagt gataacactg cggccaactt acttctgaca acgatcggag   6300
gaccgaagga gctaaccgct tttttgcaca acatggggga tcatgtaact cgccttgatc   6360
gttgggaacc ggagctgaat gaagccatac caaacgacga gcgtgacacc acgatgcctg   6420
tagcaatggc aacaacgttg cgcaaactat taactggcga actacttact ctagcttccc   6480
ggcaacaatt aatagactgg atggaggcgg ataaagttgc aggaccactt ctgcgctcgg   6540
cccttccggc tggctggttt attgctgata aatctggagc cggtgagcgt gggtctcgcg   6600
gtatcattgc agcactgggg ccagatggta agccctcccg tatcgtagtt atctacacga   6660
cggggagtca ggcaactatg gatgaacgaa atagacagat cgctgagata ggtgcctcac   6720
tgattaagca ttggtaactg tcagaccaag tttactcata tatactttag attgatttaa   6780
aacttcattt ttaatttaaa aggatctagg tgaagatcct ttttgataat ctcatgacca   6840
aaatccctta acgtgagttt tcgttccact gagcgtcaga ccccgtagaa aagatcaaag   6900
gatcttcttg agatcctttt tttctgcgcg taatctgctg cttgcaaaca aaaaaaccac   6960
cgctaccagc ggtggtttgt ttgccggatc aagagctacc aactcttttt ccgaaggtaa   7020
ctggcttcag cagagcgcag ataccaaata ctgtccttct agtgtagccg tagttaggcc   7080
accacttcaa gaactctgta gcaccgccta catacctcgc tctgctaatc ctgttaccag   7140
tggctgctgc cagtggcgat aagtcgtgtc ttaccgggtt ggactcaaga cgatagttac   7200
cggataaggc gcagcggtcg ggctgaacgg ggggttcgtg cacacagccc agcttggagc   7260
gaacgaccta caccgaactg agatacctac agcgtgagct atgagaaagc gccacgcttc   7320
ccgaagggag aaaggcggac aggtatccgg taagcggcag ggtcggaaca ggagagcgca   7380
```

cgagggagct tccaggggga aacgcctggt atctttatag tcctgtcggg tttcgccacc 7440
tctgacttga gcgtcgattt ttgtgatgct cgtcaggggg gcggagccta tggaaaaacg 7500
ccagcaacgc ggccttttta cggttcctgg ccttttgctg gccttttgct cacatgttct 7560
ttcctgcgtt atcccctgat tctgtggata accgtattac cgcctttgag tgagctgata 7620
ccgctcgccg cagccgaacg accgagcgca gcgagtcagt gagcgaggaa gcggaagagc 7680
gcccaatacg caaaccgcct ctccccgcgc gttggccgat tcattaatg 7729

<210> SEQ ID NO 41
<211> LENGTH: 7855
<212> TYPE: DNA
<213> ORGANISM: Artificial
<220> FEATURE:
<223> OTHER INFORMATION: AAV donor template

<400> SEQUENCE: 41
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctagaaattg ttttcactgc actattgaga aattaagaga taatggcaaa agtcacaaag 240
agtatattca aaaagaagta tagcactttt tccttagaaa ccactgctaa ctgaaagaga 300
ctaagatttg tcccgtcaaa aatcctggac ctatgcctaa aacacatttc acaatccctg 360
aacttttcaa aaattggtac atgctttagc tttaaactac aggcctcact ggagctagag 420
acaagaaggt aaaaaacggc tgacaaaaga agtcctggta tcctctatga tgggagaagg 480
aaactagcta aagggaagaa taaattagag aaaaactgga atgactgaat cggaacaagg 540
caaaggctat aaaaaaaatt agcagtatcc tcttgggggc cccttcccca cactatctca 600
atgcaaatat ctgtctgaaa cggtccctgg ctaaactcca cccgcggcca cggggttggg 660
gttgcgcctt ttccaaggca gccctgggtt tgcgcaggga cgcggctgct ctgggcgtgg 720
ttccgggaaa cgcagcggcg ccgaccctgg gtctcgcaca ttcttcacgt ccgttcgcag 780
cgtcacccgg atcttcgccg ctacccttgt gggccccccg gcgacgcttc ctgctccgcc 840
cctaagtcgg gaaggttcct tgcggttcgc ggcgtgccgg acgtgacaaa cggaagccgc 900
acgtctcact agtaccctcg cagacggaca gcgccaggga gcaatggcag cgcgccgacc 960
gcgatgggct gtggccaata gcggctgctc agcggggcgc gccgagagca gcggccggga 1020
aggggcggtg cgggaggcgg ggtgtggggc ggtagtgtgg gccctgttcc tgcccgcgcg 1080
gtgttccgca ttctgcaagc ctccggagcg cacgtcggca gtcggctccc tcgttgaccg 1140
aatcaccgac ctctctcccc agcggccgcg ccgccaccat ggacaaggat tgtgaaatga 1200
aacgcaccac actggacagc cctttgggga agctggagct gtctggttgt gagcagggtc 1260
tgcacgaaat aaagctcctg ggcaagggga cgtctgcagc tgatgccgtg gaggtcccag 1320
cccccgctgc ggttctcgga ggtccggagc ccctgatgca gtgcacagcc tggctgaatg 1380
cctatttcca ccagcccgag gctatcgaag agttccccgt gccggctctt caccatcccg 1440
ttttccagca agagtcgttc accagacagg tgttatggaa gctgctgaag gttgtgaaat 1500
tcggagaagt gatttcttac cagcaattag cagccctggc aggcaacccc aaagccgcgc 1560
gagcagtggg aggagcaatg agaggcaatc ctgtcaaaat cctcatcccg tgccacagag 1620
tggtctgcag cagcggagcc gtgggcaact actccggagg actggccgtg aaggaatggc 1680

-continued ttctggccca tgaaggccac cggttgggga agccaggctt gggagggagc tcaggtctgg 1740
caggggcctg gctcaaggga gcgggagcta cctcgggctc cccgcctgct ggccgaaact 1800
aacctgcagg gataatcaac ctctggatta caaaatttgt gaaagattga ctggtattct 1860
taactatgtt gctcctttta cgctatgtgg atacgctgct ttaatgcctt tgtatcatgc 1920
tattgcttcc cgtatggctt tcattttctc ctccttgtat aaatcctggt tagttcttgc 1980
cacggcggaa ctcatcgccg cctgccttgc ccgctgctgg acaggggctc ggctgttggg 2040
cactgacaat tccgtggtgt ttatttgtga aatttgtgat gctattgctt tatttgtaac 2100
cattctagct ttatttgtga aatttgtgat gctattgctt tatttgtaac cattataagc 2160
tgcaataaac aagttaacaa caacaattgc attcatttta tgtttcaggt tcagggggag 2220
atgtgggagg tttttaaag cgaattccga gatcgagacc atcctggcta acacagtgaa 2280
accccgtctc tactaaaaaa atacaaaaaa ttagccgggc ttggtggcgg gtgcctgtag 2340
tcccagctac tatggaggct gaggcgggag aatggcgtga acgcgggggg cggagcttgc 2400
agtgagcaga gatcaggggc cactgcactc cagcctgggc gacagagaga gactctgtct 2460
caaaaaaaag aaaaaaaaaa tttagtagac tagctaaaaa aatccagaga tagttattga 2520
tgcatatgta aaagtcttcc aatatttaca agtacaatga aaaaaaaata accttgaatt 2580
aagtgtagaa ctcattgaca atgtttcaaa ggatgtgagg gataaactaa aatttgggca 2640
gtacatgctg ttcctgtgta cttggaacag agggagaaaa tctgggctgg aaatattgtt 2700
ataggagtta gcacatgaag gtgacaacta aattatttgg agtagatgga gtcaccagca 2760
catgtgaata gttttagaat gaaatgaccc aagatagaac tttggagagc cccaaattt 2820
aaataaaatc agtataagag aagaggaaga aaccaaatgg tatactagtc taaattgttt 2880
cttagtgaca aaagaataac ctgaatatta gattagctgc ctatatgctc tctgaatcaa 2940
tttcattcaa catgcaacag ttctggaacc tatcagggac cacagtcagc caggcaagca 3000
catctgccca agccaagggt ggaggcatgc agctgtgggg gtctgtgaaa acacttgagg 3060
gagcagataa ctgggccaac catgactcag tgcttctgga ggccaacagg actgctgagt 3120
catcctgtgg gggtggaggt gggacaaggg aaaggggtga atggtactgc tgattacaac 3180
ctctggtgct gcctccccct cctgtttatc tgagaggcta gcgtaaatac acttgcaaag 3240
gaggatgttt ttagtagcaa tttgtactga tggtatgggg ccaagagata tatcttagag 3300
ggagggctga gggtttgaag tccaactcct aagccagtgc cagaagagcc aaggacaggt 3360
acggctgtca tcacttagac ctcaccctgt ggagccacac cctagggttg gccaatctac 3420
tcccaggagc agggagggca ggagccaggg ctgggcataa aagtcagggc agagccatct 3480
attgcttaca ctcgcttctg gaacgtctga ggttatcaat aagctcctag tccagacgcc 3540
atgggtcatt tcacagagga ggacaaggct actatcacaa gcctgtgggg caaggtgaat 3600
gtggaagatg ctggaggaga aaccctggga aggtaggctc tggtgaccag gacaagggag 3660
ggaaggaagg accctgtgcc tggcaaaagt ccaggtcgct tctcaggatt tgtggcacct 3720
tctgactgtc aaactgttct tgtcaatctc acaggctcct ggttgtctac ccatggaccc 3780
agaggttctt tgacagcttt ggcaacctgt cctctgcctc tgccatcatg ggcaacccca 3840
aagtcaaggc acatggcaag aaggtgctga cttccttggg agatgccaca aagcacctgg 3900
atgatctcaa gggcaccttt gcccagctga gtgaactgca ctgtgacaag ctgcatgtgg 3960
atcctgagaa cttcaaggtg agtccaggag atgtttcagc cctgttgcct ttagtctcga 4020
ggcaacttag acaacggagt attgatctga gcacagcagg gtgtgagctg tttgaagata 4080

-continued

```
ctggggtctc gaggtcgacg tagataagta gcatggcggg ttaatcatta actacaagga   4140
acccctagtg atggagttgg ccactccctc tctgcgcgct cgctcgctca ctgaggccgg   4200
gcgaccaaag gtcgcccgac gcccgggctt tgcccgggcg gcctcagtga gcgagcgagc   4260
gcgccagctg gcgtaatagc gaagaggccc gcaccgatcg cccttcccaa cagttgcgca   4320
gcctgaatgg cgaatggcga ttccgttgca atggctggcg gtaatattgt tctggatatt   4380
accagcaagg ccgatagttt gagttcttct actcaggcaa gtgatgttat tactaatcaa   4440
agaagtattg cgacaacggt taatttgcgt gatggacaga ctcttttact cggtggcctc   4500
actgattata aaaacacttc tcaggattct ggcgtaccgt tcctgtctaa aatcccttta   4560
atcggcctcc tgtttagctc ccgctctgat tctaacgagg aaagcacgtt atacgtgctc   4620
gtcaaagcaa ccatagtacg cgccctgtag cggcgcatta agcgcggcgg gtgtggtggt   4680
tacgcgcagc gtgaccgcta cacttgccag cgccctagcg cccgctcctt tcgctttctt   4740
cccttccttt ctcgccacgt tcgccggctt tccccgtcaa gctctaaatc gggggctccc   4800
tttagggttc cgatttagtg ctttacggca cctcgacccc aaaaaacttg attagggtga   4860
tggttcacgt agtgggccat cgccctgata gacggttttt cgccctttga cgttggagtc   4920
cacgttcttt aatagtggac tcttgttcca aactggaaca acactcaacc ctatctcggt   4980
ctattctttt gatttataag ggattttgcc gatttcggcc tattggttaa aaaatgagct   5040
gatttaacaa aaatttaacg cgaattttaa caaaatatta acgtttacaa tttaaatatt   5100
tgcttataca atcttcctgt ttttggggct tttctgatta tcaaccgggg tacatatgat   5160
tgacatgcta gttttacgat taccgttcat cgattctctt gtttgctcca gactctcagg   5220
caatgacctg atagcctttg tagagacctc tcaaaaatag ctaccctctc cggcatgaat   5280
ttatcagcta gaacggttga atatcatatt gatggtgatt tgactgtctc cggcctttct   5340
cacccgtttg aatctttacc tacacattac tcaggcattg catttaaaat atatgagggt   5400
tctaaaaatt tttatccttg cgttgaaata aaggcttctc ccgcaaaagt attacagggt   5460
cataatgttt ttggtacaac cgatttagct ttatgctctg aggctttatt gcttaatttt   5520
gctaattctt tgccttgcct gtatgattta ttggatgttg gaatcgcctg atgcggtatt   5580
ttctccttac gcatctgtgc ggtatttcac accgcatatg gtgcactctc agtacaatct   5640
gctctgatgc cgcatagtta agccagcccc gacacccgcc aacacccgct gacgcgccct   5700
gacgggcttg tctgctcccg gcatccgctt acagacaagc tgtgaccgtc tccgggagct   5760
gcatgtgtca gaggttttca ccgtcatcac cgaaacgcgc gagacgaaag ggcctcgtga   5820
tacgcctatt tttataggtt aatgtcatga taataatggt ttcttagacg tcaggtggca   5880
cttttcgggg aaatgtgcgc ggaaccccta tttgtttatt tttctaaata cattcaaata   5940
tgtatccgct catgagacaa taaccctgat aaatgcttca ataatattga aaaaggaaga   6000
gtatgagtat tcaacatttc cgtgtcgccc ttattccctt ttttgcggca ttttgccttc   6060
ctgtttttgc tcacccagaa acgctggtga aagtaaaaga tgctgaagat cagttgggtg   6120
cacgagtggg ttacatcgaa ctggatctca acagcggtaa gatccttgag agttttcgcc   6180
ccgaagaacg ttttccaatg atgagcactt ttaaagttct gctatgtggc gcggtattat   6240
cccgtattga cgccgggcaa gagcaactcg gtcgccgcat acactattct cagaatgact   6300
tggttgagta ctcaccagtc acagaaaagc atcttacgga tggcatgaca gtaagagaat   6360
tatgcagtgc tgccataacc atgagtgata acactgcggc caacttactt ctgacaacga   6420
```

```
tcggaggacc gaaggagcta accgcttttt tgcacaacat gggggatcat gtaactcgcc   6480
ttgatcgttg ggaaccggag ctgaatgaag ccataccaaa cgacgagcgt gacaccacga   6540
tgcctgtagc aatggcaaca acgttgcgca aactattaac tggcgaacta cttactctag   6600
cttcccggca acaattaata gactggatgg aggcggataa agttgcagga ccacttctgc   6660
gctcggccct tccggctggc tggtttattg ctgataaatc tggagccggt gagcgtgggt   6720
ctcgcggtat cattgcagca ctggggccag atggtaagcc ctcccgtatc gtagttatct   6780
acacgacggg gagtcaggca actatggatg aacgaaatag acagatcgct gagataggtg   6840
cctcactgat taagcattgg taactgtcag accaagttta ctcatatata ctttagattg   6900
atttaaaact tcatttttaa tttaaaagga tctaggtgaa gatccttttt gataatctca   6960
tgaccaaaat cccttaacgt gagttttcgt tccactgagc gtcagacccc gtagaaaaga   7020
tcaaaggatc ttcttgagat cctttttttc tgcgcgtaat ctgctgcttg caaacaaaaa   7080
aaccaccgct accagcggtg gtttgtttgc cggatcaaga gctaccaact ctttttccga   7140
aggtaactgg cttcagcaga gcgcagatac caaatactgt ccttctagtg tagccgtagt   7200
taggccacca cttcaagaac tctgtagcac cgcctacata cctcgctctg ctaatcctgt   7260
taccagtggc tgctgccagt ggcgataagt cgtgtcttac cgggttggac tcaagacgat   7320
agttaccgga taaggcgcag cggtcgggct gaacgggggg ttcgtgcaca cagcccagct   7380
tggagcgaac gacctacacc gaactgagat acctacagcg tgagctatga gaaagcgcca   7440
cgcttcccga agggagaaag gcggacaggt atccggtaag cggcagggtc ggaacaggag   7500
agcgcacgag ggagcttcca gggggaaacg cctggtatct ttatagtcct gtcgggtttc   7560
gccacctctg acttgagcgt cgatttttgt gatgctcgtc aggggggcgg agcctatgga   7620
aaaacgccag caacgcggcc tttttacggt tcctggcctt ttgctggcct tttgctcaca   7680
tgttctttcc tgcgttatcc cctgattctg tggataaccg tattaccgcc tttgagtgag   7740
ctgataccgc tcgccgcagc cgaacgaccg agcgcagcga gtcagtgagc gaggaagcgg   7800
aagagcgccc aatacgcaaa ccgcctctcc ccgcgcgttg gccgattcat taatg        7855
```

```
<210> SEQ ID NO 42
<211> LENGTH: 8024
<212> TYPE: DNA
<213> ORGANISM: Artificial
<220> FEATURE:
<223> OTHER INFORMATION: AAV donor template

<400> SEQUENCE: 42
```

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtagat    180
cttgaaacag tcatgattta tttcaaatag gtacggataa gtagatattg aggtaagcat    240
taggtcttat attatgtaac actaatctat tactgcgctg aaactgtggc tttatagaaa    300
ttgttttcac tgcactattg agaaattaag agataatggc aaaagtcaca aagagtatat    360
tcaaaaagaa gtatagcact tttccttag aaaccactgc taactgaaag agactaagat     420
ttgtcccgtc aaaaatcctg gacctatgcc taaaacacat ttcacaatcc ctgaactttt    480
caaaaattgg tacatgcttt agctttaaac tacaggcctc actggagcta gagacaagaa    540
ggtaaaaaac ggctgacaaa agaagtcctg gtatcctcta tgatgggaga aggaaactag    600
ctaaagggaa gaataaatta gagaaaaact ggaatgactg aatcggaaca aggcaaaggc    660
```

-continued

```
tataaaaaaa attagcagta tcctcttggg ggccccttcc ccacactatc tcaatgcaaa    720
tatctgtctg aaacggtccc tggctaaact ccacccatgg gttggccagc cttgccttga    780
caaggcaaac ttgaccaata gtcttagagt atccagtgag gccaggggcc ggcggctggc    840
tagggatgaa gaataaaagg aagcaccctt cagcagttcc acacactcgc ttctggaacg    900
tctgaggtta tcaataagct cctagtccag acgccatggt gcacctgact cctgaggaga    960
agtctgccgt tactgccctg tggggcaagg tgaacgtgga tgaagttggt ggtgaggccc   1020
tgggcaggtt ggtatcaagg ttacaagaca ggtttaagga gaccaataga aactgggcat   1080
gtggagacag agaagactct tgggtttctg ataggcactg actctctctg cctattggtc   1140
tattttccca cccttaggct gctggtggtc tacccttgga cccagaggtt ctttgagtcc   1200
tttggggatc tgtccactcc tgatgctgtt atgggcaacc ctaaggtgaa ggctcatggc   1260
aagaaagtgc tcggtgcctt tagtgatggc ctggctcacc tggacaacct caagggcacc   1320
tttgcccagc tgagtgagct gcactgtgac aagctgcacg tggatcctga gaacttcagg   1380
gtgagtctat gggacccttg atgttttctt tccccttctt ttctatggtt aagttcatgt   1440
cataggaagg ggagaagtaa cagggtacac atattgacca aatcagggta attttgcatt   1500
tgtaatttta aaaaatgctt tcttctttta atatactttt ttgtttatct tatttctaat   1560
actttcccta atctctttct ttcagggcaa taatgataca atgtatcatg cctctttgca   1620
ccattctaaa gaataacagt gataatttct gggttaaggc aatagcaata tttctgcata   1680
taaatatttc tgcatataaa ttgtaactga tgtaagaggt ttcatattgc taatagcagc   1740
tacaatccag ctaccattct gcttttattt tatggttggg ataaggctgg attattctga   1800
gtccaagcta ggcccttttg ctaatcatgt tcatacctct tatcttcctc ccacagctcc   1860
tgggcaacgt gctggtctgt gtgctggccc atcactttgg caaagaattc accccaccag   1920
tgcaggctgc ctatcagaaa gtggtggctg gtgtggctaa tgccctggcc cacaagtatc   1980
actaagctcg ctttcttgct gtccaatttc tattaaaggt tcctttgttc cctaagtcca   2040
actactaaac tgggggatat tatgaagggc cttgagcatc tggattctgc ctaataaaaa   2100
acatttattt tcattgcaat gatgtattta aattatttct gaatatttta ctaaaaaggg   2160
aatgtgggag gttgcagtgc tagtctcccg gaactatcac tctttcacag tctgctttgg   2220
aaggactggg cttagtatga aaagttagga ctgagaagaa tttgaaaggg ggctttttgt   2280
agcttgatat tcactactgt cttattaccc tatcataggc ccaccccaaa tggaagtccc   2340
attcttcctc aggatgttta agattagcat tcaggaagag atcagaggtc tgctggctcc   2400
cttatcatgt cccttatggt gcttctggct ctgcaccgcg gccacggggt tggggttgcg   2460
ccttttccaa ggcagccctg ggtttgcgca gggacgcggc tgctctgggc gtggttccgg   2520
gaaacgcagc ggcgccgacc ctgggtctcg cacattcttc acgtccgttc gcagcgtcac   2580
ccggatcttc gccgctaccc ttgtgggccc cccggcgacg cttcctgctc cgcccctaag   2640
tcgggaaggt tccttgcggt tcgcggcgtg ccggacgtga caaacggaag ccgcacgtct   2700
cactagtacc ctcgcagacg gacagcgcca gggagcaatg gcagcgcgcc gaccgcgatg   2760
ggctgtggcc aatagcggct gctcagcggg gcgcgccgag agcagcggcc gggaaggggc   2820
ggtgcgggag gcggggtgtg gggcggtagt gtgggccctg ttcctgcccg cgcggtgttc   2880
cgcattctgc aagcctccgg agcgcacgtc ggcagtcggc tccctcgttg accgaatcac   2940
cgacctctct ccccagcggc cgcgccgcca ccatggacaa ggattgtgaa atgaaacgca   3000
```

-continued

```
ccacactgga cagccctttg gggaagctgg agctgtctgg ttgtgagcag ggtctgcacg   3060
aaataaagct cctgggcaag gggacgtctg cagctgatgc cgtggaggtc ccagcccccg   3120
ctgcggttct cggaggtccg gagcccctga tgcagtgcac agcctggctg aatgcctatt   3180
tccaccagcc cgaggctatc gaagagttcc ccgtgccggc tcttcaccat cccgttttcc   3240
agcaagagtc gttcaccaga caggtgttat ggaagctgct gaaggttgtg aaattcggag   3300
aagtgatttc ttaccagcaa ttagcagccc tggcaggcaa ccccaaagcc gcgcgagcag   3360
tgggaggagc aatgagaggc aatcctgtca aaatcctcat cccgtgccac agagtggtct   3420
gcagcagcgg agccgtgggc aactactccg gaggactggc cgtgaaggaa tggcttctgg   3480
cccatgaagg ccaccggttg gggaagccag gcttgggagg gagctcaggt ctggcagggg   3540
cctggctcaa gggagcggga gctacctcgg gctccccgcc tgctggccga aacgagggca   3600
gaggaagtct tctaacatgc ggtgacgtgg aggagaatcc gggcccccct gcaggaactt   3660
caaggtgagt ccaggagatg tttcagccct gttgccttta gtctcgaggc aacttagaca   3720
acggagtatt gatctgagca cagcagggtg tgagctgttt gaagatactg gggttggggg   3780
tgaagaaact gcagaggact aactgggctg agacccagtg gtaatgtttt agggcctaag   3840
gagtgcctct aaaaatctag atggacaatt ttgactttga gaaaagagag gtggaaatga   3900
ggaaaatgac ttttctttat tagattccag tagaaagaac tttcatcttt ccctcatttt   3960
tgttgtttta aaacatctat ctggaggcag gacaagtatg gtcgttaaaa agatgcaggc   4020
agaaggcata tattggctca gtcaaagtgg ggaactttgg tggccaaaca tacattgcta   4080
aggctattcc tatatcagct ggacacatat aaaatgctgc taatgcttca ttacaaactt   4140
atatccttta attccagatg ggggcaaagt atgtccaggg gtgaggaaca attgaaacat   4200
ttgggctgga gtagattttg aaagtcagct ctgtgtgtgt gtgtgtgtgt gcgcgcgcgc   4260
gtgtcgacgt agataagtag catggcgggt taatcattaa ctacaaggaa cccctagtga   4320
tggagttggc cactccctct ctgcgcgctc gctcgctcac tgaggccggg cgaccaaagg   4380
tcgcccgacg cccgggcttt gcccgggcgg cctcagtgag cgagcgagcg cgccagctgg   4440
cgtaatagcg aagaggcccg caccgatcgc ccttcccaac agttgcgcag cctgaatggc   4500
gaatggcgat tccgttgcaa tggctggcgg taatattgtt ctggatatta ccagcaaggc   4560
cgatagtttg agttcttcta ctcaggcaag tgatgttatt actaatcaaa gaagtattgc   4620
gacaacggtt aatttgcgtg atggacagac tcttttactc ggtggcctca ctgattataa   4680
aaacacttct caggattctg gcgtaccgtt cctgtctaaa atccctttaa tcggcctcct   4740
gtttagctcc cgctctgatt ctaacgagga aagcacgtta tacgtgctcg tcaaagcaac   4800
catagtacgc gccctgtagc ggcgcattaa gcgcggcggg tgtggtggtt acgcgcagcg   4860
tgaccgctac acttgccagc gccctagcgc ccgctccttt cgctttcttc ccttcctttc   4920
tcgccacgtt cgccggcttt ccccgtcaag ctctaaatcg ggggctccct ttagggttcc   4980
gatttagtgc tttacggcac ctcgacccca aaaaacttga ttagggtgat ggttcacgta   5040
gtgggccatc gccctgatag acggtttttc gccctttgac gttggagtcc acgttcttta   5100
atagtggact cttgttccaa actggaacaa cactcaaccc tatctcggtc tattcttttg   5160
atttataagg gattttgccg atttcggcct attggttaaa aaatgagctg atttaacaaa   5220
aatttaacgc gaattttaac aaaatattaa cgtttacaat ttaaatattt gcttatacaa   5280
tcttcctgtt tttggggctt ttctgattat caaccggggt acatatgatt gacatgctag   5340
ttttacgatt accgttcatc gattctcttg tttgctccag actctcaggc aatgacctga   5400
```

tagcctttgt agagacctct caaaaatagc taccctctcc ggcatgaatt tatcagctag 5460
aacggttgaa tatcatattg atggtgattt gactgtctcc ggcctttctc acccgtttga 5520
atctttacct acacattact caggcattgc atttaaaata tatgagggtt ctaaaaattt 5580
ttatccttgc gttgaaataa aggcttctcc cgcaaaagta ttacagggtc ataatgtttt 5640
tggtacaacc gatttagctt tatgctctga ggctttattg cttaattttg ctaattcttt 5700
gccttgcctg tatgatttat tggatgttgg aatcgcctga tgcggtattt tctccttacg 5760
catctgtgcg gtatttcaca ccgcatatgg tgcactctca gtacaatctg ctctgatgcc 5820
gcatagttaa gccagccccg acacccgcca acacccgctg acgcgccctg acgggcttgt 5880
ctgctcccgg catccgctta cagacaagct gtgaccgtct ccgggagctg catgtgtcag 5940
aggttttcac cgtcatcacc gaaacgcgcg agacgaaagg gcctcgtgat acgcctattt 6000
ttataggtta atgtcatgat aataatggtt tcttagacgt caggtggcac ttttcgggga 6060
aatgtgcgcg gaacccctat ttgtttattt ttctaaatac attcaaatat gtatccgctc 6120
atgagacaat aaccctgata aatgcttcaa taatattgaa aaaggaagag tatgagtatt 6180
caacatttcc gtgtcgccct tattcccttt tttgcggcat tttgccttcc tgtttttgct 6240
cacccagaaa cgctggtgaa agtaaaagat gctgaagatc agttgggtgc acgagtgggt 6300
tacatcgaac tggatctcaa cagcggtaag atccttgaga gttttcgccc cgaagaacgt 6360
tttccaatga tgagcacttt taaagttctg ctatgtggcg cggtattatc ccgtattgac 6420
gccgggcaag agcaactcgg tcgccgcata cactattctc agaatgactt ggttgagtac 6480
tcaccagtca cagaaaagca tcttacggat ggcatgacag taagagaatt atgcagtgct 6540
gccataacca tgagtgataa cactgcggcc aacttacttc tgacaacgat cggaggaccg 6600
aaggagctaa ccgctttttt gcacaacatg ggggatcatg taactcgcct tgatcgttgg 6660
gaaccggagc tgaatgaagc cataccaaac gacgagcgtg acaccacgat gcctgtagca 6720
atggcaacaa cgttgcgcaa actattaact ggcgaactac ttactctagc ttcccggcaa 6780
caattaatag actggatgga ggcggataaa gttgcaggac cacttctgcg ctcggccctt 6840
ccggctggct ggtttattgc tgataaatct ggagccggtg agcgtgggtc tcgcggtatc 6900
attgcagcac tggggccaga tggtaagccc tcccgtatcg tagttatcta cacgacgggg 6960
agtcaggcaa ctatggatga acgaaataga cagatcgctg agataggtgc ctcactgatt 7020
aagcattggt aactgtcaga ccaagtttac tcatatatac tttagattga tttaaaactt 7080
catttttaat ttaaaaggat ctaggtgaag atcctttttg ataatctcat gaccaaaatc 7140
ccttaacgtg agttttcgtt ccactgagcg tcagaccccg tagaaaagat caaaggatct 7200
tcttgagatc ctttttttct gcgcgtaatc tgctgcttgc aaacaaaaaa accaccgcta 7260
ccagcggtgg tttgtttgcc ggatcaagag ctaccaactc tttttccgaa ggtaactggc 7320
ttcagcagag cgcagatacc aaatactgtc cttctagtgt agccgtagtt aggccaccac 7380
ttcaagaact ctgtagcacc gcctacatac ctcgctctgc taatcctgtt accagtggct 7440
gctgccagtg gcgataagtc gtgtcttacc gggttggact caagacgata gttaccggat 7500
aaggcgcagc ggtcgggctg aacggggggt tcgtgcacac agcccagctt ggagcgaacg 7560
acctacaccg aactgagata cctacagcgt gagctatgag aaagcgccac gcttcccgaa 7620
gggagaaagg cggacaggta tccggtaagc ggcagggtcg gaacaggaga gcgcacgagg 7680
gagcttccag ggggaaacgc ctggtatctt tatagtcctg tcgggtttcg ccacctctga 7740

-continued

```
cttgagcgtc gatttttgtg atgctcgtca ggggggcgga gcctatggaa aaacgccagc   7800

aacgcggcct ttttacggtt cctggccttt tgctggcctt ttgctcacat gttctttcct   7860

gcgttatccc ctgattctgt ggataaccgt attaccgcct ttgagtgagc tgataccgct   7920

cgccgcagcc gaacgaccga gcgcagcgag tcagtgagcg aggaagcgga agagcgccca   7980

atacgcaaac cgcctctccc cgcgcgttgg ccgattcatt aatg                    8024
```

<210> SEQ ID NO 43
<211> LENGTH: 7953
<212> TYPE: DNA
<213> ORGANISM: Artificial
<220> FEATURE:
<223> OTHER INFORMATION: AAV donor template

<400> SEQUENCE: 43

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac acgcgtagat    180

cttgaaacag tcatgattta tttcaaatag gtacggataa gtagatattg aggtaagcat    240

taggtcttat attatgtaac actaatctat tactgcgctg aaactgtggc tttatagaaa    300

ttgttttcac tgcactattg agaaattaag agataatggc aaaagtcaca aagagtatat    360

tcaaaaagaa gtatagcact tttccttag aaaccactgc taactgaaag agactaagat    420

ttgtcccgtc aaaaatcctg gacctatgcc taaaacacat ttcacaatcc ctgaactttt    480

caaaaattgg tacatgcttt agctttaaac tacaggcctc actggagcta gagacaagaa    540

ggtaaaaaac ggctgacaaa agaagtcctg gtatcctcta tgatgggaga aggaaactag    600

ctaaagggaa gaataaatta gagaaaaact ggaatgactg aatcggaaca aggcaaaggc    660

tataaaaaaa attagcagta tcctcttggg ggccccttcc ccacactatc tcaatgcaaa    720

tatctgtctg aaacggtccc tggctaaact ccacccatgg gttggccagc cttgccttga    780

caaggcaaac ttgaccaata gtcttagagt atccagtgag gccaggggcc ggcggctggc    840

tagggatgaa gaataaaagg aagcaccctt cagcagttcc acacactcgc ttctggaacg    900

tctgaggtta tcaataagct cctagtccag acgccatggt gcacctgact cctgaggaga    960

agtctgccgt tactgccctg tggggcaagg tgaacgtgga tgaagttggt ggtgaggccc   1020

tgggcaggtt ggtatcaagg ttacaagaca ggtttaagga gaccaataga aactgggcat   1080

gtggagacag agaagactct tgggtttctg ataggcactg actctctctg cctattggtc   1140

tattttccca cccttaggct gctggtggtc tacccttgga cccagaggtt ctttgagtcc   1200

tttggggatc tgtccactcc tgatgctgtt atgggcaacc ctaaggtgaa ggctcatggc   1260

aagaaagtgc tcggtgcctt tagtgatggc ctggctcacc tggacaacct caagggcacc   1320

tttgcccagc tgagtgagct gcactgtgac aagctgcacg tggatcctga gaacttcagg   1380

gtgagtctat gggacccttg atgttttctt tccccttctt ttctatggtt aagttcatgt   1440

cataggaagg ggagaagtaa cagggtacac atattgacca aatcagggta attttgcatt   1500

tgtaatttta aaaaatgctt tcttctttta atatactttt ttgtttatct tatttctaat   1560

actttcccta atctctttct ttcagggcaa taatgataca atgtatcatg cctctttgca   1620

ccattctaaa gaataacagt gataatttct gggttaaggc aatagcaata tttctgcata   1680

taaatatttc tgcatataaa ttgtaactga tgtaagaggt ttcatattgc taatagcagc   1740

tacaatccag ctaccattct gcttttattt tatggttggg ataaggctgg attattctga   1800
```

gtccaagcta ggccctttg ctaatcatgt tcatacctct tatcttcctc ccacagctcc 1860
tgggcaacgt gctggtctgt gtgctggccc atcactttgg caaagaattc accccaccag 1920
tgcaggctgc ctatcagaaa gtggtggctg gtgtggctaa tgccctggcc cacaagtatc 1980
actaagctcg ctttcttgct gtccaatttc tattaaaggt tcctttgttc cctaagtcca 2040
actactaaac tgggggatat tatgaagggc cttgagcatc tggattctgc ctaataaaaa 2100
acatttattt tcattgcaat gatgtattta aattatttct gaatatttta ctaaaaaggg 2160
aatgtgggag gttgcagtgc tagtctcccg gaactatcac tctttcacag tctgctttgg 2220
aaggactggg cttagtatga aaagttagga ctgagaagaa tttgaaaggg ggcttttgt 2280
agcttgatat tcactactgt cttattaccc tatcataggc ccaccccaaa tggaagtccc 2340
attcttcctc aggatgttta agattagcat tcaggaagag atcagaggtc tgctggctcc 2400
cttatcatgt ccccttatggt gcttctggct ctgcaccgcg ggaacagaga aacaggagaa 2460
tatgggccaa acaggatatc tgtggtaagc agttcctgcc ccggctcagg gccaagaaca 2520
gttggaacag cagaatatgg gccaaacagg atatctgtgg taagcagttc ctgccccggc 2580
tcagggccaa gaacagatgg tccccagatg cggtcccgcc ctcagcagtt tctagagaac 2640
catcagatgt ttccagggtg ccccaaggac ctgaaatgac cctgtgcctt atttgaacta 2700
accaatcagt tcgcttctcg cttctgttcg cgcgcttctg ctccccgagc tctatataag 2760
cagagctcgt ttagtgaacc gtcagatcgc ggccgcgccg ccaccatggt gagcaagggc 2820
gaggagctgt tcaccggggt ggtgcccatc ctggtcgagc tggacggcga cgtaaacggc 2880
cacaagttca gcgtgtccgg cgagggcgag ggcgatgcca cctacggcaa gctgaccctg 2940
aagttcatct gcaccaccgg caagctgccc gtgccctggc ccaccctcgt gaccaccctg 3000
acctacggcg tgcagtgctt cagccgctac cccgaccaca tgaagcagca cgacttcttc 3060
aagtccgcca tgcccgaagg ctacgtccag gagcgcacca tcttcttcaa ggacgacggc 3120
aactacaaga cccgcgccga ggtgaagttc gagggcgaca ccctggtgaa ccgcatcgag 3180
ctgaagggca tcgacttcaa ggaggacggc aacatcctgg ggcacaagct ggagtacaac 3240
tacaacagcc acaacgtcta tatcatggcc gacaagcaga agaacggcat caaggtgaac 3300
ttcaagatcc gccacaacat cgaggacggc agcgtgcagc tcgccgacca ctaccagcag 3360
aacaccccca tcggcgacgg ccccgtgctg ctgcccgaca accactacct gagcacccag 3420
tccgccctga gcaaagaccc caacgagaag cgcgatcaca tggtcctgct ggagttcgtg 3480
accgccgccg ggatcactct cggcatggac gagctgtaca aggagggcag aggaagtctt 3540
ctaacatgcg gtgacgtgga ggagaatccg ggccccctg caggaacttc aaggtgagtc 3600
caggagatgt ttcagccctg ttgcctttag tctcgaggca acttagacaa cggagtattg 3660
atctgagcac agcagggtgt gagctgtttg aagatactgg ggttgggggt gaagaaactg 3720
cagaggacta actgggctga gacccagtgg taatgtttta gggcctaagg agtgcctcta 3780
aaaatctaga tggacaattt tgactttgag aaaagagagg tggaaatgag gaaaatgact 3840
tttctttatt agattccagt agaaagaact ttcatctttc cctcattttt gttgttttaa 3900
aacatctatc tggaggcagg acaagtatgg tcgttaaaaa gatgcaggca gaaggcatat 3960
attggctcag tcaaagtggg gaactttggt ggccaaacat acattgctaa ggctattcct 4020
atatcagctg gacacatata aaatgctgct aatgcttcat tacaaactta tatcctttaa 4080
ttccagatgg gggcaaagta tgtccagggg tgaggaacaa ttgaaacatt tgggctggag 4140

-continued

```
tagattttga aagtcagctc tgtgtgtgtg tgtgtgtgtg cgcgcgcgcg tgtcgacgta   4200
gataagtagc atggcgggtt aatcattaac tacaaggaac ccctagtgat ggagttggcc   4260
actccctctc tgcgcgctcg ctcgctcact gaggccgggc gaccaaaggt cgcccgacgc   4320
ccgggctttg cccgggcggc ctcagtgagc gagcgagcgc gccagctggc gtaatagcga   4380
agaggcccgc accgatcgcc cttcccaaca gttgcgcagc ctgaatggcg aatggcgatt   4440
ccgttgcaat ggctggcggt aatattgttc tggatattac cagcaaggcc gatagtttga   4500
gttcttctac tcaggcaagt gatgttatta ctaatcaaag aagtattgcg acaacggtta   4560
atttgcgtga tggacagact cttttactcg gtggcctcac tgattataaa aacacttctc   4620
aggattctgg cgtaccgttc ctgtctaaaa tccctttaat cggcctcctg tttagctccc   4680
gctctgattc taacgaggaa agcacgttat acgtgctcgt caaagcaacc atagtacgcg   4740
ccctgtagcg gcgcattaag cgcggcgggt gtggtggtta cgcgcagcgt gaccgctaca   4800
cttgccagcg ccctagcgcc cgctcctttc gctttcttcc cttcctttct cgccacgttc   4860
gccggctttc cccgtcaagc tctaaatcgg gggctccctt tagggttccg atttagtgct   4920
ttacggcacc tcgaccccaa aaaacttgat tagggtgatg gttcacgtag tgggccatcg   4980
ccctgataga cggtttttcg ccctttgacg ttggagtcca cgttctttaa tagtggactc   5040
ttgttccaaa ctggaacaac actcaaccct atctcggtct attcttttga tttataaggg   5100
attttgccga tttcggccta ttggttaaaa aatgagctga tttaacaaaa atttaacgcg   5160
aattttaaca aaatattaac gtttacaatt taaatatttg cttatacaat cttcctgttt   5220
ttggggcttt tctgattatc aaccggggta catatgattg acatgctagt tttacgatta   5280
ccgttcatcg attctcttgt ttgctccaga ctctcaggca atgacctgat agcctttgta   5340
gagacctctc aaaaatagct accctctccg gcatgaattt atcagctaga acggttgaat   5400
atcatattga tggtgatttg actgtctccg gcctttctca cccgtttgaa tctttaccta   5460
cacattactc aggcattgca tttaaaatat atgagggttc taaaaatttt tatccttgcg   5520
ttgaaataaa ggcttctccc gcaaaagtat tacagggtca taatgttttt ggtacaaccg   5580
atttagcttt atgctctgag gctttattgc ttaattttgc taattctttg ccttgcctgt   5640
atgatttatt ggatgttgga atcgcctgat gcggtatttt ctccttacgc atctgtgcgg   5700
tatttcacac cgcatatggt gcactctcag tacaatctgc tctgatgccg catagttaag   5760
ccagccccga cacccgccaa cacccgctga cgcgccctga cgggcttgtc tgctcccggc   5820
atccgcttac agacaagctg tgaccgtctc cgggagctgc atgtgtcaga ggttttcacc   5880
gtcatcaccg aaacgcgcga gacgaaaggg cctcgtgata cgcctatttt tataggttaa   5940
tgtcatgata ataatggttt cttagacgtc aggtggcact tttcggggaa atgtgcgcgg   6000
aacccctatt tgtttatttt tctaaataca ttcaaatatg tatccgctca tgagacaata   6060
accctgataa atgcttcaat aatattgaaa aaggaagagt atgagtattc aacatttccg   6120
tgtcgccctt attccctttt ttgcggcatt ttgccttcct gtttttgctc acccagaaac   6180
gctggtgaaa gtaaaagatg ctgaagatca gttgggtgca cgagtgggtt acatcgaact   6240
ggatctcaac agcggtaaga tccttgagag ttttcgcccc gaagaacgtt ttccaatgat   6300
gagcactttt aaagttctgc tatgtggcgc ggtattatcc cgtattgacg ccgggcaaga   6360
gcaactcggt cgccgcatac actattctca gaatgacttg gttgagtact caccagtcac   6420
agaaaagcat cttacggatg gcatgacagt aagagaatta tgcagtgctg ccataaccat   6480
gagtgataac actgcggcca acttacttct gacaacgatc ggaggaccga aggagctaac   6540
```

-continued

```
cgctttttttg cacaacatgg gggatcatgt aactcgcctt gatcgttggg aaccggagct   6600

gaatgaagcc ataccaaacg acgagcgtga caccacgatg cctgtagcaa tggcaacaac   6660

gttgcgcaaa ctattaactg gcgaactact tactctagct tcccggcaac aattaataga   6720

ctggatggag gcggataaag ttgcaggacc acttctgcgc tcggcccttc cggctggctg   6780

gtttattgct gataaatctg gagccggtga gcgtgggtct cgcggtatca ttgcagcact   6840

ggggccagat ggtaagccct cccgtatcgt agttatctac acgacgggga gtcaggcaac   6900

tatggatgaa cgaaatagac agatcgctga gataggtgcc tcactgatta agcattggta   6960

actgtcagac caagtttact catatatact ttagattgat ttaaaacttc atttttaatt   7020

taaaaggatc taggtgaaga tcctttttga taatctcatg accaaaatcc cttaacgtga   7080

gttttcgttc cactgagcgt cagaccccgt agaaaagatc aaaggatctt cttgagatcc   7140

tttttttctg cgcgtaatct gctgcttgca aacaaaaaaa ccaccgctac cagcggtggt   7200

ttgtttgccg gatcaagagc taccaactct ttttccgaag gtaactggct tcagcagagc   7260

gcagatacca aatactgtcc ttctagtgta gccgtagtta ggccaccact tcaagaactc   7320

tgtagcaccg cctacatacc tcgctctgct aatcctgtta ccagtggctg ctgccagtgg   7380

cgataagtcg tgtcttaccg ggttggactc aagacgatag ttaccggata aggcgcagcg   7440

gtcgggctga acggggggtt cgtgcacaca gcccagcttg gagcgaacga cctacaccga   7500

actgagatac ctacagcgtg agctatgaga aagcgccacg cttcccgaag ggagaaaggc   7560

ggacaggtat ccggtaagcg gcagggtcgg aacaggagag cgcacgaggg agcttccagg   7620

gggaaacgcc tggtatcttt atagtcctgt cgggtttcgc cacctctgac ttgagcgtcg   7680

atttttgtga tgctcgtcag gggggcggag cctatggaaa aacgccagca acgcggcctt   7740

tttacggttc ctggcctttt gctggccttt tgctcacatg ttctttcctg cgttatcccc   7800

tgattctgtg gataaccgta ttaccgcctt tgagtgagct gataccgctc gccgcagccg   7860

aacgaccgag cgcagcgagt cagtgagcga ggaagcggaa gagcgcccaa tacgcaaacc   7920

gcctctcccc gcgcgttggc cgattcatta atg                                 7953
```

<210> SEQ ID NO 44
<211> LENGTH: 7553
<212> TYPE: DNA
<213> ORGANISM: Artificial
<220> FEATURE:
<223> OTHER INFORMATION: 45

<400> SEQUENCE: 44

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac acgcgtagat    180

cttccttaga aaccactgct aactgaaaga gactaagatt tgtcccgtca aaaatcctgg    240

acctatgcct aaaacacatt tcacaatccc tgaacttttc aaaaattggt acatgcttta    300

gctttaaact acaggcctca ctggagctag agacaagaag gtaaaaaacg gctgacaaaa    360

gaagtcctgg tatcctctat gatgggagaa ggaaactagc taaagggaag aataaattag    420

agaaaaactg gaatgactga atcggaacaa ggcaaaggct ataaaaaaaa ttagcagtat    480

cctcttgggg gccccttccc cacactatct caatgcaaat atctgtctga aacggtccct    540

ggctaaactc cacccatggg ttggccagcc ttgccttgac aaggcaaact tgaccaatag    600
```

-continued

```
tcttagagta tccagtgagg ccaggggccg gcggctggct agggatgaag aataaaagga    660
agcacccttc agcagttcca cacactcgct tctggaacgt ctgaggttat caataagctc    720
ctagtccaga cgccatggtg cacctgactc ctgaggagaa gtctgccgtt actgccctgt    780
ggggcaaggt gaacgtggat gaagttggtg gtgaggccct gggcaggttg gtatcaaggt    840
tacaagacag gtttaaggag accaatagaa actgggcatg tggagacaga gaagactctt    900
gggtttctga taggcactga ctctctctgc ctattggtct attttcccac ccttaggctg    960
ctggtggtct acccttggac ccagaggttc tttgagtcct ttggggatct gtccactcct   1020
gatgctgtta tgggcaaccc taaggtgaag gctcatggca agaaagtgct cggtgccttt   1080
agtgatggcc tggctcacct ggacaacctc aagggcacct ttgcccagct gagtgagctg   1140
cactgtgaca agctgcacgt ggatcctgag aacttcaggg tgagtctatg ggacccttga   1200
tgttttcttt ccccttcttt tctatggtta agttcatgtc ataggaaggg gagaagtaac   1260
agggtacaca tattgaccaa atcagggtaa ttttgcattt gtaattttaa aaaatgcttt   1320
cttcttttaa tatacttttt tgtttatctt atttctaata ctttccctaa tctctttctt   1380
tcagggcaat aatgatacaa tgtatcatgc ctctttgcac cattctaaag aataacagtg   1440
ataatttctg ggttaaggca atagcaatat ttctgcatat aaatatttct gcatataaat   1500
tgtaactgat gtaagaggtt tcatattgct aatagcagct acaatccagc taccattctg   1560
cttttatttt atggttggga taaggctgga ttattctgag tccaagctag gcccttttgc   1620
taatcatgtt catacctctt atcttcctcc cacagctcct gggcaacgtg ctggtctgtg   1680
tgctggccca tcactttggc aaagaattca ccccaccagt gcaggctgcc tatcagaaag   1740
tggtggctgg tgtggctaat gccctggccc acaagtatca ctaagctcgc tttcttgctg   1800
tccaatttct attaaaggtt cctttgttcc ctaagtccaa ctactaaact gggggatatt   1860
atgaagggcc ttgagcatct ggattctgcc taataaaaaa catttatttt cattgcaatg   1920
atgtatttaa attatttctg aatattttac taaaaaggga atgtgggagg ttgcagtgct   1980
agtctcccgg aactatcact ctttcacagt ctgctttgga aggactgggc ttagtatgaa   2040
aagttaggac tgagaagaat ttgaaagggg gctttttgta gcttgatatt cactactgtc   2100
ttattaccct atcataggcc caccccaaat ggaagtccca ttcttcctca ggatgtttaa   2160
gattagcatt caggaagaga tcagaggtct gctggctccc ttatcatgtc ccttatggtg   2220
cttctggctc tgcaccgcgg gaacagagaa acaggagaat atgggccaaa caggatatct   2280
gtggtaagca gttcctgccc cggctcaggg ccaagaacag ttggaacagc agaatatggg   2340
ccaaacagga tatctgtggt aagcagttcc tgccccggct cagggccaag aacagatggt   2400
ccccagatgc ggtcccgccc tcagcagttt ctagagaacc atcagatgtt tccagggtgc   2460
cccaaggacc tgaaatgacc ctgtgcctta tttgaactaa ccaatcagtt cgcttctcgc   2520
ttctgttcgc gcgcttctgc tccccgagct ctatataagc agagctcgtt tagtgaaccg   2580
tcagatcgcg gccgcgccgc caccatggtg agcaagggcg aggagctgtt caccggggtg   2640
gtgcccatcc tggtcgagct ggacggcgac gtaaacggcc acaagttcag cgtgtccggc   2700
gagggcgagg gcgatgccac ctacggcaag ctgaccctga agttcatctg caccaccggc   2760
aagctgcccg tgccctggcc caccctcgtg accaccctga cctacggcgt gcagtgcttc   2820
agccgctacc ccgaccacat gaagcagcac gacttcttca agtccgccat gcccgaaggc   2880
tacgtccagg agcgcaccat cttcttcaag gacgacggca actacaagac ccgcgccgag   2940
gtgaagttcg agggcgacac cctggtgaac cgcatcgagc tgaagggcat cgacttcaag   3000
```

gaggacggca acatcctggg gcacaagctg gagtacaact acaacagcca caacgtctat 3060
atcatggccg acaagcagaa gaacggcatc aaggtgaact tcaagatccg ccacaacatc 3120
gaggacggca gcgtgcagct cgccgaccac taccagcaga acacccccat cggcgacggc 3180
cccgtgctgc tgcccgacaa ccactacctg agcacccagt ccgccctgag caaagacccc 3240
aacgagaagc gcgatcacat ggtcctgctg gagttcgtga ccgccgccgg gatcactctc 3300
ggcatggacg agctgtacaa ggagggcaga ggaagtcttc taacatgcgg tgacgtggag 3360
gagaatccgg gcccccctgc aggaacttca aggtgagtcc aggagatgtt tcagccctgt 3420
tgcctttagt ctcgaggcaa cttagacaac ggagtattga tctgagcaca gcagggtgtg 3480
agctgtttga agatactggg gttgggggtg aagaaactgc agaggactaa ctgggctgag 3540
acccagtggt aatgttttag ggcctaagga gtgcctctaa aaatctagat ggacaatttt 3600
gactttgaga aaagagaggt ggaaatgagg aaaatgactt ttctttatta gattccagta 3660
gaaagaactt tcatctttcc ctcatttttg ttgttttaaa acatctatct ggaggcagga 3720
caagtatggt cgttaaaaag atgcaggcag aaggcatata ttggctcagt caaagtgggg 3780
aactttggtg ggtcgacgta gataagtagc atggcgggtt aatcattaac tacaaggaac 3840
ccctagtgat ggagttggcc actccctctc tgcgcgctcg ctcgctcact gaggccgggc 3900
gaccaaaggt cgcccgacgc ccgggctttg cccgggcggc ctcagtgagc gagcgagcgc 3960
gccagctggc gtaatagcga agaggcccgc accgatcgcc cttcccaaca gttgcgcagc 4020
ctgaatggcg aatggcgatt ccgttgcaat ggctggcggt aatattgttc tggatattac 4080
cagcaaggcc gatagtttga gttcttctac tcaggcaagt gatgttatta ctaatcaaag 4140
aagtattgcg acaacggtta atttgcgtga tggacagact cttttactcg gtggcctcac 4200
tgattataaa aacacttctc aggattctgg cgtaccgttc ctgtctaaaa tccctttaat 4260
cggcctcctg tttagctccc gctctgattc taacgaggaa agcacgttat acgtgctcgt 4320
caaagcaacc atagtacgcg ccctgtagcg gcgcattaag cgcggcgggt gtggtggtta 4380
cgcgcagcgt gaccgctaca cttgccagcg ccctagcgcc cgctcctttc gctttcttcc 4440
cttcctttct cgccacgttc gccggctttc cccgtcaagc tctaaatcgg gggctccctt 4500
tagggttccg atttagtgct ttacggcacc tcgaccccaa aaaacttgat tagggtgatg 4560
gttcacgtag tgggccatcg ccctgataga cggtttttcg ccctttgacg ttggagtcca 4620
cgttctttaa tagtggactc ttgttccaaa ctggaacaac actcaaccct atctcggtct 4680
attcttttga tttataaggg attttgccga tttcggccta ttggttaaaa aatgagctga 4740
tttaacaaaa atttaacgcg aattttaaca aaatattaac gtttacaatt taaatatttg 4800
cttatacaat cttcctgttt ttggggcttt tctgattatc aaccggggta catatgattg 4860
acatgctagt tttacgatta ccgttcatcg attctcttgt ttgctccaga ctctcaggca 4920
atgacctgat agcctttgta gagacctctc aaaaatagct accctctccg gcatgaattt 4980
atcagctaga acggttgaat atcatattga tggtgatttg actgtctccg gcctttctca 5040
cccgtttgaa tctttaccta cacattactc aggcattgca tttaaaatat atgagggttc 5100
taaaaatttt tatccttgcg ttgaaataaa ggcttctccc gcaaaagtat tacagggtca 5160
taatgttttt ggtacaaccg atttagcttt atgctctgag gctttattgc ttaattttgc 5220
taattctttg ccttgcctgt atgatttatt ggatgttgga atcgcctgat gcggtatttt 5280
ctccttacgc atctgtgcgg tatttcacac cgcatatggt gcactctcag tacaatctgc 5340

-continued tctgatgccg catagttaag ccagccccga cacccgccaa cacccgctga cgcgccctga 5400
cgggcttgtc tgctcccggc atccgcttac agacaagctg tgaccgtctc cgggagctgc 5460
atgtgtcaga ggttttcacc gtcatcaccg aaacgcgcga gacgaaaggg cctcgtgata 5520
cgcctatttt tataggttaa tgtcatgata ataatggttt cttagacgtc aggtggcact 5580
tttcggggaa atgtgcgcgg aacccctatt tgtttatttt tctaaataca ttcaaatatg 5640
tatccgctca tgagacaata accctgataa atgcttcaat aatattgaaa aaggaagagt 5700
atgagtattc aacatttccg tgtcgccctt attccctttt ttgcggcatt ttgccttcct 5760
gtttttgctc acccagaaac gctggtgaaa gtaaaagatg ctgaagatca gttgggtgca 5820
cgagtgggtt acatcgaact ggatctcaac agcggtaaga tccttgagag ttttcgcccc 5880
gaagaacgtt ttccaatgat gagcactttt aaagttctgc tatgtggcgc ggtattatcc 5940
cgtattgacg ccgggcaaga gcaactcggt cgccgcatac actattctca gaatgacttg 6000
gttgagtact caccagtcac agaaaagcat cttacggatg gcatgacagt aagagaatta 6060
tgcagtgctg ccataaccat gagtgataac actgcggcca acttacttct gacaacgatc 6120
ggaggaccga aggagctaac cgcttttttg cacaacatgg gggatcatgt aactcgcctt 6180
gatcgttggg aaccggagct gaatgaagcc ataccaaacg acgagcgtga caccacgatg 6240
cctgtagcaa tggcaacaac gttgcgcaaa ctattaactg gcgaactact tactctagct 6300
tcccggcaac aattaataga ctggatggag gcggataaag ttgcaggacc acttctgcgc 6360
tcggcccttc cggctggctg gtttattgct gataaatctg gagccggtga gcgtgggtct 6420
cgcggtatca ttgcagcact ggggccagat ggtaagccct cccgtatcgt agttatctac 6480
acgacgggga gtcaggcaac tatggatgaa cgaaatagac agatcgctga gataggtgcc 6540
tcactgatta agcattggta actgtcagac caagtttact catatatact ttagattgat 6600
ttaaaacttc atttttaatt taaaaggatc taggtgaaga tcctttttga taatctcatg 6660
accaaaatcc cttaacgtga gttttcgttc cactgagcgt cagaccccgt agaaaagatc 6720
aaaggatctt cttgagatcc tttttttctg cgcgtaatct gctgcttgca aacaaaaaaa 6780
ccaccgctac cagcggtggt ttgtttgccg gatcaagagc taccaactct ttttccgaag 6840
gtaactggct tcagcagagc gcagatacca aatactgtcc ttctagtgta gccgtagtta 6900
ggccaccact tcaagaactc tgtagcaccg cctacatacc tcgctctgct aatcctgtta 6960
ccagtggctg ctgccagtgg cgataagtcg tgtcttaccg ggttggactc aagacgatag 7020
ttaccggata aggcgcagcg gtcgggctga acggggggtt cgtgcacaca gcccagcttg 7080
gagcgaacga cctacaccga actgagatac ctacagcgtg agctatgaga aagcgccacg 7140
cttcccgaag ggagaaaggc ggacaggtat ccggtaagcg gcagggtcgg aacaggagag 7200
cgcacgaggg agcttccagg gggaaacgcc tggtatcttt atagtcctgt cgggtttcgc 7260
cacctctgac ttgagcgtcg atttttgtga tgctcgtcag gggggcggag cctatggaaa 7320
aacgccagca acgcggcctt tttacggttc ctggcctttt gctggccttt tgctcacatg 7380
ttctttcctg cgttatcccc tgattctgtg gataaccgta ttaccgcctt tgagtgagct 7440
gataccgctc gccgcagccg aacgaccgag cgcagcgagt cagtgagcga ggaagcggaa 7500
gagcgcccaa tacgcaaacc gcctctcccc gcgcgttggc cgattcatta atg 7553

<210> SEQ ID NO 45
<211> LENGTH: 7252
<212> TYPE: DNA
<213> ORGANISM: Artificial
<220> FEATURE:
<223> OTHER INFORMATION: AAV donor template

<400> SEQUENCE: 45

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtagat    180
ctagaaattg ttttcactgc actattgaga aattaagaga taatggcaaa agtcacaaag    240
agtatattca aaaagaagta tagcactttt tccttagaaa ccactgctaa ctgaaagaga    300
ctaagatttg tcccgtcaaa aatcctggac ctatgcctaa aacacatttc acaatccctg    360
aacttttcaa aaattggtac atgctttagc tttaaactac aggcctcact ggagctagag    420
acaagaaggt aaaaaacggc tgacaaaaga agtcctggta tcctctatga tgggagaagg    480
aaactagcta aagggaagaa taaattagag aaaaactgga atgactgaat cggaacaagg    540
caaaggctat aaaaaaaatt agcagtatcc tcttgggggc cccttcccca cactatctca    600
atgcaaatat ctgtctgaaa cggtccctgg ctaaactcca cccatgggtt ggccagcctt    660
gccttgacca atagccttga caaggcaaac ttgaccaata gtcttagagt atccagtgag    720
gccaggggcc ggcggctggc tagggatgaa gaataaaagg aagcaccctt cagcagttcc    780
acccgcggga acagagaaac aggagaatat gggccaaaca ggatatctgt ggtaagcagt    840
tcctgccccg gctcagggcc aagaacagtt ggaacagcag aatatgggcc aaacaggata    900
tctgtggtaa gcagttcctg ccccggctca gggccaagaa cagatggtcc ccagatgcgg    960
tcccgccctc agcagtttct agagaaccat cagatgtttc cagggtgccc caaggacctg   1020
aaatgaccct gtgccttatt tgaactaacc aatcagttcg cttctcgctt ctgttcgcgc   1080
gcttctgctc cccgagctct atataagcag agctcgttta gtgaaccgtc agatcgcctg   1140
gagacgccat ccacgctgtt ttgacttcca tagaaggcgg ccgcgccgcc accatggtga   1200
gcaagggcga ggagctgttc accggggtgg tgcccatcct ggtcgagctg gacggcgacg   1260
taaacggcca caagttcagc gtgtccggcg agggcgaggg cgatgccacc tacggcaagc   1320
tgaccctgaa gttcatctgc accaccggca agctgcccgt gccctggccc accctcgtga   1380
ccaccctgac ctacggcgtg cagtgcttca gccgctaccc cgaccacatg aagcagcacg   1440
acttcttcaa gtccgccatg cccgaaggct acgtccagga gcgcaccatc ttcttcaagg   1500
acgacggcaa ctacaagacc cgcgccgagg tgaagttcga gggcgacacc ctggtgaacc   1560
gcatcgagct gaagggcatc gacttcaagg aggacggcaa catcctgggg cacaagctgg   1620
agtacaacta caacagccac aacgtctata tcatggccga caagcagaag aacggcatca   1680
aggtgaactt caagatccgc cacaacatcg aggacggcag cgtgcagctc gccgaccact   1740
accagcagaa cacccccatc ggcgacggcc ccgtgctgct gcccgacaac cactacctga   1800
gcacccagtc cgccctgagc aaagacccca acgagaagcg cgatcacatg gtcctgctgg   1860
agttcgtgac cgccgccggg atcactctcg gcatggacga gctgtacaag taacctgcag   1920
ggataatcaa cctctggatt acaaaatttg tgaaagattg actggtattc ttaactatgt   1980
tgctcctttt acgctatgtg gatacgctgc tttaatgcct ttgtatcatg ctattgcttc   2040
ccgtatggct ttcattttct cctccttgta taaatcctgg ttagttcttg ccacggcgga   2100
actcatcgcc gcctgccttg cccgctgctg gacaggggct cggctgttgg gcactgacaa   2160
ttccgtggtg tttatttgtg aaatttgtga tgctattgct ttatttgtaa ccattctagc   2220
```

-continued

```
tttatttgtg aaatttgtga tgctattgct ttatttgtaa ccattataag ctgcaataaa   2280
caagttaaca acaacaattg cattcatttt atgtttcagg ttcaggggga gatgtgggag   2340
gtttttttaaa gcgaattctc tggaacctat cagggaccac agtcagccag gcaagcacat   2400
ctgcccaagc caagggtgga ggcatgcagc tgtgggggtc tgtgaaaaca cttgagggag   2460
cagataactg ggccaaccat gactcagtgc ttctggaggc caacaggact gctgagtcat   2520
cctgtggggg tggaggtggg acaagggaaa ggggtgaatg gtactgctga ttacaacctc   2580
tggtgctgcc tccccctcct gtttatctga gaggctagcg taaatacact tgcaaaggag   2640
gatgttttta gtagcaattt gtactgatgg tatggggcca agagatatat cttagaggga   2700
gggctgaggg tttgaagtcc aactcctaag ccagtgccag aagagccaag gacaggtacg   2760
gctgtcatca cttagacctc accctgtgga gccacaccct agggttggcc aatctactcc   2820
caggagcagg gagggcagga gccagggctg ggcataaaag tcagggcaga gccatctatt   2880
gcttacactc gcttctggaa cgtctgaggt tatcaataag ctcctagtcc agacgccatg   2940
ggtcatttca cagaggagga caaggctact atcacaagcc tgtggggcaa ggtgaatgtg   3000
gaagatgctg gaggagaaac cctgggaagg taggctctgg tgaccaggac aagggaggga   3060
aggaaggacc ctgtgcctgg caaaagtcca ggtcgcttct caggatttgt ggcaccttct   3120
gactgtcaaa ctgttcttgt caatctcaca ggctcctggt tgtctaccca tggacccaga   3180
ggttctttga cagctttggc aacctgtcct ctgcctctgc catcatgggc aaccccaaag   3240
tcaaggcaca tggcaagaag gtgctgactt ccttgggaga tgccacaaag cacctggatg   3300
atctcaaggg cacctttgcc cagctgagtg aactgcactg tgacaagctg catgtggatc   3360
ctgagaactt caaggtgagt ccaggagatg tttcagccct gttgccttta gtctcgaggc   3420
aacttagaca acggagtatt gatctgagca cagcagggtg tgagctgttt gaagatactg   3480
gggtctcgag gtcgacgtag ataagtagca tggcgggtta atcattaact acaaggaacc   3540
cctagtgatg gagttggcca ctccctctct gcgcgctcgc tcgctcactg aggccgggcg   3600
accaaaggtc gcccgacgcc cgggctttgc ccgggcggcc tcagtgagcg agcgagcgcg   3660
ccagctggcg taatagcgaa gaggcccgca ccgatcgccc ttcccaacag ttgcgcagcc   3720
tgaatggcga atggcgattc cgttgcaatg gctggcggta atattgttct ggatattacc   3780
agcaaggccg atagtttgag ttcttctact caggcaagtg atgttattac taatcaaaga   3840
agtattgcga caacggttaa tttgcgtgat ggacagactc ttttactcgg tggcctcact   3900
gattataaaa acacttctca ggattctggc gtaccgttcc tgtctaaaat ccctttaatc   3960
ggcctcctgt ttagctcccg ctctgattct aacgaggaaa gcacgttata cgtgctcgtc   4020
aaagcaacca tagtacgcgc cctgtagcgg cgcattaagc gcggcgggtg tggtggttac   4080
gcgcagcgtg accgctacac ttgccagcgc cctagcgccc gctcctttcg ctttcttccc   4140
ttcctttctc gccacgttcg ccggctttcc ccgtcaagct ctaaatcggg ggctcccttt   4200
agggttccga tttagtgctt tacggcacct cgaccccaaa aaacttgatt agggtgatgg   4260
ttcacgtagt gggccatcgc cctgatagac ggtttttcgc cctttgacgt tggagtccac   4320
gttctttaat agtggactct tgttccaaac tggaacaaca ctcaacccta tctcggtcta   4380
ttcttttgat ttataaggga ttttgccgat ttcggcctat tggttaaaaa atgagctgat   4440
ttaacaaaaa tttaacgcga attttaacaa aatattaacg tttacaattt aaatatttgc   4500
ttatacaatc ttcctgtttt tggggctttt ctgattatca accggggtac atatgattga   4560
catgctagtt ttacgattac cgttcatcga ttctcttgtt tgctccagac tctcaggcaa   4620
```

-continued tgacctgata gcctttgtag agacctctca aaaatagcta ccctctccgg catgaattta 4680
tcagctagaa cggttgaata tcatattgat ggtgatttga ctgtctccgg cctttctcac 4740
ccgtttgaat ctttacctac acattactca ggcattgcat ttaaaatata tgagggttct 4800
aaaaattttt atccttgcgt tgaaataaag gcttctcccg caaaagtatt acagggtcat 4860
aatgtttttg gtacaaccga tttagcttta tgctctgagg ctttattgct taattttgct 4920
aattctttgc cttgcctgta tgatttattg gatgttggaa tcgcctgatg cggtattttc 4980
tccttacgca tctgtgcggt atttcacacc gcatatggtg cactctcagt acaatctgct 5040
ctgatgccgc atagttaagc cagccccgac acccgccaac acccgctgac gcgccctgac 5100
gggcttgtct gctcccggca tccgcttaca gacaagctgt gaccgtctcc gggagctgca 5160
tgtgtcagag gttttcaccg tcatcaccga aacgcgcgag acgaaagggc ctcgtgatac 5220
gcctattttt ataggttaat gtcatgataa taatggtttc ttagacgtca ggtggcactt 5280
ttcggggaaa tgtgcgcgga acccctattt gtttattttt ctaaatacat tcaaatatgt 5340
atccgctcat gagacaataa ccctgataaa tgcttcaata atattgaaaa aggaagagta 5400
tgagtattca acatttccgt gtcgccctta ttcccttttt tgcggcattt tgccttcctg 5460
tttttgctca cccagaaacg ctggtgaaag taaaagatgc tgaagatcag ttgggtgcac 5520
gagtgggtta catcgaactg gatctcaaca gcggtaagat ccttgagagt tttcgccccg 5580
aagaacgttt tccaatgatg agcactttta aagttctgct atgtggcgcg gtattatccc 5640
gtattgacgc cgggcaagag caactcggtc gccgcataca ctattctcag aatgacttgg 5700
ttgagtactc accagtcaca gaaaagcatc ttacggatgg catgacagta agagaattat 5760
gcagtgctgc cataaccatg agtgataaca ctgcggccaa cttacttctg acaacgatcg 5820
gaggaccgaa ggagctaacc gcttttttgc acaacatggg ggatcatgta actcgccttg 5880
atcgttggga accggagctg aatgaagcca taccaaacga cgagcgtgac accacgatgc 5940
ctgtagcaat ggcaacaacg ttgcgcaaac tattaactgg cgaactactt actctagctt 6000
cccggcaaca attaatagac tggatggagg cggataaagt tgcaggacca cttctgcgct 6060
cggcccttcc ggctggctgg tttattgctg ataaatctgg agccggtgag cgtgggtctc 6120
gcggtatcat tgcagcactg gggccagatg gtaagccctc ccgtatcgta gttatctaca 6180
cgacggggag tcaggcaact atggatgaac gaaatagaca gatcgctgag ataggtgcct 6240
cactgattaa gcattggtaa ctgtcagacc aagtttactc atatatactt tagattgatt 6300
taaaacttca tttttaattt aaaaggatct aggtgaagat cctttttgat aatctcatga 6360
ccaaaatccc ttaacgtgag ttttcgttcc actgagcgtc agaccccgta gaaaagatca 6420
aaggatcttc ttgagatcct ttttttctgc gcgtaatctg ctgcttgcaa acaaaaaaac 6480
caccgctacc agcggtggtt tgtttgccgg atcaagagct accaactctt tttccgaagg 6540
taactggctt cagcagagcg cagataccaa atactgtcct tctagtgtag ccgtagttag 6600
gccaccactt caagaactct gtagcaccgc ctacatacct cgctctgcta atcctgttac 6660
cagtggctgc tgccagtggc gataagtcgt gtcttaccgg gttggactca agacgatagt 6720
taccggataa ggcgcagcgg tcgggctgaa cggggggttc gtgcacacag cccagcttgg 6780
agcgaacgac ctacaccgaa ctgagatacc tacagcgtga gctatgagaa agcgccacgc 6840
ttcccgaagg gagaaaggcg gacaggtatc cggtaagcgg cagggtcgga acaggagagc 6900
gcacgaggga gcttccaggg ggaaacgcct ggtatcttta tagtcctgtc gggtttcgcc 6960
acctctgact tgagcgtcga tttttgtgat gctcgtcagg ggggcggagc ctatggaaaa 7020
acgccagcaa cgcggccttt ttacggttcc tggccttttg ctggcctttt gctcacatgt 7080
tctttcctgc gttatcccct gattctgtgg ataaccgtat taccgccttt gagtgagctg 7140
ataccgctcg ccgcagccga acgaccgagc gcagcgagtc agtgagcgag gaagcggaag 7200
agcgcccaat acgcaaaccg cctctccccg cgcgttggcc gattcattaa tg 7252

<210> SEQ ID NO 46
<211> LENGTH: 6991
<212> TYPE: DNA
<213> ORGANISM: Artificial
<220> FEATURE:
<223> OTHER INFORMATION: AAV donor template

<400> SEQUENCE: 46
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctagaaattg ttttcactgc actattgaga aattaagaga taatggcaaa agtcacaaag 240
agtatattca aaaagaagta tagcactttt tccttagaaa ccactgctaa ctgaaagaga 300
ctaagatttg tcccgtcaaa aatcctggac ctatgcctaa aacacatttc acaatccctg 360
aacttttcaa aaattggtac atgctttagc tttaaactac aggcctcact ggagctagag 420
acaagaaggt aaaaaacggc tgacaaaaga agtcctggta tcctctatga tgggagaagg 480
aaactagcta aagggaagaa taaattagag aaaaactgga atgactgaat cggaacaagg 540
caaaggctat aaaaaaaatt agcagtatcc tcttgggggc cccttcccca cactatctca 600
atgcaaatat ctgtctgaaa cggtccctgg ctaaactcca cccatgggtt ggccagcctt 660
gccttgacca atagccttga caaggcaaac ttgaccaata gtcttagagt atccagtgag 720
gccaggggcc ggcggctggc tagggatgaa gaataaaagg aagcaccctt cagcagttcc 780
acccgcggga acagagaaac aggagaatat gggccaaaca ggatatctgt ggtaagcagt 840
tcctgccccg gctcagggcc aagaacagtt ggaacagcag aatatgggcc aaacaggata 900
tctgtggtaa gcagttcctg ccccggctca gggccaagaa cagatggtcc ccagatgcgg 960
tcccgccctc agcagtttct agagaaccat cagatgtttc cagggtgccc caaggacctg 1020
aaatgaccct gtgccttatt tgaactaacc aatcagttcg cttctcgctt ctgttcgcgc 1080
gcttctgctc cccgagctct atataagcag agctcgttta gtgaaccgtc agatcgcctg 1140
gagacgccat ccacgctgtt ttgacttcca tagaaggcgg ccgcgccgcc accatggtga 1200
gcaagggcga ggagctgttc accggggtgg tgcccatcct ggtcgagctg gacggcgacg 1260
taaacggcca caagttcagc gtgtccggcg agggcgaggg cgatgccacc tacggcaagc 1320
tgaccctgaa gttcatctgc accaccggca agctgcccgt gccctggccc accctcgtga 1380
ccaccctgac ctacggcgtg cagtgcttca gccgctaccc cgaccacatg aagcagcacg 1440
acttcttcaa gtccgccatg cccgaaggct acgtccagga gcgcaccatc ttcttcaagg 1500
acgacggcaa ctacaagacc cgcgccgagg tgaagttcga gggcgacacc ctggtgaacc 1560
gcatcgagct gaagggcatc gacttcaagg aggacggcaa catcctgggg cacaagctgg 1620
agtacaacta caacagccac aacgtctata tcatggccga caagcagaag aacggcatca 1680
aggtgaactt caagatccgc cacaacatcg aggacggcag cgtgcagctc gccgaccact 1740
accagcagaa cacccccatc ggcgacggcc ccgtgctgct gcccgacaac cactacctga 1800

-continued gcacccagtc cgccctgagc aaagacccca acgagaagcg cgatcacatg gtcctgctgg 1860
agttcgtgac cgccgccggg atcactctcg gcatggacga gctgtacaag taacctgcag 1920
ggataatcaa cctctggatt acaaaatttg tgaaagattg actggtattc ttaactatgt 1980
tgctcctttt acgctatgtg gatacgctgc tttaatgcct ttgtatcatg ctattgcttc 2040
ccgtatggct ttcattttct cctccttgta taaatcctgg ttagttcttg ccacggcgga 2100
actcatcgcc gcctgccttg cccgctgctg gacaggggct cggctgttgg gcactgacaa 2160
ttccgtggtg tttatttgtg aaatttgtga tgctattgct ttatttgtaa ccattctagc 2220
tttatttgtg aaatttgtga tgctattgct ttatttgtaa ccattataag ctgcaataaa 2280
caagttaaca acaacaattg cattcatttt atgtttcagg ttcaggggga gatgtgggag 2340 gtttttaaa gcgaattcgt aaatacactt gcaaaggagg atgtttttag tagcaatttg 2400
tactgatggt atggggccaa gagatatatc ttagagggag ggctgagggt ttgaagtcca 2460
actcctaagc cagtgccaga agagccaagg acaggtacgg ctgtcatcac ttagacctca 2520
ccctgtggag ccacacccta gggttggcca atctactccc aggagcaggg agggcaggag 2580
ccagggctgg gcataaaagt cagggcagag ccatctattg cttacactcg cttctggaac 2640
gtctgaggtt atcaataagc tcctagtcca gacgccatgg gtcatttcac agaggaggac 2700
aaggctacta tcacaagcct gtggggcaag gtgaatgtgg aagatgctgg aggagaaacc 2760
ctgggaaggt aggctctggt gaccaggaca agggagggaa ggaaggaccc tgtgcctggc 2820
aaaagtccag gtcgcttctc aggatttgtg gcaccttctg actgtcaaac tgttcttgtc 2880
aatctcacag gctcctggtt gtctacccat ggacccagag gttctttgac agctttggca 2940
acctgtcctc tgcctctgcc atcatgggca accccaaagt caaggcacat ggcaagaagg 3000
tgctgacttc cttgggagat gccacaaagc acctggatga tctcaagggc acctttgccc 3060
agctgagtga actgcactgt gacaagctgc atgtggatcc tgagaacttc aaggtgagtc 3120
caggagatgt ttcagccctg ttgcctttag tctcgaggca acttagacaa cggagtattg 3180
atctgagcac agcagggtgt gagctgtttg aagatactgg ggtctcgagg tcgacgtaga 3240
taagtagcat ggcgggttaa tcattaacta caaggaaccc ctagtgatgg agttggccac 3300
tccctctctg cgcgctcgct cgctcactga ggccgggcga ccaaaggtcg cccgacgccc 3360
gggctttgcc cgggcggcct cagtgagcga gcgagcgcgc cagctggcgt aatagcgaag 3420
aggcccgcac cgatcgccct tcccaacagt tgcgcagcct gaatggcgaa tggcgattcc 3480
gttgcaatgg ctggcggtaa tattgttctg gatattacca gcaaggccga tagtttgagt 3540
tcttctactc aggcaagtga tgttattact aatcaaagaa gtattgcgac aacggttaat 3600
ttgcgtgatg gacagactct tttactcggt ggcctcactg attataaaaa cacttctcag 3660
gattctggcg taccgttcct gtctaaaatc cctttaatcg gcctcctgtt tagctcccgc 3720
tctgattcta acgaggaaag cacgttatac gtgctcgtca aagcaaccat agtacgcgcc 3780
ctgtagcggc gcattaagcg cggcgggtgt ggtggttacg cgcagcgtga ccgctacact 3840
tgccagcgcc ctagcgcccg ctcctttcgc tttcttccct tcctttctcg ccacgttcgc 3900
cggctttccc cgtcaagctc taaatcgggg gctcccttta gggttccgat ttagtgcttt 3960
acggcacctc gaccccaaaa aacttgatta gggtgatggt tcacgtagtg ggccatcgcc 4020
ctgatagacg gtttttcgcc ctttgacgtt ggagtccacg ttctttaata gtggactctt 4080
gttccaaact ggaacaacac tcaaccctat ctcggtctat tcttttgatt tataagggat 4140

-continued

```
tttgccgatt tcggcctatt ggttaaaaaa tgagctgatt taacaaaaat ttaacgcgaa   4200
ttttaacaaa atattaacgt ttacaattta aatatttgct tatacaatct tcctgttttt   4260
ggggcttttc tgattatcaa ccggggtaca tatgattgac atgctagttt tacgattacc   4320
gttcatcgat tctcttgttt gctccagact ctcaggcaat gacctgatag cctttgtaga   4380
gacctctcaa aaatagctac cctctccggc atgaatttat cagctagaac ggttgaatat   4440
catattgatg gtgatttgac tgtctccggc ctttctcacc cgtttgaatc tttacctaca   4500
cattactcag gcattgcatt taaaatatat gagggttcta aaaattttta tccttgcgtt   4560
gaaataaagg cttctcccgc aaaagtatta cagggtcata atgtttttgg tacaaccgat   4620
ttagctttat gctctgaggc tttattgctt aattttgcta attctttgcc ttgcctgtat   4680
gatttattgg atgttggaat cgcctgatgc ggtattttct ccttacgcat ctgtgcggta   4740
tttcacaccg catatggtgc actctcagta caatctgctc tgatgccgca tagttaagcc   4800
agccccgaca cccgccaaca cccgctgacg cgccctgacg ggcttgtctg ctcccggcat   4860
ccgcttacag acaagctgtg accgtctccg ggagctgcat gtgtcagagg ttttcaccgt   4920
catcaccgaa acgcgcgaga cgaaagggcc tcgtgatacg cctattttta taggttaatg   4980
tcatgataat aatggtttct tagacgtcag gtggcacttt tcggggaaat gtgcgcggaa   5040
cccctatttg tttatttttc taaatacatt caaatatgta tccgctcatg agacaataac   5100
cctgataaat gcttcaataa tattgaaaaa ggaagagtat gagtattcaa catttccgtg   5160
tcgcccttat tccctttttt gcggcatttt gccttcctgt ttttgctcac ccagaaacgc   5220
tggtgaaagt aaaagatgct gaagatcagt tgggtgcacg agtgggttac atcgaactgg   5280
atctcaacag cggtaagatc cttgagagtt ttcgccccga agaacgtttt ccaatgatga   5340
gcacttttaa agttctgcta tgtggcgcgg tattatcccg tattgacgcc gggcaagagc   5400
aactcggtcg ccgcatacac tattctcaga atgacttggt tgagtactca ccagtcacag   5460
aaaagcatct tacggatggc atgacagtaa gagaattatg cagtgctgcc ataaccatga   5520
gtgataacac tgcggccaac ttacttctga caacgatcgg aggaccgaag gagctaaccg   5580
cttttttgca caacatgggg gatcatgtaa ctcgccttga tcgttgggaa ccggagctga   5640
atgaagccat accaaacgac gagcgtgaca ccacgatgcc tgtagcaatg gcaacaacgt   5700
tgcgcaaact attaactggc gaactactta ctctagcttc ccggcaacaa ttaatagact   5760
ggatggaggc ggataaagtt gcaggaccac ttctgcgctc ggcccttccg gctggctggt   5820
ttattgctga taaatctgga gccggtgagc gtgggtctcg cggtatcatt gcagcactgg   5880
ggccagatgg taagccctcc cgtatcgtag ttatctacac gacggggagt caggcaacta   5940
tggatgaacg aaatagacag atcgctgaga taggtgcctc actgattaag cattggtaac   6000
tgtcagacca agtttactca tatatacttt agattgattt aaaacttcat ttttaattta   6060
aaaggatcta ggtgaagatc ctttttgata atctcatgac caaaatccct taacgtgagt   6120
tttcgttcca ctgagcgtca gaccccgtag aaaagatcaa aggatcttct tgagatcctt   6180
tttttctgcg cgtaatctgc tgcttgcaaa caaaaaaacc accgctacca gcggtggttt   6240
gtttgccgga tcaagagcta ccaactcttt ttccgaaggt aactggcttc agcagagcgc   6300
agataccaaa tactgtcctt ctagtgtagc cgtagttagg ccaccacttc aagaactctg   6360
tagcaccgcc tacatacctc gctctgctaa tcctgttacc agtggctgct gccagtggcg   6420
ataagtcgtg tcttaccggg ttggactcaa gacgatagtt accggataag gcgcagcggt   6480
cgggctgaac ggggggttcg tgcacacagc ccagcttgga gcgaacgacc tacaccgaac   6540
```

```
tgagatacct acagcgtgag ctatgagaaa gcgccacgct tcccgaaggg agaaaggcgg   6600

acaggtatcc ggtaagcggc agggtcggaa caggagagcg cacgagggag cttccagggg   6660

gaaacgcctg gtatctttat agtcctgtcg ggtttcgcca cctctgactt gagcgtcgat   6720

ttttgtgatg ctcgtcaggg gggcggagcc tatggaaaaa cgccagcaac gcggcctttt   6780

tacggttcct ggccttttgc tggccttttg ctcacatgtt ctttcctgcg ttatcccctg   6840

attctgtgga taaccgtatt accgcctttg agtgagctga taccgctcgc cgcagccgaa   6900

cgaccgagcg cagcgagtca gtgagcgagg aagcggaaga gcgcccaata cgcaaaccgc   6960

ctctccccgc gcgttggccg attcattaat g                                  6991
```

```
<210> SEQ ID NO 47
<211> LENGTH: 7825
<212> TYPE: DNA
<213> ORGANISM: Artificial
<220> FEATURE:
<223> OTHER INFORMATION: AAV donor template

<400> SEQUENCE: 47
```

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac acgcgtagat    180

ctagaaattg ttttcactgc actattgaga aattaagaga taatggcaaa agtcacaaag    240

agtatattca aaaagaagta tagcactttt tccttagaaa ccactgctaa ctgaaagaga    300

ctaagatttg tcccgtcaaa aatcctggac ctatgcctaa aacacatttc acaatccctg    360

aacttttcaa aaattggtac atgctttagc tttaaactac aggcctcact ggagctagag    420

acaagaaggt aaaaaacggc tgacaaaaga agtcctggta tcctctatga tgggagaagg    480

aaactagcta aagggaagaa taaattagag aaaaactgga atgactgaat cggaacaagg    540

caaaggctat aaaaaaaatt agcagtatcc tcttgggggc cccttcccca cactatctca    600

atgcaaatat ctgtctgaaa cggtccctgg ctaaactcca cccgcgggaa cagagaaaca    660

ggagaatatg ggccaaacag gatatctgtg gtaagcagtt cctgccccgg ctcagggcca    720

agaacagttg gaacagcaga atatgggcca aacaggatat ctgtggtaag cagttcctgc    780

cccggctcag ggccaagaac agatggtccc cagatgcggt cccgccctca gcagtttcta    840

gagaaccatc agatgtttcc agggtgcccc aaggacctga aatgaccctg tgccttattt    900

gaactaacca atcagttcgc ttctcgcttc tgttcgcgcg cttctgctcc ccgagctcta    960

tataagcaga gctcgtttag tgaaccgtca gatcgcctgg agacgccatc cacgctgttt   1020

tgacttccat agaaggcggc cgcgccgcca ccatggtgag caagggcgag gagctgttca   1080

ccggggtggt gcccatcctg gtcgagctgg acggcgacgt aaacggccac aagttcagcg   1140

tgtccggcga gggcgagggc gatgccacct acggcaagct gaccctgaag ttcatctgca   1200

ccaccggcaa gctgcccgtg ccctggccca ccctcgtgac caccctgacc tacggcgtgc   1260

agtgcttcag ccgctacccc gaccacatga agcagcacga cttcttcaag tccgccatgc   1320

ccgaaggcta cgtccaggag cgcaccatct tcttcaagga cgacggcaac tacaagaccc   1380

gcgccgaggt gaagttcgag ggcgacaccc tggtgaaccg catcgagctg aagggcatcg   1440

acttcaagga ggacggcaac atcctggggc acaagctgga gtacaactac aacagccaca   1500

acgtctatat catggccgac aagcagaaga acggcatcaa ggtgaacttc aagatccgcc   1560
```

-continued

```
acaacatcga ggacggcagc gtgcagctcg ccgaccacta ccagcagaac acccccatcg   1620
gcgacggccc cgtgctgctg cccgacaacc actacctgag cacccagtcc gccctgagca   1680
aagaccccaa cgagaagcgc gatcacatgg tcctgctgga gttcgtgacc gccgccggga   1740
tcactctcgg catggacgag ctgtacaagt aacctgcagg gataatcaac ctctggatta   1800
caaaatttgt gaaagattga ctggtattct taactatgtt gctcctttta cgctatgtgg   1860
atacgctgct ttaatgcctt tgtatcatgc tattgcttcc cgtatggctt tcattttctc   1920
ctccttgtat aaatcctggt tagttcttgc cacggcggaa ctcatcgccg cctgccttgc   1980
ccgctgctgg acaggggctc ggctgttggg cactgacaat tccgtggtgt ttatttgtga   2040
aatttgtgat gctattgctt tatttgtaac cattctagct ttatttgtga aatttgtgat   2100
gctattgctt tatttgtaac cattataagc tgcaataaac aagttaacaa caacaattgc   2160
attcatttta tgtttcaggt tcagggggag atgtgggagg tttttaaag cgaattccga   2220
gatcgagacc atcctggcta acacagtgaa accccgtctc tactaaaaaa atacaaaaaa   2280
ttagccgggc ttggtggcgg gtgcctgtag tcccagctac tatggaggct gaggcgggag   2340
aatggcgtga acgcgggggg cggagcttgc agtgagcaga gatcaggggc cactgcactc   2400
cagcctgggc gacagagaga gactctgtct caaaaaaaag aaaaaaaaaa tttagtagac   2460
tagctaaaaa aatccagaga tagttattga tgcatatgta aaagtcttcc aatatttaca   2520
agtacaatga aaaaaaaata accttgaatt aagtgtagaa ctcattgaca atgtttcaaa   2580
ggatgtgagg gataaactaa aatttgggca gtacatgctg ttcctgtgta cttggaacag   2640
agggagaaaa tctgggctgg aaatattgtt ataggagtta gcacatgaag gtgacaacta   2700
aattatttgg agtagatgga gtcaccagca catgtgaata gttttagaat gaaatgaccc   2760
aagatagaac tttggagagc cccaaattt aaataaaatc agtataagag aagaggaaga   2820
aaccaaatgg tatactagtc taaattgttt cttagtgaca aaagaataac ctgaatatta   2880
gattagctgc ctatatgctc tctgaatcaa tttcattcaa catgcaacag ttctggaacc   2940
tatcagggac cacagtcagc caggcaagca catctgccca agccaagggt ggaggcatgc   3000
agctgtgggg gtctgtgaaa acacttgagg gagcagataa ctgggccaac catgactcag   3060
tgcttctgga ggccaacagg actgctgagt catcctgtgg gggtggaggt gggacaaggg   3120
aaaggggtga atggtactgc tgattacaac ctctggtgct gcctcccccct cctgtttatc   3180
tgagaggcta gcgtaaatac acttgcaaag gaggatgttt ttagtagcaa tttgtactga   3240
tggtatgggg ccaagagata tatcttagag ggagggctga gggtttgaag tccaactcct   3300
aagccagtgc cagaagagcc aaggacaggt acggctgtca tcacttagac ctcaccctgt   3360
ggagccacac cctagggttg gccaatctac tcccaggagc agggagggca ggagccaggg   3420
ctgggcataa aagtcagggc agagccatct attgcttaca ctcgcttctg gaacgtctga   3480
ggttatcaat aagctcctag tccagacgcc atgggtcatt tcacagagga ggacaaggct   3540
actatcacaa gcctgtgggg caaggtgaat gtggaagatg ctggaggaga aaccctggga   3600
aggtaggctc tggtgaccag gacaagggag ggaaggaagg accctgtgcc tggcaaaagt   3660
ccaggtcgct tctcaggatt tgtggcacct tctgactgtc aaactgttct tgtcaatctc   3720
acaggctcct ggttgtctac ccatggaccc agaggttctt tgacagcttt ggcaacctgt   3780
cctctgcctc tgccatcatg ggcaacccca aagtcaaggc acatggcaag aaggtgctga   3840
cttccttggg agatgccaca aagcacctgg atgatctcaa gggcaccttt gcccagctga   3900
gtgaactgca ctgtgacaag ctgcatgtgg atcctgagaa cttcaaggtg agtccaggag   3960
```

-continued atgtttcagc cctgttgcct ttagtctcga ggcaacttag acaacggagt attgatctga 4020
gcacagcagg gtgtgagctg tttgaagata ctggggtctc gaggtcgacg tagataagta 4080
gcatggcggg ttaatcatta actacaagga acccctagtg atggagttgg ccactccctc 4140
tctgcgcgct cgctcgctca ctgaggccgg gcgaccaaag gtcgcccgac gcccgggctt 4200
tgcccgggcg gcctcagtga gcgagcgagc gcgccagctg gcgtaatagc gaagaggccc 4260
gcaccgatcg cccttcccaa cagttgcgca gcctgaatgg cgaatggcga ttccgttgca 4320
atggctggcg gtaatattgt tctggatatt accagcaagg ccgatagttt gagttcttct 4380
actcaggcaa gtgatgttat tactaatcaa agaagtattg cgacaacggt taatttgcgt 4440
gatggacaga ctcttttact cggtggcctc actgattata aaaacacttc tcaggattct 4500
ggcgtaccgt tcctgtctaa aatcccttta atcggcctcc tgtttagctc ccgctctgat 4560
tctaacgagg aaagcacgtt atacgtgctc gtcaaagcaa ccatagtacg cgccctgtag 4620
cggcgcatta agcgcggcgg gtgtggtggt tacgcgcagc gtgaccgcta cacttgccag 4680
cgccctagcg cccgctcctt tcgctttctt cccttccttt ctcgccacgt tcgccggctt 4740
tccccgtcaa gctctaaatc gggggctccc tttagggttc cgatttagtg ctttacggca 4800
cctcgacccc aaaaaacttg attagggtga tggttcacgt agtgggccat cgccctgata 4860
gacggttttt cgccctttga cgttggagtc cacgttcttt aatagtggac tcttgttcca 4920
aactggaaca acactcaacc ctatctcggt ctattctttt gatttataag ggattttgcc 4980
gatttcggcc tattggttaa aaaatgagct gatttaacaa aaatttaacg cgaattttaa 5040
caaaatatta acgtttacaa tttaaatatt tgcttataca atcttcctgt ttttggggct 5100
tttctgatta tcaaccgggg tacatatgat tgacatgcta gttttacgat taccgttcat 5160
cgattctctt gtttgctcca gactctcagg caatgacctg atagcctttg tagagacctc 5220
tcaaaaatag ctaccctctc cggcatgaat ttatcagcta gaacggttga atatcatatt 5280
gatggtgatt tgactgtctc cggcctttct cacccgtttg aatctttacc tacacattac 5340
tcaggcattg catttaaaat atatgagggt tctaaaaatt tttatccttg cgttgaaata 5400
aaggcttctc ccgcaaaagt attacagggt cataatgttt ttggtacaac cgatttagct 5460
ttatgctctg aggctttatt gcttaatttt gctaattctt tgccttgcct gtatgattta 5520
ttggatgttg gaatcgcctg atgcggtatt ttctccttac gcatctgtgc ggtatttcac 5580
accgcatatg gtgcactctc agtacaatct gctctgatgc cgcatagtta agccagcccc 5640
gacacccgcc aacacccgct gacgcgccct gacgggcttg tctgctcccg gcatccgctt 5700
acagacaagc tgtgaccgtc tccgggagct gcatgtgtca gaggttttca ccgtcatcac 5760
cgaaacgcgc gagacgaaag ggcctcgtga tacgcctatt tttataggtt aatgtcatga 5820
taataatggt ttcttagacg tcaggtggca cttttcgggg aaatgtgcgc ggaaccccta 5880
tttgtttatt tttctaaata cattcaaata tgtatccgct catgagacaa taaccctgat 5940
aaatgcttca ataatattga aaaaggaaga gtatgagtat tcaacatttc cgtgtcgccc 6000
ttattccctt ttttgcggca ttttgccttc ctgtttttgc tcacccagaa acgctggtga 6060
aagtaaaaga tgctgaagat cagttgggtg cacgagtggg ttacatcgaa ctggatctca 6120
acagcggtaa gatccttgag agttttcgcc ccgaagaacg ttttccaatg atgagcactt 6180
ttaaagttct gctatgtggc gcggtattat cccgtattga cgccgggcaa gagcaactcg 6240
gtcgccgcat acactattct cagaatgact tggttgagta ctcaccagtc acagaaaagc 6300
atcttacgga tggcatgaca gtaagagaat tatgcagtgc tgccataacc atgagtgata 6360
acactgcggc caacttactt ctgacaacga tcggaggacc gaaggagcta accgcttttt 6420
tgcacaacat gggggatcat gtaactcgcc ttgatcgttg ggaaccggag ctgaatgaag 6480
ccataccaaa cgacgagcgt gacaccacga tgcctgtagc aatggcaaca acgttgcgca 6540
aactattaac tggcgaacta cttactctag cttcccggca acaattaata gactggatgg 6600
aggcggataa agttgcagga ccacttctgc gctcggccct tccggctggc tggtttattg 6660
ctgataaatc tggagccggt gagcgtgggt ctcgcggtat cattgcagca ctggggccag 6720
atggtaagcc ctcccgtatc gtagttatct acacgacggg gagtcaggca actatggatg 6780
aacgaaatag acagatcgct gagataggtg cctcactgat taagcattgg taactgtcag 6840
accaagttta ctcatatata ctttagattg atttaaaact tcatttttaa tttaaaagga 6900
tctaggtgaa gatccttttt gataatctca tgaccaaaat cccttaacgt gagttttcgt 6960
tccactgagc gtcagacccc gtagaaaaga tcaaaggatc ttcttgagat cctttttttc 7020
tgcgcgtaat ctgctgcttg caaacaaaaa aaccaccgct accagcggtg gtttgtttgc 7080
cggatcaaga gctaccaact ctttttccga aggtaactgg cttcagcaga gcgcagatac 7140
caaatactgt ccttctagtg tagccgtagt taggccacca cttcaagaac tctgtagcac 7200
cgcctacata cctcgctctg ctaatcctgt taccagtggc tgctgccagt ggcgataagt 7260
cgtgtcttac cgggttggac tcaagacgat agttaccgga taaggcgcag cggtcgggct 7320
gaacgggggg ttcgtgcaca cagcccagct tggagcgaac gacctacacc gaactgagat 7380
acctacagcg tgagctatga gaaagcgcca cgcttcccga agggagaaag gcggacaggt 7440
atccggtaag cggcagggtc ggaacaggag agcgcacgag ggagcttcca gggggaaacg 7500
cctggtatct ttatagtcct gtcgggtttc gccacctctg acttgagcgt cgatttttgt 7560
gatgctcgtc aggggggcgg agcctatgga aaaacgccag caacgcggcc tttttacggt 7620
tcctggcctt ttgctggcct tttgctcaca tgttctttcc tgcgttatcc cctgattctg 7680
tggataaccg tattaccgcc tttgagtgag ctgataccgc tcgccgcagc cgaacgaccg 7740
agcgcagcga gtcagtgagc gaggaagcgg aagagcgccc aatacgcaaa ccgcctctcc 7800
ccgcgcgttg gccgattcat taatg 7825

<210> SEQ ID NO 48
<211> LENGTH: 7111
<212> TYPE: DNA
<213> ORGANISM: Artificial
<220> FEATURE:
<223> OTHER INFORMATION: AAV donor template

<400> SEQUENCE: 48
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
ctagaaattg ttttcactgc actattgaga aattaagaga taatggcaaa agtcacaaag 240
agtatattca aaaagaagta tagcactttt tccttagaaa ccactgctaa ctgaaagaga 300
ctaagatttg tcccgtcaaa aatcctggac ctatgcctaa aacacatttc acaatccctg 360
aacttttcaa aaattggtac atgctttagc tttaaactac aggcctcact ggagctagag 420
acaagaaggt aaaaaacggc tgacaaaaga agtcctggta tcctctatga tgggagaagg 480
aaactagcta aagggaagaa taaattagag aaaaactgga atgactgaat cggaacaagg 540

-continued

```
caaaggctat aaaaaaaatt agcagtatcc tcttgggggc cccttcccca cactatctca    600
atgcaaatat ctgtctgaaa cggtccctgg ctaaactcca cccgcgggaa cagagaaaca    660
ggagaatatg ggccaaacag gatatctgtg gtaagcagtt cctgccccgg ctcagggcca    720
agaacagttg gaacagcaga atatgggcca aacaggatat ctgtggtaag cagttcctgc    780
cccggctcag ggccaagaac agatggtccc cagatgcggt cccgccctca gcagtttcta    840
gagaaccatc agatgtttcc agggtgcccc aaggacctga aatgaccctg tgccttattt    900
gaactaacca atcagttcgc ttctcgcttc tgttcgcgcg cttctgctcc ccgagctcta    960
tataagcaga gctcgtttag tgaaccgtca gatcgcctgg agacgccatc cacgctgttt   1020
tgacttccat agaaggcggc cgcgccgcca ccatggtgag caagggcgag gagctgttca   1080
ccggggtggt gcccatcctg gtcgagctgg acggcgacgt aaacggccac aagttcagcg   1140
tgtccggcga gggcgagggc gatgccacct acggcaagct gaccctgaag ttcatctgca   1200
ccaccggcaa gctgcccgtg ccctggccca ccctcgtgac caccctgacc tacggcgtgc   1260
agtgcttcag ccgctacccc gaccacatga agcagcacga cttcttcaag tccgccatgc   1320
ccgaaggcta cgtccaggag cgcaccatct tcttcaagga cgacggcaac tacaagaccc   1380
gcgccgaggt gaagttcgag ggcgacaccc tggtgaaccg catcgagctg aagggcatcg   1440
acttcaagga ggacggcaac atcctggggc acaagctgga gtacaactac aacagccaca   1500
acgtctatat catggccgac aagcagaaga acggcatcaa ggtgaacttc aagatccgcc   1560
acaacatcga ggacggcagc gtgcagctcg ccgaccacta ccagcagaac acccccatcg   1620
gcgacggccc cgtgctgctg cccgacaacc actacctgag cacccagtcc gccctgagca   1680
aagaccccaa cgagaagcgc gatcacatgg tcctgctgga gttcgtgacc gccgccggga   1740
tcactctcgg catggacgag ctgtacaagt aacctgcagg gataatcaac ctctggatta   1800
caaaatttgt gaaagattga ctggtattct taactatgtt gctcctttta cgctatgtgg   1860
atacgctgct ttaatgcctt tgtatcatgc tattgcttcc cgtatggctt tcattttctc   1920
ctccttgtat aaatcctggt tagttcttgc cacggcggaa ctcatcgccg cctgccttgc   1980
ccgctgctgg acaggggctc ggctgttggg cactgacaat tccgtggtgt ttatttgtga   2040
aatttgtgat gctattgctt tatttgtaac cattctagct ttatttgtga aatttgtgat   2100
gctattgctt tatttgtaac cattataagc tgcaataaac aagttaacaa caacaattgc   2160
attcatttta tgtttcaggt tcagggggag atgtgggagg ttttttaaag cgaattctct   2220
ggaacctatc agggaccaca gtcagccagg caagcacatc tgcccaagcc aagggtggag   2280
gcatgcagct gtgggggtct gtgaaaacac ttgagggagc agataactgg gccaaccatg   2340
actcagtgct tctggaggcc aacaggactg ctgagtcatc ctgtgggggt ggaggtggga   2400
caagggaaag gggtgaatgg tactgctgat tacaacctct ggtgctgcct ccccctcctg   2460
tttatctgag aggctagcgt aaatacactt gcaaaggagg atgtttttag tagcaatttg   2520
tactgatggt atggggccaa gagatatatc ttagagggag ggctgagggt ttgaagtcca   2580
actcctaagc cagtgccaga agagccaagg acaggtacgg ctgtcatcac ttagacctca   2640
ccctgtggag ccacacccta gggttggcca atctactccc aggagcaggg agggcaggag   2700
ccagggctgg gcataaaagt cagggcagag ccatctattg cttacactcg cttctggaac   2760
gtctgaggtt atcaataagc tcctagtcca gacgccatgg gtcatttcac agaggaggac   2820
aaggctacta tcacaagcct gtggggcaag gtgaatgtgg aagatgctgg aggagaaacc   2880
```

-continued

```
ctgggaaggt aggctctggt gaccaggaca agggagggaa ggaaggaccc tgtgcctggc   2940
aaaagtccag gtcgcttctc aggatttgtg gcaccttctg actgtcaaac tgttcttgtc   3000
aatctcacag gctcctggtt gtctacccat ggacccagag gttctttgac agctttggca   3060
acctgtcctc tgcctctgcc atcatgggca accccaaagt caaggcacat ggcaagaagg   3120
tgctgacttc cttgggagat gccacaaagc acctggatga tctcaagggc acctttgccc   3180
agctgagtga actgcactgt gacaagctgc atgtggatcc tgagaacttc aaggtgagtc   3240
caggagatgt ttcagccctg ttgcctttag tctcgaggca acttagacaa cggagtattg   3300
atctgagcac agcagggtgt gagctgtttg aagatactgg ggtctcgagg tcgacgtaga   3360
taagtagcat ggcgggttaa tcattaacta caaggaaccc ctagtgatgg agttggccac   3420
tccctctctg cgcgctcgct cgctcactga ggccgggcga ccaaaggtcg cccgacgccc   3480
gggctttgcc cgggcggcct cagtgagcga gcgagcgcgc cagctggcgt aatagcgaag   3540
aggcccgcac cgatcgccct tcccaacagt tgcgcagcct gaatggcgaa tggcgattcc   3600
gttgcaatgg ctggcggtaa tattgttctg gatattacca gcaaggccga tagtttgagt   3660
tcttctactc aggcaagtga tgttattact aatcaaagaa gtattgcgac aacggttaat   3720
ttgcgtgatg gacagactct tttactcggt ggcctcactg attataaaaa cacttctcag   3780
gattctggcg taccgttcct gtctaaaatc cctttaatcg gcctcctgtt tagctcccgc   3840
tctgattcta acgaggaaag cacgttatac gtgctcgtca aagcaaccat agtacgcgcc   3900
ctgtagcggc gcattaagcg cggcgggtgt ggtggttacg cgcagcgtga ccgctacact   3960
tgccagcgcc ctagcgcccg ctcctttcgc tttcttccct tcctttctcg ccacgttcgc   4020
cggctttccc cgtcaagctc taaatcgggg gctcccttta gggttccgat ttagtgcttt   4080
acggcacctc gaccccaaaa aacttgatta gggtgatggt tcacgtagtg ggccatcgcc   4140
ctgatagacg gtttttcgcc ctttgacgtt ggagtccacg ttctttaata gtggactctt   4200
gttccaaact ggaacaacac tcaaccctat ctcggtctat tcttttgatt tataagggat   4260
tttgccgatt tcggcctatt ggttaaaaaa tgagctgatt taacaaaaat ttaacgcgaa   4320
ttttaacaaa atattaacgt ttacaattta aatatttgct tatacaatct tcctgttttt   4380
ggggcttttc tgattatcaa ccggggtaca tatgattgac atgctagttt tacgattacc   4440
gttcatcgat tctcttgttt gctccagact ctcaggcaat gacctgatag cctttgtaga   4500
gacctctcaa aaatagctac cctctccggc atgaatttat cagctagaac ggttgaatat   4560
catattgatg gtgatttgac tgtctccggc ctttctcacc cgtttgaatc tttacctaca   4620
cattactcag gcattgcatt taaaatatat gagggttcta aaaattttta tccttgcgtt   4680
gaaataaagg cttctcccgc aaaagtatta cagggtcata atgtttttgg tacaaccgat   4740
ttagctttat gctctgaggc tttattgctt aattttgcta attctttgcc ttgcctgtat   4800
gatttattgg atgttggaat cgcctgatgc ggtattttct ccttacgcat ctgtgcggta   4860
tttcacaccg catatggtgc actctcagta caatctgctc tgatgccgca tagttaagcc   4920
agccccgaca cccgccaaca cccgctgacg cgccctgacg ggcttgtctg ctcccggcat   4980
ccgcttacag acaagctgtg accgtctccg ggagctgcat gtgtcagagg ttttcaccgt   5040
catcaccgaa acgcgcgaga cgaaagggcc tcgtgatacg cctattttta taggttaatg   5100
tcatgataat aatggtttct tagacgtcag gtggcacttt tcggggaaat gtgcgcggaa   5160
cccctatttg tttatttttc taaatacatt caaatatgta tccgctcatg agacaataac   5220
cctgataaat gcttcaataa tattgaaaaa ggaagagtat gagtattcaa catttccgtg   5280
```

tcgcccttat tccctttttt gcggcatttt gccttcctgt ttttgctcac ccagaaacgc 5340
tggtgaaagt aaaagatgct gaagatcagt tgggtgcacg agtgggttac atcgaactgg 5400
atctcaacag cggtaagatc cttgagagtt ttcgccccga agaacgtttt ccaatgatga 5460
gcacttttaa agttctgcta tgtggcgcgg tattatcccg tattgacgcc gggcaagagc 5520
aactcggtcg ccgcatacac tattctcaga atgacttggt tgagtactca ccagtcacag 5580
aaaagcatct tacggatggc atgacagtaa gagaattatg cagtgctgcc ataaccatga 5640
gtgataacac tgcggccaac ttacttctga caacgatcgg aggaccgaag gagctaaccg 5700
cttttttgca caacatgggg gatcatgtaa ctcgccttga tcgttgggaa ccggagctga 5760
atgaagccat accaaacgac gagcgtgaca ccacgatgcc tgtagcaatg gcaacaacgt 5820
tgcgcaaact attaactggc gaactactta ctctagcttc ccggcaacaa ttaatagact 5880
ggatggaggc ggataaagtt gcaggaccac ttctgcgctc ggcccttccg gctggctggt 5940
ttattgctga taaatctgga gccggtgagc gtgggtctcg cggtatcatt gcagcactgg 6000
ggccagatgg taagccctcc cgtatcgtag ttatctacac gacggggagt caggcaacta 6060
tggatgaacg aaatagacag atcgctgaga taggtgcctc actgattaag cattggtaac 6120
tgtcagacca agtttactca tatatacttt agattgattt aaaacttcat ttttaattta 6180
aaaggatcta ggtgaagatc ctttttgata atctcatgac caaaatccct taacgtgagt 6240
tttcgttcca ctgagcgtca gaccccgtag aaaagatcaa aggatcttct tgagatcctt 6300
tttttctgcg cgtaatctgc tgcttgcaaa caaaaaaacc accgctacca gcggtggttt 6360
gtttgccgga tcaagagcta ccaactcttt ttccgaaggt aactggcttc agcagagcgc 6420
agataccaaa tactgtcctt ctagtgtagc cgtagttagg ccaccacttc aagaactctg 6480
tagcaccgcc tacatacctc gctctgctaa tcctgttacc agtggctgct gccagtggcg 6540
ataagtcgtg tcttaccggg ttggactcaa gacgatagtt accggataag gcgcagcggt 6600
cgggctgaac ggggggttcg tgcacacagc ccagcttgga gcgaacgacc tacaccgaac 6660
tgagatacct acagcgtgag ctatgagaaa gcgccacgct tcccgaaggg agaaaggcgg 6720
acaggtatcc ggtaagcggc agggtcggaa caggagagcg cacgagggag cttccagggg 6780
gaaacgcctg gtatctttat agtcctgtcg ggtttcgcca cctctgactt gagcgtcgat 6840
ttttgtgatg ctcgtcaggg gggcggagcc tatggaaaaa cgccagcaac gcggcctttt 6900
tacggttcct ggccttttgc tggccttttg ctcacatgtt ctttcctgcg ttatcccctg 6960
attctgtgga taaccgtatt accgcctttg agtgagctga taccgctcgc cgcagccgaa 7020
cgaccgagcg cagcgagtca gtgagcgagg aagcggaaga gcgcccaata cgcaaaccgc 7080
ctctccccgc gcgttggccg attcattaat g 7111

<210> SEQ ID NO 49
<211> LENGTH: 8293
<212> TYPE: DNA
<213> ORGANISM: Artificial
<220> FEATURE:
<223> OTHER INFORMATION: AAV donor template

<400> SEQUENCE: 49
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgt atacatacat acctgaatat ggaatcaaat 180

-continued

```
atttttctaa gatgaaacag tcatgattta tttcaaatag gtacggataa gtagatattg    240
aggtaagcat taggtcttat attatgtaac actaatctat tactgcgctg aaactgtggc    300
tttatagaaa ttgttttcac tgcactattg agaaattaag agataatggc aaaagtcaca    360
aagagtatat tcaaaaagaa gtatagcact ttttccttag aaaccactgc taactgaaag    420
agactaagat ttgtcccgtc aaaaatcctg gacctatgcc taaaacacat ttcacaatcc    480
ctgaactttt caaaaattgg tacatgcttt agctttaaac tacaggcctc actggagcta    540
gagacaagaa ggtaaaaaac ggctgacaaa agaagtcctg gtatcctcta tgatgggaga    600
aggaaactag ctaaagggaa gaataaatta gagaaaaact ggaatgactg aatcggaaca    660
aggcaaaggc tataaaaaaa attaagcagc agtatcctct tgggggcccc ttccccacac    720
tatctcaatg caaatatctg tctgaaacgg tccctggcta aactccaccc atgggttggc    780
cagccttgcc ttgacgctag cgtaaataca cttgcaaagg aggatgtttt tagtagcaat    840
ttgtactgat ggtatggggc caagagatat atcttagagg gagggctgag ggtttgaagt    900
ccaactccta agccagtgcc agaagagcca aggacaggta cggctgtcat cacttagacc    960
tcaccctgtg gagccacacc ctagggttgg ccaatctact cccaggagca gggagggcag   1020
gagccagggc tgggcataaa agtcagggca gagccatcta ttgcttacat ttgcttctga   1080
cacaactgtg ttcactagca acctcaaaca gacaccatgg tgcacctgac tcctgaggag   1140
aagtctgccg ttactgccct gtggggcaag gtgaacgtgg atgaagttgg tggtgaggcc   1200
ctgggcaggt tggtatcaag gttacaagac aggtttaagg agaccaatag aaactgggca   1260
tgtggagaca gagaagactc ttgggtttct gataggcact gactctctct gcctattggt   1320
ctattttccc acccttaggc tgctggtggt ctacccttgg acccagaggt tctttgagtc   1380
ctttggggat ctgtccactc ctgatgctgt tatgggcaac cctaaggtga aggctcatgg   1440
caagaaagtg ctcggtgcct ttagtgatgg cctggctcac ctggacaacc tcaagggcac   1500
ctttgcccag ctgagtgagc tgcactgtga caagctgcac gtggatcctg agaacttcag   1560
ggtgagtcta tgggaccctt gatgttttct ttccccttct tttctatggt taagttcatg   1620
tcataggaag gggagaagta acagggtaca catattgacc aaatcagggt aattttgcat   1680
ttgtaatttt aaaaaatgct ttcttctttt aatatacttt tttgtttatc ttatttctaa   1740
tactttccct aatctctttc tttcagggca ataatgatac aatgtatcat gcctctttgc   1800
accattctaa agaataacag tgataatttc tgggttaagg caatagcaat atttctgcat   1860
ataaatattt ctgcatataa attgtaactg atgtaagagg tttcatattg ctaatagcag   1920
ctacaatcca gctaccattc tgcttttatt ttatggttgg gataaggctg gattattctg   1980
agtccaagct aggccctttt gctaatcatg ttcatacctc ttatcttcct cccacagctc   2040
ctgggcaacg tgctggtctg tgtgctggcc catcactttg gcaaagaatt caccccacca   2100
gtgcaggctg cctatcagaa agtggtggct ggtgtggcta atgccctggc ccacaagtat   2160
cactaagctc gctttcttgc tgtccaattt ctattaaagg ttcctttgtt ccctaagtcc   2220
aactactaaa ctgggggata ttatgaaggg ccttgagcat ctggattctg cctaataaaa   2280
aacatttatt ttcattgcaa tgatgtattt aaattatttc tgaatatttt actaaaaagg   2340
gaatgtggga ggttgcagtg ctagtctccc ggaactatca ctctttcaca gtctgctttg   2400
gaaggactgg gcttagtatg aaaagttagg actgagaaga atttgaaagg gggctttttg   2460
tagcttgata ttcactactg tcttattacc ctatcatagg cccaccccaa atggaagtcc   2520
cattcttcct caggatgttt aagattagca ttcaggaaga gatcagaggt ctgctggctc   2580
```

-continued ccttatcatg tcccttatgg tgcttctggc tctgcaccgc ggccacgggg ttggggttgc 2640
gccttttcca aggcagccct gggtttgcgc agggacgcgg ctgctctggg cgtggttccg 2700
ggaaacgcag cggcgccgac cctgggtctc gcacattctt cacgtccgtt cgcagcgtca 2760
cccggatctt cgccgctacc cttgtgggcc ccccggcgac gcttcctgct ccgcccctaa 2820
gtcgggaagg ttccttgcgg ttcgcggcgt gccggacgtg acaaacggaa gccgcacgtc 2880
tcactagtac cctcgcagac ggacagcgcc agggagcaat ggcagcgcgc cgaccgcgat 2940
gggctgtggc caatagcggc tgctcagcgg ggcgcgccga gagcagcggc cgggaagggg 3000
cggtgcggga ggcggggtgt ggggcggtag tgtgggccct gttcctgccc gcgcggtgtt 3060
ccgcattctg caagcctccg gagcgcacgt cggcagtcgg ctccctcgtt gaccgaatca 3120
ccgacctctc tccccagcgg ccgcgccgcc accatggaca aggattgtga aatgaaacgc 3180
accacactgg acagcccttt ggggaagctg gagctgtctg gttgtgagca gggtctgcac 3240
gaaataaagc tcctgggcaa ggggacgtct gcagctgatg ccgtggaggt cccagccccc 3300
gctgcggttc tcggaggtcc ggagcccctg atgcagtgca cagcctggct gaatgcctat 3360
ttccaccagc ccgaggctat cgaagagttc cccgtgccgg ctcttcacca tcccgttttc 3420
cagcaagagt cgttcaccag acaggtgtta tggaagctgc tgaaggttgt gaaattcgga 3480
gaagtgattt cttaccagca attagcagcc ctggcaggca accccaaagc cgcgcgagca 3540
gtgggaggag caatgagagg caatcctgtc aaaatcctca tcccgtgcca cagagtggtc 3600
tgcagcagcg gagccgtggg caactactcc ggaggactgg ccgtgaagga atggcttctg 3660
gcccatgaag gccaccggtt ggggaagcca ggcttgggag ggagctcagg tctggcaggg 3720
gcctggctca agggagcggg agctacctcg ggctccccgc ctgctggccg aaactaagct 3780
ttatttgtga aatttgtgat gctattgctt tatttgtaac cattataagc tgcaataaac 3840
aagttaacaa caacaattgc attcatttta tgtttcaggt tcagggggag atgtgggagg 3900 tttttaaag ccctgcaggc aatagccttg acaaggcaaa cttgaccaat agtcttagag 3960
tatccagtga ggccaggggc cggcggctgg ctagggatga agaataaaag gaagcaccct 4020
tcagcagttc cacacactcg cttctggaac gtctgaggtt atcaataagc tcctagtcca 4080
gacgccatgg gtcatttcac agaggaggac aaggctacta tcacaagcct gtggggcaag 4140
gtgaatgtgg aagatgctgg aggagaaacc ctgggaaggt aggctctggt gaccaggaca 4200
agggagggaa ggaaggaccc tgtgcctggc aaaagtccag gtcgcttctc aggatttgtg 4260
gcaccttctg actgtcaaac tgttcttgtc aatctcacag gctcctggtt gtctacccat 4320
ggacccagag gttctttgac agctttggca acctgtcctc tgcctctgcc atcatgggca 4380
accccaaagt caaggcacat ggcaagaagg tgctgacttc cttgggagat gccacaaagc 4440
acctggatga tctcaagggc acctttgccc agctgagtga actgcactgt gacaagctgc 4500
atgtggatcc tgagaacttc aaggtgagtc caggagatgt ttcagccctg ttgcctttag 4560
tctcgaggcg tcgacaggaa cccctagtga tggagttggc cactccctct ctgcgcgctc 4620
gctcgctcac tgaggccggg cgaccaaagg tcgcccgacg cccgggcttt gcccgggcgg 4680
cctcagtgag cgagcgagcg cgcagctggc gtaatagcga agaggcccgc accgatcgcc 4740
cttcccaaca gttgcgcagc ctgaatggcg aatggcgatt ccgttgcaat ggctggcggt 4800
aatattgttc tggatattac cagcaaggcc gatagtttga gttcttctac tcaggcaagt 4860
gatgttatta ctaatcaaag aagtattgcg acaacggtta atttgcgtga tggacagact 4920

```
cttttactcg gtggcctcac tgattataaa aacacttctc aggattctgg cgtaccgttc   4980
ctgtctaaaa tccctttaat cggcctcctg tttagctccc gctctgattc taacgaggaa   5040
agcacgttat acgtgctcgt caaagcaacc atagtacgcg ccctgtagcg gcgcattaag   5100
cgcggcgggt gtggtggtta cgcgcagcgt gaccgctaca cttgccagcg ccctagcgcc   5160
cgctcctttc gctttcttcc cttcctttct cgccacgttc gccggctttc cccgtcaagc   5220
tctaaatcgg gggctccctt tagggttccg atttagtgct ttacggcacc tcgaccccaa   5280
aaaacttgat tagggtgatg gttcacgtag tgggccatcg ccctgataga cggtttttcg   5340
ccctttgacg ttggagtcca cgttctttaa tagtggactc ttgttccaaa ctggaacaac   5400
actcaaccct atctcggtct attcttttga tttataaggg attttgccga tttcggccta   5460
ttggttaaaa aatgagctga tttaacaaaa atttaacgcg aattttaaca aaatattaac   5520
gtttacaatt taaatatttg cttatacaat cttcctgttt ttggggcttt tctgattatc   5580
aaccggggta catatgattg acatgctagt tttacgatta ccgttcatcg attctcttgt   5640
ttgctccaga ctctcaggca atgacctgat agcctttgta gagacctctc aaaaatagct   5700
accctctccg gcatgaattt atcagctaga acggttgaat atcatattga tggtgatttg   5760
actgtctccg gcctttctca cccgtttgaa tctttaccta cacattactc aggcattgca   5820
tttaaaatat atgagggttc taaaaatttt tatccttgcg ttgaaataaa ggcttctccc   5880
gcaaaagtat tacagggtca taatgttttt ggtacaaccg atttagcttt atgctctgag   5940
gctttattgc ttaattttgc taattctttg ccttgcctgt atgatttatt ggatgttgga   6000
atcgcctgat gcggtatttt ctccttacgc atctgtgcgg tatttcacac cgcatatggt   6060
gcactctcag tacaatctgc tctgatgccg catagttaag ccagccccga cacccgccaa   6120
cacccgctga cgcgccctga cgggcttgtc tgctcccggc atccgcttac agacaagctg   6180
tgaccgtctc cgggagctgc atgtgtcaga ggttttcacc gtcatcaccg aaacgcgcga   6240
gacgaaaggg cctcgtgata cgcctatttt tataggttaa tgtcatgata ataatggttt   6300
cttagacgtc aggtggcact tttcggggaa atgtgcgcgg aacccctatt tgtttatttt   6360
tctaaataca ttcaaatatg tatccgctca tgagacaata accctgataa atgcttcaat   6420
aatattgaaa aaggaagagt atgagtattc aacatttccg tgtcgccctt attccctttt   6480
ttgcggcatt ttgccttcct gtttttgctc acccagaaac gctggtgaaa gtaaaagatg   6540
ctgaagatca gttgggtgca cgagtgggtt acatcgaact ggatctcaac agcggtaaga   6600
tccttgagag ttttcgcccc gaagaacgtt ttccaatgat gagcactttt aaagttctgc   6660
tatgtggcgc ggtattatcc cgtattgacg ccgggcaaga gcaactcggt cgccgcatac   6720
actattctca gaatgacttg gttgagtact caccagtcac agaaaagcat cttacggatg   6780
gcatgacagt aagagaatta tgcagtgctg ccataaccat gagtgataac actgcggcca   6840
acttacttct gacaacgatc ggaggaccga aggagctaac cgcttttttg cacaacatgg   6900
gggatcatgt aactcgcctt gatcgttggg aaccggagct gaatgaagcc ataccaaacg   6960
acgagcgtga caccacgatg cctgtagcaa tggcaacaac gttgcgcaaa ctattaactg   7020
gcgaactact tactctagct tcccggcaac aattaataga ctggatggag gcggataaag   7080
ttgcaggacc acttctgcgc tcggcccttc cggctggctg gtttattgct gataaatctg   7140
gagccggtga gcgtgggtct cgcggtatca ttgcagcact ggggccagat ggtaagccct   7200
cccgtatcgt agttatctac acgacgggga gtcaggcaac tatggatgaa cgaaatagac   7260
agatcgctga gataggtgcc tcactgatta agcattggta actgtcagac caagtttact   7320
```

```
catatatact ttagattgat ttaaaacttc atttttaatt taaaaggatc taggtgaaga   7380

tcctttttga taatctcatg accaaaatcc cttaacgtga gttttcgttc cactgagcgt   7440

cagaccccgt agaaaagatc aaaggatctt cttgagatcc tttttttctg cgcgtaatct   7500

gctgcttgca aacaaaaaaa ccaccgctac cagcggtggt ttgtttgccg gatcaagagc   7560

taccaactct ttttccgaag gtaactggct tcagcagagc gcagatacca aatactgtcc   7620

ttctagtgta gccgtagtta ggccaccact tcaagaactc tgtagcaccg cctacatacc   7680

tcgctctgct aatcctgtta ccagtggctg ctgccagtgg cgataagtcg tgtcttaccg   7740

ggttggactc aagacgatag ttaccggata aggcgcagcg gtcgggctga acggggggtt   7800

cgtgcacaca gcccagcttg gagcgaacga cctacaccga actgagatac ctacagcgtg   7860

agctatgaga aagcgccacg cttcccgaag ggagaaaggc ggacaggtat ccggtaagcg   7920

gcagggtcgg aacaggagag cgcacgaggg agcttccagg gggaaacgcc tggtatcttt   7980

atagtcctgt cgggtttcgc cacctctgac ttgagcgtcg atttttgtga tgctcgtcag   8040

gggggcggag cctatggaaa aacgccagca acgcggcctt tttacggttc ctggcctttt   8100

gctggccttt tgctcacatg ttctttcctg cgttatcccc tgattctgtg gataaccgta   8160

ttaccgcctt tgagtgagct gataccgctc gccgcagccg aacgaccgag cgcagcgagt   8220

cagtgagcga ggaagcggaa gagcgcccaa tacgcaaacc gcctctcccc gcgcgttggc   8280

cgattcatta atg                                                      8293
```

<210> SEQ ID NO 50
<211> LENGTH: 8290
<212> TYPE: DNA
<213> ORGANISM: Artificial
<220> FEATURE:
<223> OTHER INFORMATION: AAV donor template

<400> SEQUENCE: 50

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt cctacgcgta gatctgtggc tttatagaaa ttgttttcac tgcactattg    180

agaaattaag agataatggc aaaagtcaca aagagtatat tcaaaaagaa gtatagcact    240

ttttccttag aaaccactgc taactgaaag agactaagat ttgtcccgtc aaaaatcctg    300

gacctatgcc taaaacacat ttcacaatcc ctgaactttt caaaaattgg tacatgcttt    360

agctttaaac tacaggcctc actggagcta gagacaagaa ggtaaaaaac ggctgacaaa    420

agaagtcctg gtatcctcta tgatgggaga aggaaactag ctaaagggaa gaataaatta    480

gagaaaaact ggaatgactg aatcggaaca aggcaaaggc tataaaaaaa attaagcagc    540

agtatcctct tgggggcccc ttccccacac tatctcaatg caaatatctg tctgaaacgg    600

tccctggcta aactccaccc atgggttggc cagccttgcc ttgacgctag cgtaaataca    660

cttgcaaagg aggatgtttt tagtagcaat ttgtactgat ggtatggggc caagagatat    720

atcttagagg gagggctgag ggtttgaagt ccaactccta agccagtgcc agaagagcca    780

aggacaggta cggctgtcat cacttagacc tcaccctgtg gagccacacc ctagggttgg    840

ccaatctact cccaggagca gggagggcag gagccagggc tgggcataaa agtcagggca    900

gagccatcta ttgcttacat ttgcttctga cacaactgtg ttcactagca acctcaaaca    960

gacaccatgg tgcacctgac tcctgaggag aagtctgccg ttactgccct gtggggcaag   1020
```

```
gtgaacgtgg atgaagttgg tggtgaggcc ctgggcaggt tggtatcaag gttacaagac   1080
aggtttaagg agaccaatag aaactgggca tgtggagaca gagaagactc ttgggtttct   1140
gataggcact gactctctct gcctattggt ctattttccc acccttaggc tgctggtggt   1200
ctacccttgg acccagaggt tctttgagtc ctttggggat ctgtccactc ctgatgctgt   1260
tatgggcaac cctaaggtga aggctcatgg caagaaagtg ctcggtgcct ttagtgatgg   1320
cctggctcac ctggacaacc tcaagggcac ctttgcccag ctgagtgagc tgcactgtga   1380
caagctgcac gtggatcctg agaacttcag ggtgagtcta tgggaccctt gatgttttct   1440
ttccccttct tttctatggt taagttcatg tcataggaag gggagaagta acagggtaca   1500
catattgacc aaatcagggt aattttgcat ttgtaatttt aaaaaatgct ttcttctttt   1560
aatatacttt tttgtttatc ttatttctaa tactttccct aatctctttc tttcagggca   1620
ataatgatac aatgtatcat gcctctttgc accattctaa agaataacag tgataatttc   1680
tgggttaagg caatagcaat atttctgcat ataaatattt ctgcatataa attgtaactg   1740
atgtaagagg tttcatattg ctaatagcag ctacaatcca gctaccattc tgcttttatt   1800
ttatggttgg gataaggctg gattattctg agtccaagct aggccctttt gctaatcatg   1860
ttcatacctc ttatcttcct cccacagctc ctgggcaacg tgctggtctg tgtgctggcc   1920
catcactttg gcaaagaatt caccccacca gtgcaggctg cctatcagaa agtggtggct   1980
ggtgtggcta atgccctggc ccacaagtat cactaagctc gctttcttgc tgtccaattt   2040
ctattaaagg ttcctttgtt ccctaagtcc aactactaaa ctgggggata ttatgaaggg   2100
ccttgagcat ctggattctg cctaataaaa aacatttatt ttcattgcaa tgatgtattt   2160
aaattatttc tgaatatttt actaaaaagg gaatgtggga ggttgcagtg ctagtctccc   2220
ggaactatca ctctttcaca gtctgctttg gaaggactgg gcttagtatg aaaagttagg   2280
actgagaaga atttgaaagg gggctttttg tagcttgata ttcactactg tcttattacc   2340
ctatcatagg cccaccccaa atggaagtcc cattcttcct caggatgttt aagattagca   2400
ttcaggaaga gatcagaggt ctgctggctc ccttatcatg tcccttatgg tgcttctggc   2460
tctgcaccgc ggccacgggg ttggggttgc gccttttcca aggcagccct gggtttgcgc   2520
agggacgcgg ctgctctggg cgtggttccg ggaaacgcag cggcgccgac cctgggtctc   2580
gcacattctt cacgtccgtt cgcagcgtca cccggatctt cgccgctacc cttgtgggcc   2640
ccccggcgac gcttcctgct ccgcccctaa gtcgggaagg ttccttgcgg ttcgcggcgt   2700
gccggacgtg acaaacggaa gccgcacgtc tcactagtac cctcgcagac ggacagcgcc   2760
agggagcaat ggcagcgcgc cgaccgcgat gggctgtggc caatagcggc tgctcagcgg   2820
ggcgcgccga gagcagcggc cgggaagggg cggtgcggga ggcggggtgt ggggcggtag   2880
tgtgggccct gttcctgccc gcgcggtgtt ccgcattctg caagcctccg gagcgcacgt   2940
cggcagtcgg ctccctcgtt gaccgaatca ccgacctctc tccccagcgg ccgcgccgcc   3000
accatggaca aggattgtga aatgaaacgc accacactgg acagcccttt ggggaagctg   3060
gagctgtctg gttgtgagca gggtctgcac gaaataaagc tcctgggcaa ggggacgtct   3120
gcagctgatg ccgtggaggt cccagccccc gctgcggttc tcggaggtcc ggagcccctg   3180
atgcagtgca cagcctggct gaatgcctat ttccaccagc ccgaggctat cgaagagttc   3240
cccgtgccgg ctcttcacca tcccgttttc cagcaagagt cgttcaccag acaggtgtta   3300
tggaagctgc tgaaggttgt gaaattcgga gaagtgattt cttaccagca attagcagcc   3360
ctggcaggca accccaaagc cgcgcgagca gtgggaggag caatgagagg caatcctgtc   3420
```

-continued

```
aaaatcctca tcccgtgcca cagagtggtc tgcagcagcg gagccgtggg caactactcc   3480
ggaggactgg ccgtgaagga atggcttctg gcccatgaag gccaccggtt ggggaagcca   3540
ggcttgggag ggagctcagg tctggcaggg gcctggctca agggagcggg agctacctcg   3600
ggctccccgc ctgctggccg aaactaagat aatcaacctc tggattacaa aatttgtgaa   3660
agattgactg gtattcttaa ctatgttgct ccttttacgc tatgtggata cgctgcttta   3720
atgcctttgt atcatgctat tgcttcccgt atggctttca ttttctcctc cttgtataaa   3780
tcctggttag ttcttgccac ggcggaactc atcgccgcct gccttgcccg ctgctggaca   3840
ggggctcggc tgttgggcac tgacaattcc gtggtgttta tttgtgaaat ttgtgatgct   3900
attgctttat ttgtaaccat tctagcttta tttgtgaaat ttgtgatgct attgctttat   3960
ttgtaaccat tataagctgc aataaacaag ttaacaacaa caattgcatt cattttatgt   4020
ttcaggttca gggggagatg tgggaggttt tttaaagccc tgcaggcaat agccttgaca   4080
aggcaaactt gaccaatagt cttagagtat ccagtgaggc caggggccgg cggctggcta   4140
gggatgaaga ataaaaggaa gcacccttca gcagttccac acactcgctt ctggaacgtc   4200
tgaggttatc aataagctcc tagtccagac gccatgggtc atttcacaga ggaggacaag   4260
gctactatca caagcctgtg gggcaaggtg aatgtggaag atgctggagg agaaaccctg   4320
ggaaggtagg ctctggtgac caggacaagg gagggaagga aggaccctgt gcctggcaaa   4380
agtccaggtc gcttctcagg atttgtggca ccttctgact gtcaaactgt tcttgtcaat   4440
ctcacaggct cctggttgtc tacccatgga cccagaggtt ctttgacagc tttggcaacc   4500
tgtcctctgc ctctgccatc atgggcaacc ccaaagtcaa ggcacatggc aagaaggtgc   4560
tgacttgtcg acaggaaccc ctagtgatgg agttggccac tccctctctg cgcgctcgct   4620
cgctcactga ggccgggcga ccaaaggtcg cccgacgccc gggctttgcc cgggcggcct   4680
cagtgagcga gcgagcgcgc agctggcgta atagcgaaga ggcccgcacc gatcgccctt   4740
cccaacagtt gcgcagcctg aatggcgaat ggcgattccg ttgcaatggc tggcggtaat   4800
attgttctgg atattaccag caaggccgat agtttgagtt cttctactca ggcaagtgat   4860
gttattacta atcaaagaag tattgcgaca acggttaatt tgcgtgatgg acagactctt   4920
ttactcggtg gcctcactga ttataaaaac acttctcagg attctggcgt accgttcctg   4980
tctaaaatcc ctttaatcgg cctcctgttt agctcccgct ctgattctaa cgaggaaagc   5040
acgttatacg tgctcgtcaa agcaaccata gtacgcgccc tgtagcggcg cattaagcgc   5100
ggcgggtgtg gtggttacgc gcagcgtgac cgctacactt gccagcgccc tagcgcccgc   5160
tcctttcgct ttcttccctt cctttctcgc cacgttcgcc ggctttcccc gtcaagctct   5220
aaatcggggg ctccctttag ggttccgatt tagtgcttta cggcacctcg accccaaaaa   5280
acttgattag ggtgatggtt cacgtagtgg gccatcgccc tgatagacgg tttttcgccc   5340
tttgacgttg gagtccacgt tctttaatag tggactcttg ttccaaactg gaacaacact   5400
caaccctatc tcggtctatt cttttgattt ataagggatt ttgccgattt cggcctattg   5460
gttaaaaaat gagctgattt aacaaaaatt taacgcgaat tttaacaaaa tattaacgtt   5520
tacaatttaa atatttgctt atacaatctt cctgtttttg gggcttttct gattatcaac   5580
cggggtacat atgattgaca tgctagtttt acgattaccg ttcatcgatt ctcttgtttg   5640
ctccagactc tcaggcaatg acctgatagc ctttgtagag acctctcaaa aatagctacc   5700
ctctccggca tgaatttatc agctagaacg gttgaatatc atattgatgg tgatttgact   5760
```

-continued

```
gtctccggcc tttctcaccc gtttgaatct ttacctacac attactcagg cattgcattt   5820
aaaatatatg agggttctaa aaatttttat ccttgcgttg aaataaaggc ttctcccgca   5880
aaagtattac agggtcataa tgtttttggt acaaccgatt tagctttatg ctctgaggct   5940
ttattgctta attttgctaa ttctttgcct tgcctgtatg atttattgga tgttggaatc   6000
gcctgatgcg gtattttctc cttacgcatc tgtgcggtat ttcacaccgc atatggtgca   6060
ctctcagtac aatctgctct gatgccgcat agttaagcca gccccgacac ccgccaacac   6120
ccgctgacgc gccctgacgg gcttgtctgc tcccggcatc cgcttacaga caagctgtga   6180
ccgtctccgg gagctgcatg tgtcagaggt tttcaccgtc atcaccgaaa cgcgcgagac   6240
gaaagggcct cgtgatacgc ctatttttat aggttaatgt catgataata atggtttctt   6300
agacgtcagg tggcactttt cggggaaatg tgcgcggaac ccctatttgt ttatttttct   6360
aaatacattc aaatatgtat ccgctcatga gacaataacc ctgataaatg cttcaataat   6420
attgaaaaag gaagagtatg agtattcaac atttccgtgt cgcccttatt cccttttttg   6480
cggcattttg ccttcctgtt tttgctcacc cagaaacgct ggtgaaagta aaagatgctg   6540
aagatcagtt gggtgcacga gtgggttaca tcgaactgga tctcaacagc ggtaagatcc   6600
ttgagagttt tcgccccgaa gaacgttttc caatgatgag cacttttaaa gttctgctat   6660
gtggcgcggt attatcccgt attgacgccg ggcaagagca actcggtcgc cgcatacact   6720
attctcagaa tgacttggtt gagtactcac cagtcacaga aaagcatctt acggatggca   6780
tgacagtaag agaattatgc agtgctgcca taaccatgag tgataacact gcggccaact   6840
tacttctgac aacgatcgga ggaccgaagg agctaaccgc ttttttgcac aacatggggg   6900
atcatgtaac tcgccttgat cgttgggaac cggagctgaa tgaagccata ccaaacgacg   6960
agcgtgacac cacgatgcct gtagcaatgg caacaacgtt gcgcaaacta ttaactggcg   7020
aactacttac tctagcttcc cggcaacaat taatagactg gatggaggcg gataaagttg   7080
caggaccact tctgcgctcg gcccttccgg ctggctggtt tattgctgat aaatctggag   7140
ccggtgagcg tgggtctcgc ggtatcattg cagcactggg gccagatggt aagccctccc   7200
gtatcgtagt tatctacacg acggggagtc aggcaactat ggatgaacga aatagacaga   7260
tcgctgagat aggtgcctca ctgattaagc attggtaact gtcagaccaa gtttactcat   7320
atatacttta gattgattta aaacttcatt tttaatttaa aaggatctag gtgaagatcc   7380
tttttgataa tctcatgacc aaaatccctt aacgtgagtt ttcgttccac tgagcgtcag   7440
accccgtaga aaagatcaaa ggatcttctt gagatccttt ttttctgcgc gtaatctgct   7500
gcttgcaaac aaaaaaacca ccgctaccag cggtggtttg tttgccggat caagagctac   7560
caactctttt tccgaaggta actggcttca gcagagcgca gataccaaat actgtccttc   7620
tagtgtagcc gtagttaggc caccacttca agaactctgt agcaccgcct acatacctcg   7680
ctctgctaat cctgttacca gtggctgctg ccagtggcga taagtcgtgt cttaccgggt   7740
tggactcaag acgatagtta ccggataagg cgcagcggtc gggctgaacg gggggttcgt   7800
gcacacagcc cagcttggag cgaacgacct acaccgaact gagataccta cagcgtgagc   7860
tatgagaaag cgccacgctt cccgaaggga gaaaggcgga caggtatccg gtaagcggca   7920
gggtcggaac aggagagcgc acgagggagc ttccaggggg aaacgcctgg tatctttata   7980
gtcctgtcgg gtttcgccac ctctgacttg agcgtcgatt tttgtgatgc tcgtcagggg   8040
ggcggagcct atggaaaaac gccagcaacg cggccttttt acggttcctg gccttttgct   8100
ggccttttgc tcacatgttc tttcctgcgt tatcccctga ttctgtggat aaccgtatta   8160
```

ccgcctttga gtgagctgat accgctcgcc gcagccgaac gaccgagcgc agcgagtcag 8220
tgagcgagga agcggaagag cgcccaatac gcaaaccgcc tctccccgcg cgttggccga 8280
ttcattaatg 8290

<210> SEQ ID NO 51
<211> LENGTH: 8222
<212> TYPE: DNA
<213> ORGANISM: Artificial
<220> FEATURE:
<223> OTHER INFORMATION: AAV donor template

<400> SEQUENCE: 51
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgt atacatacat acctgaatat ggaatcaaat 180
atttttctaa gatgaaacag tcatgattta tttcaaatag gtacggataa gtagatattg 240
aggtaagcat taggtcttat attatgtaac actaatctat tactgcgctg aaactgtggc 300
tttatagaaa ttgttttcac tgcactattg agaaattaag agataatggc aaaagtcaca 360
aagagtatat tcaaaaagaa gtatagcact ttttccttag aaaccactgc taactgaaag 420
agactaagat ttgtcccgtc aaaaatcctg gacctatgcc taaaacacat ttcacaatcc 480
ctgaactttt caaaaattgg tacatgcttt agctttaaac tacaggcctc actggagcta 540
gagacaagaa ggtaaaaaac ggctgacaaa agaagtcctg gtatcctcta tgatgggaga 600
aggaaactag ctaaagggaa gaataaatta gagaaaaact ggaatgactg aatcggaaca 660
aggcaaaggc tataaaaaaa attaagcagc agtatcctct tgggggcccc ttccccacac 720
tatctcaatg caaatatctg tctgaaacgg tccctggcta aactccaccc atgggttggc 780
cagccttgcc ttgacgctag cgtaaataca cttgcaaagg aggatgtttt tagtagcaat 840
ttgtactgat ggtatggggc caagagatat atcttagagg gagggctgag ggtttgaagt 900
ccaactccta agccagtgcc agaagagcca aggacaggta cggctgtcat cacttagacc 960
tcaccctgtg gagccacacc ctagggttgg ccaatctact cccaggagca gggagggcag 1020
gagccagggc tgggcataaa agtcagggca gagccatcta ttgcttacat ttgcttctga 1080
cacaactgtg ttcactagca acctcaaaca gacaccatgg tgcacctgac tcctgaggag 1140
aagtctgccg ttactgccct gtggggcaag gtgaacgtgg atgaagttgg tggtgaggcc 1200
ctgggcaggt tggtatcaag gttacaagac aggtttaagg agaccaatag aaactgggca 1260
tgtggagaca gagaagactc ttgggtttct gataggcact gactctctct gcctattggt 1320
ctattttccc acccttaggc tgctggtggt ctacccttgg acccagaggt tctttgagtc 1380
ctttggggat ctgtccactc ctgatgctgt tatgggcaac cctaaggtga aggctcatgg 1440
caagaaagtg ctcggtgcct ttagtgatgg cctggctcac ctggacaacc tcaagggcac 1500
ctttgcccag ctgagtgagc tgcactgtga caagctgcac gtggatcctg agaacttcag 1560
ggtgagtcta tgggaccctt gatgttttct ttccccttct tttctatggt taagttcatg 1620
tcataggaag gggagaagta acagggtaca catattgacc aaatcagggt aattttgcat 1680
ttgtaatttt aaaaaatgct ttcttctttt aatatacttt tttgtttatc ttatttctaa 1740
tactttccct aatctctttc tttcagggca ataatgatac aatgtatcat gcctctttgc 1800
accattctaa agaataacag tgataatttc tgggttaagg caatagcaat atttctgcat 1860

-continued ataaatattt ctgcatataa attgtaactg atgtaagagg tttcatattg ctaatagcag 1920
ctacaatcca gctaccattc tgcttttatt ttatggttgg gataaggctg gattattctg 1980
agtccaagct aggccctttt gctaatcatg ttcatacctc ttatcttcct cccacagctc 2040
ctgggcaacg tgctggtctg tgtgctggcc catcactttg gcaaagaatt caccccacca 2100
gtgcaggctg cctatcagaa agtggtggct ggtgtggcta atgccctggc ccacaagtat 2160
cactaagctc gctttcttgc tgtccaattt ctattaaagg ttcctttgtt ccctaagtcc 2220
aactactaaa ctgggggata ttatgaaggg ccttgagcat ctggattctg cctaataaaa 2280
aacatttatt ttcattgcaa tgatgtattt aaattatttc tgaatatttt actaaaaagg 2340
gaatgtggga ggttgcagtg ctagtctccc ggaactatca ctctttcaca gtctgctttg 2400
gaaggactgg gcttagtatg aaaagttagg actgagaaga atttgaaagg gggctttttg 2460
tagcttgata ttcactactg tcttattacc ctatcatagg cccaccccaa atggaagtcc 2520
cattcttcct caggatgttt aagattagca ttcaggaaga gatcagaggt ctgctggctc 2580
ccttatcatg tcccttatgg tgcttctggc tctgcaccgc gggaacagag aaacaggaga 2640
atatgggcca aacaggatat ctgtggtaag cagttcctgc cccggctcag ggccaagaac 2700
agttggaaca gcagaatatg ggccaaacag gatatctgtg gtaagcagtt cctgccccgg 2760
ctcagggcca agaacagatg gtccccagat gcggtcccgc cctcagcagt ttctagagaa 2820
ccatcagatg tttccagggt gccccaagga cctgaaatga ccctgtgcct tatttgaact 2880
aaccaatcag ttcgcttctc gcttctgttc gcgcgcttct gctccccgag ctctatataa 2940
gcagagctcg tttagtgaac cgtcagatcg cggccgcgcc gccaccatgg tgagcaaggg 3000
cgaggagctg ttcaccgggg tggtgcccat cctggtcgag ctggacggcg acgtaaacgg 3060
ccacaagttc agcgtgtccg gcgagggcga gggcgatgcc acctacggca agctgaccct 3120
gaagttcatc tgcaccaccg gcaagctgcc cgtgccctgg cccaccctcg tgaccaccct 3180
gacctacggc gtgcagtgct tcagccgcta ccccgaccac atgaagcagc acgacttctt 3240
caagtccgcc atgcccgaag gctacgtcca ggagcgcacc atcttcttca aggacgacgg 3300
caactacaag acccgcgccg aggtgaagtt cgagggcgac accctggtga accgcatcga 3360
gctgaagggc atcgacttca aggaggacgg caacatcctg gggcacaagc tggagtacaa 3420
ctacaacagc cacaacgtct atatcatggc cgacaagcag aagaacggca tcaaggtgaa 3480
cttcaagatc cgccacaaca tcgaggacgg cagcgtgcag ctcgccgacc actaccagca 3540
gaacaccccc atcggcgacg gccccgtgct gctgcccgac aaccactacc tgagcaccca 3600
gtccgccctg agcaaagacc ccaacgagaa gcgcgatcac atggtcctgc tggagttcgt 3660
gaccgccgcc gggatcactc tcggcatgga cgagctgtac aagtaagctt tatttgtgaa 3720
atttgtgatg ctattgcttt atttgtaacc attataagct gcaataaaca agttaacaac 3780
aacaattgca ttcattttat gtttcaggtt cagggggaga tgtgggaggt tttttaaagc 3840
cctgcaggca atagccttga caaggcaaac ttgaccaata gtcttagagt atccagtgag 3900
gccaggggcc ggcggctggc tagggatgaa gaataaaagg aagcaccctt cagcagttcc 3960
acacactcgc ttctggaacg tctgaggtta tcaataagct cctagtccag acgccatggg 4020
tcatttcaca gaggaggaca aggctactat cacaagcctg tggggcaagg tgaatgtgga 4080
agatgctgga ggagaaaccc tgggaaggta ggctctggtg accaggacaa gggagggaag 4140
gaaggaccct gtgcctggca aaagtccagg tcgcttctca ggatttgtgg caccttctga 4200
ctgtcaaact gttcttgtca atctcacagg ctcctggttg tctacccatg gacccagagg 4260

-continued ttctttgaca gctttggcaa cctgtcctct gcctctgcca tcatgggcaa ccccaaagtc 4320
aaggcacatg gcaagaaggt gctgacttcc ttgggagatg ccacaaagca cctggatgat 4380
ctcaagggca cctttgccca gctgagtgaa ctgcactgtg acaagctgca tgtggatcct 4440
gagaacttca aggtgagtcc aggagatgtt tcagccctgt tgcctttagt ctcgaggcgt 4500
cgacaggaac ccctagtgat ggagttggcc actccctctc tgcgcgctcg ctcgctcact 4560
gaggccgggc gaccaaaggt cgcccgacgc ccgggctttg cccgggcggc ctcagtgagc 4620
gagcgagcgc gcagctggcg taatagcgaa gaggcccgca ccgatcgccc ttcccaacag 4680
ttgcgcagcc tgaatggcga atggcgattc cgttgcaatg gctggcggta atattgttct 4740
ggatattacc agcaaggccg atagtttgag ttcttctact caggcaagtg atgttattac 4800
taatcaaaga agtattgcga caacggttaa tttgcgtgat ggacagactc ttttactcgg 4860
tggcctcact gattataaaa acacttctca ggattctggc gtaccgttcc tgtctaaaat 4920
ccctttaatc ggcctcctgt ttagctcccg ctctgattct aacgaggaaa gcacgttata 4980
cgtgctcgtc aaagcaacca tagtacgcgc cctgtagcgg cgcattaagc gcggcgggtg 5040
tggtggttac gcgcagcgtg accgctacac ttgccagcgc cctagcgccc gctcctttcg 5100
ctttcttccc ttcctttctc gccacgttcg ccggctttcc ccgtcaagct ctaaatcggg 5160
ggctcccttt agggttccga tttagtgctt tacggcacct cgaccccaaa aaacttgatt 5220
agggtgatgg ttcacgtagt gggccatcgc cctgatagac ggtttttcgc cctttgacgt 5280
tggagtccac gttctttaat agtggactct tgttccaaac tggaacaaca ctcaacccta 5340
tctcggtcta ttcttttgat ttataaggga ttttgccgat ttcggcctat tggttaaaaa 5400
atgagctgat ttaacaaaaa tttaacgcga attttaacaa aatattaacg tttacaattt 5460
aaatatttgc ttatacaatc ttcctgtttt tggggctttt ctgattatca accggggtac 5520
atatgattga catgctagtt ttacgattac cgttcatcga ttctcttgtt tgctccagac 5580
tctcaggcaa tgacctgata gcctttgtag agacctctca aaaatagcta ccctctccgg 5640
catgaattta tcagctagaa cggttgaata tcatattgat ggtgatttga ctgtctccgg 5700
cctttctcac ccgtttgaat ctttacctac acattactca ggcattgcat ttaaaatata 5760
tgagggttct aaaaattttt atccttgcgt tgaaataaag gcttctcccg caaaagtatt 5820
acagggtcat aatgtttttg gtacaaccga tttagcttta tgctctgagg ctttattgct 5880
taattttgct aattctttgc cttgcctgta tgatttattg gatgttggaa tcgcctgatg 5940
cggtattttc tccttacgca tctgtgcggt atttcacacc gcatatggtg cactctcagt 6000
acaatctgct ctgatgccgc atagttaagc cagccccgac acccgccaac acccgctgac 6060
gcgccctgac gggcttgtct gctcccggca tccgcttaca gacaagctgt gaccgtctcc 6120
gggagctgca tgtgtcagag gttttcaccg tcatcaccga aacgcgcgag acgaaagggc 6180
ctcgtgatac gcctattttt ataggttaat gtcatgataa taatggtttc ttagacgtca 6240
ggtggcactt ttcggggaaa tgtgcgcgga acccctattt gtttattttt ctaaatacat 6300
tcaaatatgt atccgctcat gagacaataa ccctgataaa tgcttcaata atattgaaaa 6360
aggaagagta tgagtattca acatttccgt gtcgccctta ttcccttttt tgcggcattt 6420
tgccttcctg tttttgctca cccagaaacg ctggtgaaag taaaagatgc tgaagatcag 6480
ttgggtgcac gagtgggtta catcgaactg gatctcaaca gcggtaagat ccttgagagt 6540
tttcgccccg aagaacgttt tccaatgatg agcactttta aagttctgct atgtggcgcg 6600
gtattatccc gtattgacgc cgggcaagag caactcggtc gccgcataca ctattctcag 6660
aatgacttgg ttgagtactc accagtcaca gaaaagcatc ttacggatgg catgacagta 6720
agagaattat gcagtgctgc cataaccatg agtgataaca ctgcggccaa cttacttctg 6780
acaacgatcg gaggaccgaa ggagctaacc gcttttttgc acaacatggg ggatcatgta 6840
actcgccttg atcgttggga accggagctg aatgaagcca taccaaacga cgagcgtgac 6900
accacgatgc ctgtagcaat ggcaacaacg ttgcgcaaac tattaactgg cgaactactt 6960
actctagctt cccggcaaca attaatagac tggatggagg cggataaagt tgcaggacca 7020
cttctgcgct cggcccttcc ggctggctgg tttattgctg ataaatctgg agccggtgag 7080
cgtgggtctc gcggtatcat tgcagcactg gggccagatg gtaagccctc ccgtatcgta 7140
gttatctaca cgacggggag tcaggcaact atggatgaac gaaatagaca gatcgctgag 7200
ataggtgcct cactgattaa gcattggtaa ctgtcagacc aagtttactc atatatactt 7260
tagattgatt taaaacttca tttttaattt aaaaggatct aggtgaagat cctttttgat 7320
aatctcatga ccaaaatccc ttaacgtgag ttttcgttcc actgagcgtc agaccccgta 7380
gaaaagatca aaggatcttc ttgagatcct ttttttctgc gcgtaatctg ctgcttgcaa 7440
acaaaaaaac caccgctacc agcggtggtt tgtttgccgg atcaagagct accaactctt 7500
tttccgaagg taactggctt cagcagagcg cagataccaa atactgtcct tctagtgtag 7560
ccgtagttag gccaccactt caagaactct gtagcaccgc ctacatacct cgctctgcta 7620
atcctgttac cagtggctgc tgccagtggc gataagtcgt gtcttaccgg gttggactca 7680
agacgatagt taccggataa ggcgcagcgg tcgggctgaa cggggggttc gtgcacacag 7740
cccagcttgg agcgaacgac ctacaccgaa ctgagatacc tacagcgtga gctatgagaa 7800
agcgccacgc ttcccgaagg gagaaaggcg gacaggtatc cggtaagcgg cagggtcgga 7860
acaggagagc gcacgaggga gcttccaggg ggaaacgcct ggtatcttta tagtcctgtc 7920
gggtttcgcc acctctgact tgagcgtcga tttttgtgat gctcgtcagg ggggcggagc 7980
ctatggaaaa acgccagcaa cgcggccttt ttacggttcc tggccttttg ctggcctttt 8040
gctcacatgt tctttcctgc gttatcccct gattctgtgg ataaccgtat taccgccttt 8100
gagtgagctg ataccgctcg ccgcagccga acgaccgagc gcagcgagtc agtgagcgag 8160
gaagcggaag agcgcccaat acgcaaaccg cctctccccg cgcgttggcc gattcattaa 8220
tg 8222

<210> SEQ ID NO 52
<211> LENGTH: 8126
<212> TYPE: DNA
<213> ORGANISM: Artificial
<220> FEATURE:
<223> OTHER INFORMATION: AAV donor template

<400> SEQUENCE: 52
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgt atacatacat acctgaatat ggaatcaaat 180
atttttctaa gatgaaacag tcatgattta tttcaaatag gtacggataa gtagatattg 240
aggtaagcat taggtcttat attatgtaac actaatctat tactgcgctg aaactgtggc 300
tttatagaaa ttgttttcac tgcactattg agaaattaag agataatggc aaaagtcaca 360
aagagtatat tcaaaaagaa gtatagcact tttccttag aaaccactgc taactgaaag 420

-continued

```
agactaagat ttgtcccgtc aaaaatcctg gacctatgcc taaaacacat ttcacaatcc    480
ctgaactttt caaaaattgg tacatgcttt agctttaaac tacaggcctc actggagcta    540
gagacaagaa ggtaaaaaac ggctgacaaa agaagtcctg gtatcctcta tgatgggaga    600
aggaaactag ctaaagggaa gaataaatta gagaaaaact ggaatgactg aatcggaaca    660
aggcaaaggc tataaaaaaa attaagcagc agtatcctct tgggggcccc ttccccacac    720
tatctcaatg caaatatctg tctgaaacgg tccctggcta aactccaccc atgggttggc    780
cagccttgcc ttgacaaggc aaacttgacc aatagtctta gagtatccag tgaggccagg    840
ggccggcggc tggctaggga tgaagaataa aaggaagcac ccttcagcag ttccacacac    900
tcgcttctgg aacgtctgag gttatcaata agctcctagt ccagacgcca tggtgcacct    960
gactcctgag gagaagtctg ccgttactgc cctgtggggc aaggtgaacg tggatgaagt   1020
tggtggtgag gccctgggca ggttggtatc aaggttacaa gacaggttta aggagaccaa   1080
tagaaactgg gcatgtggag acagagaaga ctcttgggtt tctgataggc actgactctc   1140
tctgcctatt ggtctatttt cccaccctta ggctgctggt ggtctaccct tggacccaga   1200
ggttctttga gtcctttggg gatctgtcca ctcctgatgc tgttatgggc aaccctaagg   1260
tgaaggctca tggcaagaaa gtgctcggtg cctttagtga tggcctggct cacctggaca   1320
acctcaaggg cacctttgcc cagctgagtg agctgcactg tgacaagctg cacgtggatc   1380
ctgagaactt cagggtgagt ctatgggacc cttgatgttt tctttcccct tcttttctat   1440
ggttaagttc atgtcatagg aaggggagaa gtaacagggt acacatattg accaaatcag   1500
ggtaattttg catttgtaat tttaaaaaat gctttcttct tttaatatac ttttttgttt   1560
atcttatttc taatactttc cctaatctct ttctttcagg gcaataatga tacaatgtat   1620
catgcctctt tgcaccattc taaagaataa cagtgataat ttctgggtta aggcaatagc   1680
aatatttctg catataaata tttctgcata taaattgtaa ctgatgtaag aggtttcata   1740
ttgctaatag cagctacaat ccagctacca ttctgctttt attttatggt tgggataagg   1800
ctggattatt ctgagtccaa gctaggccct tttgctaatc atgttcatac ctcttatctt   1860
cctcccacag ctcctgggca acgtgctggt ctgtgtgctg gcccatcact ttggcaaaga   1920
attcacccca ccagtgcagg ctgcctatca gaaagtggtg gctggtgtgg ctaatgccct   1980
ggcccacaag tatcactaag ctcgctttct tgctgtccaa tttctattaa aggttccttt   2040
gttccctaag tccaactact aaactggggg atattatgaa gggccttgag catctggatt   2100
ctgcctaata aaaaacattt attttcattg caatgatgta tttaaattat ttctgaatat   2160
tttactaaaa agggaatgtg ggaggttgca gtgctagtct cccggaacta tcactctttc   2220
acagtctgct ttggaaggac tgggcttagt atgaaaagtt aggactgaga agaatttgaa   2280
agggggcttt ttgtagcttg atattcacta ctgtcttatt accctatcat aggcccaccc   2340
caaatggaag tcccattctt cctcaggatg tttaagatta gcattcagga agagatcaga   2400
ggtctgctgg ctcccttatc atgtccctta tggtgcttct ggctctgcac cgcggccacg   2460
gggttggggt tgcgcctttt ccaaggcagc cctgggtttg cgcagggacg cggctgctct   2520
gggcgtggtt ccgggaaacg cagcggcgcc gaccctgggt ctcgcacatt cttcacgtcc   2580
gttcgcagcg tcacccggat cttcgccgct acccttgtgg gccccccggc gacgcttcct   2640
gctccgcccc taagtcggga aggttccttg cggttcgcgg cgtgccggac gtgacaaacg   2700
gaagccgcac gtctcactag taccctcgca gacggacagc gccagggagc aatggcagcg   2760
```

-continued

```
cgccgaccgc gatgggctgt ggccaatagc ggctgctcag cggggcgcgc cgagagcagc   2820
ggccgggaag gggcggtgcg ggaggcgggg tgtggggcgg tagtgtgggc cctgttcctg   2880
cccgcgcggt gttccgcatt ctgcaagcct ccggagcgca cgtcggcagt cggctccctc   2940
gttgaccgaa tcaccgacct ctctccccag cggccgcgcc gccaccatgg acaaggattg   3000
tgaaatgaaa cgcaccacac tggacagccc tttggggaag ctggagctgt ctggttgtga   3060
gcagggtctg cacgaaataa agctcctggg caaggggacg tctgcagctg atgccgtgga   3120
ggtcccagcc cccgctgcgg ttctcggagg tccggagccc ctgatgcagt gcacagcctg   3180
gctgaatgcc tatttccacc agcccgaggc tatcgaagag ttccccgtgc cggctcttca   3240
ccatcccgtt ttccagcaag agtcgttcac cagacaggtg ttatggaagc tgctgaaggt   3300
tgtgaaattc ggagaagtga tttcttacca gcaattagca gccctggcag gcaaccccaa   3360
agccgcgcga gcagtgggag gagcaatgag aggcaatcct gtcaaaatcc tcatcccgtg   3420
ccacagagtg gtctgcagca gcggagccgt gggcaactac tccggaggac tggccgtgaa   3480
ggaatggctt ctggcccatg aaggccaccg gttggggaag ccaggcttgg gagggagctc   3540
aggtctggca ggggcctggc tcaagggagc gggagctacc tcgggctccc cgcctgctgg   3600
ccgaaactaa gctttatttg tgaaatttgt gatgctattg ctttatttgt aaccattata   3660
agctgcaata aacaagttaa caacaacaat tgcattcatt ttatgtttca ggttcagggg   3720
gagatgtggg aggtttttta aagccctgca ggcaatagcc ttgacaaggc aaacttgacc   3780
aatagtctta gagtatccag tgaggccagg ggccggcggc tggctaggga tgaagaataa   3840
aaggaagcac ccttcagcag ttccacacac tcgcttctgg aacgtctgag gttatcaata   3900
agctcctagt ccagacgcca tgggtcattt cacagaggag gacaaggcta ctatcacaag   3960
cctgtggggc aaggtgaatg tggaagatgc tggaggagaa accctgggaa ggtaggctct   4020
ggtgaccagg acaagggagg gaaggaagga ccctgtgcct ggcaaaagtc caggtcgctt   4080
ctcaggattt gtggcacctt ctgactgtca aactgttctt gtcaatctca caggctcctg   4140
gttgtctacc catggaccca gaggttcttt gacagctttg gcaacctgtc ctctgcctct   4200
gccatcatgg gcaaccccaa agtcaaggca catggcaaga aggtgctgac ttccttggga   4260
gatgccacaa agcacctgga tgatctcaag ggcacctttg cccagctgag tgaactgcac   4320
tgtgacaagc tgcatgtgga tcctgagaac ttcaaggtga gtccaggaga tgtttcagcc   4380
ctgttgcctt tagtctcgag gcgtcgacag gaacccctag tgatggagtt ggccactccc   4440
tctctgcgcg ctcgctcgct cactgaggcc gggcgaccaa aggtcgcccg acgcccgggc   4500
tttgcccggg cggcctcagt gagcgagcga gcgcgcagct ggcgtaatag cgaagaggcc   4560
cgcaccgatc gcccttccca acagttgcgc agcctgaatg gcgaatggcg attccgttgc   4620
aatggctggc ggtaatattg ttctggatat taccagcaag gccgatagtt tgagttcttc   4680
tactcaggca agtgatgtta ttactaatca aagaagtatt gcgacaacgg ttaatttgcg   4740
tgatggacag actcttttac tcggtggcct cactgattat aaaaacactt ctcaggattc   4800
tggcgtaccg ttcctgtcta aaatcccttt aatcggcctc ctgtttagct cccgctctga   4860
ttctaacgag gaaagcacgt tatacgtgct cgtcaaagca accatagtac gcgccctgta   4920
gcggcgcatt aagcgcggcg ggtgtggtgg ttacgcgcag cgtgaccgct acacttgcca   4980
gcgccctagc gcccgctcct ttcgctttct tcccttcctt tctcgccacg ttcgccggct   5040
ttccccgtca agctctaaat cgggggctcc ctttagggtt ccgatttagt gctttacggc   5100
acctcgaccc caaaaaactt gattagggtg atggttcacg tagtgggcca tcgccctgat   5160
```

-continued

```
agacggtttt tcgccctttg acgttggagt ccacgttctt taatagtgga ctcttgttcc   5220
aaactggaac aacactcaac cctatctcgg tctattcttt tgatttataa gggattttgc   5280
cgatttcggc ctattggtta aaaaatgagc tgatttaaca aaaatttaac gcgaatttta   5340
acaaaatatt aacgtttaca atttaaatat ttgcttatac aatcttcctg tttttggggc   5400
ttttctgatt atcaaccggg gtacatatga ttgacatgct agttttacga ttaccgttca   5460
tcgattctct tgtttgctcc agactctcag gcaatgacct gatagccttt gtagagacct   5520
ctcaaaaata gctaccctct ccggcatgaa tttatcagct agaacggttg aatatcatat   5580
tgatggtgat ttgactgtct ccggcctttc tcacccgttt gaatctttac ctacacatta   5640
ctcaggcatt gcatttaaaa tatatgaggg ttctaaaaat ttttatcctt gcgttgaaat   5700
aaaggcttct cccgcaaaag tattacaggg tcataatgtt tttggtacaa ccgatttagc   5760
tttatgctct gaggctttat tgcttaattt tgctaattct ttgccttgcc tgtatgattt   5820
attggatgtt ggaatcgcct gatgcggtat tttctcctta cgcatctgtg cggtatttca   5880
caccgcatat ggtgcactct cagtacaatc tgctctgatg ccgcatagtt aagccagccc   5940
cgacacccgc caacacccgc tgacgcgccc tgacgggctt gtctgctccc ggcatccgct   6000
tacagacaag ctgtgaccgt ctccgggagc tgcatgtgtc agaggttttc accgtcatca   6060
ccgaaacgcg cgagacgaaa gggcctcgtg atacgcctat ttttataggt taatgtcatg   6120
ataataatgg tttcttagac gtcaggtggc acttttcggg gaaatgtgcg cggaacccct   6180
atttgtttat ttttctaaat acattcaaat atgtatccgc tcatgagaca ataaccctga   6240
taaatgcttc aataatattg aaaaaggaag agtatgagta ttcaacattt ccgtgtcgcc   6300
cttattccct tttttgcggc attttgcctt cctgtttttg ctcacccaga aacgctggtg   6360
aaagtaaaag atgctgaaga tcagttgggt gcacgagtgg gttacatcga actggatctc   6420
aacagcggta agatccttga gagttttcgc cccgaagaac gttttccaat gatgagcact   6480
tttaaagttc tgctatgtgg cgcggtatta tcccgtattg acgccgggca agagcaactc   6540
ggtcgccgca tacactattc tcagaatgac ttggttgagt actcaccagt cacagaaaag   6600
catcttacgg atggcatgac agtaagagaa ttatgcagtg ctgccataac catgagtgat   6660
aacactgcgg ccaacttact tctgacaacg atcggaggac cgaaggagct aaccgctttt   6720
ttgcacaaca tgggggatca tgtaactcgc cttgatcgtt gggaaccgga gctgaatgaa   6780
gccataccaa acgacgagcg tgacaccacg atgcctgtag caatggcaac aacgttgcgc   6840
aaactattaa ctggcgaact acttactcta gcttcccggc aacaattaat agactggatg   6900
gaggcggata aagttgcagg accacttctg cgctcggccc ttccggctgg ctggtttatt   6960
gctgataaat ctggagccgg tgagcgtggg tctcgcggta tcattgcagc actggggcca   7020
gatggtaagc cctcccgtat cgtagttatc tacacgacgg ggagtcaggc aactatggat   7080
gaacgaaata gacagatcgc tgagataggt gcctcactga ttaagcattg gtaactgtca   7140
gaccaagttt actcatatat actttagatt gatttaaaac ttcattttta atttaaaagg   7200
atctaggtga agatcctttt tgataatctc atgaccaaaa tcccttaacg tgagttttcg   7260
ttccactgag cgtcagaccc cgtagaaaag atcaaaggat cttcttgaga tccttttttt   7320
ctgcgcgtaa tctgctgctt gcaaacaaaa aaaccaccgc taccagcggt ggtttgtttg   7380
ccggatcaag agctaccaac tctttttccg aaggtaactg gcttcagcag agcgcagata   7440
ccaaatactg tccttctagt gtagccgtag ttaggccacc acttcaagaa ctctgtagca   7500
```

ccgcctacat acctcgctct gctaatcctg ttaccagtgg ctgctgccag tggcgataag 7560
tcgtgtctta ccgggttgga ctcaagacga tagttaccgg ataaggcgca gcggtcgggc 7620
tgaacggggg gttcgtgcac acagcccagc ttggagcgaa cgacctacac cgaactgaga 7680
tacctacagc gtgagctatg agaaagcgcc acgcttcccg aagggagaaa ggcggacagg 7740
tatccggtaa gcggcagggt cggaacagga gagcgcacga gggagcttcc agggggaaac 7800
gcctggtatc tttatagtcc tgtcgggttt cgccacctct gacttgagcg tcgatttttg 7860
tgatgctcgt caggggggcg gagcctatgg aaaaacgcca gcaacgcggc ctttttacgg 7920
ttcctggcct tttgctggcc ttttgctcac atgttctttc ctgcgttatc ccctgattct 7980
gtggataacc gtattaccgc ctttgagtga gctgataccg ctcgccgcag ccgaacgacc 8040
gagcgcagcg agtcagtgag cgaggaagcg gaagagcgcc caatacgcaa accgcctctc 8100
cccgcgcgtt ggccgattca ttaatg 8126

<210> SEQ ID NO 53
<211> LENGTH: 8168
<212> TYPE: DNA
<213> ORGANISM: Artificial
<220> FEATURE:
<223> OTHER INFORMATION: AAV donor template

<400> SEQUENCE: 53
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctgcggccg cgatgtgagg acacagtggg aagtcagcca cctgcaaccc 180
aggaagagag ccctgaccag gaaccagcag aaaagtgaga aaaaatcctg ttgttgaagt 240
cacccagtct atgctatttt gttatagcac cttgcactaa gtaaggcaga tgaagaaaga 300
gaaaaaaata agcttcggtg ttcagtggat tagaaaccat gtttatctca ggtttacaaa 360
tctccacttg tcctctgtgt ttcagaataa aataccaact ctactactct catctgtaag 420
atgcaaatag taagcctgag cccttctgtc taactttgaa ttctattttt tcttcaacgt 480
actttaggct tgtaatgtgt ttatatacag tgaaatgtca agttctttct ttatatttct 540
ttctttcttt tttttcctca gcctcagagt tttccacatg cccttcctac tttcaggaac 600
ttctttctcc aaacgtcttc tgcctggctc catcaaatca taaaggaccc acttcaaatg 660
ccatcactca ctaccatttc acaattcgca ctttctttct ttgtcctttt ttttttagt 720 aaaacaagtt tataaaaaat tgaaggaata aatgaatggc tacttcatag gcagagtaga 780
cgcaagggct actggttgcc gatttttatt gttatttttc aatagtatgc taaacaaggg 840
gtagattatt tatgctgccc atttttagac cataaaagat aacttcctga tgttgccatg 900
gcattttttt ccttttaatt ttatttcatt tcattttaat ttcgaaggta catgtgcagg 960
atgtgcaggc ttgttacatg ggtaaatgtg tgtctttctg gccttttagc catctgtatc 1020
aatgagcaga tataagcttt acacaggatc atgaaggatg aaagaatttc accaatatta 1080
taataatttc aatcaacctg atagcttagg ggataaacta atttgaagat acagcttgcc 1140
tccgataagc cagaattcca gagcttctgg cattataatc tagcaaggtt agagatcatg 1200
gatcactttc agagaaaaac aaaaacaaac taaccaaaag caaaacagaa ccaaaaaacc 1260
accataaata cttcctaccc tgttaatggt ccaatatgtc agaaacagca ctgtgttaga 1320
aataaagctg tctaaagtac actaatattc gagttataat agtgtgtgga ctattagtca 1380
ataaaaacaa cccttgcctc tttagagttg ttttccatgt acacgcacat cttatgtctt 1440

```
agagtaagat tccctgagaa gtgaacctag catttataca agataattaa ttctaatcca   1500
cagtacctgc caaagaacat tctaccatca tctttactga gcatagaaga gctacgccaa   1560
aaccctgggt catcagccag cacacacact tatccagtgg taaatacaca tcatctggtg   1620
tatacataca tacctgaata tggaatcaaa tatttttcta agatgaaaca gtcatgattt   1680
atttcaaata ggtacggata agtagatatt gaggtaagca ttaggtctta tattatgtaa   1740
cactaatcta ttactgcgct gaaactgtgg ctttatagaa attgttttca ctgcactatt   1800
gagaaattaa gagataatgg caaaagtcac aaagagtata ttcaaaaaga agtatagcac   1860
tttttcctta gaaaccactg ctaactgaaa gagactaaga tttgtcccgt caaaaatcct   1920
ggacctatgc ctaaaacaca tttcacaatc cctgaacttt tcaaaaattg gtacatgctt   1980
tagctttaaa ctacaggcct cactggagct agagacaaga aggtaaaaaa cggctgacaa   2040
aagaagtcct ggtatcctct atgatgggag aaggaaacta gctaaaggga agaataaatt   2100
agagaaaaac tggaatgact gaatcggaac aaggcaaagg ctataaaaaa aattagcagt   2160
atcctcttgg gggccccttc cccacactat ctcaatgcaa atatctgtct gaaacggtcc   2220
ctggctaaac tccacccatg ggttggccag ccttgccttg acaaggcaaa cttgaccaat   2280
agtcttagag tatccagtga ggccaggggc cggcggctgg ctagggatga agaataaaag   2340
gaagcaccct tcagcagttc cacacactcg cttctggaac gtctgaggtt atcaataagc   2400
tcctagtcca gacgccatgg gtcatttcac agaggaggac aaggctacta tcacaagcct   2460
gtggggcaag gtgaatgtgg aagatgctgg aggagaaacc ctgggaaggt aggctctggt   2520
gaccaggaca agggagggaa ggaaggaccc tgtgcctggc aaaagtccag gtcgcttctc   2580
aggatttgtg gcaccttctg actgtcaaac tgttcttgtc aatctcacag gctcctggtt   2640
gtctacccat ggacccagag gttctttgac agctttggca acctgtcctc tgcctctgcc   2700
atcatgggca accccaaagt caaggcacat ggcaagaagg tgctgacttc cttgggagat   2760
gccacaaagc acctggatga tctcaagggc acctttgccc agctgagtga actgcactgt   2820
gacaagctgc atgtggatcc tgagaacttc aaggtgagtc caggagatgt ttcagccctg   2880
ttgcctttag tctcgaggca acttagacaa cggagtattg atctgagcac agcagggtgt   2940
gagctgtttg aagatactgg ggttgggggt gaagaaactg cagaggacta actgggctga   3000
gacccagtgg taatgtttta gggcctaagg agtgcctcta aaaatctaga tggacaattt   3060
tgactttgag aaaagagagg tggaaatgag gaaaatgact tttctttatt agattccagt   3120
agaaagaact ttcatctttc cctcattttt gttgttttaa aacatctatc tggaggcagg   3180
acaagtatgg tcgttaaaaa gatgcaggca gaaggcatat attggctcag tcaaagtggg   3240
gaactttggt ggccaaacat acattgctaa ggctattcct atatcagctg gacacatata   3300
aaatgctgct aatgcttcat tacaaactta tatcctttaa ttccagatgg gggcaaagta   3360
tgtccagggg tgaggaacaa ttgaaacatt tgggctggag tagattttga aagtcagctc   3420
tgtgtgtgtg tgtgtgtgtg cgcgcgcgcg tgtgtgtgtg tgtgtcagcg tgtgtttctt   3480
ttaacgtctt cagcctacaa catacagggt tcatggtggc aagaagatag caagatttaa   3540
attatggcca gtgactagtg cttgaagggg aacaactacc tgcatttaat gggaaggcaa   3600
aatctcaggc tttgagggaa gttaacatag gcttgattct gggtggaagc ttggtgtgta   3660
gttatctgga ggccaggctg gagctctcag ctcactatgg gttcatcttt attgtctcct   3720
ttcatctcaa cagctcctgg gaaatgtgct ggtgaccgtt ttggcaatcc atttcggcaa   3780
```

-continued

```
agaattcacc cctgaggtgc aggcttcctg gcagaagatg gtgactgcag tggccagtgc   3840
cctgtcctcc agataccact gagctcactg cccatgattc agagctttca aggataggct   3900
ttattctgca agcaatacaa ataataaatc tattctgctg agagatcaca catgattttc   3960
ttcagctctt ttttttacat ctttttaaat atatgagcca caaagggttt atattgaggg   4020
aagtgtgtat gtgtatttct gcatgcctgt ttgtgtttgt ggtgtgtgca tgctcctcat   4080
ttatttttat atgagatgtg cattttgatg agcaaataaa agcagtaaag acacttgtac   4140
acgggagttc tgcaagtggg agtaaatggt gtaggagaaa tccggtggga agaaagacct   4200
ctataggaca ggacttctca gaaacagatg ttttggaaga gatgggaaaa ggttcagtga   4260
agacctgggg gctggattga ttgcagctga gtagcaagga tggttcttaa ggaagggaaa   4320
gtgttccaag ctttaggaat tcaaggttta gtcaggtgta gcaattctat tttattagga   4380
ggaatactat ttctaatggc acttagcttt tcacagccct tgtggatgcc taaatcggat   4440
cccctgcagg aggaacccct agtgatggag ttggccactc cctctctgcg cgctcgctcg   4500
ctcactgagg ccgggcgacc aaaggtcgcc cgacgcccgg gctttgcccg ggcggcctca   4560
gtgagcgagc gagcgcgcag ctggcgtaat agcgaagagg cccgcaccga tcgcccttcc   4620
caacagttgc gcagcctgaa tggcgaatgg cgattccgtt gcaatggctg gcggtaatat   4680
tgttctggat attaccagca aggccgatag tttgagttct tctactcagg caagtgatgt   4740
tattactaat caaagaagta ttgcgacaac ggttaatttg cgtgatggac agactctttt   4800
actcggtggc ctcactgatt ataaaaacac ttctcaggat tctggcgtac cgttcctgtc   4860
taaaatccct ttaatcggcc tcctgtttag ctcccgctct gattctaacg aggaaagcac   4920
gttatacgtg ctcgtcaaag caaccatagt acgcgccctg tagcggcgca ttaagcgcgg   4980
cgggtgtggt ggttacgcgc agcgtgaccg ctacacttgc cagcgcccta gcgcccgctc   5040
ctttcgcttt cttcccttcc tttctcgcca cgttcgccgg ctttccccgt caagctctaa   5100
atcgggggct ccctttaggg ttccgattta gtgctttacg gcacctcgac cccaaaaaac   5160
ttgattaggg tgatggttca cgtagtgggc catcgccctg atagacggtt tttcgccctt   5220
tgacgttgga gtccacgttc tttaatagtg gactcttgtt ccaaactgga acaacactca   5280
accctatctc ggtctattct tttgatttat aagggatttt gccgatttcg gcctattggt   5340
taaaaaatga gctgatttaa caaaaattta acgcgaattt taacaaaata ttaacgttta   5400
caatttaaat atttgcttat acaatcttcc tgtttttggg gcttttctga ttatcaaccg   5460
gggtacatat gattgacatg ctagttttac gattaccgtt catcgattct cttgtttgct   5520
ccagactctc aggcaatgac ctgatagcct ttgtagagac ctctcaaaaa tagctaccct   5580
ctccggcatg aatttatcag ctagaacggt tgaatatcat attgatggtg atttgactgt   5640
ctccggcctt tctcacccgt ttgaatcttt acctacacat tactcaggca ttgcatttaa   5700
aatatatgag ggttctaaaa atttttatcc ttgcgttgaa ataaaggctt ctcccgcaaa   5760
agtattacag ggtcataatg tttttggtac aaccgattta gctttatgct ctgaggcttt   5820
attgcttaat tttgctaatt ctttgccttg cctgtatgat ttattggatg ttggaatcgc   5880
ctgatgcggt attttctcct tacgcatctg tgcggtattt cacaccgcat atggtgcact   5940
ctcagtacaa tctgctctga tgccgcatag ttaagccagc cccgacaccc gccaacaccc   6000
gctgacgcgc cctgacgggc ttgtctgctc ccggcatccg cttacagaca agctgtgacc   6060
gtctccggga gctgcatgtg tcagaggttt tcaccgtcat caccgaaacg cgcgagacga   6120
aagggcctcg tgatacgcct atttttatag gttaatgtca tgataataat ggtttcttag   6180
```

```
acgtcaggtg gcacttttcg gggaaatgtg cgcggaaccc ctatttgttt atttttctaa   6240
atacattcaa atatgtatcc gctcatgaga caataaccct gataaatgct tcaataatat   6300
tgaaaaagga agagtatgag tattcaacat ttccgtgtcg cccttattcc cttttttgcg   6360
gcattttgcc ttcctgtttt tgctcaccca gaaacgctgg tgaaagtaaa agatgctgaa   6420
gatcagttgg gtgcacgagt gggttacatc gaactggatc tcaacagcgg taagatcctt   6480
gagagttttc gccccgaaga acgttttcca atgatgagca cttttaaagt tctgctatgt   6540
ggcgcggtat tatcccgtat tgacgccggg caagagcaac tcggtcgccg catacactat   6600
tctcagaatg acttggttga gtactcacca gtcacagaaa agcatcttac ggatggcatg   6660
acagtaagag aattatgcag tgctgccata accatgagtg ataacactgc ggccaactta   6720
cttctgacaa cgatcggagg accgaaggag ctaaccgctt ttttgcacaa catgggggat   6780
catgtaactc gccttgatcg ttgggaaccg gagctgaatg aagccatacc aaacgacgag   6840
cgtgacacca cgatgcctgt agcaatggca acaacgttgc gcaaactatt aactggcgaa   6900
ctacttactc tagcttcccg gcaacaatta atagactgga tggaggcgga taaagttgca   6960
ggaccacttc tgcgctcggc ccttccggct ggctggttta ttgctgataa atctggagcc   7020
ggtgagcgtg ggtctcgcgg tatcattgca gcactggggc cagatggtaa gccctcccgt   7080
atcgtagtta tctacacgac ggggagtcag gcaactatgg atgaacgaaa tagacagatc   7140
gctgagatag gtgcctcact gattaagcat tggtaactgt cagaccaagt ttactcatat   7200
atactttaga ttgatttaaa acttcatttt taatttaaaa ggatctaggt gaagatcctt   7260
tttgataatc tcatgaccaa aatcccttaa cgtgagtttt cgttccactg agcgtcagac   7320
cccgtagaaa agatcaaagg atcttcttga gatccttttt ttctgcgcgt aatctgctgc   7380
ttgcaaacaa aaaaaccacc gctaccagcg gtggtttgtt tgccggatca agagctacca   7440
actctttttc cgaaggtaac tggcttcagc agagcgcaga taccaaatac tgtccttcta   7500
gtgtagccgt agttaggcca ccacttcaag aactctgtag caccgcctac atacctcgct   7560
ctgctaatcc tgttaccagt ggctgctgcc agtggcgata agtcgtgtct taccgggttg   7620
gactcaagac gatagttacc ggataaggcg cagcggtcgg gctgaacggg gggttcgtgc   7680
acacagccca gcttggagcg aacgacctac accgaactga gatacctaca gcgtgagcta   7740
tgagaaagcg ccacgcttcc cgaagggaga aaggcggaca ggtatccggt aagcggcagg   7800
gtcggaacag gagagcgcac gagggagctt ccagggggaa acgcctggta tctttatagt   7860
cctgtcgggt ttcgccacct ctgacttgag cgtcgatttt tgtgatgctc gtcagggggg   7920
cggagcctat ggaaaaacgc cagcaacgcg gcctttttac ggttcctggc cttttgctgg   7980
ccttttgctc acatgttctt tcctgcgtta tcccctgatt ctgtggataa ccgtattacc   8040
gcctttgagt gagctgatac cgctcgccgc agccgaacga ccgagcgcag cgagtcagtg   8100
agcgaggaag cggaagagcg cccaatacgc aaaccgcctc tccccgcgcg ttggccgatt   8160
cattaatg                                                            8168
```

<210> SEQ ID NO 54
<211> LENGTH: 7556
<212> TYPE: DNA
<213> ORGANISM: Artificial
<220> FEATURE:
<223> OTHER INFORMATION: AAV donor template

<400> SEQUENCE: 54

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtagat    180
cttaagtata gcacaatgct tactaaatga gactaagact tgtcccatcg aaaatcctgg    240
acctatgcct aaaacacgtg tcacaatccc cgaacttttc aaaaattggt acatgcttta    300
actttaatct ccaggcctca ctggagctag agacaagaag gtaaaaaaag gctgacaaaa    360
gaagtcctgg tatcttctat ggtgggagaa ggaaactagc taaagggaag aataaattag    420
agaaaaattg gaatgattga atcggaacaa ggcaaaggct ataaaaaaat taagcagcag    480
tatcctcttg gggcccctt ccccacacta tctcaatgca aatatctgtc tgaaacggtc     540
cctggctaaa ctccacccat gggttggcca gtcttgcctt gacaaggcaa ccttgaccaa    600
tagtcttaga gtatcaggtg aggccagggg ccggcggctg gctagggatg aagaataaaa    660
ggaagcaccc tccagcagtt ccacacactc gcttctggaa cggctgagat tatcaataag    720
ctcctagtcc agacgccatg gtgcacctga ctcctgagga gaagtctgcc gttactgccc    780
tgtggggcaa ggtgaacgtg gatgaagttg gtggtgaggc cctgggcagg ttggtatcaa    840
ggttacaaga caggtttaag gagaccaata gaaactgggc atgtggagac agagaagact    900
cttgggtttc tgataggcac tgactctctc tgcctattgg tctattttcc cacccttagg    960
ctgctggtgg tctacccttg gacccagagg ttctttgagt cctttgggga tctgtccact   1020
cctgatgctg ttatgggcaa ccctaaggtg aaggctcatg gcaagaaagt gctcggtgcc   1080
tttagtgatg gcctggctca cctggacaac ctcaagggca cctttgccca gctgagtgag   1140
ctgcactgtg acaagctgca cgtggatcct gagaacttca gggtgagtct atgggaccct   1200
tgatgttttc tttccccttc ttttctatgg ttaagttcat gtcataggaa ggggagaagt   1260
aacagggtac acatattgac caaatcaggg taattttgca tttgtaattt taaaaaatgc   1320
tttcttcttt taatatactt ttttgtttat cttatttcta atactttccc taatctcttt   1380
ctttcagggc aataatgata caatgtatca tgcctctttg caccattcta aagaataaca   1440
gtgataattt ctgggttaag gcaatagcaa tatttctgca tataaatatt tctgcatata   1500
aattgtaact gatgtaagag gtttcatatt gctaatagca gctacaatcc agctaccatt   1560
ctgcttttat tttatggttg ggataaggct ggattattct gagtccaagc taggcccttt   1620
tgctaatcat gttcatacct cttatcttcc tcccacagct cctgggcaac gtgctggtct   1680
gtgtgctggc ccatcacttt ggcaaagaat tcaccccacc agtgcaggct gcctatcaga   1740
aagtggtggc tggtgtggct aatgccctgg cccacaagta tcactaagct cgctttcttg   1800
ctgtccaatt tctattaaag gttcctttgt tccctaagtc caactactaa actgggggat   1860
attatgaagg gccttgagca tctggattct gcctaataaa aaacatttat tttcattgca   1920
atgatgtatt taaattattt ctgaatattt tactaaaaag ggaatgtggg aggttgcagt   1980
gctagtctcc cggaactatc actctttcac agtctgcttt ggaaggactg ggcttagtat   2040
gaaaagttag gactgagaag aatttgaaag gggcttttt gtagcttgat attcactact    2100
gtcttattac cctatcatag gcccacccca aatggaagtc ccattcttcc tcaggatgtt   2160
taagattagc attcaggaag agatcagagg tctgctggct cccttatcat gtcccttatg   2220
gtgcttctgg ctctgcaccg cgggaacaga gaaacaggag aatatgggcc aaacaggata   2280
tctgtggtaa gcagttcctg ccccggctca gggccaagaa cagttggaac agcagaatat   2340
gggccaaaca ggatatctgt ggtaagcagt tcctgccccg gctcagggcc aagaacagat   2400
```

-continued ggtccccaga tgcggtcccg ccctcagcag tttctagaga accatcagat gtttccaggg 2460
tgccccaagg acctgaaatg accctgtgcc ttatttgaac taaccaatca gttcgcttct 2520
cgcttctgtt cgcgcgcttc tgctccccga gctctatata agcagagctc gtttagtgaa 2580
ccgtcagatc gcggccgcgc cgccaccatg gtgagcaagg gcgaggagct gttcaccggg 2640
gtggtgccca tcctggtcga gctggacggc gacgtaaacg gccacaagtt cagcgtgtcc 2700
ggcgagggcg agggcgatgc cacctacggc aagctgaccc tgaagttcat ctgcaccacc 2760
ggcaagctgc ccgtgccctg gcccaccctc gtgaccaccc tgacctacgg cgtgcagtgc 2820
ttcagccgct accccgacca catgaagcag cacgacttct tcaagtccgc catgcccgaa 2880
ggctacgtcc aggagcgcac catcttcttc aaggacgacg gcaactacaa gacccgcgcc 2940
gaggtgaagt tcgagggcga caccctggtg aaccgcatcg agctgaaggg catcgacttc 3000
aaggaggacg gcaacatcct ggggcacaag ctggagtaca actacaacag ccacaacgtc 3060
tatatcatgg ccgacaagca gaagaacggc atcaaggtga acttcaagat ccgccacaac 3120
atcgaggacg gcagcgtgca gctcgccgac cactaccagc agaacacccc catcggcgac 3180
ggccccgtgc tgctgcccga caaccactac ctgagcaccc agtccgccct gagcaaagac 3240
cccaacgaga agcgcgatca catggtcctg ctggagttcg tgaccgccgc cgggatcact 3300
ctcggcatgg acgagctgta caaggagggc agaggaagtc ttctaacatg cggtgacgtg 3360
gaggagaatc cgggcccccc tgcaggaact tcagggtgag tccaggagtt tcagcagttt 3420
cagagttcag tctcaaggca acttagacaa ctgagtattg atctgaggac agtcgaatct 3480
acctgctggg tgtgagctat ttgaagatac tggggttggg agtgaagaaa ctgcagagga 3540
ctaactgggc tgagaccgaa tggtaatgtt ttagggccta aggagtgcct ctaaaaatct 3600
agacggacaa ttttgacatt gacaaaagag aggtggaaat gaggaaaatg acttttcttt 3660
attagattcc ggtagaaaga actttcatct ttccctcatt tttgttattt gttttaaaac 3720
atctatctgg aggcaggaca agtatggtca ttaaaaagat gcaggcagaa ggcatatatt 3780
ggcccagtca aagtgtcgac gtagataagt agcatggcgg gttaatcatt aactacaagg 3840
aacccctagt gatggagttg gccactccct ctctgcgcgc tcgctcgctc actgaggccg 3900
ggcgaccaaa ggtcgcccga cgcccgggct ttgcccgggc ggcctcagtg agcgagcgag 3960
cgcgccagct ggcgtaatag cgaagaggcc cgcaccgatc gcccttccca acagttgcgc 4020
agcctgaatg gcgaatggcg attccgttgc aatggctggc ggtaatattg ttctggatat 4080
taccagcaag gccgatagtt tgagttcttc tactcaggca agtgatgtta ttactaatca 4140
aagaagtatt gcgacaacgg ttaatttgcg tgatggacag actcttttac tcggtggcct 4200
cactgattat aaaaacactt ctcaggattc tggcgtaccg ttcctgtcta aaatcccttt 4260
aatcggcctc ctgtttagct cccgctctga ttctaacgag gaaagcacgt tatacgtgct 4320
cgtcaaagca accatagtac gcgccctgta gcggcgcatt aagcgcggcg ggtgtggtgg 4380
ttacgcgcag cgtgaccgct acacttgcca gcgccctagc gcccgctcct ttcgctttct 4440
tcccttcctt tctcgccacg ttcgccggct ttccccgtca agctctaaat cgggggctcc 4500
ctttagggtt ccgatttagt gctttacggc acctcgaccc caaaaaactt gattagggtg 4560
atggttcacg tagtgggcca tcgccctgat agacggtttt tcgccctttg acgttggagt 4620
ccacgttctt taatagtgga ctcttgttcc aaactggaac aacactcaac cctatctcgg 4680
tctattcttt tgatttataa gggattttgc cgatttcggc ctattggtta aaaaatgagc 4740

-continued

```
tgatttaaca aaaatttaac gcgaatttta acaaaatatt aacgtttaca atttaaatat   4800
ttgcttatac aatcttcctg tttttggggc ttttctgatt atcaaccggg gtacatatga   4860
ttgacatgct agttttacga ttaccgttca tcgattctct tgtttgctcc agactctcag   4920
gcaatgacct gatagccttt gtagagacct ctcaaaaata gctaccctct ccggcatgaa   4980
tttatcagct agaacggttg aatatcatat tgatggtgat ttgactgtct ccggcctttc   5040
tcacccgttt gaatctttac ctacacatta ctcaggcatt gcatttaaaa tatatgaggg   5100
ttctaaaaat ttttatcctt gcgttgaaat aaaggcttct cccgcaaaag tattacaggg   5160
tcataatgtt tttggtacaa ccgatttagc tttatgctct gaggctttat tgcttaattt   5220
tgctaattct ttgccttgcc tgtatgattt attggatgtt ggaatcgcct gatgcggtat   5280
tttctcctta cgcatctgtg cggtatttca caccgcatat ggtgcactct cagtacaatc   5340
tgctctgatg ccgcatagtt aagccagccc cgacacccgc caacacccgc tgacgcgccc   5400
tgacgggctt gtctgctccc ggcatccgct tacagacaag ctgtgaccgt ctccgggagc   5460
tgcatgtgtc agaggttttc accgtcatca ccgaaacgcg cgagacgaaa gggcctcgtg   5520
atacgcctat ttttataggt taatgtcatg ataataatgg tttcttagac gtcaggtggc   5580
acttttcggg gaaatgtgcg cggaacccct atttgtttat ttttctaaat acattcaaat   5640
atgtatccgc tcatgagaca ataaccctga taaatgcttc aataatattg aaaaaggaag   5700
agtatgagta ttcaacattt ccgtgtcgcc cttattccct tttttgcggc attttgcctt   5760
cctgtttttg ctcacccaga aacgctggtg aaagtaaaag atgctgaaga tcagttgggt   5820
gcacgagtgg gttacatcga actggatctc aacagcggta agatccttga gagttttcgc   5880
cccgaagaac gttttccaat gatgagcact tttaaagttc tgctatgtgg cgcggtatta   5940
tcccgtattg acgccgggca agagcaactc ggtcgccgca tacactattc tcagaatgac   6000
ttggttgagt actcaccagt cacagaaaag catcttacgg atggcatgac agtaagagaa   6060
ttatgcagtg ctgccataac catgagtgat aacactgcgg ccaacttact tctgacaacg   6120
atcggaggac cgaaggagct aaccgctttt ttgcacaaca tgggggatca tgtaactcgc   6180
cttgatcgtt gggaaccgga gctgaatgaa gccataccaa acgacgagcg tgacaccacg   6240
atgcctgtag caatggcaac aacgttgcgc aaactattaa ctggcgaact acttactcta   6300
gcttcccggc aacaattaat agactggatg gaggcggata aagttgcagg accacttctg   6360
cgctcggccc ttccggctgg ctggtttatt gctgataaat ctggagccgg tgagcgtggg   6420
tctcgcggta tcattgcagc actggggcca gatggtaagc cctcccgtat cgtagttatc   6480
tacacgacgg ggagtcaggc aactatggat gaacgaaata gacagatcgc tgagataggt   6540
gcctcactga ttaagcattg gtaactgtca gaccaagttt actcatatat actttagatt   6600
gatttaaaac ttcattttta atttaaaagg atctaggtga agatcctttt tgataatctc   6660
atgaccaaaa tcccttaacg tgagttttcg ttccactgag cgtcagaccc cgtagaaaag   6720
atcaaaggat cttcttgaga tccttttttt ctgcgcgtaa tctgctgctt gcaaacaaaa   6780
aaaccaccgc taccagcggt ggtttgtttg ccggatcaag agctaccaac tctttttccg   6840
aaggtaactg gcttcagcag agcgcagata ccaaatactg tccttctagt gtagccgtag   6900
ttaggccacc acttcaagaa ctctgtagca ccgcctacat acctcgctct gctaatcctg   6960
ttaccagtgg ctgctgccag tggcgataag tcgtgtctta ccgggttgga ctcaagacga   7020
tagttaccgg ataaggcgca gcggtcgggc tgaacggggg gttcgtgcac acagcccagc   7080
ttggagcgaa cgacctacac cgaactgaga tacctacagc gtgagctatg agaaagcgcc   7140
```

acgcttcccg aagggagaaa ggcggacagg tatccggtaa gcggcagggt cggaacagga 7200
gagcgcacga gggagcttcc agggggaaac gcctggtatc tttatagtcc tgtcgggttt 7260
cgccacctct gacttgagcg tcgatttttg tgatgctcgt caggggggcg gagcctatgg 7320
aaaaacgcca gcaacgcggc ctttttacgg ttcctggcct tttgctggcc ttttgctcac 7380
atgttctttc ctgcgttatc ccctgattct gtggataacc gtattaccgc ctttgagtga 7440
gctgataccg ctcgccgcag ccgaacgacc gagcgcagcg agtcagtgag cgaggaagcg 7500
gaagagcgcc caatacgcaa accgcctctc cccgcgcgtt ggccgattca ttaatg 7556

<210> SEQ ID NO 55
<211> LENGTH: 7635
<212> TYPE: DNA
<213> ORGANISM: Artificial
<220> FEATURE:
<223> OTHER INFORMATION: AAV donor template

<400> SEQUENCE: 55
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
cttcccaact gtcacagtgt gtggcctatt agtcaattaa agcagtccct gcctctttag 240
agttgttttc catgcaatta catgtcttat gtcttagaat aagattccct gagaactgaa 300
cctagcattt atacaagata attaattcta agccatagta cctgccaaag aacattctac 360
tatcatcttt actgaacaca gaagagctac accaaaaacc tgggtcatca gccagcacac 420
acacttatcc agtgataaat acacatcatc gggtgcctac atacatacct gaataagaaa 480
aaaaaatacc tttgctgaga tgaaacacac atgatttatt tcaaataggt acagagaagt 540
agatactgaa gtaaggatta agtattatat tatattacat aacattaatc tattcctgca 600
ctgaaaccgt tgctttatat gatttttttt ttcactacac taatgagaac ttaagagata 660
atggcctaaa accacagaga gtattttcaa agataagtat agcacaatgc ttactaaatg 720
agactaagac ttgtcccatc gaaaatcctg gacctatgcc taaaacacgt gtcacaatcc 780
ccgaactttt caaaaattgg tacatgcttt aactttaatc tccaggcctc actggagcta 840
gagacaagaa ggtaaaaaaa ggctgacaaa agaagtcctg gtatcttcta tggtgggaga 900
aggaaactag ctaaagggaa gaataaatta gagaaaaatt ggaatgattg aatcggaaca 960
aggcaaaggc tataaaaaaa ttaagcagca gtatcctctt gggggcccct tccccacact 1020
atctcaatgc aaatatctgt ctgaaacggt ccctggctaa actccacccg cgggaacaga 1080
gaaacaggag aatatgggcc aaacaggata tctgtggtaa gcagttcctg ccccggctca 1140
gggccaagaa cagttggaac agcagaatat gggccaaaca ggatatctgt ggtaagcagt 1200
tcctgccccg gctcagggcc aagaacagat ggtccccaga tgcggtcccg ccctcagcag 1260
tttctagaga accatcagat gtttccaggg tgccccaagg acctgaaatg accctgtgcc 1320
ttatttgaac taaccaatca gttcgcttct cgcttctgtt cgcgcgcttc tgctccccga 1380
gctctatata agcagagctc gtttagtgaa ccgtcagatc gcctggagac gccatccacg 1440
ctgttttgac ttccatagaa ggcggccgcg ccgccaccat ggtgagcaag ggcgaggagc 1500
tgttcaccgg ggtggtgccc atcctggtcg agctggacgg cgacgtaaac ggccacaagt 1560
tcagcgtgtc cggcgagggc gagggcgatg ccacctacgg caagctgacc ctgaagttca 1620

-continued

```
tctgcaccac cggcaagctg cccgtgccct ggcccaccct cgtgaccacc ctgacctacg   1680
gcgtgcagtg cttcagccgc taccccgacc acatgaagca gcacgacttc ttcaagtccg   1740
ccatgcccga aggctacgtc caggagcgca ccatcttctt caaggacgac ggcaactaca   1800
agacccgcgc cgaggtgaag ttcgagggcg acaccctggt gaaccgcatc gagctgaagg   1860
gcatcgactt caaggaggac ggcaacatcc tggggcacaa gctggagtac aactacaaca   1920
gccacaacgt ctatatcatg gccgacaagc agaagaacgg catcaaggtg aacttcaaga   1980
tccgccacaa catcgaggac ggcagcgtgc agctcgccga ccactaccag cagaacaccc   2040
ccatcggcga cggccccgtg ctgctgcccg acaaccacta cctgagcacc cagtccgccc   2100
tgagcaaaga ccccaacgag aagcgcgatc acatggtcct gctggagttc gtgaccgccg   2160
ccgggatcac tctcggcatg gacgagctgt acaagtaacc tgcagggata atcaacctct   2220
ggattacaaa atttgtgaaa gattgactgg tattcttaac tatgttgctc cttttacgct   2280
atgtggatac gctgctttaa tgcctttgta tcatgctatt gcttcccgta tggctttcat   2340
tttctcctcc ttgtataaat cctggttagt tcttgccacg gcggaactca tcgccgcctg   2400
ccttgcccgc tgctggacag gggctcggct gttgggcact gacaattccg tggtgtttat   2460
ttgtgaaatt tgtgatgcta ttgctttatt tgtaaccatt ctagctttat ttgtgaaatt   2520
tgtgatgcta ttgctttatt tgtaaccatt ataagctgca ataaacaagt taacaacaac   2580
aattgcattc attttatgtt tcaggttcag ggggagatgt gggaggtttt ttaaagcgaa   2640
ttcgtaaata cacttgcaaa ggaggatgtt tttagtagca atttgtactg atggtatggg   2700
gccaagagat atatcttaga gggagggctg agggtttgaa gtccaactcc taagccagtg   2760
ccagaagagc caaggacagg tacggctgtc atcacttaga cctcaccctg tggagccaca   2820
ccctagggtt ggccaatcta ctcccaggag cagggagggc aggagccagg gctgggcata   2880
aaagtcaggg cagagccatc tattgcttac actcgcttct ggaacggctg agattatcaa   2940
taagctccta gtccagacgc catgggtcat ttcacagagg aggacaaggc tactatcaca   3000
agcctgtggg gcaaggtgaa tgtggaagat gctggaggag aaaccctggg aaggtaggct   3060
ctggtgacca ggacaaggaa gggaaggaag gaccctgtgc ctggcaaaag tccaggccac   3120
ttctcaggat ttgtggcact ttctgactgt caaactgctc ttgttcaatc tcacaggctc   3180
ctggttgtct acccatggac ccagaggttc tttgacagct ttggcaacct gtcctctgcc   3240
tctgccatca tgggcaaccc caaggtcaag gcacacggca agaaggtgct gacttccttg   3300
ggagatgcca taaagaacct ggatgatctc aagggcacct ttgcccagct gagtgagctg   3360
cactgtgaca agctgcatgt ggatcctgag aacttcaggg tgagtccagg agtttcagca   3420
gtttcagagt tcagtctcaa ggcaacttag acaactgagt attgatctga ggacagtcga   3480
atctacctgc tgggtgtgag ctatttgaag atactggggt tgggagtgaa gaaactgcag   3540
aggactaact gggctgagac cgaatggtaa tgttttaggg cctaaggagt gcctctaaaa   3600
atctagacgg acaattttga cattgacaaa agagaggtgg aaatgaggaa aatgactttt   3660
ctttattaga ttccggtaga aagaactttc atctttccct catttttgtt atttgtttta   3720
aaacatctat ctggaggcag gacaagtatg gtcattaaaa agatgcaggc agaaggcata   3780
tattggccca gtcaaagtgg ggaactctgg tgaccaaaca gagtctgagg ctattcctat   3840
atcagctgga cacatacaaa atgccgcctc gaggtcgacg tagataagta gcatggcggg   3900
ttaatcatta actacaagga acccctagtg atggagttgg ccactccctc tctgcgcgct   3960
cgctcgctca ctgaggccgg gcgaccaaag gtcgcccgac gcccgggctt tgcccgggcg   4020
```

```
gcctcagtga gcgagcgagc gcgccagctg gcgtaatagc gaagaggccc gcaccgatcg   4080
cccttcccaa cagttgcgca gcctgaatgg cgaatggcga ttccgttgca atggctggcg   4140
gtaatattgt tctggatatt accagcaagg ccgatagttt gagttcttct actcaggcaa   4200
gtgatgttat tactaatcaa agaagtattg cgacaacggt taatttgcgt gatggacaga   4260
ctcttttact cggtggcctc actgattata aaaacacttc tcaggattct ggcgtaccgt   4320
tcctgtctaa aatcccttta atcggcctcc tgtttagctc ccgctctgat tctaacgagg   4380
aaagcacgtt atacgtgctc gtcaaagcaa ccatagtacg cgccctgtag cggcgcatta   4440
agcgcggcgg gtgtggtggt tacgcgcagc gtgaccgcta cacttgccag cgccctagcg   4500
cccgctcctt tcgctttctt cccttccttt ctcgccacgt tcgccggctt tccccgtcaa   4560
gctctaaatc gggggctccc tttagggttc cgatttagtg ctttacggca cctcgacccc   4620
aaaaaacttg attagggtga tggttcacgt agtgggccat cgccctgata gacggttttt   4680
cgccctttga cgttggagtc cacgttcttt aatagtggac tcttgttcca aactggaaca   4740
acactcaacc ctatctcggt ctattctttt gatttataag ggattttgcc gatttcggcc   4800
tattggttaa aaaatgagct gatttaacaa aaatttaacg cgaattttaa caaaatatta   4860
acgtttacaa tttaaatatt tgcttataca atcttcctgt ttttggggct tttctgatta   4920
tcaaccgggg tacatatgat tgacatgcta gttttacgat taccgttcat cgattctctt   4980
gtttgctcca gactctcagg caatgacctg atagcctttg tagagacctc tcaaaaatag   5040
ctaccctctc cggcatgaat ttatcagcta gaacggttga atatcatatt gatggtgatt   5100
tgactgtctc cggcctttct cacccgtttg aatctttacc tacacattac tcaggcattg   5160
catttaaaat atatgagggt tctaaaaatt tttatccttg cgttgaaata aaggcttctc   5220
ccgcaaaagt attacagggt cataatgttt ttggtacaac cgatttagct ttatgctctg   5280
aggctttatt gcttaatttt gctaattctt tgccttgcct gtatgattta ttggatgttg   5340
gaatcgcctg atgcggtatt ttctccttac gcatctgtgc ggtatttcac accgcatatg   5400
gtgcactctc agtacaatct gctctgatgc cgcatagtta agccagcccc gacacccgcc   5460
aacacccgct gacgcgccct gacgggcttg tctgctcccg gcatccgctt acagacaagc   5520
tgtgaccgtc tccgggagct gcatgtgtca gaggttttca ccgtcatcac cgaaacgcgc   5580
gagacgaaag ggcctcgtga tacgcctatt tttataggtt aatgtcatga taataatggt   5640
ttcttagacg tcaggtggca cttttcgggg aaatgtgcgc ggaaccccta tttgtttatt   5700
tttctaaata cattcaaata tgtatccgct catgagacaa taaccctgat aaatgcttca   5760
ataatattga aaaaggaaga gtatgagtat tcaacatttc cgtgtcgccc ttattccctt   5820
ttttgcggca ttttgccttc ctgtttttgc tcacccagaa acgctggtga aagtaaaaga   5880
tgctgaagat cagttgggtg cacgagtggg ttacatcgaa ctggatctca acagcggtaa   5940
gatccttgag agttttcgcc ccgaagaacg ttttccaatg atgagcactt ttaaagttct   6000
gctatgtggc gcggtattat cccgtattga cgccgggcaa gagcaactcg gtcgccgcat   6060
acactattct cagaatgact tggttgagta ctcaccagtc acagaaaagc atcttacgga   6120
tggcatgaca gtaagagaat tatgcagtgc tgccataacc atgagtgata acactgcggc   6180
caacttactt ctgacaacga tcggaggacc gaaggagcta accgcttttt tgcacaacat   6240
gggggatcat gtaactcgcc ttgatcgttg ggaaccggag ctgaatgaag ccataccaaa   6300
cgacgagcgt gacaccacga tgcctgtagc aatggcaaca acgttgcgca aactattaac   6360
```

```
tggcgaacta cttactctag cttcccggca acaattaata gactggatgg aggcggataa   6420
agttgcagga ccacttctgc gctcggccct tccggctggc tggtttattg ctgataaatc   6480
tggagccggt gagcgtgggt ctcgcggtat cattgcagca ctggggccag atggtaagcc   6540
ctcccgtatc gtagttatct acacgacggg gagtcaggca actatggatg aacgaaatag   6600
acagatcgct gagataggtg cctcactgat taagcattgg taactgtcag accaagttta   6660
ctcatatata ctttagattg atttaaaact tcatttttaa tttaaaagga tctaggtgaa   6720
gatccttttt gataatctca tgaccaaaat cccttaacgt gagttttcgt tccactgagc   6780
gtcagacccc gtagaaaaga tcaaaggatc ttcttgagat cctttttttc tgcgcgtaat   6840
ctgctgcttg caaacaaaaa aaccaccgct accagcggtg gtttgtttgc cggatcaaga   6900
gctaccaact ctttttccga aggtaactgg cttcagcaga gcgcagatac caaatactgt   6960
ccttctagtg tagccgtagt taggccacca cttcaagaac tctgtagcac cgcctacata   7020
cctcgctctg ctaatcctgt taccagtggc tgctgccagt ggcgataagt cgtgtcttac   7080
cgggttggac tcaagacgat agttaccgga taaggcgcag cggtcgggct gaacgggggg   7140
ttcgtgcaca cagcccagct tggagcgaac gacctacacc gaactgagat acctacagcg   7200
tgagctatga gaaagcgcca cgcttcccga agggagaaag gcggacaggt atccggtaag   7260
cggcagggtc ggaacaggag agcgcacgag ggagcttcca gggggaaacg cctggtatct   7320
ttatagtcct gtcgggtttc gccacctctg acttgagcgt cgatttttgt gatgctcgtc   7380
aggggggcgg agcctatgga aaaacgccag caacgcggcc tttttacggt tcctggcctt   7440
ttgctggcct tttgctcaca tgttctttcc tgcgttatcc cctgattctg tggataaccg   7500
tattaccgcc tttgagtgag ctgataccgc tcgccgcagc cgaacgaccg agcgcagcga   7560
gtcagtgagc gaggaagcgg aagagcgccc aatacgcaaa ccgcctctcc ccgcgcgttg   7620
gccgattcat taatg                                                    7635
```

<210> SEQ ID NO 56
<211> LENGTH: 8285
<212> TYPE: DNA
<213> ORGANISM: Artificial
<220> FEATURE:
<223> OTHER INFORMATION: AAV donor template

<400> SEQUENCE: 56

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt cctacgcgta gatctggtgc ctacatacat acctgaataa gaaaaaaaaa    180
tacctttgct gagatgaaac acacatgatt tatttcaaat aggtacagag aagtagatac    240
tgaagtaagg attaagtatt atattatatt acataacatt aatctattcc tgcactgaaa    300
ccgttgcttt atatgatttt ttttttcact acactaatga gaacttaaga gataatggcc    360
taaaaccaca gagagtattt tcaaagataa gtatagcaca atgcttacta aatgagacta    420
agacttgtcc catcgaaaat cctggaccta tgcctaaaac acgtgtcaca atccccgaac    480
ttttcaaaaa ttggtacatg ctttaacttt aatctccagg cctcactgga gctagagaca    540
agaaggtaaa aaaaggctga caaaagaagt cctggtatct tctatggtgg gagaaggaaa    600
ctagctaaag ggaagaataa attagagaaa aattggaatg attgaatcgg aacaaggcaa    660
aggctataaa aaaattaagc agcagtatcc tcttgggggc cccttcccca cactatctca    720
atgcaaatat ctgtctgaaa cggtccctgg ctaaactcca cccatgggtt ggccagtctt    780
```

-continued

```
gccttgacgc tagcgtaaat acacttgcaa aggaggatgt ttttagtagc aatttgtact    840
gatggtatgg ggccaagaga tatatcttag agggagggct gagggtttga agtccaactc    900
ctaagccagt gccagaagag ccaaggacag gtacggctgt catcacttag acctcaccct    960
gtggagccac accctagggt tggccaatct actcccagga gcagggaggg caggagccag   1020
ggctgggcat aaaagtcagg gcagagccat ctattgctta catttgcttc tgacacaact   1080
gtgttcacta gcaacctcaa acagacacca tggtgcacct gactcctgag gagaagtctg   1140
ccgttactgc cctgtggggc aaggtgaacg tggatgaagt tggtggtgag gccctgggca   1200
ggttggtatc aaggttacaa gacaggttta aggagaccaa tagaaactgg gcatgtggag   1260
acagagaaga ctcttgggtt tctgataggc actgactctc tctgcctatt ggtctatttt   1320
cccaccctta ggctgctggt ggtctaccct tggacccaga ggttctttga gtcctttggg   1380
gatctgtcca ctcctgatgc tgttatgggc aaccctaagg tgaaggctca tggcaagaaa   1440
gtgctcggtg cctttagtga tggcctggct cacctggaca acctcaaggg cacctttgcc   1500
cagctgagtg agctgcactg tgacaagctg cacgtggatc ctgagaactt cagggtgagt   1560
ctatgggacc cttgatgttt tctttcccct tcttttctat ggttaagttc atgtcatagg   1620
aaggggagaa gtaacagggt acacatattg accaaatcag ggtaattttg catttgtaat   1680
tttaaaaaat gctttcttct tttaatatac ttttttgttt atcttatttc taatactttc   1740
cctaatctct ttctttcagg gcaataatga tacaatgtat catgcctctt tgcaccattc   1800
taaagaataa cagtgataat ttctgggtta aggcaatagc aatatttctg catataaata   1860
tttctgcata taaattgtaa ctgatgtaag aggtttcata ttgctaatag cagctacaat   1920
ccagctacca ttctgctttt attttatggt tgggataagg ctggattatt ctgagtccaa   1980
gctaggccct tttgctaatc atgttcatac ctcttatctt cctcccacag ctcctgggca   2040
acgtgctggt ctgtgtgctg gcccatcact ttggcaaaga attcacccca ccagtgcagg   2100
ctgcctatca gaaagtggtg gctggtgtgg ctaatgccct ggcccacaag tatcactaag   2160
ctcgctttct tgctgtccaa tttctattaa aggttccttt gttccctaag tccaactact   2220
aaactggggg atattatgaa gggccttgag catctggatt ctgcctaata aaaaacattt   2280
attttcattg caatgatgta tttaaattat ttctgaatat tttactaaaa agggaatgtg   2340
ggaggttgca gtgctagtct cccggaacta tcactctttc acagtctgct ttggaaggac   2400
tgggcttagt atgaaaagtt aggactgaga agaatttgaa agggggcttt ttgtagcttg   2460
atattcacta ctgtcttatt accctatcat aggcccaccc caaatggaag tcccattctt   2520
cctcaggatg tttaagatta gcattcagga agagatcaga ggtctgctgg ctcccttatc   2580
atgtccctta tggtgcttct ggctctgcac cgcggccacg ggttggggt tgcgcctttt   2640
ccaaggcagc cctgggtttg cgcagggacg cggctgctct gggcgtggtt ccgggaaacg   2700
cagcggcgcc gaccctgggt ctcgcacatt cttcacgtcc gttcgcagcg tcacccggat   2760
cttcgccgct acccttgtgg gccccccggc gacgcttcct gctccgcccc taagtcggga   2820
aggttccttg cggttcgcgg cgtgccggac gtgacaaacg gaagccgcac gtctcactag   2880
taccctcgca gacggacagc gccagggagc aatggcagcg cgccgaccgc gatgggctgt   2940
ggccaatagc ggctgctcag cggggcgcgc cgagagcagc ggccgggaag gggcggtgcg   3000
ggaggcgggg tgtggggcgg tagtgtgggc cctgttcctg cccgcgcggt gttccgcatt   3060
ctgcaagcct ccggagcgca cgtcggcagt cggctccctc gttgaccgaa tcaccgacct   3120
```

-continued

```
ctctccccag cggccgcgcc gccaccatgg acaaggattg tgaaatgaaa cgcaccacac   3180
tggacagccc tttggggaag ctggagctgt ctggttgtga gcagggtctg cacgaaataa   3240
agctcctggg caaggggacg tctgcagctg atgccgtgga ggtcccagcc cccgctgcgg   3300
ttctcggagg tccggagccc ctgatgcagt gcacagcctg gctgaatgcc tatttccacc   3360
agcccgaggc tatcgaagag ttccccgtgc cggctcttca ccatcccgtt ttccagcaag   3420
agtcgttcac cagacaggtg ttatggaagc tgctgaaggt tgtgaaattc ggagaagtga   3480
tttcttacca gcaattagca gccctggcag gcaaccccaa agccgcgcga gcagtgggag   3540
gagcaatgag aggcaatcct gtcaaaatcc tcatcccgtg ccacagagtg gtctgcagca   3600
gcggagccgt gggcaactac tccggaggac tggccgtgaa ggaatggctt ctggcccatg   3660
aaggccaccg gttggggaag ccaggcttgg gagggagctc aggtctggca ggggcctggc   3720
tcaagggagc gggagctacc tcgggctccc cgcctgctgg ccgaaactaa gctttatttg   3780
tgaaatttgt gatgctattg ctttatttgt aaccattata agctgcaata aacaagttaa   3840
caacaacaat tgcattcatt ttatgtttca ggttcagggg gagatgtggg aggtttttta   3900
aagccctgca ggcaatagcc ttgacaaggc aaccttgacc aatagtctta gagtatcagg   3960
tgaggccagg ggccggcggc tggctaggga tgaagaataa aaggaagcac cctccagcag   4020
ttccacacac tcgcttctgg aacggctgag attatcaata agctcctagt ccagacgcca   4080
tgggtcattt cacagaggag gacaaggcta ctatcacaag cctgtggggc aaggtgaatg   4140
tggaagatgc tggaggagaa accctgggaa ggtaggctct ggtgaccagg acaaggaagg   4200
gaaggaagga ccctgtgcct ggcaaaagtc caggccactt ctcaggattt gtggcacttt   4260
ctgactgtca aactgctctt gttcaatctc acaggctcct ggttgtctac ccatggaccc   4320
agaggttctt tgacagcttt ggcaacctgt cctctgcctc tgccatcatg ggcaacccca   4380
aggtcaaggc acacggcaag aaggtgctga cttccttggg agatgccata aagaacctgg   4440
atgatctcaa gggcaccttt gcccagctga gtgagctgca ctgtgacaag ctgcatgtgg   4500
atcctgagaa cttcagggtg agtccaggag tttcagcagt ttcagagttc agtctcaagg   4560
cgtcgacagg aacccctagt gatggagttg gccactccct ctctgcgcgc tcgctcgctc   4620
actgaggccg ggcgaccaaa ggtcgcccga cgcccgggct ttgcccgggc ggcctcagtg   4680
agcgagcgag cgcgcagctg gcgtaatagc gaagaggccc gcaccgatcg cccttcccaa   4740
cagttgcgca gcctgaatgg cgaatggcga ttccgttgca atggctggcg gtaatattgt   4800
tctggatatt accagcaagg ccgatagttt gagttcttct actcaggcaa gtgatgttat   4860
tactaatcaa agaagtattg cgacaacggt taatttgcgt gatggacaga ctcttttact   4920
cggtggcctc actgattata aaaacacttc tcaggattct ggcgtaccgt tcctgtctaa   4980
aatcccttta atcggcctcc tgtttagctc ccgctctgat tctaacgagg aaagcacgtt   5040
atacgtgctc gtcaaagcaa ccatagtacg cgccctgtag cggcgcatta agcgcggcgg   5100
gtgtggtggt tacgcgcagc gtgaccgcta cacttgccag cgccctagcg cccgctcctt   5160
tcgctttctt cccttccttt ctcgccacgt tcgccggctt tccccgtcaa gctctaaatc   5220
gggggctccc tttagggttc cgatttagtg ctttacggca cctcgacccc aaaaaacttg   5280
attagggtga tggttcacgt agtgggccat cgccctgata gacggttttt cgccctttga   5340
cgttggagtc cacgttcttt aatagtggac tcttgttcca aactggaaca acactcaacc   5400
ctatctcggt ctattctttt gatttataag ggattttgcc gatttcggcc tattggttaa   5460
aaaatgagct gatttaacaa aaatttaacg cgaattttaa caaaatatta acgtttacaa   5520
```

-continued

```
tttaaatatt tgcttataca atcttcctgt ttttggggct tttctgatta tcaaccgggg   5580
tacatatgat tgacatgcta gttttacgat taccgttcat cgattctctt gtttgctcca   5640
gactctcagg caatgacctg atagcctttg tagagacctc tcaaaaatag ctaccctctc   5700
cggcatgaat ttatcagcta gaacggttga atatcatatt gatggtgatt tgactgtctc   5760
cggcctttct cacccgtttg aatctttacc tacacattac tcaggcattg catttaaaat   5820
atatgagggt tctaaaaatt tttatccttg cgttgaaata aaggcttctc ccgcaaaagt   5880
attacagggt cataatgttt ttggtacaac cgatttagct ttatgctctg aggctttatt   5940
gcttaatttt gctaattctt tgccttgcct gtatgattta ttggatgttg gaatcgcctg   6000
atgcggtatt ttctccttac gcatctgtgc ggtatttcac accgcatatg gtgcactctc   6060
agtacaatct gctctgatgc cgcatagtta agccagcccc gacacccgcc aacacccgct   6120
gacgcgccct gacgggcttg tctgctcccg gcatccgctt acagacaagc tgtgaccgtc   6180
tccgggagct gcatgtgtca gaggttttca ccgtcatcac cgaaacgcgc gagacgaaag   6240
ggcctcgtga tacgcctatt tttataggtt aatgtcatga taataatggt ttcttagacg   6300
tcaggtggca cttttcgggg aaatgtgcgc ggaaccccta tttgtttatt tttctaaata   6360
cattcaaata tgtatccgct catgagacaa taaccctgat aaatgcttca ataatattga   6420
aaaaggaaga gtatgagtat tcaacatttc cgtgtcgccc ttattccctt ttttgcggca   6480
ttttgccttc ctgtttttgc tcacccagaa acgctggtga aagtaaaaga tgctgaagat   6540
cagttgggtg cacgagtggg ttacatcgaa ctggatctca acagcggtaa gatccttgag   6600
agttttcgcc ccgaagaacg ttttccaatg atgagcactt ttaaagttct gctatgtggc   6660
gcggtattat cccgtattga cgccgggcaa gagcaactcg gtcgccgcat acactattct   6720
cagaatgact tggttgagta ctcaccagtc acagaaaagc atcttacgga tggcatgaca   6780
gtaagagaat tatgcagtgc tgccataacc atgagtgata acactgcggc caacttactt   6840
ctgacaacga tcggaggacc gaaggagcta accgcttttt tgcacaacat gggggatcat   6900
gtaactcgcc ttgatcgttg ggaaccggag ctgaatgaag ccataccaaa cgacgagcgt   6960
gacaccacga tgcctgtagc aatggcaaca acgttgcgca aactattaac tggcgaacta   7020
cttactctag cttcccggca acaattaata gactggatgg aggcggataa agttgcagga   7080
ccacttctgc gctcggccct tccggctggc tggtttattg ctgataaatc tggagccggt   7140
gagcgtgggt ctcgcggtat cattgcagca ctggggccag atggtaagcc ctcccgtatc   7200
gtagttatct acacgacggg gagtcaggca actatggatg aacgaaatag acagatcgct   7260
gagataggtg cctcactgat taagcattgg taactgtcag accaagttta ctcatatata   7320
ctttagattg atttaaaact tcatttttaa tttaaaagga tctaggtgaa gatccttttt   7380
gataatctca tgaccaaaat cccttaacgt gagttttcgt tccactgagc gtcagacccc   7440
gtagaaaaga tcaaaggatc ttcttgagat cctttttttc tgcgcgtaat ctgctgcttg   7500
caaacaaaaa aaccaccgct accagcggtg gtttgtttgc cggatcaaga gctaccaact   7560
ctttttccga aggtaactgg cttcagcaga gcgcagatac caaatactgt ccttctagtg   7620
tagccgtagt taggccacca cttcaagaac tctgtagcac cgcctacata cctcgctctg   7680
ctaatcctgt taccagtggc tgctgccagt ggcgataagt cgtgtcttac cgggttggac   7740
tcaagacgat agttaccgga taaggcgcag cggtcgggct gaacgggggg ttcgtgcaca   7800
cagcccagct tggagcgaac gacctacacc gaactgagat acctacagcg tgagctatga   7860
```

```
gaaagcgcca cgcttcccga agggagaaag gcggacaggt atccggtaag cggcagggtc   7920

ggaacaggag agcgcacgag ggagcttcca gggggaaacg cctggtatct ttatagtcct   7980

gtcgggtttc gccacctctg acttgagcgt cgatttttgt gatgctcgtc aggggggcgg   8040

agcctatgga aaaacgccag caacgcggcc tttttacggt tcctggcctt ttgctggcct   8100

tttgctcaca tgttctttcc tgcgttatcc cctgattctg tggataaccg tattaccgcc   8160

tttgagtgag ctgataccgc tcgccgcagc cgaacgaccg agcgcagcga gtcagtgagc   8220

gaggaagcgg aagagcgccc aatacgcaaa ccgcctctcc ccgcgcgttg gccgattcat   8280

taatg                                                                8285
```

<210> SEQ ID NO 57
<211> LENGTH: 8214
<212> TYPE: DNA
<213> ORGANISM: Artificial
<220> FEATURE:
<223> OTHER INFORMATION: AAV donor template

<400> SEQUENCE: 57

```
cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt cctacgcgta gatctggtgc ctacatacat acctgaataa gaaaaaaaaa    180

tacctttgct gagatgaaac acacatgatt tatttcaaat aggtacagag aagtagatac    240

tgaagtaagg attaagtatt atattatatt acataacatt aatctattcc tgcactgaaa    300

ccgttgcttt atatgatttt tttttcact acactaatga gaacttaaga gataatggcc    360

taaaaccaca gagagtattt tcaaagataa gtatagcaca atgcttacta aatgagacta    420

agacttgtcc catcgaaaat cctggaccta tgcctaaaac acgtgtcaca atccccgaac    480

ttttcaaaaa ttggtacatg ctttaacttt aatctccagg cctcactgga gctagagaca    540

agaaggtaaa aaaaggctga caaaagaagt cctggtatct tctatggtgg gagaaggaaa    600

ctagctaaag ggaagaataa attagagaaa aattggaatg attgaatcgg aacaaggcaa    660

aggctataaa aaaattaagc agcagtatcc tcttgggggc cccttcccca cactatctca    720

atgcaaatat ctgtctgaaa cggtccctgg ctaaactcca cccatgggtt ggccagtctt    780

gccttgacgc tagcgtaaat acacttgcaa aggaggatgt ttttagtagc aatttgtact    840

gatggtatgg ggccaagaga tatatcttag agggagggct gagggtttga agtccaactc    900

ctaagccagt gccagaagag ccaaggacag gtacggctgt catcacttag acctcaccct    960

gtggagccac accctagggt tggccaatct actcccagga gcagggaggg caggagccag   1020

ggctgggcat aaaagtcagg gcagagccat ctattgctta catttgcttc tgacacaact   1080

gtgttcacta gcaacctcaa acagacacca tggtgcacct gactcctgag gagaagtctg   1140

ccgttactgc cctgtggggc aaggtgaacg tggatgaagt tggtggtgag gccctgggca   1200

ggttggtatc aaggttacaa gacaggttta aggagaccaa tagaaactgg gcatgtggag   1260

acagagaaga ctcttgggtt tctgataggc actgactctc tctgcctatt ggtctatttt   1320

cccaccctta ggctgctggt ggtctaccct tggacccaga ggttctttga gtcctttggg   1380

gatctgtcca ctcctgatgc tgttatgggc aaccctaagg tgaaggctca tggcaagaaa   1440

gtgctcggtg cctttagtga tggcctggct cacctggaca acctcaaggg cacctttgcc   1500

cagctgagtg agctgcactg tgacaagctg cacgtggatc ctgagaactt cagggtgagt   1560

ctatgggacc cttgatgttt tctttcccct tcttttctat ggttaagttc atgtcatagg   1620
```

aaggggagaa gtaacagggt acacatattg accaaatcag ggtaattttg catttgtaat 1680
tttaaaaaat gctttcttct tttaatatac ttttttgttt atcttatttc taatactttc 1740
cctaatctct ttctttcagg gcaataatga tacaatgtat catgcctctt tgcaccattc 1800
taaagaataa cagtgataat ttctgggtta aggcaatagc aatatttctg catataaata 1860
tttctgcata taaattgtaa ctgatgtaag aggtttcata ttgctaatag cagctacaat 1920
ccagctacca ttctgctttt attttatggt tgggataagg ctggattatt ctgagtccaa 1980
gctaggccct tttgctaatc atgttcatac ctcttatctt cctcccacag ctcctgggca 2040
acgtgctggt ctgtgtgctg gcccatcact ttggcaaaga attcacccca ccagtgcagg 2100
ctgcctatca gaaagtggtg gctggtgtgg ctaatgccct ggcccacaag tatcactaag 2160
ctcgctttct tgctgtccaa tttctattaa aggttccttt gttccctaag tccaactact 2220
aaactggggg atattatgaa gggccttgag catctggatt ctgcctaata aaaaacattt 2280
attttcattg caatgatgta tttaaattat ttctgaatat tttactaaaa agggaatgtg 2340
ggaggttgca gtgctagtct cccggaacta tcactctttc acagtctgct ttggaaggac 2400
tgggcttagt atgaaaagtt aggactgaga agaatttgaa agggggcttt ttgtagcttg 2460
atattcacta ctgtcttatt accctatcat aggcccaccc caaatggaag tcccattctt 2520
cctcaggatg tttaagatta gcattcagga agagatcaga ggtctgctgg ctcccttatc 2580
atgtccctta tggtgcttct ggctctgcac cgcgggaaca gagaaacagg agaatatggg 2640
ccaaacagga tatctgtggt aagcagttcc tgccccggct cagggccaag aacagttgga 2700
acagcagaat atgggccaaa caggatatct gtggtaagca gttcctgccc cggctcaggg 2760
ccaagaacag atggtcccca gatgcggtcc cgccctcagc agtttctaga gaaccatcag 2820
atgtttccag ggtgccccaa ggacctgaaa tgaccctgtg ccttatttga actaaccaat 2880
cagttcgctt ctcgcttctg ttcgcgcgct tctgctcccc gagctctata taagcagagc 2940
tcgtttagtg aaccgtcaga tcgcggccgc gccgccacca tggtgagcaa gggcgaggag 3000
ctgttcaccg gggtggtgcc catcctggtc gagctggacg gcgacgtaaa cggccacaag 3060
ttcagcgtgt ccggcgaggg cgagggcgat gccacctacg gcaagctgac cctgaagttc 3120
atctgcacca ccggcaagct gcccgtgccc tggcccaccc tcgtgaccac cctgacctac 3180
ggcgtgcagt gcttcagccg ctaccccgac cacatgaagc agcacgactt cttcaagtcc 3240
gccatgcccg aaggctacgt ccaggagcgc accatcttct tcaaggacga cggcaactac 3300
aagacccgcg ccgaggtgaa gttcgagggc gacaccctgg tgaaccgcat cgagctgaag 3360
ggcatcgact tcaaggagga cggcaacatc ctggggcaca agctggagta caactacaac 3420
agccacaacg tctatatcat ggccgacaag cagaagaacg gcatcaaggt gaacttcaag 3480
atccgccaca acatcgagga cggcagcgtg cagctcgccg accactacca gcagaacacc 3540
cccatcggcg acggccccgt gctgctgccc gacaaccact acctgagcac ccagtccgcc 3600
ctgagcaaag accccaacga gaagcgcgat cacatggtcc tgctggagtt cgtgaccgcc 3660
gccgggatca ctctcggcat ggacgagctg tacaagtaag ctttatttgt gaaatttgtg 3720
atgctattgc tttatttgta accattataa gctgcaataa acaagttaac aacaacaatt 3780
gcattcattt tatgtttcag gttcaggggg agatgtggga ggtttttttaa agccctgcag 3840
gcaatagcct tgacaaggca accttgacca atagtcttag agtatcaggt gaggccaggg 3900
gccggcggct ggctagggat gaagaataaa aggaagcacc ctccagcagt tccacacact 3960

-continued

```
cgcttctgga acggctgaga ttatcaataa gctcctagtc cagacgccat gggtcatttc   4020
acagaggagg acaaggctac tatcacaagc ctgtggggca aggtgaatgt ggaagatgct   4080
ggaggagaaa ccctgggaag gtaggctctg gtgaccagga caaggaaggg aaggaaggac   4140
cctgtgcctg gcaaaagtcc aggccacttc tcaggatttg tggcactttc tgactgtcaa   4200
actgctcttg ttcaatctca caggctcctg gttgtctacc catggaccca gaggttcttt   4260
gacagctttg gcaacctgtc ctctgcctct gccatcatgg gcaaccccaa ggtcaaggca   4320
cacggcaaga aggtgctgac ttccttggga gatgccataa agaacctgga tgatctcaag   4380
ggcacctttg cccagctgag tgagctgcac tgtgacaagc tgcatgtgga tcctgagaac   4440
ttcagggtga gtccaggagt ttcagcagtt tcagagttca gtctcaaggc gtcgacagga   4500
acccctagtg atggagttgg ccactccctc tctgcgcgct cgctcgctca ctgaggccgg   4560
gcgaccaaag gtcgcccgac gcccgggctt tgcccgggcg gcctcagtga gcgagcgagc   4620
gcgcagctgg cgtaatagcg aagaggcccg caccgatcgc ccttcccaac agttgcgcag   4680
cctgaatggc gaatggcgat tccgttgcaa tggctggcgg taatattgtt ctggatatta   4740
ccagcaaggc cgatagtttg agttcttcta ctcaggcaag tgatgttatt actaatcaaa   4800
gaagtattgc gacaacggtt aatttgcgtg atggacagac tcttttactc ggtggcctca   4860
ctgattataa aaacacttct caggattctg gcgtaccgtt cctgtctaaa atccctttaa   4920
tcggcctcct gtttagctcc cgctctgatt ctaacgagga aagcacgtta tacgtgctcg   4980
tcaaagcaac catagtacgc gccctgtagc ggcgcattaa gcgcggcggg tgtggtggtt   5040
acgcgcagcg tgaccgctac acttgccagc gccctagcgc ccgctccttt cgctttcttc   5100
ccttcctttc tcgccacgtt cgccggcttt ccccgtcaag ctctaaatcg ggggctccct   5160
ttagggttcc gatttagtgc tttacggcac ctcgacccca aaaaacttga ttagggtgat   5220
ggttcacgta gtgggccatc gccctgatag acggtttttc gccctttgac gttggagtcc   5280
acgttcttta atagtggact cttgttccaa actggaacaa cactcaaccc tatctcggtc   5340
tattcttttg atttataagg gattttgccg atttcggcct attggttaaa aaatgagctg   5400
atttaacaaa aatttaacgc gaattttaac aaaatattaa cgtttacaat ttaaatattt   5460
gcttatacaa tcttcctgtt tttggggctt ttctgattat caaccggggt acatatgatt   5520
gacatgctag ttttacgatt accgttcatc gattctcttg tttgctccag actctcaggc   5580
aatgacctga tagcctttgt agagacctct caaaaatagc taccctctcc ggcatgaatt   5640
tatcagctag aacggttgaa tatcatattg atggtgattt gactgtctcc ggcctttctc   5700
acccgtttga atctttacct acacattact caggcattgc atttaaaata tatgagggtt   5760
ctaaaaattt ttatccttgc gttgaaataa aggcttctcc cgcaaaagta ttacagggtc   5820
ataatgtttt tggtacaacc gatttagctt tatgctctga ggctttattg cttaattttg   5880
ctaattcttt gccttgcctg tatgatttat tggatgttgg aatcgcctga tgcggtattt   5940
tctccttacg catctgtgcg gtatttcaca ccgcatatgg tgcactctca gtacaatctg   6000
ctctgatgcc gcatagttaa gccagccccg acacccgcca acacccgctg acgcgccctg   6060
acgggcttgt ctgctcccgg catccgctta cagacaagct gtgaccgtct ccgggagctg   6120
catgtgtcag aggttttcac cgtcatcacc gaaacgcgcg agacgaaagg gcctcgtgat   6180
acgcctattt ttataggtta atgtcatgat aataatggtt tcttagacgt caggtggcac   6240
ttttcgggga aatgtgcgcg gaacccctat ttgtttattt ttctaaatac attcaaatat   6300
gtatccgctc atgagacaat aaccctgata aatgcttcaa taatattgaa aaaggaagag   6360
```

```
tatgagtatt caacatttcc gtgtcgccct tattcccttt tttgcggcat tttgccttcc   6420

tgtttttgct cacccagaaa cgctggtgaa agtaaaagat gctgaagatc agttgggtgc   6480

acgagtgggt tacatcgaac tggatctcaa cagcggtaag atccttgaga gttttcgccc   6540

cgaagaacgt tttccaatga tgagcacttt taaagttctg ctatgtggcg cggtattatc   6600

ccgtattgac gccgggcaag agcaactcgg tcgccgcata cactattctc agaatgactt   6660

ggttgagtac tcaccagtca cagaaaagca tcttacggat ggcatgacag taagagaatt   6720

atgcagtgct gccataacca tgagtgataa cactgcggcc aacttacttc tgacaacgat   6780

cggaggaccg aaggagctaa ccgctttttt gcacaacatg ggggatcatg taactcgcct   6840

tgatcgttgg gaaccggagc tgaatgaagc cataccaaac gacgagcgtg acaccacgat   6900

gcctgtagca atggcaacaa cgttgcgcaa actattaact ggcgaactac ttactctagc   6960

ttcccggcaa caattaatag actggatgga ggcggataaa gttgcaggac cacttctgcg   7020

ctcggccctt ccggctggct ggtttattgc tgataaatct ggagccggtg agcgtgggtc   7080

tcgcggtatc attgcagcac tggggccaga tggtaagccc tcccgtatcg tagttatcta   7140

cacgacgggg agtcaggcaa ctatggatga acgaaataga cagatcgctg agataggtgc   7200

ctcactgatt aagcattggt aactgtcaga ccaagtttac tcatatatac tttagattga   7260

tttaaaactt catttttaat ttaaaaggat ctaggtgaag atcctttttg ataatctcat   7320

gaccaaaatc ccttaacgtg agttttcgtt ccactgagcg tcagaccccg tagaaaagat   7380

caaaggatct tcttgagatc ctttttttct gcgcgtaatc tgctgcttgc aaacaaaaaa   7440

accaccgcta ccagcggtgg tttgtttgcc ggatcaagag ctaccaactc tttttccgaa   7500

ggtaactggc ttcagcagag cgcagatacc aaatactgtc cttctagtgt agccgtagtt   7560

aggccaccac ttcaagaact ctgtagcacc gcctacatac ctcgctctgc taatcctgtt   7620

accagtggct gctgccagtg gcgataagtc gtgtcttacc gggttggact caagacgata   7680

gttaccggat aaggcgcagc ggtcgggctg aacggggggt tcgtgcacac agcccagctt   7740

ggagcgaacg acctacaccg aactgagata cctacagcgt gagctatgag aaagcgccac   7800

gcttcccgaa gggagaaagg cggacaggta tccggtaagc ggcagggtcg gaacaggaga   7860

gcgcacgagg gagcttccag ggggaaacgc ctggtatctt tatagtcctg tcgggtttcg   7920

ccacctctga cttgagcgtc gatttttgtg atgctcgtca ggggggcgga gcctatggaa   7980

aaacgccagc aacgcggcct ttttacggtt cctggccttt tgctggcctt ttgctcacat   8040

gttctttcct gcgttatccc ctgattctgt ggataaccgt attaccgcct ttgagtgagc   8100

tgataccgct cgccgcagcc gaacgaccga gcgcagcgag tcagtgagcg aggaagcgga   8160

agagcgccca atacgcaaac cgcctctccc cgcgcgttgg ccgattcatt aatg          8214
```

<210> SEQ ID NO 58
<211> LENGTH: 15824
<212> TYPE: DNA
<213> ORGANISM: Artificial
<220> FEATURE:
<223> OTHER INFORMATION: TALEN plasmid sequence

<400> SEQUENCE: 58

```
gcgtataatg gactattgtg tgctgataag gagaacataa gcgcagaaca atatgtatct     60

attccggtgt tgtgttcctt tgttattctg ctattatgtt ctcttatagt gtgacgaaag    120

cagcataatt aatcgccact tgttctttga ttgtgttacg atatccagag acttagaaac    180
```

-continued

```
gggggaaccg ggatgagcaa ggtaaaaatc ggtgagttga tcaacacgct tgtgaatgag    240
gtagaggcaa ttgatgcctc agaccgccca caaggcgaca aaacgaagag aattaaagcc    300
gcagccgcac ggtataagaa cgcgttattt aatgataaaa gaaagttccg tgggaaagga    360
ttgcagaaaa gaataaccgc gaatactttt aacgcctata tgagcagggc aagaaagcgg    420
tttgatgata aattacatca tagctttgat aaaaatatta ataaattatc ggaaaagtat    480
cctctttaca gcgaagaatt atcttcatgg ctttctatgc ctacggctaa tattcgccag    540
cacatgtcat cgttacaatc taaattgaaa gaaataatgc cgcttgccga agagttatca    600
aatgtaagaa taggctctaa aggcagtgat gcaaaaatag caagactaat aaaaaaatat    660
ccagattgga gttttgctct tagtgattta aacagtgatg attggaagga gcgccgtgac    720
tatctttata agttattcca acaaggctct gcgttgttag aagaactaca ccagctcaag    780
gtcaaccatg aggttctgta ccatctgcag ctaagccctg cggagcgtac atctatacag    840
caacgatggg ccgatgttct gcgcgagaag aagcgtaatg ttgtggttat tgactaccca    900
acatacatgc agtctatcta tgatattttg aataatcctg cgactttatt tagtttaaac    960
actcgttctg gaatggcacc tttggccttt gctctggctg cggtatcagg gcgaagaatg   1020
attgagataa tgtttcaggg tgaatttgcc gtttcaggaa agtatacggt taatttctca   1080
gggcaagcta aaaaacgctc tgaagataaa agcgtaacca gaacgattta tactttatgc   1140
gaagcaaaat tattcgttga attattaaca gaattgcgtt cttgctctgc tgcatctgat   1200
ttcgatgagg ttgttaaagg atatggaaag gatgatacaa ggtctgagaa cggcaggata   1260
aatgctattt tagcaaaagc atttaaccct tgggttaaat catttttcgg cgatgaccgt   1320
cgtgtttata aagatagccg cgctatttac gctcgcatcg cttatgagat gttcttccgc   1380
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaaacacc aggctggtgg ctctgcagaa actggacgat   1560
gaaatgccag gctttgccag aggtgacgct ggcgtccgtc tgcatgaaac cgttaagcag   1620
ctggtggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg aaaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacggacatc gccgtcccga ctgcagggac   2220
ttccccgcgt aaagcggggc ttaaattcgg gctggccaac cctatttttc tgcaatcgct   2280
ggcgatgtta gtttcgtgga tagcgtttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg cgcggcggag agccatccag   2580
```

-continued

```
acgccgctaa cccatgcgtt acggtactga aaactttgtg ctatgtcgtt tatcaggccc   2640
cgaagttctt ctttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagaggccag attccgatac cacatttact tccctggcca tccgatcaag tttttgtgcc   2880
tcggttaaac cgagggtcaa tttttcatca tgatccagct tacgcaatgc atcagaaggg   2940
ttggctatat tcaatgcagc acagatatcc agcgccacaa accacgggtc accaccgaca   3000
agaaccaccc gtatagggtg gctttcctga aatgaaaaga cggagagagc cttcattgcg   3060
cctccccgga tttcagctgc tcagaaaggg acagggagca gccgcgagct tcctgcgtga   3120
gttcgcgcgc gacctgcaga agttccgcag cttcctgcaa atacagcgtg gcctcataac   3180
tggagatagt gcggtgagca gagcccacaa gcgcttcaac ctgcagcagg cgttcctcaa   3240
tcgtcttcag caggccctgg gcgtttaact gaatctggtt catgcgatca cctcgctgac   3300
cgggatacgg gctgacagaa cgaggacaaa acggctggcg aactggcgac gagcttctcg   3360
ctcggatgat gcagtggtgg aaaggcggtg gatatgggat tttttgtccg tgcggacgac   3420
agctgcaaat ttgaatttga acatggtatg cattcctatc ttgtataggg tgctaccacc   3480
agagttgaga atctctatag gggtggtagc ccagacaggg ttctcaacac cggtacaaga   3540
agaaaccggc ccaaccgaag ttggccccat ctgagccacc ataattcagg tatgcgcaga   3600
tttaacacac aaaaaaacac gctggcgcgt gttgtgcgct tcttgtcatt cggggttgag   3660
aggcccggct gcagattttg ctgcagcggg gtaactctac cgccaaagca gaacgcacgt   3720
caataattta ggtggatatt ttaccccgtg accagtcacg tgcacaggtg tttttatagt   3780
ttgctttact gactgatcag aacctgatca gttattggag tccggtaatc ttattgatga   3840
ccgcagccac cttagatgtt gtctcaaacc ccatacggcc acgaatgagc cactggaacg   3900
gaatagtcag caggtacagc ggaacgaacc acaaacggtt cagacgctgc cagaacgtcg   3960
catcacgacg ttccatccat tcggtattgt cgacgacctg gtaagcgtat tgtcctggcg   4020
tttttgctgc ttccgagtag caatcctctt caccacaaag aaagttactt atctgcttcc   4080
agttttcgaa cccttcttct ttgagccgct tttccagctc attcctccac aaaacaggca   4140
cccatcctct gcgataaatc atgattattt gtcctttaaa taaggctgta gaactgcaaa   4200
atcgctctcg ttcacatgct gtacgtagat gcgtagcaaa ttgccgttcc atccctgtaa   4260
tccaccttct ttggaaagat cgtccttgac ctcacgaaga actttatcca atagccctgc   4320
ggcacaagaa attgcctgct ctggatcagc aaattcatat tgattaatag gtgattgcca   4380
cacaccaaaa acaggaatca tcttttcggc taaacgcctc tcctgttctt tcttaatctc   4440
aagttgtaag cggaccagct caccatccat catttttttgt agatcatgcg ccactattca   4500
cccccactgg ccatcagcaa ataaagcttc atactcggac accggcaggc ggcttccacg   4560
gattgaaagg tcaagccaac cacgtccaga tgggtcagcc ttatccgatt cttcccaccg   4620
ttctgcagct gtagcaacca ggcattctac cgccttcatg tagtcttctg tacggaacca   4680
gccgtagtta atgccaccat cagtaactgc ccaggccatc tttttctctt cggcctcaat   4740
agcccggatg cggttatcgc acagctcgcg acagtacttc agctgttcgt aatccagttg   4800
cttcaggaac tctggtgtcg acgtcatagt ggcttcacct tataggcttt tagaagcgcc   4860
ctggcttcgt ctgtgtggtc ttccatgctc ttatcgctgg caatgcagca ataaactccc   4920
```

-continued

```
tcactatctg agaacccgtt catccgaatg atcgtgaatg gaagttcccg gccagtttta   4980
taatcgctat agcttgtcgc gtcgtggctg accttgacca cataagggtc gtagccctcc   5040
acgatgacaa ggcattcccg ttgttttccc attacccctc cggttatatc gccacggctt   5100
gccgctggct tagaaacgct ttcagcagcc ttatttcgcg tactgatagc aggtccataa   5160
attcggtcat gtacagcgag gcgaacgttc tcgcgatgct ggccactggc cacaggcgta   5220
ccgcctccat ttcggttgct ggcaacgcgt tctccgccca cgcctccggt accgccaccg   5280
ggatagcctc cagtgcctgg ataattactg attgtggggc gtccggaacg tgctctgttt   5340
tggatcgagg gttaccatgt atatctatat ttagatccaa atcgcgatcc acttcgatgg   5400
tggtttttc caccttacgt gcgtgaattg ataaaccggc ctcgcggcgc ttctccacga   5460
tattcatgag gaactcgacc gagtccgggt caatggaacg catcgtgggg cgtgcatcgc   5520
catctctggc gcgtctggtc ttactggata gccccataga ctccaggatg cctatgcaga   5580
ggtctgcagg cgctttcttc ttgcctttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggtttttg gatcgatacc gcagtcgcgg aagtactgct   5760
gcagcgtcgc cgatttgagg gtgtagaaac cacgcatgcc tatctcaaca gcaggggtcg   5820
atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact tttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360
cggctttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgattttt tccggatcgg tttcacgttt accgcgaagc ttgtcgaaac   6540
cgataatgta ttcctgagct gtacggtcgc ggcgcagcat ctggatggcg tcgctgggga   6600
ccacttcgcc gcagaacatg ccgaaatggc ggtggaagtg tttctcctca atcgatacac   6660
ctgaagatat cgacgggctg tagatgaggc cgtcatattt tttcaccatc actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900
gatttttctc ggtataaaat acgcggatag gcttgttggt ttcgcggttg cgaacgtcga   6960
ccgggagttc aatcacgtga atttgcagcc aggcaggtag gcccagctcc tcgcgtcgct   7020
tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
```

cggctttcgc gcctttccct tcggtcatca tttcatgcag gccgcctatc agggatacgc 7380
ggtgcgcgac ggaaacgcca cgcgtggact gcagcatcag tggacgcagg aggcctgtcg 7440
atttacccga ccccatcccg gcgcggacaa taacgatgcc ctgcagctgt gcggcgtatg 7500
tcatcacctc atcggtcatc ctggaggttt caaaccgttt gtaagtgatg tgtgacgggc 7560
gaaggttcgg gttggtgatg cgttcactga acgaacgtga tgtttgcgcg gcacggcatt 7620
tgcgattcaa ccggcgcgta atgtgatctt taacggtacc gttataaatt tctgcgatac 7680
ccatatcccg cagcgtgctg ctgaaaaggc gcataagttc tttcgggctg tttggtaccg 7740
ggcatgtcag catgccaata tcaacggcgc gaagcagttc tttggcaaaa gtgcgtctgt 7800
tcagacgcgg gagagtacgc agcttattca gcgtgatcga caacagatcg gttgcacggc 7860
tcagatgatt tctcgttaac tggcgagcga cttccttcag ccctctcagg ctgtgcaggt 7920
cgttaaaatc gctgcattcc agctcagggt catcctcaaa agttgggtaa acacatttga 7980
cgccggaaaa cttctccatg atgtcgaatc cggtgcggag gcctgtgttg ccttttcctt 8040
cagctgagga tttgcggtcg ttatcgagag cgcaagtgat ttgcgcagcc gggtacatgt 8100
tcaccagctg ctcgacaacg tgaatcatgt tgttagcgga aaccgcaatg actaccgcgt 8160
caaagcgttt tttcgggtcg tttctggtcg ccagccagat ggatgccccg gtggcgaaac 8220
cctctgcagt cgcaattttt tgcgcccccct gcaggtcgcc aataacaaag catgcaccga 8280
cgaaatcacc gttagtgatg gcgctggtct ggaacttgcc accattcaga tcgatacgtt 8340
gccagccaac aatccgcccg tcttttcttc cgtccaggtg ggacagaggt atcgccatgt 8400
aagttgttgg tccacggctc catttcgcac tgtcgtgact ggtcacgcga cgtatatcac 8460
aagcgccaaa tacgtcacga attccctttt ttaccgcata aggccaggag ccatcttcag 8520
ctggcgaatg ttcccaggcg cgatggaaag ccaaccatcc aagcaggcgt tcctgctcca 8580
tctgattgtt ttttaaatca ttaacgcgtt gttgttcagc tcggaggcgg cgtgcttcag 8640
cctggcgctc catgcgtgca cgttcttctt ccggctgagc gaccacggtc gcaccattcc 8700
gttgctgttc acggcgatac tccgaaaaca ggaatgaaaa gccactccag gagccagcgt 8760
catgcgcttt ttcaacgaag ttaacgaaag gataactgat gccatccttg ctctgctcaa 8820
ggcgtgaata gatttccaca cggcctttaa ggctcttctg cagagcttcc ggggaggaat 8880
tattgtaggt ggtatagcgc tctacaccac cgcgcggatt gagctgaatc ttatcagcac 8940
acgcaggcca gttgataccg gccatcttcg ccagctcagt cagctcatca cgtgccgcgt 9000
caagcagtga aaacggatcg ctgccaaagc gctccgcgta gaattcttgt aaggtcattt 9060
tttagccttt ccatgcgaat tagcattttt tcgggttgaa aaaatccgca ggagcagcca 9120
caataaacgc actatctttc tgaaggacgt atctgcgtta tcgtggctac ttcctgaaaa 9180
aggcccgagt ttgccgactc ggtttttttt tcgtcttttt tcggctgcta cggtctggtt 9240
caaccccgac aaagtataga tcggattaaa ccagaattat agtcagcaat aaaccctgtt 9300
attgtatcat ctaccctcaa ccatgaacga tttgatcgta ccgactactt ggtgcacaaa 9360
ttgaagatca cttttatcat ggataacccg ttgagagtta gcactatcaa ggtagtaatg 9420
ctgctcgtca taacgggcta atcgttgaat tgtgatctcg ccgttattat cacaaaccag 9480
tacatcctca cccggtacaa gcgtaagtga agaatcgacc aggataacat ctcccggctg 9540
gtagtttcgc tgaatctggt tcccgaccgt cagtgcgtaa acggtgttcc gttgactcac 9600
gaacggcagg aatcgctctg tgttggcagg ttctccaggc tgccagtctc tatccggtcc 9660

-continued

```
tgtctctgtc gtaccaataa caggaacgcg gtctggatca gattcagtgc catacagtat   9720
ccattgcacg ggcttacgca ggcattttgc cagcgatagc ccgatctcca gcgacggcat   9780
cacgtcgcca cgttctaagt tttggacgcc cggaagagag attcctacag cttctgccac   9840
ttgcttcagc gtcagtttca gctctaaacg gcgtgctttc agtcgttcgc ctcgtgtttt   9900
cataccctta atcataaatg atctctttat agctggctat aatttttata aattatacct   9960
agctttaatt ttcacttatt gattataata atccccatga aacccgaaga acttgtgcgc  10020
catttcggcg atgtggaaaa agcagcggtt ggcgtgggcg tgacacccgg cgcagtctat  10080
caatggctgc aagctgggga gattccacct ctacgacaaa gcgatataga ggtccgtacc  10140
gcgtacaaat taaagagtga tttcacctct cagcgcatgg gtaaggaagg gcataacaag  10200
gggatcctct agacgcagaa aggcccaccc gaaggtgagc cagtgtgatt acatttgcgg  10260
cctaactgtg gccagtccag ttacgctgga gtcactagtg cggccgcgac aacttgtcta  10320
gggcccaatg gcccatacac ttagtgtaat acgactcact atagggagag cggccgcttt  10380
ttcagcaaga ttaagccgcc accatggcgc cgcggcctcc taagaagaag cggaaagtcg  10440
aattcgtgga tctgcgaaca ctgggctata gccagcagca gcaggagaag atcaaaccca  10500
aggtgaggtc cacagtcgca cagcaccatg aagccctggt gggccacggg ttcactcacg  10560
ctcatattgt cgcactgtct cagcatccag ccgctctggg aaccgtggca gtcacatacc  10620
agcacatcat tactgccctg cccgaggcta cccatgaaga catcgtggga gtcggcaaac  10680
agtggagcgg cgcacgggcc ctggaggctc tgctgaccga cgcaggggaa ctgagaggac  10740
cccctctgca gctggataca gggcagctgg tgaagattgc taagagggga ggggtgacag  10800
caatggaagc cgtccacgca agcaggaacg cactgacagg ggcccccctg aacctgaccc  10860
cggaccaagt ggtggctatc gccagcaatc acggcggcaa gcaagcgctc gaaacggtgc  10920
agcggctgtt gccggtgctg tgccaggacc atggcctgac cccggaccaa gtggtggcta  10980
tcgccagcaa tcacggcggc aagcaagcgc tcgaaacggt gcagcggctg ttgccggtgc  11040
tgtgccagga ccatggcctg accccggacc aagtggtggc tatcgccagc aatcacggcg  11100
gcaagcaagc gctcgaaacg gtgcagcggc tgttgccggt gctgtgccag gaccatggcc  11160
tgaccccgga ccaagtggtg gctatcgcca gcaacggtgg cggcaagcaa gcgctcgaaa  11220
cggtgcagcg gctgttgccg gtgctgtgcc aggaccatgg cctgaccccg gaccaagtgg  11280
tggctatcgc cagcaacggt ggcggcaagc aagcgctcga aacggtgcag cggctgttgc  11340
cggtgctgtg ccaggaccat ggcctgaccc cggaccaagt ggtggctatc gccagcaatc  11400
acggtggaaa acaggccctt gaaacggtgc agcggctgtt gccggtgctg tgccaggacc  11460
atggcctgac cccggaccaa gtggtggcta tcgccagcaa tcacggcggc aagcaagcgc  11520
tcgaaacggt gcagcggctg ttgccggtgc tgtgccagga ccatggcctg actccggacc  11580
aagtggtggc tatcgccagc cacgatggcg gcaagcaagc gctcgaaacg gtgcagcggc  11640
tgttgccggt gctgtgccag gaccatggcc tgactccgga ccaagtggtg gctatcgcca  11700
gccacgatgg cggcaagcaa gcgctcgaaa cggtgcagcg gctgttgccg gtgctgtgcc  11760
aggaccatgg cctgaccccg gaccaagtgg tggctatcgc cagcaacatt ggcggcaagc  11820
aagcgctcga aacggtgcag cggctgttgc cggtgctgtg ccaggaccat ggcctgaccc  11880
cggaccaagt ggtggctatc gccagcaatc acggcggcaa gcaagcgctc gaaacggtgc  11940
agcggctgtt gccggtgctg tgccaggacc atggcctgac tccggaccaa gtggtggcta  12000
tcgccagcca cgatggcggc aagcaagcgc tcgaaacggt gcagcggctg ttgccggtgc  12060
```

-continued

```
tgtgccagga ccatggcctg actccggacc aagtggtggc tatcgccagc cacgatggcg  12120
gcaagcaagc gctcgaaacg gtgcagcggc tgttgccggt gctgtgccag gaccatggcc  12180
tgaccccgga ccaagtggtg gctatcgcca gcaacggtgg cggcaagcaa gcgctcgaaa  12240
cggtgcagcg gctgttgccg gtgctgtgcc aggaccatgg cctgaccccg gaccaagtgg  12300
tggctatcgc cagcaacggt ggcggcaagc aagcgctcga aacggtgcag cggctgttgc  12360
cggtgctgtg ccaggaccat ggcctgaccc cggaccaagt ggtggctatc gccagcaatc  12420
acggcggcaa gcaagcgctc gaaagcattg tggcccagct gagccggcct gatccggcgt  12480
tggccgcgtt gaccaacgac cacctggtcg ctctggcttg cctgggagga cgccctgcta  12540
tggacgctgt gaagaaagga ctgccccacg cacccgaact gattagacgg gtgaaccgga  12600
gaatcggcga gagaacatcc catagggtgg caatctctag aactcagctg gtcaagagtg  12660
aactggagga aaagaaatca gagctgcgcc acaagctgaa atacgtgcct catgagtata  12720
tcgaactgat cgagattgct cgcaattcaa cccaggaccg gatcctggaa atgaaagtga  12780
tggagttctt tatgaaagtc tacggatatc gggggaaaca cctgggaggg agcagaaagc  12840
cagatggggc catctacaca gtgggatccc ccatcgacta tggcgtgatt gtcgatacta  12900
aagcctacag cggaggctat aacctgccta tcggccaggc tgacgagatg cagagatacg  12960
tggaggaaaa ccagacccgc aataagcata ttaaccccaa tgaatggtgg aaagtgtatc  13020
ctagctccgt cacagagttc aagtttctgt tcgtgagcgg acactttaag ggcaactaca  13080
aagcacagct gactaggctg aatcatatca ccaactgcaa tggagccgtg ctgtctgtcg  13140
aggaactgct gatcggggga gagatgatta aggctggcac actgactctg gaggaagtga  13200
ggcgcaagtt caacaatggg gaaatcaact tctaacctgc aggatgataa gctagccccg  13260
ggcgtacgga aaaaaaaaaa aaaaaaaaaa aaaaaaaaaa aaaaaaaaaa aaaaaaaaaa  13320
aaaaaaaaaa aaaaaaaaaa aaaaaaaaaa aaaaaaaaaa aaaaaaaaaa aaaaaaaaaa  13380
aaaaaaaaaa aaaaaaaaaa aaaaaaaaaa aaaaaaaaaa aaaaaaaaaa aaaaaaaaaa  13440
aaaaaaaaaa aaaaaaaaaa aaaaaaaaaa aaaaaaaaaa aaaaaaaaaa aaaaaaaaaa  13500
aaaaaaaaaa aaaaaaaaaa aaaaaaaaaa aaaaaaaaaa aaaaaaaaaa aaaaaaaaaa  13560
aaaaaaaaaa aaaaaaaaaa aaaaaaaaaa aaaacgagac cttagggcca ttagacttga  13620
agtcaagcgg ccgcttacaa ctggaccttg ctggtacata gaactgatta actgaccatt  13680
taaatcatac caacatggtc aaataaaacg aaaggctcag tcgaaagact gggcctttcg  13740
ttttaatctg atcggcacgt aagaggttcc aactttcacc ataatgaaat aagatcacta  13800
ccgggcgtat tttgagttat cgagattttc aggagctaag gaagctaaaa tgagccatat  13860
tcaacgggaa acgtcttgct cgaggccgcg attaaattcc aacatggatg ctgatttata  13920
tgggtataaa tgggctcgcg ataatgtcgg gcaatcaggt gcgacaatct atcgattgta  13980
tgggaagccc gatgcgccag agttgtttct gaaacatggc aaaggtagcg ttgccaatga  14040
tgttacagat gagatggtca ggctaaactg gctgacggaa tttatgcctc ttccgaccat  14100
caagcatttt atccgtactc ctgatgatgc atggttactc accactgcga tccccaggaa  14160
aacagcattc caggtattag aagaatatcc tgattcaggt gaaaatattg ttgatgcgct  14220
ggcagtgttc ctgcgccggt tgcattcgat tcctgtttgt aattgtcctt ttaacggcga  14280
tcgcgtattt cgtctggctc aggcgcaatc acgaatgaat aacggtttgg ttggtgcgag  14340
tgattttgat gacgagcgta atggctggcc tgttgaacaa gtctggaaag aaatgcataa  14400
```

acttttgcca ttctcaccgg attcagtcgt cactcatggt gatttctcac ttgataacct 14460
tatttttgac gaggggaaat taataggttg tattgatgtt ggacgagtcg gaatcgcaga 14520
ccgataccag gatcttgcca tcctatggaa ctgcctcggt gagttttctc cttcattaca 14580
gaaacggctt tttcaaaaat atggtattga taatcctgat atgaataaat tgcagtttca 14640
cttgatgctc gatgagtttt tctaacctag gtgacagaag tcaaaagcct ccggtcggag 14700
gcttttgact ttctgctaga tctgtttcaa tgcggtgaag ggccaggcag ctggggatta 14760
tgtccagacc cggccagcat gttggtttta tcgcatattc agcgttgtcg cgtttaccca 14820
ggtaaaatgg aagcagtgta tcgtctgcgt gaatgtgcaa atcaggaacg taaccgtggt 14880
acatagatgc agtcccttgc gggtcgttcc cttcaacgag taggacgcgg tgcccttgca 14940
aggctaacca ttgcgcctgg tgtactgcag atgaggtttt ataaacccct cccttgtgtg 15000
acataacgga aagtacaacc gggtttttat cgtcaggtct ttggtttggg ttaccaaaca 15060
cactccgcat atggctaatt tggtcaattg tgtagccagc gcgacgttct actcggcccc 15120
tcatctcaaa atcaggagcc ggtagacgac cagctttttc cgcatctctg atagcctgcg 15180
gtgttacgcc gatcaggtct gcaacttctg ttatacccca gcggcgagta atacgacgcg 15240
cttccgggct gtcatcgccg aactgtgcga tggcaatagc gcgcgtcatt tcctgaccgc 15300
gattgataca gtctttcagc aaattaatta acgacatcct gtttcctctc aaacatgccc 15360
ttatctttgt gtttttcatc atactttacg tttttaaagc aaagcaacat aaaaaaagca 15420
aagtgactta gaaaacgcaa agttaaggtt caaatcaatt ttttgatgcg ctacagaagc 15480
tatttagctt catctaagcg caacggtatt acttacgttg gtatatttaa aacctaactt 15540
aatgatttta aatgataata aatcatacca attgctatca aaagttaagc gaacatgctg 15600
attttcacgc tgtttataca ctttgaggca tctctatctc ttctgtctct atattgaaac 15660
acaatcaaag aacatcaatc catgtgacat cccccactat ctaagaacac cataacagaa 15720
cacaacatag gaatgcaaca ttaatgtatc aataattcgg aacatatgca ctatatcata 15780
tctcaattac ggaacatatc agcacacaat tgcccattat acgc 15824

<210> SEQ ID NO 59
<211> LENGTH: 16028
<212> TYPE: DNA
<213> ORGANISM: Artificial
<220> FEATURE:
<223> OTHER INFORMATION: TALEN plasmid sequence

<400> SEQUENCE: 59
gcgtataatg gactattgtg tgctgataag gagaacataa gcgcagaaca atatgtatct 60
attccggtgt tgtgttcctt tgttattctg ctattatgtt ctcttatagt gtgacgaaag 120
cagcataatt aatcgccact tgttctttga ttgtgttacg atatccagag acttagaaac 180
gggggaaccg ggatgagcaa ggtaaaaatc ggtgagttga tcaacacgct tgtgaatgag 240
gtagaggcaa ttgatgcctc agaccgccca caaggcgaca aaacgaagag aattaaagcc 300
gcagccgcac ggtataagaa cgcgttattt aatgataaaa gaaagttccg tgggaaagga 360
ttgcagaaaa gaataaccgc gaatactttt aacgcctata tgagcagggc aagaaagcgg 420
tttgatgata aattacatca tagctttgat aaaaatatta ataaattatc ggaaaagtat 480
cctctttaca gcgaagaatt atcttcatgg ctttctatgc ctacggctaa tattcgccag 540
cacatgtcat cgttacaatc taaattgaaa gaaataatgc cgcttgccga agagttatca 600
aatgtaagaa taggctctaa aggcagtgat gcaaaaatag caagactaat aaaaaaatat 660

-continued ccagattgga gttttgctct tagtgattta aacagtgatg attggaagga gcgccgtgac 720
tatctttata agttattcca acaaggctct gcgttgttag aagaactaca ccagctcaag 780
gtcaaccatg aggttctgta ccatctgcag ctaagccctg cggagcgtac atctatacag 840
caacgatggg ccgatgttct gcgcgagaag aagcgtaatg ttgtggttat tgactaccca 900
acatacatgc agtctatcta tgatattttg aataatcctg cgactttatt tagtttaaac 960
actcgttctg gaatggcacc tttggccttt gctctggctg cggtatcagg gcgaagaatg 1020
attgagataa tgtttcaggg tgaatttgcc gtttcaggaa agtatacggt taatttctca 1080
gggcaagcta aaaaacgctc tgaagataaa agcgtaacca gaacgattta tactttatgc 1140
gaagcaaaat tattcgttga attattaaca gaattgcgtt cttgctctgc tgcatctgat 1200
ttcgatgagg ttgttaaagg atatggaaag gatgatacaa ggtctgagaa cggcaggata 1260
aatgctattt tagcaaaagc atttaaccct tgggttaaat catttttcgg cgatgaccgt 1320
cgtgtttata aagatagccg cgctatttac gctcgcatcg cttatgagat gttcttccgc 1380
gtcgatccac ggtggaaaaa cgtcgacgag gatgtgttct tcatggagat tctcggacac 1440
gacgatgaga acacccagct gcactataag cagttcaagc tggccaactt ctccagaacc 1500
tggcgacctg aagttgggga tgaaaacacc aggctggtgg ctctgcagaa actggacgat 1560
gaaatgccag gctttgccag aggtgacgct ggcgtccgtc tgcatgaaac cgttaagcag 1620
ctggtggagc aggacccatc agcaaaaata accaacagca ctctccgggc ctttaaattt 1680
agcccgacga tgattagccg gtacctggag tttgccgctg atgcattggg gcagttcgtt 1740
ggcgagaacg ggcagtggca gctgaagata gagacacctg caatcgtcct gcctgatgaa 1800
gaatccgttg aaaccatcga cgaaccggat gatgagtccc aagacgacga gctggatgaa 1860
gatgaaattg agctcgacga gggtggcggc gatgaaccaa ccgaagagga agggccagaa 1920
gaacatcagc caactgctct aaaacccgtc ttcaagcctg caaaaaataa cggggacgga 1980
acgtacaaga tagagtttga atacgatgga aagcattatg cctggtccgg ccccgccgat 2040
agccctatgg ccgcaatgcg atccgcatgg gaaacgtact acagctaaaa gaaaagccac 2100
cggtgttaat cggtggcttt tttattgagg cctgtcccta cccatcccct gcaagggacg 2160
gaaggattag gcggaaactg cagctgcaac tacggacatc gccgtcccga ctgcagggac 2220
ttccccgcgt aaagcggggc ttaaattcgg gctggccaac cctatttttc tgcaatcgct 2280
ggcgatgtta gtttcgtgga tagcgtttcc agcttttcaa tggccagctc aaaatgtgct 2340
ggcagcacct tctccagttc cgtatcaata tcggtgatcg gcagctctcc acaagacata 2400
ctccggcgac cgccacgaac tacatcgcgc agcagctccc gttcgtagac acgcatgttg 2460
cccagagccg tttctgcagc cgttaatatc cggcgcagct cggcgatgat tgccgggaga 2520
tcatccacgg ttattgggtt cggtgatggg ttcctgcagg cgcggcggag agccatccag 2580
acgccgctaa cccatgcgtt acggtactga aaactttgtg ctatgtcgtt tatcaggccc 2640
cgaagttctt ctttctgccg ccagtccagt ggttcaccgg cgttcttagg ctcaggctcg 2700
acaaaagcat actcgccgtt tttccggata gctggcagaa cctcgttcgt cacccacttg 2760
cggaaccgcc aggctgtcgt cccctgtttc accgcgtcgc ggcagcggag gattatggtg 2820
tagaggccag attccgatac cacatttact tccctggcca tccgatcaag tttttgtgcc 2880
tcggttaaac cgagggtcaa tttttcatca tgatccagct tacgcaatgc atcagaaggg 2940
ttggctatat tcaatgcagc acagatatcc agcgccacaa accacgggtc accaccgaca 3000

-continued

```
agaaccaccc gtatagggtg gctttcctga aatgaaaaga cggagagagc cttcattgcg   3060
cctccccgga tttcagctgc tcagaaaggg acagggagca gccgcgagct tcctgcgtga   3120
gttcgcgcgc gacctgcaga agttccgcag cttcctgcaa atacagcgtg gcctcataac   3180
tggagatagt gcggtgagca gagcccacaa gcgcttcaac ctgcagcagg cgttcctcaa   3240
tcgtcttcag caggccctgg gcgtttaact gaatctggtt catgcgatca cctcgctgac   3300
cgggatacgg gctgacagaa cgaggacaaa acggctggcg aactggcgac gagcttctcg   3360
ctcggatgat gcagtggtgg aaaggcggtg gatatgggat tttttgtccg tgcggacgac   3420
agctgcaaat ttgaatttga acatggtatg cattcctatc ttgtataggg tgctaccacc   3480
agagttgaga atctctatag ggtggtagcc ccagacaggg ttctcaacac cggtacaaga   3540
agaaaccggc ccaaccgaag ttggccccat ctgagccacc ataattcagg tatgcgcaga   3600
tttaacacac aaaaaaacac gctggcgcgt gttgtgcgct tcttgtcatt cggggttgag   3660
aggcccggct gcagattttg ctgcagcggg gtaactctac cgccaaagca gaacgcacgt   3720
caataattta ggtggatatt ttaccccgtg accagtcacg tgcacaggtg tttttatagt   3780
ttgctttact gactgatcag aacctgatca gttattggag tccggtaatc ttattgatga   3840
ccgcagccac cttagatgtt gtctcaaacc ccatacggcc acgaatgagc cactggaacg   3900
gaatagtcag caggtacagc ggaacgaacc acaaacggtt cagacgctgc cagaacgtcg   3960
catcacgacg ttccatccat tcggtattgt cgacgacctg gtaagcgtat tgtcctggcg   4020
tttttgctgc ttccgagtag caatcctctt caccacaaag aaagttactt atctgcttcc   4080
agttttcgaa cccttcttct ttgagccgct tttccagctc attcctccac aaaacaggca   4140
cccatcctct gcgataaatc atgattattt gtcctttaaa taaggctgta gaactgcaaa   4200
atcgctctcg ttcacatgct gtacgtagat gcgtagcaaa ttgccgttcc atccctgtaa   4260
tccaccttct ttggaaagat cgtccttgac ctcacgaaga actttatcca atagccctgc   4320
ggcacaagaa attgcctgct ctggatcagc aaattcatat tgattaatag gtgattgcca   4380
cacaccaaaa acaggaatca tcttttcggc taaacgcctc tcctgttctt tcttaatctc   4440
aagttgtaag cggaccagct caccatccat catttttttgt agatcatgcg ccactattca   4500
cccccactgg ccatcagcaa ataaagcttc atactcggac accggcaggc ggcttccacg   4560
gattgaaagg tcaagccaac cacgtccaga tgggtcagcc ttatccgatt cttcccaccg   4620
ttctgcagct gtagcaacca ggcattctac cgccttcatg tagtcttctg tacggaacca   4680
gccgtagtta atgccaccat cagtaactgc ccaggccatc tttttctctt cggcctcaat   4740
agcccggatg cggttatcgc acagctcgcg acagtacttc agctgttcgt aatccagttg   4800
cttcaggaac tctggtgtcg acgtcatagt ggcttcacct tataggcttt tagaagcgcc   4860
ctggcttcgt ctgtgtggtc ttccatgctc ttatcgctgg caatgcagca ataaactccc   4920
tcactatctg agaacccgtt catccgaatg atcgtgaatg gaagttcccg gccagtttta   4980
taatcgctat agcttgtcgc gtcgtggctg accttgacca cataagggtc gtagccctcc   5040
acgatgacaa ggcattcccg ttgttttccc attacccctc cggttatatc gccacggctt   5100
gccgctggct tagaaacgct ttcagcagcc ttatttcgcg tactgatagc aggtccataa   5160
attcggtcat gtacagcgag gcgaacgttc tcgcgatgct ggccactggc cacaggcgta   5220
ccgcctccat ttcggttgct ggcaacgcgt tctccgccca cgcctccggt accgccaccg   5280
ggatagcctc cagtgcctgg ataattactg attgtggggc gtccggaacg tgctctgttt   5340
tggatcgagg gttaccatgt atatctatat ttagatccaa atcgcgatcc acttcgatgg   5400
```

-continued

```
tggttttttc caccttacgt gcgtgaattg ataaaccggc ctcgcggcgc ttctccacga   5460
tattcatgag gaactcgacc gagtccgggt caatggaacg catcgtgggg cgtgcatcgc   5520
catctctggc gcgtctggtc ttactggata gccccataga ctccaggatg cctatgcaga   5580
ggtctgcagg cgctttcttc ttgcctttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggtttttg gatcgatacc gcagtcgcgg aagtactgct   5760
gcagcgtcgc cgatttgagg gtgtagaaac cacgcatgcc tatctcaaca gcaggggtcg   5820
atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact tttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360
cggctttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgattttt tccggatcgg tttcacgttt accgcgaagc ttgtcgaaac   6540
cgataatgta ttcctgagct gtacggtcgc ggcgcagcat ctggatggcg tcgctgggga   6600
ccacttcgcc gcagaacatg ccgaaatggc ggtggaagtg tttctcctca atcgatacac   6660
ctgaagatat cgacgggctg tagatgaggc cgtcatattt tttcaccatc actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900
gatttttctc ggtataaaat acgcggatag gcttgttggt ttcgcggttg cgaacgtcga   6960
ccgggagttc aatcacgtga atttgcagcc aggcaggtag gcccagctcc tcgcgtcgct   7020
tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gcctttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg gcacggcatt   7620
tgcgattcaa ccggcgcgta atgtgatctt taacggtacc gttataaatt tctgcgatac   7680
ccatatcccg cagcgtgctg ctgaaaaggc gcataagttc tttcgggctg tttggtaccg   7740
```

-continued

```
ggcatgtcag catgccaata tcaacggcgc gaagcagttc tttggcaaaa gtgcgtctgt   7800
tcagacgcgg gagagtacgc agcttattca gcgtgatcga caacagatcg gttgcacggc   7860
tcagatgatt tctcgttaac tggcgagcga cttccttcag ccctctcagg ctgtgcaggt   7920
cgttaaaatc gctgcattcc agctcagggt catcctcaaa agttgggtaa acacatttga   7980
cgccggaaaa cttctccatg atgtcgaatc cggtgcggag gcctgtgttg ccttttcctt   8040
cagctgagga tttgcggtcg ttatcgagag cgcaagtgat ttgcgcagcc gggtacatgt   8100
tcaccagctg ctcgacaacg tgaatcatgt tgttagcgga aaccgcaatg actaccgcgt   8160
caaagcgttt tttcgggtcg tttctggtcg ccagccagat ggatgccccg gtggcgaaac   8220
cctctgcagt cgcaattttt tgcgcccccct gcaggtcgcc aataacaaag catgcaccga   8280
cgaaatcacc gttagtgatg gcgctggtct ggaacttgcc accattcaga tcgatacgtt   8340
gccagccaac aatccgcccg tcttttcttc cgtccaggtg ggacagaggt atcgccatgt   8400
aagttgttgg tccacggctc catttcgcac tgtcgtgact ggtcacgcga cgtatatcac   8460
aagcgccaaa tacgtcacga attccctttt ttaccgcata aggccaggag ccatcttcag   8520
ctggcgaatg ttcccaggcg cgatggaaag ccaaccatcc aagcaggcgt tcctgctcca   8580
tctgattgtt ttttaaatca ttaacgcgtt gttgttcagc tcggaggcgg cgtgcttcag   8640
cctggcgctc catgcgtgca cgttcttctt ccggctgagc gaccacggtc gcaccattcc   8700
gttgctgttc acggcgatac tccgaaaaca ggaatgaaaa gccactccag gagccagcgt   8760
catgcgcttt ttcaacgaag ttaacgaaag gataactgat gccatccttg ctctgctcaa   8820
ggcgtgaata gatttccaca cggcctttaa ggctcttctg cagagcttcc ggggaggaat   8880
tattgtaggt ggtatagcgc tctacaccac cgcgcggatt gagctgaatc ttatcagcac   8940
acgcaggcca gttgataccg gccatcttcg ccagctcagt cagctcatca cgtgccgcgt   9000
caagcagtga aaacggatcg ctgccaaagc gctccgcgta gaattcttgt aaggtcattt   9060
tttagccttt ccatgcgaat tagcattttt tcgggttgaa aaaatccgca ggagcagcca   9120
caataaacgc actatctttc tgaaggacgt atctgcgtta tcgtggctac ttcctgaaaa   9180
aggcccgagt ttgccgactc ggtttttttt tcgtcttttt tcggctgcta cggtctggtt   9240
caaccccgac aaagtataga tcggattaaa ccagaattat agtcagcaat aaaccctgtt   9300
attgtatcat ctaccctcaa ccatgaacga tttgatcgta ccgactactt ggtgcacaaa   9360
ttgaagatca cttttatcat ggataacccg ttgagagtta gcactatcaa ggtagtaatg   9420
ctgctcgtca taacgggcta atcgttgaat tgtgatctcg ccgttattat cacaaaccag   9480
tacatcctca cccggtacaa gcgtaagtga agaatcgacc aggataacat ctcccggctg   9540
gtagtttcgc tgaatctggt tcccgaccgt cagtgcgtaa acggtgttcc gttgactcac   9600
gaacggcagg aatcgctctg tgttggcagg ttctccaggc tgccagtctc tatccggtcc   9660
tgtctctgtc gtaccaataa caggaacgcg gtctggatca gattcagtgc catacagtat   9720
ccattgcacg ggcttacgca ggcattttgc cagcgatagc ccgatctcca gcgacggcat   9780
cacgtcgcca cgttctaagt tttggacgcc cggaagagag attcctacag cttctgccac   9840
ttgcttcagc gtcagtttca gctctaaacg gcgtgctttc agtcgttcgc ctcgtgtttt   9900
catacccctta atcataaatg atctctttat agctggctat aatttttata aattatacct   9960
agctttaatt ttcacttatt gattataata atccccatga aacccgaaga acttgtgcgc  10020
catttcggcg atgtggaaaa agcagcggtt ggcgtgggcg tgacacccgg cgcagtctat  10080
caatggctgc aagctgggga gattccacct ctacgacaaa gcgatataga ggtccgtacc  10140
```

gcgtacaaat taaagagtga tttcacctct cagcgcatgg gtaaggaagg gcataacaag 10200
gggatcctct agacgcagaa aggcccaccc gaaggtgagc cagtgtgatt acatttgcgg 10260
cctaactgtg gccagtccag ttacgctgga gtcactagtg cggccgcgac aacttgtcta 10320
gggcccaatg gcccatacac ttagtgtaat acgactcact atagggagag cggccgcttt 10380
ttcagcaaga ttaagccgcc accatggcgc cgcggcctcc taagaagaag cggaaagtcg 10440
aattcgtgga tctgcgaaca ctgggctata gccagcagca gcaggagaag atcaaaccca 10500
aggtgaggtc cacagtcgca cagcaccatg aagccctggt gggccacggg ttcactcacg 10560
ctcatattgt cgcactgtct cagcatccag ccgctctggg aaccgtggca gtcacatacc 10620
agcacatcat tactgccctg cccgaggcta cccatgaaga catcgtggga gtcggcaaac 10680
agtggagcgg cgcacgggcc ctggaggctc tgctgaccga cgcaggggaa ctgagaggac 10740
cccctctgca gctggataca gggcagctgg tgaagattgc taagagggga ggggtgacag 10800
caatggaagc cgtccacgca agcaggaacg cactgacagg ggccccccctg aacctgaccc 10860
cggaccaagt ggtggctatc gccagcaatc acggcggcaa gcaagcgctc gaaacggtgc 10920
agcggctgtt gccggtgctg tgccaggacc atggcctgac cccggaccaa gtggtggcta 10980
tcgccagcaa tcacggcggc aagcaagcgc tcgaaacggt gcagcggctg ttgccggtgc 11040
tgtgccagga ccatggcctg accccggacc aagtggtggc tatcgccagc aacggtggcg 11100
gcaagcaagc gctcgaaacg gtgcagcggc tgttgccggt gctgtgccag gaccatggcc 11160
tgactccgga ccaagtggtg gctatcgcca gccacgatgg cggcaagcaa gcgctcgaaa 11220
cggtgcagcg gctgttgccg gtgctgtgcc aggaccatgg cctgaccccg gaccaagtgg 11280
tggctatcgc cagcaacatt ggcggcaagc aagcgctcga aacggtgcag cggctgttgc 11340
cggtgctgtg ccaggaccat ggcctgaccc cggaccaagt ggtggctatc gccagcaaca 11400
ttggtggaaa acaggccctt gaaacggtgc agcggctgtt gccggtgctg tgccaggacc 11460
atggcctgac cccggaccaa gtggtggcta tcgccagcaa tcacggcggc aagcaagcgc 11520
tcgaaacggt gcagcggctg ttgccggtgc tgtgccagga ccatggcctg accccggacc 11580
aagtggtggc tatcgccagc aacggtggcg gcaagcaagc gctcgaaacg gtgcagcggc 11640
tgttgccggt gctgtgccag gaccatggcc tgaccccgga ccaagtggtg gctatcgcca 11700
gcaacggtgg cggcaagcaa gcgctcgaaa cggtgcagcg gctgttgccg gtgctgtgcc 11760
aggaccatgg cctgaccccg gaccaagtgg tggctatcgc cagcaacggt ggcggcaagc 11820
aagcgctcga aacggtgcag cggctgttgc cggtgctgtg ccaggaccat ggcctgaccc 11880
cggaccaagt ggtggctatc gccagcaatc acggcggcaa gcaagcgctc gaaacggtgc 11940
agcggctgtt gccggtgctg tgccaggacc atggcctgac tccggaccaa gtggtggcta 12000
tcgccagcca cgatggcggc aagcaagcgc tcgaaacggt gcagcggctg ttgccggtgc 12060
tgtgccagga ccatggcctg actccggacc aagtggtggc tatcgccagc cacgatggcg 12120
gcaagcaagc gctcgaaacg gtgcagcggc tgttgccggt gctgtgccag gaccatggcc 12180
tgaccccgga ccaagtggtg gctatcgcca gcaacggtgg cggcaagcaa gcgctcgaaa 12240
cggtgcagcg gctgttgccg gtgctgtgcc aggaccatgg cctgaccccg gaccaagtgg 12300
tggctatcgc cagcaacggt ggcggcaagc aagcgctcga aacggtgcag cggctgttgc 12360
cggtgctgtg ccaggaccat ggcctgaccc cggaccaagt ggtggctatc gccagcaatc 12420
acggcggcaa gcaagcgctc gaaacggtgc agcggctgtt gccggtgctg tgccaggacc 12480

-continued atggcctgac cccggaccaa gtggtggcta tcgccagcaa cggtggcggc aagcaagcgc 12540
tcgaaacggt gcagcggctg ttgccggtgc tgtgccagga ccatggcctg accccggacc 12600
aagtggtggc tatcgccagc cacgatggcg gcaagcaagc gctcgaaagc attgtggccc 12660
agctgagccg gcctgatccg gcgttggccg cgttgaccaa cgaccacctg gtcgctctgg 12720
cttgcctggg aggacgccct gctatggacg ctgtgaagaa aggactgccc cacgcacccg 12780
aactgattag acgggtgaac cggagaatcg gcgagagaac atcccatagg gtggcaatct 12840
ctagaactca gctggtcaag agtgaactgg aggaaaagaa atcagagctg cgccacaagc 12900
tgaaatacgt gcctcatgag tatatcgaac tgatcgagat tgctcgcaat tcaacccagg 12960
accggatcct ggaaatgaaa gtgatggagt tctttatgaa agtctacgga tatcggggga 13020
aacacctggg agggagcaga aagccagatg ggccatcta cacagtggga tcccccatcg 13080
actatggcgt gattgtcgat actaaagcct acagcggagg ctataacctg cctatcggcc 13140
aggctgacga gatgcagaga tacgtggagg aaaaccagac ccgcaataag catattaacc 13200
ccaatgaatg gtggaaagtg tatcctagct ccgtcacaga gttcaagttt ctgttcgtga 13260
gcggacactt taagggcaac tacaaagcac agctgactag gctgaatcat atcaccaact 13320
gcaatggagc cgtgctgtct gtcgaggaac tgctgatcgg gggagagatg attaaggctg 13380
gcacactgac tctggaggaa gtgaggcgca agttcaacaa tggggaaatc aacttctaac 13440
ctgcaggatg ataagctagc cccgggcgta cggaaaaaaa aaaaaaaaaa aaaaaaaaaa 13500
aaaaaaaaaa aaaaaaaaaa aaaaaaaaaa aaaaaaaaaa aaaaaaaaaa aaaaaaaaaa 13560
aaaaaaaaaa aaaaaaaaaa aaaaaaaaaa aaaaaaaaaa aaaaaaaaaa aaaaaaaaaa 13620
aaaaaaaaaa aaaaaaaaaa aaaaaaaaaa aaaaaaaaaa aaaaaaaaaa aaaaaaaaaa 13680
aaaaaaaaaa aaaaaaaaaa aaaaaaaaaa aaaaaaaaaa aaaaaaaaaa aaaaaaaaaa 13740
aaaaaaaaaa aaaaaaaaaa aaaaaaaaaa aaaaaaaaaa aaaaaaaaaa aaaaaaaacg 13800
agaccttagg gccattagac ttgaagtcaa gcggccgctt acaactggac cttgctggta 13860
catagaactg attaactgac catttaaatc ataccaacat ggtcaaataa aacgaaaggc 13920
tcagtcgaaa gactgggcct ttcgttttaa tctgatcggc acgtaagagg ttccaacttt 13980
caccataatg aaataagatc actaccgggc gtattttgag ttatcgagat tttcaggagc 14040
taaggaagct aaaatgagcc atattcaacg ggaaacgtct tgctcgaggc cgcgattaaa 14100
ttccaacatg gatgctgatt tatatgggta taaatgggct cgcgataatg tcgggcaatc 14160
aggtgcgaca atctatcgat tgtatgggaa gcccgatgcg ccagagttgt ttctgaaaca 14220
tggcaaaggt agcgttgcca atgatgttac agatgagatg gtcaggctaa actggctgac 14280
ggaatttatg cctcttccga ccatcaagca ttttatccgt actcctgatg atgcatggtt 14340
actcaccact gcgatcccag ggaaaacagc attccaggta ttagaagaat atcctgattc 14400
aggtgaaaat attgttgatg cgctggcagt gttcctgcgc cggttgcatt cgattcctgt 14460
ttgtaattgt ccttttaacg gcgatcgcgt atttcgtctg gctcaggcgc aatcacgaat 14520
gaataacggt ttggttggtg cgagtgattt tgatgacgag cgtaatggct ggcctgttga 14580
acaagtctgg aaagaaatgc ataaactttt gccattctca ccggattcag tcgtcactca 14640
tggtgatttc tcacttgata accttatttt tgacgagggg aaattaatag gttgtattga 14700
tgttggacga gtcggaatcg cagaccgata ccaggatctt gccatcctat ggaactgcct 14760
cggtgagttt tctccttcat tacagaaacg gctttttcaa aaatatggta ttgataatcc 14820
tgatatgaat aaattgcagt ttcacttgat gctcgatgag tttttctaac ctaggtgaca 14880

-continued gaagtcaaaa gcctccggtc ggaggctttt gactttctgc tagatctgtt tcaatgcggt 14940
gaagggccag gcagctgggg attatgtcca gacccggcca gcatgttggt tttatcgcat 15000
attcagcgtt gtcgcgttta cccaggtaaa atggaagcag tgtatcgtct gcgtgaatgt 15060
gcaaatcagg aacgtaaccg tggtacatag atgcagtccc ttgcgggtcg ttcccttcaa 15120
cgagtaggac gcggtgccct tgcaaggcta accattgcgc ctggtgtact gcagatgagg 15180
ttttataaac ccctcccttg tgtgacataa cggaaagtac aaccgggttt ttatcgtcag 15240
gtctttggtt tgggttacca aacacactcc gcatatggct aatttggtca attgtgtagc 15300
cagcgcgacg ttctactcgg cccctcatct caaaatcagg agccggtaga cgaccagctt 15360
tttccgcatc tctgatagcc tgcggtgtta cgccgatcag gtctgcaact tctgttatac 15420
cccagcggcg agtaatacga cgcgcttccg ggctgtcatc gccgaactgt gcgatggcaa 15480
tagcgcgcgt catttcctga ccgcgattga tacagtcttt cagcaaatta attaacgaca 15540
tcctgtttcc tctcaaacat gcccttatct ttgtgttttt catcatactt tacgttttta 15600
aagcaaagca acataaaaaa agcaaagtga cttagaaaac gcaaagttaa ggttcaaatc 15660 aatttttga tgcgctacag aagctattta gcttcatcta agcgcaacgg tattacttac 15720
gttggtatat ttaaaaccta acttaatgat tttaaatgat aataaatcat accaattgct 15780
atcaaaagtt aagcgaacat gctgattttc acgctgttta tacactttga ggcatctcta 15840
tctcttctgt ctctatattg aaacacaatc aaagaacatc aatccatgtg acatccccca 15900
ctatctaaga acaccataac agaacacaac ataggaatgc aacattaatg tatcaataat 15960
tcggaacata tgcactatat catatctcaa ttacggaaca tatcagcaca caattgccca 16020
ttatacgc 16028

<210> SEQ ID NO 60
<211> LENGTH: 19
<212> TYPE: PRT
<213> ORGANISM: Artificial
<220> FEATURE:
<223> OTHER INFORMATION: polynucleotide sequence for exemplary 2A sites

<400> SEQUENCE: 60

Leu Leu Asn Phe Asp Leu Leu Lys Leu Ala Gly Asp Val Glu Ser Asn
1               5                   10                  15

Pro Gly Pro

<210> SEQ ID NO 61
<211> LENGTH: 19
<212> TYPE: PRT
<213> ORGANISM: Artificial
<220> FEATURE:
<223> OTHER INFORMATION: polynucleotide sequence for exemplary 2A sites

<400> SEQUENCE: 61

Thr Leu Asn Phe Asp Leu Leu Lys Leu Ala Gly Asp Val Glu Ser Asn
1               5                   10                  15

Pro Gly Pro

<210> SEQ ID NO 62
<211> LENGTH: 14
<212> TYPE: PRT
<213> ORGANISM: Artificial
<220> FEATURE:
<223> OTHER INFORMATION: polynucleotide sequence for exemplary 2A sites

<400> SEQUENCE: 62

Leu Leu Lys Leu Ala Gly Asp Val Glu Ser Asn Pro Gly Pro
1 5 10

<210> SEQ ID NO 63
<211> LENGTH: 17
<212> TYPE: PRT
<213> ORGANISM: Artificial
<220> FEATURE:
<223> OTHER INFORMATION: polynucleotide sequence for exemplary 2A sites

<400> SEQUENCE: 63

Asn Phe Asp Leu Leu Lys Leu Ala Gly Asp Val Glu Ser Asn Pro Gly
1 5 10 15

Pro

<210> SEQ ID NO 64
<211> LENGTH: 20
<212> TYPE: PRT
<213> ORGANISM: Artificial
<220> FEATURE:
<223> OTHER INFORMATION: polynucleotide sequence for exemplary 2A sites

<400> SEQUENCE: 64

Gln Leu Leu Asn Phe Asp Leu Leu Lys Leu Ala Gly Asp Val Glu Ser
1 5 10 15

Asn Pro Gly Pro
20

<210> SEQ ID NO 65
<211> LENGTH: 24
<212> TYPE: PRT
<213> ORGANISM: Artificial
<220> FEATURE:
<223> OTHER INFORMATION: polynucleotide sequence for exemplary 2A sites

<400> SEQUENCE: 65

Ala Pro Val Lys Gln Thr Leu Asn Phe Asp Leu Leu Lys Leu Ala Gly
1 5 10 15

Asp Val Glu Ser Asn Pro Gly Pro
20

<210> SEQ ID NO 66
<211> LENGTH: 40
<212> TYPE: PRT
<213> ORGANISM: Artificial
<220> FEATURE:
<223> OTHER INFORMATION: polynucleotide sequence for exemplary 2A sites

<400> SEQUENCE: 66

Val Thr Glu Leu Leu Tyr Arg Met Lys Arg Ala Glu Thr Tyr Cys Pro
1 5 10 15

Arg Pro Leu Leu Ala Ile His Pro Thr Glu Ala Arg His Lys Gln Lys
20 25 30

Ile Val Ala Pro Val Lys Gln Thr
35 40

<210> SEQ ID NO 67
<211> LENGTH: 18
<212> TYPE: PRT
<213> ORGANISM: Artificial
<220> FEATURE:
<223> OTHER INFORMATION: polynucleotide sequence for exemplary 2A sites

<400> SEQUENCE: 67

Leu Asn Phe Asp Leu Leu Lys Leu Ala Gly Asp Val Glu Ser Asn Pro
1               5                   10                  15

Gly Pro

<210> SEQ ID NO 68
<211> LENGTH: 40
<212> TYPE: PRT
<213> ORGANISM: Artificial
<220> FEATURE:
<223> OTHER INFORMATION: polynucleotide sequence for exemplary 2A sites

<400> SEQUENCE: 68

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 69
<211> LENGTH: 33
<212> TYPE: PRT
<213> ORGANISM: Artificial
<220> FEATURE:
<223> OTHER INFORMATION: polynucleotide sequence for exemplary 2A sites

<400> SEQUENCE: 69

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 70
<211> LENGTH: 3
<212> TYPE: PRT
<213> ORGANISM: Artificial
<220> FEATURE:
<223> OTHER INFORMATION: linker sequence

<400> SEQUENCE: 70

Gly Gly Gly
1

<210> SEQ ID NO 71
<211> LENGTH: 5
<212> TYPE: PRT
<213> ORGANISM: Artificial
<220> FEATURE:
<223> OTHER INFORMATION: linker sequence

<400> SEQUENCE: 71

Asp Gly Gly Gly Ser
1               5

<210> SEQ ID NO 72
<211> LENGTH: 5
<212> TYPE: PRT
<213> ORGANISM: Artificial
<220> FEATURE:
<223> OTHER INFORMATION: linker sequence

<400> SEQUENCE: 72

-continued

Thr Gly Glu Lys Pro
1 5

<210> SEQ ID NO 73
<211> LENGTH: 4
<212> TYPE: PRT
<213> ORGANISM: Artificial
<220> FEATURE:
<223> OTHER INFORMATION: linker sequence

<400> SEQUENCE: 73

Gly Gly Arg Arg
1

<210> SEQ ID NO 74
<211> LENGTH: 5
<212> TYPE: PRT
<213> ORGANISM: Artificial
<220> FEATURE:
<223> OTHER INFORMATION: linker sequence

<400> SEQUENCE: 74

Gly Gly Gly Gly Ser
1 5

<210> SEQ ID NO 75
<211> LENGTH: 14
<212> TYPE: PRT
<213> ORGANISM: Artificial
<220> FEATURE:
<223> OTHER INFORMATION: linker sequence

<400> SEQUENCE: 75

Glu Gly Lys Ser Ser Gly Ser Gly Ser Glu Ser Lys Val Asp
1 5 10

<210> SEQ ID NO 76
<211> LENGTH: 18
<212> TYPE: PRT
<213> ORGANISM: Artificial
<220> FEATURE:
<223> OTHER INFORMATION: linker sequence

<400> SEQUENCE: 76

Lys Glu Ser Gly Ser Val Ser Ser Glu Gln Leu Ala Gln Phe Arg Ser
1 5 10 15

Leu Asp

<210> SEQ ID NO 77
<211> LENGTH: 8
<212> TYPE: PRT
<213> ORGANISM: Artificial
<220> FEATURE:
<223> OTHER INFORMATION: linker sequence

<400> SEQUENCE: 77

Gly Gly Arg Arg Gly Gly Gly Ser
1 5

<210> SEQ ID NO 78
<211> LENGTH: 9
<212> TYPE: PRT
<213> ORGANISM: Artificial
<220> FEATURE:
<223> OTHER INFORMATION: linker sequence

<400> SEQUENCE: 78

Leu Arg Gln Arg Asp Gly Glu Arg Pro
1               5

<210> SEQ ID NO 79
<211> LENGTH: 12
<212> TYPE: PRT
<213> ORGANISM: Artificial
<220> FEATURE:
<223> OTHER INFORMATION: linker sequence

<400> SEQUENCE: 79

Leu Arg Gln Lys Asp Gly Gly Gly Ser Glu Arg Pro
1               5                   10

<210> SEQ ID NO 80
<211> LENGTH: 12
<212> TYPE: PRT
<213> ORGANISM: Artificial
<220> FEATURE:
<223> OTHER INFORMATION: linker sequence

<400> SEQUENCE: 80

Leu Arg Gln Lys Asp Gly Gly Gly Ser Glu Arg Pro
1               5                   10

<210> SEQ ID NO 81
<211> LENGTH: 61
<212> TYPE: DNA
<213> ORGANISM: Homo sapiens

<400> SEQUENCE: 81
ccagccttgc cttgaccaat agccttgaca aggcaaactt gaccaatagt cttagagtat     60
c                                                                     61

<210> SEQ ID NO 82
<211> LENGTH: 61
<212> TYPE: DNA
<213> ORGANISM: Homo sapiens

<400> SEQUENCE: 82
catgggttgg ccagccttgc cttgaccaat agccttgaca aggcaaactt gaccaatagt     60
c                                                                     61

<210> SEQ ID NO 83
<211> LENGTH: 41
<212> TYPE: DNA
<213> ORGANISM: Homo sapiens

<400> SEQUENCE: 83
cttgaccaat agccttgaca aggcaaactt gaccaatagt c                         41

<210> SEQ ID NO 84
<211> LENGTH: 87
<212> TYPE: DNA
<213> ORGANISM: Artificial
<220> FEATURE:
<223> OTHER INFORMATION: ddPCR assay

<400> SEQUENCE: 84
aaactacagg cctcactgga atcctctatg atgggagaag gaaactcctt gaccaatagc     60
cttgacaaaa aggaagcacc cttcagc                                         87

<210> SEQ ID NO 85
<211> LENGTH: 87
<212> TYPE: DNA
<213> ORGANISM: Artificial
<220> FEATURE:
<223> OTHER INFORMATION: ddPCR assay

<400> SEQUENCE: 85
aaactacagg cctcactgga atcttctatg gtgggagaag aaaactcctt gaccaatagc 60
cttgacaaaa aggaagcacc cttcagc 87

<210> SEQ ID NO 86
<211> LENGTH: 38
<212> TYPE: DNA
<213> ORGANISM: Homo sapiens

<400> SEQUENCE: 86
ggccagcctt gccttgacca atagccttga caaggcaa 38

<210> SEQ ID NO 87
<211> LENGTH: 40
<212> TYPE: DNA
<213> ORGANISM: Homo sapiens

<400> SEQUENCE: 87
ccttgaccaa tagccttgac aaggcaaact tgaccaatag 40

<210> SEQ ID NO 88
<211> LENGTH: 40
<212> TYPE: DNA
<213> ORGANISM: Homo sapiens

<400> SEQUENCE: 88
gggttggcca gtcttgccaa tagccttgac aaggcaacct 40

<210> SEQ ID NO 89
<211> LENGTH: 44
<212> TYPE: DNA
<213> ORGANISM: Homo sapiens

<400> SEQUENCE: 89
gggttggcca gtcttgcctt gaaatagcct tgacaaggca acct 44

<210> SEQ ID NO 90
<211> LENGTH: 43
<212> TYPE: DNA
<213> ORGANISM: Homo sapiens

<400> SEQUENCE: 90
gggttggcca gtcttgcctt gaatagcctt gacaaggcaa cct 43

<210> SEQ ID NO 91
<211> LENGTH: 33
<212> TYPE: DNA
<213> ORGANISM: Homo sapiens

<400> SEQUENCE: 91
gggttggcca gtcttgcctt gacaaggcaa cct 33

<210> SEQ ID NO 92
<211> LENGTH: 45
<212> TYPE: DNA
<213> ORGANISM: Homo sapiens -continued

```
<400> SEQUENCE: 92

gggttggcca gtcttgcctt gacaatagcc ttgacaaggc aacct                  45


<210> SEQ ID NO 93
<211> LENGTH: 42
<212> TYPE: DNA
<213> ORGANISM: Homo sapiens

<400> SEQUENCE: 93

gggttggcca gtcttgcctt gatagccttg acaaggcaac ct                     42
```